United States Patent
Stamford et al.

(10) Patent No.: US 8,361,959 B2
(45) Date of Patent: Jan. 29, 2013

(54) SPIRO-IMIDAZOLONE DERIVATIVES AS GLUCAGON RECEPTOR ANTAGONISTS

(75) Inventors: Andrew Stamford, Chatham Township, NJ (US); Michael W. Miller, Scotch Plains, NJ (US); Duane Eugene DeMong, Somerset, NJ (US); William J. Greenlee, Teaneck, NJ (US); Joseph A. Kozlowski, Princeton, NJ (US); Brian J. Lavey, New Providence, NJ (US); Michael K. C. Wong, Somerset, NJ (US); Wensheng Yu, Edison, NJ (US); Xing Dai, Cranford, NJ (US); De-Yi Yang, Morris Plains, NJ (US); Guowei Zhou, Somerset, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 72 days.

(21) Appl. No.: 13/121,725

(22) PCT Filed: Sep. 30, 2009

(86) PCT No.: PCT/US2009/058963
§ 371 (c)(1),
(2), (4) Date: Mar. 30, 2011

(87) PCT Pub. No.: WO2010/039789
PCT Pub. Date: Apr. 8, 2010

(65) Prior Publication Data
US 2011/0178007 A1  Jul. 21, 2011

Related U.S. Application Data

(60) Provisional application No. 61/102,565, filed on Oct. 3, 2008.

(51) Int. Cl.
*A61F 7/10* (2006.01)
*A61K 31/4184* (2006.01)
*C07D 235/02* (2006.01)

(52) U.S. Cl. ....... 514/5.9; 514/381; 548/251; 548/300.7
(58) Field of Classification Search .................. 514/5.9, 514/381; 548/251, 300.7
See application file for complete search history.

(56) References Cited

U.S. PATENT DOCUMENTS

| | | |
|---|---|---|
| 2005/0272794 A1 | 12/2005 | Parmee et al. |
| 2006/0084681 A1 | 4/2006 | Parmee et al. |
| 2007/0088071 A1 | 4/2007 | Kim et al. |
| 2007/0105930 A1 | 5/2007 | Parmee et al. |
| 2007/0203186 A1 | 8/2007 | Beeson et al. |
| 2008/0085926 A1 | 4/2008 | Stelmach et al. |
| 2008/0108620 A1 | 5/2008 | Brockunier et al. |
| 2008/0161347 A1 | 7/2008 | Stelmach et al. |
| 2009/0054506 A1 | 2/2009 | Liang et al. |
| 2009/0054662 A1 | 2/2009 | Tan et al. |
| 2009/0105310 A1 | 4/2009 | Kim et al. |
| 2009/0176854 A1 | 7/2009 | Parmee et al. |
| 2009/0209564 A1 | 8/2009 | Kim et al. |
| 2009/0215825 A1 | 8/2009 | Parmee et al. |
| 2010/0144824 A1 | 6/2010 | Stelmach et al. |
| 2011/0065634 A1 | 3/2011 | Greenlee et al. |
| 2011/0172256 A1 | 7/2011 | Lin et al. |
| 2011/0251248 A1 | 10/2011 | Lin et al. |
| 2011/0281795 A1 | 11/2011 | Lin et al. |
| 2011/0301082 A1 | 12/2011 | Lin et al. |
| 2011/0306524 A1 | 12/2011 | Lin et al. |
| 2011/0312911 A1 | 12/2011 | Kats-Kagan et al. |
| 2012/0010262 A1 | 1/2012 | Chung et al. |

FOREIGN PATENT DOCUMENTS

| | | | |
|---|---|---|---|
| WO | 2005/058845 | | 6/2005 |
| WO | WO 2007/104762 | * | 8/2007 |
| WO | 2007/106181 | | 9/2007 |
| WO | 2007/111864 | | 10/2007 |
| WO | 2007/114855 | | 10/2007 |
| WO | 2010/080971 | | 7/2010 |
| WO | 2010/144664 | | 12/2010 |
| WO | 2011/037815 | | 3/2011 |
| WO | 2011/119541 | | 9/2011 |
| WO | 2011/119559 | | 9/2011 |

OTHER PUBLICATIONS

Int'l Search Report at PCT/US2009/058963, dated Feb. 4, 2010.
Int'l Preliminary Report on Patentability of PCT/US2009/058963, dated Apr. 5, 2011.

* cited by examiner

*Primary Examiner* — Susannah Chung
(74) *Attorney, Agent, or Firm* — Anna L. Cocuzzo; Joan C. Todaro

(57) ABSTRACT

The present invention relates to compounds of the general formula: (I) wherein ring A, ring B, $R^1$, $R^3$, Z, $L^1$, and $L^2$ are selected independently of each other and are as defined herein, to compositions comprising the compounds, and to methods of using the compounds as glucagon receptor antagonists and for the treatment or prevention of type 2 diabetes and conditions related thereto.

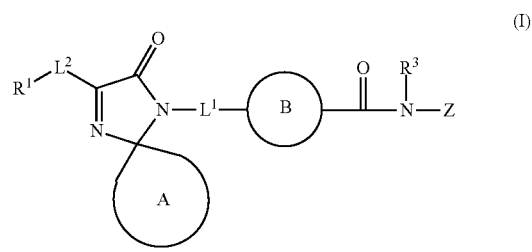

18 Claims, No Drawings

SPIRO-IMIDAZOLONE DERIVATIVES AS GLUCAGON RECEPTOR ANTAGONISTS

CROSS-REFERENCE TO RELATED APPLICATION

This application claims priority to provisional application U.S. Ser. No. 61/102,565, filed Oct. 3, 2008, incorporated by reference.

FIELD OF THE INVENTION

The present invention relates to certain novel compounds as glucagon receptor antagonists, compositions comprising these compounds, and methods for their use in treating, preventing, or delaying the onset of type 2 diabetes and related conditions.

BACKGROUND OF THE INVENTION

Diabetes refers to a disease state or process derived from multiple causative factors and is characterized by elevated levels of plasma glucose (hyperglycemia) in the fasting state or after administration of glucose during a glucose tolerance test. Persistent or uncontrolled hyperglycemia is associated with a wide range of pathologies. Diabetes mellitus, is associated with elevated fasting blood glucose levels and increased and premature cardiovascular disease and premature mortality. It is also related directly and indirectly to various metabolic conditions, including alterations of lipid, lipoprotein, apolipoprotein metabolism and other metabolic and hemodynamic diseases. As such, the diabetic patient is at increased risk of macrovascular and microvascular complications. Such complications can lead to diseases and conditions such as coronary heart disease, stroke, peripheral vascular disease, hypertension, nephropathy, neuropathy, and retinopathy. Accordingly, therapeutic control and correction of glucose homeostasis is regarded as important in the clinical management and treatment of diabetes mellitus.

There are two generally recognized forms of diabetes. In type 1 diabetes, or insulin-dependent diabetes mellitus (IDDM), the diabetic patient's pancreas is incapable of producing adequate amounts of insulin, the hormone which regulates glucose uptake and utilization by cells. In type 2 diabetes, or noninsulin dependent diabetes mellitus (NIDDM), patients often produce plasma insulin levels comparable to those of nondiabetic subjects; however, the cells of patients suffering from type 2 diabetes develop a resistance to the effect of insulin, even in normal or elevated plasma levels, on glucose and lipid metabolism, especially in the main insulin-sensitive tissues (muscle, liver and adipose tissue).

Insulin resistance is not associated with a diminished number of cellular insulin receptors but rather with a post-insulin receptor binding defect that is not well understood. This cellular resistance to insulin results in insufficient insulin activation of cellular glucose uptake, oxidation, and storage in muscle, and inadequate insulin repression of lipolysis in adipose tissue, and of glucose production and secretion in the liver. A net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

The available treatments for type 2 diabetes, some of which have not changed substantially in many years, are used alone and in combination. Many of these treatments have recognized limitations, however. For example, while physical exercise and reductions in dietary intake of fat, high glycemic carbohydrates, and calories can dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic beta-cells to secrete more insulin, and/or by injection of insulin when sulfonylureas or meglitinide become ineffective, can result in insulin concentrations high enough to stimulate insulin-resistance in tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a separate class of agents that can increase insulin sensitivity and bring about some degree of correction of hyperglycemia. These agents, however, can induce lactic acidosis, nausea and diarrhea.

The glitazones (i.e. 5-benzylthiazolidine-2,4-diones) are another class of compounds that have proven useful for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination thereof, and in many cases are chemically different from the glitazones (i.e., they are not thiazolidinediones). Serious side effects (e.g. liver toxicity) have been noted in some patients treated with glitazone drugs, such as troglitazone.

Compounds that are inhibitors of the dipeptidyl peptidase-IV (DPP-IV) enzyme are also under investigation as drugs that may be useful in the treatment of diabetes, and particularly type 2 diabetes.

Additional methods of treating hyperglycemia and diabetes are currently under investigation. New biochemical approaches include treatment with alpha-glucosidase inhibitors (e.g. acarbose) and protein tyrosine phosphatase-1B (PTP-1B) inhibitors.

Other approaches to treating hyperglycemia, diabetes, and indications attendant thereto have focused on the glucagon hormone receptor. Glucagon and insulin are the two primary hormones regulating plasma glucose levels. Insulin, released in response to a meal, increases the uptake of glucose into insulin-sensitive tissues such as skeletal muscle and fat. Glucagon, which is secreted by alpha cells in pancreatic islets in response to decreased postprandial glucose levels or during fasting, signals the production and release of glucose from the liver. Glucagon binds to specific receptors in liver cells that trigger glycogenolysis and an increase in gluconeogenesis through cAMP-mediated events. These responses generate increases in plasma glucose levels (e.g., hepatic glucose production), which help to regulate glucose homeostasis.

Type 2 diabetic patients typically have fasting hyperglycemia that is associated with elevated rates of hepatic glucose production. This is due to increased gluconeogenesis coupled with hepatic insulin resistance. Such patients typically have a relative deficiency in their fasting and postprandial insulin-to-glucagon ratio that contributes to their hyperglycemic state. Several studies have demonstrated that hepatic glucose production correlates with fasting plasma glucose levels, suggesting that chronic hepatic glucagon receptor antagonism should improve this condition. In addition, defects in rapid postprandial insulin secretion, as well as ineffective suppression of glucagon secretion, lead to increased glucagon levels that elevate hepatic glucose production and contribute to hyperglycemia. Suppression of elevated postprandial glucagon levels in type 2 diabetics with somatostatin has been shown to lower blood glucose concentrations. This indicates that acute postprandial glucagon receptor antagonism would also be beneficial. Based on these and other data, glucagon receptor antagonism holds promise as a potential treatment of type 2 diabetes by reducing hyperglycemia. There is thus a need in the art for small-molecule glucagon receptor antagonists with good safety profiles and efficacy that are useful for the treatment of hyperglycemia, diabetes, and related metabolic diseases and indications. The present invention addresses that need.

SUMMARY OF THE INVENTION

In one embodiment, the compounds of the invention have the general structure shown in Formula (A):

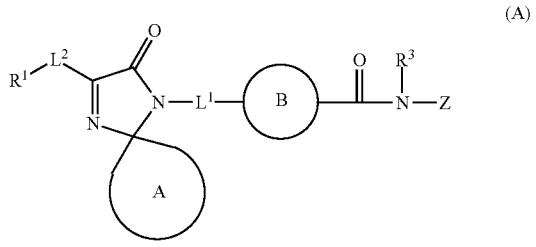

(A)

and include pharmaceutically acceptable salts, solvates, esters, prodrugs, tautomers, and isomers of said compounds, wherein ring A, ring B, $L^1$, $L^2$, $R^1$, $R^3$, and Z are selected independently of each other and are as defined below.

The invention also relates to compositions, including pharmaceutically acceptable compositions, comprising the compounds of the invention (alone and in combination with one or more additional therapeutic agents), and to methods of using such compounds and compositions as glucagon receptor antagonists and for the treatment or prevention of type 2 diabetes and conditions related thereto.

DETAILED DESCRIPTION OF THE INVENTION

In one embodiment, the compounds of the invention have the general structure shown in Formula (A):

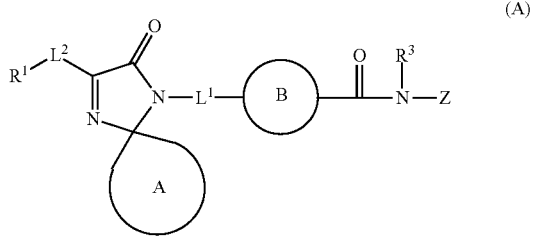

(A)

and include pharmaceutically acceptable salts, solvates, esters, prodrugs, tautomers, and isomers of said compounds, wherein ring A, ring B, $L^2$, $R^1$, $R^3$, and Z are selected independently of each other and wherein:

$L^1$ is selected from the group consisting of a bond, $-N(R^4)-$, $-N(R^4)-C(R^{5A})_2-(C(R^5)_2)_q-$, $-C(R^{5A})_2-(C(R^5)_2)_r-C(R^{5A})_2-N(R^4)-$, $-O-$, $-O-(C(R^{5A})_2)-(C(R^5)_2)_q-$, $-(C(R^{5A})_2)-(C(R^5)_2)_r-(C(R^{5A})_2)-O-$, and $-(C(R^{5A})_2)-(C(R^5)_2)_s-$, each q is independently an integer from 0 to 5;
each r is independently an integer from 0 to 3;
s is an integer from 0 to 5;

$L^2$ is selected from the group consisting of a bond, $-N(R^4)-$, $-N(R^4)-(C(R^{5A})_2)-(C(R^5)_2)_t-$, $-(C(R^5)_2)_u-(C(R^{5A})_2)-N(R^4)-$, $-O-$, $-O-(C(R^{5A})_2)-(C(R^5)_2)_t-$, $-(C(R^5)_2)_u-(C(R^{5A})_2)-O-$, $-S-$, $-S-(C(R^{5A})_2)-(C(R^5)_2)_r-$, $-(C(R^5)_2)_u-(C(R^{5A})_2)-S-$, $-S(O)-$, $-S(O)-(C(R^{5A})_2)-(C(R^5)_2)_t-$, $-(C(R^5)_2)_u-(C(R^{5A})_2)-S(O)-$, $-S(O)_2-$, $-S(O)_2-(C(R^{5A})_2)-(C(R^5)_2)_t-$, $-(C(R^5)_2)_u-(C(R^{5A})_2)-S(O)_2-$, $-(C(R^3)_2)_v-$;

each t is independently an integer from 0 to 3;
each u is independently an integer from 0 to 3;
v is an integer from 1 to 5;

ring A represents a spirocycloalkyl ring or a spirocycloalkenyl ring, wherein said ring A is substituted on one or more available ring carbon atoms with from 0 to 5 independently selected $R^2$ groups, or, alternatively, ring A represents a spiroheterocycloalkyl ring or a spiroheterocycloalkenyl ring, wherein said ring A is substituted on one or more available ring carbon atoms with from 0 to 5 independently selected $R^2$ groups, and wherein said ring A is optionally further substituted on one or more available ring nitrogen atoms (when present) with from 0 to 3 $R^{2A}$ groups;

ring B is a phenyl ring, wherein said phenyl ring is (in addition to the and $-C(O)N(R^3)-Z$ moieties shown) optionally further substituted with one or more substituents $R^a$, wherein each $R^a$ (when present) is independently selected from the group consisting of halo, $-OH$, $-SF_5$, $-OSF_5$, alkyl, haloalkyl, heteroalkyl, hydroxyalkyl, alkoxy, and $-O$-haloalkyl, or ring B is a 5-membered heteroaromatic ring containing from 1 to 3 ring heteroatoms independently selected from N, O, and S, wherein said 5-membered heteroaromatic ring is (in addition to the $-L^1-$ and $-C(O)N(R^3)-Z$ moieties shown) optionally further substituted with one or more substituents $R^a$, wherein each $R^a$ (when present) is independently selected from the group consisting of halo, $-OH$, $-SF_5$, $-OSF_5$, alkyl, haloalkyl, heteroalkyl, hydroxyalkyl, alkoxy, and $-O$-haloalkyl, or ring B is a 6-membered heteroaromatic ring containing from 1 to 3 ring nitrogen atoms, wherein said 6-membered heteroaromatic ring is (in addition to $-L^1-$ and $-C(O)N(R^3)Z$ moieties shown) optionally further substituted with one or more substituents $R^a$, wherein each $R^a$ (when present) is independently selected from the group consisting of halo, $-OH$, $-SF_5$, $-OSF_5$, alkyl, haloalkyl, hydroxyalkyl, alkoxy, and $-O$-haloalkyl;

$R^1$ is independently selected from the group consisting of aryl and heteroaryl, wherein said aryl and said heteroaryl of $R^1$ are unsubstituted or substituted with one or more groups independently selected from:

(1) halo, $-OH$, $-CO_2R^6$, $-C(O)R^6$, $-SR^7$, $-S(O)R^7$, $-SO_2R^7$, $-SF_5$, $-OSF_5$, $CN$, $NO_2$, $-C(O)NR^8R^9$, $-NR^8R^9$, $-NR^{10}-C(O)-NR^8R^9$, $-NR^{10}-CO_2R^6$, $-NR^{10}-C(O)R^6$, $-NR^{10}-SO_2R^6$, $-SO_2-NR^8R^9$, $-C(O)NR^8R^9$, and $-OC(O)NR^8R^9$, (2) alkyl, alkoxy, heteroalkyl, —O-heteroalkyl, alkenyl, heteroalkenyl, alkynyl, and heteroalkynyl,
wherein each of said alkyl, alkoxy, heteroalkyl, —O-heteroalkyl, alkenyl, heteroalkenyl, alkynyl, and heteroalkynyl, are unsubstituted or optionally independently substituted with one or more groups each independently selected from:
halo, OH, —$CO_2R^6$, —$C(O)R^6$, —$SR^7$, —$S(O)R^7$, —$SO_2R^7$, CN, $NO_2$, —$C(O)NR^8R^9$, —$NR^8R^9$, —O-haloalkyl, —$NR^{10}$—C(O)—$NR^8R^9$, —$NR^{10}$—$CO_2R^6$, —$NR^{10}$—$C(O)R^6$, —$NR^{10}SO_2R^6$, —$SO_2$—$NR^8R^9$, —$C(O)NR^8R^9$, and —$OC(O)NR^8R^9$, and
(3) aryl, —O-aryl, —C(O)-aryl, —S-aryl, —S(O)-aryl, —$S(O)_2$-aryl, —$N(R_4)$-aryl, —C(O)—$N(R_4)$-aryl, —$N(R_4)$—C(O)-aryl, heteroaryl, —O-heteroaryl, —C(O)-heteroaryl, —S-heteroaryl, —S(O)-heteroaryl, —$S(O)_2$-heteroaryl, —$N(R_4)$-heteroaryl, —C(O)—$N(R_4)$-heteroaryl, —$N(R_4)$—C(O)-heteroaryl, cycloalkyl, —O-cycloalkyl, —C(O)-cycloalkyl, —S-cycloalkyl, —S(O)-cycloalkyl, —$S(O)_2$-cycloalkyl, —$N(R_4)$-cycloalkyl, —C(O)—$N(R_4)$-cycloalkyl, —$N(R_4)$—C(O)-cycloalkyl, heterocycloalkyl, —O-heterocycloalkyl, —C(O)-heterocycloalkyl, —S-heterocycloalkyl, —S(O)-heterocycloalkyl, —$S(O)_2$-heterocycloalkyl, —$N(R_4)$-heterocycloalkyl, —C(O)—$N(R_4)$-heterocycloalkyl, —$N(R_4)$—C(O)-heterocycloalkyl, cycloalkenyl, —O-cycloalkenyl, —C(O)-cycloalkenyl, —S-cycloalkenyl, —S(O)-cycloalkenyl, —$S(O)_2$-cycloalkenyl, —$N(R_4)$-cycloalkenyl, —C(O)—$N(R_4)$-cycloalkenyl, —$N(R_4)$—C(O)-cycloalkenyl, heterocycloalkenyl, —O— heterocycloalkenyl, —C(O)-heterocycloalkenyl, —S-heterocycloalkenyl, —S(O)-heterocycloalkenyl, —$S(O)_2$-heterocycloalkenyl, —$N(R_4)$-heterocycloalkenyl, —C(O)—$N(R_4)$-heterocycloalkenyl, and —$N(R_4)$—C(O)-heterocycloalkenyl,
each of which is unsubstituted or optionally independently substituted with from 1 to 2 groups each independently selected from (1) and (2) above;

each $R^2$ (when present) is independently selected from the group consisting of:
(a) phenyl substituted with from 0 to 5 groups independently selected from —OH, halo, alkyl, haloalkyl, hydroxyalkyl, alkyl substituted with from 1 to 2 —$CO_2R^6$ groups, alkoxy, —O-haloalkyl, hydroxyalkoxy, alkoxy substituted with from 1 to 2 —$CO_2R^6$ groups, —$C(O)R^6$, —$CO_2R^6$, CN, —$SO_2R^7$, —$SF_5$, —$OSF_5$, —$C(O)NR^8R^9$, and —$NO_2$,
(b) alkyl or heteroalkyl, each substituted with from 0 to 5 groups independently selected from —OH, oxo, halo, heteroalkyl, deuteroalkyl, alkoxy, —O-haloalkyl, —$CO_2R^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —$CO_2R^6$, CN, —$S(O)R^7$, —$S(O)_2R^7$, —$SF_5$, —$OSF_5$, —$C(O)NR^8R^9$, and —$NO_2$,
(c) —$NR^{10}$—C(O)—$NR^8R^9$, —$NR^{10}$—$CO_2R^6$, —$NR^{10}$—$C(O)R^6$, —$NR^8R^9$, —$NR^{10}SO_2R^6$, —$SO_2$—$NR^8R^9$, —$C(O)NR^8R^9$, and —OC(O)—$NR^8R^9$;
(d) cycloalkyl, cycloalkenyl, heterocycloalkyl, or heterocycloalkenyl, each substituted with from 0 to 5 groups independently selected from —OH, oxo, halo, heteroalkyl, alkoxy, —O-haloalkyl, —$CO_2R^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —$CO_2R^6$, CN, —$S(O)R^7$, —$S(O)_2R^7$, —$SF_5$, —$OSF_5$, —$C(O)NR^8R^9$, —$NR^{10}$—$C(O)R^6$, —$SO_2$—$NR^8R^9$, and —$NO_2$,
(e) heteroaryl substituted from 0 to 5 groups independently selected from —OH, oxo, halo, heteroalkyl, alkoxy, —O-haloalkyl, —$CO_2R^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —$CO_2R^6$, CN, —$S(O)R^7$, —$S(O)_2R^7$, —$C(O)NR^8R^9$, —$NR^{10}$—$C(O)R^6$, —$SO_2$—$NR^8R^9$, —$SF_5$, —$OSF_5$, and —$NO_2$, and
(f) —$Si(alkyl)_3$;
or, alternatively, two $R^2$ groups attached to the same atom of ring A are taken together to form a moiety selected from the group consisting of carbonyl, oxime, substituted oxime (said oxime substituents being independently selected from the group consisting of alkyl, haloalkyl, hydroxyl-substituted alkyl, and cycloalkyl), spirocycloalkyl, spiroheterocycloalkyl, spirocycloalkenyl, and spiroheterocycloalkenyl;
or, alternatively, two $R^2$ groups attached to adjacent ring atoms of ring A are taken together to form a 5-6-membered aromatic or heteroaromatic ring;
each $R^{2A}$ (when present) is independently selected from the group consisting of —$C(O)NR^8R^9$, —$CO_2R^6$, —$C(O)R^6$, —$SO_2R^7$, alkyl, heteroalkyl, haloalkyl, hydroxyl-substituted alkyl, cycloalkyl, heterocycloalkyl, aryl, arylalkyl-, heteroaryl,
$R^3$ is selected from H and lower alkyl;
Z is a moiety selected from —$(C(R^{11})_2)$—$(C(R^{12}R^{13}))_m$—C(O)OH, —$(C(R^{11})_2)$—$(C(R^{14})_2)_n$—C(O)OH, from —$(C(R^{11})_2)$—$(C(R^{12}R^{13}))_m$—C(O)Oalkyl, —$(C(R^{11})_2)$—$(C(R^{14})_2)_n$—C(O)Oalkyl,

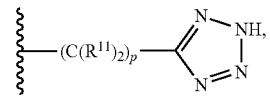

—$(C(R^{11})_2)$—$(C(R^{12}R^{13}))_m$, and —$(C(R^{11})_2)$—$(C(R^{14})_2)_n$,
wherein Q is a moiety selected from the group consisting of:

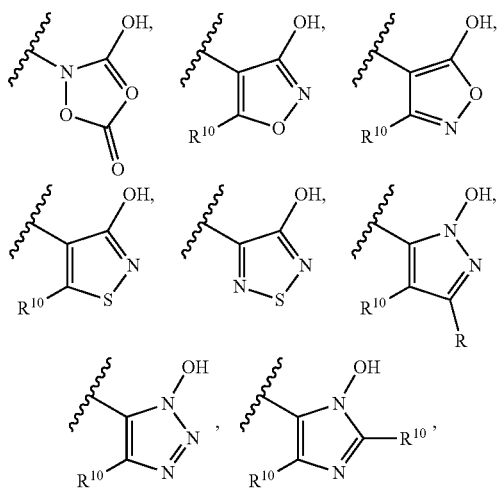

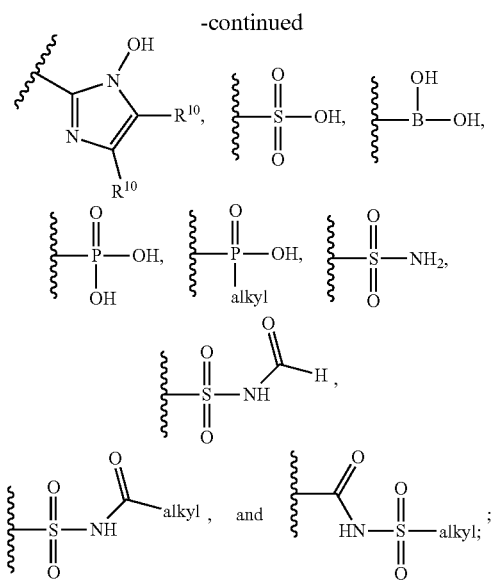

m is an integer from 0 to 5;
n is an integer from 0 to 5;
p is an integer from 0 to 5;
each $R^4$ is independently selected from H, —OH, lower alkyl, haloalkyl, alkoxy, heteroalkyl, cyano-substituted lower alkyl, hydroxy-substituted lower alkyl, cycloalkyl, —O-cycloalkyl, —O-alkyl-cycloalkyl, and heterocycloalkyl, —O-heterocycloalkyl, and —O-alkyl-heterocycloalkyl;
each $R^{5A}$ is independently selected from H, alkyl, -alkyl-Si(CH$_3$)$_3$, haloalkyl, heteroalkyl, cyano-substituted alkyl, hydroxy-substituted alkyl, cycloalkyl, -alkyl-cycloalkyl, and heterocycloalkyl, -alkyl-heterocycloalkyl,
or, alternatively, two $R^{5A}$ groups are taken together with the carbon atom to which they are attached to form a carbonyl group, a spirocycloalkyl group, a spiroheterocycloalkyl group, an oxime group, or a substituted oxime group (said oxime substituents being independently selected from alkyl, haloalkyl, hydroxyl-substituted alkyl, and cycloalkyl);
each $R^5$ is independently selected from H, —OH, alkyl, -alkyl-Si(CH$_3$)$_3$, haloalkyl, alkoxy, heteroalkyl, cyano-substituted alkyl, hydroxy-substituted alkyl, cycloalkyl, -alkyl-cycloalkyl, —O-cycloalkyl, —O-alkyl-cycloalkyl, and heterocycloalkyl, -alkyl-heterocycloalkyl, —O-heterocycloalkyl, and —O-alkyl-heterocycloalkyl,
or, alternatively, two $R^5$ groups bound to the same carbon atom are taken together with the carbon atom to which they are attached to form a carbonyl group, a spirocycloalkyl group, a spiroheterocycloalkyl group, an oxime group, or a substituted oxime group (said oxime substituents being independently selected from alkyl, haloalkyl, hydroxyl-substituted alkyl, and cycloalkyl);
each $R^6$ is independently selected from H, alkyl, haloalkyl, heteroalkyl, alkenyl, heteroalkenyl, alkynyl, and heteroalkynyl;
each $R^7$ is independently selected from H, alkyl, heteroalkyl, and haloalkyl;
each $R^8$ is independently selected from H and alkyl;
each $R^9$ is independently selected from H and alkyl,
or alternatively $R^8$ and $R^9$ are taken together with the nitrogen to which they are attached to form a 5-, 6-, or 7-membered saturated heterocyclic ring, or a 5-, 6-, or 7-membered unsaturated heterocyclic ring, which ring contains (including said nitrogen) from 1 to 2 ring heteroatoms each independently selected from N,N-oxide, O, S, S(O), or S(O)$_2$,
or alternatively $R^8$ and $R^9$ are taken together with the nitrogen to which they are attached to form a 5-membered heteroaromatic ring containing (including the nitrogen to which $R^8$ and $R^9$ are attached) from 1 to 3 ring nitrogens;
each $R^{10}$ is independently selected from H and alkyl;
each $R^{11}$ is independently selected from H and lower alkyl;
each $R^{12}$ is independently selected from H, lower alkyl, —OH, hydroxy-substituted lower alkyl;
each $R^{13}$ is independently selected from H, unsubstituted lower alkyl, lower alkyl substituted with one or more groups each independently selected from hydroxyl and alkoxy, or $R^{12}$ and $R^{13}$ are taken together to form an oxo; and
each $R^{14}$ is independently selected from H and fluoro.

In one embodiment, in Formula (A), ring A represents a 3-8-membered spirocycloalkyl or spirocycloalkenyl ring.

In one embodiment, in Formula (A), ring A represents a 3-8-membered spirocycloalkyl or spirocycloalkenyl ring, which ring is substituted with from 1 to 5 independently selected $R^2$ groups, which $R^2$ groups may be attached to the same or different ring carbon atom(s).

In one embodiment, in Formula (A), ring A represents a 3-8-membered spirocycloalkyl or spirocycloalkenyl ring, which ring is substituted with from 1 to 3 independently selected $R^2$ groups, which $R^2$ groups may be attached to the same or different ring carbon atom(s).

In one embodiment, in Formula (A), ring A represents a 3-8-membered spirocycloalkyl or spirocycloalkenyl ring, which ring is substituted with from 1 to 2 independently selected $R^2$ groups, which $R^2$ groups may be attached to the same or different ring carbon atom(s).

In one embodiment, in Formula (A), ring A represents a 3-8-membered spirocycloalkyl or spirocycloalkenyl ring, which ring is substituted with 1 $R^2$ group.

In one embodiment, in Formula (A), ring A represents a 4-6-membered spirocycloalkyl or spirocycloalkenyl ring.

In one embodiment, in Formula (A), ring A represents a 4-6-membered spirocycloalkyl or spirocycloalkenyl ring, which ring is substituted with from 1 to 5 independently selected $R^2$ groups, which $R^2$ groups may be attached to the same or different ring carbon atom(s).

In one embodiment, in Formula (A), ring A represents a 4-6-membered spirocycloalkyl or spirocycloalkenyl ring, which ring is substituted with from 1 to 3 independently selected $R^2$ groups, which $R^2$ groups may be attached to the same or different ring carbon atom(s).

In one embodiment, in Formula (A), ring A represents a 4-6-membered spirocycloalkyl or spirocycloalkenyl ring, which ring is substituted with from 1 to 2 independently selected $R^2$ groups, which $R^2$ groups may be attached to the same or different ring carbon atom(s).

In one embodiment, in Formula (A), ring A represents a 4-6-membered spirocycloalkyl or spirocycloalkenyl ring, which ring is substituted with 1 $R^2$ group.

Non-limiting examples of ring A when ring A represents a spirocycloalkyl ring, which may be unsubstituted or substituted as described herein, include: sprirocyclobutyl, spirocyclopentyl, spirocyclohexyl, spirocycloheptyl, spirocyclooctyl, spironorbornanyl, and spiroadamantanyl.

Non-limiting examples of ring A when ring A represents a spirocycloalkenyl ring, which may be unsubstituted or substituted as described herein, include partially or fully unsaturated versions of the spirocycloalkyl moieties described above. Non-limiting examples include: spirocyclopentenyl, spirocyclohexenyl, spirocycloheptenyl, and spirocyclooctenyl.

In one embodiment, in Formula (A), ring A represents a 3-8-membered spiroheterocycloalkyl ring containing up to 3 ring heteroatoms, 1-3 of which are selected from O, S, S(O), S(O)$_2$, and N or N-oxide.

In one embodiment, in Formula (A), ring A represents a 3-8-membered spiroheterocycloalkenyl ring containing up to 3 ring heteroatoms, 1-3 of which are selected from O, S, S(O), S(O)$_2$, and N or N-oxide.

In one embodiment, in Formula (A), ring A represents a 3-8-membered spiroheterocycloalkyl ring containing up to 3 ring heteroatoms, 0-1 of which are O, S, S(O), and S(O)$_2$, and 1-2 of which are N or N-oxide, which ring A is substituted on one or more available ring carbon atom(s) with from 1 to 5 independently selected R$^2$ groups, and which ring A is optionally further substituted on one or more available ring nitrogen atoms with from 0 to 2 independently selected R$^{2A}$ groups.

In one embodiment, in Formula (A), ring A represents a 3-8-membered spiroheterocycloalkenyl ring containing up to 3 ring heteroatoms, 0-1 of which are O, S, S(O), and S(O)$_2$, and 1-2 of which are N or N-oxide, which ring A is substituted on one or more available ring carbon atom(s) with from 1 to 5 independently selected R$^2$ groups, and which ring A is optionally further substituted on one or more available ring nitrogen atoms with 0 to 2 independently selected R$^{2A}$ groups.

In one embodiment, in Formula (A), ring A represents a 4-8-membered spiroheterocycloalkyl ring containing up to 3 ring heteroatoms, 0-1 of which are O, S, S(O), and S(O)$_2$, and 1-2 of which are N or N-oxide, which ring A is substituted on one or more available ring carbon atom(s) with from 1 to 5 independently selected R$^2$ groups, and which ring A is optionally further substituted on one or more available ring nitrogen atoms with 0 to 2 independently selected R$^{2A}$ groups.

In one embodiment, in Formula (A), ring A represents a 4-8-membered spiroheterocycloalkenyl ring containing up to 3 ring heteroatoms, 0-1 of which are O, S, S(O), and S(O)$_2$, and 1-2 of which are N or N-oxide, which ring A is substituted on one or more available ring carbon atom(s) with from 1 to 5 independently selected R$^2$ groups, and which ring A is optionally further substituted on one or more available ring nitrogen atoms with 0 to 2 independently selected R$^{2A}$ groups.

In one embodiment, in Formula (A), ring A represents a spiropiperidinyl ring.

In one embodiment, in Formula (A), ring A represents a spiropiperidinyl ring, which ring A is substituted on one or more available ring carbon atom(s) with from 1 to 5 independently selected R$^2$ groups, and which ring A is optionally further substituted on the spiropiperidinyl nitrogen with R$^{2A}$.

In one embodiment, in Formula (A), ring A represents a spiropiperidinyl ring, which ring A is substituted on one or more available ring carbon atom(s) with from 1 to 3 independently selected R$^2$ groups.

In one embodiment, in Formula (A), ring A represents a spiropiperidinyl ring, which ring A is substituted on one or more available ring carbon atom(s) with from 1 to 2 independently selected R$^2$ groups.

In one embodiment, in Formula (A), ring A represents a spiropiperidinyl ring, which ring A is substituted on one or more available ring carbon atom(s) with an R$^2$ group.

Additional non-limiting examples of ring A when ring A represents a spiroheterocycloalkyl ring, which may be unsubstituted or substituted as described herein, include: spiropyrrolidinyl, spirodioxolanyl, spiroimidazolidinyl, spiropyrazolidinyl, spiropiperidinyl, spirodioxanyl, spiromorpholinyl, spirotetrahydropyranyl, spirodithianyl, spirothiomorpholinyl, spriro piperazinyl, and spirotrithianyl.

Additional non-limiting examples of ring A when ring A represents a spiroheterocycloalkyenyl ring, which may be unsubstituted or substituted as described herein, include unsaturated versions of the following moieties spiropyrrolidinyl, spirodioxolanyl, spiroimidazolidinyl, spiropyrazolidinyl, spiropiperidinyl, spirodioxanyl, spiromorpholinyl, spirodithianyl, spirothiomorpholinyl, spriro piperazinyl, and spirotrithianyl.

In one embodiment, the compounds of the invention have the general structure shown in Formula (A-1):

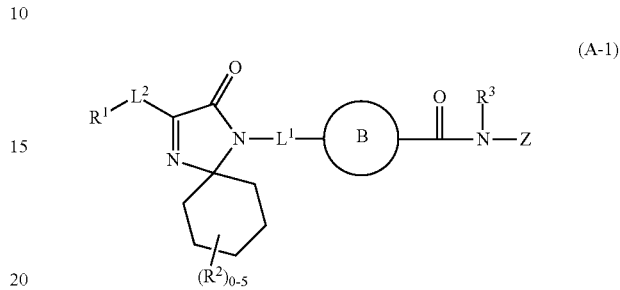

(A-1)

and include pharmaceutically acceptable salts, solvates, esters, prodrugs, tautomers, and isomers of said compounds, wherein ring B, L$^1$, L$^2$, R$^1$, each R$^2$, R$^3$, and Z are selected independently of each other and as defined in Formula (A).

In one embodiment, the compounds of the invention have the general structure shown in Formula (A-1a):

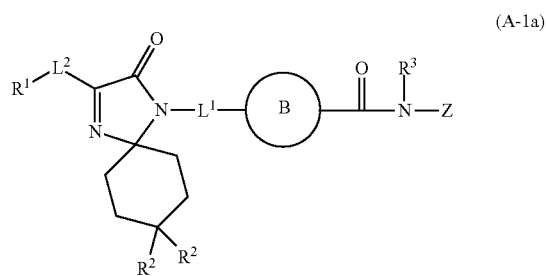

(A-1a)

and include pharmaceutically acceptable salts, solvates, esters, prodrugs, tautomers, and isomers of said compounds, wherein ring B, L$^1$, L$^2$, R$^1$, each R$^2$, R$^3$, and Z are selected independently of each other and as defined in Formula (A).

In one embodiment, the compounds of the invention have the general structure shown in Formula (A-1b):

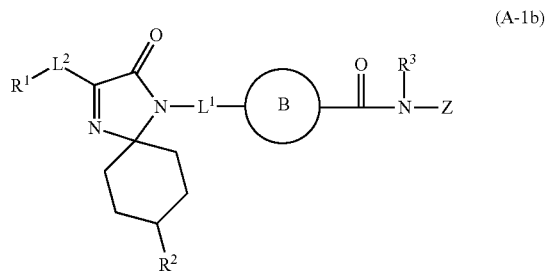

(A-1b)

and include pharmaceutically acceptable salts, solvates, esters, prodrugs, tautomers, and isomers of said compounds, wherein ring B, L$^1$, L$^2$, R$^1$, R$^2$, R$^3$, and Z are selected independently of each other and as defined in Formula (A).

In one embodiment, the compounds of the invention have the general structure shown in Formula (A-2a):

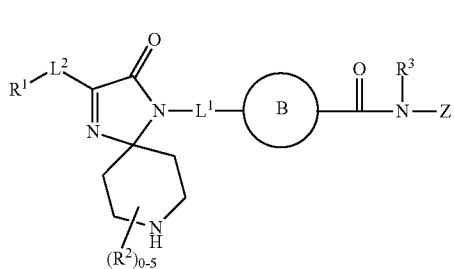

(A-2a)

and include pharmaceutically acceptable salts, solvates, esters, prodrugs, tautomers, and isomers of said compounds, wherein ring B, $L^1$, $L^2$, $R^1$, each $R^2$, $R^3$, and Z are selected independently of each other and as defined in Formula (A).

In one embodiment, the compounds of the invention have the general structure shown in Formula (A-2b):

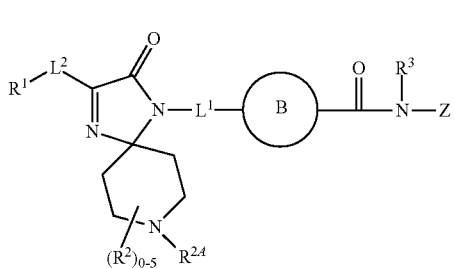

(A-2b)

and include pharmaceutically acceptable salts, solvates, esters, prodrugs, tautomers, and isomers of said compounds, wherein ring B, $L^1$, $L^2$, $R^1$, each $R^2$, $R^3$, and Z are selected independently of each other and as defined in Formula (A).

In one embodiment, the compounds of the invention have the general structure shown in Formula (A-2c):

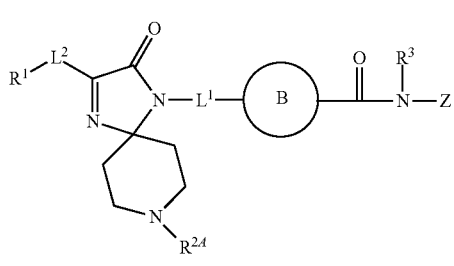

(A-2c)

and include pharmaceutically acceptable salts, solvates, esters, prodrugs, tautomers, and isomers of said compounds, wherein ring B, $L^1$, $L^2$, $R^1$, $R^2$, $R^3$, and Z are selected independently of each other and as defined in Formula (A).

In one embodiment, the compounds of the invention have the general structure shown in Formula (A-2d):

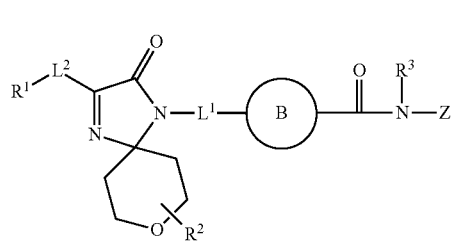

(A-2d)

and include pharmaceutically acceptable salts, solvates, esters, prodrugs, tautomers, and isomers of said compounds, wherein ring B, $L^1$, $L^2$, $R^1$, $R^2$, $R^3$, and Z are selected independently of each other and as defined in Formula (A).

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a phenyl ring wherein the -$L^1$- and the —C(O)N($R^3$)Z moieties shown in the formula are bound to said phenyl ring in a 1,4-relationship, and wherein said phenyl ring is (in addition to the -$L^1$- and —C(O)N($R^3$)—Z moieties shown) optionally further substituted with one or more substituents $R^a$, wherein each $R^a$ (when present) is independently selected from the group consisting of halo, alkyl, and haloalkyl, In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 5-membered heteroaromatic ring containing from 1 to 3 ring heteroatoms independently selected from N, O, and S, wherein the -$L^1$- and the —C(O)N($R^3$)—Z moieties shown in the formula are bound to said 5-membered ring in a 1,3-relationship, and wherein said 5-membered heteroaromatic ring is (in addition to the -$L^1$- and —C(O)N($R^3$)—Z moieties shown) optionally further substituted with one or more substituents $R^a$, wherein each $R^a$ (when present) is independently selected from the group consisting of halo, alkyl, and haloalkyl, In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 6-membered heteroaromatic ring containing from 1 to 3 ring nitrogen atoms, wherein the -$L^1$- and the —C(O)N($R^3$)—Z moieties shown in the formula are bound to said 6-membered ring in a 1,4-relationship, and wherein said 6-membered heteroaromatic ring is (in addition to -$L^1$- and —C(O)N($R^3$)Z moieties shown) optionally further substituted with one or more substituents $R^a$, wherein each $R^a$ (when present) is independently selected from the group consisting of halo, alkyl, and haloalkyl;

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is phenyl.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is phenyl which, in addition to the moieties -$L^1$- and —C(O)N($R^3$)—Z shown in the formula, is further substituted with one or more independently selected $R^a$ groups.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a phenyl which, in addition to the moieties -L$^1$- and —C(O)N(R$^3$)—Z shown in the formula, is further substituted with from 1 to 2 substituents, each independently selected from halo, alkyl, and haloalkyl.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 5-membered heteroaromatic ring having from 1 to 3 ring heteroatoms independently selected from N, O, and S, wherein said ring B is not further substituted.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 6-membered heteroaromatic ring having from 1 to 3 ring nitrogen atoms, wherein said ring B is not further substituted.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 5-membered heteroaromatic ring having from 1 to 3 ring heteroatoms independently selected from N, O, and S, wherein said ring B is further substituted with one or more substituents. Said further substituents in such embodiments may be bound to one or more available ring carbon atoms and/or ring nitrogen atoms.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 6-membered heteroaromatic ring having from 1 to 3 ring nitrogen atoms wherein said ring B is further substituted with one or more substituents. Said further substituents in such embodiments may be bound to one or more available ring carbon atoms and/or ring nitrogen atoms.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 5-membered heteroaromatic ring having from 1 to 3 ring heteroatoms independently selected from N, O, and S, wherein said 5-membered heteroaromatic ring is further substituted with from 1 to 2 substituents, each substituent being independently selected from halo, alkyl, and haloalkyl. In one such embodiment, ring B contains two said substituents. In another such embodiment, ring B contains one said substitutent.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 5-membered heteroaromatic ring, non-limiting examples of such rings include, but are not limited to: furan, thiophene, pyrrole, imidazole, pyrazole, 1,2,3-triazole, 1,2,4-triazole, thiazole, thiadiazole, oxazole, oxadiazole, and isoxazole, each of which may be optionally further substituted as described herein. Non-limiting examples of ring B (shown connected to moieties L$^1$ and —C(O)—N (R$^3$)—Z) include:

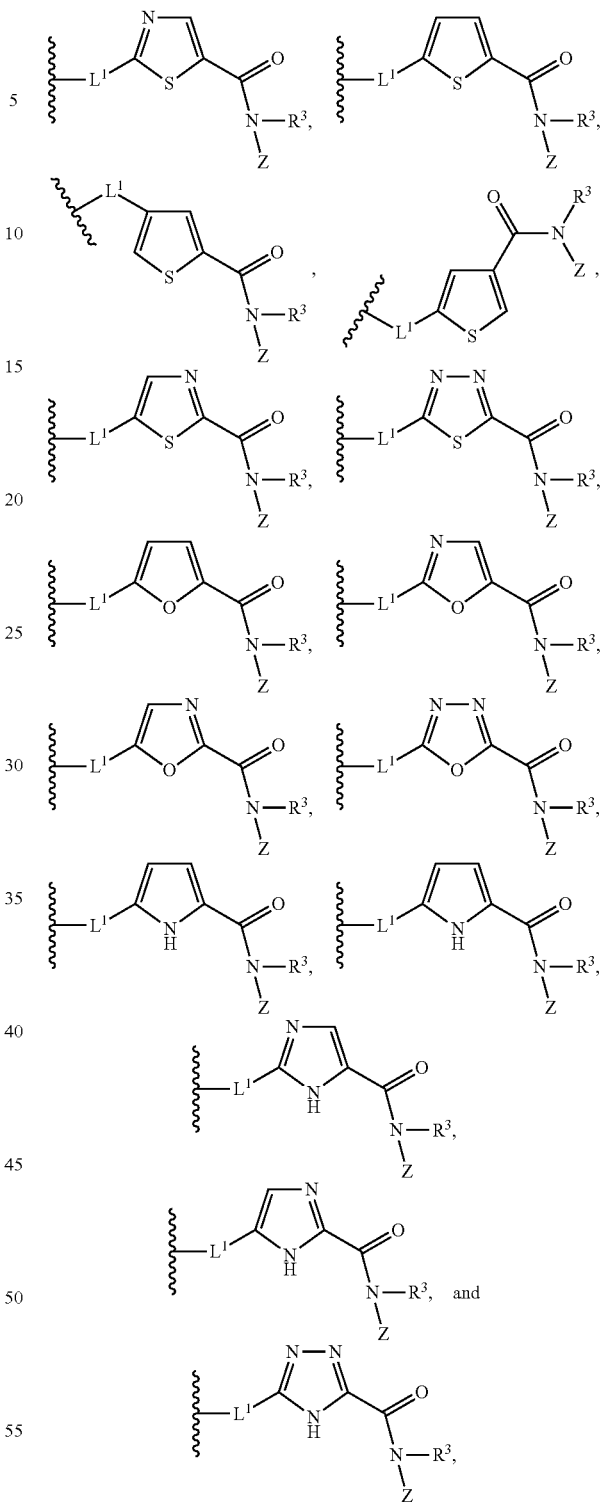

wherein each ring B shown is optionally further substituted on an available ring carbon atom or ring nitrogen atom with one or more groups R$^a$, wherein each R$^a$, when attached to a ring carbon atom, is independently selected from halo, alkyl, and haloalkyl, and wherein each R$^a$, when attached to a ring nitrogen atom, is independently selected from alkyl, and haloalkyl. Non-limiting examples of such groups substituted on an available ring nitrogen atom include:

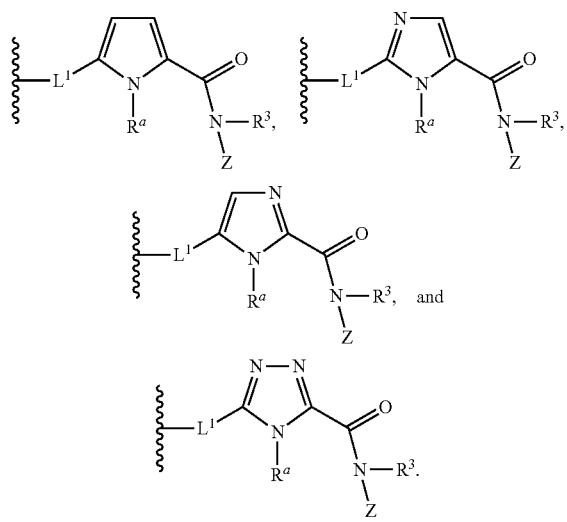

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), ring B is a 6-membered heteroaromatic ring having from 1 to 3 ring nitrogen atoms, wherein said ring B is further substituted with from 1 to 3 substituents, each substituent being independently selected from halo, alkyl, and haloalkyl. In one such embodiment, ring B contains three said substituents. In one such embodiment, ring B contains two said substituents. In another such embodiment, ring B contains one said substitutent.

When, in each of Formula (A), Formula (A-1), Formula (A-1a), Formula (A-1b), Formula (A-2a), Formula (A-2b), Formula (A-2c), ring B is a 6-membered heteroaromatic ring, non-limiting examples of such rings include: pyridine, pyrimidine, pyrazine, pyridazine, and triazine, each of which may be optionally further substituted as described herein. Non-limiting examples of ring B (shown connected to moieties $L^1$ and —C(O)—N($R^3$)—Z) include:

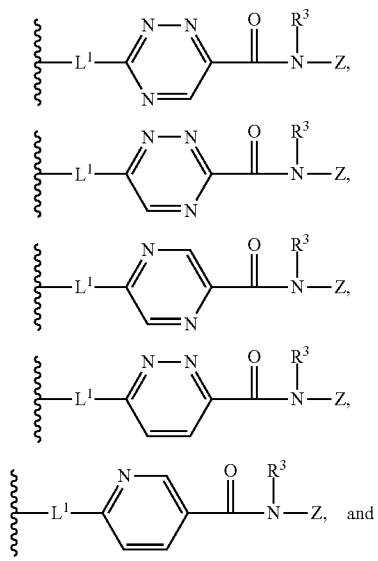

-continued

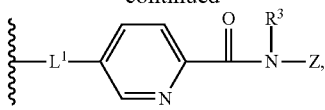

wherein any of such moieties may be optionally further substituted with one or more groups $R^a$, wherein each $R^a$ is independently selected from halo, alkyl, and haloalkyl.

In the various embodiments of the compounds of the invention described herein, functional groups for $L^1$ and $L^2$ are to be read from left to right unless otherwise stated.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), $L^1$ is selected from the group consisting of: a bond, —N($R^4$)—, —N($R^4$)—(C($R^{5A}$)$_2$)—, —O—, —O—(C($R^{5A}$)$_2$)—, and —(C($R^{5A}$)$_2$)—(C($R^5$)$_2$)$_s$—, wherein s is an integer from 0 to 3.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), $L^1$ is selected from the group consisting of: a bond and —(C($R^{5A}$)$_2$)—(C($R^5$)$_2$)$_s$—, wherein s is an integer from 0 to 1, and wherein each $R^5$ and each $R^{5A}$ is independently selected from the group consisting of H, lower alkyl, -lower alkyl-Si(CH$_3$)$_3$, lower haloalkyl, and lower alkyl substituted with one or more groups independently selected from hydroxyl and cyano. In one such embodiment, s is 0. In one such embodiment, s is 1.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), $L^1$ is selected from the group consisting of lower branched alkyl and -lower alkyl-Si(CH$_3$)$_3$.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), $L^1$ is a bond.

In one embodiment, in each of Formula (A), Formula (A-1), Formula (A-1a), Formula (A-1b), Formula (A-2a), Formula (A-2b), Formula (A-2c), and Formula (A-2d), and Formula (A-2d), $L^1$ is —N($R^4$)—(C($R^{5A}$)$_2$)—, wherein each $R^{5A}$ is independently selected from H, lower alkyl, lower haloalkyl, and lower alkyl substituted with one or more hydroxyl and $R^4$ is selected from H and lower alkyl.

In one embodiment, in each of Formula (A), Formula (A-1), Formula (A-1a), Formula (A-1b), Formula (A-2a), Formula (A-2b), Formula (A-2c), and Formula (A-2d), $L^1$ is —O—(C($R^{5A}$)$_2$)—, wherein each $R^{5A}$ is independently selected from H, lower alkyl, lower haloalkyl, and lower alkyl substituted with one or more hydroxyl.

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of a bond, —NH—(CH$_2$)$_2$—, —O—(CH$_2$)$_2$—, —O—, —NH—, —N(CH$_3$)—, —CH$_2$—, —CH(CH$_3$)—, and —CH$_2$CH$_2$—.

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of —CH$_2$—, —CH(CH$_3$)—, and —CH$_2$CH$_2$—.

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of: —CH(cycloalkylalkyl)- and —CH(heterocycloalkylalkyl)-.

In one embodiment, in each of Formula (A), Formula (A-1), Formula (A-1a), Formula (A-1b), Formula (A-2a), Formula (A-2b), Formula (A-2c), and Formula (A-2d), $L^1$ is —C($R^{5A}$)$_2$—, wherein each $R^{5A}$ is independently selected from the group consisting of H, lower alkyl, -lower alkyl-Si(CH$_3$)$_3$, haloalkyl, heteroalkyl, cyano-substituted lower alkyl, hydroxy-substituted lower alkyl, cycloalkyl, cycloalkylalkyl-, heterocycloalkyl, and heterocycloalkylalkyl-.

In one embodiment, in each of Formula (A), Formula (A-1), Formula (A-1a), Formula (A-1b), Formula (A-2a), Formula (A-2b), Formula (A-2c), and Formula (A-2d), $L^1$ is —CH($R^{5A}$)—, wherein $R^{5A}$ is selected from the group consisting of H, lower alkyl, -lower alkyl-Si(CH$_3$)$_3$, haloalkyl, heteroalkyl, cyano-substituted lower alkyl, hydroxy-substituted lower alkyl, cycloalkyl, cycloalkylalkyl-, heterocycloalkyl, and heterocycloalkylalkyl-.

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of:

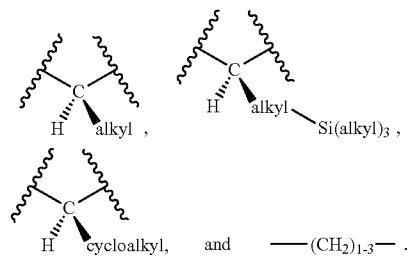

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of

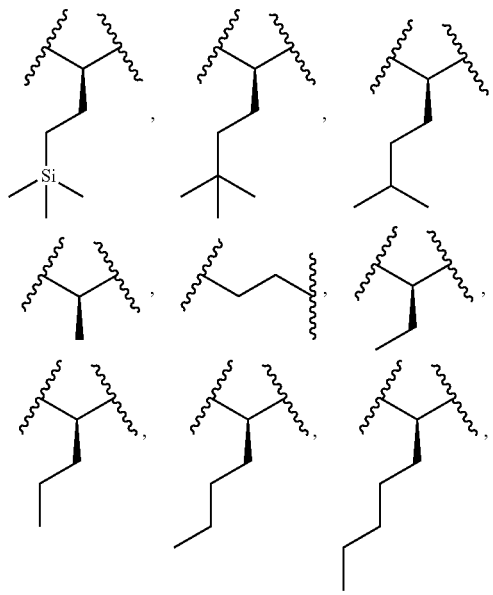

-continued

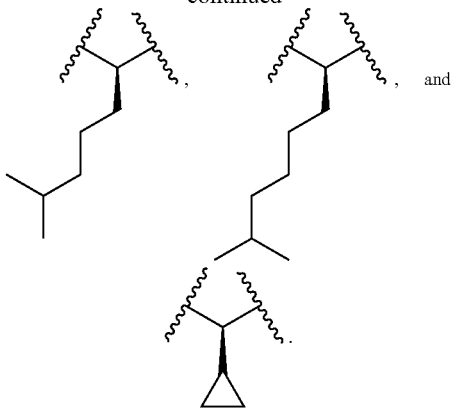

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of

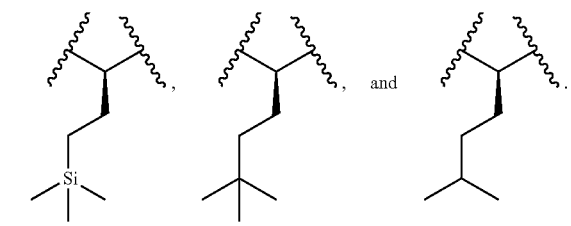

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of

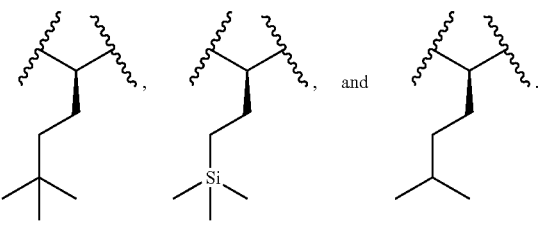

In one embodiment, in each of Formula (A), Formula (A-1), Formula (A-1a), Formula (A-1b), Formula (A-2a), Formula (A-2b), Formula (A-2c), and Formula (A-2d), $L^1$ is selected from the group consisting of:

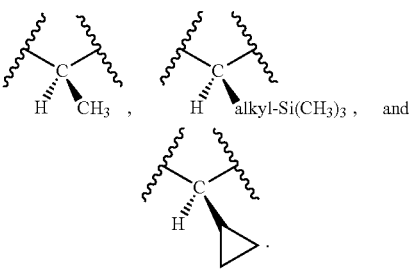

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of:

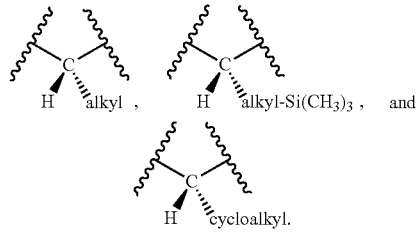

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of:

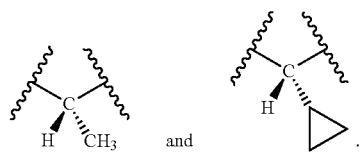

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of:

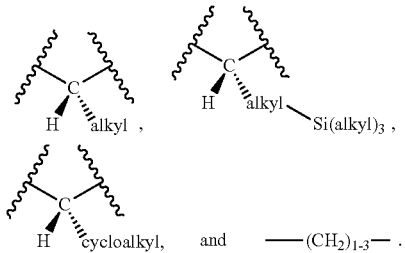

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of

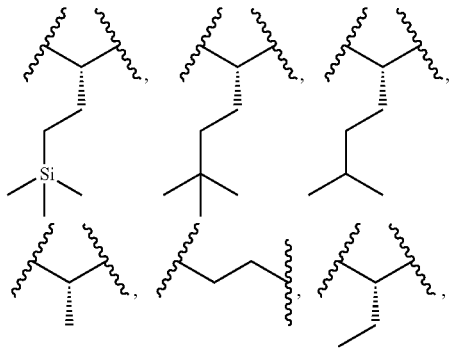

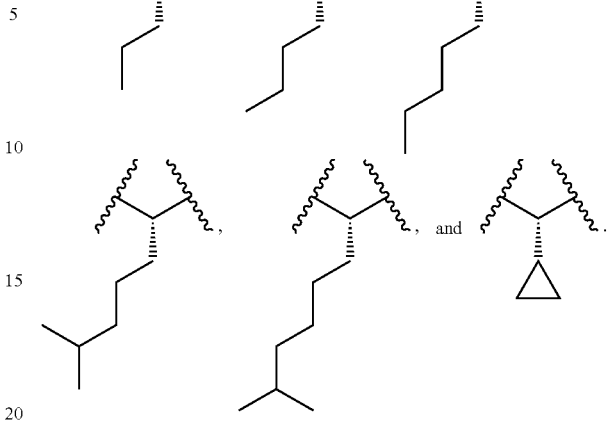

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of

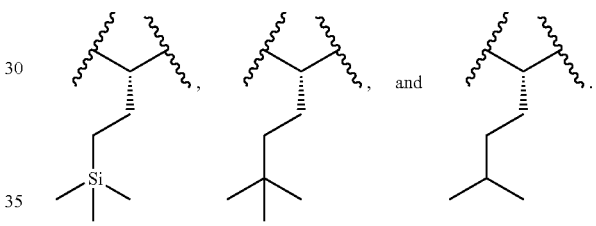

In one embodiment, in each of Formula (A), Formula (A-1), Formula (A-1a), Formula (A-1b), Formula (A-2a), Formula (A-2b), Formula (A-2c), and Formula (A-2d), L¹ is selected from the group consisting of

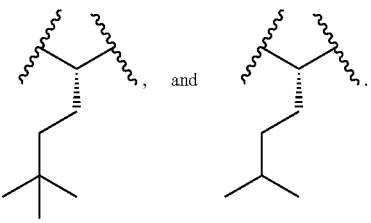

In one embodiment, in each of Formula (A), Formula (A-1), Formula (A-1a), Formula (A-1b), Formula (A-2a), Formula (A-2b), Formula (A-2c), $L^2$ is selected from the group consisting of a bond, —N($R^4$)—, —N($R^4$)—(C($R^{5A}$)$_2$)—, —(C($R^5$)$_2$)$_u$—, —(C($R^{5A}$)$_2$)—N($R^4$)—, wherein u is 0 to 2, —O—, —O—(C($R^{5A}$)$_2$)—, and —(C($R^5$)$_2$)$_v$—, wherein v is 1-3, and each $R^5$ and each $R^{5A}$ is independently selected from the group consisting of H, lower alkyl, lower haloalkyl, and lower alkyl substituted with one or more groups independently selected from hydroxyl and cyano, and wherein each $R^4$ is independently selected from the group consisting of H, lower alkyl, lower haloalkyl, and lower alkyl substituted with one or more groups independently selected from hydroxyl and cyano.

In one embodiment, in each of Formula (A), Formula (A-1), Formula (A-1a), Formula (A-1b), Formula (A-2a), Formula (A-2b), Formula (A-2c), L² is selected from the group consisting of a —(C(R⁵)₂)ᵤ—(C(R⁵ᴬ)₂)—N(R⁴)—, wherein u is 0 to 2, —O—, and each R⁴, each R⁵, and each R⁵ᴬ is independently selected from the group consisting of H and lower alkyl.

In one embodiment, in each of Formula (A), Formula (A-1), Formula (A-1a), Formula (A-1b), Formula (A-2a), Formula (A-2b), Formula (A-2c), and Formula (A-2d), L² is selected from a bond and —(C(R⁵)₂)ᵥ—, wherein v is 1-2, and each R⁵ is independently selected from the group consisting of H, —OH, lower alkyl, loweralkoxy, lower haloalkyl, and lower alkyl substituted with one or more groups independently selected from hydroxyl and cyano. In one such embodiment, v is 1 and each R⁵ is independently selected from H and lower alkyl. In another such embodiment, v is 1 and each R⁵ is independently selected from H, lower alkyl, and OH.

In one embodiment, in each of Formula (A), Formula (A-1), Formula (A-1a), Formula (A-1b), Formula (A-2a), Formula (A-2b), Formula (A-2c), L² is a bond.

In one embodiment, in each of Formula (A), Formula (A-1), Formula (A-1a), Formula (A-1b), Formula (A-2a), Formula (A-2b), Formula (A-2c), and Formula (A-2d), L² is selected from the group consisting of —CH₂—, —CH(CH₃)—, —CH₂CH₂—, —CH(OH)—, —CH(CH₃)—CH₂—, —CH₂—CH(CH₃)—, —CH(OH)—CH₂—, and —CH₂—CH(OH)—.

In one embodiment, in each of Formula (A), Formula (A-1), Formula (A-1a), Formula (A-1b), Formula (A-2a), Formula (A-2b), Formula (A-2c), and Formula (A-2d), L² is selected from the group consisting of:

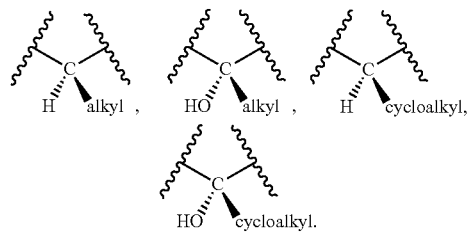

In one embodiment, in each of Formula (A), Formula (A-1), Formula (A-1a), Formula (A-1b), Formula (A-2a), Formula (A-2b), Formula (A-2c), and Formula (A-2d), L² is selected from the group consisting of:

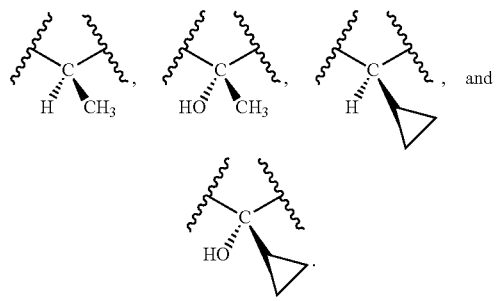

In one embodiment, in each of Formula (A), Formula (A-1), Formula (A-1a), Formula (A-1b), Formula (A-2a), Formula (A-2b), Formula (A-2c), and Formula (A-2d), L² is selected from the group consisting of:

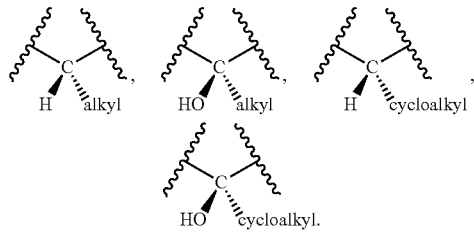

In one embodiment, in each of Formula (A), Formula (A-1), Formula (A-1a), Formula (A-1b), Formula (A-2a), Formula (A-2b), Formula (A-2c), and Formula (A-2d), L² is selected from the group consisting of:

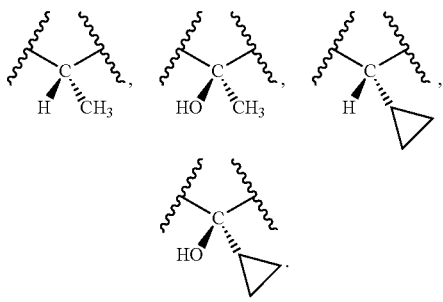

In embodiments wherein either L¹ or L² (or both) contains a group —(C(R⁵ᴬ)₂)—, any two R⁵ᴬ groups bound to the same carbon atom may be taken together to form a carbonyl group, an oxime group, or a substituted oxime group. As indicated herein, each R⁵ᴬ group is selected independently. Similarly, in embodiments wherein either L¹ or L² (or both) contains a group —(C(R⁵)₂)—, any two R⁵ groups bound to the same carbon atom may be taken together to form a carbonyl group, an oxime group, or a substituted oxime group. For illustrative purposes only, such oxime groups, when present, may be pictured as:

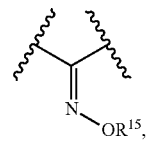

wherein each wavy line presents a point of attachment to the rest of the molecule and wherein R¹⁵ is selected from the group consisting of H, alkyl, haloalkyl, hydroxyl-substituted alkyl, and cycloalkyl.

In one embodiment, in each of Formula (A), Formula (A-1), Formula (A-1a), Formula (A-1b), Formula (A-2a), Formula (A-2b), Formula (A-2c), and Formula (A-2d), R¹ is selected from the group consisting of:
  aryl and heteroaryl,
  wherein each of said aryl and said heteroaryl are unsubstituted or substituted with from 1 to 3 groups each independently selected from:
  (1) halo, —SO₂R⁷, —SF₅, —OSF₅, CN,
  (2) alkyl, alkoxy, heteroalkyl, —O-heteroalkyl, wherein each of said alkyl, alkoxy, heteroalkyl, and —O-heteroalkyl, is unsubstituted or optionally independently substituted with from 1 to 3 groups each independently selected from:
halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, —O-haloalkyl, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and
(3) aryl, —O-aryl, —S-aryl, —S(O)-aryl, —S(O)$_2$-aryl, heteroaryl, cycloalkyl, cycloalkenyl, and heterocycloalkenyl,
each of which is unsubstituted or optionally independently substituted with from 1 to 2 groups each independently selected from (1) and (2) above.

In one embodiment, in each of Formula (A), Formula (A-1), Formula (A-1a), Formula (A-1b), Formula (A-2a), Formula (A-2b), Formula (A-2c), and Formula (A-2d), R$^1$ is selected from the group consisting of:
phenyl or naphthyl,
wherein said phenyl and said naphthyl are unsubstituted or substituted with from 1 to 3 groups each independently selected from:
(1) halo, —SO$_2$R$^7$, —SF$_5$, —OSF$_5$, CN,
(2) alkoxy, haloalkyl, —O-haloalkyl, heteroalkyl, —O-heteroalkyl,
(3) aryl, —O-aryl, —S-aryl, —S(O)-aryl, —S(O)$_2$-aryl, heteroaryl, cycloalkyl, cycloalkenyl, and heterocycloalkenyl,
each of which is unsubstituted or optionally independently substituted with from 1 to 2 groups each independently selected from (1) and (2) above.

In one embodiment, in each of Formula (A), Formula (A-1), Formula (A-1a), Formula (A-1b), Formula (A-2a), Formula (A-2b), Formula (A-2c), and Formula (A-2d), R$^1$ is selected from the group consisting of:
phenyl,
wherein said phenyl is unsubstituted or substituted with one or more groups each independently selected from:
halo, alkyl, haloalkyl, heteroalkyl, haloheteroalkyl, alkoxy, —O-haloalkyl, and cycloalkyl.

In one embodiment, in each of Formula (A), Formula (A-1), Formula (A-1a), Formula (A-1b), Formula (A-2a), Formula (A-2b), Formula (A-2c), and Formula (A-2d), R$^1$ is selected from the group consisting of:
heteroaryl,
wherein said heteroaryl is unsubstituted or substituted with one or more groups each independently selected from:
halo, alkyl, haloalkyl, alkoxy, —O-haloalkyl, and cycloalkyl.

In one embodiment, in each of Formula (A), Formula (A-1), Formula (A-1a), Formula (A-1b), Formula (A-2a), Formula (A-2b), Formula (A-2c), and Formula (A-2d), each R$^2$ is independently selected from the group consisting of:
phenyl substituted with from 0 to 5 groups independently selected from —OH, halo, alkyl, haloalkyl, hydroxyalkyl, alkyl substituted with from 1 to 2 —CO$_2$R$^6$ groups, alkoxy, —O-haloalkyl, hydroxyalkoxy, alkoxy substituted with from 1 to 2 —CO$_2$R$^6$ groups, —CO$_2$R$^6$, CN, —SO$_2$R$^7$, —C(O)NR$^8$R$^9$, and —NO$_2$.

In one embodiment, in each of Formula (A), Formula (A-1), Formula (A-1a), Formula (A-1b), Formula (A-2a), Formula (A-2b), Formula (A-2c), and Formula (A-2d), ring A represents a spirocycloalkyl ring or a spirocycloalkenyl ring, wherein said ring A is substituted on one or more available ring carbon atoms with from 1 to 5 independently selected R$^2$ groups.

In one embodiment, in each of Formula (A), Formula (A-1), Formula (A-1a), Formula (A-1b), Formula (A-2a), Formula (A-2b), Formula (A-2c), and Formula (A-2d), ring A represents a spirocycloalkyl ring, wherein said ring A is substituted on one or more available ring carbon atoms with from 1 to 5 independently selected R$^2$ groups.

In one embodiment, in each of Formula (A), Formula (A-1), Formula (A-1a), Formula (A-1b), Formula (A-2a), Formula (A-2b), Formula (A-2c), and Formula (A-2d), each R$^2$ is independently selected from the group consisting of:
phenyl substituted with from 0 to 5 groups independently selected from —OH, halo, alkyl, haloalkyl, alkoxy, —O-haloalkyl, hydroxyalkoxy, —CO$_2$R$^6$, CN, —SO$_2$R$^7$, —C(O)NR$^8$R$^9$, and —NO$_2$.

In one embodiment, in each of Formula (A), Formula (A-1), Formula (A-1a), Formula (A-1b), Formula (A-2a), Formula (A-2b), Formula (A-2c), and Formula (A-2d), each R$^2$ is independently selected from the group consisting of:
unsubstituted phenyl.

In one embodiment, in each of Formula (A), Formula (A-1), Formula (A-1a), Formula (A-1b), Formula (A-2a), Formula (A-2b), Formula (A-2c), and Formula (A-2d), each R$^2$ is independently selected from the group consisting of:
phenyl substituted with from 1 to 5 groups independently selected from halo.

In one embodiment, in each of Formula (A), Formula (A-1), Formula (A-1a), Formula (A-1b), Formula (A-2a), Formula (A-2b), Formula (A-2c), and Formula (A-2d), each R$^2$ is independently selected from the group consisting of:
alkyl substituted with from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, heteroalkyl, haloalkyl, haloheteroalkyl, —CO$_2$R$^6$, CN, —S(O)R$^7$, —S(O)$_2$R$^7$, —C(O)NR$^8$R$^9$, and —NO$_2$.

In one embodiment, in each of Formula (A), Formula (A-1), Formula (A-1a), Formula (A-1b), Formula (A-2a), Formula (A-2b), Formula (A-2c), and Formula (A-2d), each R$^2$ is selected from the group consisting of t-butyl and —Si(CH$_3$)$_3$.

In one embodiment, in each of Formula (A), Formula (A-1), Formula (A-1a), Formula (A-1b), Formula (A-2a), Formula (A-2b), Formula (A-2c), and Formula (A-2d), each R$^2$ is t-butyl, In one embodiment, in each of Formula (A), Formula (A-1), Formula (A-1a), Formula (A-1b), Formula (A-2a), Formula (A-2b), Formula (A-2c), and Formula (A-2d), each R$^2$ is deuteroalkyl, In one embodiment, in each of Formula (A), Formula (A-1), Formula (A-1a), Formula (A-1b), Formula (A-2a), Formula (A-2b), Formula (A-2c), and Formula (A-2d), each R$^2$ is —C(CD$_3$)$_3$.

In one embodiment, in each of Formula (A), Formula (A-1), Formula (A-1a), Formula (A-1b), Formula (A-2a), Formula (A-2b), Formula (A-2c), and Formula (A-2d), each R$^2$ is cycloalkyl or substituted cycloalkyl. Non-limiting examples of R$^2$ when R$^2$ is cycloalkyl include: cyclopropyl, cyclobutyl, cyclopentyl, cyclohexyl, cycloheptyl, and cyclooctyl. Non-limiting examples of said substituents when R$^2$ when R$^2$ is substituted cycloalkyl —OH, halo, aryl, substituted aryl, alkyl, alkoxy, heteroalkyl, haloalkyl, haloheteroalkyl, —CO$_2$R$^6$, CN, —S(O)R$^7$, —S(O)$_2$R$^7$, —C(O)

$NR^8R^9$, and $-NO_2$. Non-limiting illustrations of points of attachment of such substituents include:

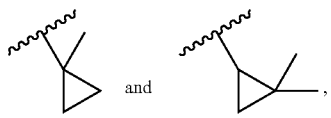

where the wavy line represents the point of attachment of $R^2$ to ring A.

In one embodiment, in each of Formula (A), Formula (A-1), Formula (A-1a), Formula (A-1b), Formula (A-2a), Formula (A-2b), Formula (A-2c), and Formula (A-2d), each $R^2$ is heterocycloalkyl or substituted heterocycloalkyl. Non-limiting examples of $R^2$ when $R^2$ is heterocycloalkyl include piperidyl, pyrrolidinyl, piperazinyl, morpholinyl, thiomorpholinyl, thiazolidinyl, 1,4-dioxanyl, tetrahydropyranyl, tetrahydrofuranyl, tetrahydrothiophenyl, lactam, lactone, oxetanes, and the like. Non-limiting illustrations of points of attachment of such substituents when $R^2$ is substituted heterocycloalkyl (such as an oxetane or substituted oxetane) include:

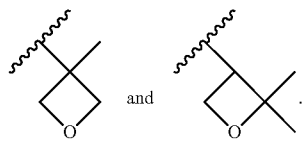

In one embodiment, in each of Formula (A), Formula (A-1), Formula (A-1a), Formula (A-1b), Formula (A-2a), Formula (A-2b), Formula (A-2c), and Formula (A-2d), each $R^2$ is $-Si(alkyl)_3$.

In one embodiment, in each of Formula (A), Formula (A-1), Formula (A-1a), Formula (A-1b), Formula (A-2a), Formula (A-2b), Formula (A-2c), and Formula (A-2d), each $R^2$ is $-Si(CH_3)_3$.

In one embodiment, in each of Formula (A), Formula (A-1), Formula (A-1a), Formula (A-1b), Formula (A-2a), Formula (A-2b), Formula (A-2c), and Formula (A-2d), $R^3$ is H.

In one embodiment, in each of Formula (A), Formula (A-1), Formula (A-1a), Formula (A-1b), Formula (A-2a), Formula (A-2b), Formula (A-2c), and Formula (A-2d), $R^3$ is selected from methyl, ethyl, n-propyl, and isopropyl.

In one embodiment, in each of Formula (A), Formula (A-1), Formula (A-1a), Formula (A-1b), Formula (A-2a), Formula (A-2b), Formula (A-2c), each $R^8$ is independently selected from H and alkyl.

In one embodiment, in each of Formula (A), Formula (A-1), Formula (A-1a), Formula (A-1b), Formula (A-2a), Formula (A-2b), Formula (A-2c), each $R^9$ is independently selected from H and alkyl.

In one embodiment, in each of Formula (A), Formula (A-1), Formula (A-1a), Formula (A-1b), Formula (A-2a), Formula (A-2b), Formula (A-2c), $R^8$ and $R^9$ are taken together with the nitrogen to which they are attached to form a 5-, 6-, or 7-membered heteroaromatic ring, which ring contains (including said nitrogen to which $R^8$ and $R^9$ are attached) from 1 to 2 ring heteroatoms.

In one embodiment, in each of Formula (A), Formula (A-1), Formula (A-1a), Formula (A-1b), Formula (A-2a), Formula (A-2b), Formula (A-2c), $R^8$ and $R^9$ are taken together with the nitrogen to which they are attached to form a 5-, 6-, or 7-membered saturated heterocyclic ring, which ring contains (including said nitrogen to which $R^8$ and $R^9$ are attached) from 1 to 2 ring heteroatoms.

In one embodiment, in each of Formula (A), Formula (A-1), Formula (A-1a), Formula (A-1b), Formula (A-2a), Formula (A-2b), Formula (A-2c), $R^8$ and $R^9$ are taken together with the nitrogen to which they are attached to form a 5-, 6-, or 7-membered partially or fully unsaturated heterocyclic ring, which ring contains (including said nitrogen to which $R^8$ and $R^9$ are attached) form 1 to 2 ring heteroatoms.

In one embodiment, in each of Formula (A), Formula (A-1), Formula (A-1a), Formula (A-1b), Formula (A-2a), Formula (A-2b), Formula (A-2c), $R^8$ and $R^9$ are taken together with the nitrogen to which they are attached to form a 5-, or 6-membered saturated, or partially or fully unsaturated, heterocyclic ring, which ring contains (including said nitrogen to which $R^8$ and $R^9$ are attached) form 1 to 2 ring heteroatoms.

In one embodiment, in each of Formula (A), Formula (A-1), Formula (A-1a), Formula (A-1b), Formula (A-2a), Formula (A-2b), Formula (A-2c), $R^8$ and $R^9$ are taken together with the nitrogen to which they are attached to form a 5-, 6-, or 7-membered ring moiety, non-limiting examples of such moieties include pyrroline, imidazolidine, piperazine, morpholine, thiomorpholine, oxazolidine, and thiazolidine.

In one embodiment, in each of Formula (A), Formula (A-1), Formula (A-1a), Formula (A-1b), Formula (A-2a), Formula (A-2b), Formula (A-2c), Z is $-(C(R^{11})_2)-(C(R^{12})(R^{13}))_m-C(O)OH$. Pharmaceutically acceptable salts of such acids are also contemplated as being within the scope of the invention. Thus, in another embodiment, in each of Formula (A), Formula (A-1), Formula (A-1a), Formula (A-1b), Formula (A-2a), Formula (A-2b), Formula (A-2c), Z is $-(C(R^{11})_2)-(C(R^{12})(R^{13}))_m-C(O)O^-Na^+$. Additional non-limiting salts contemplated as alternatives to the sodium salt are known to those of ordinary skill in the art and/or are as described herein.

In one embodiment, in each of Formula (A), Formula (A-1), Formula (A-1a), Formula (A-1b), Formula (A-2a), Formula (A-2b), Formula (A-2c), Z is $-(CH_2)-(CH(CH_3))-C(O)OH$.

In one embodiment, in each of Formula (A), Formula (A-1), Formula (A-1a), Formula (A-1b), Formula (A-2a), Formula (A-2b), Formula (A-2c), Z is $-(CH_2)-(CH_2)-(CH_2)-C(O)OH$.

In one embodiment, in each of Formula (A), Formula (A-1), Formula (A-1a), Formula (A-1b), Formula (A-2a), Formula (A-2b), Formula (A-2c), Z is $-(CH_2)-C(CH_3)_2-C(O)OH$.

In one embodiment, in each of Formula (A), Formula (A-1), Formula (A-1a), Formula (A-1b), Formula (A-2a), Formula (A-2b), Formula (A-2c), Z is $-(CH_2)-C(CH_3)(OH)-C(O)OH$.

In one embodiment, in each of Formula (A), Formula (A-1), Formula (A-1a), Formula (A-1b), Formula (A-2a), Formula (A-2b), Formula (A-2c), Z is $-CH_2-CH_2-C(O)OH$.

In one embodiment, in each of Formula (A), Formula (A-1), Formula (A-1a), Formula (A-1b), Formula (A-2a), Formula (A-2b), Formula (A-2c), Z is $-CH_2-CH(OH)-C(O)OH$.

In one embodiment, in each of Formula (A), Formula (A-1), Formula (A-1a), Formula (A-1b), Formula (A-2a), Formula (A-2b), Formula (A-2c), Z is $-CH(CH_3)-CH_2-C(O)OH$.

In one embodiment, in each of Formula (A), Formula (A-1), Formula (A-1a), Formula (A-1b), Formula (A-2a), Formula (A-2b), Formula (A-2c), Z is —C(CH$_2$)$_2$—CH$_2$—C(O)OH.

In one embodiment, in each of Formula (A), Formula (A-1), Formula (A-1a), Formula (A-1b), Formula (A-2a), Formula (A-2b), Formula (A-2c), Z is —(C(R$^{11}$)$_2$)—(C(R$^{14}$)$_2$)$_n$—C(O)OH.

In one embodiment, in each of Formula (A), Formula (A-1), Formula (A-1a), Formula (A-1b), Formula (A-2a), Formula (A-2b), Formula (A-2c), Z is —CH$_2$—CH(F)—C(O)OH.

In one embodiment, in each of Formula (A), Formula (A-1), Formula (A-1a), Formula (A-1b), Formula (A-2a), Formula (A-2b), Formula (A-2c), Z is —CH$_2$—CF$_2$—C(O)OH.

In one embodiment, in each of Formula (A), Formula (A-1), Formula (A-1a), Formula (A-1b), Formula (A-2a), Formula (A-2b), Formula (A-2c), Z is —CH(CH$_3$)—CF$_2$—C(O)OH.

In one embodiment, in each of Formula (A), Formula (A-1), Formula (A-1a), Formula (A-1b), Formula (A-2a), Formula (A-2b), Formula (A-2c), Z is —CH$_2$—CH$_2$—CF$_2$—C(O)OH.

In one embodiment, in each of Formula (A), Formula (A-1), Formula (A-1a), Formula (A-1b), Formula (A-2a), Formula (A-2b), Formula (A-2c), Z is

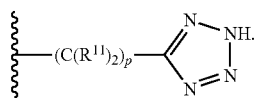

In one embodiment, in each of Formula (A), Formula (A-1), Formula (A-1a), Formula (A-1b), Formula (A-2a), Formula (A-2b), Formula (A-2c), Z is

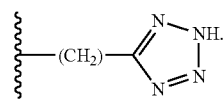

In one embodiment, in each of Formula (A), Formula (A-1), Formula (A-1a), Formula (A-1b), Formula (A-2a), Formula (A-2b), Formula (A-2c), Z is

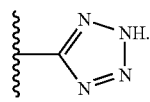

In one embodiment, in each of Formula (A), Formula (A-1), Formula (A-1a), Formula (A-1b), Formula (A-2a), Formula (A-2b), Formula (A-2c), when Z is a moiety selected from —(C(R$^{11}$)$_2$)—(C(R$^{12}$R$^{13}$))$_m$—C(O)OH, or —(C(R$^{11}$)$_2$)—(C(R$^{14}$)$_2$)$_n$—C(O)OH, the —C(O)OH group may be replaced by a moiety -Q, wherein Q is selected from the group consisting of:

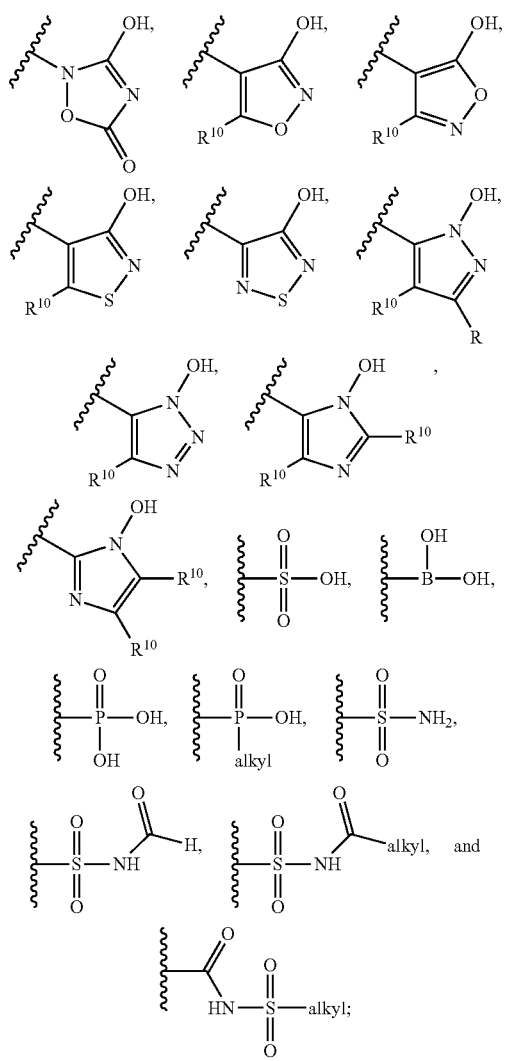

Such moieties Q are readily available to those skilled in the art and may be made, for example, by methods according to Stensbol et al., J. Med. Chem., 2002, 45, 19-31, or according to Moreira Lima et al., Current Med. Chem., 2005, 12, 23-49.

In one embodiment, in each of Formula (A), Formula (A-1), Formula (A-1a), Formula (A-1b), Formula (A-2a), Formula (A-2b), Formula (A-2c), the compounds of the invention have the general structure shown in Formula (I):

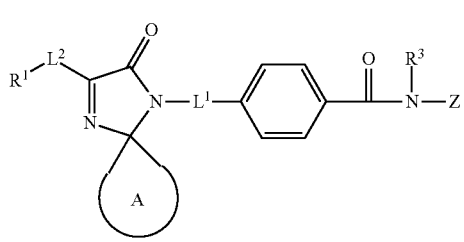

(I)

and include pharmaceutically acceptable salts, solvates, esters, prodrugs, tautomers, and isomers of said compounds, wherein ring A, $L^1$, $L^2$, $R^1$, $R^3$, and Z are selected independently of each other and wherein:

ring A and $R^1$ are as defined in Formula (A);

$L^1$ is selected from the group consisting of: a bond, —N($R^4$)—, —N($R^4$)—(C($R^{5A}$)$_2$)—, —O—, —O—(C($R^{5A}$)$_2$)—, and —(C($R^{5A}$)$_2$)—(C($R^5$)$_2$)$_s$—;

s is 0-3;

$L^2$ is selected from the group consisting of bond, —N($R^4$)—, —N($R^4$)—(C($R^{5A}$)$_2$)—, —(C($R^5$)$_2$)$_u$—(C($R^{5A}$)$_2$)—N($R^4$)—, —(C($R^{5A}$)$_2$)—N($R^4$)—, —O—, —O—(C($R^{5A}$)$_2$)—, —(C($R^{5A}$)$_2$)—O— and —(C($R^5$)$_2$)$_v$—, wherein v is 1-3;

$R^3$ is selected from the group consisting of H and lower alkyl;

Z is a moiety selected from —(C($R^{11}$)$_2$)—(C($R^{12}R^{13}$))$_m$—C(O)OH, —(C($R^{11}$)$_2$)—(C($R^{14}$)$_2$)$_n$—C(O)OH, and

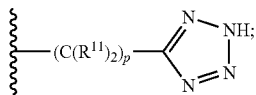

m is an integer from 0 to 5;
n is an integer from 0 to 5;
p is an integer from 0 to 5;

each $R^4$ is independently selected from H, lower alkyl, cycloalkyl, heterocycloalkyl, heteroalkyl, and haloalkyl;

each $R^{5A}$ is independently selected from H, lower alkyl, -lower alkyl-Si(CH$_3$)$_3$, -lower alkyl-Si(CH$_3$)$_3$, lower haloalkyl, and hydroxy-substituted lower alkyl;

each $R^5$ is independently selected from H, —OH, lower alkyl, -lower alkyl-Si(CH$_3$)$_3$, -lower alkyl-Si(CH$_3$)$_3$, lower haloalkyl, and hydroxy-substituted lower alkyl;

each $R^6$ is independently selected from H, alkyl, and haloalkyl;

each $R^7$ is independently selected from H, alkyl, heteroalkyl, and haloalkyl;

each $R^8$ is independently selected from H and alkyl;

each $R^9$ is independently selected from H and alkyl, each $R^{11}$ is independently selected from H and lower alkyl;

each $R^{12}$ is independently selected from H, lower alkyl, —OH, hydroxy-substituted lower alkyl;

each $R^{13}$ is independently selected from H, unsubstituted lower alkyl, lower alkyl substituted with one or more groups each independently selected from hydroxyl and alkoxy, or $R^{12}$ and $R^{13}$ are taken together to form an oxo; and each $R^{14}$ is independently selected from H and fluoro.

In one embodiment, in Formula (I):

ring A represents a spirocycloalkyl ring or a spirocycloalkenyl ring, wherein said ring A is substituted on one or more available ring carbon atoms with from 0 to 5 independently selected $R^2$ groups;

$R^1$ is selected from the group consisting of:
aryl and heteroaryl,
wherein each of said aryl and said heteroaryl are unsubstituted or substituted with from 1 to 3 groups each independently selected from:
(1) halo, —SO$_2$R$^7$, —SF$_5$, —OSF$_5$, CN,
(2) alkyl, alkoxy, heteroalkyl, —O-heteroalkyl,
wherein each of said alkyl, alkoxy, heteroalkyl, and —O-heteroalkyl, is unsubstituted or optionally independently substituted with from 1 to 3 groups each independently selected from:
halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, —O-haloalkyl, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (3) aryl, —O-aryl, —S-aryl, —S(O)-aryl, —S(O)$_2$-aryl, heteroaryl, cycloalkyl, cycloalkenyl, and heterocycloalkenyl,
each of which is unsubstituted or optionally independently substituted with from 1 to 2 groups each independently selected from (1) and (2) above; and each $R^2$ (when present) is independently selected from the group consisting of —Si(CH$_3$)$_3$ and alkyl, wherein said alkyl substituted with from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, —O-haloalkyl, heteroalkyl, haloalkyl, haloheteroalkyl, —CO$_2$R$^6$, CN, —S(O)R$^7$, —S(O)$_2$R$^7$, —SF$_5$, —OSF$_5$, —C(O)NR$^8$R$^9$, and —NO$_2$.

In one embodiment, in Formula (I):

ring A represents a spirocycloalkyl ring or a spirocycloalkenyl ring, wherein said ring A is substituted on one or more available ring carbon atoms with from 0 to 5 independently selected $R^2$ groups;

$R^1$ is selected from the group consisting of:
phenyl,
wherein said phenyl and is unsubstituted or substituted with from 1 to 3 groups each independently selected from:
(1) halo, —SO$_2$R$^7$, —SF$_5$, —OSF$_5$, CN,
(2) alkyl, alkoxy, haloalkyl, —O-haloalkyl, heteroalkyl, —O-heteroalkyl,
(3) aryl, —O-aryl, —S-aryl, —S(O)-aryl, —S(O)$_2$-aryl, heteroaryl, cycloalkyl, cycloalkenyl, and heterocycloalkenyl,
each of which said aryl, —O-aryl, —S-aryl, —S(O)-aryl, —S(O)$_2$-aryl, heteroaryl, cycloalkyl, cycloalkenyl, and heterocycloalkenyl, is unsubstituted or optionally independently substituted with from 1 to 2 groups each independently selected from (1) and (2) above; and each $R^2$ (when present) is independently selected from the group consisting of —Si(CH$_3$)$_3$ and alkyl, wherein said alkyl is substituted with from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, heteroalkyl, haloalkyl, haloheteroalkyl, —CO$_2$R$^6$, CN, —S(O)R$^7$, —S(O)$_2$R$^7$, —C(O)NR$^8$R$^9$, and —NO$_2$.

In one embodiment, the compounds of the invention have the general structure shown in Formula (I-1):

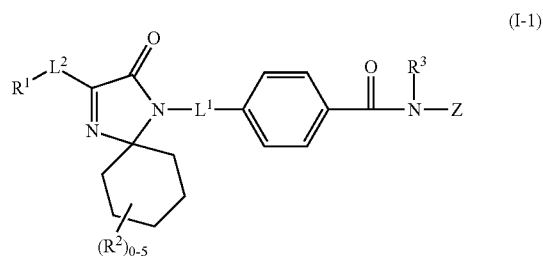

(I-1)

and include pharmaceutically acceptable salts, solvates, esters, prodrugs, tautomers, and isomers of said compounds, wherein $L^2$, $L^2$, $R^1$, each $R^2$, $R^3$, and Z are selected independently of each other and as defined in Formula (I).

In one embodiment, the compounds of the invention have the general structure shown in Formula (II):

(II)

and include pharmaceutically acceptable salts, solvates, esters, prodrugs, tautomers, and isomers of said compounds, wherein $L^2$, $R^1$, each $R^2$, $R^3$, and Z are selected independently of each other and wherein:

$L^1$ is selected from the group consisting of: a bond and —$(C(R^{5A})_2)$—$(C(R^5)_2)_s$—;

s is 0-1;

$L^2$ is selected from the group consisting of: a bond, —$(C(R^5)_2)_u$—$(C(R^5)_2)$—$N(R^4)$—, and —$(C(R^5)_2)_v$—;

u is 0 to 2;

v is 1-2;

$R^1$ is selected from the group consisting of:
phenyl,
wherein said phenyl is unsubstituted or substituted with one or more groups each independently selected from: halo, alkyl, haloalkyl, heteroalkyl, haloheteroalkyl, alkoxy, —O-haloalkyl, and cycloalkyl;

each $R^2$ is independently selected from the group consisting of —$Si(CH_3)_3$ and alkyl, wherein said alkyl is substituted with from 0 to 5 groups independently selected from —OH, halo, alkyl, haloalkyl, hydroxyalkyl, alkyl substituted with from 1 to 2 —$CO_2R^6$ groups, alkoxy, —O-haloalkyl, hydroxyalkoxy, alkoxy substituted with from 1 to 2 —$CO_2R^6$ groups, —$CO_2R^6$, CN, —$SO_2R^7$, —$C(O)NR^8R^9$, and —$NO_2$;

$R^3$ is selected from the group consisting of H and lower alkyl;

Z is a moiety selected from the group consisting of:
—$(CH_2)$—$(CH(CH_3))$—$C(O)OH$, —$(CH_2)$—$(CH_2)$—$(CH_2)$—$C(O)OH$, —$(CH_2)$—$C(CH_3)_2$—$C(O)OH$, —$(CH_2)$—$C(CH_3)(OH)$—$C(O)OH$, —$CH_2$—$CH_2$—$C(O)OH$, —$CH_2$—$CH(OH)$—$C(O)OH$, —$CH(CH_3)$—$CH_2$—$C(O)OH$, —$C(CH_3)_2$—$CH_2$—$C(O)OH$, —$CH_2$—$CH(F)$—$C(O)OH$, —$CH_2$—$CF_2$—$C(O)OH$, —$CH(CH_3)$—$CF_2$—$C(O)OH$, —$CH_2$—$CH_2$—$CF_2$—$C(O)OH$, and wherein p is an integer from 0 to 1, and $R^{11}$ (when present) is selected from the group consisting of H and lower alkyl;

each $R^{5A}$ is independently selected from H, lower alkyl, -lower alkyl-$Si(CH_3)_3$, lower haloalkyl, and lower alkyl substituted with from 1 to 2 hydroxyl;

each $R^5$ is independently selected from H, —OH, lower alkyl, -lower alkyl-$Si(CH_3)_3$, lower haloalkyl, and lower alkyl substituted with from 1 to 2 hydroxyl;

each $R^6$ is independently selected from H, alkyl, and haloalkyl;

each $R^7$ is independently selected from H, alkyl, heteroalkyl, and haloalkyl;

each $R^8$ is independently selected from H and alkyl; and each $R^9$ is independently selected from H and alkyl.

In one embodiment, the compounds of the invention have the general structure shown in Formula (II-a):

(II-a)

and include pharmaceutically acceptable salts, solvates, esters, prodrugs, tautomers, and isomers of said compounds, wherein $L^1$, $L^2$, $R^1$, each $R^2$, $R^3$, and Z are selected independently of each other and as defined in Formula (II).

In one embodiment, the compounds of the invention have the general structure shown in Formula (II-b):

(II-b)

and include pharmaceutically acceptable salts, solvates, esters, prodrugs, tautomers, and isomers of said compounds, wherein $L^1$, $L^2$, $R^1$, $R^2$, $R^3$, and Z are selected independently of each other and as defined in Formula (II).

In one embodiment, in each of Formula (II), Formula (II-a), and Formula (II-b):

$L^1$ is selected from the group consisting of: a bond, straight or branched lower alkyl, and —(CH(-lower alkyl-$Si(CH_3)_3$)—;

$L^2$ is selected from the group consisting of: a bond and straight or branched lower alkyl;

$R^1$ is selected from the group consisting of:
phenyl,
wherein said phenyl is unsubstituted or substituted with from 1 to 3 groups each independently selected from: halo, alkyl, haloalkyl, heteroalkyl, haloheteroalkyl, alkoxy, and —O-haloalkyl;

each $R^2$ is independently selected from the group consisting of H, straight or branched lower alkyl, and —$Si(CH_3)_3$;

$R^3$ is selected from the group consisting of H and lower alkyl;

Z is a moiety selected from the group consisting of:
—$(CH_2)$—$(CH(CH_3))$—$C(O)OH$, —$(CH_2)$—$(CH_2)$—$(CH_2)$—$C(O)OH$, —$(CH_2)$—$C(CH_3)_2$—$C(O)OH$, —$(CH_2)$—$C(CH_3)(OH)$—$C(O)OH$, —$CH_2$—$CH_2$—$C(O)OH$, —$CH_2$—$CH(OH)$—$C(O)OH$, —$CH(CH_3)$—$CH_2$—$C(O)OH$, —$C(CH_3)_2$—$CH_2$—$C(O)OH$, —$(C(R^{11})_2)$—(C $-(R^{14})_2)_n-C(O)OH$, $-CH_2-CH(F)-C(O)OH$, $-CH_2-CF_2-C(O)OH$, $-CH(CH_3)-CF_2-C(O)OH$, $-CH_2-CH_2-CF_2-C(O)OH$, $-(CH_2)-(CH(CH_3))-C(O)OCH_3$, $-(CH_2)-(CH_2)-(CH_2)-C(O)OCH_3$, $-(CH_2)-C(CH_3)_2-C(O)OCH_3$, $-(CH_2)-C(CH_3)(OH)-C(O)OCH_3$, $-CH_2-CH_2-C(O)OCH_3$, $-CH_2-CH(OH)-C(O)OCH_3$, $-CH(CH_3)-CH_2-C(O)OCH_3$, $-C(CH_3)_2-CH_2-C(O)OCH_3$, $-(C(R^{11})_2)-(C(R^{14})_2)_n-C(O)OCH_3$, $-CH_2-CH(F)-C(O)OCH_3$, $-CH_2-CF_2-C(O)OCH_3$, $-CH(CH_3)-CF_2-C(O)OCH_3$, $-CH_2-CH_2-CF_2-C(O)OCH_3$, and

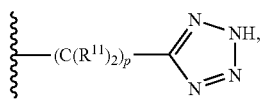

wherein p is an integer from 0 to 1, and $R^{11}$ (when present) is selected from the group consisting of H and lower alkyl;

each $R^5$ is independently selected from H, —OH, lower alkyl, -lower alkyl-Si(CH$_3$)$_3$, lower haloalkyl, and lower alkyl substituted with from 1 to 2 hydroxyl;

each $R^6$ is independently selected from H, alkyl, and haloalkyl;

each $R^7$ is independently selected from H, alkyl, heteroalkyl, and haloalkyl;

each $R^8$ is independently selected from H and alkyl; and each $R^9$ is independently selected from H and alkyl.

In one embodiment, in each of Formula (II), Formula (II-a), and Formula (II-b), $L^1$ is selected from the group consisting of: a bond,

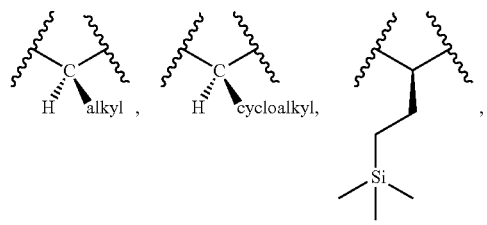

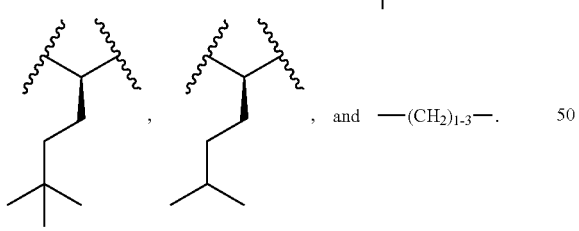, and $-(CH_2)_{1-3}-$.

In one such embodiment, $L^1$ is selected from the group consisting of:

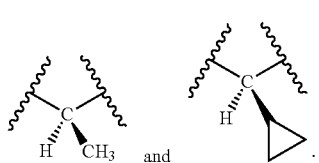

In one such embodiment, $L^1$ is

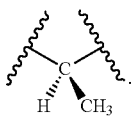

In one such embodiment, $L^1$ is

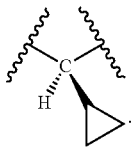

In one such embodiment, $L^1$ is

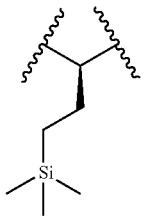

In one such embodiment, $L^1$ is

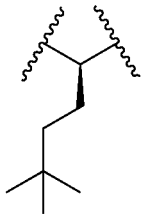

In one such embodiment, $L^1$ is

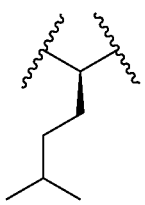

In one embodiment, in each of Formula (II), Formula (II-a), and Formula (II-b):

$L^1$ is selected from the group consisting of:

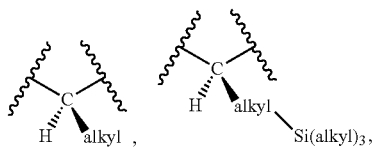

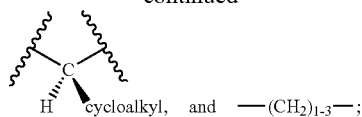

$L^2$ is selected from the group consisting of: a bond and straight or branched lower alkyl;

$R^1$ is selected from the group consisting of:
phenyl,
wherein said phenyl is unsubstituted or substituted with from 1 to 3 groups each independently selected from: halo, alkyl, haloalkyl, heteroalkyl, haloheteroalkyl, alkoxy, and —O-haloalkyl;

each $R^2$ is independently selected from the group consisting of H, straight or branched lower alkyl, and —Si(CH$_3$)$_3$;

$R^3$ is selected from the group consisting of H and lower alkyl; and

Z is selected from the group consisting of —CH$_2$—CH$_2$—C(O)OH and

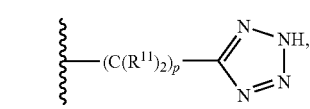

wherein p is 1 and $R^{11}$ is H.

In one embodiment, in each of Formula (II), Formula (II-a), and Formula (II-b):

$L^1$ is selected from the group consisting of

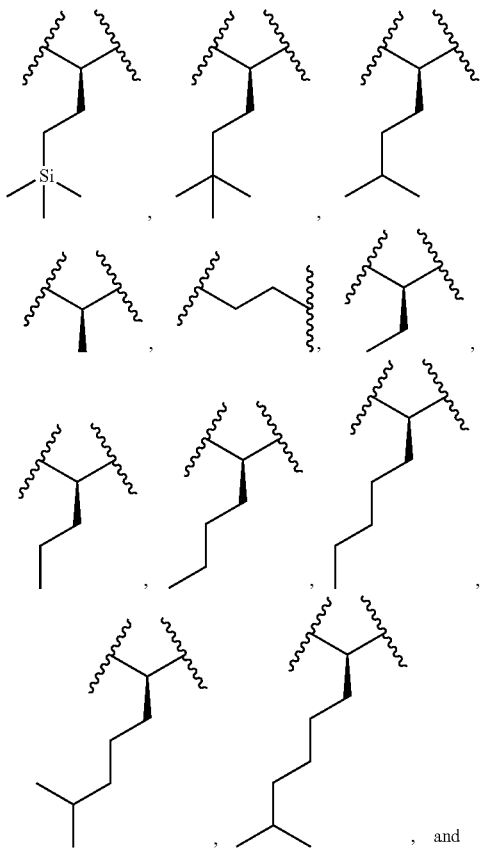

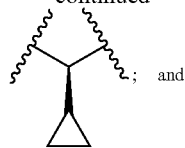

$L^2$ is a bond;
$R^1$ is selected from the group consisting of:
phenyl,
wherein said phenyl is unsubstituted or substituted with from 1 to 3 groups each independently selected from: halo;

each $R^2$ is independently selected from the group consisting of iso-propyl, tert-butyl and tert-pentyl;

$R^3$ is H; and

Z is selected from the group consisting of —CH$_2$—CH$_2$—C(O)OH and

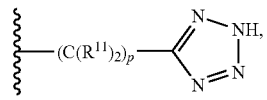

wherein p is 1 and $R^{11}$ is H.

In one embodiment, the compounds of the invention have the general structure shown in the tables below, and include pharmaceutically acceptable salts, solvates, esters, prodrugs, tautomers, and isomers of said compounds.

In the various embodiments described herein, variables of each of the general formulas not explicitly defined in the context of the respective formula are as defined in Formula (A).

In one embodiment, a compound or compounds of the invention is/are in isolated or purified form.

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"Mammal" means humans and other mammalian animals.

A "patient" is a human or non-human mammal. In one embodiment, a patient is a human. In another embodiment, a patient is a non-human mammal, including, but not limited to, a monkey, baboon, mouse, rat, horse, dog, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "impaired glucose tolerance" (IGT) as used herein, is defined as a two-hour glucose level of 140 to 199 mg per dL (7.8 to 11.0 mmol) as measured using the 75-g oral glucose tolerance test. A patient is said to be under the condition of impaired glucose tolerance when he/she has an intermediately raised glucose level after 2 hours, wherein the level is less than would qualify for type 2 diabetes mellitus.

The term "impaired fasting glucose" (IFG) as used herein, is defined as a fasting plasma glucose level of 100 to 125 mg/dL; normal fasting glucose values are below 100 mg per dL.

The term "effective amount" as used herein, refers to an amount of Compound of Formula (I) and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl. Additional non-limiting examples of branched lower alkyl include -loweralkyl-isopropyl, (e.g., —CH$_2$CH$_2$CH(CH$_3$)$_2$), -loweralkyl-t-butyl (e.g., —CH$_2$CH$_2$C(CH$_3$)$_3$).

The term "haloalkyl" as used herein, refers to an alkyl group, as defined above, wherein one or more of the alkyl group's hydrogen atoms have been independently replaced with —F, —Cl, —Br or —I. Non-limiting illustrative examples of haloalkyl groups include —CH$_2$F, —CHF$_2$, —CF$_3$, —CH$_2$CHF$_2$, —CH$_2$CF$_3$, —CCl$_3$, —CH$_2$Cl, and —CH$_2$CHCl$_3$.

The term "deuterioalkyl" (or "deuteroalkyl") as used herein, refers to an alkyl group, as defined above, wherein one or more of the alkyl group's hydrogen atoms have been independently replaced with deuterium.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. Further non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. More generally, the suffix "ene" on alkyl, aryl, heterocycloalkyl, etc. indicates a divalent moiety, e.g., —CH$_2$CH$_2$— is ethylene, and

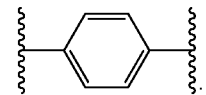

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Heteroalkynyl" means an alkynyl moiety as defined above, having one or more carbon atoms, for example one, two or three carbon atoms, replaced with one or more heteroatoms, which may be the same or different, where the point of attachment to the remainder of the molecule is through a carbon atom of the heteroalkynyl radical.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The bond to the parent moiety may be through an available carbon or nitrogen atom.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, 2-decalinyl, norbornyl, adamantyl and the like. Further non-limiting examples of cycloalkyl include the following:

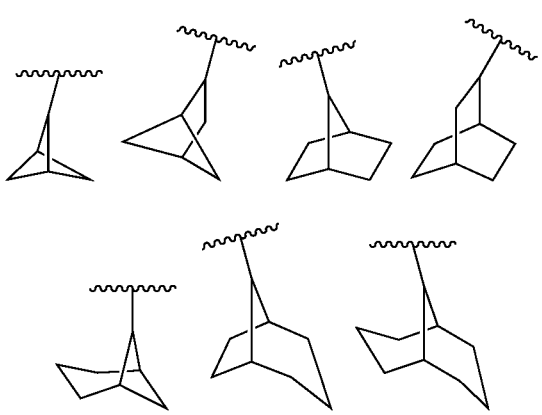

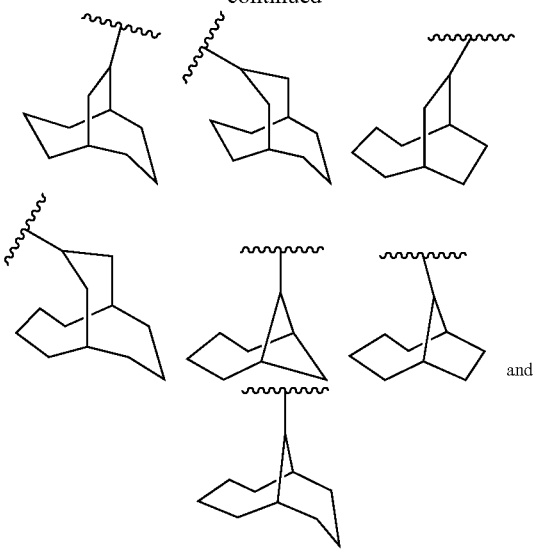

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidinyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." Example of such moiety is pyrrolidinone (or pyrrolidone):

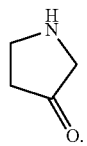

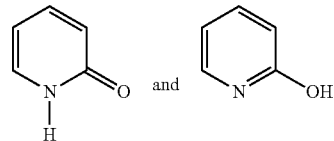 [SMILES: O=c1cccc[nH]1 ; Oc1ccccn1]

are considered equivalent in certain embodiments of this invention. Thus, for example, when a compound of the invention contains a

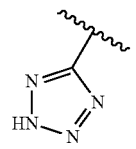

group,

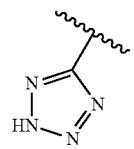 [SMILES: *c1nn[nH]n1]

is equivalent to

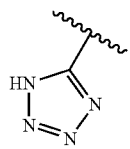

It should be understood that for hetero-containing functional groups described herein, e.g., heterocycloalkyl, heterocycloalkenyl, heteroalkyl, heteroaryl, and arylheterocycloalkyl (e.g., benzo-fused heterocycloalkyl), the bond to the parent moiety can be through an available carbon or heteroatom (e.g., nitrogen atom).

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

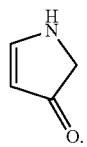

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

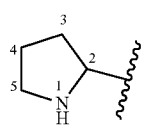

there is no —OH attached directly to carbons marked 2 and 5.

It should also be noted that tautomeric forms such as, for example, the moieties:

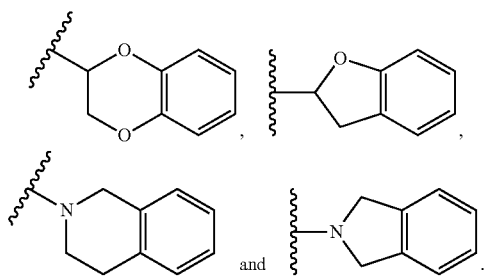

The bond to the parent moiety is through a non-aromatic carbon atom.

It is also understood that the terms "arylfused aryl", "arylfused cycloalkyl", "arylfused cycloalkenyl", "arylfused heterocycloalkyl", "arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl", "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Spirocycloalkyl" means a monocyclic or multicyclic cycloalkyl group attached to a parent moiety by replacement of two available hydrogen atoms attached to the same carbon atom. The spirocycloalkyl may optionally be substituted as described herein. Non-limiting examples of suitable monocyclic spirocycloalkyl groups include spirocyclopropyl, spirocyclobutyl, spirocycloheptyl, spirocyclohexyl, and spirocyclooctyl. Non-limiting examples of suitable multicyclic spirocycloalkyl groups include the moiety:

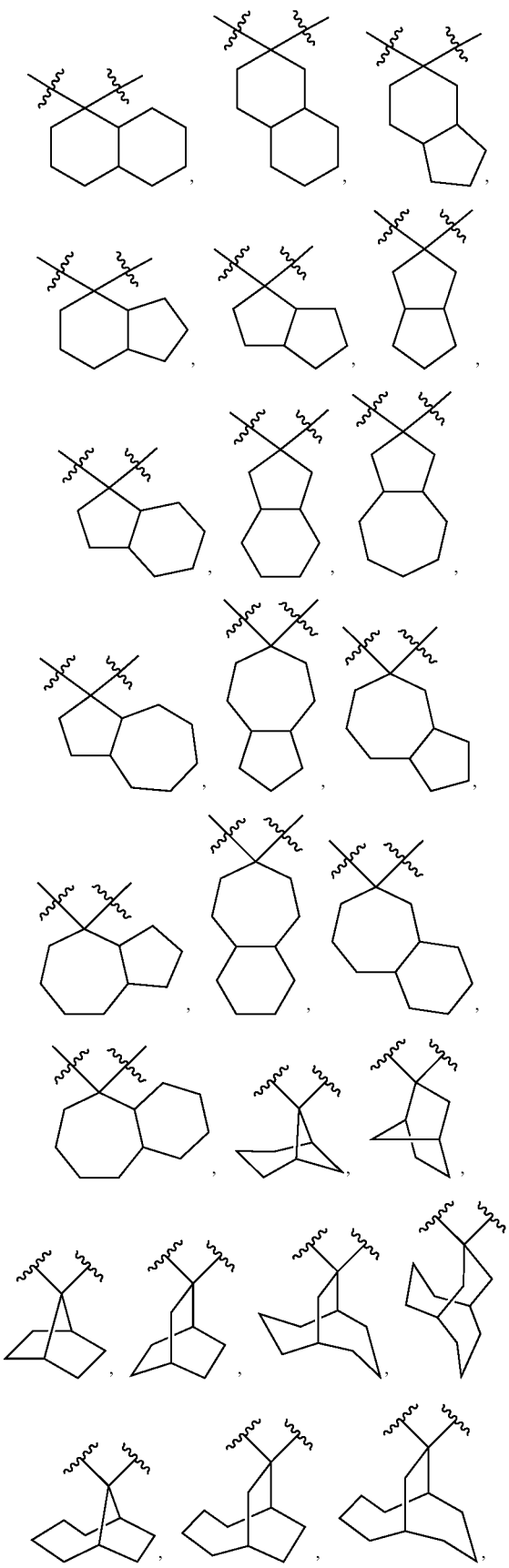

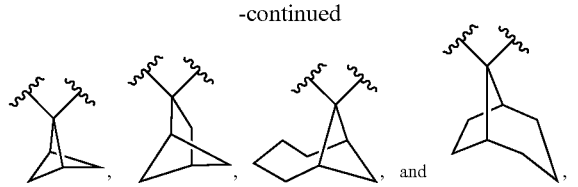

and the like.

"Spirocycloalkenyl" means a spirocycloalkyl group which contains at least one carbon-carbon double bond. Preferred spirocycloalkenyl rings contain about 5 to about 7 ring atoms. The spirocycloalkenyl can be optionally substituted as described herein. Non-limiting examples of suitable monocyclic cycloalkenyls include spirocyclopentenyl, spirocyclohexenyl, spirocyclohepta-1,3-dienyl, and the like. Non-limiting example of a suitable multicyclic spirocycloalkenyl include

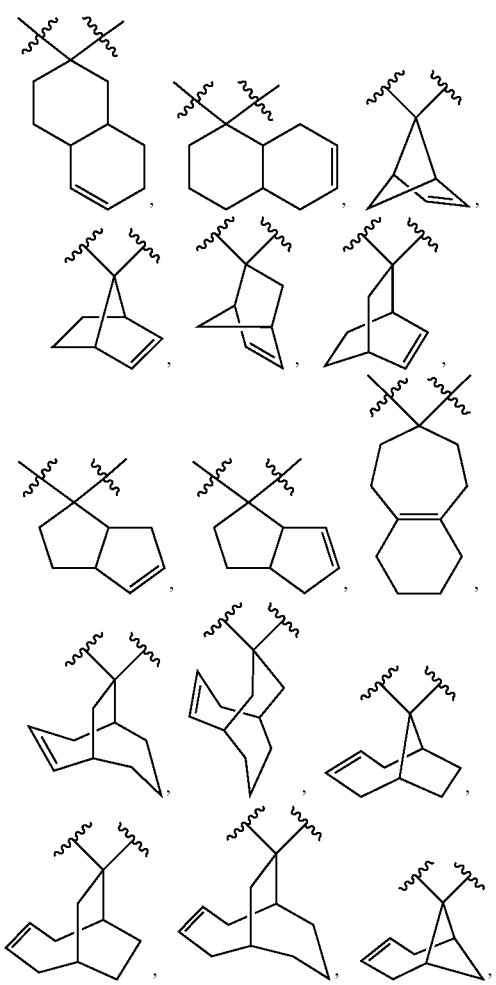

and the like.

"Sprioheterocycloalkyl" means a monocyclic or multicyclic heterocycloalkyl group (include oxides thereof) attached to the parent moiety by replacement of two available hydrogen atoms attached to the same carbon atom. The spiroheterocycloalkyl may be optionally substituted as described herein. Non-limiting examples of suitable multicyclic spiroheterocycloalkyl include

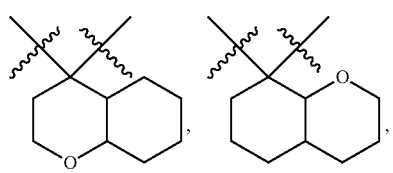

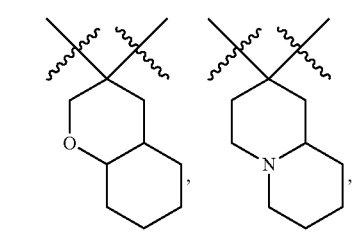

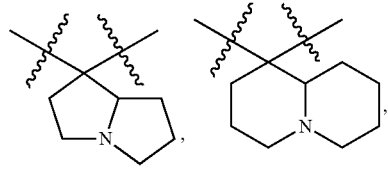

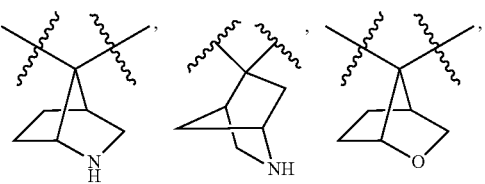

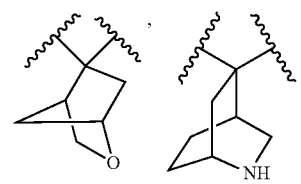

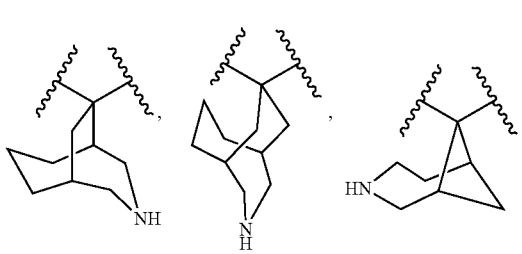

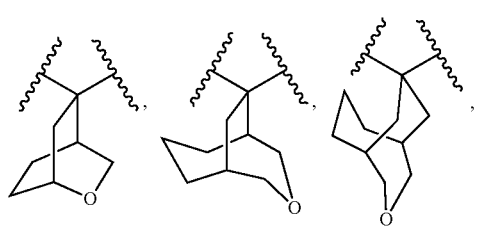

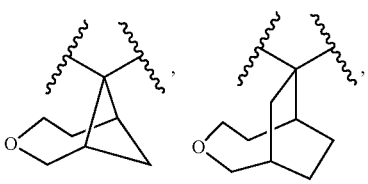

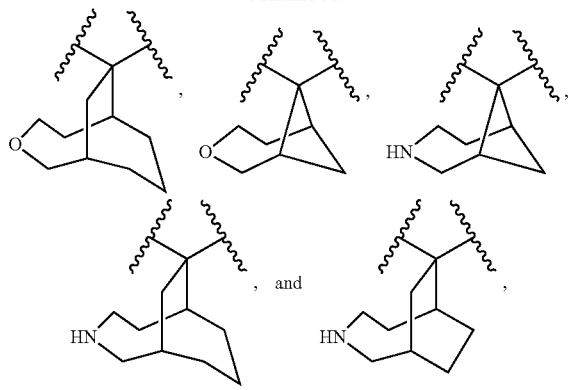

and the like.

"Spiroheterocycloalkenyl" (or "spiroheterocyclenyl") means a spiroheterocycloalkyl group which contains at least one carbon-carbon double bond. Non-limiting examples of suitable multicyclic spiroheterocycloalkenyl include:

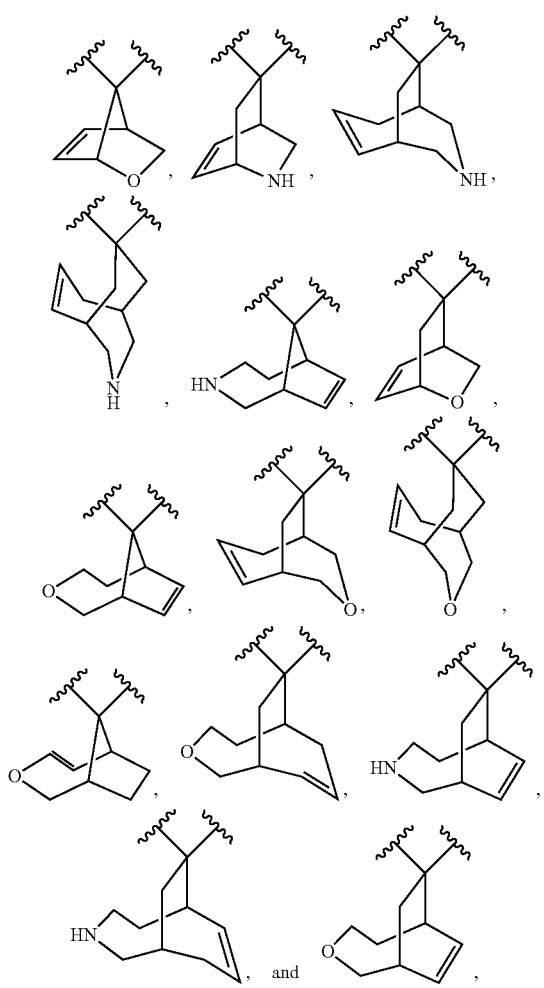

and the like.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in —N($R^8$)$_2$, or a variable appears more than once in a structure presented herein such as Formula (I), the variables can be the same or different.

The term, "compound(s) of the invention," as used herein, refers, collectively or independently, to any of the compounds embraced by the general formulas described herein, e.g., Formula (A), Formula (I), Formula (II-A), Formula (II-B), Formula (II-B1), Formula (II-B2), Formula (II-B3), Formula (II-B4), Formula (II-B5), Formula (II-C), Formula (II-C1), Formula (II-C2), Formula (II-C3), Formula (II-C4), Formula (II-C5), Formula (II-D), Formula (II-D1), Formula (II-D2), Formula (III), Formula (IV), Formula (IV), Formula (V), and Formula (VI), and the example compounds thereof.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (I)," one to three compounds of the invention, e.g., of Formula (I) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C(CH$_3$)$_2$— and the like which form moieties such as, for example:

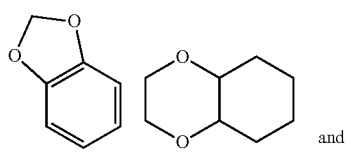 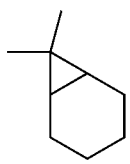 and 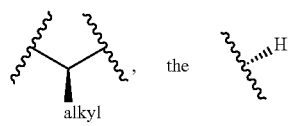.

As used herein, the term "composition" is intended to encompass a product comprising the specified ingredients in the specified amounts, as well as any product which results, directly or indirectly, from combination of the specified ingredients in the specified amounts.

The line ----, as a bond generally indicates a mixture of, or either of, the possible isomers, e.g., containing (R)- and (S)-stereochemistry. For example:

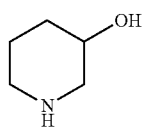

means containing both

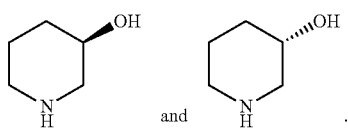 [SMILES: O[C@@H]1CCCNC1 ; O[C@H]1CCCNC1]

In the structure

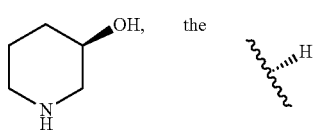 the 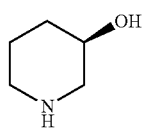

is implied. Thus, the structure

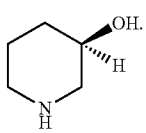

is equivalent to

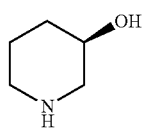

Similarly, and by way of additional non-limiting example, when -L$^1$- is

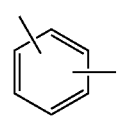, the 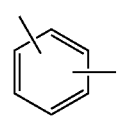

is implied. Thus,

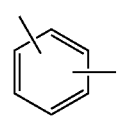

is equivalent to

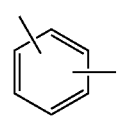

The wavy line ～, as used herein, indicates a point of attachment to the rest of the compound. For example, each wavy line in the following structure:

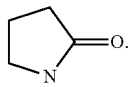

indicates a point of attachment to the core structure, as described herein.

Lines drawn into the ring systems, such as, for example:

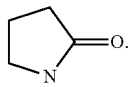

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

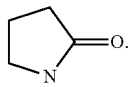

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

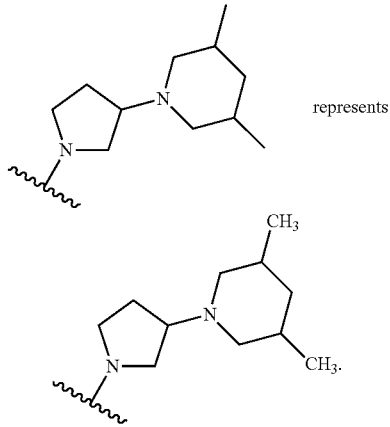

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1999), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-$((C_1-C_6)$ alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O) $(OH)_2$, —P(O)(O$(C_1-C_6)_{alkyl})_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or an unnatural α-aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N- or di-N,N-$(C_1-C_6)$alkylaminoalkyl, —C($Y^4$)$Y^5$ wherein $Y^4$ is H or methyl and $Y^5$ is mono-N- or di-N,N-$(C_1-C_6)$alkylamino morpholino, piperidin-1-yl or pyrrolidin-1-yl, and the like.

Compounds of the invention wherein Z is an ester moiety, such as those selected from —$(C(R^{11})_2)$—$(C(R^{12}R^{13}))_m$—C(O)Oalkyl, and —$(C(R^{11})_2)$—$(C(R^{14})_2)_n$—C(O)Oalkyl, are also expected to form prodrugs.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3) 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1) article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("Inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

By way of further non-limiting example, compounds of the invention having the general structure shown in Formula (II-b):

In one embodiment, the compounds of the invention have the general structure shown in Formula (II-b):

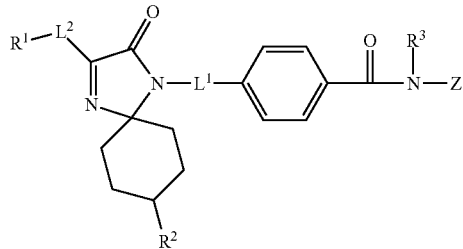

(II-b)

encompass compounds of the formula

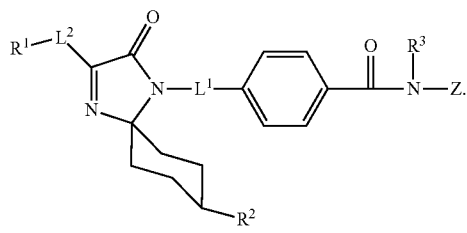

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent. Such compounds are within the scope of the compounds of the invention. Non-limiting examples of deuterated compounds are described herein, including examples 1.369, 1.371, 1.371, 1.372, and 1.312, and elsewhere.

Polymorphic forms of the compounds of the invention, and of the salts, solvates, esters and prodrugs of the compounds of the invention, are intended to be included in the present invention.

EXPERIMENTALS

Abbreviations Used in the Experimentals May Include the Following:

| | |
|---|---|
| ACN | Acetonitrile |
| AcOH | Acetic acid |
| Aq | Aqueous |
| Bn | Benzyl |
| BOC | tert-Butoxycarbonyl |
| BOC$_2$O | BOC Anhydride |
| Bu | Butyl |
| C (or ° C.) | degrees Celsius |
| Cbz | benzyloxycarbonyl |
| DBU | 1,8-Diazabicyclo[5.4.0]undec-7-ene |
| DCM | Dichloromethane |
| DIPEA | Diisopropylethylamine |
| DMA | N,N-Dimethylacetamide |
| DMAP | 4-Dimethylaminopyridine |
| DME | 1,2-dimethoxyethane |
| DMF | Dimethylformamide |
| DMSO | Dimethyl sulfoxide |
| DPPF | 1,1'-(bis-diphenylphosphino) ferrocene |
| EDCI | 1-(3-Dimethylaminopropyl)-3-ethylcarbodiimide hydrochloride |
| EDC | 1-(3-Dimethylaminopropyl)-3-ethylcarbodiimide hydrochloride |
| EI | Electron ionization |
| Eq | Equivalents |
| Et | Ethyl |
| EtOAc | Ethyl acetate |
| EtOH | Ethanol |
| g | grams |
| h | hours |
| hr | hours |
| $^1$H | proton |
| HATU | N,N,N',N'-Tetramethyl-O-(7-Azabenzotriazol-1-yl)Uronium hexafluorophosphate |
| Hex | hexanes |
| HOBT | 1-Hydroxybenzotriazole |
| HOBT•H$_2$O | 1-Hydroxybenzotriazole hydrate |
| HOTS | para-toluene sulfonic acid (see also TsOH) |
| HOTS•H$_2$O | para-toluene sulfonic acid hydrate (see also TsOH•H$_2$O) |
| HMPA | hexamethylphosphoramide |
| HPLC | High pressure liquid chromatography |
| IPA | isopropanol, 2-propanol |
| LDA | lithium diisopropylamide |
| M | Molar |
| mmol | milimolar |
| mCPBA | meta-Chloroperoxybenzoic acid |
| Me | Methyl |

| | |
|---|---|
| MeCN | Acetonitrile |
| MeOH | Methanol |
| min | Minutes |
| mg | Milligrams |
| MHZ | Megahertz |
| mL (or ml) | Milliliter |
| mol sieves | molecular sieves |
| N | normal |
| NMR | Nuclear Magnetic Resonance |
| MS | Mass Spectroscopy |
| NBS | N-Bromosuccinimide |
| NMM | N-Methylmorpholine |
| NMP | 1-methyl-2-pyrrolidone |
| ON | Overnight |
| PTLC | Preparative thin layer chromatography |
| PyBrOP | Bromo-tris-pyrrolidino-phosphonium hexafluorophosphate |
| PyBOP | (Benzotriazol-1-yloxy)tripyrrolidinophosphonium hexa-fluorophosphate |
| Pyr | Pyridine |
| Quant | quantitative |
| RT or rt | Room temperature |
| sat (or sat. or sat'd.) | Saturated |
| SFC | supercritical fluid chromatography |
| sgc | Silica gel 60 chromatography |
| SiO$_2$ | Silica gel |
| tBOC | tert-Butoxycarbonyl |
| t-Bu | tert-butyl |
| TEA | Triethylamine |
| Tf | Trifluoromethane sulfonyl |
| TFA | Trifluoroacetic acid |
| THF | Tetrahydrofuran |
| TLC | Thin layer chromatography |
| Ts | Toluene sulfonyl |
| TsOH | para-toluene sulfonic acid |
| TsOH•H$_2$O | para-toluene sulfonic acid hydrate |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Microwave chemistry is performed in sealed glass tubes in a Biotage microwave oven.

General Synthetic Schemes

The general approach to these types of spiro-heterocycles is depicted in Scheme I. The Boc-amino acid i can be coupled to an appropriately substituted amine ii using standard conditions to provide amides iii. The BOC group in iii can be removed under acid conditions which provide amino-amides iv. Amino-amides iv can be reacted with ketones v to provide spiro-amino amides such as vi (e.g. microwave mediated—Feliu, L., Font, D., Soley, R., Tailhades, J., Martinez, J., Amblard, M. *ARKIVOC* 2007, 65; thermal conditions—Gomes, P., Araujo, M. J., Rodrigues, M., Vale, N., Azevedo, Z., Iley, J., Chanbel, P., Morals, J., Moreira, R. *Tetrahedron* 2004, 60, 5551 and Cheng, S., Wu, H., Hu. X. *Syn. Comm.* 2007, 37, 297); TsOH mediated cyclization as described herein. The amino intermediates such as vi can be oxidized to the spiro-imidazolone intermediates vii (e.g. Dean, A. W., Porter, R. A., WO 2007014762). The ester in vii can be hydrolyzed to provide the acid viii. The acid can be coupled to amines using standard protocols to provide the amides such as x. One skilled in the art would recognize that there are numerous coupling conditions for formation of amides.

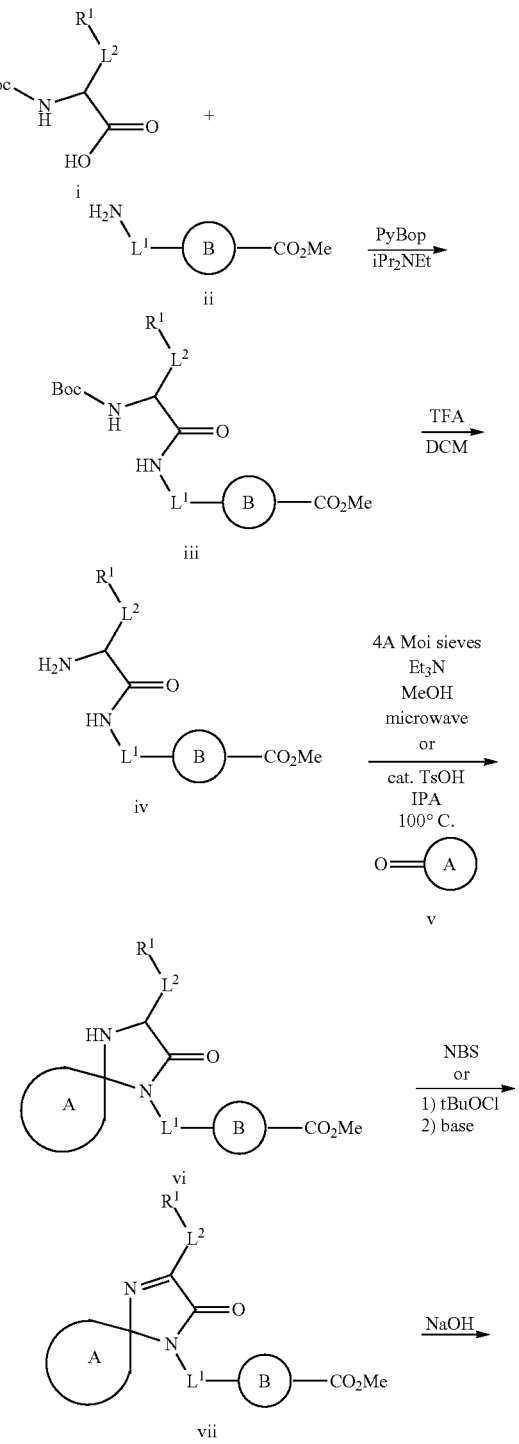

Scheme I

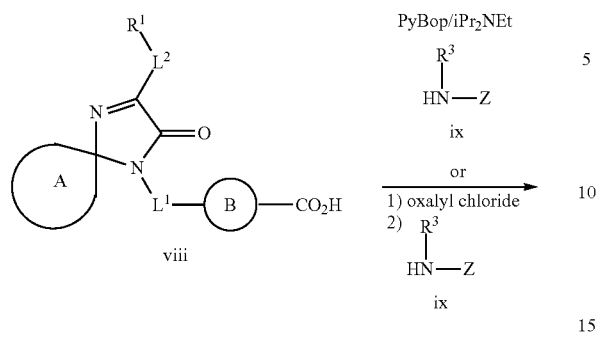

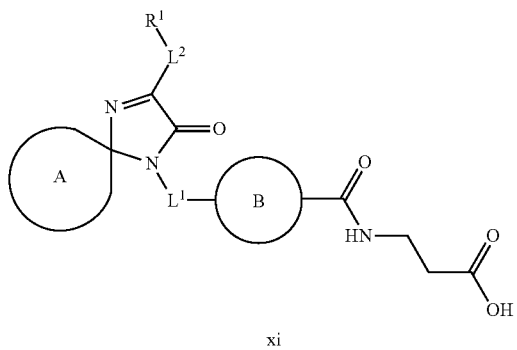

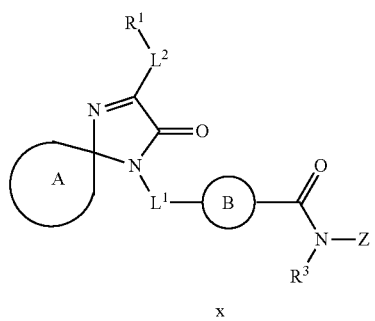

When the HN(R³)Z is an amine containing an additional protected acid moiety (e.g. R³═H, Z═—CH₂CH₂CO₂tert-Butyl xa or R³═H, Z═—CH₂CH₂CO₂Me xb, respectively), the moiety can be deprotected using standards conditions to provide the acid analogs xi.

When HN(R³)Z is 5-amino tetrazole, acids viii will produce amino-tetrazole terminated compounds such as xc using standard amide bond coupling procedures that are known to those skilled in the art.

Scheme III

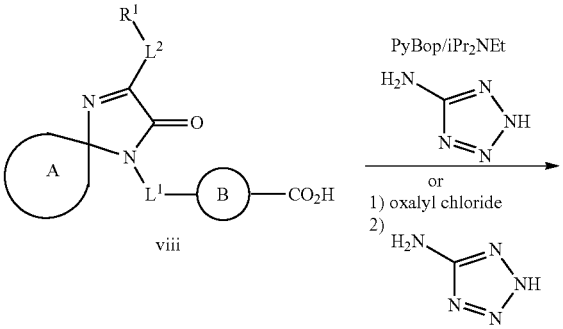

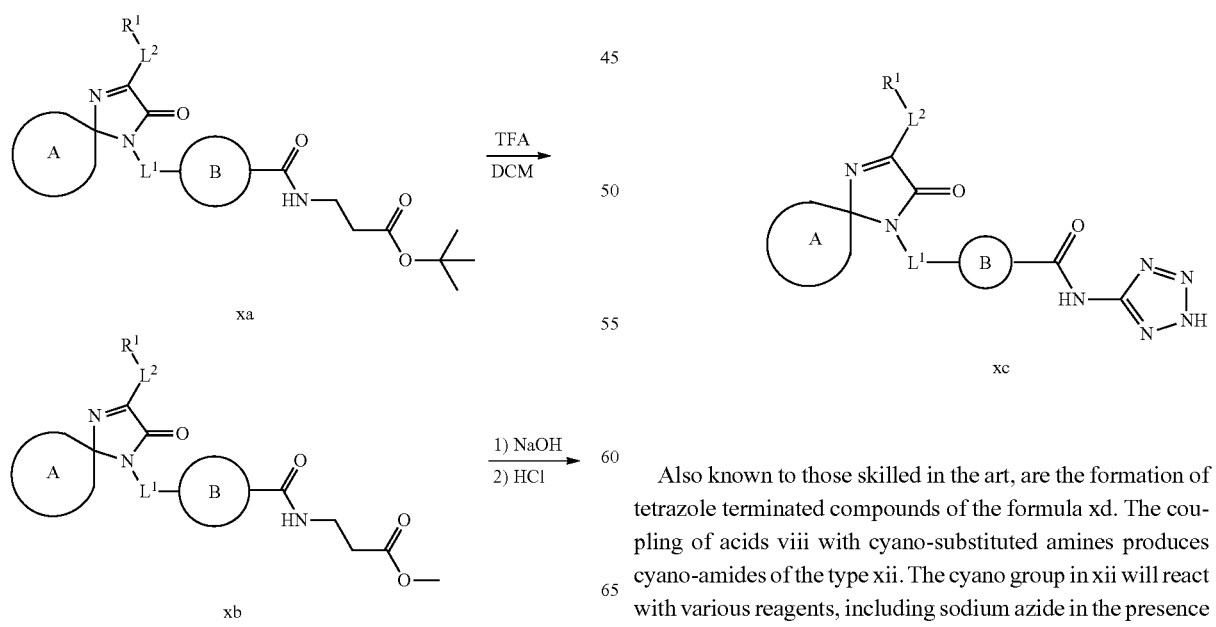

Also known to those skilled in the art, are the formation of tetrazole terminated compounds of the formula xd. The coupling of acids viii with cyano-substituted amines produces cyano-amides of the type xii. The cyano group in xii will react with various reagents, including sodium azide in the presence of an alkyl amine hydrochloride, to provide compounds xd.

Scheme IV

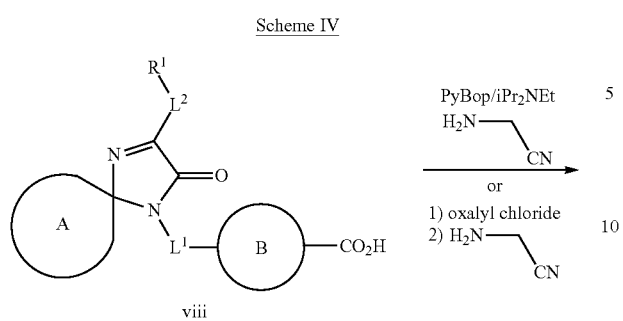

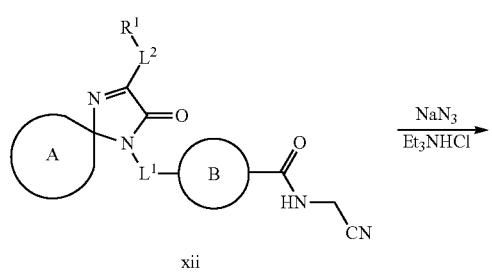

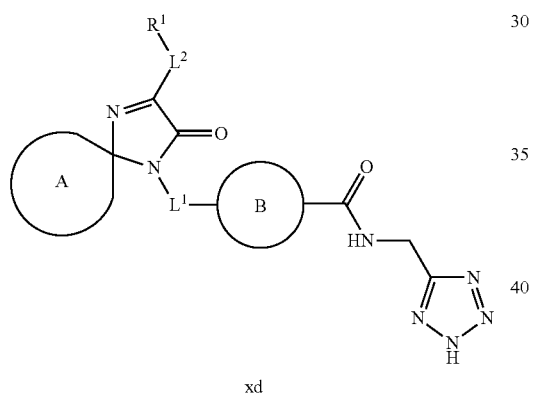

Alternatively, those skilled in the art can utilize the reaction depicted in Scheme V for the formation of tetrazole analogs xd. The coupling reaction of acids viii with amino tetrazoles provides compounds xd using standard amide bond coupling procedures that are known to those skilled in the art.

Scheme V

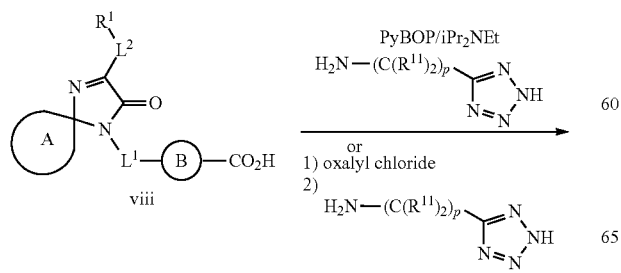

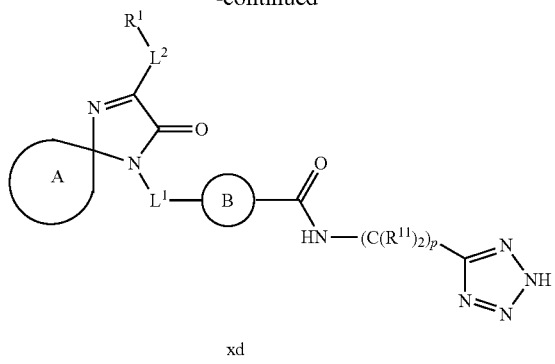

A general approach to enantiomerically enriched amines xvii and xiv is illustrated in Scheme VI. This approach is familiar to one skilled in the art, and numerous examples exist in the literature (for example see: Cogan, D. A.; Liu, G.; Ellman, J. A. *Tetrahedron* 1999, 55, 8883-8904). The condensation of the sulfinamide xiii with aldehydes xiv provides the imines xv. Organometallic reagents (such as grignards: $R^{5A}$MgBr) add to imines xv to provide diastereomeric mixtures of the sulfinamides xvi and xvii. These diastereomers can be purified by crystallization or chiral HPLC methods that are known to those skilled in the art. The pure diastereomers xvi and xvii can be treated with HCl to provide the enantiomerically enriched amine HCl salt xviii and xix, respectively.

Scheme VI

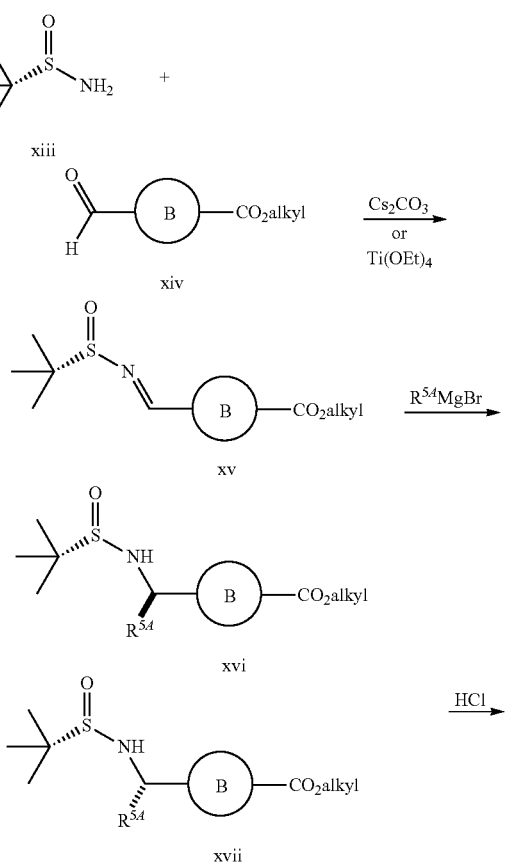

-continued

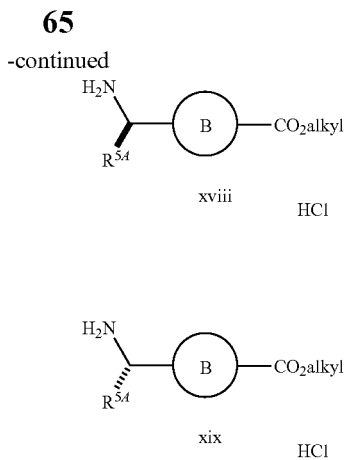

xviii HCl xix HCl

A related approach to these types of enantiomericaly enriched amine HCl salts is illustrated in Scheme VII. The condensation of the sulfinamide xiii with the ketones such as xx provide imines xxi. The imines can be reduced (see Tanuwidjaja, J.; Peltier, H. M.; Ellman, J. A. *J. Org. Chem.* 2007, 72, 626) with various reducing reagents to provide sulfinamides such as xvi and xvii. As previously, these can be treated with HCl to provide the enantiomerically enriched amine HCl salts xviii and xix.

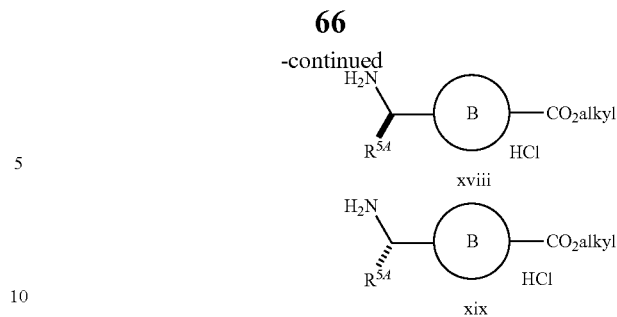

xviii HCl xix HCl

The N—BOC glycine xxii can be processed heterocycles such as xxvi using previously described procedures. The heterocycles can be treated with m-CPBA to provide the hydroxy intermediates xxvii. The hydroxy intermediates xxvii can be converted into the corresponding triflate intermediates xxviii. The triflate intermediates xxviii can be converted into the arylated analogs xxix using standard palladium catalyzed chemistry that is known by those skilled in the art. Further transformation of the arylated intermediates xxix into the desired compounds has previously been described.

Scheme VII

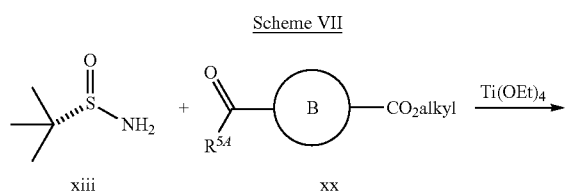

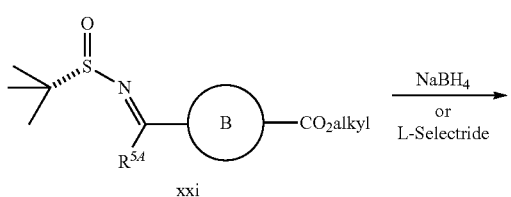

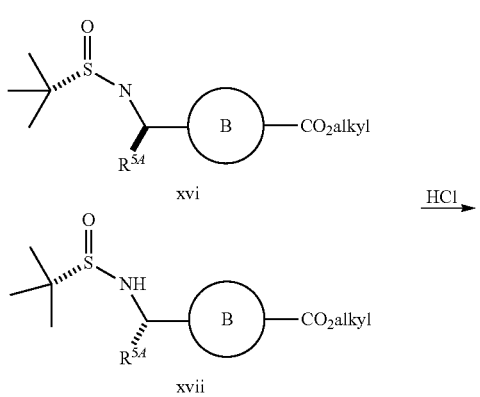

Scheme VIII

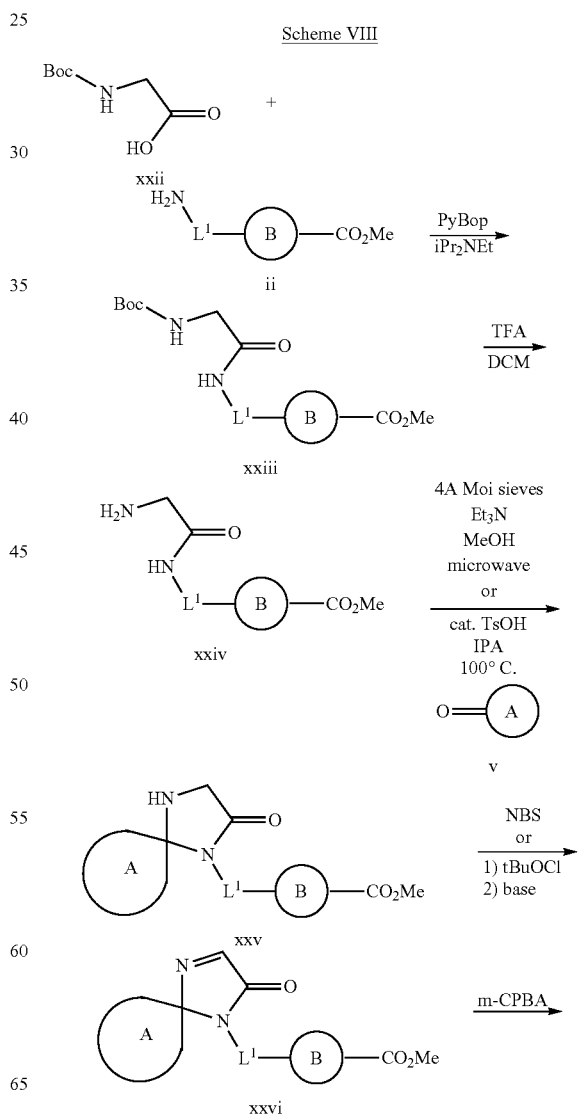

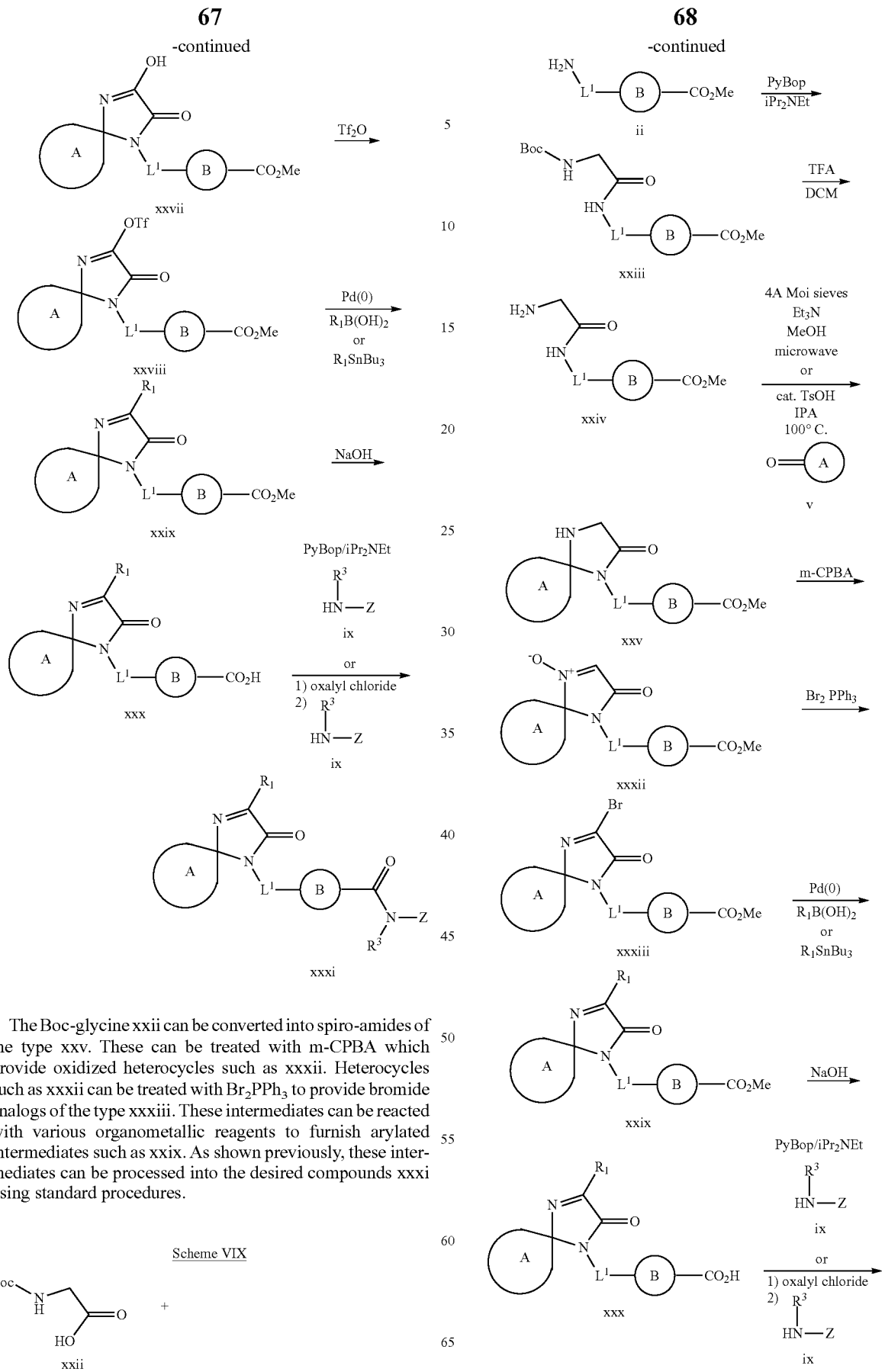

The Boc-glycine xxii can be converted into spiro-amides of the type xxv. These can be treated with m-CPBA which provide oxidized heterocycles such as xxxii. Heterocycles such as xxxii can be treated with $Br_2PPh_3$ to provide bromide analogs of the type xxxiii. These intermediates can be reacted with various organometallic reagents to furnish arylated intermediates such as xxix. As shown previously, these intermediates can be processed into the desired compounds xxxi using standard procedures.

Scheme VIX

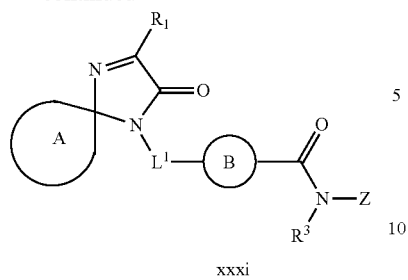
xxxi
Procedures/Examples
Scheme A
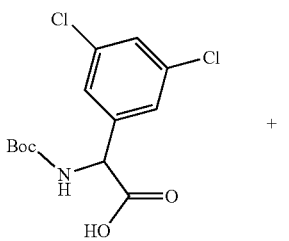
+
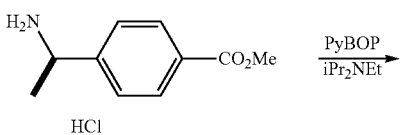
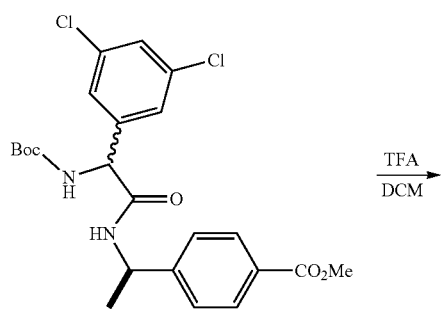
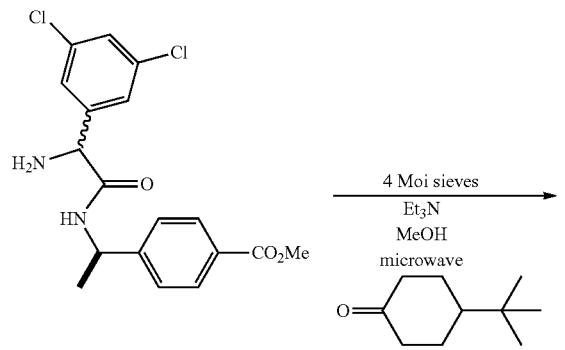
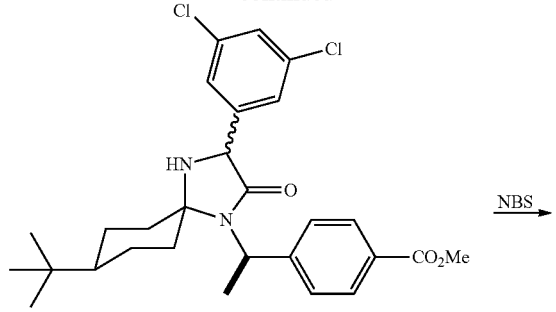
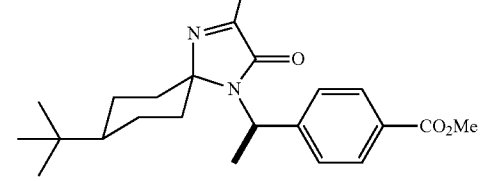
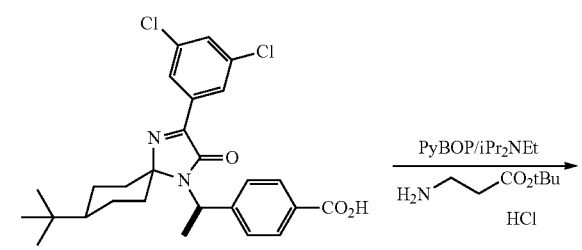
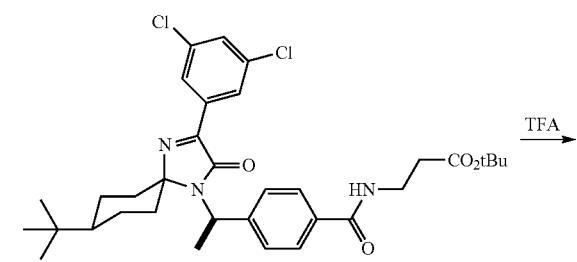
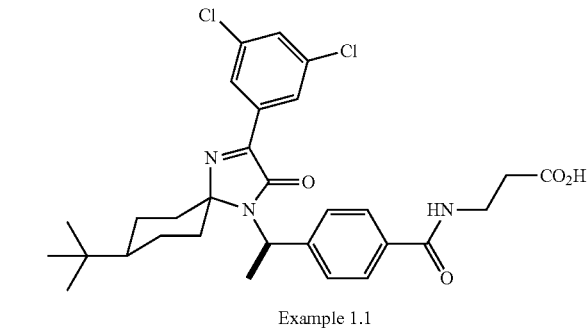
Example 1.1

Step 1

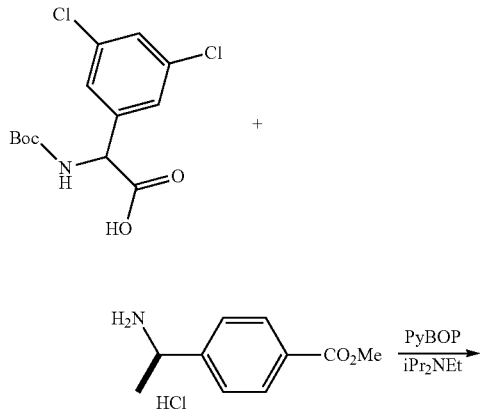

+

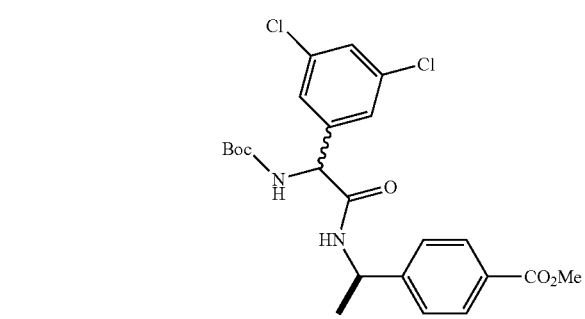

Racemic 2-(tert-butoxycarbonylamino)-2-(3,5-dichlorophenyl)acetic acid (1.64 g, 5.1 mmol), (R)-methyl 4-(1-aminoethyl)benzoate HCl (1.0 g, 4.65 mmol), PyBOP (2.66 g, 5.1 mmol), and iPr₂NEt (2.4 mL) were taken up in CH₃CN (35 mL), and the solution was stirred at room temperature for 18 hours. The solution was concentrated, and the residue was partitioned between EtOAc and sat. NaHCO₃₍aq.₎. The aqueous layer was extracted with EtOAc, and the combined organic layers were dried over MgSO₄. The mixture was filtered and concentrated which provided a yellow oil. The residue was purified by gradient flash chromatography (Analogix, 0 to 60% EtOAc in hexanes, SiO₂) gave 2.2 grams (100%) of the amide as a white solid.

Step 2

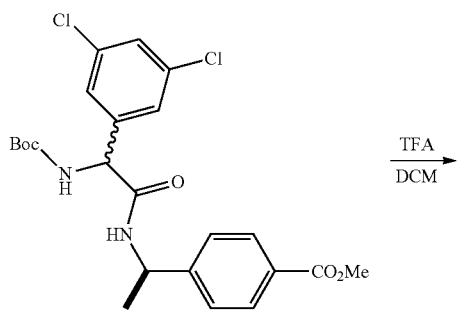

The product from Step 1 (2.2 g, 4.5 mmol) was taken up in DCM (35 mL), and TFA (10 mL) was added at room temperature. The solution was stirred at room temperature for 18 hours. The solution was concentrated, and the residue was partitioned between DCM and 1 N NaOH₍aq.₎. The aqueous layer was extracted with DCM. The combined organic layers were dried (MgSO₄), filtered and concentrated which furnished 1.6 g (94%) of the amine as a colorless oil.

Step 3

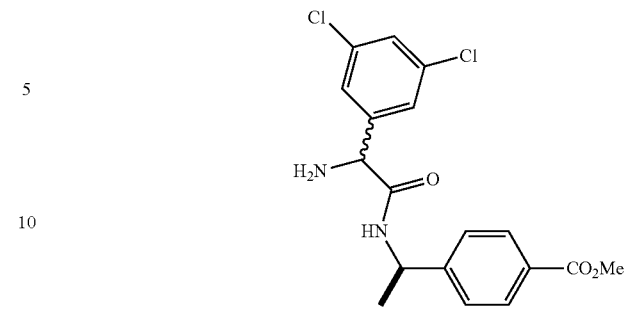

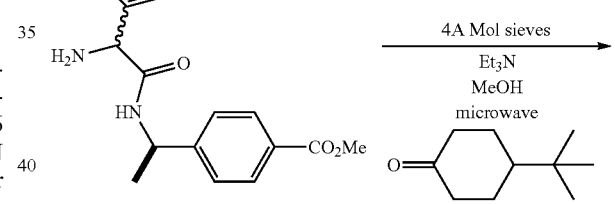

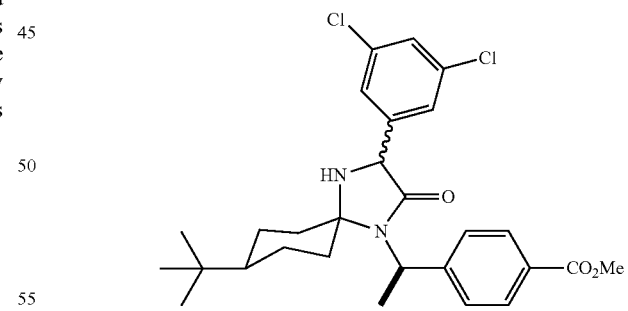

The product from Step 2 (890 mg, 2.3 mmol), 4-tert-butyl-cyclohexanone (719 mg, 4.6 mmol), 4 Å mol sieves (900 mg), and Et₃N (0.65 mL) were taken up in MeOH (12 mL). The mixture was heated in a microwave (130° C., 2 h). The mixture was filtered, and the solution was concentrated. The residue was purified via gradient flash chromatography (Analogix®, 0-35% EtOAc in hexanes, SiO₂) which furnished 570 mg (48%) of the spiro-amine as a colorless oil.

Step 4

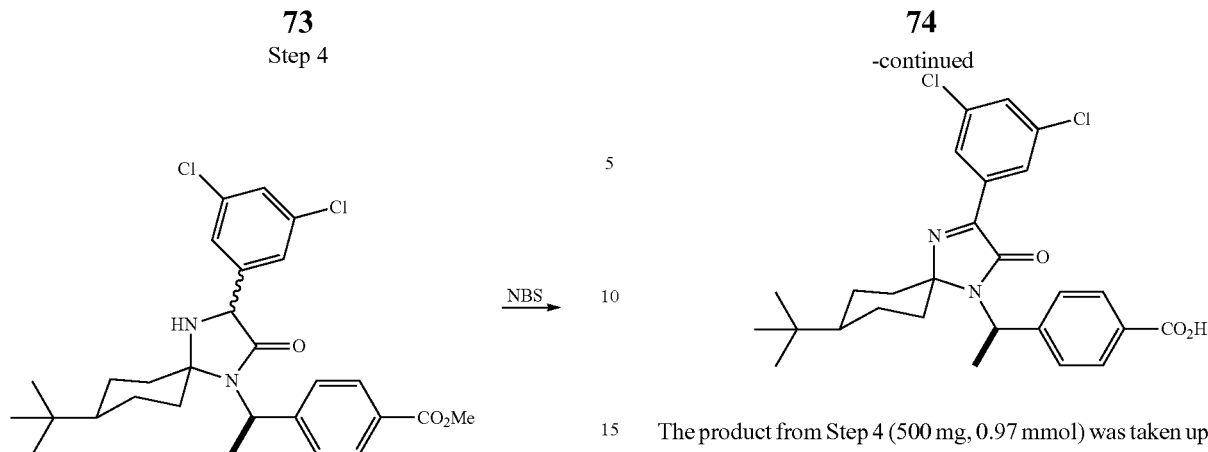

The product from Step 3 (570 mg, 1.1 mmol) was taken up in DCM (35 mL), and N-bromosuccinimide (196 mg, 2.2 mmol) were added to the solution at room temperature. After the solution was stirred at room temperature for 5 hours, the solution was partitioned between 10% NaHSO$_3$(aq.). The aqueous layer was extracted with DCM. The combined organic layers were dried (MgSO$_4$), filtered, and concentrated which gave a yellow oil. The residue was purified via gradient flash chromatography (Analogix, 0-15% EtOAc in hexanes, SiO$_2$) which furnished 500 mg (88%) of the imidazolone as a colorless oil.

Step 5

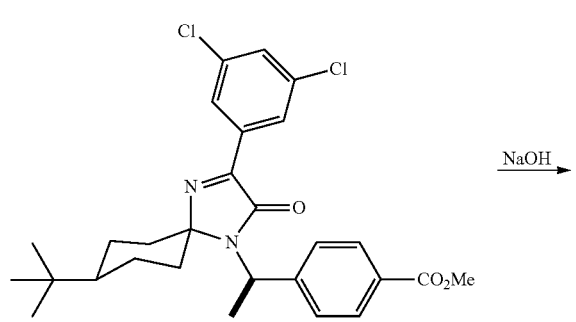

-continued

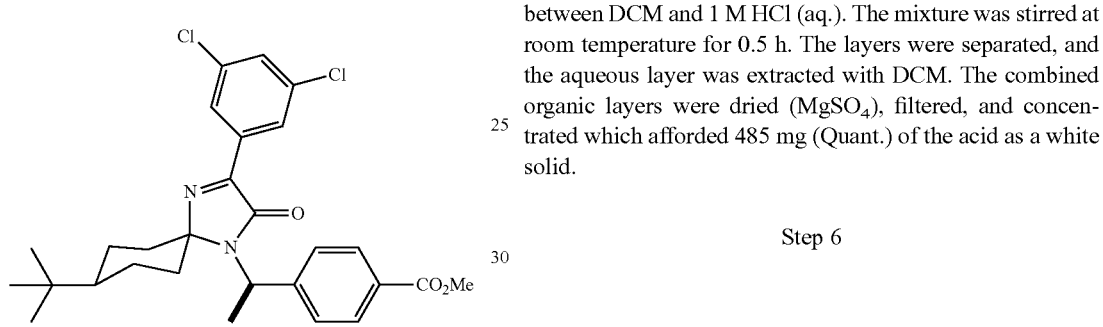

The product from Step 4 (500 mg, 0.97 mmol) was taken up in 1 N NaOH$_{(aq.)}$/dioxane/MeOH (1/1/1, 90 ml total), and the solution was heated at 65° C. for 5 hours. The solution was cooled and stirred at room temperature for 16 hours. The solution was concentrated. The residue was partitioned between DCM and 1 M HCl (aq.). The mixture was stirred at room temperature for 0.5 h. The layers were separated, and the aqueous layer was extracted with DCM. The combined organic layers were dried (MgSO$_4$), filtered, and concentrated which afforded 485 mg (Quant.) of the acid as a white solid.

Step 6

The product from Step 5 (200 mg, 0.40 mmol), PyBOP (311 mg, 0.60 mmol), iPr$_2$NEt (0.2 mL), and β-alanine, tert-butyl ester HCl salt (109 mg, 0.60 mmol) were taken up in CH$_3$CN (20 mL), and the solution was stirred at room temperature for 18 hours. The solution was concentrated, and the residue was partitioned between EtOAc and sat. NaHCO$_{3(aq)}$. The aqueous layer was extracted with EtOAc. The combined organic layers were washed with brine and dried (MgSO$_4$). Filtration and concentration provided a yellow oil. The residue was purified via thin-layer preparative chromatography (2/1 hexanes/EtOAc, SiO$_2$) which provided 170 mg (67%) of the tert-butyl ester as a colorless oil.

75
Step 7
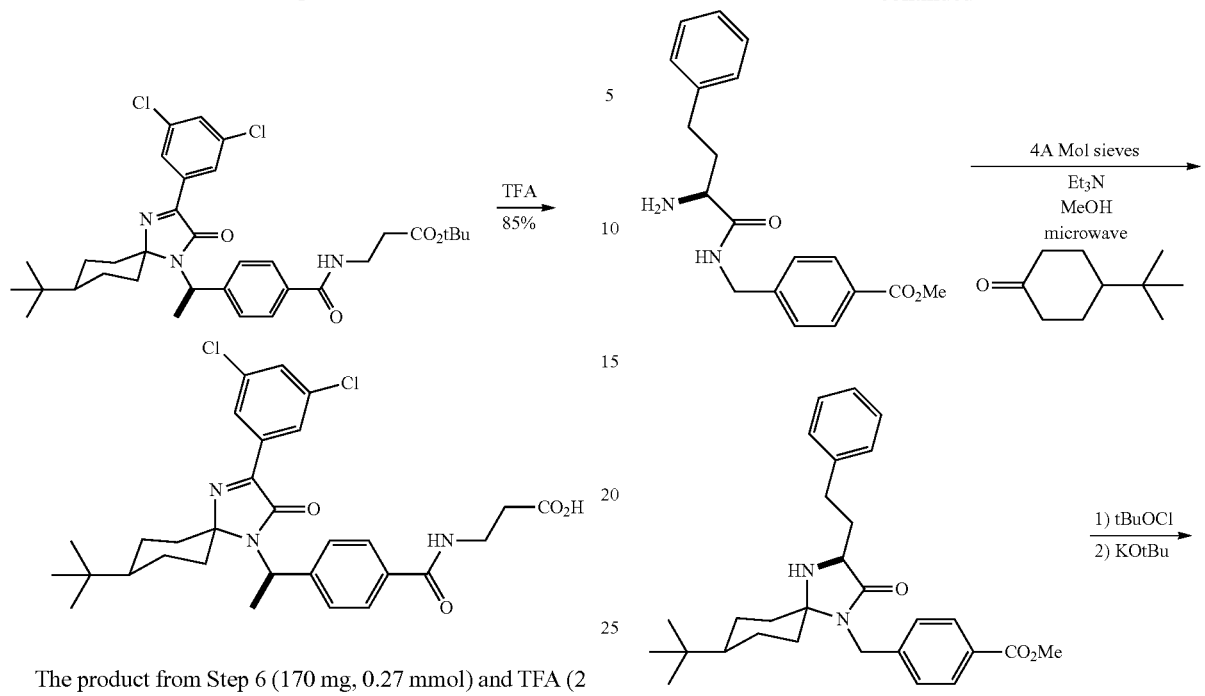
The product from Step 6 (170 mg, 0.27 mmol) and TFA (2 mL) were taken up in DCM (15 mL), and the solution was stirred at room temperature for 18 hours. The solution was concentrated and dried under high vacuum which provided 132 mg (85%) of Example 1.1 as an off-white solid. LC/MS ret. time (6.4 min); (MH)$^+$ 572. HRMS calc'd for $C_{30}H_{35}Cl_2N_3NaO_2$ (M+Na)$^+$ 594.1902; found 594.1926.
Scheme B
76
-continued
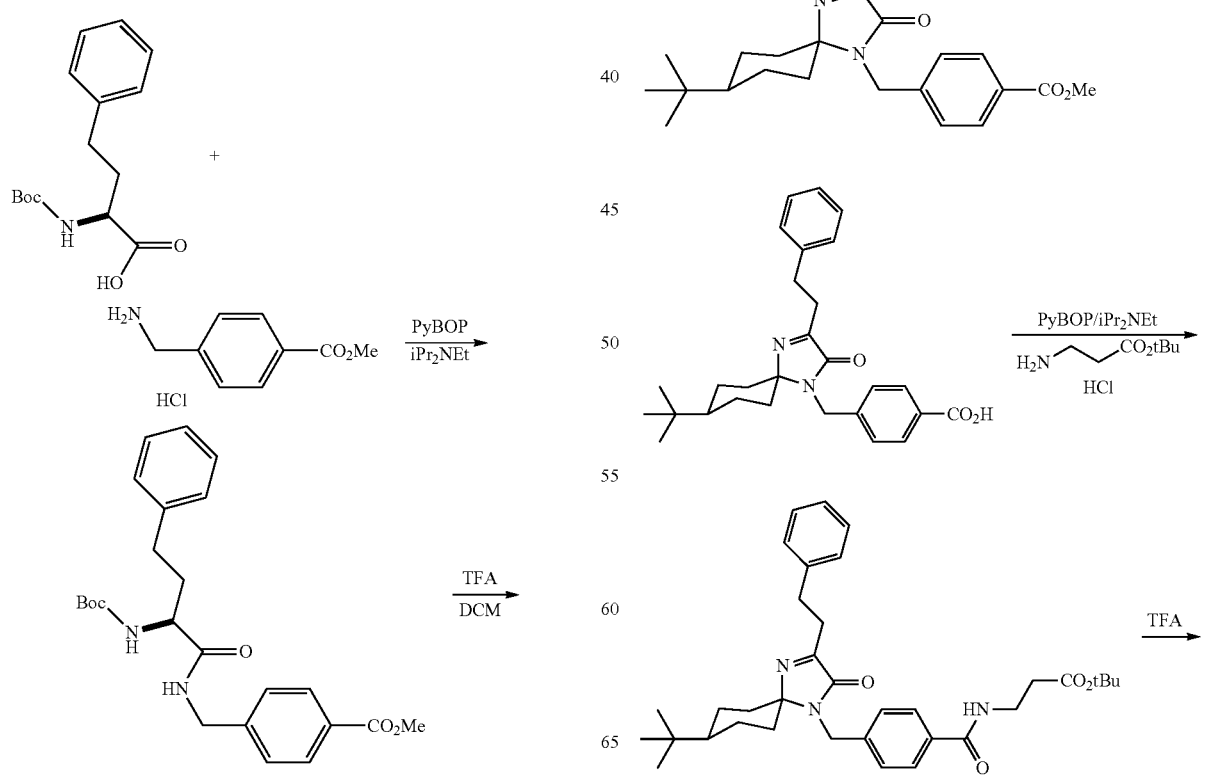

77
-continued

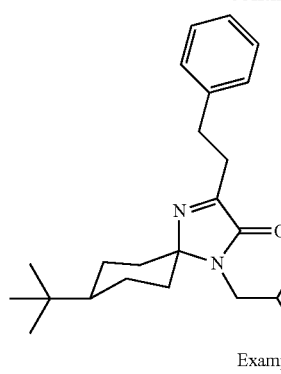

Example 1.2

Step 1

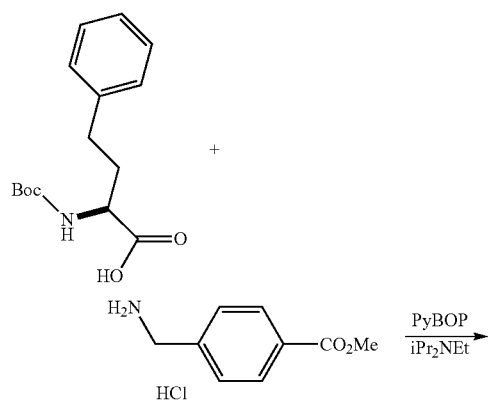

(S)-Boc-homo-phenyl alanine (3.0 g, 10.7 mmol), PyBOP (6.1 g, 11.8 mmol), iPr₂NEt (5.6 mL), and methyl 4-(aminomethyl)benzoate HCl (2.4 g, 11.8 mmol) were reacted according to the procedure outlined in Step 1 of Scheme A to afford 4.5 g (98%) of the amide a colorless foam.

78
Step 2

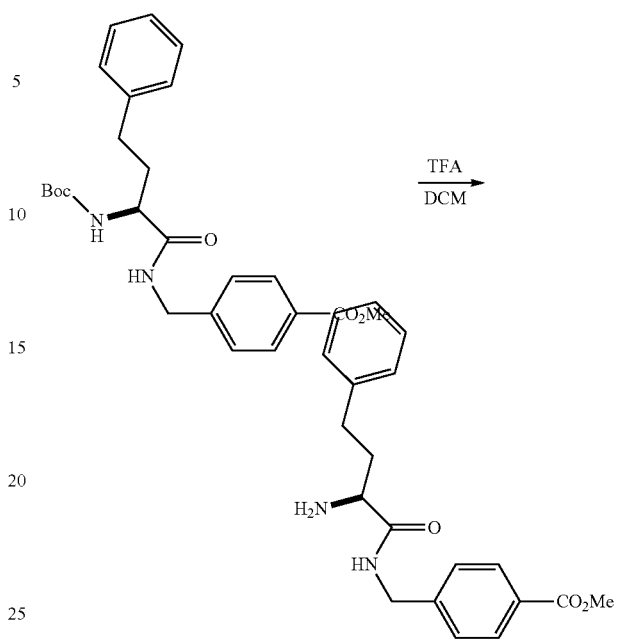

The product from Step 1 (4.53 g, 10.6 mmol) and 20 mL of TFA were reacted according to the procedure outlined in Step 2 of Scheme A to afford 3.25 g (93%) of the amine as a white solid.

Step 3

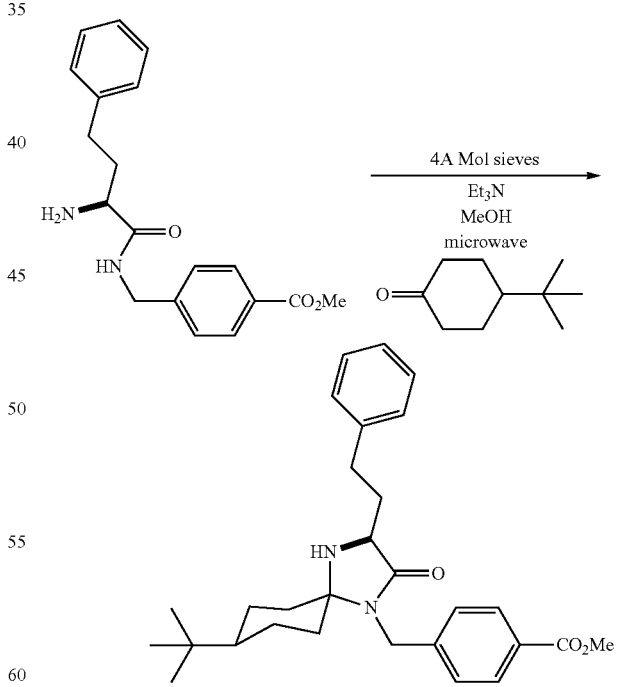

The product from Step 2 (2.5 g, 7.7 mmol), 4-tert-butyl cyclohexanone (2.4 g, 15.3 mmol), 4 Å mol sieves (2.5 g), and Et₃N (2.1 mL) were reacted according to the procedure outlined in Step 3 of Scheme A to afford 3.3 grams (94%) of the spiro-amine as a white solid.

Step 4

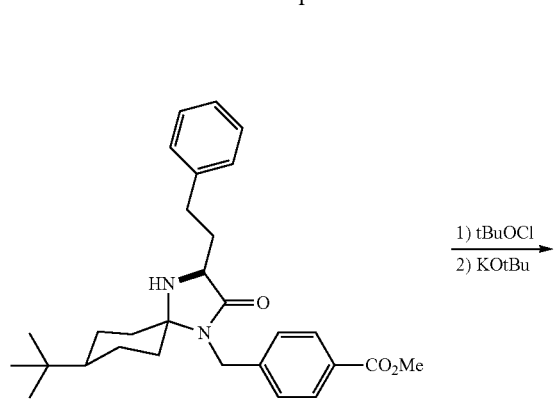

The product from Step 3 (500 mg, 1.2 mmol) was taken up in dioxane (15 mL), and the solution was cooled to 0° C. tert-Butyl hypochlorite (0.2 mL) was added, and the solution was warmed to room temperature. After the solution had stirred at room temperature for 30 minutes, potassium tert-butoxide (300 mg) was added. The resulting mixture was stirred at room temperature for 2 hours. The mixture was partitioned between EtOAc and sat. $NH_4Cl_{(aq.)}$. The aqueous layer was extracted with EtOAc, and the combined organic layers were washed with 10% $Na_2S_2O_{3(aq.)}$. The combined organic layers were dried ($MgSO_4$), filtered, and concentrated. The residue was purified via gradient flash chromatography (Analogix, 0-15% EtOAc in hexanes, $SiO_2$) which afforded 310 mg (56%) of the imidazolone as a colorless oil.

Step 5

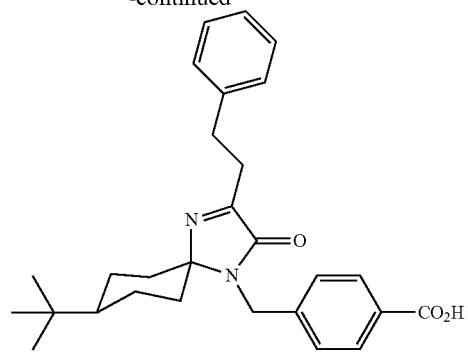

The product from Step 4 (310 mg, 0.67 mmol) was reacted according to the procedure outlined in Step 5 of Scheme A to afford 300 mg (Quant.) of the acid as a yellow solid.

Step 6

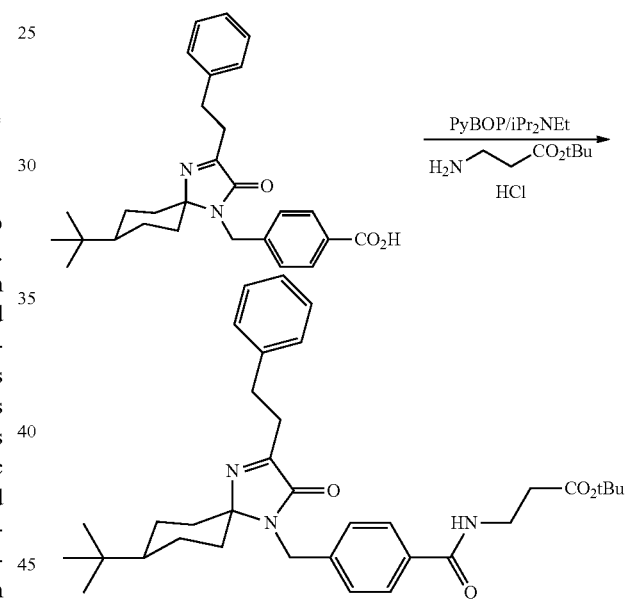

The product from Step 5 (300 mg, 0.67 mmol) was reacted according to the procedure outlined in Step 6 of Scheme A to afford 300 mg (78%) of the tert-butyl ester as a colorless oil.

Step 7

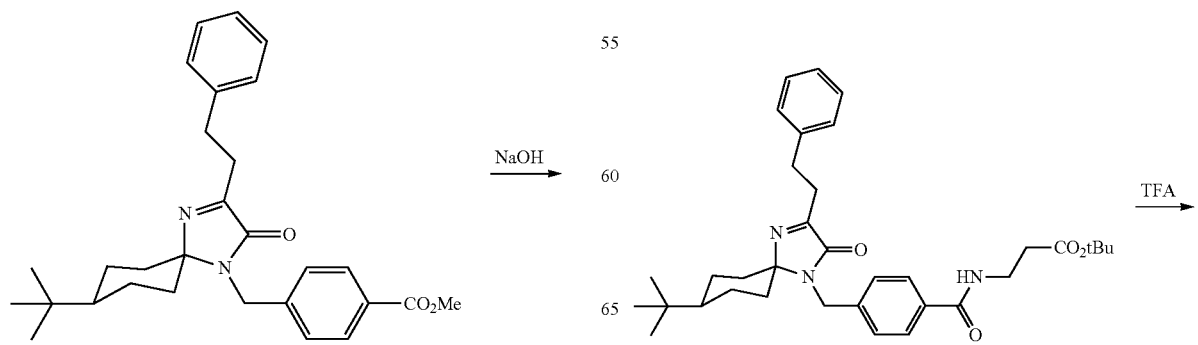

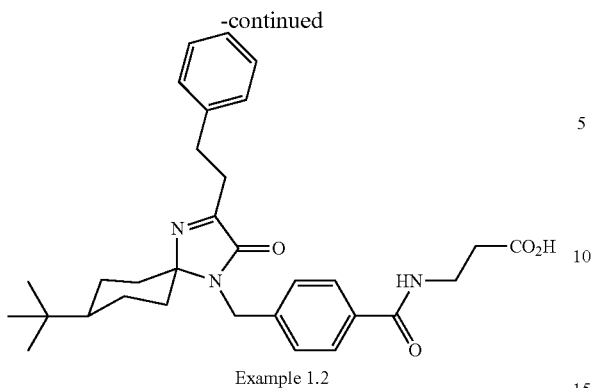

Example 1.2

The product from Step 6 (300 mg, 0.52 mmol) was reacted according to the procedure outlined in Step 7 of Scheme A to afford 87 mg (32%) of Example 1.2 as a white solid. LC/MS ret. time (4.9 min); (MH)$^+$ 516.

Scheme C

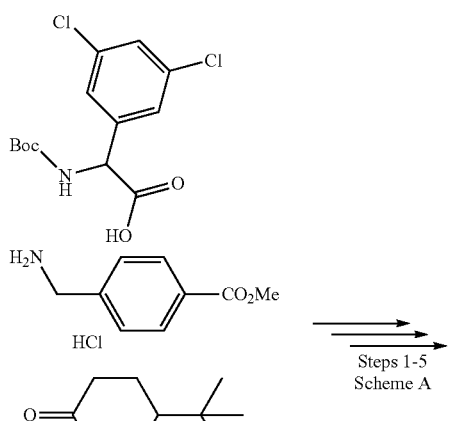

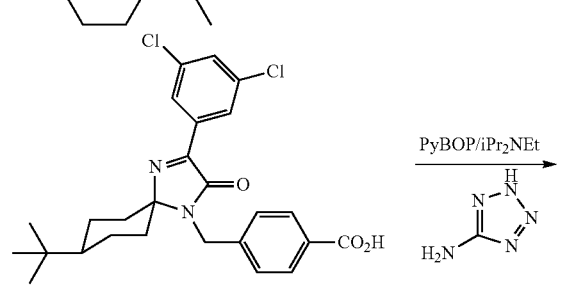

Example 1.3

The benzoic acid in Scheme C was prepared according to the procedure outlined in Scheme A (Steps 1-5) using the amino acid, ketone, and amine. The benzoic acid (65 mg, 0.13 mmol), PyBOP (83 mg, 0.16 mmol), iPr$_2$NEt (0.1 mL), and aminotetrazole hydrate (20 mg) were taken up in CH$_3$CN (10 mL). The solution was heated to 80° C. until everything had dissolved. The solution was stirred at room temperature (18 hours). The formed solid was collected and washed with Et$_2$O which provided 24 mg (33%) of Example 1.3 as a white solid. LC/MS ret. time (6.0 min); (MH)$^+$ 554. HRMS calc'd for C$_{27}$H$_{29}$Cl$_2$N$_3$NaO$_2$ (M+Na)$^+$ 576.1658; found 576.1642.

Scheme D

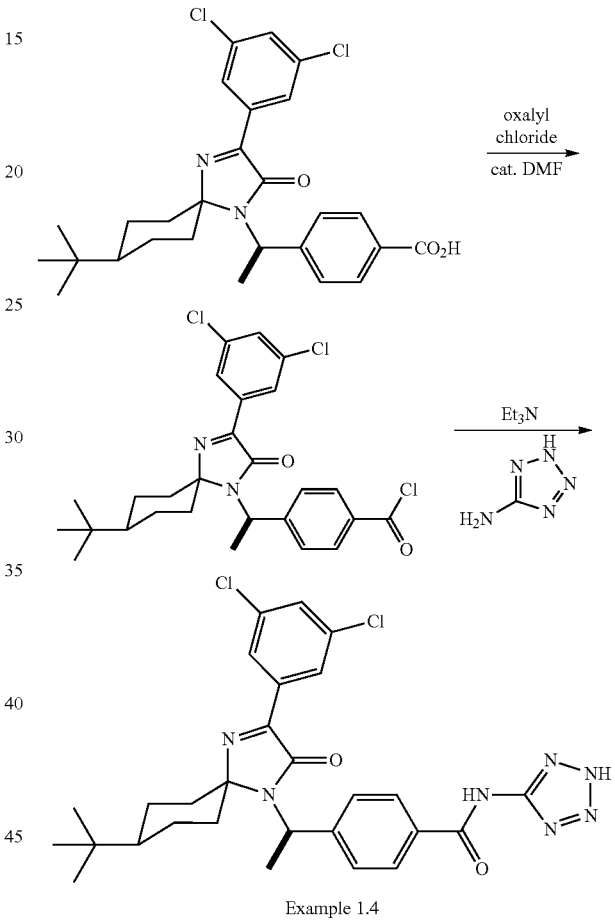

Example 1.4

Step 1

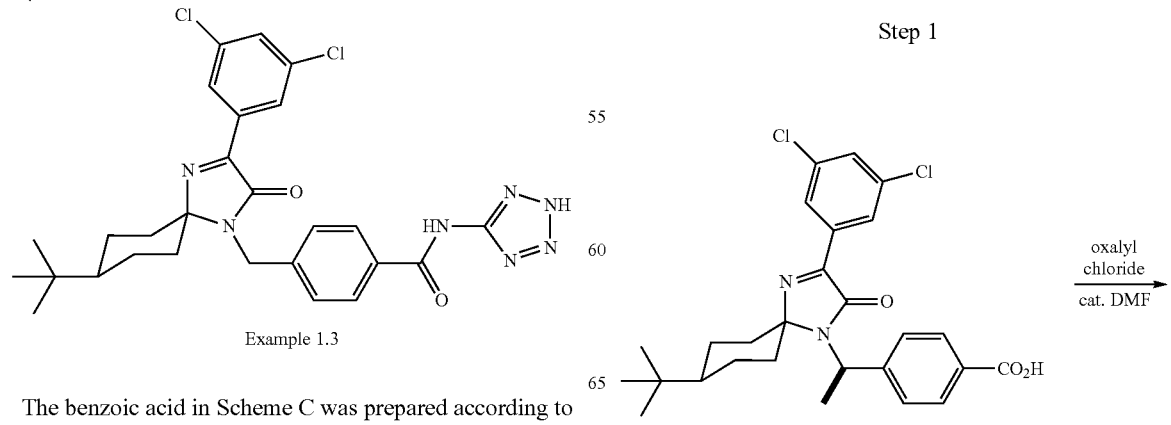

-continued

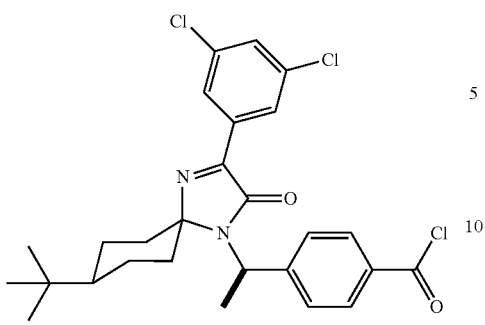

The benzoic acid (Product of Step 5, Scheme A; 150 mg, 0.30 mmol) was suspended in DCM (20 mL). Oxalyl chloride (113 mg) was added followed by two drops of DMF, and the solution was stirred at room temperature for 20 minutes. More oxalyl chloride (113 mg) was added, and after an additional 30 minutes at room temperature, the solution was concentrated. The acid chloride was used directly in the next step.

Step 2

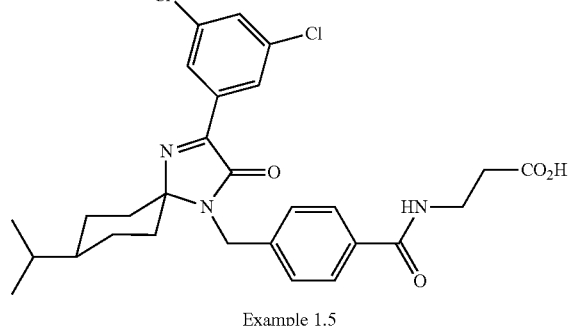

Example 1.4

The acid chloride from Step 1 and $Et_3N$ (100 mg) were taken up in DCM (20 mL), and aminotetrazole hydrate (30 mg) was added to the solution. After stirring at room temperature for 2 hours, the solution was washed with sat. $NaHCO_{3(aq.)}$. The aqueous layer was extracted with DCM. The combined organic layers were dried ($MgSO_4$), filtered, and concentrated. The residue was purified via preparative thin-layer chromatography (16% MeOH in DCM, $SiO_2$) which gave 81 mg (48%) of Example 1.4 as a white solid. LC/MS ret. time (6.2 min); $(MH)^+$ 568.

Scheme E

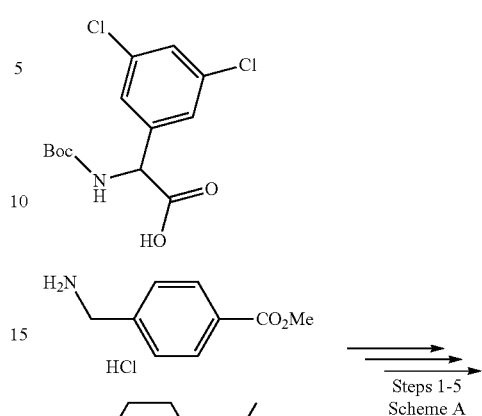

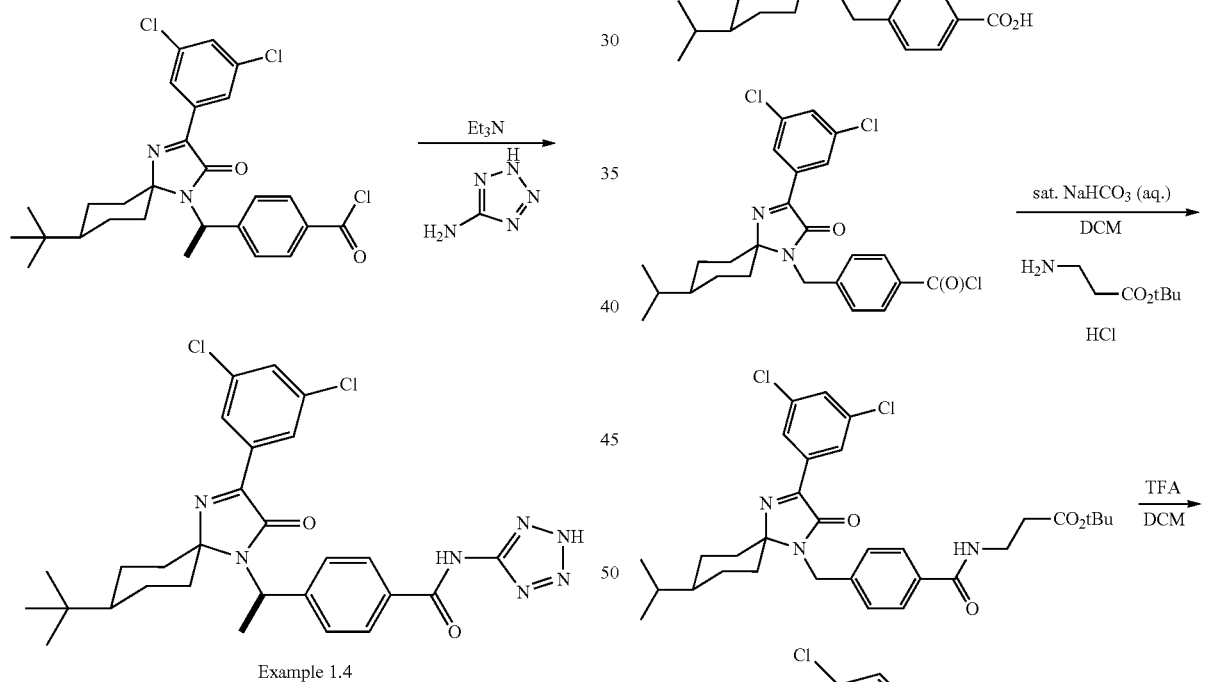

Example 1.5

Step 1

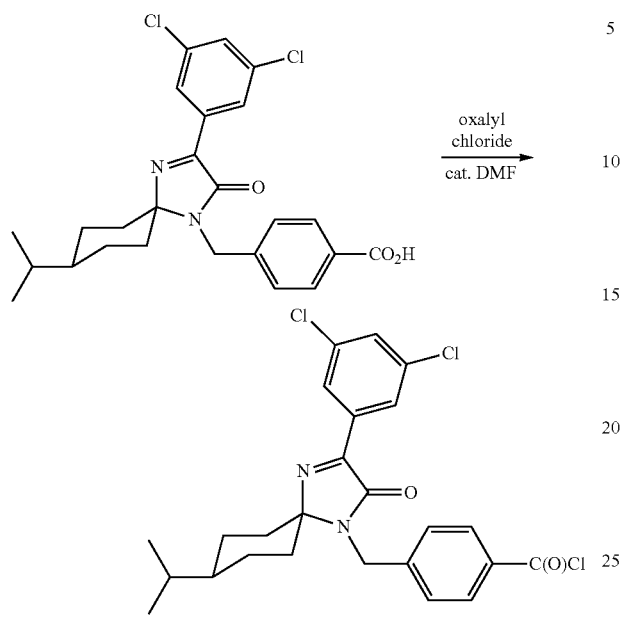

The benzoic acid in Scheme E was prepared according to the procedure outlined in Scheme A (Steps 1-5) using the requisite amino acid, ketone, and amine. The benzoic acid (200 mg, 0.42 mmol) was suspended in DCM (35 mL). Oxalyl chloride (0.1 mL) followed by 3-4 drops of DMF was added. The solution was stirred at room temperature for 2.5 hours. The solution was concentrated. The crude acid chloride was used without further purification.

Step 2

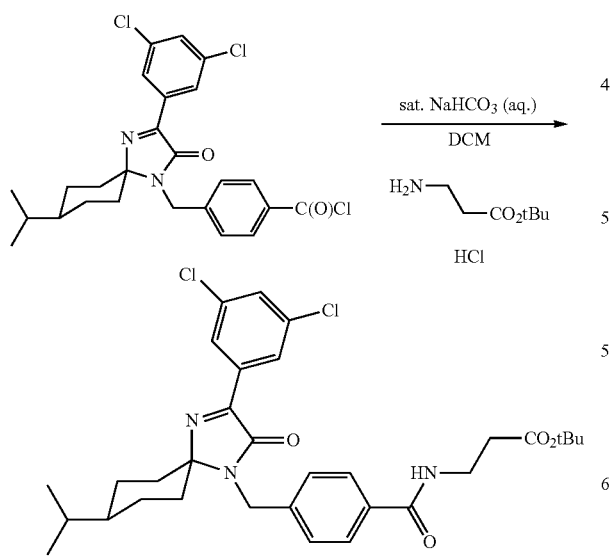

The acid chloride from Step 1, was partitioned between DCM and sat. NaHCO$_{3(aq.)}$. The β-alanine tert-butyl ester HCl salt (115 mg, 0.63 mmol) was added, and the mixture was stirred at room temperature for 2 hours. The layers were separated, and the aqueous layer was extracted with DCM. The combined organic layers were dried (MgSO$_4$), filtered, and concentrated. The residue was purified via gradient flash chromatography (Analogix, 0-35% EtOAc in hexanes, SiO$_2$) which afforded 194 mg (77%) of the tert-butyl ester as a colorless foam.

Step 3

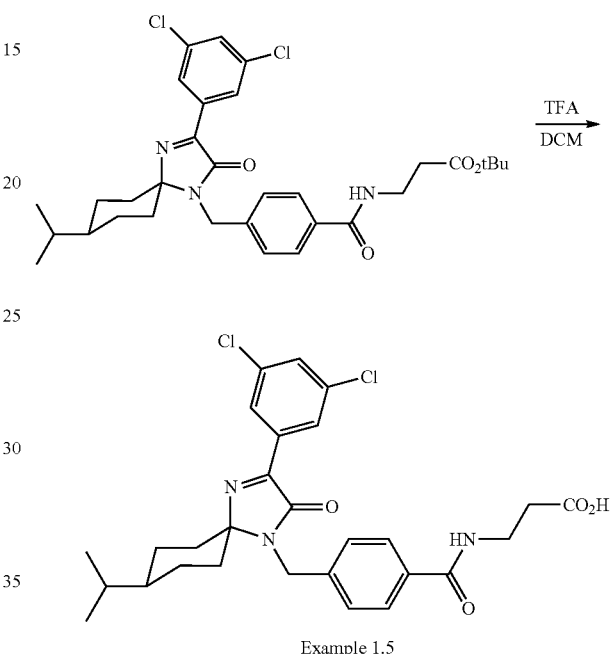

Example 1.5

The tert-butyl ester (194 mg, 0.32 mmol) was reacted according to the procedure outlined in Step 7 of Scheme A which afforded 124 mg (71%) of Example 1.5. LC/MS ret. time (5.8 min); (MH)$^+$ 544.

Scheme F

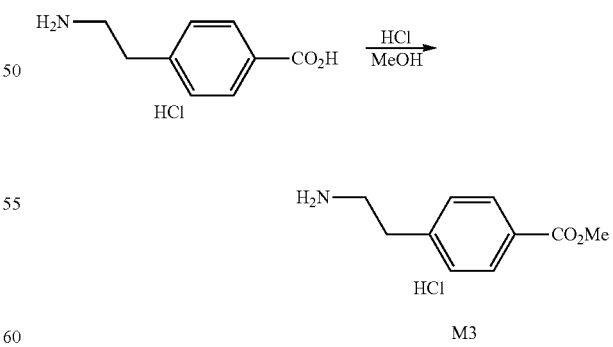

M3

4-(2-Aminoethyl)benzoic acid HCl (20 g, 99 mmol) and 4 M HCl in dioxane (20 mL) were taken up in MeOH (200 mL) and heated at 85° C. for 24 hours. The solution was cooled to room temperature at which time a solid precipitated. The solid was collected. The mother liquor was concentrated to afford a solid that was washed with Et₂O. The two crops were combined to afford 20 g (94%) of the methyl ester HCl salt as a white solid.

Scheme G

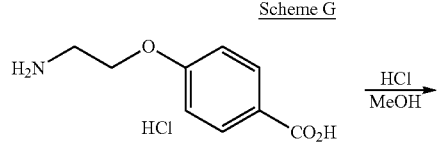

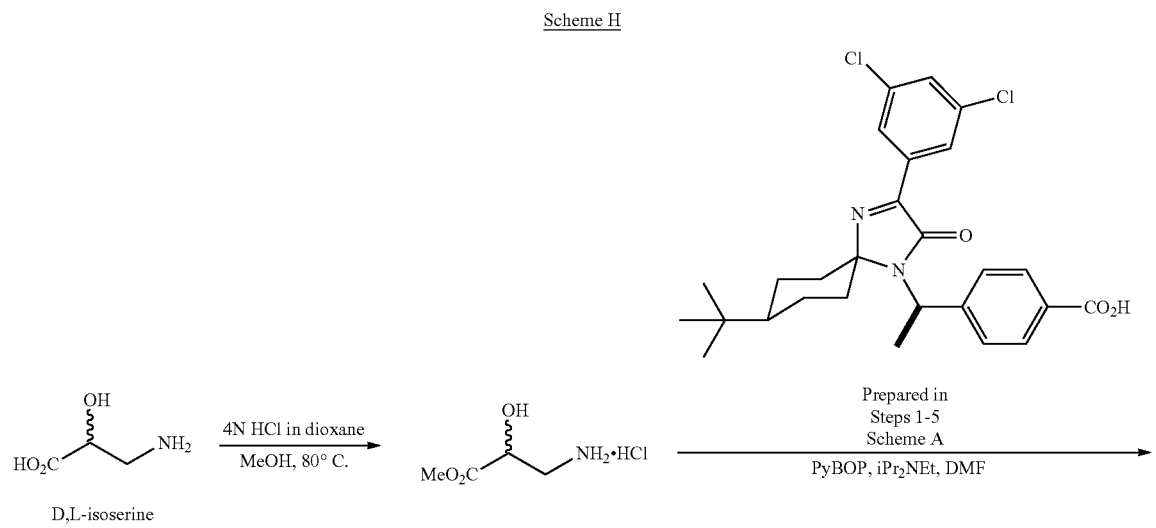

4-(2-Aminoethoxy)benzoic acid HCl salt (1.5 g, 6.9 mmol) was taken up in MeOH (75 mL) and 4 M HCl in dioxane (15 mL). The solution was heated at 70° C. for 18 hours. The solution was concentrated which provided a yellow solid. This material was used without further purification.

Scheme H

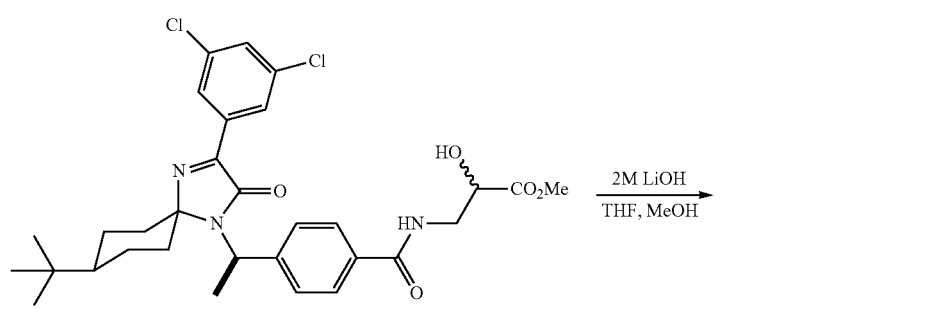

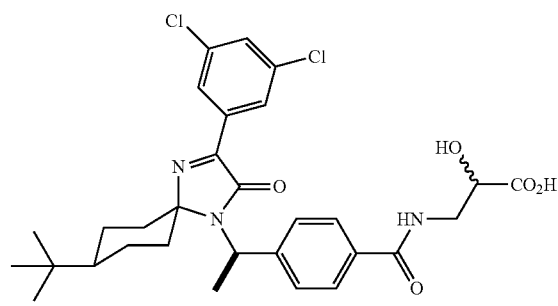

Example 1.6

Step 1

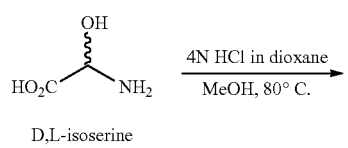

A solution of D,L-isoserine (1 g, 9.52 mmol), MeOH (20 mL) and 4N HCl in dioxane (20 mL) in a round bottomed flask with a reflux condenser attached was heated 3 h in an 80° C. oil bath. The reaction mixture was then cooled and evaporated to afford the desired methyl ester hydrochloride salt as an oil which was used without further purification.

Step 2

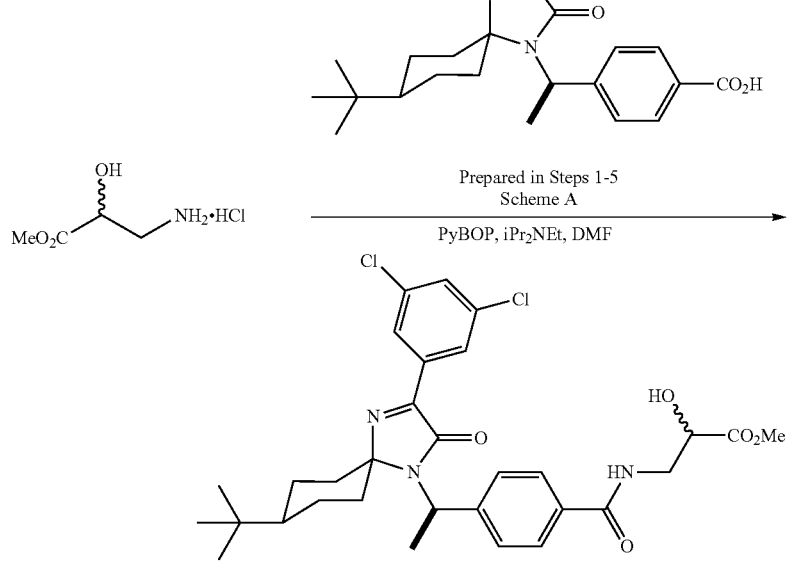

A solution of the methyl ester prepared in Step 1 (62 mg, 0.40 mmol, 1 eq), the benzoic acid prepared in Scheme A, steps 1-5 (200 mg, 0.40 mmol, 1 eq), PyBOP (208 mg, 0.40 mmol, 1 eq) and iPr$_2$NEt (0.28 mL, 1.60 mmol, 4 eq) in DMF (3 mL) was stirred 16 h at room temperature. The reaction was then partitioned between EtOAc and brine diluted with aqueous HCl. After discarding the aqueous layer, the organic layer was washed successively with brine, saturated NaHCO$_3$ $_{(aq)}$, and again with brine. The organic layer was dried over anhydrous sodium sulfate, filtered, and evaporated to afford a crude residue which was purified via silica gel chromatography (gradient elution 10% to 100% EtOAc in hexanes, SiO$_2$) to afford the desired product (188 mg, 78%) as a 1:1 mixture of diastereomers.

Step 3

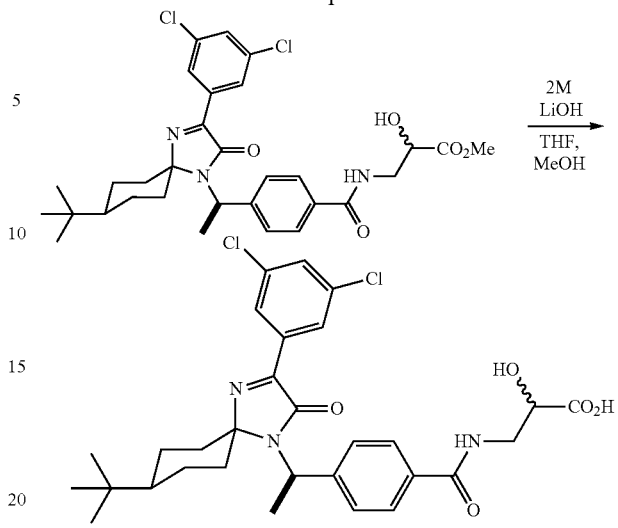

A solution of the coupling product from Step 2 (188 mg, 0.31 mmol, 1 eq) in MeOH (1.5 mL) and THF (3 mL) was treated with 2M LiOH$_{(aq)}$ (1.5 mL, 3 mmol, 10 eq) and stirred at room temperature. Upon completion of the reaction (2 h), the reaction was acidified with 4N HCl in dioxane and evaporated. The white solid was suspended in water with 0.1% formic acid and stirred for 16 h at room temperature. The suspension was transferred to a polypropylene tube, centrifuged, and the liquid decanted. The solid was then re-suspended in water with 0.1% formic acid, centrifuged, and decanted again. Dissolution of the wet solid in THF was followed by transfer to a round bottomed flask and concentration in vacuo to afford Example 1.6 as a white foam (111 mg, 61%).

Scheme I
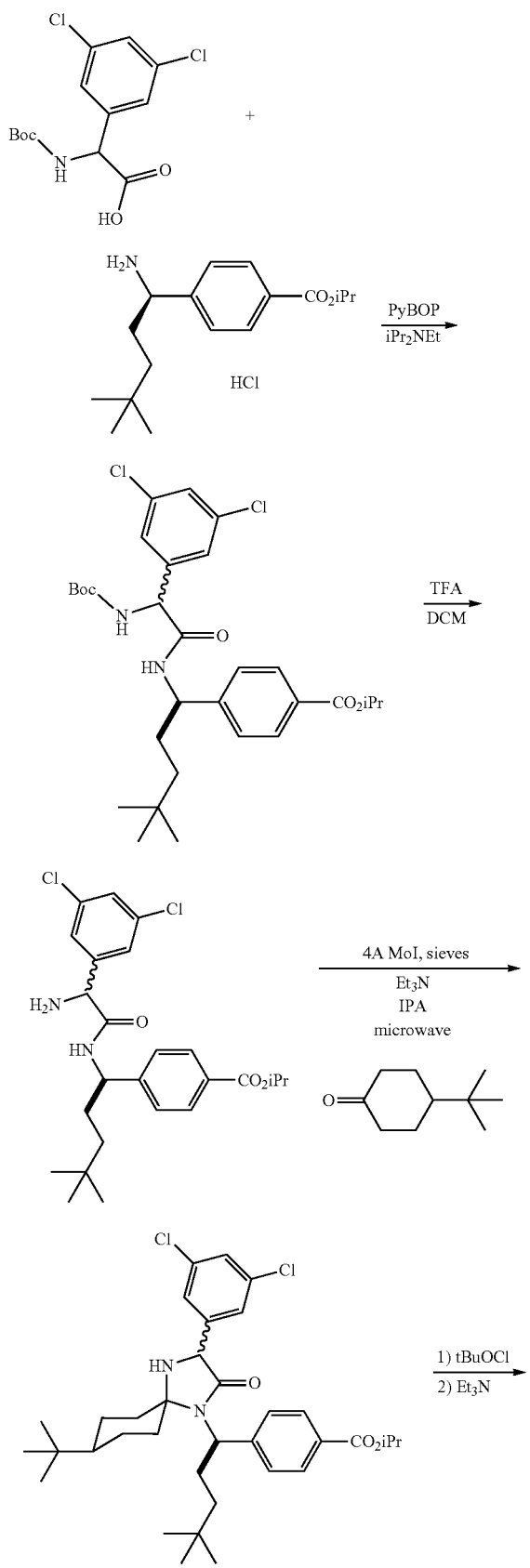
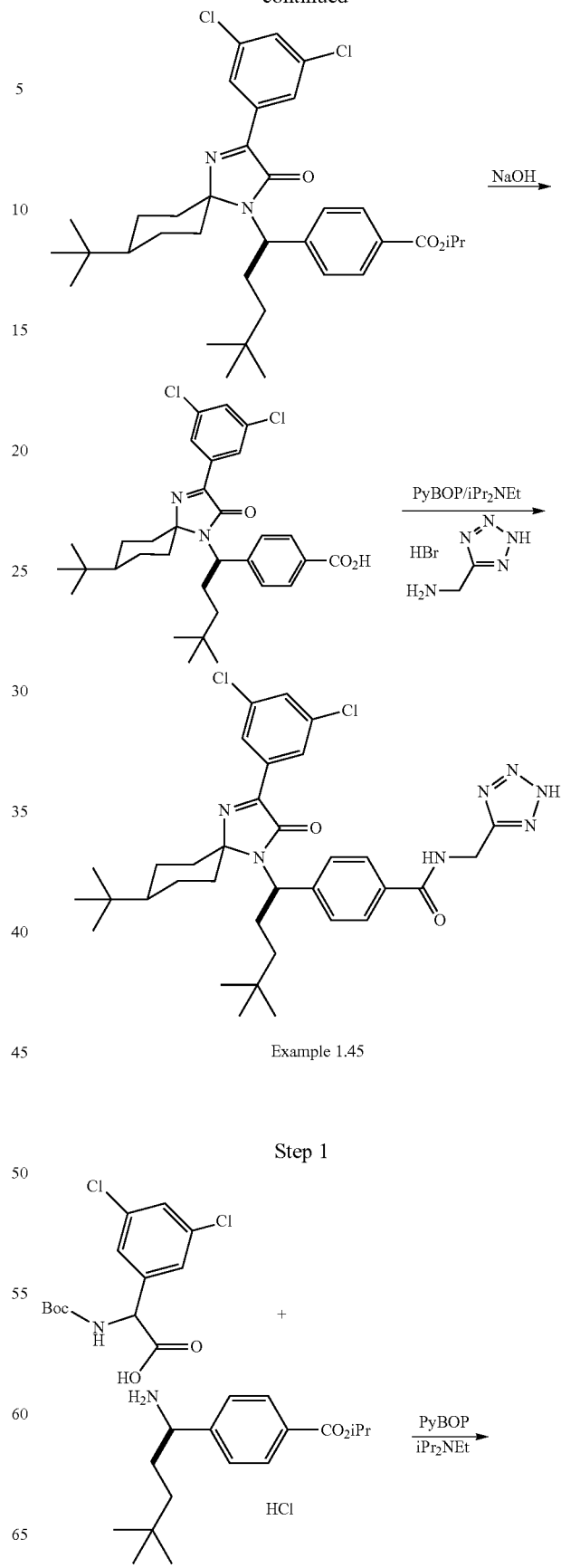
Example 1.45
Step 1

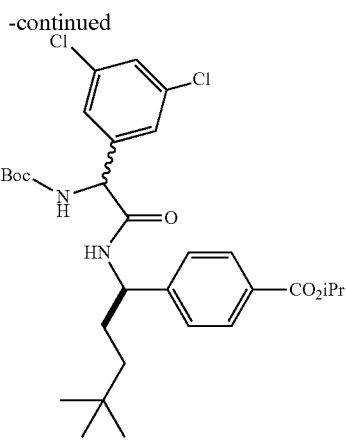

The amine (1.1 grams, 3.5 mmol), the N—BOC amino acid (1.1 g, 3.5 mmol), PyBOP (2.2 g, 4.2 mmol), and i-Pr$_2$NEt (1.8 g, 14 mmol) were taken up in CH$_3$CN (20 ml), and the resulting solution was stirred at 25° C. for 18 h. The solution was concentrated, and the residue was partitioned between EtOAc and 1 N NaOH$_{(aq.)}$. The aqueous layer was extracted with EtOAc. The combined organic layers were washed with brine and dried (MgSO$_4$). The solution was filtered and concentrated. The residue was purified via gradient flash chromatography (Analogix, 0-30% EtOAc in hexanes, SiO$_2$) which provided 1.6 g (79%) of the BOG protected peptide as an oil.

Step 2

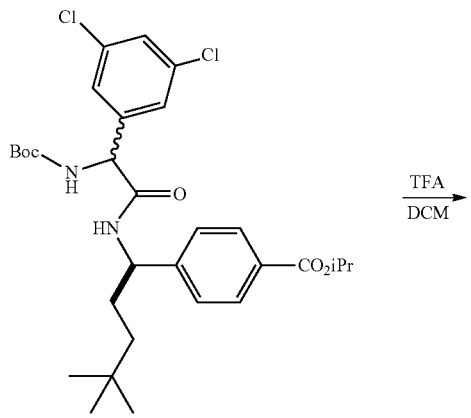

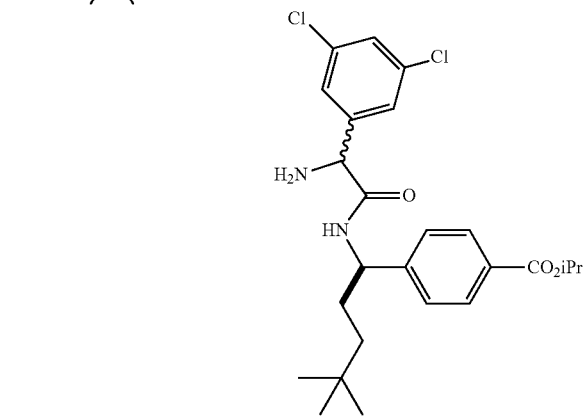

The Boc-protected peptide (1.6 g, 2.76 mmol) and TFA (3 ml) were taken up in DCM (10 ml), and the solution was stirred at 25° C. for 18 h. The solution was concentrated. The residue was partitioned between DCM and 1 N NaOH$_{(aq.)}$. The aqueous layer was extracted with DCM. The combined organic layers were dried (MgSO$_4$), filtered, and concentrated. The amino-peptide (1.3 g, Quant.) was used without further purification.

Step 3

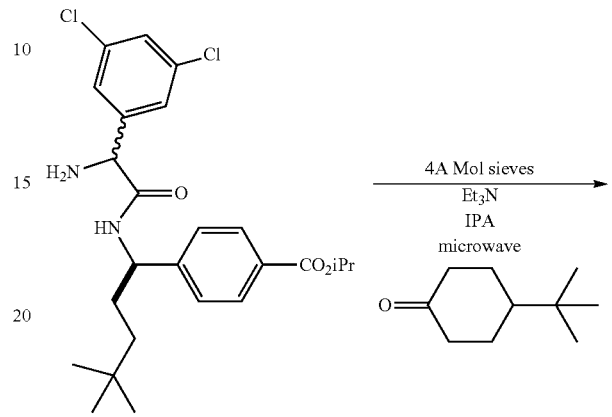

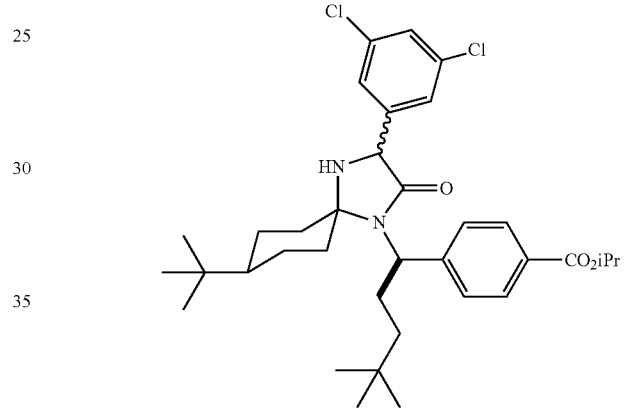

The amino-peptide (0.39 g, 0.67 mmol), 4-tert-butyl-cyclohexanone (0.21 g, 1.3 mmol), Et$_3$N (0.14 g, 1.3 mmol), and powdered 4 Å mol. sieves (0.5 g) were taken up in IPA (10 ml). The mixture was heated in a microwave (130° C., 5 h). The mixture was filtered and concentrated. The residue was purified via gradient flash chromatography (Analogix, 0-20% EtOAc in hexanes, SiO$_2$) to afford 0.43 g (50%) of the spiroamide as a colorless oil.

Step 4

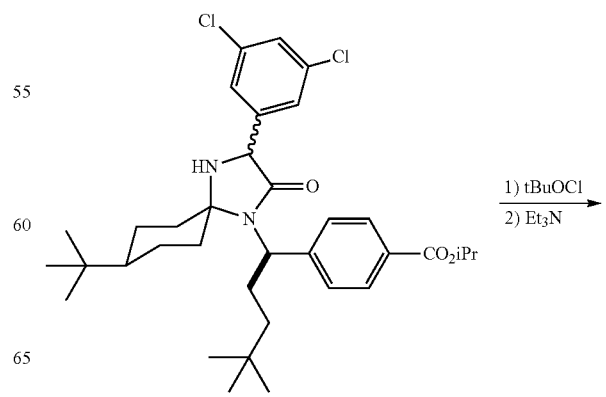

-continued

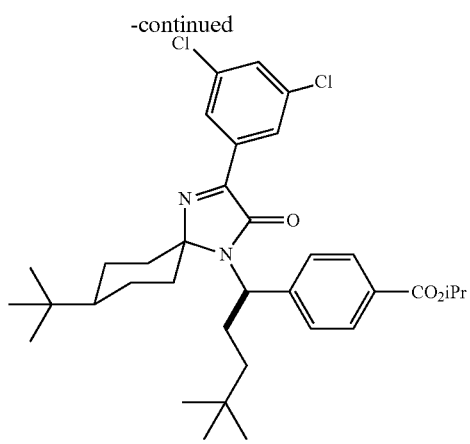

The spiro-amine (0.43 g, 0.7 mmol) was taken up in DCM (20 ml), and t-BuOCl (100 mg, 0.84 mmol) was added dropwise. After 2 hours, Et₃N (0.283 g, 2.8 mmol) was added, and the resulting solution was stirred at 25° C. for 1 h. The solution was diluted with DCM and washed with NaHSO$_{3(aq.)}$. The aqueous layer was extracted with DCM. The combined organic layers were dried (MgSO₄), filtered, and concentrated. The residue was purified via gradient flash chromatography (Analogix, 0-50% DCM in hexanes, SiO₂) which provided 0.28 g (65%) of the imidazolone-ester as a colorless oil.

Step 5

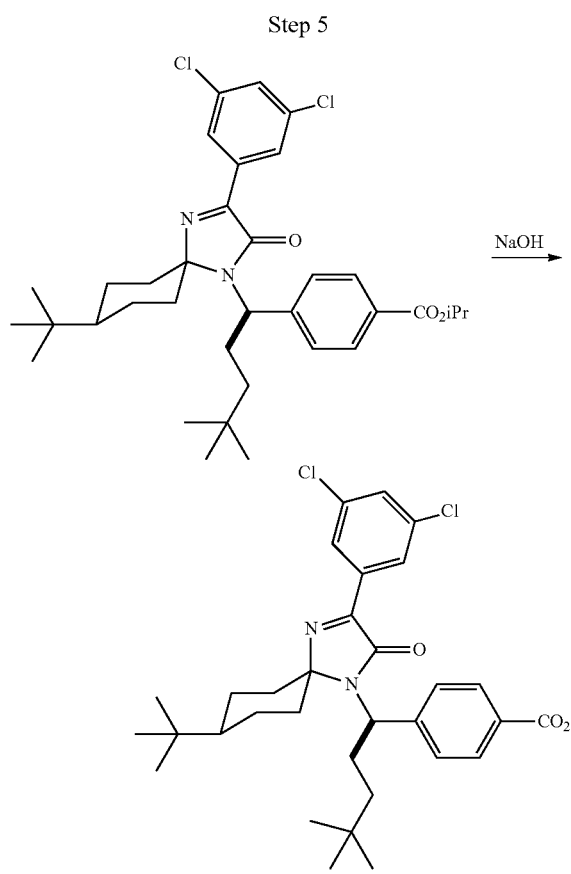

The ester (0.28 g, 0.46 mmol) was taken up in MeOH/dioxane/1 N NaOH$_{(aq.)}$ (10/5/1 mL), and the resulting solution was stirred at 25° C. for 18 h. The solution was concentrated, and the residue was partitioned between DCM and 1 M HCl$_{(aq.)}$. The aqueous layer was extracted with DCM. The combined organic layers were dried (MgSO₄), filtered, and concentrated. This provided 0.25 g (96%) of the acid as a colorless foam.

Step 6

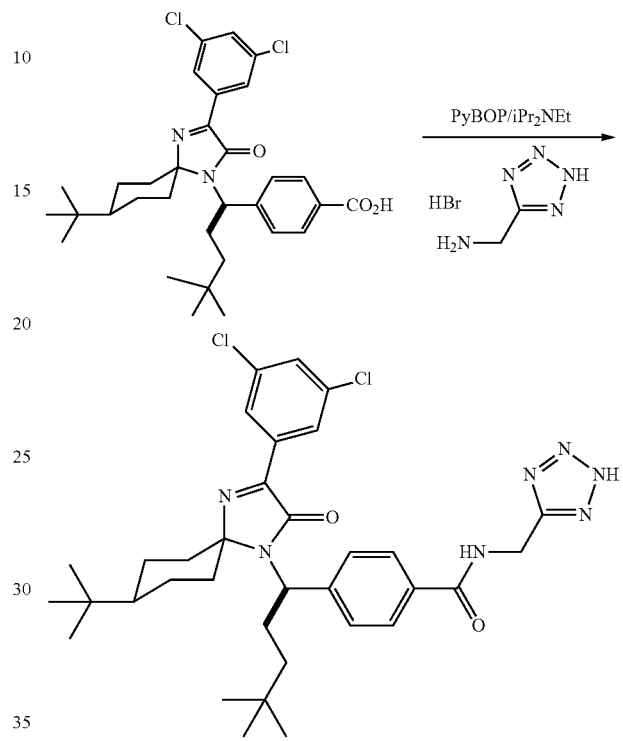

Example 1.45

The acid (0.25 g, 0.44 mmol), PyBOP (0.27 g, 0.53 mmol), iPr₂NEt (0.17 g, 1.3 mmol), and the amino-methyl tetrazole HBr salt (0.12 g, 0.66 mmol) were taken up in DMF (5 mL), and the resulting solution was heated at 70° C. for 18 h. The solution was concentrated, and the residue was purified via reversed-phase chromatography (Biotage, water/CH₃CN gradient) which provided 0.22 g (77%) of Ex 1.45 as a colorless solid.

Scheme J

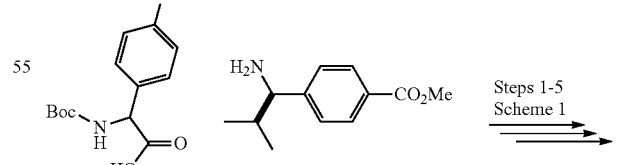

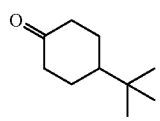

97

-continued

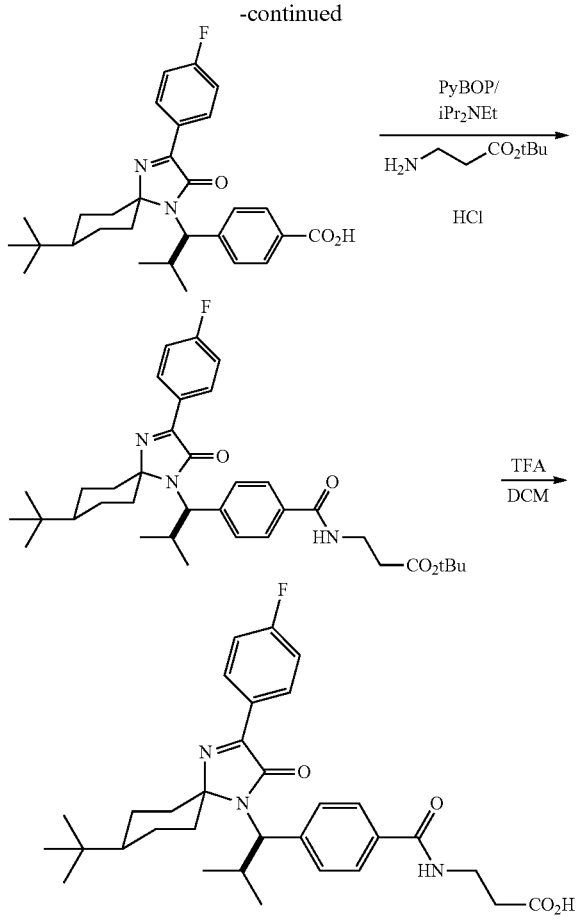

Example 1.46

Step 1

The amino acid, amine, and ketone were used according to Steps 1-5 in Scheme I to afford the benzoic acid. The benzoic

98 acid (240 mg, 0.50 mmol), β-alanine tert-butyl ester HCl (110 mg, 0.60 mmol), PyBOP (313 mg, 0.6 mmol), and iPr$_2$NEt (260 mg, 2 mmol) were taken up in CH$_3$CN (5 mL), and the resulting solution was stirred at 25° C. for 18 h. The solution was concentrated. The residue was partitioned between EtOAc and 1 N NaOH$_{(aq.)}$. The aqueous layer was extracted with EtOAc. The combined organic layers were washed with brine and dried (MgSO$_4$). Filtration and concentration gave a yellow oil. The residue was purified via thin-layer preparative chromatography (1/1 hexanes/EtOAc, SiO$_2$) which gave 180 mg (60%) of the tert-butyl ester as a colorless oil.

Step 2

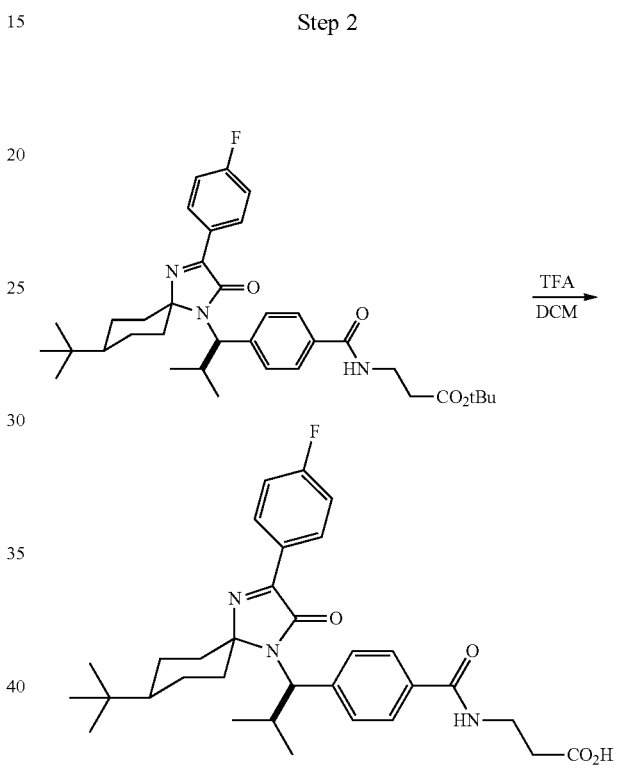

Example 1.46

The tert-butyl ester (180 mg, 0.30 mmol) was taken up in TFA (2.5 mL) and DCM (15 ml). The solution was stirred at 25° C. for 18 h. The solution was concentrated. The residue was co-evaporated with DCM 3 times (25 mL) which provided 170 mg (Quant.) of Example 1.46 as a colorless foam.

Scheme K

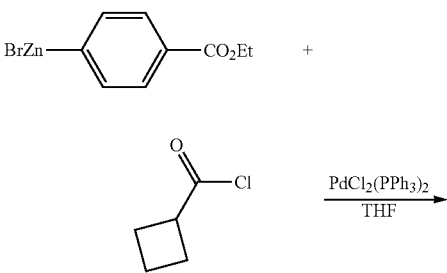

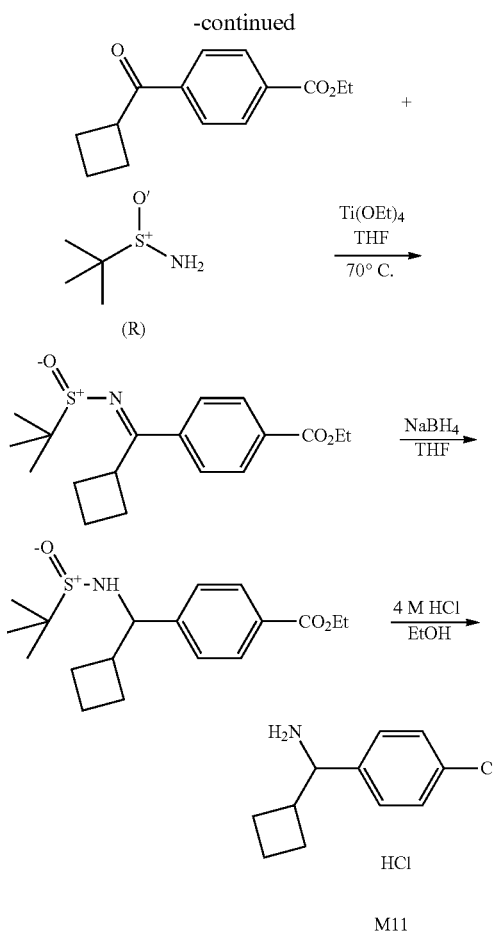

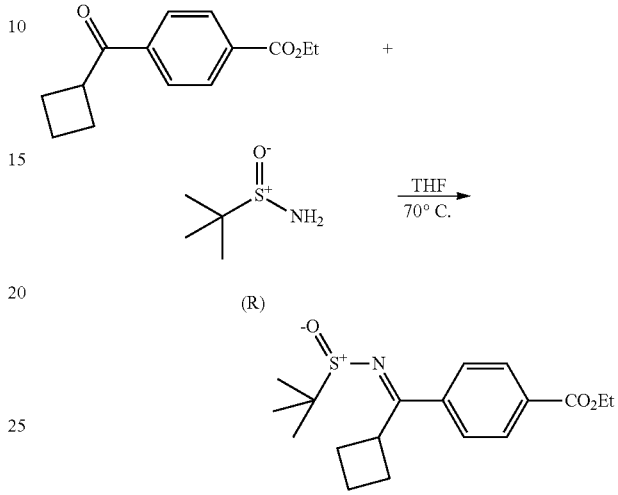

via gradient flash chromatography (0-5% EtOAc in hexanes, SiO$_2$, Analogix) which provided 866 mg (74%) of the ketone as a yellow oil.

Step 2

The ketone (866 mg, 3.7 mmol), Ti(OEt)$_4$ (0.94 mL, 4.5 mmol), and the (R) sulfinamide (493 mg, 4 mmol) were taken up in THF (40 mL). The resulting solution was heated at 70° C. for 16 h. The solution of the imine was used without further purification.

Step 3

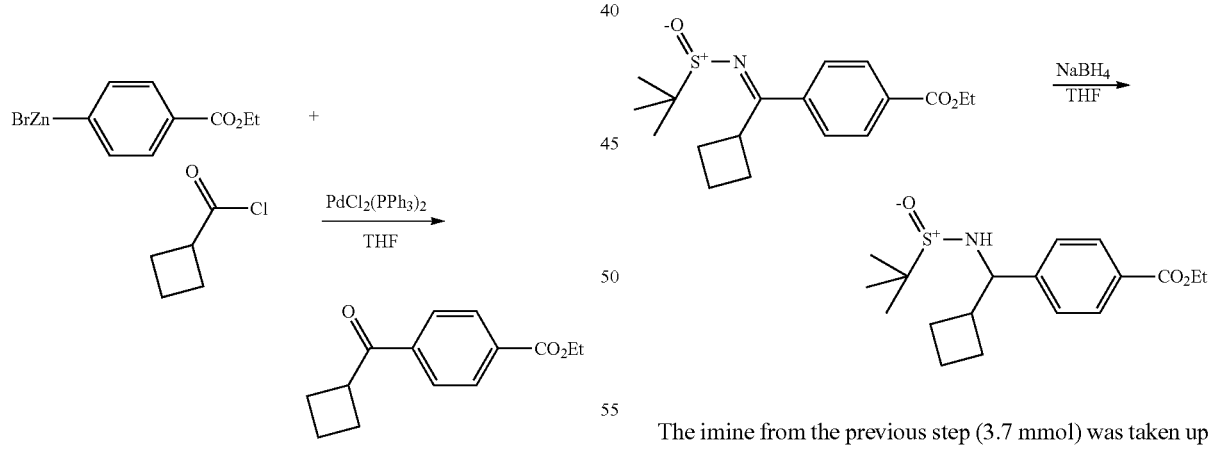

Step 1

Cyclobutyl carbonyl chloride (0.6 mL, 5.2 mmol) and PdCl$_2$(PPh$_3$)$_3$ (176 mg, 0.25 mmol) were taken up in THF (35 mL). The aryl zinc reagent (10 mL of a 0.5 M solution in THF, 5 mmol) was added to the reaction at 25° C. The resulting dark solution was stirred at 25° C. (5 hr). The yellow solution was partitioned between Et$_2$O and sat. NH$_4$Cl (aq.). The aqueous layer was extracted with Et$_2$O. The combined organic layers were washed with brine and dried (MgSO$_4$). Filtration and concentration provided a yellow oil. The residue was purified The imine from the previous step (3.7 mmol) was taken up in THF (20 ml), and the resulting solution was cooled to −78° C. Sodium borohydride (420 mg, 11.1 mmol) was added at −78° C., and the resulting solution was allowed to warm to 25° C. over 18 h. The residue was partitioned between EtOAc and sat. NH$_4$Cl (aq.). The aqueous layer was extracted with EtOAc. The combined organic layers were washed with brine and dried (MgSO$_4$). Filtration and concentration provided a yellow oil. The residue was purified via gradient flash chromatography (0-40% EtOAc in hexanes, SiO$_2$, Analgogix) which provided 580 mg (46%) of the sulfinimide as a mixture of diastereomers (3/1).

Step 4

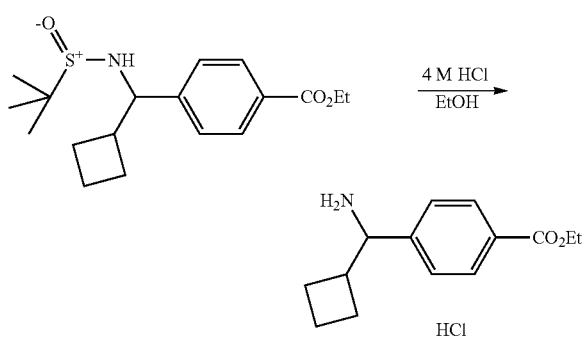

The sulfinamide (580 mg, 1.7 mmol) was taken up in EtOH (30 ml) at 25° C. Dioxane (4.0 M HCl, 15 mL) was added, and the solution was stirred at 25° C. for 18 h. The solution was concentrated and dried which provided the amine HCl salt as a white solid. The material was used without further purification. All final compounds prepared from this amine are a 3/1 mix of enantiomers.

Scheme LD

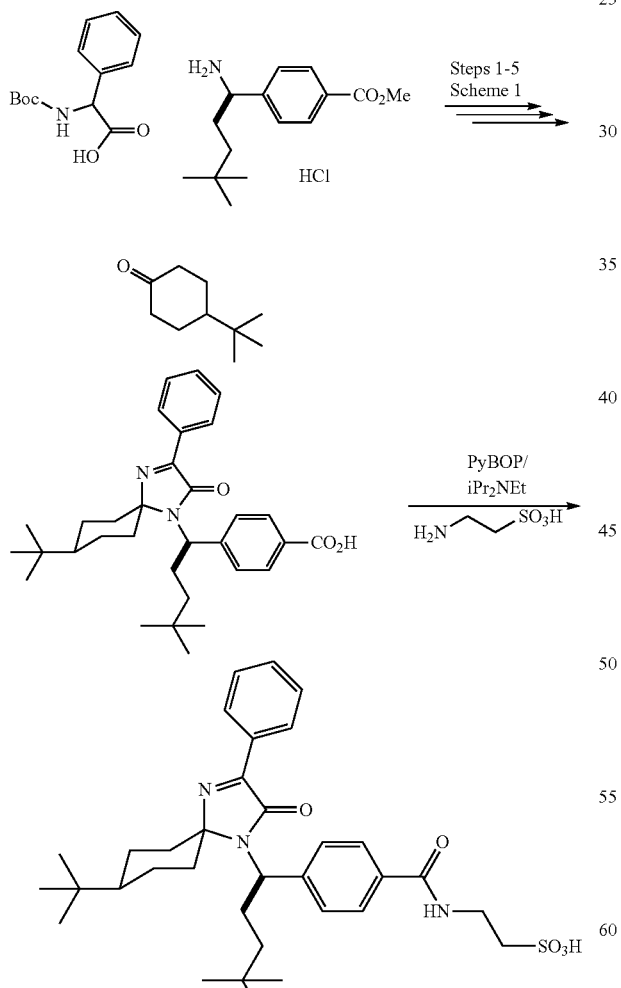

Example 1.72

The benzoic acid was prepared according to Scheme I (Steps 1-5) using the appropriate amino acid, amine, and ketone. The benzoic acid (90 mg, 0.18 mmol), iPr$_2$NEt (0.12 mL, 0.72 mmol), PyBOP (122 mg, 0.23 mmol), and taurine (34 mg, 0.27 mmol) were taken up in DMF (4 mL), and the resulting solution was heated at 80° C. for 2.5 h. The reaction was concentrated. The residue was purified via reversed-phase chromatography (water/CH$_3$CN gradient) which provided 85 mg (77%) of Example 1.72 as a colorless foam.

Scheme M

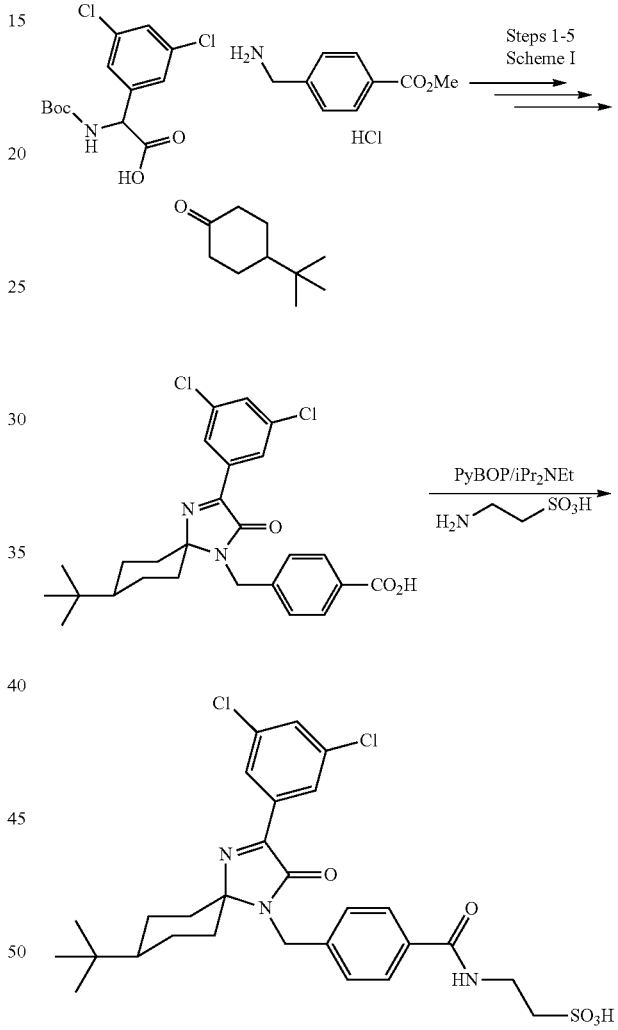

Example 1.73

The benzoic acid was prepared according to Scheme I (Steps 1-5) using the appropriate amino acid, amine, and ketone. The benzoic acid (200 mg, 0.4 mmol), iPr$_2$NEt (158 mg), HOBt (83 mg), EDCl (117 mg), and taurine (76 mg) were taken up in DMF (3 mL), and the resulting solution was stirred at 25° C. for 3 days. The reaction was quenched with 1 M HCl$_{(aq.)}$. The resulting solid was collected and purified via reversed-phase chromatography (water/CH$_3$CN gradient) which provided 33 mg (14%) of Example 1.73 as a colorless foam.

Scheme N

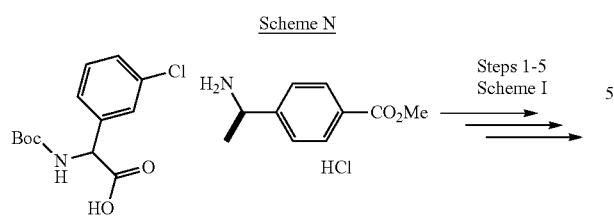

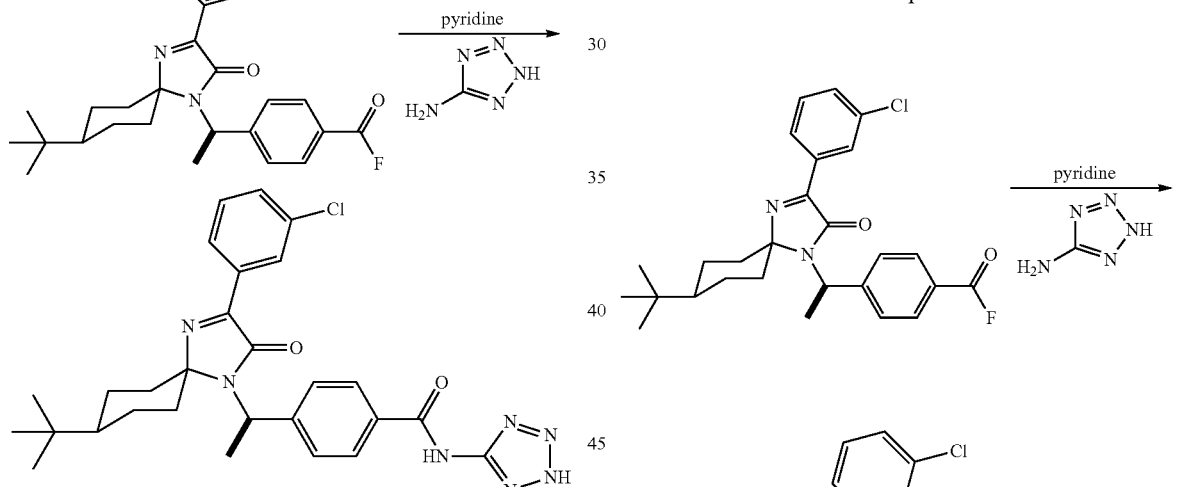

Example 1.76

Step 1

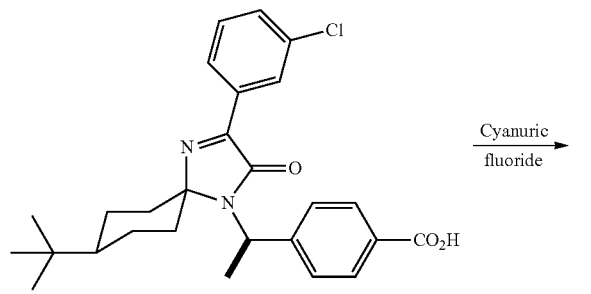

-continued

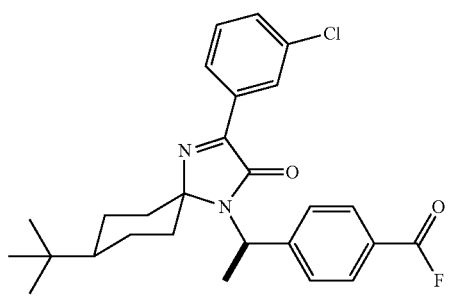

The benzoic acid was prepared according to Scheme I (Steps 1-5) using the appropriate amino acid, amine, and ketone. The benzoic acid (320 mg, 0.71 mmol) and pyridine (0.2 mL) were taken up in DCM (15 mL) at 0° C. Cyanuric fluoride (0.13 ml) was added, and the resulting solution was stirred at 0° C. for 2 h. The solution was diluted with DCM and washed with sat. $NaHCO_3$(aq.). The aqueous layer was extracted with DCM. The combined organic layers were dried ($MgSO_4$), filtered and concentrated. The acid fluoride was used without further purification.

Step 2

Example 1.76

The acid fluoride (0.7 mmol) from the previous step and amino-tetrazole hydrate (70 mg) were taken up in pyridine and stirred at 25° C. for 18 h. The solution was concentrated. The residue was purified via reversed-phase chromatography (water/$CH_3CN$ gradient) provided 47 mg (12%) of Example 1.76 as a colorless solid.

Scheme O

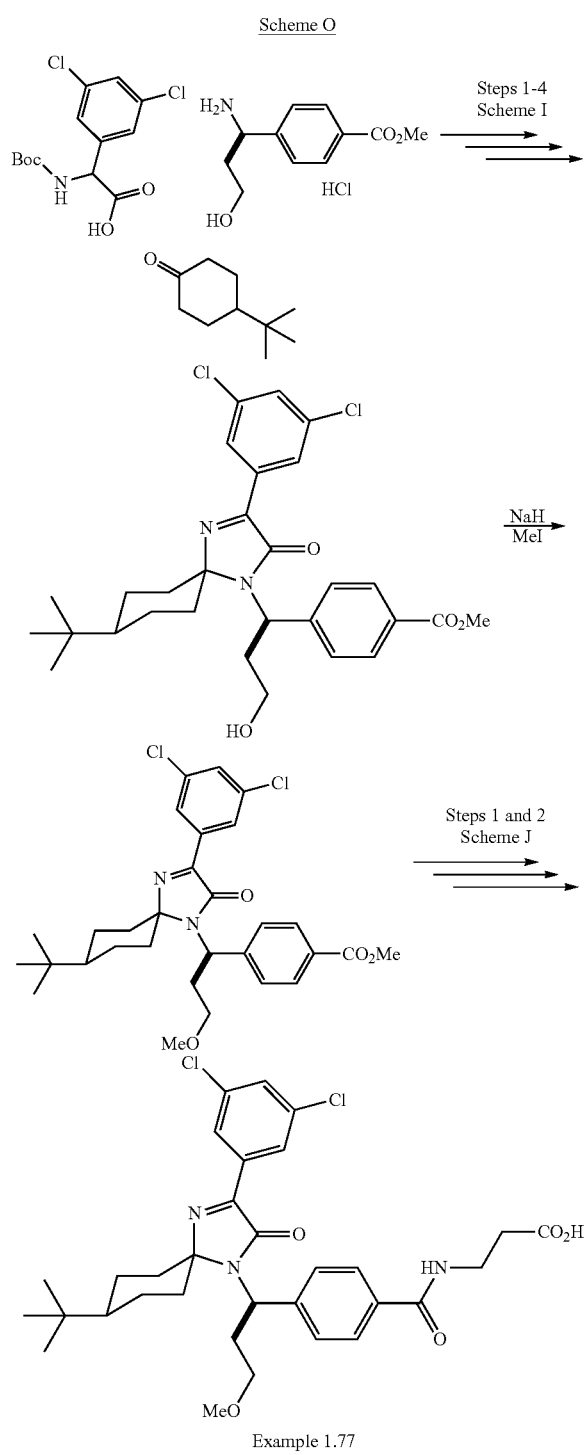

Example 1.77

The methyl ester was prepared according to Scheme I (Step 1-4) using the appropriate amino acid, amine, and ketone. The methyl ester (350 mg, 0.6 mmol) was taken up in DMF (5 mL). Sodium hydride (40 mg, 60% wt dispersion in oil) was added. The solution was stirred at 25° C. for 1 hr. Methyl iodide (150 mg) was added, and the solution was stirred at 25° C. for 3 h. More NaH and MeI were added, and the resulting solution was stirred at 25° C. for 18 h. The solution was partitioned between Et$_2$O and water. The aqueous layer was extracted with Et$_2$O. The combined organic layers were washed with brine and dried (MgSO$_4$). Filtration and concentration gave an orange oil. The residue was purified via gradient flash chromatography (0-25% EtOAc in hexanes, SiO$_2$) which provided 220 mg (61%) of the methyl ether as a colorless oil.

The methyl ester from the previous step was converted into Example 1.77 according to Scheme J (Steps 1 and 2).

Scheme P

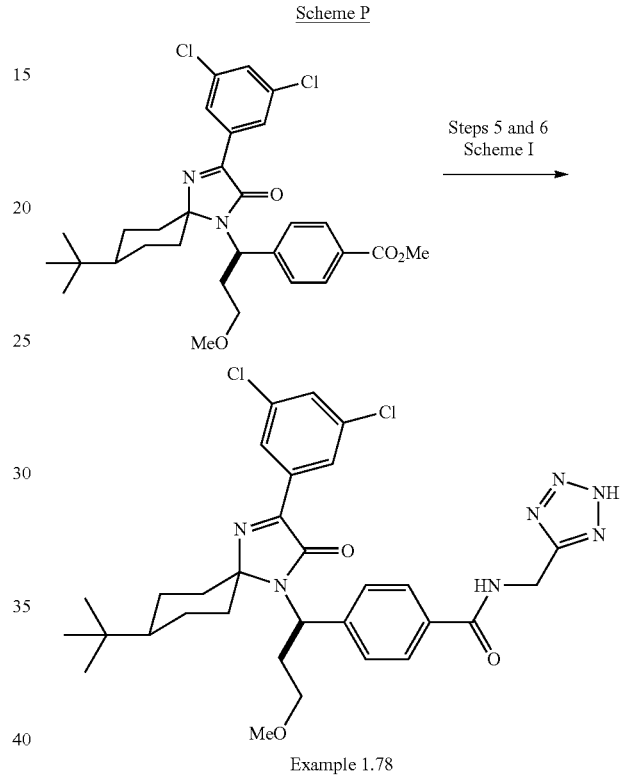

Example 1.78

The methyl ester (Scheme O) was converted into Example 138 according to Scheme I (Steps 5 and 6).

Scheme Q

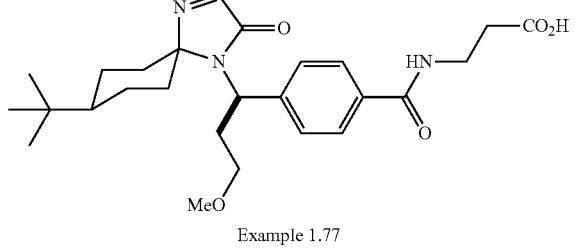

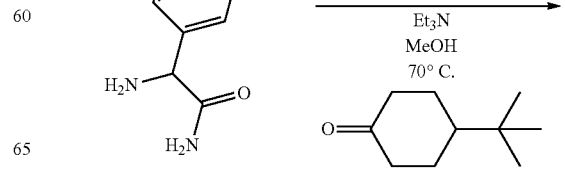

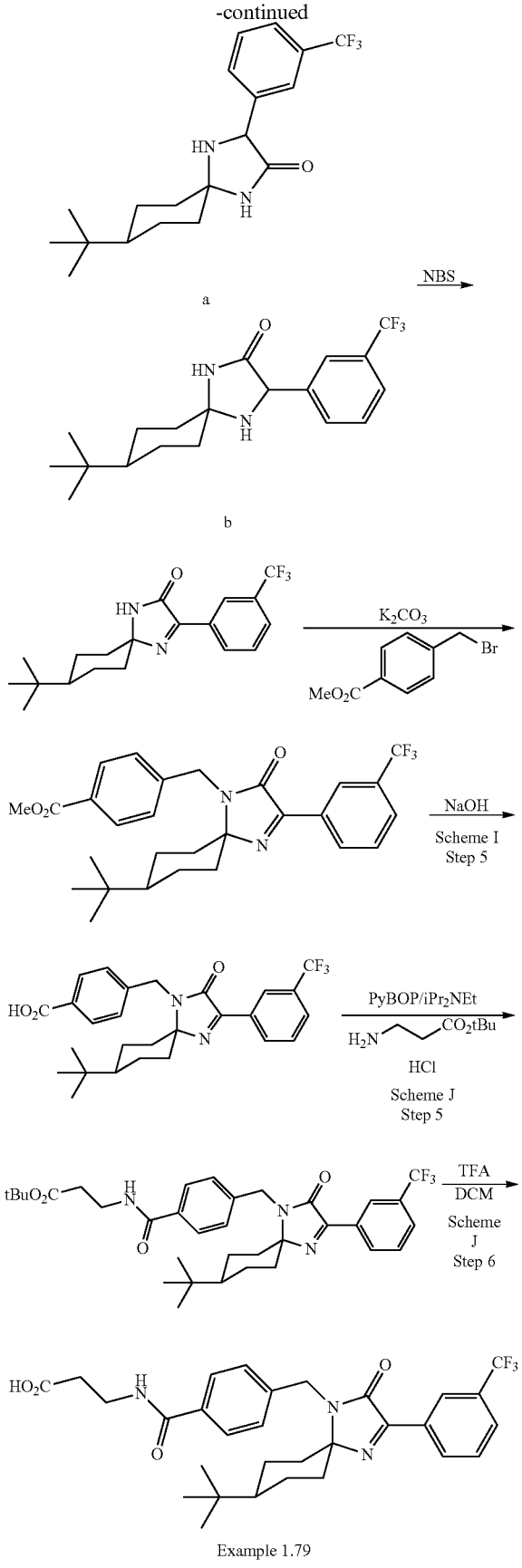

Example 1.79

Step 1

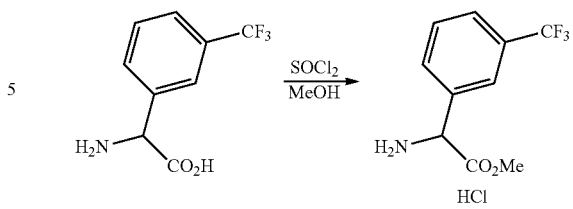

Thionyl chloride (1.5 mL) was added dropwise to MeOH (35 mL) at 0° C. After stirring at 0° C. for 45 minutes, the phenyl glycine (3 g, 13.7 mmol) was added, and the resulting solution was heated at 45° C. for 16 h. The solution was concentrated. The residue was triturated with Et$_2$O. The solid was collected and dried which furnished 3.5 g (94%) of the methyl ester HCl salt.

Step 2

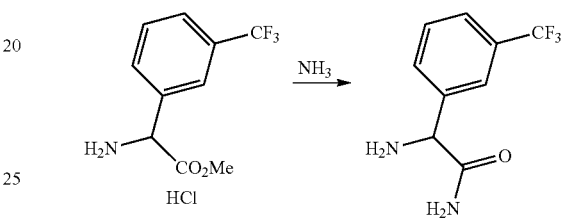

The methyl ester HCl salt (3.5 g, 13 mmol) was taken up in MeOH (45 ml). A methanol solution containing NH$_3$ (7 N, 80 mL) was added, and the resulting solution was stirred at 25° C. for 50 h. The solution was concentrated. The residue was partitioned between DCM and water. The aqueous layer was extracted with DCM. The combined organic layers were dried (MgSO$_4$), filtered, and concentrated. This provided 2.7 g (95%) of the amino-amide as a colorless solid.

Step 3

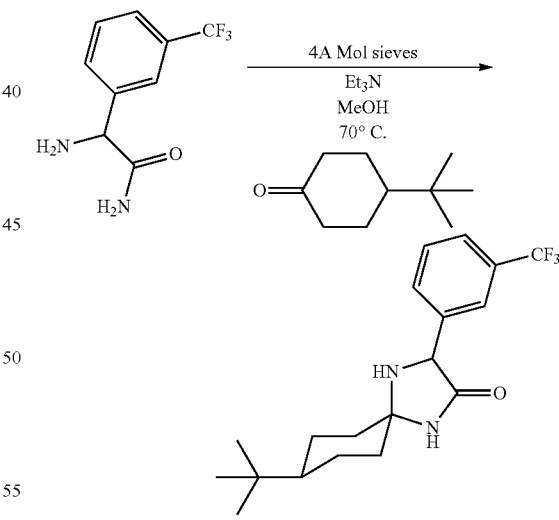

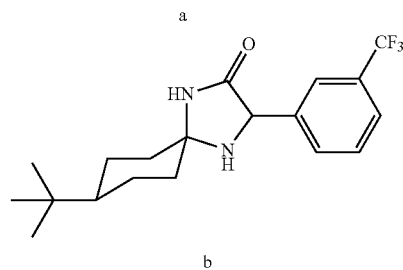

The amino-amide (1.1 g, 5.0 mol), ketone (1.5 g), 4 Å mol sieves (3 g), and Et₃N (1.5 g) were taken up in MeOH (20 ml), and the resulting mixture was heated at 70° C. for 18 h. The solution was filtered and concentrated. The residue was purified via gradient flash chromatography (0-50% EtOAc in hexanes, SiO₂) which provided 500 mg (28%) of the spiro-amide a and 660 mg (37%) the spiro-amine b as a colorless oil.

Step 4

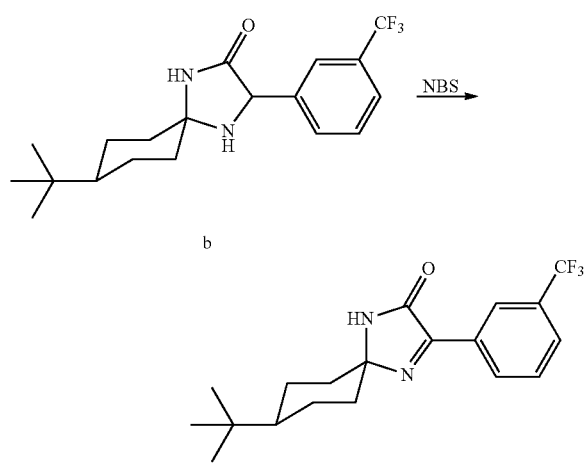

b

The spiro-amine b (660 mg, 1.86 mmol) was taken up in DCM (35 mL), and NBS (400 mg) was added. The solution was stirred at 25° C. for 18 h. The solution was diluted with DCM and washed with 10% NaHSO₃(aq.). The aqueous layer was extracted with DCM. The combined organic layers were washed with 10% NaHCO₃(aq.), dried (MgSO₄), filtered, and concentrated. The residue was purified via gradient flash chromatography (0-50% EtOAc in hexanes, SiO₂) which provided 95 mg (14%) of the imidazolone as a colorless solid.

Step 5

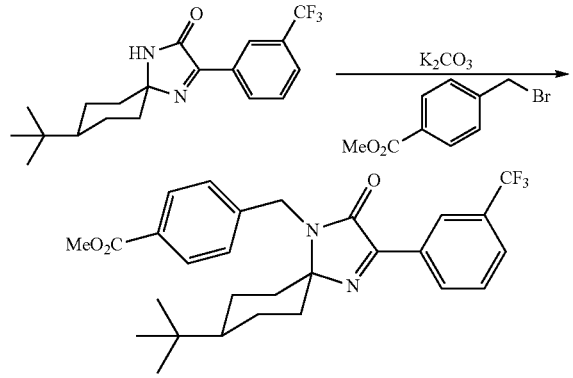

The imidazolone (95 mg, 0.27 mmol), K₂CO₃ (48 mg), and the benzyl bromide (310 mg) were taken up in acetone (20 mL), and the resulting solution was heated at 65° C. for 18 h. The solution was filtered and concentrated. The residue was purified via thin-layer preparative chromatography (14% Et₂O in hexanes, SiO₂) which provided 40 mg (30%) of the methyl ester as a colorless oil.

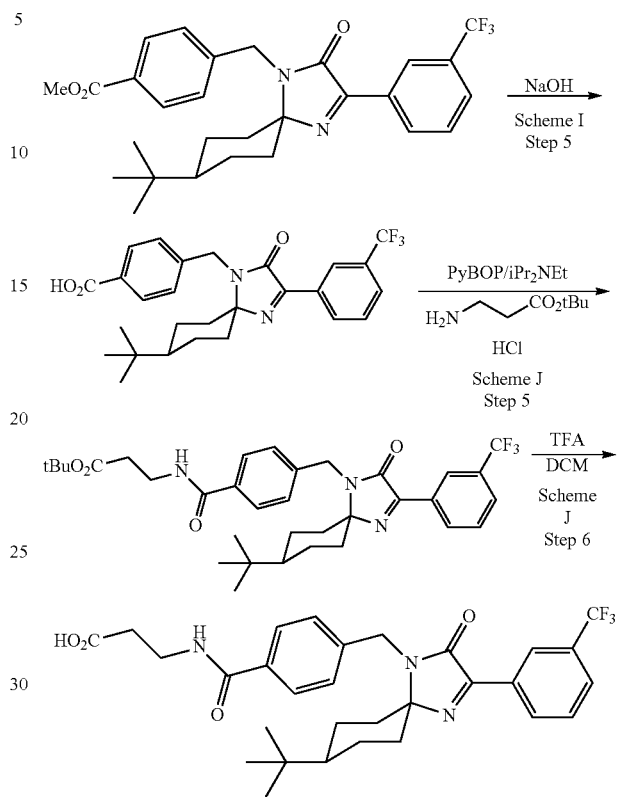

Example 1.79

The methyl ester was converted into Example 1.79 according to the procedures outlined in Scheme I (Step 5) and Scheme J (Steps 1 and 2).

Scheme R

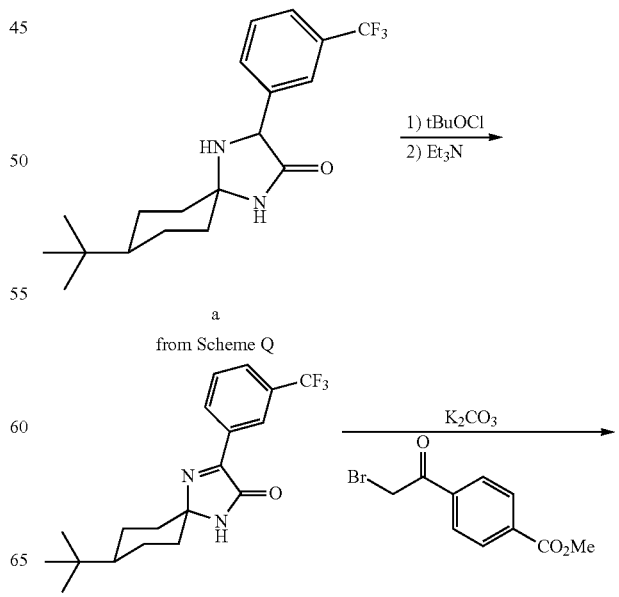

a
from Scheme Q

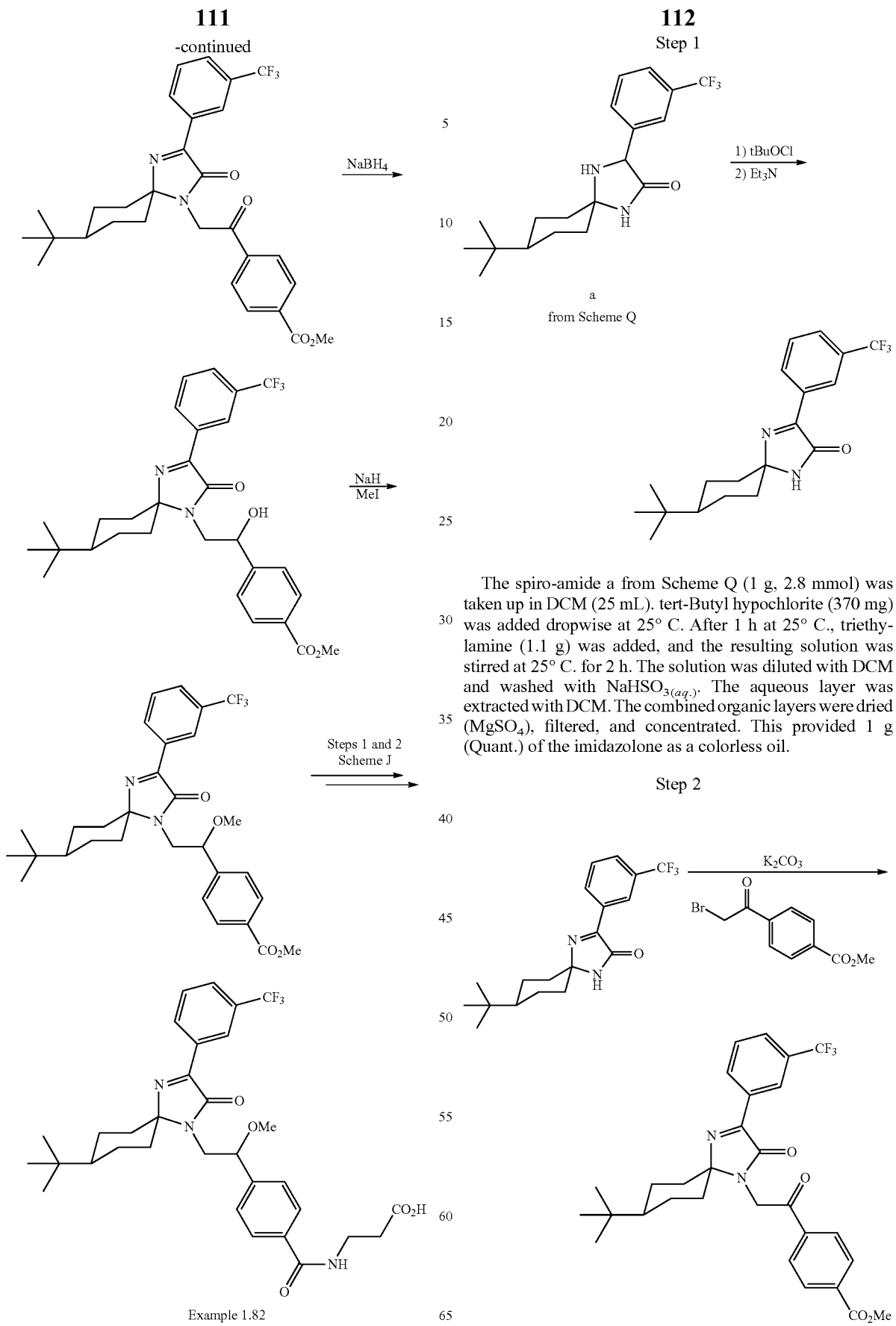

Step 1

The spiro-amide a from Scheme Q (1 g, 2.8 mmol) was taken up in DCM (25 mL). tert-Butyl hypochlorite (370 mg) was added dropwise at 25° C. After 1 h at 25° C., triethylamine (1.1 g) was added, and the resulting solution was stirred at 25° C. for 2 h. The solution was diluted with DCM and washed with NaHSO$_{3(aq.)}$. The aqueous layer was extracted with DCM. The combined organic layers were dried (MgSO$_4$), filtered, and concentrated. This provided 1 g (Quant.) of the imidazolone as a colorless oil.

Step 2

The imidazolone (1 g, 2.85 mmol), K$_2$CO$_3$ (786 mg), and the bromide (1.46 g) were reacted according to the procedure outlined in Step 5 of Scheme Q which provided 720 mg (48%) of the ketone as a colorless oil.

Step 3

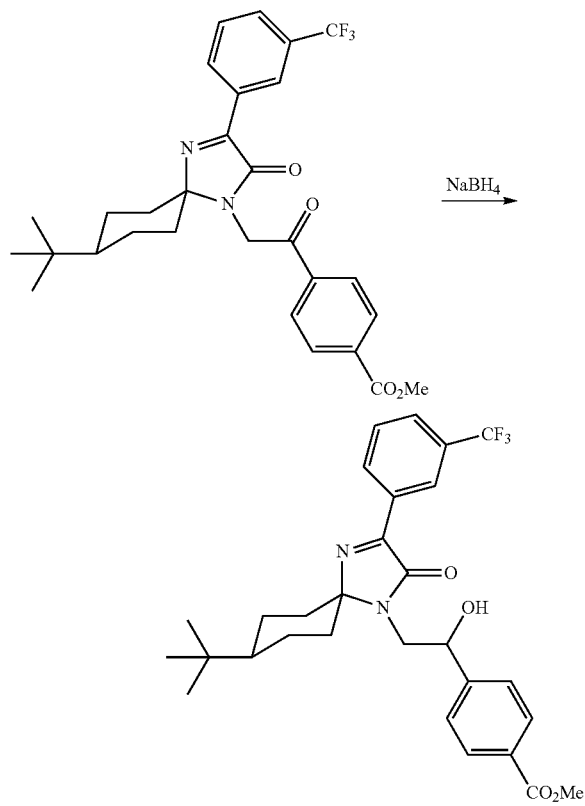

The ketone (360 mg, 0.68 mmol) was taken up in MeOH (20 mL), and sodium borohydride (40 mg) was added. After stirring at 25° C. for 2 hr, the solution was concentrated. The residue was partitioned between EtOAc and water. The aqueous layer was extracted with EtOAc. The combined organic layers were washed with brine and dried (MgSO$_4$). Filtration and concentration provided 345 mg (95%) of the alcohol as a yellow oil.

Step 4

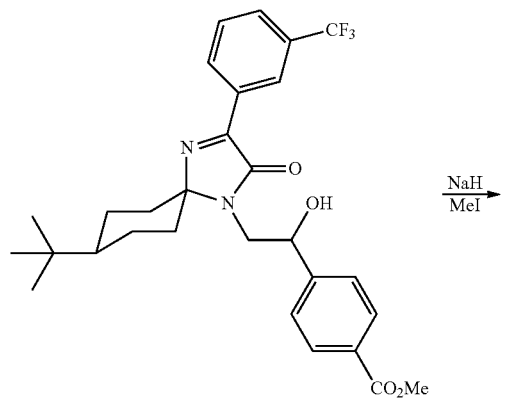

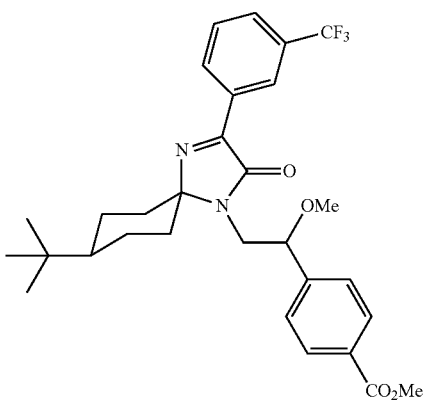

The alcohol (345 mg, 0.65 mmol) was taken up in THF (8 mL), and sodium hydride (30 mg, 60 wt % dispersion in oil) was added. After 15 minutes, methyl iodide (100 mg) was added. After stirring at 25° C. for 1 h, the solution was concentrated. The residue was partitioned between EtOAc and brine. The aqueous layer was extracted with EtOAc. The combined organic layers were dried (MgSO$_4$), filtered, and concentrated. The residue was purified via gradient flash chromatography (0-30% EtOAc in hexanes, SiO$_2$) which provided 180 mg (50%) of the methyl ether as a colorless oil.

The methyl ether was converted into Example 1.82 according to the procedures outlined in Scheme J (Steps 1 and 2).

Scheme S

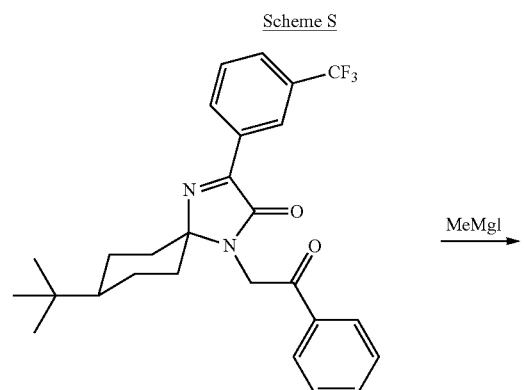

115

-continued

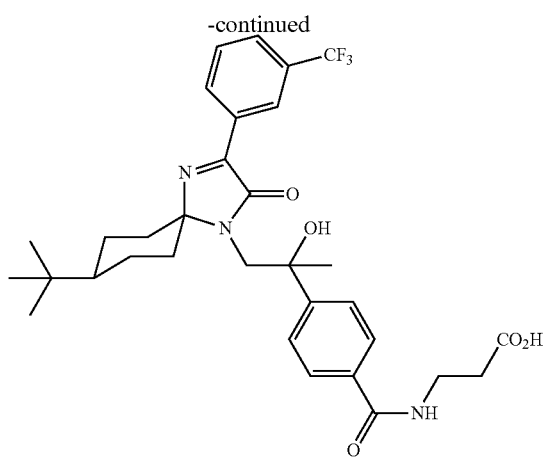

Example 1.83

Step 1

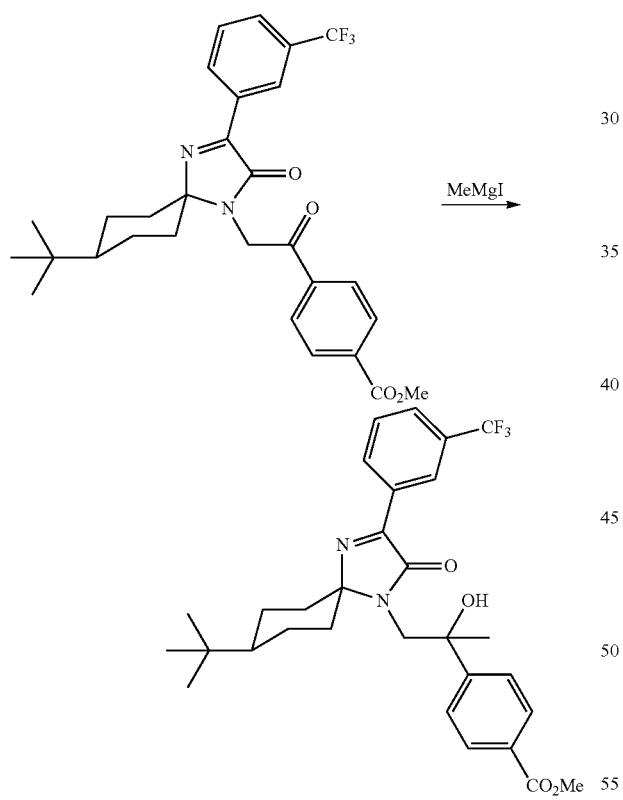

The ketone from Scheme R (Step 2) (140 mg, 0.26 mmol) was taken up in Et$_2$O (8 ml) at 0° C. Methyl magnesium iodide (0.15 mL of a 3 M solution in Et$_2$O) was added at 0° C. After one hour at 0° C., the solution was partitioned between Et$_2$O and sat. NH$_4$Cl$_{(aq.)}$. The aqueous layer was extracted with Et$_2$O. The combined Et$_2$O layers were washed with brine and dried (MgSO$_4$). Filtration and concentration provided a yellow oil. The residue was purified via gradient flash chromatography (0-30% EtOAc in hexanes, Analogix) which provided 40 mg (28%) of the alcohol as a colorless oil.

116

The alcohol was converted into Example 1.83 according to the procedures outlined in Scheme J (Steps 1 and 2).

Scheme T

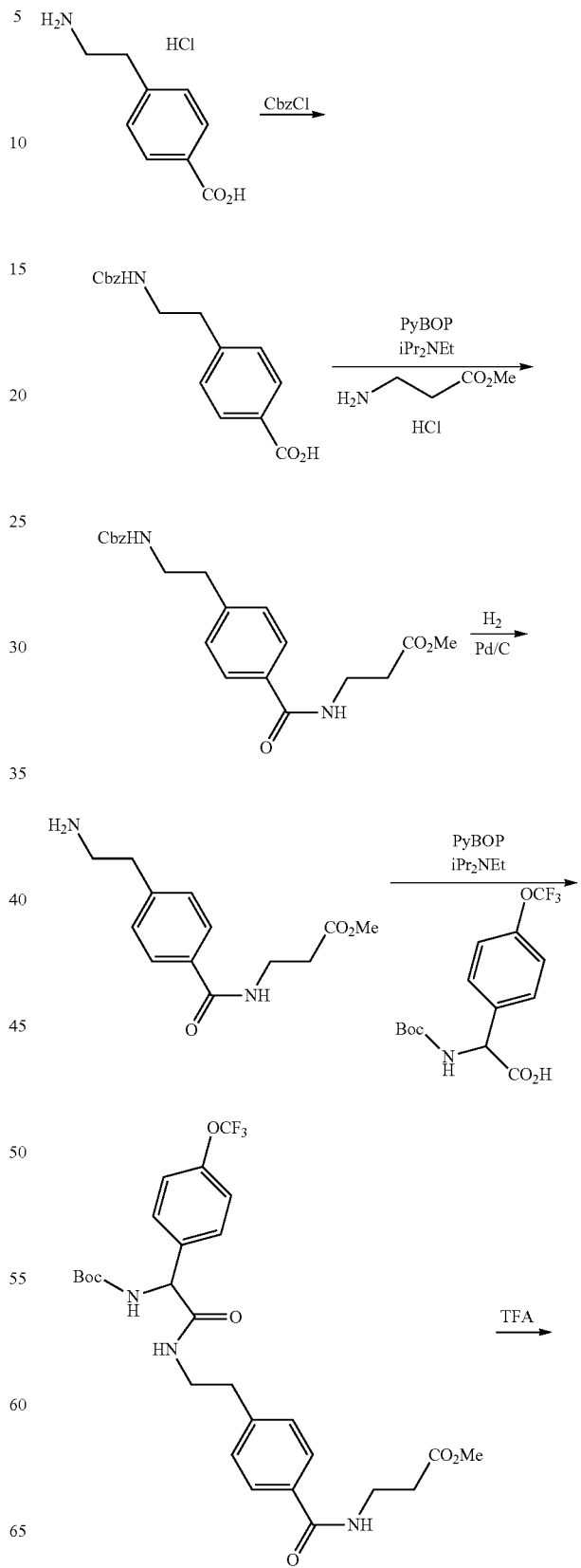

-continued

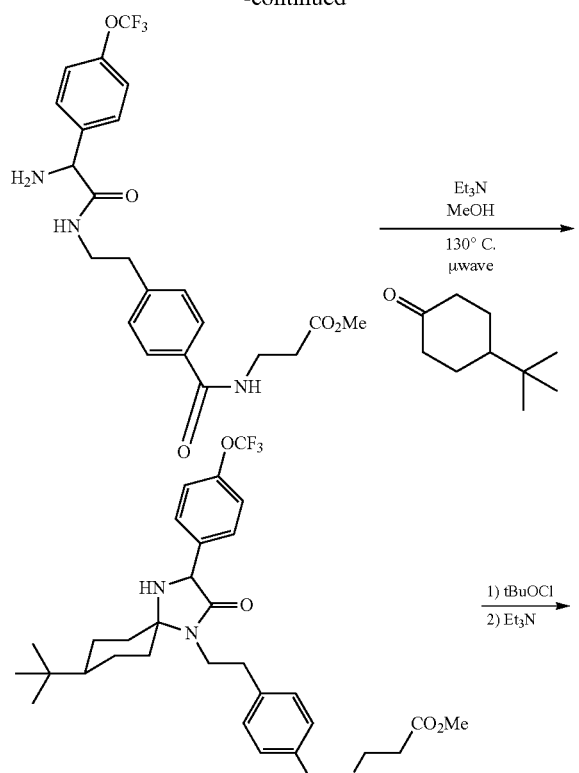

Example 1.98

Step 1

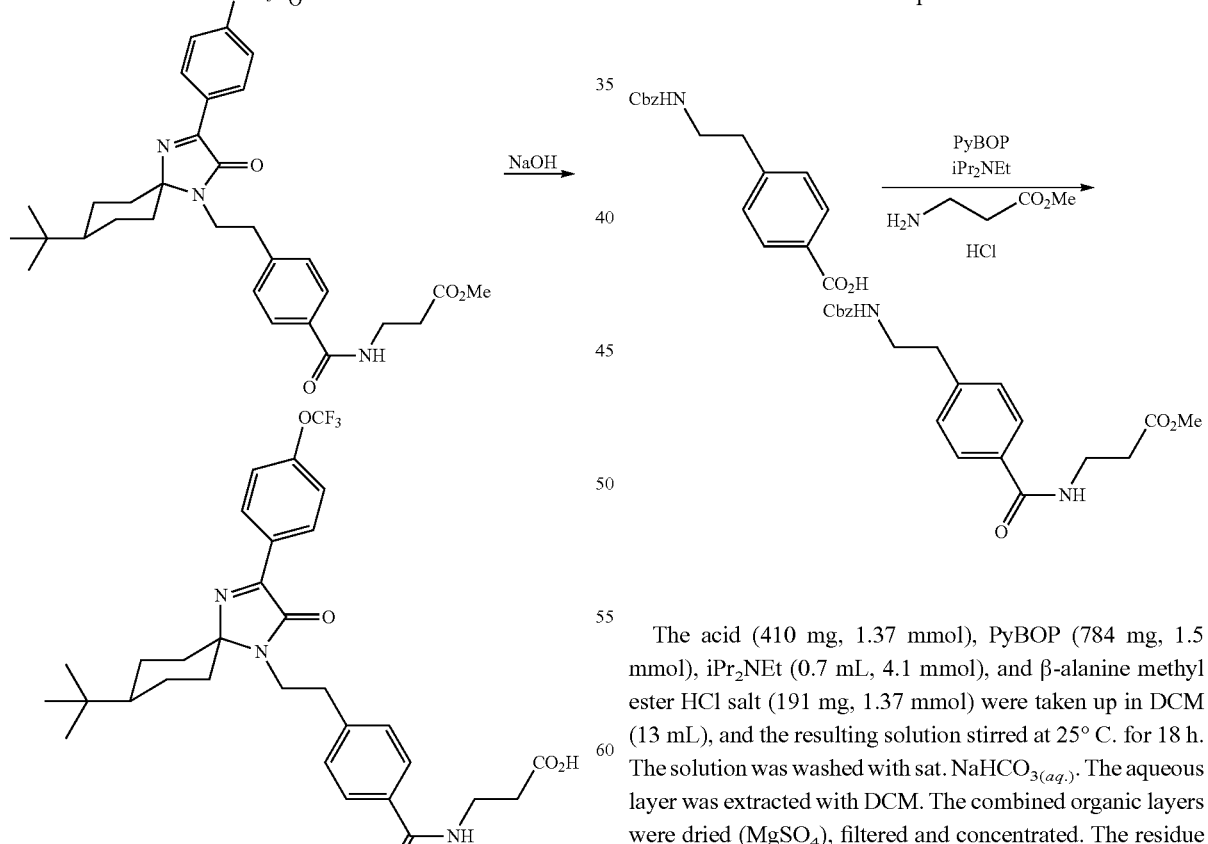

The amine 5.07 g (25 mmol) and CbzCl 19.3 g (113 mmol) were partitioned in water (100 mL). A sodium hydroxide solution (2 N, 15 mL) was added at 25° C. Additional aqueous sodium hydroxide solution was added at later time points (10 min –5 mL and 30 min 10 mL of 2 N NaOH). The mixture was stirred at 25° C. for 18 h. Diethyl ether was added (30 mL), and the mixture was stirred. The layers were separated. The aqueous layer was cooled to 0° C., and acidified via careful addition of conc. HCl until pH=3.0. The formed white solid was collected and washed with water. The white solid was dried under vacuum to provide 7.1 g (94%) of the Cbz protected acid.

Step 2

The acid (410 mg, 1.37 mmol), PyBOP (784 mg, 1.5 mmol), iPr$_2$NEt (0.7 mL, 4.1 mmol), and β-alanine methyl ester HCl salt (191 mg, 1.37 mmol) were taken up in DCM (13 mL), and the resulting solution stirred at 25° C. for 18 h. The solution was washed with sat. NaHCO$_{3(aq.)}$. The aqueous layer was extracted with DCM. The combined organic layers were dried (MgSO$_4$), filtered and concentrated. The residue was purified via gradient flash chromatography (0-80% EtOAc in hexanes, SiO$_2$) which provided 260 mg (49%) of the amide as a white solid.

Step 3

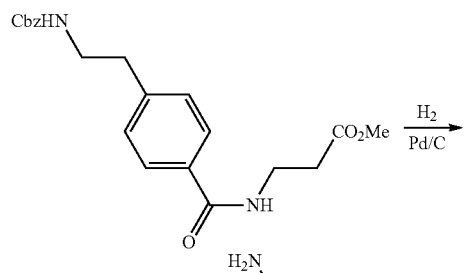

The Cbz protected amine (260 mg, 0.7 mmol) and 10% Pd/C (220 mg) were stirred in MeOH (7 mL) under H₂ (1 atm) for 18 h. The mixture was filtered through Celite®. The solution was concentrated which provided 170 mg (Quant.) of the amine as a colorless foam.

Step 4

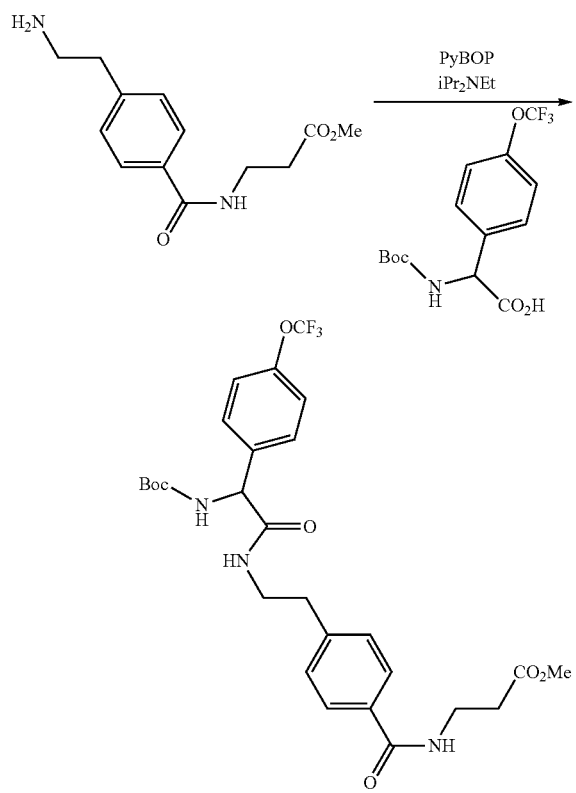

The amine (170 mg, 0.7 mmol), N—BOC phenyl glycine (234 mg, 0.7 mmol), PyBOP (400 mg, 0.77 mmol), and iPr₂NEt (0.4 mL) were taken up in DMF (20 mL), and the resulting solution was stirred at 25° C. for 18 h. The solution was partitioned between 1 N NaOH$_{(aq.)}$ and EtOAc. The aqueous layer was extracted with EtOAc. The combined organic layers were dried (MgSO₄), filtered, and concentrated. The residue was purified via gradient flash chromatography (50-100% EtOAc in hexanes, SiO₂) which provided 114 mg (29%) of the BOC protected peptide as a foam.

Step 5

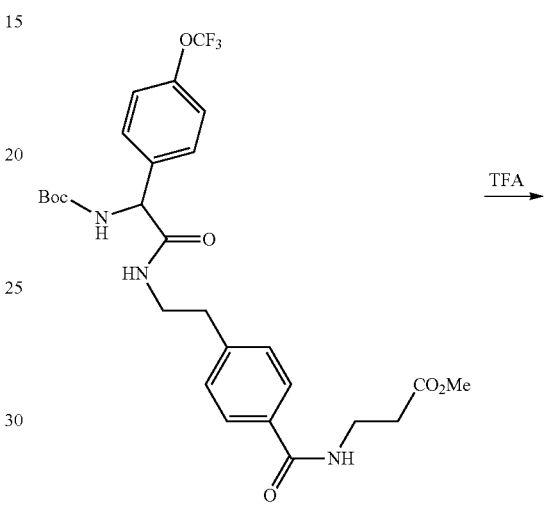

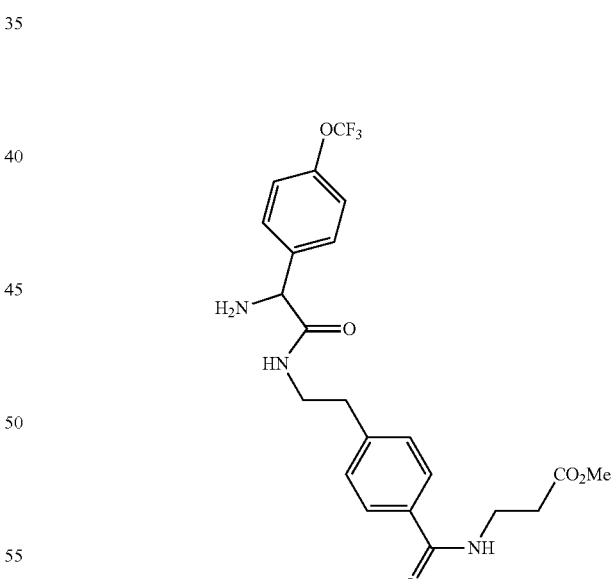

The BOC protected amine (114 mg, 0.2 mmol) and TFA (1 mL) were taken up in DCM (1 mL), and the solution was stirred at 25° C. for 3 h. The solution was concentrated. The residue was partitioned between DCM and 1 N NaOH$_{(aq.)}$. The aqueous layer was extracted with DCM. The combined organic layers were dried (MgSO₄), filtered, and concentrated. The amine was used without further purification.

Step 6

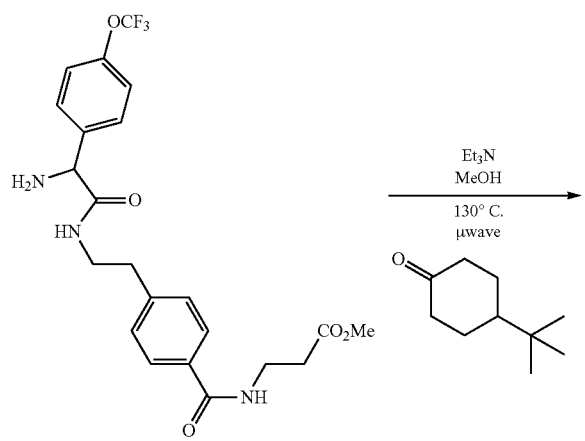

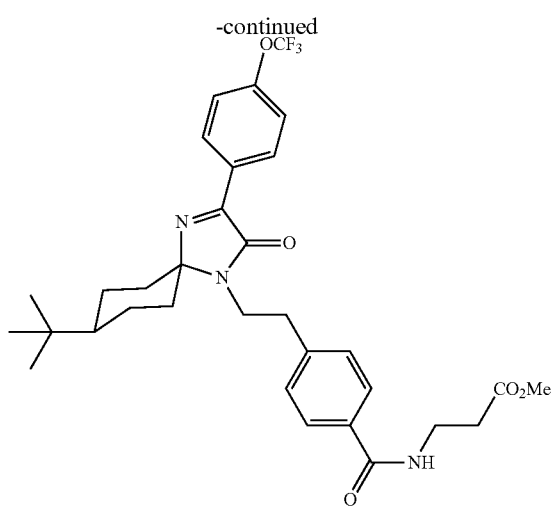

The spiro-amide (88 mg, 0.146 mmol), tBuOCl (40 μL), and Et₃N (100 μL) were used according to Step 4 of Scheme I to provide the imidazolone. The material was purified via gradient flash chromatography (30-50% EtOAc in hexanes, SiO₂) which provide 80 mg (90%) of the methyl ester as a colorless oil.

Step 8

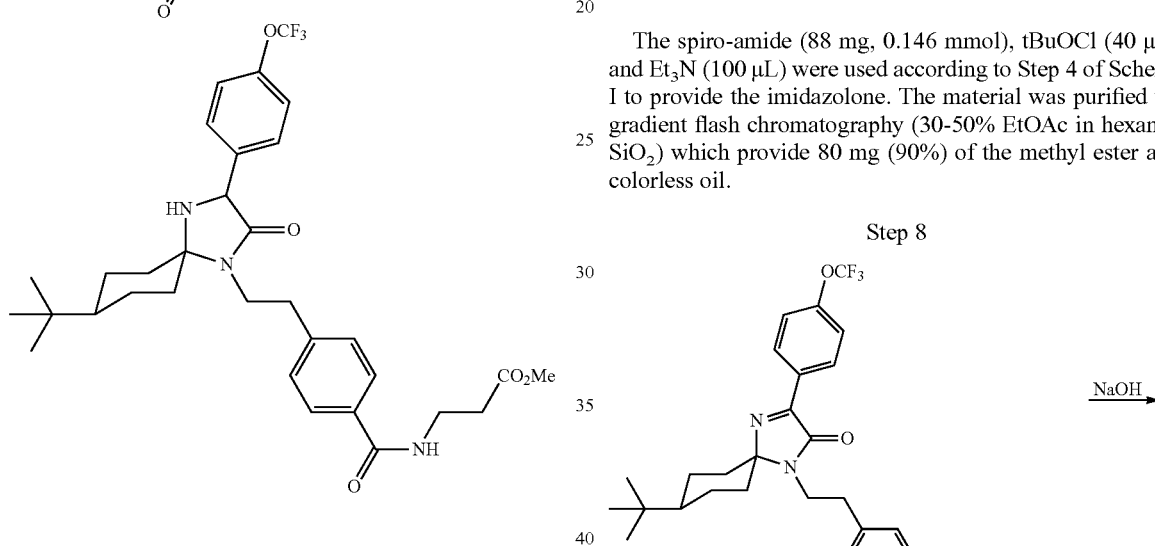

The amine (0.2 mmol), ketone (79 mg, 0.5 mmol), Et₃N (0.1 mL), 4 A mol sieves (125 mg), and MeOH (2 mL) were processed according to Step 3 of Scheme I. The crude material was purified via gradient flash chromatography (30-70% EtOAc in hexanes, SiO₂) which provided 88 mg (73%) of the spiro-amide.

Step 7

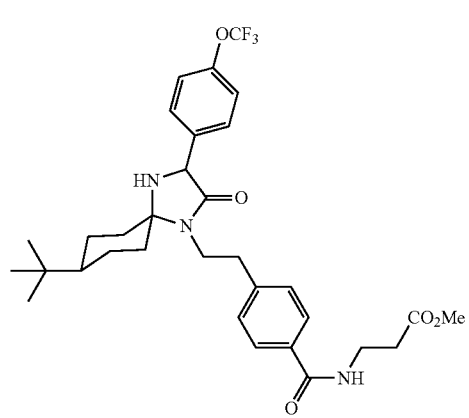

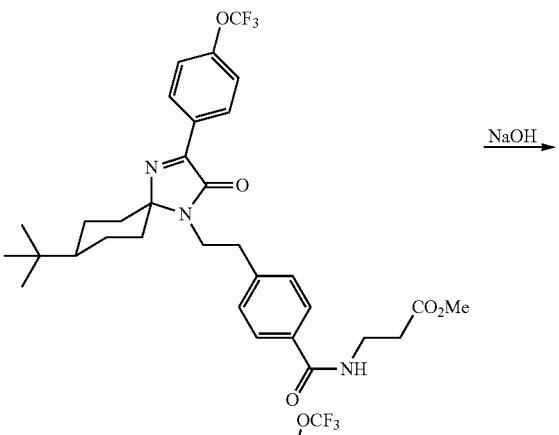

Example 1.98

The methyl ester (80 mg, 0.13 mmol) was taken up in 1 N NaOH(aq.)/MeOH/dioxane (1/1/1, 4.5 ml). The solution was stirred at 25° C. for 18 h. The reaction was concentrated. The residue was acidified with 1 N HCl$_{(aq.)}$. The solution was extracted with EtOAc. The combined organic layers were dried (MgSO$_4$), filtered, and concentrated. The residue was purified via gradient flash chromatography (10-30% MeOH in DCM, SiO$_2$) which provided 75 mg (Quant.) of Example 1.98 as a colorless solid after freeze drying.

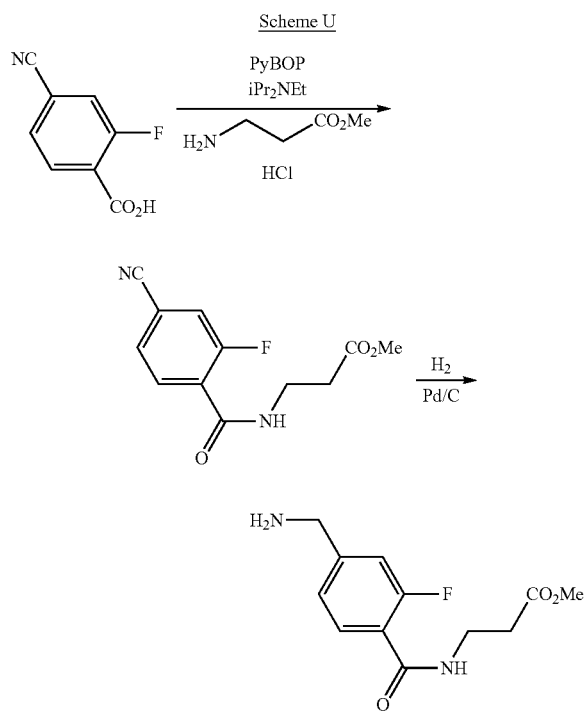

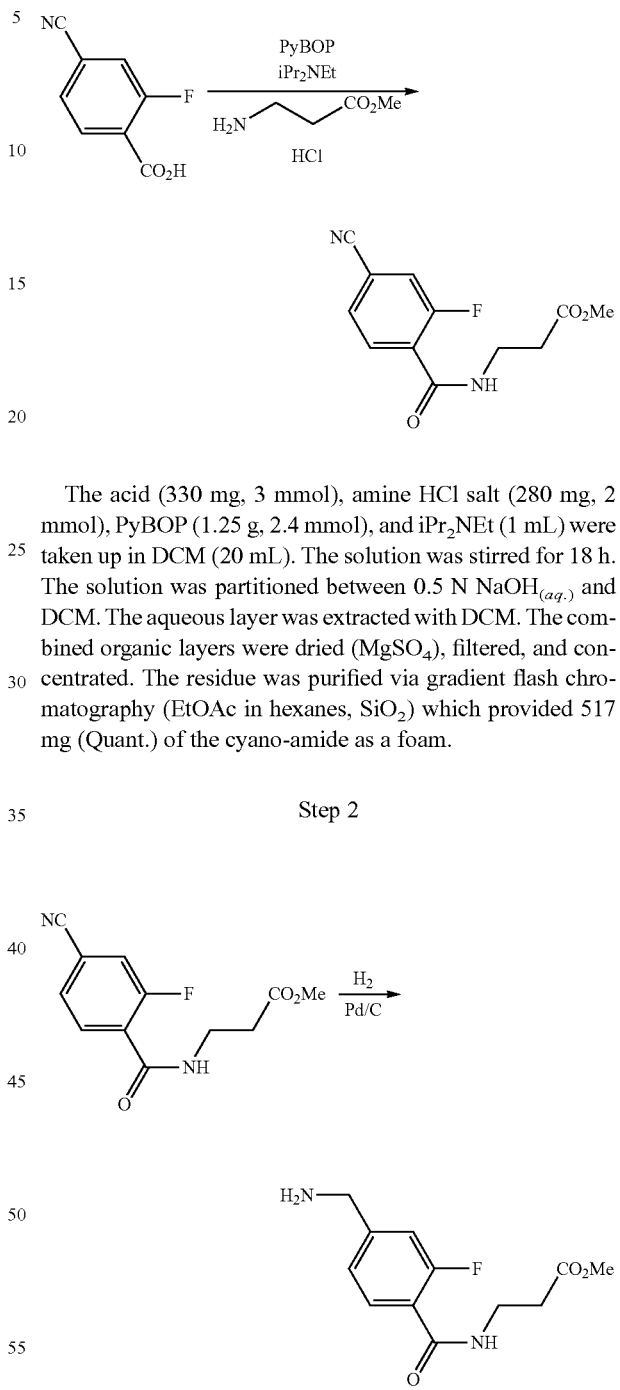

Step 1

The acid (330 mg, 3 mmol), amine HCl salt (280 mg, 2 mmol), PyBOP (1.25 g, 2.4 mmol), and iPr$_2$NEt (1 mL) were taken up in DCM (20 mL). The solution was stirred for 18 h. The solution was partitioned between 0.5 N NaOH$_{(aq.)}$ and DCM. The aqueous layer was extracted with DCM. The combined organic layers were dried (MgSO$_4$), filtered, and concentrated. The residue was purified via gradient flash chromatography (EtOAc in hexanes, SiO$_2$) which provided 517 mg (Quant.) of the cyano-amide as a foam.

Step 2

The cyano-amide (517 mg, 2 mmol) and 10% Pd/C (200 mg) were taken up in EtOH/water/HOAc (10 mL/3 mL/0.3 mL), and the resulting solution was charged with 50 psi H$_2$. After 0.5 h, the solution was filtered (Celite®) and concentrated. The residue was basified with 0.5 N NaOH to pH=11. The solution was extracted with DCM. The DCM layers were dried (MgSO$_4$), filtered, and concentrated which provided 394 mg (79%) of the amine as a colorless oil.

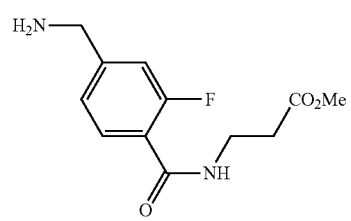
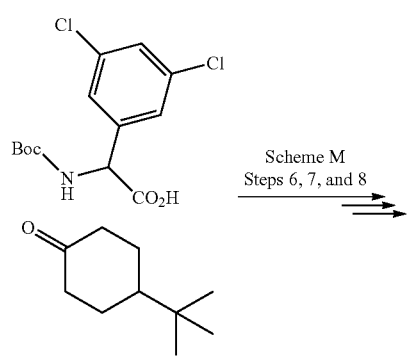
Scheme M
Steps 6, 7, and 8
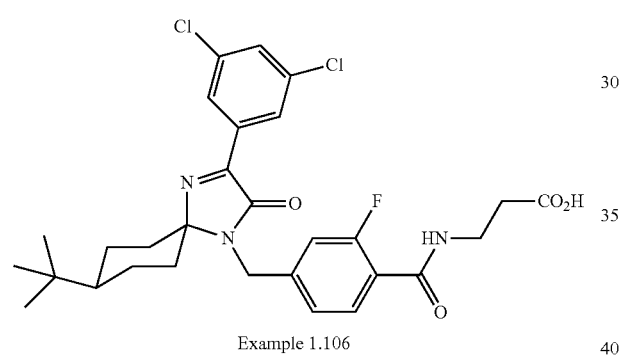
Example 1.106
The amine, N—BOC phenyl glycine, and ketone were processed into Example 1.106 according to the procedures outlined in Scheme M (Steps 6, 7 and 8).
Scheme V
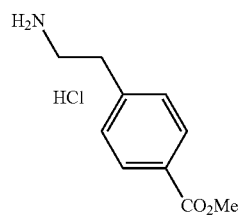
+
Scheme I
Step 1
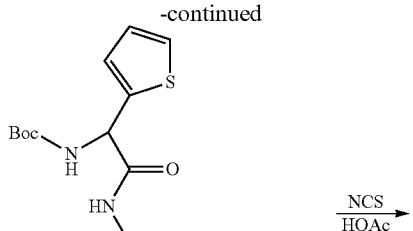
NCS
HOAc
Scheme M
Steps 5-8
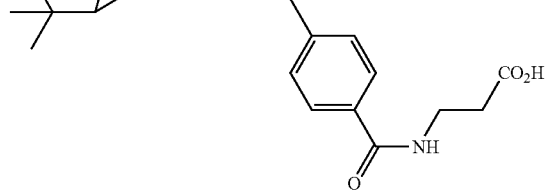
Example 1.110
Step 2
NCS
HOAc

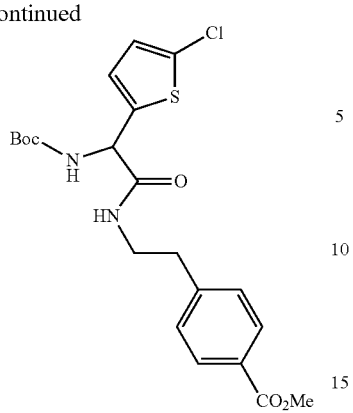

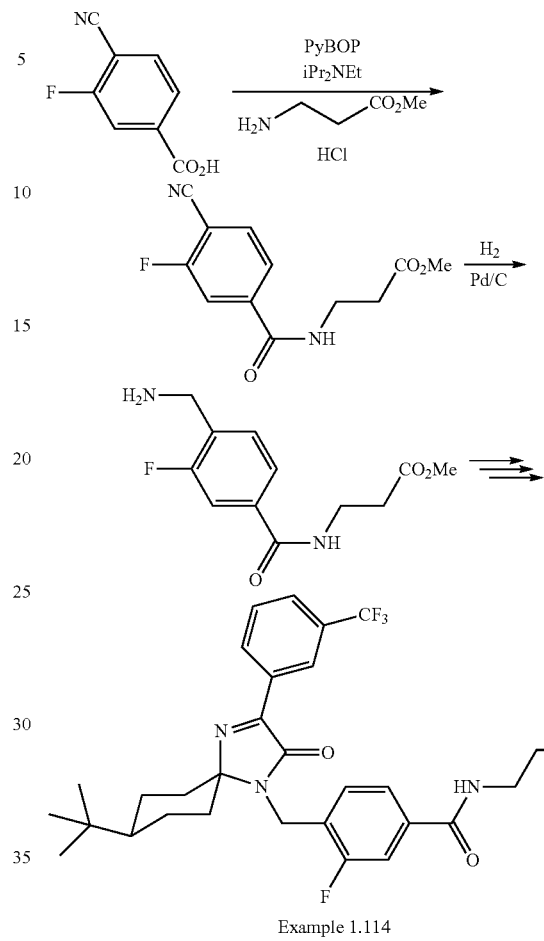

Scheme W

The Boc-amide (1.25 g, 3.0 mmol; prepared according to Scheme I—Step 1 using the appropriate amine and acid) and NCS (1.25 g) were taken up in CHCl$_3$/HOAc (1/1, 50 mL). The solution was heated at reflux for 6 h. The solution was concentrated. The residue was purified via gradient flash chromatography (10-50% EtOAc in hexanes, SiO$_2$) which provided 1.1 g (81%) of the chloro thiophene as a colorless oil.

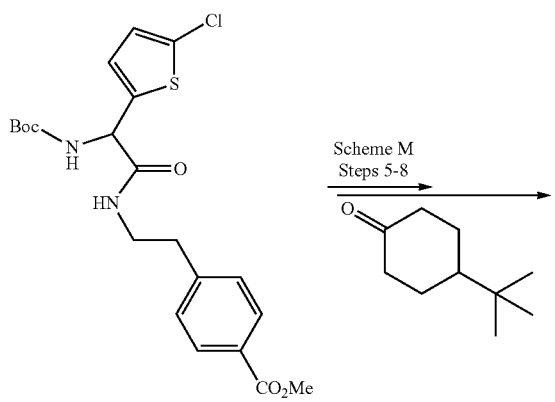

Example 1.114

The benzoic acid in Scheme W was processed according to the procedures outlined in Scheme U to provide Example 1.114.

Scheme X

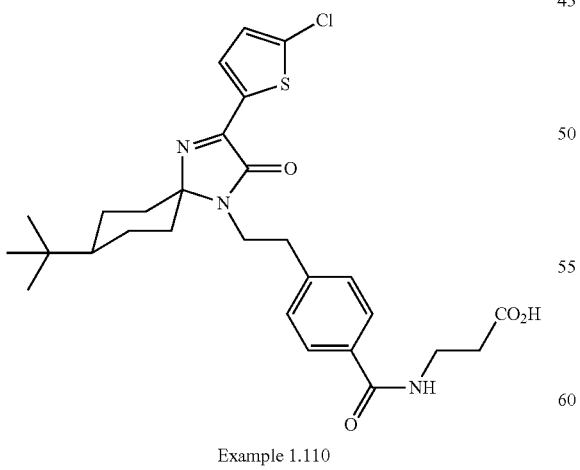

Example 1.110

The BOC protected chloro thiophene was processed according to the procedures outlined in Scheme M (Steps 5-8) to provide Example 1.110.

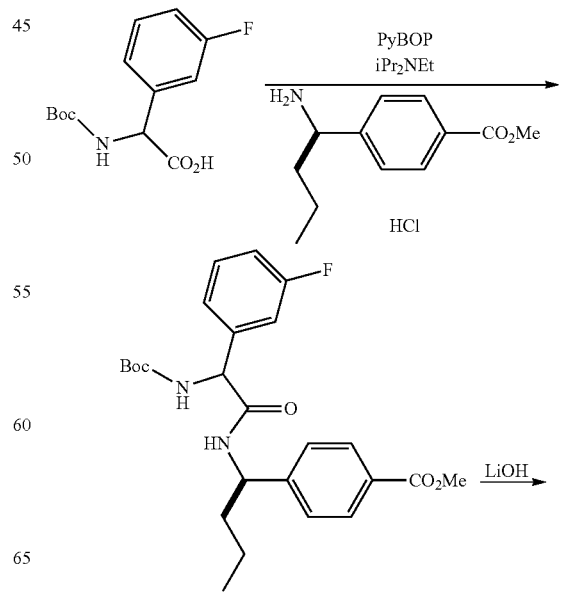

-continued

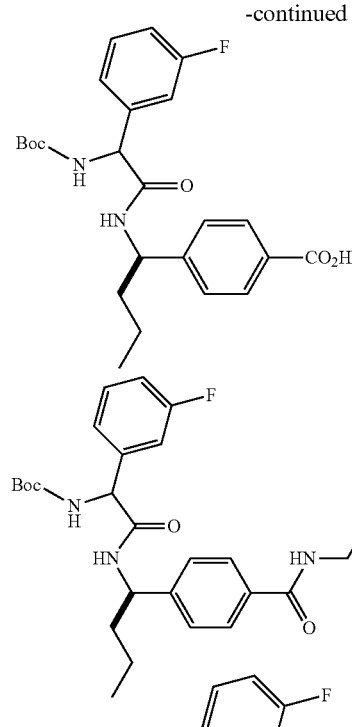

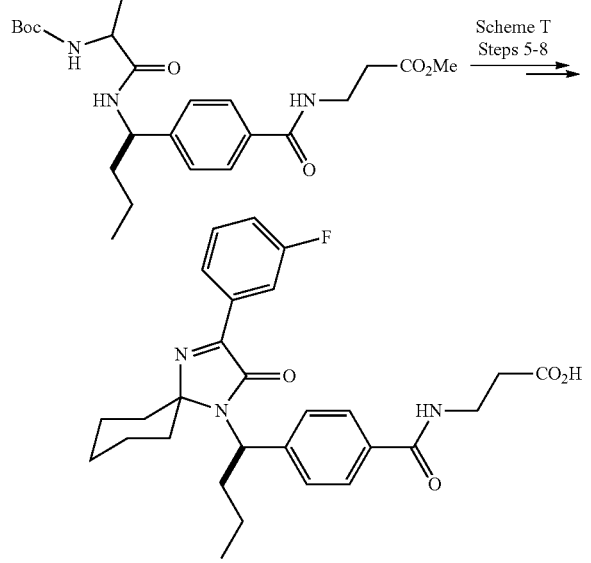

Example 1.117

Step 1

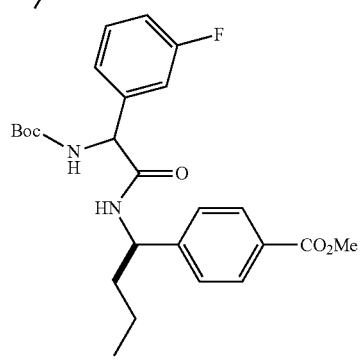

The N—BOC phenyl glycine (1.56 g, 5.8 mmol), amine (1.41 g, 5.8 mmol), PyBOP (3.64 g, 7 mmol), and iPr₂NEt (2.3 mL) were reacted according to the procedure outlined in Scheme I (Step 1) to provide 2.78 g (100%) of the amide as a colorless foam.

Step 2

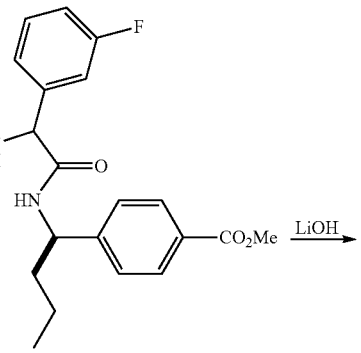

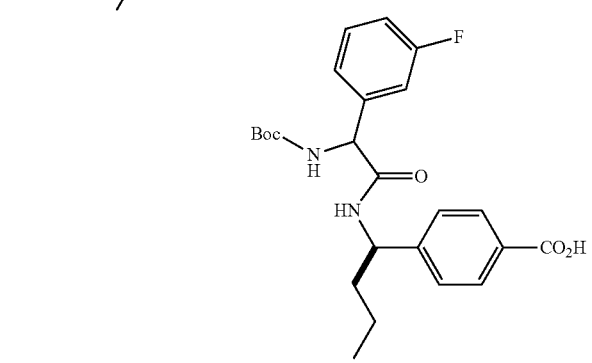

The methyl ester (2.78 g, 6.1 mmol) was dissolved in THF (30 mL), MeOH (10 mL), and 2 M LiOH (12.2 mL). The solution was stirred at 25° C. for 2 h and at 80° C. for 1 h. The solution was concentrated. The residue was taken up in water and neutralized with 2 N HCl (pH=3). The mixture was extracted with DCM. The combined organic layers were dried (MgSO₄), filtered, and concentrated which provided 2.52 g (94%) of the acid as a colorless foam.

Step 3

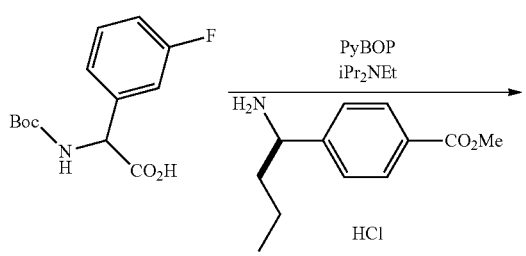

-continued
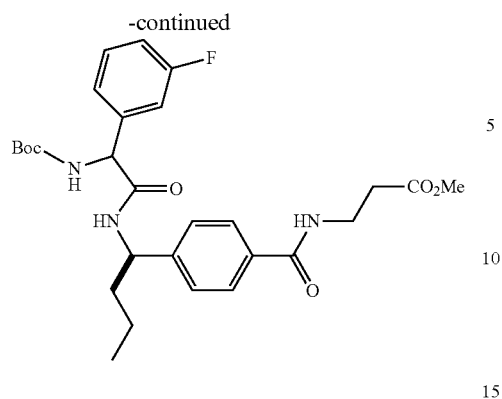
The acid (2.5 g, 5.7 mmol), amine HCl salt (800 mg, 5.7 mmol), PyBOP (3.56 g, 6.84 mmol), and iPr$_2$NEt (3 mL) were processed according to Scheme T (Step 2) to provide the 2.7 g (91%) of the Boc-amine as a colorless foam.
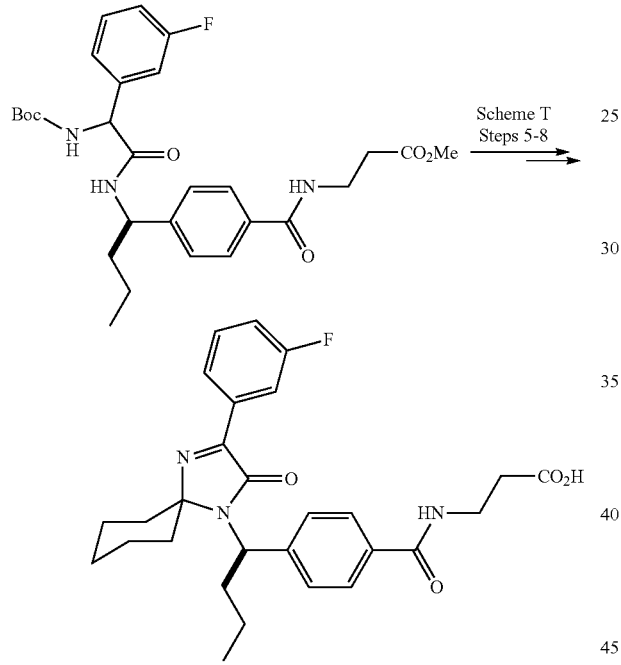
Example 1.117
The BOC amine was processed according to Scheme T (Steps 5-8) to provide Example 1.117.
Scheme Y
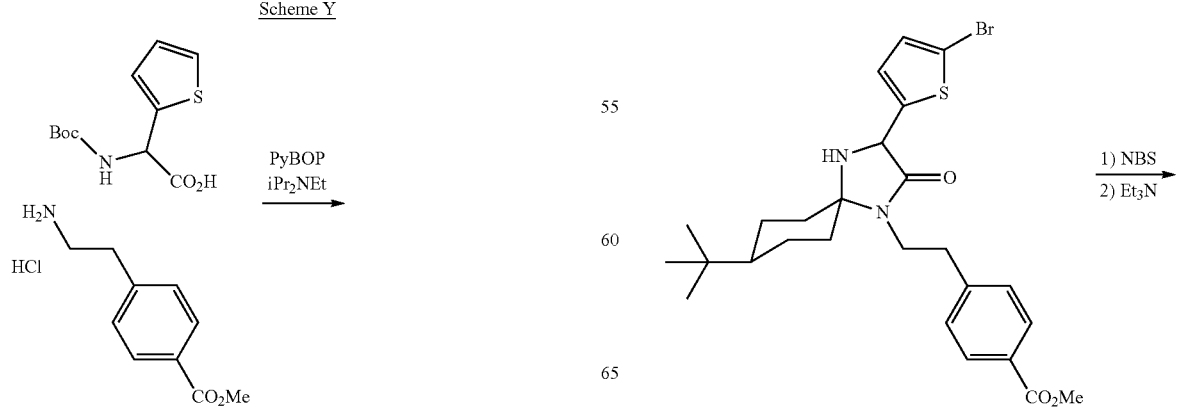
-continued
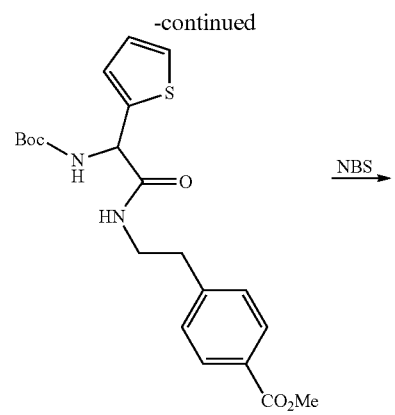
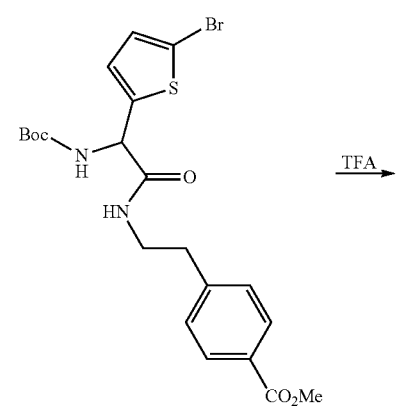
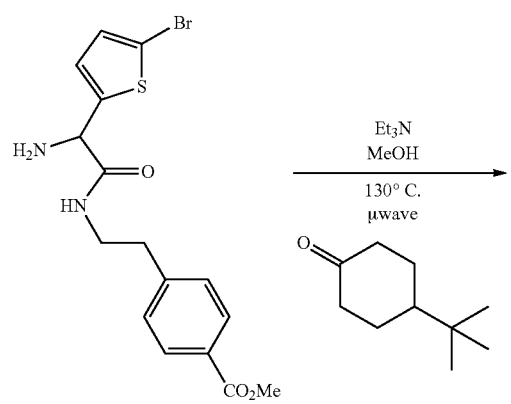

133
-continued
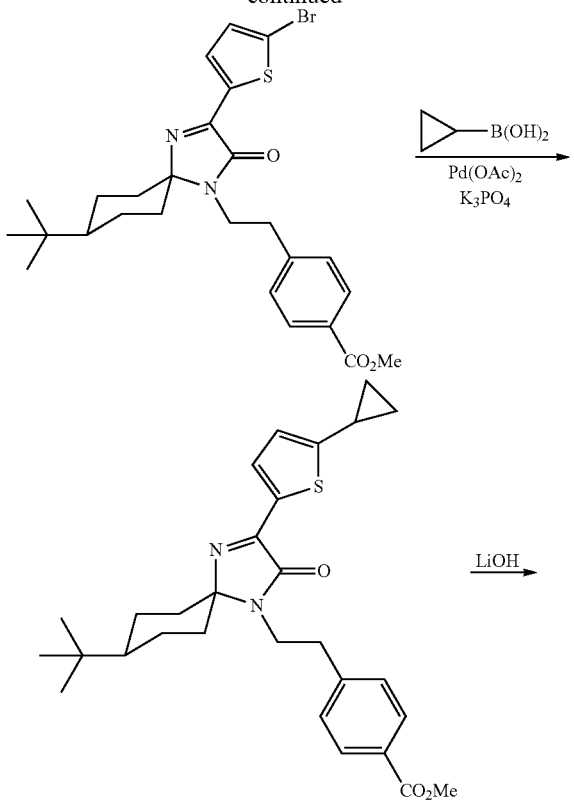
134
Step 1
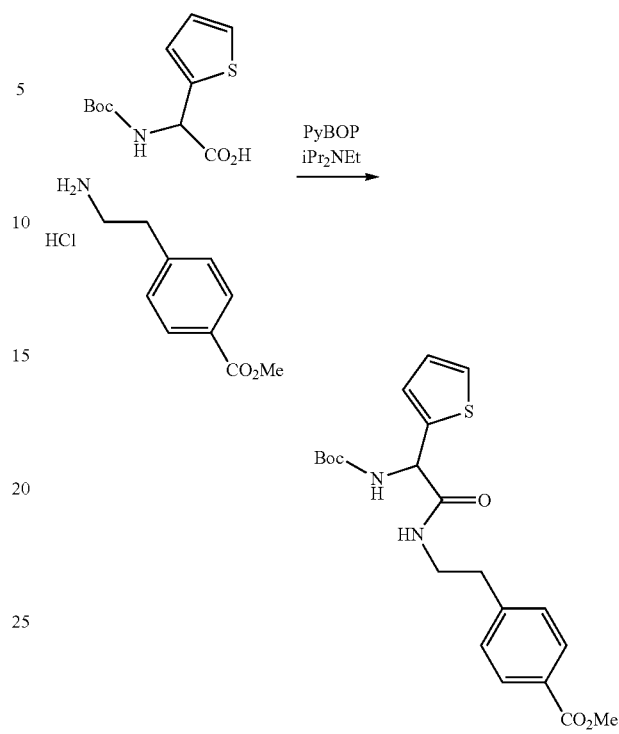
The N—BOC acid and the amine HCl salt were processed according to the procedure outlined in Scheme I (Step 1) to provide the BOC protected amide.
Step 2
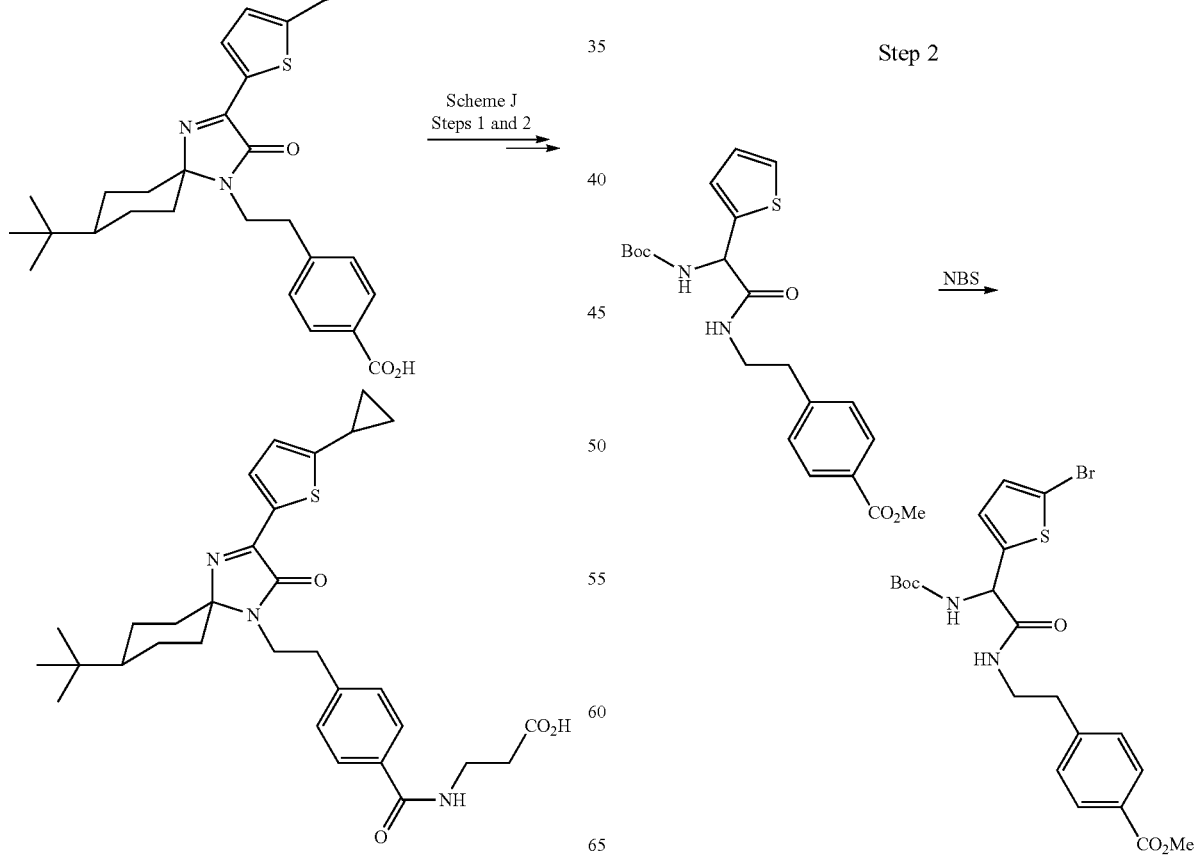

135

The Boc-amide (1.62 g, 3.87 mmol) and NBS (688 mg, 3.87 mmol) were taken up in CHCl₃/HOAc (1/1, 50 mL). The solution was heated at 80° C. for 1 h. The solution was concentrated. The residue was partitioned between EtOAc and sat. NaHCO₃ $_{(aq)}$. The aqueous layer was extracted with EtOAc. The combined organic layers were dried (MgSO₄), filtered, and concentrated. The residue was purified via gradient flash chromatography (0-30% EtOAc in hexanes, SiO₂) provided 424 mg (22%) of the bromo thiophene as an oil.

Step 3

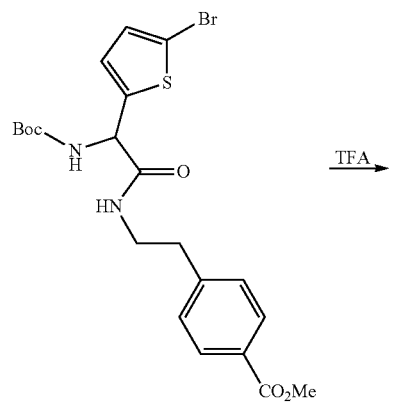

The Boc-amine was processed into the amine using the conditions outlined in Scheme T Step 5.

Step 4

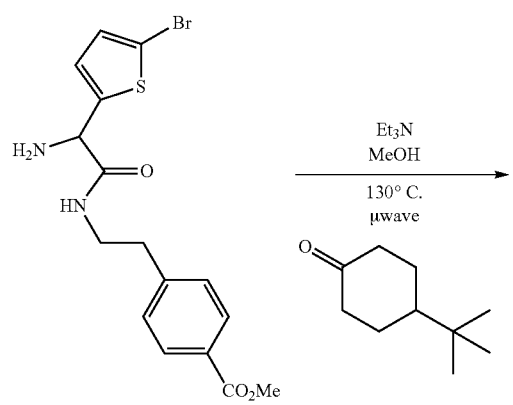

136

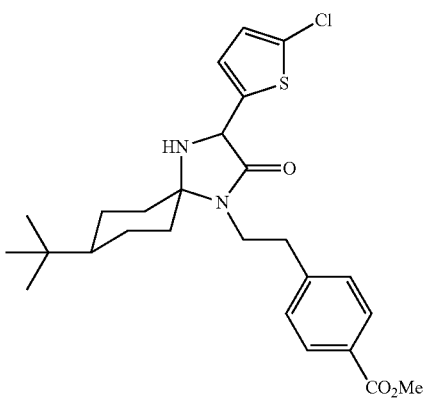

The amine was processed into the spiro-amide using conditions outlined in Scheme T Step 6.

Step 5

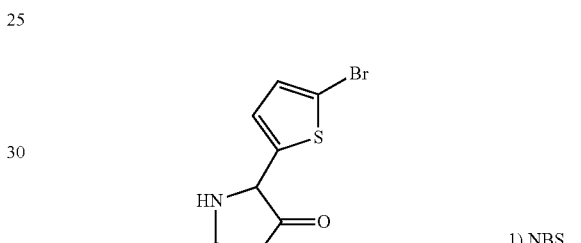

The spiro-amide (589 mg, 1.1 mmol) was taken up in DCM (20 ml), and NBS (235 mg, 1.32 mmol) was added. After stirring at 25° C. for 1 h, triethylamine (445 mg, 4.4 mmol) was added, and the solution was stirred at 25° C. for 2 h. The solution was concentrated. The residue was purified via gradient flash chromatography (0-20% EtOAc in hexanes, SiO₂) which provided 386 mg (66%) of the bromo thiophene as a white solid.

Step 6

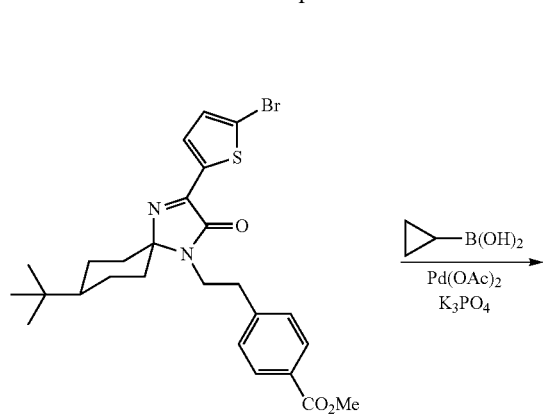

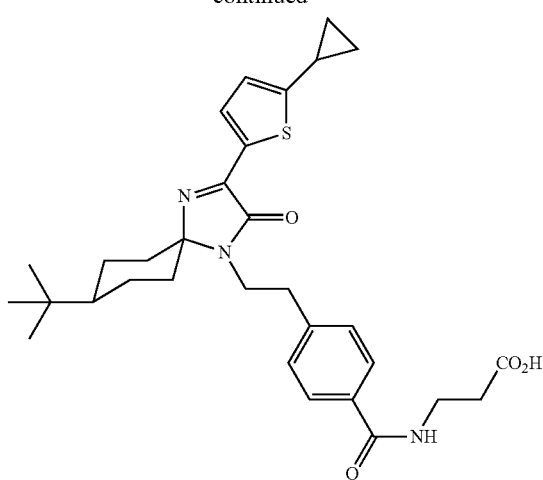

Example 1.120

The product from the previous step was processed according to Scheme J (Steps 1 and 2) to furnish Example 1.120.

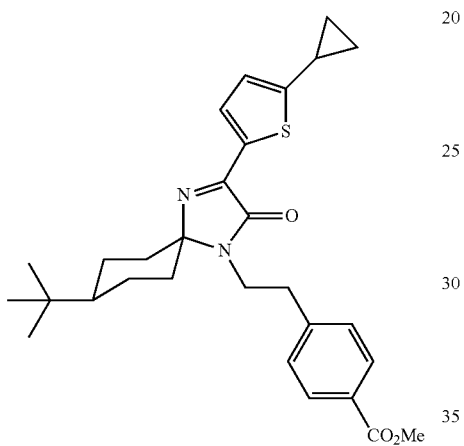

The bromo thiophene (55 mg, 0.1 mmol), cyclopropyl boronic acid (12 mg, 0.13 mmol), Pd(OAc)$_2$ (1 mg), PCy$_3$ (3 mg), and K$_3$PO$_4$·H$_2$O (83 mg, 0.36 mmol) were taken up in toluene/water (2 mL/0.1 mL), and the mixture was heated in a sealed tube at 100° C. for 3 h. The mixture was diluted with EtOAc, filtered, and concentrated. The residue was purified via gradient flash chromatography (0-20% EtOAc in hexanes, SiO$_2$) which provided 40 mg (79%) of the cyclopropyl thiophene as a white solid.

Scheme Z

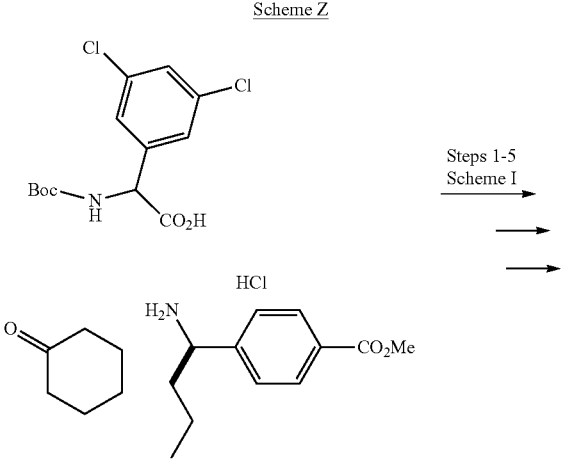

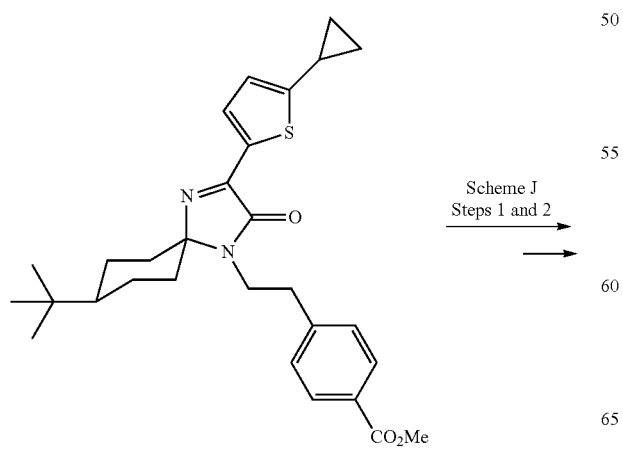

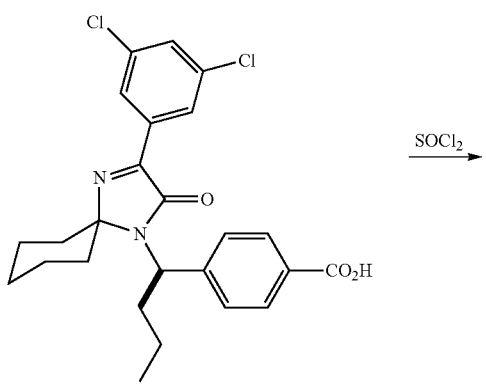

Step 1

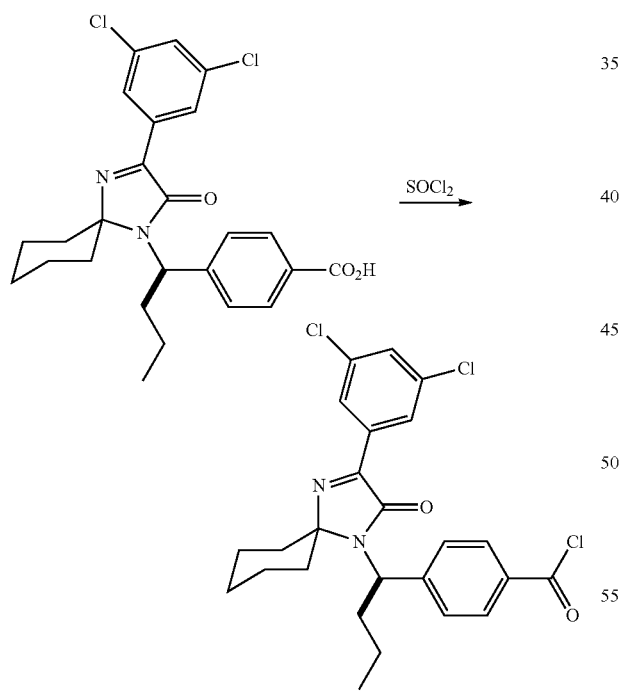

The acid (106 mg, 0.22 mol; prepared according to Scheme I Steps 1-5 using the appropriate amino acid, amine, and ketone) was taken up in DCM (8 mL), and thionyl chloride (0.5 mL, 0.72 mmol) was added. The solution was heated at 55° C. for 3 h. The solution was concentrated with 3 volumes of DCM. The residue was dried under high vacuum for 18 h which provided the acid chloride as a foam. This material was used without further purification.

Step 2

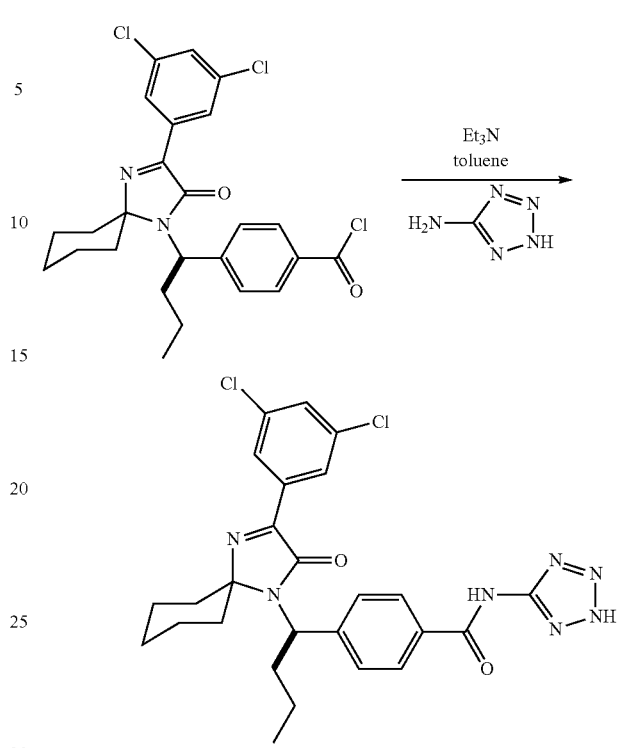

Example 1.140

The acid chloride from the previous step was processed into Example 1.140 using the conditions described in Scheme D Step 2.

Scheme AA

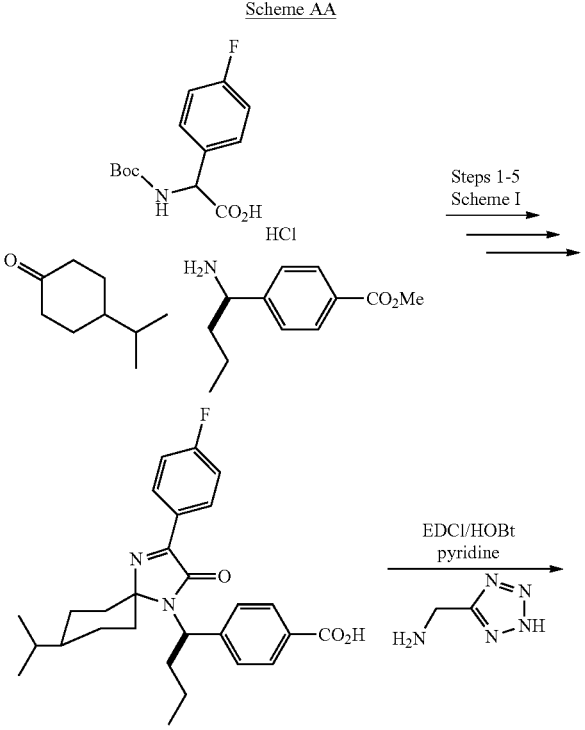

Scheme AB

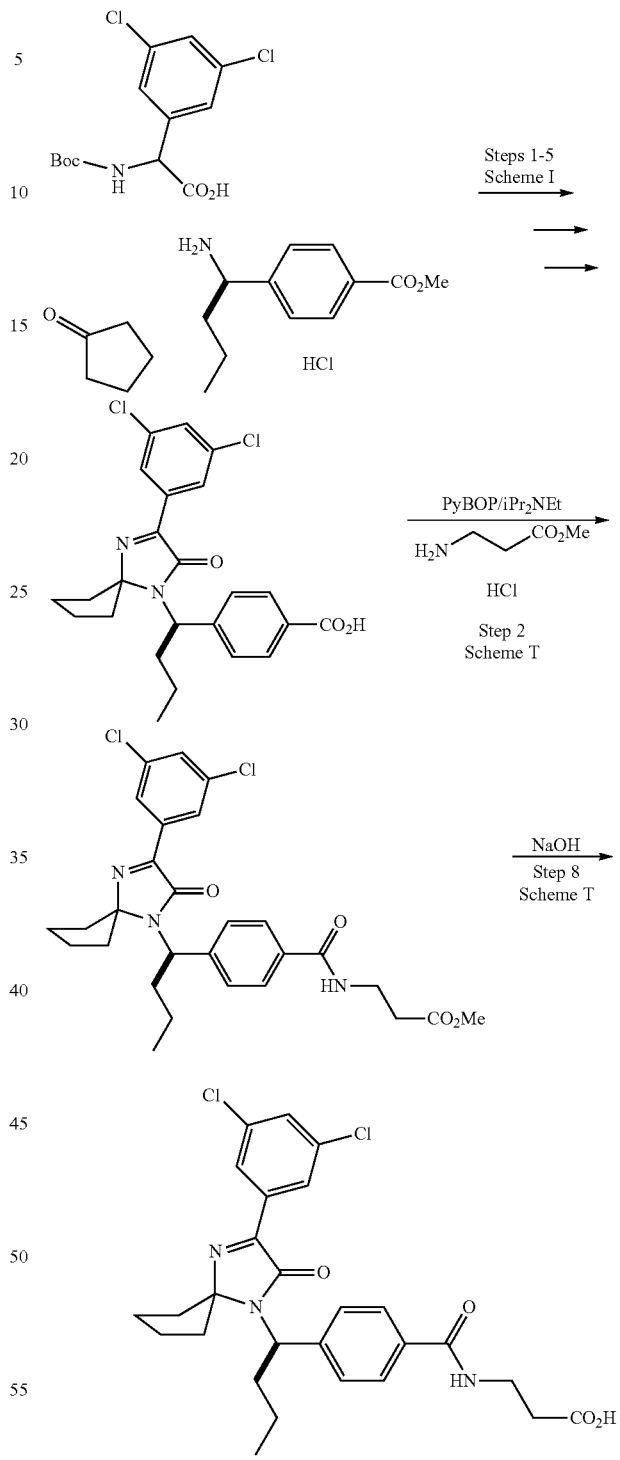

Step 1

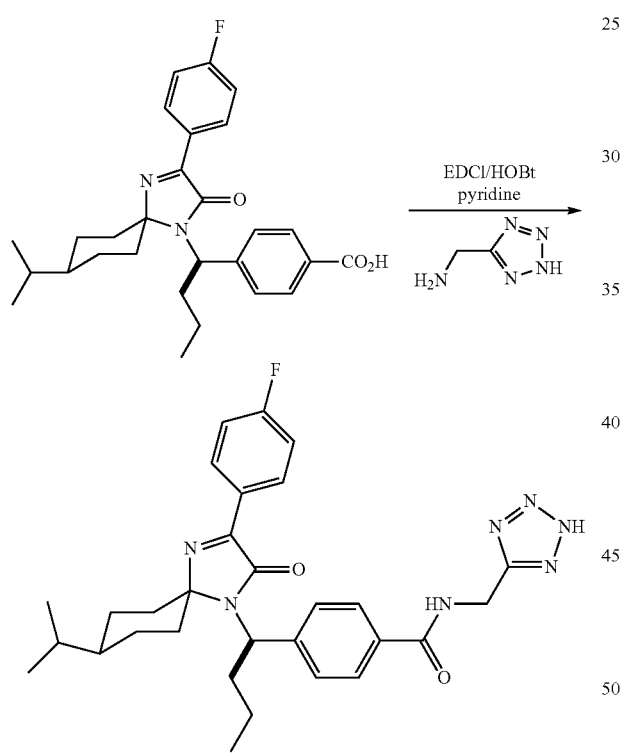

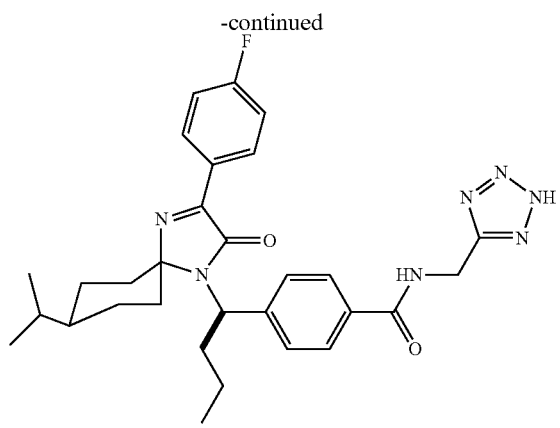

Example 1.145

The acid (220 mg, 0.47 mmol; prepared according to Scheme I (Steps 1-5) using the appropriate amino acid, amine, and ketone), EDCl (150 mg, 0.78 mmol), 4 Å mol. sieves (100 mg), and HOBt (106 mg, 0.78 mmol) were taken up in pyridine (6 mL). The mixture was stirred at 50° C. for 3 h and then at 25° C. for 18 h. The solution was concentrated. The residue was purified via gradient flash chromatography (0-10% MeOH in DCM, SiO$_2$). Additional purification using preparative thin-layer chromatography (10/2/0.3 DCM/MeOH/HOAc, SiO$_2$) provided 55 mg (21%) of Example 1.145 as an off-white solid.

The amino acid, amine, and ketone were converted into the acid using procedures outlined in Scheme I (Steps 1-5). The acid was subsequently converted into Example 1.149 using Steps 2 and 8 of Scheme T.

143
Scheme AC
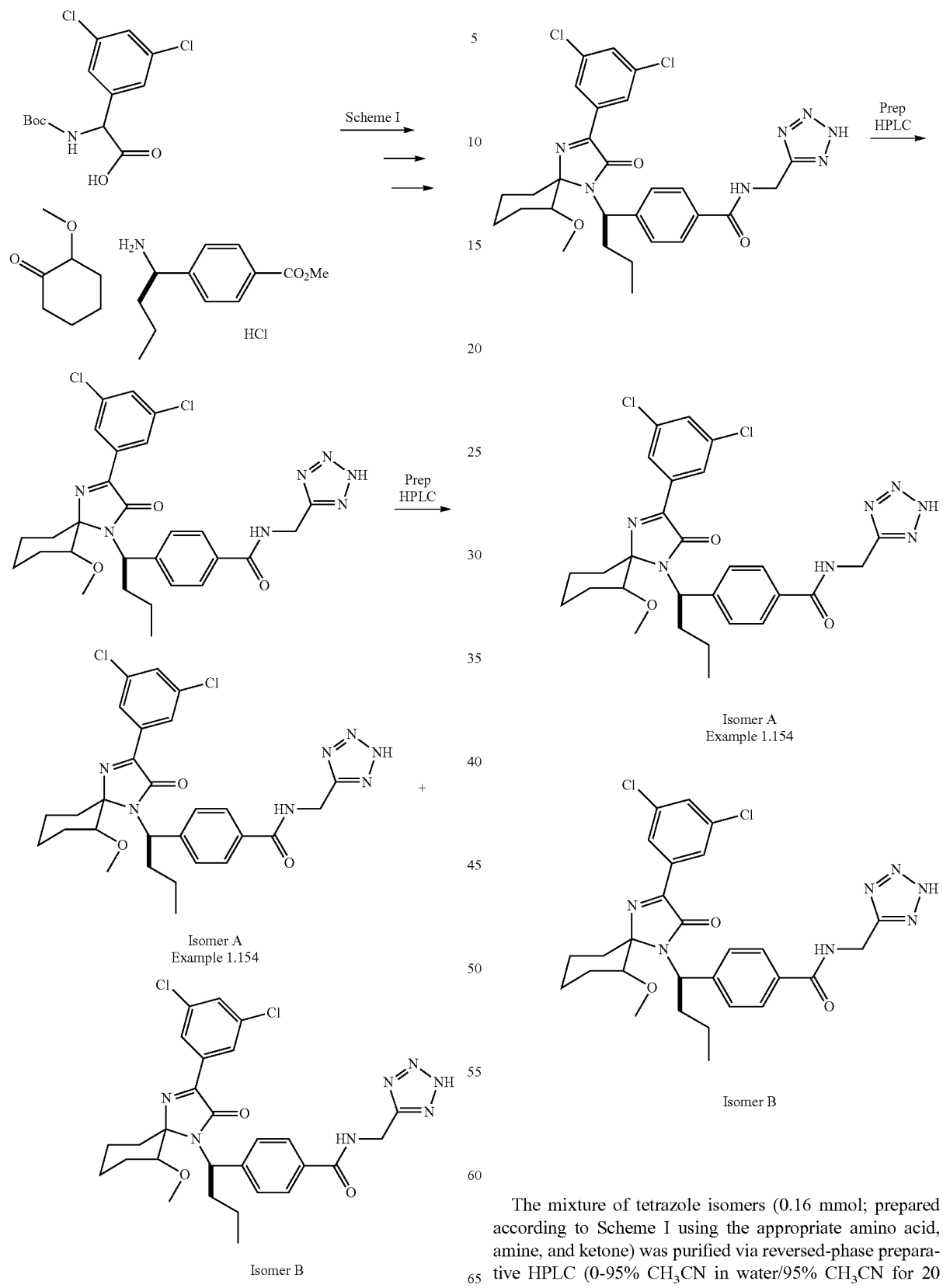
Step 1
The mixture of tetrazole isomers (0.16 mmol; prepared according to Scheme I using the appropriate amino acid, amine, and ketone) was purified via reversed-phase preparative HPLC (0-95% CH$_3$CN in water/95% CH$_3$CN for 20 minutes) to provide 29 mg (31%) of Example 1.154 (Isomer A; faster eluting) and 31 mg (33%) of Isomer B.

Scheme AD
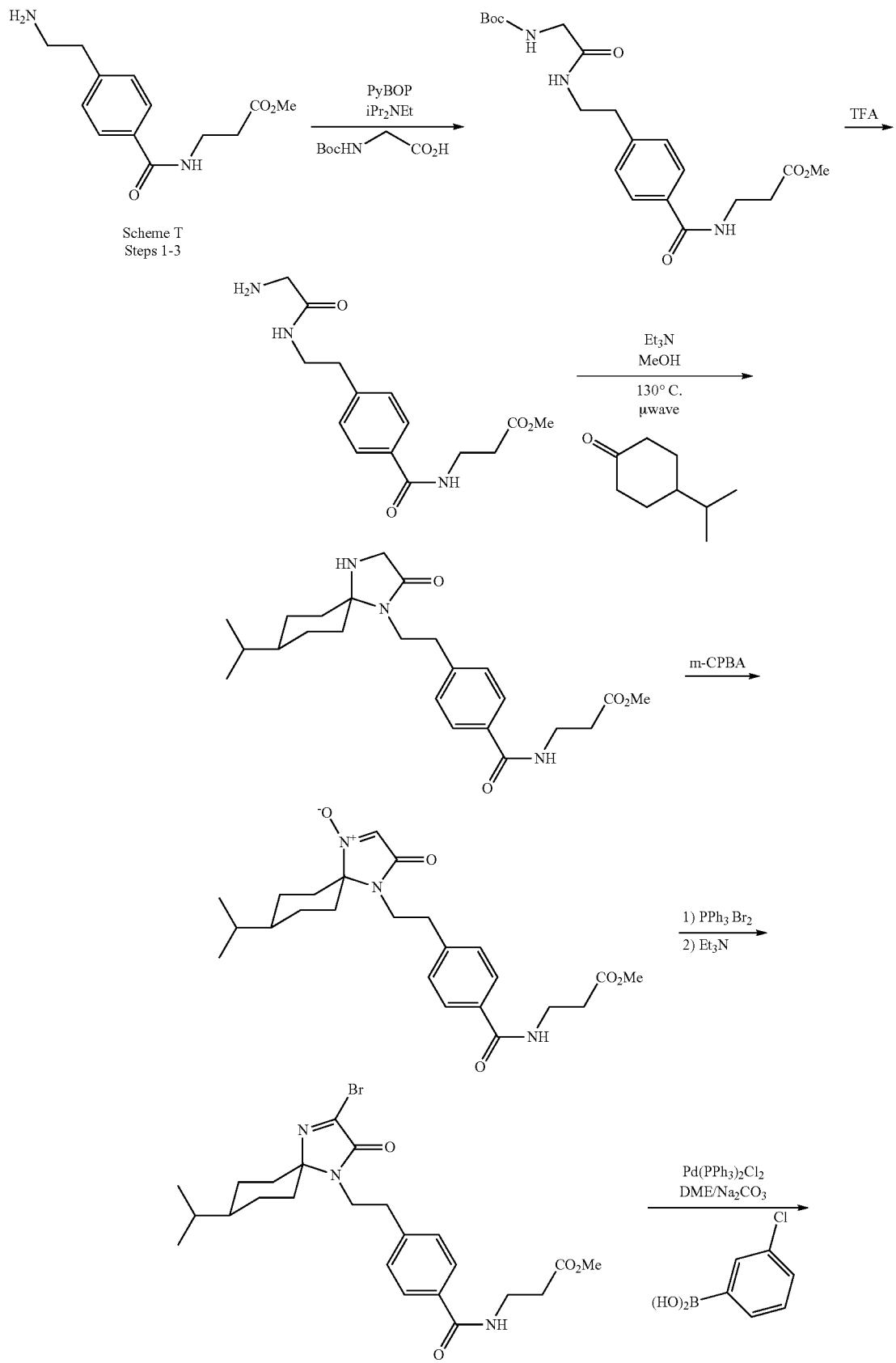

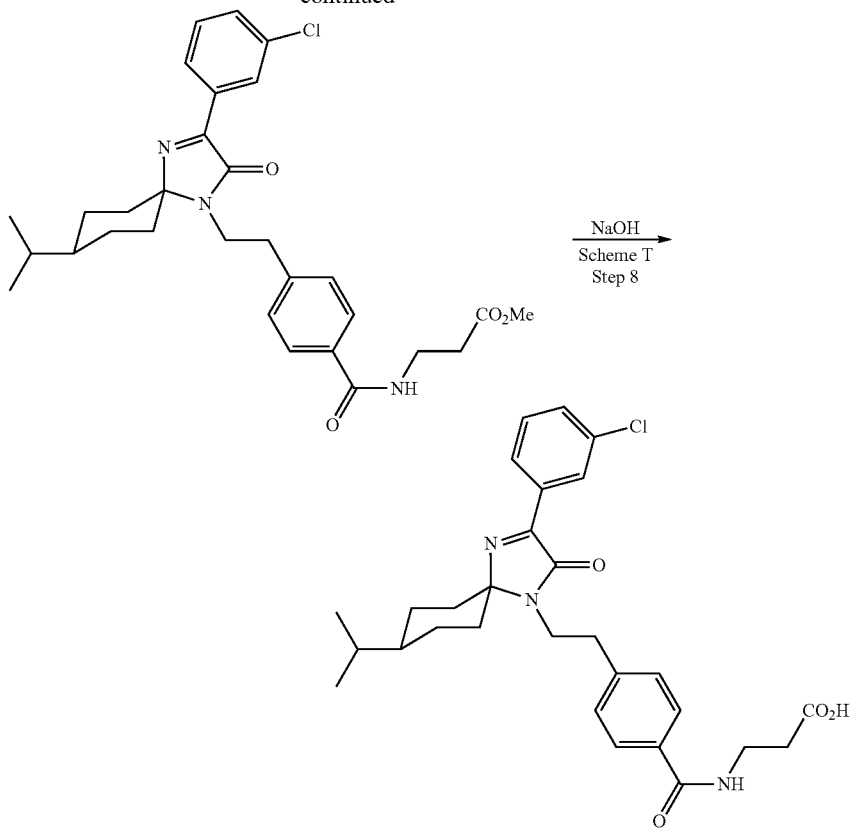

Example 2.1

Step 1

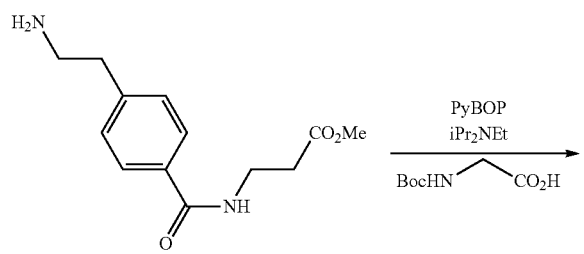

The amine (572 mg, 2 mmol; prepared according to Scheme T Steps 1-3), N—BOC glycine (350 mg, 2 mmol), PyBOP (1.2 g, 2.4 mmol), and iPr₂NEt (1 mL) were taken up in DMF (10 mL), and the resulting solution was stirred at 25° C. for 18 h. The solution was partitioned between EtOAc and sat. NaHCO$_{3(aq.)}$. The aqueous layer was extracted with EtOAc. The combined organic layers were washed with brine and dried (MgSO₄). The mixture was filtered and concentrated. The residue was purified via gradient flash chromatography (0-30% MeOH in DCM, SiO₂) provided the desired product contaminated with the PyBOP by-product. The residue was treated with 20 mL of EtOAc. The formed precipitate was collected and dried under high vac. This provided 730 mg (90%) of the Boc-protected amide.

Step 2

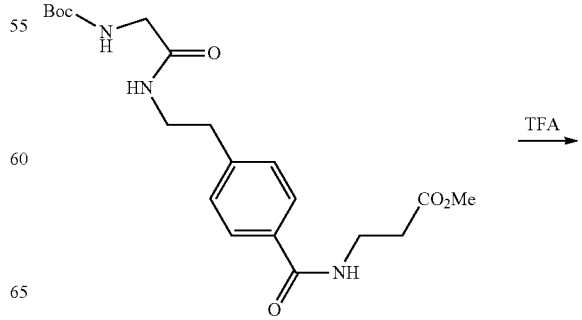

-continued

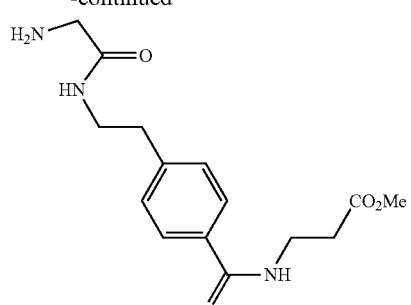

The Boc-amine (370 mg, 0.9 mmol) and TFA (4 mL) were taken up in DCM (4 mL). The solution was stirred at 25° C. for 18 h. The solution was concentrated, and the residue was partitioned between DCM and 1 N NaOH. The aqueous layer was extracted with DCM. The combined organic layers were dried (MgSO$_4$), filtered, and concentrated. The amine was used without further purification.

Step 3

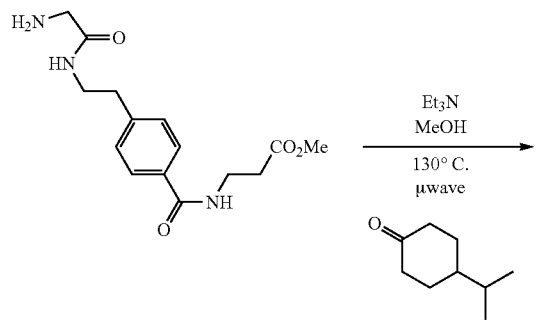

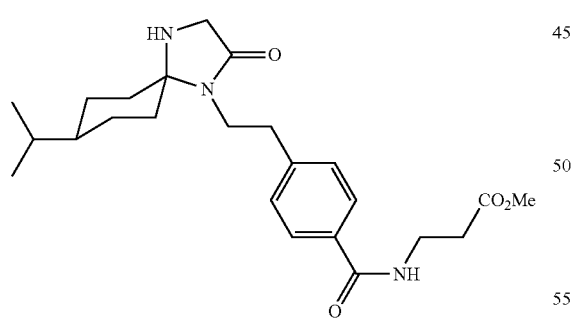

The amine from the previous step (0.9 mmol), ketone (3 mmol), Et$_3$N (3 mmol), and 4 A mol. sieves (1 g) were taken up in MeOH (8 ml), and the mixture was subjected to microwave conditions (Biotage—130° C. for 4 h). The mixture was filtered and concentrated. The residue was purified via gradient flash chromatography (0-100% EtOAc in hexanes, SiO$_2$) to provide 281 mg (73%) of the spiro-amide as a pale yellow solid.

Step 4

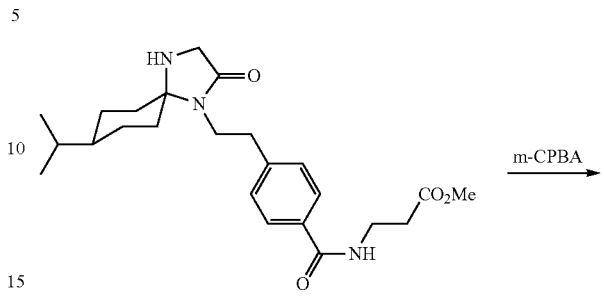

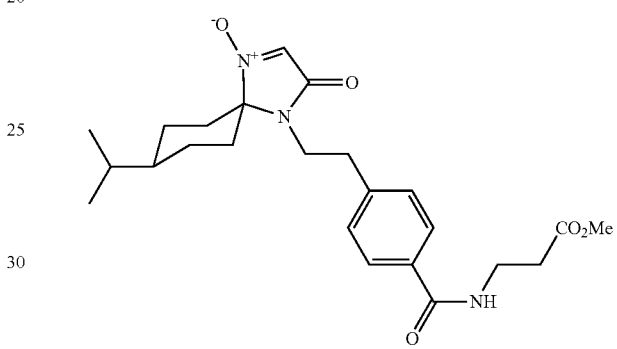

The spiro-amide (280 mg, 0.65 mmol) was taken up in DCM (4 mL) at 0° C., and m-CPBA (440 mg, 1.96 mmol; 77%) was added at 0° C. After stirring at 0° C. for 3 h, the reaction was quenched with 3 ml of 10% Na$_2$S$_2$O$_3$ solution. The mixture was partitioned between sat. NaHCO$_3$ and DCM. The aqueous layer was extracted with DCM. The combined organic layers were dried (MgSO$_4$), filtered, and concentrated. The residue was purified via flash chromatography (EtOAc, SiO$_2$) which provided 250 mg (87%) of the nitrone as an oil.

Step 5

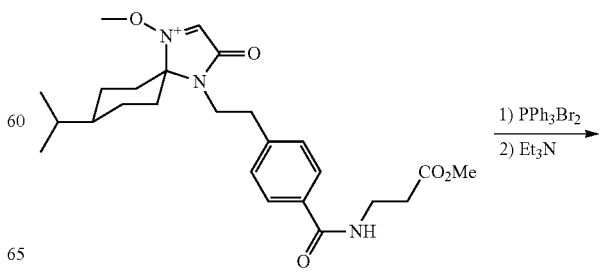

-continued

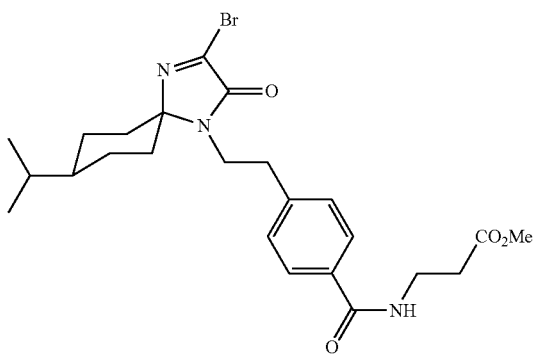

Triphenylphosphine (220 mg, 0.84 mmol) was taken up in DCM (1 mL), and bromine (40 μL) was added at 0° C. After stirring at 0° C. for 15 minutes, the nitrone (250 mg, 0.56 mmol) and triethylamine (0.17 mmol) was added at 0° C. The solution was warmed to 25° C. and stirred at that temperature for 1 h. The solution was diluted with DCM and washed with brine. The aqueous layer was extracted with DCM. The combined organic layers were dried (MgSO$_4$), filtered, and concentrated. The residue was purified via gradient flash chromatography (0-40% EtOAc in hexanes, SiO$_2$) to provide the desired product contaminated with triphenylphosphine oxide. The material was purified via gradient flash chromatography (0-30% EtOAc in hexanes, SiO$_2$) which provided 60 mg (21%) of the bromide as an oil.

Step 6

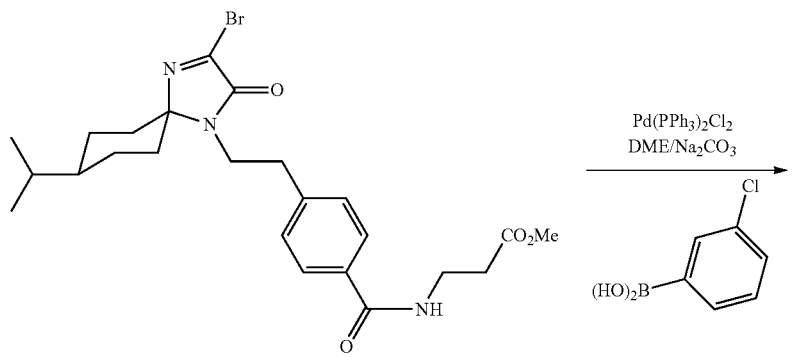

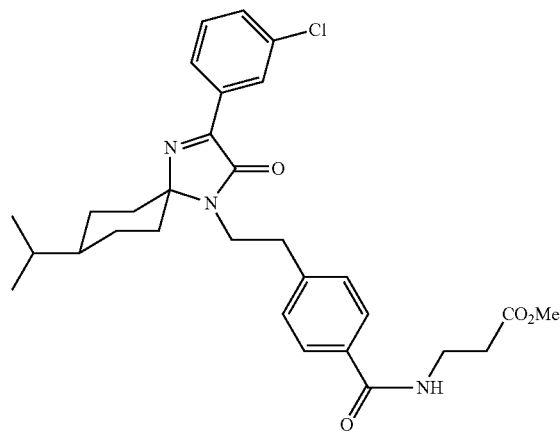

The bromide (60 mg, 0.12 mmol), Pd(PPh$_3$)$_2$Cl$_2$ (4 mg), Na$_2$CO$_3$ (0.5 mL of a 2 M solution), and the boronic acid (40 mg, 0.24 mmol) were taken up in DME (1 mL) and heated at 85° C. for 4 h in a sealed tube. The reaction was partitioned between 1 M HCl and EtOAc. The aqueous layer was extracted with EtOAc. The combined organic layers were washed with brine and dried (Na$_2$SO$_4$). The mixture was filtered and concentrated. The residue was purified via gradient flash chromatography (0-30% EtOAc in hexanes, SiO$_2$) provided 50 mg (77%) of the arylated imidazolone as a colorless oil.

Step 7

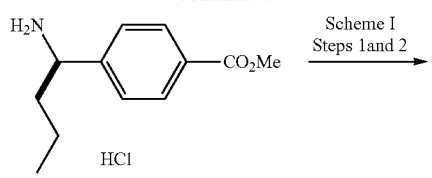

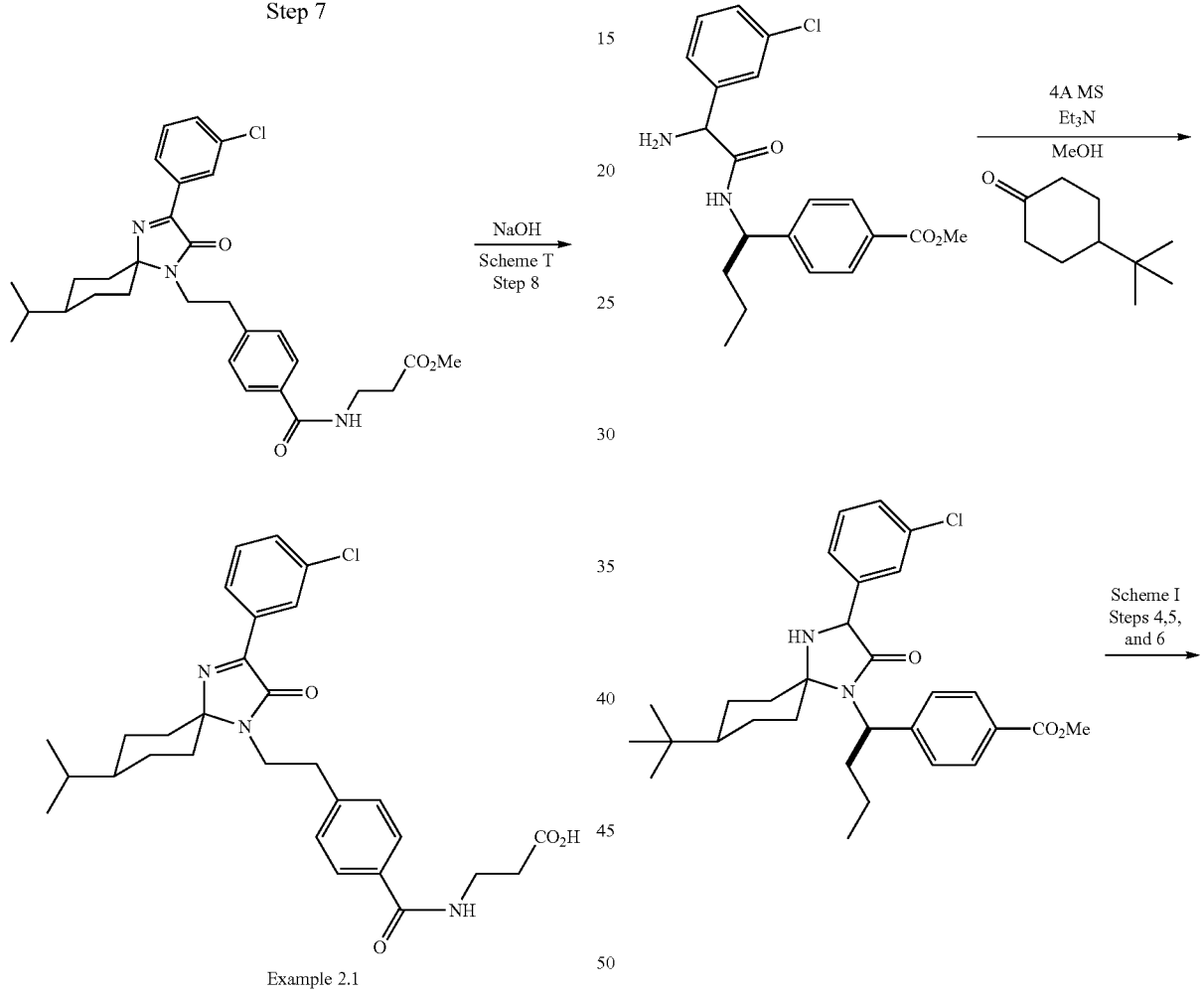

Example 2.1

The methyl ester was processed into Example 2.1 using the conditions outlined in Scheme T (Step 8).

Scheme AE

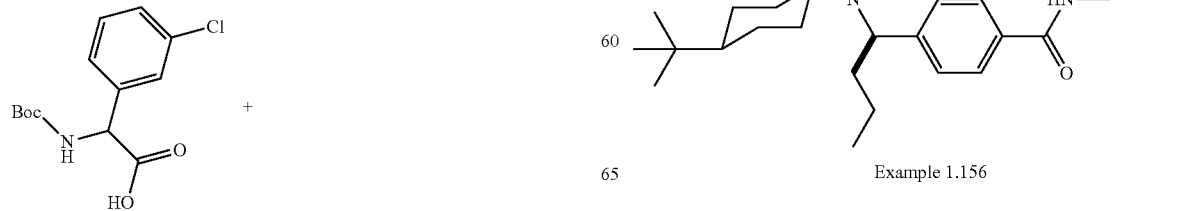

Example 1.156

Step 1

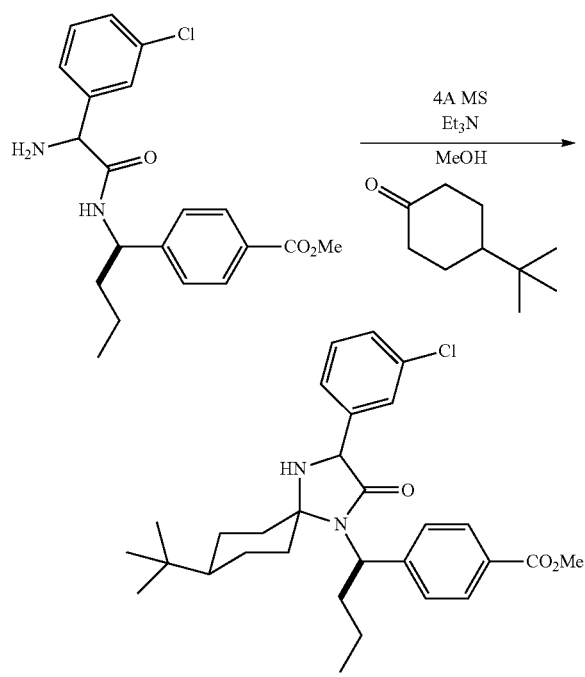

The amine (1 g, 3.5 mmol; prepared according to Scheme I (Steps 1 and 2), 4 Å mol. sieves (1 g), Et$_3$N (3 ml), and the ketone (3.3 g, 21 mmol) were taken up in MeOH (15 ml). The mixture was placed into a sealed tube and heated at 100° C. for 7 h. The mixture was filtered and concentrated. The residue was purified via gradient flash chromatography (2-10% MeOH in DCM, SiO$_2$) which provided the spiro-amide (2.5 g) contaminated with ~15% of the ketone. This material was used without further purification.

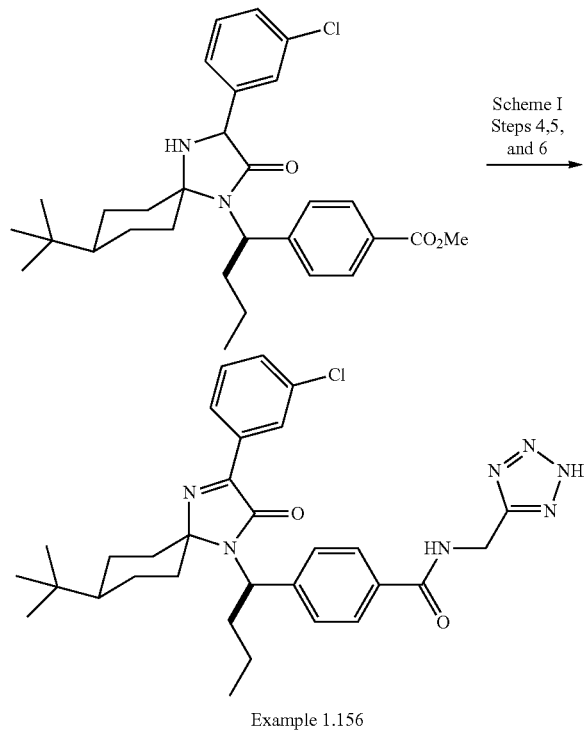

Example 1.156

The spiro-amide was processed into Example 1.156 using the conditions outlined in Scheme I (Steps 4, 5, and 6)

Scheme AF

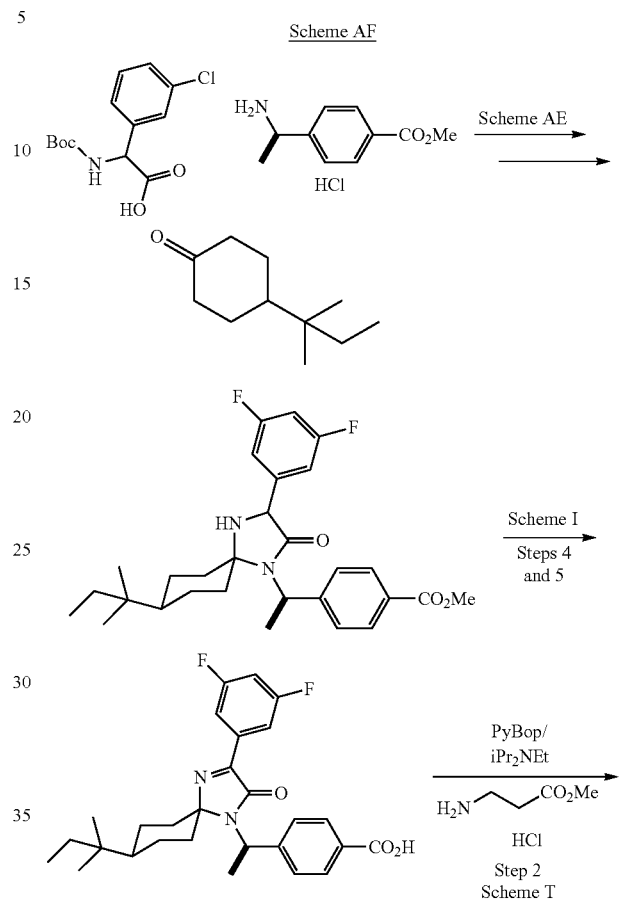

Example 1.164

The amino acid, amine, and ketone were converted into the methyl ester using procedures outlined in Scheme AE. The methyl ester was subsequently converted into Example 1.164 using Steps 2 and 8 of Scheme T.

Scheme AG

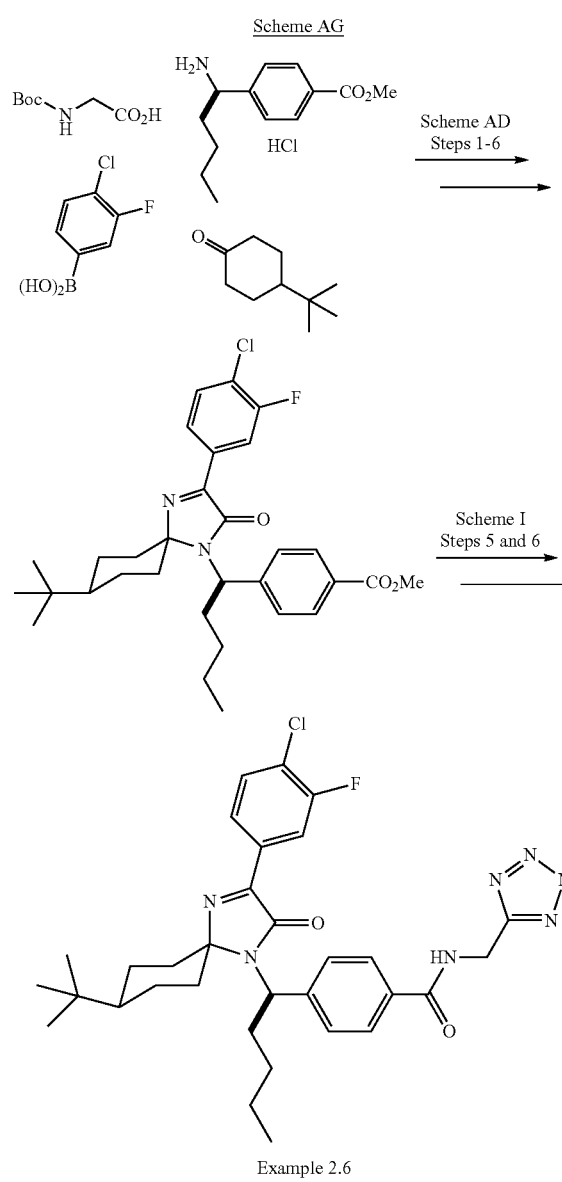

Example 2.6

The Boc-protected amino acid, amine, ketone, and boronic acid were converted into the methyl ester following procedures outlined in Scheme AD (Steps 1-5). The methyl ester was converted into Example 2.6 using Steps 5 and 6 of Scheme I.

Scheme AH

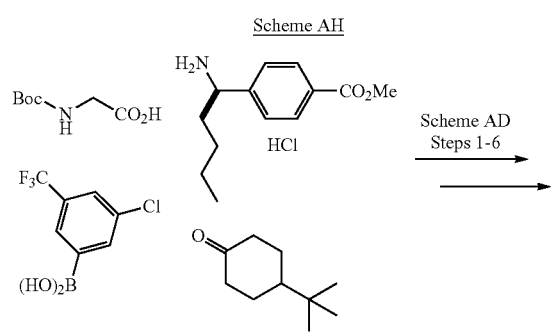

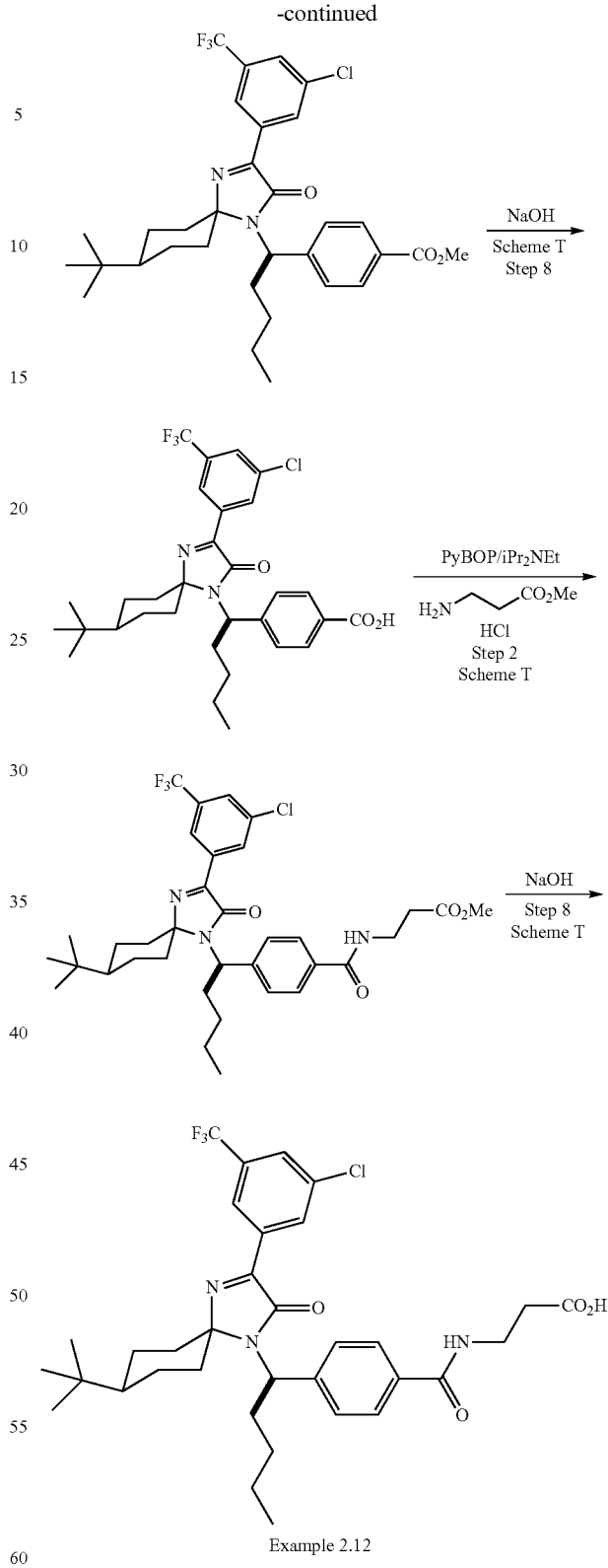

Example 2.12

The Boc-protected amino acid, amine, ketone, and boronic acid were converted into the methyl ester following procedures outlined in Scheme AD (Steps 1-5). The methyl ester was converted into Example 2.12 using Steps 2 and 8 of Scheme T.

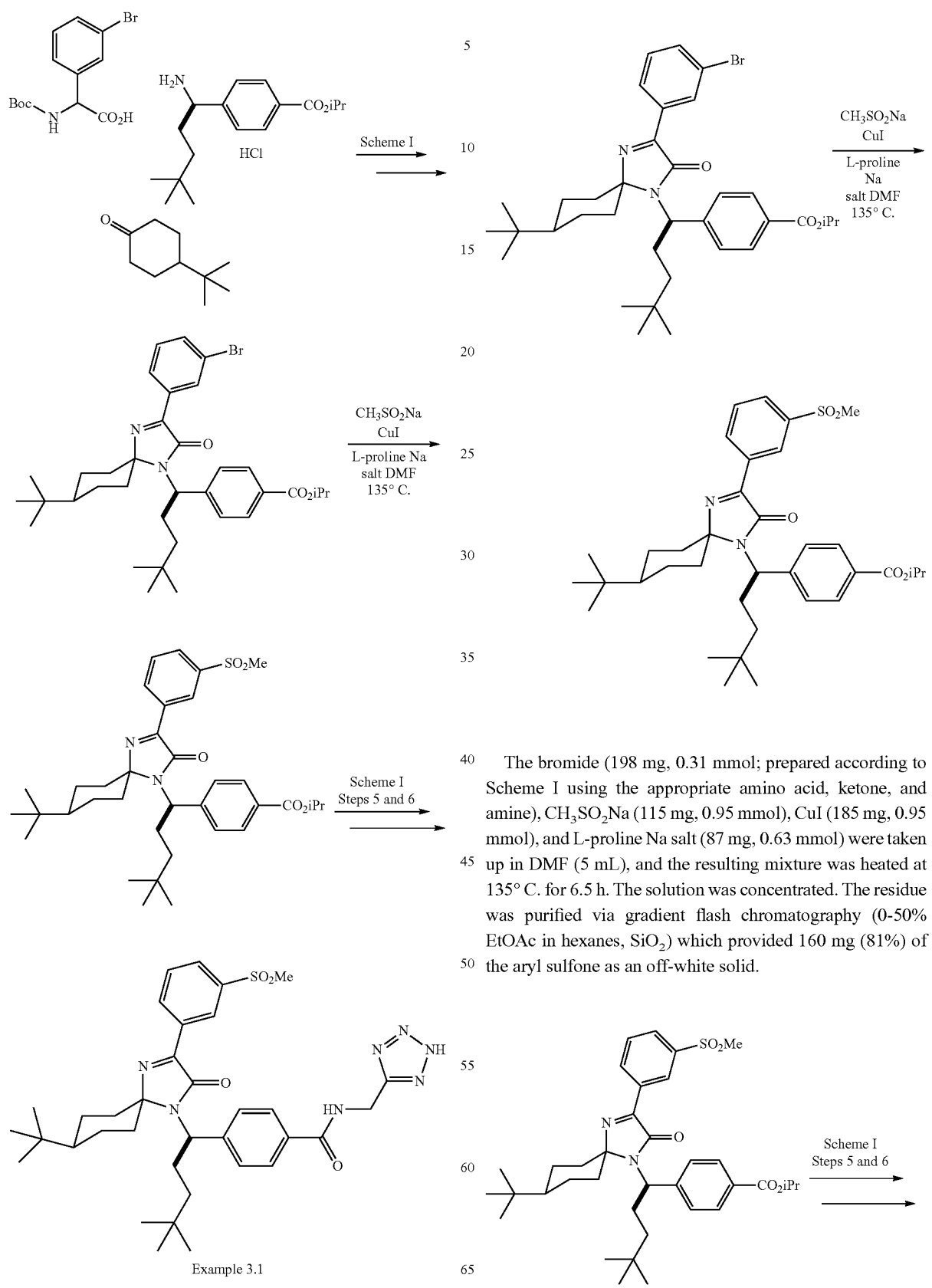

Step 1

The bromide (198 mg, 0.31 mmol; prepared according to Scheme I using the appropriate amino acid, ketone, and amine), $CH_3SO_2Na$ (115 mg, 0.95 mmol), CuI (185 mg, 0.95 mmol), and L-proline Na salt (87 mg, 0.63 mmol) were taken up in DMF (5 mL), and the resulting mixture was heated at 135° C. for 6.5 h. The solution was concentrated. The residue was purified via gradient flash chromatography (0-50% EtOAc in hexanes, $SiO_2$) which provided 160 mg (81%) of the aryl sulfone as an off-white solid.

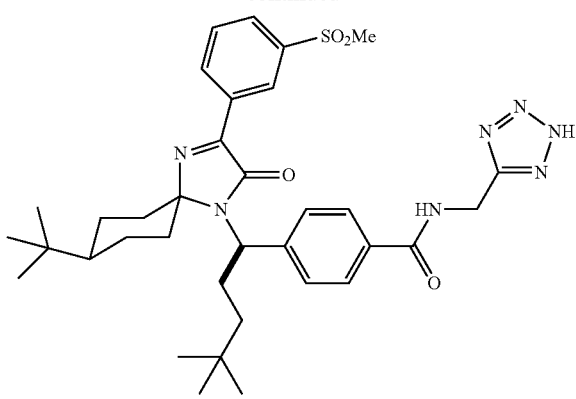
Example 3.1
The aryl sulfone was processed into Example 3.1 using condition outlined in Scheme I (Steps 5 and 6).
Scheme AJ
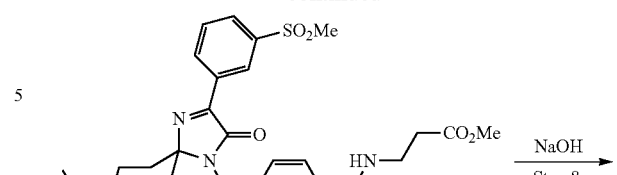
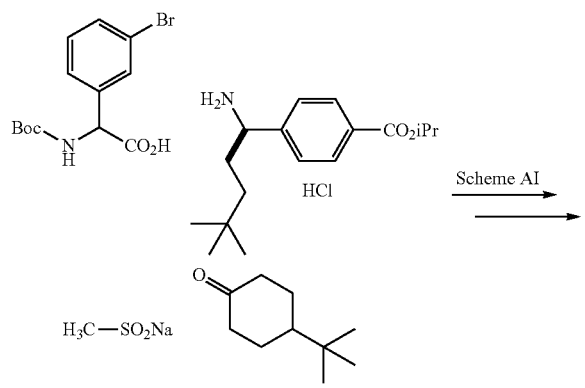
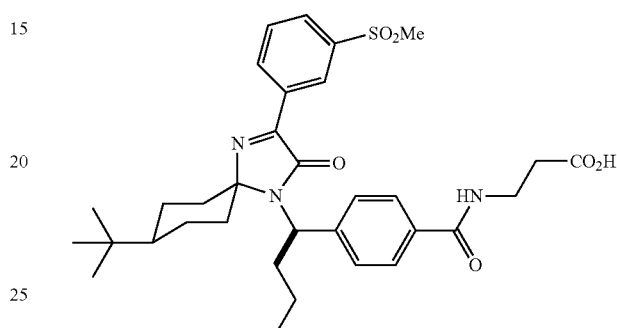
Example 3.3
The sulfone was prepared according the procedures outlined in Scheme AI. The ester was processed using conditions outlined in Scheme T to provide Example 3.3.
Scheme AK
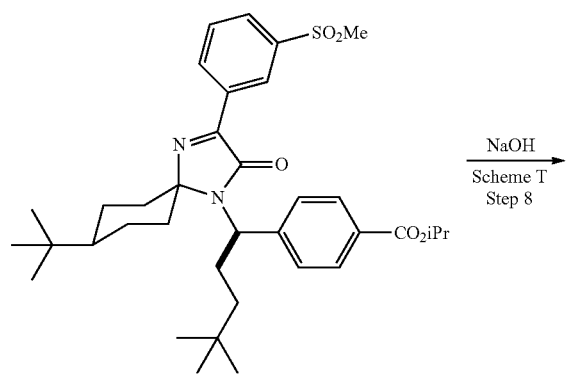
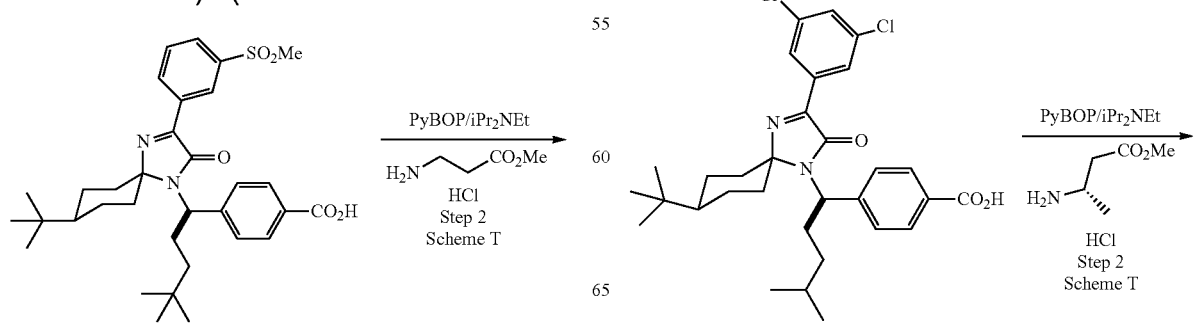

163
-continued
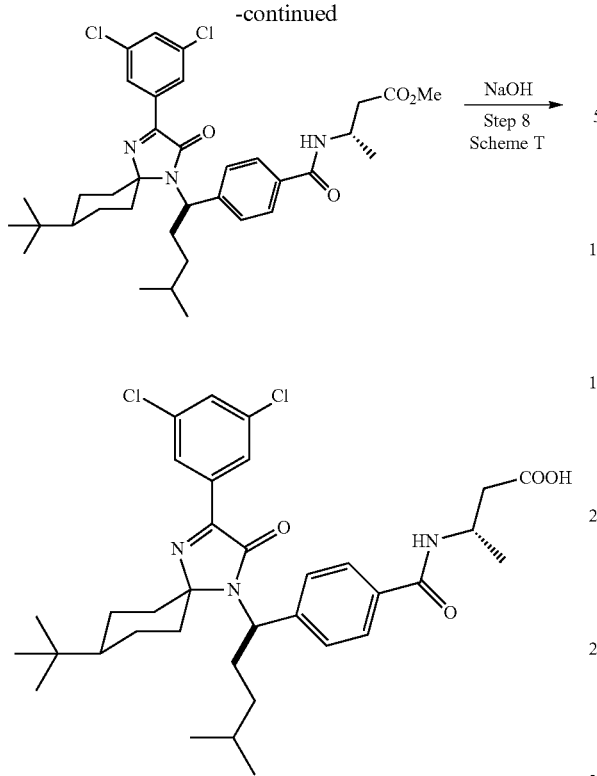
Example 4.1
Example 4.1 was prepared according to the procedures outlined in Scheme T using Steps 2 and 8.
164
-continued
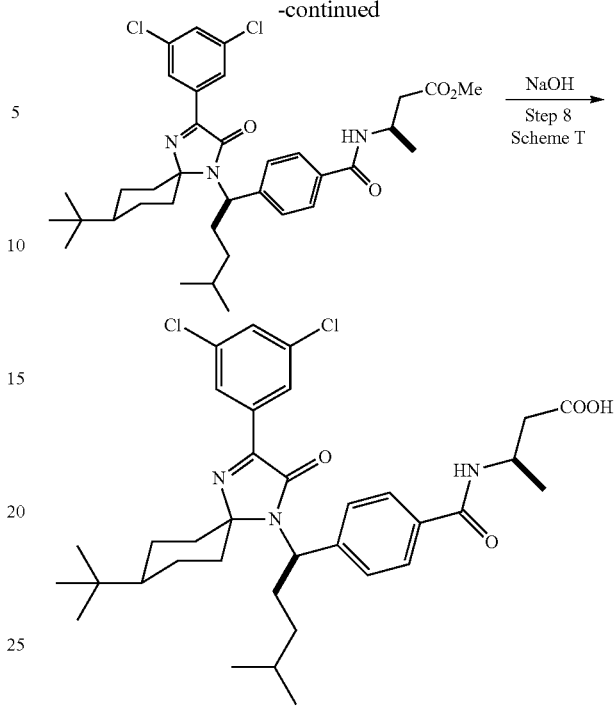
Example 4.2
Example 4.2 was prepared according to the procedures outlined in Scheme T using Steps 2 and 8.
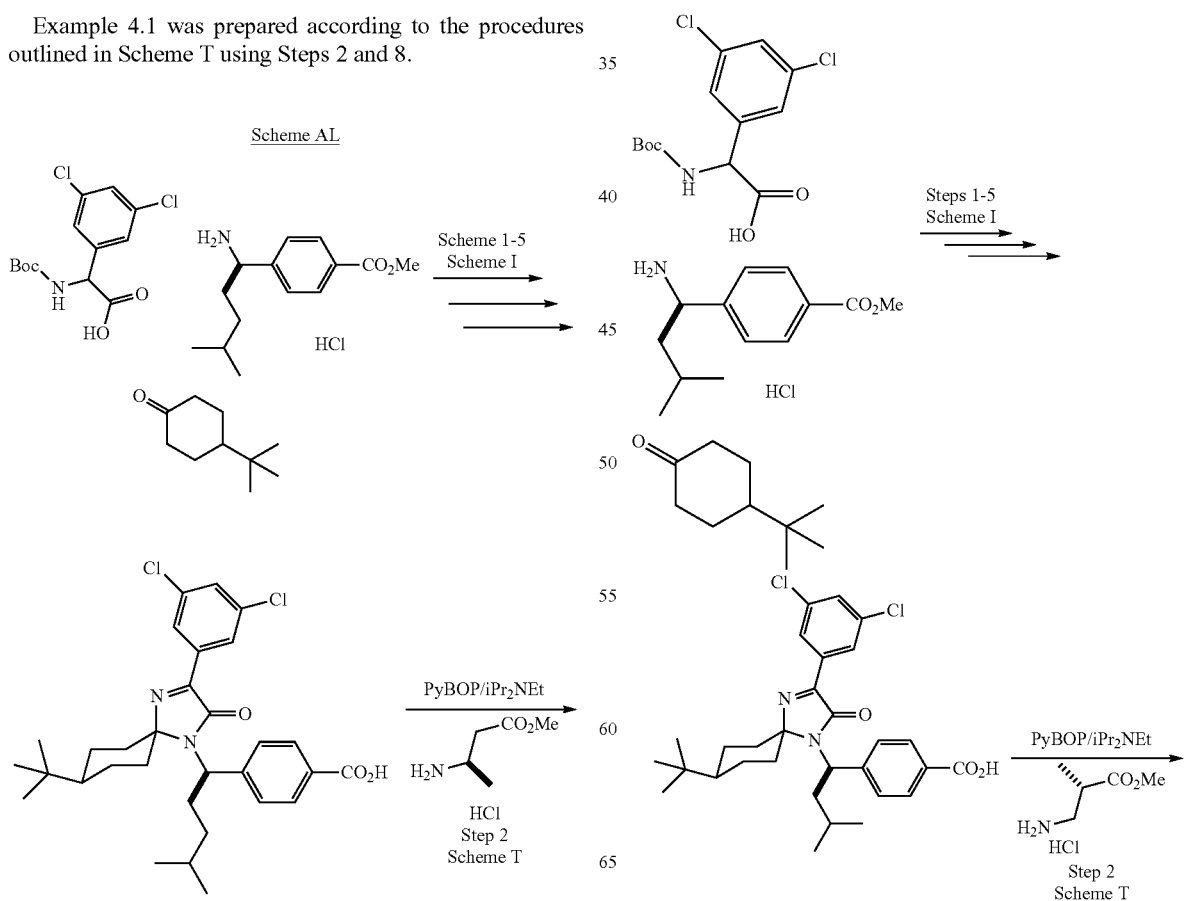

165
-continued
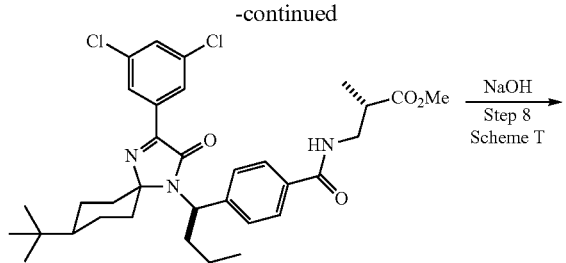
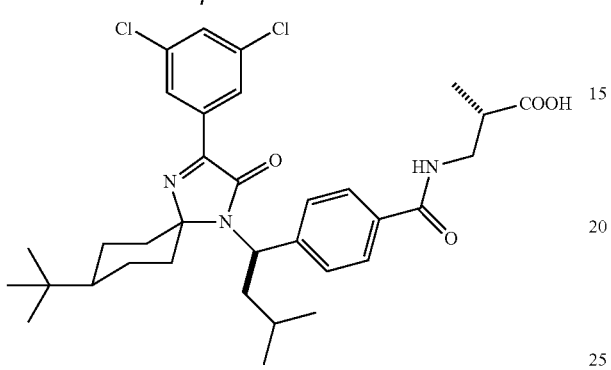
Example 4.11
Example 4.11 was prepared according to the procedures outlined in Scheme T using Steps 2 and 8.
Scheme AN
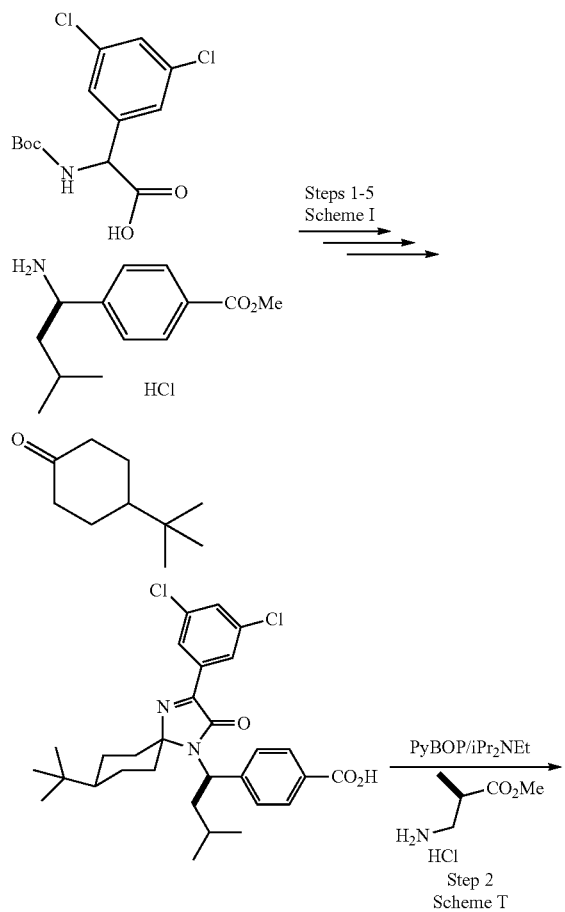
166
-continued
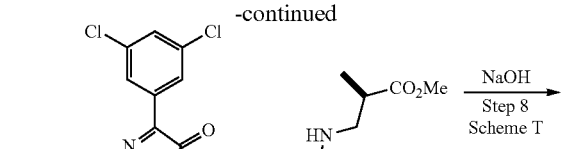
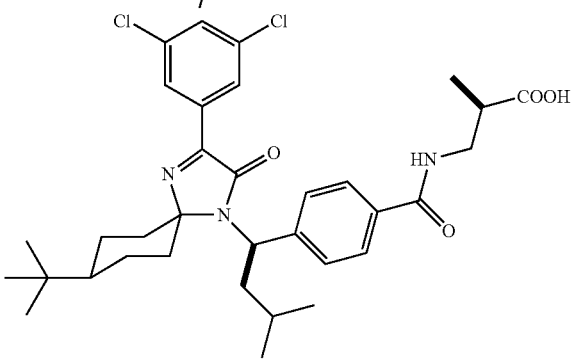
Example 4.12
Example 4.12 was prepared according to the procedures outlined in Scheme T using the Steps 2 and 8.
Scheme AO
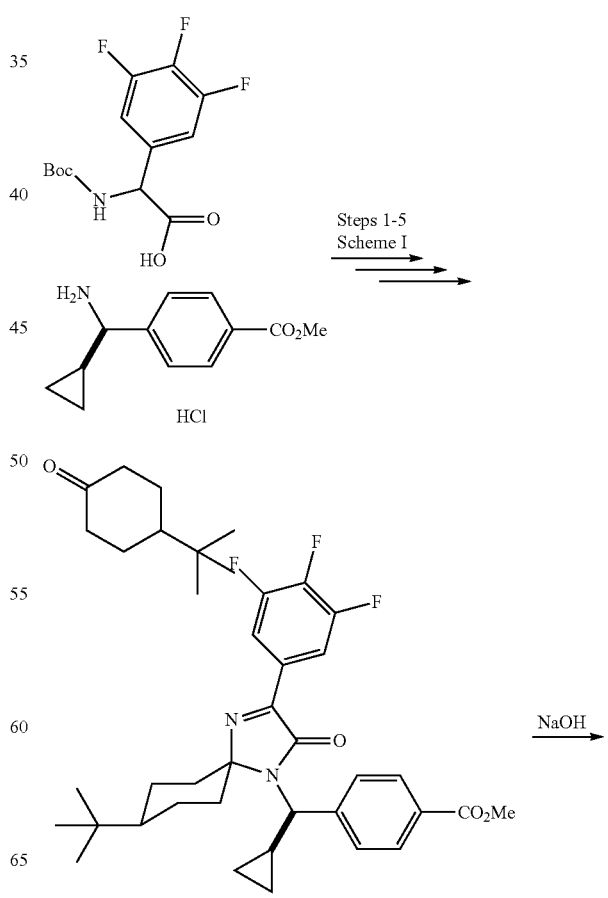

167
-continued

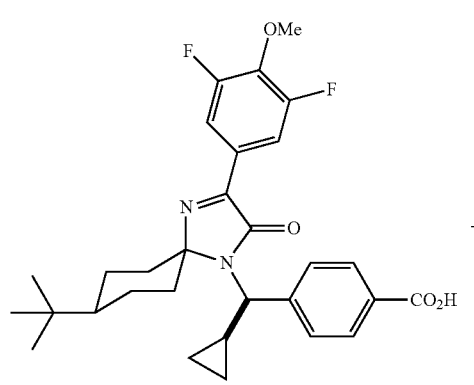

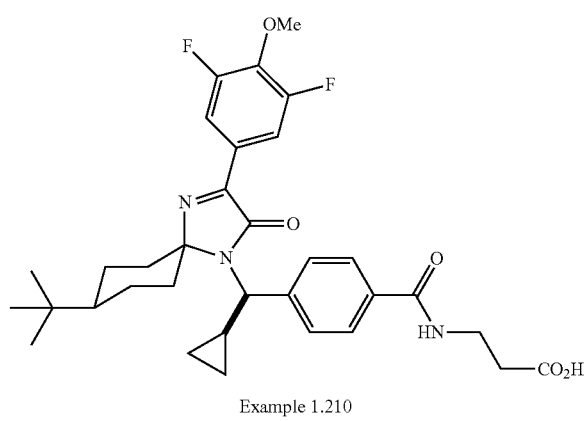

Example 1.210

168
Step 1

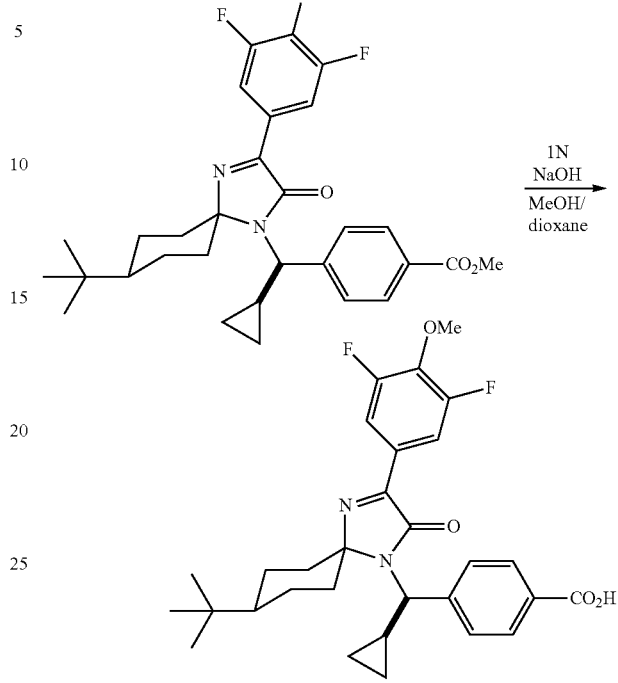

The starting material (prepared according to Scheme I—Steps 1-5) was taken up in 1 N NaOH$_{(aq.)}$/dioxane/MeOH [1/1/1, 10 mL], and the solution was heated at 60° C. for 14 hours. The solution was cooled to the room temperature. The solution was concentrated. The residue was partitioned between DCM and 1 M HCl$_{(aq.)}$. The mixture was stirred at room temperature for 0.5 h. The layers were separated, and the aqueous layer was extracted with DCM. The combined organic layers were dried (Na$_2$SO$_4$), filtered, and concentrated which afforded the acid as a white solid.

The acid was processed using conditions described in Scheme J (Steps 1 and 2) to provide Example 1.210.

Scheme AP

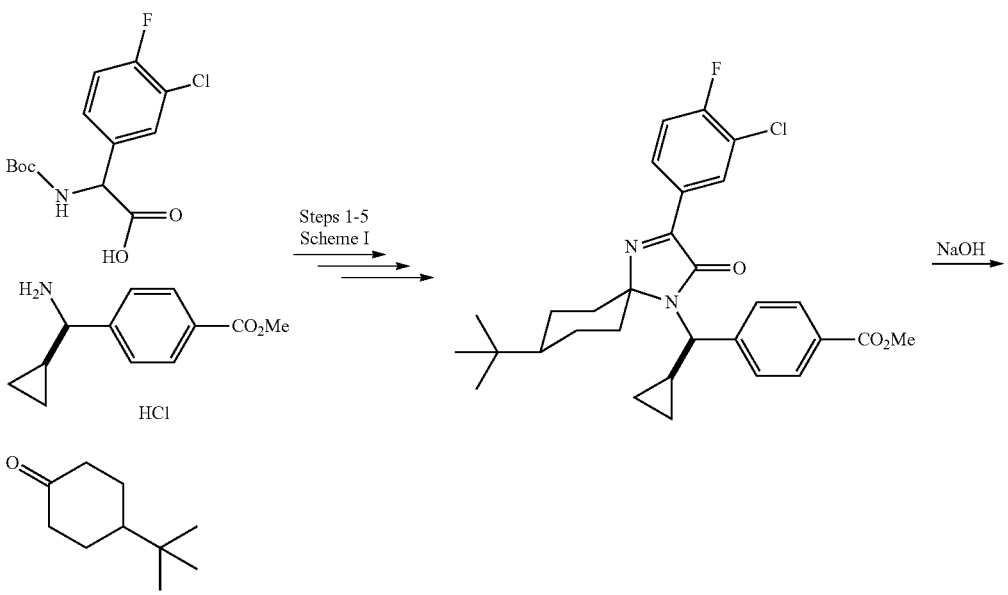

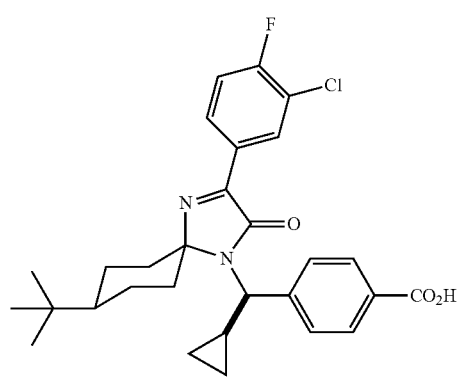

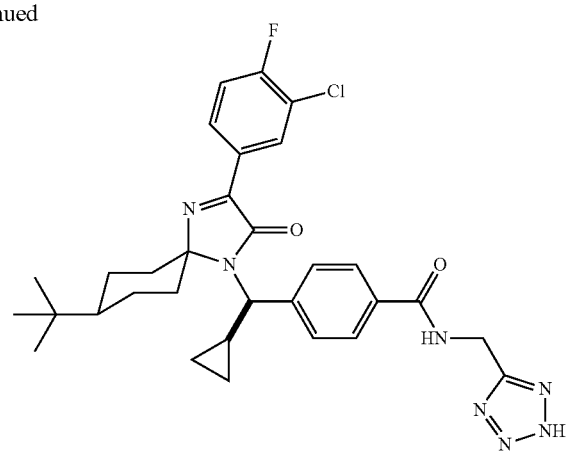

Example 1.224

Step 6
Scheme I

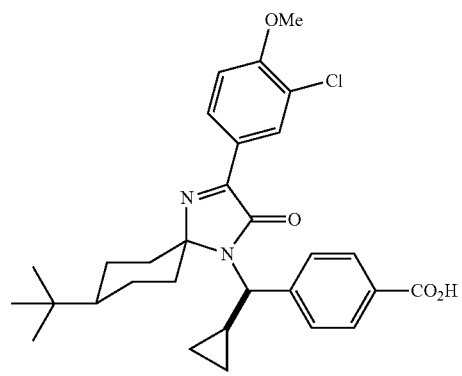

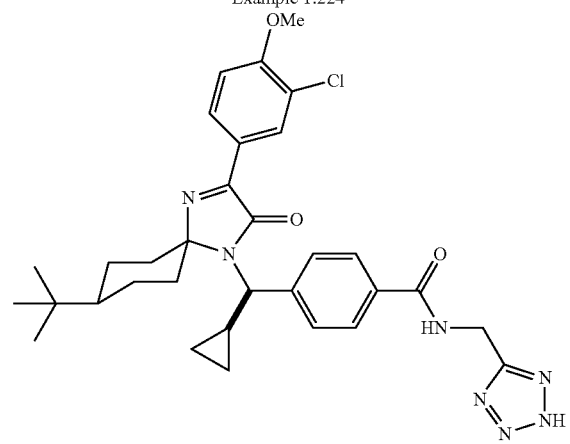

Example 1.225

Step 1

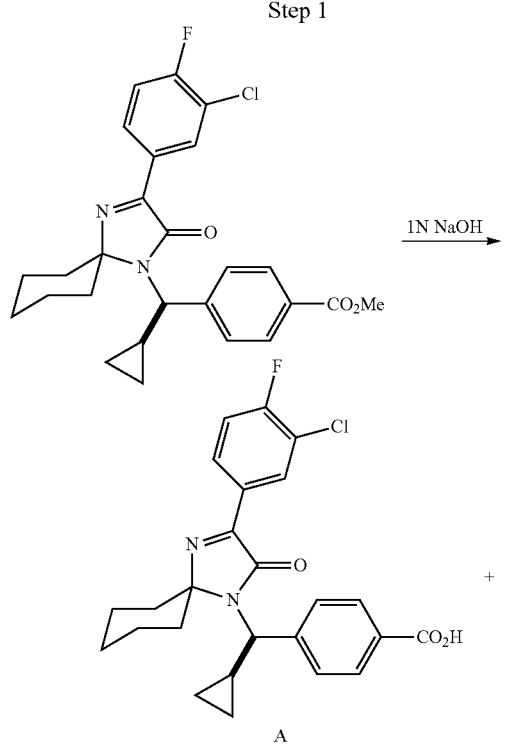

-continued

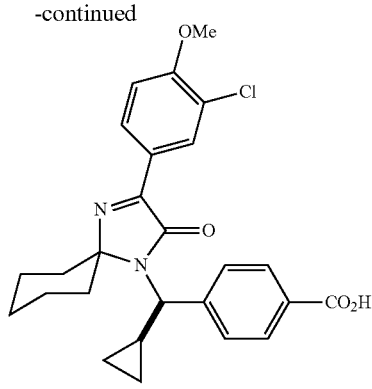

B (A:B = 3:1)

The methyl ester (prepared according to Scheme J—Steps 1-5 using the appropriate amino acid, ketone, and amine was taken up in 1 N NaOH$_{(aq.)}$/dioxane/MeOH [1/1/1, 10 mL], and the solution was heated at 60° C. for 14 hours. The solution was cooled to room temperature. The solution was concentrated. The residue was partitioned between DCM and 1 M HCl$_{(aq.)}$. The mixture was stirred at room temperature for 0.5 h. The layers were separated, and the aqueous layer was extracted with DCM. The combined organic layers were dried (Na₂SO₄), filtered, and concentrated which afforded the acids A and B as a mixture (A:B=3:1). This mixture was carried on to the coupling step directly.

The mixture of A and B were processed into Example 1.224 and 1.225 using the conditions described in Scheme I Step 6.

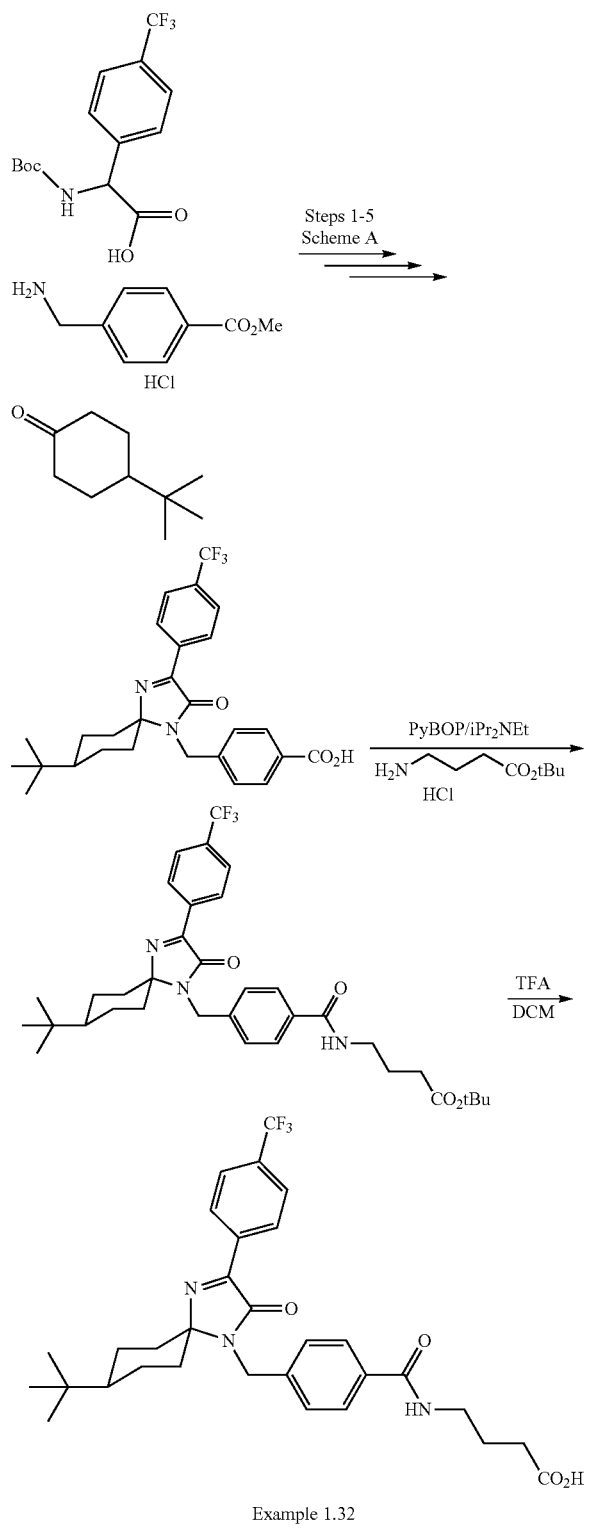

Scheme AQ

Example 1.32

The corresponding N—BOC phenyl glycine, amine, and ketone were processed to the benzoic acid intermediate using procedures outlined in Scheme A (Steps 1-5). The benozoic acid was processed into Example 1.32 using similar conditions outlined in Scheme A (Steps 6 and 7) using tert-butyl 4-aminobutanoate HCl salt as depicted in Scheme AQ.

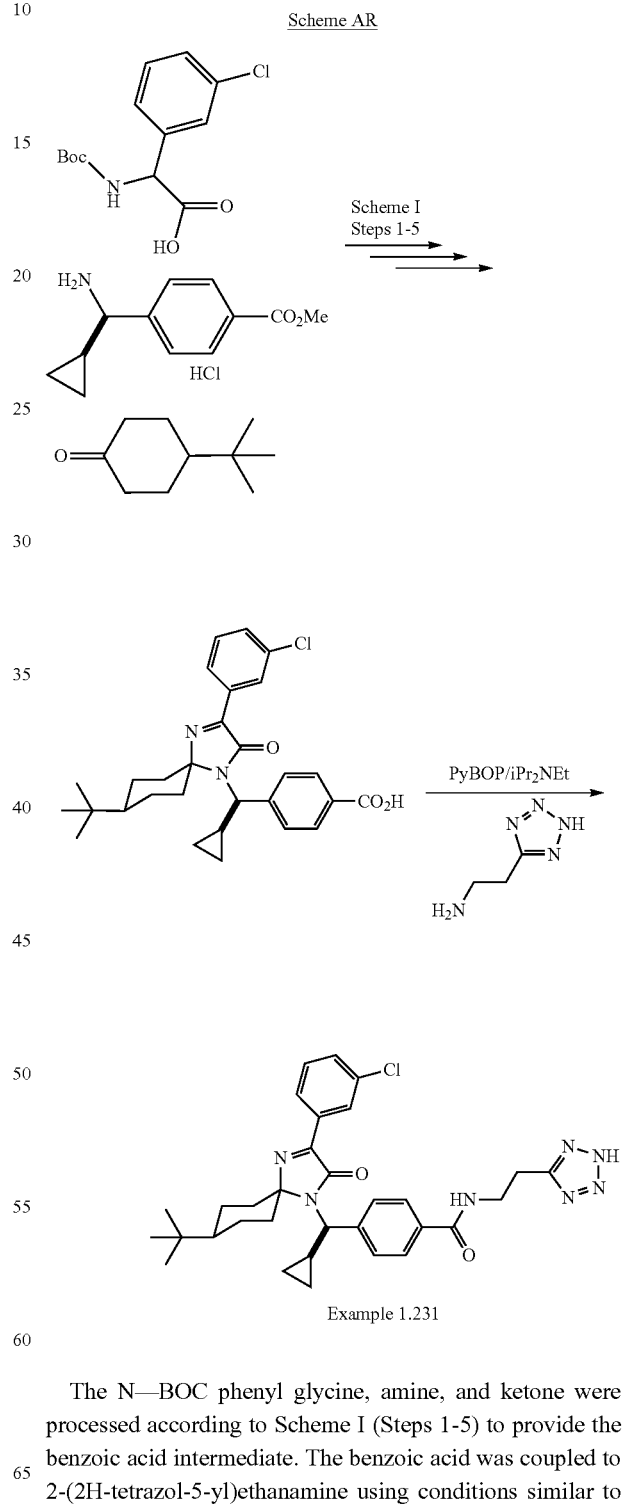

Scheme AR

Example 1.231

The N—BOC phenyl glycine, amine, and ketone were processed according to Scheme I (Steps 1-5) to provide the benzoic acid intermediate. The benzoic acid was coupled to 2-(2H-tetrazol-5-yl)ethanamine using conditions similar to those in Scheme I (Step 6) which provided Example 1.231.

Scheme IA
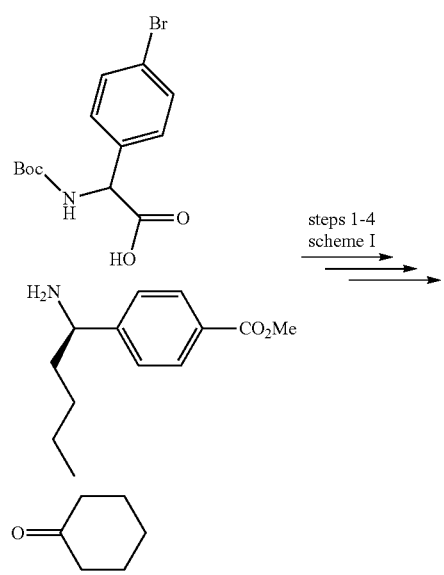
steps 1-4
scheme I
⟹
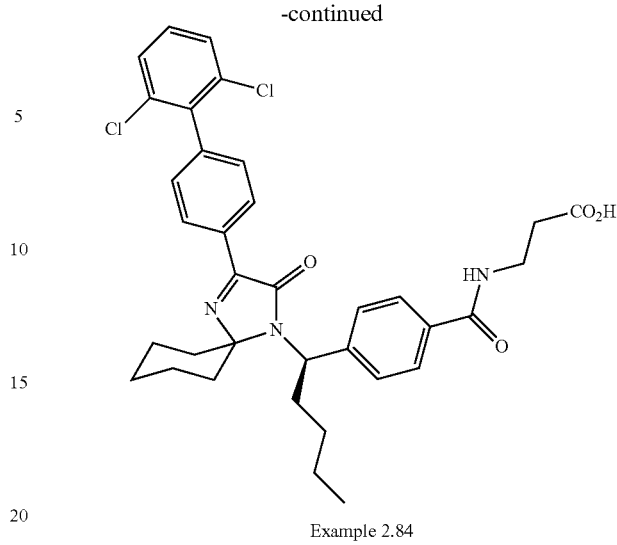
Example 2.84
Step 1
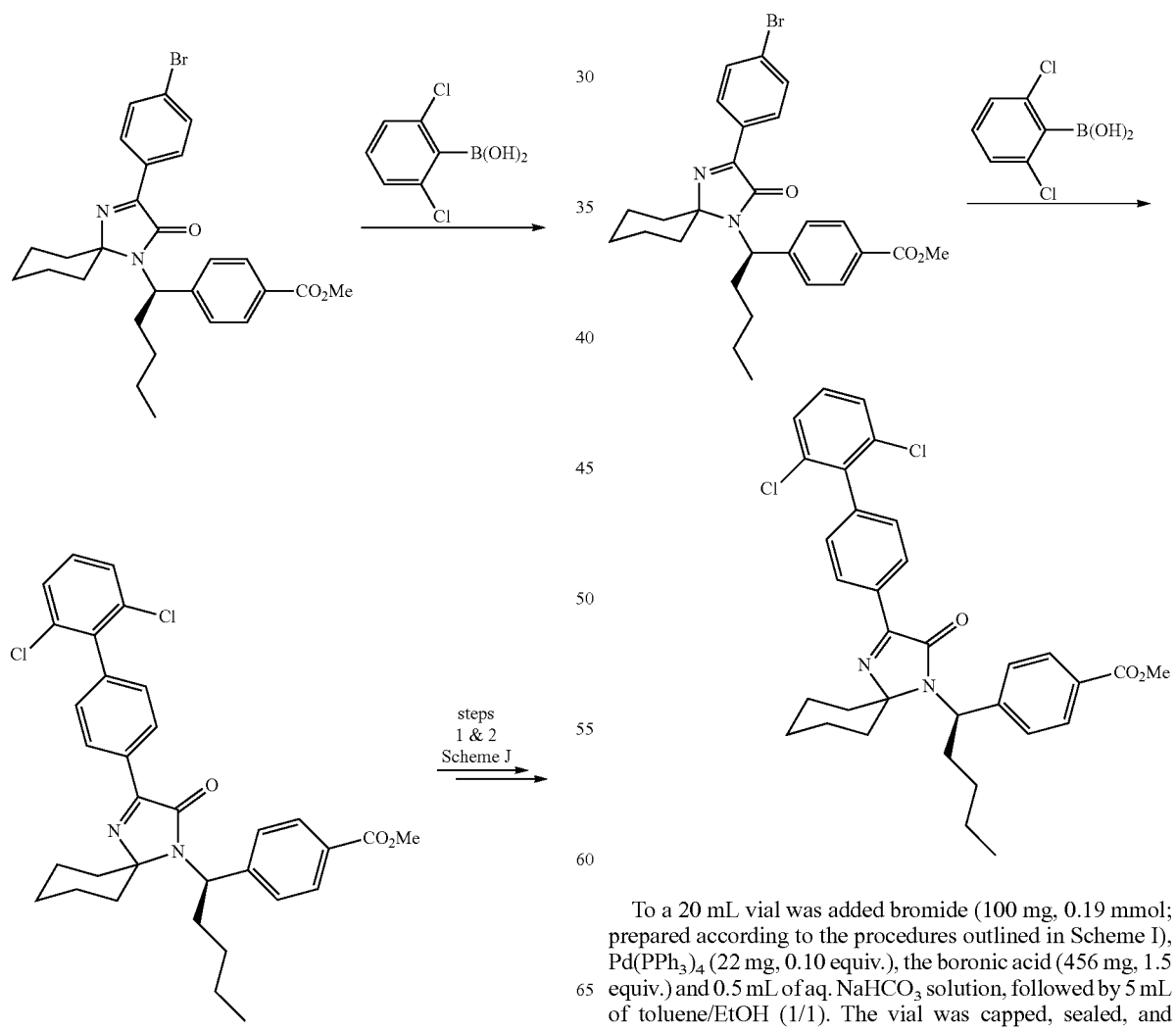
To a 20 mL vial was added bromide (100 mg, 0.19 mmol; prepared according to the procedures outlined in Scheme I), Pd(PPh$_3$)$_4$ (22 mg, 0.10 equiv.), the boronic acid (456 mg, 1.5 equiv.) and 0.5 mL of aq. NaHCO$_3$ solution, followed by 5 mL of toluene/EtOH (1/1). The vial was capped, sealed, and heated at 110° C. overnight. The mixture was cooled to RT, diluted with ether, filtered through Celite®, and concentrated. The residue was purified via gradient flash chromatography (ISCO, 0-50% EtOAc in hexanes, SiO$_2$) to furnish the desired compound (103 mg, 91% yield).

The methyl ester was processed into Example 2.84 using conditions outlined in Scheme J (Steps 1 and 2).

Scheme IB

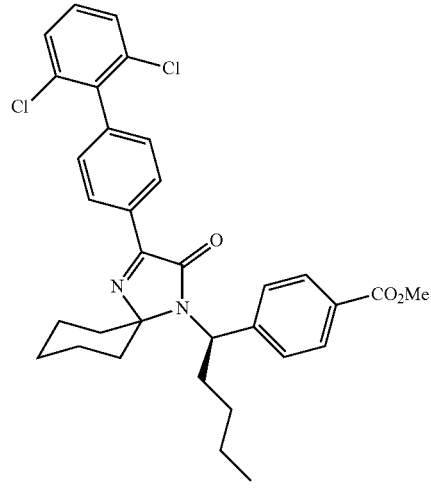

Scheme IA steps 5 & 6
Scheme I

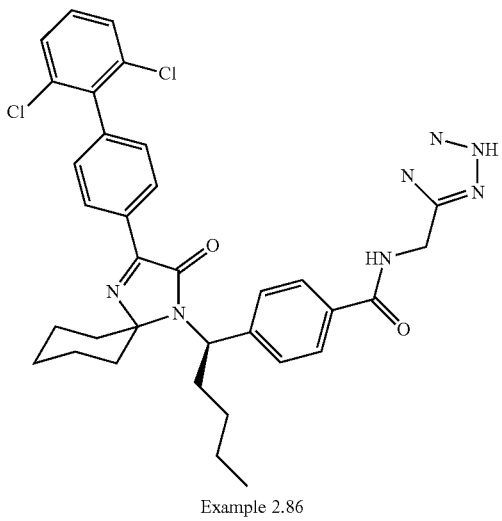

Example 2.86

The methyl ester (Scheme IA) was processed into Example 2.86 using conditions outlined in Scheme I (Steps 5 and 6).

Scheme IC

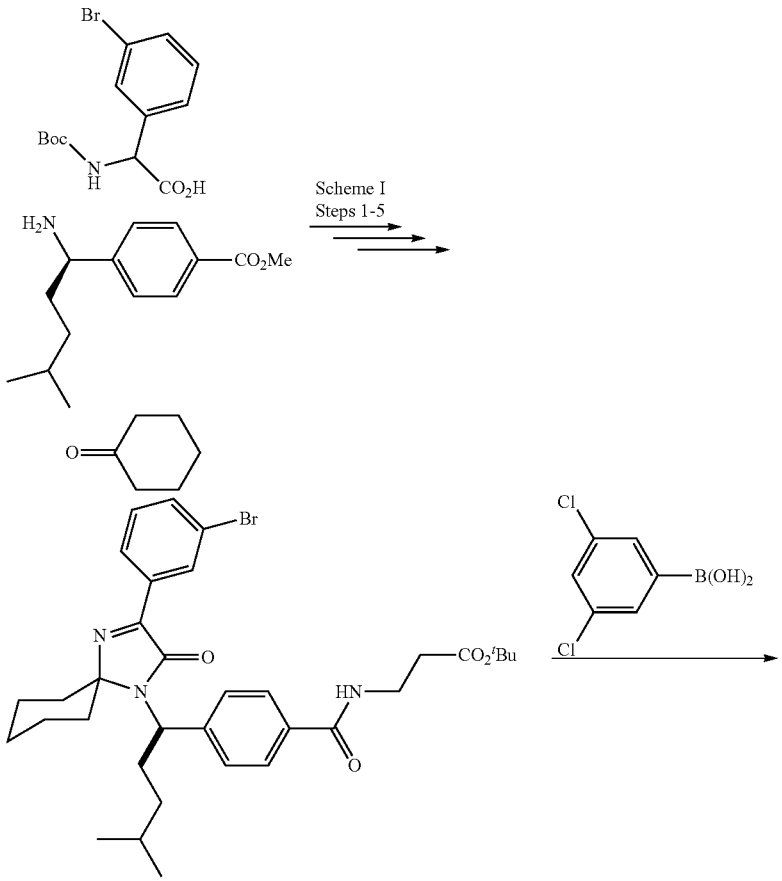

-continued
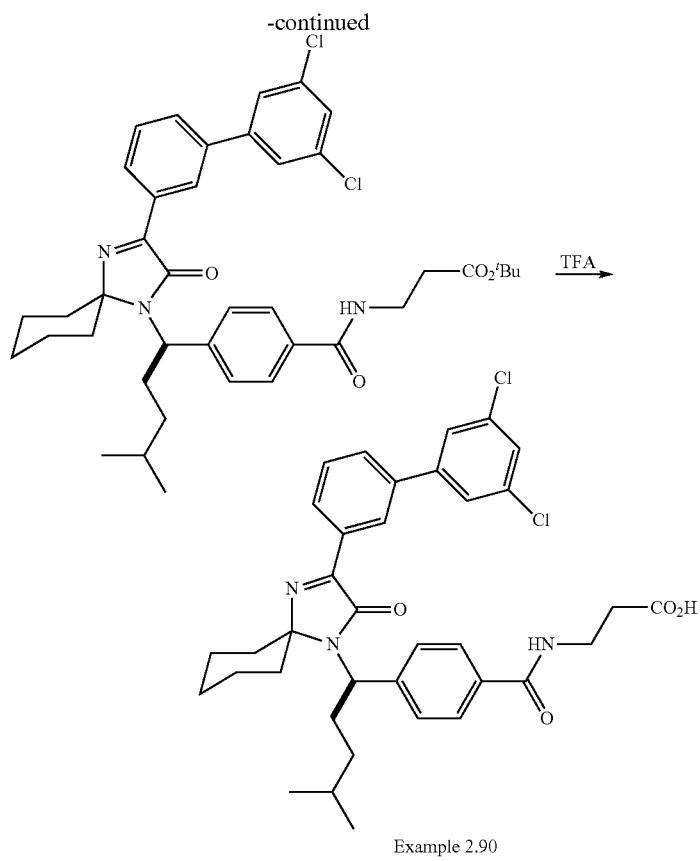
Example 2.90
Step 1
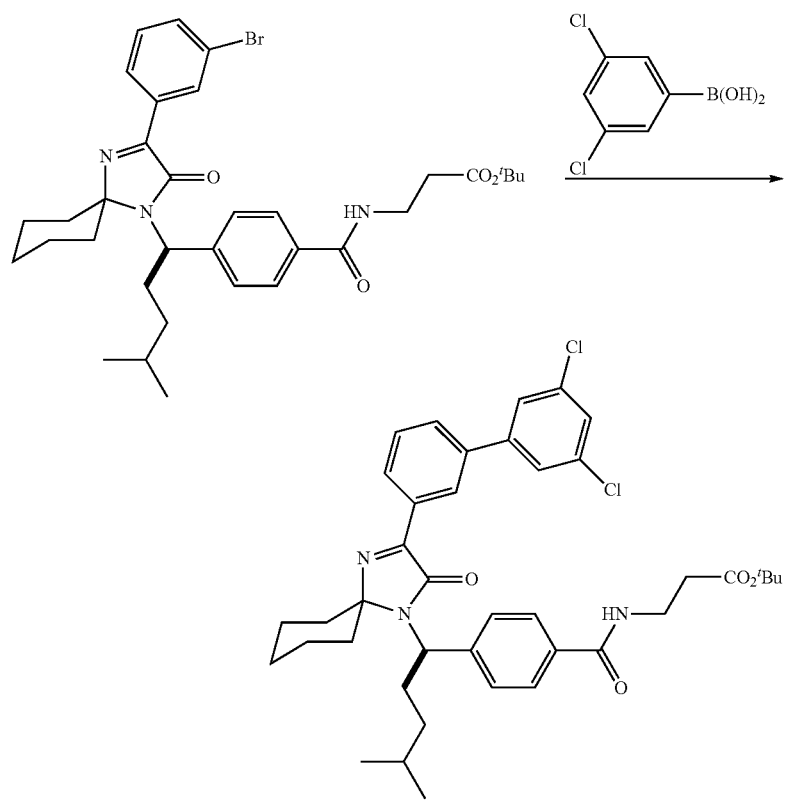

The bromide was prepared according to the Scheme I (Steps 1-5) using the requisite amino acid, amine, and ketone.

To a 20 mL vial was added bromide (100 mg, 0.15 mmol), Pd(PPh₃)₄ (18 mg, 0.10 equiv.), boronic acid (45 mg, 1.5 equiv.) and 0.5 mL of aq. NaHCO₃ solution, followed by 5 mL of toluene/EtOH (1/1). The vial was capped, sealed, and heated at 110° C. overnight. The mixture was cooled to RT and diluted with ether and filtered through Celite® and concentrated. The residue was purified via gradient flash chromatography (ISCO, 0-50% EtOAc in hexanes, SiO₂) which furnished the desired compound (100 mg, 92% yield).

The tert-butyl ester was processed into Example 2.90 using conditions outlined in Scheme J (Step 2).

Scheme ID

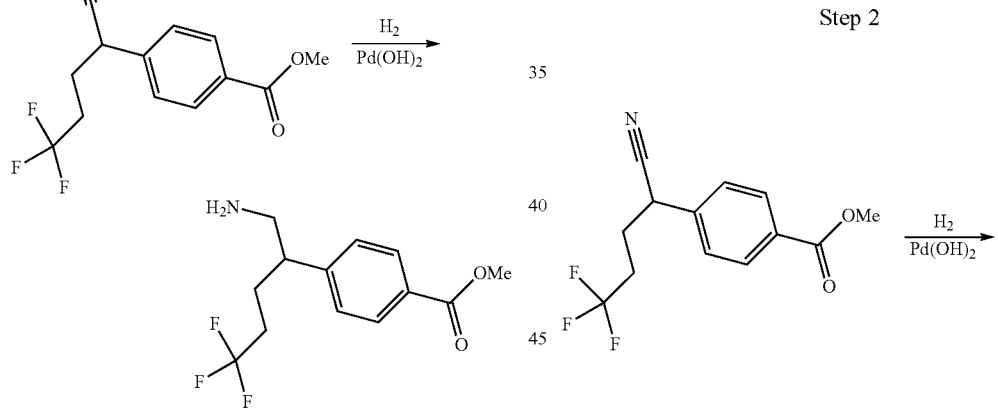

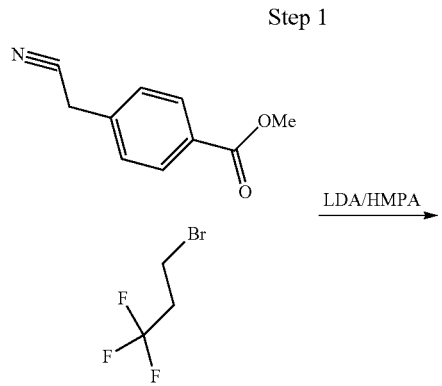

Step 1

LDA was generated in situ from n-BuLi (6.85 mL, 17.1 mmol, 2.5 M in hexanes, SiO₂) and diisopropylamine (2.40 mL, 17.1 mmol) in THF (10 mL). Benzyl cyanide (3.0 g, 20.0 mmol) was added to a solution of LDA at −78° C. Then the solution was warmed to 0° C. and stirred for 10 min. To this solution was added 4-bromo 1,1,1-trifluorobutane (1.92 mL, 18.0 mmol) followed by HMPA (2.5 mL, 14.0 mmol) in 5 min. The reaction was allowed to warm to room temperature gradually overnight. Then the reaction was partitioned between EtOAc and 1N HCl. The aqueous layer was discarded and the organic layer washed with 1N HCl and brine then dried (Na₂SO₄). Filtration and concentration provided a yellow oil. The residue was purified via gradient flash chromatography (ISCO, 0-40% EtOAc in hexanes, SiO₂) which provided the cyano-ester 1.92 g (41% yield).

Step 2

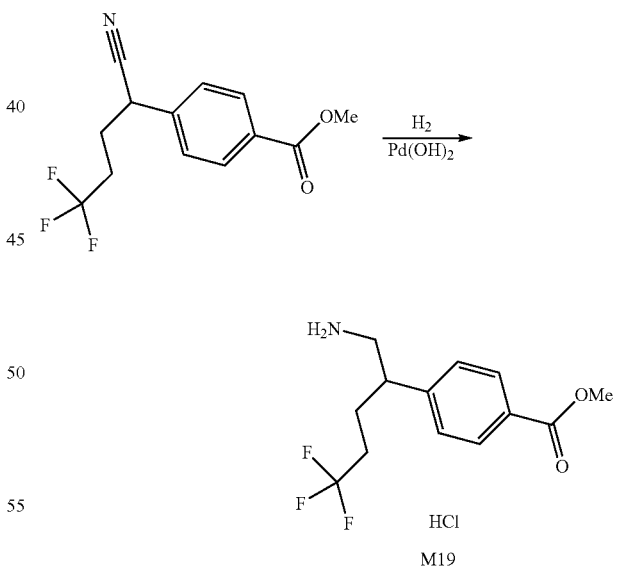

A mixture of cyano-ester (1.92 g), Pd(OH)₂/C (300 mg 10 mol %) in 50 mL MeOH and 5 mL con. HCl was stirred under 50 atm H₂ overnight (20 h). The reaction was purged with nitrogen, filtered through Celite®, and concentrated. This provided the crude product 1.93 g (99% yield), which was used without further purification.

Scheme IE

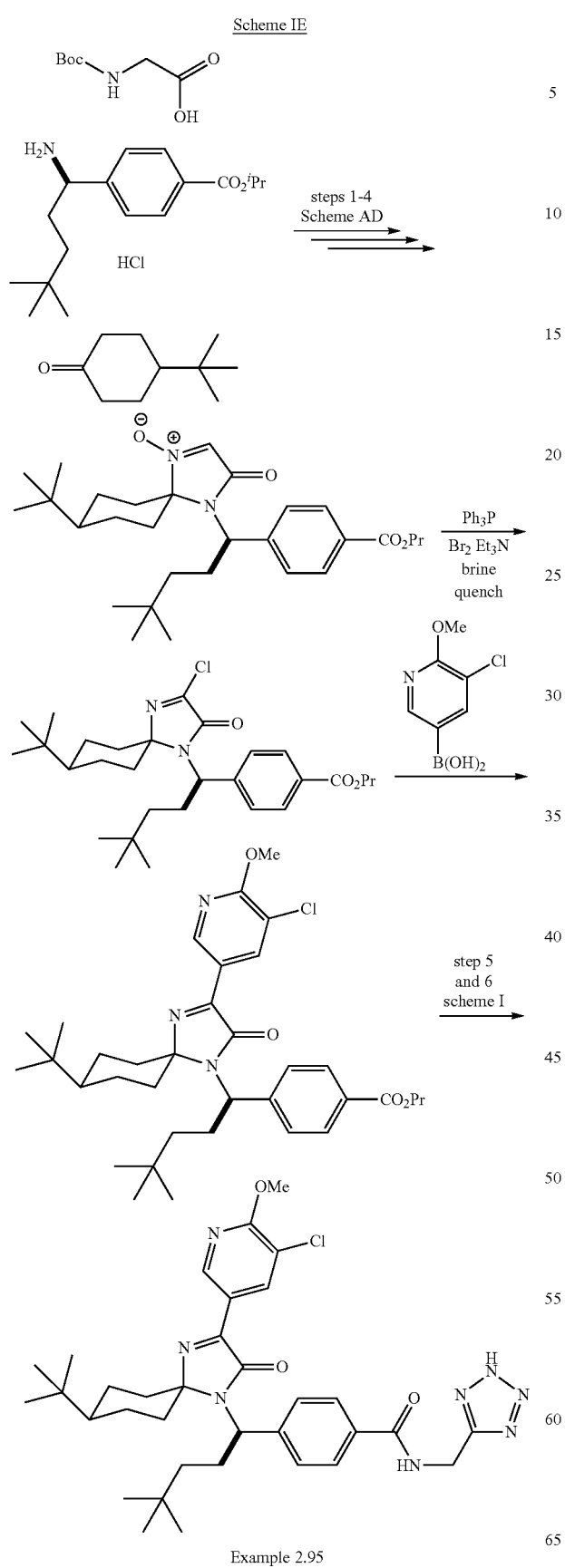

Example 2.95

Step 1

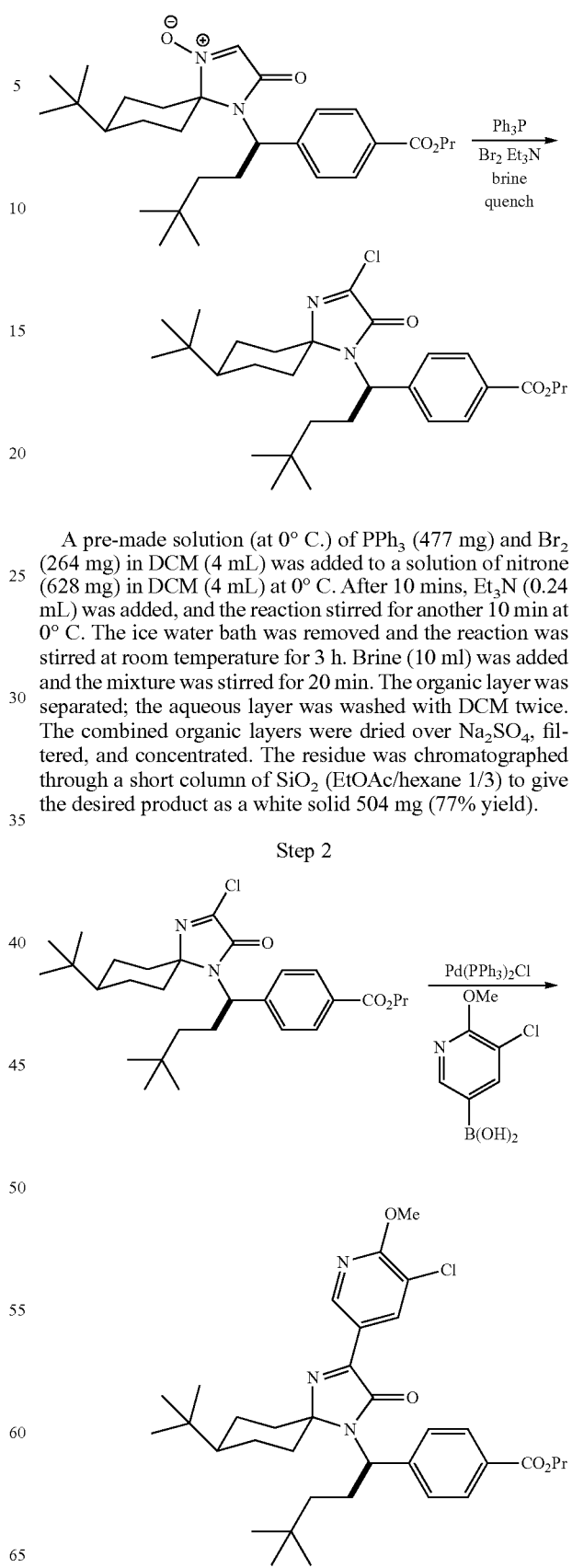

A pre-made solution (at 0° C.) of PPh$_3$ (477 mg) and Br$_2$ (264 mg) in DCM (4 mL) was added to a solution of nitrone (628 mg) in DCM (4 mL) at 0° C. After 10 mins, Et$_3$N (0.24 mL) was added, and the reaction stirred for another 10 min at 0° C. The ice water bath was removed and the reaction was stirred at room temperature for 3 h. Brine (10 ml) was added and the mixture was stirred for 20 min. The organic layer was separated; the aqueous layer was washed with DCM twice. The combined organic layers were dried over Na$_2$SO$_4$, filtered, and concentrated. The residue was chromatographed through a short column of SiO$_2$ (EtOAc/hexane 1/3) to give the desired product as a white solid 504 mg (77% yield).

Step 2

To a 20 mL vial was added chloride (100 mg, 0.20 mmol), Pd(PPh$_3$)$_2$Cl$_2$ (14 mg, 0.10 equiv.), boronic acid (56 mg, 1.5 equiv.) and 0.5 mL of aq. Na$_2$CO$_3$ solution, followed by 5 mL of dioxane. The vial was capped and heated at 110° C. overnight. The mixture was cooled to RT, diluted with ether, filtered through Celite®, and concentrated. The residue was purified via gradient flash chromatography (ISCO, 0-50% EtOAc in hexanes, SiO$_2$) to furnish the desired compound (87 mg, 72% yield).

The product from above was processed into Example 2.95 according to the procedures outlined in Scheme I (Steps 5 and 6).

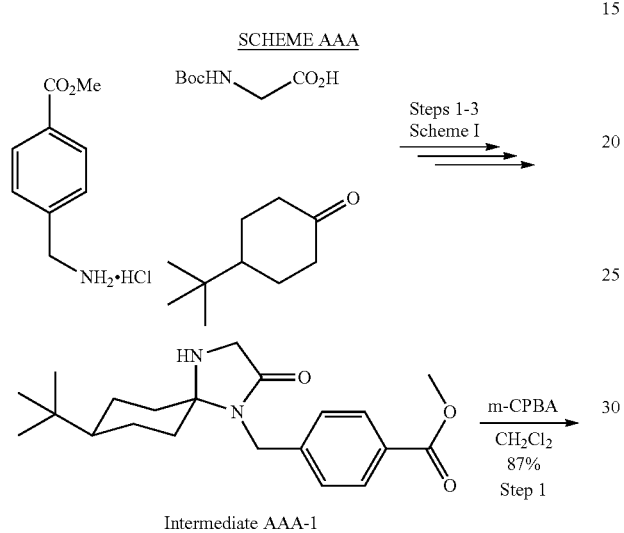

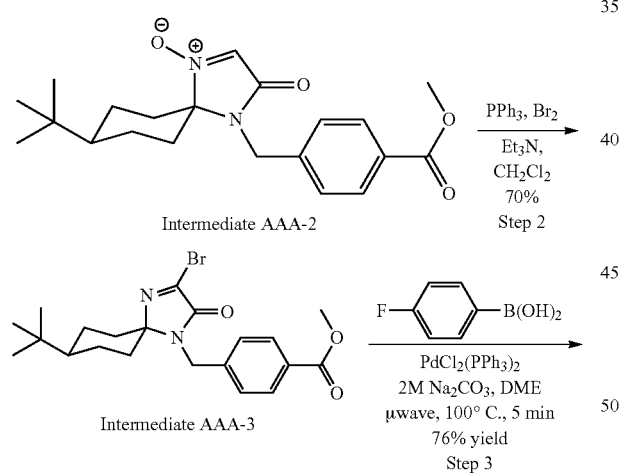

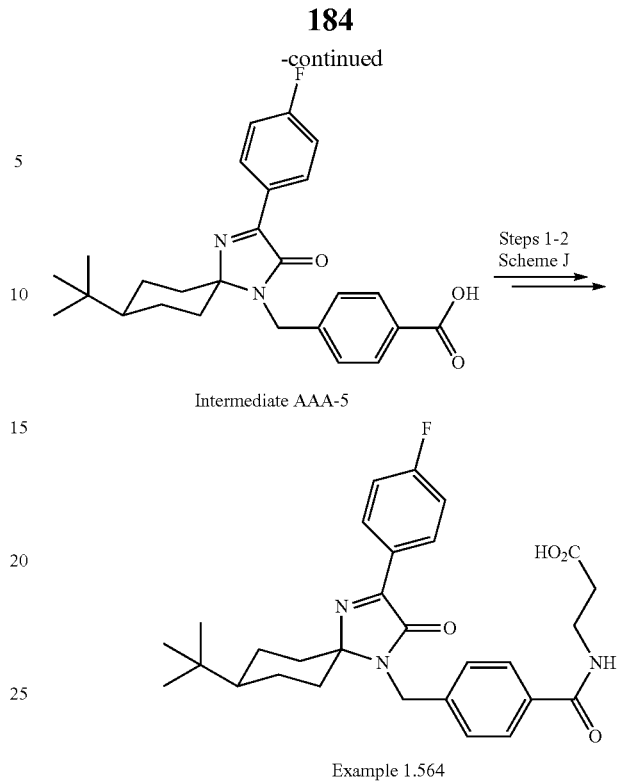

Methyl 4-(aminomethyl)benzoate hydrochloride, N-Boc-glycine, and 4-tert-butylcyclohexanone were used according to Steps 1-3 in Scheme I to afford the desired Intermediate AAA-1. Intermediate AAA-1 (200 mg, 0.558 mmol, 1 eq) was dissolved in CH$_2$Cl$_2$ (2.4 mL), cooled to 0° C., and treated with m-CPBA (77% w/w with water, 280 mg, 1.25 mmol, 2.24 eq) in three portions over 2.5 hours. Upon completion of the reaction by TLC, 10% sodium thiosulfate$_{(aq.)}$ (0.66 mL) and saturated NaHCO$_{3(aq.)}$ were added. The resulting biphasic mixture was stirred until both layers were clear. The layers were separated and both were saved. The aqueous layer was extracted twice with CH$_2$Cl$_2$. The combined organic layers were washed with saturated NaHCO$_{3(aq.)}$, and brine, were dried over anhydrous sodium sulfate, filtered, and evaporated to afford the desired nitrone (181 mg, 87%) which was used in the next step without further purification.

Step 2

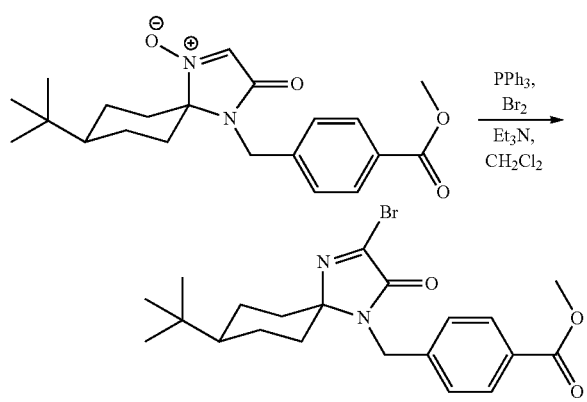

Triphenylphosphine (69 mg, 0.263 mmol, 1.4 eq) was dissolved in CH$_2$Cl$_2$ (0.3 mL) and was cooled to 0° C. Bromine (0.013 mL, 0.24 mmol, 1.3 eq) was added and the resulting mixture was stirred for 10 minutes at 0° C. The nitrone from Step 1 (70 mg, 0.20 mmol, 1 eq) was added, followed by triethylamine (0.035 mL, 0.25 mmol, 1.3 eq) at 0° C. After stirring the resulting mixture for 10 minutes at 0° C., the ice bath was removed and the reaction was stirred for 2 hours at room temperature. The reaction was partitioned between CH$_2$Cl$_2$ and brine. The organic layer was separated and saved. The aqueous layer was extracted with CH$_2$Cl$_2$. The organic layers were combined and evaporated to afford a residue which was purified via silica gel chromatography (gradient elution, 0% to 100% EtOAc in hexanes, SiO$_2$) to afford the desired product as a clear film (57 mg, 70%).

Step 3

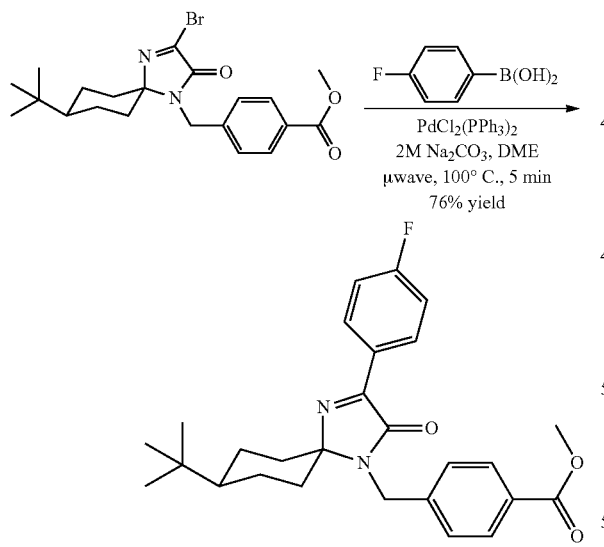

A solution of the bromoimidazolone prepared in Step 2 (57 mg, 0.13 mmol, 1 eq), bis(triphenylphosphino)palladium(II) chloride (4 mg, 0.006 mmol, 0.05 eq), 2M Na$_2$CO$_{3(aq.)}$ (0.5 mL), and 4-fluorophenylboronic acid (20 mg, 0.14 mmol, 1.1 eq) in DME (1 mL) in a Biotage microwave vial was subjected to microwave heating (100° C., min, very high absorption). The reaction mixture was then partitioned between water and EtOAc. The organic layer was removed and saved and the aqueous layer was extracted with EtOAc. The organic layers were combined, dried over anhydrous sodium sulfate, filtered, and evaporated to afford a residue which was purified via silica gel chromatography (gradient elution, 0% to 100% EtOAc in hexanes, SiO$_2$) to afford the desired product (45 mg, 76%).

Step 4

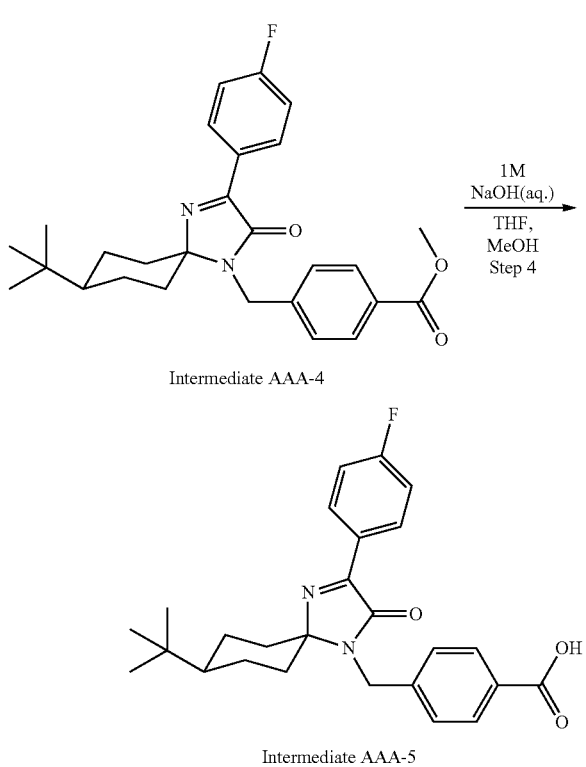

Intermediate AAA-4

Intermediate AAA-5

A solution of the coupling product from Step 3 (45 mg, 0.10 mmol, 1 eq) in THF (2 mL) and MeOH (1 mL) was treated with 1M NaOH(aq.) (1 mL, 1.00 mmol, 10 eq). The resulting solution was stirred overnight at room temperature. The reaction mixture was then partitioned between CH$_2$Cl$_2$ and 1M HCl(aq.). The organic layer was removed and saved and the aqueous layer was extracted with CH$_2$Cl$_2$. The organic layers were combined, washed with brine, dried over anhydrous sodium sulfate, filtered, and evaporated to afford the desired product, which was used in the next step without further purification.

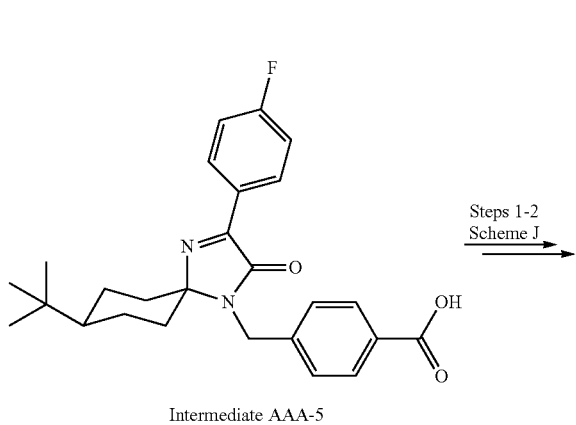

Intermediate AAA-5

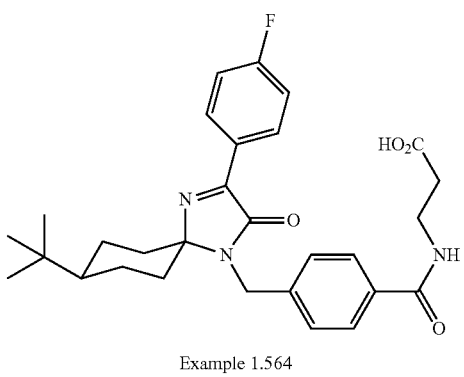 [SMILES: CC(C)(C)C1CCC2(CC1)N=C(c1ccc(F)cc1)C(=O)N2Cc1ccc(C(=O)NCCC(=O)O)cc1]

Example 1.564

The benzoic acid prepared in Step 4 was converted to the desired Example 1.564 using the method outlined in Steps 1 and 2 of Scheme J.

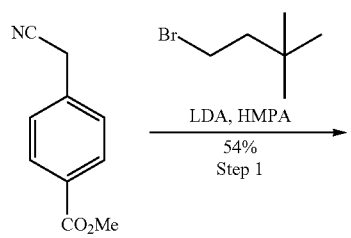

Scheme AAB

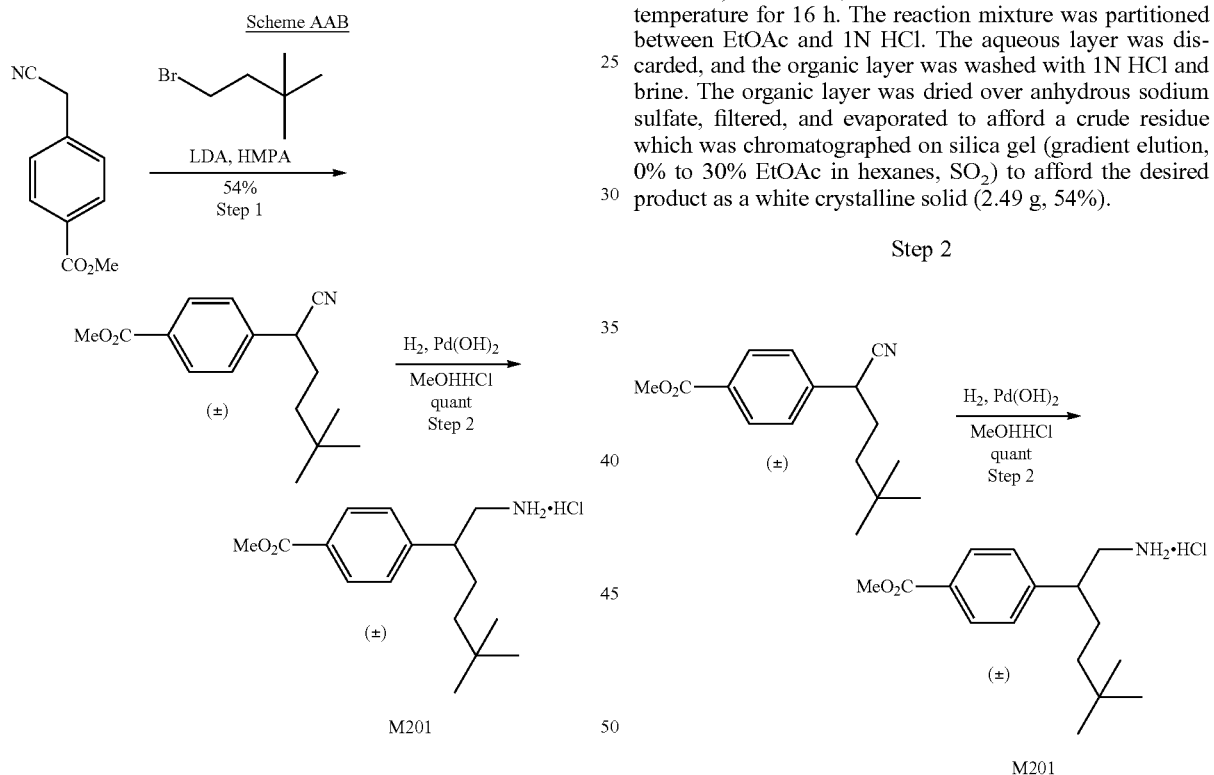

Step 1

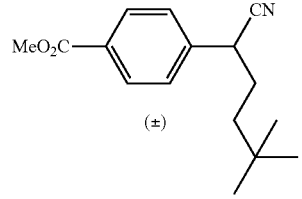

A solution of N,N-diisopropylethylamine (2.4 mL, 17.1 mmol, 1 eq) in THF (10 mL) was cooled to −78° C. A solution of n-butyllithium in hexanes (2.5M, 6.85 mL, 17.1 eq) was added dropwise with stirring. The solution was warmed to 0° C. for 10 min, then cooled again to −78° C. At −78° C., a solution of methyl 4-(cyanomethyl)benzoate (3 g, 20 mmol, 1 eq) in THF (8 mL) was added dropwise to the LDA solution (a dark red slurry formed). After stirring the resulting slurry for 10 minutes at −78° C., 1-bromo-3,3-dimethylbutane (2.46 mL, 17.9 mmol, 1.05 eq) was added rapidly. The reaction was stirred for 30 minutes at −78° C. then was warmed to room temperature. After 1 h, hexamethylphosphoramide (2.5 mL, 14 mmol) was added, and the reaction was stirred at room temperature for 16 h. The reaction mixture was partitioned between EtOAc and 1N HCl. The aqueous layer was discarded, and the organic layer was washed with 1N HCl and brine. The organic layer was dried over anhydrous sodium sulfate, filtered, and evaporated to afford a crude residue which was chromatographed on silica gel (gradient elution, 0% to 30% EtOAc in hexanes, $SO_2$) to afford the desired product as a white crystalline solid (2.49 g, 54%).

Step 2

A solution of the product from Step 1 (2.49 g, 9.60 mmol, 1 eq) and conc. HCl (5 mL, 60 mmol, 6 eq) in MeOH (100 mL) was added to a Parr hydrogenation bottle containing 20% Pd(OH)$_2$ on carbon (50% w/w water, 660 mg, 0.94 mmol, 0.098 eq). The resulting heterogeneous mixture was purged with nitrogen, then pressurized with hydrogen (60 psi). The bottle was shaken for 16 hours at room temperature, refilling the hydrogen to 60 psi. as necessary. After releasing the hydrogen pressure and purging the vessel with nitrogen, the reaction mixture was filtered through Celite®, and the Celite® pad was washed with MeOH. The resulting filtrates were combined and evaporated to afford the desired amine hydrochloride salt (2.87 g) which was used in the next step without further purification.

TABLE AAB

Using the conditions described in Scheme AB and the requisite
alkyl halide, the following intermediate was prepared:

| alkyl halide | intermediate |
|---|---|
| methyl iodide | 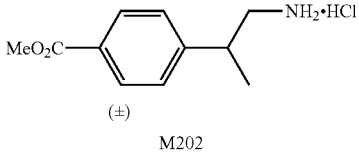<br>(±)<br>M202 |

Scheme AAC

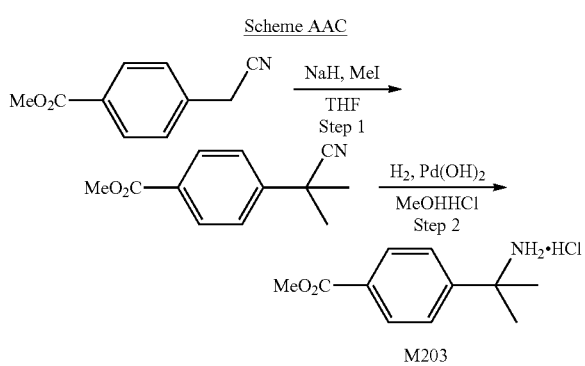

Step 1

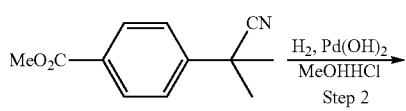

Methyl 4-(cyanomethyl)benzoate (1.8 g, 10 mmol, 1 eq) was dissolved in THF (100 mL) and cooled to 0° C. Sodium hydride (60% w/w in mineral oil, 820 mg, 20 mmol, 2 eq) was added portionwise and the mixture was stirred for 10 minutes. Methyl iodide (1.3 mL, 20 mmol, 2 eq) was added dropwise and the reaction was stirred at 0° C. until the starting material was consumed by TLC (2 hours). The reaction mixture was quenched with water and was partitioned between EtOAc and brine. The aqueous layer was discarded, and the organic layer was washed with brine, dried over anhydrous sodium sulfate, filtered, and evaporated to afford a crude residue which was chromatographed on silica gel (gradient elution, 0% to 50% EtOAc in hexanes, SiO$_2$) to afford the desired product as a white crystalline solid (1.88 g, 74%).

Step 2

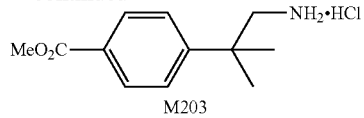

M203

A solution of the product from Step 1 (1.88 g, 7.40 mmol, 1 eq) and 10% Palladium on carbon (50% w/w water, 660 mg, 0.310 mmol, 0.4 eq) in MeOH (100 mL) was purged with nitrogen, then with hydrogen. A balloon of hydrogen was affixed to the flask, and the reaction was stirred overnight. Concentrated aqueous HCl (~12M, 5 mL, 60 mmol, 8 eq) was added to the reaction and stirring was continued under a balloon of hydrogen for 24 h. The incomplete reaction was purged with nitrogen and transferred to a Parr hydrogenation bottle containing 20% Pd(OH)$_2$ on carbon (50% w/w water, 660 mg, 0.94 mmol, 0.13 eq). The resulting heterogeneous mixture was purged with nitrogen, then pressurized with hydrogen (50 psi). The bottle was shaken for 72 hours at room temperature, refilling the hydrogen to 50 psi. as necessary. After releasing the hydrogen pressure and purging the vessel with nitrogen, the reaction mixture was filtered through Celite®, and the Celite® pad was washed with MeOH. The resulting filtrates were combined and evaporated to afford the desired amine hydrochloride salt (2.08 g, quant.) which was used in the next step without further purification.

Scheme AAD

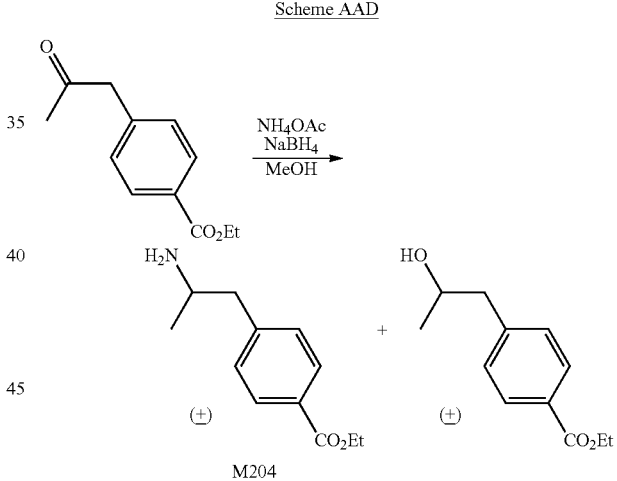

Ethyl 4-(2-oxopropyl)benzoate (2.25 g, 10.9 mmol, 1 eq) and ammonium acetate (8.40 g, 109 mmol, 9.97 eq) were dissolved in MeOH (45 mL). While stirring at room temperature, sodium borohydride (684 mg, 18.1 mmol, 1.65 eq) was added. The resulting reaction mixture was stirred overnight at room temperature. The reaction was concentrated and partitioned between CH$_2$Cl$_2$ and 1M NaOH (aq.). The organic layer was removed and saved and the aqueous layer was extracted with CH$_2$Cl$_2$. The organic layers were combined, washed with brine, dried over anhydrous sodium sulfate, filtered, and evaporated to afford a residue which was purified via silica gel chromatography (gradient elution, 0% to 100% EtOAc in hexanes, SiO$_2$) to afford ethyl 4-(2-hydroxypropyl)benzoate (1.18 g, 52%). The same silica gel column was then subjected to a second set of chromatography conditions (gradient elution, 0% to 80% MeOH in EtOAc) to afford racemic ethyl 4-(2-aminopropyl)benzoate (610 mg, 27%).

Scheme AAE
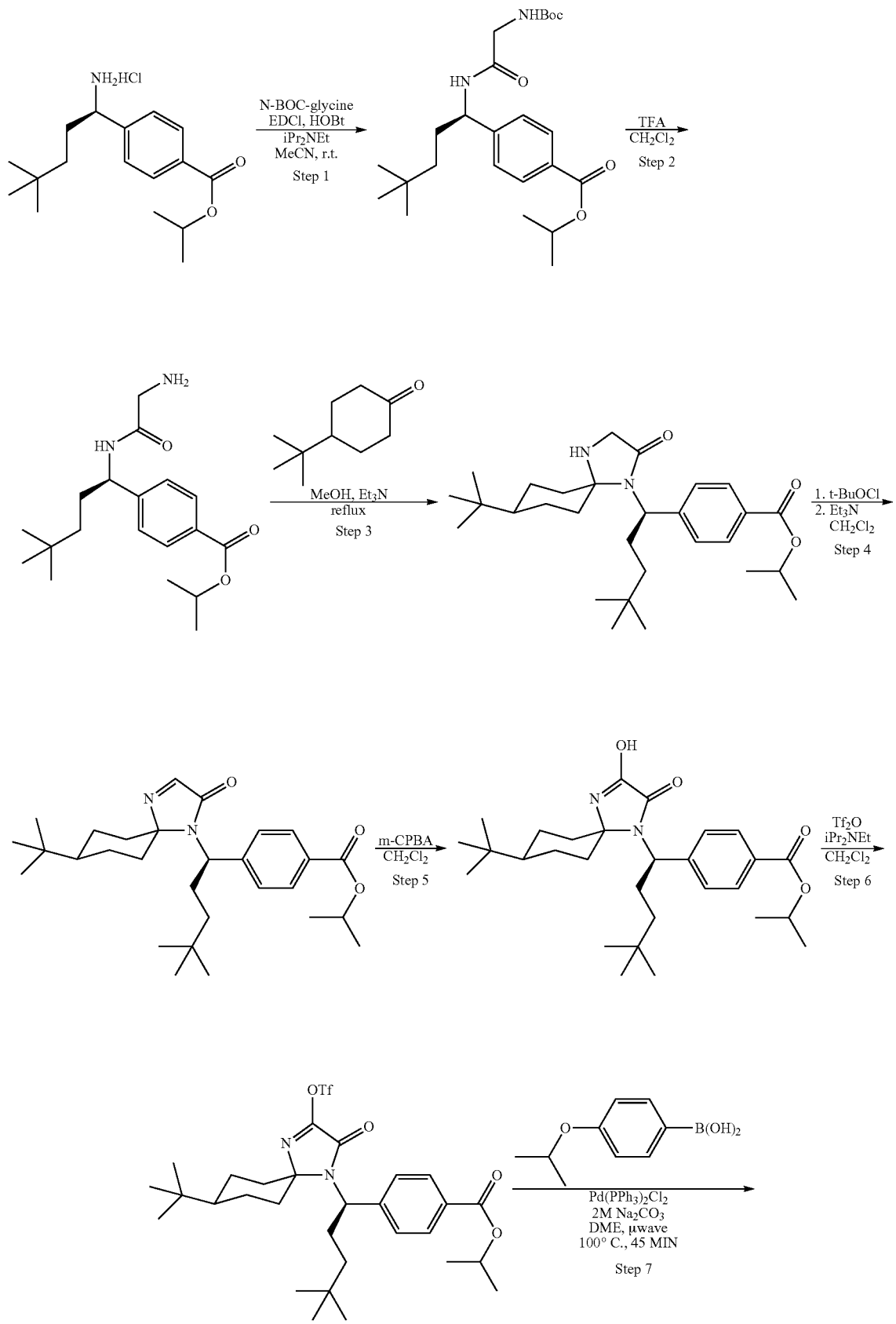

-continued
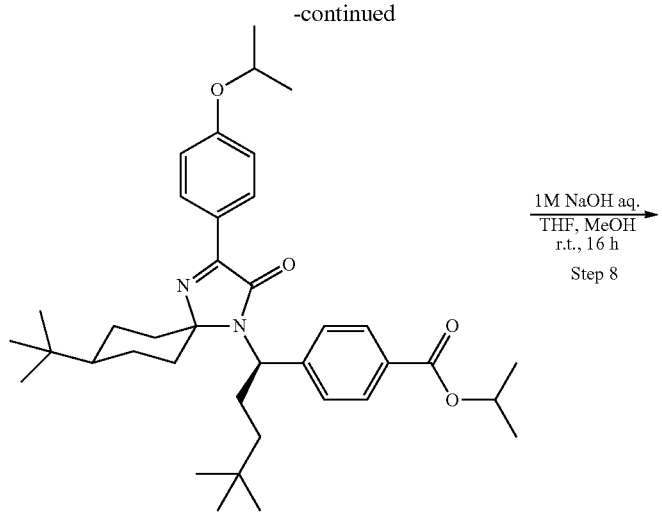
1M NaOH aq.
THF, MeOH
r.t., 16 h
Step 8
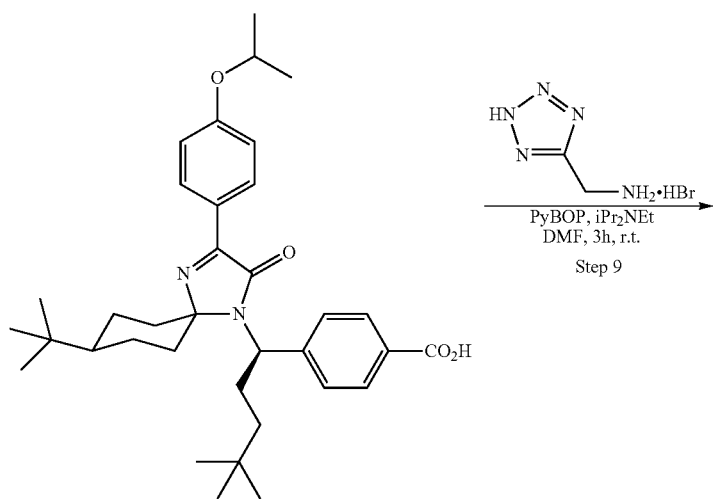
PyBOP, iPr₂NEt
DMF, 3h, r.t.
Step 9
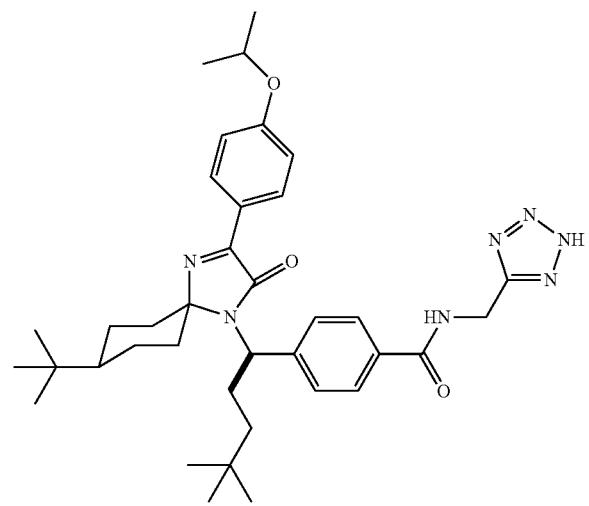
Example 2.117

Step 1

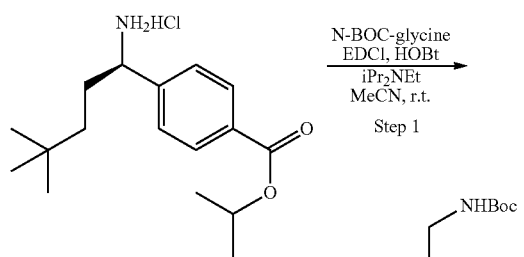

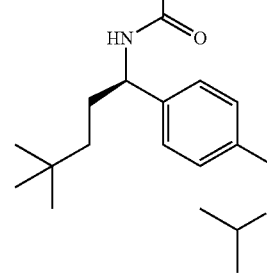

A solution of N—BOC-glycine (6.13 g, 35.0 mmol, 1.10 eq), HOBt (2.68 g, 17.5 mmol, 0.55 eq), and iPr₂NEt (18.3 mL, 105 mmol, 3.29 eq) in MeCN (100 mL) at 0° C. was treated with EDCl (6.71 g, 35.0 mmol, 1.10 eq) followed by the amine hydrochloride salt (10.00 g, 31.9 mmol, 1.00 eq). The resulting mixture was stirred at 0° C. for 15 minutes. The reaction was allowed to warm to room temperature and was stirred 16 h. The reaction was partitioned between EtOAc and a mixture of 1N HCl$_{(aq.)}$ and brine. The aqueous layer was discarded and the organic layer was washed successively with saturated NaHCO₃$_{(aq.)}$ and brine, was dried over anhydrous sodium sulfate, filtered and evaporated to afford the desired product (14.1 g, quant.) which was used in the next step without further purification.

Step 2

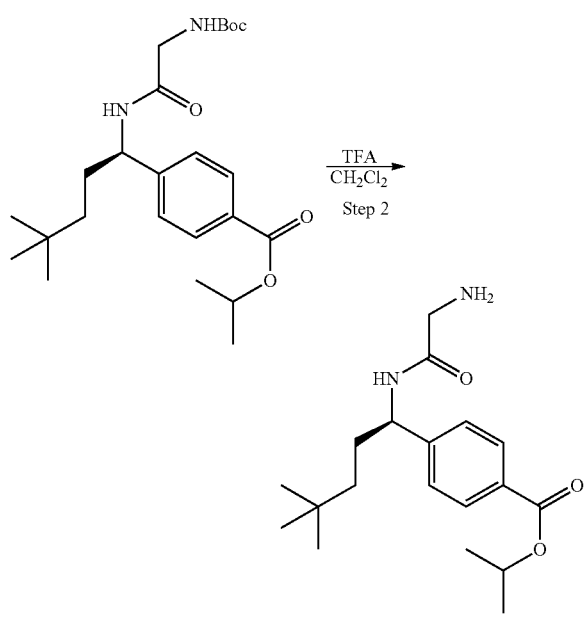

The product from Step 1 (14.1 g, 32.4 mmol, 1 eq) was dissolved in CH₂Cl₂ (200 mL) and treated with TFA (20 mL). After 2 hours, TLC showed the reaction to be incomplete. An additional amount of TFA (20 mL) was added and the reaction was stirred for 2 hours more, at which point, the voltiles were removed in vacuo to afford an oily residue. The crude residue was partitioned between CH₂Cl₂ and 1M NaOH$_{(aq.)}$. The organic layer was saved and the aqueous layer was extracted with CH₂Cl₂. The organic layers were combined, washed with brine, dried over anhydrous sodium sulfate, filtered, and evaporated to afford the desired product (10.51 g, 97%), which was used in the next step without further purification.

Step 3

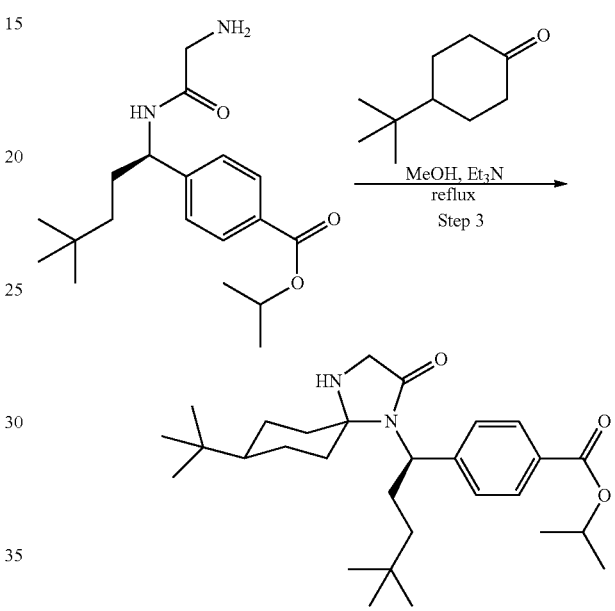

A solution of the product from Step 2 (2.63 g, 7.86 mmol, 1.00 eq), 4-tert-butylcyclohexanone (3.63 g, 23.5 mmol, 2.99 eq), and triethylamine (5.90 mL, 42.3 mmol, 5.38 eq) in MeOH (45 mL) in a round bottomed flask was charged with powdered, 4 angstrom molecular sieves (3.6 g, dried under vacuum, 72 hours at 130° C.). A reflux condenser and nitrogen line were attached and the mixture was refluxed 24 h. The reaction was cooled to room temperature and filtered through Celite®. The Celite® pad was washed with MeOH. The filtrates were combined and concentrated to afford a residue which was purified via silica gel chromatography (gradient elution, 0% to 100% EtOAc in hexanes, SiO₂) to afford the desired product (1.78 g, 48%) as a viscous oil.

Step 4

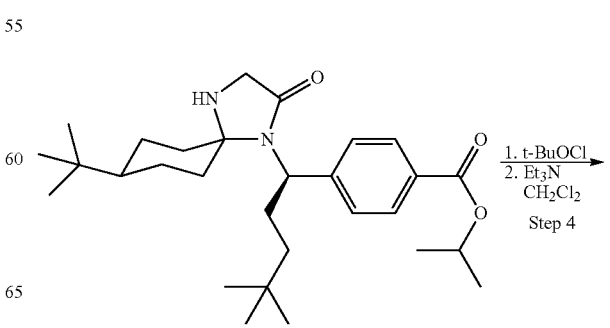

-continued

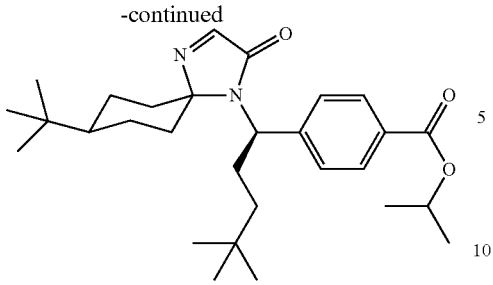

A solution of the product from Step 3 (1.00 g, 2.12 mmol, 1.00 eq) in CH$_2$Cl$_2$ (30 mL) at room temperature was treated with tert-butyl hypochlorite (0.29 mL, 2.55 mmol, 1.20 eq). After stirring for 45 minutes, triethylamine (1.2 mL, 8.50 mmol, 4.00 eq) was added dropwise, and the resulting solution was stirred for 45 minutes more. The reaction was quenched by adding 10% sodium bisulfite$_{(aq.)}$ while stirring. The organic layer was removed and saved, and the aqueous layer was extracted with CH$_2$Cl$_2$. The organic layers were combined, washed with brine, dried over anhydrous sodium sulfate, filtered, and evaporated to afford a crude residue which was purified via silica gel chromatography (gradient elution, 0% to 30% EtOAc in hexanes, SiO$_2$) to afford the desired product (730 mg, 73%) as a white foam.

Step 5

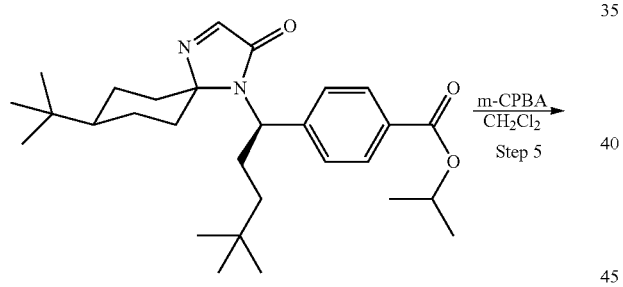

The product from Step 4 (730 mg, 1.6 mmol, 1.0 eq) was dissolved in CH$_2$Cl$_2$ (10 mL), and treated with m-CPBA (77% w/w with water, 1.05 g, 4.67 mmol, 3.00 eq) and stirred at room temperature overnight. The reaction was quenched with 10% sodium thiosulfate$_{(aq.)}$ and saturated NaHCO$_{3(aq.)}$. The resulting biphasic mixture was stirred until both layers were clear. The layers were separated and both were saved. The aqueous layer was extracted with CH$_2$Cl$_2$. The combined organic layers were washed with brine, dried over anhydrous sodium sulfate, filtered, and evaporated to afford a crude product which was purified via silica gel chromatography (gradient elution, 0% to 100% EtOAc in hexanes, SiO$_2$) to afford the desired product (560 mg, 74%) as a white foam.

Step 6

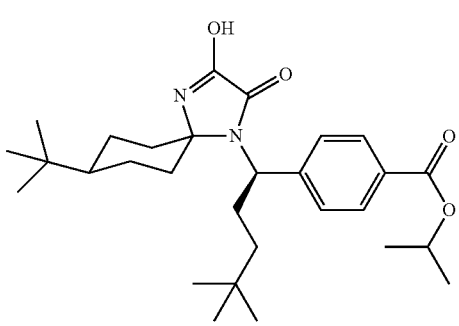

The product from Step 5 (560 mg, 1.16 mmol, 1.00 eq) and iPr$_2$NEt (0.50 mL, 2.89 mmol, 2.5 eq) were dissolved in CH$_2$Cl$_2$ (30 mL) and cooled to −10° C. Trifluoromethanesulfonic anhydride (0.233 mL, 1.39 mmol, 1.20 eq) was added dropwise and the mixture was stirred for 30 minutes at −10° C. An additional amount of trifluoromethanesulfonic anhydride (0.2 mL) was added and the reaction was stirred for an additional 30 minutes. An additional amount of iPr$_2$NEt (1.0 mL, 5.78 mmol, 5 eq) was added and the reaction was stirred for 5 minutes. The reaction mixture was partitioned between CH$_2$Cl$_2$ and brine. The layers were separated and both were saved. The aqueous layer was extracted with CH$_2$Cl$_2$. The combined organic layers were dried over anhydrous sodium sulfate, filtered, and evaporated to afford a crude product which was purified via silica gel chromatography (gradient elution, 0% to 20% EtOAc in hexanes, SiO$_2$) to afford the desired product (478 mg, 67%).

Step 7

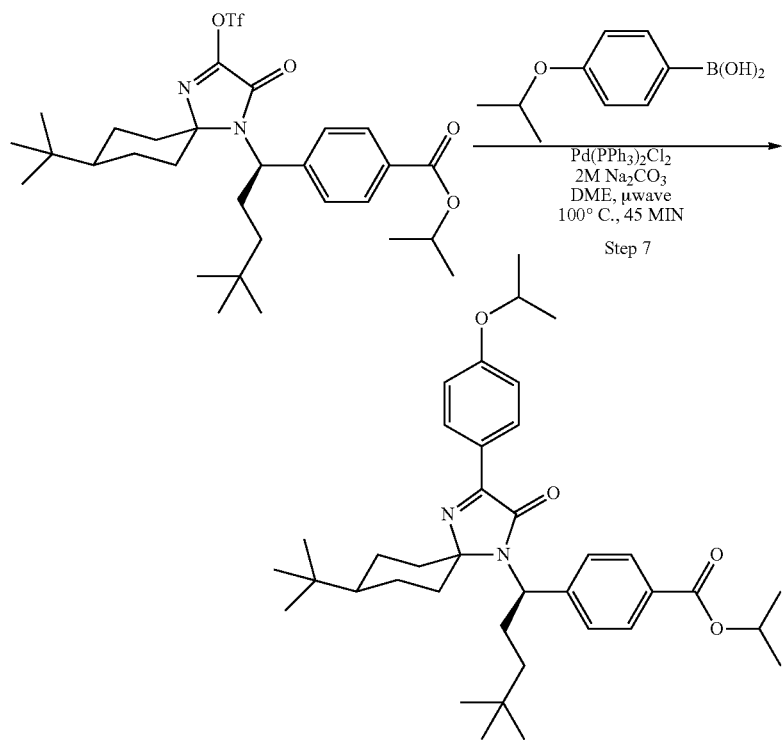

The product from Step 6 (120 mg, 0.194 mmol, 1.00 eq), 4-isopropoxyphenylboronic acid (52 mg, 0.29 mmol, 1.5 eq), and bis(triphenylphosphino)palladium(II)chloride (7 mg, 0.01 mmol, 0.05 eq) were combined with 2M $Na_2CO_{3(aq.)}$ (0.7 mL) and DME (1 mL) in a Biotage microwave vial. The reaction underwent microwave heating (45 minutes, 100° C., very high absorption). The organic layer of the reaction was removed and saved. The aqueous layer was extracted with EtOAc. The organic layers were combined and evaporated to afford a crude product which was purified via silica gel chromatography (gradient elution, 0% to 100% EtOAc in hexanes, $SiO_2$) to afford the desired product (71 mg, 60%).

Step 8

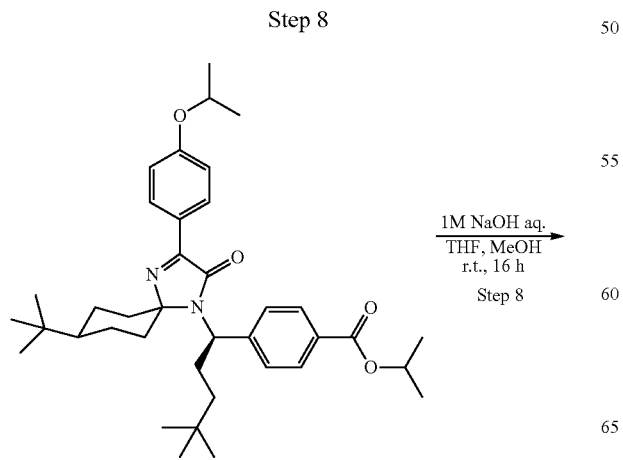

-continued

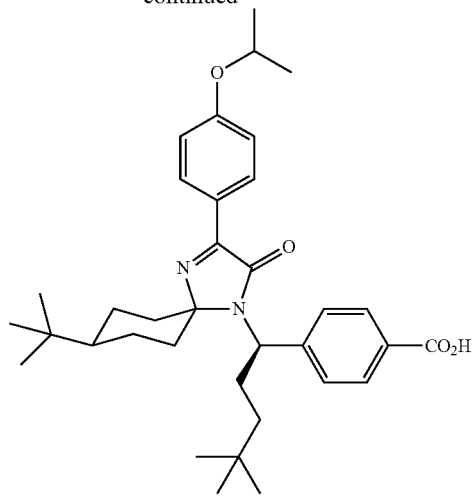

A solution of the product from Step 7 (71 mg, 0.12 mmol, 1 eq) in THF (3 mL) and MeOH (3 mL) was treated with 1M $NaOH_{(aq.)}$ (1.5 mL, 1.50 mmol, 13 eq). The resulting solution was stirred overnight at room temperature. The reaction mixture was then partitioned between EtOAc and 1M $HCl_{(aq.)}$. The aqueous layer was discarded, and the organic layer was washed with brine, dried over anhydrous sodium sulfate, filtered, and evaporated to afford the desired product (70 mg, quant.), which was used in the next step without further purification.

203

Step 9

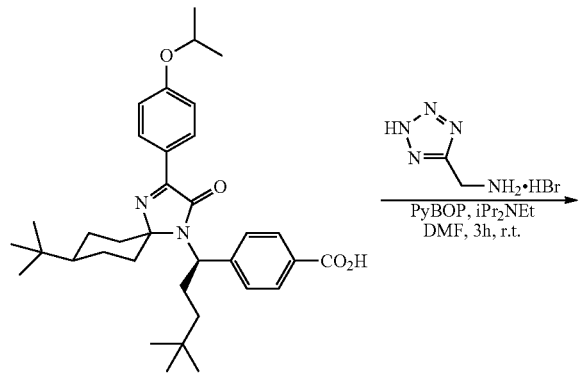

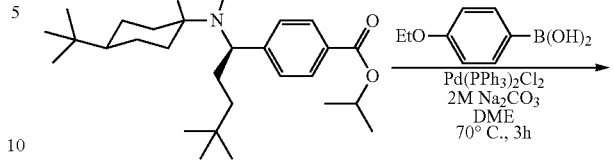

-continued

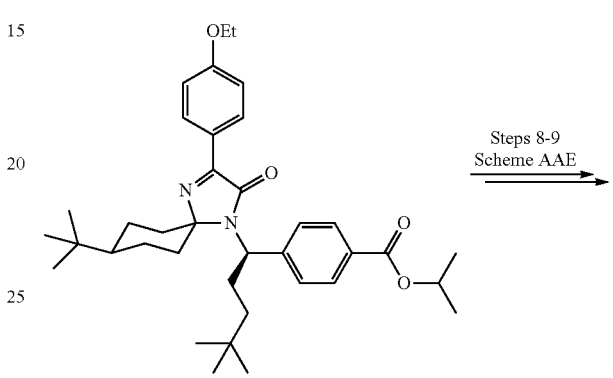

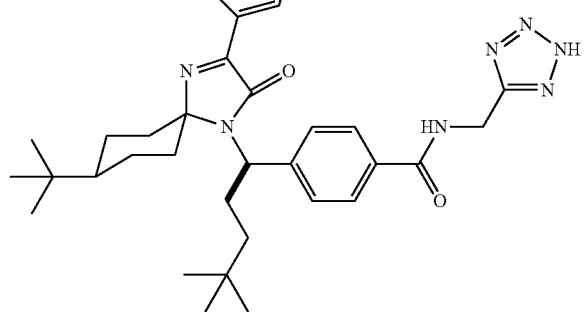

Example 2.117

The product from Step 8 (70 mg, 0.12 mmol, 1.0 eq), (2H-tetrazol-5-yl)methanamine hydrobromide (34 mg, 0.19 mmol, 1.5 eq), iPr$_2$NEt (0.065 mL, 0.37 mmol, 3.0 eq), and PyBOP (78 mg, 0.15 mmol, 1.2 eq) were combined in DMF (1 mL) and were stirred at room temperature for 3 hours. The solvent was removed in vacuo to afford a crude residue which was dissolved in DMSO and purified via reversed-phase C18 chromatography (gradient elution, 10% MeCN in water with 0.1% HCOOH to 100% MeCN with 0.1% HCOOH) to afford Example 2.117.

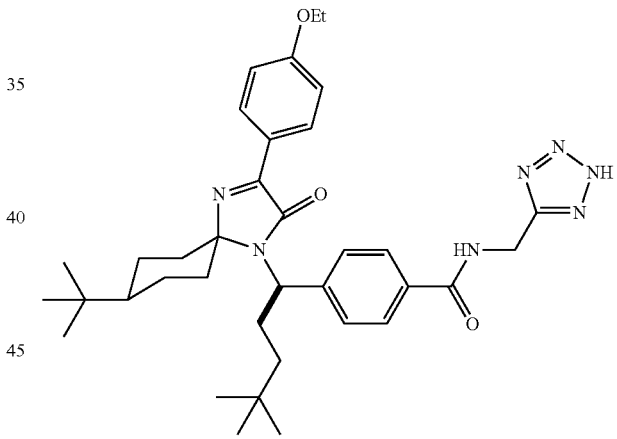

Example 2.137

Step 1

Scheme AAF

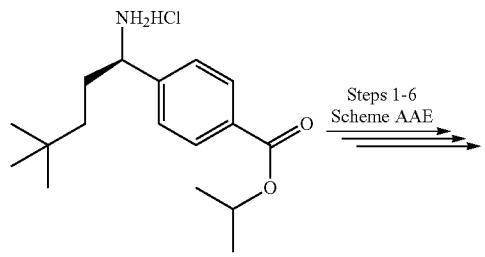

Steps 1-6
Scheme AAE

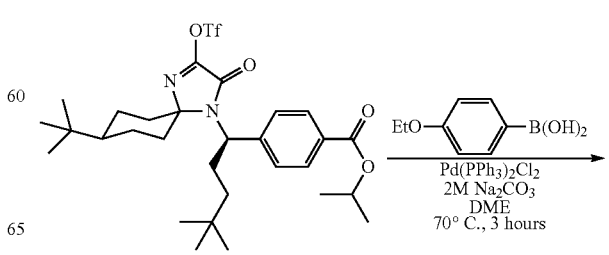

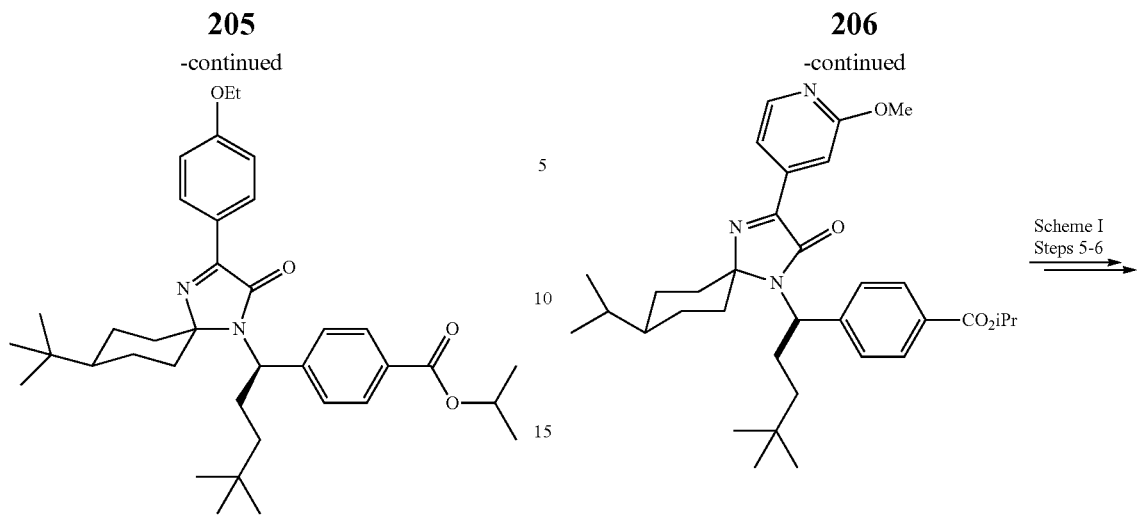

The product from Scheme AAE, Step 6 (200 mg, 0.324 mmol, 1 eq), 4-ethoxyphenylboronic acid (81 mg, 0.49 mmol, 1.5 eq), and bis(triphenylphosphino)palladium(II)chloride (10 mg, 0.02 mmol, 0.05 eq) were combined with 2M $Na_2CO_{3(aq.)}$ (1.5 mL) and DME (3 mL) in a scintillation vial. The reaction was heated in a heating block at 70° C. for 3 h. The reaction was cooled and was partitioned between EtOAc and water. The organic layer was removed and saved, and the aqueous layer was extracted with EtOAc. The organic layers were combined, washed with brine, dried over anhydrous sodium sulfate, filtered, and evaporated to afford a crude product which was purified via silica gel chromatography (gradient elution, 0% to 100% EtOAc in hexanes, $SiO_2$) to afford the desired product (77 mg, 40%).

The product from Step 1 was converted to Example 2.137 using the conditions outlined in Steps 8-9 of Scheme AAE.

The requisite amine, ketone, and N—BOC glycine were converted into the bromide using the Scheme AAA (Steps 1 and 2). The bromide was reacted according to the conditions outlined in Scheme AD Step 6 to provide the arylated intermediate. This intermediate was processed according to the Scheme I (Steps 5 and 6) which provided Example 2.97.

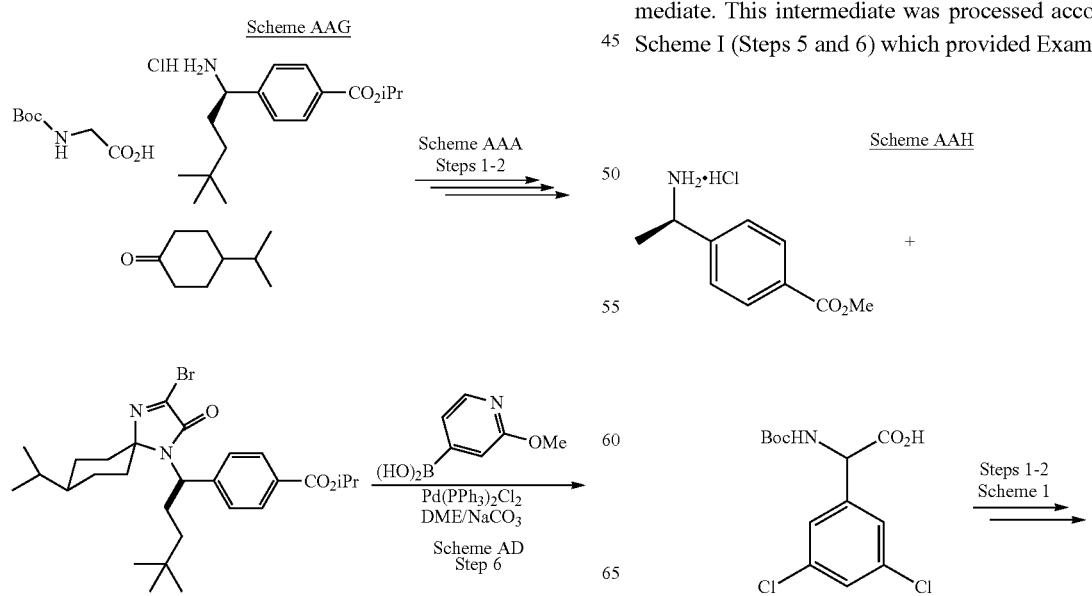

-continued

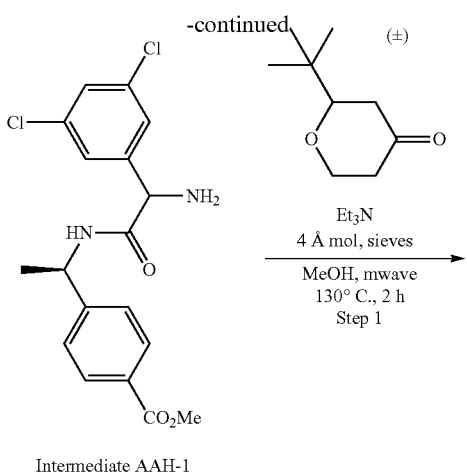

Intermediate AAH-1

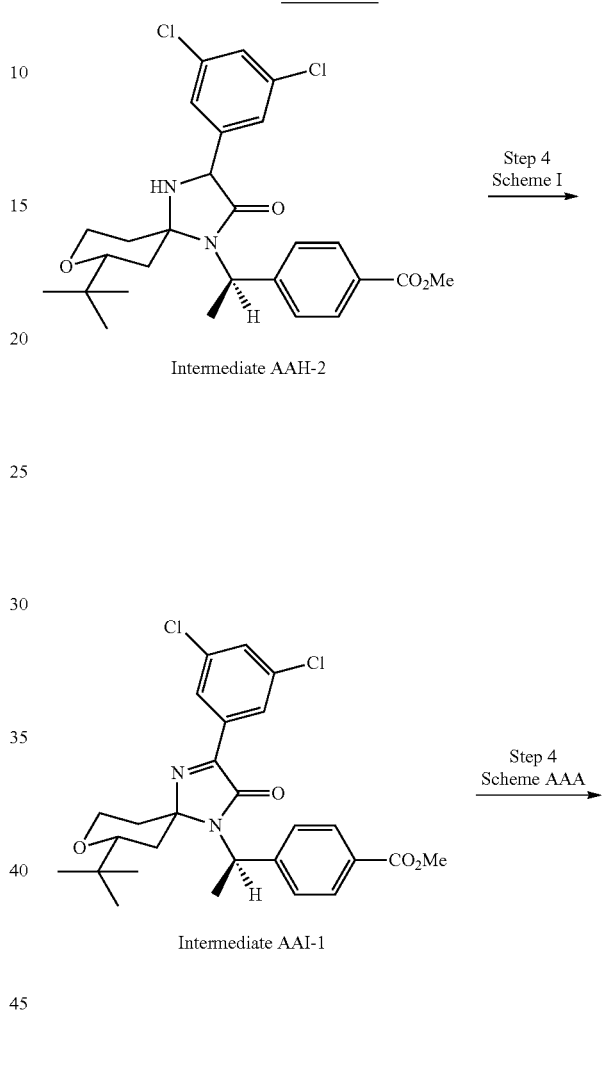

SiO$_2$) to afford the two diastereomeric mixtures Intermediate AAH-2 (68 mg) and Intermediate AAH-3 (290 mg) which were used in the next step without further purification.

(R)-Methyl 4-(1-aminoethyl)benzoate hydrochloride and 2-(tert-butoxycarbonylamino)-2-(3,5-dichlorophenyl)acetic acid were converted to Intermediate AAH-1 via a method similar to that outlined in Steps 1-2 in Scheme 1.

Step 1

Intermediate AAH-1 (400 mg, 1.05 mmol, 1 eq), (±)-2-tert-butyldihydro-2H-pyran-4(3M)-one (328 mg, 2.1 mmol, 2 eq), Et$_3$N (0.29 mL, 2.1 mmol, 2 eq), and powdered 4 Å molecular sieves (400 mg) were taken up in methanol (10 mL). The mixture was heated in a microwave (130° C., high absorption) for 2 h. The mixture was cooled to room temperature, filtered, and concentrated. The residue was purified via silica gel chromatography (gradient elution, 0-50% EtOAc in hexanes,

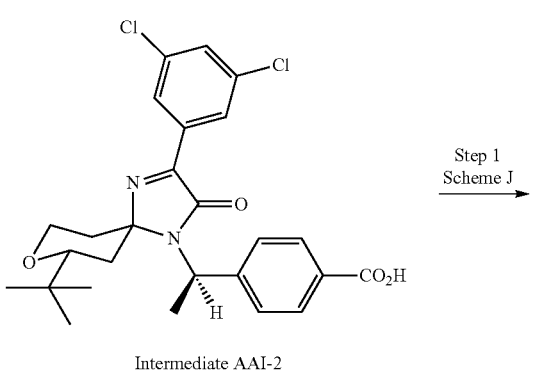

-continued

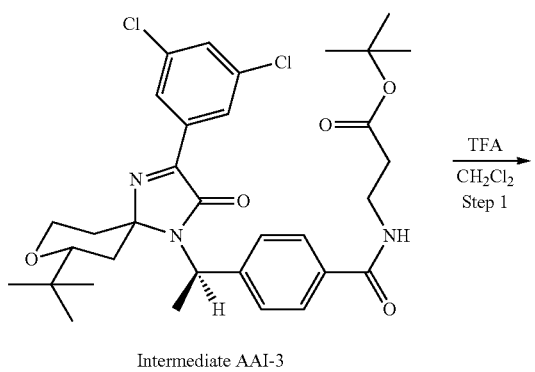

Intermediate AAI-3

Example 1.557

Intermediate AAH-2 was converted to Intermediate AAI-1 via a method similar to that described in Step 4 of Scheme I.

Intermediate AAI-1 was converted to Intermediate AAI-2 via a method similar to that described in Step 4 of Scheme AAA.

Intermediate AAI-2 was converted to Intermediate AAI-3 via a method similar to that described in Step 1 of Scheme AAA.

Scheme AAI, Step 1

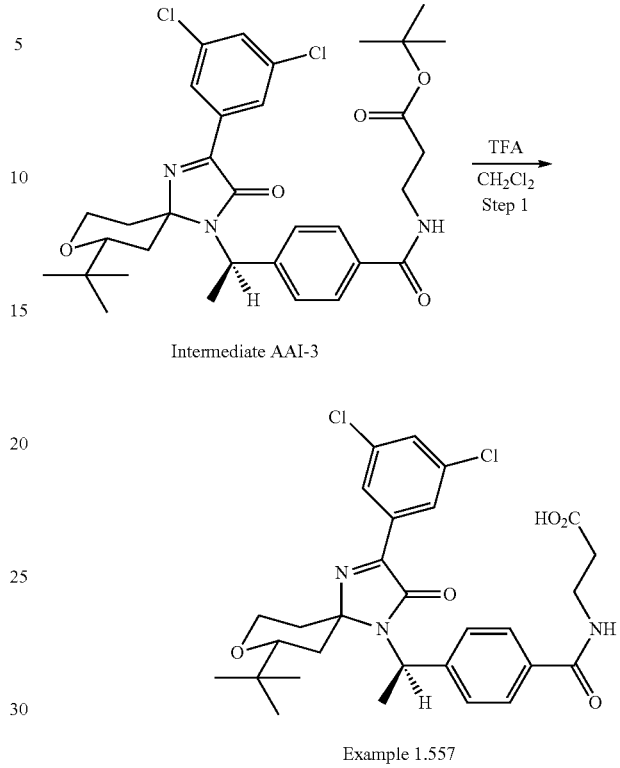

Intermediate AAI-3

Example 1.557

Intermediate AAI-3 (33 mg, 0.052 mmol, 1 eq) was dissolved in $CH_2Cl_2$ (6 mL). Trifluoroacetic acid (3 mL) was added and the reaction was stirred for 3 h at room temperature. The volatiles were removed in vacuo to afford a crude residue which was purified via reversed-phase, C-18 column chromatography (gradient elution, 10% to 80% MeCN in water with 0.1% HCOOH) to afford Example 1.557 (20 mg) as a white solid.

TABLE AAI

Using the requisite starting material, and the method outlined in Scheme AAI, the following examples were prepared:

| Starting Material | Example Number | Example Structure |
|---|---|---|
| Intermediate AAH-3 | 1.527 | |

Scheme AAJ

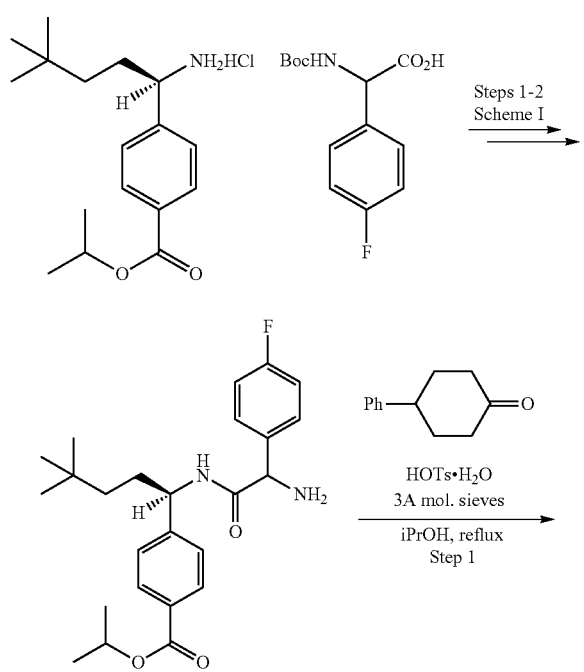

Intermediate AAJ-1

Intermediate AAJ-2

Intermediate AAJ-3

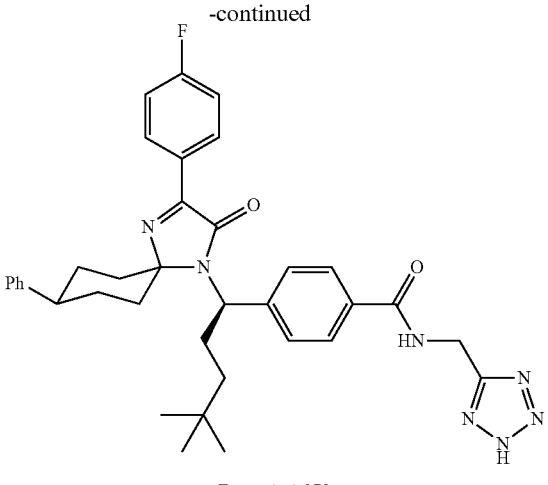

Example 1.373

The amine hydrochloride salt and 2-(tert-butoxycarbonylamino)-2-(4-fluorophenyl)acetic acid were used according to Steps 1-2 in Scheme I to afford the desired Intermediate AAJ-1.

Step 1

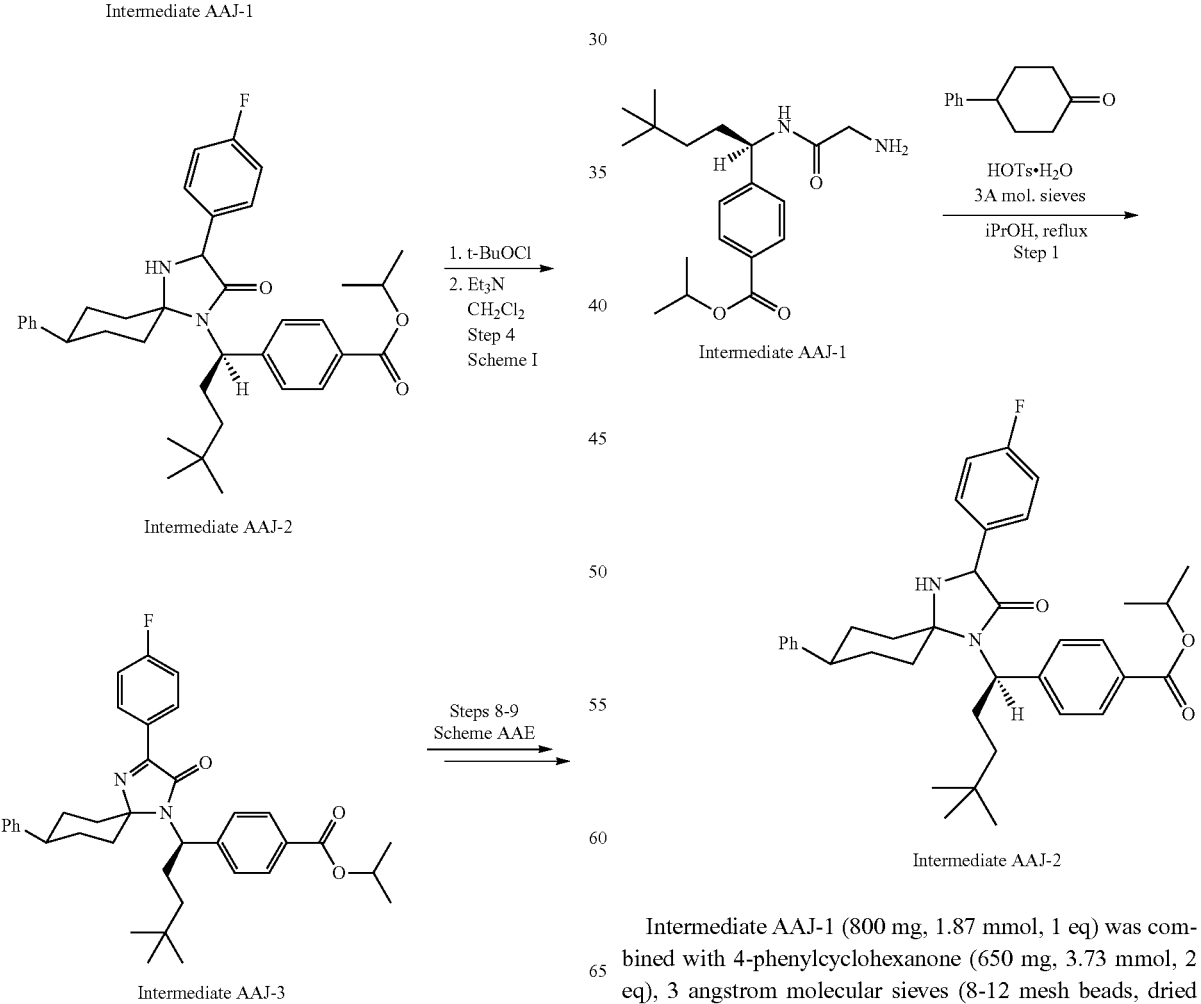

Intermediate AAJ-1

Intermediate AAJ-2

Intermediate AAJ-1 (800 mg, 1.87 mmol, 1 eq) was combined with 4-phenylcyclohexanone (650 mg, 3.73 mmol, 2 eq), 3 angstrom molecular sieves (8-12 mesh beads, dried under vacuum at 130° C., 1.6 g), and para-toluenesulfonic acid monohydrate (36 mg, 0.19 mmol, 0.1 eq) in isopropanol (10 mL) under a nitrogen atmosphere. A reflux condenser was attached, and the reaction was heated at reflux (105° C. oil bath) for 16 h. The reaction was then cooled to room temperature, filtered through Celite® and the resulting filter cake washed with isopropanol. The filtrates were combined and evaporated to afford a crude residue with was partitioned between EtOAc and saturated NaHCO$_{3(aq.)}$. The aqueous layer was discarded and the organic layer was washed with brine, dried over anhydrous sodium sulfate, filtered and evaporated to afford a crude product which was purified via silica gel chromatography (gradient elution, 0% to 40% EtOAc in hexanes, SiO$_2$) to afford the desired product (Intermediate AAJ-2, 1.05 g, 96%) as an inseparable mixture of diastereomers.

Intermediate AAJ-3 was prepared from Intermediate AAJ-2 in a manner similar to that described in Scheme I, Step 4.

Preparation of Example 1.373

Preparation of Intermediate AAJ-3

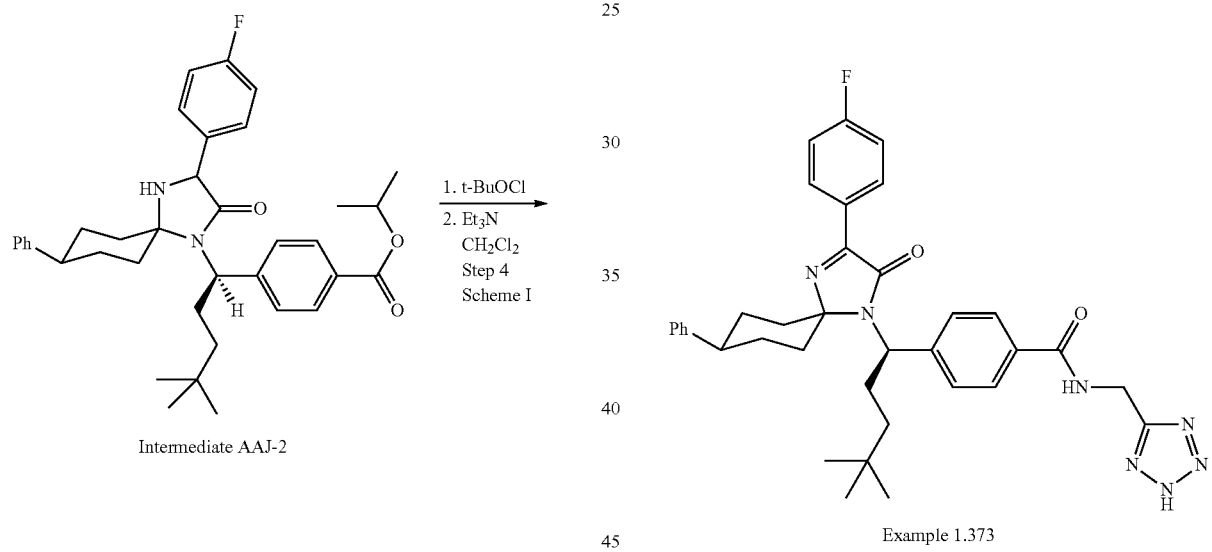

Using a method similar to that outlined in Steps 8-9 of Scheme AAE, Intermediate AAJ-3 was converted to Example 1.373.

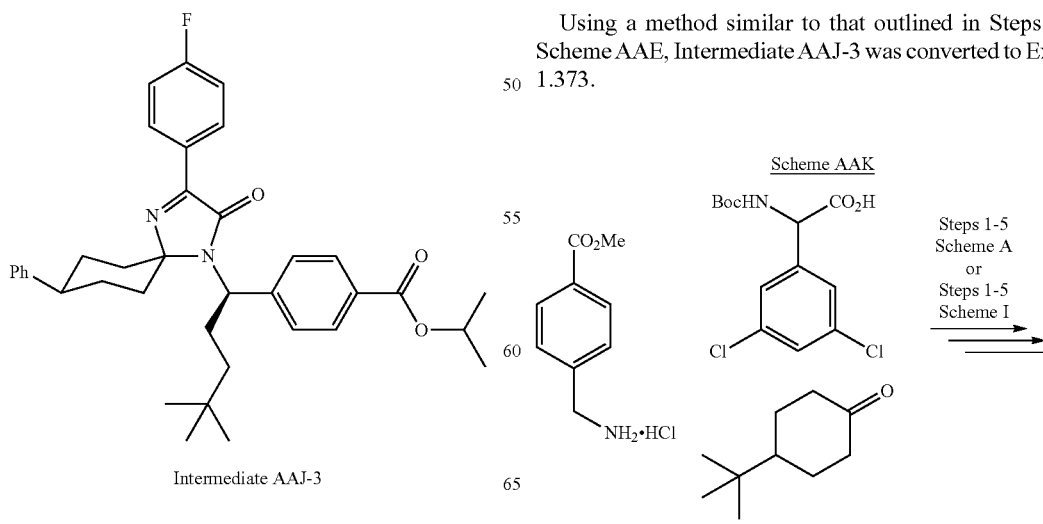

215
-continued

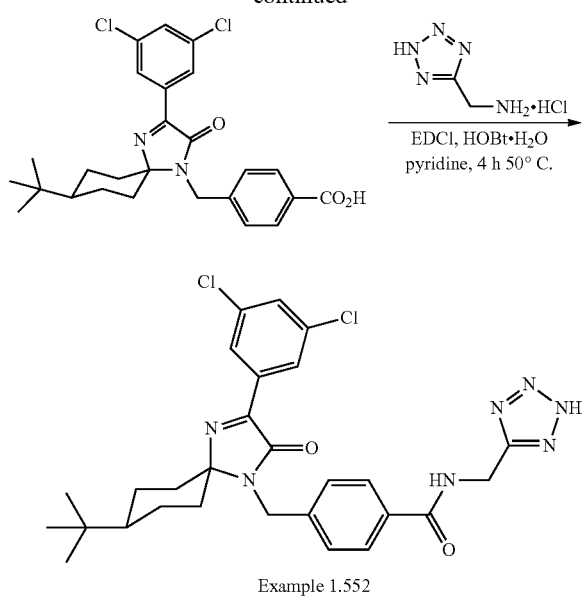

Example 1.552

The benzoic acid prepared from the requisite starting materials via a method similar to that outlined in either Steps 1-5 of Scheme A or Steps 1-5 of Scheme I (195 mg, 0.40 mmol), (2H-tetrazol-5-yl)methanamine hydrochloride (81 mg, 0.60 mmol), HOBt.H$_2$O (89 mg, 0.66 mmol), and EDCl (127 mg, 0.66 mmol) were combined in pyridine (3 mL) and were stirred at 50° C. for 4 hours. The reaction was cooled to room temperature and concentrated to afford a dark residue, which was dissolved in DMSO and chromatographed via reversed-phase C-18 column chromatography (gradient elution, 10% to 100% MeCN in water with 0.1% HCOOH) to afford Example 1.552 (110 mg) as a white solid.

Scheme AAL

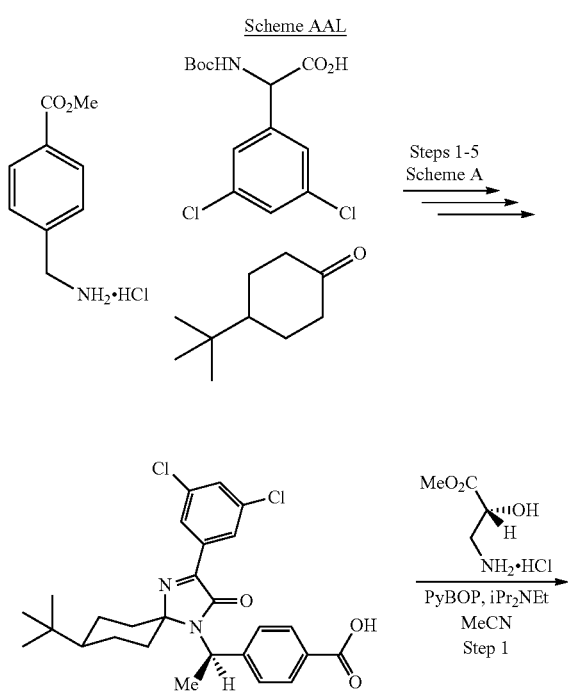

216
-continued

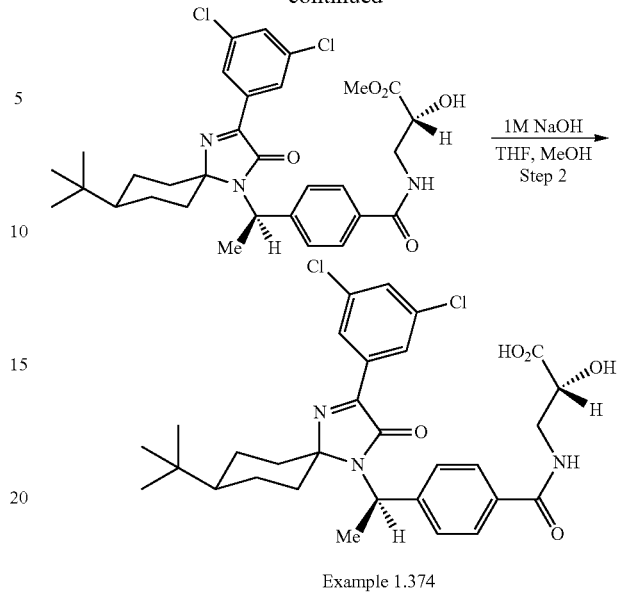

Example 1.374

Step 1

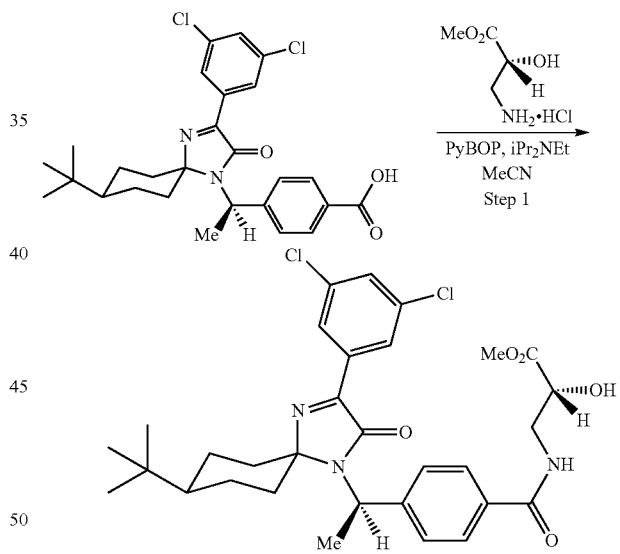

The benzoic acid prepared in Steps 1-5 of Scheme A (106 mg, 0.21 mmol, 1 eq), (R)-methyl 3-amino-2-hydroxypropanoate hydrochloride (33 mg, 0.21 mmol, 1 eq), PyBOP (111 mg, 0.21 mmol, 1 eq), and iPr$_2$NEt (0.11 mL, 0.64 mmol, 3 eq) were combined in MeCN (2 mL) at room temperature. After stirring overnight at room temperature, the reaction mixture was partitioned between EtOAc and 1M HCl$_{(aq.)}$/brine. The aqueous layer was discarded and the organic layer was washed with saturated NaHCO$_{3(aq.)}$ and brine, was dried over anhydrous Na$_2$SO$_4$, was filtered, and was evaporated to afford a crude material. Silica gel chromatography (gradient elution, 0% to 100% EtOAc in hexanes, SiO$_2$) afforded the desired product (137 mg, quant.) as a clear, colorless film.

217

Step 2

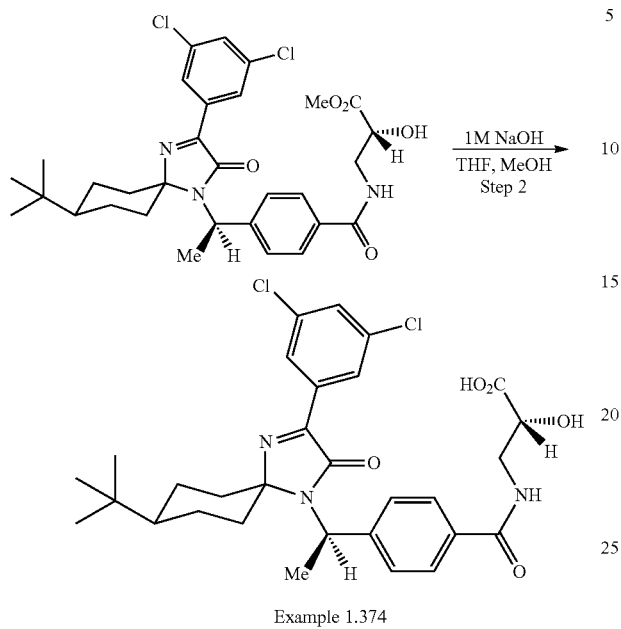

Example 1.374

A solution of the product from Step 1 (137 mg, 0.23 mmol, 1 eq) in MeOH (2 mL) and THF (4 mL) was treated with 1M NaOH$_{(aq.)}$ (1.14 mL, 1.14 mmol, 5 eq). The resulting mixture was stirred for 2 h at room temperature. After adding 1M HCl$_{(aq.)}$ (1 mL) to the reaction mixture, the reaction was concentrated. The crude residue was dissolved in DMSO and purified via reversed-phase C18 chromatography (gradient elution, 10% MeCN in water with 0.1% HCOOH to 100% MeCN with 0.1% HCOOH) to afford Example 1.374 (93 mg, 67%) as a white solid.

Scheme AAM

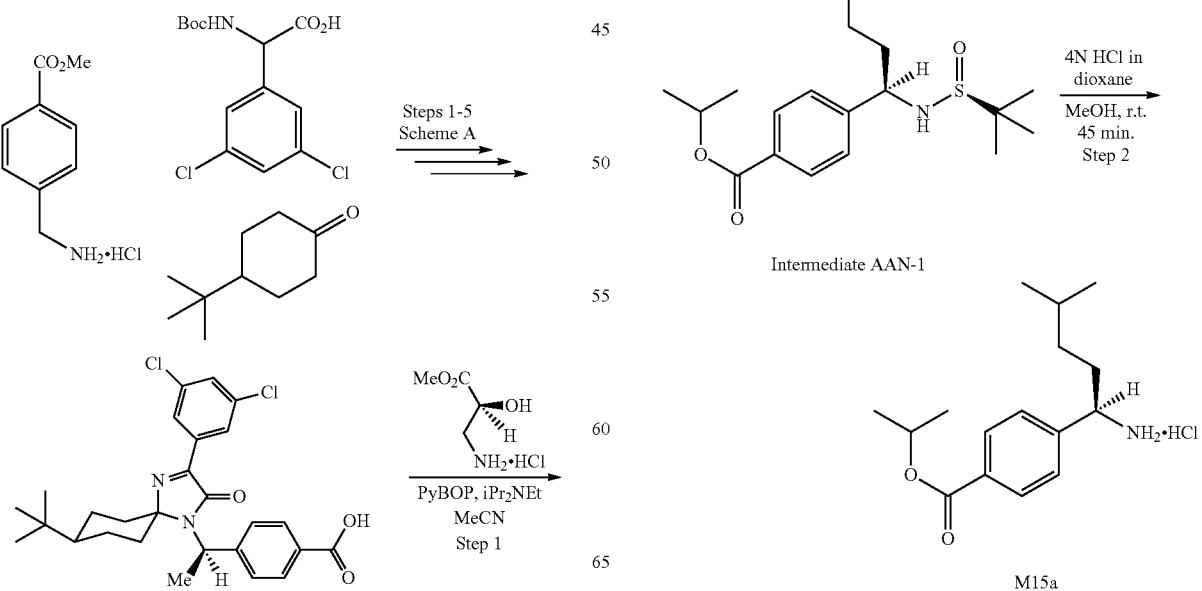

218

-continued

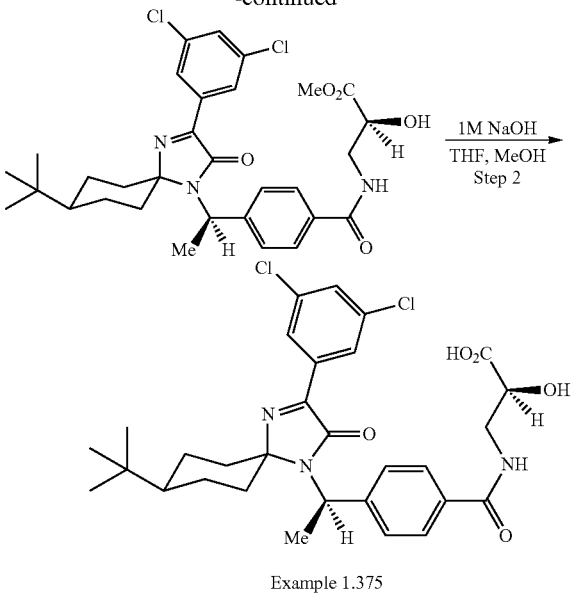

Example 1.375

Example 1.375 was prepared in a manner similar to that described in Steps 1-2 of Scheme AAL with the exception that (S)-methyl 3-amino-2-hydroxypropanoate hydrochloride was substituted for (R)-methyl 3-amino-2-hydroxypropanoate hydrochloride.

Scheme AAN

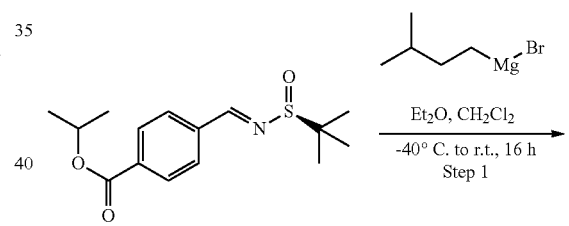

Step 1

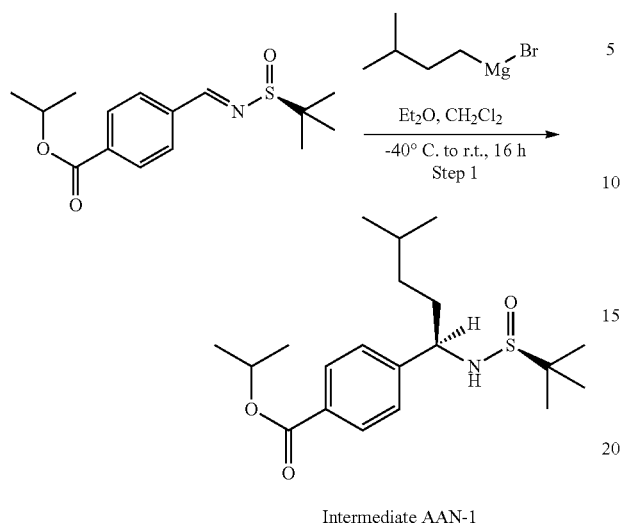

Intermediate AAN-1

Magnesium turnings (14.6 g, 600 mmol, 1 eq) were added to Et$_2$O (400 mL) under a nitrogen atmosphere in a round bottomed flask with a reflux condenser attached. A crystal of iodine was added to the mixture, followed by 1-bromo-3-methylbutane (20 mL). The mixture was gently warmed to 30° C., at which point the reaction initiated and a vigorous refluxing ensued. Additional aliquots of 1-bromo-3-methylbutane were added at a rate such that the refluxing was maintained. After completion of the addition of 1-bromo-3-methylbutane (total amount: 72 mL, 601.1 mmol, 1 eq), the mixture was refluxed for 2 h. The reaction was then cooled to room temperature, affording the requisite isopentylmagnesium bromide solution.

The sulfinimine (90.0 g, 305 mmol, 1.00 eq) was dissolved in CH$_2$Cl$_2$ (1000 mL), and the solution was cooled to −40° C. The previously prepared isopentylmagnesium bromide solution was added dropwise over a one hour period via a dropping funnel to the sulfinimine solution. The reaction was stirred at −40° C. for 4 h. The reaction was stirred for an additional 16 h, during which time the cold bath was allowed to expire. Saturated ammonium chloride$_{(aq.)}$ was added to the reaction and the resulting murky suspension was stirred for 30 min. An attempt to filter the reaction through Celite® resulted in a clogged filter pad. The crude reaction, including the clogged Celite® pad was transferred to an Erlenmeyer flask. EtOAc (2000 mL) and 20% sodium citrate$_{(aq.)}$ (2000 mL) were added to the crude mixture and the solution was stirred for 2 h. The biphasic solution was filtered, and the Celite® left behind in the filter was washed with EtOAc and water. The combined biphasic filtrate was separated. The aqueous layer was extracted with EtOAc. The organic layers were combined, washed with brine twice, dried over anhydrous MgSO$_4$, filtered, and evaporated to afford a viscous green oil. Silica chromatography (performed in two batches, each on a 600 g silica gel column, gradient elution, 0% to 100% EtOAc in hexanes, SiO$_2$) afforded the desired addition product as a 5.6:1 mixture of diastereomers. The latter fractions of the product peak were collected separately, as they were enriched in the major diastereomer. The enriched material was recrystallized from hot hexanes to afford the major diastereomer (Intermediate AAN-1, 9.71 g, 99.8:0.1 dr, ChiralPak AD, 95:5 hexanes:isopropanol, 1 mL/min, 254 nm) as white crystals. Additional crops of crystals can be obtained from the mixed fractions.

Step 2

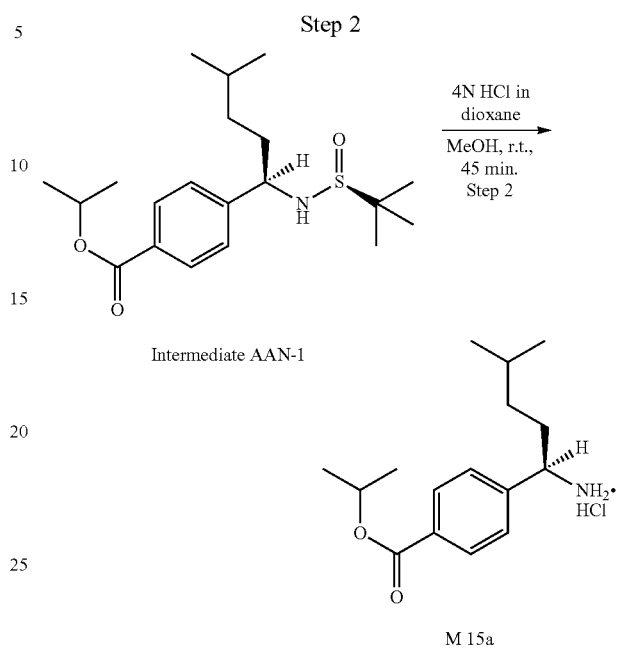

M 15a

A solution of Intermediate AAN-1 (22.2 g) in MeOH (100 mL) at room temperature was treated with 4N HCl in dioxane (28 mL). The resulting solution was stirred for 45 min at room temperature. The reaction was concentrated and treated with Et$_2$O (500 mL) to afford a white solid, which was collected via filtration, washed with Et$_2$O and dried under vacuum to afford Intermediate Amine HCl salt M15a as a white solid (14.7 g).

Scheme AAO

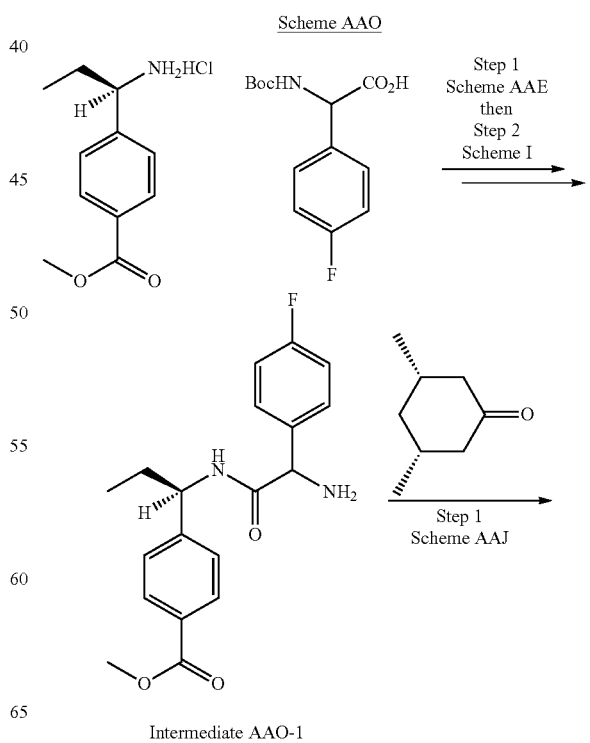

Intermediate AAO-1

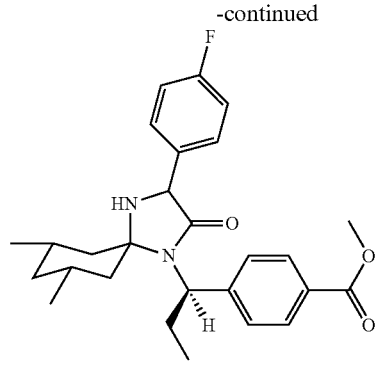

Intermediate AAO-2

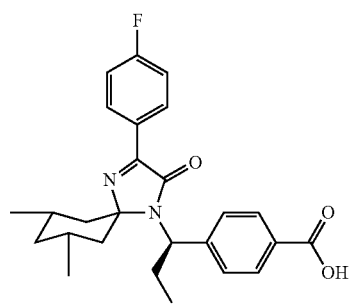

Intermediate AAO-3

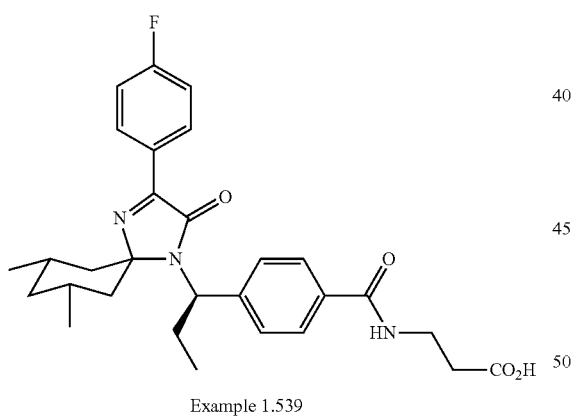

Example 1.539

Intermediate AAO-1 was prepared in two steps from the requisite starting materials in a manner similar to that described in Step 1 of Scheme AAE followed by Step 2 of Scheme I.

Intermediate AAO-2 was prepared from Intermediate AAO-1 in a manner similar to that described in Step 1 of Scheme AAJ.

Intermediate AAO-3 was prepared from Intermediate AAO-2 in a manner similar to that described in Steps 4-5 of Scheme I.

Example 1.539 was prepared from Intermediate AAO-3 in a manner similar to that described in Steps 1-2 of Scheme J.

Scheme AAP

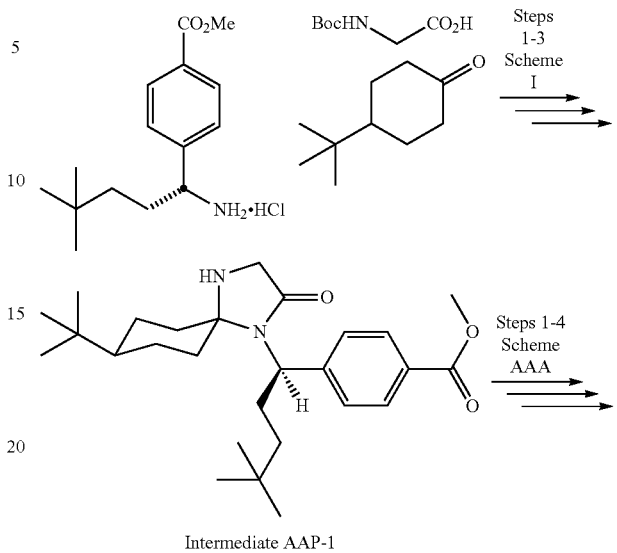

Intermediate AAP-1

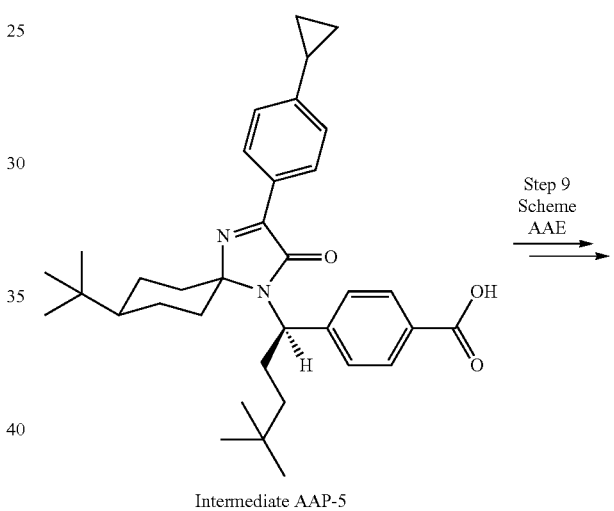

Intermediate AAP-5

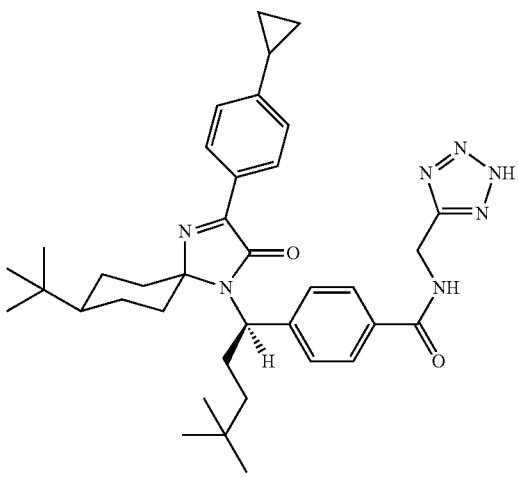

Example 2.118

Intermediate AAP-1 was prepared from the requisite starting materials in a manner similar to that described in Steps 1-3 of Scheme I.

Intermediate AAP-2 was prepared from Intermediate AAP-1 in a manner similar to that described in Steps 1-4 of Scheme AAA.

Example 2.118 was prepared from Intermediate AAP-2 in a manner similar to that described in Step 9 of Scheme AAE.

Scheme AAQ

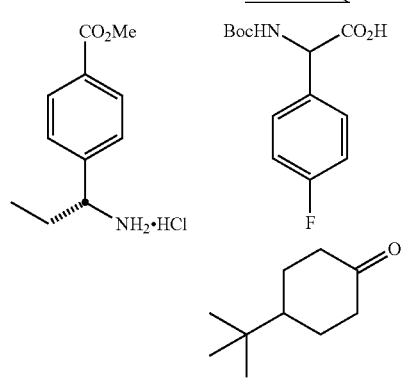
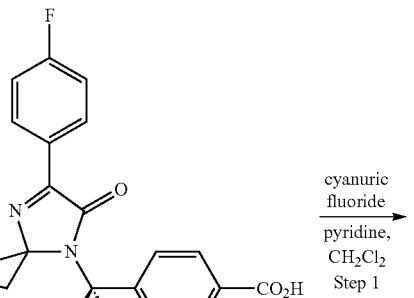
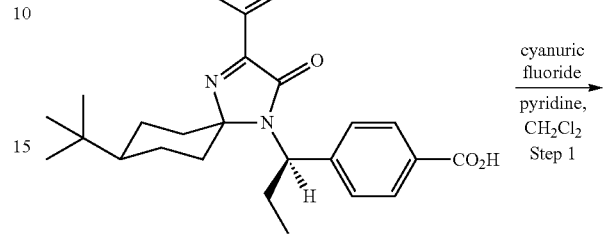

Step 1

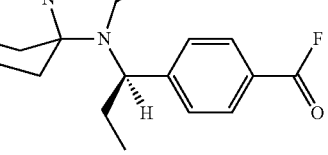

The benzoic acid (200 mg, 0.430 mmol, 1 eq) (prepared according to Scheme AAQ) was dissolved in methylene chloride (3 mL) and pyridine (0.14 mL). The resulting solution was cooled to 0° C. and cyanuric fluoride (0.075 mL, 0.861 mmol, 2 eq) was added. After stirring the reaction at 0° C. for 30 min, saturated NaHCO$_{3(aq.)}$ was added and the mixture was stirred 5 min at 0° C. The organic layer was removed, dried over anhydrous Na$_2$SO$_4$, filtered, and evaporated to afford the desired acid fluoride (215 mg, quant.) which was used in the next step without further purification.

Step 2

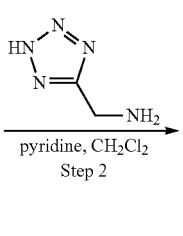

Example 1.551

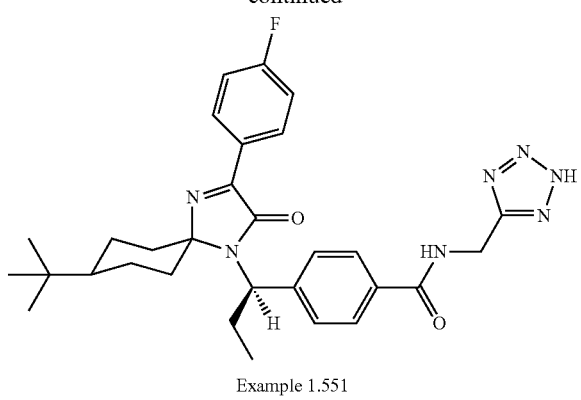

Example 1.551

A solution of the acid fluoride prepared in Step 1 (201 mg, 0.43 mmol, 1 eq) and (2H-tetrazol-5-yl)methanamine (49 mg, 0.50 mmol, 1.15 eq) were added to pyridine (2 mL) and methylene chloride (2 mL) at room temperature. The resulting suspension was stirred at room temperature for 72 h. The reaction was concentrated, dissolved in DMSO, and chromatographed via reversed-phase C-18 column chromatography (gradient elution, 10% to 100% MeCN in water with 0.1% HCOOH) to afford Example 1.551 (62 mg, 26%) as an off-white foam.

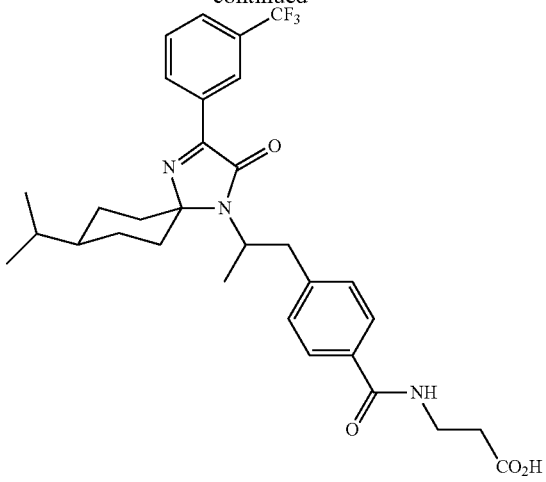

Example 1.556

Using the appropriate starting materials, Example 1356 was prepared using a method similar to that described in Step 1 of Scheme AAE followed by Steps 2-5 of Scheme I then Steps 1-2 of Scheme J.

Scheme AAR

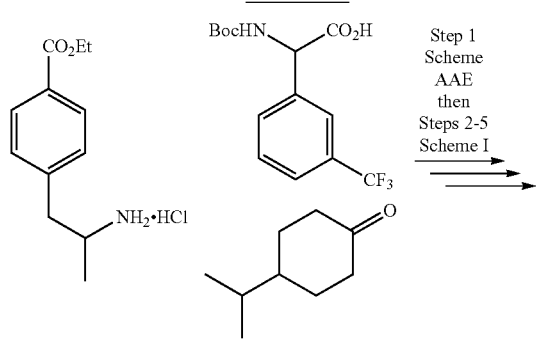

Scheme AAS

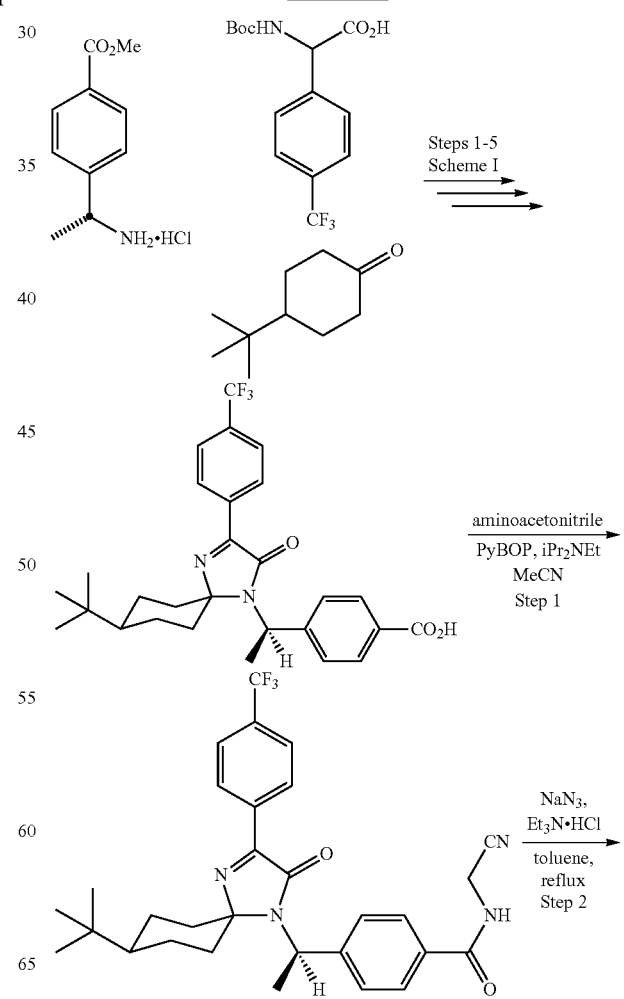

-continued

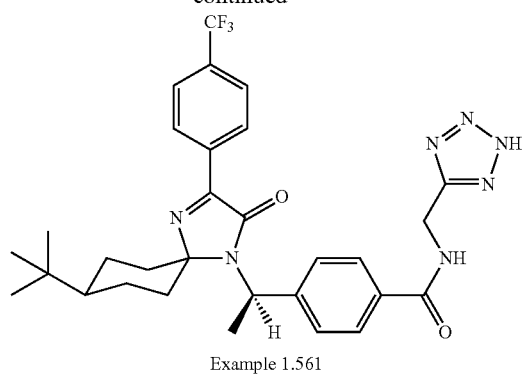

Example 1.561

Step 1

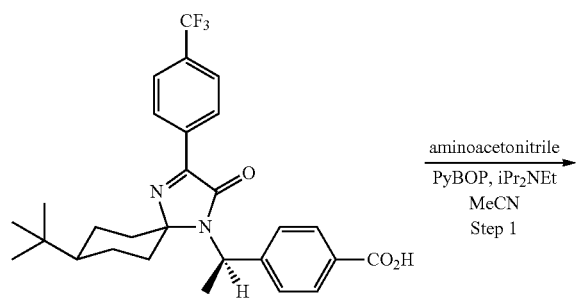

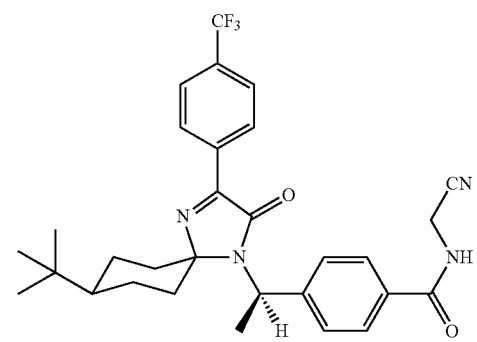

The benzoic acid (Prepared from the requisite starting materials via a method similar to that described in Steps 1-5 of Scheme 1,166 mg, 0.33 mmol, 1 eq), aminoacetonitrile (19 mg, 0.33 mmol, 1 eq), iPr$_2$NEt (0.12 mL, 0.66 mmol, 2 eq), and PyBOP (171 mg, 0.33 mmol, 1 eq) were combined in MeCN (5 mL) and were stirred overnight at room temperature. The reaction was partitioned between EtOAc and 1N HCl$_{(aq.)}$/brine. The aqueous layer was discarded and the organic layer was washed with saturated NaHCO$_{3(aq.)}$ and brine, was dried over anhydrous Na$_2$SO$_4$, was filtered, and was evaporated to afford a crude yellow foam. Silica gel chromatography (gradient elution, 10% to 100% EtOAc in hexanes, SiO$_2$) afforded the desired amide (175 mg, 98%) as a glass.

Step 2

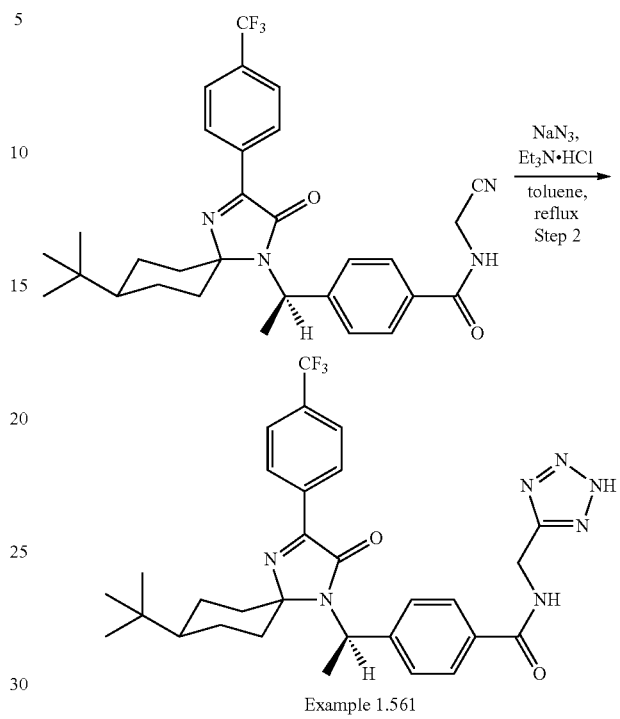

Example 1.561

The benzamide prepared in Step 1 (160 mg, 0.30 mmol, 1 eq), sodium azide (59 mg, 0.90 mmol, 3 eq), and triethylamine hydrochloride (123 mg, 0.90 mmol, 3 eq) were combined in toluene and were heated at reflux for 16 h. Additional amounts of sodium azide (59 mg, 0.90 mmol, 3 eq) and triethylamine hydrochloride (123 mg, 0.90 mmol, 3 eq) were added and the reaction heated at reflux for an additional 6 h. The solvent was removed in vacuo to afford a crude residue which was dissolved in methanol, and chromatographed via reversed-phase C-18 column chromatography (gradient elution, 10% to 100% MeCN in water with 0.1% HCOOH) to afford a mixture of starting material and product. This mixture was then subjected to silica gel chromatography (gradient elution, 0% to 100% EtOAc in hexanes, SiO$_2$ then gradient elution 20% to 50% MeOH in EtOAc) to afford Example 1.561 (126 mg) as a foam.

Scheme AAT

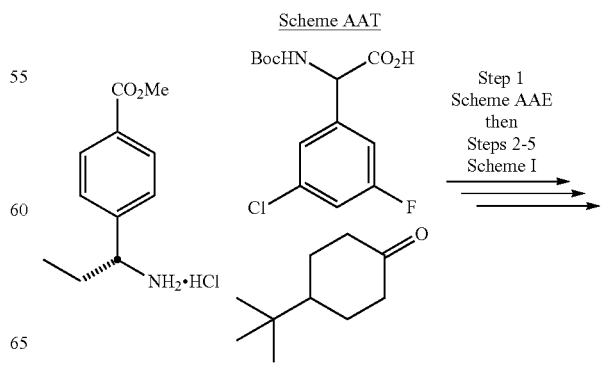

229
-continued

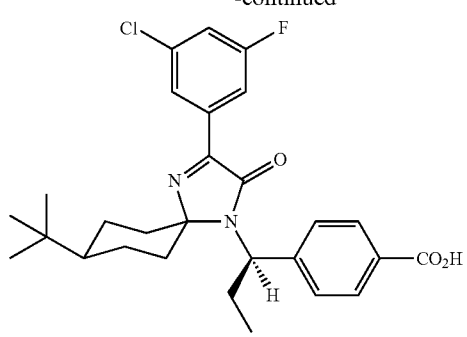

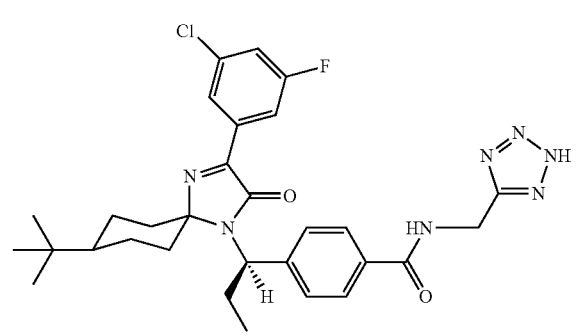

Example 1.532

The benzoic acid intermediate in Scheme AAT was prepared from the requisite starting materials using a method similar to that described in Step 1 of Scheme AAE followed by Steps 2-5 of Scheme I.

Example 1.532 was prepared from the benzoic acid in a manner similar to that described in Step 9 of Scheme AAE.

Scheme AAU

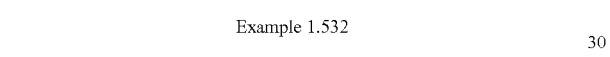
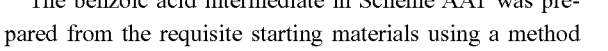

Intermediate AAU-1

230
-continued

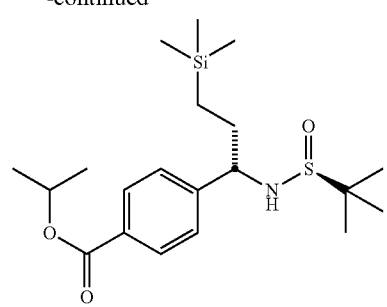

Intermediate AAU-2

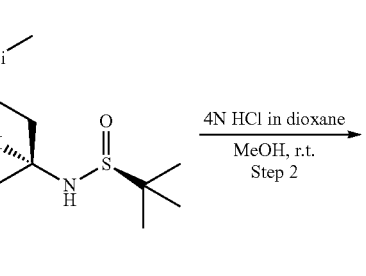

Intermediate AAU-1

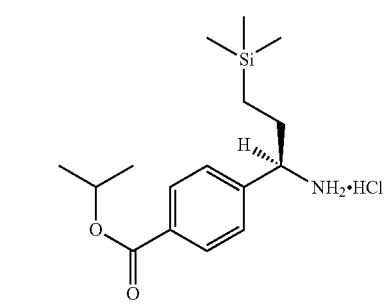

M205

Step 1

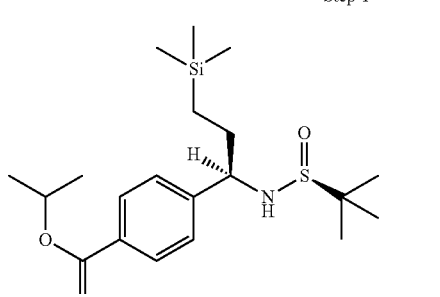

Isomer A

231
-continued

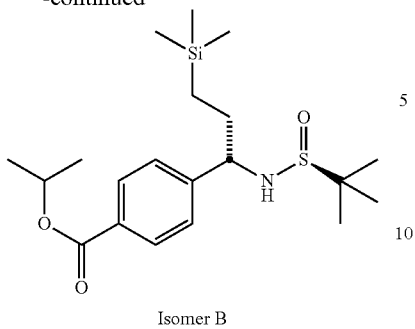

Isomer B

Magnesium turnings (3.85 g, 158 mmol, 1 eq) were added to Et$_2$O (100 mL) under a nitrogen atmosphere in a round bottomed flask with a reflux condenser attached. A crystal of iodine was added to the mixture, followed by (2-bromoethyl) trimethyl silane (5 mL). The mixture was gently warmed to 32° C., at which point the reaction initiated and a vigorous refluxing ensued. Additional aliquots of (2-bromoethyl) trimethyl silane were added at a rate such that the refluxing was maintained. After completion of the addition of (2-bromoethyl) trimethyl silane(total amount: 25 mL, 158.7 mmol, 1 eq), the mixture was refluxed for 1 h. The reaction was then cooled to room temperature, affording the requisite (2-(trimethylsilyl)ethyl)magnesium bromide solution.

The sulfinimine (23.8 g, 80.7 mmol, 1.00 eq) was dissolved in CH$_2$Cl$_2$ (300 mL), and the solution was cooled to –40° C. The previously prepared (2-(trimethylsilyl)ethyl)magnesium bromide solution was added dropwise over a one hour period via a dropping funnel to the sulfinimine solution. The reaction was stirred at –40° C. for 3 h. The reaction was stirred for an additional 16 h, during which time the cold bath was allowed to expire. A 20% sodium citrate$_{(aq.)}$ solution (300 mL) was added to quench the reaction, and the resulting mixture was stirred for 30 min. The biphasic solution was separated. The aqueous layer was extracted with CH$_2$Cl$_2$. The organic layers were combined, washed with brine, dried over anhydrous Na$_2$SO$_4$, filtered, and evaporated to afford a viscous oil which was subjected to silica gel chromatography (gradient elution, 0% to 60% EtOAc in hexanes, SiO$_2$) to afford the desired addition product as a 1:1 mixture of diastereomers (7.59 g). The diastereomeric mixture of addition products was dissolved in 50 mL of hot heptane and was then allowed to slowly cool to room temperature. The solution was allowed to stand at room temperature for 4 days, during which time clusters of white needles formed, which were collected via filtration, washed with heptane and dried to afford pure Intermediate AAU-1 (2.72 g, 8.5% yield).

Step 2

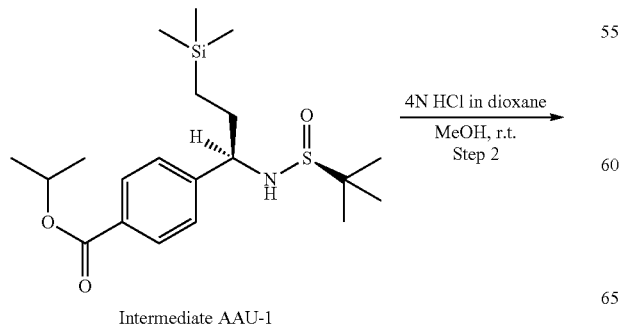

Intermediate AAU-1

232
-continued

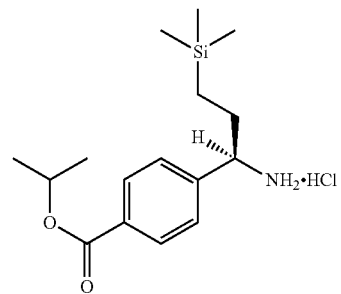

M205

A solution of Intermediate AAU-1 (2.7 g) in MeOH (40 mL) at room temperature was treated with 4N HCl in dioxane (4 mL). The resulting solution was stirred for 2 h at room temperature. The reaction was concentrated and treated with Et$_2$O to afford a white solid, which was collected via filtration, washed with Et$_2$O and dried under vacuum to afford amine HCl salt M205 as a white solid (1.4 g).

Scheme L

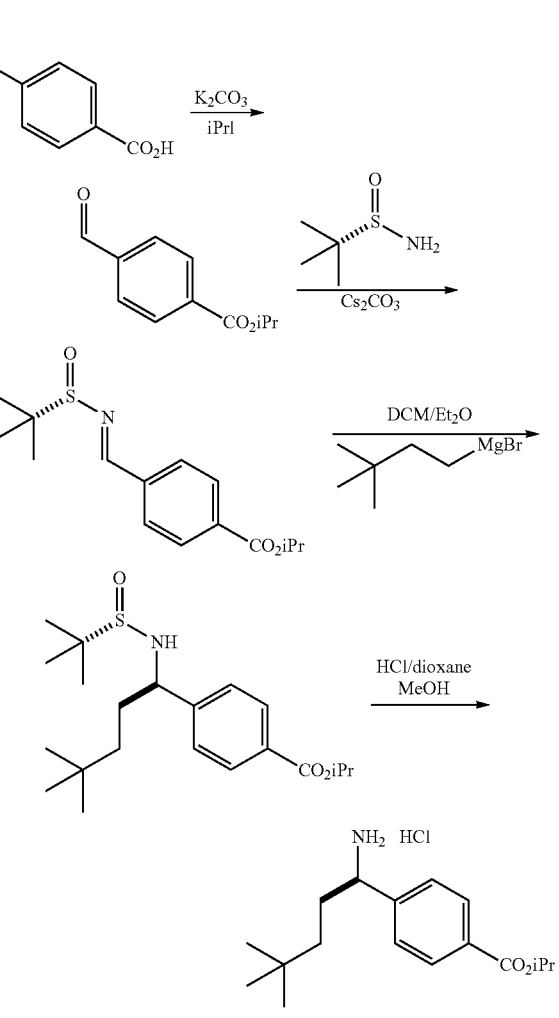

M6

Step 1

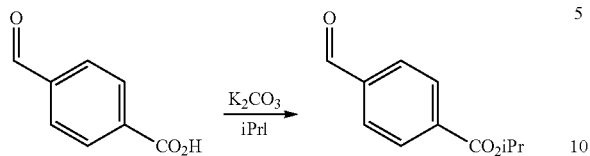

The aldehyde (20 g, 133 mmol), isopropyl iodide (68 g, 399 mmol), and K$_2$CO$_3$ (37 g, 266 mmol) were taken up in THF/DMF (2/1, 300 ml), and the mixture was heated at 70° C. for 64 h. The solution was partitioned between EtOAc and water. The aqueous layer was extracted with EtOAc. The combined organic layers were washed with brine and dried (MgSO$_4$). The solution was filtered and concentrated which yielded 20.3 g (79%) of the ester as an oil that solidified upon standing.

Step 2

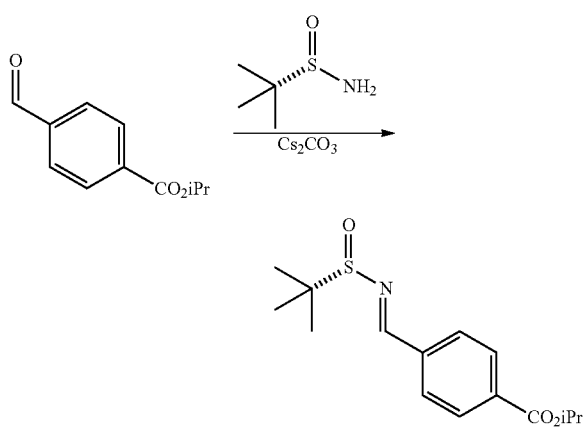

The aldehyde (21.2 g, 110 mmol), (S)-2-methylpropane-2-sulfinamide (13.4 g, 110 mmol), and Cs$_2$CO$_3$ (36 g. 110 mmol) were taken up in DCM (400 ml), and the mixture was stirred at 42° C. for 30 h. The solution was filtered and concentrated. This yielded 32.2 g (99%) of the imine as an oil that solidified upon standing.

Step 3

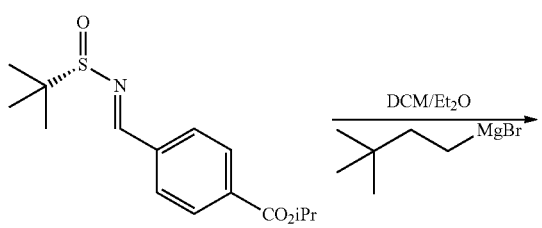

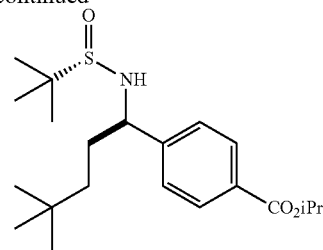

The grignard reagent was made as follows: Magnesium turnings (2.4 g, 100 mmol) were suspended in dry Et$_2$O (150 ml) under N$_2$. A few iodine crystals were added to the mixture. The 1-bromo-3,3-dimethyl butane (16.5 g, 100 mmol) in Et$_2$O (50 ml) was added in portions over ~45 minutes to maintain gentle reflux. After the addition of all of the 1-bromo-3,3-dimethyl butane, the reaction was refluxed for 2 hr. The gringnard solution was used as is in the next step.

The grignard reagent (100 mmol in 200 ml of Et$_2$O) was added to a solution of the imine (9.9 g, 33.5 mmol) at −78° C. The solution was slowly warmed to RT. After stirring at RT for 2 h, the reaction was quenched with sat. NH$_4$Cl$_{(aq.)}$ at 0° C. Ethyl acetate was added, and the mixture was stirred at RT for 1 h. The layers were separated, and the aqueous layer was extracted with EtOAc. The combined organic layers were washed with brine and dried (MgSO$_4$). The mixture was filtered and concentrated. The residue was purified via gradient flash chromatography (0-40% EtOAc in hexanes, SiO$_2$). The major fraction was recrystallized from heptane/IPA which yielded 2.8 g of the desired product. The mother liquor was recrystallized once again to provide an additional 1.3 g (32% total).

Step 4

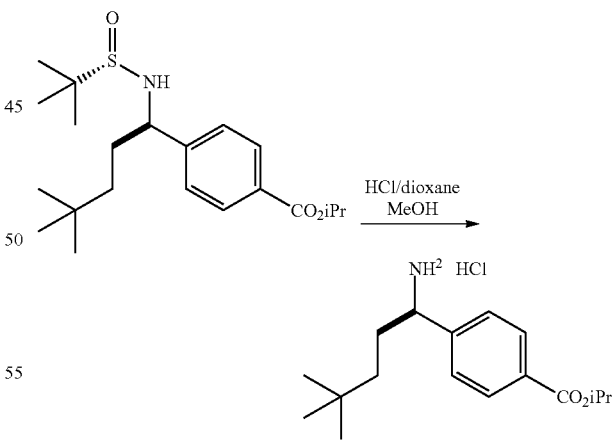

The sulfinamide (3.18 g, 8.3 mmol) was taken up in MeOH (30 ml), and 4 M HCl in dioxane (4.1 ml) was added at RT. The solution was stirred at RT for 1.5 h. The solution was concentrated, and ether was added which resulted in the formation of a white solid. The solid was collected and rinsed with ether. The solid was dried which provided 2.2 g (84%) of the amine HCl salt M6.

Scheme LA

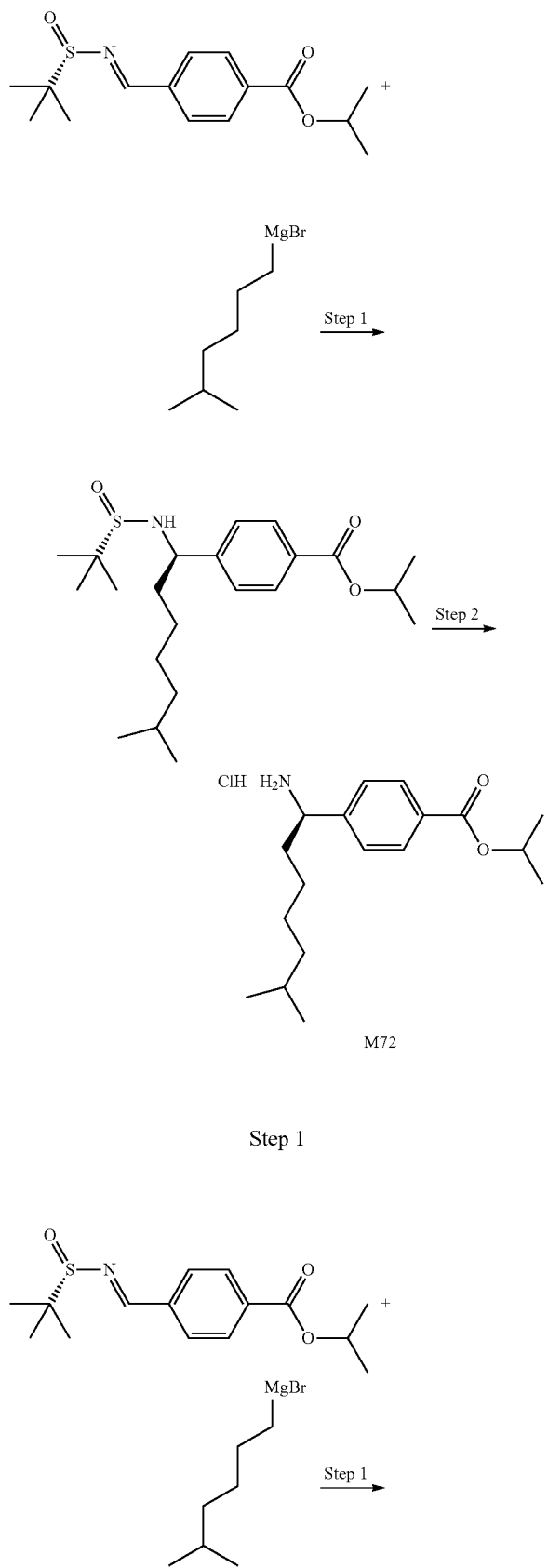

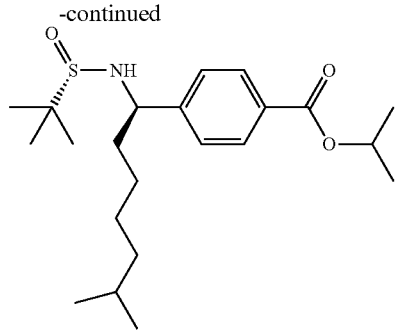

Step 1

Magnesium turnings (2.21 g, 90.9 mmol) were stirred with a magnetic stir bar overnight in a 500 ml round-bottom flask. Anhydrous ethyl ether 9173 ml) was added. 1-Bromo-5-methylhexane (15.0 g, 90.9 mmol) was added dropwise over 40 minutes. The solution was stirred at RT for 3.5 hours. The grignard solution was added to (S)-isopropyl 4-((tert-butylsulfinylimino)methyl)benzoate (13.4 g, 45.4 mmol) in 100 mL anhydrous DCM at −48° C. The solution was allowed to gradually warm to RT and was stirred at RT for 18 h. Saturated $NH_4Cl$ (150 ml) and EtOAc (200 mL) were added. The aqueous layer was separated and extracted with EtOAc (100 mL). The organic layers were washed with brine (200 mL), dried over anhydrous $Na_2SO_4$, filtered, and concentrated. The product was purified by $SiO_2$ chromatography (200 g, Hexane/EtOAc, 25% to 33%) to give a mixture of R isomer and S isomer of isopropyl 4-(1-((S)-1,1-dimethylethylsulfinamido)-6-methylheptyl)benzoate (14.8 g, 82.4%, R:S=2:1). This mixture of two isomers (6 g) was resolved by Chiralpak AD column (4% isopropyl alcohol in hexane) to give isopropyl 4-((R)-1-((S)-1,1-dimethylethylsulfinamido)-6-methylheptyl)benzoate (2.61 g).

Step 2

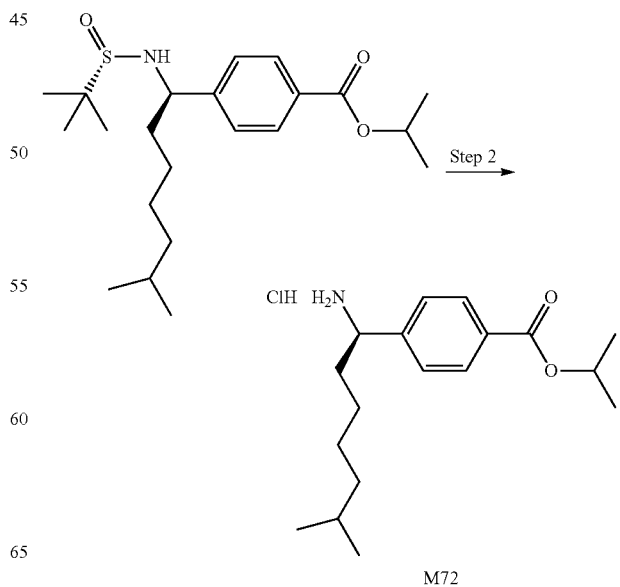

4-((R)-1-((S)-1,1-dimethylethylsulfinamido)-6-methylheptyl)benzoate (2.60 g, 6.81 mmol) was dissolved in MeOH (10 mL). HCl (4N in dioxane, 4.3 mL, 17.0 mmol) was added. The reaction mixture was stirred at RT overnight. The solvent was removed via use of a rotary evaporator. The residue was stirred with ethyl ether (100 mL) for 10 minutes. The solid was collected by filtration. The solid was washed with ethyl ether 910 mL) twice which furnished upon drying (R)-isopropyl 4-(1-amino-6-methylheptyl)benzoate hydrochloride M72 (1.50 g 75.6%).

Scheme LB

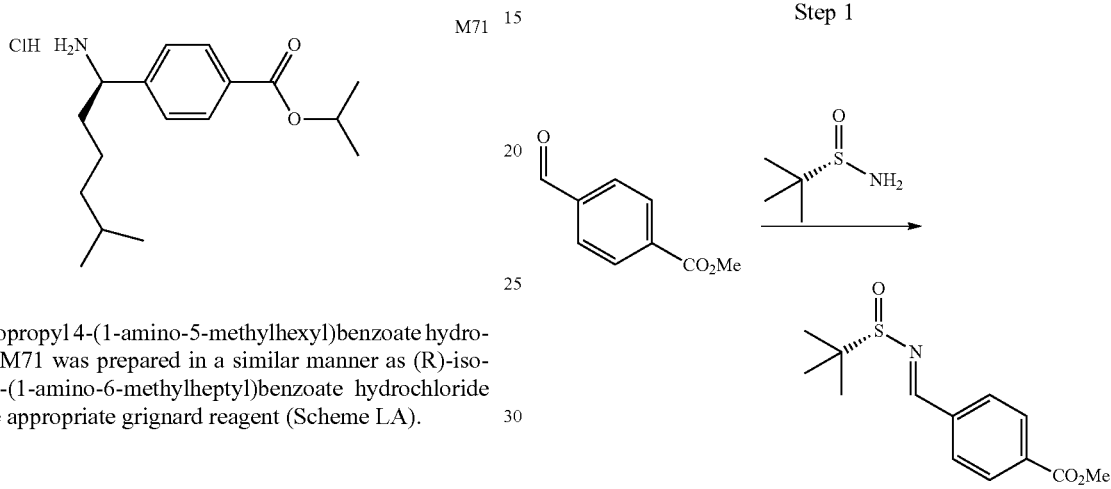

M71

(R)-Isopropyl 4-(1-amino-5-methylhexyl)benzoate hydrochloride M71 was prepared in a similar manner as (R)-isopropyl 4-(1-amino-6-methylheptyl)benzoate hydrochloride using the appropriate grignard reagent (Scheme LA).

Scheme MA

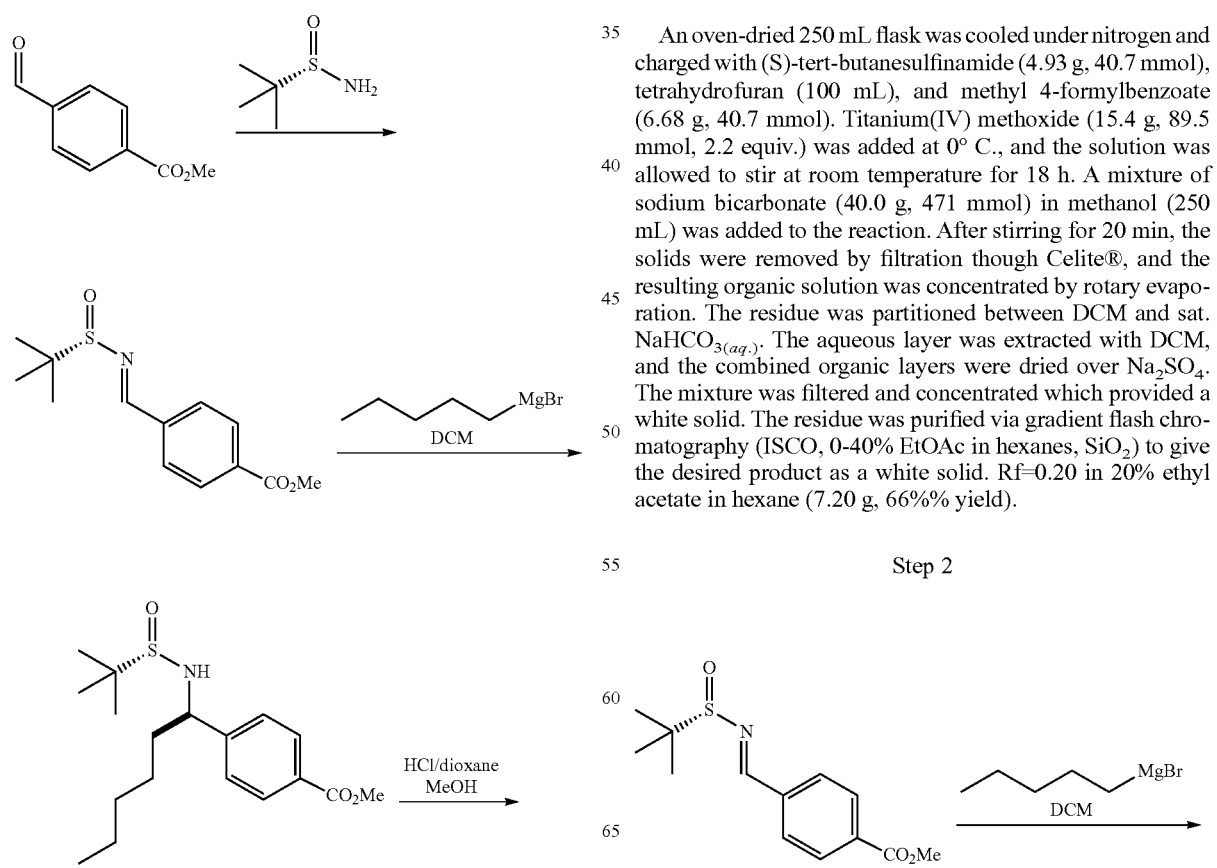

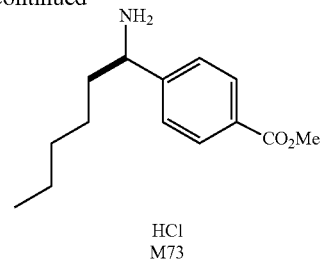

HCl
M73

Step 1

An oven-dried 250 mL flask was cooled under nitrogen and charged with (S)-tert-butanesulfinamide (4.93 g, 40.7 mmol), tetrahydrofuran (100 mL), and methyl 4-formylbenzoate (6.68 g, 40.7 mmol). Titanium(IV) methoxide (15.4 g, 89.5 mmol, 2.2 equiv.) was added at 0° C., and the solution was allowed to stir at room temperature for 18 h. A mixture of sodium bicarbonate (40.0 g, 471 mmol) in methanol (250 mL) was added to the reaction. After stirring for 20 min, the solids were removed by filtration though Celite®, and the resulting organic solution was concentrated by rotary evaporation. The residue was partitioned between DCM and sat. NaHCO$_3$$_{(aq.)}$. The aqueous layer was extracted with DCM, and the combined organic layers were dried over Na$_2$SO$_4$. The mixture was filtered and concentrated which provided a white solid. The residue was purified via gradient flash chromatography (ISCO, 0-40% EtOAc in hexanes, SiO$_2$) to give the desired product as a white solid. Rf=0.20 in 20% ethyl acetate in hexane (7.20 g, 66%% yield).

Step 2

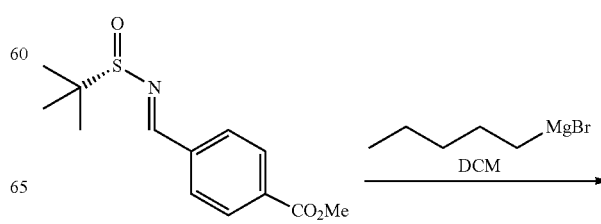

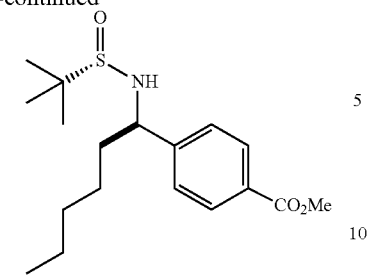

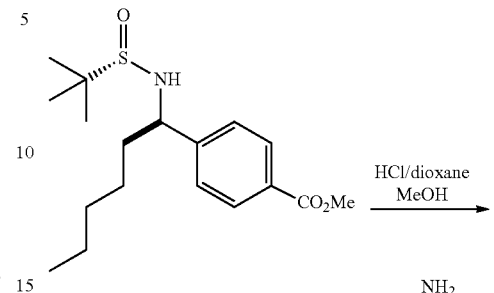

Step 3

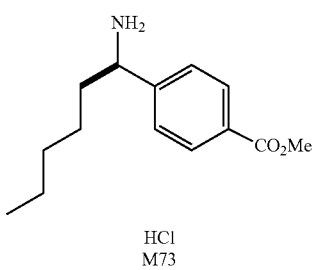

An oven-dried 125 mL flask was cooled under nitrogen, and it was charged with (S)-methyl 4-((tert-butylsulfinylimino)methyl)benzoate (2.67 g, 10.0 mmol) and dichloromethane (60 mL). The colorless solution was cooled to −48° C. (CH$_3$CN/CO$_2$). Pentylmagnesium bromide (6.0 mL, 12 mmol, 2.0M in Et$_2$O) was added dropwise. The mixture was stirred at −48° C. for 6 h, then allowed to warm to room temperature. After stirring at room temperature for 18 h, the reaction mixture was quenched with 25 mL of saturated ammonium chloride aqueous solution, and the aqueous layer was extracted with EtOAc (30 mL×3). The combined organic layers were dried over Na$_2$SO$_4$. The mixture was filtered and concentrated which provided a white solid. The residue was purified via gradient flash chromatography (ISCO, 0-40% EtOAc in hexanes, SiO$_2$) to give the desired product as a white solid (1.20 g, 36% yield, with dr ratio>7/1). Recrystallization from hexanes gave the pure isomer (820 mg, 24% yield).

The sulfinamide derivative (820 mg) in 2.5 mL MeOH and 1.21 mL of 4M HCl 1,4-dioxane solution were stirred at RT for 1 h. The solution was concentrated, and diethyl ether was added to precipitate the amine hydrochloride salt M73 (620 mg, 95% yield, $[\alpha]_D^{20}$=−20.3 (c=1.22, MeOH)).

Scheme MB

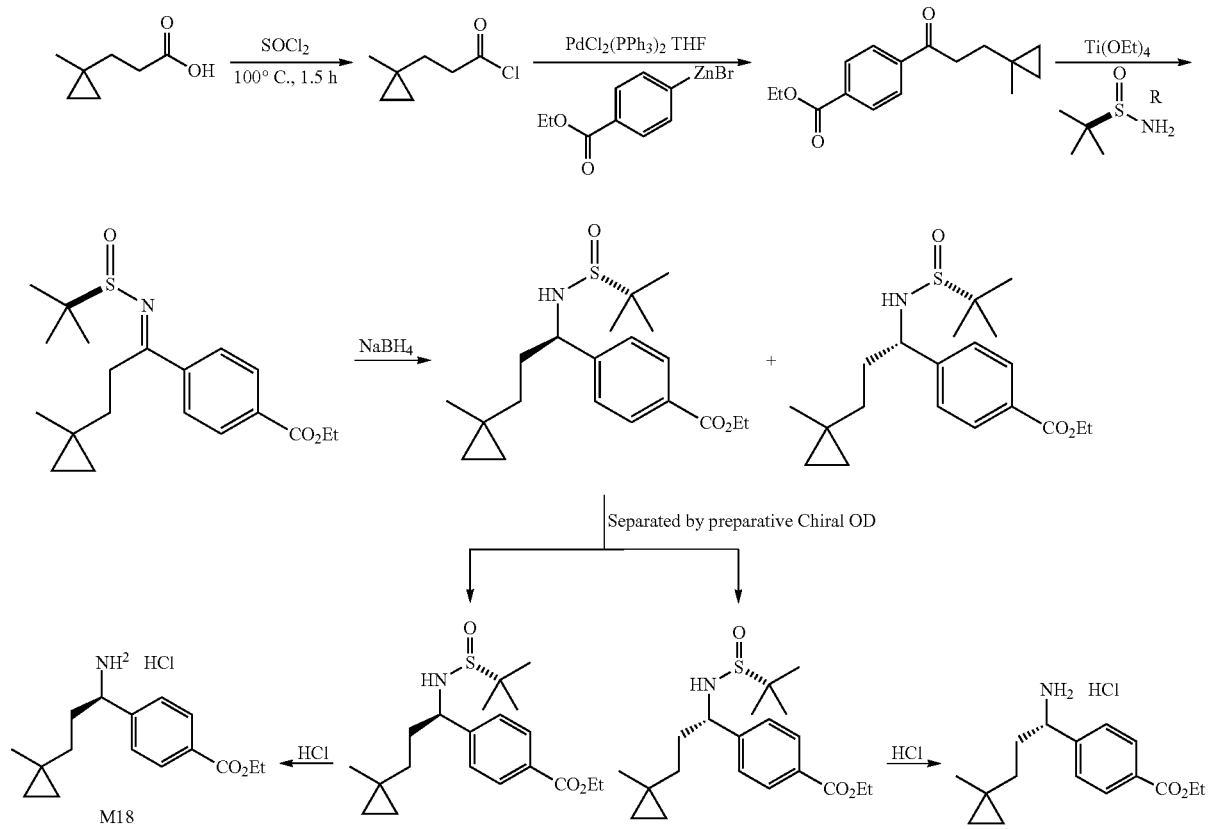

Step 1

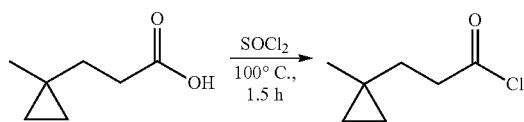

The acid (5.0 g, 39.1 mmol) and SOCl₂ (4.24 mL) were added to a flame-dried 50 mL round flask. The resulting mixture was heated at 100° C. for 1.5 h. The resulting brown mixture was carefully distilled under vacuum to give the desired product as colorless oil (4.20 g, 74% yield).

Step 2

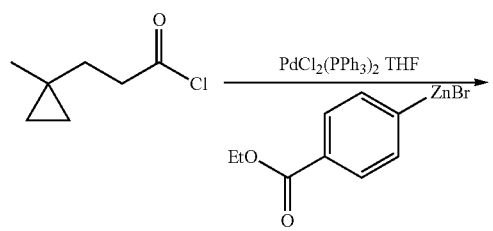

The acid chloride (4.20 g, 28.8 mmol), PdCl₂(PPh₃)₂ (960 mg, 5 mol %), and zinc reagent (55 ml, 27.45 mmol, 0.5 M in THF) were taken up in 60 mL THF at RT. The resulted mixture was stirred at RT for 4 h. The reaction was quenched by addition of a 1N HCl solution. The mixture was then extracted with diethyl ether, and the organic layer was washed with brine, dried with Na₂SO₄ and evaporated under reduced pressure. The residue was purified via gradient flash chromatography (ISCO, 0-20% EtOAc in hexanes, SiO₂) to give the desired product as a colorless oil (5.0 g, 67% yield).

Step 3

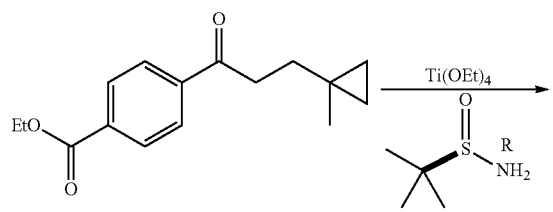

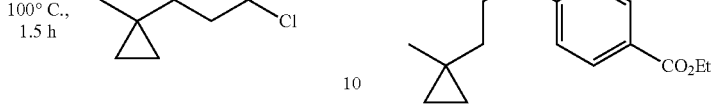

An oven-dried 250 mL flask was cooled under nitrogen and charged with (R)-tert-butanesulfinamide (2.33 g, 19.2 mmol, 1.00 equiv.), tetrahydrofuran (40 mL), and Ti(OEt)₄ (8.76 g, 38.4 mmol, 2.0 equiv) and ketone (5.0 g, 19.2 mmol, 1.0 equiv). The mixture was heated to 70° C. for 18 hours and then cooled to rt. While rapidly stirring, the reaction was quenched by adding an equal volume of brine. The mixture was diluted with EtOAc and stirred vigorously for 20 min. The resulting mixture was filtered through a pad of Celite®, and the pad of Celite® was washed with EtOAc. The filtrate was transferred to a separatory funnel and washed with brine. The brine was then extracted with a small amount of EtOAc. The combined organic layers were dried over Na₂SO₄ and concentrated. The material was purified by silica gel chromatography (0-40% EtOAc in hexanes) to give the desired product (4.33 g, 62% yield).

Step 4

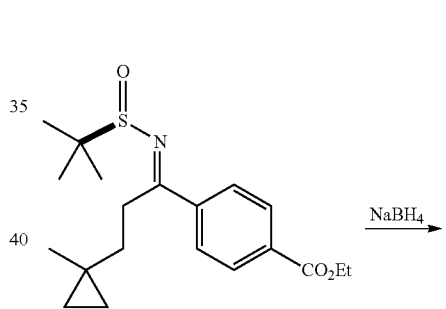

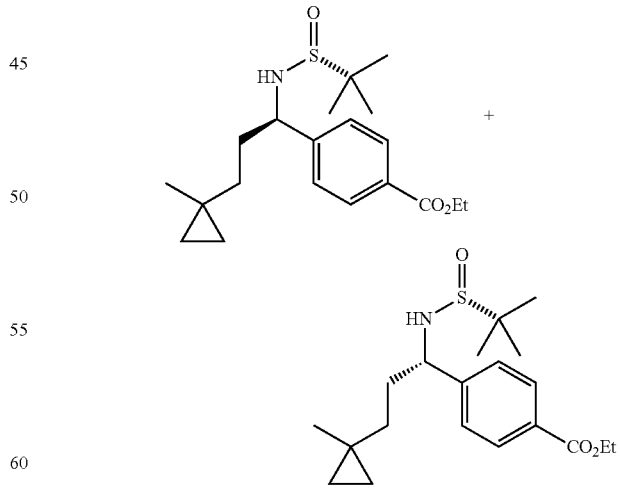

Sodium borohydride (907 mg, 23.9 mmol) was added to a solution of the imine (4.33 g, 11.9 mmol) in 50 mL THF at −78° C. The resulting mixture was allowed warm to RT, and the resulting solution was stirred at RT for 18 h. The reaction was quenched by addition of water (carefully). The mixture was then extracted with diethyl ether, and the organic layer was washed with brine, dried with $Na_2SO_4$ and evaporated under reduced pressure. The residue was purified via gradient flash chromatography (ISCO, 0-20% EtOAc in hexanes, $SiO_2$) which furnished the desired product as a mixture of two diasteromers. The two diasteromers were separated by preparative HPLC (Chiral OD, 5% iPr/Hexanes, 30 mL/min) to give the (R,R) isomer (2.88 g, 67% yield) and the (R,S) isomer (583 mg, 14% yield).

Step 5

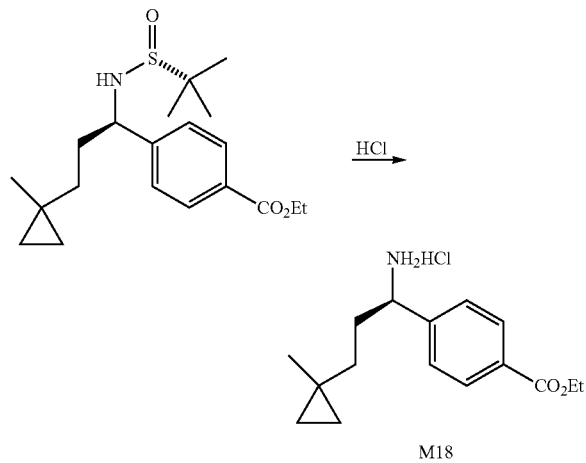

The sulfinamide derivative (2.88 g, 7.89 mmol) in 7 mL MeOH and 3.95 mL of 4N HCl 1,4-dioxane solution were stirred at RT for 1 h. The solution was concentrated, and diethyl ether was added to precipitate the amine hydrochloride salt M18. The mixture was filtered to give the desired product 2.0 g (85% yield). $[\alpha]_D^{25}=-19.5$ (c=0.72, MeOH) as a white solid.

(The (S) isomer was deprotected in a similar fashion)

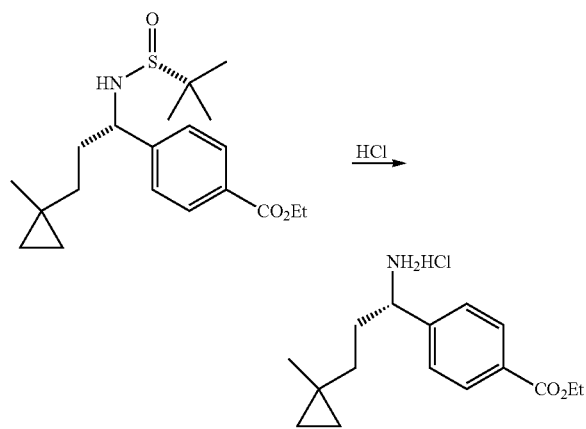

The sulfinamide derivative (583 mg) in 1.5 mL MeOH and 0.80 mL of 4M HCl 1,4-dioxane solution were stirred at RT for 1 h. The solution was concentrated, and diethyl ether was added to precipitate the amine hydrochloride. The mixture was filtered to provide the desired product 420 mg (89% yield). $[\alpha]_D^{25}=+21.0$ (c=0.70, MeOH).

Scheme KA

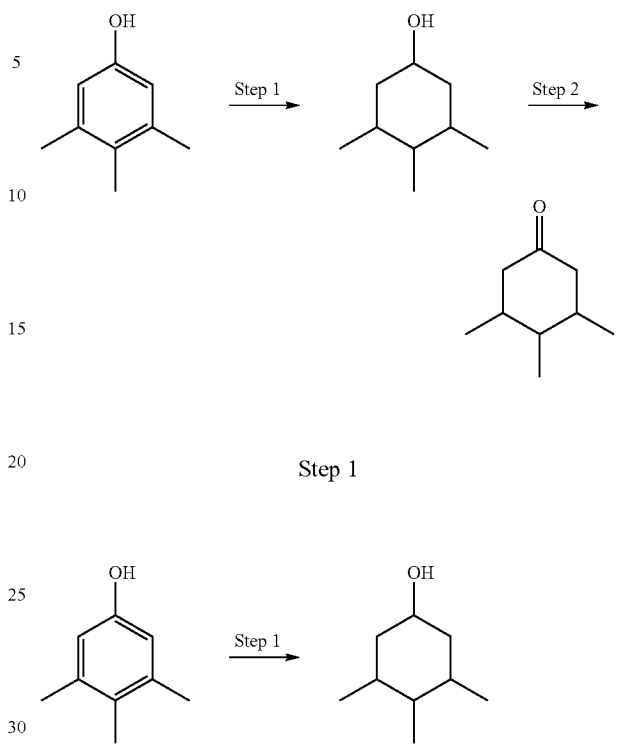

Step 1

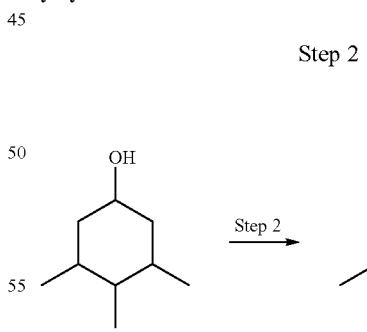

3,4,5-trimethylphenol (1.0 g, 7.34 mmol) was suspended in a mixture of hexane 915 mL) and buffer (pH=7.4, 15 mL). tetra-n-Butylammonium sulfate (426 mg, 0.736 mmol) and ruthenium(III) chloride monohydrate (167 mg, 0.734 mmol) was added. The reaction mixture was shaken under a hydrogen atmosphere at 60 psi for two days. The reaction mixture was filtered through a short pad of Celite®. The organic layer was separated. The aqueous layer was extracted with EtOAc (30 mL×3). The organic layers were combined, washed by brine (50 mL), dried over anhydrous $Na_2SO_4$, filtered, and concentrated by rotary evaporator. The crude 3,4,5-trimethylcyclohexanol was used without further purification.

Step 2

3,4,5-trimethylcyclohexanol obtained in step 1 was dissolved in dichloromethane. Dess-Martin reagent (3.1 g, 7.34 mmol) was added in one portion. Trifluoroacetic acid anhydride (0.56 mL, 7.34 mmol) was added, and the solution was stirred at RT for 18 h. Sodium hydroxide (1 N, 30 mL) and diethyl ether (100 mL) were added. The reaction mixture was stirred at RT for one hour. The organic layer was washed with NaOH (1N, 30 ml), brine 930 ml), dried over anhydrous $Na_2SO_4$, filtered, and concentrated. The product was purified by SiO₂ chromatography (Hexane/EtOAc 5:1) to give 3,4,5-trimethylcyclohexanone (758 mg, 73.6% from 3,4,5-trimethylphenol).
Scheme BA
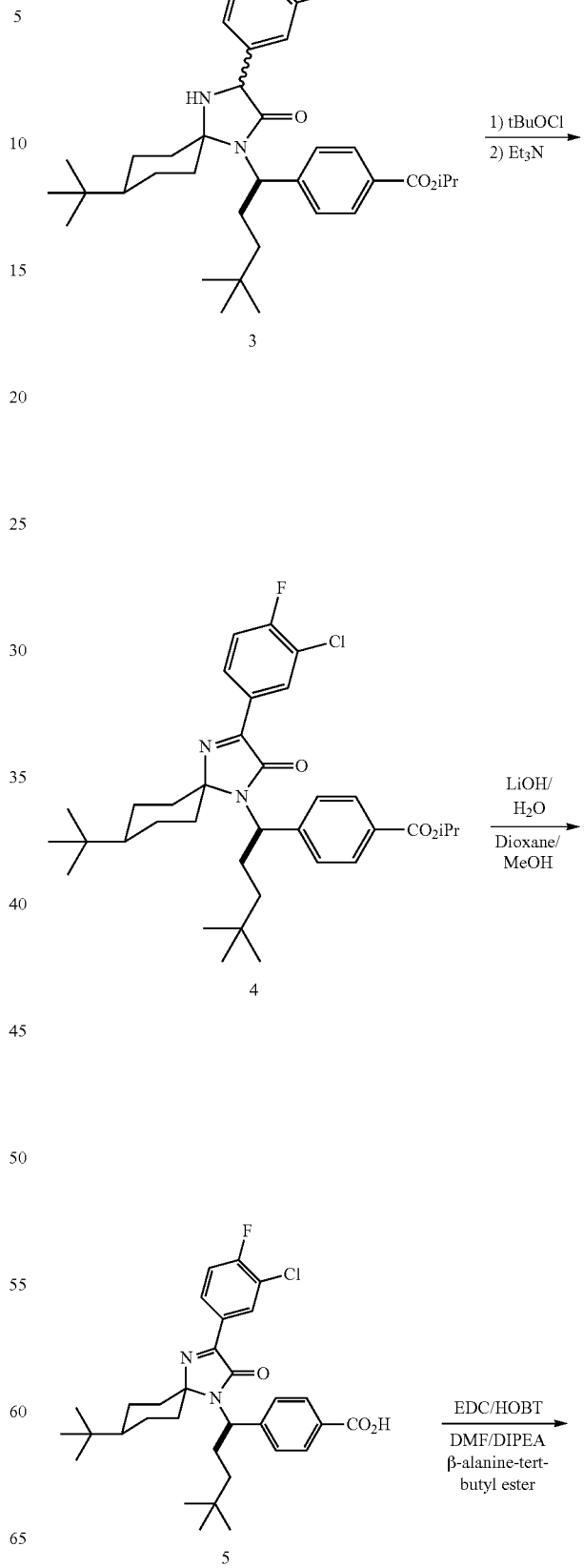

-continued

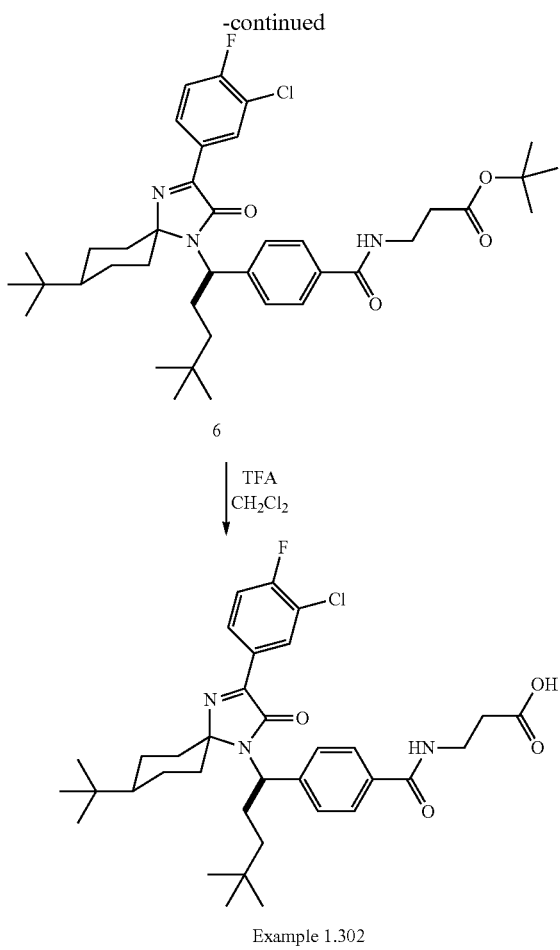

Example 1.302

Compound BA-4 was prepared using procedures similar to those described in Scheme I (Steps 1-4).

BA-4 (387 mg, 0.65 mmol) was dissolved in dioxane (4 mL) and methanol (2 mL). Aq 1.0 M lithium hydroxide was added (1.3 mL). The reaction mixture was stirred at RT overnight. After 20 h, additional aq 1.0 M LiOH was added (1.0 mL). About 7 h later, the reaction mixture was concentrated to near dryness. EtOAc (80 mL) and 1.0 M aq $NaHSO_4$ (10 mL) were added. The layers were separated. The aqueous layer was extracted with EtOAc. The combined organic layer was gravity filtered and concentrated to dryness giving compound BA-5 as a white foam (0.33 g).

BA-5 (14.5 mg, 0.026 mmol, 1.0 eq), beta alanine tert butyl ester hydrochloride (5.4 mg, 0.03 mmol), and HOBT (3.6 mg, 0.026 mmol), were added to a 1 dram vial equipped with a stir bar. $CH_2Cl_2$ (0.3 mL) and DIPEA (15 µL, 0.087 mmol), were added followed by EDC (6 mg, 0.031 mmol). The vial was capped and the reaction mixture was left stirring at RT over the weekend. The reaction mixture was diluted with $CH_2Cl_2$ and washed with aq $NH_4Cl$, water, and brine. The resulting organic solution was gravity filtered and concentrated to dryness. The crude product was purified via flash sgc using a 15% to 30% EtOAc/Hex gradient as the mobile phase. The major peak was collected as product to give 12 mg of BA-6 as a clear oil.

Compound BA-6 was dissolved in a solution consisting of $CH_2Cl_2$ (8 mL) and TFA (2 mL). The reaction mixture was stirred at RT for 7 h, then concentrated to dryness on the rotovap. $CH_2Cl_2$ and hexanes were added and the solution was concentrated to dryness. The crude product was purified via reversed-phase chromatography on a 13 g Isco C-18 cartridge using a 80% to 100% $CH_3CN/H_2O$ gradient as the mobile phase. Each component of the mobile phase contained formic acid (0.1% by volume). The major peak was collected as product to give 8 mg of Example 1.302.

Scheme BB

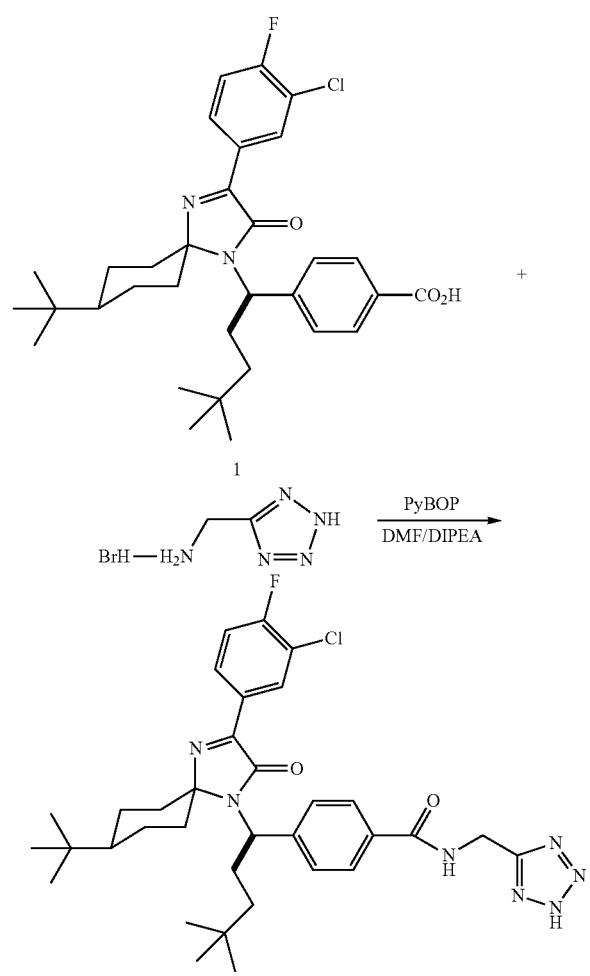

Example 1.305

Compound BB-1 was prepared using procedures similar to those described in Scheme BA-(Steps 1-5).

Compound BB-1 (228 mg, 0.41 mmol, 1.0 eq) and (1-H-tetrazol-5-ylmethyl) amine hydrobromide (89 mg, 0.49 mmol, purchased from ChemBridge) were dissolved in DMF (4 mL). DIPEA (1.6 mL) was added, followed by PyBOP (260 mg, 0.5 mmol). The reaction mixture was placed under $N_2$. The flask was placed in an oil bath and warmed to 70° C. The reaction mixture was stirred at 70° C. for 2 h and at 50 C for 1 h. The heat was turned off and the reaction mixture was left stirring overnight at RT under $N_2$ The reaction mixture was partially concentrated on the rotovap, then purified via reversed-phase chromatography using a 50 g Varian C-18 cartridge. The column was eluted using a 50% to 100% $CH_3CN/H_2O$ gradient as the mobile phase. Each component of the mobile phase contained formic acid (0.1% by volume). The major peak was collected as product to give Example 1.305 (0.23 g) as a clear oil.

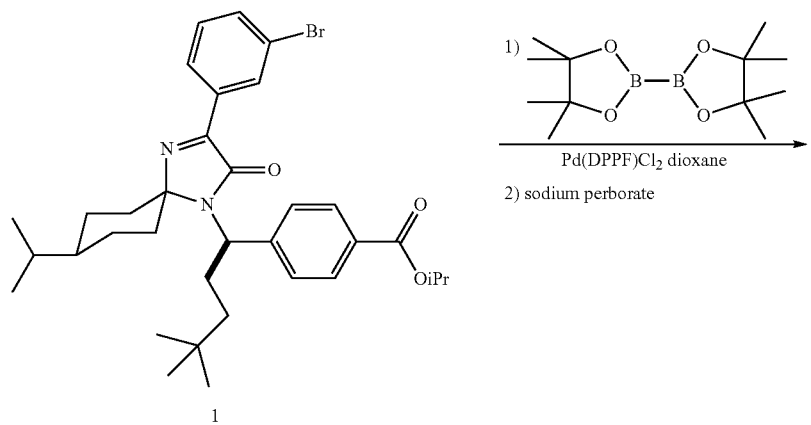
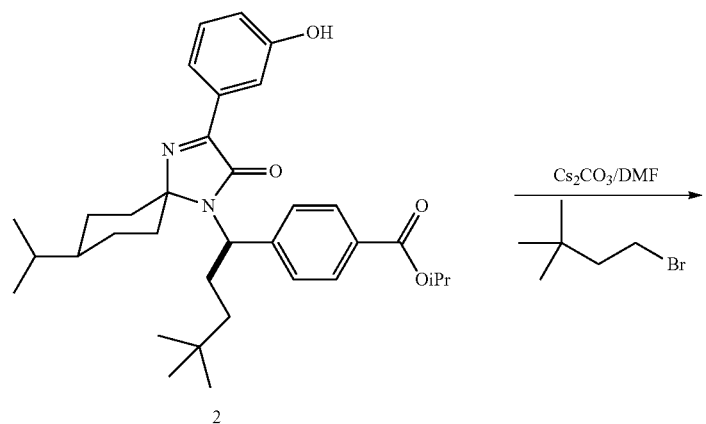
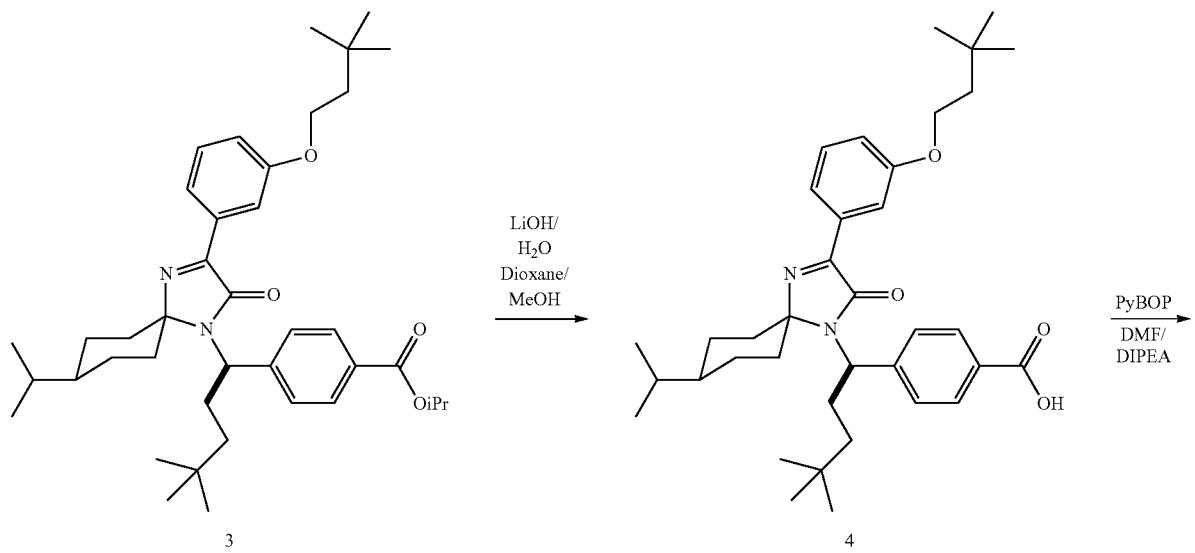

-continued

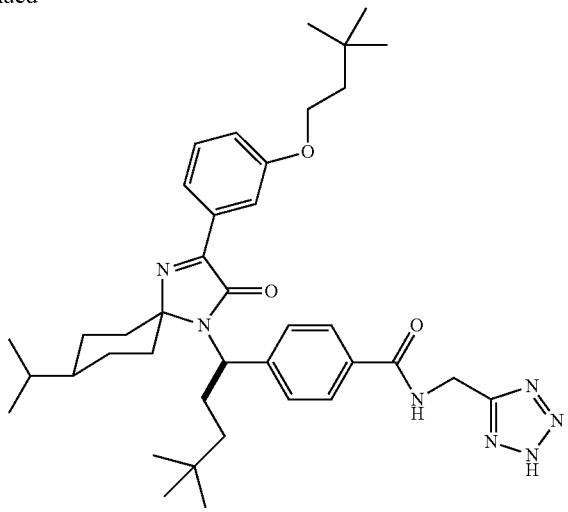

Example 1.317

Compound BC-1 was prepared using procedures similar to those described in Scheme I, (Steps 1-4) using the appropriate phenyl glycine, amine, and ketone.

Compound BC-1 (0.55 g, 0.90 mmol, 1.0 eq), pinacolatodiboron (0.69 g, 2.7 mmol, 3.0 eq), Pd(dppf)Cl$_2$ (7.3 mg, 0.01 mmol, 0.1 eq), and potassium acetate (0.18 g, 1.8 mmol, 2.0 eq) were added to a 100 mL round bottomed flask equipped with a stir bar. The flask was equipped with a septum and connected to a vacuum manifold via a syringe needle and tubing. The air in the flask was removed and replaced with N$_2$ by cycling between vacuum and nitrogen several times. Dioxane (10 mL, anhydrous) was added via syringe. The reaction mixture was heated at 90° C. for 3 h under N$_2$ then left stirring overnight at rt. Sodium perborate (1.38 g, 10 eq) and water (3 mL) were added. The reaction mixture was stirred at RT overnight. The resulting reaction mixture was poured into 200 mL of EtOAc, then washed with 1% aq HCl solution and water. The organic layer was concentrated to dryness on the rotovap. The crude product was purified via flash silica gel chromatography using a 5%-80% EtOAc/hexanes gradient on a 24 g Isco SiO$_2$ cartridge to give 0.36 g of compound BC-2.

Compound BC-2 (0.20 g, 0.366 mmol, 1.0 eq) was added to a 50 mL round bottomed flask equipped with a stir bar. DMF (3 mL), cesium carbonate (0.18 g, 1.5 eq), and 1-bromo-3,3-dimethylbutane (91 mg, 1.5 eq) were added. The reaction mixture was stirred overnight at rt. After about 16 h, the reaction mixture was heated for 5 h at 70° C. The reaction mixture was poured into 100 mL of EtOAc. The resulting mixture was washed with water (2×20 mL) and concentrated to dryness. The crude product was purified via flash sgc using an Isco 24 g SiO$_2$ cartridge and a 5%-60% EtOAC/hexanes gradient as the mobile phase giving 0.17 g of BC-3.

Compound BC-3 was converted to BC-4 and to Example 1.317 using procedures similar to those described in Schemes BA and BB.

Scheme BD

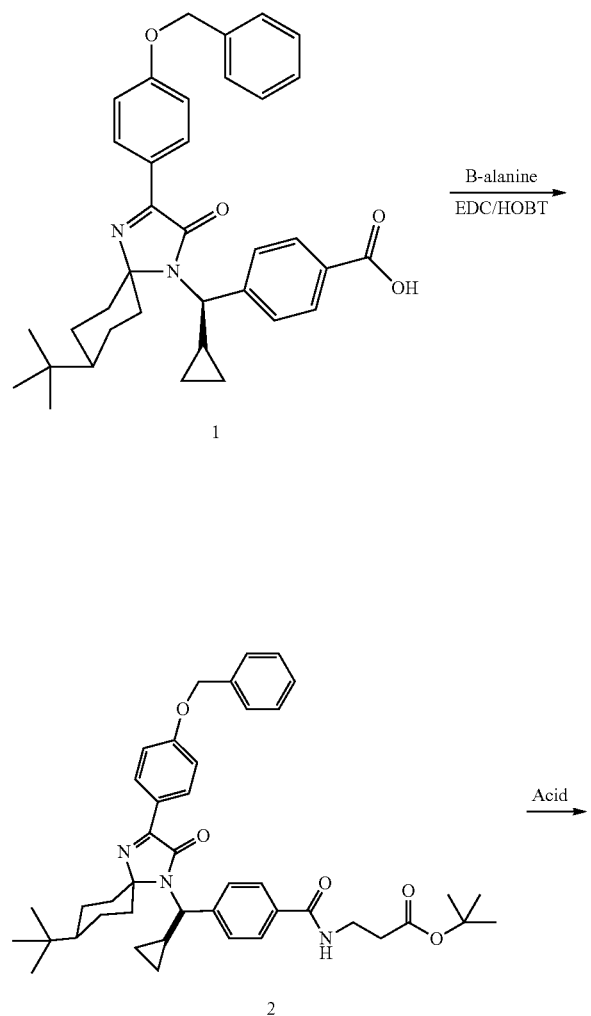

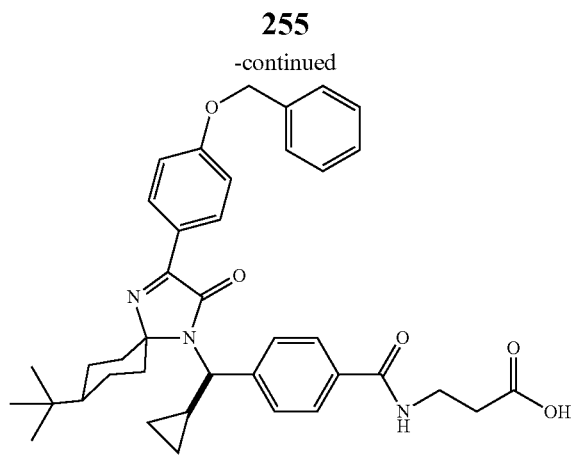

Example 1.321

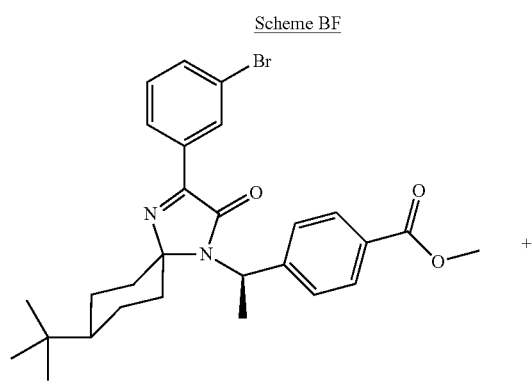

Example 1.339

Compound BD-1 was prepared using procedures similar to those described in Scheme BA. BD-1 was converted to Example 1.321 using procedures similar to those described in Scheme BA.

Compound BF-1 may be prepared using procedures similar to those described in Scheme I (Steps 1-4).

Compound BF-1 (0.1 g, 0.19 mmol, 1.0 eq), BF-2 (48 mg, 2 eq), and Pd(dppf)Cl$_2$ (16 mg, 0.1 eq) were added to a rb flask equipped with a stir bar. The flask was capped with a septum and connected to a vacuum manifold via a syringe and tubing. The flask was cycled between vacuum and nitrogen several times to blanket the reaction mixture with nitrogen. Acetonitrile (1.4 mL) and 1M aq K$_2$CO$_3$ (1.4 mL) were added via syringe. The reaction was heated to 80° C. in an oil bath and left stirring at 80° C. overnight under N$_2$. The reaction mixture was removed from the oil bath and diluted with EtOAc and brine. The layers were separated. The organic layer was concentrated to dryness. The crude product was purified via flash sgc using a 0.5% to 6% MeOH/CH$_2$Cl$_2$ gradient as the mobile phase to give 70 mg of BF-3.

Compound BF-3 may be converted to Example 1.339 using procedures similar to those described in Scheme BA (Steps 5-7).

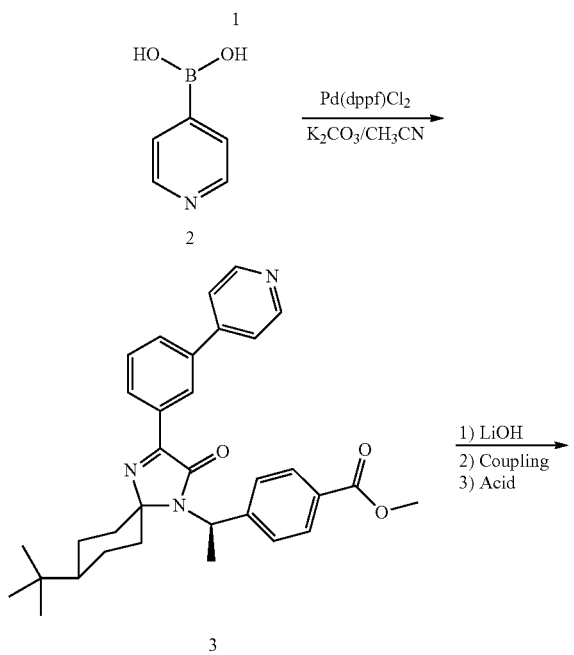

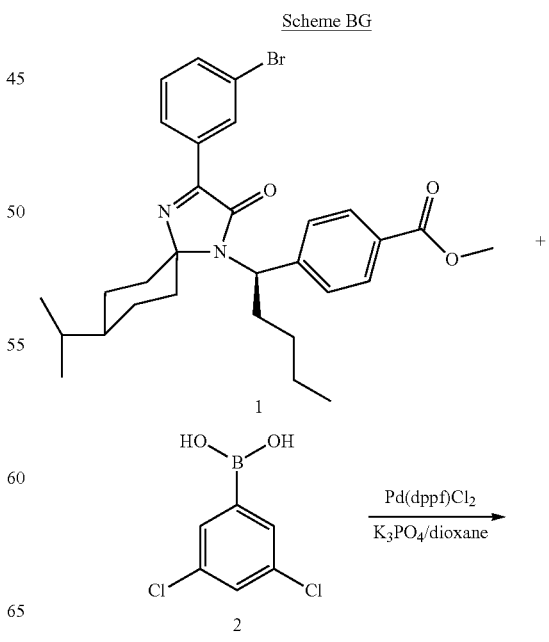

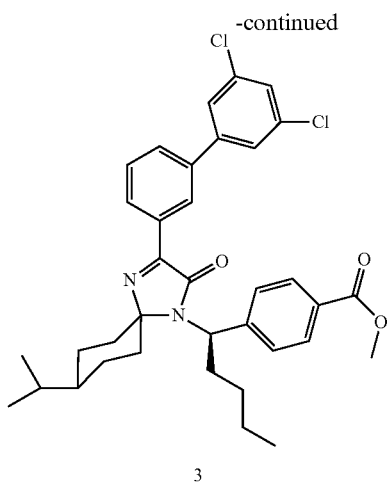

3

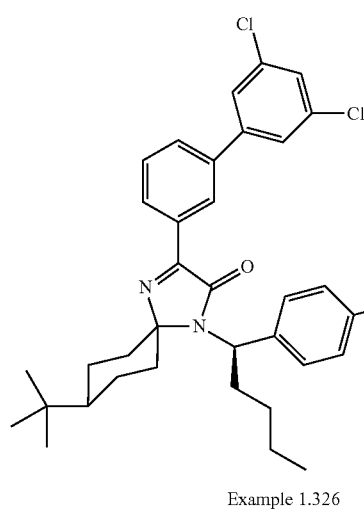

Example 1.326

Compound BG-1 may be prepared using procedures similar to those described in Scheme I (Steps 1-4).

Compound BG-2 (73 mg, 2 eq) Pd(dppf)Cl$_2$ (16 mg, 0.1 eq) and tripotassium phosphate (0.2 g, 5 eq) were added to a 5 mL microwave vial equipped with a stir bar. The vial was capped and connected to a vacuum manifold via a syringe and tubing. The flask was cycled between vacuum and nitrogen several times to blanket the reaction mixture with nitrogen. Compound BG-1 (0.11 g, 0.19 mmol, 1.0 eq) was dissolved in 2 mL of anhydrous dioxane. The resulting solution was added via syringe, and the reaction mixture was heated overnight in an oil bath at 110° C. under N$_2$. The reaction mixture was poured into 100 mL of EtOAc and washed with water (2×20 mL). the resulting organic solution was concentrated to dryness. The crude product was purified via sgc on a 12 g Isco SiO$_2$ cartridge using a 5%-20% EtOAc/Hexanes gradient as the mobile phase to give 48 mg of BG-3.

Compound BG-3 was converted to Example 1.326 using procedures similar to those described in Schemes BA and BB.

Scheme BH

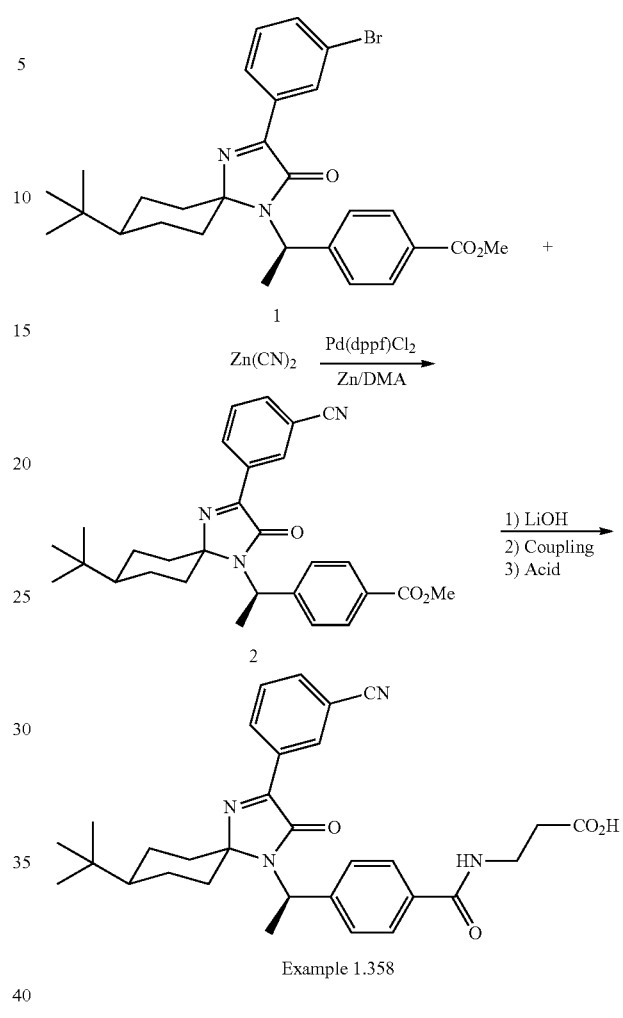

Example 1.358

Compound BH-1 may be prepared using procedures similar to those described in Scheme I. (Steps 1-4).

Compound BF-1 (0.1 g, 0.19 mmol, 1.0 eq), Zn(CN)$_2$ (27 mg, 0.05 eq), zinc (1.5 mg, 0.12 eq) and Pd(dppf)Cl$_2$ (8 mg, 0.1 eq) were added to a rb flask equipped with a stir bar. The flask was capped with a septum and connected to a vacuum manifold via a syringe and tubing. The flask was cycled between vacuum and nitrogen several times to blanket the reaction mixture with nitrogen. N,N-Dimethyl acetamide (1.0 mL) was added via syringe and the reaction mixture was stirred overnight at 120° C. under N$_2$. TLC showed SM remained. The reaction mixture was heated overnight at 140° C. under N$_2$. The reaction mixture was allowed to cool to RT and diluted with EtOAc. The resulting solution was washed with water and concentrated to dryness. The crude product was purified via sgc using a 5%-70% EtOAc/hexanes gradient as the mobile phase. The major peak was isolated as product to give 48 mg of BH-2.

Compound BH-2 may be converted to compound Example 1.358 using procedures similar to those described in Scheme BA (Steps 5-7).

Scheme BI

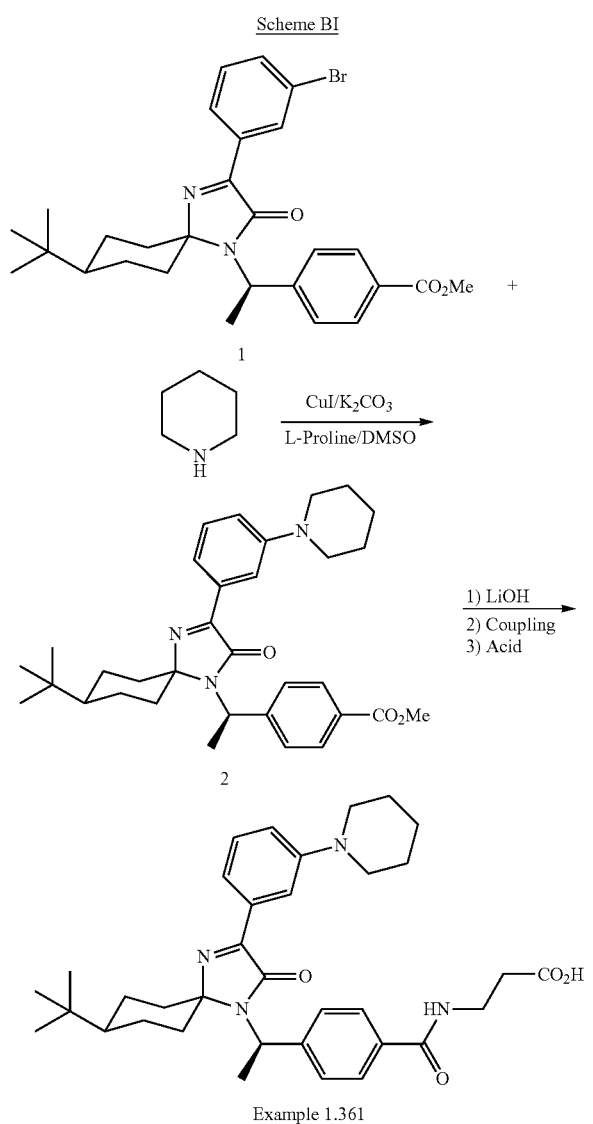

Example 1.361

Compound BI-1 may be prepared using procedures similar to those described in Scheme I (Steps 1-4).

Compound BI-1 (0.1 g, 0.19 mmol, 1.0 eq), CuI (6 mg, 0.1 eq), L-proline (6 mg, 0.18 eq) and $K_2CO_3$ (80 mg, 2.0 eq) were added to a rb flask equipped with a stir bar. The flask was capped with a septum and connected to a vacuum manifold via a syringe and tubing. The flask was cycled between vacuum and nitrogen several times to blanket the reaction mixture with nitrogen. A solution of piperidine (37 mg, 1.5 eq) in 2 mL of DMSO was added via syringe. The reaction mixture was stirred overnight at 140° C. under $N_2$. The reaction mixture was allowed to cool to RT and was diluted with EtOAc. The resulting solution was washed with water and concentrated to dryness on the rotovap. The crude product was purified via flash chromatography using a 0.5%-6% $CH_3OH/CH_2Cl_2$ gradient as the mobile phase to give 39 mg of impure BI-2. The fractions containing BI-2 were purified a second time via flash sgc using a 5%-80% EtOAc/Hexanes gradient as the mobile phase with 0.5% formic acid (by volume) in the EtOAc component of the mobile phase to give 32 mg of BI-2.

Compound BI-2 was converted to Example 1.361 using procedures similar to those described in Scheme BA (Steps 5-7).

Scheme BM

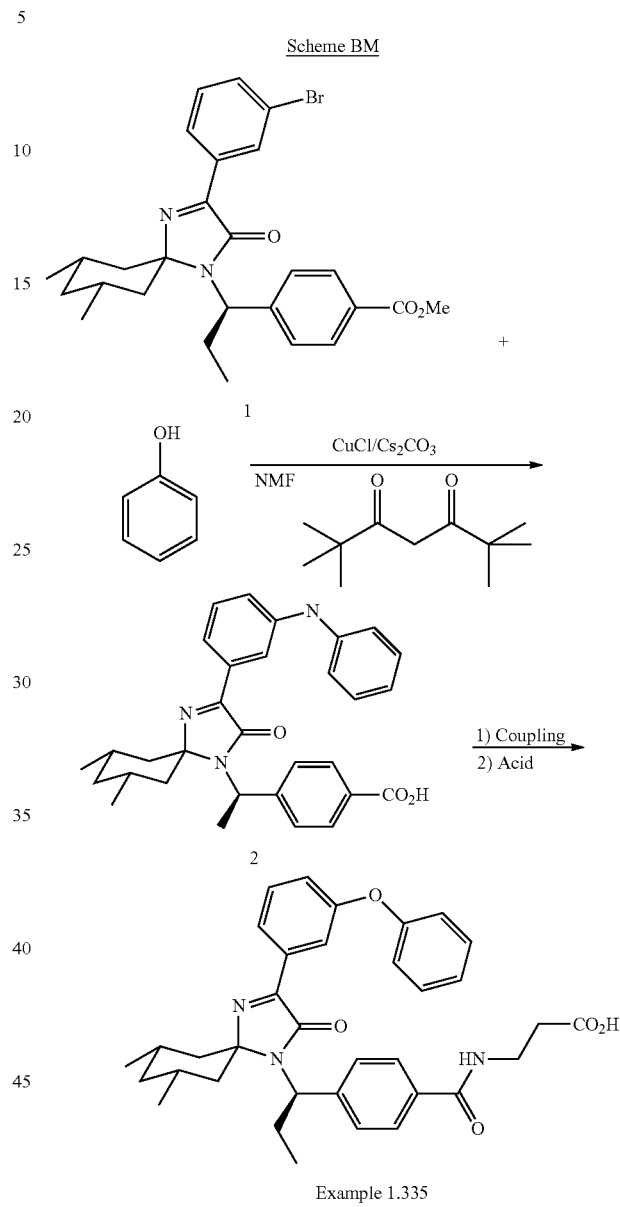

Example 1.335

Compound BM-1 may be prepared using procedures similar to those described in Scheme I (Steps 1-4).

Compound BM-1 (0.1 g, 0.19 mmol, 1.0 eq), CuCl (2 mg, 0.1 eq), phenol (45 mg, 2.5 eq), 2,2,6,6 tetraethylheptane-3,5-dione (5 mg, 0.1 eq), and $Cs_2CO_3$ (0.12 g, 2.0 eq) were added to a 5 mL microwave vial equipped with a stir bar. The vial was capped and connected to a vacuum manifold via a syringe and tubing. The flask was cycled between vacuum and nitrogen several times to blanket the reaction mixture with nitrogen. N-methylpyrrolidinone was added via syringe and the reaction mixture was heated overnight in an oil bath at 140° C. The reaction mixture allowed to cool and was diluted with 100 mL of EtOAc. The resulting solution was washed with saturated aq $NH_4Cl$ and water (20 mL), then concentrated to dryness. The crude product was purified via sgc on a 12 gram Isco $SiO_2$ cartridge using a 5%-100% EtOAc/hexanes gradient in which 0.5% formic acid (by volume) had been added to the EtOAc, giving compound BM-2 mixed with some of the des-bromo analog of BM-1. The product was used in the next step without further purification.

Compound BM-2 may be converted to Example 1.335 using chemistry similar to that described in Scheme BA (Steps 5-7).

night with stirring. The reaction mixture was allowed to cool to RT and diluted with EtOAc and water. The layers were separated. The organic layer was concentrated to dryness. The crude product was purified via sgc using a 5%-80% EtOAc/hexanes gradient as the mobile phase to give 79 mg of BN-2.

Compound BN-2 may be converted to Example 1.340 using chemistry similar to that described in Scheme BA (Steps 5-7).

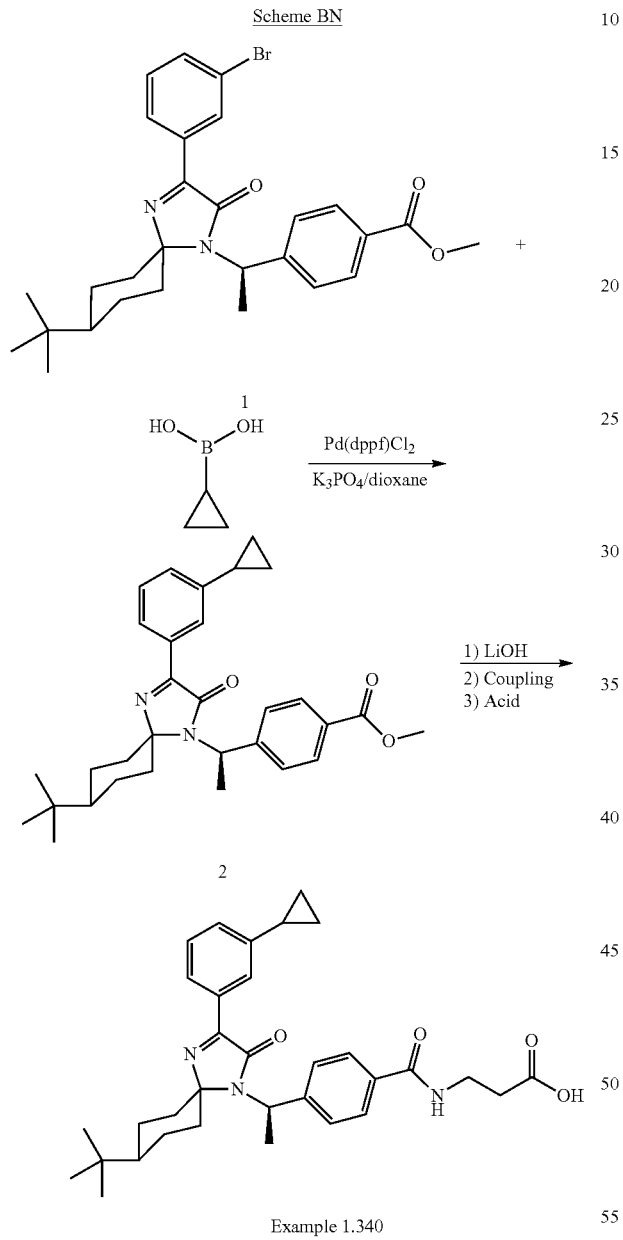

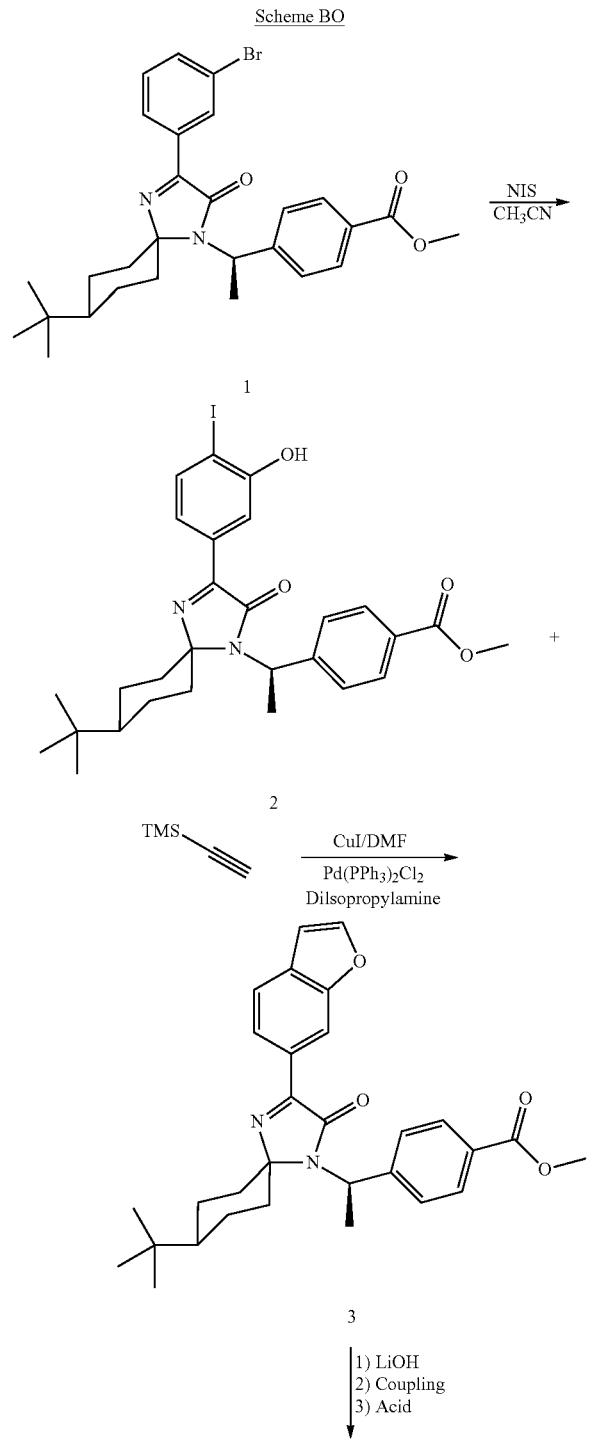

Compound BN-1 may be prepared using procedures similar to those described in Scheme I (Steps 1-4).

Compound BN-1 (0.1 g, 0.19 mmol, 1.0 eq), cyclopropyl boronic acid (21 mg, 1.3 eq), and Pd(dppf)Cl₂ (16 mg, 0.1 eq), K₃PO₄ (0.1 g, 2.5 eq) were added to a 5 mL microwave vial equipped with a stir bar. The flask was capped and connected to a vacuum manifold via a syringe and tubing. The vial was cycled between vacuum and nitrogen several times to blanket the reaction mixture with nitrogen. Dioxane (2 mL) was added via syringe. The reaction was heated at 135° C. over-

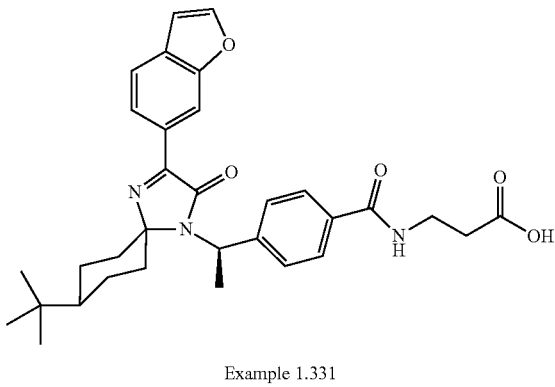 [SMILES: C[C@H](c1ccc(C(=O)NCCC(=O)O)cc1)N1C(=O)C(c2ccc3ccoc3c2)=NC12CCC(C(C)(C)C)CC2]

Example 1.331

Compound BO-1 may be prepared using procedures similar to those described in Scheme BC. (Step 1 to compound BC-2)

Compound BO-1 (84 mg, 0.18 mmol) was added to a 50 mL rb flask equipped with a stir bar. Acetonitrile (1 mL) was added with stirring, followed by N-iodosuccinamide (45 mg, 1.1 eq). The reaction mixture was stirred at RT ON. The reaction mixture was concentrated to dryness. The crude product was purified via flash sgc using an Isco 12 g $SiO_2$ cartridge and a 5%-60% EtOAc/hexanes gradient as the mobile phase to give 50 mg of BO-2.

Compound BO-2 (50 mg, 0.085 mmol, 1.0 eq), CuI (2 mg, 0.011 mmol, 0.12 eq.), and $Pd(PPh_3)_2Cl_2$ (2 mg, 0.003 mmol, 0.03 eq.) were added to a 5 mL microwave vial equipped with a stir bar. The vial was capped and connected to a vacuum manifold via a syringe and tubing. The vial was cycled between vacuum and nitrogen several times to blanket the reaction mixture with nitrogen. A solution of TMS acetylene (12 mg, 1.5 eq) and diisopropylamine (50 μL) dissolved in DMF (1 mL) was added via syringe. The reaction mixture was placed in an oil bath and stirred at 80° C. under $N_2$ overnight. The reaction mixture was poured into 50 mL of EtOAc and 30 mL of water. The layers were separated. The organic layer was washed with 2×20 mL of water, then concentrated to dryness. The crude product was purified via prep TLC on $SiO_2$ plates using a 1:1 EtOAc:Hexanes solution as the mobile phase to give 21 mg of BO-3.

Compound BO-3 was converted to Example 1.331 using procedures similar to those described in Scheme BA (Steps 5-7).

Scheme BP

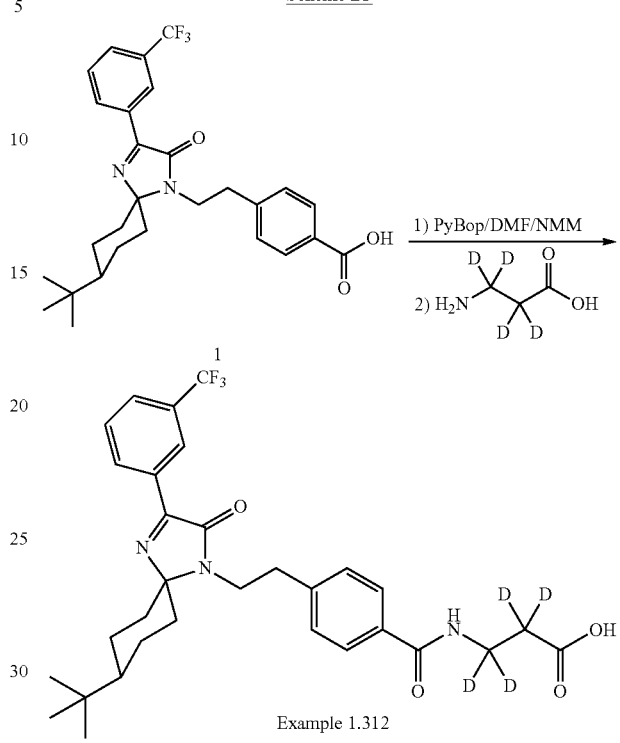

Example 1.312

Compound BP-1 was prepared using procedures similar to those described in Scheme BA (Steps 1-5).

Compound BP-1 (120 mg, 0.24 mmol, 1.0 eq) and PyBOP (137 mg, 0.26 mmol, 1.1 eq) were added to a 40 mL vial equipped with a stir bar. DMF and N-methyl morpholine were added. The vial was capped and the reaction mixture was stirred at RT for 3 h. Tetradeuterated beta-alanine (2,2,3,3-D4) was added (CAS number 116173-67-2, purchased from CDN Isotopes). The reaction mixture was left stirring at rt. for 26 h. The reaction mixture was diluted with EtOAc (120 mL) and 0.5 M citric acid (20 mL). The layers were separated. The organic layer was washed with water and brine, dried with $MgSO_4$, and filtered. The resulting solution was concentrated to a clear oil. The crude product was purified via sgc using a 12 g Isco $SiO_2$ cartridge and an EtOAc/Hex gradient (15%-70%) as the mobile phase. The EtOAc contained 0.5% (by volume) formic acid. The major peak was collected as product. The product was purified further via reversed-phase HPLC on a C-18 column using a 60%-99% $CH_3CN/H_2O$ gradient as the mobile phase. Formic acid (0.1% by volume) was added to each component of the mobile phase. Example 1.312 (0.07 g) was obtained as a clear oil.

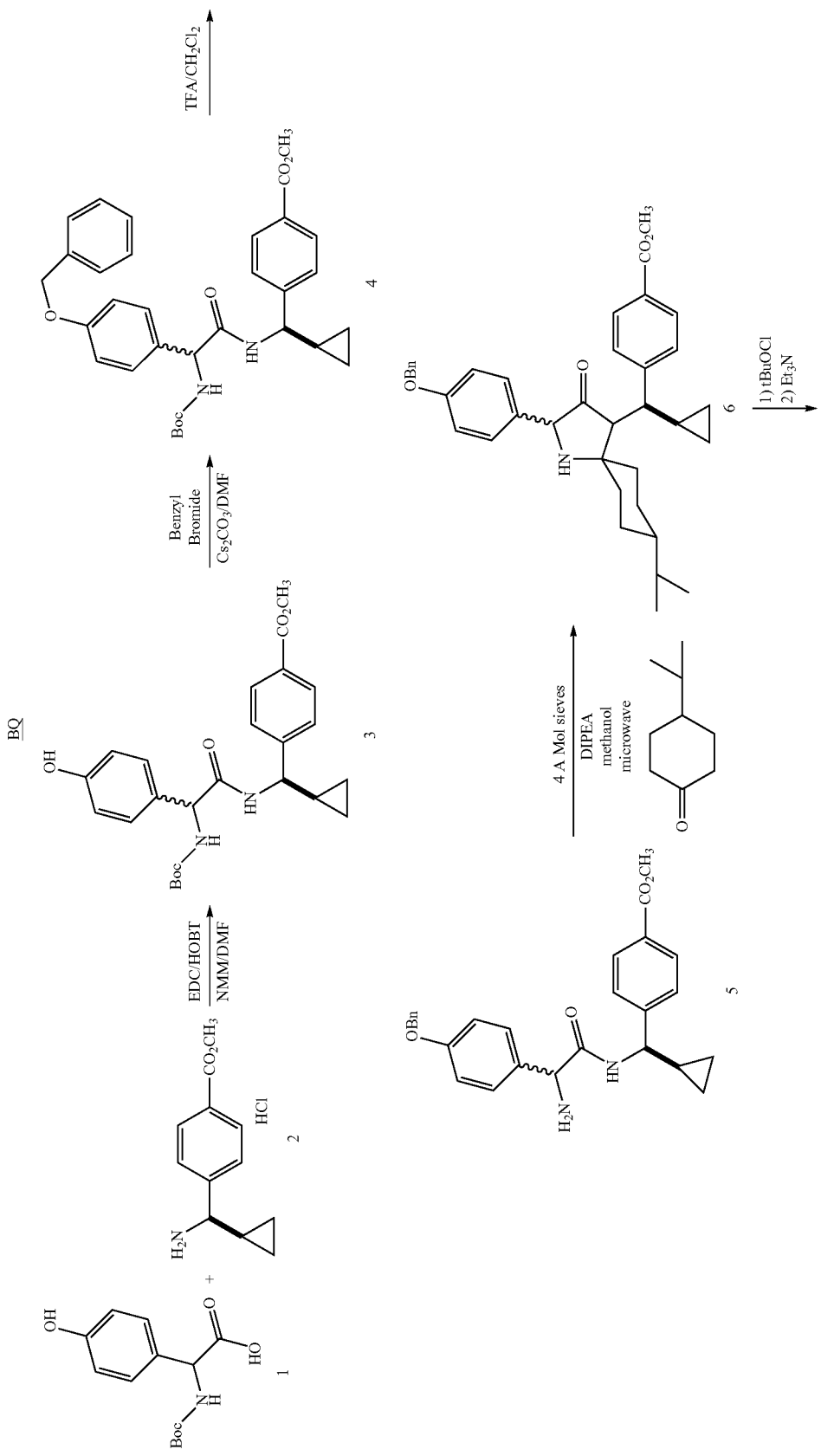

-continued
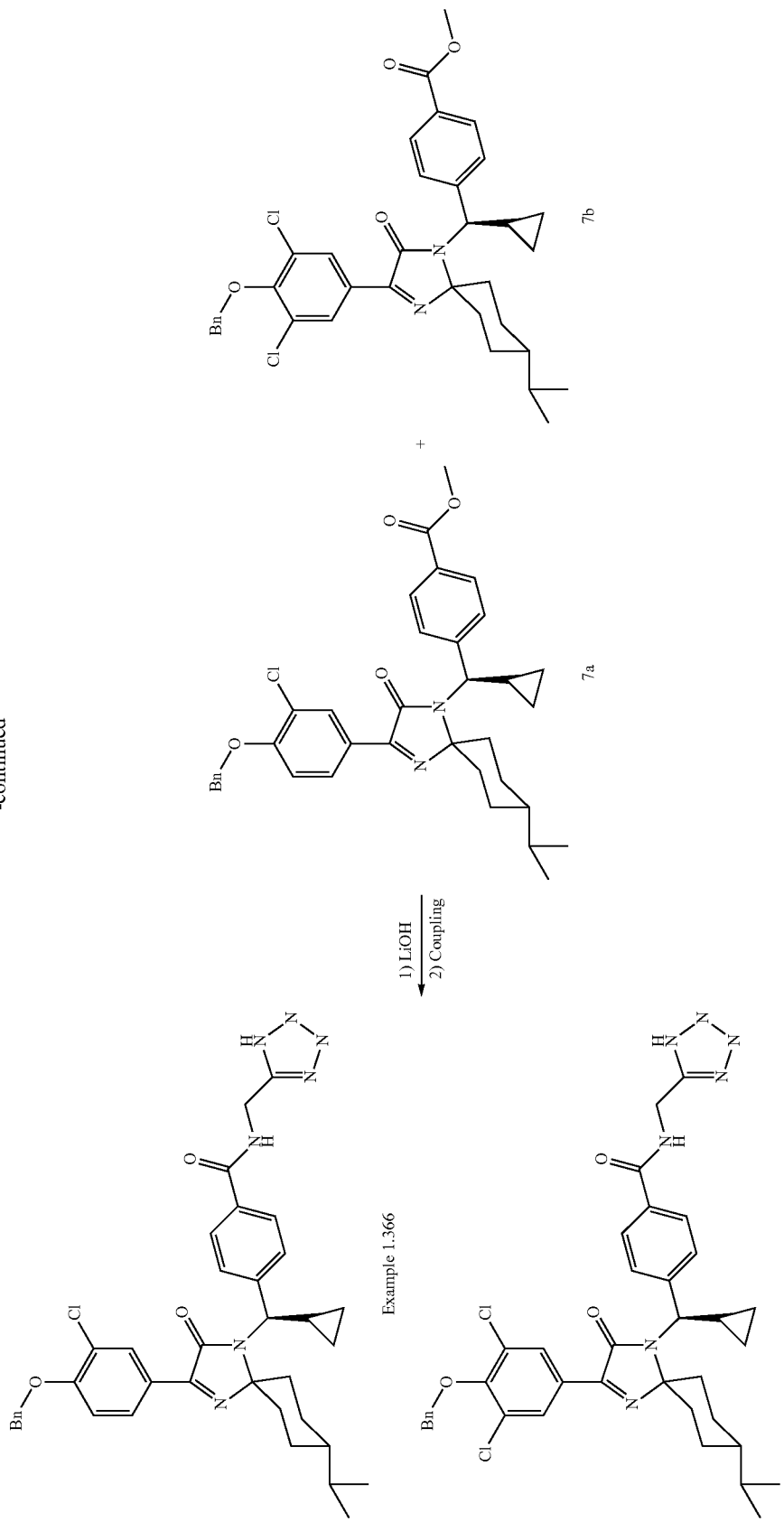

Compound BQ-1 (1.0 g, 3.74 mmol, 1.0 eq), compound BQ-2 (0.90 g, 1.0 eq), HOBT (0.51 g, 1.0 eq), N-methyl morpholine (1.13 g, 3.0 eq), DMF (15 mL), and EDCl (1.08 g, 1.5 eq). were added to a 250 mL rb flask and stirred at RT ON. The reaction mixture was diluted with 300 mL of EtOAc and washed with water (2×100 mL). The organic layer was concentrated to dryness to give BQ-3 (1.78 g).

Compound BQ-3 (0.93 g, 2.0 mmol, 1.0 eq), cesium carbonate (0.73 g, 1.1 eq) and DMF (10 mL) were added to a 250 mL rb flask. Benzyl bromide (0.38 g, 1.1 eq), dissolved in 1 mL of DMF was added slowly to the reaction mixture with stirring. The reaction mixture was stirred ON at rt, then concentrated to near dryness on the rotovap. The residue was diluted with 200 mL of EtOAc then washed with water (2×200 mL). The resulting organic solution was concentrated to dryness. The crude product was purified via sgc using a 40 gram Isco $SiO_2$ cartridge and a 10%-100% EtOAc/Hexanes gradient as the mobile phase to give 0.84 g of compound BQ-4.

Compound BQ-4 was converted to compound BQ-6 using procedures that are similar to those described in Scheme A-(Step 3) and Scheme I-(Step 4).

Compound BQ-6 (0.53 g, 0.94 mmol, 1.0 eq) was dissolved in 20 mL of $CH_2Cl_2$ in a 250 mL flask equipped with a stir bar. The flask was cooled in an ice-water bath. tert-Butyl hypochlorite (0.12 g, 1.2 eq) was added dropwise. The reaction mixture was stirred at 0° C. for 1 h. The bath was removed and the reaction mixture was warmed to rt. The reaction mixture was stirred at RT for 3 h. Triethylamine (0.47 g, 5.0 eq) was added and the reaction mixture was stirred overnight at rt. The reaction mixture was concentrated to dryness. The crude product was purified via sgc using a 23 g $SiO_2$ cartridge and a 5%-80% EtOAc/hexanes gradient as the mobile phase. Two fractions were isolated as impure compound BQ-7a and BQ-7b (0.25 g). The fraction containing BQ-7a was repurified via reversed-phase HPLC on a semi-preparative C-18 column using a 70%-100% $CH_3CN/H_2O$ gradient over 20 min as the mobile phase. Formic acid (0.1% by volume) was added to each component of the mobile phase. Compounds BQ-7a (156 mg) and BQ-7b (47 mg) were isolated as product.

Compound BQ-7a was converted to Example 1.366 using procedures similar to those described in Scheme BB.

Compound BQ-7b was converted to Example 1.359 using procedures similar to those described in Scheme BB.

Scheme BR

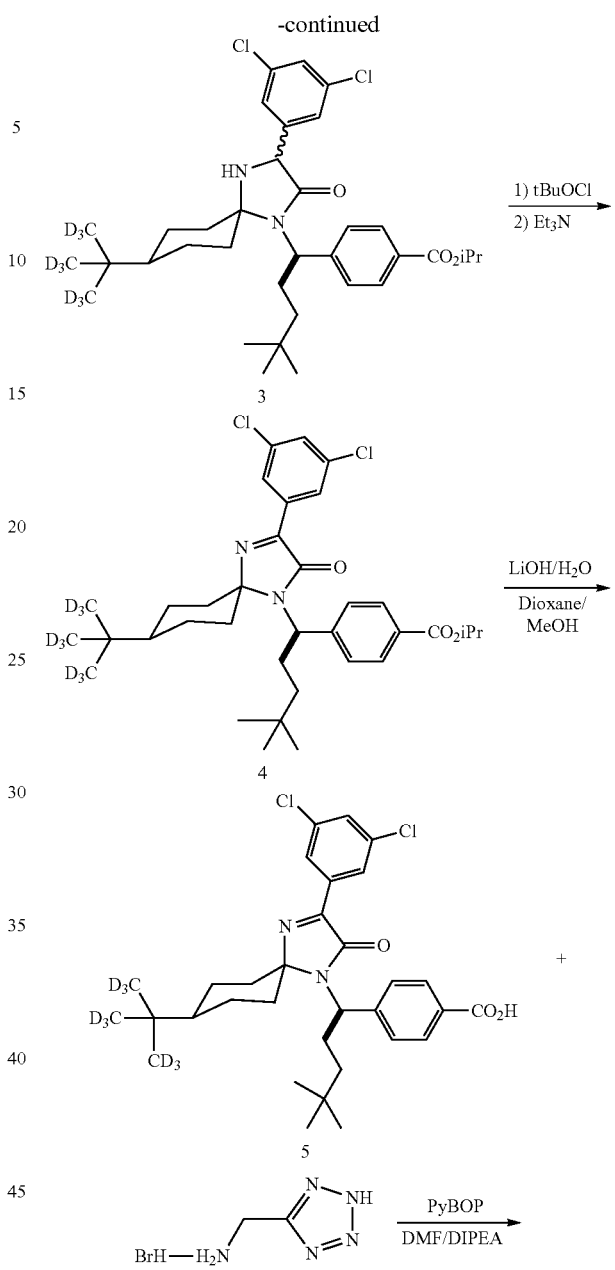

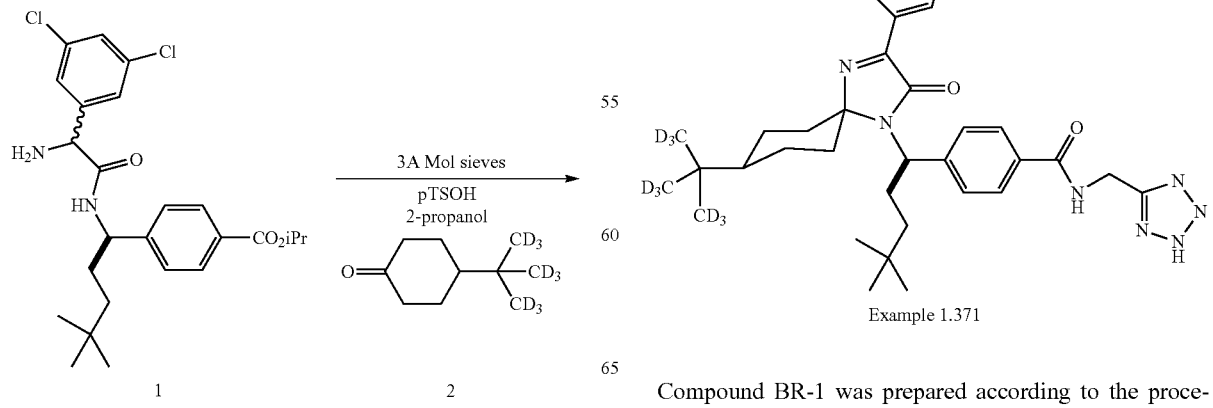

Example 1.371

Compound BR-1 was prepared according to the procedures described in Scheme I.

Compound BR-1 (0.54 g, 0.91 mmol, 1.0 eq), compound BR-2 (4-tert-butyl cyclohexanone [$^2H_9$]— purchased from Isosciences, LLC- (270 mg, 1.65 mmol, 1.8 eq)), and para-toluene sulfonic acid monohydrate (18 mg, 0.09 mmol, 0.10 eq) were added to a 20 mL microwave vial equipped with a stir bar. Molecular sieves (3 Å, 2.03 g) were added, followed by 2-propanol. $N_2$ was blown over the reaction mixture and the vial was capped. The vial was placed in an oil bath and heated to 102° C. The reaction was stirred at 102° C. for 15 h, then allowed to cool to rt. The reaction mixture was diluted with $CH_2Cl_2$ and gravity filtered. The filtrate was concentrated to a brown oil. The oil was chromatographed on a 50 g Supelco $SiO_2$ cartridge using a 5% to 25% EtOAc/hexanes gradient as the mobile phase. The second large peak off the column was collected as product to give 0.29 g of BR-3.

Compound BR-3 was converted to Example 1.371 using procedures similar to those described in Scheme BA and Scheme BB.

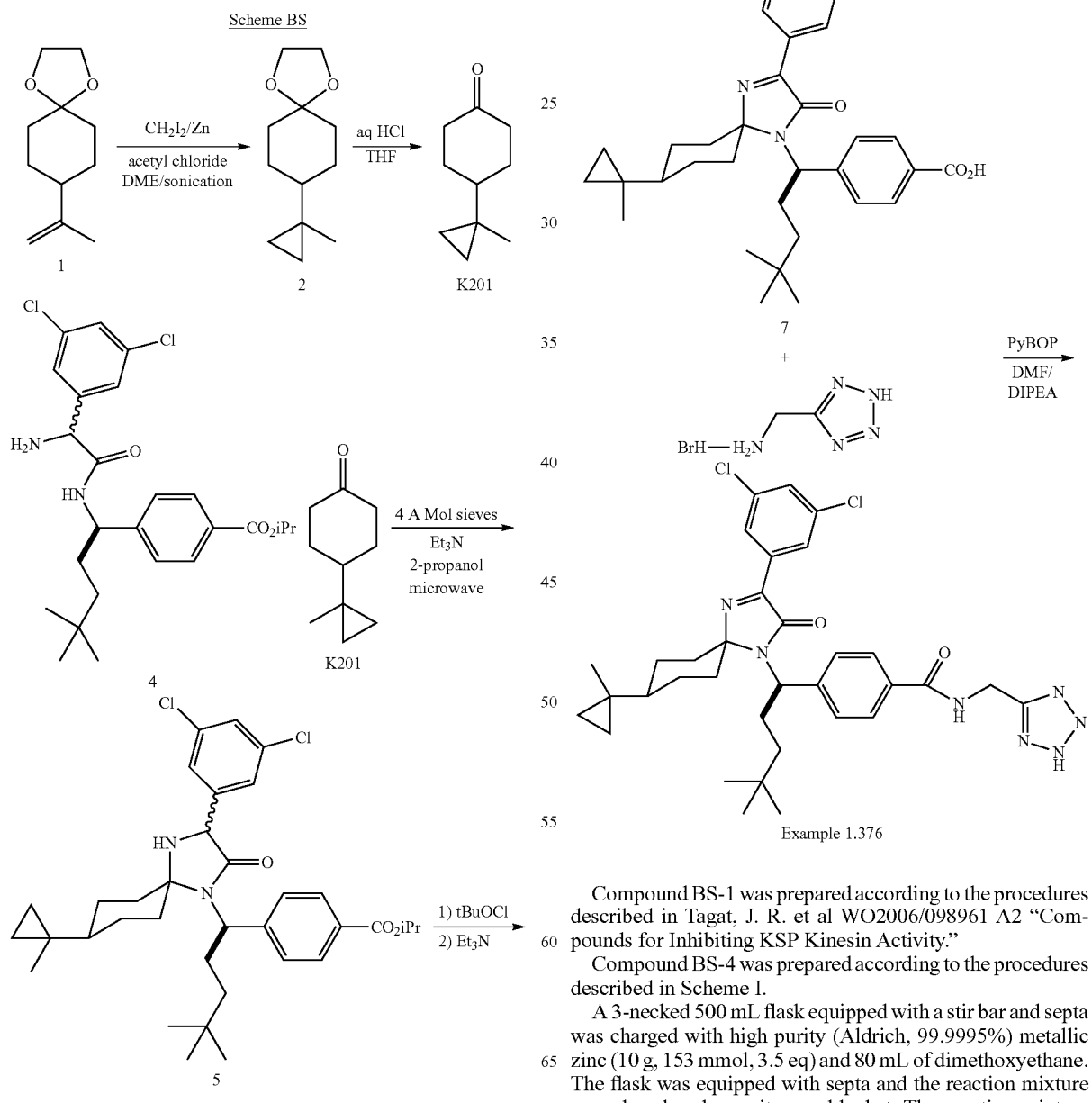

Example 1.376

Compound BS-1 was prepared according to the procedures described in Tagat, J. R. et al WO2006/098961 A2 "Compounds for Inhibiting KSP Kinesin Activity."

Compound BS-4 was prepared according to the procedures described in Scheme I.

A 3-necked 500 mL flask equipped with a stir bar and septa was charged with high purity (Aldrich, 99.9995%) metallic zinc (10 g, 153 mmol, 3.5 eq) and 80 mL of dimethoxyethane. The flask was equipped with septa and the reaction mixture was placed under a nitrogen blanket. The reaction mixture was sonicated and heated using a Fisher Scientific 150 watt FS60 sonicating bath. Acetyl chloride (0.34 g, 5.1 mmol) was added via syringe, followed by compound BS-1 (8.0 g, 43.9 mmol, 1.0 eq) and diiodomethane (42.3 g, 158 mmol, 3.6 eq), which were also added via syringe. The reaction mixture was sonicated and heated at 60° C. for 5 h under $N_2$. The sonication and heating were stopped and the reaction mixture was allowed to stand at RT under $N_2$ overnight. The reaction mixture was quenched with saturated aq $NH_4Cl$ solution and poured into 1 L of EtOAc. The layers were separated. The organic layer was washed with saturated aq $NH_4Cl$ and dried over sodium sulfate. The resulting mixture was filtered and the filtrate was concentrated to dryness, giving 10.16 g of impure BS-2. The crude product was used in the next step without further purification. (See also Repic, O. et al *Tetrahedron Letters* 1982, 23, 2729-2732 for a leading reference on the use of sonication in the Simmons-Smith reaction.)

In a 250 mL round bottomed flask, compound BS-2 (10.16 g) was dissolved in 20 mL of THF Aqueous 4 N HCl was added (20 mL) and the resulting solution was stirred at RT overnight. The resulting reaction mixture was partially concentrated on the rotovap then added to 1 L of EtOAc. The organic layer was washed with 2×100 mL of water and dried over sodium sulfate. The solution was gravity filtered and concentrated to dryness. The crude K201 was purified via flash sgc on a 120 g Isco $SiO_2$ cartridge using a 0%-40% EtOAc/hexanes gradient as the mobile phase to give 4.34 g of K201 (65% yield over the two steps).

Compound K201 was converted to Example 1.376 using procedures similar to those described in Scheme BA and Scheme BB.

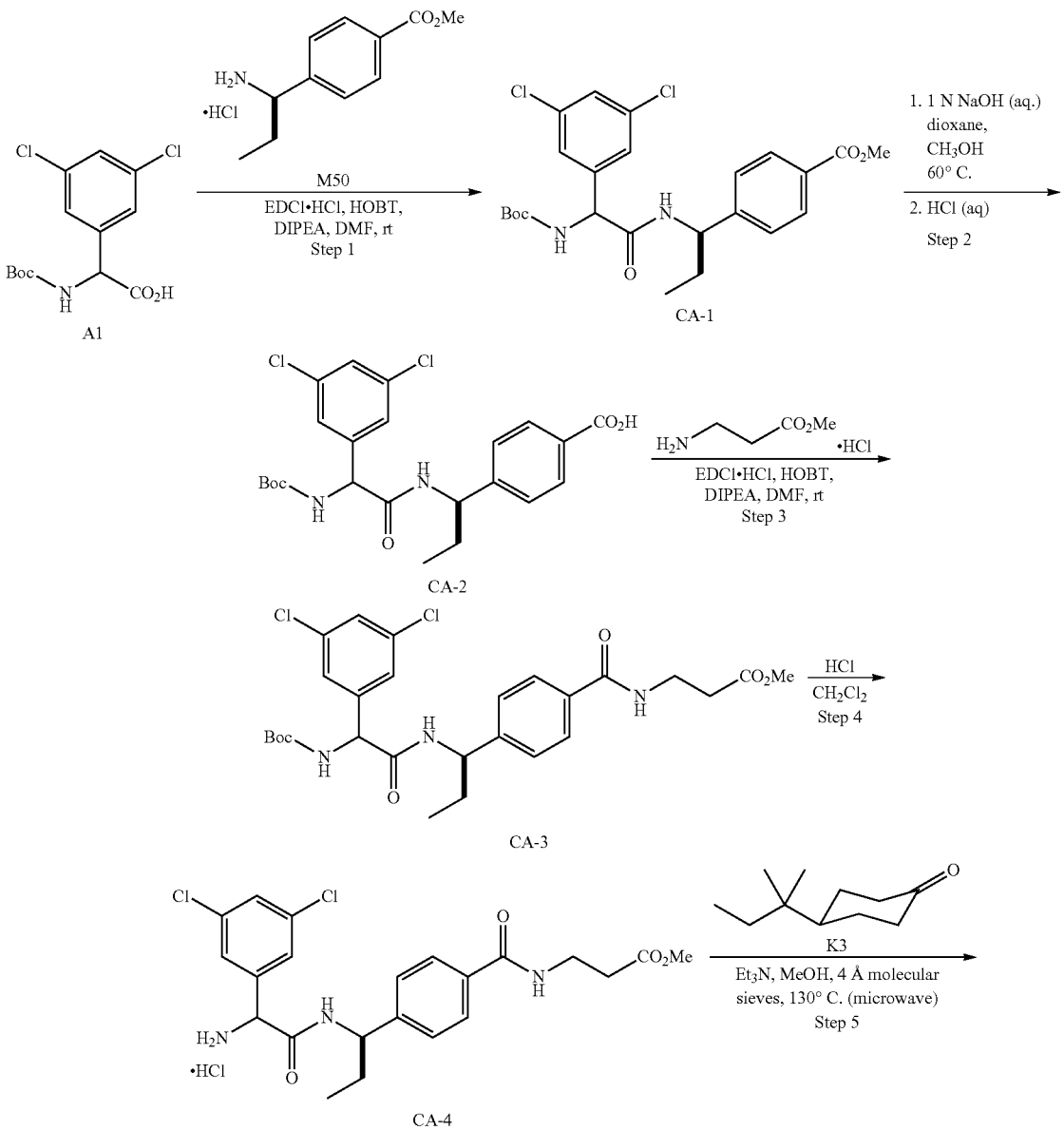

Scheme CA

Preparation of Example 1.931

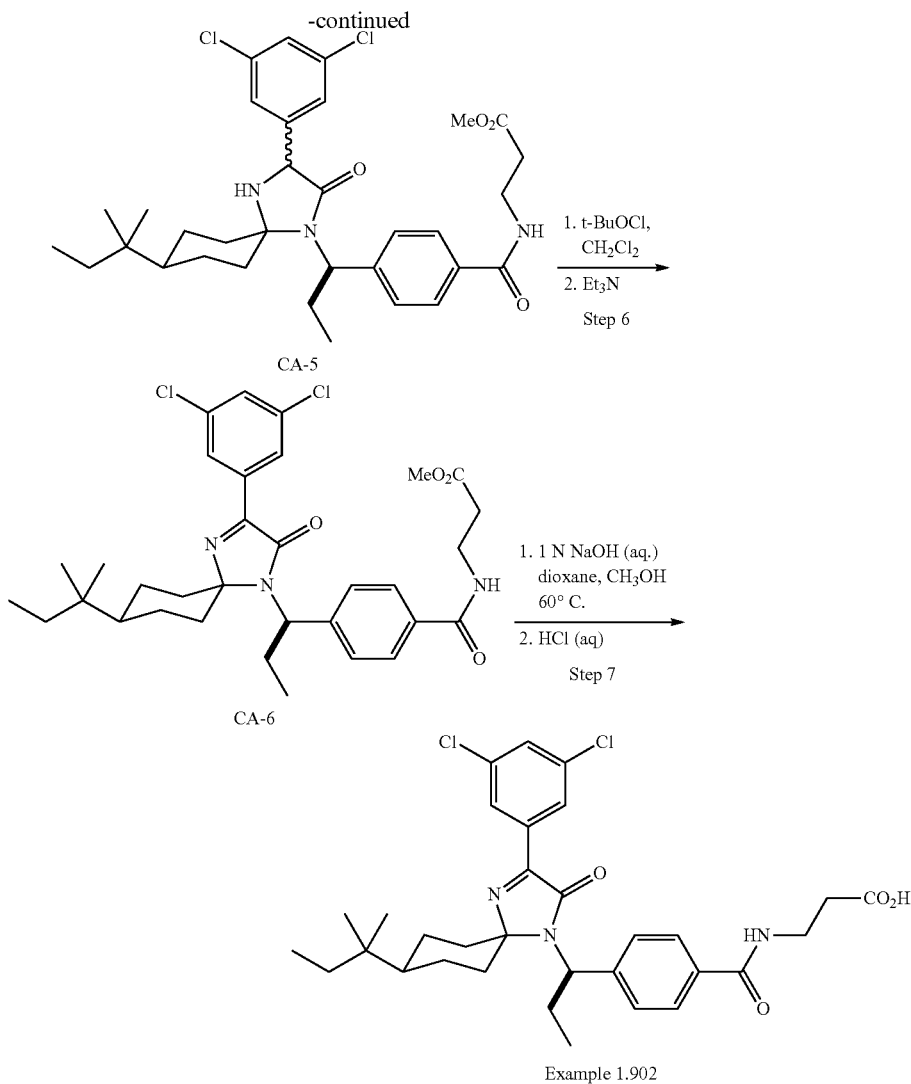

Example 1.902

Step 1

In a 125-mL round-bottom flask, amino acid A1 (1.0 g, 3.1 mmol), amine hydrochloride salt M50 (652 mg, 2.8 mmol), EDCl.HCl (817 mg, 4.3 mmol) and HOBT.H₂O (423 mg, 3.1 mmol), and DIPEA (1.5 mL, 1.1 g, 8.5 mmol) were combined and collectively dissolved in DMF (5.7 mL). The resulting solution was stirred overnight at rt, then diluted with EtOAc (80 mL) and water (40 mL). The organic layer was separated and washed sequentially with water (3×20 mL) and brine (20 mL), then dried over anhydrous MgSO₄, filtered, and concentrated under reduced pressure. The residue was purified by flash chromatography (Ism Combiflash Rf®; 40 g RediSep silica gel cartridge, 0-30% EtOAc/hexanes over 16 column volumes @ 40 mL/min). The desired product CA-1 was obtained as a pale yellow oil (1.22 g, 86%).

Step 2

In a 500-mL round-bottom flask, Compound CA-1 (1.22 g, 2.46 mmol) was dissolved in a mixture of dioxane (11 mL) and methanol (5.5 mL) and the solution was treated with 1 N aq. NaOH. The reaction mixture was heated with stirring at 60° C. for 2 h and then was then allowed to cool to rt. The solvent was removed by rotary evaporation under reduced pressure. The residue was redissolved in water (50 mL) and then acidified to pH 2 using 2 N aq. HCl. EtOAc (100 mL) was added. The aq. layer was separated and extracted with EtOAc (3×30 mL). The combined organic phases were washed with brine (~50 mL), dried over anhydrous MgSO₄, filtered, and concentrated by rotary evaporation under reduced pressure to afford Compound CA-2 as a white foam (1.16 g, 97%), which was used without further purification.

Step 3

In a 250-mL round-bottom flask, the carboxylic acid CA-2 (1.16 g, 2.41 mmol), beta-alanine methyl ester hydrochloride (505 mg, 3.61 mmol), EDCl.HCl (693 mg, 3.61 mmol), HOBT.H₂O (360 mg), and DIPEA (1.3 mL, 934 mg, 7.23 mmol) were mixed and collectively dissolved in DMF (8 mL). The resulting solution was stirred overnight at rt. The reaction mixture was diluted with EtOAc (60 mL). Water (30 mL) was added. The organic layer was separated, washed with water (3×10 mL) and brine (10 mL), dried over anhydrous MgSO₄, filtered, and concentrated by rotary evaporation under reduced pressure to afford a crude product CA-3 (off-white solid, 1.34 g, 98% yield), which was used without further purification.

Step 4

In a 250-mL round-bottom flask, a solution of Compound CA-3 (1.34 g, 2.37 mmol) in dichloromethane (4.7 mL) was treated with HCl (24 mL, 2 M in diethyl ether; 48 mmol) and the reaction was allowed to proceed overnight at rt. The solvent was removed by rotary evaporation under reduced pressure to give a crude product, Compound CA-4, as a light yellow solid (1.27 g, in excess of theoretical yield). Compound CA-4 was used without further purification.

Step 5

In a Biotage® 20-mL microwave tube, Compound CA-4 (118 mg, 0.235 mmol), 4-t-pentylcyclohexanone (Compound K3; 316 mg, 1.88 mmol), triethylamine (0.2 mL, 142 mg, 1.4 mmol) and 4 Å molecular sieves (100 mg, 0.4-0.8 mm beads) were admixed and suspended in dry methanol (0.94 mL). The tube was sealed and the reaction was allowed to proceed at 130° C. (microwave heating) for 6 h. The reaction mixture was filtered through a Celite®® pad, which was then washed with dichloromethane (~10 mL). The filtrate was concentrated under reduced pressure and the residue was purified by flash silica gel chromatography (Isco Combiflash Rf®; 12 g RediSep silica gel cartridge, 0-30% EtOAc/hexanes over 28 column volumes @ 30 mL/min). The desired product CA-5 was obtained as a pale yellow oil (122 mg, 84% yield).

Step 6

In a 125-mL round-bottom flask, Compound CA-5 (122 mg, 0.197 mmol) was dissolved in dichloromethane (2 mL) and treated with t-butyl hypochlorite (0.03 mL, 27 mg, 0.24 mmol). The reaction mixture was stirred at RT for 1 h. Triethylamine (0.11 mL, 80 mg, 0.80 mmol) was added and the reaction was allowed to proceed at RT for 1 h. The reaction mixture was then diluted with dichloromethane (30 mL) and washed sequentially with 1 N aq. NaHSO$_3$ (5 mL), water (5 mL), and brine (5 mL). The organic layer was dried over anhydrous MgSO$_4$, filtered, and concentrated by rotary evaporation under reduced pressure. The resulting residue was purified by flash silica gel chromatography (Isco Combiflash Rf®; 12 g RediSep silica gel cartridge, 0-30% EtOAc/hexanes over 28 column volumes @ 30 mL/min) to give desired product CA-6 as a yellow oil (89 mg, 74% yield).

Step 7

In a 125-mL round-bottom flask, substrate CA-6 (89 mg, 0.145 mmol) was dissolved in dioxane (0.64 mL) and methanol (0.32 mL) and the resulting solution was treated with 1 N aq. NaOH (0.160 mL). The reaction mixture was stirred at 60° C. for 2 h, then allowed to cool to rt, and was concentrated under reduced pressure. The resulting residue was redissolved in water (15 mL) and the solution was acidified to pH 2 using 2 N aq. HCl. EtOAc (30 mL) was added. The aq. layer was separated and extracted with further amounts of EtOAc (3×15 mL). The combined organic layers were washed with brine (~25 mL), dried over anhydrous MgSO$_4$, filtered, and concentrated by rotary evaporation under reduced pressure. The resulting residue was purified by flash silica gel chromatography (Isco Combiflash Rf®; 12 g RediSep silica gel cartridge, 0-100% EtOAc/hexanes over 28 column volumes @ 30 mL/min) to give Example 1.902 as a yellow oil (76 mg, 86% yield).

Scheme CB

Preparation of Example 1.931

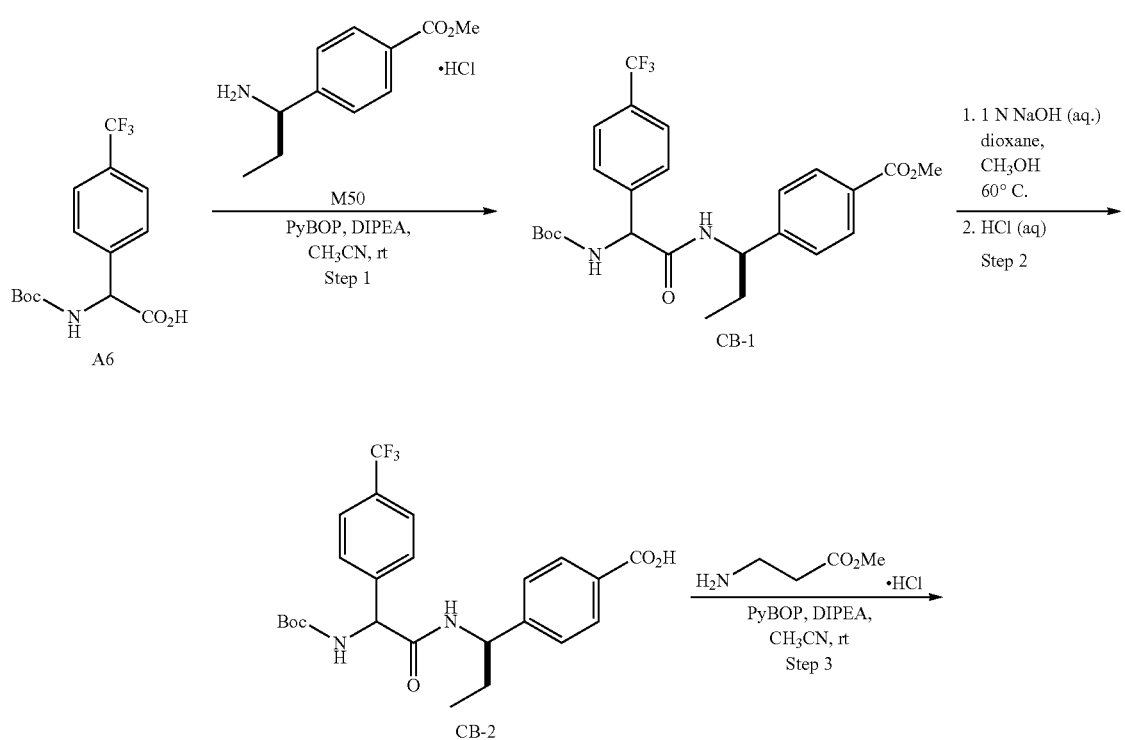

-continued
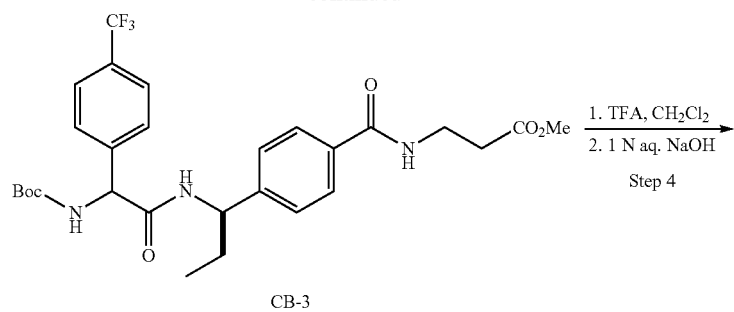
CB-3
1. TFA, CH$_2$Cl$_2$
2. 1 N aq. NaOH
Step 4
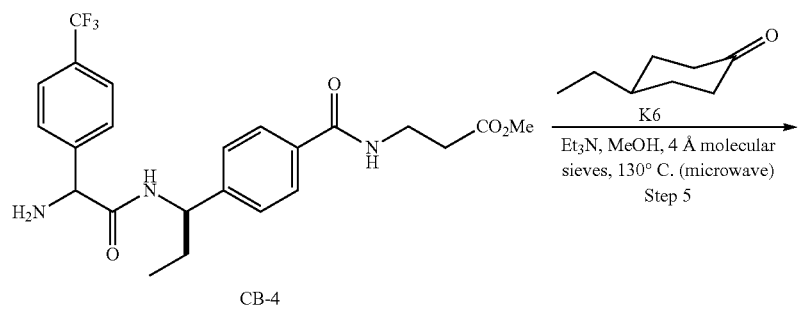
CB-4
K6
Et$_3$N, MeOH, 4 Å molecular sieves, 130° C. (microwave)
Step 5
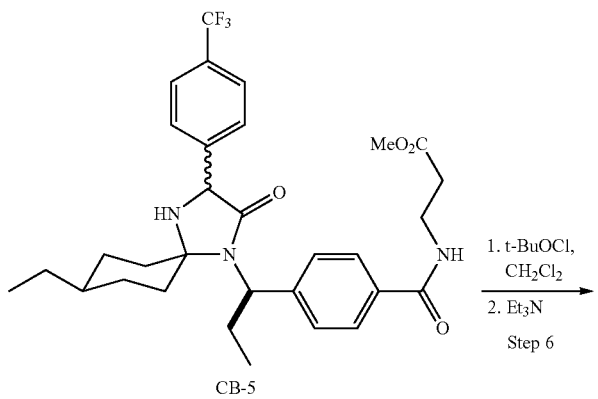
CB-5
1. t-BuOCl, CH$_2$Cl$_2$
2. Et$_3$N
Step 6
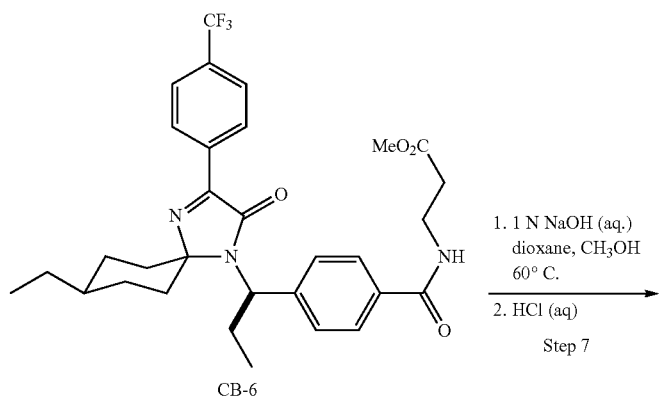
CB-6
1. 1 N NaOH (aq.) dioxane, CH$_3$OH 60° C.
2. HCl (aq)
Step 7

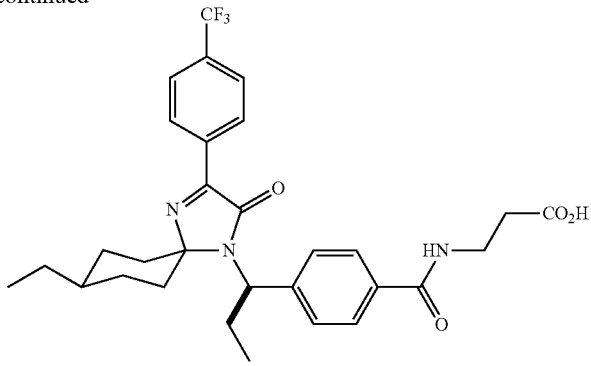

Example 1.931

Step 1

In a 250-mL round-bottom flask, an admixture of Compound A6 (4.37 g, 13.7 mmol), Compound M50 (2.86 g, 12.4 mmol), and PyBOP (7.12 g, 13.7 mmol) was dissolved in dry acetonitrile (54 mL). The solution was stirred at RT for 3 days. The solvent was removed by rotary evaporation under reduced pressure. The residue was purified directly by flash silica gel chromatography (Isco Combiflash Rf®; 80 g RediSep silica gel cartridge, 0-30% EtOAc/hexanes over 20 column volumes 80 mL/min) to afford Compound CB-1 as a yellow solid (5.81 g, 94% yield).

Step 2

Compound CB-1 was converted to Compound CB-2 following the procedure in Scheme CA, Step 2.

Step 3

In a 1-L round-bottom flask, an admixture of Compound CB-2 (5.36 g, 11.2 mmol), beta-alanine methyl ester hydrochloride (2.34 g, 16.7 mmol), DIPEA (7.7 mL, 5.8 g, 45 mmol), and PyBOP (6.38 g, 12.3 mmol) was dissolved in dry acetonitrile (55 mL). The solution was stirred overnight at rt. The solvent was removed by rotary evaporation under reduced pressure. The residue was purified directly by flash silica gel chromatography (Isco Combiflash Rf®; 80 g RediSep silica gel cartridge, 0-30% EtOAc/hexanes over 20 column volumes @ 80 mL/min) to afford Compound CB-3 as an off-white solid (6.05 g, 96% yield).

Step 4

In a 100-mL round-bottom flask, TFA (3.0 mL, 4.6 g, 41 mmol) was added to a stirred solution of Compound CB-3 (2.3 g, 4.1 mmol) in dichloromethane (16 mL). The reaction mixture was stirred overnight at rt. The solvent and other volatile components were removed by rotary evaporation under reduced pressure. The residue was redissolved in dichloromethane (150 mL) and the solution was washed with 1 N aq. NaOH (~50 mL). The organic layer was set aside while the aqueous layer was extracted with dichloromethane (3×25 mL). The combined organic phases were dried over anhydrous MgSO$_4$, filtered, and concentrated under reduced pressure to afford Compound CB-4 as an off-white solid (1.77 g, 94% yield).

Steps 5 and 6

Compound CB-4 was converted to Compound CB-6 by sequential application of procedures given in steps 5 and 6 of Scheme CA, and substituting Compound K6 for Compound K3 in step 5.

Step 7

Compound CB-6 was converted to Example 1.931 following the procedure of Scheme CA, step 7.

Scheme CC

Preparation of Example 1.951

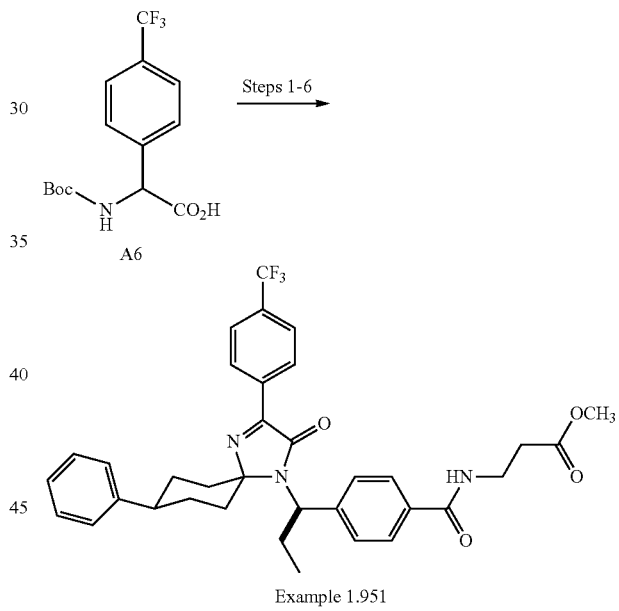

Example 1.951

Steps 1-6

Compound A6 was converted to Example 1.951 by sequential application of procedures given in steps 1-6 of Scheme CB, substituting Compound K11 for Compound K6 in step 5.

Scheme CD

Preparation of Compound K95

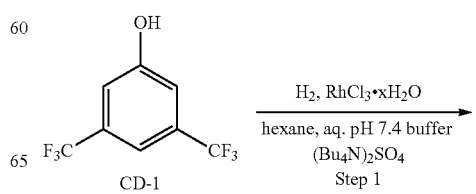

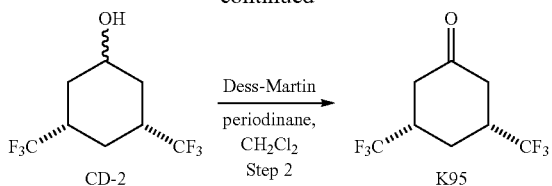

Step 1

In a 500-mL Parr® hydrogenation vessel, Compound CD-1 (8.74 g, 38 mmol) was dissolved in hexane (20 mL) and aqueous pH 7.4 buffer (20 mL; Fisher Scientific: SB110-1; potassium phosphate monobasic-sodium hydroxide buffer, 0.05 M). $RhCl_3 \cdot xH_2O$ (1.0 g, 3.8 mmol; Alfa Aesar) and tetrabutylammonium sulfate solution (4.4 mL, 50 wt % in $H_2O$; 4.4 g, 3.8 mmol) were added sequentially. The biphasic mixture was shaken under hydrogen atmosphere (53 psi) for 14 days at rt. The reaction mixture was filtered through a Celite® pad. The aq. layer was separated and extracted with EtOAc (3×15 mL). The combined organic layers was washed with brine (~25 mL), dried over anhydrous $MgSO_4$, filtered, and concentrated by rotary evaporation under reduced pressure. The crude product was purified by flash silica gel chromatography (Isco Combiflash Rf®; 80 g RediSep silica gel cartridge, 0-100% EtOAc/hexanes over 20 column volumes @ 80 mL/min). Eluent from column volumes 1-6, containing unreacted Compound CD-1, were discarded, while column volumes 7-20 were combined and concentrated to give desired product, Compound CD-2, as an off-white solid (6.67 g, 74% yield).

Step 2

A solution of Compound CD-2 (6.67 g, 28.3 mmol) in dichloromethane (113 mL) was treated with solid Dess-Martin periodinane (18 g, 42 mmol). The reaction mixture was stirred overnight at rt. The reaction mixture was diluted with diethyl ether (385 mL) and 1 N aq. NaOH (185 mL) was added slowly. The resulting solution was stirred at RT for 1.5 h. The organic layer was separated and washed sequentially with 1 N aq. NaOH (90 mL), brine (~50 mL), dried over anhydrous $MgSO_4$, filtered, and concentrated by rotary evaporation under reduced pressure to afford the desired product, Compound K95, as a yellow oil (6.55 g, 99% yield). Compound K95 was used without subsequent purification.

Scheme CE

Preparation of Example 1.966

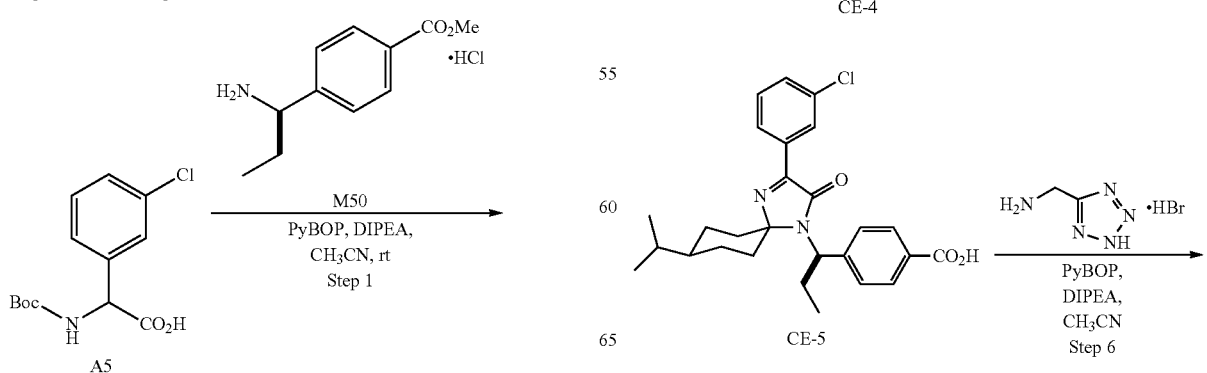

285

-continued

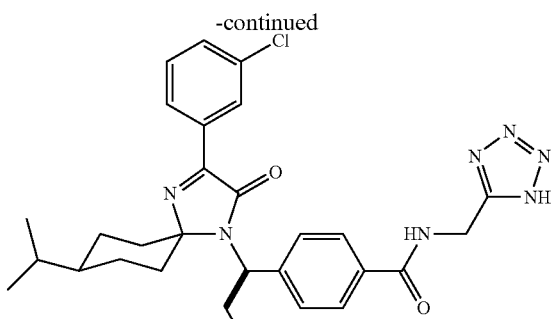

Example 1.966

Step 1

Compound CE-1 was prepared following the procedure given in Step 1 of Scheme CB, substituting Compound A5 (707 mg, 2.47 mmol) for Compound A6.

Step 2

In a 250-mL round-bottom flask, Compound CE-1 (1.08 g, 2.47 mmol) was dissolved in dichloromethane (10 mL). Neat TFA (5 mL) was added and the resulting solution was stirred at RT for 16 h. The reaction mixture was concentrated by rotary evaporation under reduced pressure. The resulting syrup was redissolved in dichloromethane (50 mL) and the solution was washed sequentially with 1 N aq. NaOH (~25 mL), water (~25 mL), and brine (~25 mL). The organic layer was dried over anhydrous $MgSO_4$, filtered, and concentrated to afford a clear, colorless oil. Said oil was redissolved in dichloromethane (25 mL). HCl solution (2.0 mL, 2.0 M in diethyl ether; 4.0 mmol) was added and the solvent was removed under reduced pressure to afford Compound CE-2 as a white solid (822 mg, 92% yield over two steps).

Step 3

In a Biotage® 5-mL microwave tube, Compound CE-2 (316 mg, 0.80 mmol) was dissolved in dry methanol (2.6 mL) with the aid of stirring and occasional sonication. 4-Isopropylcyclohexanone (Compound K2; 891 mg, 6.37 mmol), triethylamine (0.447 mL, 322 mg, 3.18 mmol) and 4 Å molecular sieves (1.3 g, 0.4-0.8 mm beads) were added. The reaction mixture was heated at 130° C. for 6 h under microwave conditions. The reaction mixture was diluted with dichloromethane (5 mL) and filtered through a Celite®® pad. The pad was rinsed with a further portion of dichloromethane (25

286 mL) and methanol (5 mL). The combined filtrates were concentrated under reduced pressure. The resulting orange, liquid residue was purified by flash silica gel chromatography (Isco Combiflash Rf®; 24 g RediSep silica gel cartridge, 0-30% EtOAc/hexanes over 12 column volumes @ 30 mL/min) to afford Compound CE-3 (667 mg), which was contaminated with an undetermined amount of Compound K2. Compound CE-3 was used without further purification.

Step 4

Compound CE-3 (667 mg, impure) was converted to Compound CE-4 following the procedure given in Scheme CA, Step 6. An undetermined amount of Compound K2 remained after chromatography, but the desired product Compound CE-4 (281 mg) was used without further purification.

Step 5

Compound CE-4 (281 mg, impure) was dissolved in methanol (1.5 mL) and 1,4-dioxane (3 mL). 1 N aq. NaOH (0.65 mL, 0.65 mmol) was added and the reaction flask was immersed into a preheated, 60° C. oil bath. The reaction was allowed to proceed at 60° C. for 22 h. The reaction mixture was concentrated to dryness under reduced pressure. The residue was taken up in water (10 mL) and acidified with 1 N aq. HCl (1 mL). The suspension was extracted with EtOAc (2×~30 mL). The combined organic phases were washed with brine (~20 mL), dried over anhydrous $MgSO_4$, filtered, and concentrated under reduced pressure to afford an oily solid. Purification by flash silica gel chromatography (Isco Combiflash Rf®; 40 g RediSep silica gel cartridge, 0-50% EtOAc/hexanes over 13 column volumes @ 30 mL/min, then 50-80% EtOAc/hexanes over 30 CV) gave pure Compound CE-5 as a white solid (151 mg, 41% yield over three steps).

Step 6

In a 50-mL round-bottom flask, Compound CE-5 (58 mg, 0.124 mmol) was dissolved in dry DMF (1.0 mL). Aminomethyltetrazole hydrobromide (27 mg, 0.149 mmol), DIPEA (0.065 mL, 48 mg, 0.373 mmol), and PyBOP (78 mg, 0.149 mmol) were added sequentially. The reaction flask was immersed into a preheated 70° C. oil bath and the reaction was allowed to proceed with stirring at 70° C. for 4 h. The reaction mixture was allowed to cool to rt, was filtered, and purified directly by reverse-phase, C-18 chromatography (40-100% MeCN (+0.05% TFA) in water (+0.05% TFA) over 20 min @ 20 mL/min) to afford Example 1.966 as a white solid (55 mg, 81% yield).

Scheme CF

Preparation of Example 1.963

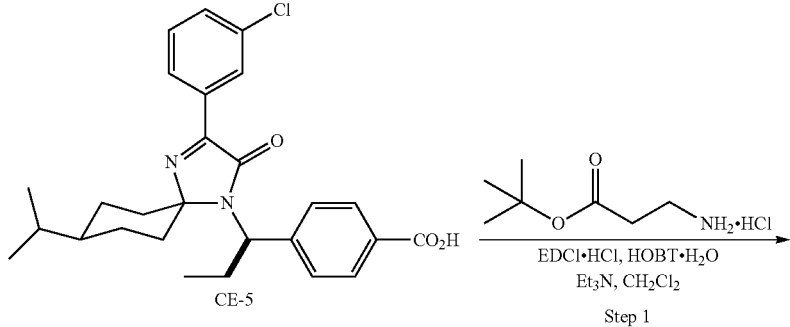

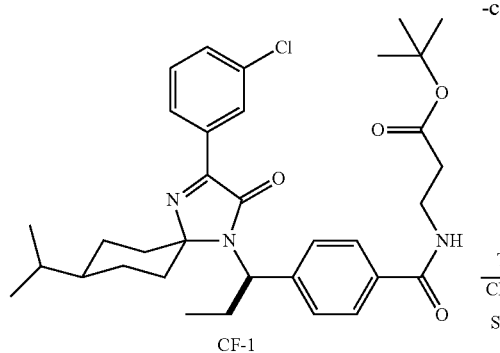

CF-1

TFA
CH₂Cl₂
Step 2

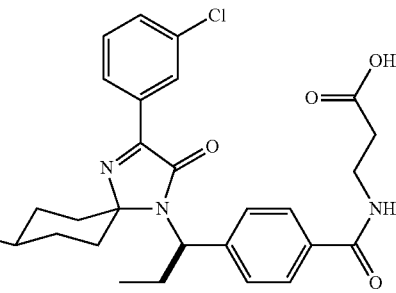

Example 1.963

Step 1

Compound CE-5 (50 mg, 0.11 mmol), prepared as described in Scheme CE, was dissolved in dichloromethane (1.1 mL). Triethylamine (0.060 mL, 43 mg, 0.43 mmol), EDCl.HCl (25 mg, 0.13 mmol), HOBT.H₂O (20 mg, 0.13 mmol), and beta-alanine t-butyl ester hydrochloride (24 mg, 0.13 mmol) were added sequentially. The reaction mixture was stirred overnight at rt. The solvent was removed by rotary evaporation under reduced pressure. The residue was purified by flash silica gel chromatography (Isco Combiflash Rf®; 4 g RediSep silica gel cartridge, 0-40% EtOAc/hexanes over 77 column volumes @ 18 mL/min) to afford Compound CF-1 as a white solid (58 mg, 91% yield).

Step 2

Compound CF-1 (56 mg, 0.094 mmol) was dissolved in dichloromethane (1 mL) and TFA (0.210 mL, 323 mg, 2.83 mmol) was added. The reaction mixture was stirred at RT for 18 h. The reaction mixture was diluted with dichloromethane (~10 mL) and then concentrated by rotary evaporation to dryness. The resulting syrup was co-evaporated with 1:1 dichloromethane-hexanes (20 mL) to afford a pale yellow foam. The foam was purified by reverse-phase C-18 chromatography (Gilson®; 20-100% MeCN (+0.05% TFA) in water (+0.05% formic acid) over 20 min @ 20 mL/min) to give Example 1.963 as a white solid (39 mg, 77% yield).

Scheme CG

Preparation of M90

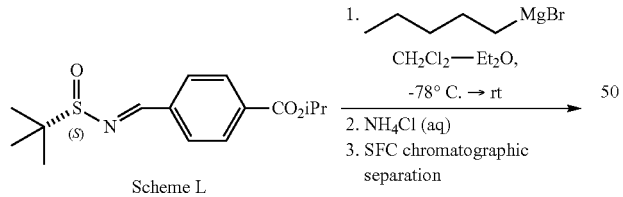

Scheme L
Step 2

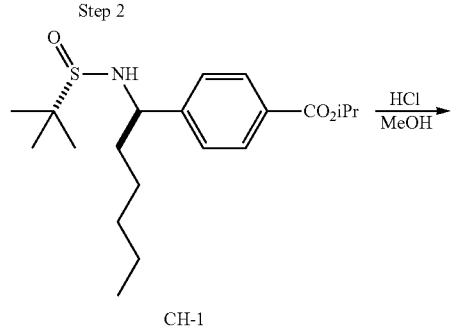

CH-1

HCl
MeOH

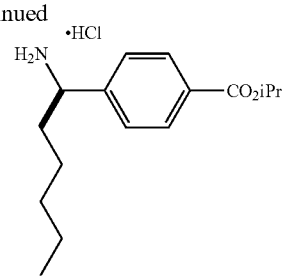

M90

Step 1

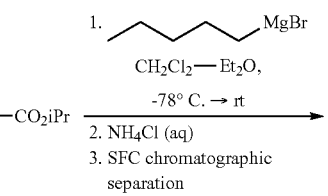

Scheme L
Step 2

1. ~~~MgBr
CH₂Cl₂—Et₂O,
-78° C. → rt
2. NH₄Cl (aq)
3. SFC chromatographic separation

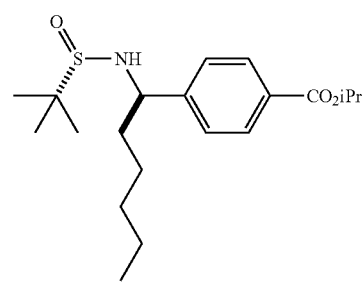

CH-1

The imine (260.4 g, 0.802 mol; prepared according to Scheme L Step 2) was dissolved in anhydrous dichloromethane (5.0 L) and the resulting solution was cooled to −73° C. (internal) using a Dry Ice/acetone bath. n-Pentylmagnesium bromide (765 mL, 2 M in diethyl ether; 1.53 mol) was added slowly over 1 h. The reaction mixture was allowed to gradually warm to rt, and was stirred overnight at rt. The reaction mixture was poured slowly a mixture of cold, saturated aq. ammonium chloride (1.25 L) and ice (~500 mL). The mixture was stirred for 5 min, and then extracted with EtOAc (1×5 L, 1×2 L). The organic layers were combined and washed sequentially with water (2×2.5 L) and brine (1×2 L), dried over anhydrous MgSO₄, filtered, and concentrated by rotary evaporation under reduced pressure to afford the crude product (332 g, yellow oil). The crude product was purified by flash column chromatography [9.3 L silica gel pre-packed in hexanes (12 L); eluted with 15% EtOAc/hexanes, followed by 25% EtOAc/hexanes (24 L), then 30% EtOAc/hexanes (8 L), and finally 35% EtOAc/hexanes (48 L)] to obtain the desired product as a ~3.5:1 mixture of diastereomers (148.5 g, 46% yield).

The diastereomers were separated in two batches by SFC chromatography (Chiralpak® AD-H, 50×250 mm column; 15% MeOH/CO₂, 100 bar back-pressure, 35° C., 300 mL/min; UV detection at λ=200 nm). In the first batch, a solution of crude product (25 g) was dissolved in MeOH (200 mL) and injected in 2.0 mL aliquots. Retention times for the two separated components were 1.97 min and 2.70 min. In the second batch, a solution of crude product (118 g) was dissolved in MeOH (500 mL) and injected in 2.5 mL aliquots. Retention times for the two separated components were 2.03 min and 2.73 min. All fractions that eluted at retention times 1.97 min and 2.03 min were combined and concentrated by rotary evaporation under reduced pressure to afford Compound CH-1 (74 g) as a white solid.

Step 2

A solution of Compound CH-1 (1.53 g, 4.15 mmol) in methanol (14.4 mL) was treated with hydrogen chloride (2.2 mL; 4 M solution in 1,4-dioxane; 8.7 mmol). The reaction mixture was stirred at RT for 40 min. The solvents were removed by rotary evaporation under reduced pressure. The residue was suspended in diethyl ether (25 mL). Solvent was removed by rotary evaporation to afford the amine M90 as a yellow solid (1.24 g, 100% yield).

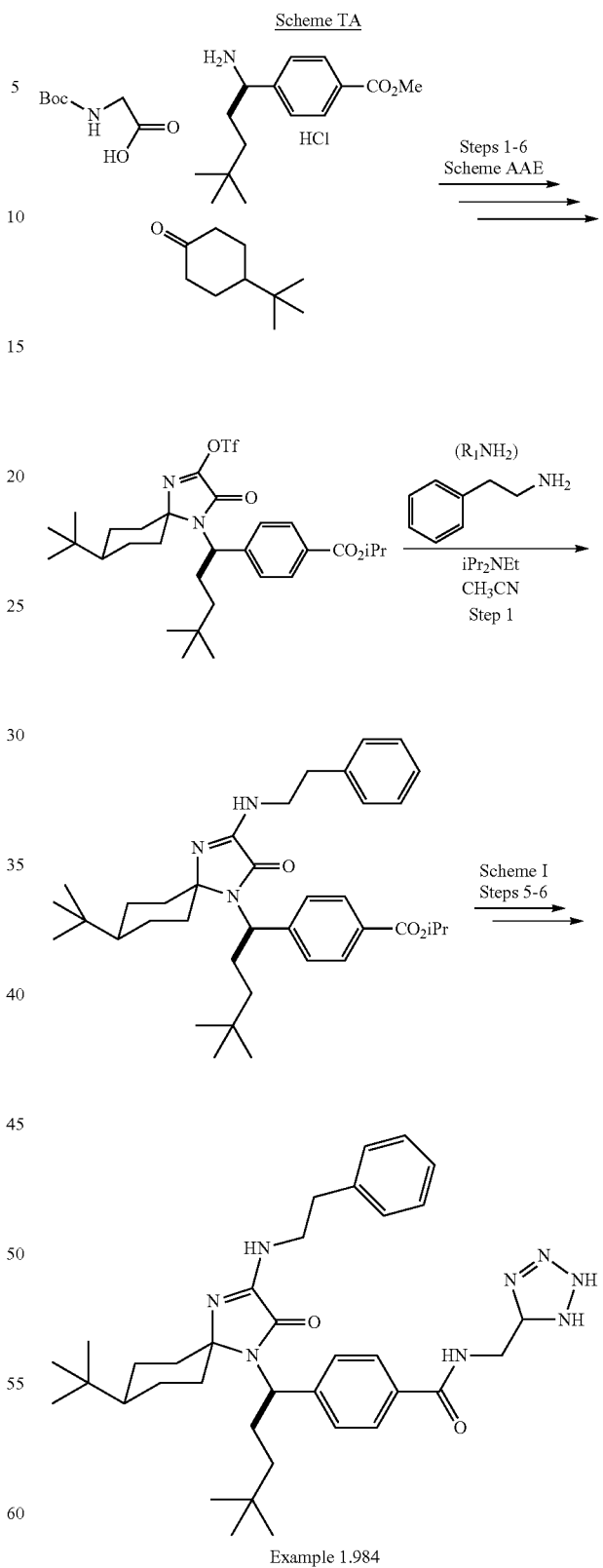

N—BOC glycine, the amine HCl salt, and ketone were processed according to Scheme AAE (Steps 1-6) to provide the triflate.

Step 1

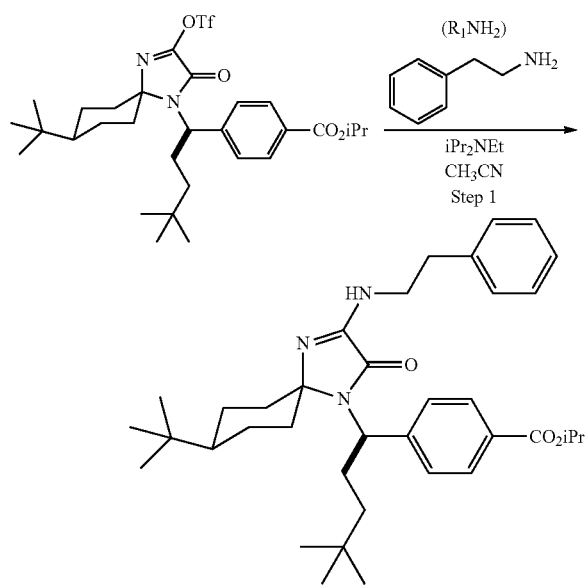

The trifate (99 mg, 0.16 mmol), 2-phenylethanamine (61 mg, 0.5 mmol), and iPr$_2$NEt (83 mg, 0.64 mmol) were taken up in 2 ml of CH$_3$CN and heated at 70° C. for 2 h. The solution was concentrated. The residue was purified via gradient flash chromatography (0-30% EtOAc in hexanes, SiO$_2$) which provided 65 mg (58%) of the amino-imidazolone.

The product of Step 1 was processed into Example 1.984 using conditions outlined in Scheme I Steps 5 and 6.

In one embodiment, the compounds of the invention have the general structure shown in Table 1 below, and include pharmaceutically acceptable salts, solvates, esters, prodrugs, tautomers, and isomers of said compounds. The compounds of Table 1 were prepared according to the detailed procedures described above. The Schemes indicated in the Table by letter correspond to the procedures described above. The ketones, amino acids, and amines used as indicated in Table 1 are depicted in Table 2.

TABLE 1
| Scheme | Ketone | Amino acid | Amine | Ex. | | LCMS | |
|---|---|---|---|---|---|---|---|
| | | | | | LC | Ret (min) | (MH)+ |
| A | K1 | A1 | M4 | 1.1 | 4 | 6.4 | 572 |
| B | K1 | A13 | M1 | 1.2 | 4 | 4.9 | 516 |
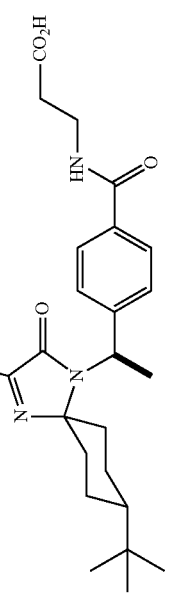
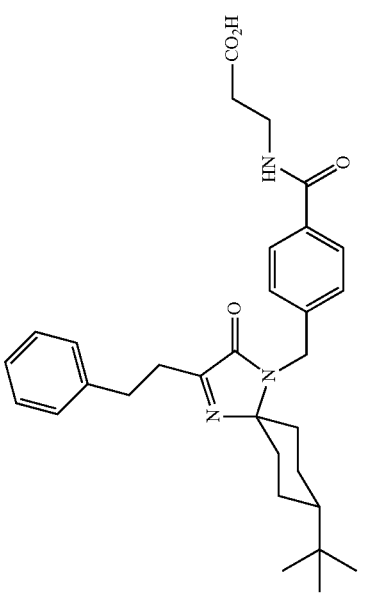

TABLE 1-continued

| | | | | | | |
|---|---|---|---|---|---|---|
| C | K1 | A1 | M1 | 1.3 | | 4 | 6.0 | 554 |
| D | K1 | A1 | M4 | 1.4 | | 4 | 6.2 | 568 |
| E | K2 | A1 | M1 | 1.5 | | 4 | 5.8 | 544 |

TABLE 1-continued

| H | K1 | A1 | M4 | 1.6 | (structure) | 4 | 5.80 | 588 |
| A | K1 | A1 | M1 | 1.7 | (structure) | 4 | 5.8 | 558 |
| A | K1 | A2 | M1 | 1.8 | (structure) | 4 | 5.2 | 558 |

TABLE 1-continued
| | | | | | | | |
|---|---|---|---|---|---|---|---|
| A | K1 | A3 | M1 | 1.9 | 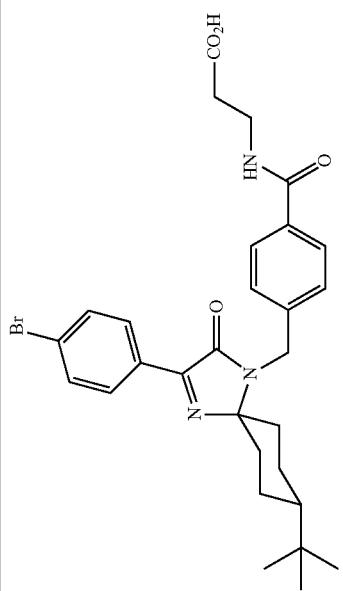 | 4 | 5.5 | 568 |
| A | K1 | A4 | M1 | 1.10 | 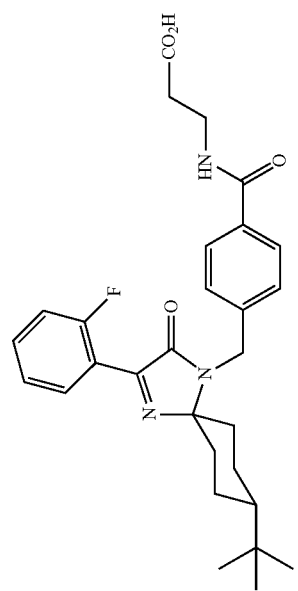 | 4 | 4.7 | 508 |
| A | K1 | A5 | M1 | 1.11 | 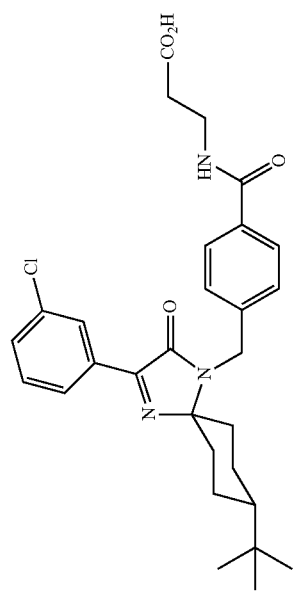 | 4 | 5.4 | 524 |

TABLE 1-continued

| | | | | | | | |
|---|---|---|---|---|---|---|---|
| A | K1 | A6 | M1 | 1.12 | *structure* | 4 | 5.2 | 558 |
| A | K1 | A1 | M2 | 1.13 | *structure* | 4 | 6.0 | 572 |
| A | K1 | A7 | M1 | 1.14 | *structure* | 4 | 5.3 | 524 |

TABLE 1-continued

| | | | | | | | |
|---|---|---|---|---|---|---|---|
| A | K1 | A8 | M1 | 1.15 | (structure) | 4 | 5.8 | 558 |
| C | K1 | A9 | M1 | 1.16 | (structure) | 4 | 4.9 | 486 |
| A | K1 | A10 | M1 | 1.17 | (structure) | 4 | 5.5 | 574 |

TABLE 1-continued

| | | | | | | |
|---|---|---|---|---|---|---|
| A | K1 | A9 | M1 | 1.18 | (structure) | 4 | 4.8 | 490 |
| A | K1 | A11 | M1 | 1.19 | (structure) | 4 | 4.9 | 524 |
| C | K1 | A12 | M1 | 1.20 | (structure) | 4 | 5.3 | 554 |

TABLE 1-continued

| A | K1 | A1 | M3 | 1.21 | ![structure with 3,5-dichlorophenyl] | 4 | 6.4 | 572 |
| A | K1 | A2 | M3 | 1.22 | ![structure with 3-CF3 phenyl] | 4 | 5.5 | 572 |

TABLE 1-continued

| | | | | | | |
|---|---|---|---|---|---|---|
| E | K1 | A2 | M4 | 1.23 | | 4 | 5.6 | 572 |
| E | K3 | A1 | M1 | 1.24 | | 4 | 6.1 | 572 |
| D | K1 | A1 | M3 | 1.25 | | 4 | 6.3 | 568 |

TABLE 1-continued

| A | K1 | A1 | M5 | 1.26 | [structure] | 4 | 6.2 | 588 |
| A | K1 | A4 | M4 | 1.27 | [structure] | 4 | 4.8 | 522 |

TABLE 1-continued

| A | K1 | A4 | M3 | 1.28 | [structure] | 4 | 4.9 | 522 |
| A | K1 | A9 | M3 | 1.29 | [structure] | 4 | 5.5 | 504 |

TABLE 1-continued

| A | K1 | A5 | M3 | 1.30 | | 4 | 6.0 | 538 |
| A | K4 | A1 | M1 | 1.31 | | 4 | 5.1 | 502 |

TABLE 1-continued

| | | | | | | |
|---|---|---|---|---|---|---|
| AQ | K1 | A6 | M3 | 1.32 | (structure) | 4 5.9 572 |
| A | K1 | A6 | M4 | 1.33 | (structure) | 4 5.9 572 |

TABLE 1-continued

| | | | | | | | |
|---|---|---|---|---|---|---|---|
| H | K1 | A6 | M4 | 1.34 | (structure) | 4 | 5.4 | 588 |
| H | K1 | A12 | M4 | 1.35 | (structure) | 4 | 5.1 | 538 |
| A | K1 | A12 | M4 | 1.36 | (structure) | 4 | 5.2 | 522 |

TABLE 1-continued
| | | | | | | | |
|---|---|---|---|---|---|---|---|
| A | K1 | A14 | M3 | 1.37 | 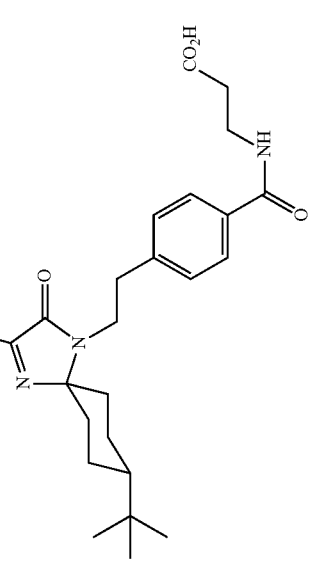 | 4 | 5.2 | 522 |
| I | K1 | A9 | M6 | 1.38 | 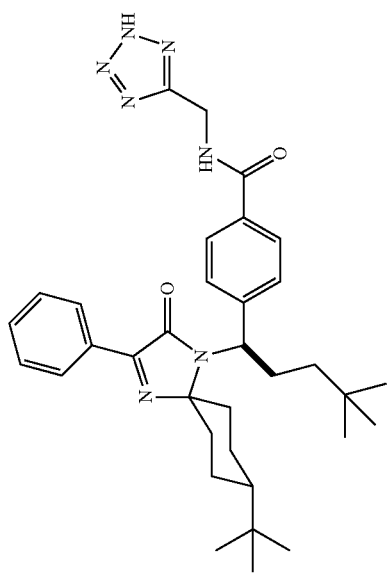 | 3 | 2.5 | 584 |

TABLE 1-continued

| I | K3 | A14 | M6 | 1.39 | [structure] | 3 | 2.6 | 616 |
| I | K1 | A15 | M7 | 1.40 | [structure] | 3 | 2.6 | 594 |

TABLE 1-continued
| | | | | | | |
|---|---|---|---|---|---|---|
| I | K2 | A1 | M7 | 1.41 | 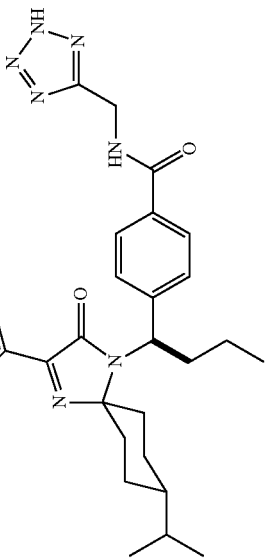 | 3 2.7 596 |
| I | K1 | A12 | M8 | 1.42 | 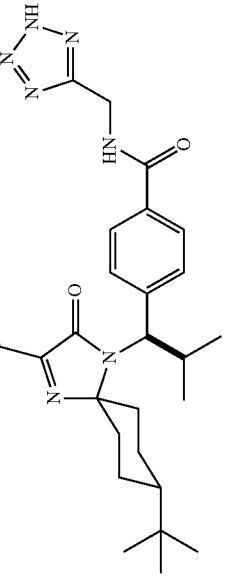 | 4 7.1 560 |

TABLE 1-continued
| I | K3 | A15 | M7 | 1.43 | 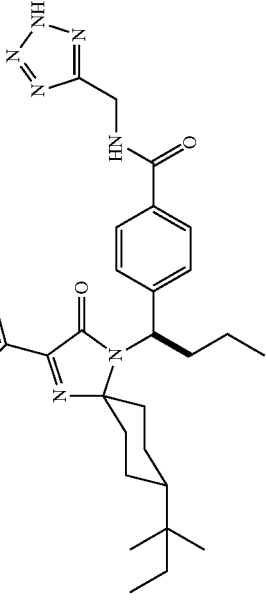 | 3 | 2.6 | 608 |
| I | K2 | A15 | M7 | 1.44 | 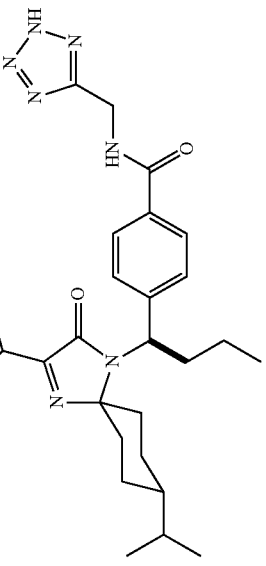 | 3 | 2.5 | 580 |

TABLE 1-continued
| | | | | | | |
|---|---|---|---|---|---|---|
| I | K1 | A1 | M6 | 1.45 | | |
| J | K1 | A12 | M8 | 1.46 | | |
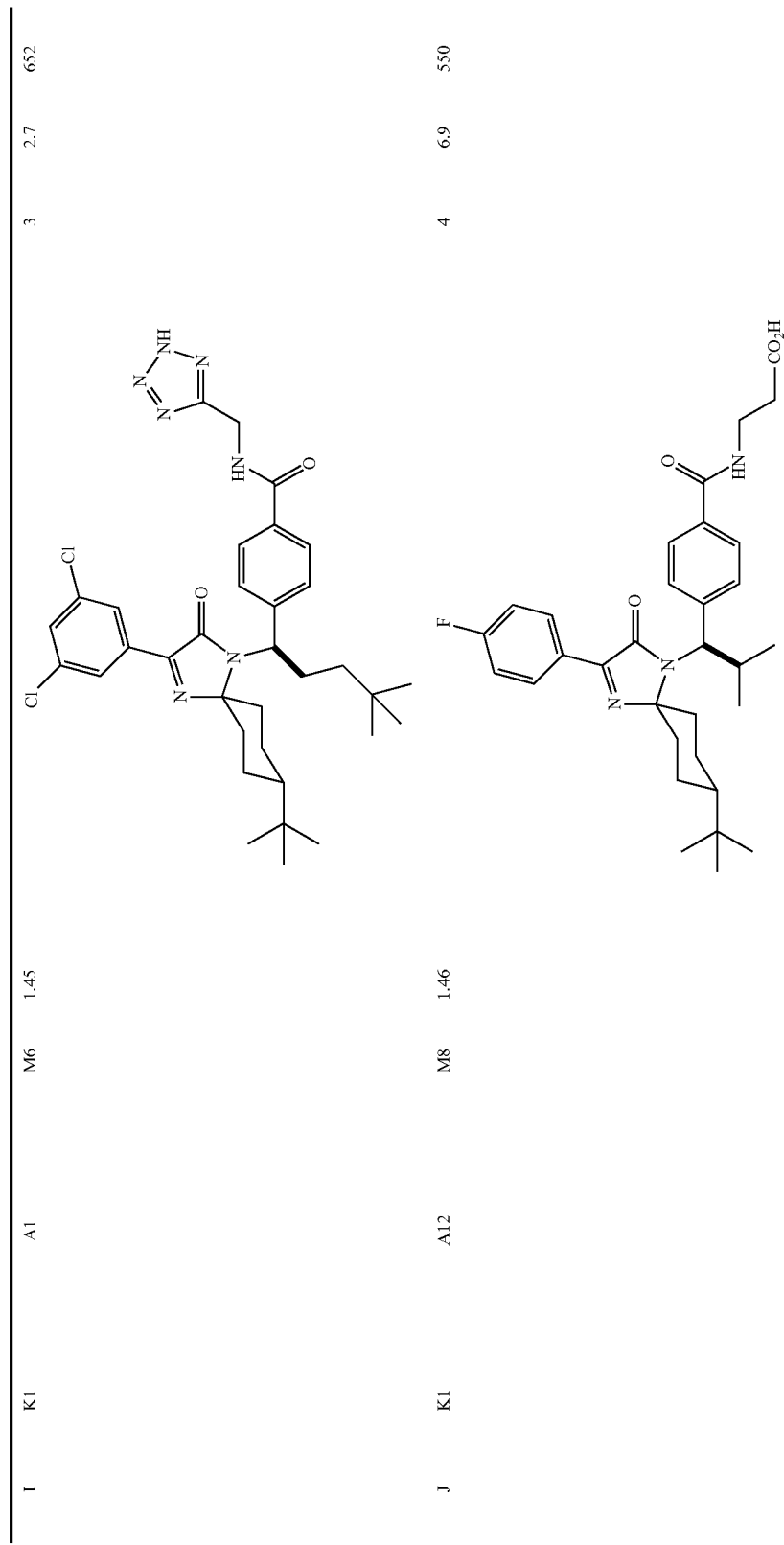
| | |
|---|---|
| 3  2.7  652 | |
| 4  6.9  550 | |

TABLE 1-continued

| | K3 | A14 | M6 | 1.47 | [structure with 3-fluorophenyl] | 3 | 2.6 | 606 |
| J | K1 | A9 | M6 | 1.48 | [structure with phenyl] | 3 | 2.5 | 574 |
| J | K3 | A1 | M4 | 1.49 | [structure with 3,5-dichlorophenyl] | 4 | 6.2 | 586 |
| J | | | | | | | | |

TABLE 1-continued
| J | K3 | A15 | M7 | 1.50 | | 3 | 2.6 | 598 |
| J | K1 | A2  | M7 | 1.60 | | 4 | 6.1 | 600 |
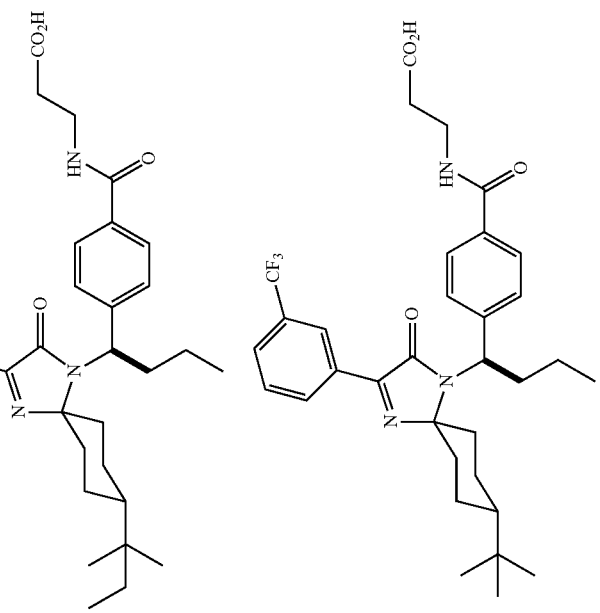

TABLE 1-continued
| J | K2 | A15 | M7 | 1.61 | 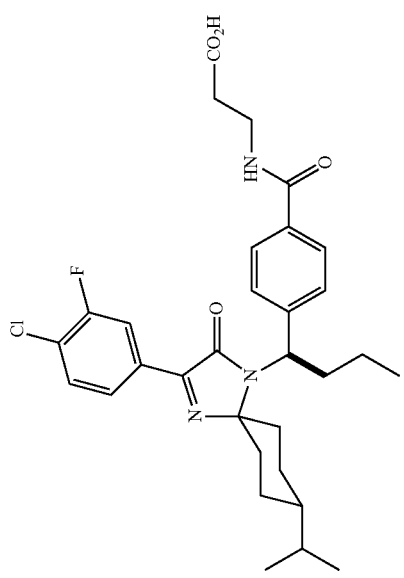 | 3 | 2.5 | 570 |
| J | K1 | A14 | M4 | 1.62 | 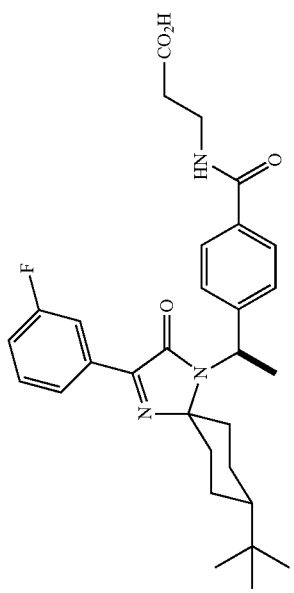 | 4 | 3.1 | 522 |

TABLE 1-continued

| J | K1 | A14 | M3 | 1.63 | | 4 | 5.2 | 522 |
| J | K1 | A1 | M9 | 1.64 | | 4 | 4.8 | 600 |

TABLE 1-continued

| | | | | | | |
|---|---|---|---|---|---|---|
| J | K1 | A15 | M7 | 1.65 | | 3 | 2.6 | 584 |
| A | K1 | A9 | M1 | 1.66 | | 4 | 4.8 | 490 |
| J | K1 | A1 | M10 | 1.67 | | 4 | 6.6 | 588 |

TABLE 1-continued
| | | | | | | |
|---|---|---|---|---|---|---|
| A | K1 | A5 | M4 | 1.68 | 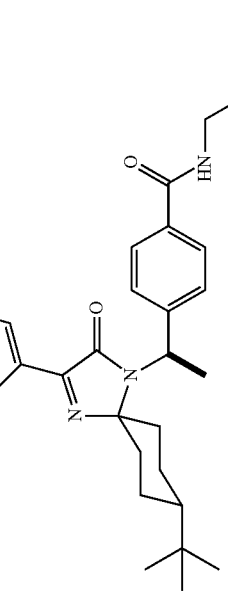 | 4 | 5.6 | 538 |
| J | K1 | A1 | M7 | 1.69 | 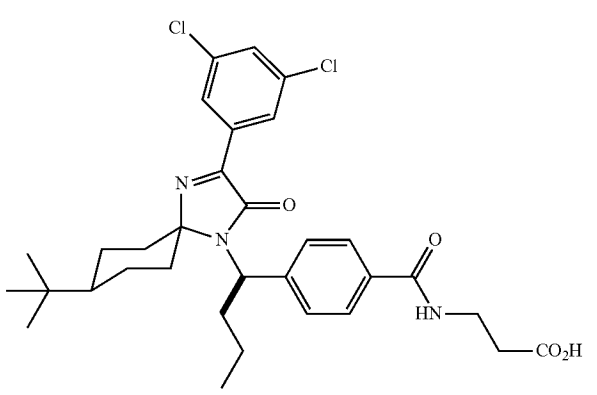 [SMILES: CCC[C@H](c1ccc(C(=O)NCCC(=O)O)cc1)N1C(=O)C(c2cc(Cl)cc(Cl)c2)=NC12CCC(C(C)(C)C)CC2] | 4 | 6.5 | 600 |
| I | K1 | A12 | M11 | 1.70 | 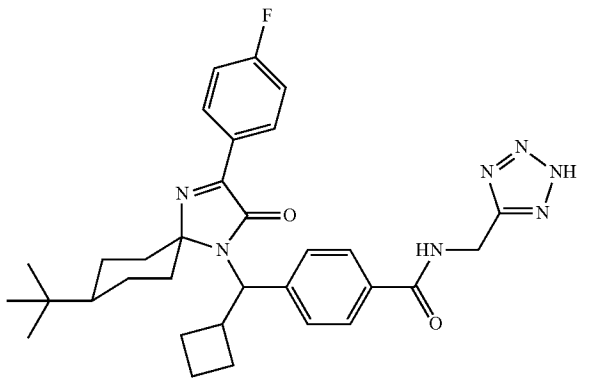 [SMILES: CC(C)(C)C1CCC2(CC1)N=C(c1ccc(F)cc1)C(=O)N2C(c1ccc(C(=O)NCc2nn[nH]n2)cc1)C1CCC1] | 3 | 2.4 | 572 |

TABLE 1-continued

| | | | | | | |
|---|---|---|---|---|---|---|
| J | K1 | A12 | M11 | 1.71 | [structure] | 3 | 2.4 | 562 |
| LD | K1 | A9 | M6 | 1.72 | [structure] | 3 | 2.4 | 610 |

TABLE 1-continued

| | | | | | | |
|---|---|---|---|---|---|---|
| M | K1 | A1 | M1 | 1.73 | 3   2.3   594 | |
| C | K1 | A1 | M7 | 1.74 | 4   6.9   596 | |

TABLE 1-continued

| | | | | |
|---|---|---|---|---|
| C | K1 | A9 | M6 | 1.75 | 3 | 2.6 | 570 |
| N | K1 | A5 | M4 | 1.76 | 4 | 5.8 | 534 |
| O | K1 | A1 | M12 | 1.77 | 3 | 2.6 | 616 |

TABLE 1-continued

| | | | | | | |
|---|---|---|---|---|---|---|
| P | K1 | A1 | M12 | 1.78 | 3 | 2.6 | 626 |
| Q | K1 | A2 | NA* | 1.79 | 4 | 5.2 | 558 |
| J | K5 | A5 | M3 | 1.80 | 4 | 5.9 | 496 |

TABLE 1-continued
| | | | | | | |
|---|---|---|---|---|---|---|
| J | K5 | A1 | M7 | 1.81 | 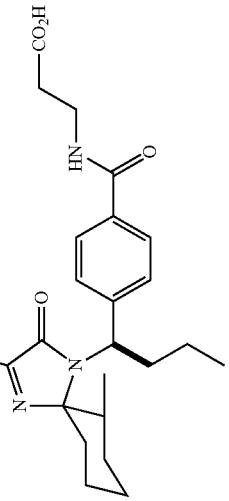 | 4 | 7.5 | 558 |
| R | K1 | A2 | NA* | 1.82 | 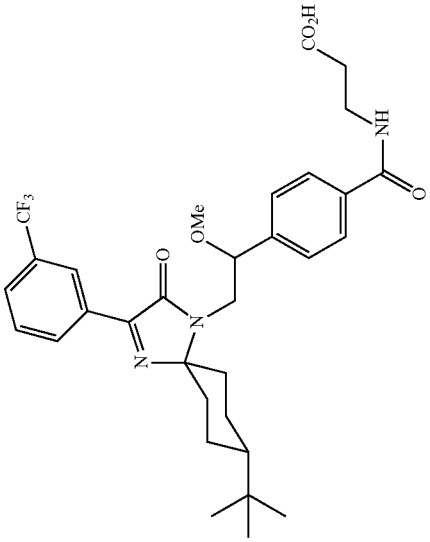 | 4 | 7.1 | 602 |

TABLE 1-continued

| | | | | | | |
|---|---|---|---|---|---|---|
| S | K1 | A2 | NA* | 1.83 | (structure) | 4 5.3 602 |
| I | K5 | A1 | M7 | 1.84 | (structure, +/-) | 3 2.5 568 |

TABLE 1-continued

| | | | | | | | |
|---|---|---|---|---|---|---|---|
| J | K1 | A11 | M3 | 1.85 | | 5 | 21.6 (25) | 538.0 |
| J | K1 | A11 | M4 | 1.86 | | 5 | 22.1 (25) | 538.3 |
| J | K1 | A8 | M4 | 1.87 | | 5 | 19.0 (25) | 572.5 |

TABLE 1-continued
| | | | | | | | |
|---|---|---|---|---|---|---|---|
| J | K1 | A10 | M4 | 1.88 |  | 5 | 17.2 (25) | 588.3 |
| J | K1 | A12 | M7 | 1.89 | 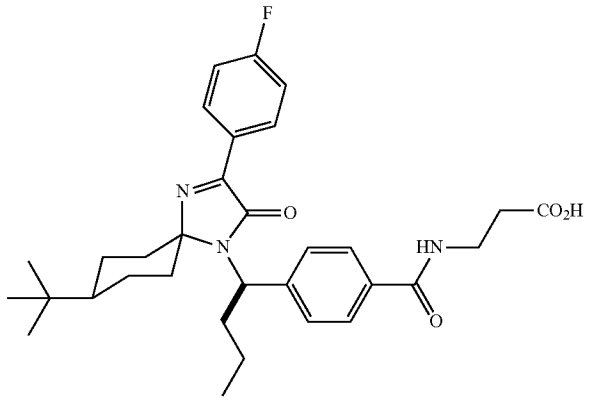 [SMILES: CCC[C@H](c1ccc(C(=O)NCCC(=O)O)cc1)N1C(=O)C(c2ccc(F)cc2)=NC12CCC(C(C)(C)C)CC2] | 5 | 17.6 (25) | 550.1 |

TABLE 1-continued
| J | K4 | A1 | M7 | 1.90 | 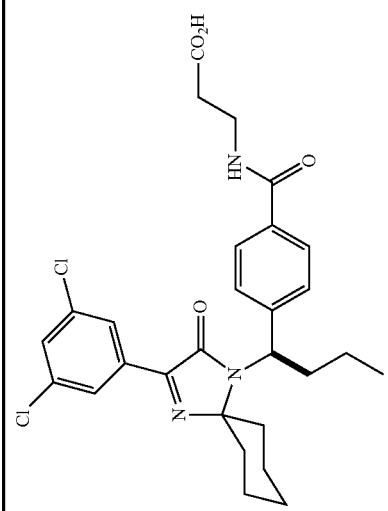 | 5 | 18.1 (25) | 544.2 |
| J | K2 | A12 | M7 | 1.91 | 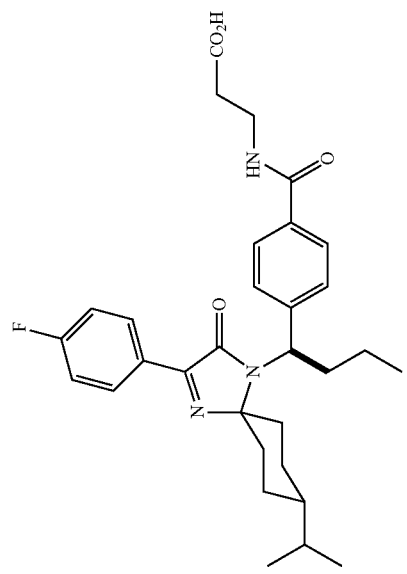 | 5 | 16.7 (23) | 536.3 |

TABLE 1-continued

| | | | | | | | | |
|---|---|---|---|---|---|---|---|---|
| J | K6 | A12 | M7 | 1.92 | | 5 | 15.5 (23) | 522.2 |
| J | K6 | A2 | M7 | 1.93 | | 5 | 17.1 (25) | 572.3 |
| J | K4 | A2 | M7 | 1.94 | | 5 | 15.3 (25) | 544.2 |

TABLE 1-continued

| | | | | | | | |
|---|---|---|---|---|---|---|---|
| J | K6 | A1 | M7 | 1.95 | [structure] | 5 | 20.8 (25) | 572.2 |
| J | K2 | A1 | M7 | 1.96 | [structure] | 5 | 22.0 (25) | 586.2 |

TABLE 1-continued
| | | | | | | | |
|---|---|---|---|---|---|---|---|
| J | K2 | A16 | M3 | 1.97 | 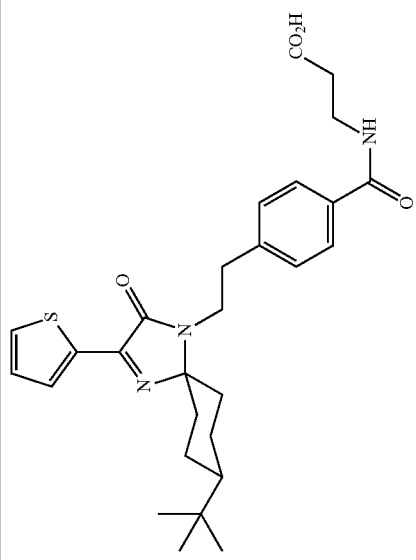 | 5 | 15.2 (23) | 510.4 |
| T | K1 | A10 | M3 | 1.98 | 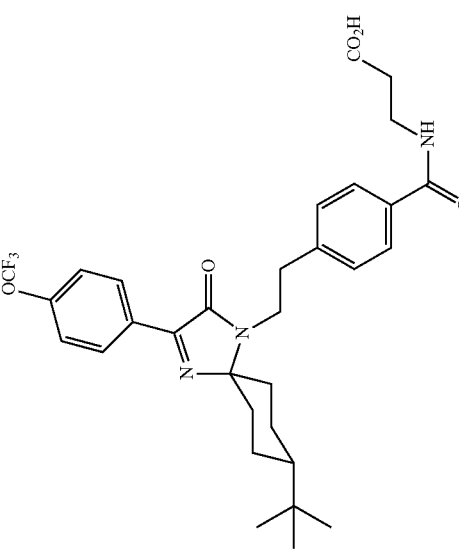 | 5 | 13.9 (23) | 588.2 |

TABLE 1-continued

| | | | | | | | |
|---|---|---|---|---|---|---|---|
| J | K7 | A1 | M7 | 1.99 | | 5 | 13.3 (23) | 558.2 |
| T | K6 | A1 | M3 | 1.100 | | 5 | 18.1 (25) | 544 |

TABLE 1-continued

| | | | | | | | |
|---|---|---|---|---|---|---|---|
| J | K4 | A5 | M7 | 1.101 | | 5 | 15.2 (22) | 510.2 |
| J | K2 | A5 | M7 | 1.102 | | 5 | 18.1 (22) | 552.3 |
| J | K1 | A5 | M7 | 1.103 | | 5 | 19.3 (22) | 566.2 |

TABLE 1-continued

| | | | | | | | |
|---|---|---|---|---|---|---|---|
| J | K2 | A2 | M7 | 1.104 | [structure with CF₃, isopropyl cyclohexyl, butyl, benzamide-CH₂CH₂CO₂H] | 5 | 18.3 (22) | 586.3 |
| T | K2 | A1 | M3 | 1.105 | [structure with 3,5-dichlorophenyl, isopropyl cyclohexyl, CH₂CH₂-benzamide-CH₂CH₂CO₂H] | 5 | 22.5 (25) | 557.8 |
| U | K1 | A1 | NA* | 1.106 | [structure with 3,5-dichlorophenyl, tert-butyl cyclohexyl, CH₂-(2-F-benzamide)-CH₂CH₂CO₂H] | 5 | 22.4 (25) | 576.1 |

TABLE 1-continued
| | | | | | | |
|---|---|---|---|---|---|---|
| U | K1 | A2 | NA* | 1.107 | 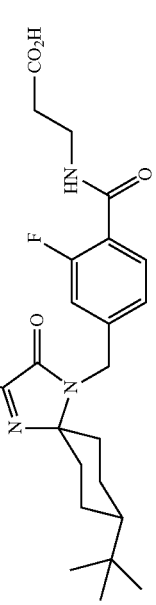 | 5 | 18.8 (20) | 576.1 |
| T | K1 | A17 | M3 | 1.108 | 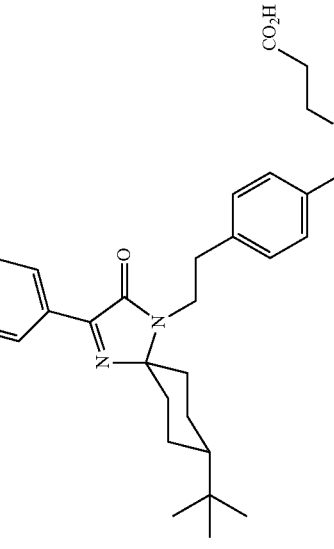 | 5 | 17.0 (22) | 556.2 |

TABLE 1-continued
| | | | | | | |
|---|---|---|---|---|---|---|
| T | K1 | A18 | M3 | 1.109 | 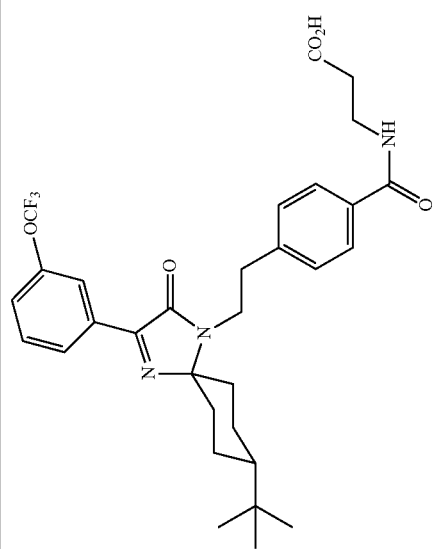 | 5 16.9 (22) 588.3 |
| V | K1 | A16 | M3 | 1.110 | 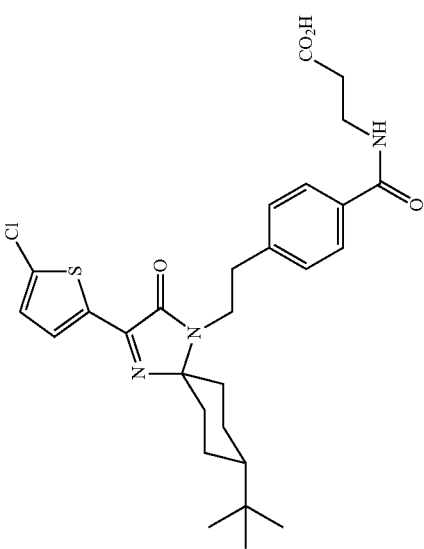 | 5 13.7 (22) 544.8 |

TABLE 1-continued

| T | K2 | A2 | M3 | 1.111 | ![structure with CF3, isopropyl cyclohexyl, benzamide, CO2H] | 5 | 26.2 (30) | 558.2 |
| T | K6 | A2 | M3 | 1.112 | ![structure with CF3, ethyl cyclohexyl, benzamide, CO2H] | 5 | 25.0 (30) | 544.2 |

TABLE 1-continued
| | | | | | | |
|---|---|---|---|---|---|---|
| J | K1 | A19 | M3 | 1.113 | 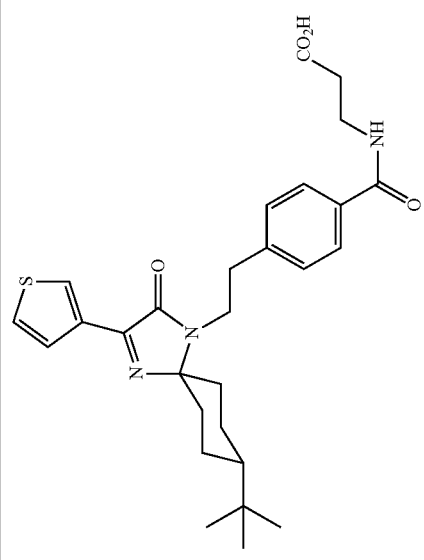 | 5 | 14.7 (22) | 510.2 |
| W | K1 | A2 | NA* | 1.114 | 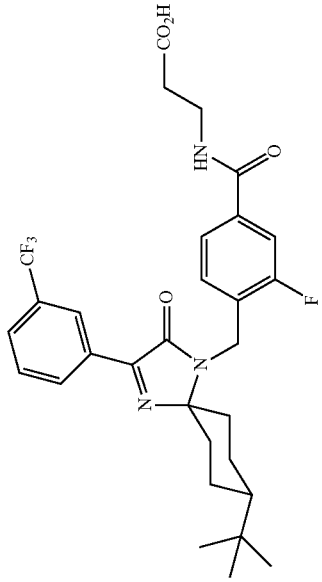 | 5 | 10.2 (22) | 576.1 |

TABLE 1-continued

| T | K8 | A2 | M3 | 1.115 | *structure* | 5 | 13.7 (23) | 544.2 |
| T | K8 | A1 | M3 | 1.116 | *structure* | 5 | 17.1 (23) | 544.1 |

TABLE 1-continued

| X | K4 | A14 | M7 | 1.117 | | 5 | 16.3 (22) | 494.1 |
| X | K9 | A14 | M7 | 1.118 | | 5 | 17.5 (23) | 508.2 |
| W | K1 | A1 | NA* | 1.119 | | 5 | 19.4 (22) | 576.2 |

TABLE 1-continued

| Y | K1 | A16 | M3 | 1.120 | | 5 | 19.1 (23) | 550.3 |
|---|----|-----|----|----|---|---|---|---|
| X | K6 | A14 | M7 | 1.121 | | 5 | 18.9 (23) | 522.2 |

TABLE 1-continued

| X | K8 | A14 | M7 | 1.122 | ![structure] | 5 | 18.3 (23) | 522.2 |
| X | K4 | A12 | M7 | 1.123 | ![structure] | 5 | 16.2 (23) | 494.3 |

TABLE 1-continued

| T | K1 | A20 | M3 | 1.124 | | 5 | 14.1 (22) | 556.2 |
| T | K1 | A21 | M3 | 1.125 | | 5 | 14.1 (22) | 556.2 |

TABLE 1-continued
| X | K2 | A14 | M7 | 1.126 | 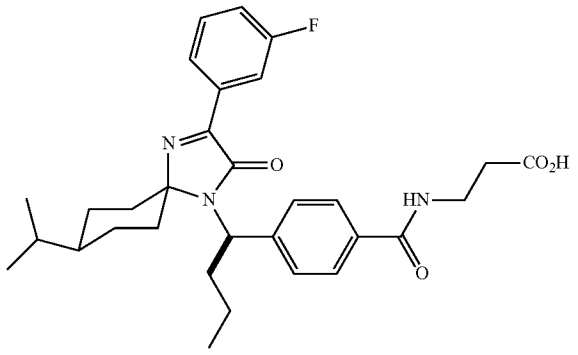 [SMILES: CCC[C@H](c1ccc(C(=O)NCCC(=O)O)cc1)N1C(=O)C(c2cccc(F)c2)=NC12CCC(C(C)C)CC2] | 5 | 20.1 (23) | 536.2 |
| T | K2 | A22 | M3 | 1.127 | 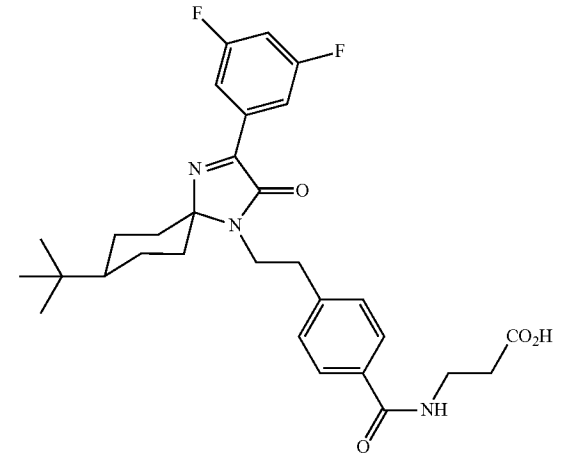 | 5 | 17.3 (23) | 540.3 |

TABLE 1-continued

| X | K9 | A12 | M7 | 1.128 | [structure] | 5 | 17.5 (23) | 508.3 |
| X | K2 | A12 | M7 | 1.129 | [structure] | 5 | 20.5 (23) | 532.3 |

TABLE 1-continued

| X | | | | | | |
|---|---|---|---|---|---|---|
| X | K7 | A14 | M7 | 1.130 | (structure) | 5 | 17.1 (23) | 508.1 |
| X | K8 | A21 | M4 | 1.131 | (structure) | 5 | 13.8 (23) | 527.6 |
| X | K2 | A21 | M4 | 1.132 | (structure) | 5 | 15.0 (22) | 541.7 |

TABLE 1-continued

| X | | | | | | | |
|---|---|---|---|---|---|---|---|
| X | K9 | A1 | M7 | 1.133 | (structure) | 5 | 19.1 (22) | 557.6 |
| X | K8 | A1 | M7 | 1.134 | (structure) | 5 | 20.2 (22) | 571.7 |

TABLE 1-continued

| X | K10 | A1 | M7 | 1.135 | [structure] | 5 | 16.4 (22) | 545.6 |
| X | K1 | A21 | M4 | 1.136 | [structure] | 5 | 15.7 (22) | 555.7 |
| X | K6 | A21 | M4 | 1.137 | [structure] | 5 | 17.6 (22) | 527.6 |

TABLE 1-continued
| X | K8 | A12 | M7 | 1.138 | 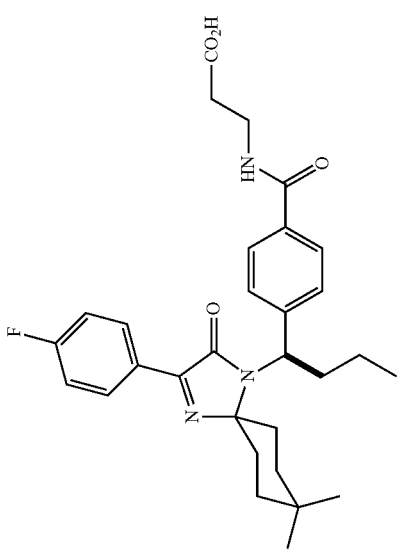 | 5 | 18.1 (22) | 521.8 |
| T | K11 | A2 | M3 | 1.139 | 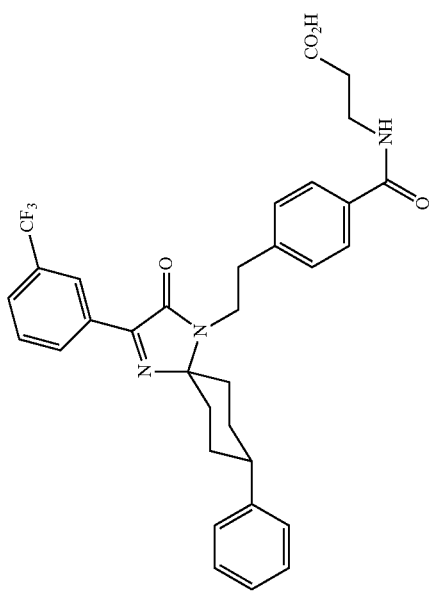 | 5 | 17.0 (22) | 592.0 |

TABLE 1-continued

| | | | | | | | |
|---|---|---|---|---|---|---|---|
| Z | K4 | A1 | M7 | 1.140 | | 5 | 18.3 (22) | 539.7 |
| X | K2 | A23 | M4 | 1.141 | | 5 | 18.5 (22) | 541.6 |
| X | K8 | A23 | M4 | 1.142 | | 5 | 13.4 (22) | 527.6 |

TABLE 1-continued
| T | K2 | A10 | M3 | 1.143 | 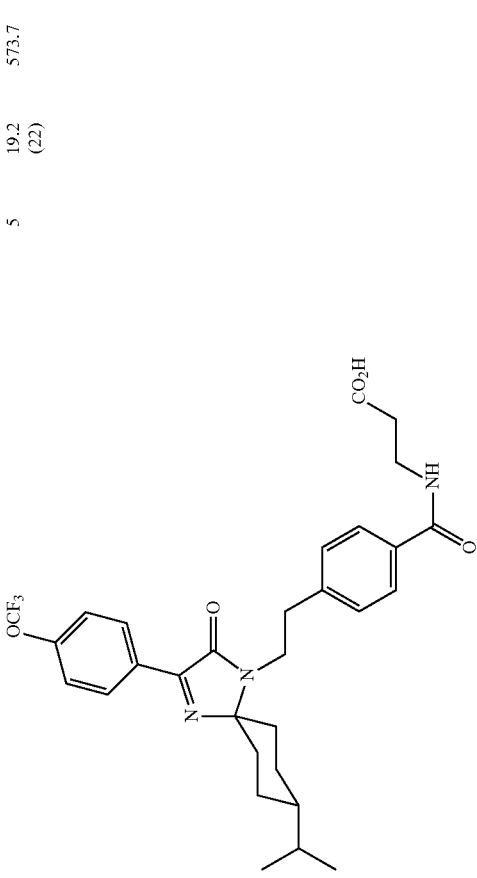 | 5 | 19.2 (22) | 573.7 |
| T | K11 | A10 | M3 | 1.144 | 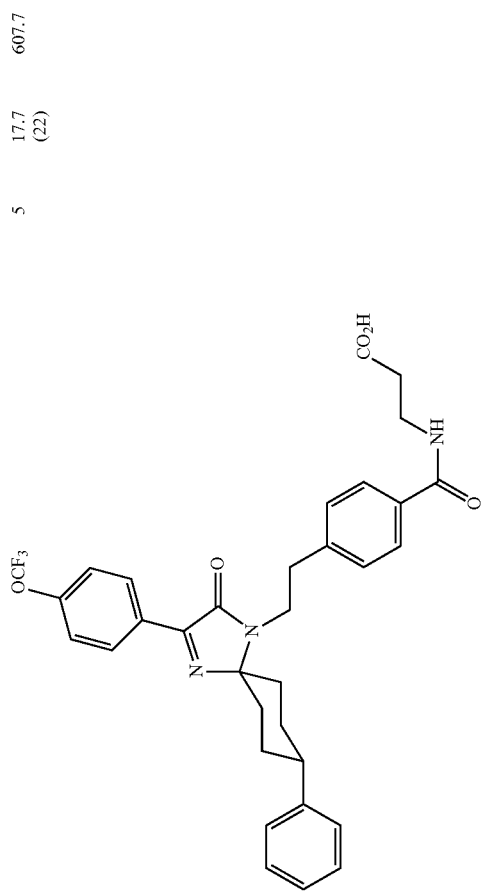 | 5 | 17.7 (22) | 607.7 |

TABLE 1-continued
| AA | K2 | A12 | M7 | 1.145 | 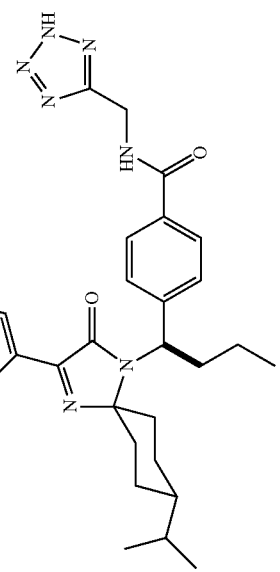 | 5 | 19.6 (22) | 545.8 |
| AA | K4 | A1 | M7 | 1.146 | 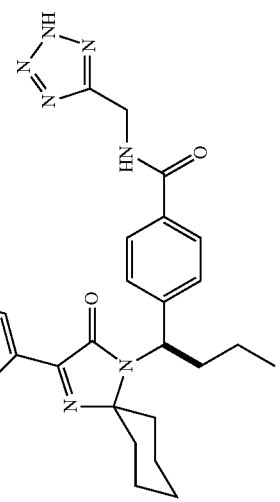 | 5 | 17.2 (22) | 553.7 |

TABLE 1-continued

| X | | | | | | |
|---|---|---|---|---|---|---|
| X | K7 | A12 | M7 | 1.147 | (structure) | 5 | 16.9 (22) | 507.8 |
| T | K12 | A2 | M3 | 1.148 | (structure) | 5 | 16.2 (22) | 546.0 |

TABLE 1-continued

| AB | K13 | A1 | M3 | 1.149 | | 5 | 19.4 (22) | 529.7 |
| T | K1 | A24 | M3 | 1.150 | | 5 | 16.2 (22) | 539.8 |

TABLE 1-continued

| X | K1 | A23 | 1.151 | M4 | [structure] | 5 | 15.6 (22) | 556.2 |
| X | K6 | A23 | 1.152 | M4 | [structure] | 5 | 17.0 (22) | 528.2 |
| T | K1 | A25 | 1.153 | M3 | [structure] | 5 | 20.9 (22) | 556.3 |

TABLE 1-continued
| AC | K12 | A1 | M7 | 1.154 | 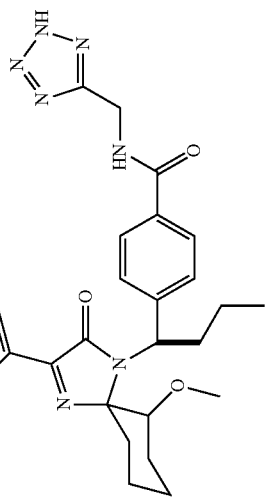 | 5 | 18.4 (22) | 584.2 |
| T | K2 | A25 | M3 | 1.155 | 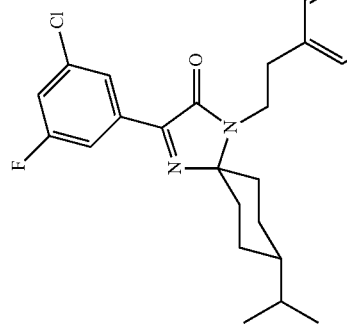 | 5 | 20.1 (22) | 542.3 |

TABLE 1-continued
| | | | | | | | |
|---|---|---|---|---|---|---|---|
| AE | K1 | A5 | M7 | 1.156 | 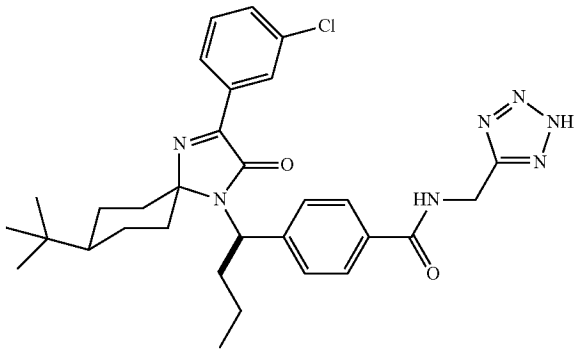 | 5 | 17.6 (25) | 576.2 |
| I | K6 | A12 | M7 | 1.157 | 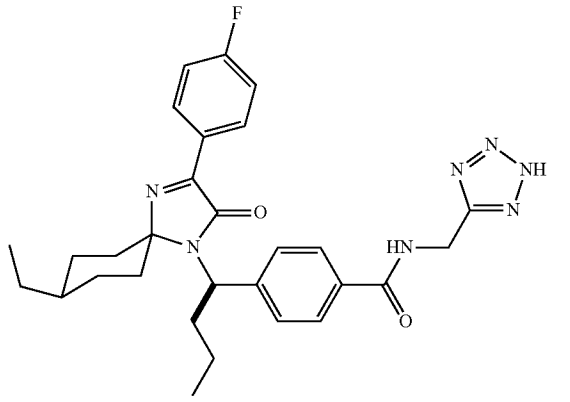 [SMILES: CCC[C@H](c1ccc(C(=O)NCc2nn[nH]n2)cc1)N1C(=O)C(c2ccc(F)cc2)=NC12CCC(CC)CC2] | 5 | 16.7 (22) | 532.2 |

TABLE 1-continued
| | | | | | | | |
|---|---|---|---|---|---|---|---|
| T | K11 | A1 | M3 | 1.158 | 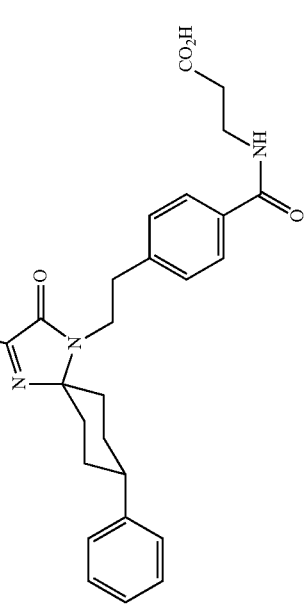 | 5 | 18.8 (22) | 592.1 |
| X | K12 | A1 | M7 | 1.159 | 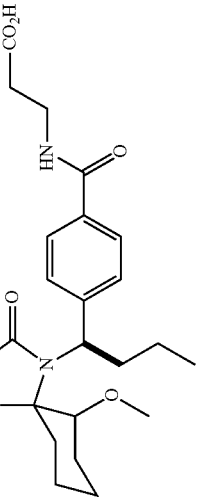 | 5 | 18.5 AND 19.8 (22) | 574.1 |

TABLE 1-continued

| T | K2 | A26 | M3 | 1.160 | | 5 | 15.6 (22) | 526.2 |
| T | K1 | A26 | M3 | 1.161 | | 5 | 16.2 (22) | 540.3 |

TABLE 1-continued

| T | K2 | A27 | M3 | 1.162 | | 5 | 15.4 (22) | 526.3 |
| T | K1 | A27 | M3 | 1.163 | | 5 | 16.0 (22) | 540.3 |

TABLE 1-continued

| | | | | | | | |
|---|---|---|---|---|---|---|---|
| AF | K3 | A22 | M4 | 1.164 | | 5 | 16.5 (25) | 554.0 |
| AF | K1 | A22 | M4 | 1.165 | | 5 | 14.9 (25) | 540.1 |
| T | K12 | A1 | M3 | 1.166 | | 5 | 17.2 (22) | 546.1 |

TABLE 1-continued

| | | | | | | |
|---|---|---|---|---|---|---|
| I | K3 | A26 | M7 | 1.167 | (structure) | 5 | 19.3 (25) | 592.3 |
| I | K14 | A26 | M7 | 1.168 | (structure) | 5 | 15.0 (25) | 550.3 |
| AB | K3 | A26 | M7 | 1.169 | (structure) | 5 | 19.5 (25) | 582.3 |

TABLE 1-continued
| AB | K14 | A23 | M7 | 1.170 | 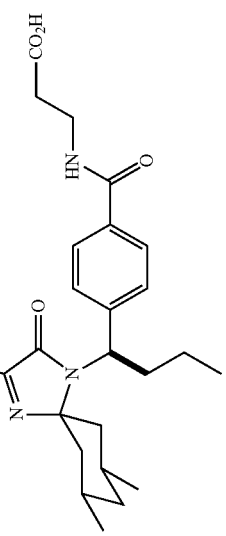 | 5 | 15.2 (25) | 540.3 |
| I | K1 | A8 | M13 | 1.171 | 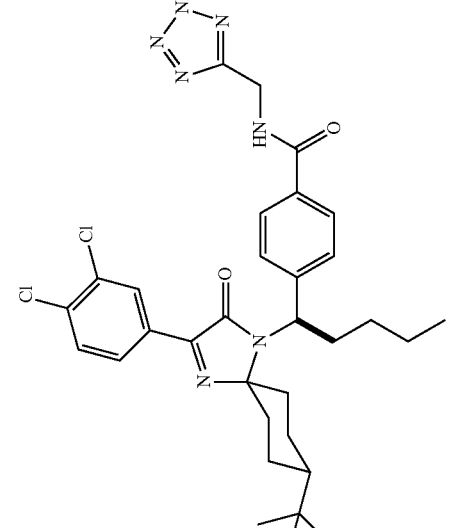 | 5 | 20.5 (25) | 624.3 |

TABLE 1-continued
| | | | | | | |
|---|---|---|---|---|---|---|
| AF | K1 | A8 | M13 | 1.172 | 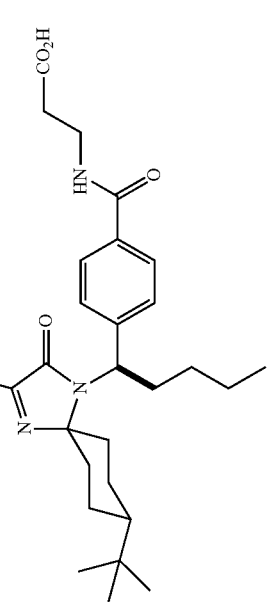 | 5 | 20.8 (25) | 614.2 |
| AE | K1 | A12 | M13 | 1.173 | 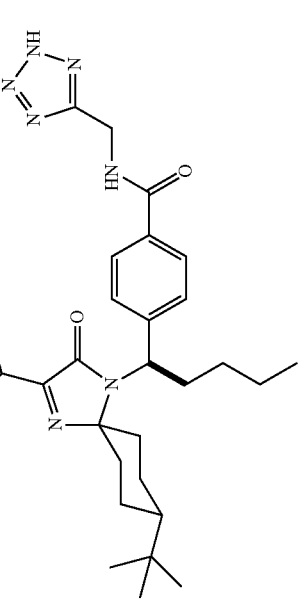 | 5 | 16.1 (25) | 574.2 |

TABLE 1-continued
| | | | | | | | |
|---|---|---|---|---|---|---|---|
| AF | K1 | A12 | M13 | 1.174 | 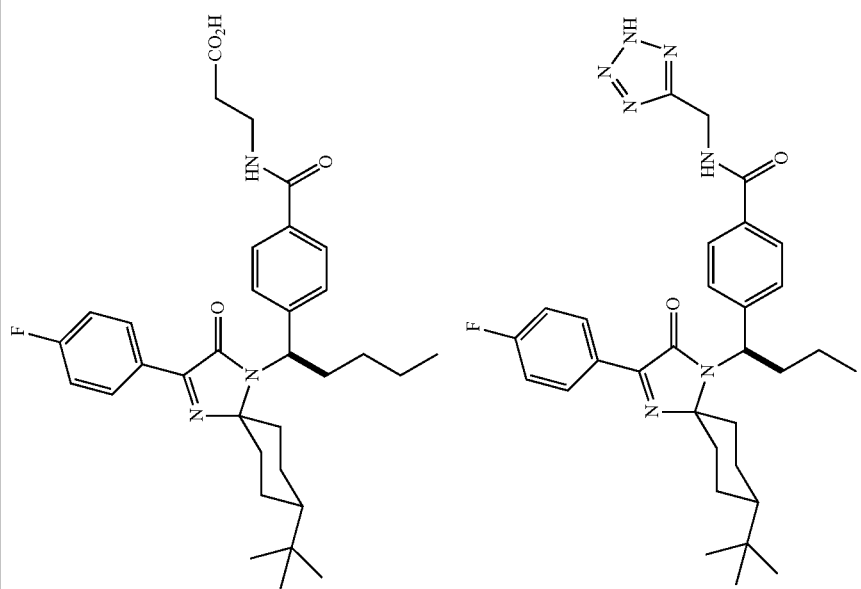 | 5 | 16.3 (26) 564.2 |
| AE | K1 | A12 | M7 | 1.175 | | 5 | 15.2 (26) 560.4 |

TABLE 1-continued
| | | | | | | | |
|---|---|---|---|---|---|---|---|
| AE | K1 | A8 | M7 | 1.176 | 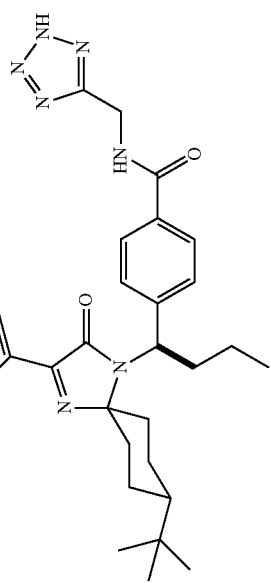 | 5 | 19.6 (26) | 610.2 |
| AF | K1 | A8 | M7 | 1.177 | 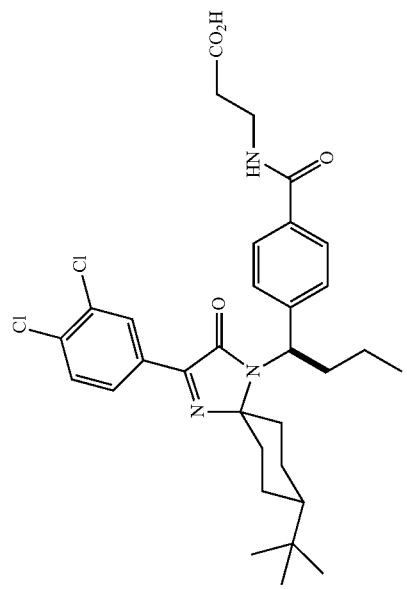 | 5 | 19.6 (26) | 600.1 |

TABLE 1-continued
| | | | | | | | |
|---|---|---|---|---|---|---|---|
| AE | K3 | A8 | M7 | 1.178 | 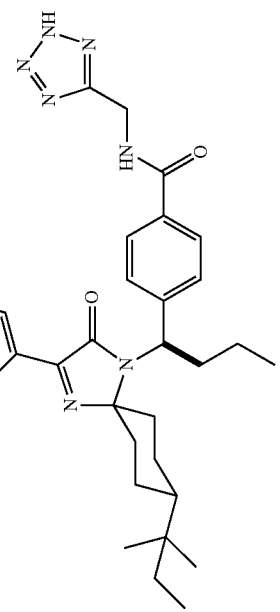 | 5 | 20.1 (28) | 624.4 |
| AF | K3 | A8 | M7 | 1.179 | 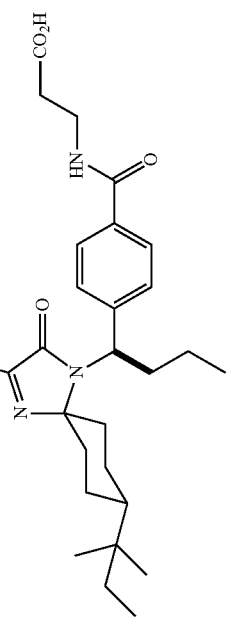 | 5 | 20.1 (28) | 614.4 |

TABLE 1-continued
| | | | | | | | |
|---|---|---|---|---|---|---|---|
| AF | K2 | A8 | M7 | 1.180 | 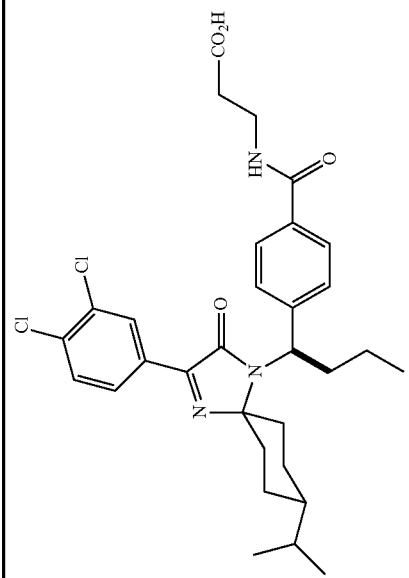 | 5 | 17.2 (28) | 586.4 |
| AE | K2 | A8 | M7 | 1.181 | 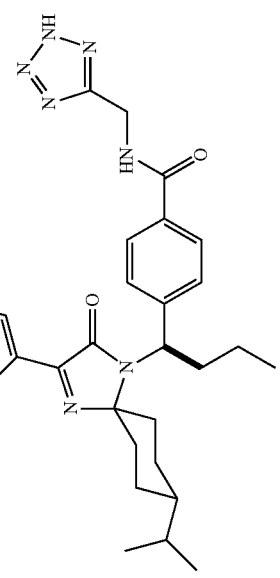 | 5 | 17.1 (28) | 596.4 |

TABLE 1-continued
| I | AF | K1 | A18 | M6 | 1.182 | 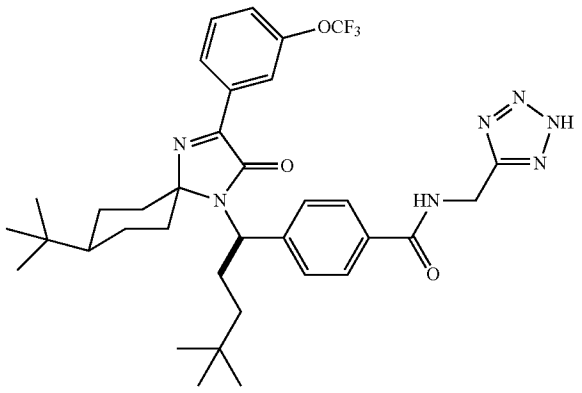 [SMILES: CC(C)(C)CC[C@H](c1ccc(C(=O)NCc2nn[nH]n2)cc1)N1C(=O)C(c2cccc(OC(F)(F)F)c2)=NC12CCC(C(C)(C)C)CC2] | 5 | 21.9 (34) | 668.5 |
| | AF | K2 | A10 | M7 | 1.183 | 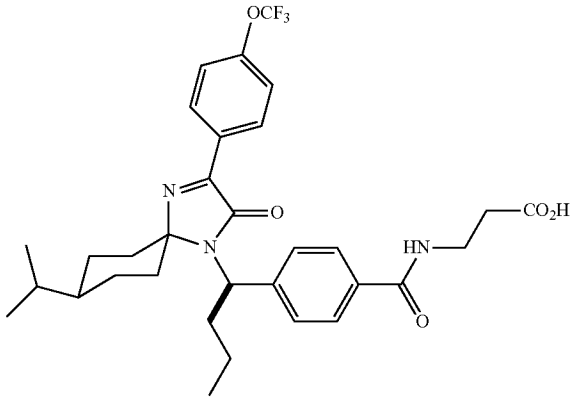 [SMILES: CCC[C@H](c1ccc(C(=O)NCCC(=O)O)cc1)N1C(=O)C(c2ccc(OC(F)(F)F)cc2)=NC12CCC(C(C)C)CC2] | 5 | 16.2 (26) | 602.5 |

TABLE 1-continued
| | | | | | | |
|---|---|---|---|---|---|---|
| AF | K1 | A10 | M6 | 1.184 | 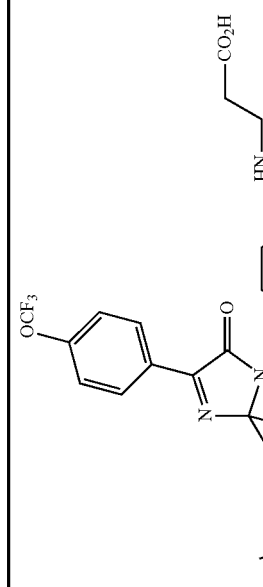 | 5 22.0 (34) 658.6 |
| I | K1 | A10 | M6 | 1.185 | 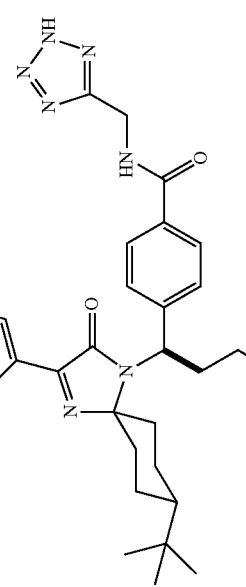 | 5 22.3 (34) 668.5 |

TABLE 1-continued

| | | | | | | | |
|---|---|---|---|---|---|---|---|
| I | K1 | A10 | M6 | 1.186 | [structure] | 5 | 21.2 (34) | 654.5 |
| J | K1 | A10 | M6 | 1.187 | [structure] | 5 | 21.1 (34) | 644.2 |

TABLE 1-continued

| | | | | | | | |
|---|---|---|---|---|---|---|---|
| J | K1 | A1 | M13 | 1.188 | | 4 | 6.81 | 614.3 |
| J | K1 | A1 | M8 | 1.189 | | 4 | 6.60 | 600.3 |
| J | K1 | A1 | M51 | 1.190 | | 4 | 6.28 | 598.3 |

TABLE 1-continued
| | | | | | | | | |
|---|---|---|---|---|---|---|---|---|
| J | K1 | A2 | M13 | 1.191 | 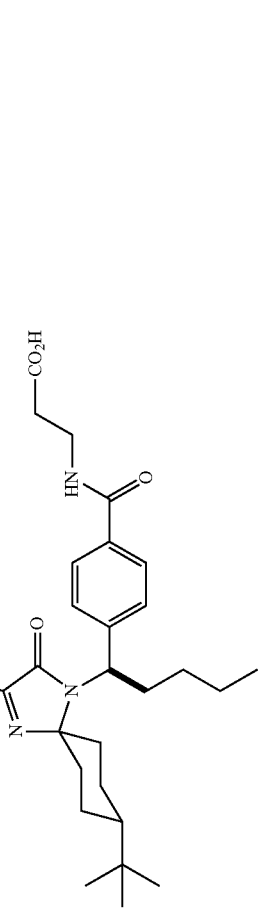 | 5 | 6.32 | 614.3 |
| J | K1 | A2 | M8 | 1.192 | 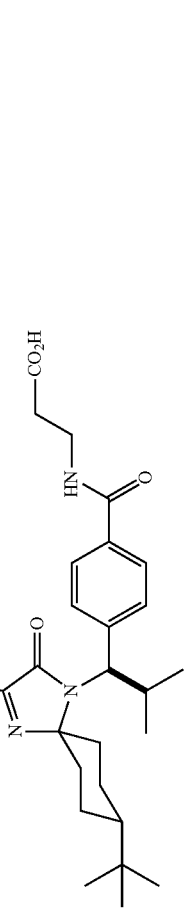 | 4 | 6.15 | 600.3 |
| J | K1 | A2 | M51 | 1.193 | 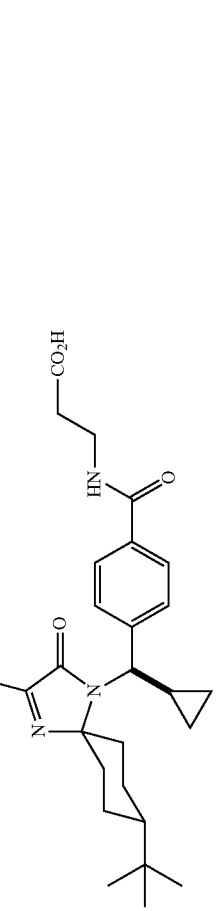 | 4 | 5.87 | 598.3 |

TABLE 1-continued

| | | | | | | | |
|---|---|---|---|---|---|---|---|
| I | K1 | A1 | M13 | 1.194 | 4 | 7.21 | 624.3 |
| I | K1 | A1 | M8 | 1.195 | 4 | 6.87 | 610.3 |
| I | K1 | A1 | M51 | 1.196 | 4 | 6.50 | 608.3 |

TABLE 1-continued

| | | | | | | | | |
|---|---|---|---|---|---|---|---|---|
| J | K2 | A1 | M51 | 1.197 | [structure] | 4 | 6.32 | 584.3 |
| J | K13 | A1 | M51 | 1.198 | [structure] | 4 | 5.26 | 528.3 |
| J | K1 | A1 | M14 | 1.199 | [structure] | 4 | 6.34 | 584.3 |

TABLE 1-continued

| | | | | | | | |
|---|---|---|---|---|---|---|---|
| J | K1 | A11 | M51 | 1.200 | | 4 | 5.21 | 564.3 |
| J | K1 | A5 | M51 | 1.201 | | 4 | 5.88 | 564.3 |
| J | K1 | A7 | M51 | 1.202 | | 4 | 5.82 | 564.3 |

TABLE 1-continued
| | | | | | | |
|---|---|---|---|---|---|---|
| J | K1 | A1 | M15 | 1.203 | 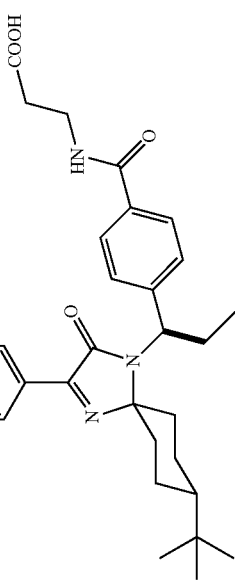 | 4 7.34 628.3 |
| J | K1 | A1 | M16 | 1.204 | 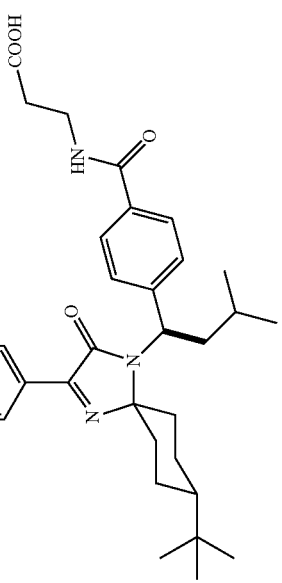 | 4 6.94 614.3 |

TABLE 1-continued
| | | | | | | | |
|---|---|---|---|---|---|---|---|
| J | K1 | A1 | M6 | 1.205 | 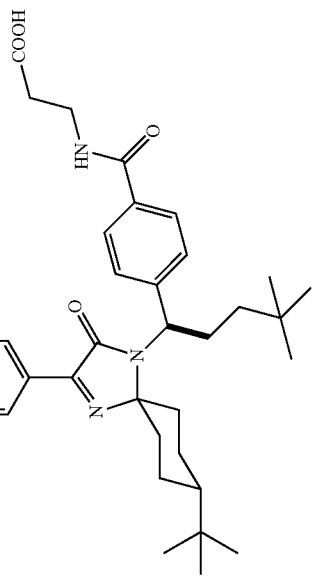 | 4 | 8.85 | 642.4 |
| J | K1 | A1 | M17 | 1.206 | 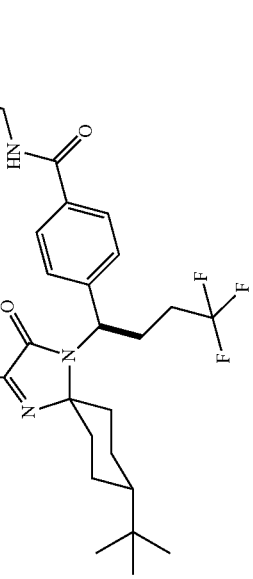 | 4 | 6.19 | 654.4 |

TABLE 1-continued
| | | | | | | | |
|---|---|---|---|---|---|---|---|
| J | K4 | A1 | M15 | 1.207 | 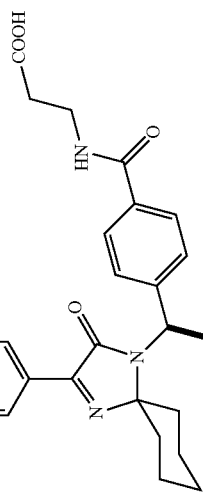 | 4 | 6.18 | 572.3 |
| J | K4 | A1 | M6 | 1.208 | 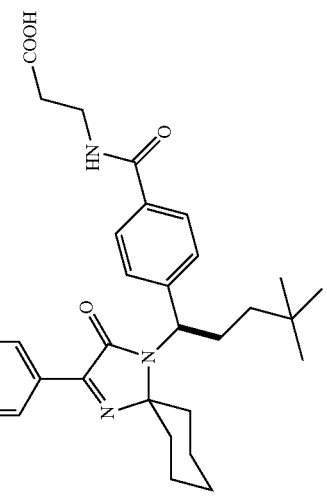 | 4 | 6.44 | 586.3 |

TABLE 1-continued
| | | | | | | |
|---|---|---|---|---|---|---|
| J | K4 | A1 | M17 | 1.209 | 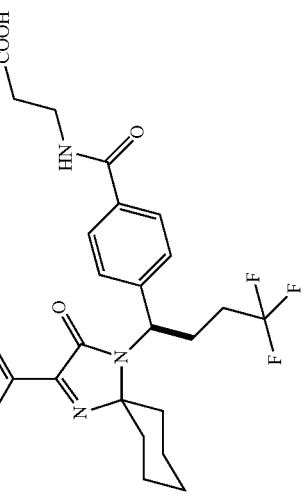 | 4 5.63 598.3 |
| AO | K1 | A28 | M51 | 1.210 | 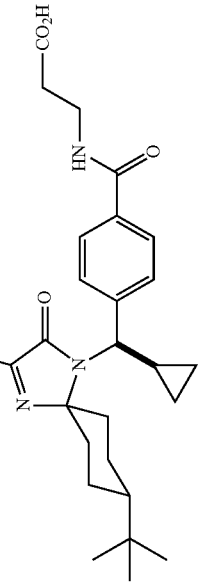 | 4 7.03 596.3 |

TABLE 1-continued

| | | | | | | | |
|---|---|---|---|---|---|---|---|
| J | K1 | A17 | M51 | 1.211 | (structure) | 4 | 7.28 | 582.3 |
| J | K1 | A12 | M51 | 1.212 | (structure) | 4 | 6.79 | 548.3 |
| AO | K4 | A28 | M51 | 1.213 | (structure) | 4 | 6.02 | 540.3 |

TABLE 1-continued

| | | | | | | | |
|---|---|---|---|---|---|---|---|
| I | K4 | A17 | M51 | 1.214 | | 4 | 6.24 | 526.3 |
| I | K4 | A12 | M51 | 1.215 | | 4 | 5.71 | 492.3 |
| I | K1 | A11 | M51 | 1.216 | | 4 | 5.12 | 574.3 |

TABLE 1-continued
| | | | | | | | |
|---|---|---|---|---|---|---|---|
| I | K1 | A5 | M51 | 1.217 | 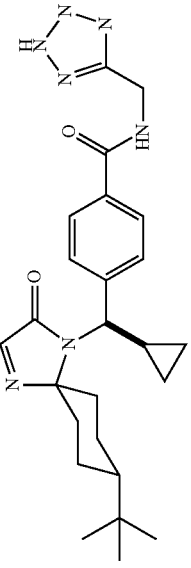 | 4 | 5.90 | 574.3 |
| I | K1 | A7 | M51 | 1.218 | 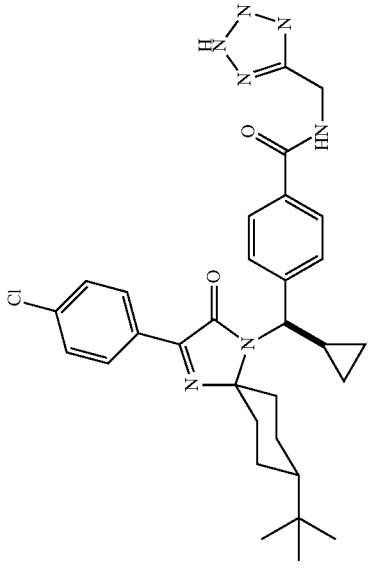 | 4 | 7.28 | 574.3 |
| J | K4 | A9 | M13 | 1.219 | 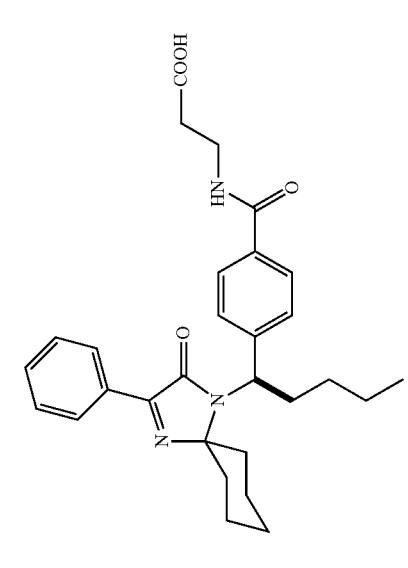 | 4 | 6.14 | 490.4 |

TABLE 1-continued

| | | | | | | | |
|---|---|---|---|---|---|---|---|
| I | K1 | A1 | M15 | 1.220 | | 4 | 8.72 | 638.4 |
| I | K1 | A1 | M16 | 1.221 | | 4 | 8.45 | 624.3 |
| I | K1 | A1 | M17 | 1.222 | | 44 | 7.74 | 664.4 |

TABLE 1-continued

| | | | | | Structure | | | |
|---|---|---|---|---|---|---|---|---|
| I | K1 | A28 | M51 | 1.223 | (3,5-diF-4-OMe-phenyl, tBu-cyclohexyl, cyclopropyl, benzamide-CH2-tetrazole) | 4 | 7.04 | 606.3 |
| AP | K1 | A17 | M51 | 1.224 | (3-Cl-4-F-phenyl, tBu-cyclohexyl, cyclopropyl, benzamide-CH2-tetrazole) | 4 | 7.30 | 592.3 |
| AP | K1 | A17 | M51 | 1.225 | (3-Cl-4-OMe-phenyl, tBu-cyclohexyl, cyclopropyl, benzamide-CH2-tetrazole) | 4 | 6.96 | 604.3 |

TABLE 1-continued
| | | | | | | |
|---|---|---|---|---|---|---|
| AO | K4 | A28 | M51 | 1.226 | 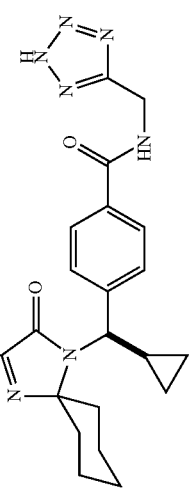 | 4 5.80 550.3 |
| AP | K4 | A17 | M51 | 1.227 | 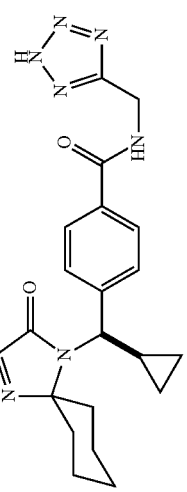 | 4 5.89 548.3 |

TABLE 1-continued

| | | | | | | |
|---|---|---|---|---|---|---|
| AP | K4 | A17 | M51 | 1.228 | 4 | 5.05 | 536.3 |
| J | K4 | A29 | M15 | 1.229 | 4 | 7.28 | 584.3 |

TABLE 1-continued

| J | K4 | A3 | M15 | 1.230 | [structure] | 4 | 7.23 | 584.3 |
| AR | K1 | A5 | M51 | 1.231 | [structure] | 4 | 7.18 | 588.3 |

TABLE 1-continued
| | | | | | | | |
|---|---|---|---|---|---|---|---|
| I | K1 | A5 | M15 | 1.232 | 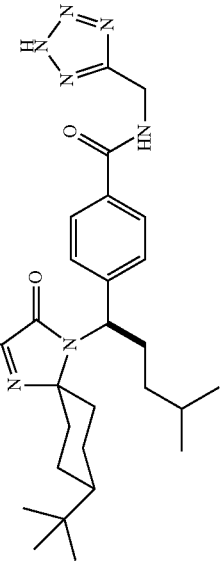 | 4 | 4.52 | 604.3 |
| I | K14 | A5 | M15 | 1.233 | 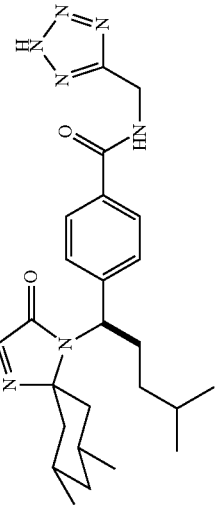 | 4 | 4.27 | 576.3 |
| I | K1 | A12 | M15 | 1.234 | 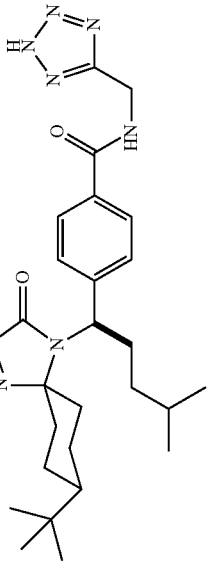 | 4 | 4.29 | 588.3 |

TABLE 1-continued
| | | | | | | |
|---|---|---|---|---|---|---|
| I | K14 | A12 | M15 | 1.235 | 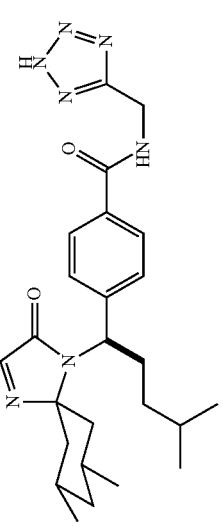 | 4 | 3.99 | 560.3 |
| J | K1 | A5 | M15 | 1.236 | 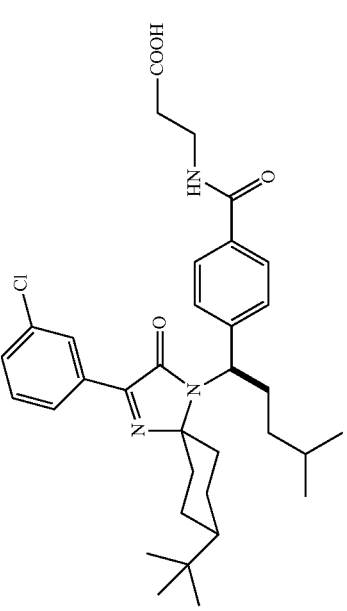 | 4 | 4.56 | 594.3 |

TABLE 1-continued
| | | | | | |
|---|---|---|---|---|---|
| J | K14 | A5 | M15 | 1.237 | 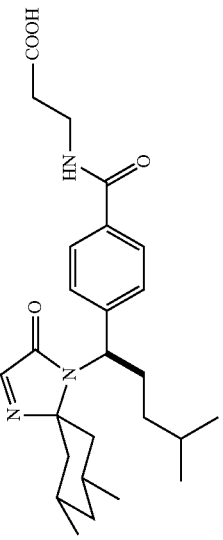 4 4.30 566.3 |
| J | K1 | A12 | M15 | 1.238 |  4 7.56 578.6 |

TABLE 1-continued

| | | | | | | |
|---|---|---|---|---|---|---|
| J | K14 | A12 | M15 | 1.239 | | 4 | 7.02 | 550.5 |
| J | K1 | A1 | M73 | 1.240 | | 4 | 8.72 | 628.3 |

TABLE 1-continued
| | | | | | | |
|---|---|---|---|---|---|---|
| J | K2 | A1 | M73 | 1.241 |  | 4 | 8.57 | 614.3 |
| J | K14 | A1 | M73 | 1.242 | 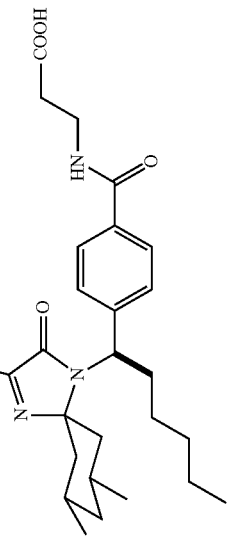 | 4 | 8.35 | 600.3 |

TABLE 1-continued

| | | | | | | |
|---|---|---|---|---|---|---|
| J | K14 | A22 | M15 | 1.243 | | 4 | 7.40 | 568.3 |
| J | K1 | A25 | M15 | 1.244 | | 4 | 8.21 | 612.3 |

TABLE 1-continued
| J | K2 | A25 | M15 | 1.245 | 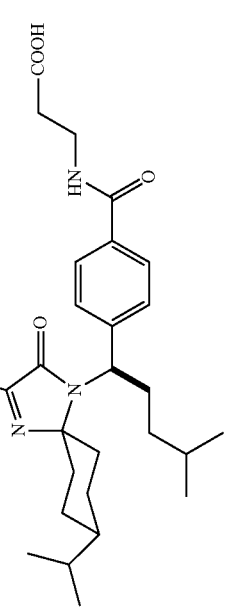 | 4 | 8.09 | 598.3 |
| J | K14 | A25 | M15 | 1.246 | 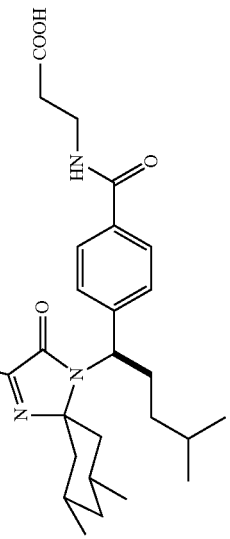 | 4 | 7.83 | 584.3 |

TABLE 1-continued

| | | | | | | |
|---|---|---|---|---|---|---|
| I | K1 | A1 | M73 | 1.247 | | 4 | 8.63 | 638.4 |
| I | K2 | A1 | M73 | 1.248 | | 4 | 8.50 | 624.3 |

TABLE 1-continued
| | | | | | | |
|---|---|---|---|---|---|---|
| I | K14 | A1 | M73 | 1.249 | 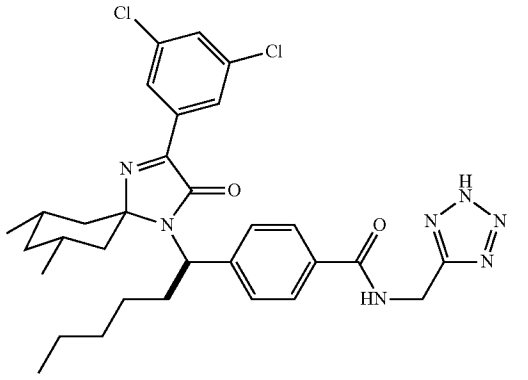 [SMILES: CCCCC[C@H](c1ccc(C(=O)NCc2nn[nH]n2)cc1)N1C(=O)C(c2cc(Cl)cc(Cl)c2)=NC12CC(C)CC(C)C2] | 4 | 8.28 | 610.5 |
| I | K14 | A22 | M15 | 1.250 | 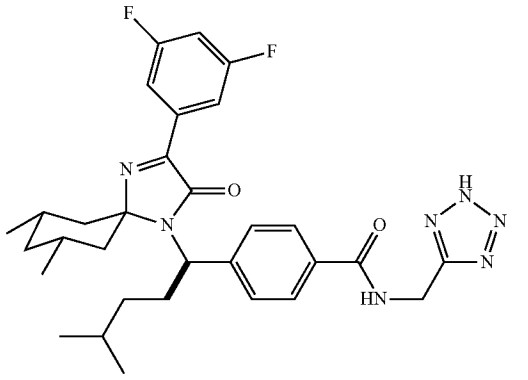 [SMILES: CC(C)CC[C@H](c1ccc(C(=O)NCc2nn[nH]n2)cc1)N1C(=O)C(c2cc(F)cc(F)c2)=NC12CC(C)CC(C)C2] | 4 | 7.36 | 578.3 |

TABLE 1-continued

| | | | | | | | |
|---|---|---|---|---|---|---|---|
| I | K1 | A25 | M15 | 1.251 | | 4 | 8.17 | 622.3 |
| I | K2 | A25 | M15 | 1.252 | | 4 | 8.00 | 608.3 |

TABLE 1-continued

| | | | | | | |
|---|---|---|---|---|---|---|
| I | K14 | A25 | M15 | 1.253 | | 4 | 7.69 | 594.3 |
| I | K1 | A22 | M15 | 1.254 | | 4 | 7.94 | 606.3 |

TABLE 1-continued
| | | | | | | | |
|---|---|---|---|---|---|---|---|
| I | K2 | A22 | M15 | 1.255 | 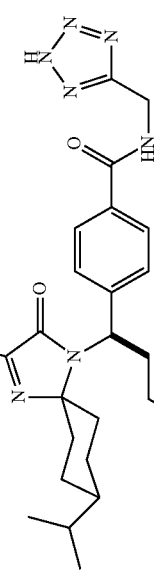 | 4 | 7.80 | 592.3 |
| I | K1 | A1 | M18 | 1.256 | 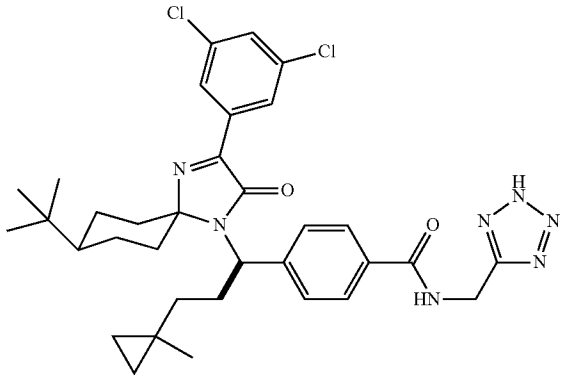 [SMILES: CC1(CC[C@H](c2ccc(C(=O)NCc3nn[nH]n3)cc2)N2C(=O)C(c3cc(Cl)cc(Cl)c3)=NC23CCC(C(C)(C)C)CC3)CC1] | 4 | 8.73 | 650.4 |

TABLE 1-continued

| I | K2 | A1 | M18 | 1.257 | ![structure] | 4 | 8.52 | 636.3 |
| I | K14 | A1 | M18 | 1.258 | ![structure] | 4 | 8.26 | 622.3 |

TABLE 1-continued

| | | | | | | |
|---|---|---|---|---|---|---|
| I | K1 | A22 | M18 | 1.259 | | 4 | 7.83 | 618.3 |
| I | K2 | A22 | M18 | 1.260 | | 4 | 4.25 | 604.3 |

TABLE 1-continued

| | | | | | | |
|---|---|---|---|---|---|---|
| I | K14 | A22 | M18 | 1.261 | [structure] | 4 | 7.37 | 590.3 |
| I | K1 | A25 | M18 | 1.262 | [structure] | 4 | 4.55 | 634.3 |

TABLE 1-continued

| | | | | | | |
|---|---|---|---|---|---|---|
| I | K2 | A25 | M18 | 1.263 | [structure] | 4 | 8.05 | 620.3 |
| I | K1 | A22 | M73 | 1.264 | [structure] | 4 | 7.86 | 606.3 |

TABLE 1-continued

| I | K2 | A22 | M73 | 1.265 | | 4 | 7.72 | 592.3 |
| I | K1 | A25 | M73 | 1.266 | | 4 | 8.20 | 622.3 |

TABLE 1-continued
| | | | | | | |
|---|---|---|---|---|---|---|
| I | K2 | A25 | M73 | 1.267 | 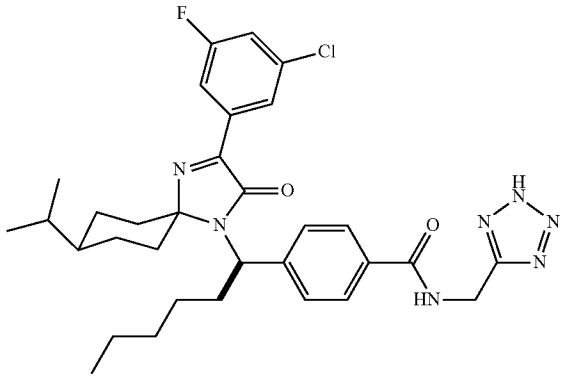 [SMILES: CCCCC[C@H](c1ccc(C(=O)NCc2nn[nH]n2)cc1)N1C(=O)C(c2cc(F)cc(F)c2)=NC12CCC(C(C)C)CC2] | 4 | 8.07 | 608.3 |
| I | K14 | A25 | M18 | 1.268 | 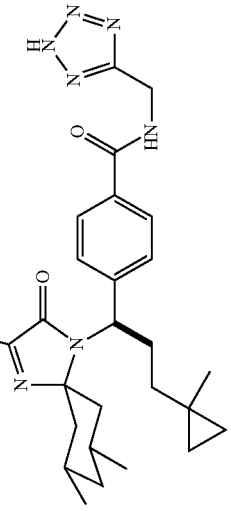 | 4 | 7.74 | 606.3 |

TABLE 1-continued
| | | | | | | | |
|---|---|---|---|---|---|---|---|
| I | K16 | A1 | M6 | 1.269 | 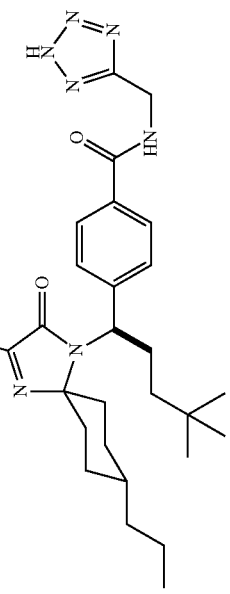 | 4 | 4.76 | 638.4 |
| I | K17 | A1 | M6 | 1.270 | 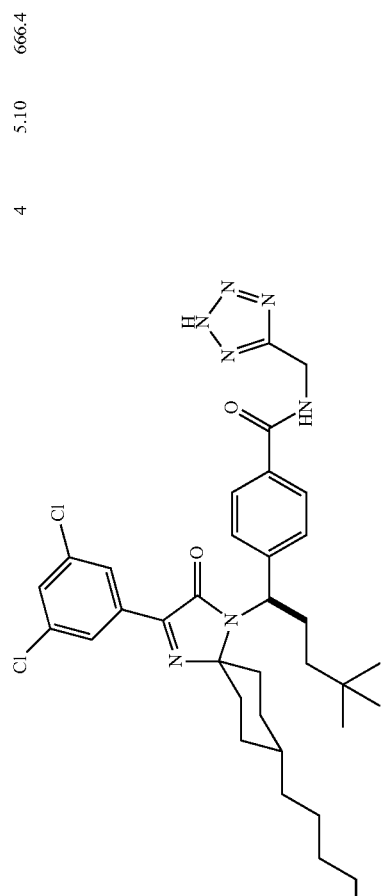 | 4 | 5.10 | 666.4 |

TABLE 1-continued
| I | K8 | A1 | M6 | 1.271 | 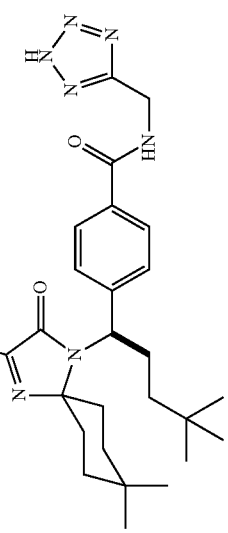 | 4 | 4.49 | 624.3 |
| I | K4 | A31 | M19 | 1.272 | 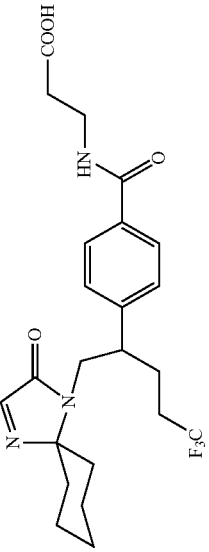 | 4 | 6.93 | 600.3 |

TABLE 1-continued
| | | | | | | |
|---|---|---|---|---|---|---|
| I | K4 | A31 | M19 | 1.273 | 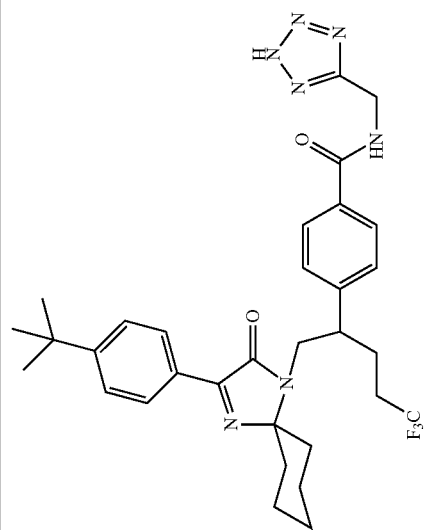 | 4 | 6.80 | 610.3 |
| J | K1 | A71 | M4 | 1.274 | 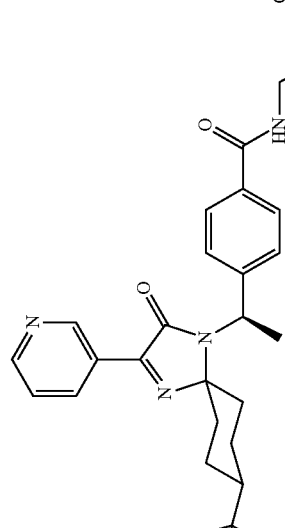 | 4 | 3.38 | 505.3 |

TABLE 1-continued
| J | K1 | A71 | M51 | 1.275 | 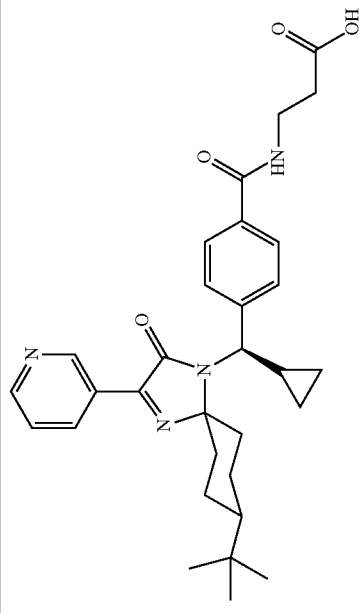 | 4 | 3.58 | 531.3 |
| I | K1 | A71 | M51 | 1.276 | 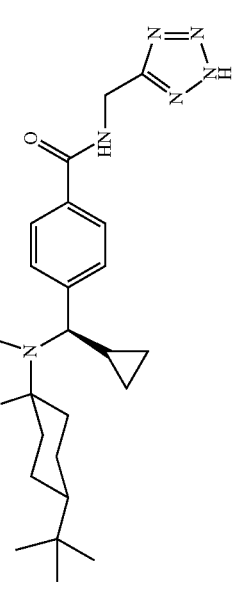 | 4 | 4.99 | 541.3 |

TABLE 1-continued
| | | | | | | |
|---|---|---|---|---|---|---|
| J | K14 | A1 | M51 | 1.277 | 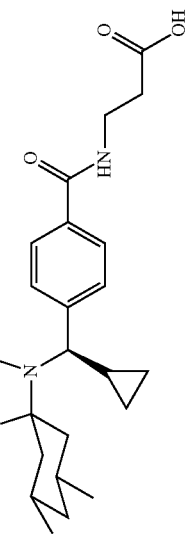 | 4 | 7.43 | 570.3 |
| I | K14 | A1 | M7 | 1.278 | 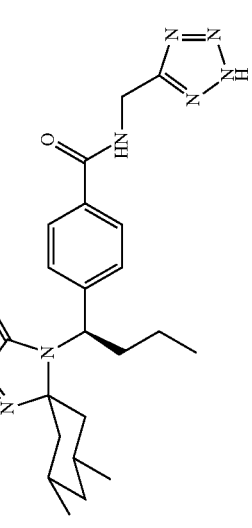 | 4 | 2.54 | 582 |

| | | | | | | |
|---|---|---|---|---|---|---|
| J | K14 | A1 | M7 | 1.279 | | 1 | 2.55 | 574 |
| I | K14 | A1 | M6 | 1.280 | | 1 | 1.85 | 624 |

TABLE 1-continued
| | | | | | | | |
|---|---|---|---|---|---|---|---|
| J | K72 | A1 | M51 | 1.281 |  | 1 | 2.53 | 586.2 |
| I | K1 | A22 | M6 | 1.282 |  | 1 | 2.60 | 620.3 |

TABLE 1-continued
| I | K2 | A1 | M6 | 1.283 | 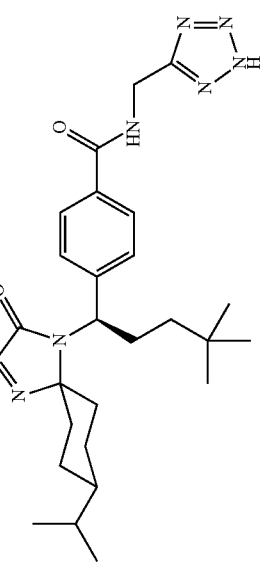 | 1 | 2.85 | 638.3 |
| I | K1 | A25 | M6 | 1.284 | 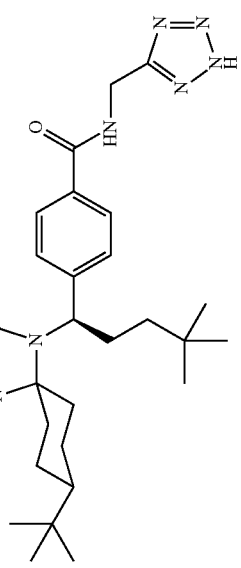 | 1 | 2.73 | 636.3 |

TABLE 1-continued
| | | | | | |
|---|---|---|---|---|---|
| I | K14 | A22 | M6 | 1.285 | 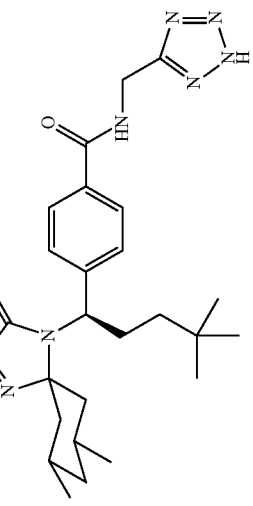 | 1 | 2.47 | 592.3 |
| I | K14 | A25 | M6 | 1.286 | 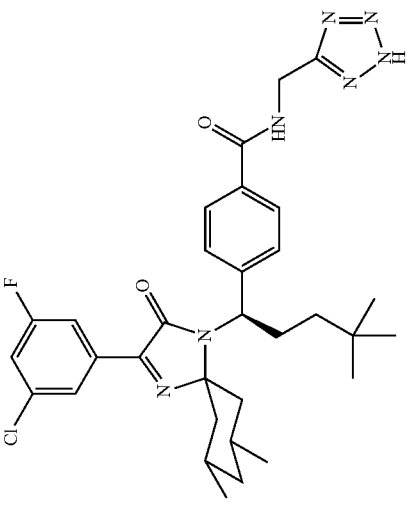 | 1 | 2.59 | 608.3 |

TABLE 1-continued
| I | K14 | A5 | M6 | 1.287 | 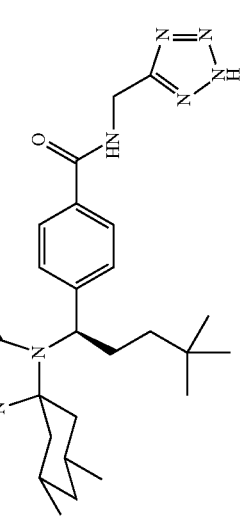 | 1 | 2.53 | 590.3 |
| I | K1 | A5 | M6 | 1.288 | 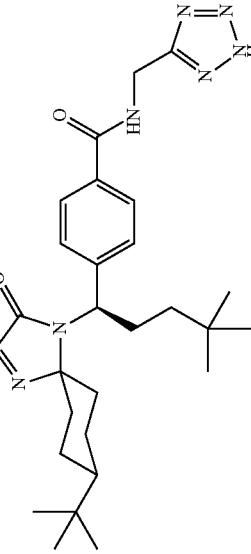 | 1 | 2.66 | 618.3 |

TABLE 1-continued
| I | K3 | A1 | M6 | 1.289 | 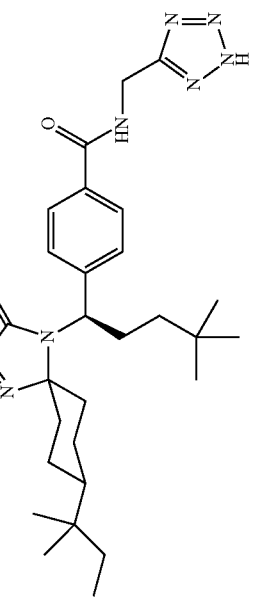 | 1 | 3.04 | 666.3 |
| I | K3 | A25 | M6 | 1.290 | 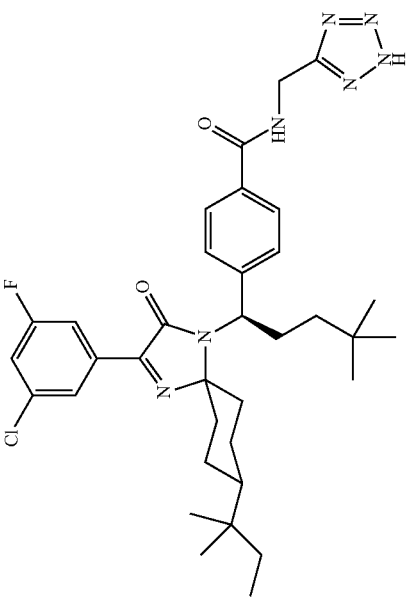 | 1 | 2.83 | 650.3 |

TABLE 1-continued
| | | | | | | | |
|---|---|---|---|---|---|---|---|
| I | K3 | A22 | M6 | 1.291 | 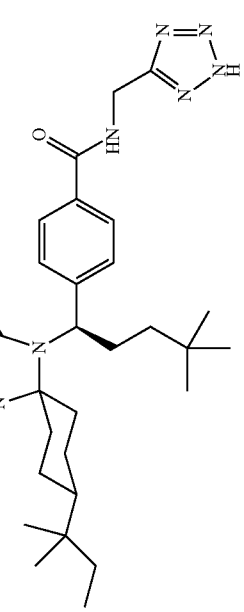 | 1 | 2.68 | 634.3 |
| I | K3 | A5 | M6 | 1.292 | 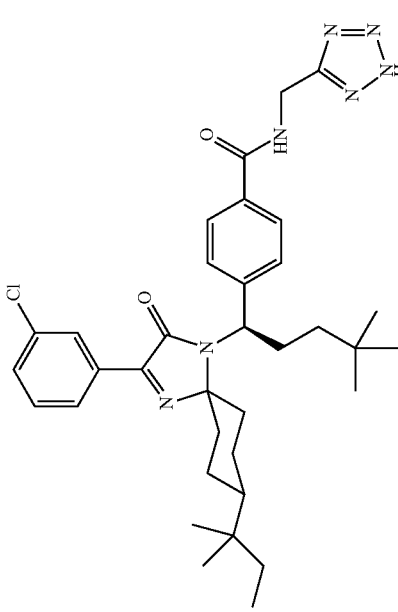 | 1 | 2.76 | 632.3 |

TABLE 1-continued
| | | | | | | |
|---|---|---|---|---|---|---|
| I | K3 | A22 | M71 | 1.293 | 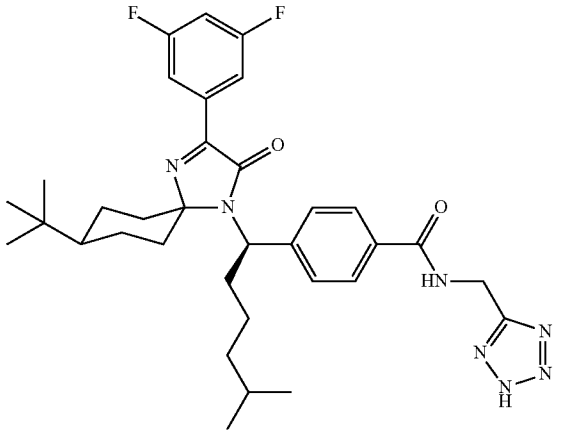 [SMILES: CC(C)CCC[C@H](c1ccc(C(=O)NCc2nn[nH]n2)cc1)N1C(=O)C(c2cc(F)cc(F)c2)=NC12CCC(C(C)(C)C)CC2] | 1 | 2.62 | 620.3 |
| I | K2 | A22 | M71 | 1.294 | 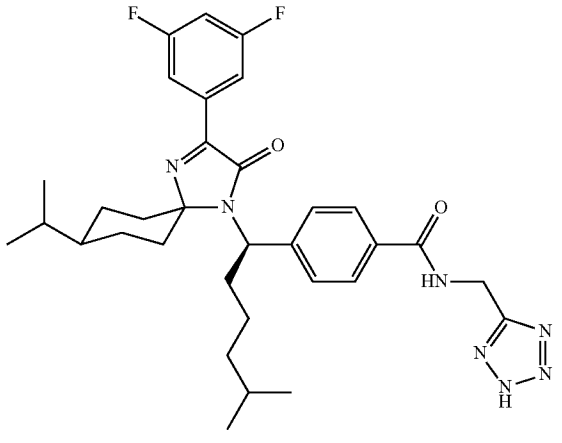 [SMILES: CC(C)CCC[C@H](c1ccc(C(=O)NCc2nn[nH]n2)cc1)N1C(=O)C(c2cc(F)cc(F)c2)=NC12CCC(C(C)C)CC2] | 1 | 2.57 | 606.3 |

TABLE 1-continued

| I | K2 | A22 | M6 | 1.295 | [structure] | 1 | 2.54 | 606.3 |
| I | K2 | A25 | M6 | 1.296 | [structure] | 1 | 2.67 | 622.3 |

TABLE 1-continued
| | | | | | | | |
|---|---|---|---|---|---|---|---|
| I | K2 | A5 | M6 | 1.297 | 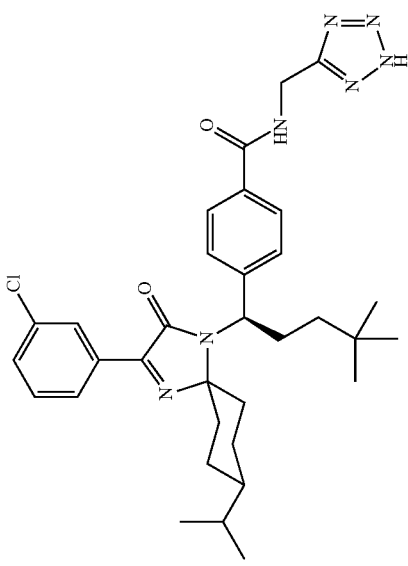 | 1 | 2.60 | 604.3 |
| I | K2 | A22 | M72 | 1.298 | 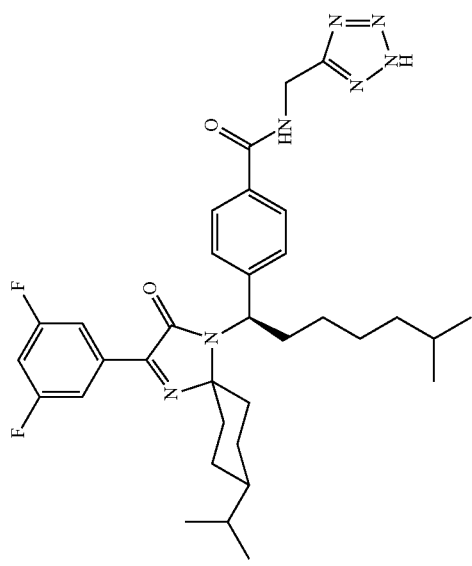 | 1 | 2.75 | 620.3 |

TABLE 1-continued
| | | | | | | |
|---|---|---|---|---|---|---|
| I | K1 | A22 | M72 | 1.299 | 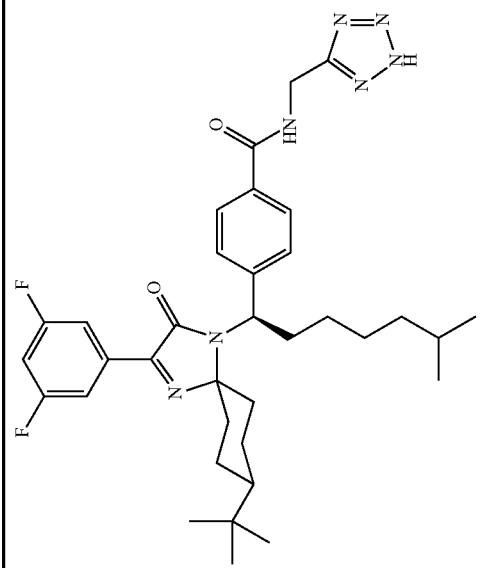 | 1 2.76 634.3 |
| I | K1 | A1 | M72 | 1.300 | 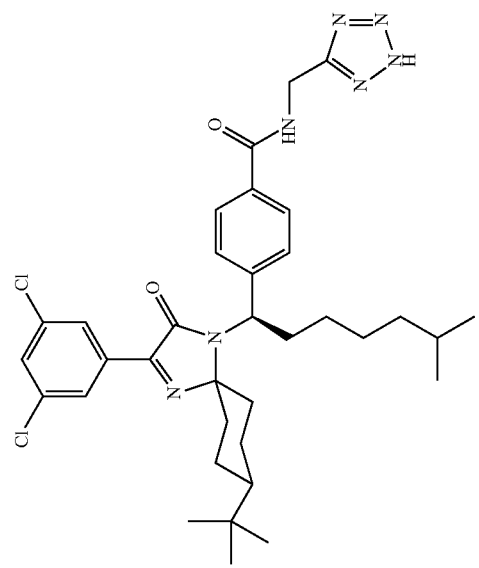 | 1 2.88 666.3 |

TABLE 1-continued
| BA | K3 | A17 | M6 | 1.301 | 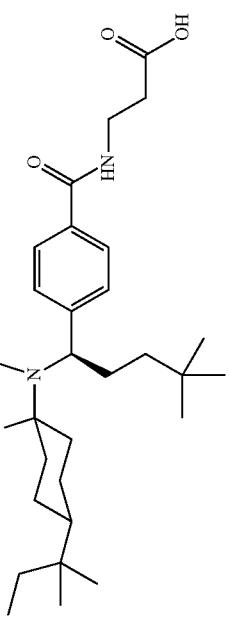 | 4 | 6.82 | 640.4 |
| BA | K1 | A17 | M6 | 1.302 | 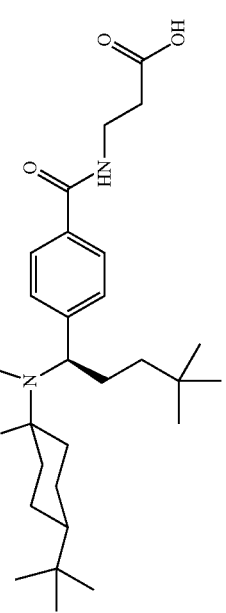 | 4 | 6.53 | 626.3 |

TABLE 1-continued

| BA | K2 | A17 | M6 | 1.303 | | 4 | 6.41 | 612.3 |
| BA | K1 | A2 | M6 | 1.304 | | 4 | 6.31 | 642.4 |

TABLE 1-continued
| | | | | | | | |
|---|---|---|---|---|---|---|---|
| BB | K1 | A17 | M6 | 1.305 | 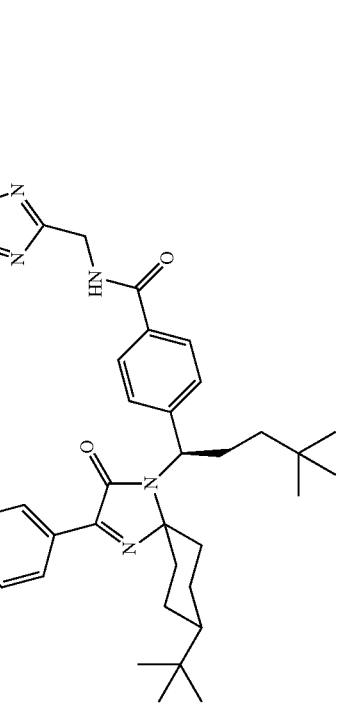 | 4 | 4.56 | 636.3 |
| BA | K2 | A2 | M6 | 1.306 | 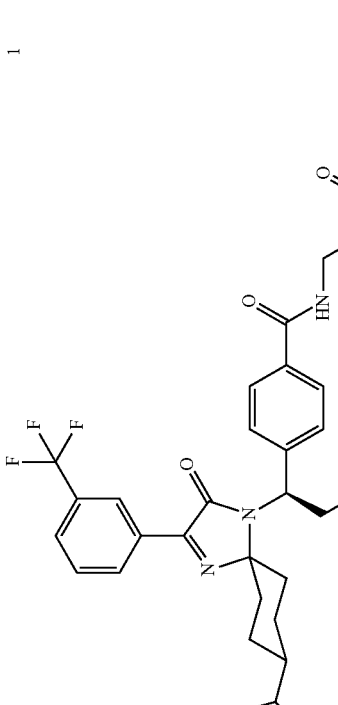 | 1 | 2.53 | 628.3 |

TABLE 1-continued
| BB | K2 | A17 | M6 | 1.307 | 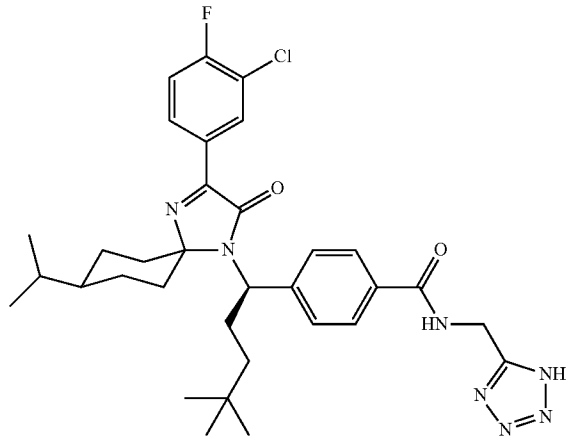 [SMILES: CC(C)C1CCC2(CC1)N=C(c1ccc(F)c(Cl)c1)C(=O)N2[C@H](CCC(C)(C)C)c1ccc(C(=O)NCc2nnn[nH]2)cc1] | 4 | 4.45 | 622.3 |
| BB | K3 | A17 | M6 | 1.308 | 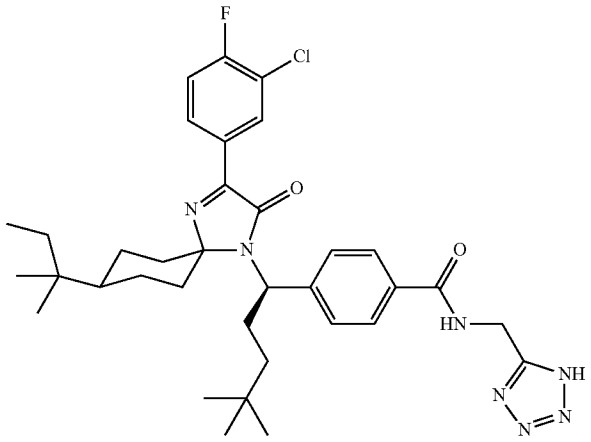 [SMILES: CCC(C)(C)C1CCC2(CC1)N=C(c1ccc(F)c(Cl)c1)C(=O)N2[C@H](CCC(C)(C)C)c1ccc(C(=O)NCc2nnn[nH]2)cc1] | 4 | 6.81 | 650.4 |

TABLE 1-continued
| | | | | | | | |
|---|---|---|---|---|---|---|---|
| BB | K1 | A2 | M6 | 1.309 | 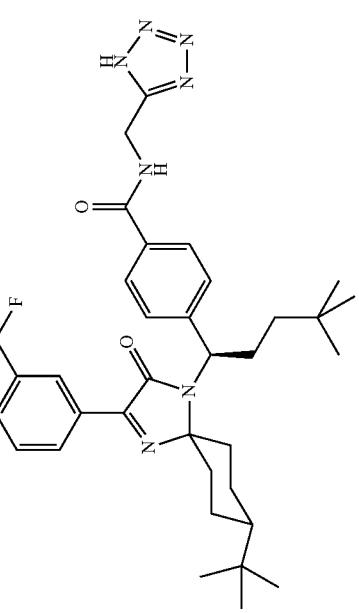 | 4 | 8.06 | 652.4 |
| BB | K3 | A2 | M6 | 1.310 | 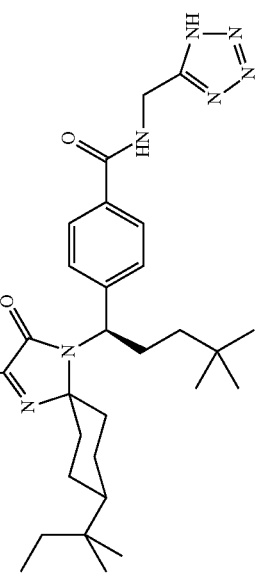 | 1 | 3.46 | 666.4 |

TABLE 1-continued

| | | | | | | |
|---|---|---|---|---|---|---|
| BB | K3 | A2 | M6 | 1.311 | [structure] | 1 | 3.25 | 638.3 |
| BP | K1 | A2 | M3 | 1.312 | [structure] | 4 | 6.84 | 576.4 |

| BA | K1 | A2 | M4 | 1.313 | 4 | 6.88 | 586.3 | 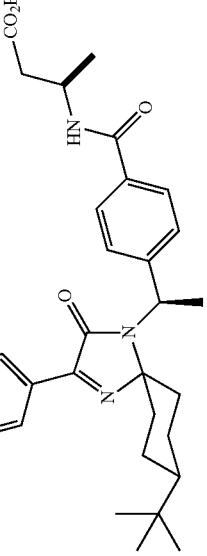 |
| BA | K1 | A2 | M3 | 1.314 | 4 | 6.88 | 586.3 | 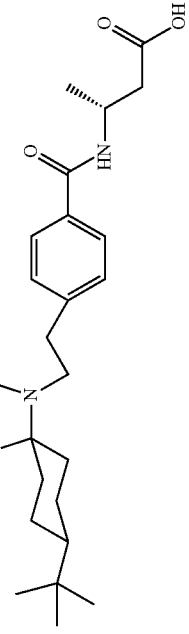 |

TABLE 1-continued

| BE | K1 | A2 | M3 | 1.315 | [structure] | 4 | 6.9 | 586.3 |
| BE | K1 | A2 | M3 | 1.316 | [structure] | 4 | 7.79 | 586.3 |

TABLE 1-continued
| | | | | | | |
|---|---|---|---|---|---|---|
| BC | K2 | A50 | M6 | 1.317 | 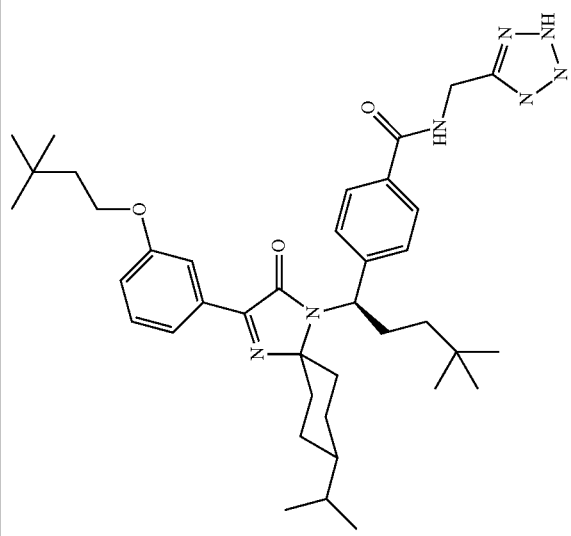 | 4 7.06 670.4 |
| BF | K1 | A50 | M50 | 1.318 | 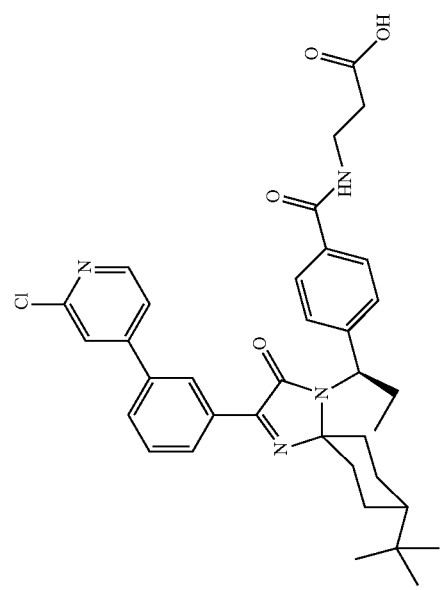 | 4 7.11 629.3 |

TABLE 1-continued
| | | | | | | |
|---|---|---|---|---|---|---|
| BF | K1 | A50 | M4 | 1.319 | 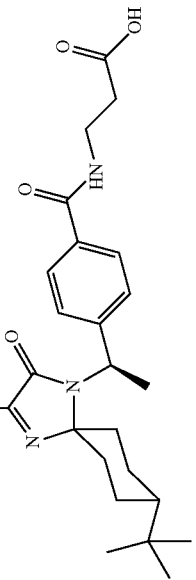 | 4 5.65 615.3 |
| BD | K14 | A51 | M51 | 1.320 | 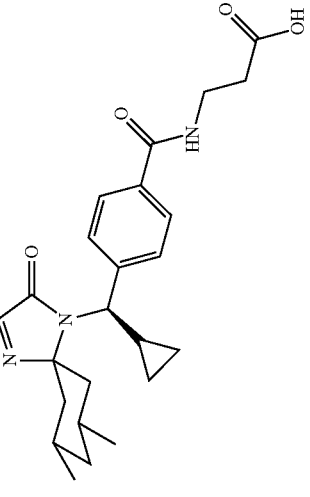 | 4 5.54 608.3 |

TABLE 1-continued
| | | | | | | | |
|---|---|---|---|---|---|---|---|
| BD | K1 | A51 | M51 | 1.321 | 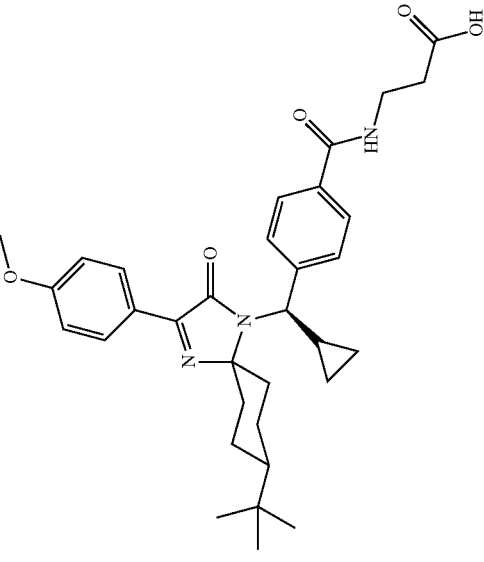 | 4 | 7.21 | 636.3 |
| BA | K14 | A22 | M13 | 1.322 | 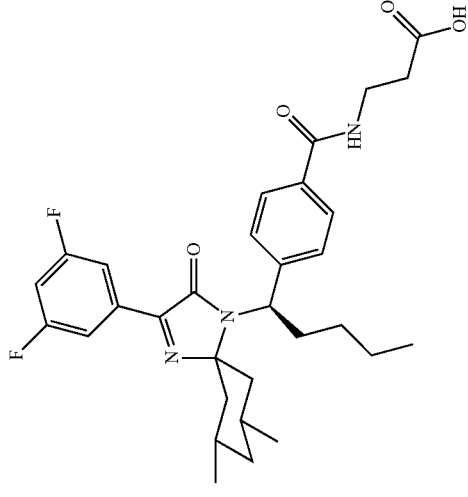 | 4 | 7.3 | 554.3 |

TABLE 1-continued

| | | | | | |
|---|---|---|---|---|---|
| BA | K1 | A3 | M50 | 1.323 | (structure) | 4 | 7.51 | 596.2 |
| BC | K2 | A40 | M6 | 1.324 | (structure) | 4 | 6.27 | 628.3 |

TABLE 1-continued
| BF | K1 | A3 | M50 | 1.325 | | | 4 | 7.43 | 624.3 |
|----|----|----|-----|-------|--|--|---|------|-------|
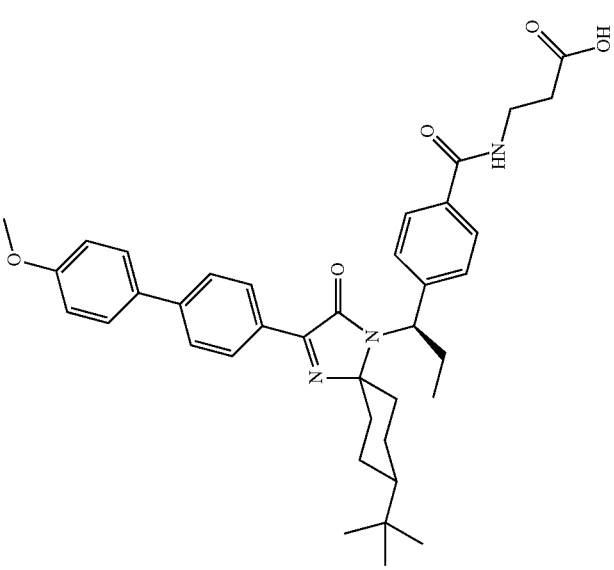

TABLE 1-continued
| | | | | | | |
|---|---|---|---|---|---|---|
| BG | K1 | A50 | M13 | 1.326 | 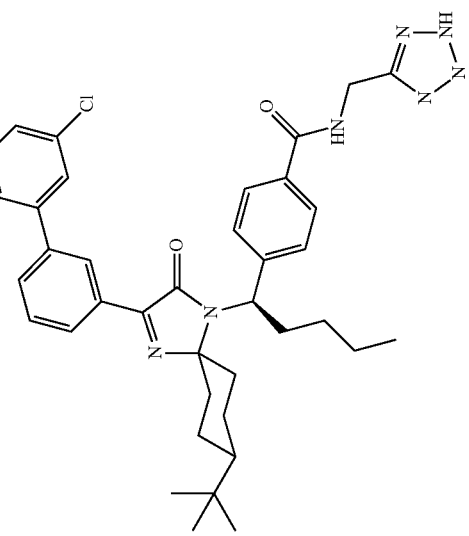 | 4 | 7.34 | 700.4 |
| BA | K3 | A22 | M13 | 1.327 | 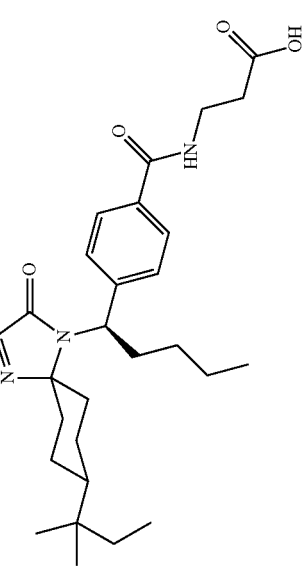 | 4 | 4.41 | 596.3 |

TABLE 1-continued
| BF | K1 | A3 | M50 | 1.328 | | 4 | 4.11 | 629.3 |
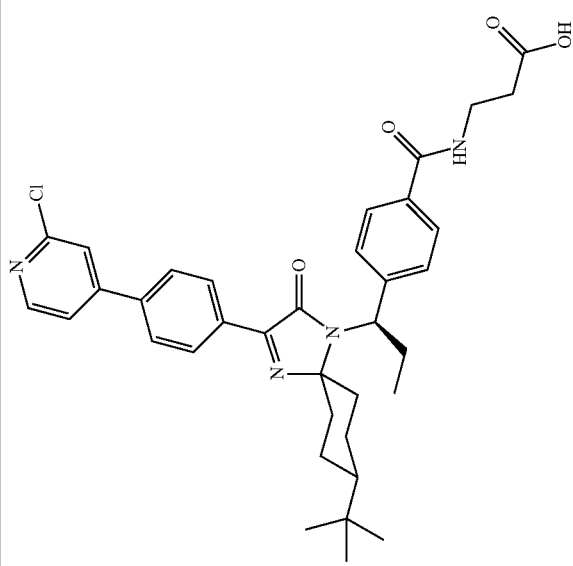

TABLE 1-continued
| | | | | | | |
|---|---|---|---|---|---|---|
| BD | K2 | A51 | M51 | 1.329 | 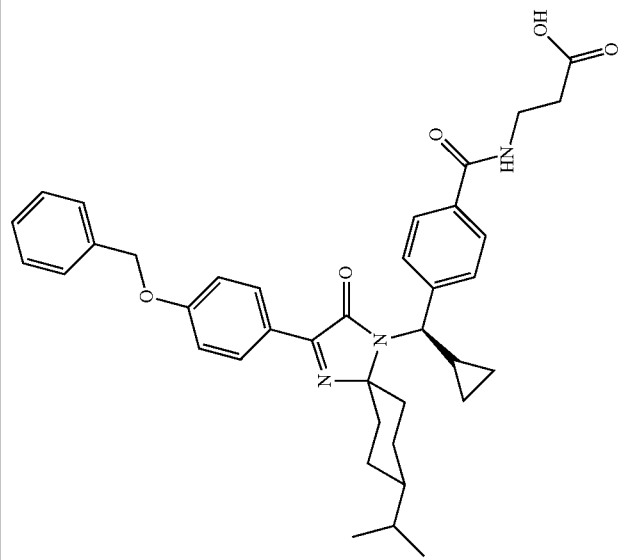 | 4 7.11 622.3 |
| BA | K2 | A22 | M13 | 1.330 | 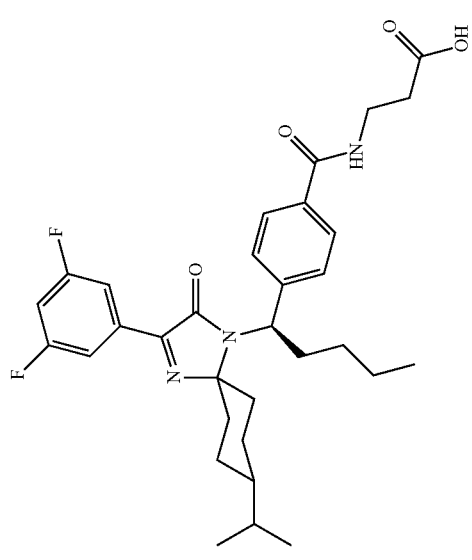 | 4 7.59 568.3 |

TABLE 1-continued

| | | | | | | |
|---|---|---|---|---|---|---|
| BO | K1 | A50 | M4 | 1.331 | 4 | 4.2 | 666.4 |
| BF | K1 | A50 | M50 | 1.332 | 4 | 6.9 | 613.3 |

TABLE 1-continued
| BA | K1 | A22 | M13 | 1.333 | 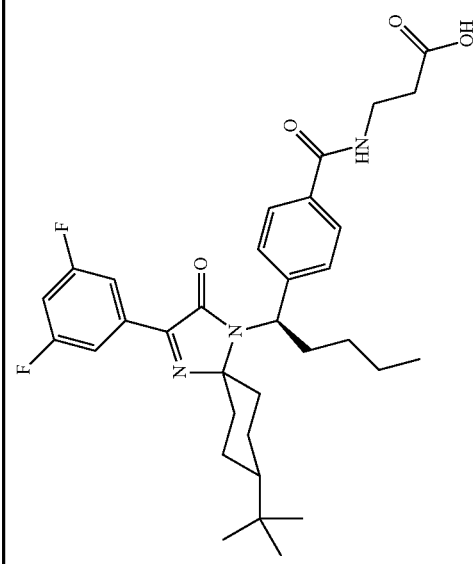 | 4 | 4.24 | 582.3 |
| BA | K1 | A50 | M4  | 1.334 | 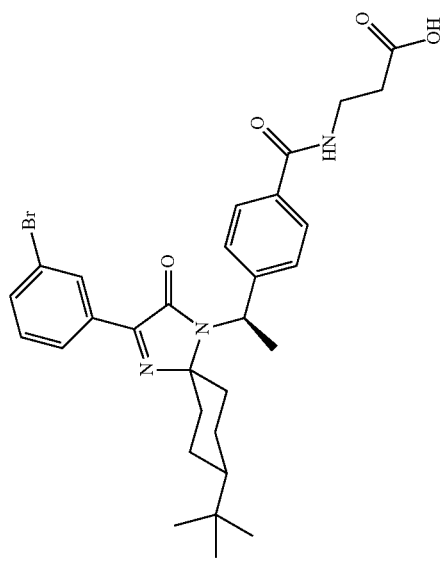 | 4 | 5.67 | 582.3 |

TABLE 1-continued

| BM | K14 | A3 | M50 | 1.335 | | 4 | 3.94 | 582.3 |
| BC | K2 | A50 | M6 | 1.336 | | 4 | 6.22 | 640.4 |

TABLE 1-continued
| | | | | | | |
|---|---|---|---|---|---|---|
| BB | K3 | A22 | M13 | 1.337 | 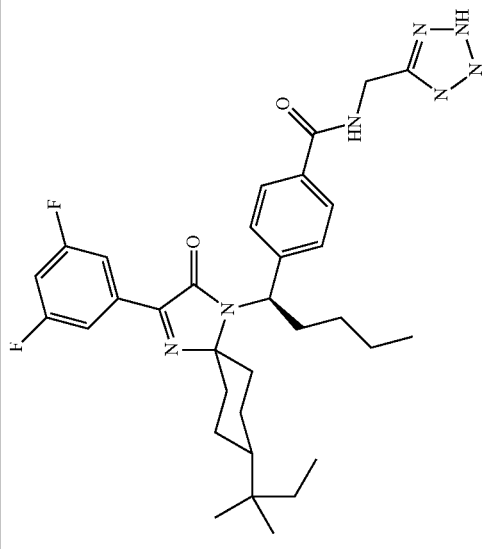 | 4 | 7.97 | 606.3 |
| BF | K14 | A3 | M50 | 1.338 | 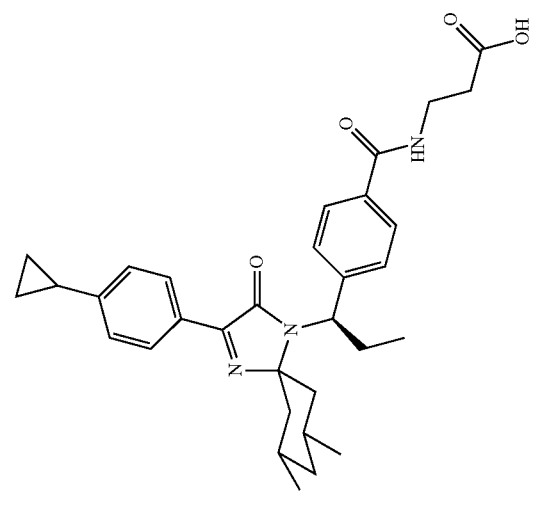 | 4 | 5.58 | 530.3 |

TABLE 1-continued
| BF | K1 | A50 | M4 | 1.339 | 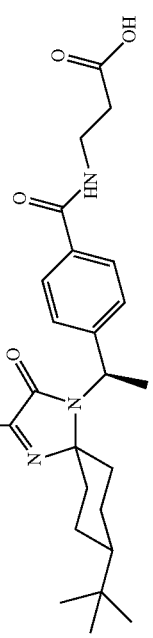 | 4 | 3.58 | 581.3 |
| BF | K1 | A50 | M4 | 1.340 | 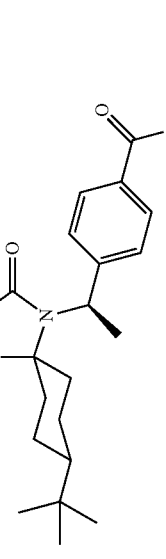 | 4 | 5.57 | 544.4 |

TABLE 1-continued
| BF | K1 | A50 | M4 | 1.341 | 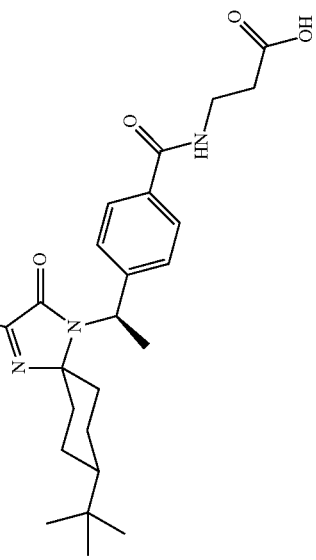 | 4 | 6.58 | 599.3 |
| BF | K14 | A3 | M50 | 1.342 | 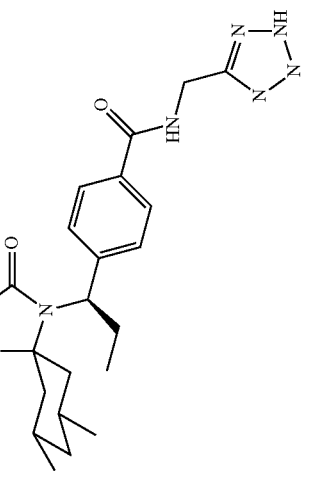 | 4 | 8.05 | 644.4 |

TABLE 1-continued
| | | | | | | | |
|---|---|---|---|---|---|---|---|
| BC | K2 | A50 | M6 | 1.343 | 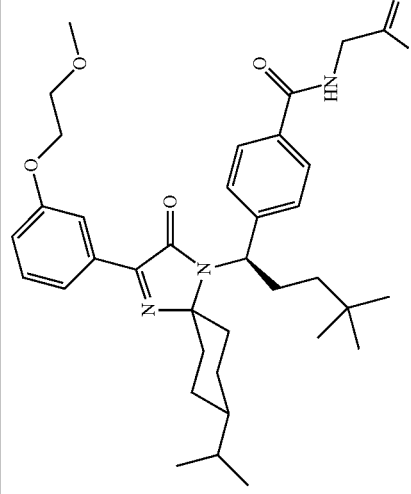 | 4 | 7.17 | 644.4 |
| BF | K1 | A50 | M4 | 1.344 | 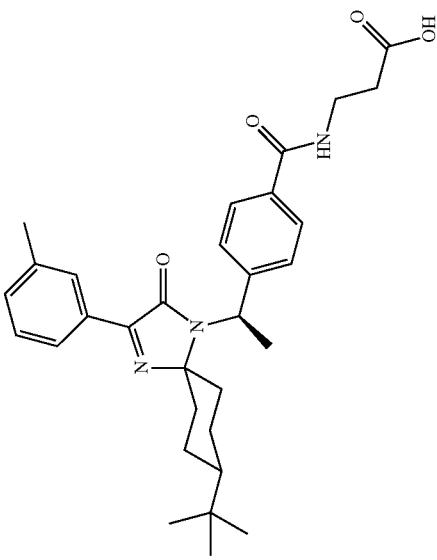 | 4 | 5.41 | 518.3 |

TABLE 1-continued

| | | | | | | |
|---|---|---|---|---|---|---|
| BB | K2 | A22 | M13 | 1.345 | (structure) | 4 7.56 578.3 |
| BF | K1 | A50 | M4 | 1.346 | (structure) | 4 3.8 599.3 |

TABLE 1-continued

| | | | | | | |
|---|---|---|---|---|---|---|
| BB | K1 | A22 | M13 | 1.347 | | 4 | 4.19 | 592.3 |
| BG | K1 | A3 | M50 | 1.348 | | 4 | 8.01 | 638.4 |

TABLE 1-continued
| BB | K14 | A22 | M13 | 1.349 | 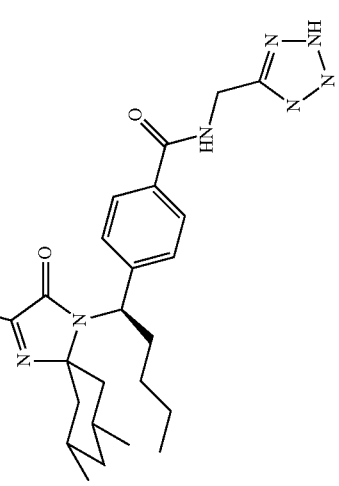 | 4 | 7.2 | 564.3 |
| BF | K1 | A50 | M4 | 1.350 | 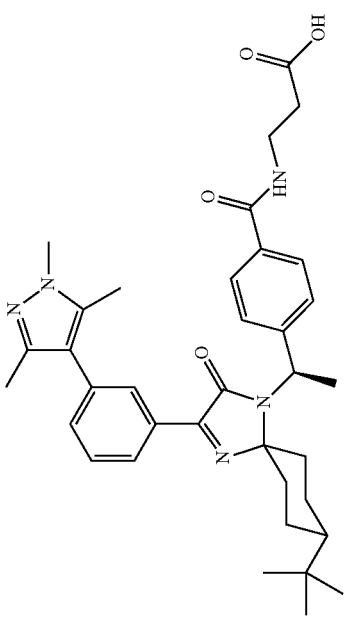 | 4 | 4.48 | 612.3 |

TABLE 1-continued

| BG | K1 | A3 | M50 | 1.351 | | 4 | 6.36 | 618.3 |

TABLE 1-continued

| | | | | | | |
|---|---|---|---|---|---|---|
| BC | K14 | A3 | M50 | 1.352 | 4 | 7.78 | 600.3 |
| BN | K1 | A50 | M13 | 1.353 | 4 | 7.76 | 596.4 |

TABLE 1-continued

| BG | K1 | A50 | M13 | 1.354 | [structure] | 4 | 4.27 | 667.3 |
| BG | K1 | A3 | M50 | 1.355 | [structure] | 4 | 7.44 | 634.3 |

TABLE 1-continued

| | | | | | | | |
|---|---|---|---|---|---|---|---|
| BC | K2 | A50 | M50 | 1.356 | | 4 | 6.25 | 614.3 |
| BM | K14 | A3 | M50 | 1.357 | | 4 | 3.93 | 592.3 |

TABLE 1-continued
| | | | | | | |
|---|---|---|---|---|---|---|
| BH | K1 | A50 | M4 | 1.358 | 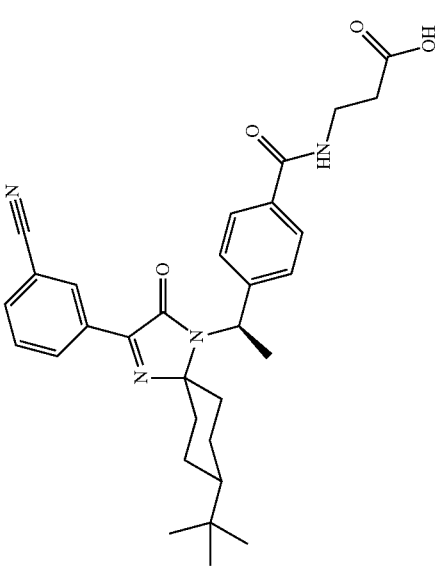 | 4 | 5.03 | 529.3 |
| BQ | K2 | A51 | M51 | 1.359 | 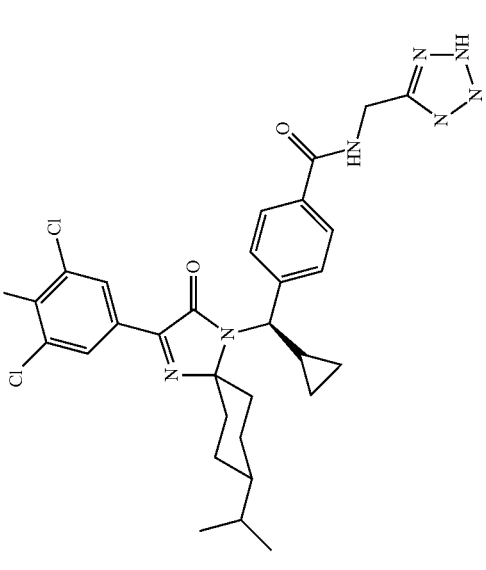 | 4 | 6.54 | 700.4 |

TABLE 1-continued

| | | | | | | |
|---|---|---|---|---|---|---|
| BF | K1 | A50 | M4 | 1.360 | [structure with quinoline-phenyl, tert-butylcyclohexyl imidazolinone, phenyl-CH(CH₃)-benzamide-NH-CH₂CH₂-COOH] | 4 4.04 631.3 |
| BI | K1 | A50 | M4 | 1.361 | [structure with piperidinyl-phenyl, tert-butylcyclohexyl imidazolinone, phenyl-CH(CH₃)-benzamide-NH-CH₂CH₂-COOH] | 4 4.71 587.3 |

TABLE 1-continued

| BN | K14 | A3 | M50 | 1.362 | | 4 | 3.66 | 540.3 |
|----|-----|-----|-----|-------|---|---|------|-------|
| BF | K1 | A50 | M4 | 1.363 | | 4 | 4.33 | 597.3 |

TABLE 1-continued
| | | | | | | |
|---|---|---|---|---|---|---|
| BI | K1 | A50 | M4 | 1.364 | 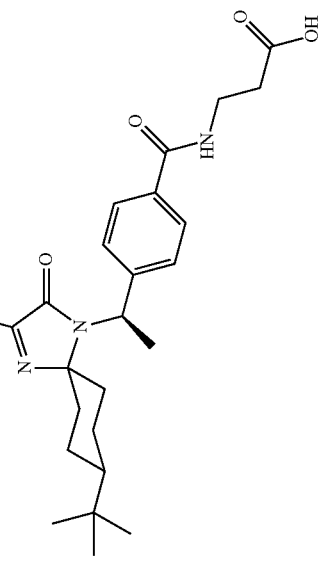 | 4 6.2 570.3 |
| BA | K14 | A12 | M4 | 1.365 | 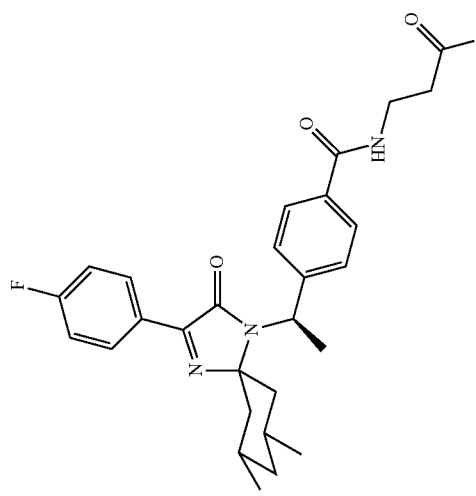 | 4 5.9 494.3 |

TABLE 1-continued
| | | | | | | |
|---|---|---|---|---|---|---|
| BQ | K2 | A51 | M51 | 1.366 | 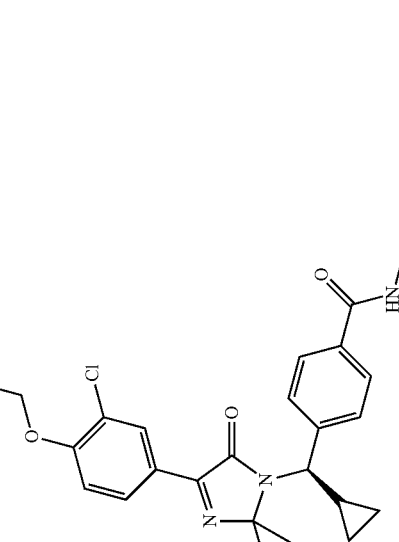 | 4 4.2 666.4 |
| BD | K1 | A51 | M51 | 1.367 | 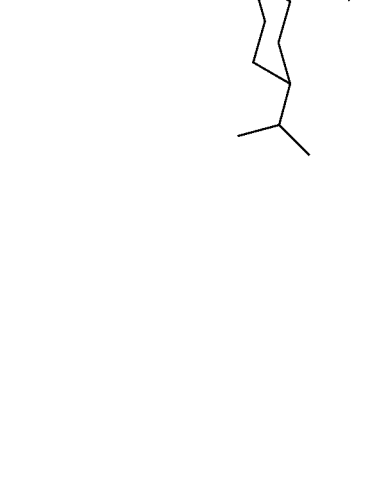 | 4 5.6 546.3 |

TABLE 1-continued
| | | | | | | |
|---|---|---|---|---|---|---|
| BC | K2 | A51 | M51 | 1.368 | 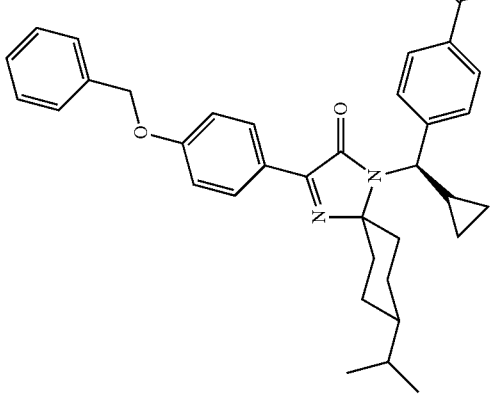 | 4 | 7.24 | 632.3 |
| BR | K100 | A1 | M15a | 1.369 | 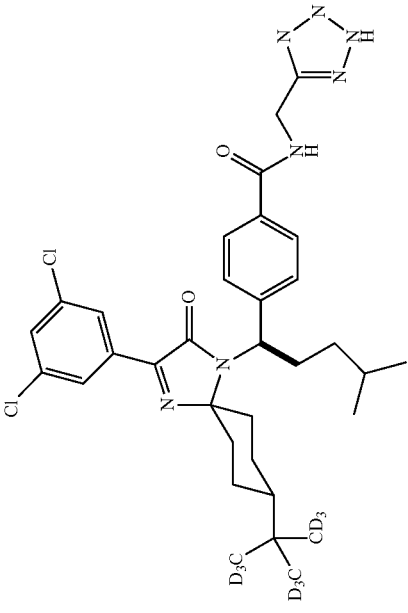 | 1 | 2.69 | 647.3 |

TABLE 1-continued
| | | | | | | |
|---|---|---|---|---|---|---|
| BR | K100 | A22 | M15a | 1.370 | 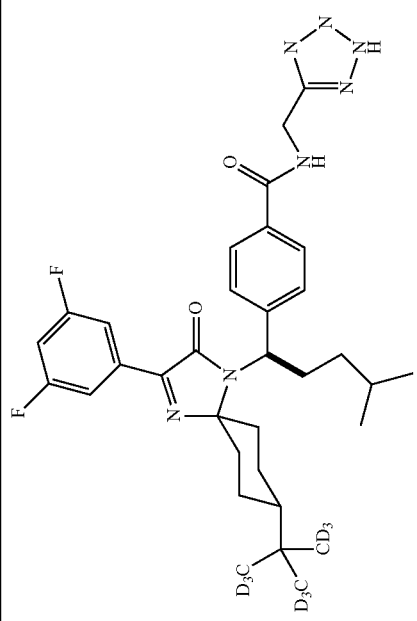 | 1 | 2.46 | 615.4 |
| BR | K100 | A1 | M6 | 1.371 | 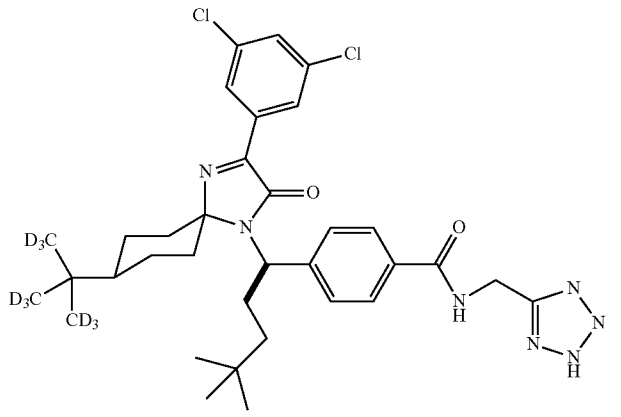 | 1 | 2.68 | 661.3 |

TABLE 1-continued
| BR | K100 | A22 | M6 | 1.372 | 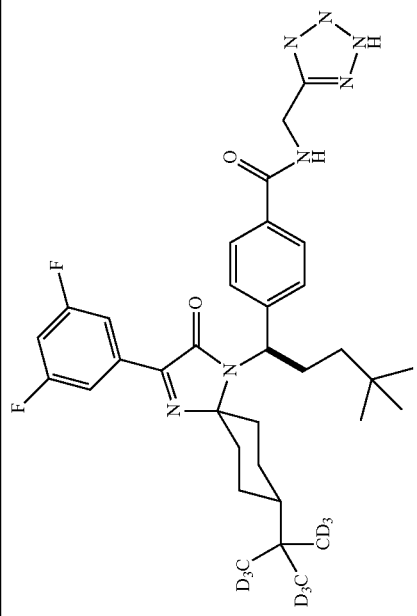 | 1 | 2.47 | 629.4 |
| AAJ | K11 | A12 | M6 | 1.373 | | 3 | 2.39 | 622.4 |

TABLE 1-continued

| | | | | | | |
|---|---|---|---|---|---|---|
| AAL | K1 | A1 | M4 | 1.374 | | 3 | 2.53 | 588.2 |
| AAM | K1 | A1 | M4 | 1.375 | | 3 | 2.53 | 588.0 |
| BS | K201 | A1 | M6 | 1.376 | | 4 | 8.49 | 650.4 |

TABLE 1-continued

| BS | K201 | A22 | M6 | 1.377 | | 4 | 4.19 | 618.3 |
| I | K202 | A1 | M6 | 1.378 | | 5 | 29.7 (34) | 668.3 |

TABLE 1-continued
| | | | | | | | |
|---|---|---|---|---|---|---|---|
| AB | K202 | A1 | M6 | 1.379 | 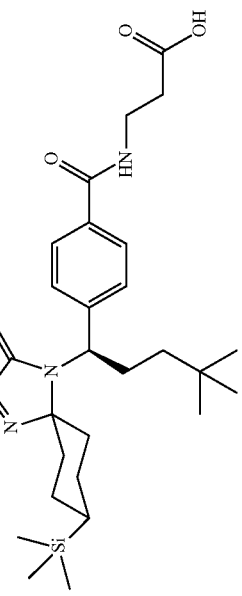 | 5 | 29.2 (34) | 658.3 |
| AAJ | K1 | A1 | M205 | 1.380 | 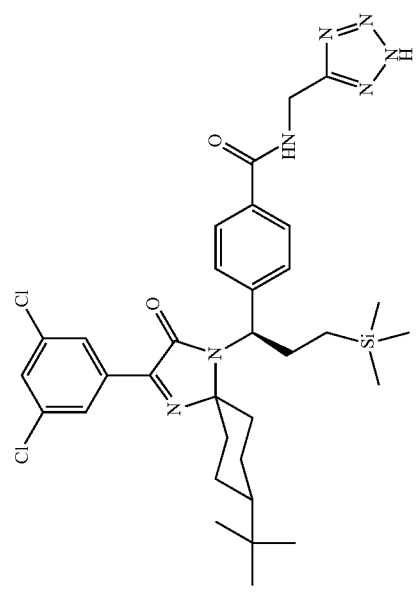 | 4 | 2.67 | 668 |

TABLE 1-continued

| AAR | K1 | A25 | M50 | 1.500 | [structure] | 3 | 2.56 | 570.2 |
| AAR | K2 | A25 | M50 | 1.501 | [structure] | 3 | 2.53 | 556.2 |

TABLE 1-continued
| | | | | | | |
|---|---|---|---|---|---|---|
| J | K2 | A14 | M6 | 1.502 | 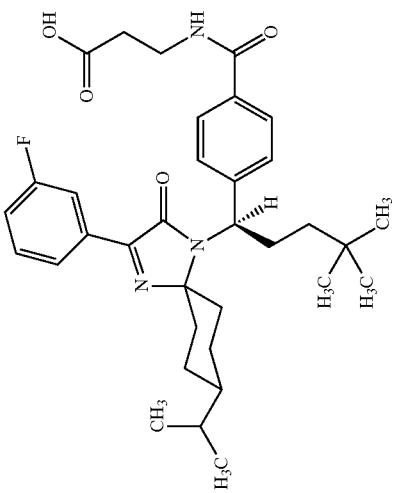 | 3 2.49 578.5 |
| AH | K1 | A25 | A25 | 1.503 | 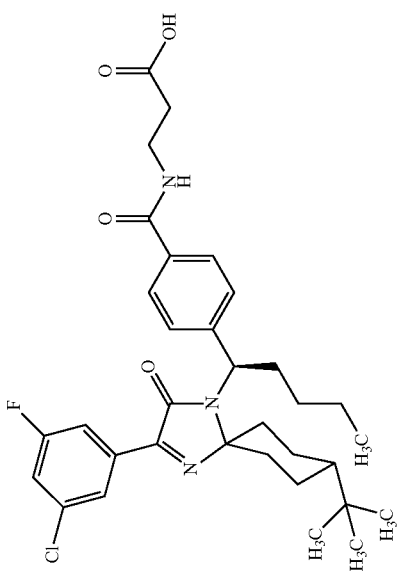 | 5 22.7 (25) 598.2 |

TABLE 1-continued

| | | | | | | | |
|---|---|---|---|---|---|---|---|
| AAJ | K2 | A12 | M6a | 1.504 | | 3 | 2.56 | 578.3 |
| AF | K3 | A22 | M7 | 1.505 | | 5 | 20.0 (25) | 582.5 |

TABLE 1-continued

| | | | | | | |
|---|---|---|---|---|---|---|
| AAJ | K3 | A12 | M6a | 1.506 | 3 | 2.60 | 606.4 |
| AAR | K1 | A12 | M50 | 1.507 | 4 | 5.57 | 536.3 |

TABLE 1-continued
| | | | | | | | |
|---|---|---|---|---|---|---|---|
| AAR | K3 | A1 | M15 | 1.508 | 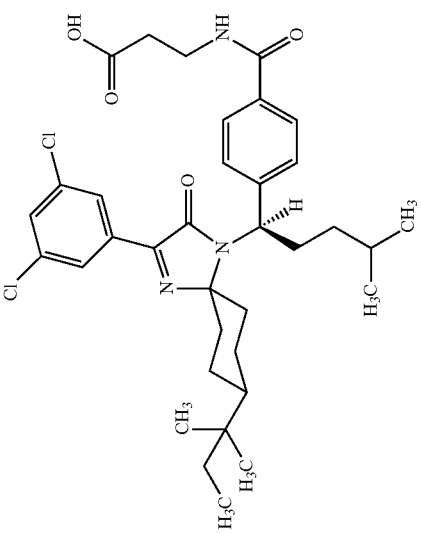 | 3 | 2.92 | 642.2 |
| AAT | K3 | A1 | M15 | 1.509 | 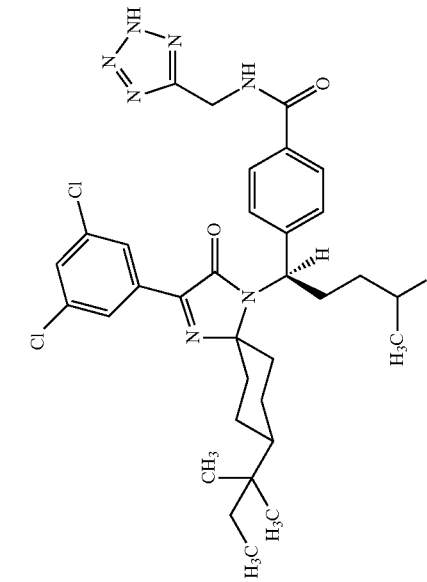 | 3 | 2.86 | 652.2 |

TABLE 1-continued

| AAR | | | | | | |
|---|---|---|---|---|---|---|
| J | K2 | A1 | M15 | 1.510 | 3 | 2.77 | 614.2 |
| J | K1 | A25 | M4 | 1.511 | 4 | 7.07 | 556.3 |

TABLE 1-continued
| AAR | | | | | |
|---|---|---|---|---|---|
| K14 | A25 | M50 | 1.512 |  | 3 2.46 542.2 |
| K1 | A22 | M7 | 1.513 | 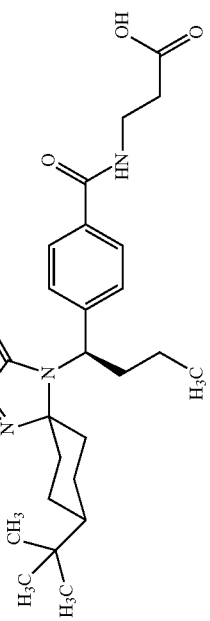 | 5 14.8 (25) 568.3 |
| AF | | | | | |

TABLE 1-continued
| | | | | | | |
|---|---|---|---|---|---|---|
| AAR | K1 | A12 | M6a | 1.514 | 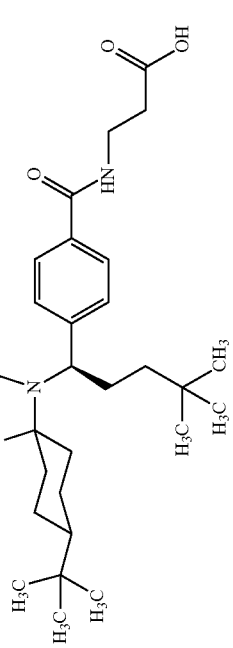 | 3 2.62 592.3 |
| AAJ | K3 | A12 | M6a | 1.515 | 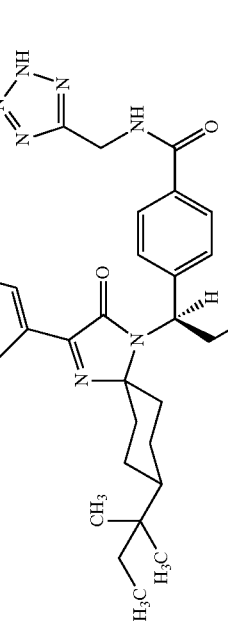 | 3 2.60 616.2 |

TABLE 1-continued

| I | K1 | A14 | M6 | 1.516 | | 3 | 2.58 | 602.2 |
| AAR | K1 | A1 | M204 | 1.517 | | 4 | 4.48 | 586.3 |

TABLE 1-continued

| AAT | K2 | A1 | M15 | 1.518 | 3 | 2.74 | 624.2 |
| J | K1 | A1 | M50 | 1.519 | 4 | 6.28 | 586.3 |

TABLE 1-continued
| I | K2 | A14 | M6a | 1.520 | 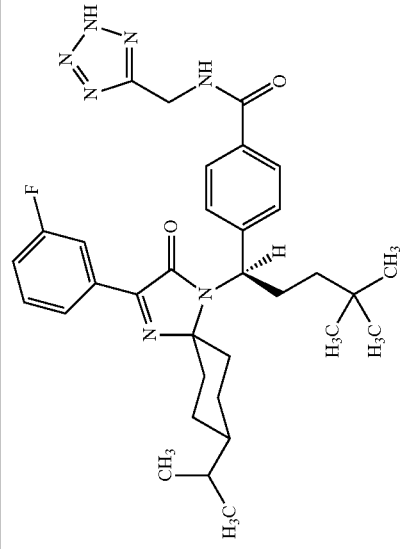 | 3 | 2.50 | 588.3 |
| I | K1 | A1 | M4 | 1.520 | 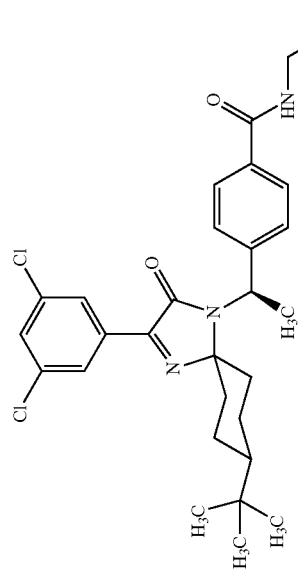 | 4 | 6.17 | 582 |

TABLE 1-continued
| | | | | | | |
|---|---|---|---|---|---|---|
| AAT | K1 | A1 | M7 | 1.521 | 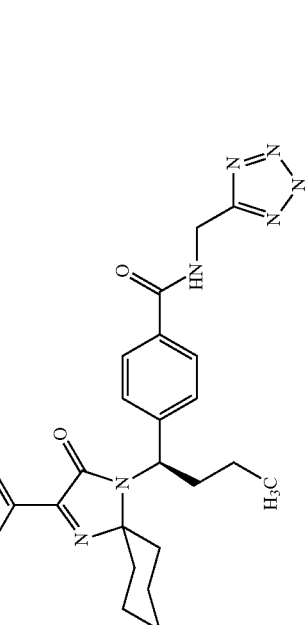 | 4 7.92 610.3 |
| AAT | K1 | A12 | M6a | 1.522 | 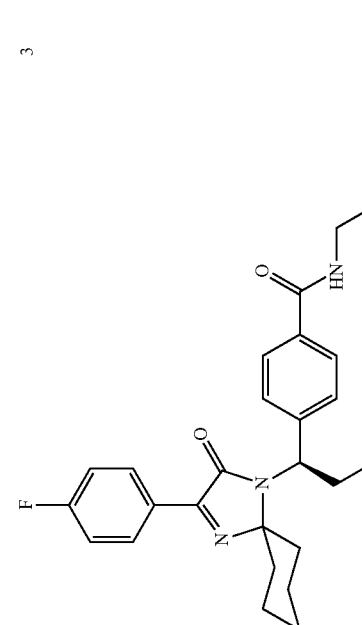 | 3 2.60 602.4 |

| | | | | | | |
|---|---|---|---|---|---|---|
| AF | K1 | A31 | M7 | 1.523 | 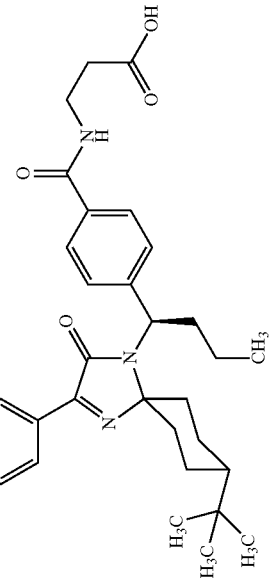 | 5 17.8 (25) 568.3 |
| AAT | K2 | A25 | M50 | 1.524 | 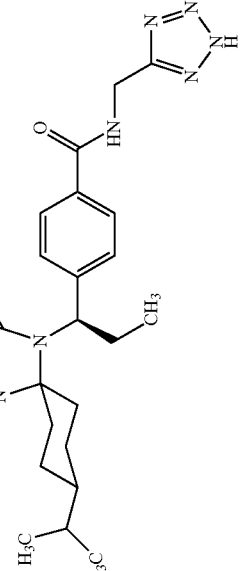 | 3 2.51 566.2 |

TABLE 1-continued

| AAT | K2 | A12 | M6a | 1.525 | [structure] | 3 | 2.55 | 588.2 |
| AF | K14 | A22 | M4 | 1.526 | [structure] | 5 | 18.1 (22) | 540.3 |

TABLE 1-continued
| | | | | | | |
|---|---|---|---|---|---|---|
| AAH, AAI | K200 | A1 | M4 | 1.527 | 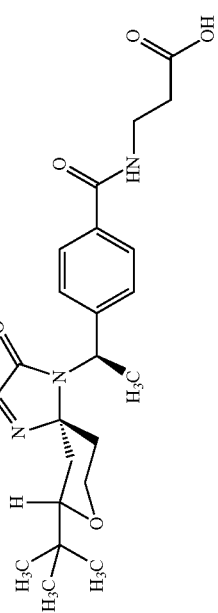 | 4 | 5.28 | 574.3 |
| AAR | K1 | A1 | M202 | 1.528 | 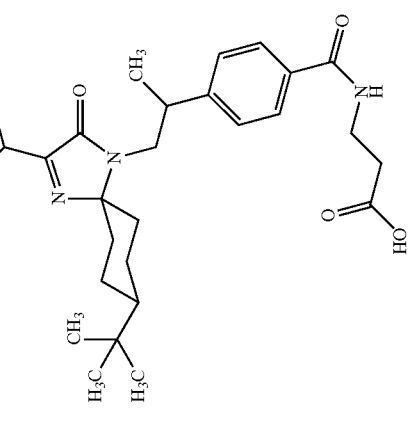 | 4 | 6.19 | 586.3 |

TABLE 1-continued
| I | K1 | A1 | M50 | 1.529 | 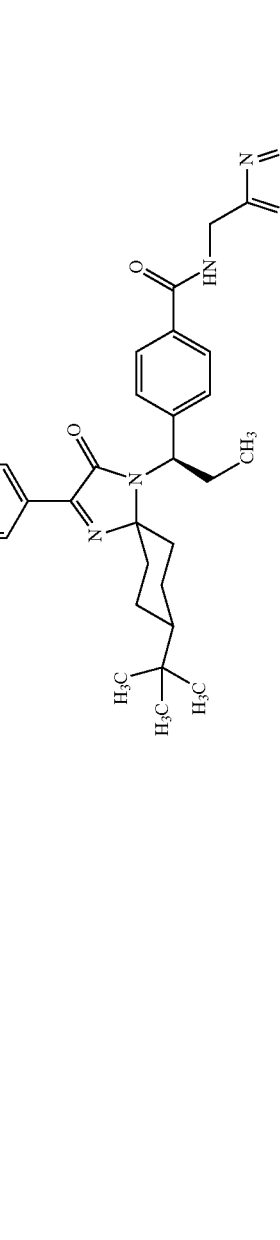 | 3 | 2.67 | 596.2 |
| af | K2 | A31 | M7 | 1.530 | 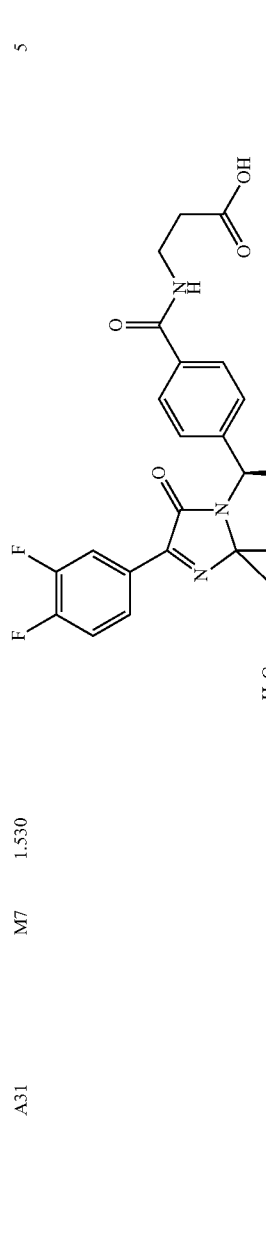 | 5 | 16.7 (25) | 554.3 |

TABLE 1-continued
| | | | | | |
|---|---|---|---|---|---|
| AAR | K1 | A2 | M204 | 1.531 | 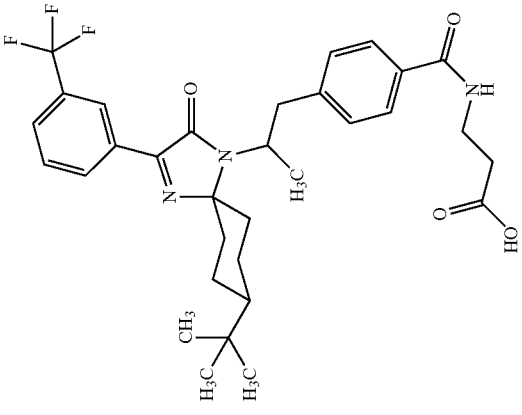 4 7.00 586.3 |
| AAT | K1 | A25 | M50 | 1.532 | 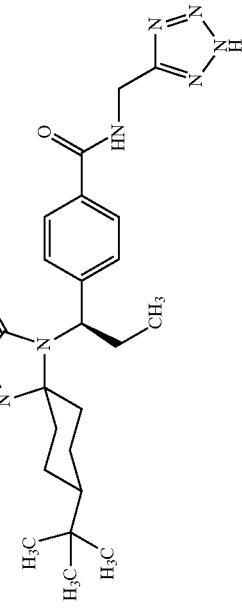 3 2.55 580.2 |

TABLE 1-continued

| AAT | K1 | A25 | M7 | 1.533 | | 3 | 2.61 | 594.2 |
| AAT | K14 | A25 | M7 | 1.534 | | 3 | 2.51 | 566.2 |

TABLE 1-continued

| | | | | | | |
|---|---|---|---|---|---|---|
| AAT | K2 | A25 | M7 | 1.535 | 3 | 2.56 | 580.2 |
| J | K1 | A12 | M4 | 1.536 | 4 | 5.18 | 522.3 |

TABLE 1-continued
| AAR | | K1 | M4 | M4 | 1.537 | 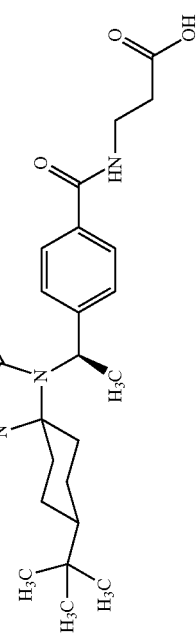 | 4 | 5.66 | 556.3 |
| J | | K1 | A2 | M50 | 1.538 | 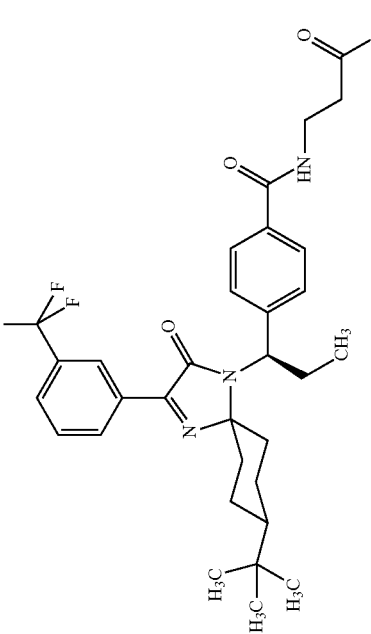 | 4 | 5.64 | 586.3 |

TABLE 1-continued
| | | | | | | | |
|---|---|---|---|---|---|---|---|
| AAO | K14 | A12 | M50 | 1.539 | 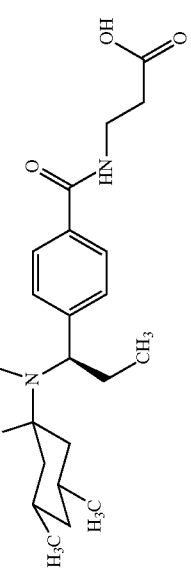 | 3 | 2.32 | 508.2 |
| J | K11 | A1 | M4 | 1.540 | 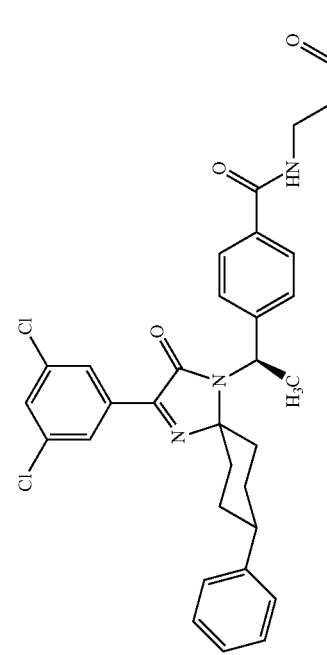 | 4 | 5.69 | 592.3 |

TABLE 1-continued

| | | | | | | | |
|---|---|---|---|---|---|---|---|
| I | K3 | A22 | M7 | 1.541 | 5 | 19.7 (25) | 592.1 |
| J | K1 | A9 | M4 | 1.542 | 4 | 5.06 | 504.3 |

TABLE 1-continued

| J | K1 | A12 | M3 | 1.543 | | 4 | 5.16 | 522.3 |
| J | K6 | A12 | M50 | 1.544 | | 4 | 6.53 | 508.3 |

TABLE 1-continued

| | | | | | | |
|---|---|---|---|---|---|---|
| AAK | K3 | A1 | M4 | 1.545 | | 4 | 4.58 | 596.3 |
| I | K1 | A22 | M7 | 1.546 | | 5 | 20.4 (22) | 578.4 |

TABLE 1-continued
| | | | | | | |
|---|---|---|---|---|---|---|
| I | K1 | A31 | M7 | 1.547 | 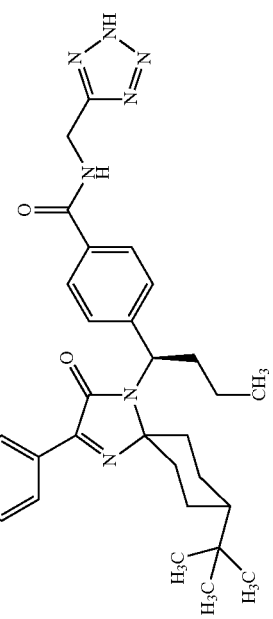 | 5 17.4 (25) 578.4 |
| AAR | K1 | A18 | M4 | 1.548 | 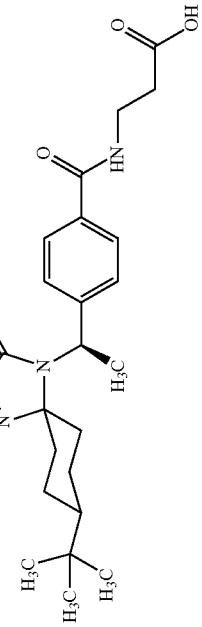 | 4 5.65 588.3 |

TABLE 1-continued

| AAR | K1 | A2 | M202 | 1.549 | | 4 | 5.61 | 586.3 |
|---|---|---|---|---|---|---|---|---|
| J | K1 | A6 | M4 | 1.550 | | 4 | 5.90 | 572.3 |

TABLE 1-continued

| | | | | | | | |
|---|---|---|---|---|---|---|---|
| AAQ | K1 | A12 | M50 | 1.551 | [structure] | 3 | 2.43 | 546.2 |
| AAK | K1 | A1 | M1 | 1.552 | [structure] | 4 | 5.98 | 568.3 |

TABLE 1-continued

| | | | | | | | |
|---|---|---|---|---|---|---|---|
| AAT | K14 | A25 | M50 | 1.553 | [structure] | 3 | 2.45 | 552.2 |
| I | K1 | A2 | M7 | 1.554 | [structure] | 3 | 2.52 | 610.2 |

TABLE 1-continued

| I | AAR | K2 | A31 | M7 | 1.555 | [structure] | 5 | 16.6 (25) | 564.3 |
| | | K2 | A2 | M204 | 1.556 | [structure] | 4 | 3.94 | 572.3 |

TABLE 1-continued
| | | | | | |
|---|---|---|---|---|---|
| AAI | K200 | A1 | M4 | 1.557 |  | 4 | 5.42 | 574.3 |
| I | K1 | A22 | M4 | 1.558 | 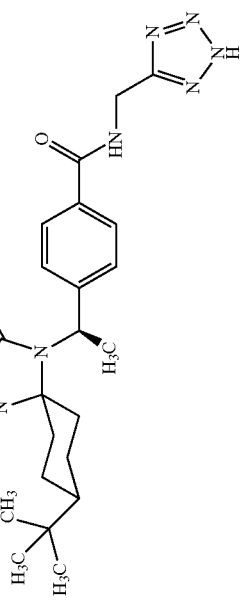 | 5 | 14.8 (25) | 550.1 |

TABLE 1-continued

| | | | | | |
|---|---|---|---|---|---|
| I | K3 | A22 | M4 | 1.559 | 5 16.3 (25) 564.4 |
| J | K1 | A6 | M3 | 1.560 | 4 5.86 572.3 |

TABLE 1-continued
| AAS | | A | M | | | | |
|---|---|---|---|---|---|---|---|
| I | K1 | A6 | M4 | 1.561 | 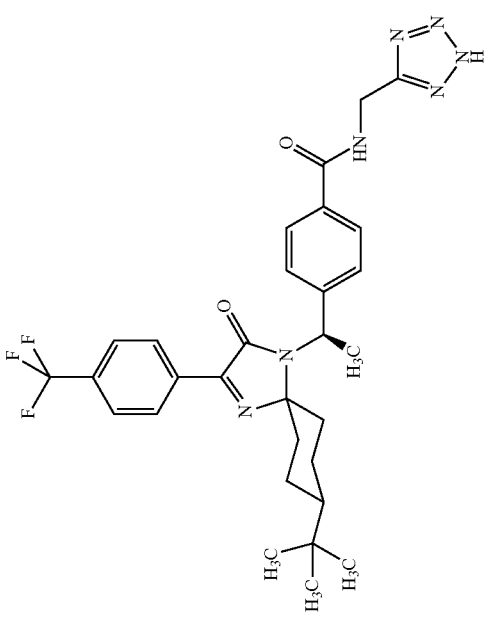 | 4 | 5.42 | 582.3 |
| I | K14 | A22 | M7 | 1.562 | 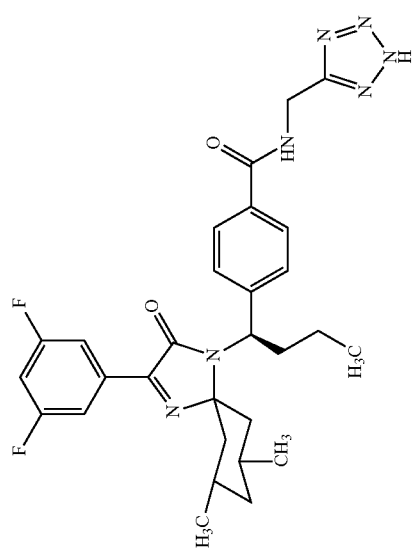 | 5 | 18.0 (22) | 550.1 |

TABLE 1-continued

| AAR | K1 | A2 | M203 | 1.563 | | 4 | 6.94 | 600.3 |
| AAA | K1 | A12 | M1 | 1.564 | | 4 | 6.05 | 508.3 |

TABLE 1-continued
| | | | | | | |
|---|---|---|---|---|---|---|
| J | K4 | A1 | M4 | 1.565 | 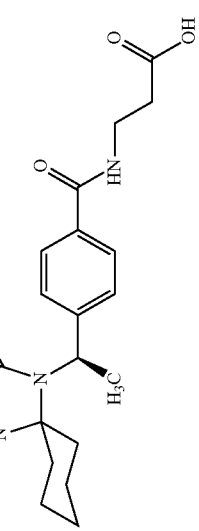 | 4 5.23 516.3 |
| AAK | K1 | A2 | M50 | 1.566 | 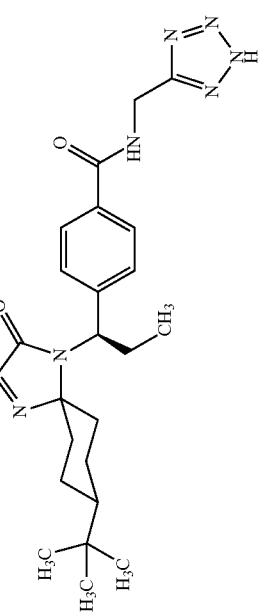 | 4 5.86 596.3 |

TABLE 1-continued
| | | | | | | |
|---|---|---|---|---|---|---|
| AAT | K1 | A25 | M4 | 1.567 | 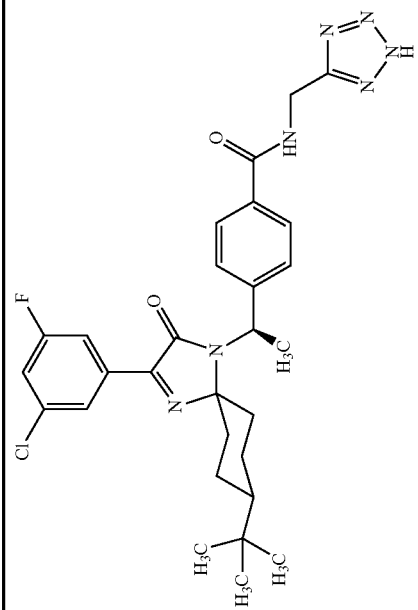 | 3 2.49 566.2 |
| AAJ | K14 | A12 | M50 | 1.568 | 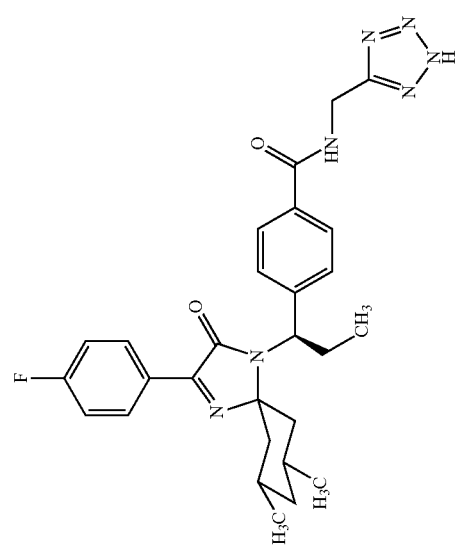 | 3 2.31 518.2 |

TABLE 1-continued
| AAR | | | | | | |
|---|---|---|---|---|---|---|
| I | K1 | A12 | M203 | 1.569 | 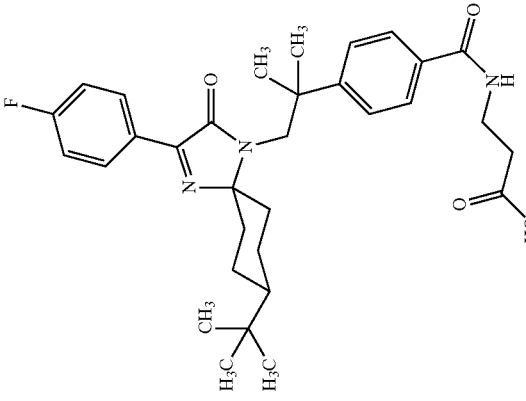 | 4 6.49 550.3 |
| | K1 | A9 | M4 | 1.570 | 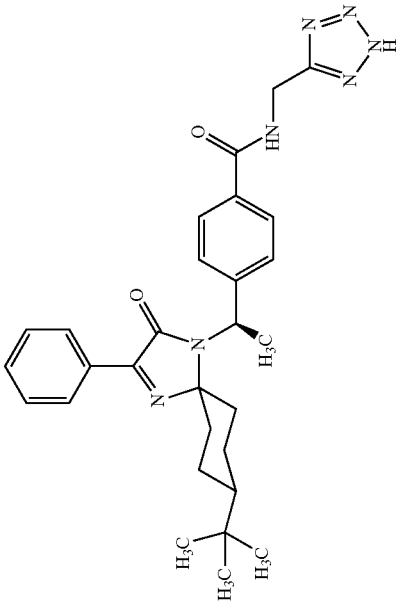 | 4 5.32 514.3 |

| AAK | K1 | A2 | M4 | 1.571 | ![structure] | 4 | 5.31 | 582.3 |
| AAK | K1 | A2 | M3 | 1.572 | ![structure] | 4 | 6.72 | 582.3 |

TABLE 1-continued
| AAR | K5 | A1 | M204 | 1.573 | 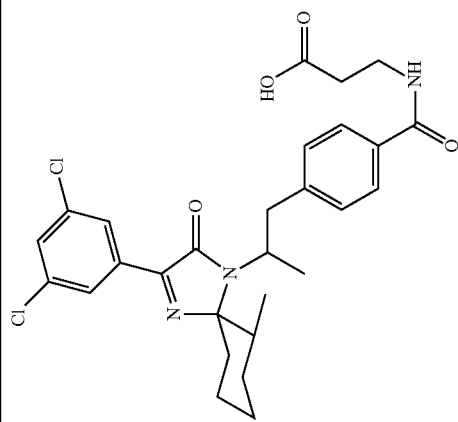 (±)-mixture of diastereomers | 3 | 2.45, 2.47 | 544 |
| H | K1 | A6 | M4 | 1.574 | 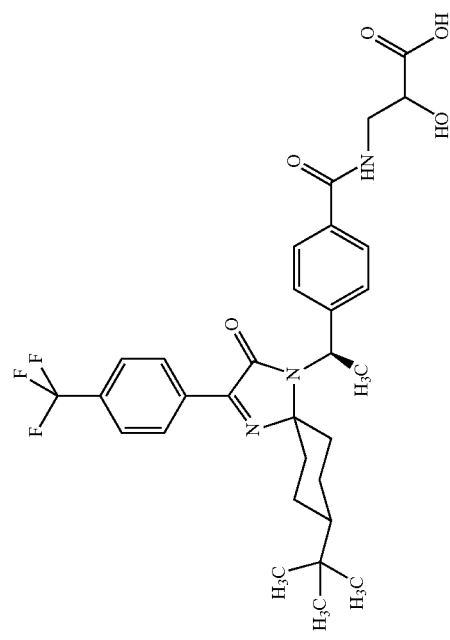 | 4 | 5.42 | 588.3 |

TABLE 1-continued
| | | | | | | | |
|---|---|---|---|---|---|---|---|
| H | K1 | A12 | M4 | 1.575 | 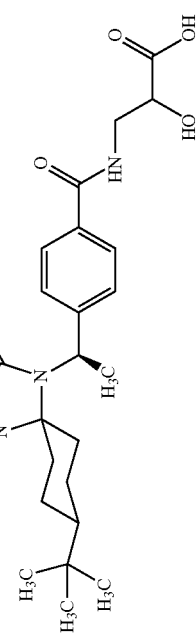 | 4 | 5.08 | 538.3 |
| CA | K90 | A1 | M50 | 1.900 | 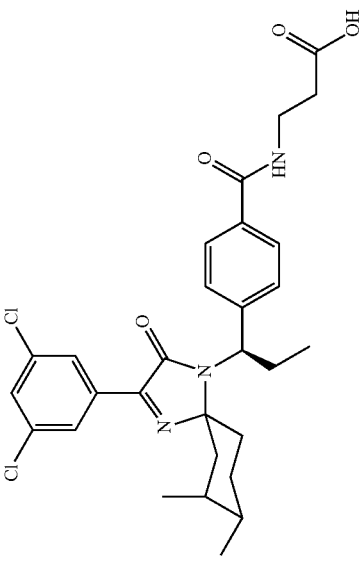 | 4 | 7.4 | 558.3 |

TABLE 1-continued

| | | | | | | |
|---|---|---|---|---|---|---|
| J | K14 | A1 | M50 | 1.901 | [structure] | 4 | 7.7 | 558.3 |
| CA | K3 | A1 | M50 | 1.902 | [structure] | 4 | 8.3 | 600.3 |
| CA | K92 | A1 | M50 | 1.903 | [structure] | 4 | 6.8 | 598.3 |

TABLE 1-continued
| J | K3 | A1 | M13 | 1.904 | 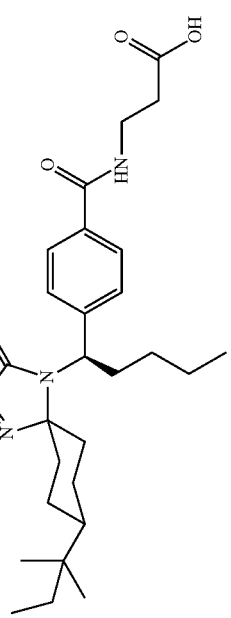 | 4 | 8.8 | 628.3 |
| CA | K91 | A1 | M50 | 1.905 | 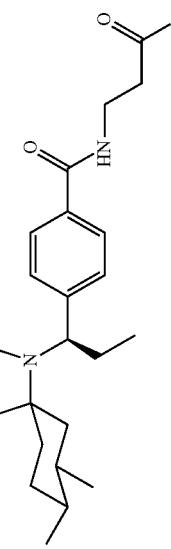 | 4 | 8.1 | 558.3 |

TABLE 1-continued
| | | | | | | |
|---|---|---|---|---|---|---|
| J | K14 | A17 | M50 | 1.906 | 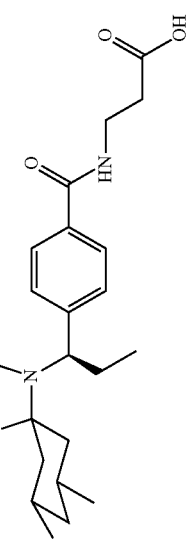 | 4 | 3.9 | 542.3 |
| J | K1 | A17 | M50 | 1.907 | 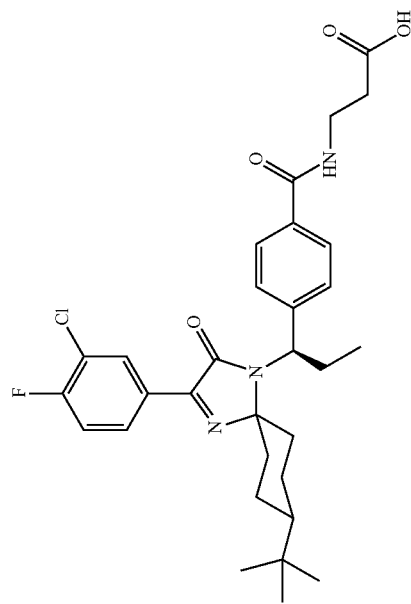 | 4 | 5.9 | 570.3 |

TABLE 1-continued
| J | K95 | A1 | M50 | 1.908 | 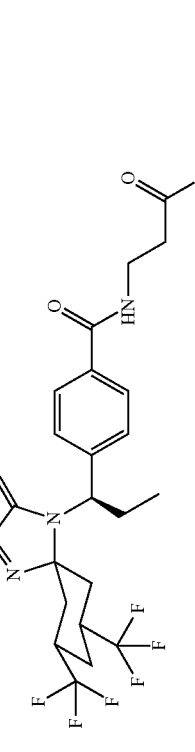 | 4 | 6.9 | 666.4 |
| J | K3 | A17 | M50 | 1.909 | 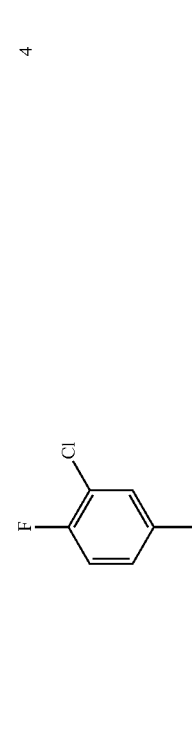 | 4 | 6.0 | 584.3 |

TABLE 1-continued
| | | | | | | |
|---|---|---|---|---|---|---|
| J | K3 | A17 | M7 | 1.910 | 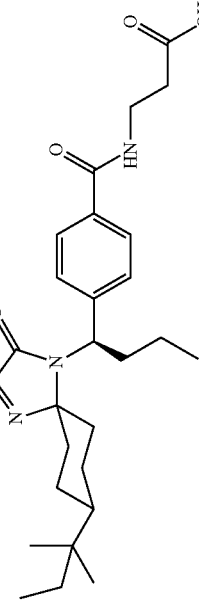 | 4 | 8.0 | 598.3 |
| CA | K92 | A1 | M50 | 1.911 | 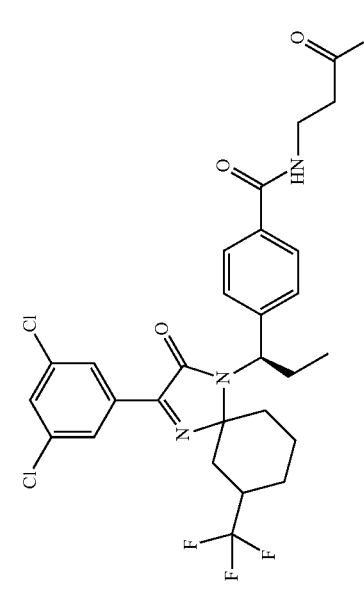 | 4 | 6.8 | 598.3 |

| | | | | | | |
|---|---|---|---|---|---|---|
| J | K1 | A5 | M90 | 1.912 | 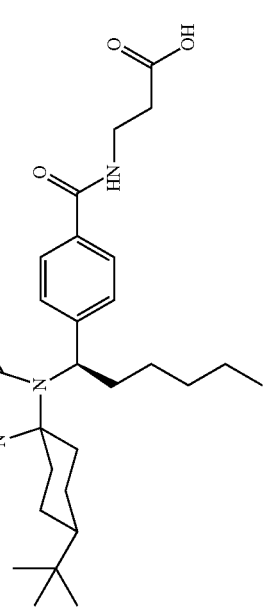 | 4 | 6.5 | 594.3 |
| J | K14 | A17 | M13 | 1.913 | 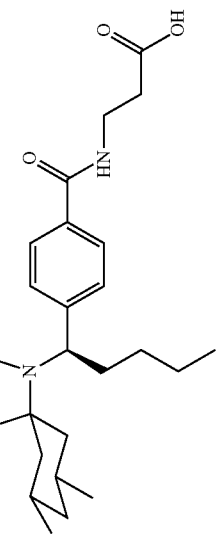 | 4 | 7.5 | 570.3 |

| | | | | | | |
|---|---|---|---|---|---|---|
| I | K3 | A1 | M3 | 1.914 | 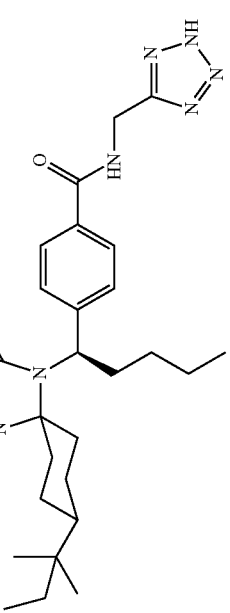 | 4 | 8.9 | 638.4 |
| J | K1 | A17 | M90 | 1.915 | 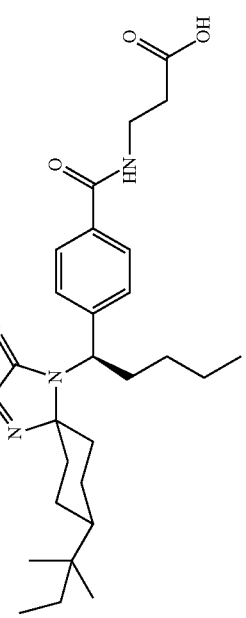 | 4 | 8.2 | 612.3 |

TABLE 1-continued
| J | K2 | A17 | M13 | 1.916 | 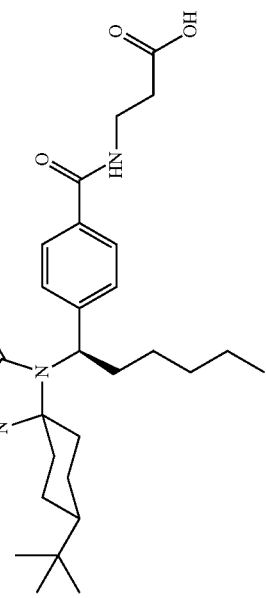 | 4 | 6.6 | 612.3 |
| J | K2 | A17 | M13 | 1.917 | 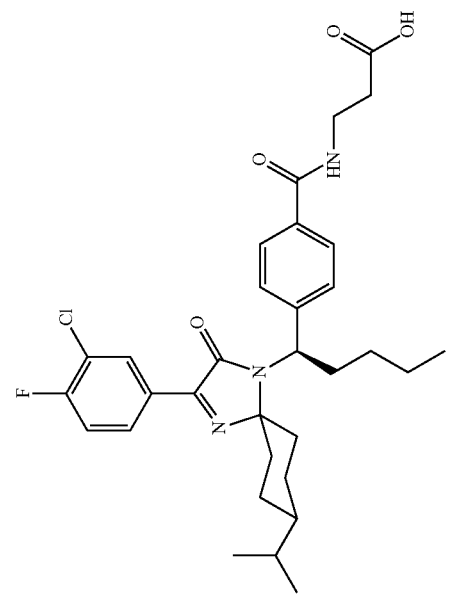 | 4 | 7.8 | 584.3 |

TABLE 1-continued

| I | K3 | A1 | M7 | 1.918 | | 4 | 4.7 | 624.3 |
| I | K3 | A1 | M50 | 1.919 | | 4 | 8.1 | 610.3 |

TABLE 1-continued
| | | | | | | | |
|---|---|---|---|---|---|---|---|
| I | K14 | A1 | M50 | 1.920 | 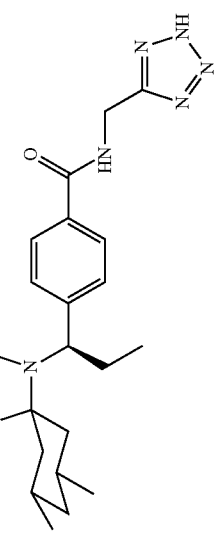 | 4 | 7.4 | 568.3 |
| I | K1 | A5 | M90 | 1.921 | 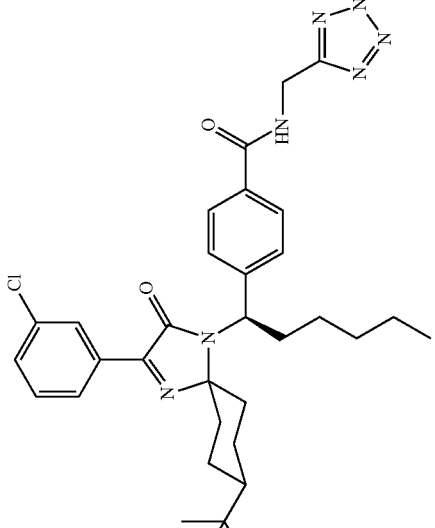 | 4 | 8.2 | 604.3 |

TABLE 1-continued
| | | | | | |
|---|---|---|---|---|---|
| CB | K14 | A6 | M50 | 1.922 | 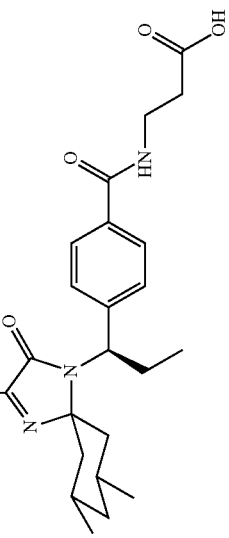 4 6.9 558.3 |
| I | K1 | A17 | M90 | 1.923 | 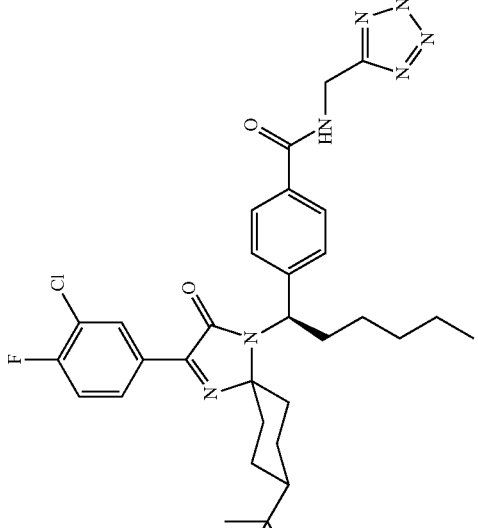 4 8.3 622.3 |

TABLE 1-continued

| CB | K92 | A6 | M50 | 1.924 | | 4 | 6.5 | 598.3 |
| I | K2 | A17 | M13 | 1.925 | | 4 | 7.7 | 594.3 |

TABLE 1-continued
| | | | | | | | |
|---|---|---|---|---|---|---|---|
| I | K1 | A17 | M50 | 1.926 | 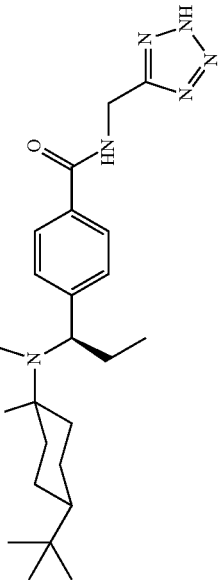 | 4 | 7.3 | 580.3 |
| I | K3 | A17 | M13 | 1.927 | 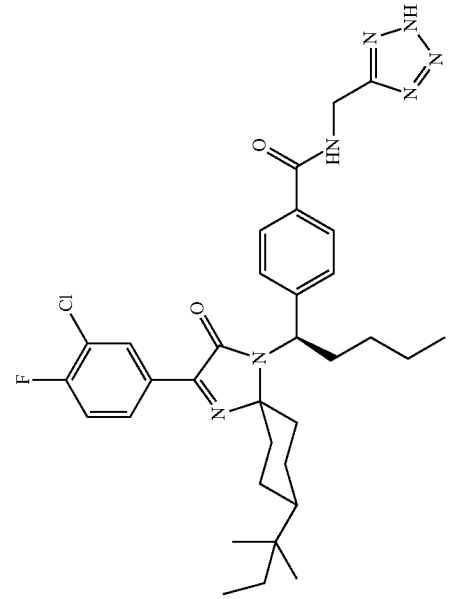 | 4 | 8.1 | 622.3 |

TABLE 1-continued

| J | K1 | A5 | M90 | 1.928 | *[structure]* | 4 | 6.4 | 594.3 |
| J | K4 | A17 | M13 | 1.929 | *[structure]* | 4 | 6.9 | 542.3 |

TABLE 1-continued
| I | K3 | A17 | M50 | 1.930 | 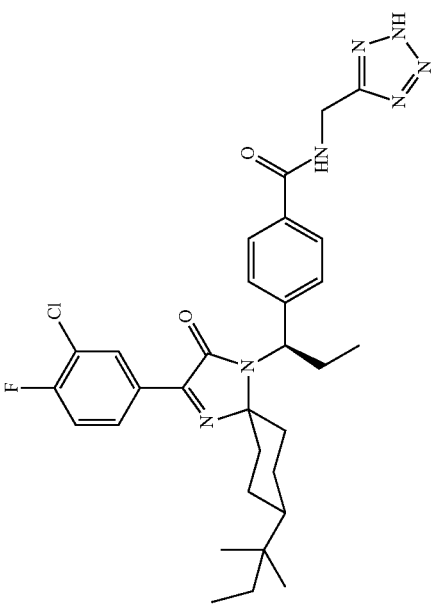 | 4 | 7.7 | 594.32 |
| CB | K6 | A6 | M50 | 1.931 | 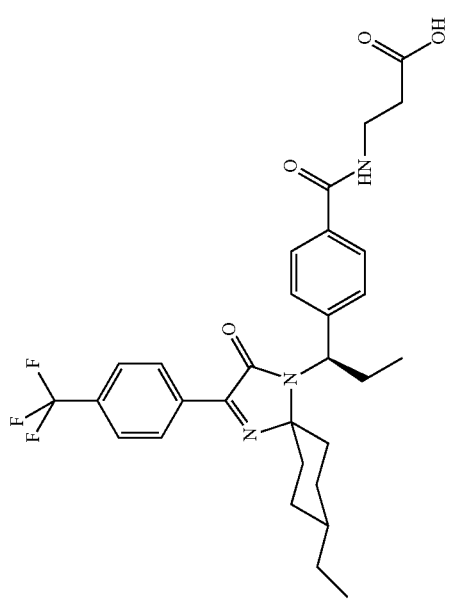 | 4 | 7.0 | 558.3 |

TABLE 1-continued

| | | | | | | |
|---|---|---|---|---|---|---|
| I | K3 | A17 | M7 | 1.932 | 4 | 8.0 | 608.3 |
| I | K14 | A17 | M13 | 1.933 | 4 | 7.4 | 580.3 |

TABLE 1-continued
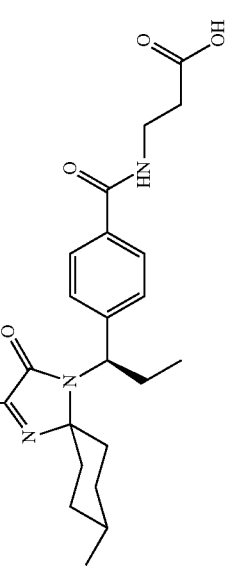
| CB | K9 | A6 | M50 | 1.934 | | 4 | 6.7 | 544.3 |
| I | K14 | A17 | M50 | 1.935 | | 4 | 3.8 | 552.3 |

TABLE 1-continued
| CB | K11 | A6 | M50 | 1.936 | 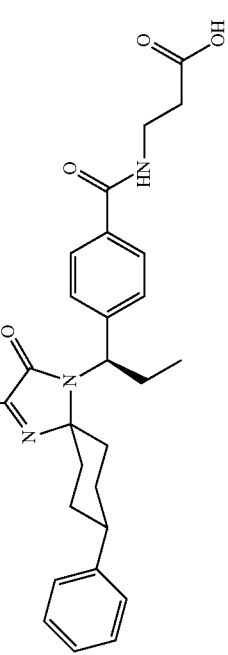 | 4 | 6.9 | 606.3 |
| J | K92 | A1 | M4 | 1.937 | 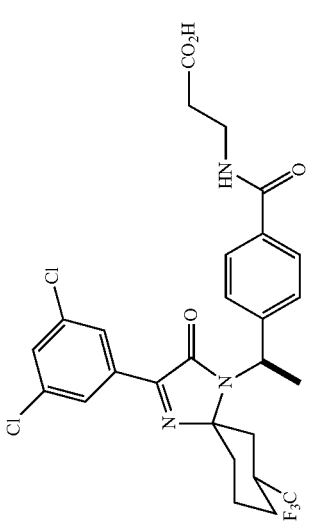 | 4 | 5.3 | 584.3 |

TABLE 1-continued

| | | | | | | |
|---|---|---|---|---|---|---|
| I | K95 | A22 | M6 | 1.938 | (structure) | 4 | 7.3 | 700.4 |
| J | K93 | A1 | M4 | 1.939 | (structure) Isomer 2 | 4 | 5.4 | 584.3 |

TABLE 1-continued
| CB | K92 | A6 | M50 | 1.940 | 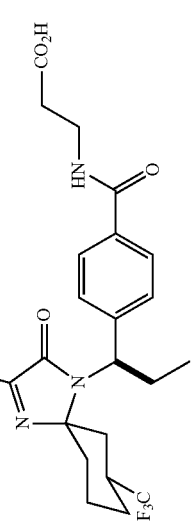 Isomer 1 | 4 | 6.6 | 598.3 |
| CB | K93 | A6 | M50 | 1.941 | 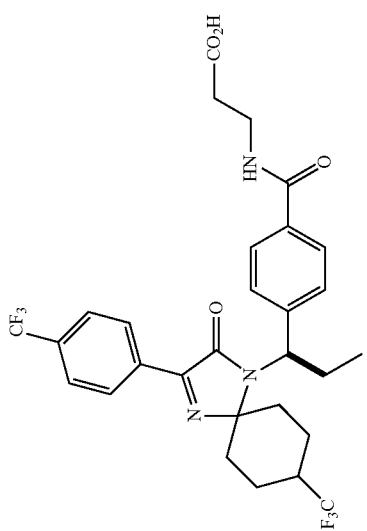 Isomer 2 | 4 | 6.5 | 598.3 |

TABLE 1-continued

| | | | | | | |
|---|---|---|---|---|---|---|
| J | K93 | A1 | M4 | 1.942 | | 4 | 5.3 | 584.3 |
| CB | K4 | A6 | M50 | 1.943 | Isomer 1 | 4 | 6.4 | 530.3 |

TABLE 1-continued
| I | K4 | A17 | M13 | 1.944 | 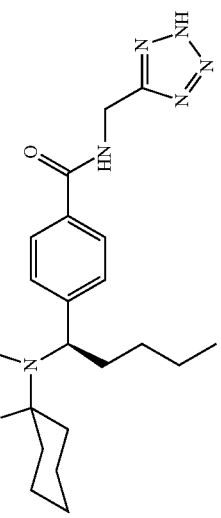 | 4 | 6.9 | 552.3 |
| CB | K94 | A6 | M50 | 1.945 | 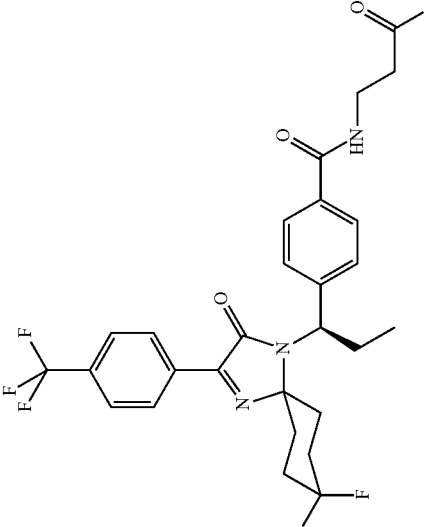 | 4 | 6.1 | 566.3 |

TABLE 1-continued
| CB | K93 | A6 | M50 | 1.946 | 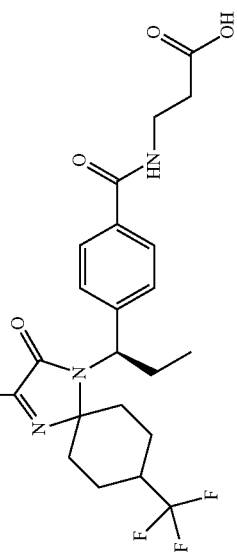 Isomer 1 | 4 | 6.4 | 598.3 |
| J | K92 | A1 | M4 | 1.947 | 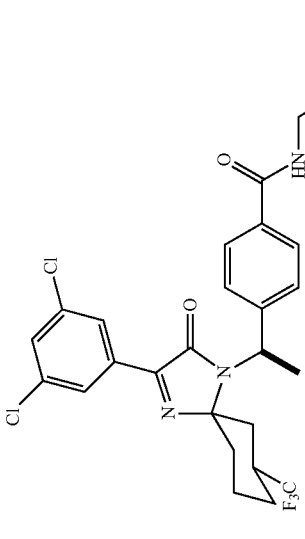 Isomer 1 | 4 | 5.4 | 584.3 |

TABLE 1-continued
| | | | | | | | |
|---|---|---|---|---|---|---|---|
| I | K1 | A5 | M91 | 1.948 | 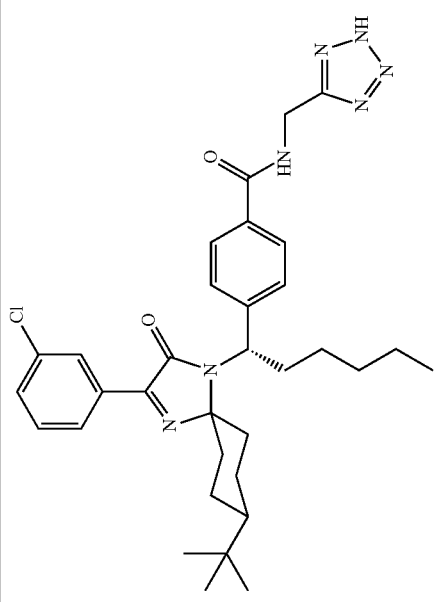 | 4 | 6.4 | 604.3 |
| J | K1 | A2 | M92 | 1.949 | 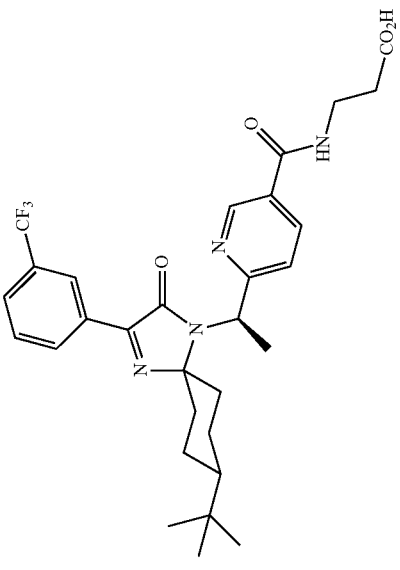 | 4 | 5.3 | 573.3 |

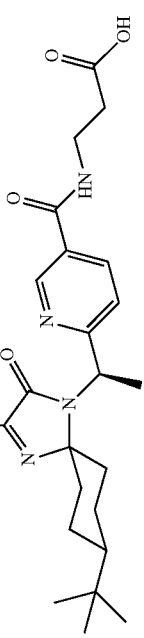

TABLE 1-continued

| CF | K2 | A1 | M50 | 1.952 | [structure with 3,5-dichlorophenyl, isopropylcyclohexyl spiro, propyl, 4-(carboxyethylaminocarbonyl)phenyl] | 4 | 6.3 | 572.3 |
| CF | K1 | A5 | M50 | 1.953 | [structure with 3-chlorophenyl, tert-butylcyclohexyl spiro, propyl, 4-(carboxyethylaminocarbonyl)phenyl] | 4 | 5.9 | 552.3 |

TABLE 1-continued
| CF | K2 | A6 | M50 | 1.954 | 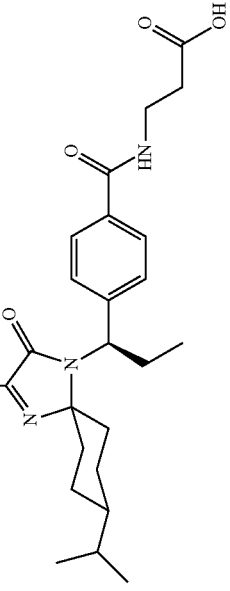 | 4 | 5.7 | 572.3 |
| CF | K1 | A6 | M50 | 1.955 | 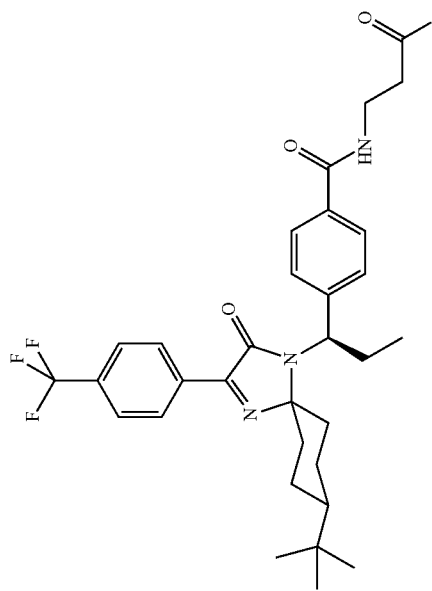 | 4 | 5.8 | 586.3 |

TABLE 1-continued
| CF | K1 | A1 | M94 | 1,956 | 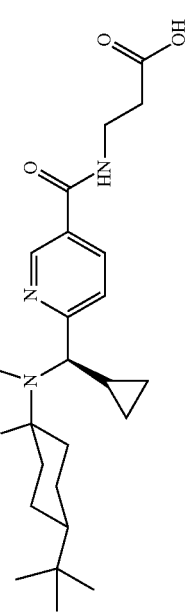 | 4 | 6.2 | 599.3 |
| CF | K1 | A71 | M50 | 1,957 | 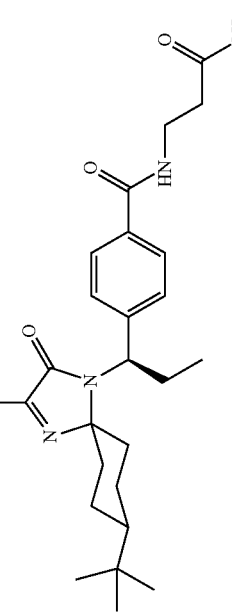 | 4 | 3.5 | 519.3 |

TABLE 1-continued
| | | | | | | | |
|---|---|---|---|---|---|---|---|
| CF | K1 | A2 | M94 | 1.958 | 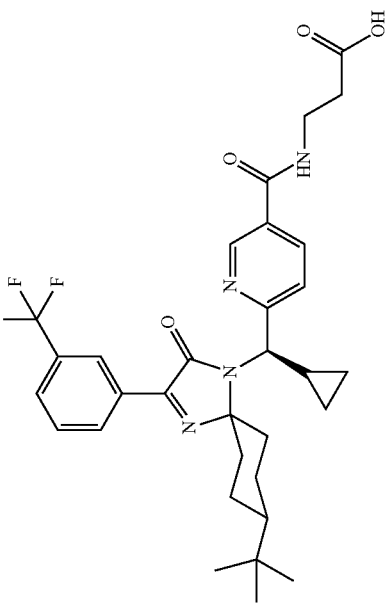 | 4 | 5.5 | 599.3 |
| CE | K2 | A1 | M3 | 1.959 | 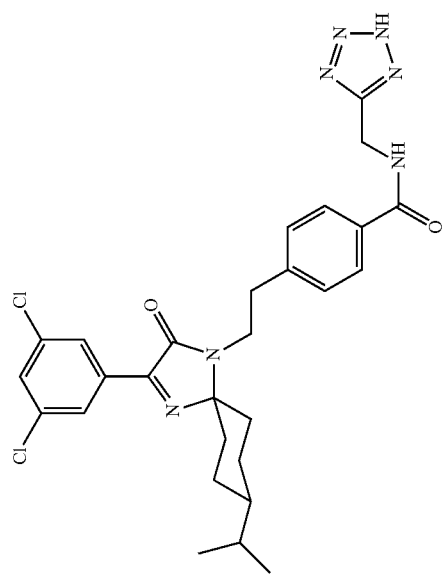 | 4 | 6.0 | 568.3 |

TABLE 1-continued

| CB | K3 | A6 | M50 | 1.960 | | 3 | 2.5 | 600 |
| CF | K1 | A71 | M8 | 1.961 | | 4 | 4.7 | 533.3 |

TABLE 1-continued

| | | | | | | |
|---|---|---|---|---|---|---|
| CF | K1 | A71 | M7 | 1,962 | *(structure)* | 4 | 4.8 | 533.3 |
| CF | K2 | A5 | M50 | 1,963 | *(structure)* | 4 | 7.1 | 538.3 |
| CF | K3 | A5 | M50 | 1,964 | *(structure)* | 1 | 2.5 | 566 |

TABLE 1-continued

| CE | K1 | A5 | M50 | 1.965 | [structure] | 2 | 5.2 | 562 |
|----|----|----|-----|-------|-------------|---|-----|-----|
| CE | K2 | A5 | M50 | 1.966 | [structure] | 1 | 2.3 | 548 |

TABLE 1-continued
| CE | K1 | A17 | M7 | 1.967 | 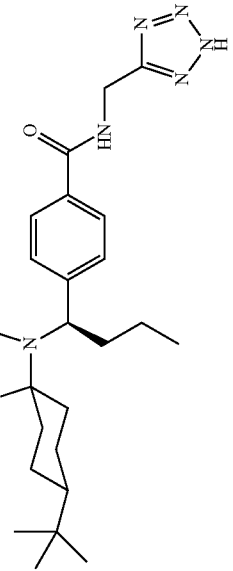 | 2 | 5.5 | 594.3 |
| CE | K3 | A2 | M7 | 1.969 | 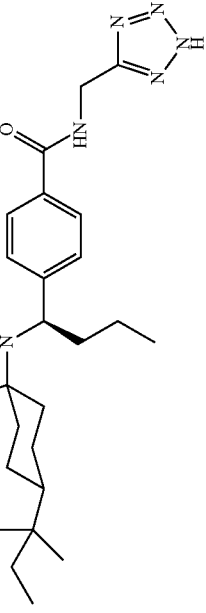 | 2 | 5.6 | 624 |

TABLE 1-continued
| CE | K14 | A2 | M7 | 1.970 | 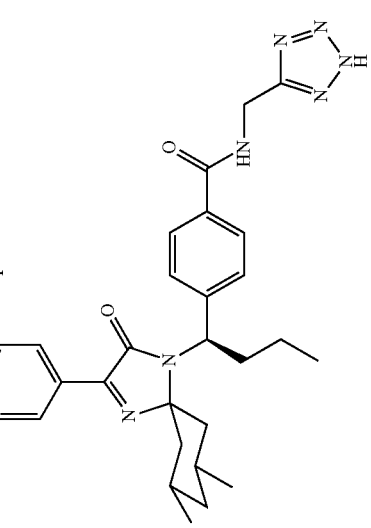 | 1 | 2.3 | 582 |
| CF | K1 | A17 | M7 | 1.971 | 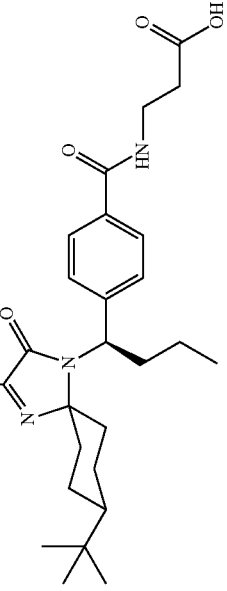 | 1 | 2.5 | 584.3 |

TABLE 1-continued

| CE | K3 | A5 | M13 | 1.972 | [structure] | 1 | 2.6 | 604.3 |
| CE | K2 | A5 | M13 | 1.973 | [structure] | 1 | 2.5 | 576.3 |

TABLE 1-continued

| CE | K3 | A5 | M7 | 1.974 | | 1 | 2.5 | 590.3 |
| CE | K14 | A5 | M13 | 1.975 | | 1 | 2.4 | 562.3 |

TABLE 1-continued
| | | | | | | | |
|---|---|---|---|---|---|---|---|
| CF | K1 | A1 | K93 | 1.976 | 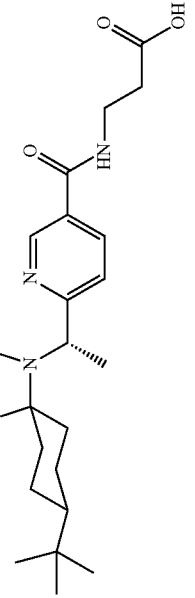 | 1 | 2.9 | 573 |
| CE | K1 | A1 | M13 | 1.977 | 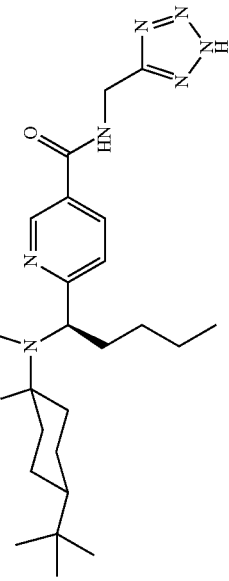 | 1 | 2.7 | 625.3 |
| CF | K1 | A2 | M95 | 1.978 | 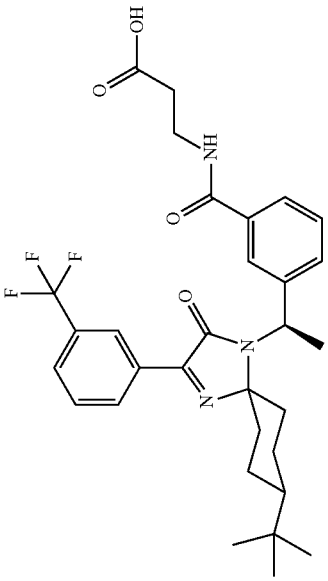 | 3 | 2.6 | 572 |

TABLE 1-continued
| | | | | | | | | |
|---|---|---|---|---|---|---|---|---|
| CF | K1 | A1 | M95 | 1.979 | 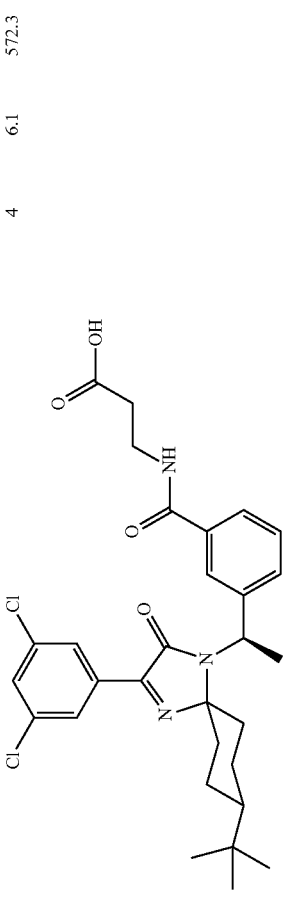 | 4 | 6.1 | 572.3 |
| J | K203 | A1 | M51 | 1.980 | 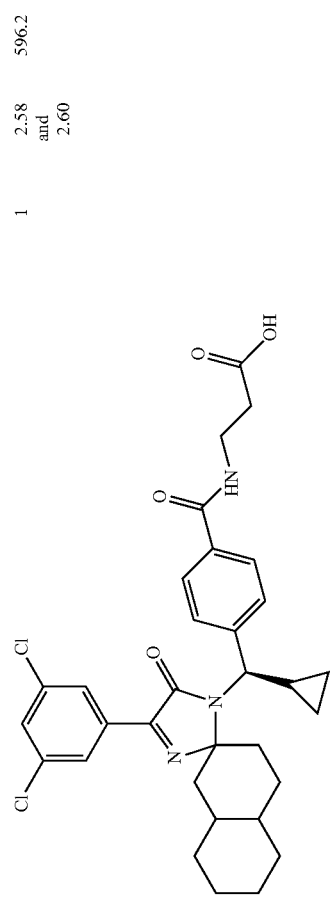<br>Mixture of isomers | 1 | 2.58 and 2.60 | 596.2 |
| J | K203 | A1 | M6 | 1.981 | 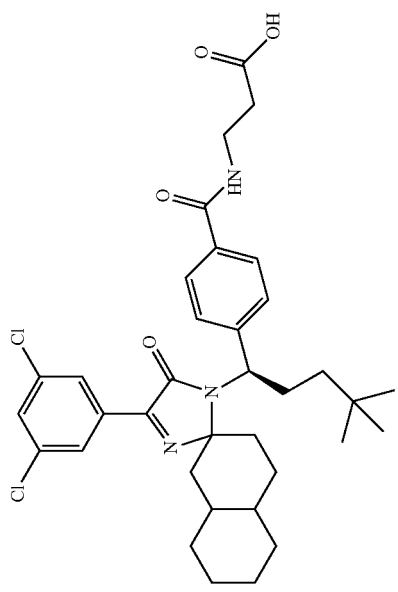<br>Mixture of isomers | 4 | 7.21 | 640.4 |

TABLE 1-continued
| | K203 | A1 | M6 | 1.982 | | 4 | 4.77 | 650.4 |
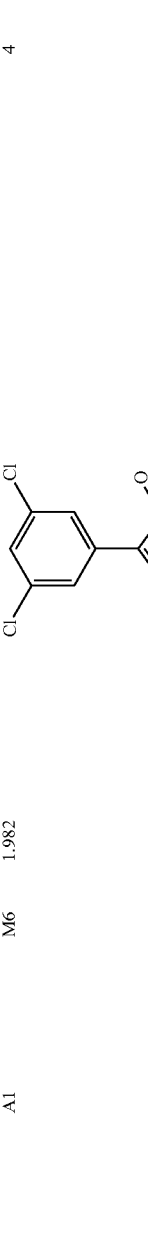
Mixture of isomers
| Scheme | Ketone | Boronic acid | Amine | Ex. | | LC | Ret (min) | LCMS (MH)+ |
|---|---|---|---|---|---|---|---|---|
| AD | K2 | (HO)₂B–(3-Cl-C₆H₄) | M3 | 2.1 | | 5 | 20.9 (22) | 524.2 |

TABLE 1-continued

| | | | | | | | |
|---|---|---|---|---|---|---|---|
| AD | K1 | ![3,5-bis(CF3)phenylboronic acid] | M3 | 2.2 | ![structure with F3C, CF3, tert-butyl adamantane, benzamide-NHCH2CH2CO2H] | 5 | 21.3 (22) | 640.2 |
| AD | K14 | ![4-OCF3 phenylboronic acid] | M3 | 2.3 | ![structure with OCF3, adamantane, benzamide-NHCH2CH2CO2H] | 5 | 18.1 (22) | 560.2 |

TABLE 1-continued

| AD | K14 | ![3-fluorophenylboronic acid] | M3 | 2.4 | ![structure with 3-fluorophenyl] | 5 | 16.1 (22) | 494.3 |
| AD | K14 | ![3,5-difluorophenylboronic acid] | M3 | 2.5 | ![structure with 3,5-difluorophenyl] | 5 | 17.1 (22) | 512.3 |

TABLE 1-continued
| AG | K1 | 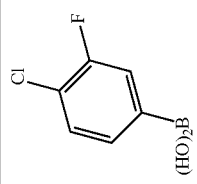 | M13 | 2.6 | 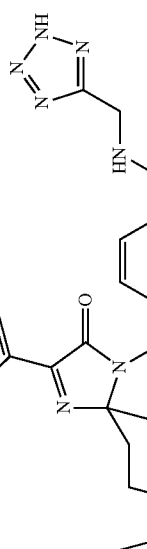 | 5 | 21.4 (25) | 608.1 |
| AG | K1 | 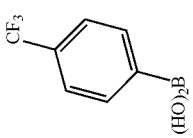 | M13 | 2.7 | 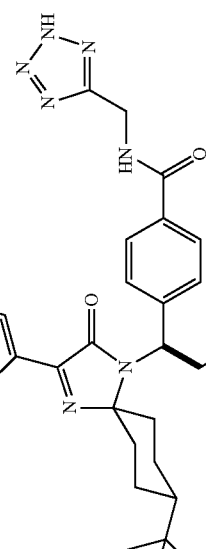 | 5 | 19.8 (25) | 624.1 |

TABLE 1-continued

| AG | K1 | [structure: 4-Cl, 3-F phenyl boronic acid] | M13 | 2.8 | [structure: biaryl imidazolone with 4-Cl-3'-F substitution, tetrazolylmethyl benzamide] | 5 | 22.5 (26) | 702.2 |
| AG | K1 | [structure: 3-Cl, 5-CF3 phenyl boronic acid] | M13 | 2.9 | [structure: 3,5-disubstituted phenyl imidazolone with tetrazolylmethyl benzamide] | 5 | 20.4 (25) | 658.3 |

TABLE 1-continued

| | | | | | | | |
|---|---|---|---|---|---|---|---|
| AG | K1 | ![F3C, F, (HO)2B aryl] | M13 | 2.10 | ![structure] | 5 | 21.0 (25) | 642.3 |
| AH | K1 | ![F3C, Cl, (HO)2B aryl] | M13 | 2.11 | ![structure] | 5 | 20.3 (25) | 648.3 |

TABLE 1-continued
| | | | | | | | | |
|---|---|---|---|---|---|---|---|---|
| AH |  | K1 | M13 | 2.12 |  | 5 | 21.4 (25) | 632.3 |
| AG | 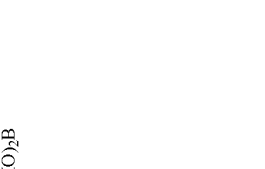 | K1 | M13 | 2.13 | 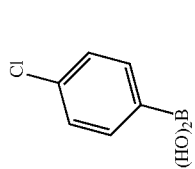 | 5 | 20.6 (25) | 590.2 |

TABLE 1-continued
| AG | K1 | 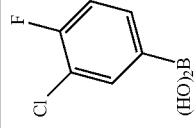 | M13 | 2.14 | 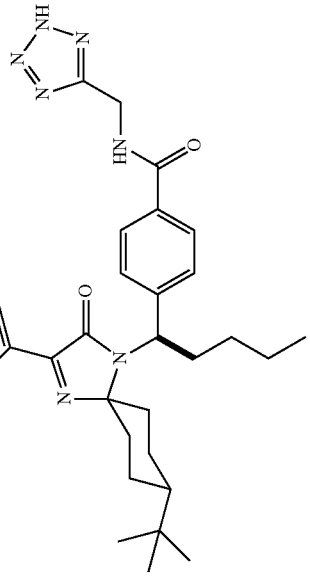 | 5 | 21.1 (25) | 608.1 |
| AG | K1 | 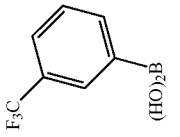 | M13 | 2.15 | 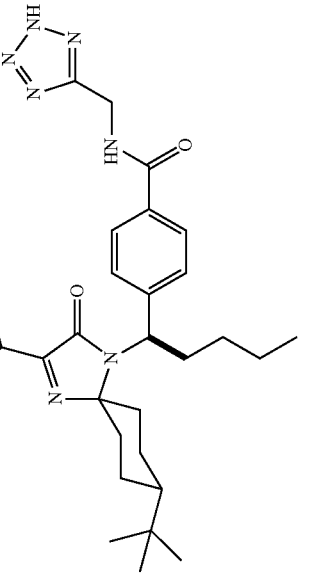 | 5 | 16.4 (25) | 624.4 |

TABLE 1-continued

| AH | K1 | Cl-C6H4-B(OH)2 | M13 | 2.16 | [structure: 4-Cl-phenyl imidazolone with cyclohexyl-tBu, pentyl chain, benzamide-NH-CH2CH2-CO2H] | 5 | 19.6 (25) | 580.3 |
| AH | K1 | 3-Cl-4-F-C6H3-B(OH)2 | M13 | 2.17 | [structure: 3-Cl-4-F-phenyl imidazolone with cyclohexyl-tBu, pentyl chain, benzamide-NH-CH2CH2-CO2H] | 5 | 21.6 (25) | 598.3 |

TABLE 1-continued

| AH | K1 | ![3-fluoro-4-chlorophenylboronic acid] | M13 | 2.18 | ![structure 809] | 5 | 18.9 (26) | 598.3 |
| AH | K1 | ![3-fluoro-4-chlorophenylboronic acid] | M13 | 2.19 | ![structure 810] | 5 | 22.5 (26) | 692.4 |

TABLE 1-continued

| | | | | | | | |
|---|---|---|---|---|---|---|---|
| AH | K1 | CF3-C6H4-B(OH)2 | M13 | 2.20 | | 5 | 20.3 (25) | 614.2 |
| AG | K1 | OCF3-C6H4-B(OH)2 | M13 | 2.21 | | 5 | 18.2 (26) | 640.3 |

TABLE 1-continued

| | | | | | | | |
|---|---|---|---|---|---|---|---|
| AH | K1 | [4-OCF3-phenyl-B(OH)2] | M13 | 2.22 | [structure] | 5 | 18.0 (26) | 630.3 |
| AG | K1 | [3-CF3-phenyl-B(OH)2] | M13 | 2.23 | [structure] | 5 | 19.5 (34) | 640.1 |

TABLE 1-continued
| AH | K1 | 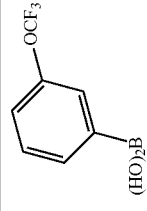 | M13 | 2.24 | 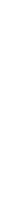 | 5 | 19.7 (34) | 630.3 |
| AH | K1 | | M13 | 2.25 | | 5 | 20.3 (34) | 580.3 |

TABLE 1-continued

| AG | K3 | ![3-fluorophenylboronic acid] | M7 | 2.26 | ![structure] | 5 | 19.8 (25) | 574.3 |
| AG | K3 | ![3-fluoro-5-trifluoromethylphenylboronic acid] | M7 | 2.27 | ![structure] | 5 | 22.0 (25) | 642.4 |
| AG | K2 | ![3-fluorophenylboronic acid] | M7 | 2.28 | ![structure] | 5 | 16.0 (25) | 547.3 |

TABLE 1-continued
| AG | K2 | 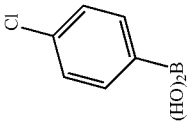 | M7 | 2.29 | 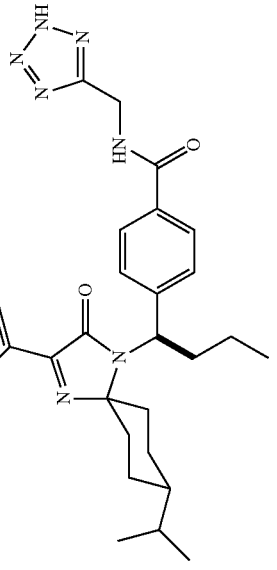 | 5 | 18.0 (25) | 563.3 |
| AG | K2 | 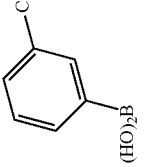 | M7 | 2.30 | 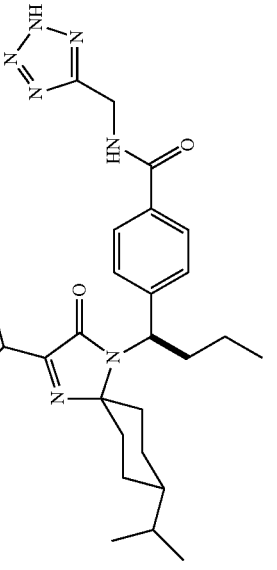 | 5 | 18.1 (25) | 563.3 |

TABLE 1-continued

| | | | | | | |
|---|---|---|---|---|---|---|
| AG | K2 | M7 | 2.31 | | 5 | 21.2 (25) 631.3 |
| AG | K3 | M7 | 2.32 | | 5 | 21.1 (26) 658.3 |
| AH | K3 | M7 | 2.33 | | 5 | 16.5 (26) 564.3 |

TABLE 1-continued

| AH | K3 | ![3-fluoro-5-trifluoromethylphenylboronic acid] | M7 | 2.34 | ![structure 823] | 5 | 18.6 (26) | 632.3 |
| AH | K3 | ![3-chloro-5-trifluoromethylphenylboronic acid] | M7 | 2.35 | ![structure 824] | 5 | 21.1 (26) | 648.3 |

TABLE 1-continued

| AG | K1 | OCF₃ ⟨phenyl⟩-B(OH)₂ | M7 | 2.36 | ⟨structure⟩ | 5 | 17.0 (26) | 626.4 |
| AG | K1 | OCF₃ ⟨phenyl⟩-B(OH)₂ | M7 | 2.37 | ⟨structure⟩ | 5 | 16.7 (26) | 626.4 |

TABLE 1-continued

| AH | K2 | (structure: 4-Cl-C6H4-B(OH)2) | M7 | 2.38 | (compound structure) | 5 | 18.3 (25) | 552.1 |
| AH | K2 | (structure: 3-Cl-5-CF3-C6H3-B(OH)2) | M7 | 2.39 | (compound structure) | 5 | 21.6 (25) | 620.2 |

TABLE 1-continued
| AG | K3 | 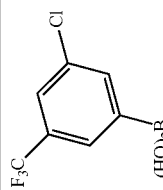 | M7 | 2.40 | 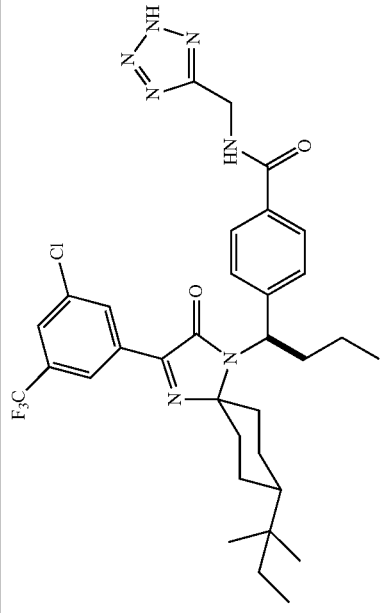 | 5 | 17.6 (26) | 608.3 |
| AG | K3 | 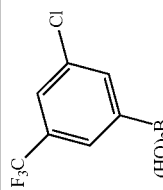 | M7 | 2.41 | 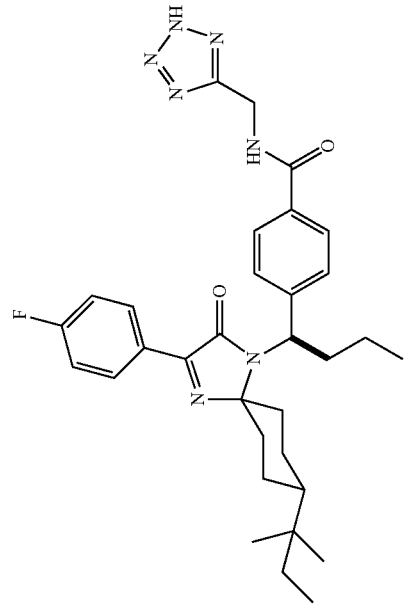 | 5 | 13.6 (26) | 574.3 |

TABLE 1-continued
| | | | | | | | |
|---|---|---|---|---|---|---|---|
| AG | K3 | 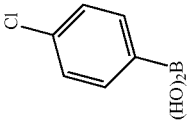 | M7 | 2.42 | 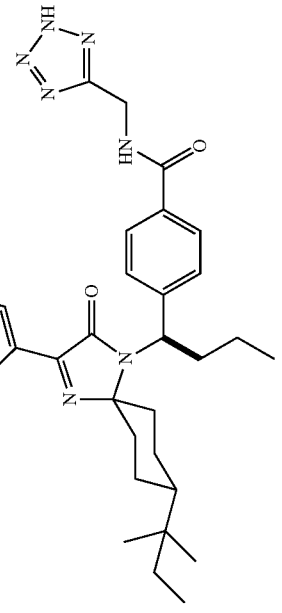 | 5 | 16.5 (26) | 590.3 |
| AH | K1 | 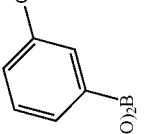 | M7 | 2.43 | | 5 | 16.7 (26) | 616.4 |

TABLE 1-continued

| AG | K1 | F3C-C6H3(Cl)-B(OH)2 | M7 | 2.44 | [structure] | 5 | 19.3 (26) | 644.3 |
| AG | K1 | CF3-C6H4-B(OH)2 | M7 | 2.45 | [structure] | 5 | 16.2 (26) | 610.4 |

TABLE 1-continued

| AG | K1 | (3-F,5-CF₃-phenyl)B(OH)₂ | M7 | 2.46 | [structure with tert-butyl cyclohexyl] | 5 | 16.8 (26) | 628.4 |
| AG | K2 | (3-F,5-CF₃-phenyl)B(OH)₂ | M7 | 2.47 | [structure with isopropyl cyclohexyl] | 5 | 18.5 (25) | 614.2 |

TABLE 1-continued
| | | | | | | | |
|---|---|---|---|---|---|---|---|
| AH | K2 | 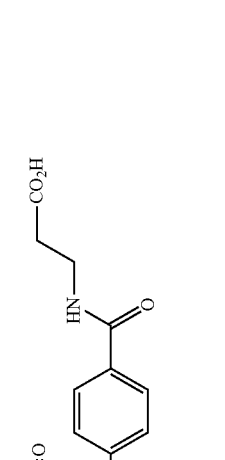 | M7 | 2.48 | 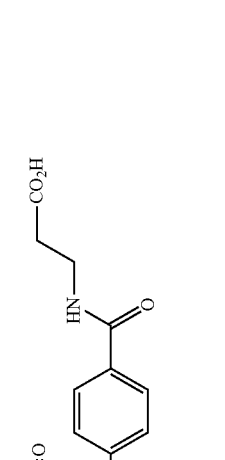 | 5 | 19.0 (25) | 604.3 |
| AG | K2 |  | M7 | 2.49 |  | 5 | 18.0 (25) | 612.2 |
| AG | K3 |  | M7 | 2.50 |  | 5 | 18.3 (26) | 640.3 |

TABLE 1-continued
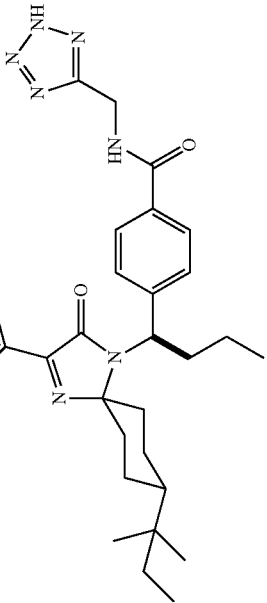

TABLE 1-continued

| AH | K1 | ![OCF3 phenylboronic acid] | M7 | 2.53 | ![structure with OCF3 aryl, imidazolone, cyclohexyl-tBu, butyl, benzamide-propanoic acid] | 5 | 16.9 (26) | 616.4 |
| AH | K1 | ![3-Cl-5-CF3 phenylboronic acid] | M7 | 2.54 | ![structure with 3-Cl-5-CF3 aryl, imidazolone, cyclohexyl-tBu, butyl, benzamide-propanoic acid] | 5 | 19.4 (26) | 634.3 |

TABLE 1-continued

| AH | K1 | ![4-CF3-phenylboronic acid] | M7 | 2.55 | ![structure K1] | 5 | 16.4 (26) | 600.4 |
| AH | K2 | ![3-OCF3-phenylboronic acid] | M7 | 2.56 | ![structure K2] | 5 | 18.6 (25) | 602.1 |

TABLE 1-continued

| AG | K2 | OCF₃-C₆H₄-B(OH)₂ | M7 | 2.57 | [structure with OCF₃ aryl] | 5 | 16.2 (26) | 612.4 |
| AG | K2 | CF₃-C₆H₄-B(OH)₂ | M7 | 2.58 | [structure with 3-CF₃ aryl] | 5 | 15.7 (26) | 596.4 |

TABLE 1-continued

| | | | | | | | |
|---|---|---|---|---|---|---|---|
| AH | K1 | (structure: 3-F, 5-CF$_3$ phenylboronic acid) | M7 | 2.59 | (structure) | 5 | 17.4 (26) | 618.4 |
| AH | K3 | (structure: 3-Cl, 5-F phenylboronic acid) | M7 | 2.60 | (structure) | 5 | 20.1 (26) | 598.4 |

TABLE 1-continued
| | | | | | | | |
|---|---|---|---|---|---|---|---|
| AH | K3 |  | M7 | 2.61 | 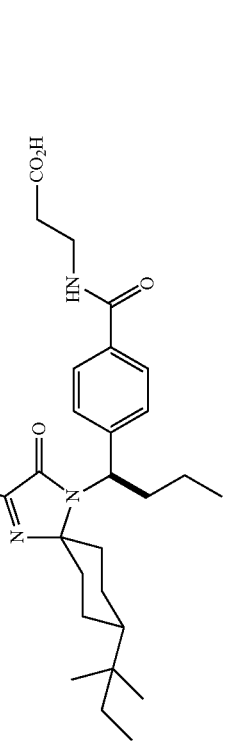 | 5 | 16.5 (26) | 564.5 |
| AH | K3 |  | M7 | 2.62 |  | 5 | 18.7 (26) | 580.4 |

TABLE 1-continued

| AH | K3 | OCF3 (HO)2B | M7 | 2.63 | | 5 | 18.3 (26) | 630.4 |
| AH | K3 | OCF3 (HO)2B | M7 | 2.64 | | 5 | 18.5 (26) | 630.4 |

TABLE 1-continued
| | | | | | | |
|---|---|---|---|---|---|---|
| AH | K3 | 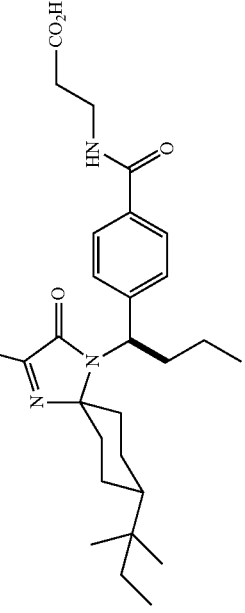 | M7 | 2.65 | 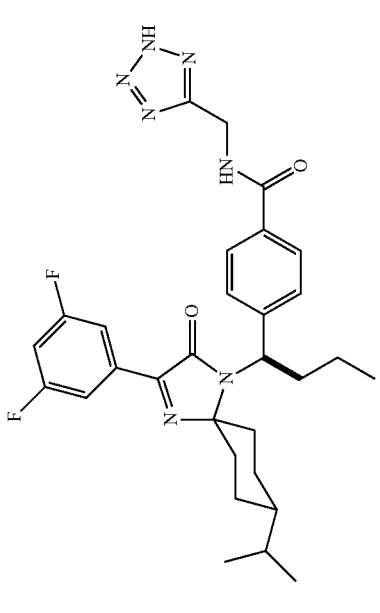 | 5 | 18.3 (26) | 586.5 |
| AG | K2 | 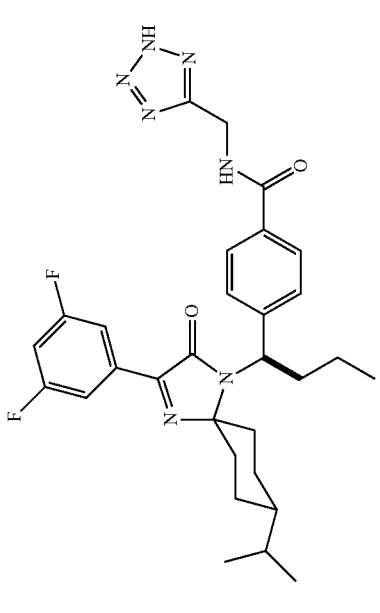 | M7 | 2.66 | | 5 | 17.1 (25) | 564.4 |

TABLE 1-continued

| AG | K2 | [3-chloro-4-fluorophenylboronic acid] | M7 | 2.67 | [structure] | 5 | 18.7 (25) | 580.3 |
| AG | K1 | [3-fluorophenylboronic acid] | M7 | 2.68 | [structure] | 5 | 16.4 (34) | 560.5 |

TABLE 1-continued

| | | | | | | | |
|---|---|---|---|---|---|---|---|
| AG | K1 | Cl-C6H4-B(OH)2 | M7 | 2.69 | [structure with 4-Cl-phenyl, cyclohexyl-tBu, butyl, benzamide-CH2-tetrazole] | 5 | 18.5 (34) | 576.5 |
| AH | K1 | F-C6H4-B(OH)2 | M7 | 2.70 | [structure with 3-F-phenyl, cyclohexyl-tBu, butyl, benzamide-CH2CH2-CO2H] | 5 | 16.6 (34) | 550.5 |

TABLE 1-continued
| AH | K2 | F-⌬-F (HO)₂B | M7 | 2.71 | 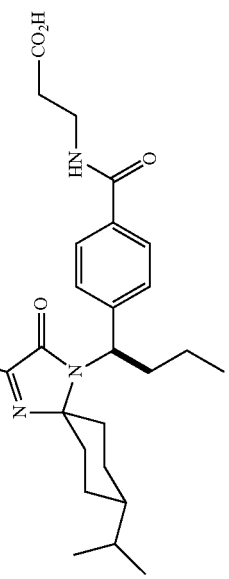 | 5 | 16.8 (34) | 554.3 |
| AH | K2 | Cl-⌬-F (HO)₂B | M7 | 2.72 | 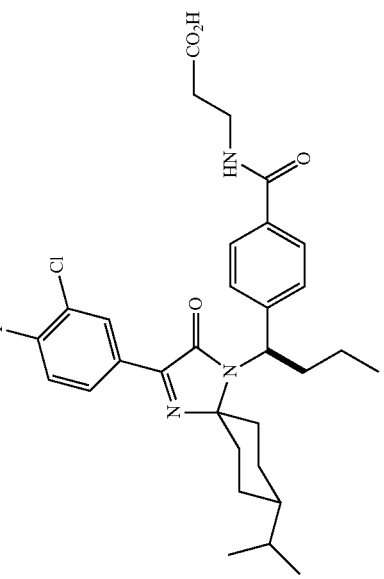 | 5 | 16.4 (34) | 570.3 |

TABLE 1-continued

| AG | K1 | M6 | 2.73 | | 5 | 22.4 (34) | 670.6 |
| AG | K2 | M7 | 2.74 | | 5 | 15.6 (26) | 596.3 |

TABLE 1-continued
| AH | K1 | 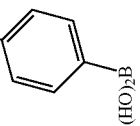 | M7 | 2.75 | 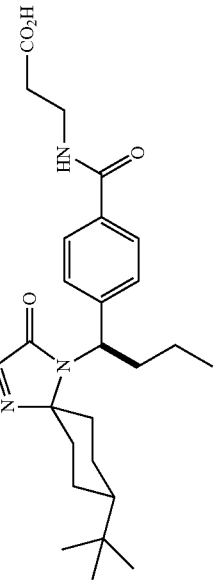 | 5 | 17.2 (26) | 566.3 |
| AH | K2 | 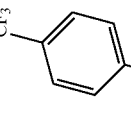 | M7 | 2.76 | 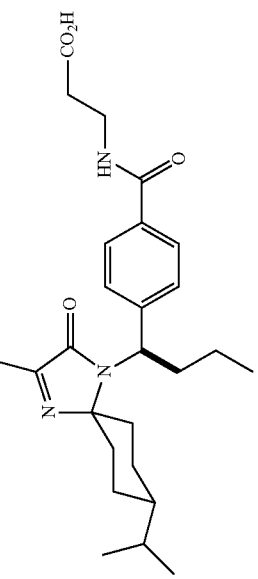 | 5 | 15.8 (26) | 586.3 |

TABLE 1-continued

| AH | K1 | ![3-OCF3 phenylboronic acid] | M6 | 2.77 | ![structure with OCF3] | 5 | 22.0 (34) | 659.6 |
| AH | K1 | ![3-F-5-CF3 phenylboronic acid] | M6 | 2.78 | ![structure with F and CF3] | 5 | 22.6 (34) | 660.5 |

TABLE 1-continued

| AG | K1 | [pyrimidine boronic acid structure] | M6 | 2.79 | [compound structure with pyrimidine, tetrazole] | 5 | 13.5 (26) | 586.5 |
| AG | K2 | [OCF3 phenyl boronic acid structure] | M6 | 2.80 | [compound structure with OCF3-phenyl, tetrazole] | 5 | 20.8 (34) | 654.3 |

TABLE 1-continued

| AG | K2 | (4-CF3-phenyl)B(OH)2 | M6 | 2.81 | [structure] | 5 | 20.2 (34) | 638.4 |
| AG | K1 | (3-Cl-5-CF3-phenyl)B(OH)2 | M6 | 2.82 | [structure] | 5 | 25.5 (34) | 687.0 |

TABLE 1-continued

| IA | K4 | ![3,5-dichlorophenylboronic acid] | M13 | 2.83 | ![structure 871] | 4 | 6.50 | 634.3 |
| IA | K4 | ![2,6-dichlorophenylboronic acid] | M13 | 2.84 | ![structure 872] | 4 | 5.96 | 634.3 |

TABLE 1-continued

| | | | | | | |
|---|---|---|---|---|---|---|
| IA | K15 | 2,6-dimethylphenylboronic acid | M13 | 2.85 | [structure with 2,6-dimethylphenyl, imidazolone-spirocyclohexane, pentyl, benzamide-NH-CH2CH2-COOH] | 4 | 7.72 | 594.3 |
| IB | K4 | 2,6-dichlorophenylboronic acid | M13 | 2.86 | [structure with 2,6-dichlorobiphenyl, imidazolone-spirocyclohexane, pentyl, benzamide-NH-CH2-tetrazole] | 4 | 7.29 | 644.4 |

TABLE 1-continued
| IA | K1 | M13 | 2.87 | 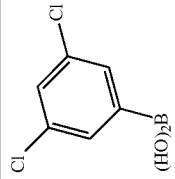 | 4 | 8.67 | 692.4 |
| IA | K4 | M15 | 2.88 | 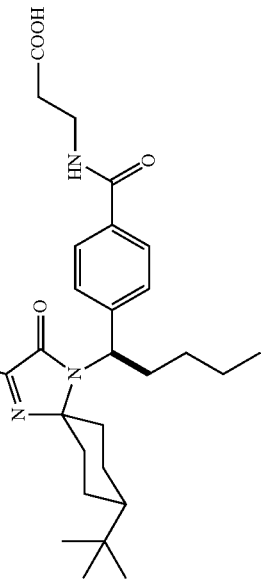 | 4 | 8.18 | 648.4 |

TABLE 1-continued

| | | | | | | |
|---|---|---|---|---|---|---|
| IA | K4 | 4-fluorophenylboronic acid | M15 | 2.89 | 4 | 7.29 598.3 |
| IC | K4 | 3,5-dichlorophenylboronic acid | M15 | 2.90 | 4 | 8.14 648.4 |

TABLE 1-continued

| IC | K4 | F-C6H4-B(OH)2 | M15 | 2.91 | [structure: 4'-fluorobiphenyl imidazolone with cyclohexyl, isohexyl, and 4-(N-(2-carboxyethyl)carbamoyl)phenyl substituents] | 4 | 7.29 | 598.3 |
| IC | K4 | Cl-C6H4-B(OH)2 (3-Cl) | M15 | 2.92 | [structure: 3'-chlorobiphenyl imidazolone with cyclohexyl, isohexyl, and 4-(N-(2-carboxyethyl)carbamoyl)phenyl substituents] | 4 | 7.88 | 614.3 |

TABLE 1-continued

| IE | K1 | | M6 | 2.93 | | 4 | 5.05 | 613.3 |
| IE | K1 | | M6 | 2.94 | | 4 | 5.12 | 599.3 |

TABLE 1-continued
| | | | | | | | |
|---|---|---|---|---|---|---|---|
| IE | K1 | 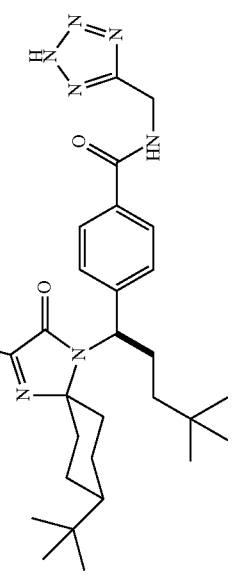 | M6 | 2.95 | 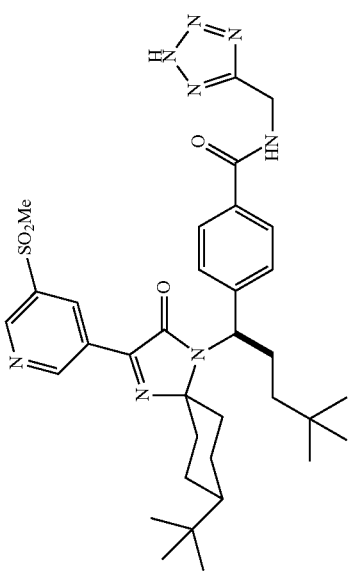 | 4 | 8.02 649.4 |
| IE | K1 | 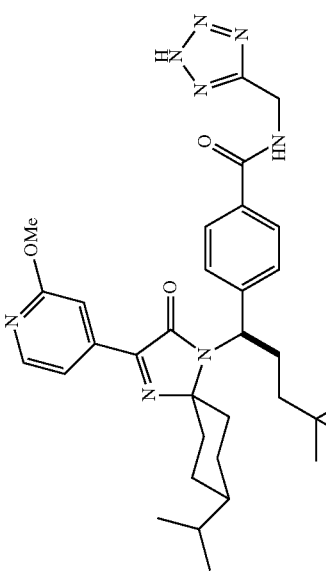 | M6 | 2.96 | 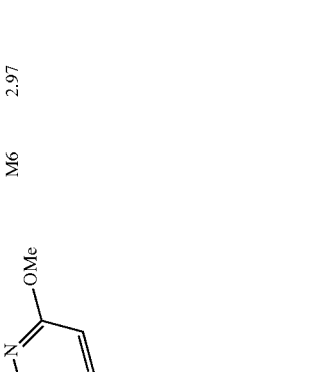 | 4 | 6.27 663.4 |
| AAG | K2 | | M6 | 2.97 | | 4 | 7.18 601.3 |

TABLE 1-continued

| | | | | | | | |
|---|---|---|---|---|---|---|---|
| AAG | K2 | pyridine-OEt boronic acid | M6 | 2.98 | structure | 4 | 7.51 | 615.3 |
| AAG | K2 | pyridine-F boronic acid | M6 | 2.99 | structure | 4 | 6.87 | 589.3 |
| AAG | K2 | pyridine-Cl boronic acid | M6 | 2.100 | structure | 1 | 2.72 | 605.2 |

TABLE 1-continued

| | | | | | | |
|---|---|---|---|---|---|---|
| AAG | K2 | (structure with OMe-pyridine boronic acid) | M6 | 2.101 | (structure 2.101) | 1 | 2.29 | 601.3 |
| AAF | K1 | (structure with CF3-pyridine boronic acid) | M6 | 2.102 | (structure 2.102) | 4 | 4.05 | 653.4 |
| AAF | K1 | (structure with OCHF2-phenyl boronic acid) | M6 | 2.103 | (structure 2.103) | 4 | 4.12 | 650.4 |

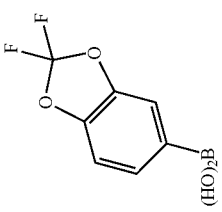

TABLE 1-continued
| AAF | K1 | 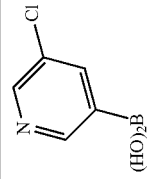 | M6 | 2.106 |  | 4 | 4.07 | 619.3 |
| AAF | K1 | 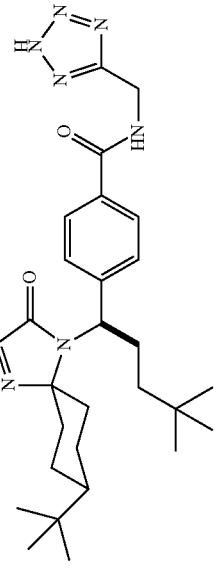 | M6 | 2.107 | 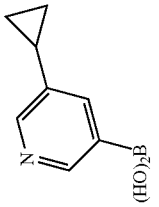 | 4 | 5.54 | 625.6 |

TABLE 1-continued

| | | | | | | |
|---|---|---|---|---|---|---|
| AAF | K1 | (structure) | M6 | 2.108 | (structure) | 4 | 4.18 | 633.3 |
| AAA | K1 | (structure) | M6 | 2.109 | (structure) | 3 | 2.64 | 642.2 |

TABLE 1-continued
| AAA | K1 | | M3 | 2.110 | | 3 | 2.59 | 560.2 |
|---|---|---|---|---|---|---|---|---|
| AAA | K1 | | M6a | 2.111 | | 3 | 2.62 | 610.2 |

TABLE 1-continued
| | | | | | | |
|---|---|---|---|---|---|---|
| AAA | K1 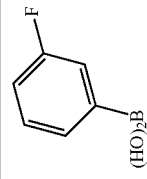 | M6a | 2.112 | 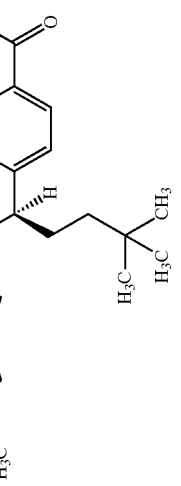 | 3 | 2.60 | 592.3 |
| AAP | K1 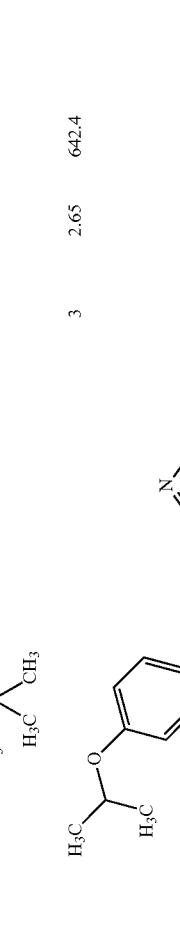 | M6a | 2.113 | | 3 | 2.65 | 642.4 |

TABLE 1-continued

| | | | | | | | |
|---|---|---|---|---|---|---|---|
| AAE | K1 | [structure] | M6 | 2.114 | [structure] | 3 | 2.55 | 628.6 |
| AAP | K1 | [structure] | M6a | 2.115 | [structure] | 3 | 2.63 | 652.2 |

TABLE 1-continued
| | | | | | | | |
|---|---|---|---|---|---|---|---|
| AAP | K1 | 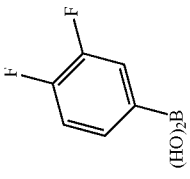 | M6a | 2.116 | 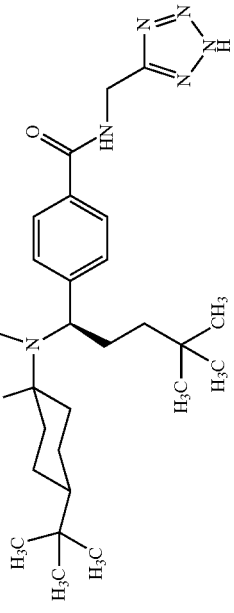 | 3 | 2.60 | 620.3 |
| AAE | K1 | 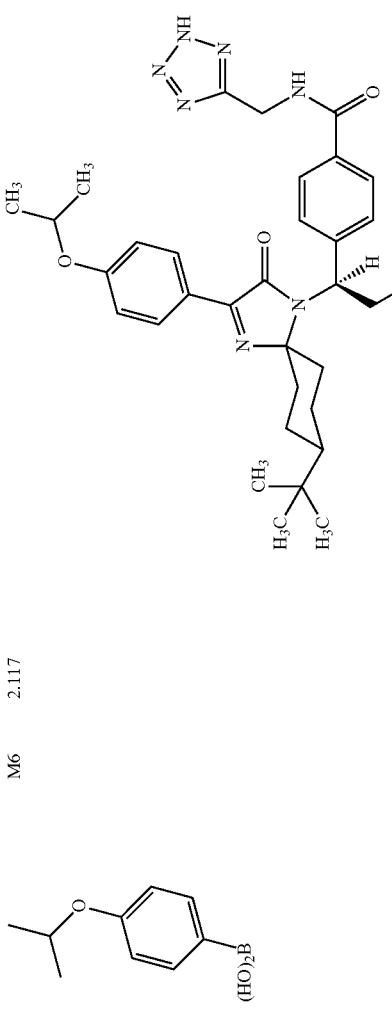 | M6 | 2.117 | 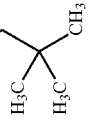 | 3 | 2.59 | 642.6 |

TABLE 1-continued

| | | | | | | |
|---|---|---|---|---|---|---|
| AAP | K1 | M6a | 2.118 | [structure] | 3 | 2.66 624.4 |
| AD | K1 | M3 | 2.119 | [structure] | 5 | 19.4 (22) 580.3 |

TABLE 1-continued

| | | | | | | | |
|---|---|---|---|---|---|---|---|
| AG | K1 | ![3-chloro-5-fluorophenylboronic acid] | M13 | 2.120 | ![structure] | 5 | 22.3 (25) | 608.3 |
| AD | K1 | ![3,5-dimethylphenylboronic acid] | M3 | 2.121 | ![structure] | 5 | 19.8 (22) | 532.2 |

TABLE 1-continued

| AD | K1 | | M3 | 2.122 | | 5 | 18.6 (22) | 554.2 |

(naphthalen-2-yl boronic acid structure)

(compound structure with naphthalene)

| AD | K1 | | M3 | 2.123 | | 5 | 19.7 (22) | 580.3 |

(biphenyl-4-yl boronic acid structure)

(compound structure with biphenyl)

TABLE 1-continued

| | | | | | | | |
|---|---|---|---|---|---|---|---|
| AD | K1 | (naphthalen-1-yl)B(OH)₂ | M3 | 2.124 | [structure] | 5 | 16.3 (22) | 554.3 |
| AG | K1 | (3-chlorophenyl)B(OH)₂ | M13 | 2.125 | [structure] | 5 | 20.8 (25) | 590.1 |

TABLE 1-continued

| AAA | K4 | (HO)₂B-C₆H₅ | M201 | 2.126 | [structure 911] | 3 | 2.38 | 532.2 |
| AAA | K4 | (HO)₂B-C₆H₄-CF₃ | M201 | 2.127 | [structure 912] | 3 | 2.48 | 600 |

TABLE 1-continued
| | K1 | 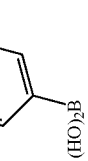 | M3 | 2.128 | 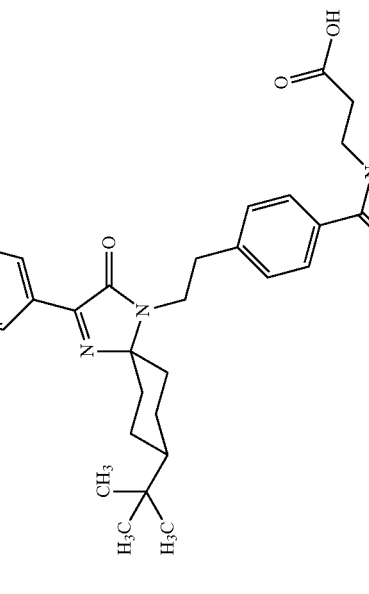 | 3 | 2.40 | 540 |
| AAA | | | | | | | | |
| AD | K1 | 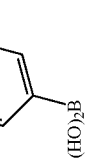 | M3 | 2.129 | 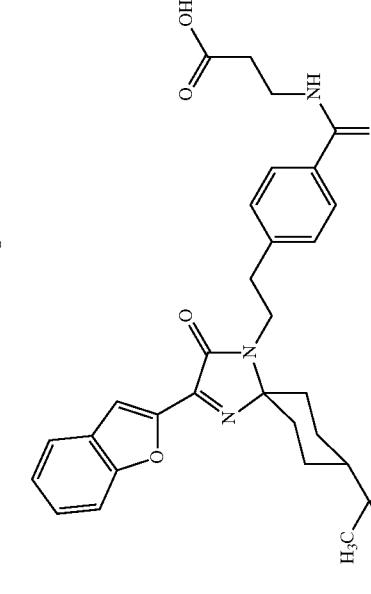 | 5 | 14.8 (22) | 544.2 |

TABLE 1-continued

| AD | K1 | [1,3-benzodioxol-5-yl-B(OH)₂] | M3 | 2.130 | [structure] | 5 | 15.3 (22) | 548.3 |
| AD | K1 | [quinolin-3-yl-B(OH)₂] | M3 | 2.131 | [structure] | 5 | 11.2 (22) | 555.3 |

| AD | K14 | 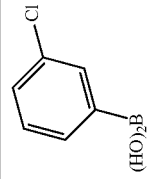 | M3 | 2.132 | 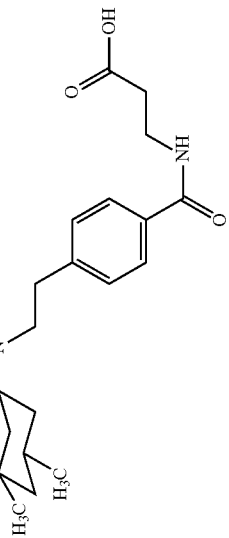 | 5 | 18.0 (22) | 510.2 |
| AD | K14 | 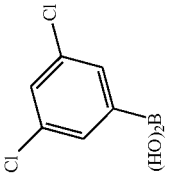 | M3 | 2.133 | 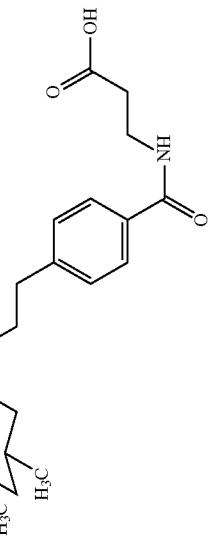 | 5 | 19.8 (22) | 544.2 |

TABLE 1-continued
| AD | K14 | 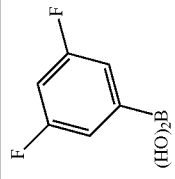 | M3 | 2.134 | 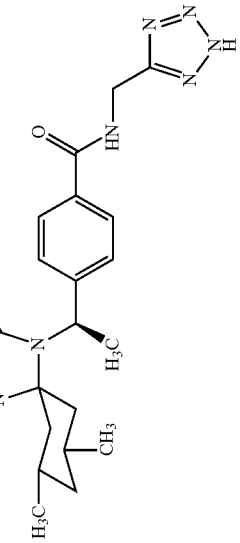 | 5 | 20.0 (22) | 582.5 |
| AD | K1 | 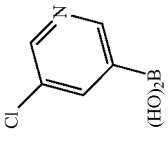 | M3 | 2.135 | 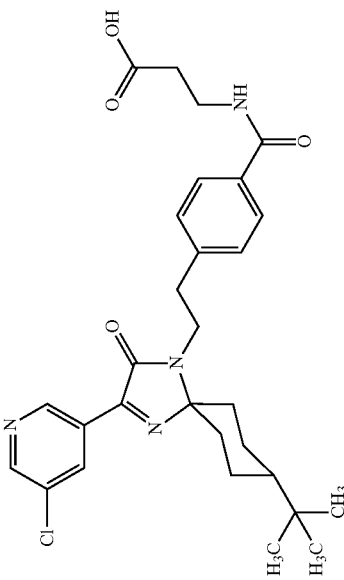 | 5 | 16.2 (22) | 539.3 |

TABLE 1-continued

| | | | | | | | |
|---|---|---|---|---|---|---|---|
| AD | K14 | ![CF3-phenylboronic acid] | M3 | 2.136 | ![structure] | 5 | 15.7 (22) | 544.2 |
| AAF | K1 | ![OEt-phenylboronic acid] | M6 | 2.137 | ![structure] | 4 | 2.48 | 628 |

TABLE 1-continued

| Scheme | Ketone | RSO₂Na | Amine | Ex. | | | LCMS | |
|---|---|---|---|---|---|---|---|---|
| | | | | | | LC | Ret (min) | (MH)⁺ |
| AAA | K1 | | M6 | 2.138 | 4 | | 2.67 | 632 |
| AI | K1 | H₃C—SO₂Na | M6 | 3.1 | 5 | | 13.6 (26) | 662.4 |

TABLE 1-continued
| Scheme | Ketone | Amino acid | Amine | Ex. | | | |
|---|---|---|---|---|---|---|---|
| AJ | K1 | H₃C—SO₂Na | M6 | 3.3 | 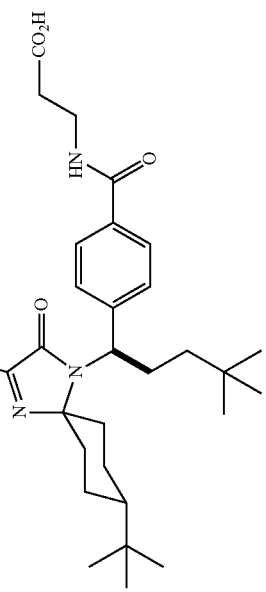 | 5 | 13.7 (26) | 652.5 |
| | | | | | | LCMS | |
| | | | | | LC | Ret (min) | (MH)⁺ |
| Scheme | Ketone | Amino acid | Amine | Ex. | | | |
| AK | K1 | A1 | M15 | 4.1 | 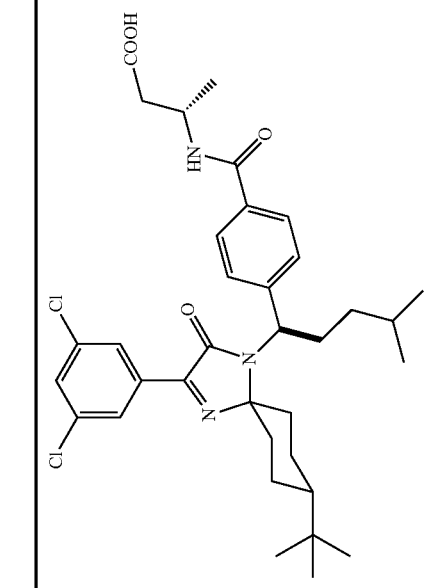 | 4 | 7.47 | 642.4 |

TABLE 1-continued

| | | | | | | |
|---|---|---|---|---|---|---|
| AL | K1 | A1 | M15 | 4.2 | [structure] | 4 7.46 642.4 |
| AK | K1 | A1 | M16 | 4.3 | [structure] | 4 7.08 628.3 |

TABLE 1-continued

| | | | | | | |
|---|---|---|---|---|---|---|
| AL | K1 | A1 | M16 | 4.4 | (structure) | 4 | 7.05 | 628.3 |
| AK | K1 | A1 | M6 | 4.5 | (structure) | 4 | 7.50 | 656.4 |

TABLE 1-continued

| AL | K1 | A1 | M6 | 4.6 | (structure) | 4 | 7.50 | 656.4 |
| AK | K1 | A1 | M17 | 4.7 | (structure) | 4 | 6.26 | 668.4 |

| | | | | | | |
|---|---|---|---|---|---|---|
| AL | K1 | A1 | M17 | 4.8 | 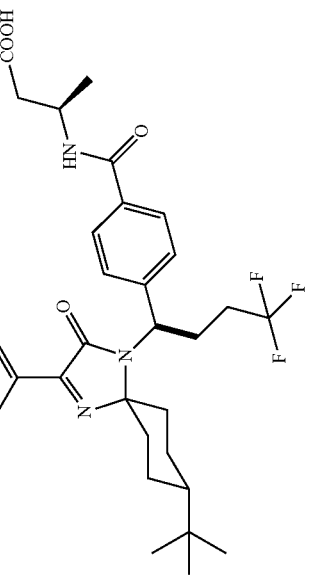 | 4 | 6.22 | 668.4 |
| AK | K4 | A1 | M15 | 4.9 | 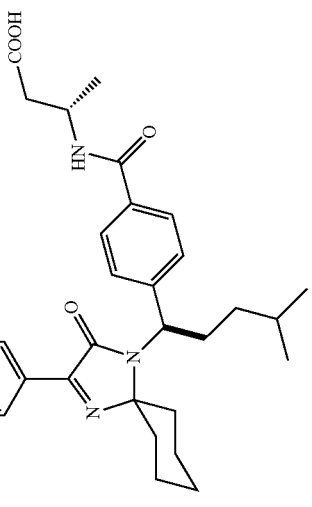 | 4 | 6.27 | 586.3 |

TABLE 1-continued
| | | | | | |
|---|---|---|---|---|---|
| AL | K4 | A1 | M15 | 4.10 | 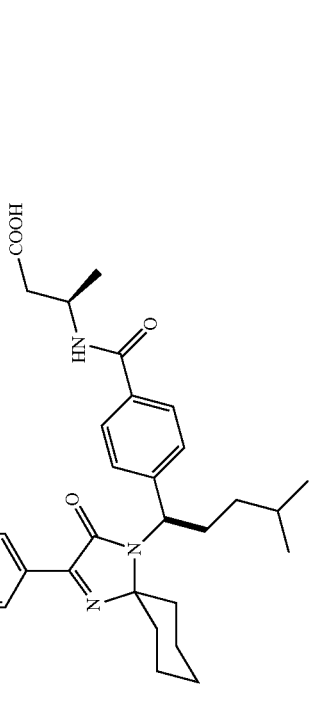 4 6.24 586.3 |
| AM | K1 | A1 | M16 | 4.11 | 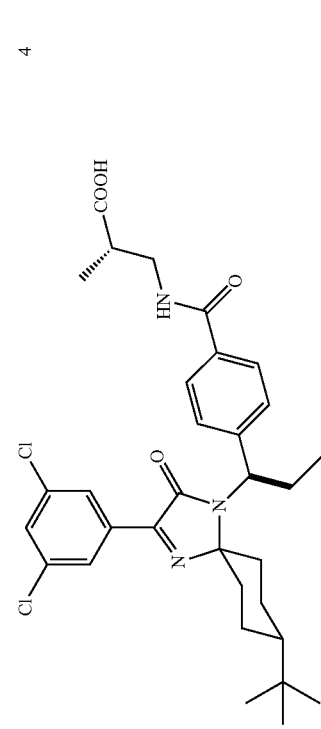 4 8.51 628.3 |

TABLE 1-continued

| Scheme | Ketone | R¹NH2 | Amine | Ex. | AN | K1 | A1 | M16 | 4.12 | 4 | 8.52 | 628.3 |
|---|---|---|---|---|---|---|---|---|---|---|---|---|
| | | | | | | | | | | | LCMS | |
| | | | | | | | | | | LC | Ret (min) | (MH)+ |
| TA | K1 | phenethylamine-NH2 | M6 | 1.983 | | | | | | 5 | 16.8 (25) | 627 |

TABLE 1-continued
| TA | | | | | | |
|----|----|----|----|----|----|----|
|  | M6 | 1.984 |  | 5 | 17.4 (25) | 613 |
| K1 | | | | | | |
| 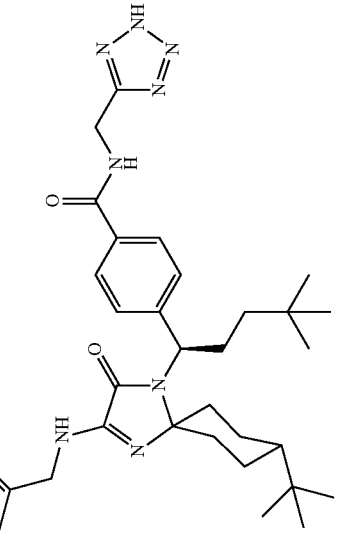 | M15a | 1.985 | 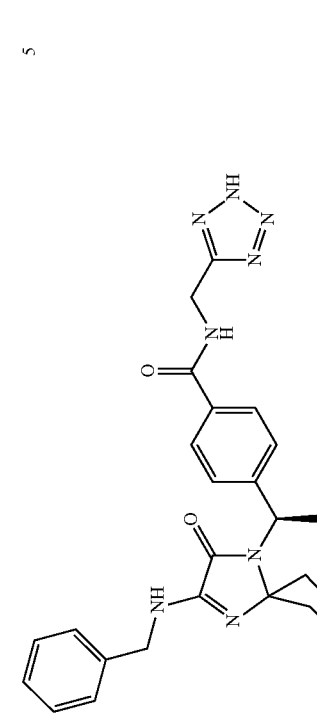 | 5 | 13.3 (25) | 599 |
| K1 | | | | | | |
NA*—not applicable/see indicated scheme for preparation TABLE 2
| Ketone | | | |
|---|---|---|---|
| K1 | 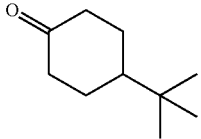 | K2 | 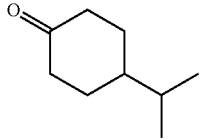 |
| K3 | 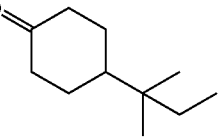 | K4 | 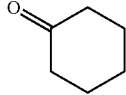 |
| K5 | 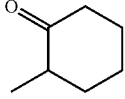 | K6 | 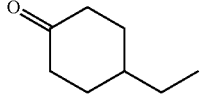 |
| K7 | 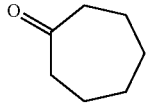 | K8 | 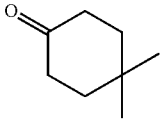 |
| K9 | 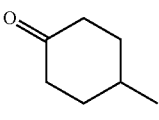 | K10 | 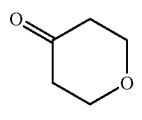 |
| K11 | 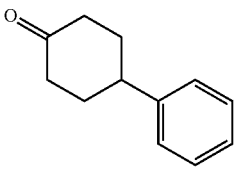 [SMILES: O=C1CCC(c2ccccc2)CC1] | K12 | 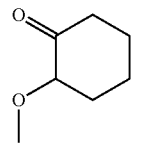 |
| K13 | 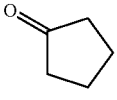 | K14 | 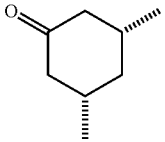 |
| K15 | 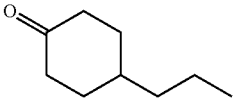 | K16 | 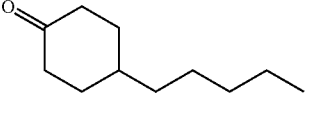 |
| K72 | 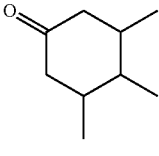 | K90 | 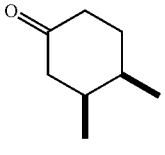 |
| K91 | 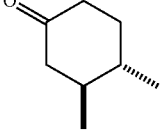 | K92 | 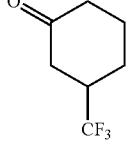 |
| K93 | 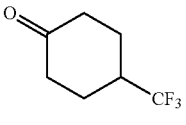 | K94 | 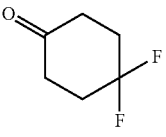 |

TABLE 2-continued
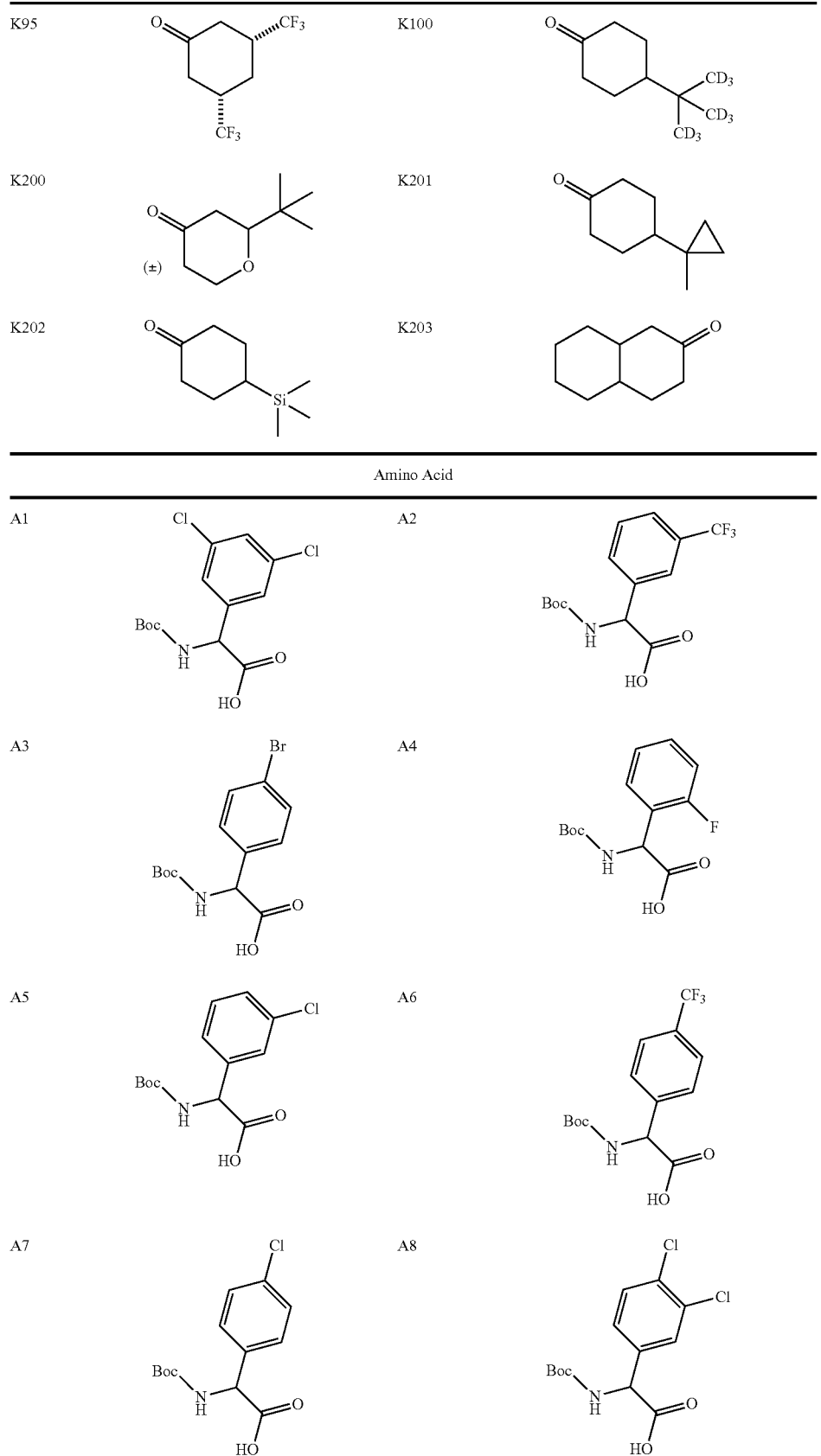

TABLE 2-continued
| | | | |
|---|---|---|---|
| A9 | 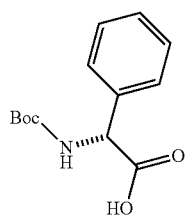 [SMILES: CC(C)(C)OC(=O)N[C@@H](C(=O)O)c1ccccc1] | A10 | 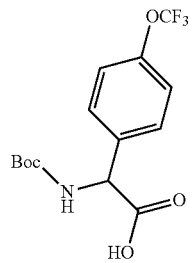 [SMILES: CC(C)(C)OC(=O)NC(C(=O)O)c1ccc(OC(F)(F)F)cc1] |
| A11 | 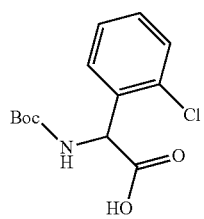 [SMILES: CC(C)(C)OC(=O)NC(C(=O)O)c1ccccc1Cl] | A12 | 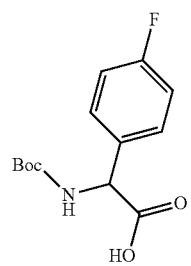 [SMILES: CC(C)(C)OC(=O)NC(C(=O)O)c1ccc(F)cc1] |
| A13 | 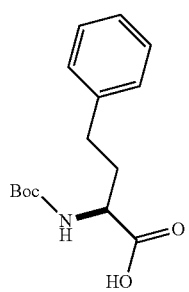 [SMILES: CC(C)(C)OC(=O)N[C@@H](CCc1ccccc1)C(=O)O] | A14 | 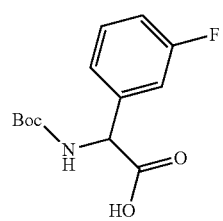 [SMILES: CC(C)(C)OC(=O)NC(C(=O)O)c1cccc(F)c1] |
| A15 | 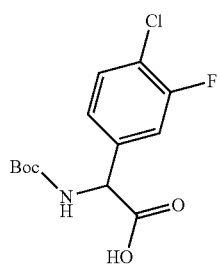 [SMILES: CC(C)(C)OC(=O)NC(C(=O)O)c1ccc(Cl)c(F)c1] | A16 | 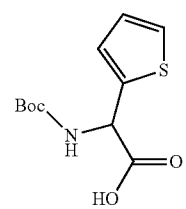 [SMILES: CC(C)(C)OC(=O)NC(C(=O)O)c1cccs1] |
| A17 | 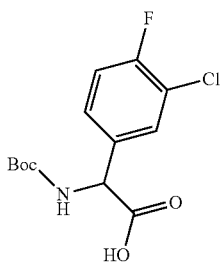 [SMILES: CC(C)(C)OC(=O)NC(C(=O)O)c1ccc(F)c(Cl)c1] | A18 | 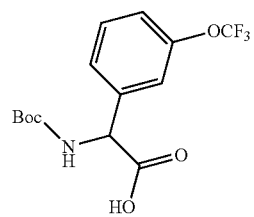 [SMILES: CC(C)(C)OC(=O)NC(C(=O)O)c1cccc(OC(F)(F)F)c1] |
| A19 | 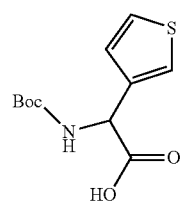 | A20 | 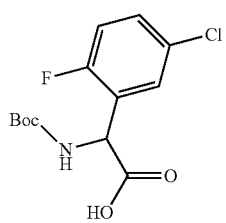 [SMILES: CC(C)(C)OC(=O)NC(C(=O)O)c1cc(Cl)ccc1F] |

TABLE 2-continued
| | | | |
|---|---|---|---|
| A21 | 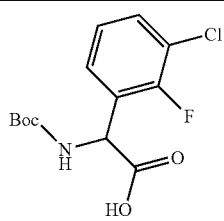 | A22 | 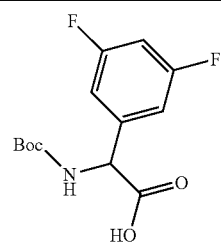 |
| A23 | 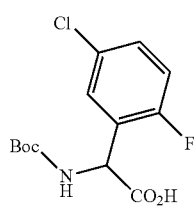 [SMILES: CC(C)(C)OC(=O)NC(C(=O)O)c1cc(Cl)ccc1F] | A24 | 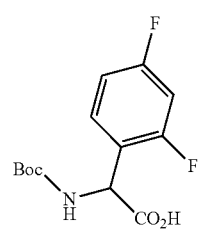 |
| A25 | 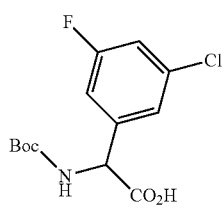 | A26 | 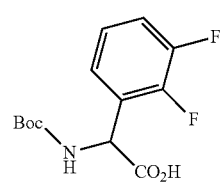 |
| A27 | 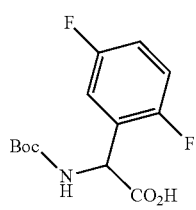 [SMILES: CC(C)(C)OC(=O)NC(C(=O)O)c1cc(F)ccc1F] | A28 | 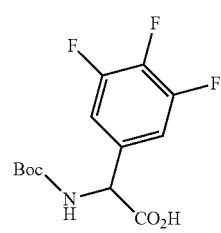 |
| A29 | 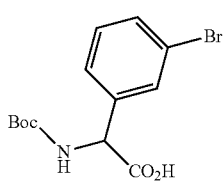 [SMILES: CC(C)(C)OC(=O)NC(C(=O)O)c1cccc(Br)c1] | A30 | 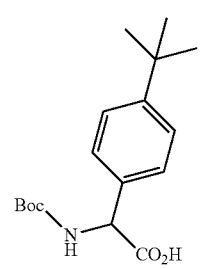 [SMILES: CC(C)(C)OC(=O)NC(C(=O)O)c1ccc(C(C)(C)C)cc1] |
| A31 | 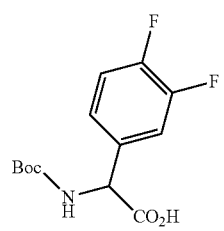 [SMILES: CC(C)(C)OC(=O)NC(C(=O)O)c1ccc(F)c(F)c1] | A71 | 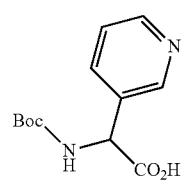 [SMILES: CC(C)(C)OC(=O)NC(C(=O)O)c1cccnc1] |
Amine
| | | | |
|---|---|---|---|
| M1 | 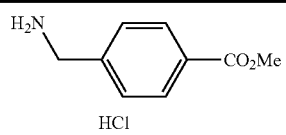 | M2 | 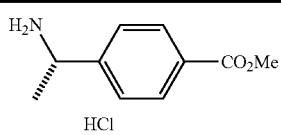 |

TABLE 2-continued

| | | | |
|---|---|---|---|
| M3 | H2N-CH2CH2-C6H4-CO2Me · HCl | M4 | H2N-CH(CH3)-C6H4-CO2Me · HCl |
| M5 | H2N-CH2CH2-O-C6H4-CO2Me · HCl | M6 | H2N-CH(CH2CH2C(CH3)3)-C6H4-CO2iPr · HCl |
| M7 | H2N-CH(CH2CH2CH3)-C6H4-CO2Me · HCl | M8 | H2N-CH(CH(CH3)2)-C6H4-CO2Me · HCl |
| M9 | H2N-CH(CH(CH3)2)-C6H4-CO2Me · HCl | M10 | H2N-CH(CH2OH)-C6H4-CO2Me · HCl |
| M11 | H2N-CH(cyclobutyl)-C6H4-CO2Et · HCl | M12 | H2N-CH(CH2CH2OH)-C6H4-CO2Me · HCl |
| M13 | H2N-CH(n-butyl)-C6H4-CO2Me · HCl | M14 | H2N-C(cyclopropyl)-C6H4-CO2Me · HCl |
| M15 | H2N-CH(CH2CH(CH3)2)-C6H4-CO2Me · HCl | M16 | H2N-CH(CH2CH(CH3)2)-C6H4-CO2Me · HCl |
| M17 | H2N-CH(CH2CF3)-C6H4-CO2Me · HCl | M18 | H2N-CH(CH2CH2-(1-methylcyclopropyl))-C6H4-CO2Et · HCl |

TABLE 2-continued
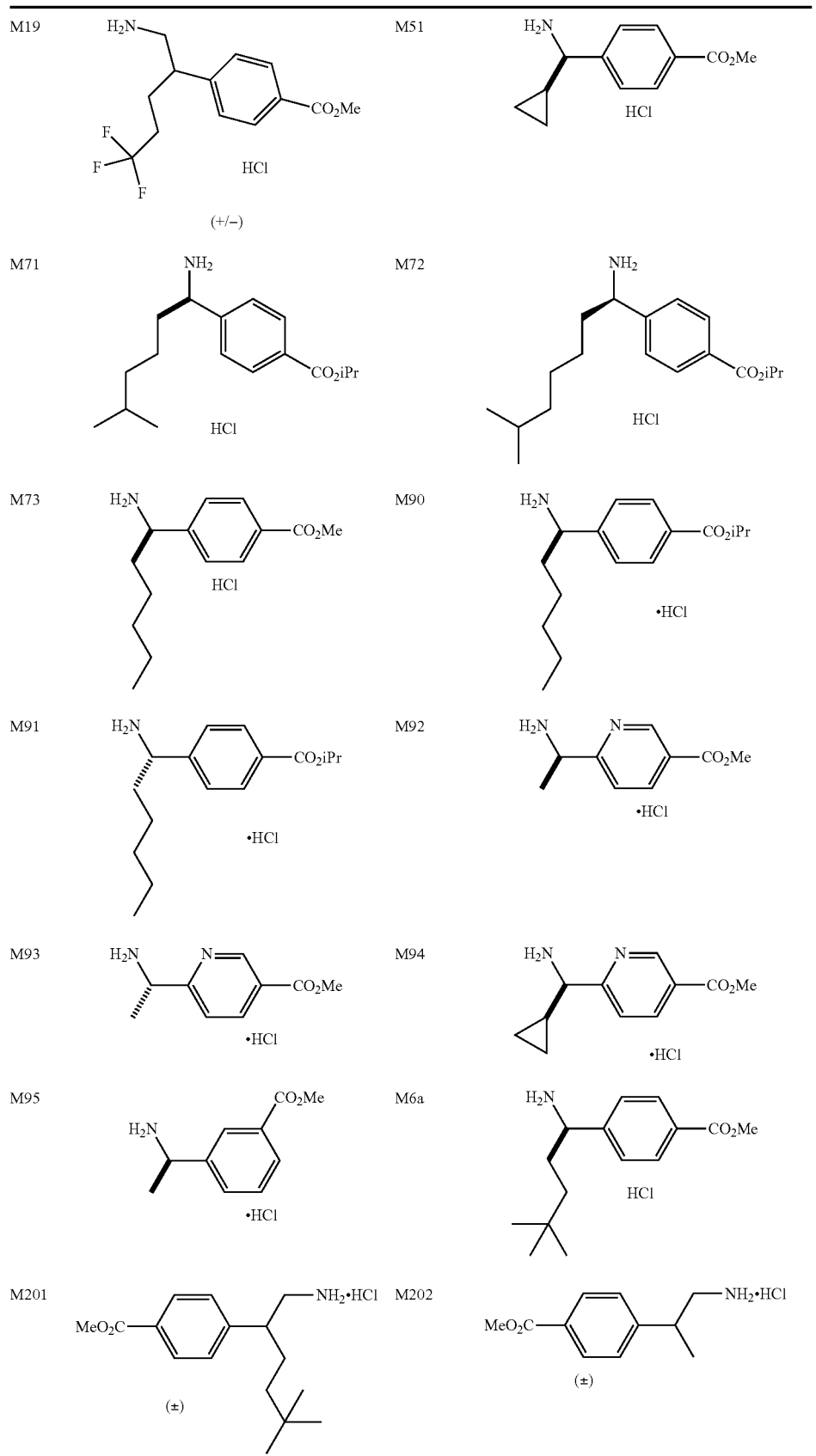

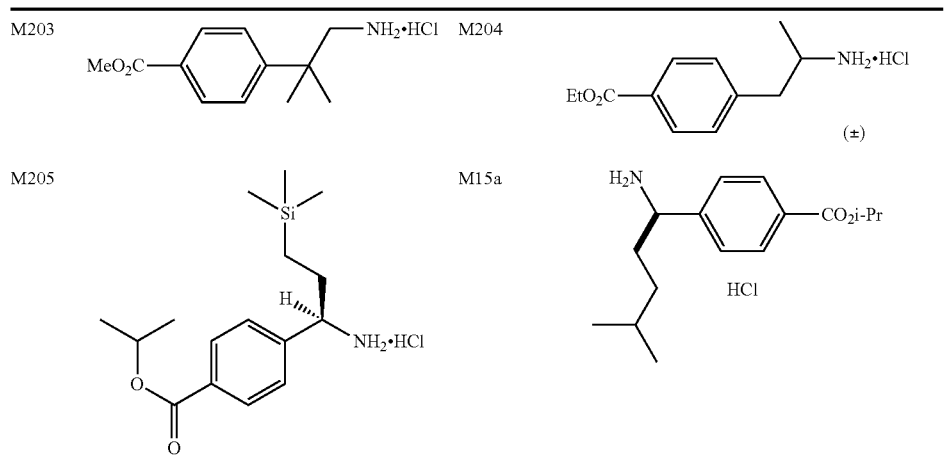

LC Refers to LCMS Conditions
LC

LC-1: LCMS spectra were obtained on an Agilent 6140 Quadrupole LCMS, using a Zorbax SB-C-18 column (1.8 micron) and a flow rate of 1.0 mL/min. The mobile phase consisted of acetonitrile and water, each of which contains 0.1% trifluoroacetic acid by volume. Gradient Table Time: 0 min=10% $CH_3CN$/90% water, 1.5 min=95% $CH_3CN$/95% water, 2.7 min=95% $CH_3CN$/5% water, 2.8 min=10% $CH_3CN$/90% water. Stop Time=3.60 min. Post Time=1.5 min, Column Temperature=50° C.

LC-2: LCMS spectra were obtained on an Agilent 6140 Quadrupole LCMS, using a Zorbax SB-C-18 column (1.8 micron) and a flow rate of 1.0 mL/min. The mobile phase consisted of acetonitrile and water, each of which contains 0.1% trifluoroacetic acid by volume. Gradient Table: Time 0 min=10% $CH_3CN$/90% water, 5.30 min=95% $CH_3CN$/95% water, 6.50 min=95% $CH_3CN$/5% water, 6.56 min=10% $CH_3CN$/90% water. Stop Time=7.5 min. Post Time=1.5 min, Column Temperature=50° C.

LC-3 Column: Agilent Zorbax SB-C18 (3.0×50 mm) 1.8 uM Mobile phase: A: 0.1% Trifluoroacetic acid in water B: 0.1% Trifluoroacetic acid in acetonitrile Gradient: 90:10 (A:B) for 0.3 min, 90:10 to 5:95 (A:B) over 1.2 min, 5:95 (A:B) for 1.2 min. Flow rate: 1.0 mL/min UV detection: 254 and 220 nm. Mass spectrometer: Agilent 6140 quadrupole.

LC-4: Column: Gemini C-18, 50×4.6 mm, 5 micron, obtained from Phenomenex. Mobile phase: A: 0.05% Trifluoroacetic acid in water B: 0.05% Trifluofloacetic acid in acetonitrile Gradient: 90:10 to 5:95 (A:B) over 5 min. Flow rate: 1.0 mL/min UV detection: 254 nm. ESI-MS: Electro Spray Ionization Liquid chromatography-mass spectrometry (ESI-LC/MS) was performed on a PE SCIEX API-150EX, single quadrupole mass spectrometer.

LC-5: HPLC conditions for the retention time were as follows: Column: Luna C18 100A, 5 µM: A: 0.025% TFA in water B: 0.025% TFA in acetonitrile: Gradient: 98:2 to 2:98 (A:B) over indicated time in parenthesis (below retention time provided in corresponding Table followed by a 2 minute gradient back to 98:2 (A:B)). Flow rate: 1.0 ml/min UV detection: 254 nm. Mass spec were obtained by one of the following methods: a) Multimode (ESI and APCI). b) ESI The following amines were purchased from NetChem (New Brunswick, N.J.): M2, M4, M7, M8, M9, M10, M12, M13, M15, M16, M17, and M51. The 4-TMS cyclohexanone K202 was prepared according to the literature procedure:

Tang, S.-X.; Li, Y.-M.; Cao, Y.-R.; Wang, X.-L. *Chinese Journal of Chemistry* 1991, 68-75.

Scheme 3.1

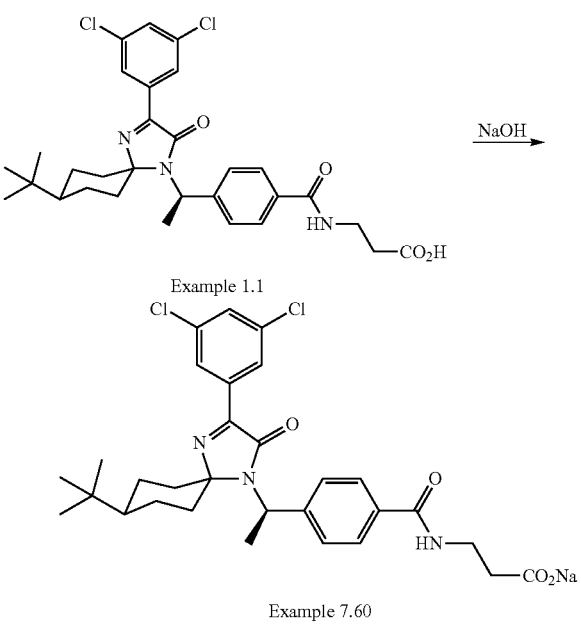

The acid (SM-Ex) Example 1.1 (300 mg, 0.52 mmol) was taken up in MeOH (50 mL), and 0.51 mL of a 0.1019 N $NaOH_{(aq.)}$ solution was added. The solution was stirred for a few minutes at room temperature. The solution was filtered and concentrated which provided 227 mg (73%) of the sodium salt Example 7.60 as a white solid.

As stated above, in one embodiment, in each of Formula (A), Formula (A-1), Formula (A-1a), Formula (A-1b), Formula (A-2a), Formula (A-2b), Formula (A-2c), Z contains a carboxylic acid moiety or a tetrazole moiety. Pharmaceutically acceptable salts of such acids are also contemplated as being within the scope of the invention. Table 3 depicts non-limiting examples of sodium salts prepared according to the procedure outlined in Scheme 3.1 using the appropriate starting acid or tetrazole (SM).

TABLE 3

| SM-Ex | Ex. | Structure |
|---|---|---|
| 1.900 | 7.1 | 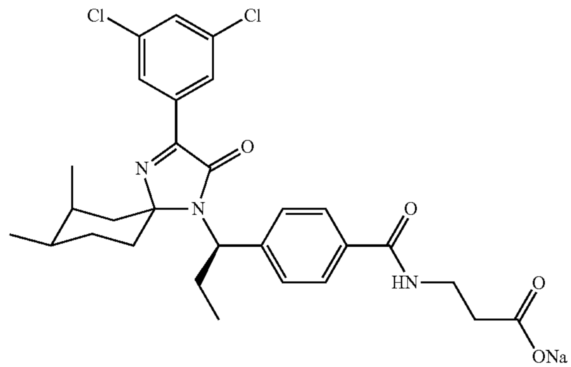 |
| 1.277 | 7.2 | 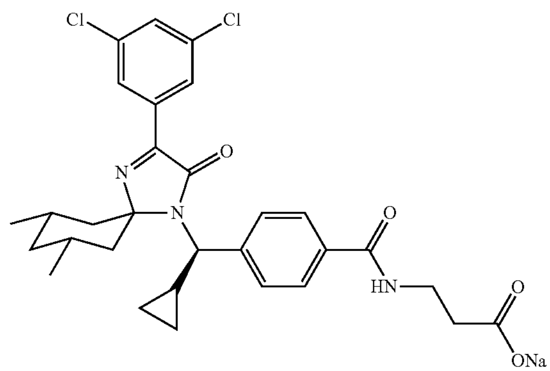 |
| 1.901 | 7.3 | 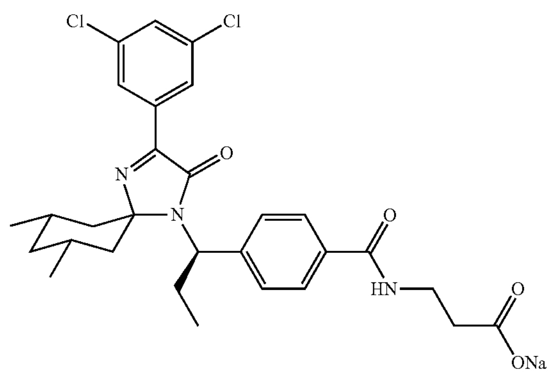 |
| 1.960 | 7.4 | 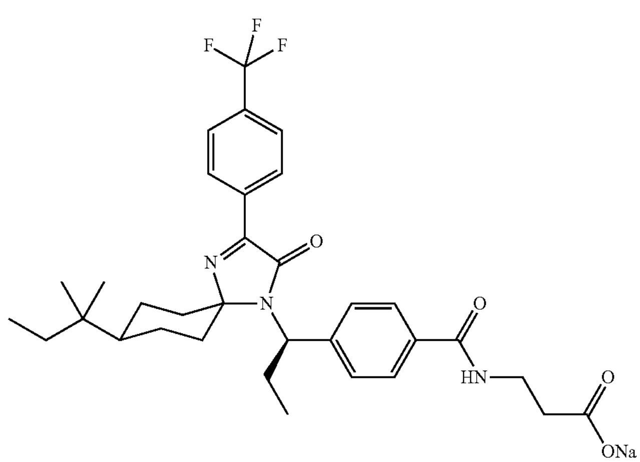 |

TABLE 3-continued
| SM-Ex | Ex. | Structure |
|---|---|---|
| 1.46 | 7.5 | 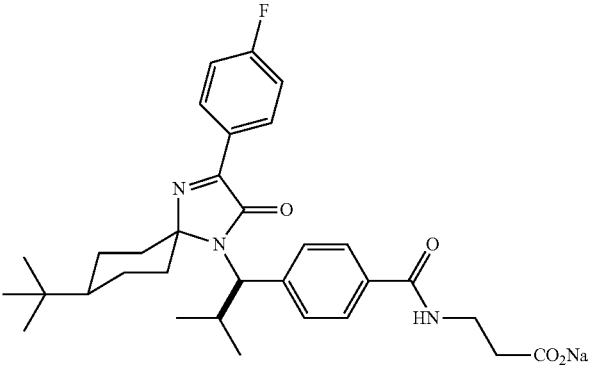 |
| 1.902 | 7.6 | 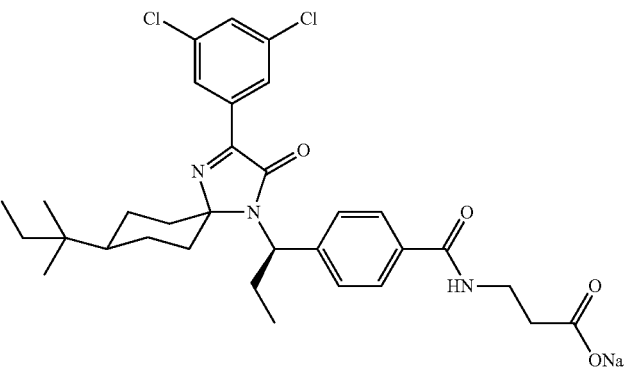 |
| 1.952 | 7.7 | 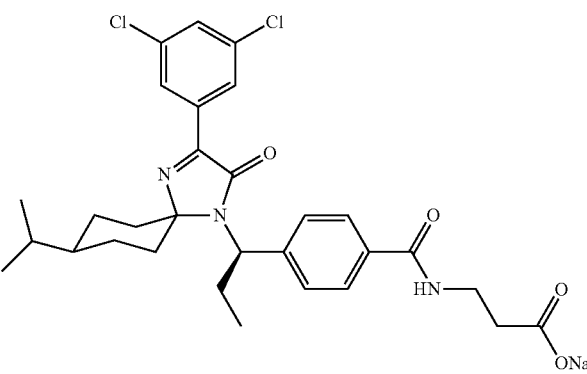 |
| 1.103 | 7.8 | 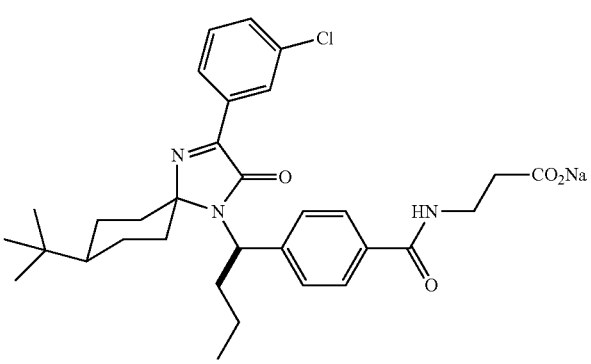 |

TABLE 3-continued
| SM-Ex | Ex. | Structure |
|---|---|---|
| 1.513 | 7.9 | 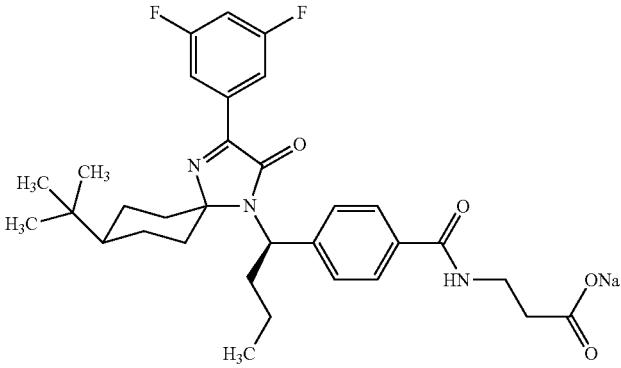 |
| 1.954 | 7.10 | 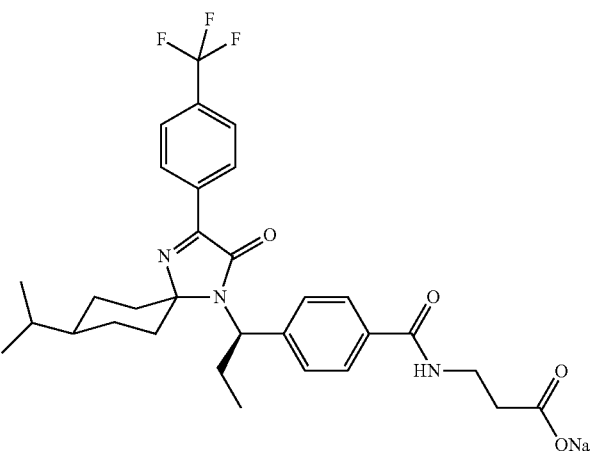 |
| 1.164 | 7.11 | 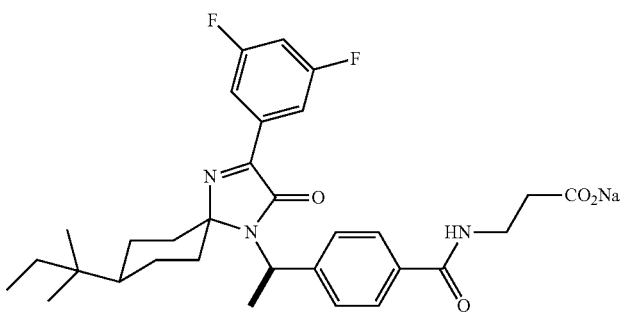 |
| 1.126 | 7.12 | 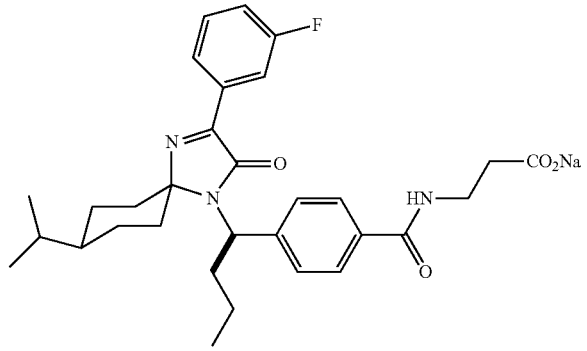 |

TABLE 3-continued

| SM-Ex | Ex. | Structure |
|---|---|---|
| 1.96 | 7.13 | 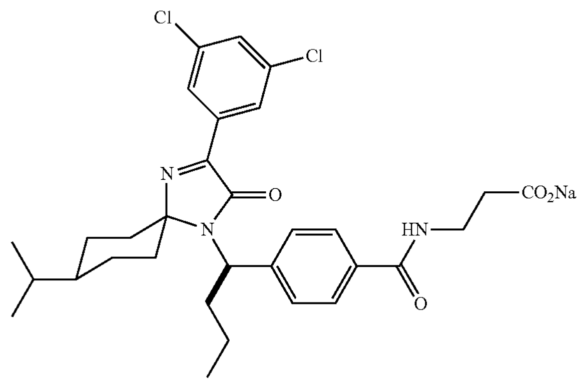 |
| 1.282 | 7.14 | 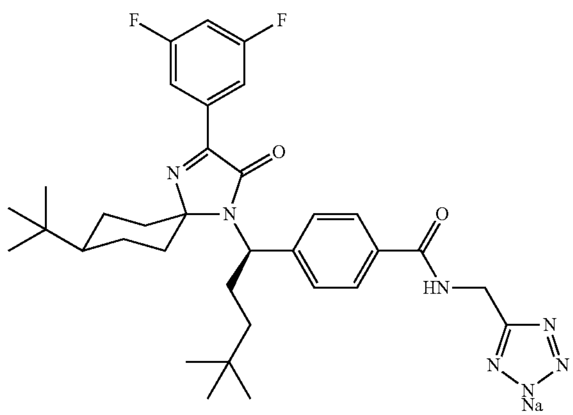 |
| 1.512 | 7.15 | 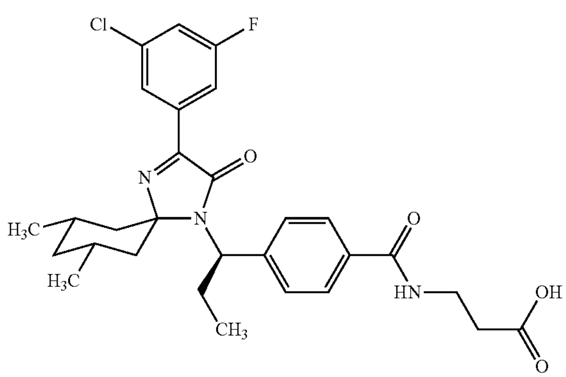 [SMILES: CC[C@H](c1ccc(C(=O)NCCC(=O)O)cc1)N1C(=O)C(c2cc(F)cc(Cl)c2)=NC12CC(C)CC(C)C2] |
| 1.511 | 7.16 | 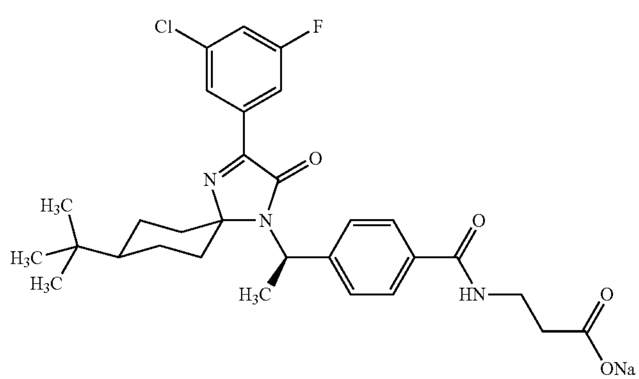 |

TABLE 3-continued

| SM-Ex | Ex. | Structure |
|---|---|---|
| 1.910 | 7.17 | 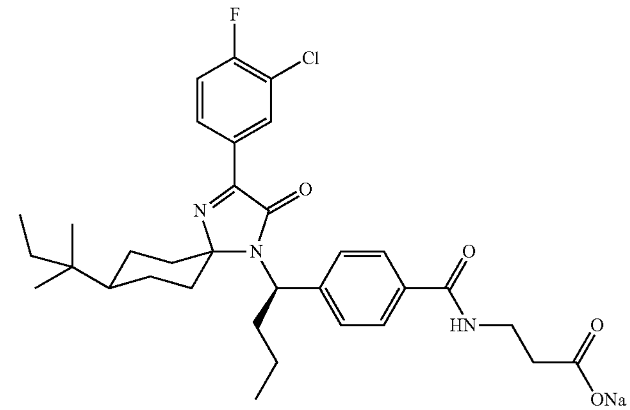 |
| 1.165 | 7.18 | 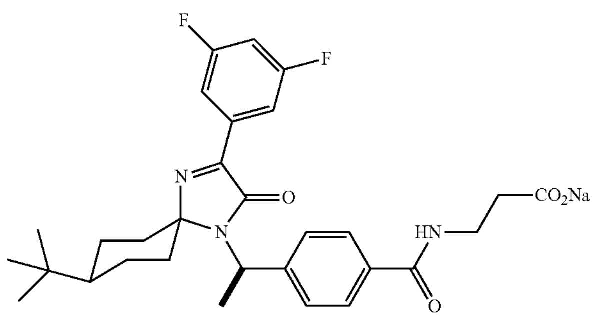 |
| 1.964 | 7.19 | 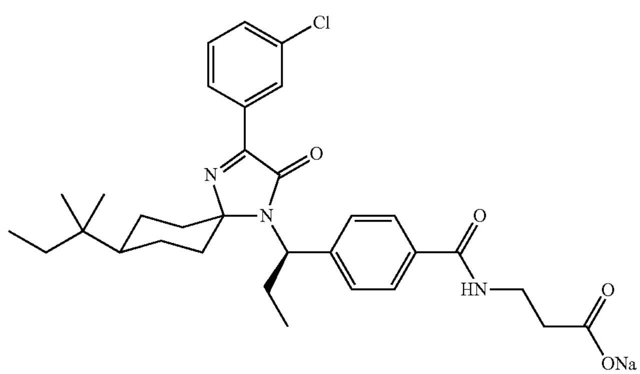 |
| 1.909 | 7.20 | 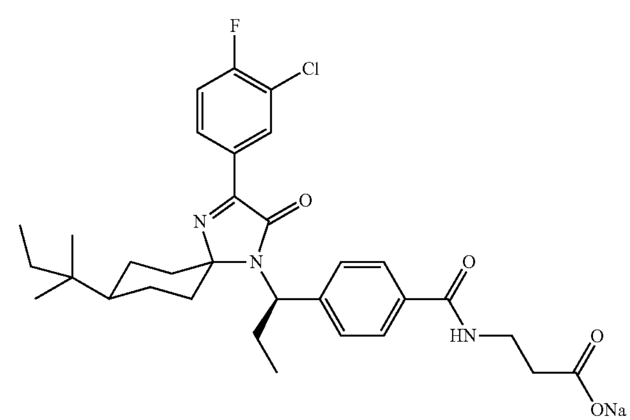 |

TABLE 3-continued
| SM-Ex | Ex. | Structure |
|---|---|---|
| 1.507 | 7.21 | 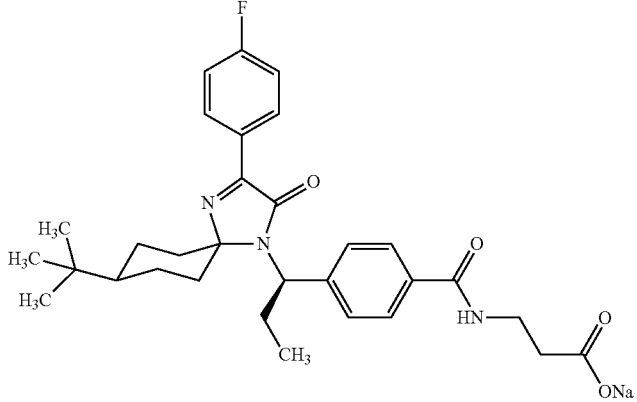 |
| 1.320 | 7.22 | 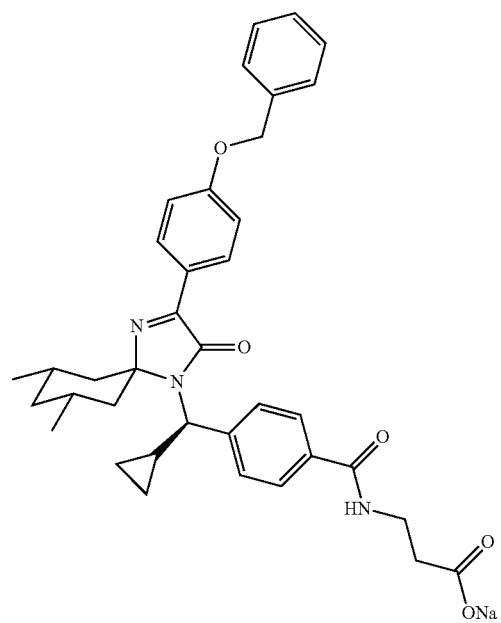 |
| 1.319 | 7.23 | 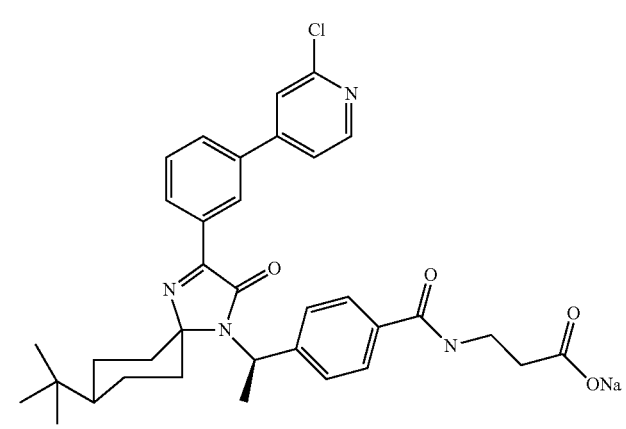 |

TABLE 3-continued
| SM-Ex | Ex. | Structure |
|---|---|---|
| 1.908 | 7.24 | 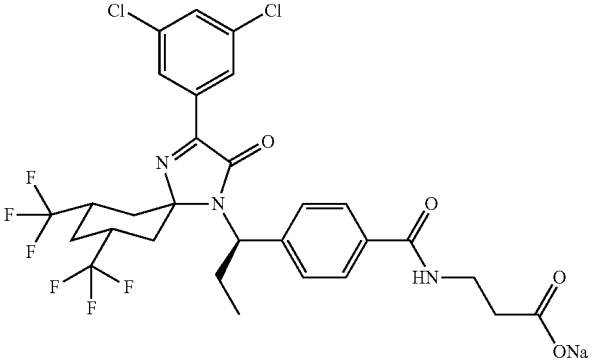 |
| 1.505 | 7.25 | 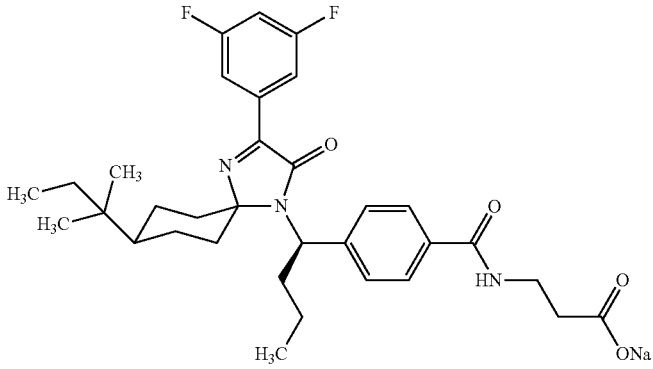 |
| 1.953 | 7.26 | 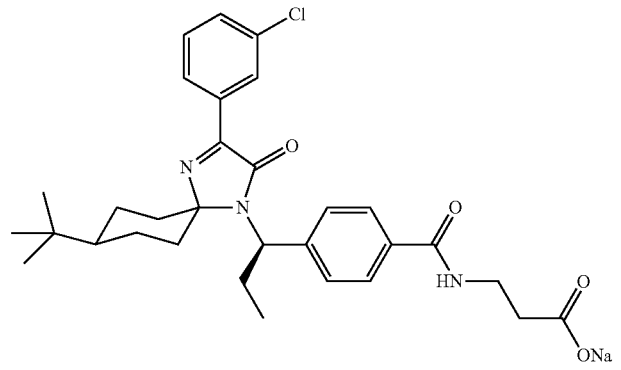 |
| 1.907 | 7.27 | 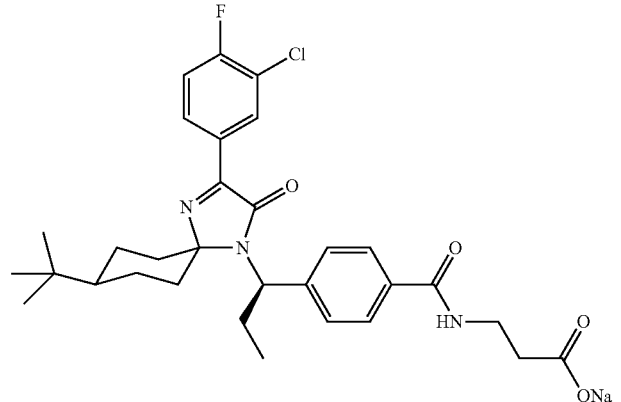 |

TABLE 3-continued
| SM-Ex | Ex. | Structure |
|---|---|---|
| 1.102 | 7.28 | 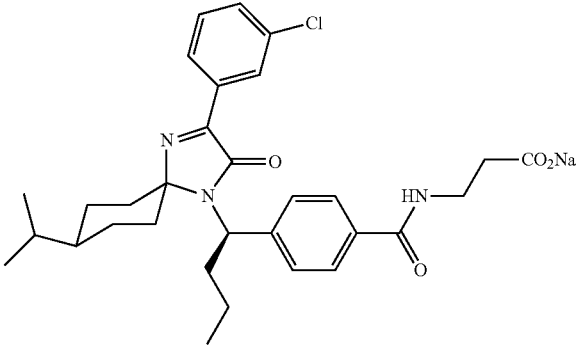 |
| 1.906 | 7.29 | 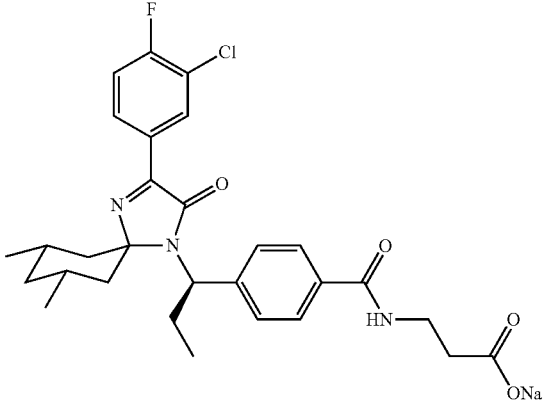 |
| 1.283 | 7.30 | 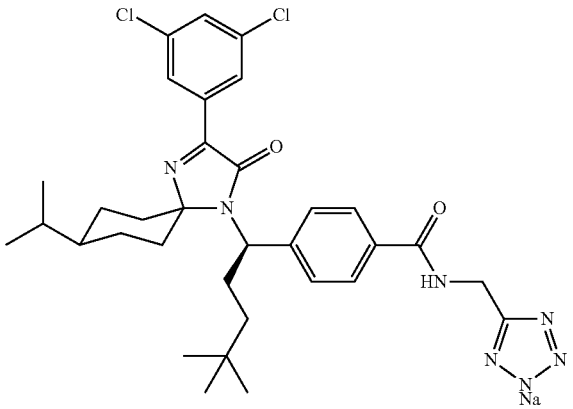 |
| 1.905 | 7.31 | 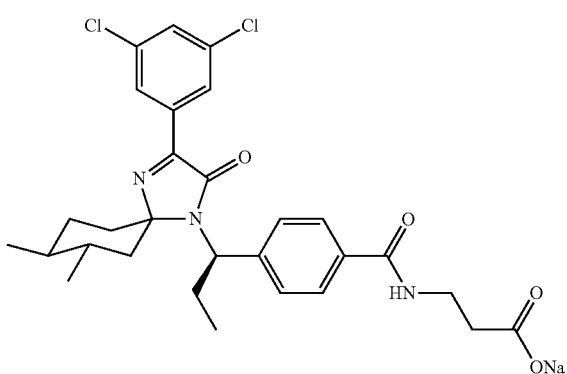 |

TABLE 3-continued
| SM-Ex | Ex. | Structure |
|---|---|---|
| 1.904 | 7.32 | 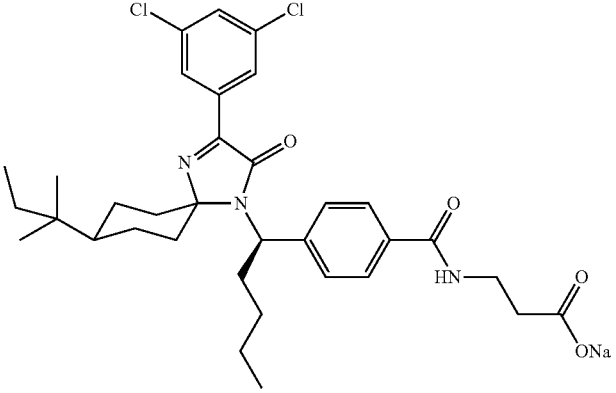 |
| 1.45 | 7.34 | 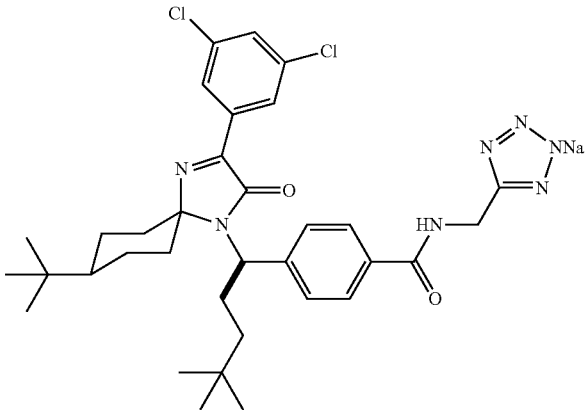 |
| 1.190 | 7.35 | 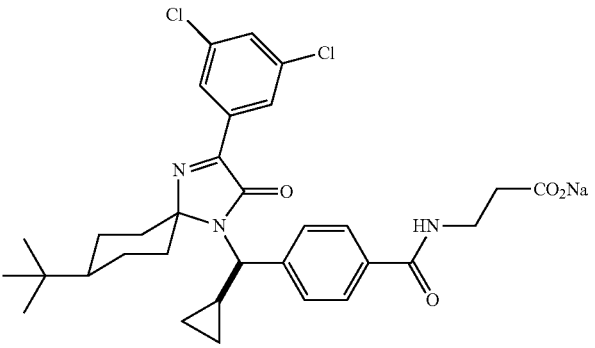 |
| 1.500 | 7.36 | 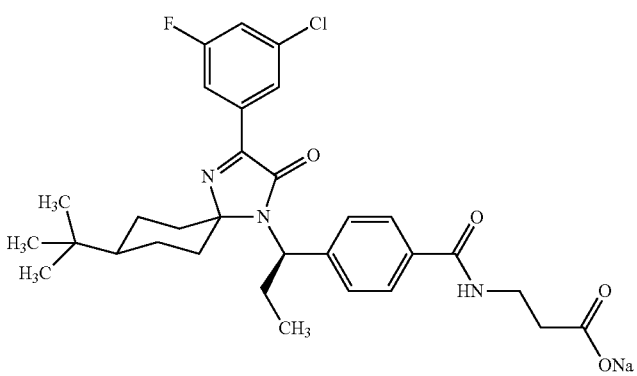 |

TABLE 3-continued

| SM-Ex | Ex. | Structure |
|---|---|---|
| 1.188 | 7.37 | 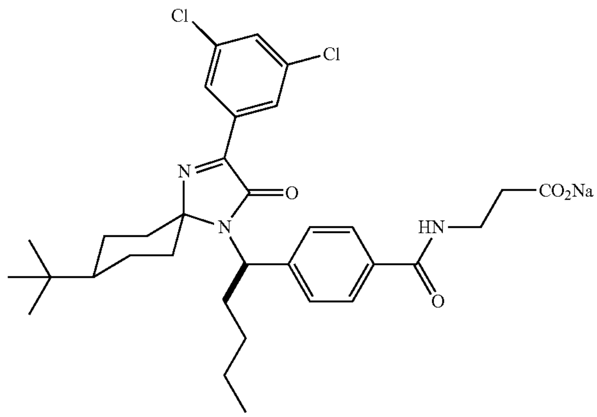 |
| 1.105 | 7.38 | 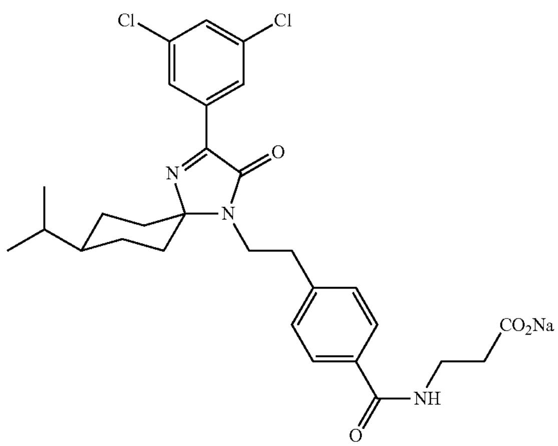 |
| 1.60 | 7.39 | 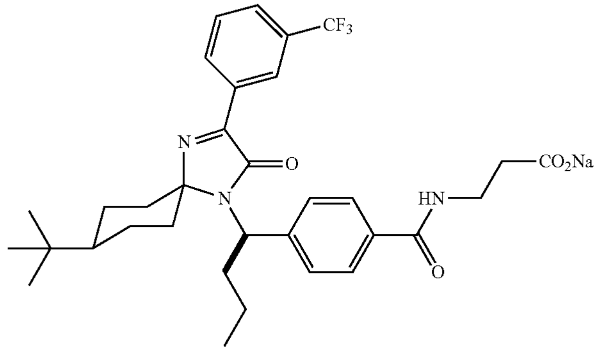 |

TABLE 3-continued
| SM-Ex | Ex. | Structure |
|---|---|---|
| 1.528 | 7.40 | 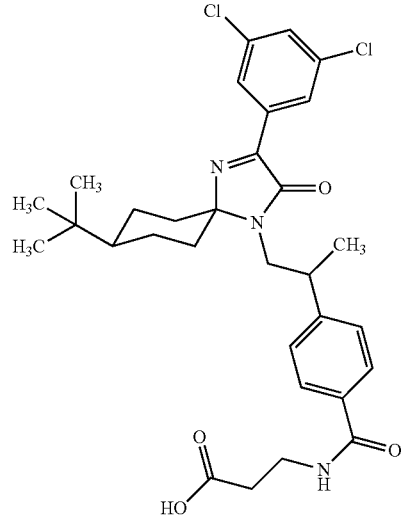 [SMILES: CC(CN1C(=O)C(c2cc(Cl)cc(Cl)c2)=NC12CCC(C(C)(C)C)CC2)c1ccc(C(=O)NCCC(=O)O)cc1] |
| 1.526 | 7.41 | 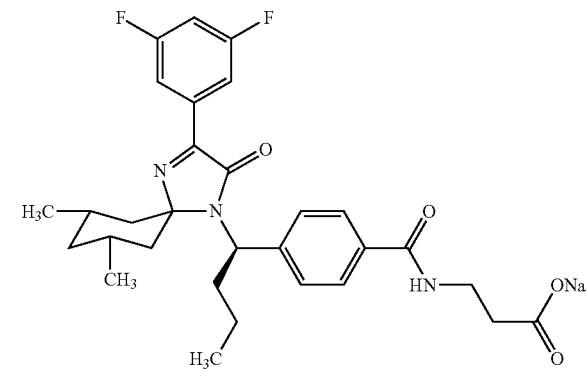 |
| 1.49 | 7.42 | 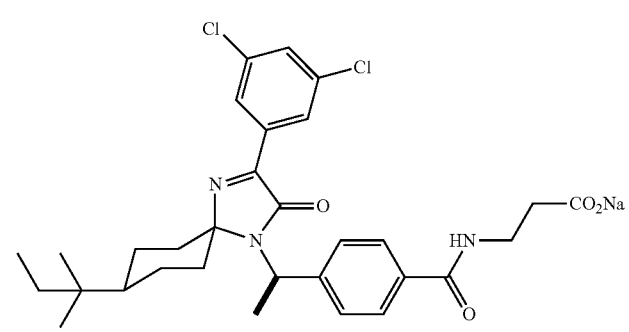 |
| 1.169 | 7.43 | 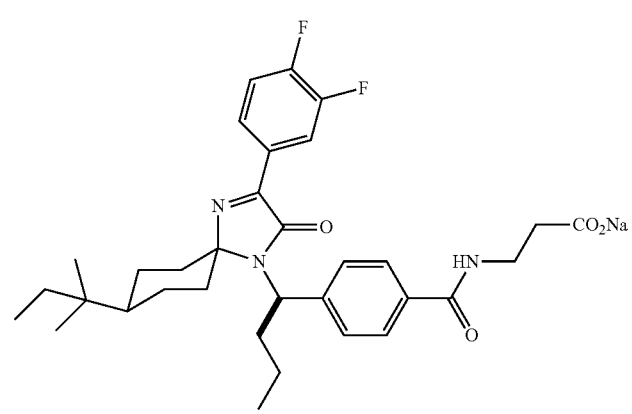 |

TABLE 3-continued

| SM-Ex | Ex. | Structure |
|---|---|---|
| 1.134 | 7.44 | 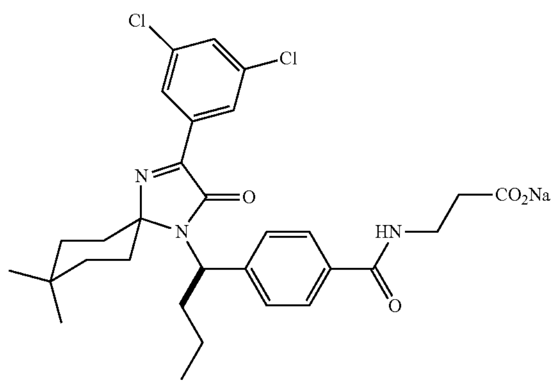 |
| 1.523 | 7.45 | 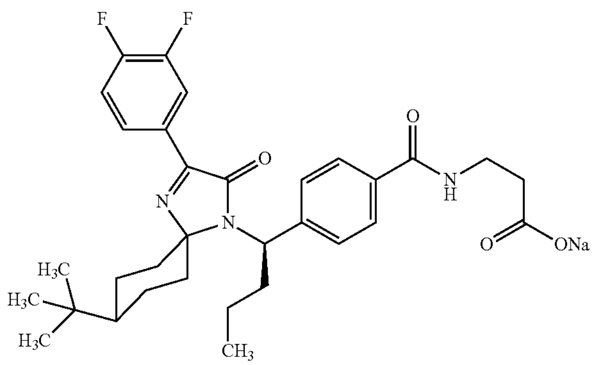 |
| 1.917 | 7.46 | 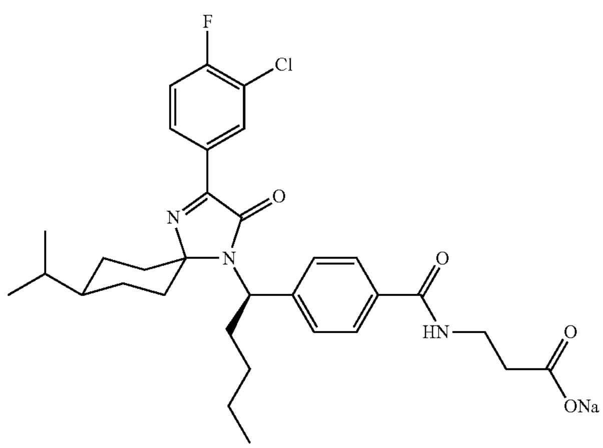 |
| 1.91 | 7.47 | 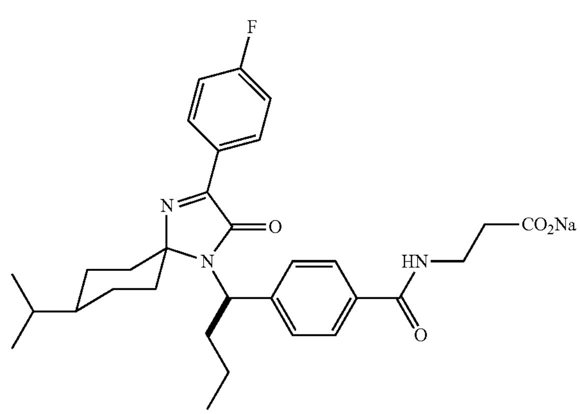 |

TABLE 3-continued
| SM-Ex | Ex. | Structure |
|---|---|---|
| 1.522 | 7.48 | 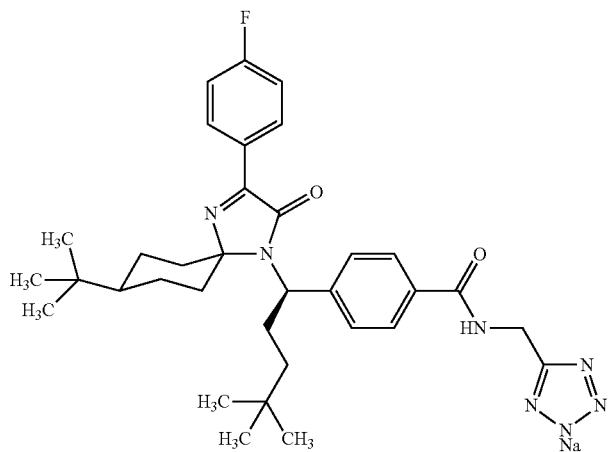 |
| 1.915 | 7.49 | 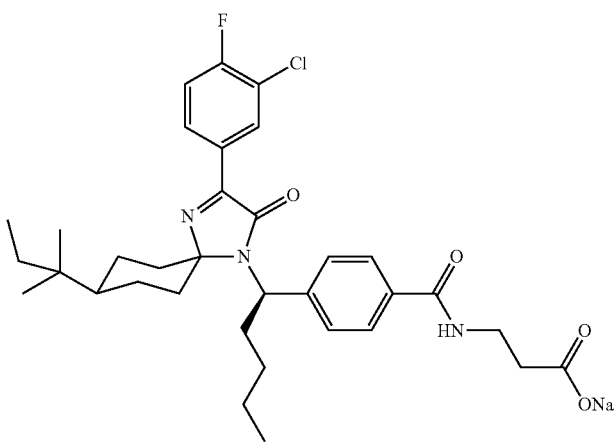 |
| 1.100 | 7.50 | 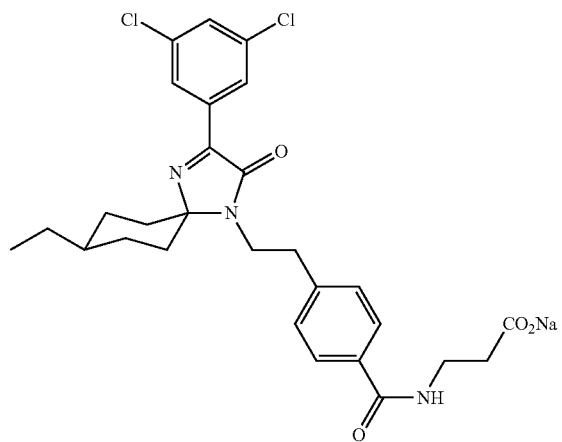 |

TABLE 3-continued
| SM-Ex | Ex. | Structure |
|---|---|---|
| 1.334 | 7.51 | 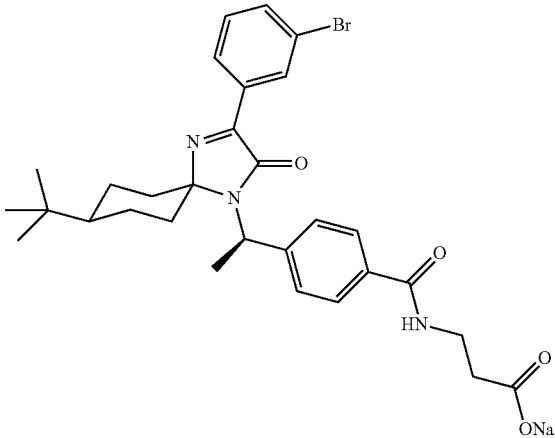 |
| 1.133 | 7.52 | 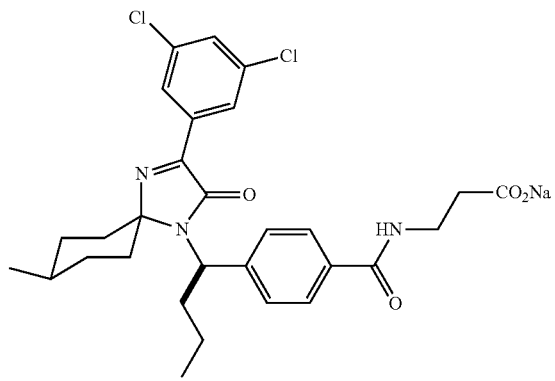 |
| 1.955 | 7.53 | 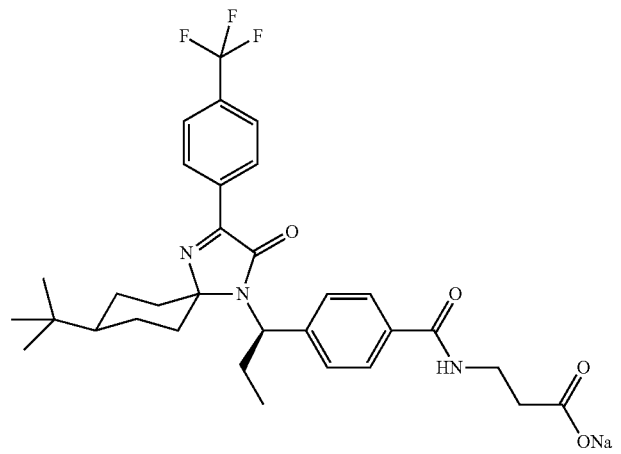 |

TABLE 3-continued
| SM-Ex | Ex. | Structure |
|---|---|---|
| 1.104 | 7.54 | 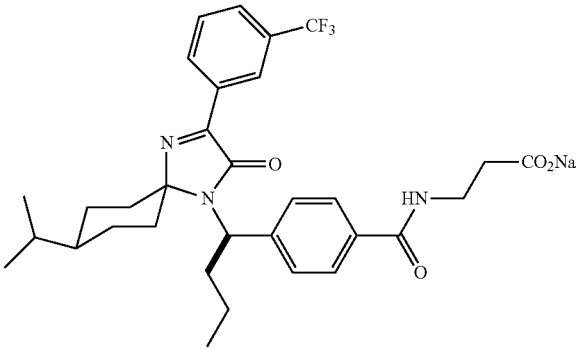 |
| 1.913 | 7.55 | 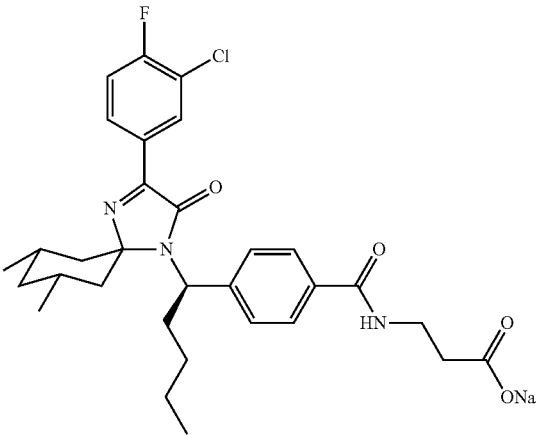 |
| 1.332 | 7.56 | 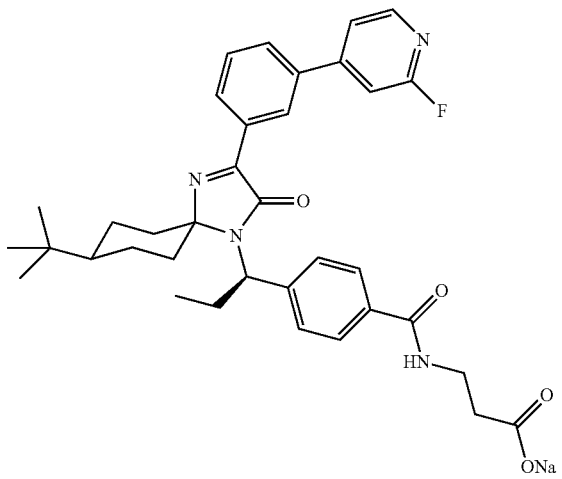 |

TABLE 3-continued
| SM-Ex | Ex. | Structure |
|---|---|---|
| 1.331 | 7.57 | 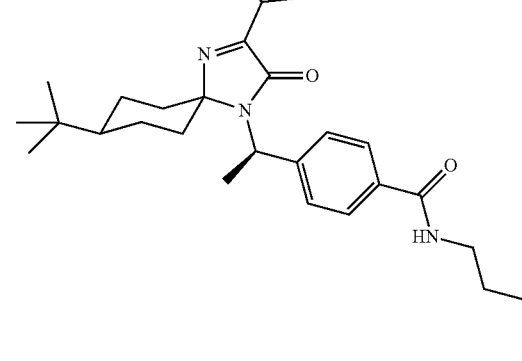 |
| 1.21 | 7.58 | 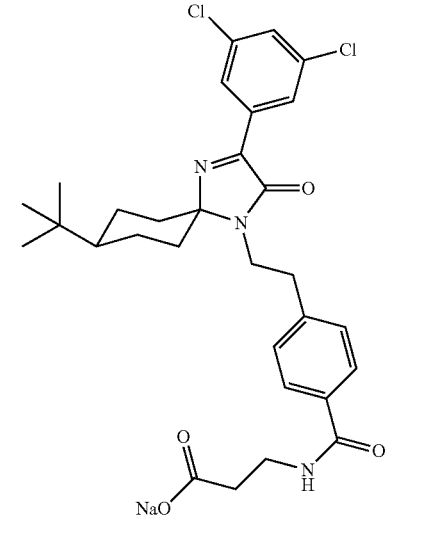 |
| 1.189 | 7.59 | 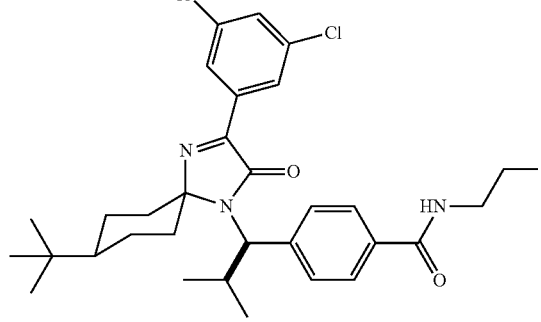 |

TABLE 3-continued
| SM-Ex | Ex. | Structure |
|---|---|---|
| 1.1 | 7.60 | 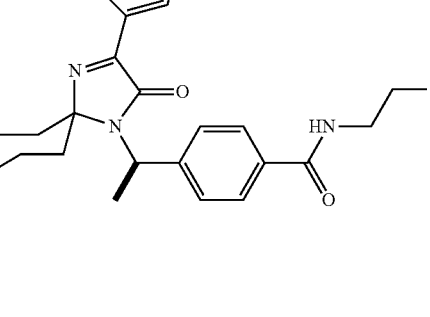 |
| 1.517 | 7.61 | 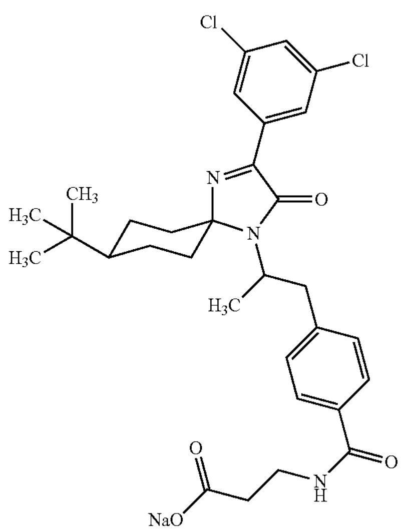 |
| 1.95 | 7.62 | 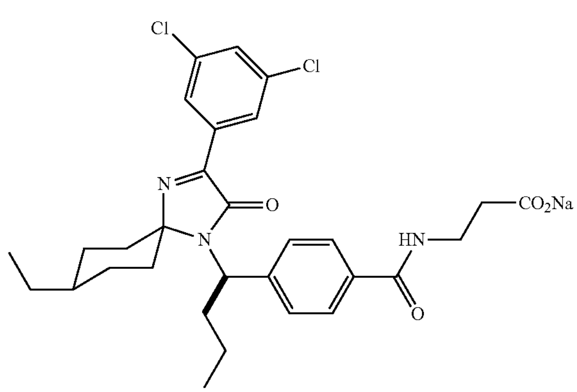 |

TABLE 3-continued
| SM-Ex | Ex. | Structure |
|---|---|---|
| 1.516 | 7.63 | 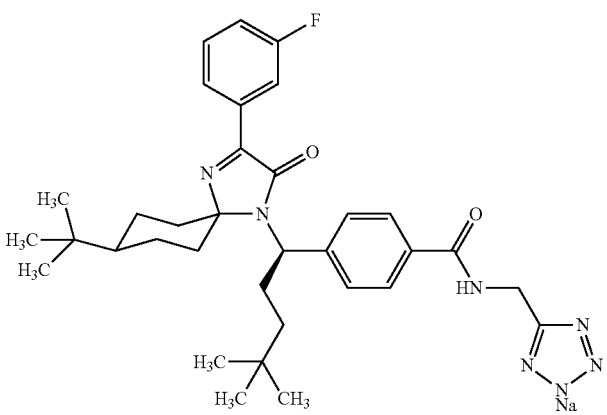 |
| 1.514 | 7.64 | 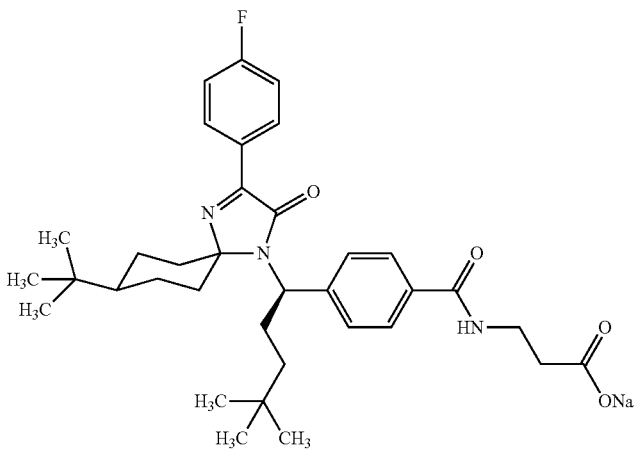 |
| 1.288 | 7.65 | 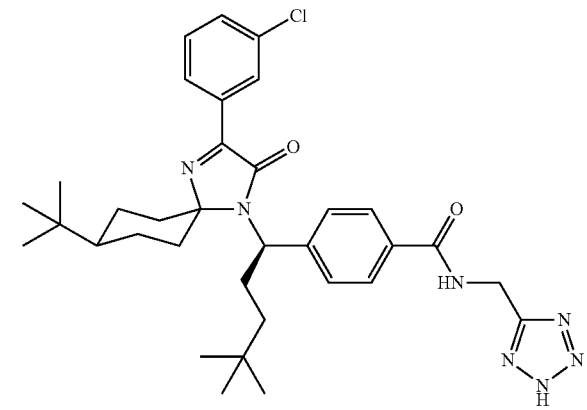 |

TABLE 3-continued

| SM-Ex | Ex. | Structure |
|---|---|---|
| 1.344 | 7.66 | 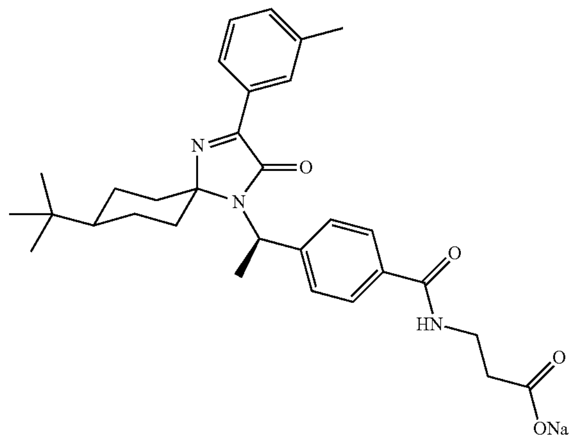 |
| 1.281 | 7.67 | 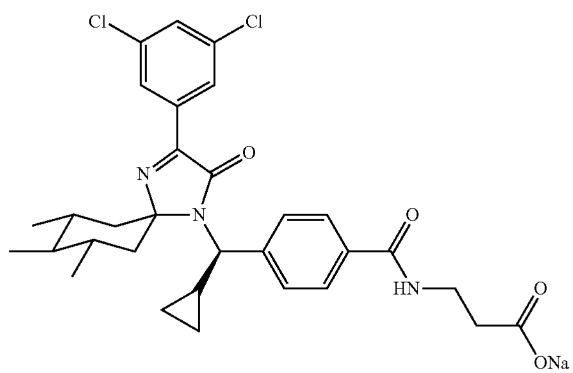 |
| 1.69 | 7.68 | 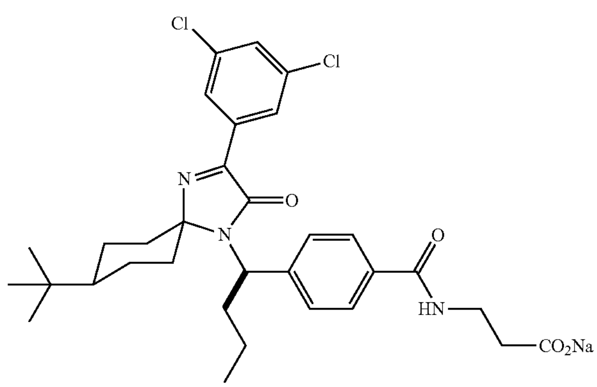 |
| 1.538 | 7.69 | 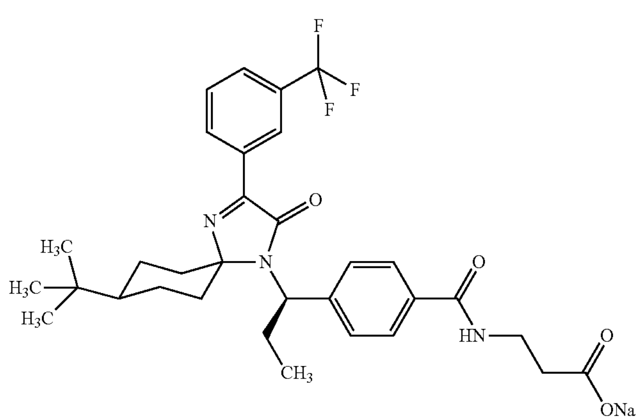 |

TABLE 3-continued
| SM-Ex | Ex. | Structure |
|---|---|---|
| 1.90 | 7.70 | 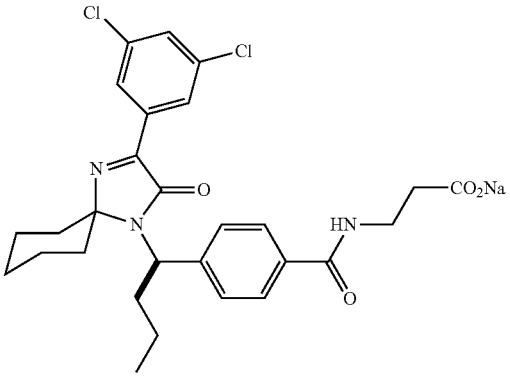 |
| 1.101 | 7.71 | 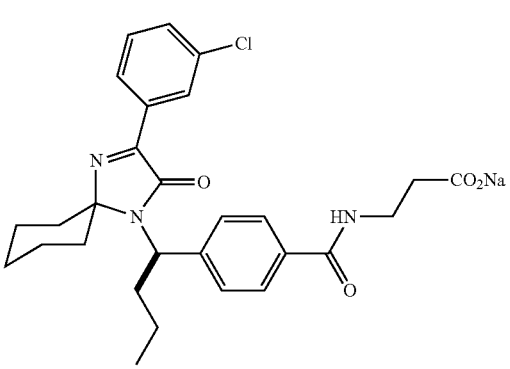 |
| 1.82 | 7.72 | 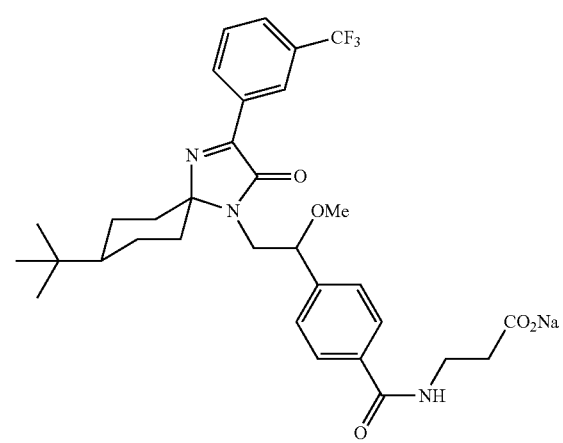 |
| 1.537 | 7.73 | 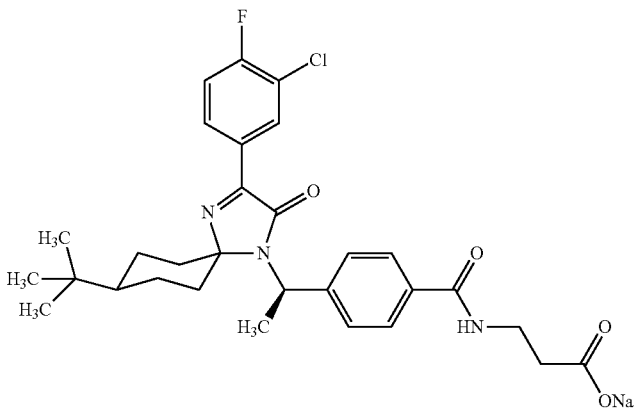 |

TABLE 3-continued
| SM-Ex | Ex. | Structure |
|---|---|---|
| 1.36 | 7.74 | 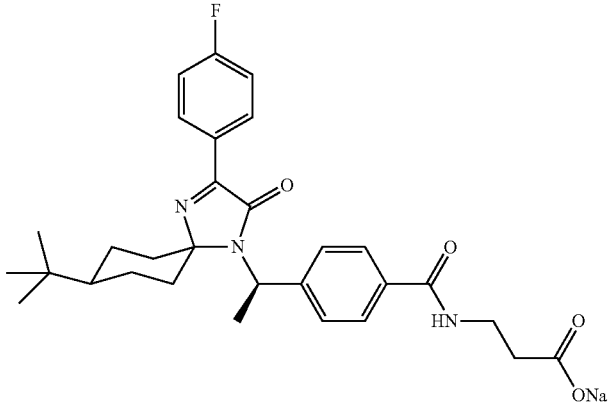 |
| 1.98 | 7.75 | 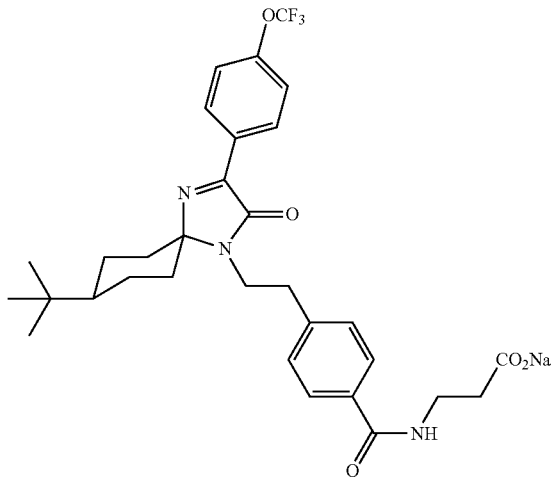 |
| 1.158 | 7.76 | 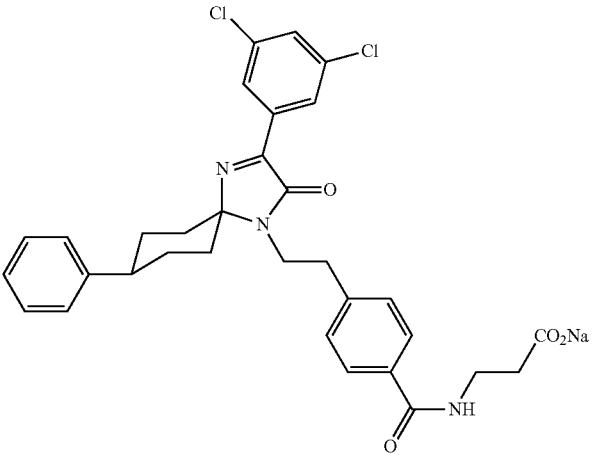 |

TABLE 3-continued
| SM-Ex | Ex. | Structure |
|---|---|---|
| 1.341 | 7.77 | 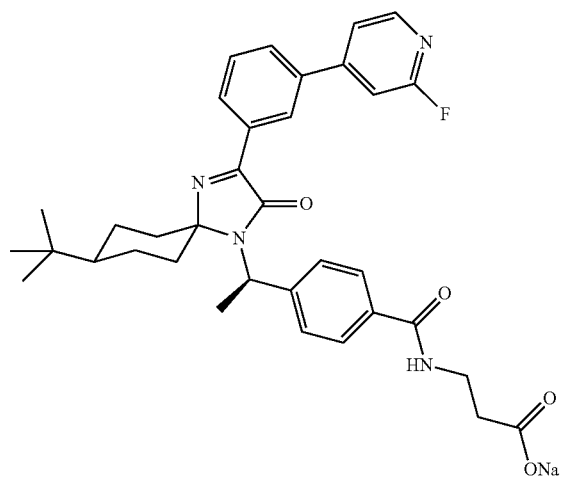 |
| 1.93 | 7.78 | 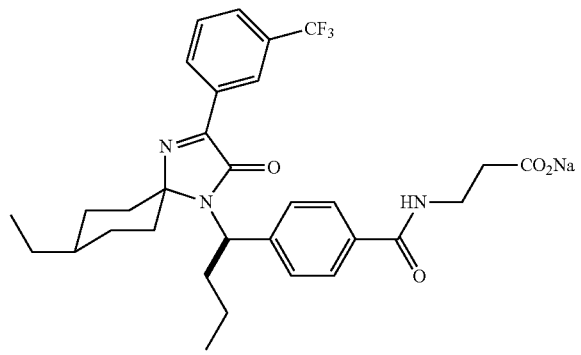 |
| 1.30 | 7.79 | 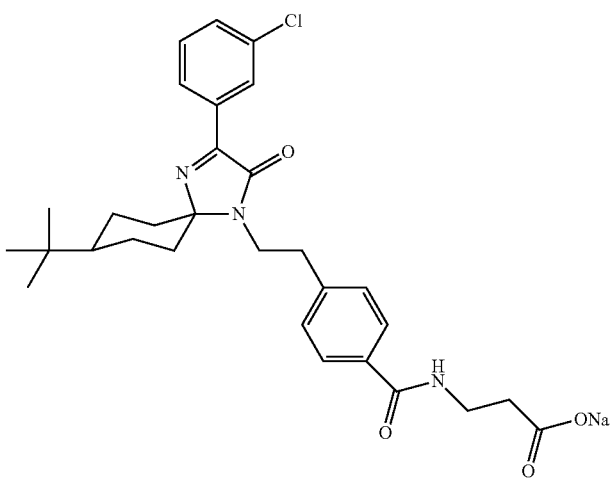 |

TABLE 3-continued

| SM-Ex | Ex. | Structure |
|---|---|---|
| 1.153 | 7.80 | 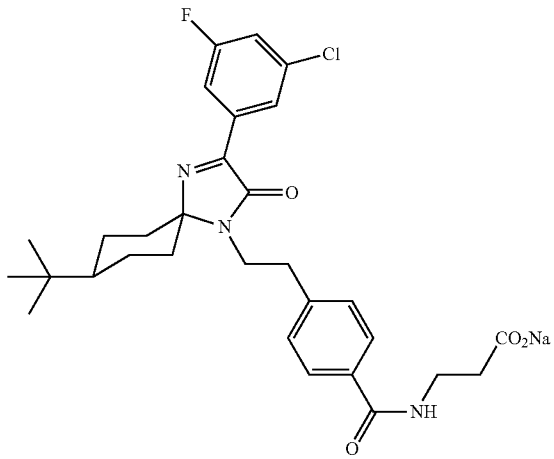 |
| 1.27 | 7.81 | 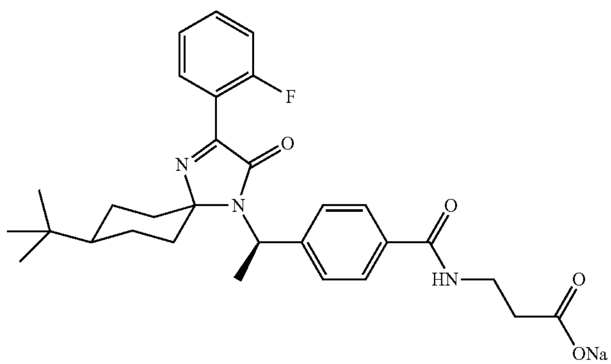 |
| 1.922 | 7.82 | 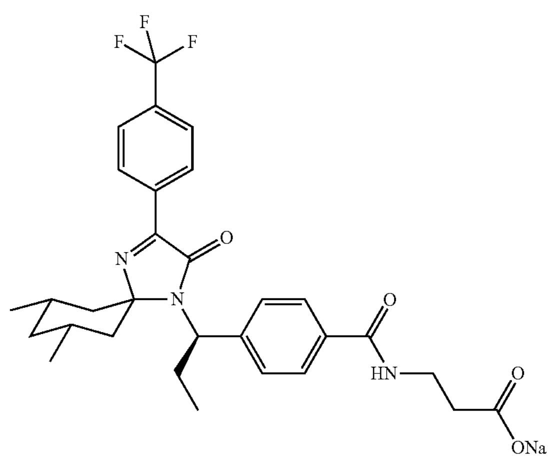 |

TABLE 3-continued

| SM-Ex | Ex. | Structure |
|---|---|---|
| 1.340 | 7.83 | 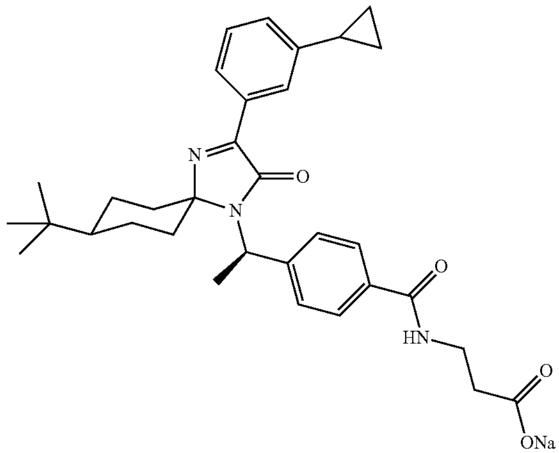 |
| 1.127 | 7.84 | 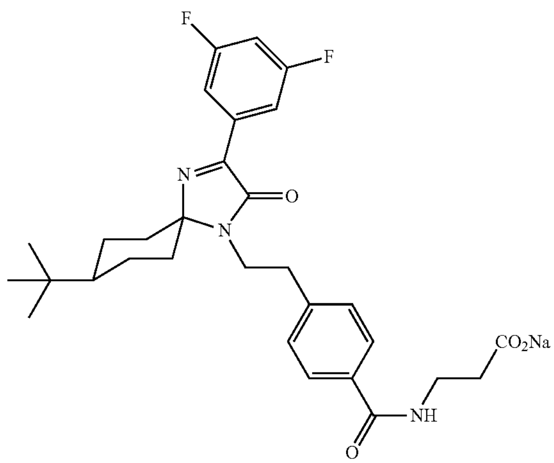 |
| 1.339 | 7.85 | 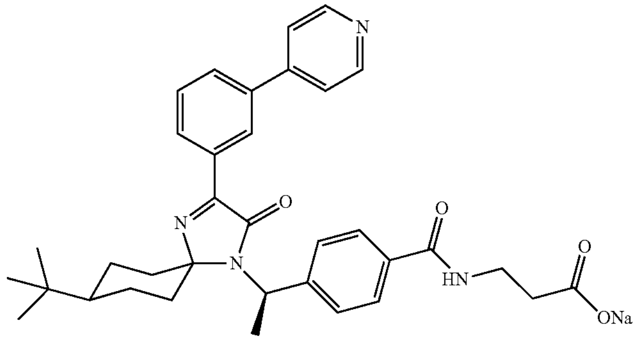 |
| 1.192 | 7.86 | 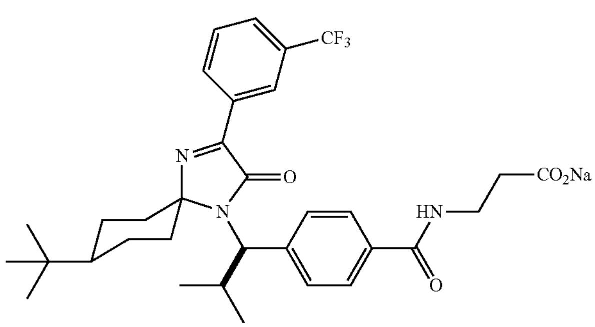 |

TABLE 3-continued
| SM-Ex | Ex. | Structure |
|---|---|---|
| 1.531 | 7.87 | 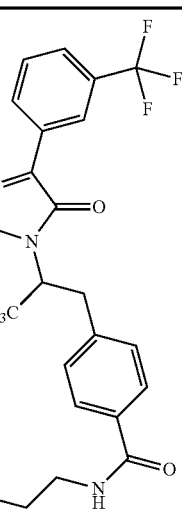 |
| 1.92 | 7.88 | 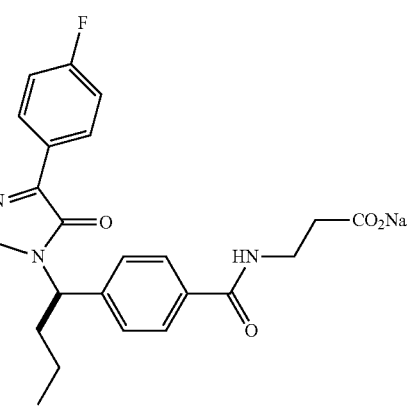 |
| 1.530 | 7.89 | 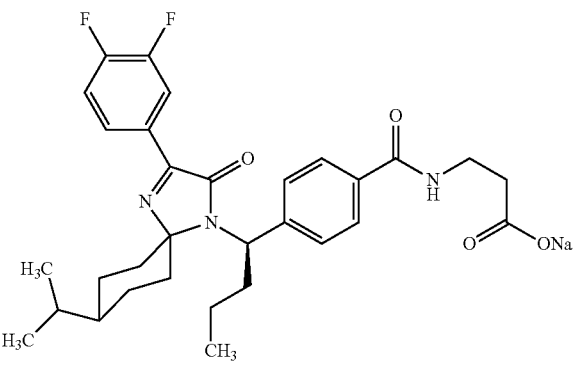 |
| 1.193 | 7.90 | 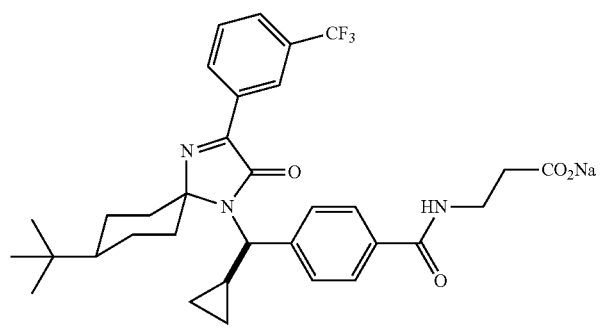 |

TABLE 3-continued

| SM-Ex | Ex. | Structure |
|---|---|---|
| 1.29 | 7.91 | 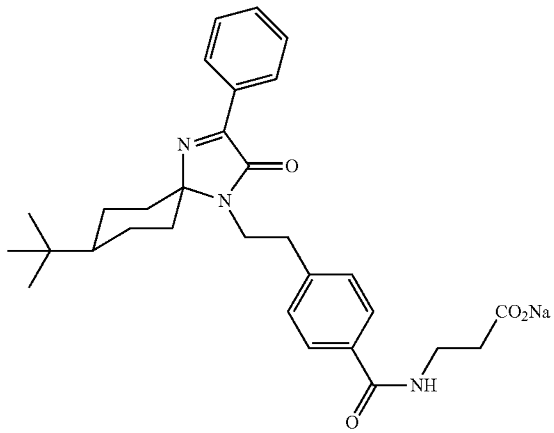 |
| 1.7 | 7.92 | 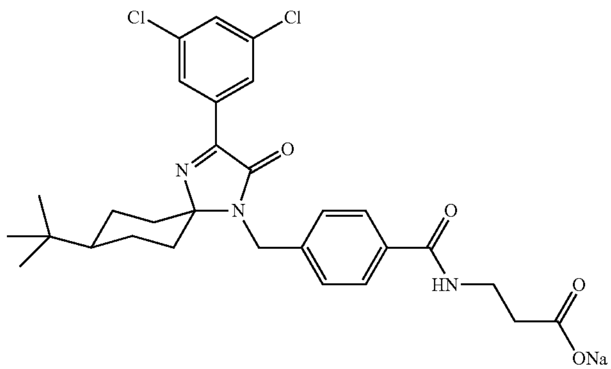 |
| 1.23 | 7.93 | 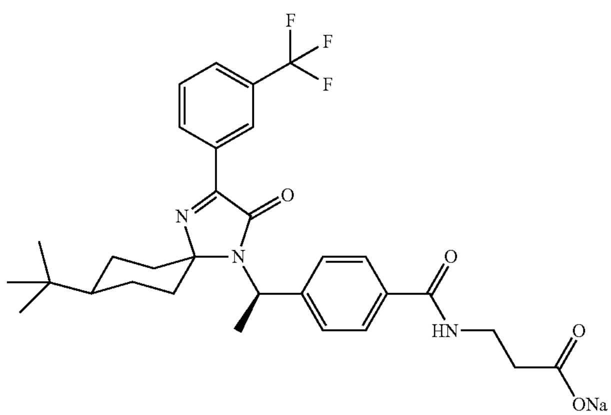 |
| 1.99 | 7.94 | 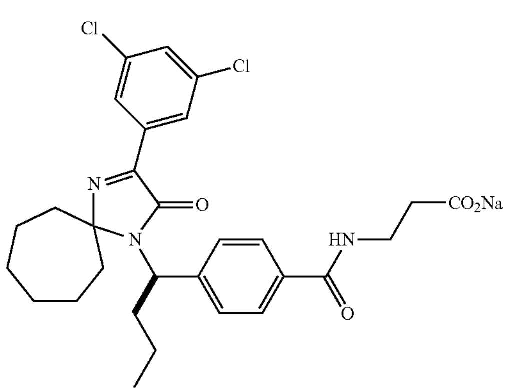 |

TABLE 3-continued
| SM-Ex | Ex. | Structure |
|---|---|---|
| 1.119 | 7.95 | 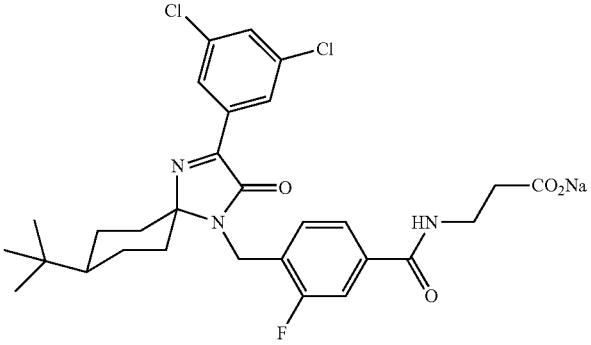 |
| 1.141 | 7.96 | 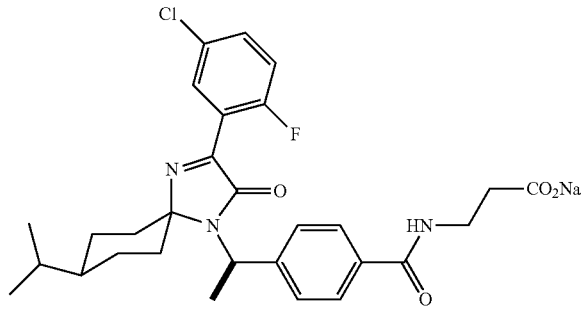 |
| 1.161 | 7.97 | 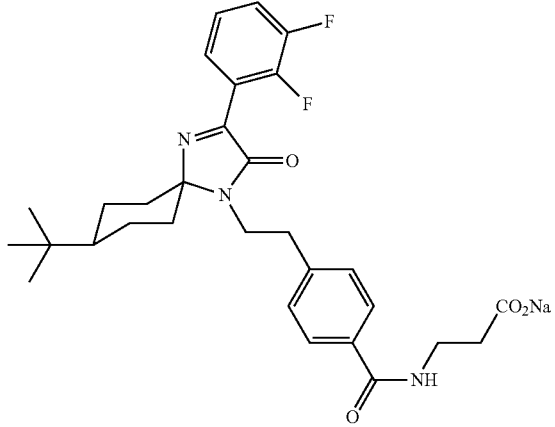 |
| 1.116 | 7.98 | 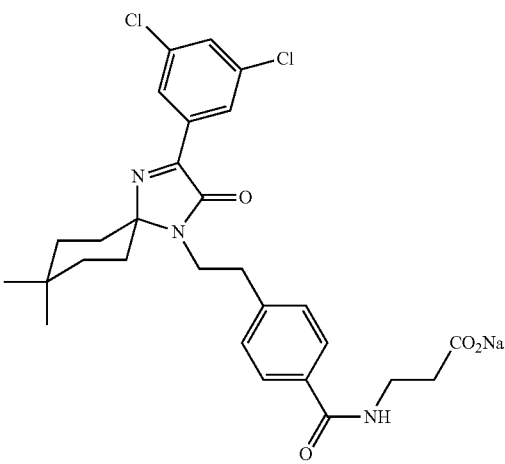 |

TABLE 3-continued
| SM-Ex | Ex. | Structure |
|---|---|---|
| 1.94 | 7.99 | 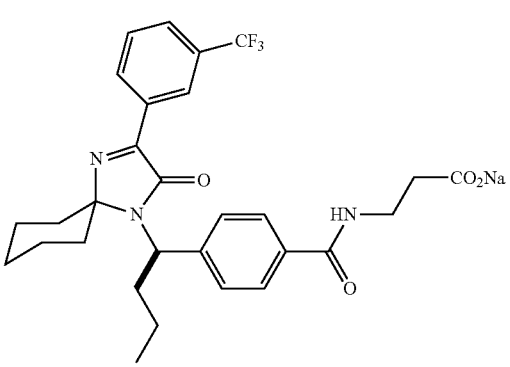 |
| 1.931 | 7.100 | 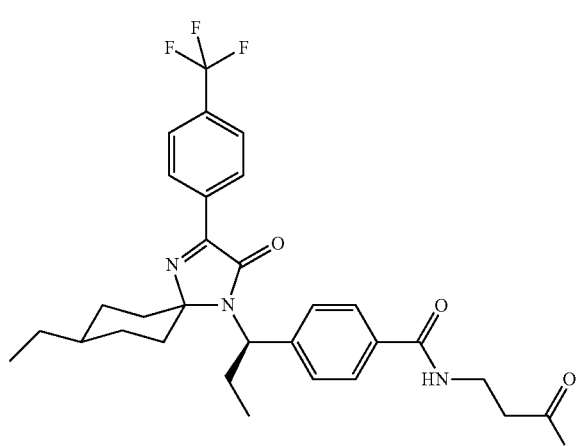 |
| 1.549 | 7.101 | 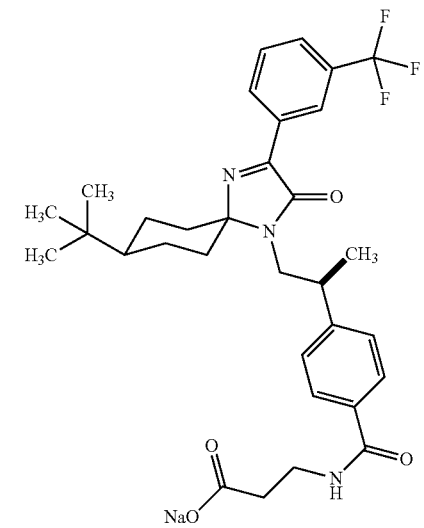 |

TABLE 3-continued

| SM-Ex | Ex. | Structure |
|---|---|---|
| 1.97 | 7.102 | 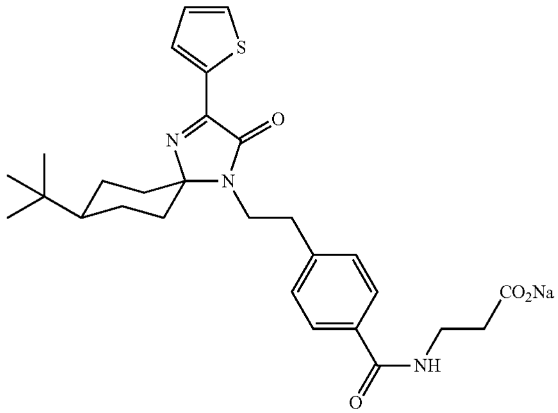 |
| 1.350 | 7.103 | 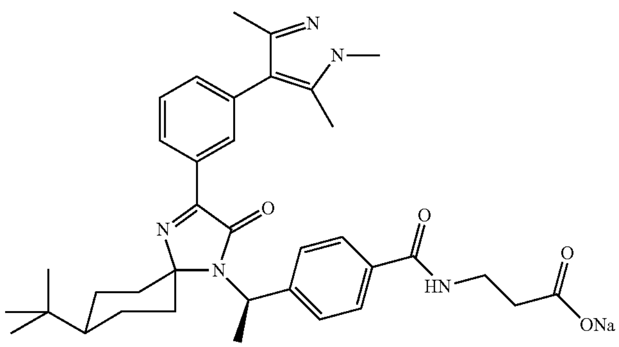 |
| 1.118 | 7.104 | 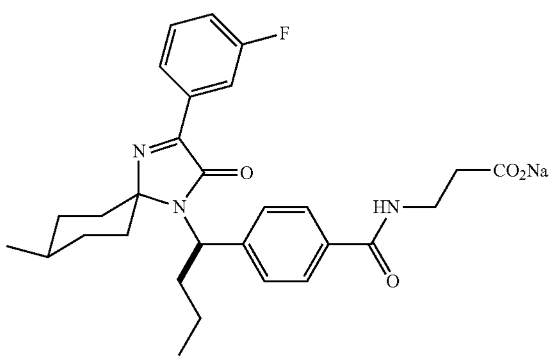 |
| 1.929 | 7.105 | 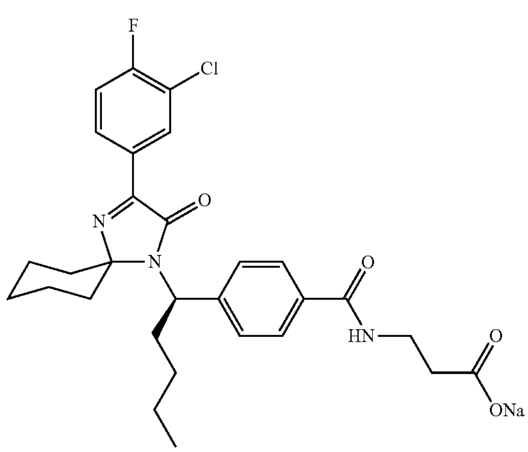 |

TABLE 3-continued

| SM-Ex | Ex. | Structure |
|---|---|---|
| 1.151 | 7.106 | 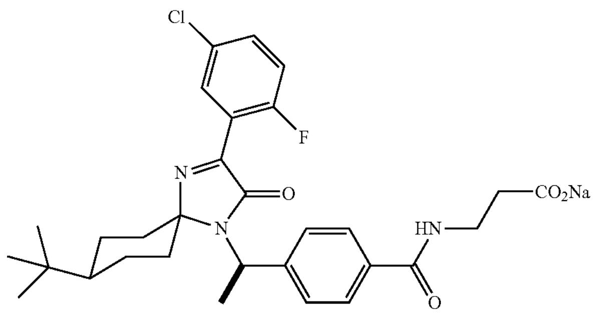 |
| 1.143 | 7.107 | 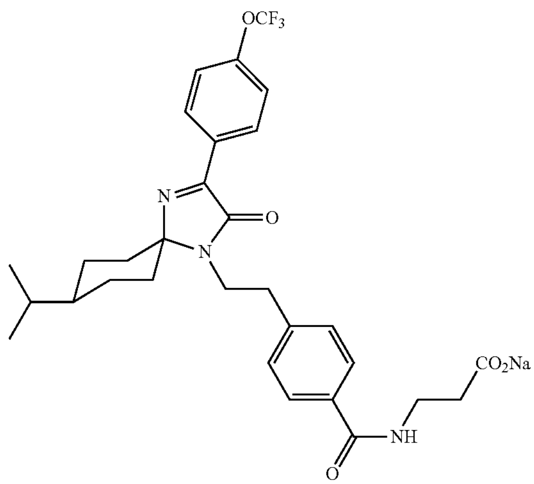 |
| 1.22 | 7.108 | 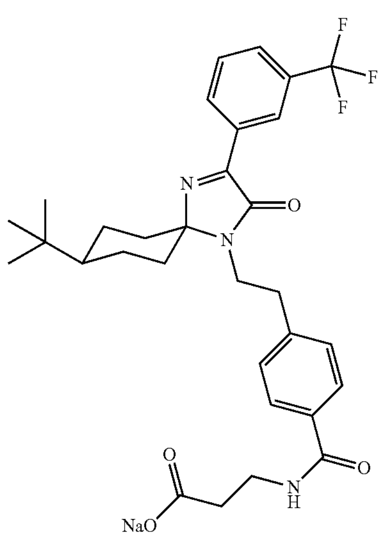 |

TABLE 3-continued
| SM-Ex | Ex. | Structure |
|---|---|---|
| 1.155 | 7.109 | 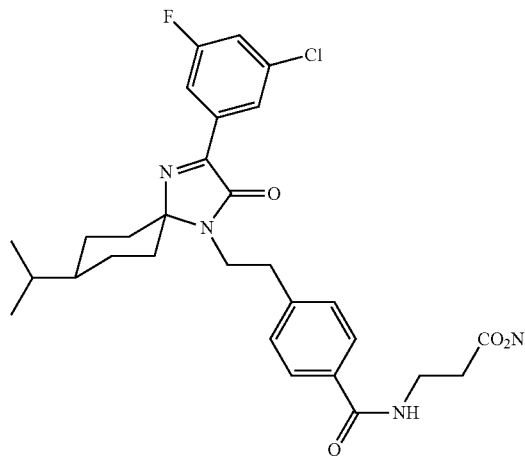 |
| 1.128 | 7.110 | 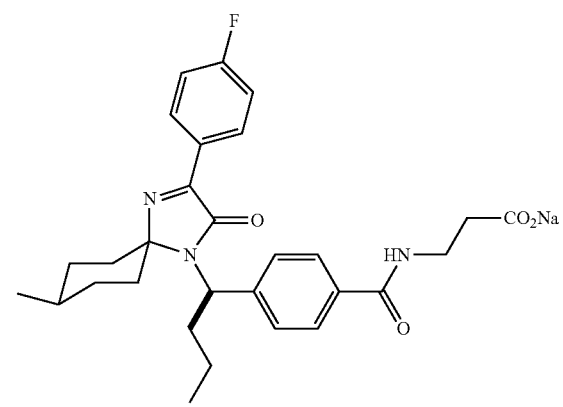 |
| 1.136 | 7.111 | 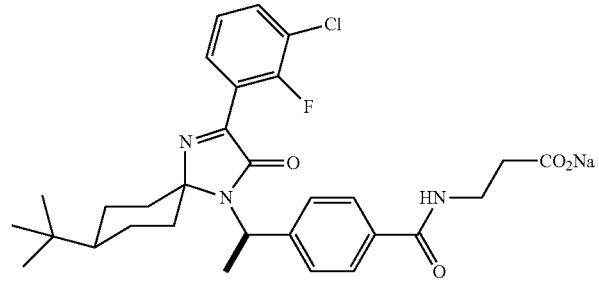 |
| 1.542 | 7.112 | 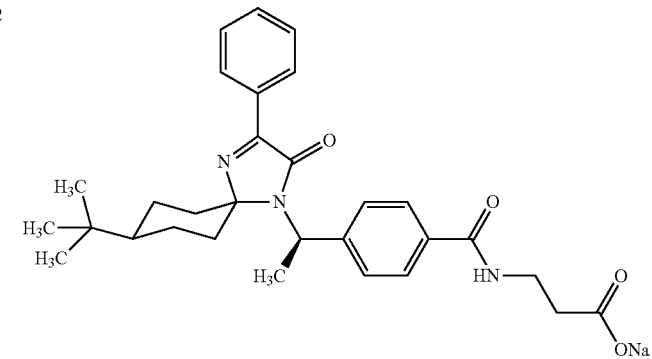 |

TABLE 3-continued
| SM-Ex | Ex. | Structure |
|---|---|---|
| 1.106 | 7.113 | 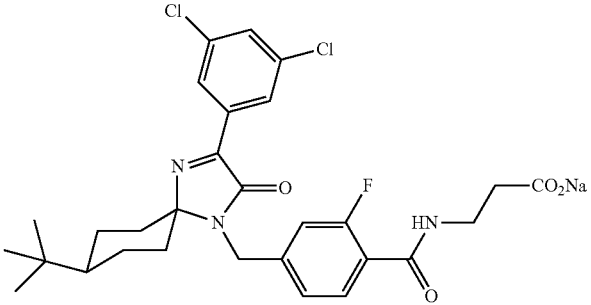 |
| 1.926 | 7.114 | 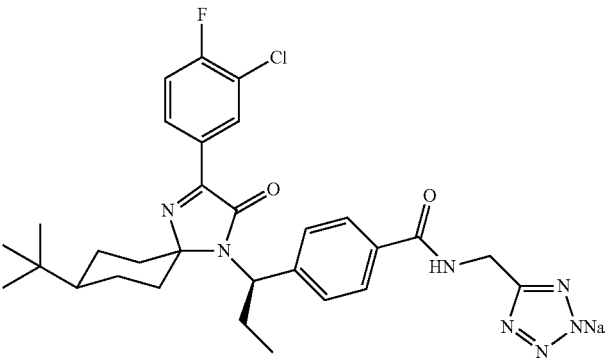 |
| 1.62 | 7.115 | 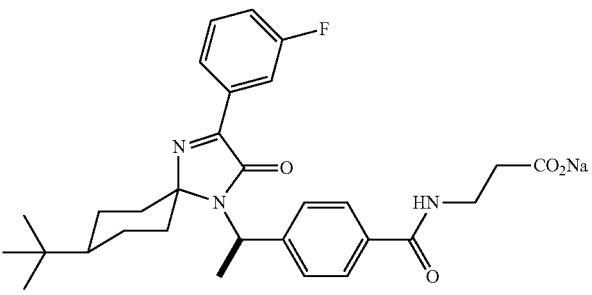 |
| 1.540 | 7.116 | 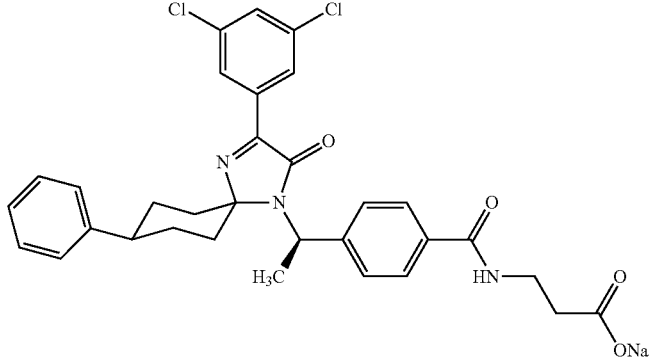 |

TABLE 3-continued
| SM-Ex | Ex. | Structure |
|---|---|---|
| 1.87 | 7.117 | 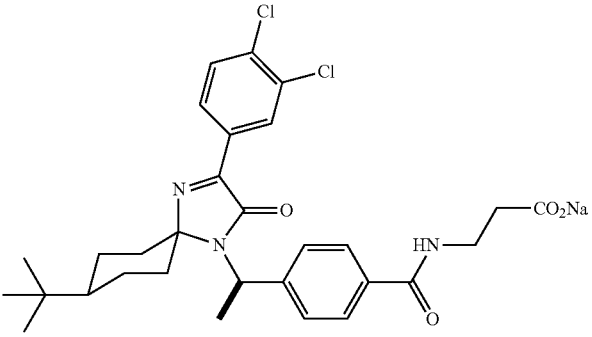 |
| 2.1 | 7.118 | 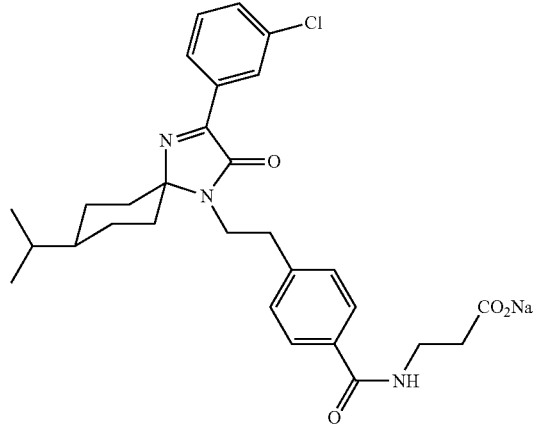 |
| 1.924 | 7.119 | 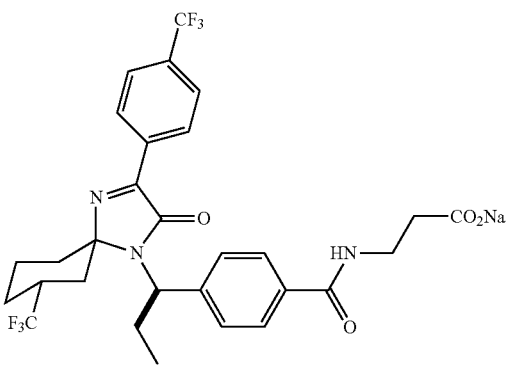<br>Isomer 2 |
| 1.89 | 7.120 | 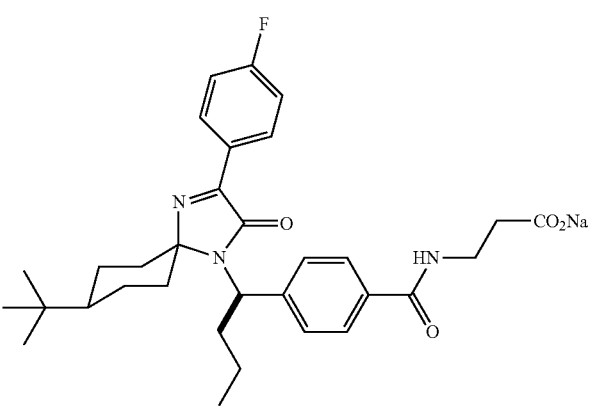 |

TABLE 3-continued
| SM-Ex | Ex. | Structure |
|---|---|---|
| 1.170 | 7.121 | 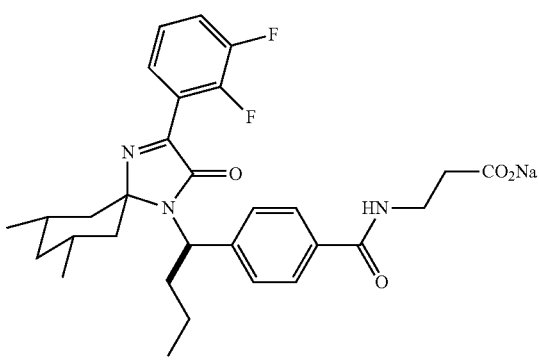 |
| 1.117 | 7.122 | 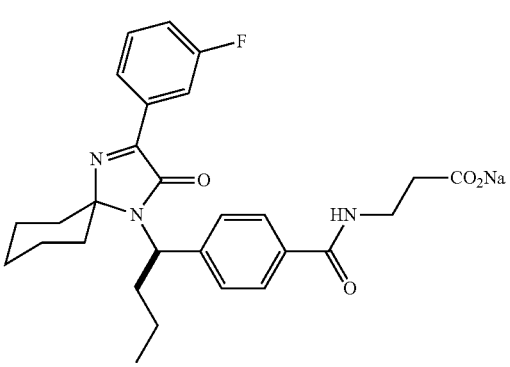 |
| 1.941 | 7.123 | 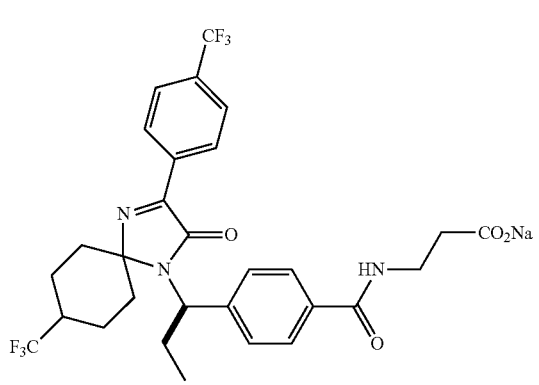<br>isomer 2 |
| 1.940 | 7.124 | 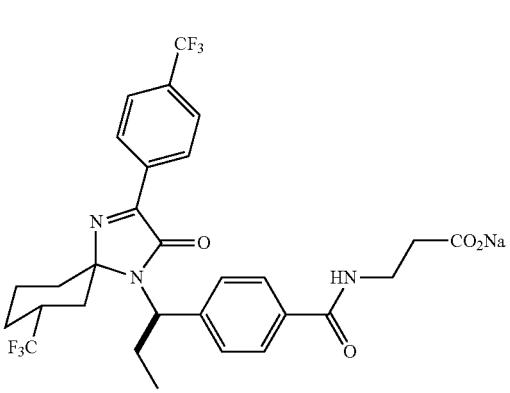<br>Isomer 1 |

TABLE 3-continued
| SM-Ex | Ex. | Structure |
|---|---|---|
| 1.122 | 7.125 | 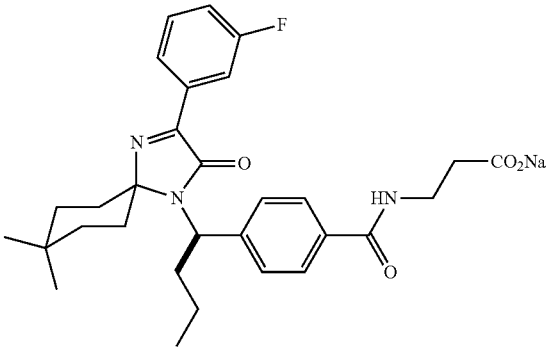 |
| 1.313 | 7.126 | 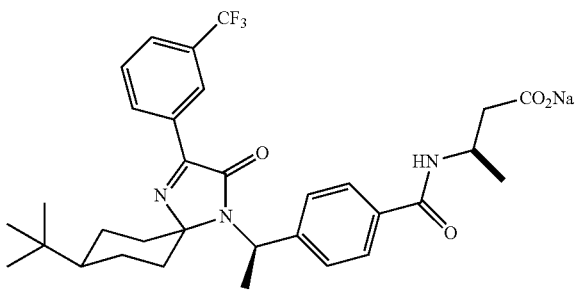 |
| 1.139 | 7.127 | 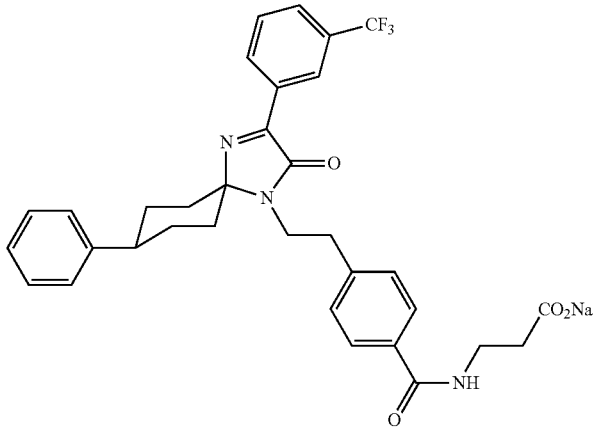 |
| 1.939 | 7.128 | 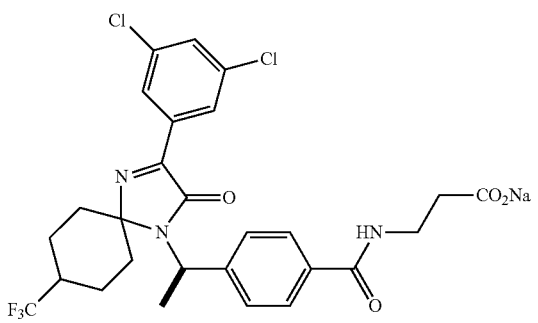 Isomer 2 |

TABLE 3-continued
| SM-Ex | Ex. | Structure |
|---|---|---|
| 1.120 | 7.129 | 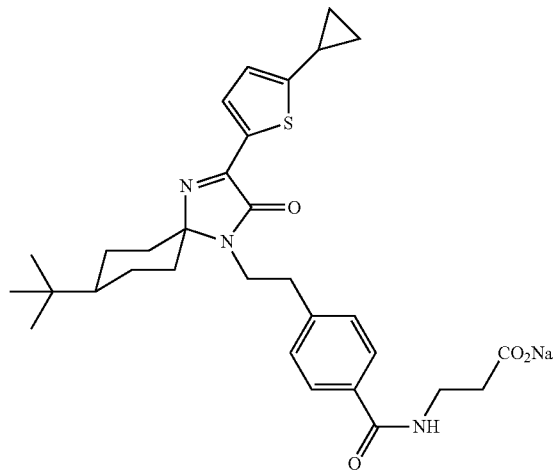 |
| 1.111 | 7.130 | 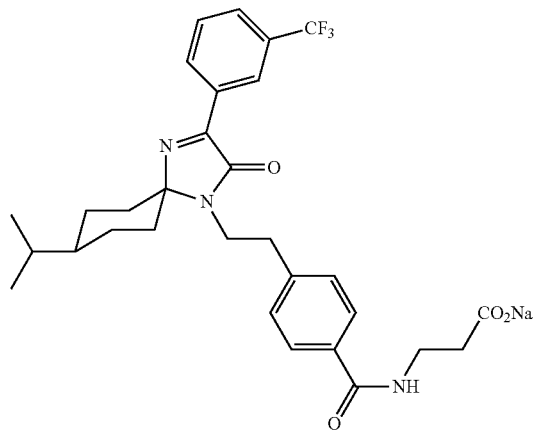 |
| 1.937 | 7.131 | 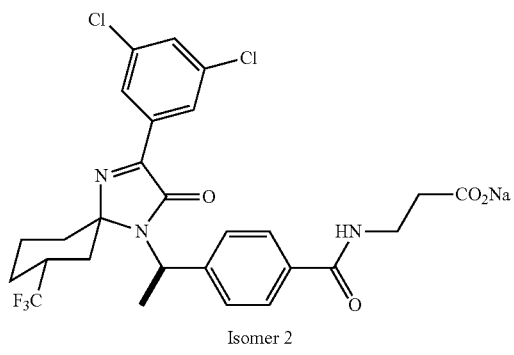 |

TABLE 3-continued
| SM-Ex | Ex. | Structure |
|---|---|---|
| 1.112 | 7.132 | 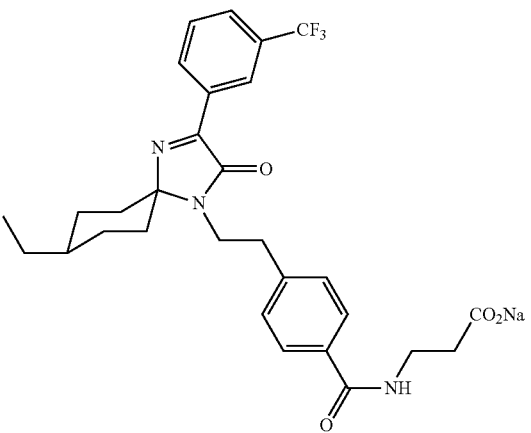 |
| 1.936 | 7.133 | 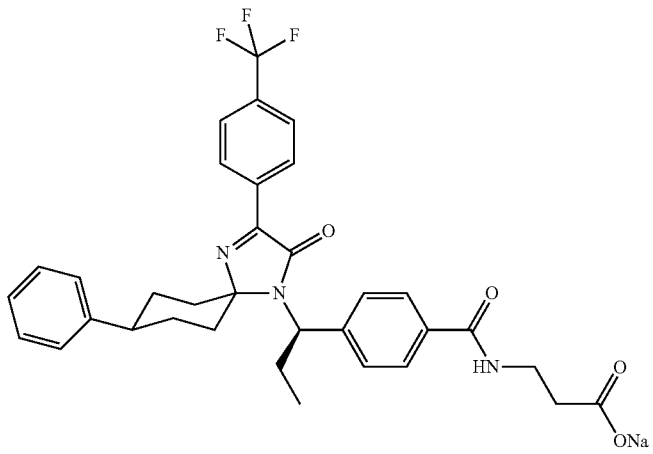 |
| 1.113 | 7.134 | 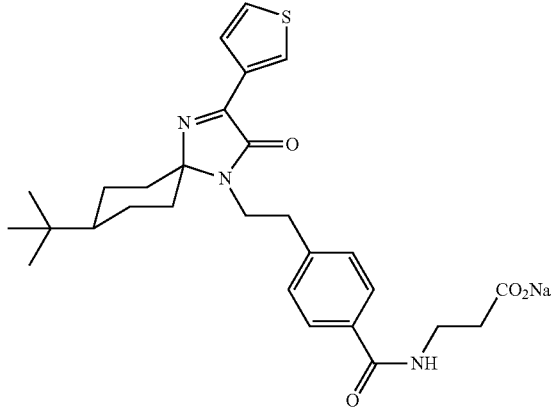 |
| 1.132 | 7.135 | 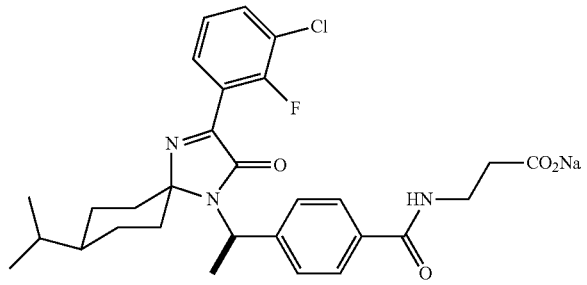 |

TABLE 3-continued
| SM-Ex | Ex. | Structure |
|---|---|---|
| 1.108 | 7.136 | 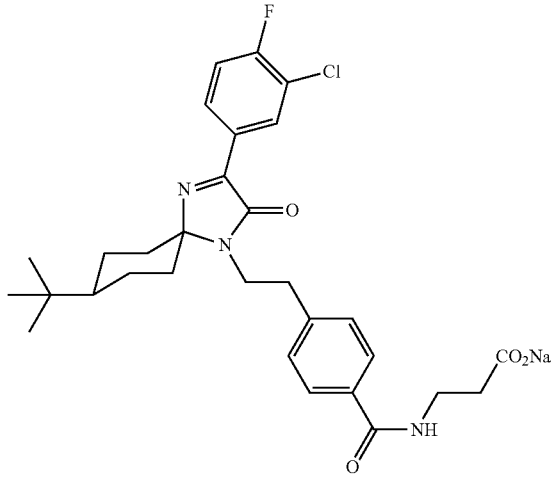 |
| 1.358 | 7.137 | 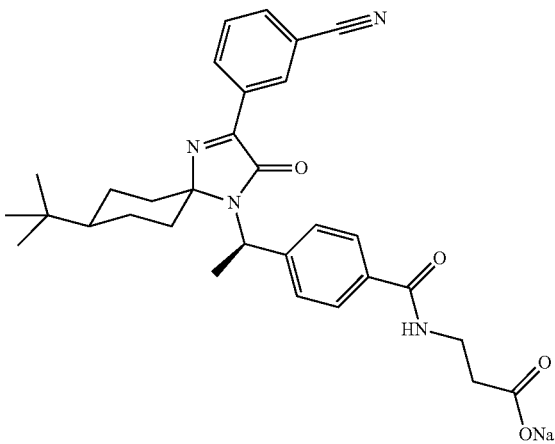 |
| 1.191 | 7.138 | 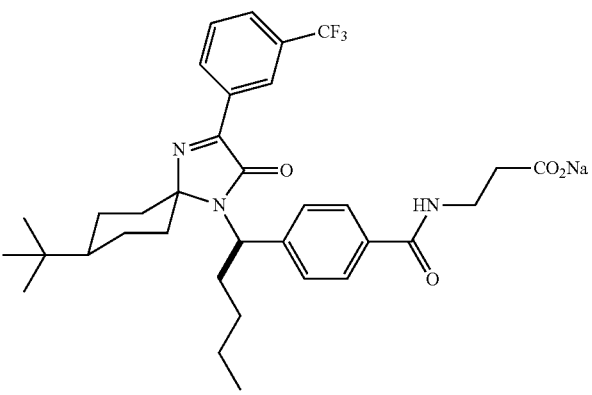 |

TABLE 3-continued
| SM-Ex | Ex. | Structure |
|---|---|---|
| 1.934 | 7.139 | 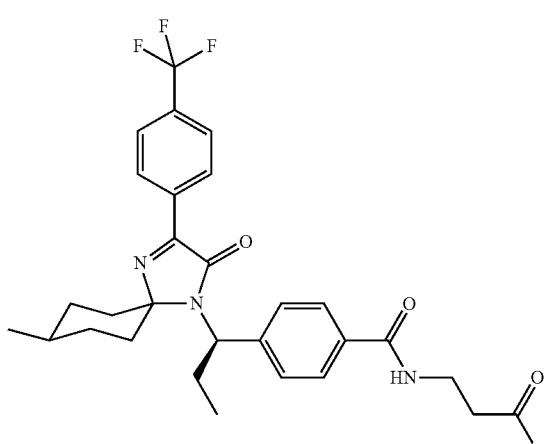 |
| 1.121 | 7.140 | 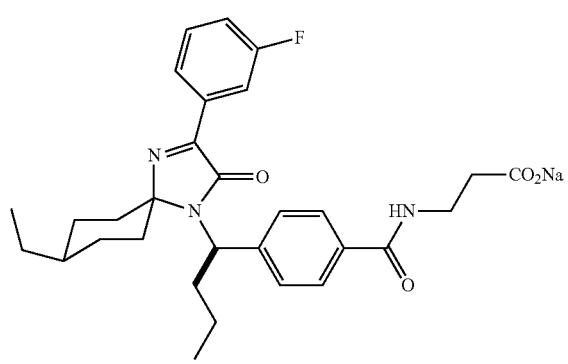 |
| 1.88 | 7.141 | 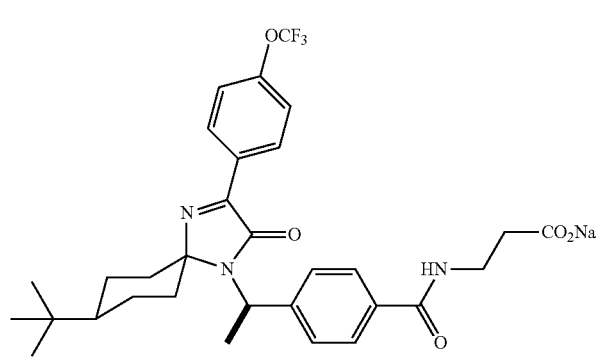 |

TABLE 3-continued
| SM-Ex | Ex. | Structure |
|---|---|---|
| 1.556 | 7.142 | 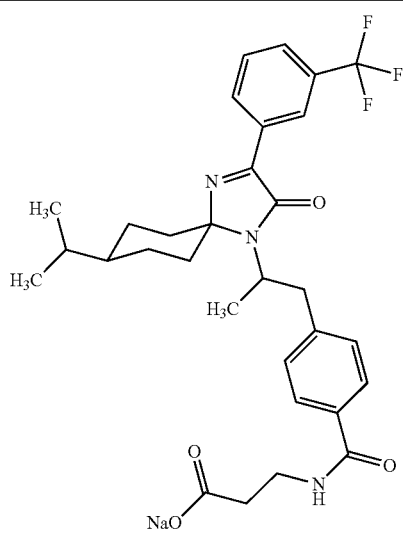 |
| 1.110 | 7.143 | 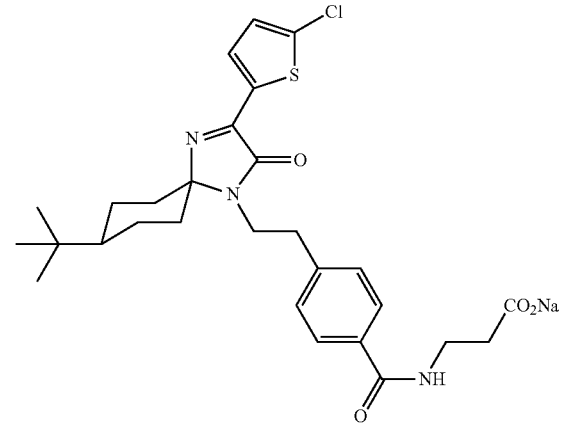 |
| 7.109 | 7.144 | 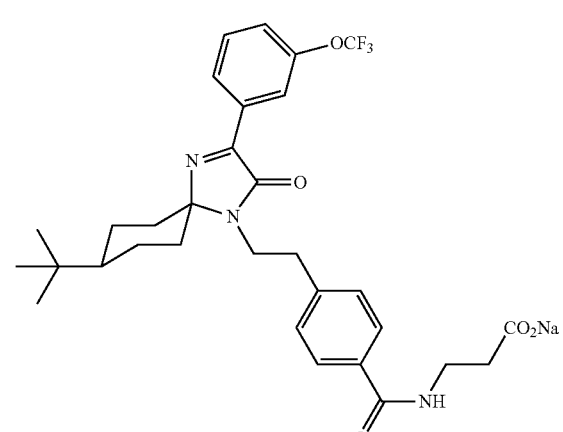 |

TABLE 3-continued
| SM-Ex | Ex. | Structure |
|---|---|---|
| 1.138 | 7.145 | 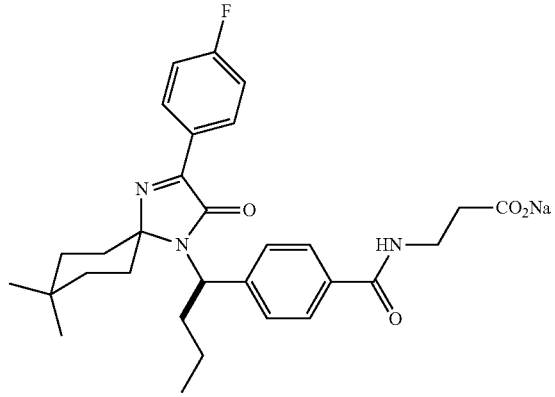 |
| 1.131 | 7.146 | 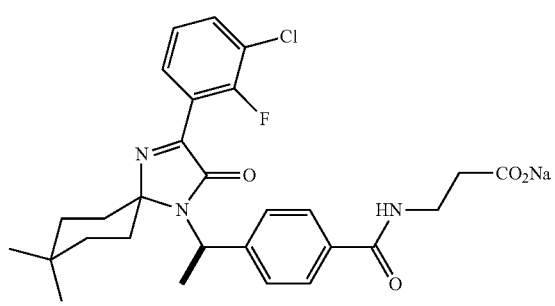 |
| 1.80 | 7.147 | 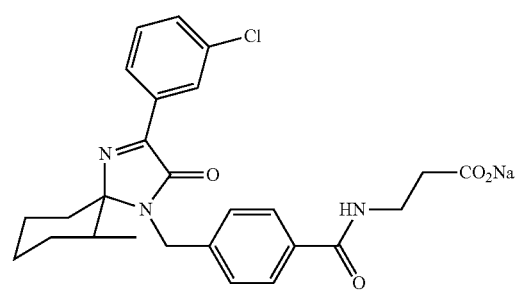 |
| 1.123 | 7.148 | 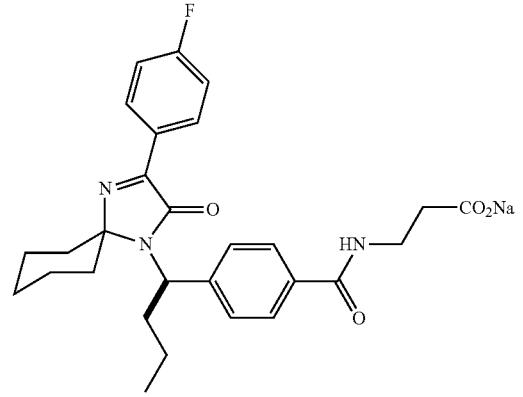 |

TABLE 3-continued
| SM-Ex | Ex. | Structure |
|---|---|---|
| 1.73 | 7.149 | 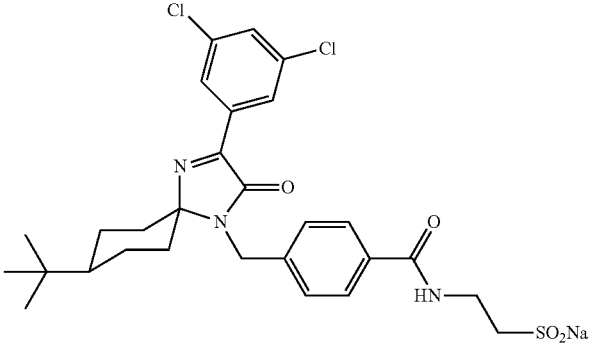 |
| 1.142 | 7.150 | 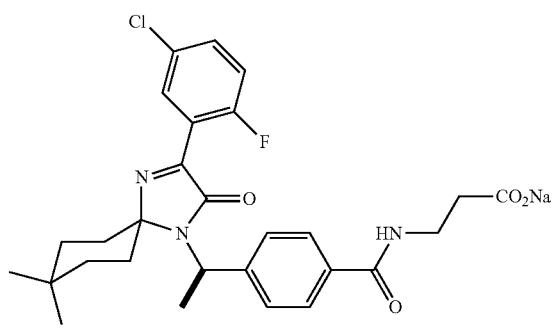 |
| 1.150 | 7.151 | 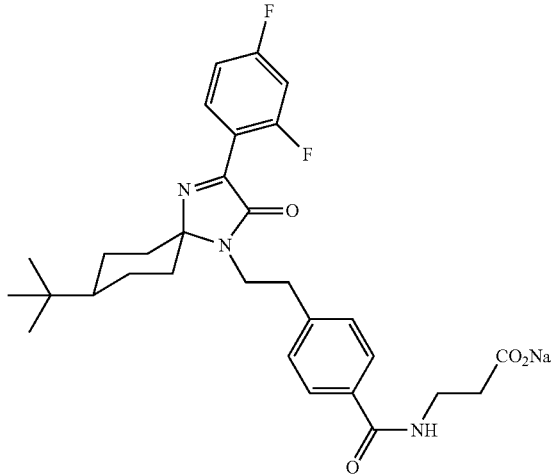 |
| 1.160 | 7.152 | 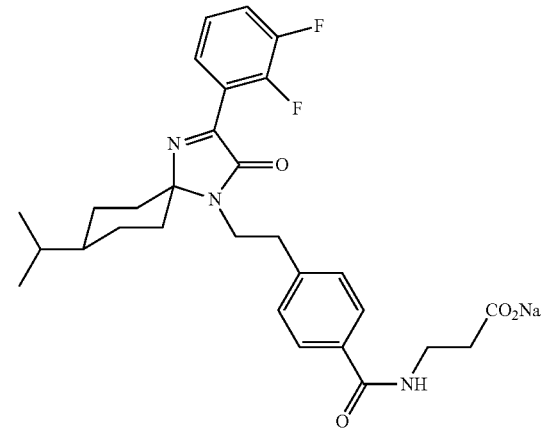 |

TABLE 3-continued
| SM-Ex | Ex. | Structure |
|---|---|---|
| 1.107 | 7.153 | 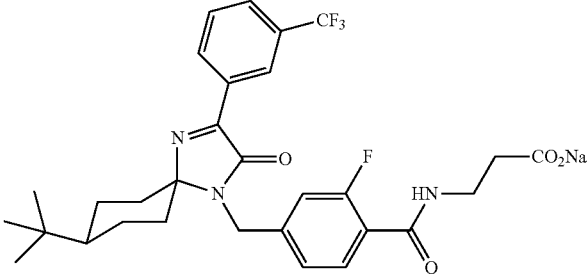 |
| 1.114 | 7.154 | 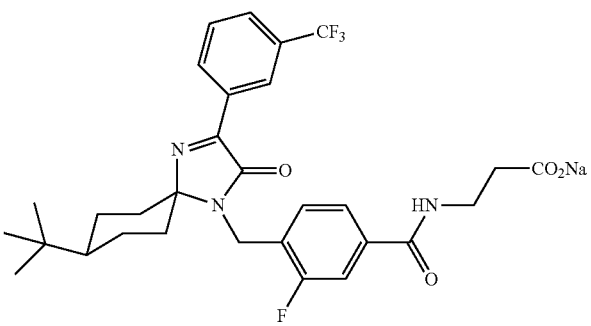 |
| 1.85 | 7.155 | 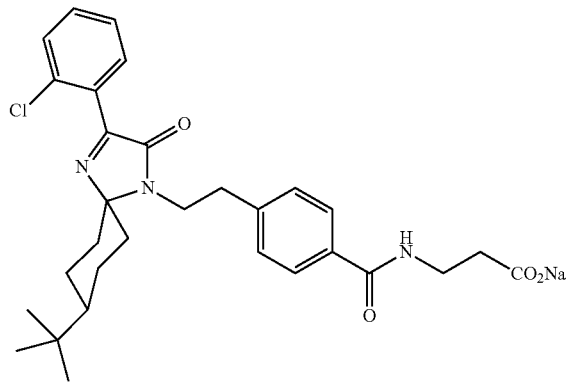 |
| 1.137 | 7.156 | 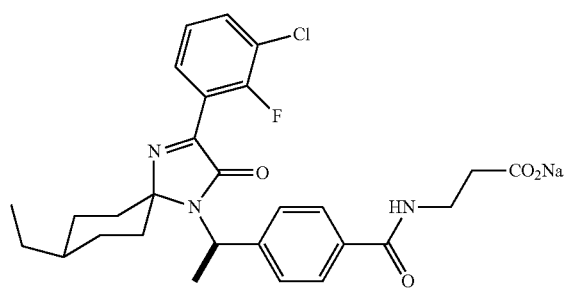 |

TABLE 3-continued
| SM-Ex | Ex. | Structure |
|---|---|---|
| 1.67 | 7.157 | 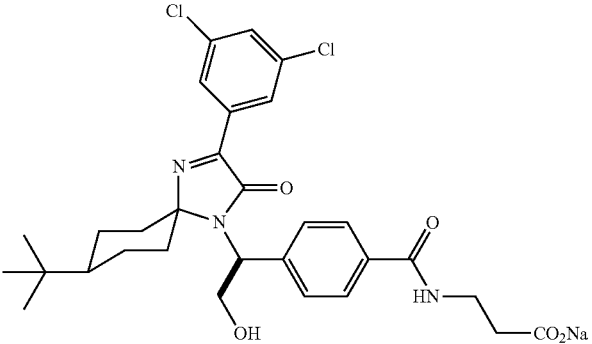 |
| 1.125 | 7.158 | 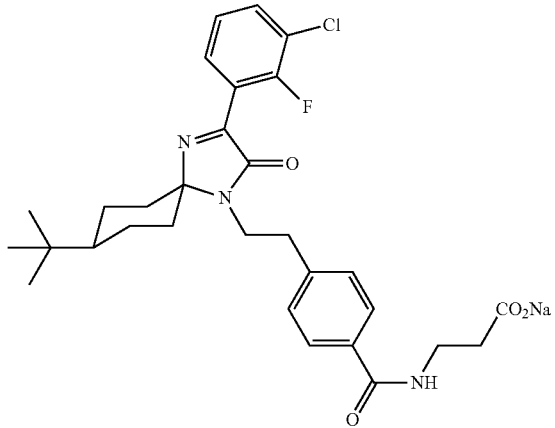 |
| 1.947 | 7.159 | 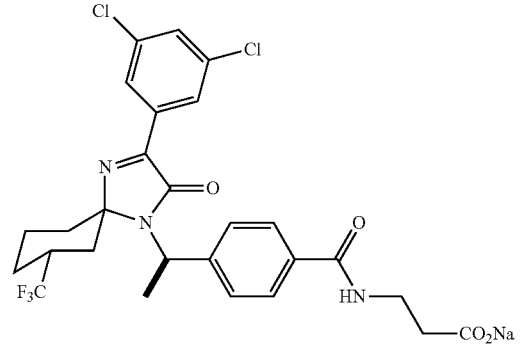<br>Isomer 1 |

TABLE 3-continued

| SM-Ex | Ex. | Structure |
|---|---|---|
| 1.365 | 7.160 | 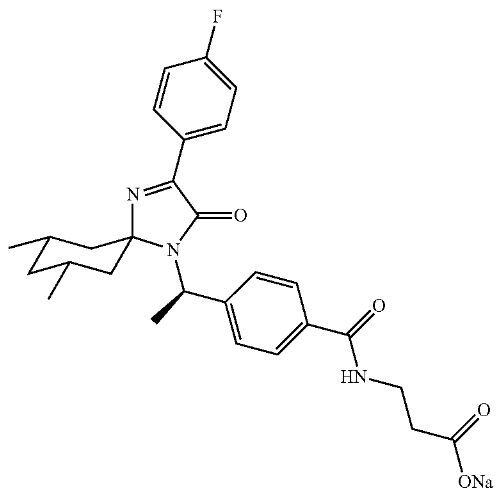 |
| 1.86 | 7.161 | 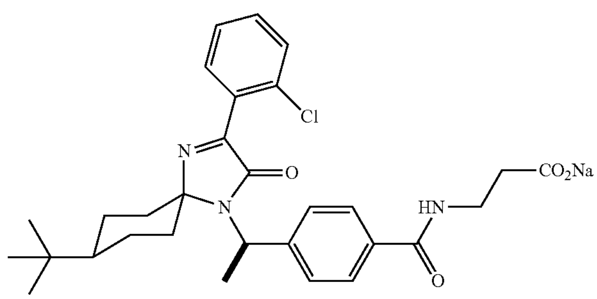 |
| 1.162 | 7.162 | 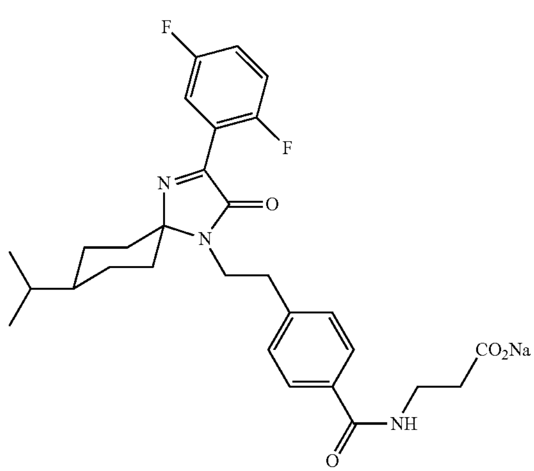 |

TABLE 3-continued
| SM-Ex | Ex. | Structure |
|---|---|---|
| 1.163 | 7.163 | 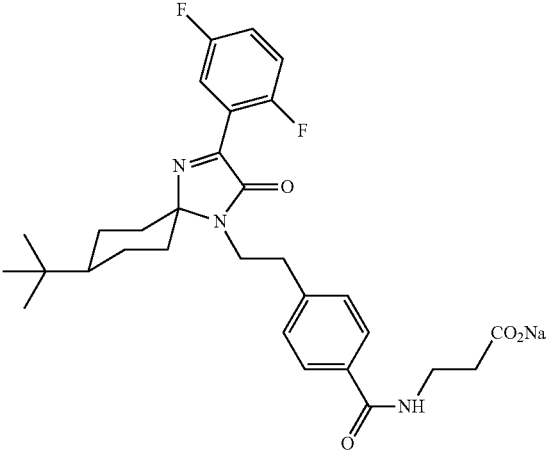 |
| 1.945 | 7.164 | 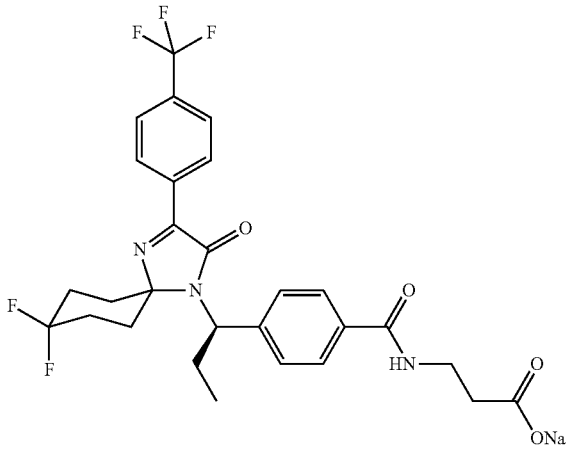 |
| 1.943 | 7.165 | 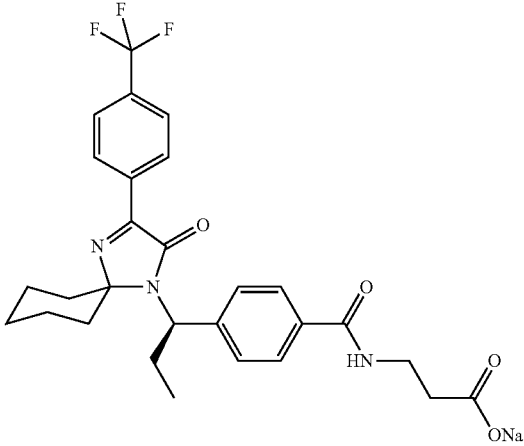 |

TABLE 3-continued
| SM-Ex | Ex. | Structure |
|---|---|---|
| 1.144 | 7.166 | 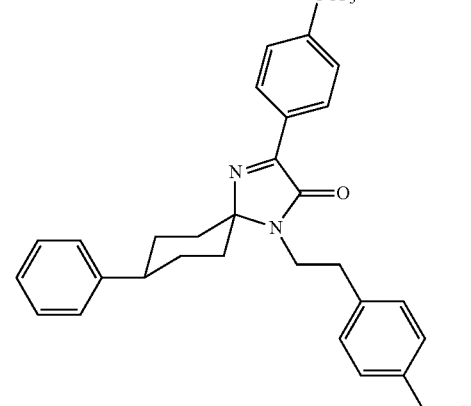 |
| 1.115 | 7.167 | 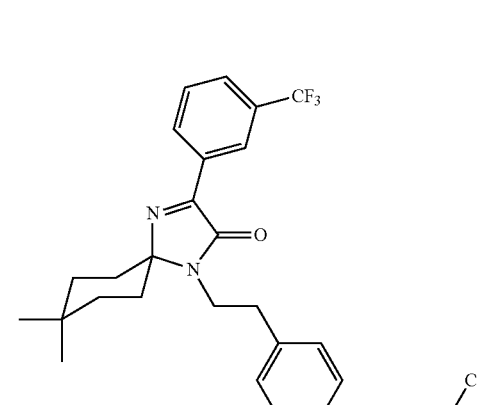 |
Scheme 4.1
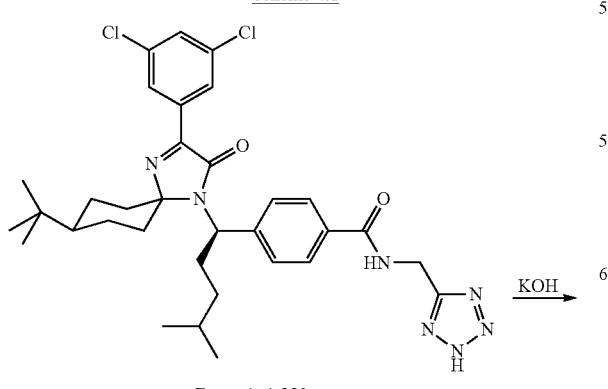
Example 1.220
-continued
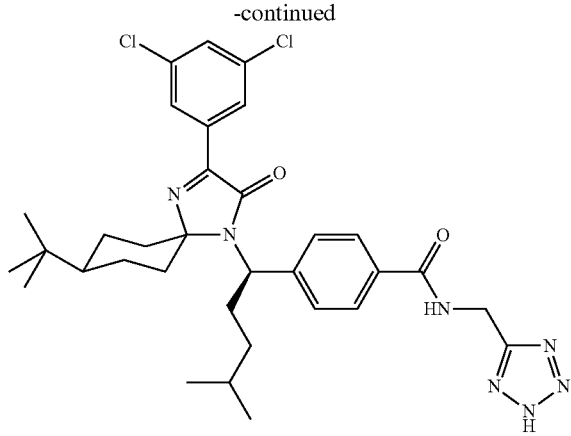
Example 8.6

The tetrazole (SM-EX) Example 1.220 (110 mg, 0.17 mmol) was taken up in MeOH (10 mL), and 0.174 mL of a 1.00 N KOH$_{(aq.)}$ solution was added. The solution was stirred for a few minutes at room temperature. The solution was filtered and concentrated which provided 102 mg (87%) of the potassium salt Example 8.6 as a white solid.

As stated above, in one embodiment, in each of Formula (A), Formula (A-1), Formula (A-1a), Formula (A-1b), Formula (A-2a), Formula (A-2b), Formula (A-2c), Z contains a carboxylic acid or tetrazole moiety. Pharmaceutically acceptable salts of such acids are also contemplated as being within the scope of the invention. Table 4 depicts non-limiting examples of potassium salts prepared according the procedure outlined in Scheme 4.1 using the appropriate starting tetrazole (SM).

TABLE 4

| SM-Ex | Ex. | Structure |
|---|---|---|
| 1.254 | 8.1 | 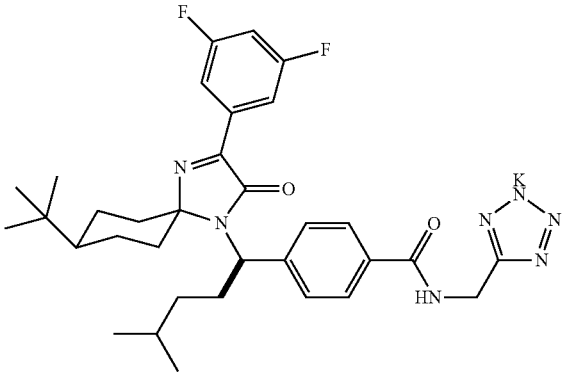 |
| 1.522 | 8.2 | 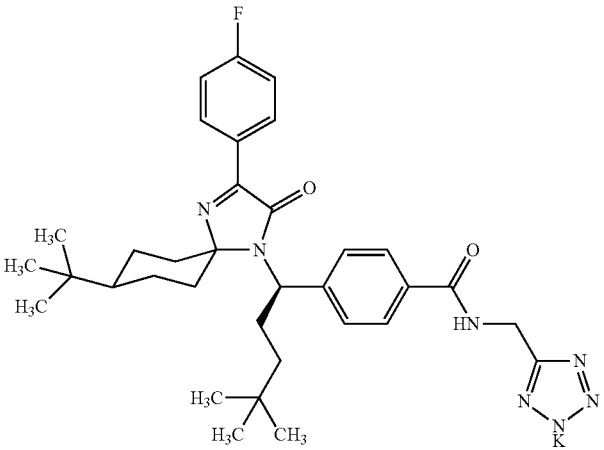 |
| 1.521 | 8.3 | 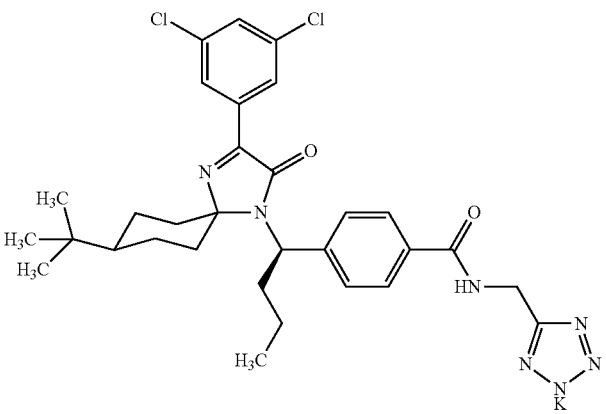 |

TABLE 4-continued
| SM-Ex | Ex. | Structure |
|---|---|---|
| 1.39 | 8.4 | 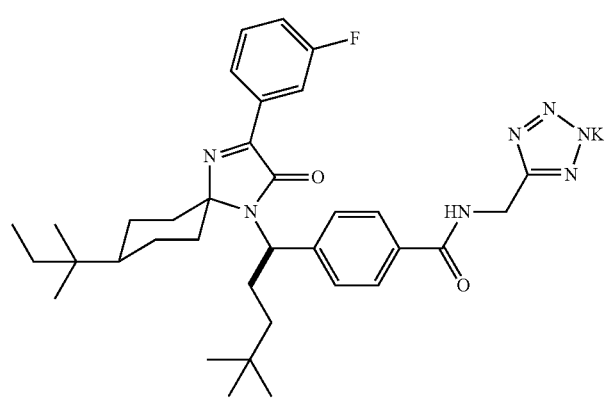 |
| 1.308 | 8.5 | 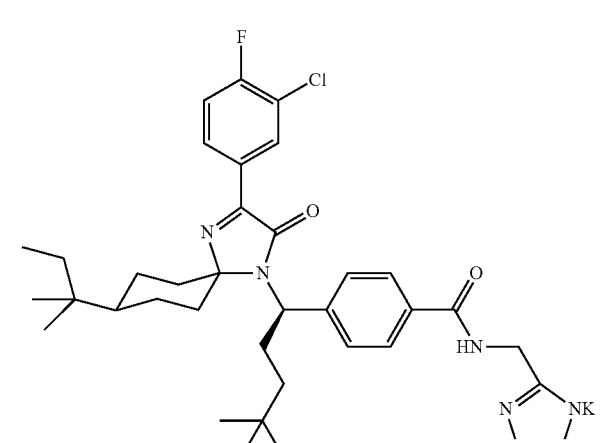 |
| 1.220 | 8.6 | 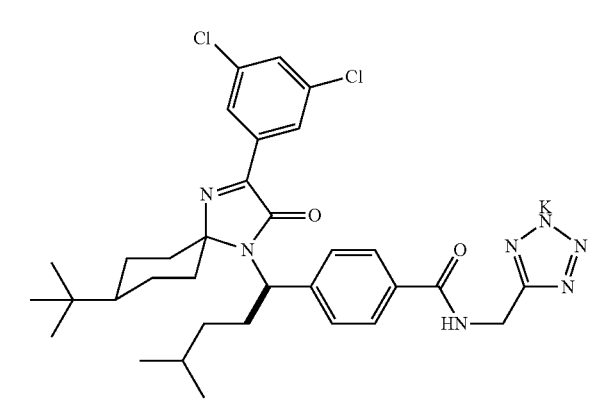 |

TABLE 4-continued
| SM-Ex | Ex. | Structure |
|---|---|---|
| 1.307 | 8.7 | 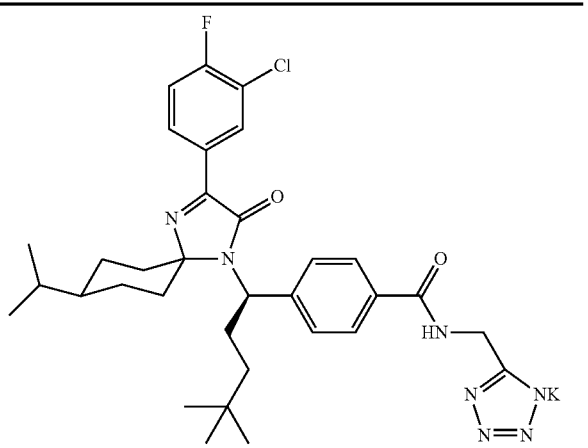 |
| 1.516 | 8.8 | 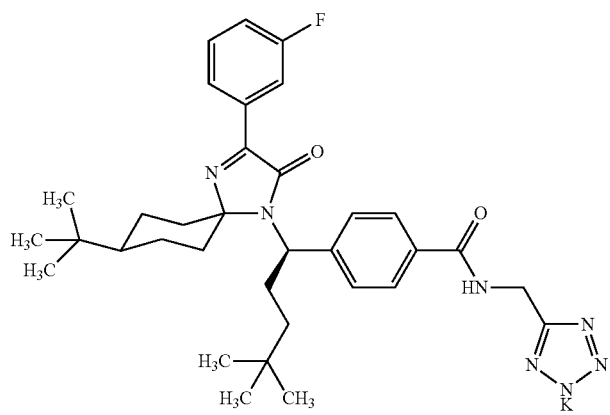 |
| 1.515 | 8.9 | 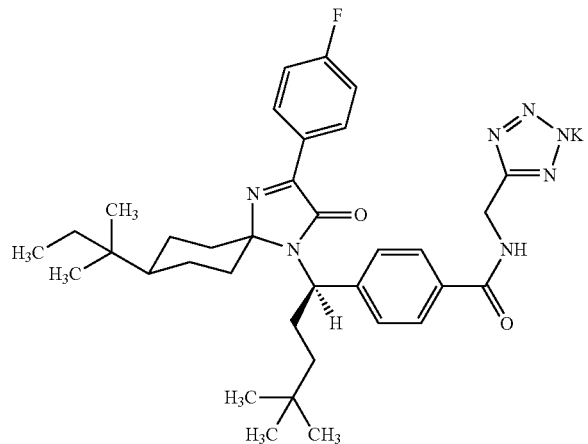 |

TABLE 4-continued
| SM-Ex | Ex. | Structure |
|---|---|---|
| 1.288 | 8.10 | 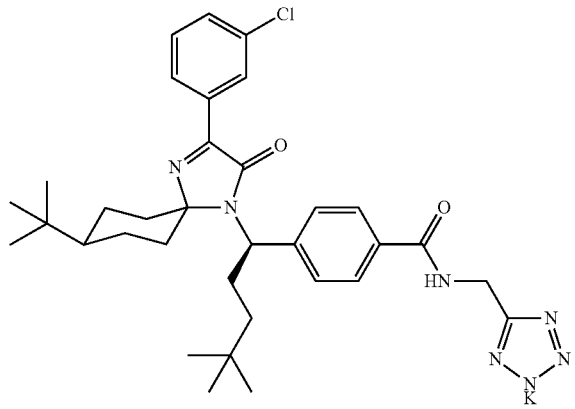 |
| 1.282 | 8.11 | 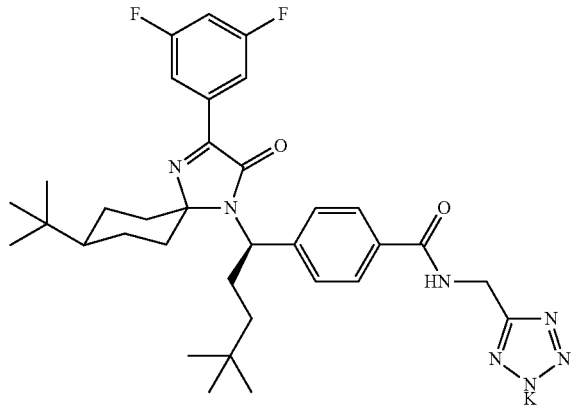 |
| 1.305 | 8.12 | 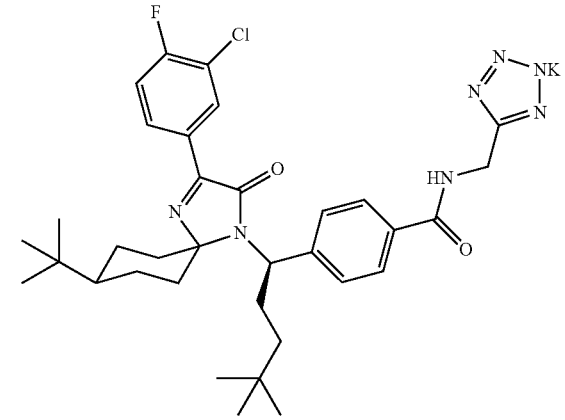 |

TABLE 4-continued
| SM-Ex | Ex. | Structure |
|---|---|---|
| 1.283 | 8.13 | 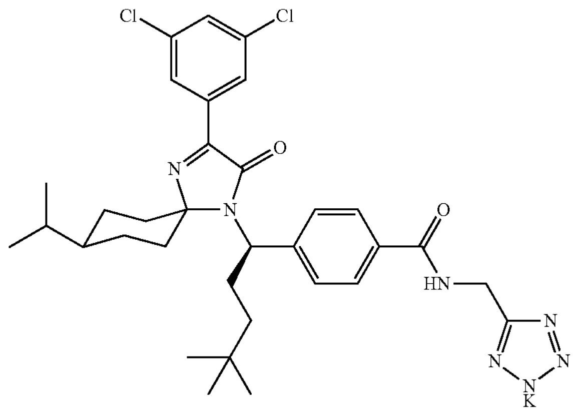 |
| 1.45 | 8.14 | 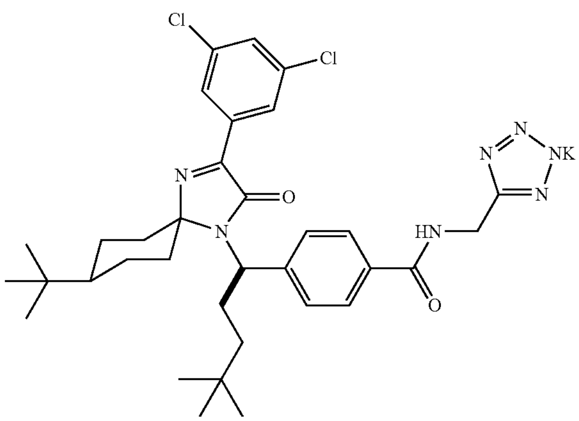 |
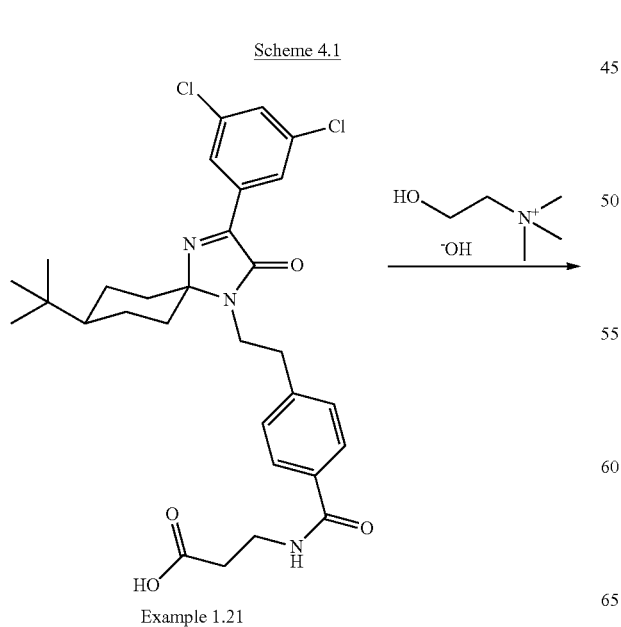
Example 1.21
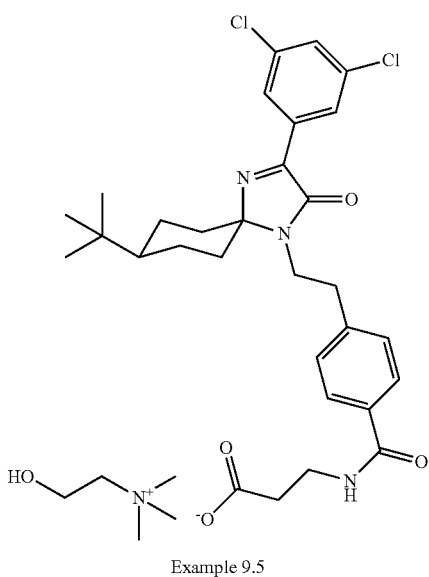
Example 9.5

The acid (SM-EX) Example 1.21 (32 mg, 0.056 mmol) was taken up in MeOH (10 mL), and 0.066 mL of a 10% aqueous choline hydroxide solution was added. The solution was stirred at RT for 18 h. The solution was concentrated, and the residue was taken up in EtOH. The EtOH was removed under reduced pressure. Ethanol/hexanes has added to the residue, and the solution was concentrated and dried under high vacuum. This provided 38 mg (Quant.) of the choline salt Example 9.5 as a white solid.

As stated above, in one embodiment, in each of Formula (A), Formula (A-1), Formula (A-1a), Formula (A-1b), Formula (A-2a), Formula (A-2b), Formula (A-2c), Z contains a carboxylic acid or tetrazole moiety. Pharmaceutically acceptable salts of such acids are also contemplated as being within the scope of the invention. Table 5 depicts non-limiting examples of choline salts prepared according the procedure outlined in Scheme 4.1 using the appropriate starting acid or tetrazole (SM-Ex).

TABLE 5

| SM-Ex | Ex. | Structure |
|---|---|---|
| 1.22 | 9.1 | 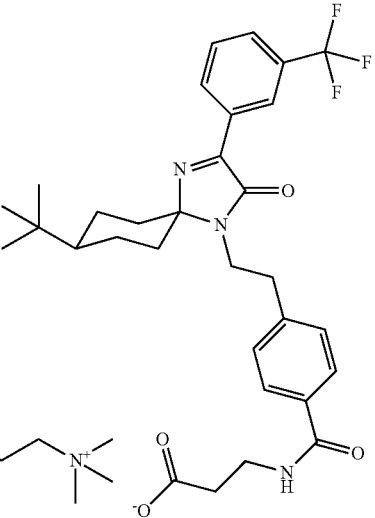 |
| 1.23 | 9.2 | 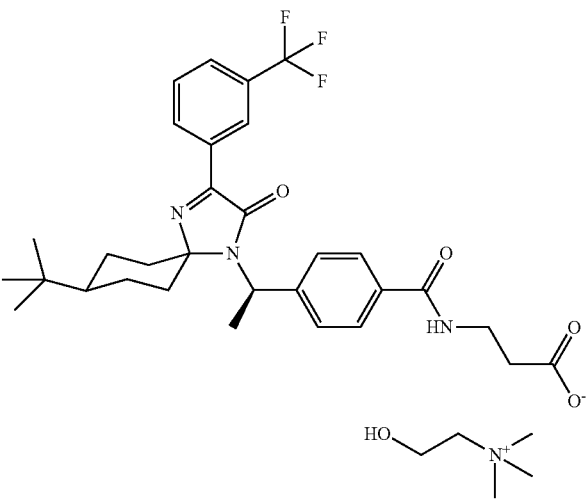 |

TABLE 5-continued
| SM-Ex | Ex. | Structure |
|---|---|---|
| 1.522 | 9.3 | 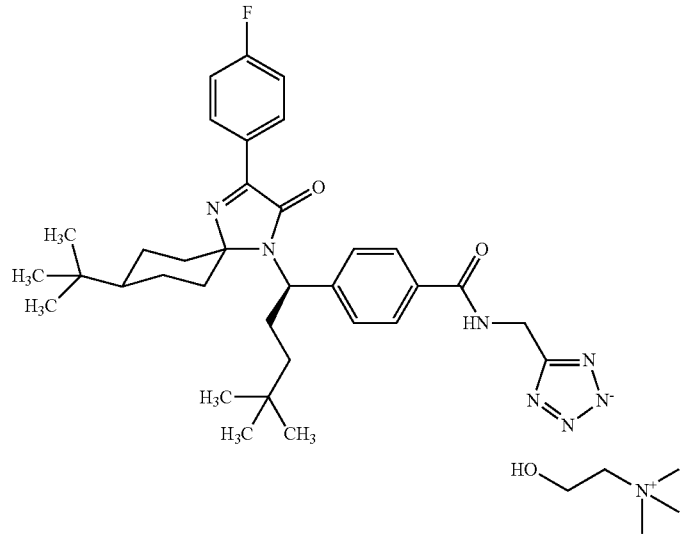 |
| 2.88 | 9.4 | 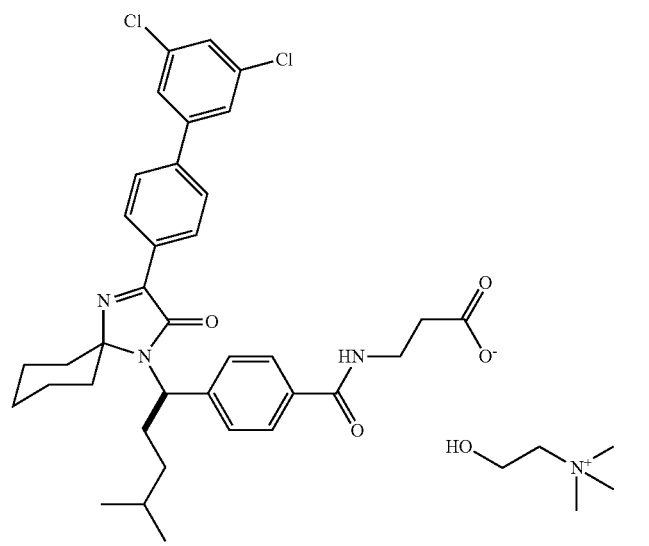 |
| 1.21 | 9.5 | 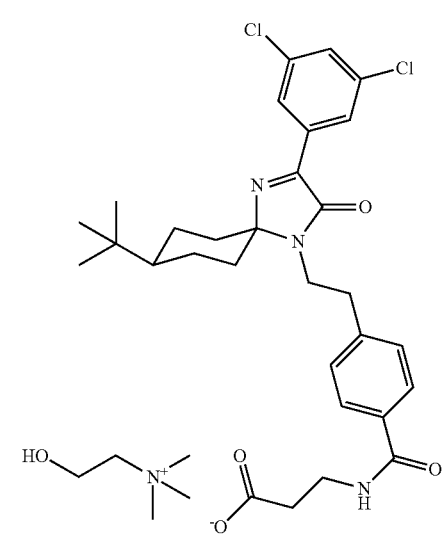 |

TABLE 5-continued
| SM-Ex | Ex. | Structure |
|---|---|---|
| 1.516 | 9.6 | 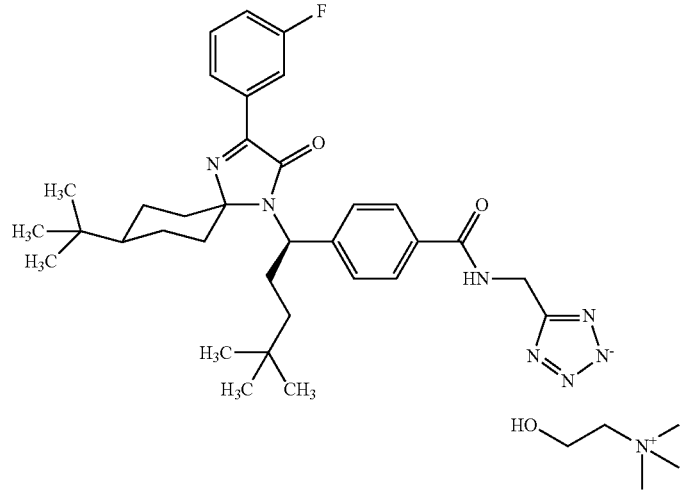 |
| 1.288 | 9.7 | 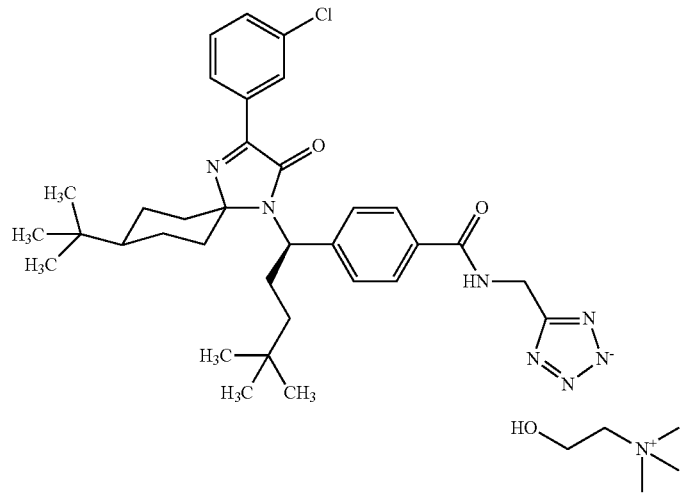 |
| 1.282 | 9.8 | 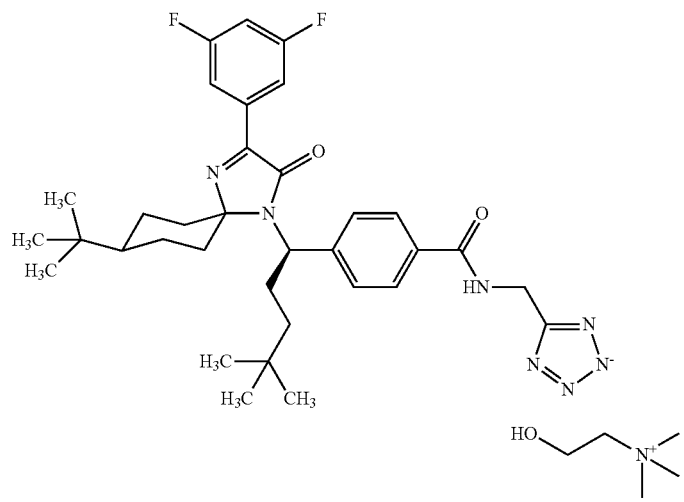 |

TABLE 5-continued

| SM-Ex | Ex. | Structure |
|---|---|---|
| 1.283 | 9.9 | 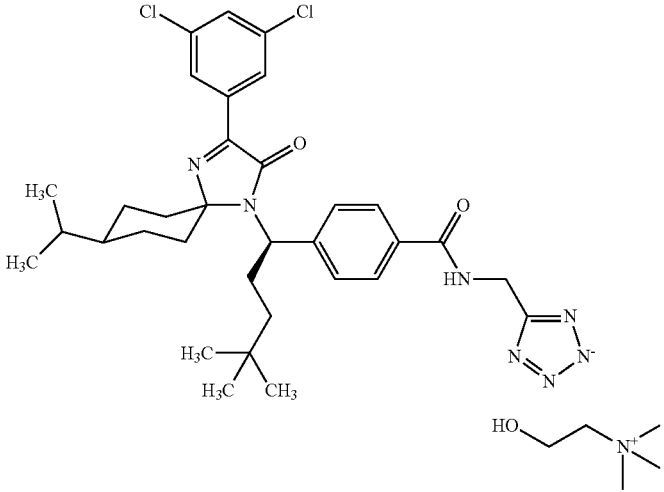 |
| 1.45 | 9.10 | 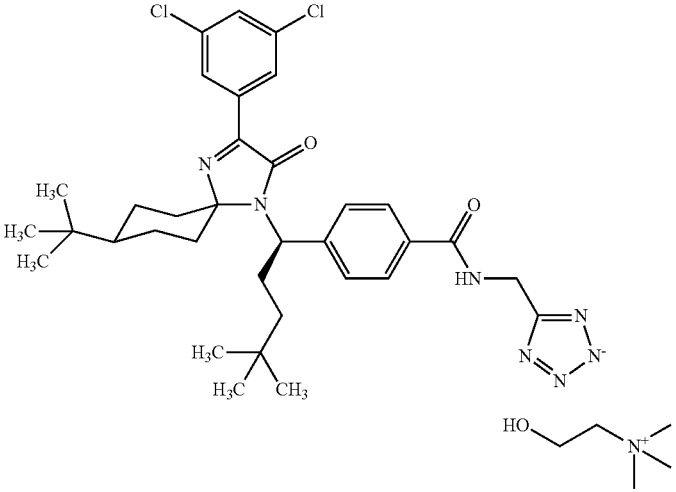 |

Microwave Reactions

All microwave reactions were performed using a Biotage Initiator Sixty microwave reactor, a Biotage Initiator Eight™ reactor, or a Biotage Creator Microwaver™ reactor.

Biological Assays

The ability of the compounds of the invention to inhibit the binding of glucagon and their utility in treating or preventing type 2 diabetes mellitus and related conditions can be demonstrated by the following in vitro assays.

Glucagon Receptor Binding Assay

Recombinant human glucagon receptor (huGlucR) membranes and mouse glucagon receptor (mGlucR) membranes were prepared in-house from huGlucR/clone 103 c/CHO and mouse liver tissue, respectively. 0.03 ug/li huGluR membranes (or 0.5 ug/ml mGlucR) was incubated in assay buffer containing 0.05 nM $^{125}$I-Glucagon (Perkin Elmer, NEX 207) and varying concentrations of antagonist at room temperature for 60 to 90 min. (assay buffer: 50 mM HEPES, 1 mM MgCl2, 1 mM CaCl2, 1 mg/ml BSA, COMPLETE protease inhibitor cocktail, pH 7.4). The total volume of the assay was 200 ul with 4% final DMSO concentration. The assay was performed at room temperature using 96-deep well plate. Compound 4c, racemic diastereomer 1 (D1), (1.0 μM final concentration), described by G. H. Ladouceur et al. in Bioorganic and Medicinal Chemistry Letters, 12 (2002), 3421-3424, was used to determine non-specific binding. Following incubation, the reaction was stopped by rapid filtration through Unfilter-96 GF/C glass fiber filter plates (Perkin Elmer) presoaked in 0.5% polyethyleneimine. The filtrate was washed using 50 mM Tris-HCl, pH 7.4. Dried filter plates containing bound radioactivity were counted in the presence of scintillation fluid (Microscint 0, Perkin-Elmer) using a Topcount scintillation counter. Data was analyzed using the software program Prism (GraphPad). $IC_{50}$ values were calculated using non-linear regression analysis assuming single site competition.

Inhibition of Glucagon-Stimulated Intracellular cAMP Assay

Chinese hamster ovary (CHO) cells expressing the recombinant human glucagon receptor were harvested with the aid of non-enzymatic cell dissociation solution (GIBCO 13151-014). The cells were then pelleted and suspended in the stimulation buffer (1×HBSS, 5 mM Hepes, 0.1% BSA, pH7.4 in presence of complete protease inhibitor and phosphodiesterase inhibitor). The adenylate cyclase assay was conducted following the LANCE cAMP Kit (Perkin Elmer, AD0262) instructions. Briefly, cells were preincubated with anti-cAMP antibody in the stimulation buffer with a final concentration of 3% DMSO for 30 minutes and then stimulated with 300 pM glucagon for 45 minutes. The reaction was stopped by incubating with the detection buffer containing Europium chelate of the Eu-SA/Biotin-cAMP tracer for 20 hours. The fluorescence intensity emitted from the assay was measured at 665 nm using PheraStar instruments. Basal activity (100% inhibition) was determined using the DMSO control and 0% inhibition was defined as cAMP stimulation produced by 300 pM glucagon. Standard cAMP concentrations were conducted concurrently for conversion of fluorescence signal to cAMP level. Data was analyzed using GraphPad Prism. $IC_{50}$ values were calculated using non-linear regression analysis assuming single site competition. $IC_{50}$ values for all of the compounds of the invention shown in the examples measured less than about 10 μM in this functional assay. Some of the compounds of the invention shown in the examples measured less than about 5 μM in this assay; other examples measured less than about 500 nM; others less than about 100 nM. The $IC_{50}$ results in this assay are given below for the indicated compound.

tors. In one embodiment, said glucagon receptors are part of a glucagon receptor assay. Non-limiting examples of such assays include glucagon receptor assays and glucagon-strimuloated intracellular cAMP formation assays such as those described above. In one embodiment, said glucagon receptors are expressed in a population of cells. In one embodiment, the population of cells is in in vitro. In one embodiment, the population of cells is in ex viva. In one embodiment, the population of cells is in a patient.

Methods of Treatment, Compositions, and Combination Therapy

In another embodiment, the present invention provides a method of treating type 2 diabetes mellitus in a patient in need of such treatment comprising administering to said patient a compound of the invention or a composition comprising a compound of the invention in an amount effective to treat type 2 diabetes mellitus.

In another embodiment, the present invention provides a method of delaying the onset of type 2 diabetes mellitus in a patient in need of such treatment comprising administering to said patient a compound of the invention or a composition comprising a compound of the invention in an amount effective to delay the onset of type 2 diabetes mellitus.

| Example | | $IC_{50}$ (nM) |
|---|---|---|
| 1.156 | 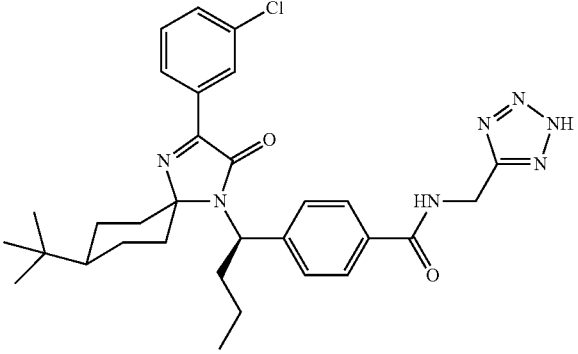 [SMILES: CCC[C@H](c1ccc(C(=O)NCc2nn[nH]n2)cc1)N1C(=O)C(c2cccc(Cl)c2)=NC12CCC(C(C)(C)C)CC2] | 452 |
| 1.212 | 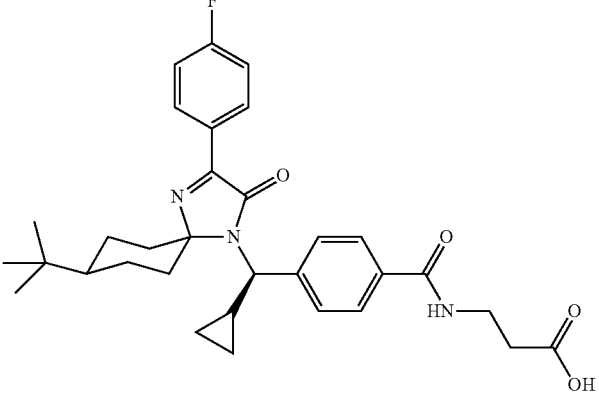 | 57 |

In another embodiment, the present invention provides a pharmaceutical composition comprising a compound of the invention described above in combination with a pharmaceutically acceptable carrier.

In another embodiment, the present invention provides a method for inhibiting glucagon receptors comprising exposing an effective amount of a compound or a composition comprising a compound of the invention to glucagon receptors.

In another embodiment, the present invention provides a method of treating hyperglycemia, diabetes, or insulin resistance in a patient in need of such treatment comprising administering to said patient a compound of the invention, or a composition comprising a compound of the invention, in an amount that is effective to treat hyperglycemia, diabetes, or insulin resistance.

In another embodiment, the present invention provides a method of treating non-insulin dependent diabetes mellitus in a patient in need of such treatment comprising administering to said patient an anti-diabetic effective amount of a compound of the invention or a composition comprising an effective amount of a compound of the invention.

In another embodiment, the present invention provides a method of treating obesity in a patient in need of such treatment comprising administering to said patient a compound of the invention or a composition comprising a compound of the invention in an amount that is effective to treat obesity.

In another embodiment, the present invention provides a method of treating one or more conditions associated with Syndrome X (also known as metabolic syndrome, metabolic syndrome X, insulin resistance syndrome, Reaven's syndrome) in a patient in need of such treatment comprising administering to said patient a compound of the invention or a composition comprising an effective amount of a compound of the invention in an amount that is effective to treat Syndrome X.

In another embodiment, the present invention provides a method of treating a lipid disorder in a patient in need of such treatment comprising administering to said patient a compound of the invention, or a composition comprising a compound of the invention, in an amount that is effective to treat said lipid disorder. Non-limiting examples of such lipid disorders include: dyslipidemia, hyperlipidemia, hypertriglyceridemia, hypercholesterolemia, low HDL and high LDL, and metabolic syndrome.

In another embodiment, the present invention provides a method of treating atherosclerosis in a patient in need of such treatment comprising administering to said patient a compound of the invention or a composition comprising a compound of the invention, in an amount effective to treat atherosclerosis.

In another embodiment, the present invention provides a method of delaying the onset of, or reducing the risk of developing, atherosclerosis in a patient in need of such treatment comprising administering to said patient a compound of the invention or a composition comprising a compound of the invention, in an amount effective to delay the onset of, or reduce the risk of developing, atherosclerosis.

In another embodiment, the present invention provides a method of treating a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to treat said condition or conditions.

In another embodiment, the present invention provides a method of delaying the onset of a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to delay the onset said condition or conditions.

In another embodiment, the present invention provides a method of reducing the risk of developing a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance or hyperglycemia is a component, in a patient in need thereof, comprising administering to said patient a compound of the invention, or a composition comprising a compound of the invention, in an amount that is effective to reduce the risk of developing said condition or conditions.

In another embodiment, the present invention provides a method of treating a condition selected from type 2 diabetes mellitus, hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient effective amounts of a compound of the invention and one or more additional active agents.

Non-limiting examples of such additional active agents include the following:

DPP-IV inhibitors. Non-limiting examples of DPP-IV inhibitors include alogliptin (Takeda), linagliptin, saxagliptin (Brystol-Myers Squibb), sitagliptin (Januvia™, Merck), vildagliptin (Galvus™, Novartis), denagliptin (GlaxoSmithKline), ABT-279 and ABT-341 (Abbott), ALS-2-0426 (Alantos), ARI-2243 (Arisaph), BI-A and BI-B (Boehringer Ingelheim), SYR-322 (Takeda), compounds disclosed in U.S. Pat. No. 6,699,871, MP-513 (Mitsubishi), DP-893 (Pfizer), RO-0730699 (Roche) and combinations thereof. Non-limiting examples of such combinations include Janumet™, a combination of sitagliptin/metformin HCl (Merck).

Insulin sensitizers. Non-limiting examples of insulin sensitizers include PPAR agonists and biguanides. Non-limiting examples of PPAR agonists include glitazone and thiaglitazone agents such as rosiglitazone, rosiglitazone maleate (AVANDIA™, GlaxoSmithKline), pioglitazone, pioglitazone hydrochloride (ACTOS™, Takeda), ciglitazone and MCC-555 (Mitstubishi Chemical Co.), troglitazone and englitazone. Non-limiting example of biguanides include phenformin, metformin, metformin hydrochloride (such as GLUCOPHAGE®, Bristol-Myers Squibb), mefformin hydrochloride with glyburide (such as GLUCOVANCE™, Bristol-Myers Squibb) and buformin. Other non-limiting examples of insulin sensitizers include PTP-1B inhibitors; and glucokinase activators, such as miglitol, acarbose, and voglibose.

Insulin and insulin mimetics. Non-limiting examples of orally administrable insulin and insulin containing compositions include AL-401 (Autoimmune), and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Sulfonylureas and other insulin secretagogues. Non-limiting examples of sulfonylureas and other secretagogues include glipizide, tolbutamide, glyburide, glimepiride, chlorpropamide, acetohexamide, gliamilide, gliclazide, glibenclamide, tolazamide, GLP-1, GLP-1 mimetics, exendin, GIP, secretin, nateglinide, meglitinide, glibenclamide, and repaglinide. Non-limiting examples of GLP-1 mimetics include Byetta™ (exenatide), liraglutide, CJC-1131 (ConjuChem), exenatide-LAR (Amylin), BIM-51077 (Ipsen/LaRoche), ZP-10 (Zealand Pharmaceuticals), and compounds disclosed in International Publication No. WO 00/07617.

Glucosidase inhibitors and alpha glucosidase inhibitors.

Glucagon receptor antagonists other than compounds of the invention.

Hepatic glucose output lowering agents other than a glucagon receptor antagonist. Non-limiting examples of hepatic glucose output lowering agents include Glucophage and Glucophage XR.

An antihypertensive agent. Non-limiting examples of antihypertensive agents include beta-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

A meglitinide. Non-limiting examples of meglitinides useful in the present methods for treating diabetes include repaglinide and nateglinide.

An agent that blocks or slows the breakdown of starches or sugars in vivo. Non-limiting examples of antidiabetic agents that slow or block the breakdown of starches and sugars in vivo include alpha-glucosidase inhibitors and certain peptides for increasing insulin production; Alpha-glucosidase inhibitors (which help the body to lower blood sugar by delaying the digestion of ingested carbohydrates, thereby resulting in a smaller rise in blood glucose concentration following meals). Non-limiting examples of alpha-glucosidase inhibitors include acarbose; miglitol; camiglibose; certain polyamines as disclosed in WO 01/47528 (incorporated herein by reference); and voglibose.

Peptides for increasing insulin production. Non-limiting examples of suitable peptides for increasing insulin production including amlintide (CAS Reg. No. 122384-88-7, Amylin); pramlintide, exendin, certain compounds having Glucagon-like peptide-1 (GLP-1) agonistic activity as disclosed in WO 00/07617 (incorporated herein by reference).

A histamine $H_3$ receptor antagonist. Non-limiting examples of histamine $H_3$ receptor antagonist agents include the following compound:

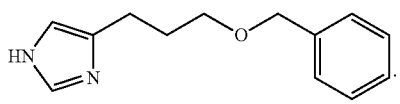

A sodium glucose uptake transporter 2 (SGLT-2) inhibitor. Non-limiting examples of SGLT-2 inhibitors useful in the present methods include dapagliflozin and sergliflozin, AVE2268 (Sanofi-Aventis) and T-1095 (Tanabe Seiyaku).

PACAP (pituitary adenylate cyclase activating polypeptide agonists) and PACAP mimetics.

Cholesterol lowering agents. Non-limiting examples of cholesterol lowering agents include HMG-CoA reductase inhibitors, sequestrants, nicotinyl alcohol, nicotinic acid and salts thereof, PPAR alpha agonists, PPAR alpha/gamma dual agonists, inhibitors of cholesterol absorption (such as ezetimibe (Zetia®)), combinations of HMG-CoA reductase inhibitors and cholesterol absorption agents (such as Vytorin®), acyl CoA:cholesterol acyltransferase inhibitors, anti-oxidants, LXR modulators, and CETP (cholesterolester transfer protein) inhibitors such as Torcetrapib™ (Pfizer) and Anacetrapib™ (Merck).

Agents capable of raising serum HDL cholesterol levels. Non-limiting examples include niacin (vitamin B-3), such as Niaspan™ (Kos). Niacin may be administered alone or optionally combined with one or more additional active agents such as: niacin/lovastatin (Advicor™, Abbott), niacin/simvastatin (Simcor™, Abbott), and/or niacin/aspirin.

PPAR Delta Agonists.

Antiobesity agents. Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat.

Ileal Bile Acid Transporter Inhibitors.

Anti-inflammatory agents, such as NSAIDs. Non-limiting examples of NSAIDS include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizole or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Anti-pain medications, including NSAIDs as discussed above, and opiates. Non-limiting examples of opiates include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Antidepressants. Non-limiting examples of tricyclic antidepressants useful in the present methods for treating pain include amitryptyline, carbamazepine, gabapentin or pregabalin.

Protein Tyrosine Phosphatase-1B (PTP-1B) Inhibitors.

CB1 antagonists/inverse agonists. Non-limiting examples of CB1 receptor antagonists and inverse agonists include rimonabant and those disclosed in WO03/077847A2, published Sep. 25, 2003, WO05/000809, published Jan. 6, 2005, and WO2006/060461, published Jun. 8, 2006.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with a statin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with one or more statins, wherein the cholesterol absorption inhibitor is selected from ezetimibe, ezetimibe/simvastatin combination (Vytorin®), and a stanol.

In another embodiment, the present invention provides a pharmaceutical composition comprising (1) a compound according to the invention; (2) one or more compounds or agents selected from DPP-IV inhibitors, insulin sensitizers, insulin and insulin mimetics, a sulfonylurea, an insulin secretagogue, a glucosidase inhibitor, an alpha glucosidase inhibitor, a glucagon receptor antagonists other than a compound of the invention, a hepatic glucose output lowering agent other than a glucagon receptor antagonist, an antihypertensive agent, a meglitinide, an agent that blocks or slows the breakdown of starches or sugars in vivo, an alpha-glucosidase inhibitor, a peptide capable of increasing insulin production, a histamine $H_3$ receptor antagonist, a sodium glucose uptake transporter 2 (SGLT-2) inhibitor, a peptide that increases insulin production, a GIP cholesterol lowering agent, a PACAP, a PACAP mimetic, a PACAP receptor 3 agonist, a cholesterol lowering agent, a PPAR delta agonist, an antiobesity agent, an ileal bile acid transporter inhibitor, an anti-inflammatory agent, an anti-pain medication, an antidepressant, a protein tyrosine phosphatase-1B (PTP-1B) inhibitor, a CB1 antagonist, and a CB1 inverse agonist; and (3) one or more pharmaceutically acceptable carriers.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more compounds of the invention is administered during at time when the additional therapeutic agent(s) exert their prophylactic or therapeutic effect, or vice versa.

In another embodiment, the one or more compounds of the invention and the additional therapeutic agent(s) are administered in doses commonly employed when such agents are used as monotherapy for treating a condition.

In another embodiment, the one or more compounds of the invention and the additional therapeutic agent(s) are administered in doses lower than the doses commonly employed when such agents are used as monotherapy for treating a condition.

In still another embodiment, the one or more compounds of the invention and the additional therapeutic agent(s) act synergistically and are administered in doses lower than the doses commonly employed when such agents are used as monotherapy for treating a condition.

In one embodiment, the one or more compounds of the invention and the additional therapeutic agent(s) are present in the same composition. In one embodiment, this composition is suitable for oral administration. In another embodiment, this composition is suitable for intravenous administration.

The one or more compounds of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more compounds of the invention and the additional therapeutic agent(s) may inhibit the resistance of a condition to the agent(s).

In one embodiment, when the patient is treated for diabetes, a diabetic complication, impaired glucose tolerance or impaired fasting glucose, the other therapeutic is an antidiabetic agent which is not a compound of the invention. In another embodiment, when the patient is treated for pain, the other therapeutic agent is an analgesic agent which is not a compound of the invention.

In another embodiment, the other therapeutic agent is an agent useful for reducing any potential side effect of a compound of the invention. Non-limiting examples of such potential side effects include nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

The doses and dosage regimen of the other agents used in the combination therapies of the present invention for the treatment or prevention of a condition described herein can be determined by the attending clinician, taking into consideration the approved doses and dosage regimen in the package insert; the age, sex and general health of the patient; and the type and severity of the viral infection or related disease or disorder. When administered in combination, the compound(s) of the invention and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more compounds of the invention and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

As indicated above, in one embodiment, the invention provides compositions comprising an effective amount of one or more compounds of the invention or a pharmaceutically acceptable salt, solvate, ester or prodrug thereof, and a pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound of the invention is administered orally.

In another embodiment, the compound of the invention is administered parenterally.

In another embodiment, the compound of the invention is administered intravenously.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of at least one compound of the invention and an additional therapeutic agent, the two active components may be co-administered simultaneously or sequentially, or a single pharmaceutical composition comprising at least one compound of the invention and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

Thus, the term "pharmaceutical composition" is also intended to encompass both the bulk composition and individual dosage units comprised of more than one (e.g., two) pharmaceutically active agents such as, for example, a compound of the present invention and an additional agent selected from the various the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

In one embodiment, the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one embodiment, the present invention provides a kit comprising a effective amount of one or more compounds of the invention, or a pharmaceutically acceptable salt or solvate thereof, and a pharmaceutically acceptable carrier, vehicle or diluent.

In another aspect the present invention provides a kit comprising an amount of one or more compounds of the invention, or a pharmaceutically acceptable salt or solvate thereof, and an amount of at least one additional therapeutic agent described above, wherein the combined amounts are effective for treating or preventing a condition described herein in a patient.

When the components of a combination therapy regime are to are to be administered in more than one composition, they can be provided in a kit comprising in a single package, one container comprising a compound of the invention in pharmaceutically acceptable carrier, and one or more separate containers, each comprising one or more additional therapeutic agents in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

We claim:

1. A compound, or a pharmaceutically acceptable salt, solvate, tautomer, or isomer of said compound, said compound having the general structure shown in Formula (A):

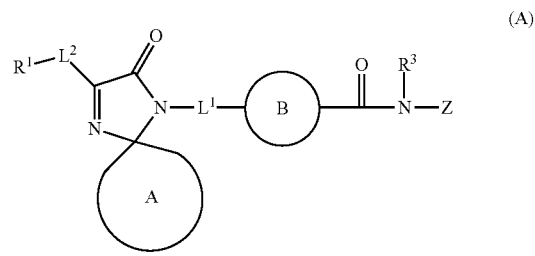

wherein ring A, ring B, $L^1$, $L^2$, $R^1$, $R^3$, and Z are selected independently of each other and wherein:

$L^1$ is selected from the group consisting of a bond, —N($R^4$)—, —N($R^4$)—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—N($R^4$)—, —O—, —O—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—O—, and —(C($R^{5A}$)$_2$)—(C($R^5$)$_2$)$_s$—, each q is independently an integer from 0 to 5;
each r is independently an integer from 0 to 3;
s is an integer from 0 to 5;

$L^2$ is selected from the group consisting of a bond, —N($R^4$)—, —N($R^4$)—(C($R^{5A}$)$_2$)—(C($R^5$)$_2$)$_t$—, —(C($R^5$)$_2$)$_u$—(C($R^{5A}$)$_2$)—N($R^4$)—, —O—, —O—(C($R^{5A}$)$_2$)—(C($R^5$)$_2$)$_t$—, —(C($R^5$)$_2$)$_u$—(C($R^{5A}$)$_2$)—O—, —S—, —S—(C($R^{5A}$)$_2$)—(C($R^5$)$_2$)$_t$—, (C($R^5$)$_2$)$_u$—(C($R^{5A}$)$_2$)—S—, —S(O)—, —S(O)—(C($R^{5A}$)$_2$)—(C($R^5$)$_2$)$_t$—, —(C($R^5$)$_2$)$_u$—(C($R^{5A}$)$_2$)—S(O)—, —S(O)$_2$—, —S(O)$_2$—(C($R^{5A}$)$_2$)—(C($R^5$)$_2$)$_t$—, —(C($R^5$)$_2$)$_u$—(C($R^{5A}$)$_2$)—S(O)$_2$—, —(C($R^5$)$_2$)$_v$—;

each t is independently an integer from 0 to 3;
each u is independently an integer from 0 to 3;
v is an integer from 1 to 5;

ring A represents a spirocycloalkyl ring or a spirocycloalkenyl ring, wherein said ring A is substituted on one or more available ring carbon atoms with from 0 to 5 independently selected $R^2$ groups, or, alternatively, ring A represents a spiroheterocycloalkyl ring or a spiroheterocycloalkenyl ring, wherein said ring A is substituted on one or more available ring carbon atoms with from 0 to 5 independently selected $R^2$ groups, and wherein said ring A is optionally further substituted on one or more available ring nitrogen atoms (when present) with from 0 to 3 $R^{2A}$ groups;

ring B is a phenyl ring, wherein said phenyl ring is (in addition to the -L$^1$- and —C(O)N(R$^3$)—Z moieties shown) optionally further substituted with one or more substituents R$^a$, wherein each R$^a$ (when present) is independently selected from the group consisting of halo, —OH, —SF$_5$, —OSF$_5$, alkyl, haloalkyl, heteroalkyl, hydroxyalkyl, alkoxy, and —O-haloalkyl, or ring B is a 5-membered heteroaromatic ring containing from 1 to 3 ring heteroatoms independently selected from N, O, and S, wherein said 5-membered heteroaromatic ring is (in addition to the -L$^1$- and —C(O)N(R$^3$)—Z moieties shown) optionally further substituted with one or more substituents R$^a$, wherein each R$^a$ (when present) is independently selected from the group consisting of halo, —OH, —SF$_5$, —OSF$_5$, alkyl, haloalkyl, heteroalkyl, hydroxyalkyl, alkoxy, and —O-haloalkyl, or ring B is a 6-membered heteroaromatic ring containing from 1 to 3 ring nitrogen atoms, wherein said 6-membered heteroaromatic ring is (in addition to -L$^1$- and —C(O)N(R$^3$)Z moieties shown) optionally further substituted with one or more substituents R$^a$, wherein each R$^a$ (when present) is independently selected from the group consisting of halo, —OH, —SF$_5$, —OSF$_5$, alkyl, haloalkyl, hydroxyalkyl, alkoxy, and —O-haloalkyl;

R$^1$ is independently selected from the group consisting of aryl and heteroaryl,
  wherein said aryl and said heteroaryl of R$^1$ are unsubstituted or substituted with one or more groups independently selected from:
  (1) halo, —OH, —CO$_2$R$^6$, —C(O)R$^6$, —SR$^7$, —S(O)R$^7$, —SO$_2$R$^7$, —SF$_5$, —OSF$_5$, CN, NO$_2$, —C(O)NR$^8$R$^9$, —NR$^8$R$^9$, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$,
  (2) alkyl, alkoxy, heteroalkyl, —O-heteroalkyl, alkenyl, heteroalkenyl, alkynyl, and heteroalkynyl,
    wherein each of said alkyl, alkoxy, heteroalkyl, —O-heteroalkyl, alkenyl, heteroalkenyl, alkynyl, and heteroalkynyl, are unsubstituted or optionally independently substituted with one or more groups each independently selected from: halo, OH, —CO$_2$R$^6$, —C(O)R$^6$, —SR$^7$, —S(O)R$^7$, —SO$_2$R$^7$, CN, NO$_2$, —C(O)NR$^8$R$^9$, —NR$^8$R$^9$, —O-haloalkyl, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and
  (3) aryl, —O-aryl, —C(O)-aryl, —S-aryl, —S(O)-aryl, —S(O)$_2$-aryl, —N(R$_4$)-aryl, —C(O)—N(R$_4$)-aryl, —N(R$_4$)—C(O)-aryl, heteroaryl, —O-heteroaryl, —C(O)-heteroaryl, —S-heteroaryl, —S(O)-heteroaryl, —S(O)$_2$-heteroaryl, —N(R$_4$)-heteroaryl, —C(O)—N(R$_4$)-heteroaryl, —N(R$_4$)—C(O)-heteroaryl, cycloalkyl, —O—cycloalkyl, —C(O)-cycloalkyl, —S-cycloalkyl, —S(O)-cycloalkyl, —S(O)$_2$-cycloalkyl, —N(R$_4$)— cycloalkyl, —C(O)—N(R$_4$)-cycloalkyl, —N(R$_4$)—C(O)-cycloalkyl, heterocycloalkyl, —O-heterocycloalkyl, —C(O)— heterocycloalkyl, —S-heterocycloalkyl, —S(O)-heterocycloalkyl, —S(O)$_2$-heterocycloalkyl, —N(R$_4$)-heterocycloalkyl, —C(O)—N(R$_4$)-heterocycloalkyl, —N(R$_4$)—C(O)-heterocycloalkyl, cycloalkenyl, —O-cycloalkenyl, —C(O)-cycloalkenyl, —S-cycloalkenyl, —S(O)-cycloalkenyl, —S(O)$_2$-cycloalkenyl, —N(R$_4$)-cycloalkenyl, —C(O)—N(R$_4$)-cycloalkenyl, —N(R$_4$)—C(O)-cycloalkenyl, heterocycloalkenyl, —O-heterocycloalkenyl, —C(O)-heterocycloalkenyl, —S-heterocycloalkenyl, —S(O)-heterocycloalkenyl, —S(O)$_2$-heterocycloalkenyl, —N(R$_4$)-heterocycloalkenyl, —C(O)—N(R$_4$)-heterocycloalkenyl, and —N(R$_4$)—C(O)-heterocycloalkenyl,
    each of which is unsubstituted or optionally independently substituted with from 1 to 2 groups each independently selected from (1) and (2) above;

each R$^2$ (when present) is independently selected from the group consisting of:
(a) phenyl substituted with from 0 to 5 groups independently selected from —OH, halo, alkyl, haloalkyl, hydroxyalkyl, alkyl substituted with from 1 to 2 —CO$_2$R$^6$ groups, alkoxy, —O-haloalkyl, hydroxyalkoxy, alkoxy substituted with from 1 to 2 —CO$_2$R$^6$ groups, —C(O)R$^6$, —CO$_2$R$^6$, CN, —SO$_2$R$^7$, —SF$_5$, —OSF$_5$, —C(O)NR$^8$R$^9$, and —NO$_2$,
(b) alkyl or heteroalkyl, each substituted with from 0 to 5 groups independently selected from —OH, oxo, halo, heteroalkyl, deuteroalkyl, alkoxy, —O-haloalkyl, —CO$_2$R$^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —CO$_2$R$^6$, CN, —S(O)R$^7$, —S(O)$_2$R$^7$, —SF$_5$, —OSF$_5$, —C(O)NR$^8$R$^9$, and —NO$_2$,
(c) —NR$^{10}$—C(O)—NR$^8$R$^9$, —NR$^{10}$—CO$_2$R$^6$, —NR$^{10}$—C(O)R$^6$, —NR$^8$R$^9$, —NR$^{10}$SO$_2$R$^6$, —SO$_2$—NR$^8$R$^9$, —C(O)NR$^8$R$^9$, and —OC(O)—NR$^8$R$^9$;
(d) cycloalkyl, cycloalkenyl, heterocycloalkyl, or heterocycloalkenyl, each substituted with from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —CO$_2$R$^6$, CN, —S(O)R$^7$, —S(O)$_2$R$^7$, —SF$_5$, —OSF$_5$, —C(O)NR$^8$R$^9$, —NR$^{10}$—C(O)R$^6$, —SO$_2$—NR$^8$R$^9$, and —NO$_2$,
(e) heteroaryl substituted from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, heteroalkyl, haloalkyl, —O-haloalkyl, haloheteroalkyl, —CO$_2$R$^6$, CN, —S(O)R$^7$, —S(O)$_2$R$^7$, —C(O)NR$^8$R$^9$, —NR$^{10}$—C(O)R$^6$, —SO$_2$—NR$^8$R$^9$, —SF$_5$, —OSF$_5$, and —NO$_2$, and
(f) —Si(alkyl)$_3$;

or, alternatively, two R$^2$ groups attached to the same atom of ring A are taken together to form a moiety selected from the group consisting of carbonyl, oxime, substituted oxime (said oxime substituents being independently selected from the group consisting of alkyl, haloalkyl, hydroxyl-substituted alkyl, and cycloalkyl), spirocycloalkyl, spiroheterocycloalkyl, spirocycloalkenyl, and spiroheterocycloalkenyl;

or, alternatively, two R$^2$ groups attached to adjacent ring atoms of ring A are taken together to form a 5-6-membered aromatic or heteroaromatic ring;

each R$^{2A}$ (when present) is independently selected from the group consisting of —C(O)NR$^8$R$^9$, —CO$_2$R$^6$, —C(O)

$R^6$, —$SO_2R^7$, alkyl, heteroalkyl, haloalkyl, hydroxyl-substituted alkyl, cycloalkyl, heterocycloalkyl, aryl, arylalkyl-, heteroaryl, $R^3$ is selected from H and lower alkyl;

Z is a moiety selected from —$(C(R^{11})_2)$—$(C(R^{12}R^{13}))_m$—C(O)OH, —$(C(R^{11})_2)$—$(C(R^{14})_2)_n$—C(O)OH, from —$(C(R^{11})_2)$—$(C(R^{12}R^{13}))_m$—C(O)Oalkyl, —$(C(R^{11})_2)$—$(C(R^{14})_2)_n$—C(O)Oalkyl,

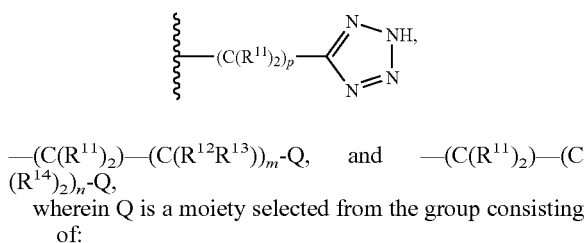

—$(C(R^{11})_2)$—$(C(R^{12}R^{13}))_m$-Q, and —$(C(R^{11})_2)$—$(C(R^{14})_2)_n$-Q, wherein Q is a moiety selected from the group consisting of:

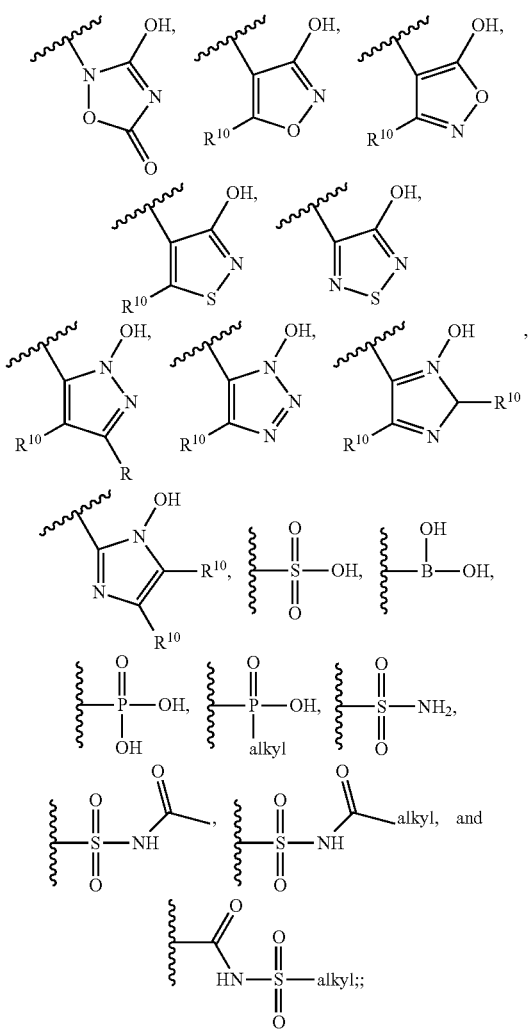

m is an integer from 0 to 5;
n is an integer from 0 to 5;
p is an integer from 0 to 5;
each $R^4$ is independently selected from H, —OH, lower alkyl, haloalkyl, alkoxy, heteroalkyl, cyano-substituted lower alkyl, hydroxy-substituted lower alkyl, cycloalkyl, —O-cycloalkyl, —O-alkyl-cycloalkyl, and heterocycloalkyl, —O-heterocycloalkyl, and —O-alkyl-heterocycloalkyl;

each $R^{5A}$ is independently selected from H, alkyl, -alkyl-Si(CH$_3$)$_3$, haloalkyl, heteroalkyl, cyano-substituted alkyl, hydroxy-substituted alkyl, cycloalkyl, -alkyl-cycloalkyl, and heterocycloalkyl, -alkyl-heterocycloalkyl, or, alternatively, two $R^{5A}$ groups are taken together with the carbon atom to which they are attached to form a carbonyl group, a spirocycloalkyl group, a spiroheterocycloalkyl group, an oxime group, or a substituted oxime group (said oxime substituents being independently selected from alkyl, haloalkyl, hydroxyl-substituted alkyl, and cycloalkyl);

each $R^5$ is independently selected from H, —OH, alkyl, -alkyl-Si(CH$_3$)$_3$, haloalkyl, alkoxy, heteroalkyl, cyano-substituted alkyl, hydroxy-substituted alkyl, cycloalkyl, -alkyl-cycloalkyl, —O-cycloalkyl, —O-alkyl-cycloalkyl, and heterocycloalkyl, -alkyl-heterocycloalkyl, —O-heterocycloalkyl, and —O-alkyl-heterocycloalkyl, or, alternatively, two $R^5$ groups bound to the same carbon atom are taken together with the carbon atom to which they are attached to form a carbonyl group, a spirocycloalkyl group, a spiroheterocycloalkyl group, an oxime group, or a substituted oxime group (said oxime substituents being independently selected from alkyl, haloalkyl, hydroxyl-substituted alkyl, and cycloalkyl);

each $R^6$ is independently selected from H, alkyl, haloalkyl, heteroalkyl, alkenyl, heteroalkenyl, alkynyl, and heteroalkynyl;

each $R^7$ is independently selected from H, alkyl, heteroalkyl, and haloalkyl;

each $R^8$ is independently selected from H and alkyl;

each $R^9$ is independently selected from H and alkyl, or alternatively $R^8$ and $R^9$ are taken together with the nitrogen to which they are attached to form a 5-, 6-, or 7-membered saturated heterocyclic ring, or a 5-, 6-, or 7-membered unsaturated heterocyclic ring, which ring contains (including said nitrogen) from 1 to 2 ring heteroatoms each independently selected from N,N-oxide, 0, S, S(O), or S(O)$_2$, or alternatively $R^8$ and $R^9$ are taken together with the nitrogen to which they are attached to form a 5-membered heteroaromatic ring containing (including the nitrogen to which $R^8$ and $R^9$ are attached) from 1 to 3 ring nitrogens;

each $R^{10}$ is independently selected from H and alkyl;

each $R^{11}$ is independently selected from H and lower alkyl;

each $R^{12}$ is independently selected from H, lower alkyl, —OH, hydroxy-substituted lower alkyl;

each $R^{13}$ is independently selected from H, unsubstituted lower alkyl, lower alkyl substituted with one or more groups each independently selected from hydroxyl and alkoxy, or $R^{12}$ and $R^{13}$ are taken together to form an oxo; and each $R^{14}$ is independently selected from H and fluoro.

2. A compound of claim 1, or a pharmaceutically acceptable salt, solvate, tautomer, or isomer of said compound, said compound having the general structure shown in Formula (A-1):

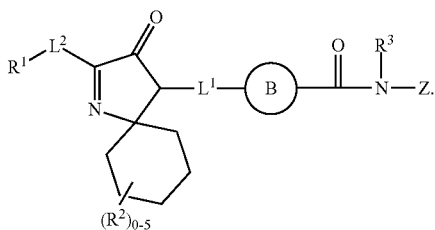

(A-1)

3. A compound of claim 1, or a pharmaceutically acceptable salt, solvate, tautomer, or isomer of said compound, said compound having the general structure shown in Formula (A-1a):

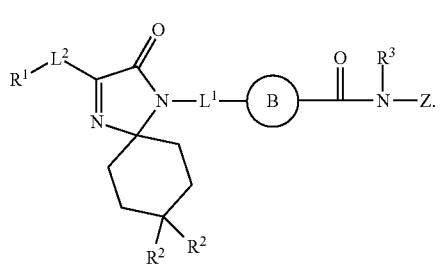

(A-1a)

4. A compound of claim 1, or a pharmaceutically acceptable salt, solvate, tautomer, or isomer of said compound, said compound having the general structure shown in Formula (A-1b):

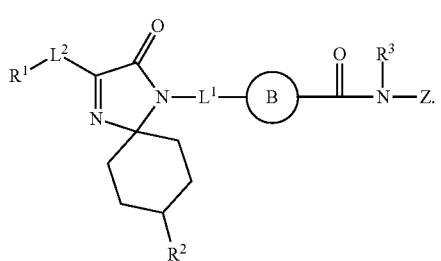

(A-1b)

5. A compound according to claim 1, or a pharmaceutically acceptable salt, solvate, tautomer, or isomer of said compound, said compound having the general structure shown Formula (I):

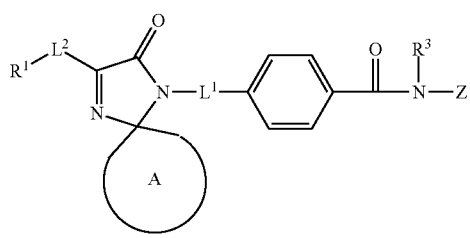

(I)

wherein ring A, $L^1$, $L^2$, $R^1$, $R^3$, and Z are selected independently of each other and wherein:

$L^1$ is selected from the group consisting of: a bond, $-N(R^4)-$, $-N(R^4)-(C(R^{5A})_2)-$, $-O-$, $-O-(C(R^{5A})_2)-$, and $-(C(R^{5A})_2)-(C(R^5)_2)_s-$;

s is 0-3;

$L^2$ is selected from the group consisting of bond, $-N(R^4)-$, $-N(R^4)-(C(R^{5A})_2)-$, $-(C(R^{5A})_2)-N(R^4)-$, $-(C(R^5)_2)_u-(C(R^{5A})_2)-N(R^4)-$, $-O-$, $-O-(C(R^{5A})_2)-$, $-(C(R^{5A})_2)-O-$ and $-(C(R^5)_2)_v-$, wherein u is 0 to 2 and v is 1-3;

$R^3$ is selected from the group consisting of H and lower alkyl;

Z is a moiety selected from $-(C(R^{11})_2)-(C(R^{12}R^{13}))$, $-C(O)OH$, $-(C(R^{11})_2)-(C(R^{14})_2)_n-C(O)OH$, and

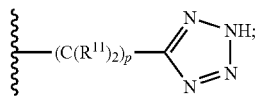

m is an integer from 0 to 5;
n is an integer from 0 to 5;
p is an integer from 0 to 5;
each $R^4$ is independently selected from H, lower alkyl, cycloalkyl, heterocycloalkyl, heteroalkyl, and haloalkyl;
each $R^{5A}$ is independently selected from H, lower alkyl, -lower alkyl-$Si(CH_3)_3$, lower haloalkyl, and hydroxy-substituted lower alkyl;
each $R^5$ is independently selected from H, $-OH$, lower alkyl, -lower alkyl-$Si(CH_3)_3$, lower haloalkyl, and hydroxy-substituted lower alkyl;
each $R^6$ is independently selected from H, alkyl, and haloalkyl;
each $R^7$ is independently selected from H, alkyl, heteroalkyl, and haloalkyl;
each $R^8$ is independently selected from H and alkyl;
each $R^9$ is independently selected from H and alkyl,
each $R^{11}$ is independently selected from H and lower alkyl;
each $R^{12}$ is independently selected from H, lower alkyl, $-OH$, hydroxy-substituted lower alkyl;
each $R^{13}$ is independently selected from H, unsubstituted lower alkyl, lower alkyl substituted with one or more groups each independently selected from hydroxyl and alkoxy, or $R^{12}$ and $R^{13}$ are taken together to form an oxo; and
each $R^{14}$ is independently selected from H and fluoro.

6. A compound of claim 5, or a pharmaceutically acceptable salt, solvate, tautomer, or isomer of said compound, wherein:
ring A represents a spirocycloalkyl ring or a spirocycloalkenyl ring, wherein said ring A is substituted on one or more available ring carbon atoms with from 0 to 5 independently selected $R^2$ groups;
$R^1$ is selected from the group consisting of:
aryl and heteroaryl,
wherein each of said aryl and said heteroaryl are unsubstituted or substituted with from 1 to 3 groups each independently selected from:
(1) halo, $-SO_2R^7$, $-SF_5$, $-OSF_5$, CN,
(2) alkyl, alkoxy, heteroalkyl, $-O$-heteroalkyl,
wherein each of said alkyl, alkoxy, heteroalkyl, and $-O$-heteroalkyl, is unsubstituted or optionally independently substituted with from 1 to 3 groups each independently selected from:
halo, OH, $-CO_2R^6$, $-C(O)R^6$, $-SR^7$, $-S(O)R^7$, $-SO_2R^7$, CN, $NO_2$, $-C(O)NR^8R^9$, $-NR^8R^9$, —O-haloalkyl, —NR$^{10}$—C(O)—NR$^8$R$^9$, —NR$^{10}$—CO$_2$R$^6$, —NR$^{10}$—C(O)R$^6$, —NR$^{10}$—SO$_2$R$^6$, —SO$_2$—NR$^8$R$^9$, —C(O)NR$^8$R$^9$, and —OC(O)NR$^8$R$^9$, and (3) aryl, —O-aryl, —S-aryl, —S(O)-aryl, —S(O)$_2$-aryl, heteroaryl, cycloalkyl, cycloalkenyl, and heterocycloalkenyl, each of which is unsubstituted or optionally independently substituted with from 1 to 2 groups each independently selected from (1) and (2) above; and each R$^2$ (when present) is independently selected from the group consisting of —Si(CH$_3$)$_3$ and alkyl, wherein said alkyl is substituted with from 0 to 5 groups independently selected from —OH, oxo, halo, heteroalkyl, alkoxy, —O-haloalkyl, —CO$_2$R$^6$, and phenyl substituted with from 0 to 5 groups independently selected from —OH, halo, aryl, substituted aryl, alkyl, alkoxy, —O-haloalkyl, heteroalkyl, haloalkyl, haloheteroalkyl, —CO$_2$R$^6$, CN, —S(O)R$^7$, —S(O)$_2$R$^7$, —SF$_5$, —C(O)NR$^8$R$^9$, and —NO$_2$.

7. A compound, or a pharmaceutically acceptable salt, solvate, tautomer, or isomer of said compound, having the general structure shown in Formula (II):

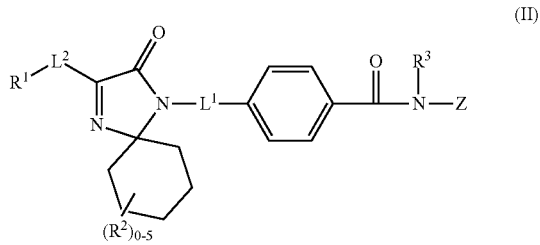

(II)

wherein L$^1$, L$^2$, R$^1$, each R$^2$, R$^3$, and Z are selected independently of each other and wherein:

L$^1$ is selected from the group consisting of: a bond, and —(C(R$^{5A}$)$_2$)—(C(R$^5$)$_2$)$_s$—;

s is 0-1;

L$^2$ is selected from the group consisting of: a bond, —(C(R$^5$)$_2$)$_u$—(C(R$^{5A}$)$_2$)—N(R$^4$)—, and —(C(R$^5$)$_2$)$_v$—;

u is 0-2;

v is 1-2;

R$^1$ is selected from the group consisting of:
phenyl,
wherein said phenyl is unsubstituted or substituted with one or more groups each independently selected from:
halo, alkyl, haloalkyl, heteroalkyl, haloheteroalkyl, alkoxy, —O-haloalkyl, and cycloalkyl;

each R$^2$ is independently selected from the group consisting of —Si(CH$_3$)$_3$ and alkyl, wherein said alkyl is substituted with from 0 to 5 groups independently selected from —OH, halo, alkyl, haloalkyl, hydroxyalkyl, alkyl substituted with from 1 to 2 —CO$_2$R$^6$ groups, alkoxy, —O-haloalkyl, hydroxyalkoxy, alkoxy substituted with from 1 to 2 —CO$_2$R$^6$ groups, —CO$_2$R$^6$, CN, —SO$_2$R$^7$, —C(O)NR$^8$R$^9$, and —NO$_2$;

R$^3$ is selected from the group consisting of H and lower alkyl;

Z is a moiety selected from the group consisting of:
—(CH$_2$)—(CH(CH$_3$))—C(O)OH, —(CH$_2$)—(CH$_2$)—(CH$_2$)—C(O)OH, —(CH$_2$)—C(CH$_3$)$_2$—C(O)OH, —(CH$_2$)—C(CH$_3$)(OH)—C(O)OH, —CH$_2$—CH$_2$—C(O)OH, —CH$_2$—CH(OH)—C(O)OH, —CH(CH$_3$)—CH$_2$—C(O)OH, —C(CH$_3$)$_2$—CH$_2$—C(O)OH, —CH$_2$—CH(F)—C(O)OH, —CH$_2$—CF$_2$—C(O)OH, —CH(CH$_3$)—CF$_2$—C(O)OH, —CH$_2$—CH$_2$—CF$_2$—C(O)OH, and

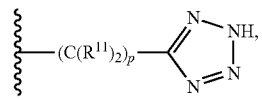

wherein p is an integer from 0 to 1, and R$^{11}$ (when present) is selected from the group consisting of H and lower alkyl;

each R$^{5A}$ is independently selected from H, lower alkyl, -lower alkyl-Si(CH$_3$)$_3$, lower haloalkyl, and lower alkyl substituted with from 1 to 2 hydroxyl;

each R$^5$ is independently selected from H, —OH, lower alkyl, -lower alkyl-Si(CH$_3$)$_3$, lower haloalkyl, and lower alkyl substituted with from 1 to 2 hydroxyl;

each R$^6$ is independently selected from H, alkyl, and haloalkyl;

each R$^7$ is independently selected from H, alkyl, heteroalkyl, and haloalkyl;

each R$^8$ is independently selected from H and alkyl; and each R$^9$ is independently selected from H and alkyl.

8. A compound of claim 7, or a pharmaceutically acceptable salt, solvate, tautomer, or isomer of said compound, said compound having the general structure shown in Formula (II-a):

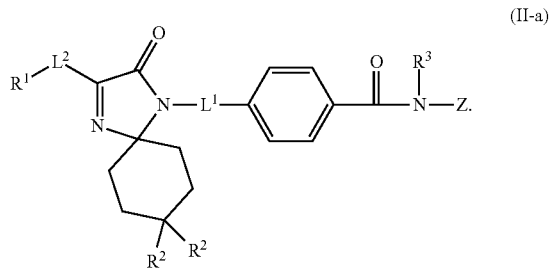

(II-a)

9. A compound of claim 7, or a pharmaceutically acceptable salt, solvate, tautomer, or isomer of said compound, said compound having the general structure shown in Formula (II-b):

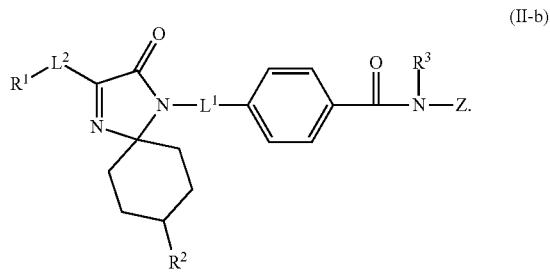

(II-b)

10. A compound of claim 9, or a pharmaceutically acceptable salt, solvate, tautomer, or isomer of said compound, wherein:

L$^1$ is selected from the group consisting of: a bond, straight or branched lower alkyl, and —CH(lower alkyl-Si(CH$_3$)$_3$)—;

$L^2$ is selected from the group consisting of: a bond and straight or branched lower alkyl;

$R^1$ is selected from the group consisting of:

phenyl,
  wherein said phenyl is unsubstituted or substituted with from 1 to 3 groups each independently selected from:
  halo, alkyl, haloalkyl, heteroalkyl, haloheteroalkyl, alkoxy, and —O-haloalkyl;

each $R^2$ is independently selected from the group consisting of H, straight or branched lower alkyl, and —Si(CH$_3$)$_3$;

$R^3$ is selected from the group consisting of H and lower alkyl;

Z is a moiety selected from the group consisting of: —(CH$_2$)—(CH(CH$_3$))—C(O)OH, —(CH$_2$)—(CH$_2$)—(CH$_2$)—C(O)OH, —(CH$_2$)—C(CH$_3$)$_2$—C(O)OH, —(CH$_2$)—C(CH$_3$)(OH)—C(O)OH, —CH$_2$—CH$_2$—C(O)OH, —CH$_2$—CH(OH)—C(O)OH, —CH(CH$_3$)—CH$_2$—C(O)OH, —C(CH$_3$)$_2$—CH$_2$—C(O)OH, —(C(R$^{11}$)$_2$)—(C(R$^{14}$)$_2$)$_n$—C(O)OH, —CH$_2$—CH(F)—C(O)OH, —CH$_2$—CF$_2$—C(O)OH, —CH(CH$_3$)—CF$_2$—C(O)OH, —CH$_2$—CH$_2$—CF$_2$—C(O)OH, —(CH$_2$)—(CH(CH$_3$))—C(O)OCH$_3$, —(CH$_2$)—(CH$_2$)—(CH$_2$)—C(O)OCH$_3$, —(CH$_2$)—C(CH$_3$)$_2$—C(O)OCH$_3$, —(CH$_2$)—C(CH$_3$)(OH)—C(O)OCH$_3$, —CH$_2$—CH$_2$—C(O)OCH$_3$, —CH$_2$—CH(OH)—C(O)OCH$_3$, —CH(CH$_3$)—CH$_2$—C(O)OCH$_3$, —C(CH$_3$)$_2$—CH$_2$—C(O)OCH$_3$, —(C(R$^{11}$)$_2$)—(C(R$^{14}$)$_2$)$_n$—C(O)OCH$_3$, —CH$_2$—CH(F)—C(O)OCH$_3$, —CH$_2$—CF$_2$—C(O)OCH$_3$, —CH(CH$_3$)—CF$_2$—C(O)OCH$_3$, —CH$_2$—CH$_2$—CF$_2$—C(O)OCH$_3$, and

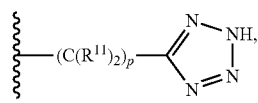

wherein p is an integer from 0 to 1, and R$^{11}$ (when present) is selected from the group consisting of H and lower alkyl;

each $R^5$ is independently selected from H, —OH, lower alkyl, lower haloalkyl, and lower alkyl substituted with from 1 to 2 hydroxyl;

each $R^6$ is independently selected from H, alkyl, and haloalkyl;

each $R^7$ is independently selected from H, alkyl, heteroalkyl, and haloalkyl;

each $R^8$ is independently selected from H and alkyl; and each $R^9$ is independently selected from H and alkyl.

11. A compound of claim 10, or a pharmaceutically acceptable salt, solvate, tautomer, or isomer of said compound, wherein:

$L^1$ is selected from the group consisting of: a bond,

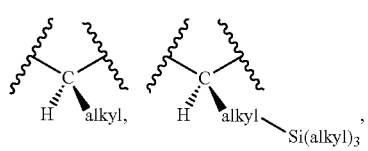

-continued

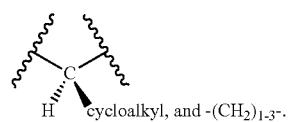

12. A compound of claim 10, or a pharmaceutically acceptable salt, solvate, tautomer, or isomer of said compound, wherein:

$L^1$ is selected from the group consisting of

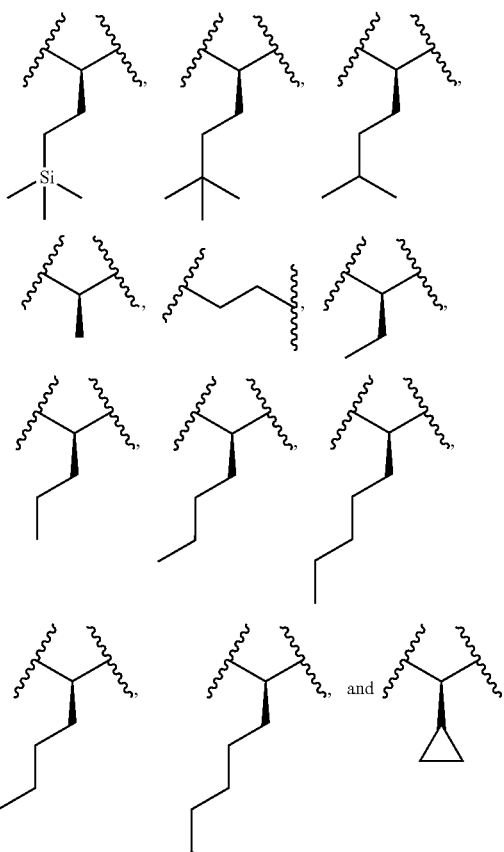

and

Z is selected from the group consisting of —CH$_2$—CH$_2$OC(O)OH and

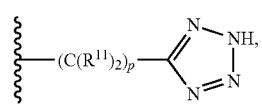

wherein p is 1 and R$^{11}$ is H.

13. A compound of claim 1, or a pharmaceutically acceptable salt or tautomer of said compound, said compound selected from the group consisting of:

| Ex. | Structure |
|---|---|
| 2.1 | 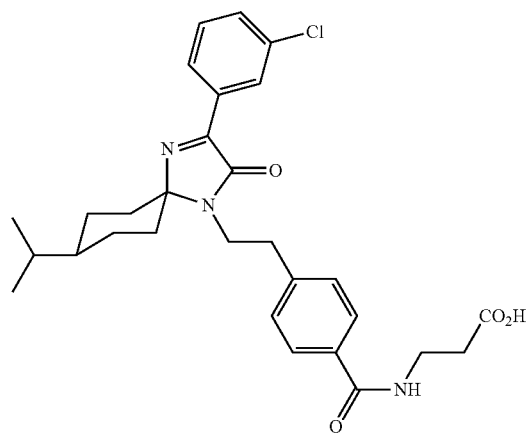 [SMILES: CC(C)C1CCC2(CC1)N=C(c1cccc(Cl)c1)C(=O)N2CCc1ccc(C(=O)NCCC(=O)O)cc1] |
| 2.2 | 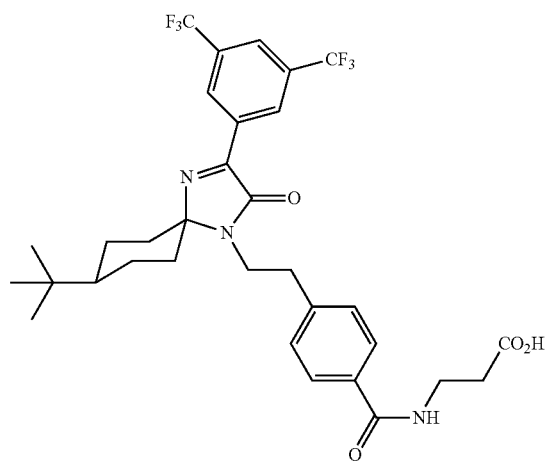 [SMILES: CC(C)(C)C1CCC2(CC1)N=C(c1cc(C(F)(F)F)cc(C(F)(F)F)c1)C(=O)N2CCc1ccc(C(=O)NCCC(=O)O)cc1] |
| 2.3 | 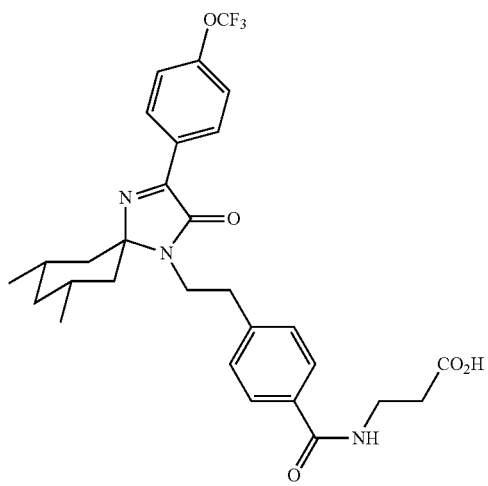 [SMILES: CC1CC(C)CC2(C1)N=C(c1ccc(OC(F)(F)F)cc1)C(=O)N2CCc1ccc(C(=O)NCCC(=O)O)cc1] |

| Ex. | Structure |
|---|---|
| 2.4 | 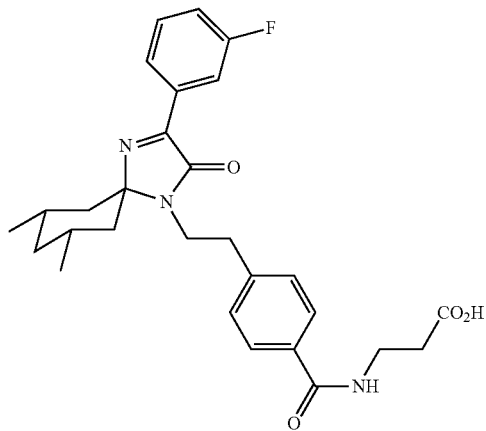 [SMILES: CC1CC(C)CC2(C1)N=C(c1cccc(F)c1)C(=O)N2CCc1ccc(C(=O)NCCC(=O)O)cc1] |
| 2.5 | 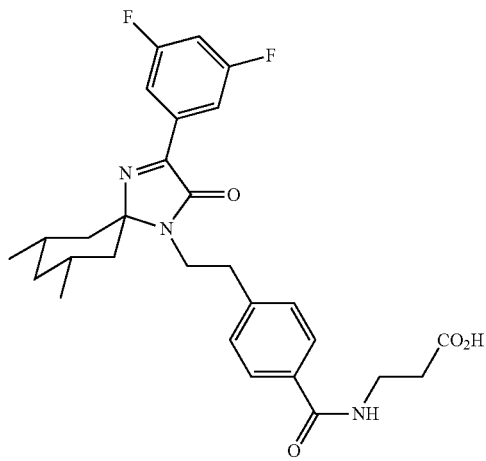 [SMILES: CC1CC(C)CC2(C1)N=C(c1cc(F)cc(F)c1)C(=O)N2CCc1ccc(C(=O)NCCC(=O)O)cc1] |
| 2.6 | 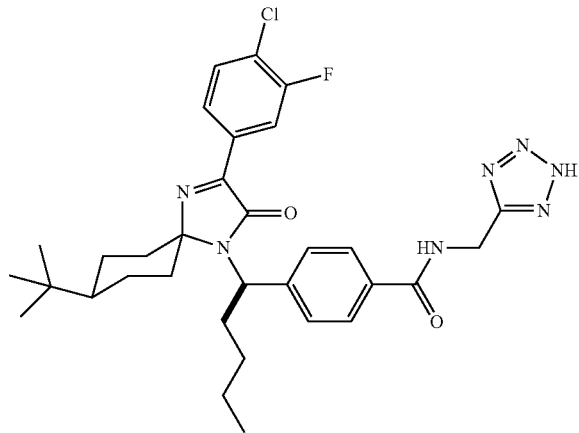 [SMILES: CCCC[C@H](c1ccc(C(=O)NCc2nn[nH]n2)cc1)N1C(=O)C(c2ccc(Cl)c(F)c2)=NC12CCC(C(C)(C)C)CC2] |

-continued
| Ex. | Structure |
|---|---|
| 2.7 | 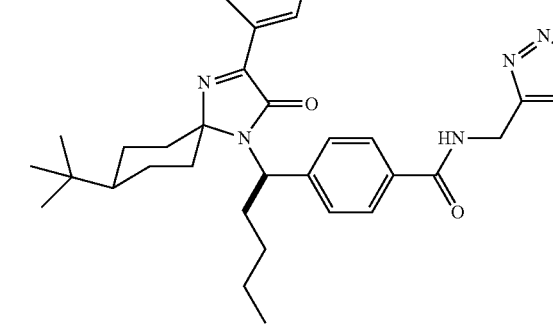 |
| 2.8 | 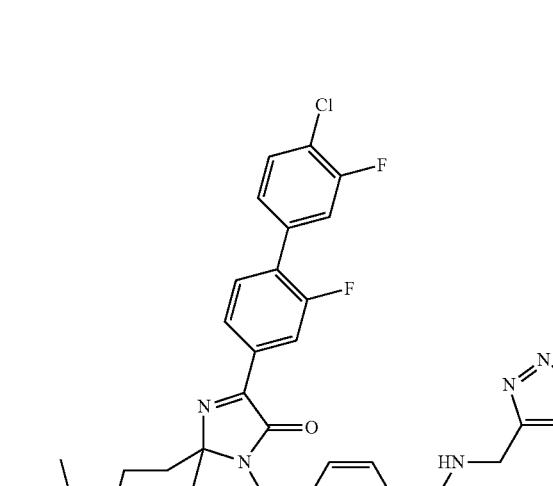 |
| 2.9 | 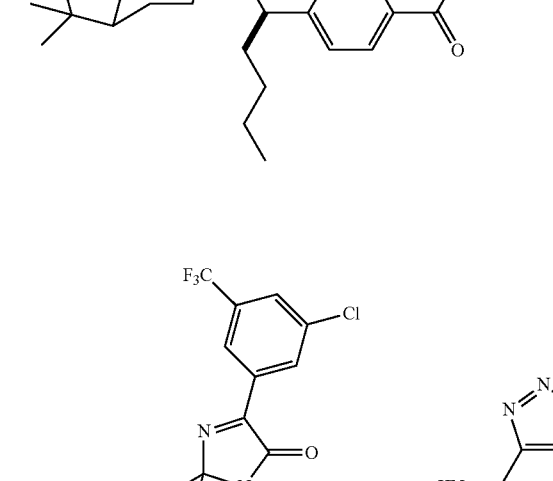 |

| Ex. | Structure |
|---|---|
| 2.10 | 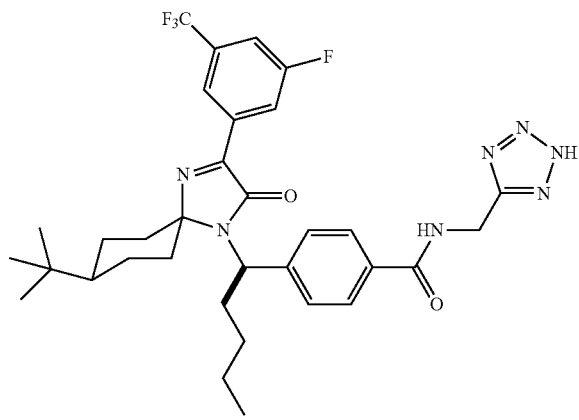 [SMILES: CCCC[C@H](c1ccc(C(=O)NCc2nn[nH]n2)cc1)N1C(=O)C(c2cc(F)cc(C(F)(F)F)c2)=NC12CCC(C(C)(C)C)CC2] |
| 2.11 | 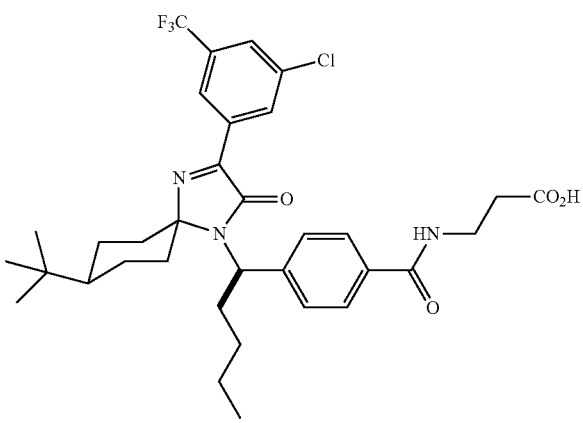 |
| 2.12 | 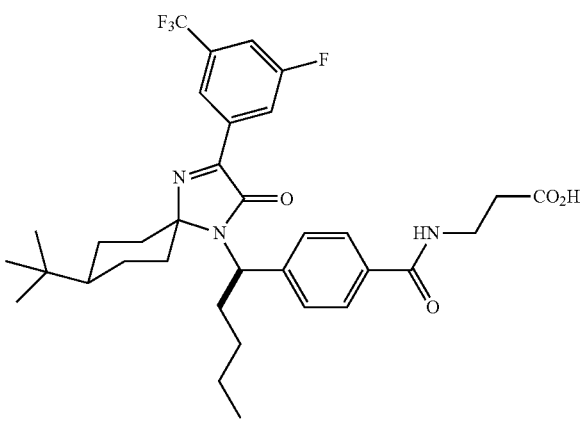 |

| Ex. | Structure |
|---|---|
| 2.13 | 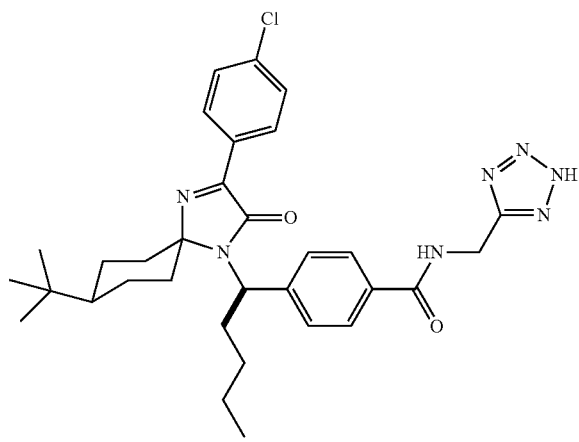 |
| 2.14 | 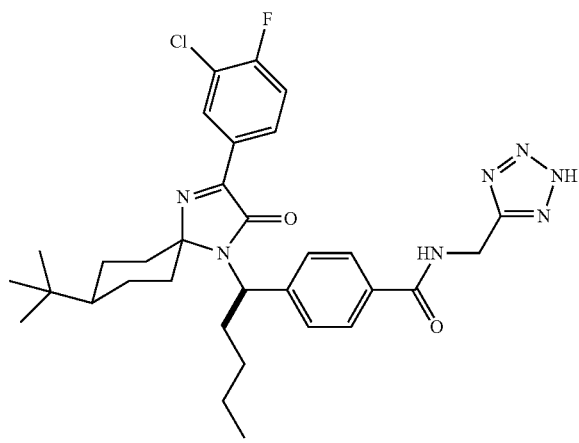 |
| 2.15 | 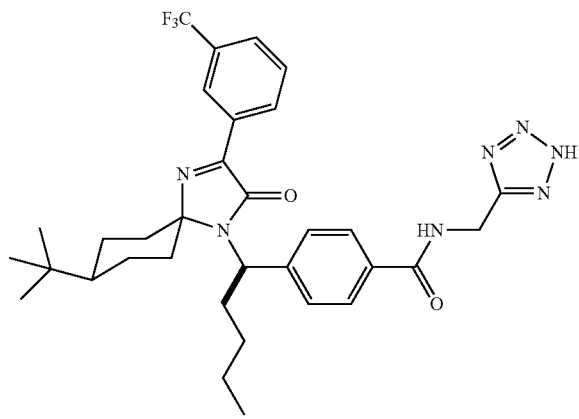 [SMILES: CCCC[C@H](c1ccc(C(=O)NCc2nn[nH]n2)cc1)N1C(=O)C(c2cccc(C(F)(F)F)c2)=NC12CCC(C(C)(C)C)CC2] |

| Ex. | Structure |
|---|---|
| 2.16 | 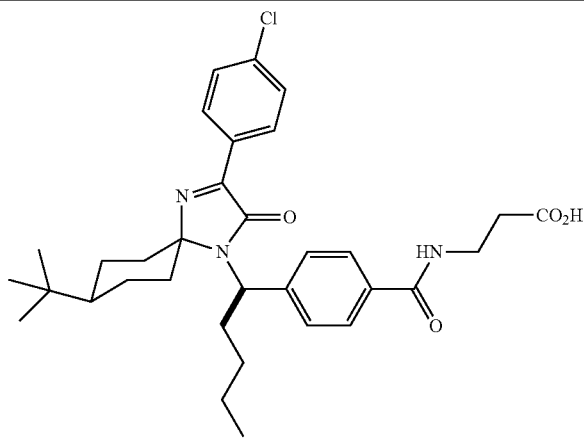 |
| 2.17 | 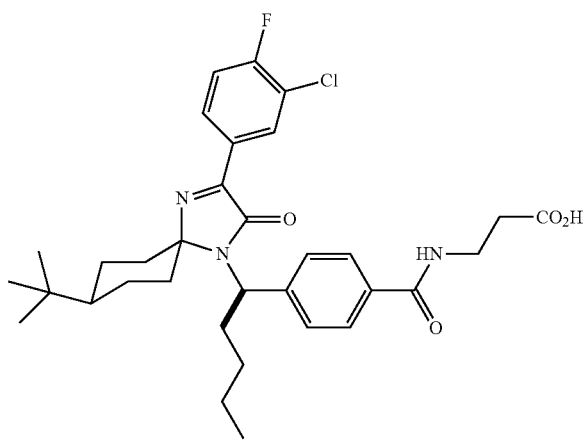 |
| 2.18 | 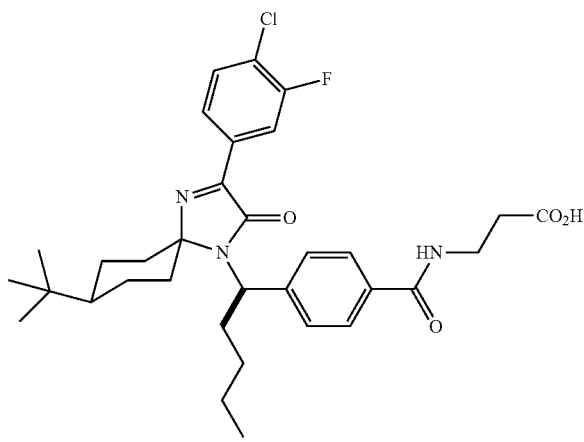 |

-continued
| Ex. | Structure |
|---|---|
| 2.19 | 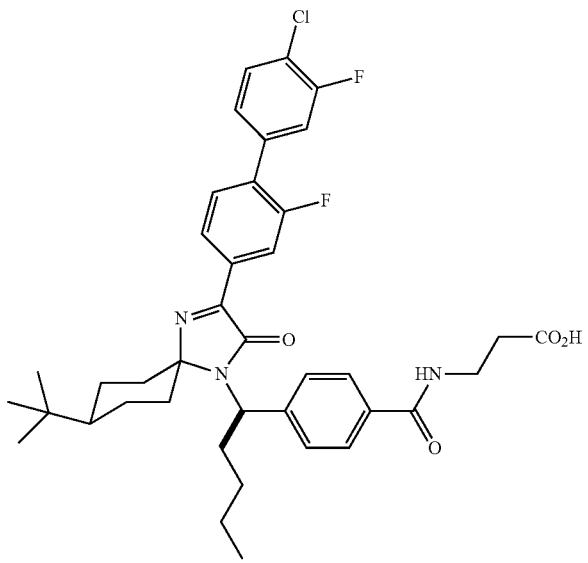 [SMILES: CCCC[C@H](c1ccc(C(=O)NCCC(=O)O)cc1)N1C(=O)C(c2ccc(-c3ccc(Cl)c(F)c3)c(F)c2)=NC12CCC(C(C)(C)C)CC2] |
| 2.20 | 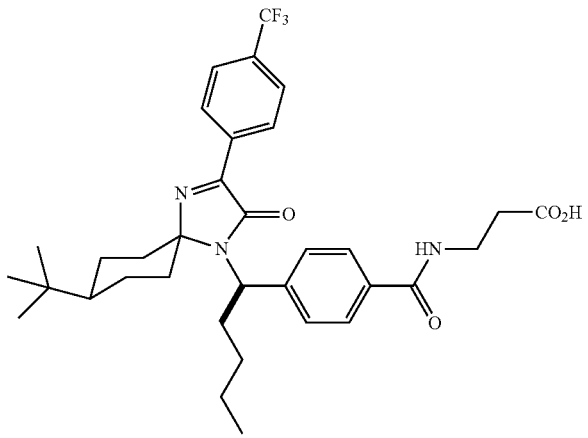 [SMILES: CCCC[C@H](c1ccc(C(=O)NCCC(=O)O)cc1)N1C(=O)C(c2ccc(C(F)(F)F)cc2)=NC12CCC(C(C)(C)C)CC2] |
| 2.21 | 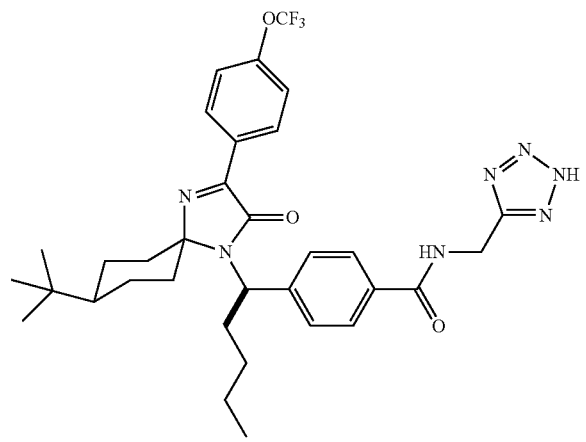 [SMILES: CCCC[C@H](c1ccc(C(=O)NCc2nn[nH]n2)cc1)N1C(=O)C(c2ccc(OC(F)(F)F)cc2)=NC12CCC(C(C)(C)C)CC2] |

-continued
| Ex. | Structure |
|---|---|
| 2.22 | 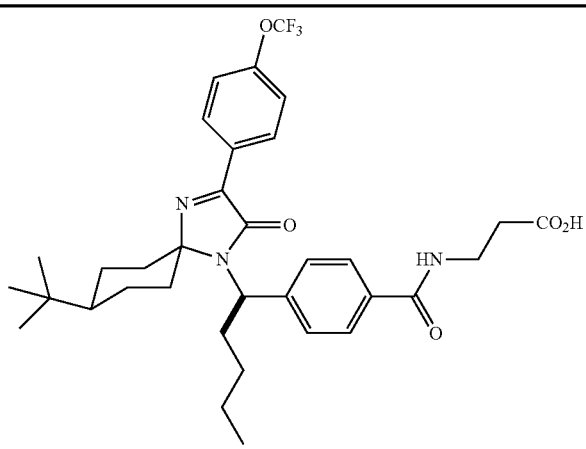 |
| 2.23 | 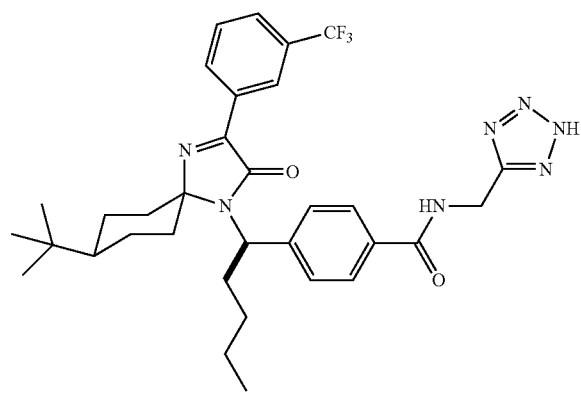 [SMILES: CCCC[C@H](c1ccc(C(=O)NCc2nn[nH]n2)cc1)N1C(=O)C(c2cccc(C(F)(F)F)c2)=NC12CCC(C(C)(C)C)CC2] |
| 2.24 | 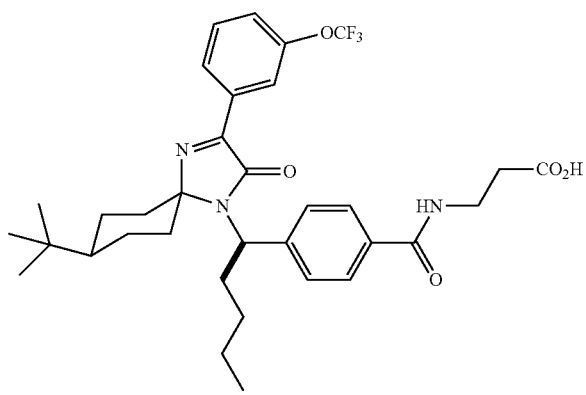 |
| 2.25 | 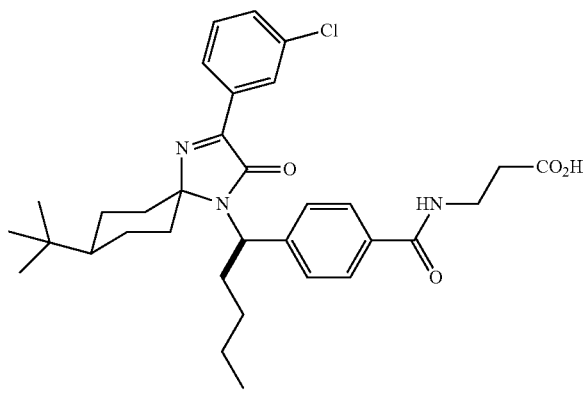 [SMILES: CCCC[C@H](c1ccc(C(=O)NCCC(=O)O)cc1)N1C(=O)C(c2cccc(Cl)c2)=NC12CCC(C(C)(C)C)CC2] |

| Ex. | Structure |
|---|---|
| 2.26 | 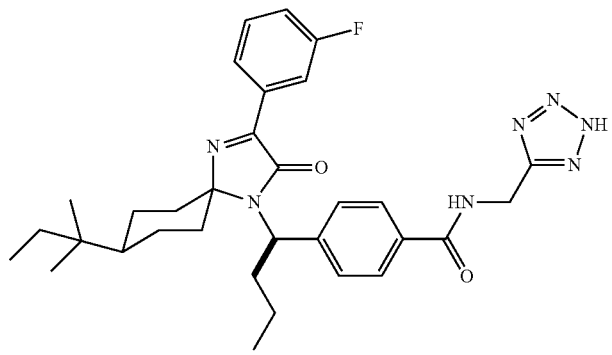 |
| 2.27 | 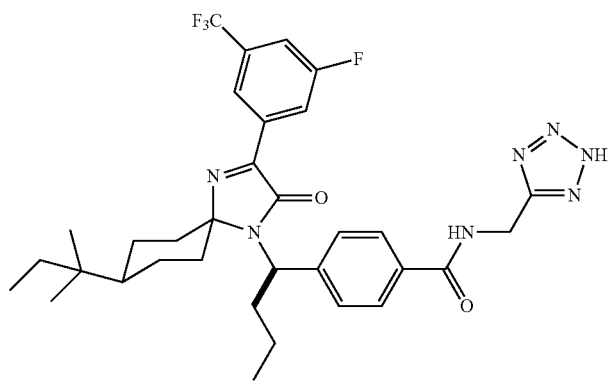 |
| 2.33 | 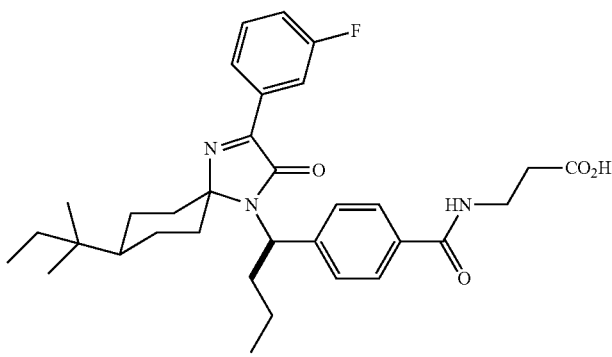 [SMILES: CCC[C@H](c1ccc(C(=O)NCCC(=O)O)cc1)N1C(=O)C(c2cccc(F)c2)=NC12CCC(C(C)(C)CC)CC2] |
| 2.34 | 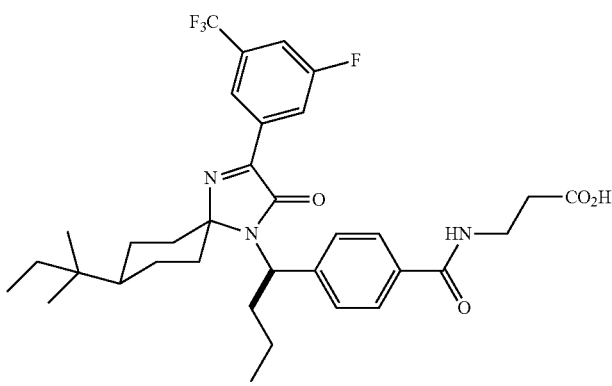 |

| Ex. | Structure |
|---|---|
| 2.28 | 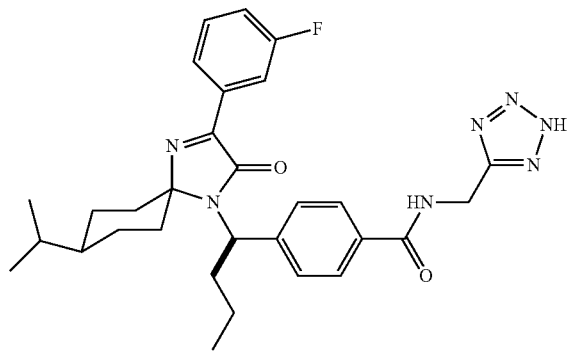 [SMILES: CCC[C@H](c1ccc(C(=O)NCc2nn[nH]n2)cc1)N1C(=O)C(c2cccc(F)c2)=NC12CCC(C(C)C)CC2] |
| 2.29 | 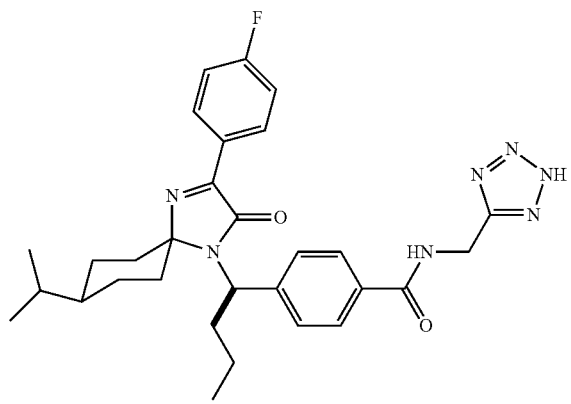 |
| 2.30 | 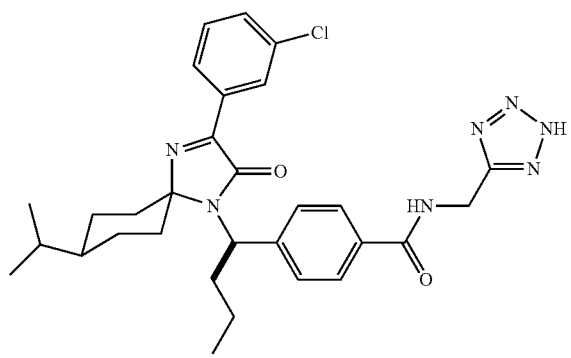 |
| 2.31 | 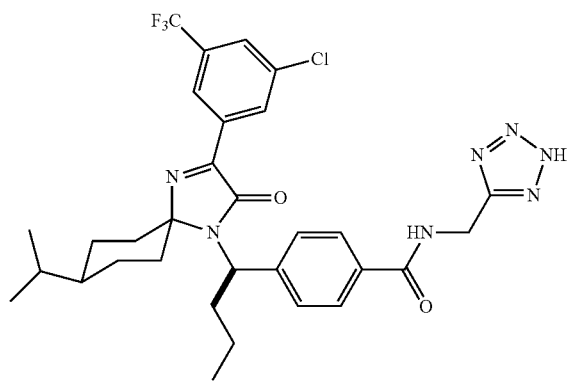 [SMILES: CCC[C@H](c1ccc(C(=O)NCc2nn[nH]n2)cc1)N1C(=O)C(c2cc(Cl)cc(C(F)(F)F)c2)=NC12CCC(C(C)C)CC2] |

| Ex. | Structure |
|---|---|
| 2.32 | 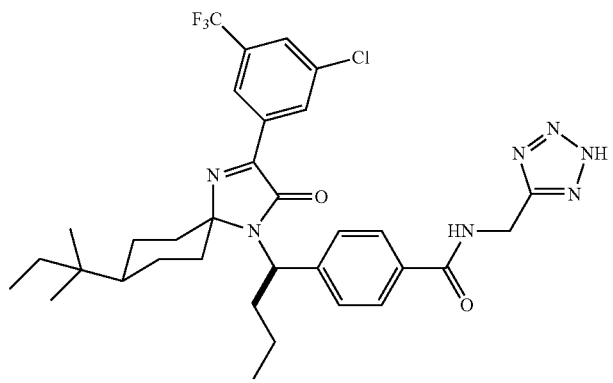 [SMILES: CCC[C@H](c1ccc(C(=O)NCc2nn[nH]n2)cc1)N1C(=O)C(c2cc(Cl)cc(C(F)(F)F)c2)=NC12CCC(C(C)(C)CC)CC2] |
| 2.41 | 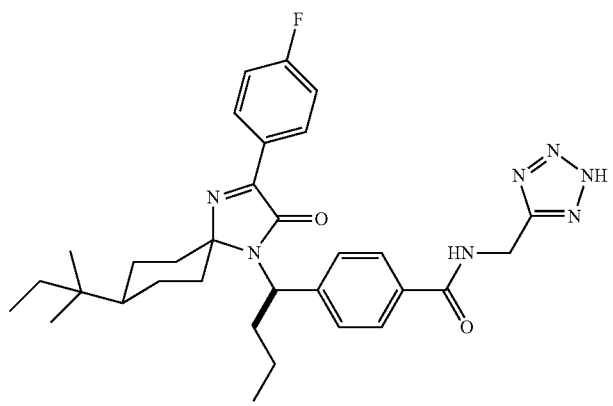 [SMILES: CCC[C@H](c1ccc(C(=O)NCc2nn[nH]n2)cc1)N1C(=O)C(c2ccc(F)cc2)=NC12CCC(C(C)(C)CC)CC2] |
| 2.42 | 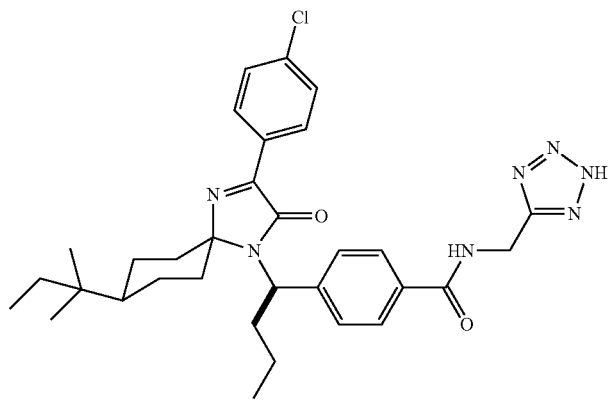 [SMILES: CCC[C@H](c1ccc(C(=O)NCc2nn[nH]n2)cc1)N1C(=O)C(c2ccc(Cl)cc2)=NC12CCC(C(C)(C)CC)CC2] |
| 2.35 | 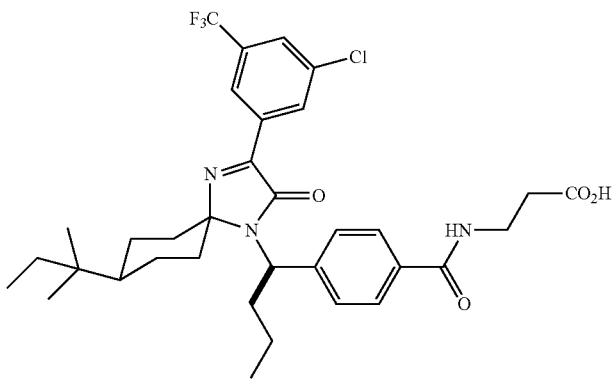 |

-continued
| Ex. | Structure |
|---|---|
| 2.36 | 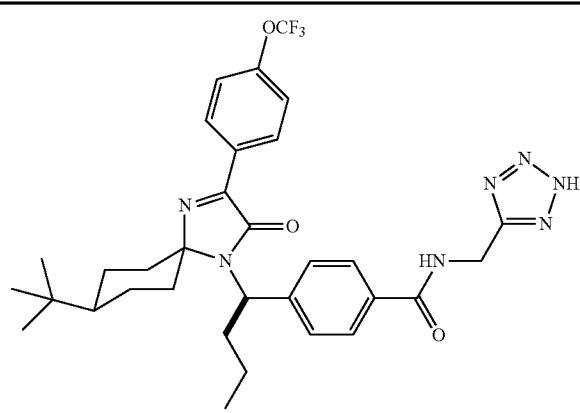 |
| 2.37 | 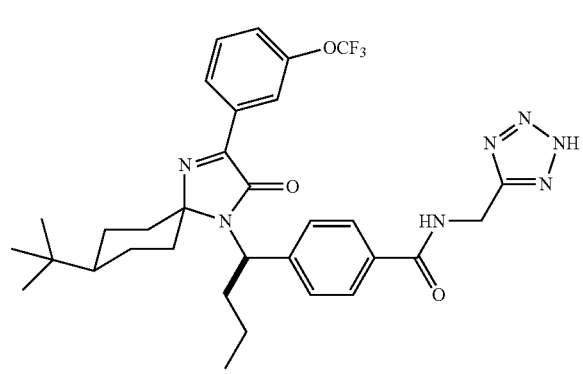 [SMILES: CCC[C@H](c1ccc(C(=O)NCc2nn[nH]n2)cc1)N1C(=O)C(c2cccc(OC(F)(F)F)c2)=NC12CCC(C(C)(C)C)CC2] |
| 2.38 | 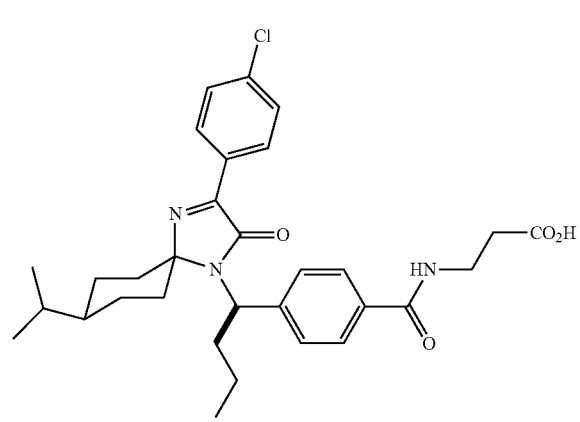 |
| 2.39 | 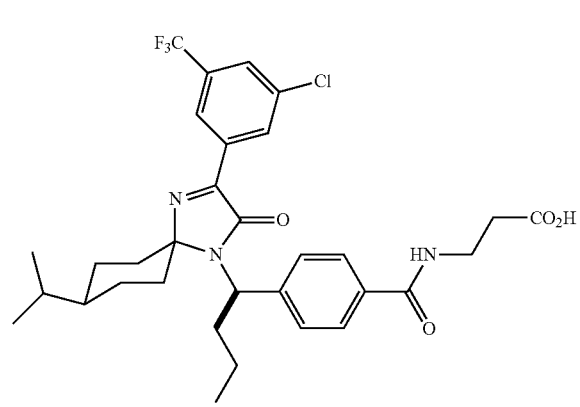 |

| Ex. | Structure |
|---|---|
| 2.40 | 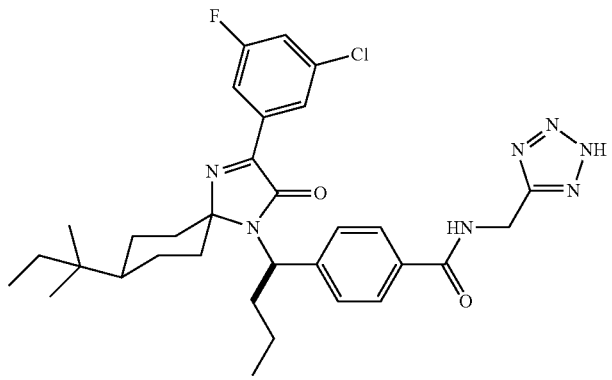 [SMILES: CCC[C@H](c1ccc(C(=O)NCc2nn[nH]n2)cc1)N1C(=O)C(c2cc(F)cc(Cl)c2)=NC12CCC(C(C)(C)CC)CC2] |
| 2.47 | 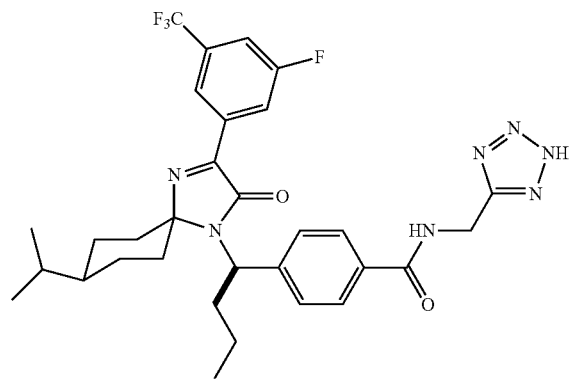 |
| 2.43 | 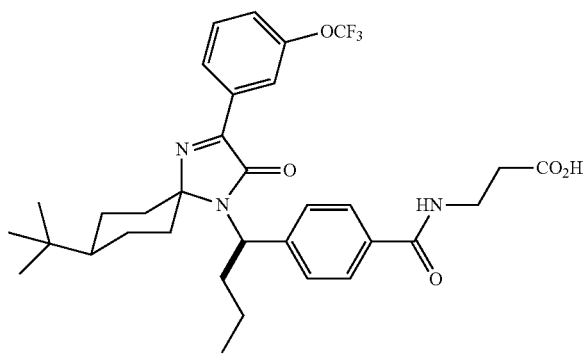 [SMILES: CCC[C@H](c1ccc(C(=O)NCCC(=O)O)cc1)N1C(=O)C(c2cccc(OC(F)(F)F)c2)=NC12CCC(C(C)(C)C)CC2] |
| 2.44 | 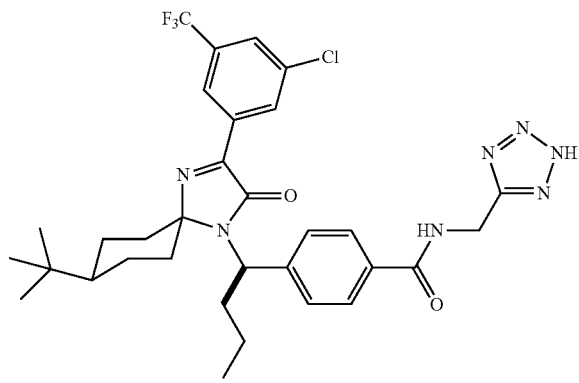 [SMILES: CCC[C@H](c1ccc(C(=O)NCc2nn[nH]n2)cc1)N1C(=O)C(c2cc(Cl)cc(C(F)(F)F)c2)=NC12CCC(C(C)(C)C)CC2] |

-continued

| Ex. | Structure |
|---|---|
| 2.45 | 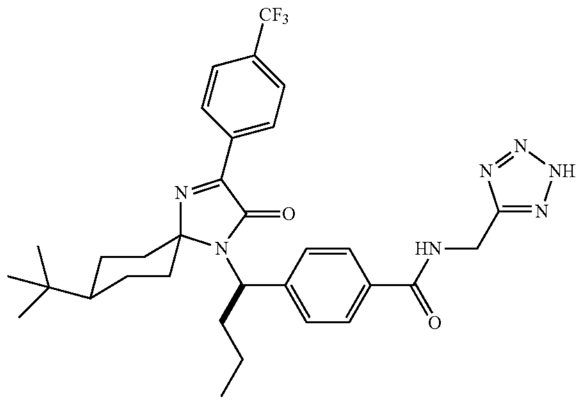 |
| 2.46 | 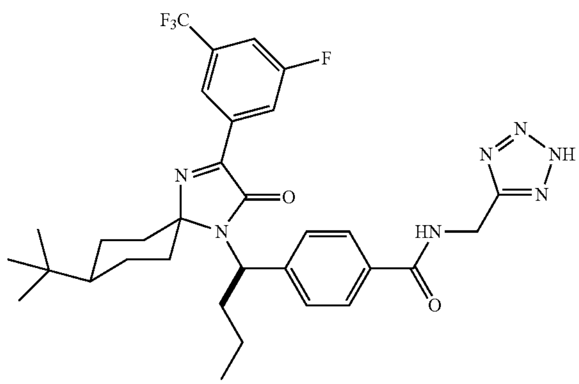 [SMILES: CCC[C@H](c1ccc(C(=O)NCc2nn[nH]n2)cc1)N1C(=O)C(c2cc(F)cc(C(F)(F)F)c2)=NC12CCC(C(C)(C)C)CC2] |
| 2.53 | 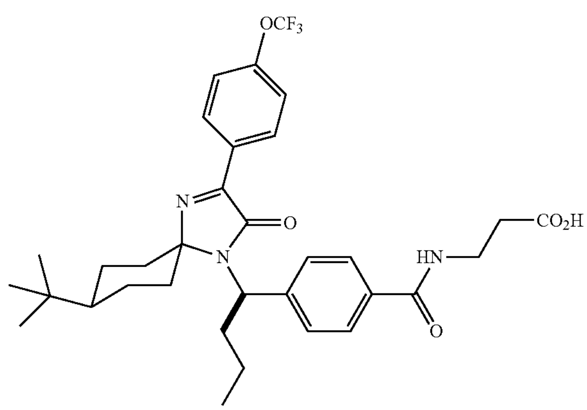 |
| 2.54 | 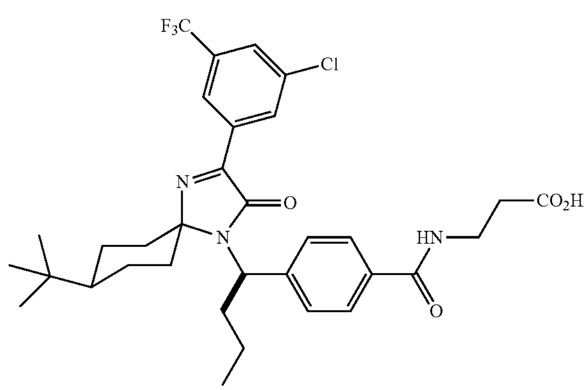 [SMILES: CCC[C@H](c1ccc(C(=O)NCCC(=O)O)cc1)N1C(=O)C(c2cc(Cl)cc(C(F)(F)F)c2)=NC12CCC(C(C)(C)C)CC2] |

| Ex. | Structure |
|---|---|
| 2.55 | 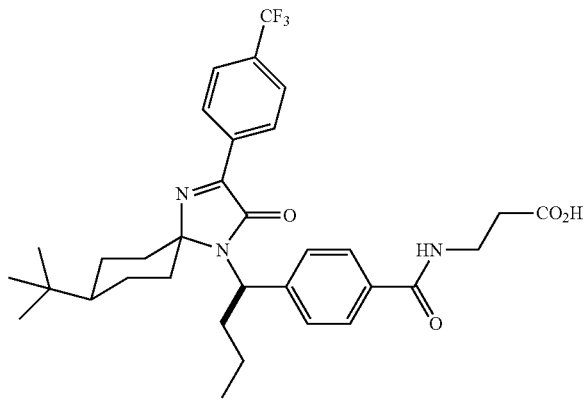 |
| 2.48 | 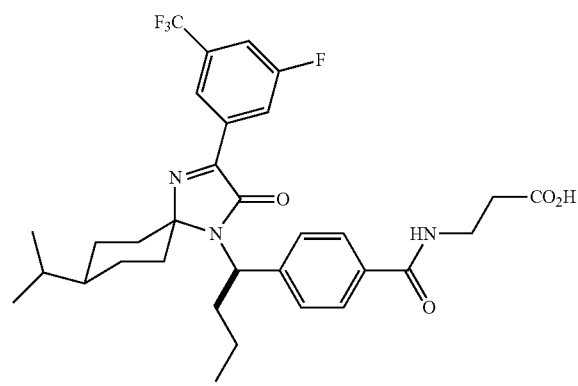 |
| 2.49 | 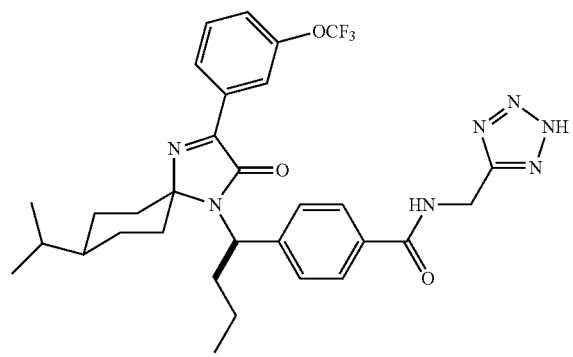 |
| 2.50 | 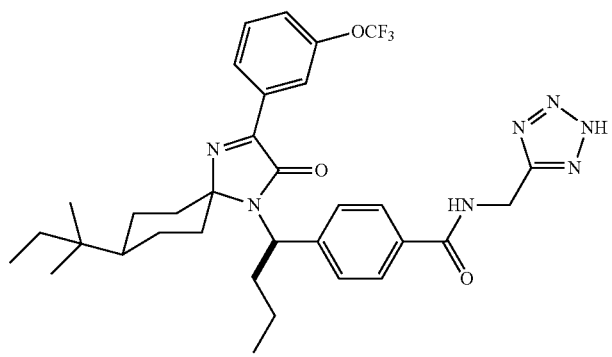 [SMILES: CCC[C@H](c1ccc(C(=O)NCc2nn[nH]n2)cc1)N1C(=O)C(c2cccc(OC(F)(F)F)c2)=NC12CCC(C(C)(C)CC)CC2] |

-continued
| Ex. | Structure |
|---|---|
| 2.51 | 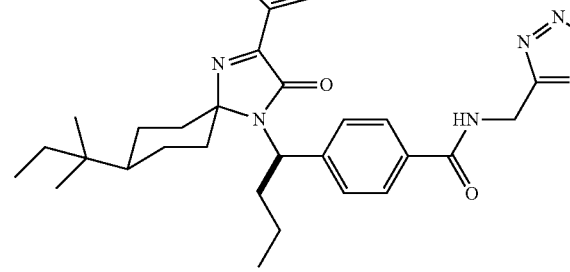 |
| 2.52 | 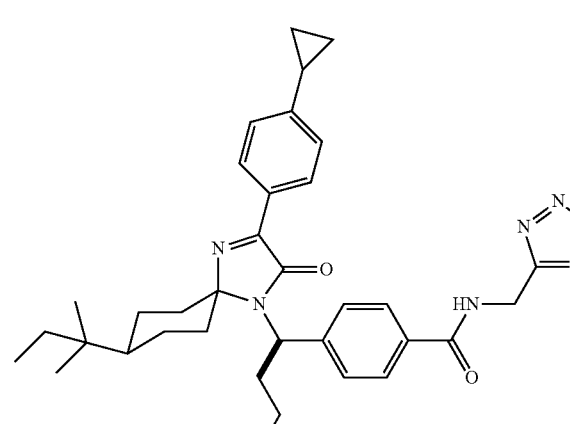 |
| 2.59 | 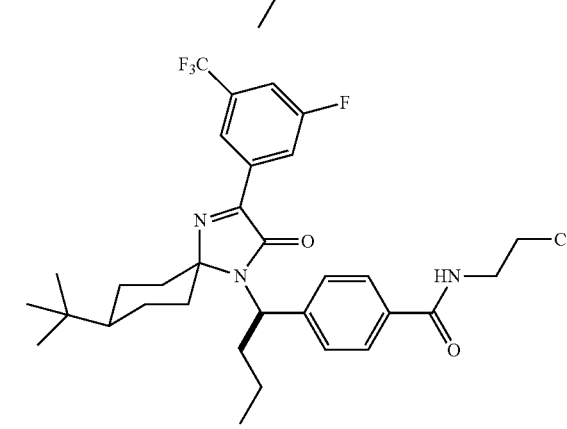 |
| 2.60 | 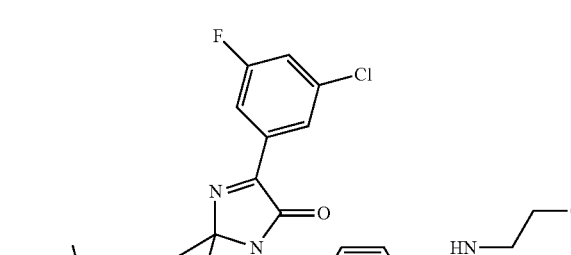 |

-continued
| Ex. | Structure |
|---|---|
| 2.56 | 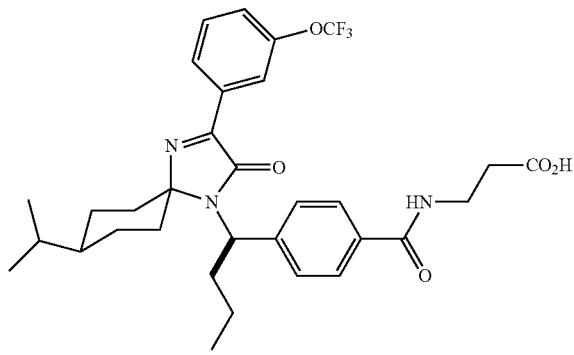 [SMILES: CCC[C@H](c1ccc(C(=O)NCCC(=O)O)cc1)N1C(=O)C(c2cccc(OC(F)(F)F)c2)=NC12CCC(C(C)C)CC2] |
| 2.57 | 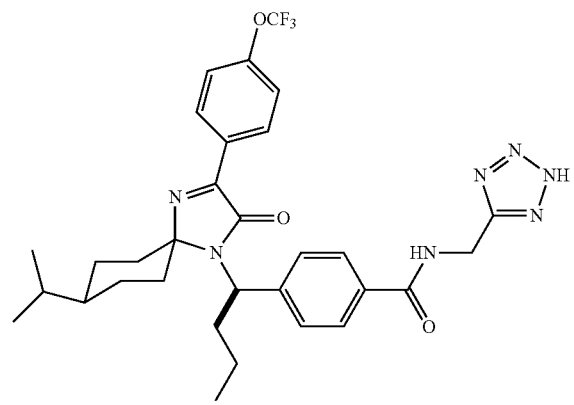 [SMILES: CCC[C@H](c1ccc(C(=O)NCc2nn[nH]n2)cc1)N1C(=O)C(c2ccc(OC(F)(F)F)cc2)=NC12CCC(C(C)C)CC2] |
| 2.58 | 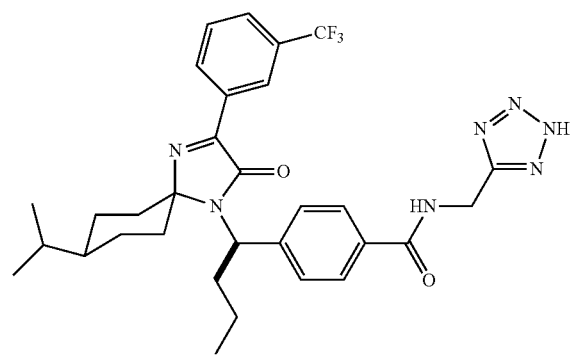 [SMILES: CCC[C@H](c1ccc(C(=O)NCc2nn[nH]n2)cc1)N1C(=O)C(c2cccc(C(F)(F)F)c2)=NC12CCC(C(C)C)CC2] |
| 2.66 | 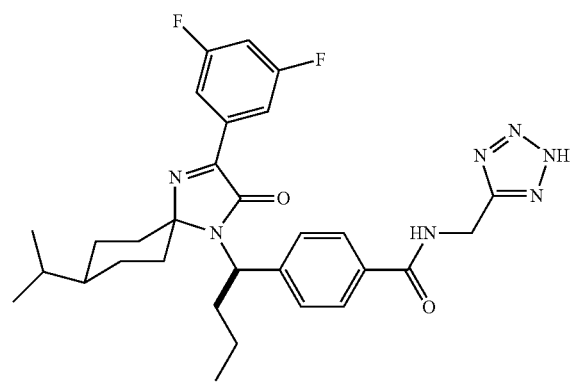 [SMILES: CCC[C@H](c1ccc(C(=O)NCc2nn[nH]n2)cc1)N1C(=O)C(c2cc(F)cc(F)c2)=NC12CCC(C(C)C)CC2] |

-continued
| Ex. | Structure |
|---|---|
| 2.67 | 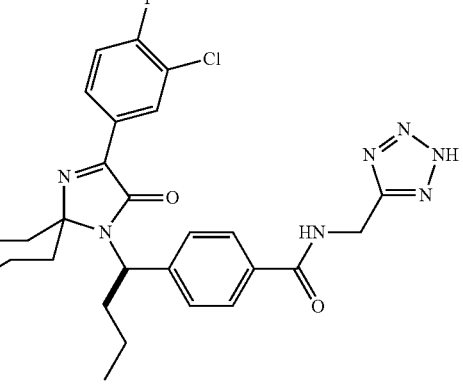 |
| 2.68 | 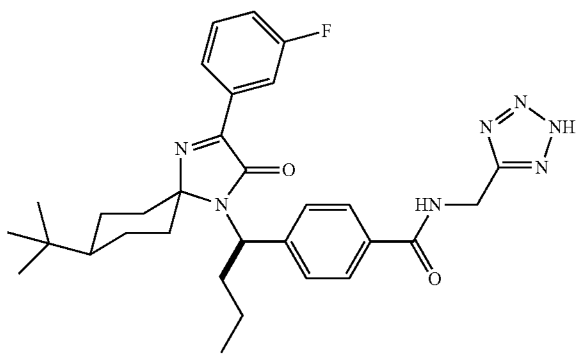 [SMILES: CCC[C@H](c1ccc(C(=O)NCc2nn[nH]n2)cc1)N1C(=O)C(c2cccc(F)c2)=NC12CCC(C(C)(C)C)CC2] |
| 2.69 | 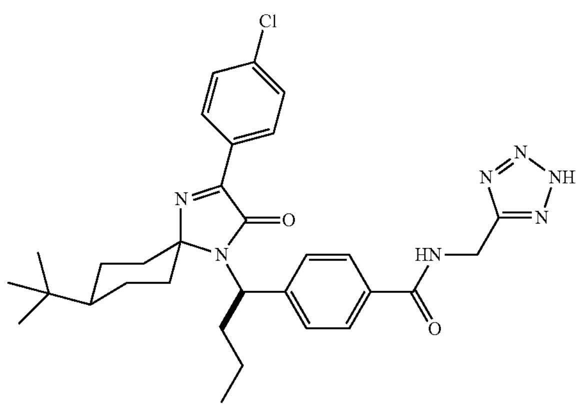 |
| 2.61 | 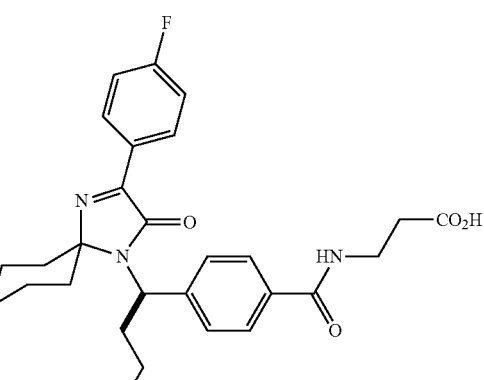 |

-continued
| Ex. | Structure |
|---|---|
| 2.62 | 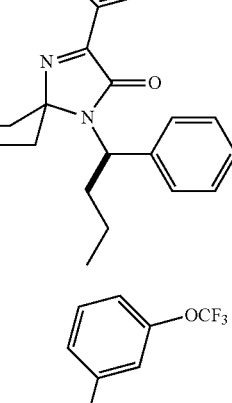 |
| 2.63 | 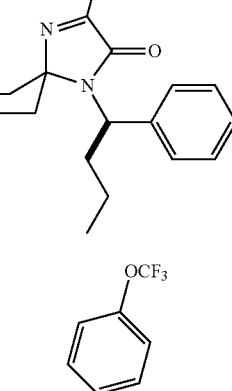 |
| 2.64 | 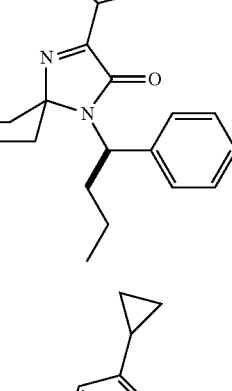 |
| 2.65 | 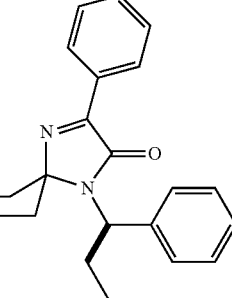 |

-continued

| Ex. | Structure |
|---|---|
| 2.72 | 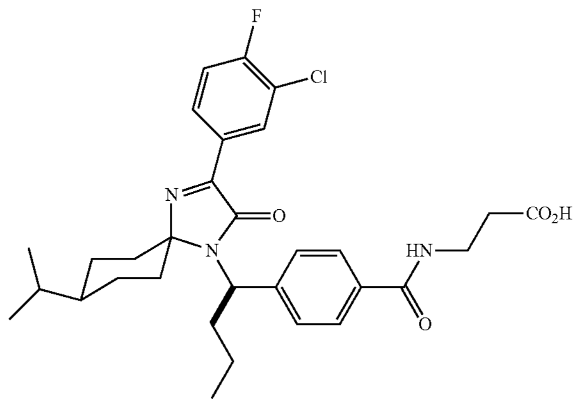 [SMILES: CCC[C@H](c1ccc(C(=O)NCCC(=O)O)cc1)N1C(=O)C(c2ccc(F)c(Cl)c2)=NC12CCC(C(C)C)CC2] |
| 2.73 | 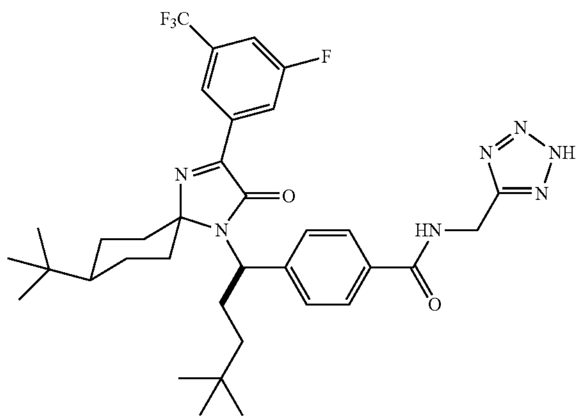 [SMILES: CC(C)(C)CC[C@H](c1ccc(C(=O)NCc2nn[nH]n2)cc1)N1C(=O)C(c2cc(F)cc(C(F)(F)F)c2)=NC12CCC(C(C)(C)C)CC2] |
| 2.70 | 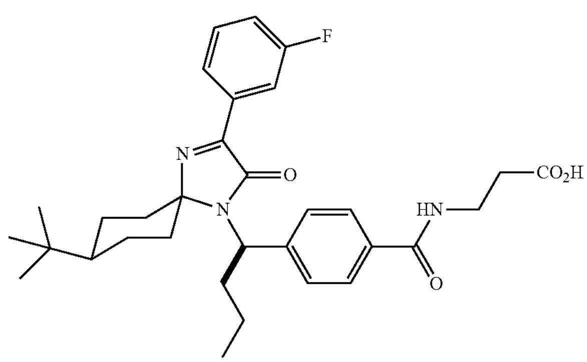 |
| 2.71 | 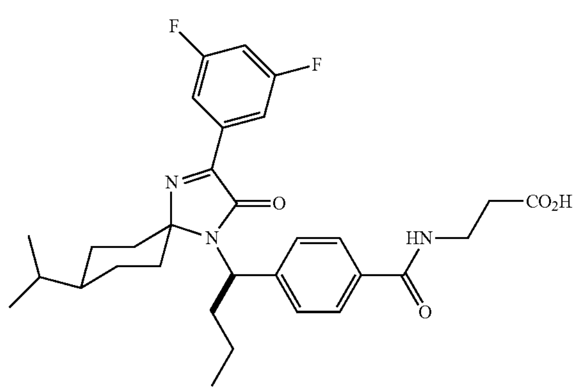 [SMILES: CCC[C@H](c1ccc(C(=O)NCCC(=O)O)cc1)N1C(=O)C(c2cc(F)cc(F)c2)=NC12CCC(C(C)C)CC2] |

| Ex. | Structure |
|---|---|
| 2.78 | 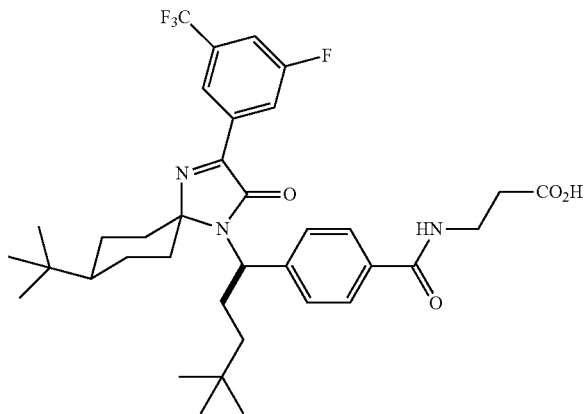 [SMILES: CC(C)(C)CC[C@H](c1ccc(C(=O)NCCC(=O)O)cc1)N1C(=O)C(c2cc(F)cc(C(F)(F)F)c2)=NC12CCC(C(C)(C)C)CC2] |
| 2.79 | 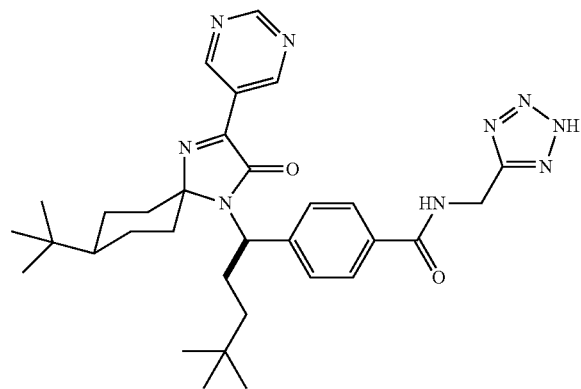 [SMILES: CC(C)(C)CC[C@H](c1ccc(C(=O)NCc2nn[nH]n2)cc1)N1C(=O)C(c2cncnc2)=NC12CCC(C(C)(C)C)CC2] |
| 2.80 | 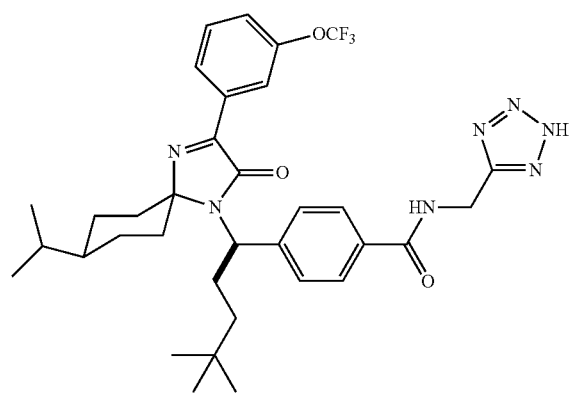 [SMILES: CC(C)C1CCC2(CC1)N=C(c1cccc(OC(F)(F)F)c1)C(=O)N2[C@H](CCC(C)(C)C)c1ccc(C(=O)NCc2nn[nH]n2)cc1] |

-continued
| Ex. | Structure |
|---|---|
| 2.81 | 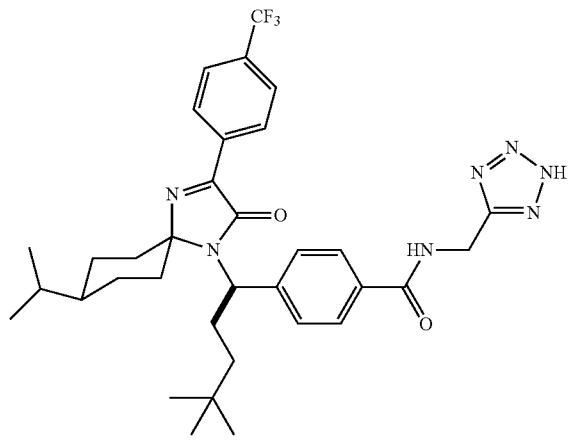 |
| 2.82 | 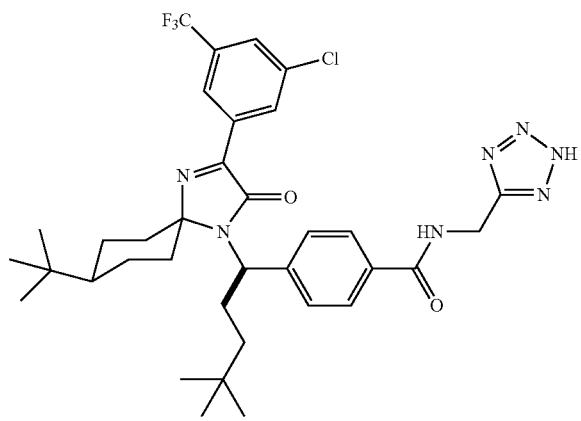 [SMILES: CC(C)(C)CC[C@H](c1ccc(C(=O)NCc2nn[nH]n2)cc1)N1C(=O)C(c2cc(Cl)cc(C(F)(F)F)c2)=NC12CCC(C(C)(C)C)CC2] |
| 2.74 | 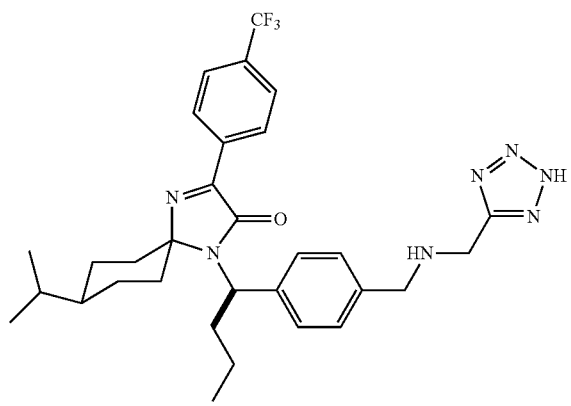 [SMILES: CCC[C@H](c1ccc(CNCc2nn[nH]n2)cc1)N1C(=O)C(c2ccc(C(F)(F)F)cc2)=NC12CCC(C(C)C)CC2] |

| Ex. | Structure |
|---|---|
| 2.75 | 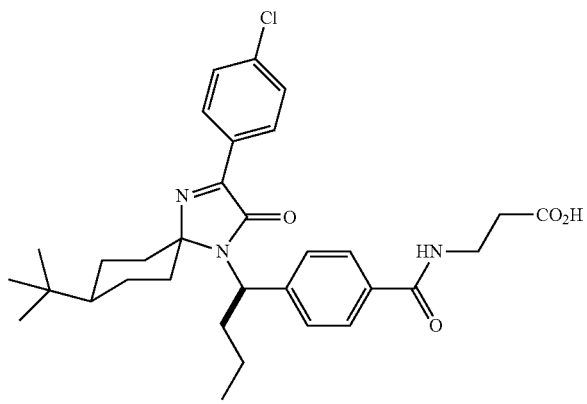 [SMILES: CCC[C@H](c1ccc(C(=O)NCCC(=O)O)cc1)N1C(=O)C(c2ccc(Cl)cc2)=NC12CCC(C(C)(C)C)CC2] |
| 2.76 | 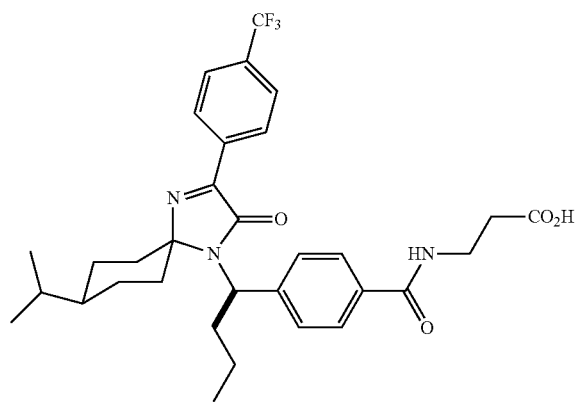 [SMILES: CCC[C@H](c1ccc(C(=O)NCCC(=O)O)cc1)N1C(=O)C(c2ccc(C(F)(F)F)cc2)=NC12CCC(C(C)C)CC2] |
| 2.77 | 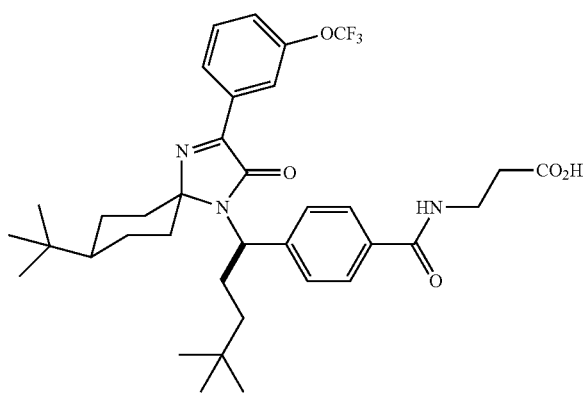 [SMILES: CC(C)(C)CC[C@H](c1ccc(C(=O)NCCC(=O)O)cc1)N1C(=O)C(c2cccc(OC(F)(F)F)c2)=NC12CCC(C(C)(C)C)CC2] |

-continued
| Ex. | Structure |
|---|---|
| 2.87 | 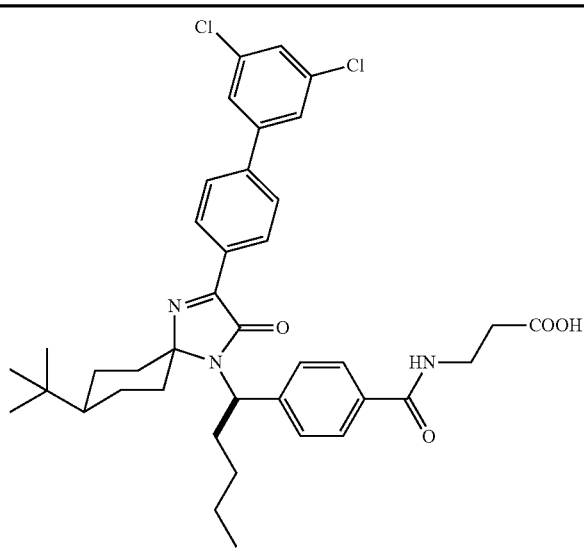 |
| 2.83 | 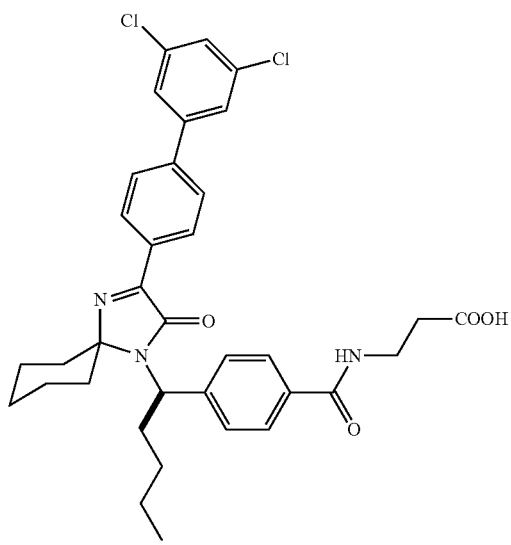 [SMILES: CCCC[C@H](c1ccc(C(=O)NCCC(=O)O)cc1)N1C(=O)C(c2ccc(-c3cc(Cl)cc(Cl)c3)cc2)=NC12CCCCC2] |
| 2.84 | 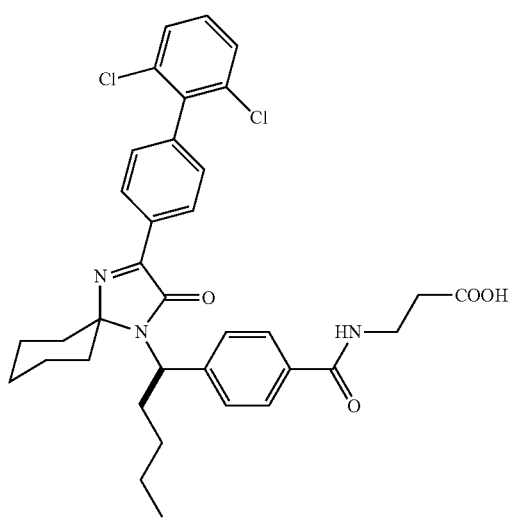 [SMILES: CCCC[C@H](c1ccc(C(=O)NCCC(=O)O)cc1)N1C(=O)C(c2ccc(-c3c(Cl)cccc3Cl)cc2)=NC12CCCCC2] |

| Ex. | Structure |
|---|---|
| 2.85 | 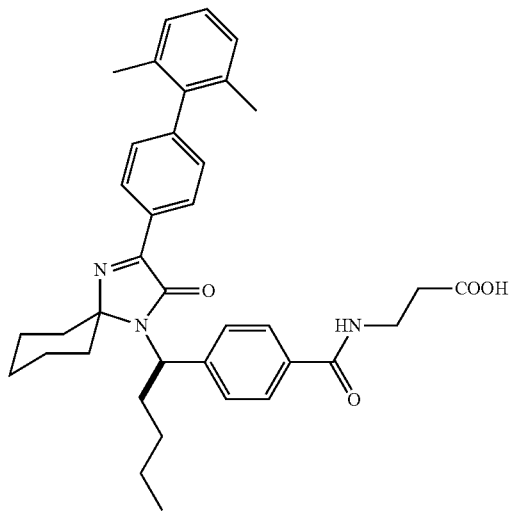 [SMILES: CCCC[C@H](c1ccc(C(=O)NCCC(=O)O)cc1)N1C(=O)C(c2ccc(-c3c(C)cccc3C)cc2)=NC12CCCCC2] |
| 2.86 | 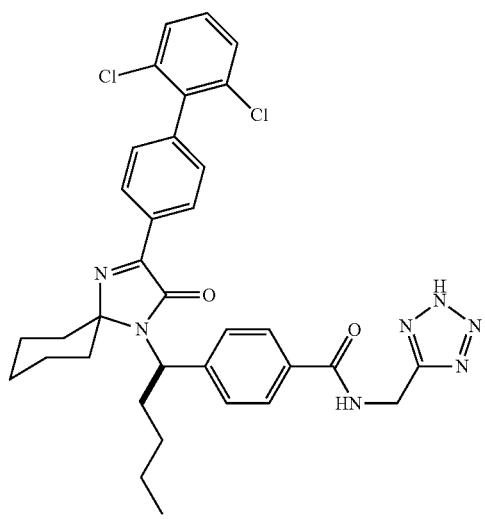 [SMILES: CCCC[C@H](c1ccc(C(=O)NCc2nn[nH]n2)cc1)N1C(=O)C(c2ccc(-c3c(Cl)cccc3Cl)cc2)=NC12CCCCC2] |
| 2.97 | 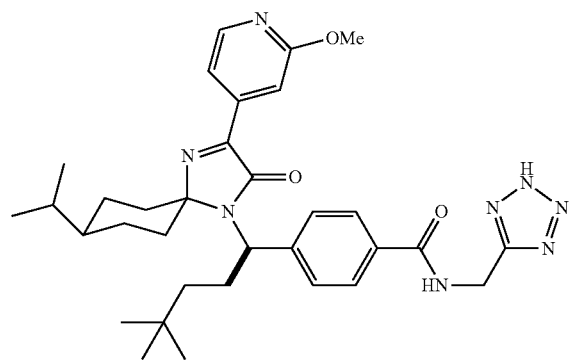 |

| Ex. | Structure |
|---|---|
| 2.88 | 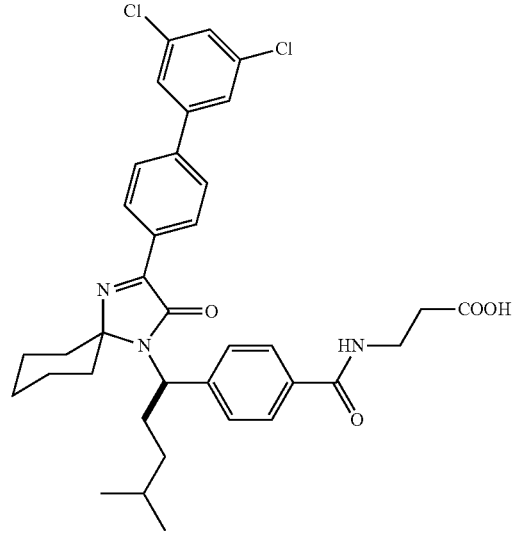 [SMILES: CC(C)CC[C@H](c1ccc(C(=O)NCCC(=O)O)cc1)N1C(=O)C(c2ccc(-c3cc(Cl)cc(Cl)c3)cc2)=NC12CCCCC2] |
| 2.89 | 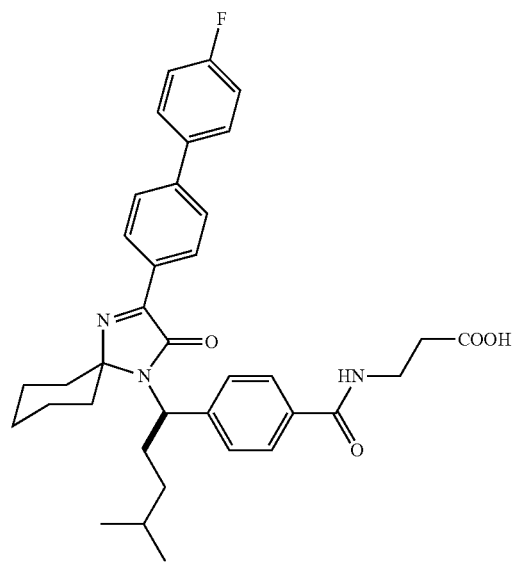 [SMILES: CC(C)CC[C@H](c1ccc(C(=O)NCCC(=O)O)cc1)N1C(=O)C(c2ccc(-c3ccc(F)cc3)cc2)=NC12CCCCC2] |
| 2.90 | 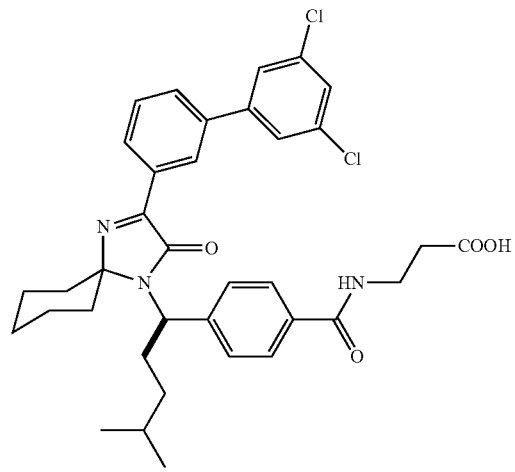 [SMILES: CC(C)CC[C@H](c1ccc(C(=O)NCCC(=O)O)cc1)N1C(=O)C(c2cccc(-c3cc(Cl)cc(Cl)c3)c2)=NC12CCCCC2] |

-continued
| Ex. | Structure |
|---|---|
| 2.91 | 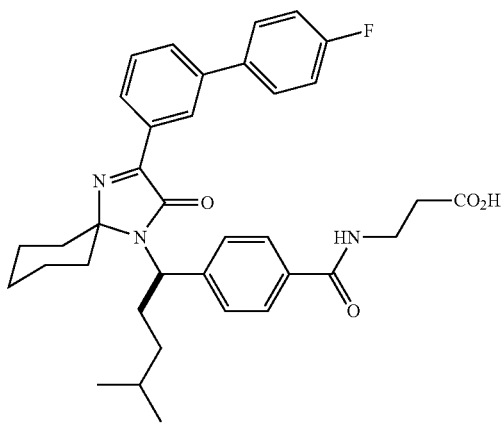 [SMILES: CC(C)CC[C@H](c1ccc(C(=O)NCCC(=O)O)cc1)N1C(=O)C(c2cccc(-c3ccc(F)cc3)c2)=NC12CCCCC2] |
| 2.92 | 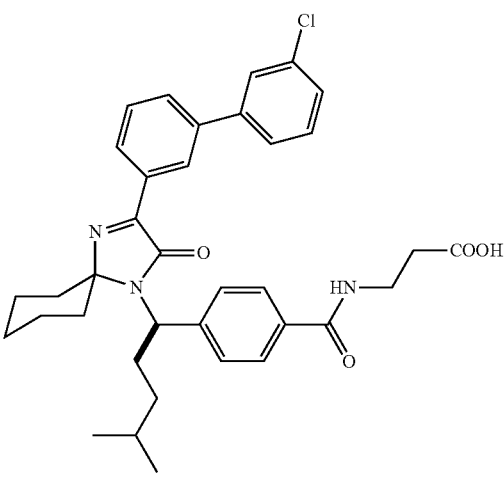 [SMILES: CC(C)CC[C@H](c1ccc(C(=O)NCCC(=O)O)cc1)N1C(=O)C(c2cccc(-c3cccc(Cl)c3)c2)=NC12CCCCC2] |
| 2.98 | 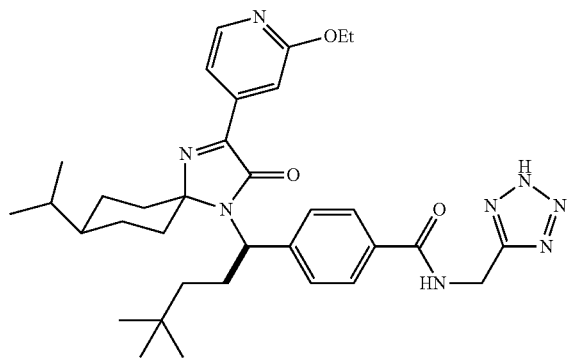 |
| 2.99 | 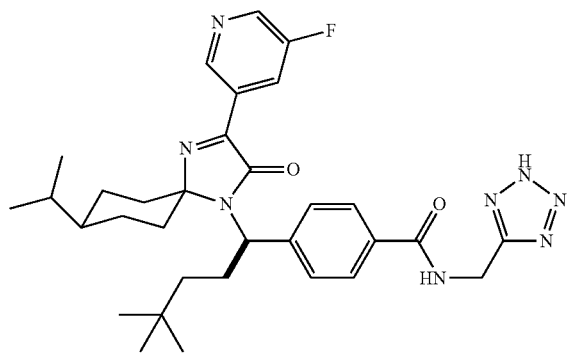 |

| Ex. | Structure |
|---|---|
| 2.100 | 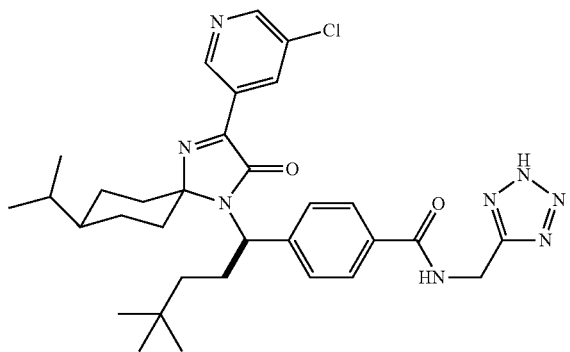 |
| 2.101 | 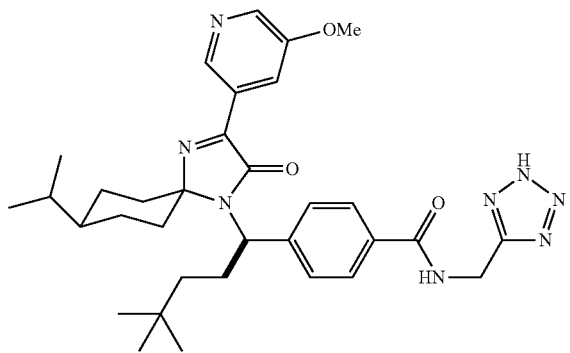 [SMILES: COc1cncc(C2=NC3(CCC(C(C)C)CC3)N([C@H](CCC(C)(C)C)c3ccc(C(=O)NCc4nn[nH]n4)cc3)C2=O)c1] |
| 2.102 | 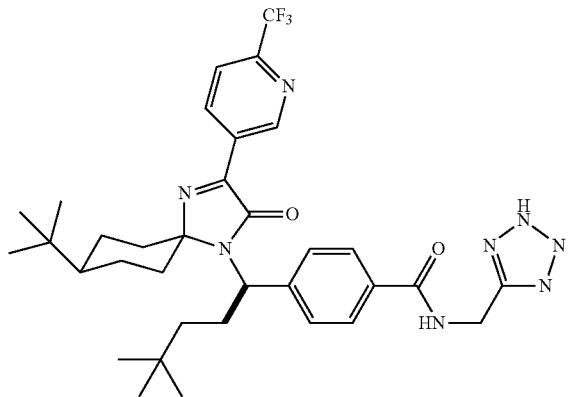 |
| 2.93 | 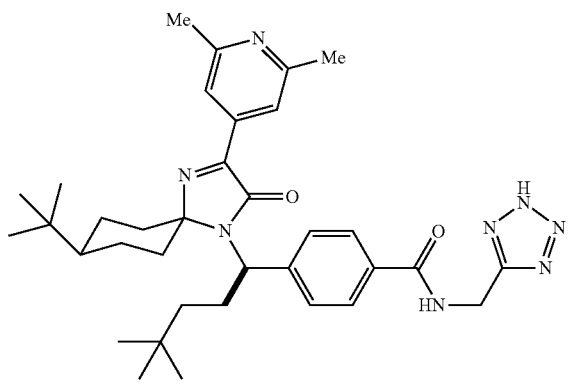 [SMILES: Cc1cc(C2=NC3(CCC(C(C)(C)C)CC3)N([C@H](CCC(C)(C)C)c3ccc(C(=O)NCc4nn[nH]n4)cc3)C2=O)cc(C)n1] |

-continued
| Ex. | Structure |
|---|---|
| 2.94 | 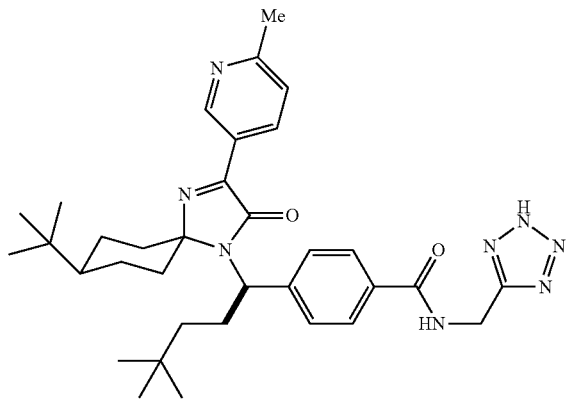 [SMILES: Cc1ccc(C2=NC3(CCC(C(C)(C)C)CC3)N([C@H](CCC(C)(C)C)c3ccc(C(=O)NCc4nn[nH]n4)cc3)C2=O)cn1] |
| 2.95 | 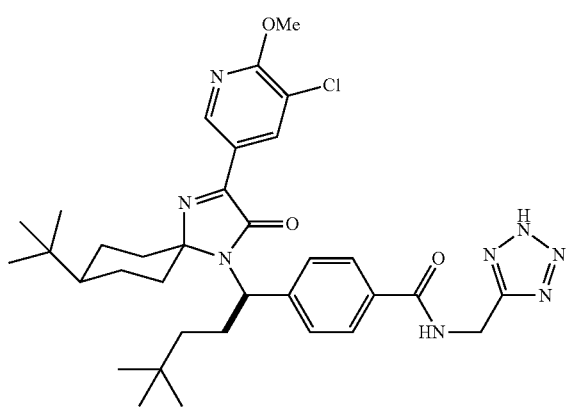 |
| 2.96 | 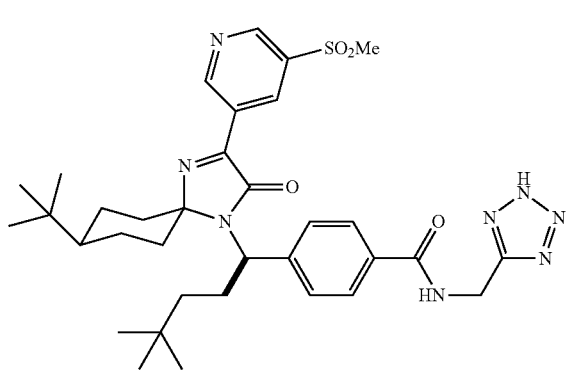 [SMILES: CC(C)(C)CC[C@H](c1ccc(C(=O)NCc2nn[nH]n2)cc1)N1C(=O)C(c2cncc(S(C)(=O)=O)c2)=NC12CCC(C(C)(C)C)CC2] |
| 2.104 | 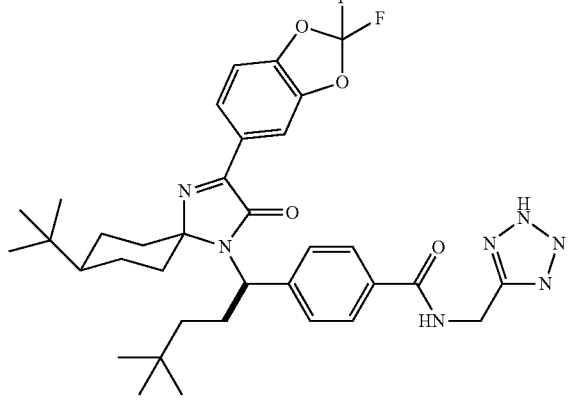 |

-continued
| Ex. | Structure |
|---|---|
| 2.105 | 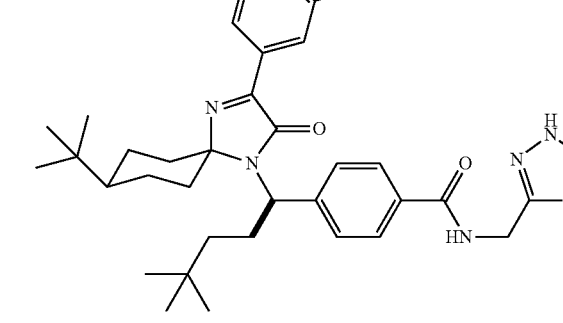 |
| 2.106 | 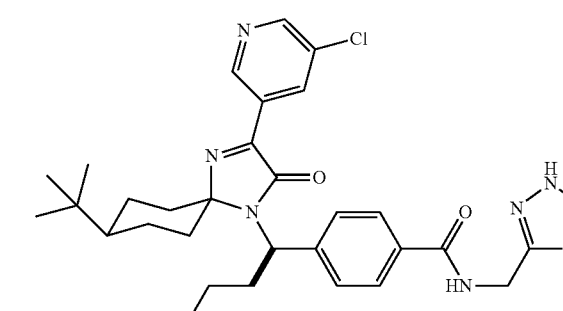 |
| 2.103 | 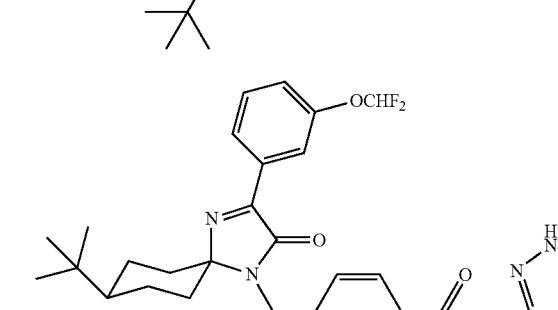 |
| 2.116 | 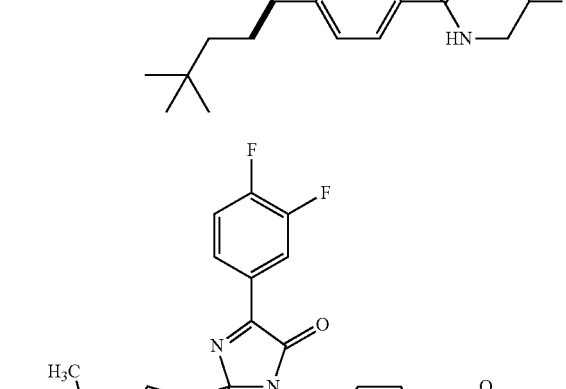 |

| Ex. | Structure |
|---|---|
| 2.117 | 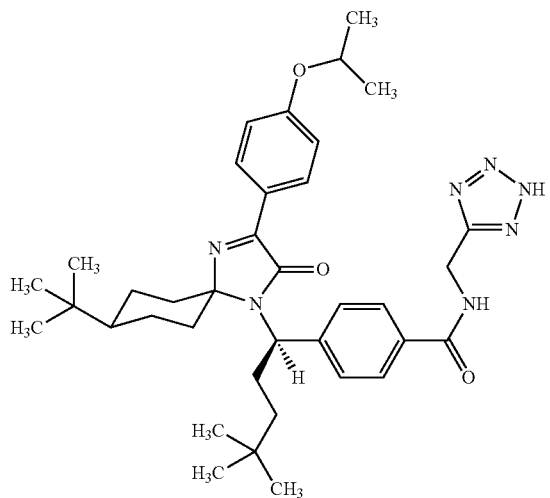 [SMILES: CC(C)Oc1ccc(C2=NC3(CCC(C(C)(C)C)CC3)N([C@H](CCC(C)(C)C)c3ccc(C(=O)NCc4nn[nH]n4)cc3)C2=O)cc1] |
| 2.118 | 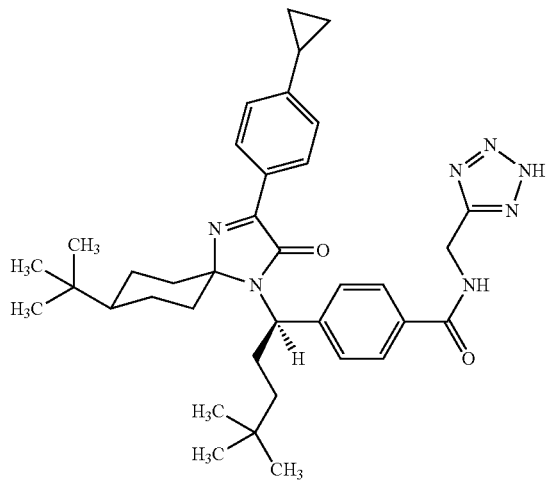 [SMILES: CC(C)(C)CC[C@H](c1ccc(C(=O)NCc2nn[nH]n2)cc1)N1C(=O)C(c2ccc(C3CC3)cc2)=NC12CCC(C(C)(C)C)CC2] |
| 2.119 | 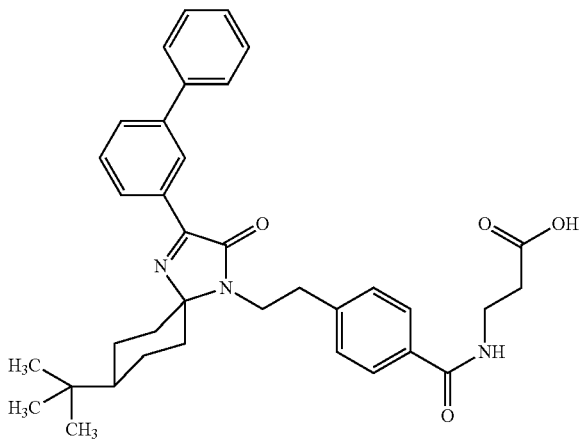 [SMILES: CC(C)(C)C1CCC2(CC1)N=C(c1cccc(-c3ccccc3)c1)C(=O)N2CCc1ccc(C(=O)NCCC(=O)O)cc1] |

-continued
| Ex. | Structure |
|---|---|
| 2.120 | 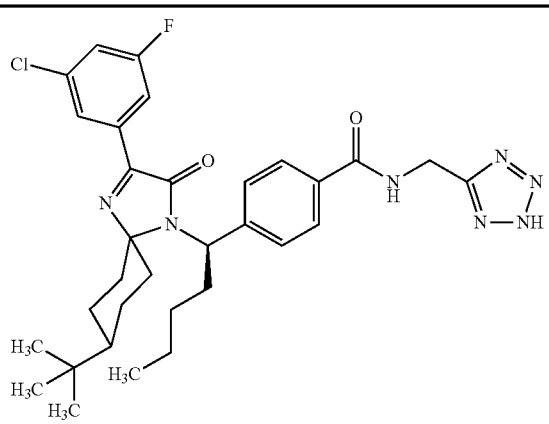 |
| 2.121 | 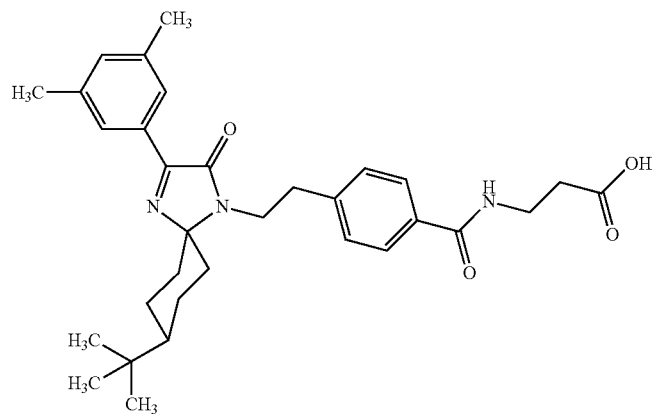 [SMILES: Cc1cc(C)cc(C2=NC3(CCC(C(C)(C)C)CC3)N(CCc3ccc(C(=O)NCCC(=O)O)cc3)C2=O)c1] |
| 2.107 | 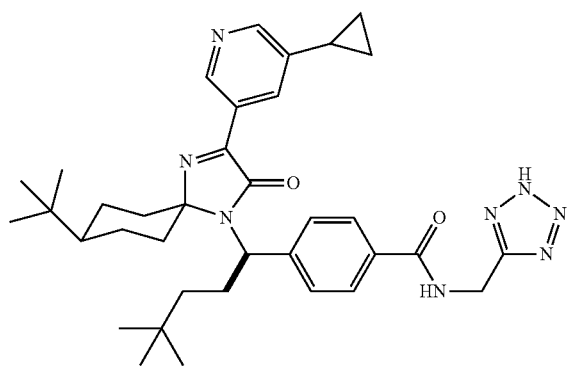 [SMILES: CC(C)(C)CC[C@H](c1ccc(C(=O)NCc2nn[nH]n2)cc1)N1C(=O)C(c2cncc(C3CC3)c2)=NC12CCC(C(C)(C)C)CC2] |
| 2.108 | 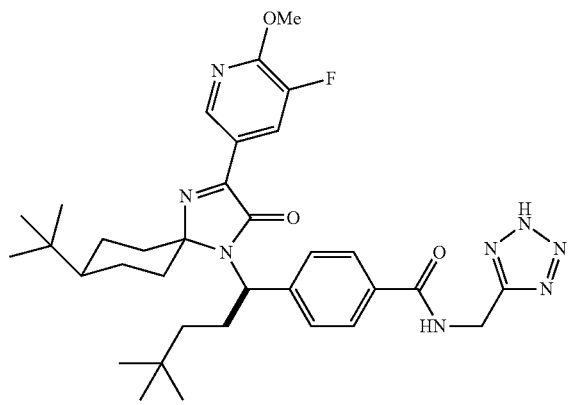 [SMILES: COc1ncc(C2=NC3(CCC(C(C)(C)C)CC3)N([C@H](CCC(C)(C)C)c3ccc(C(=O)NCc4nn[nH]n4)cc3)C2=O)cc1F] |

| Ex. | Structure |
|---|---|
| 2.109 | 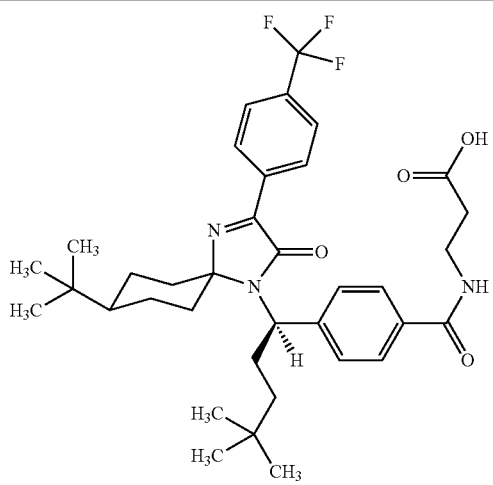 [SMILES: CC(C)(C)CC[C@H](c1ccc(C(=O)NCCC(=O)O)cc1)N1C(=O)C(c2ccc(C(F)(F)F)cc2)=NC12CCC(C(C)(C)C)CC2] |
| 2.110 | 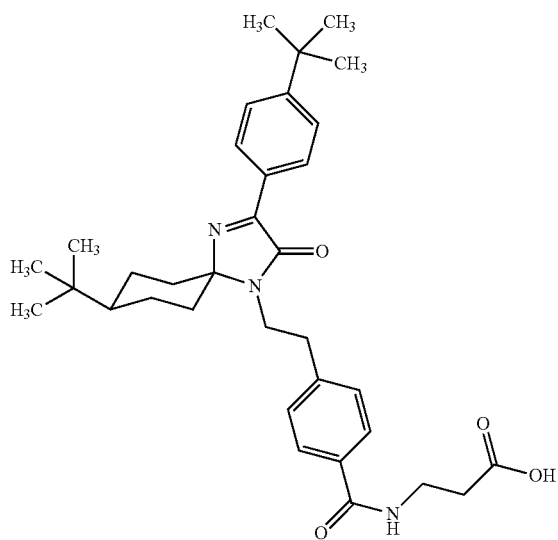 [SMILES: CC(C)(C)c1ccc(C2=NC3(CCC(C(C)(C)C)CC3)N(CCc3ccc(C(=O)NCCC(=O)O)cc3)C2=O)cc1] |
| 2.111 | 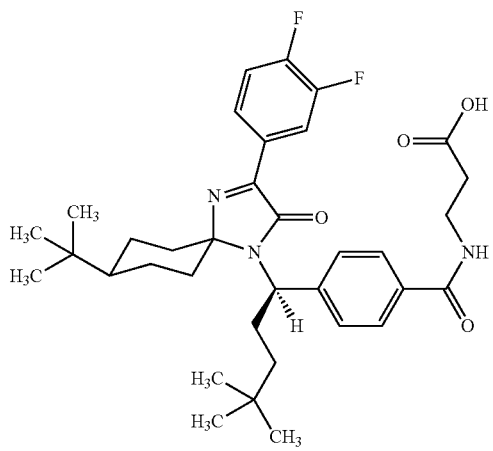 [SMILES: CC(C)(C)CC[C@H](c1ccc(C(=O)NCCC(=O)O)cc1)N1C(=O)C(c2ccc(F)c(F)c2)=NC12CCC(C(C)(C)C)CC2] |

| Ex. | Structure |
|---|---|
| 2.112 | 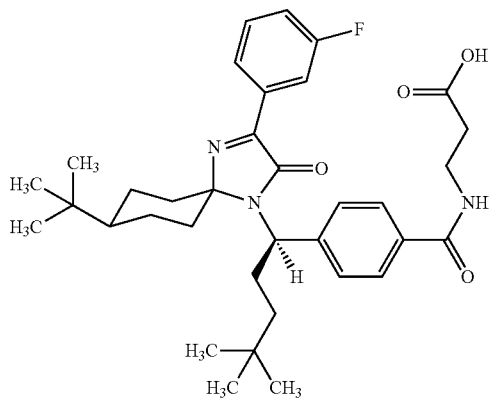 [SMILES: CC(C)(C)CC[C@H](c1ccc(C(=O)NCCC(=O)O)cc1)N1C(=O)C(c2cccc(F)c2)=NC12CCC(C(C)(C)C)CC2] |
| 2.122 | 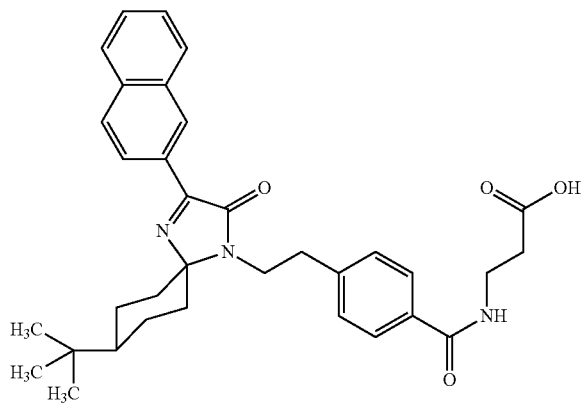 [SMILES: CC(C)(C)C1CCC2(CC1)N=C(c1ccc3ccccc3c1)C(=O)N2CCc1ccc(C(=O)NCCC(=O)O)cc1] |
| 2.123 | 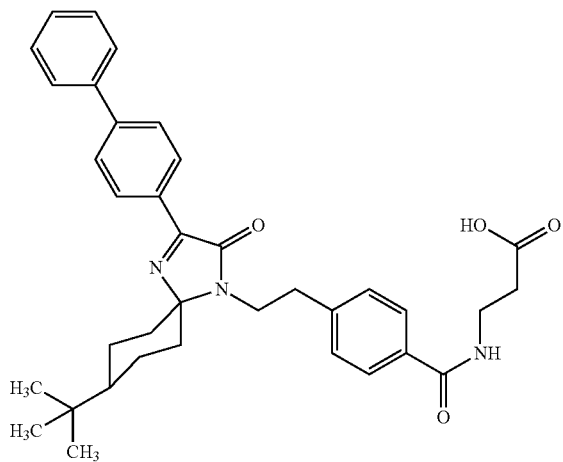 [SMILES: CC(C)(C)C1CCC2(CC1)N=C(c1ccc(-c3ccccc3)cc1)C(=O)N2CCc1ccc(C(=O)NCCC(=O)O)cc1] |

| Ex. | Structure |
|---|---|
| 2.124 | 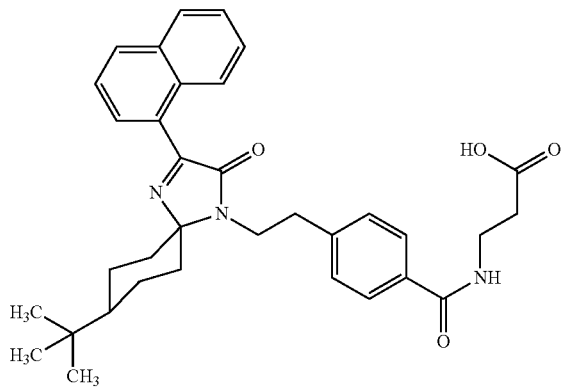 [SMILES: CC(C)(C)C1CCC2(CC1)N=C(c1cccc3ccccc13)C(=O)N2CCc1ccc(C(=O)NCCC(=O)O)cc1] |
| 2.125 | 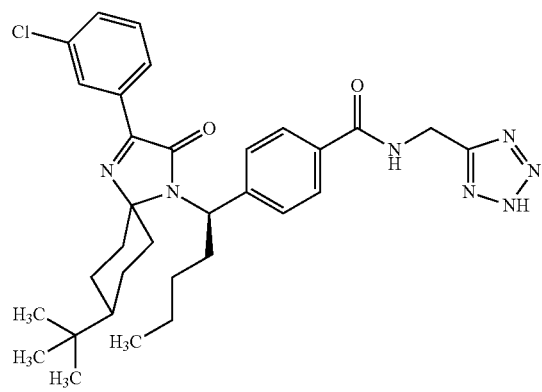 [SMILES: CCCC[C@H](c1ccc(C(=O)NCc2nn[nH]n2)cc1)N1C(=O)C(c2cccc(Cl)c2)=NC12CCC(C(C)(C)C)CC2] |
| 2.126 | 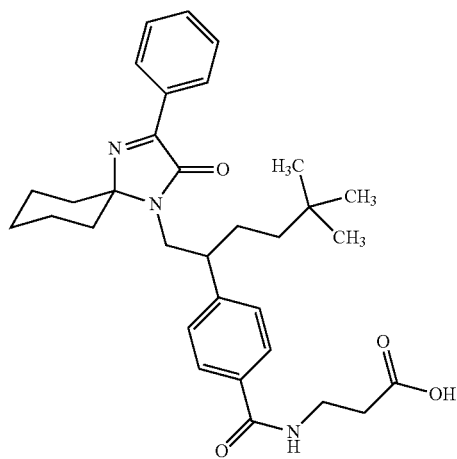 [SMILES: CC(C)(C)CCC(CN1C(=O)C(c2ccccc2)=NC12CCCCC2)c1ccc(C(=O)NCCC(=O)O)cc1] |

-continued
| Ex. | Structure |
|---|---|
| 2.127 | 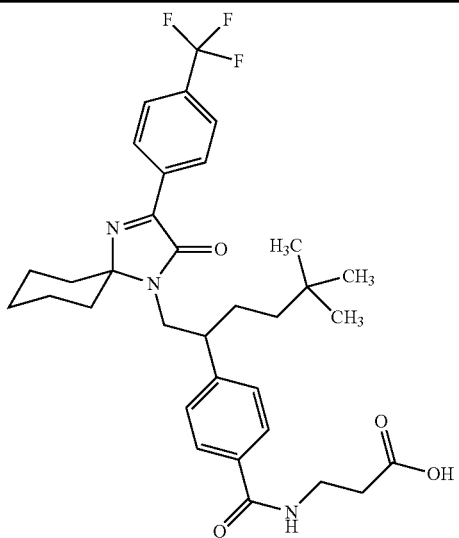 |
| 2.113 | 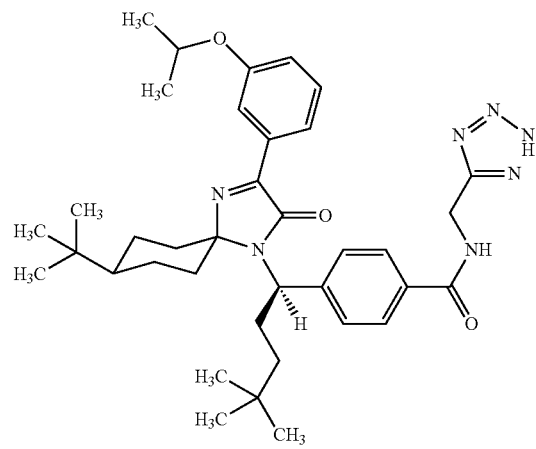 |
| 2.114 | 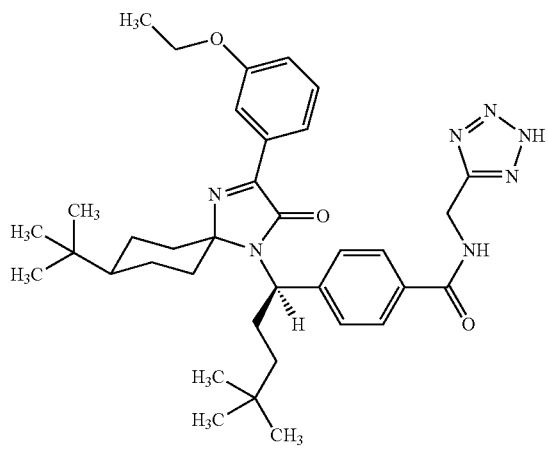 [SMILES: CCOc1cccc(C2=NC3(CCC(C(C)(C)C)CC3)N([C@H](CCC(C)(C)C)c3ccc(C(=O)NCc4nn[nH]n4)cc3)C2=O)c1] |

| Ex. | Structure |
|---|---|
| 2.115 | 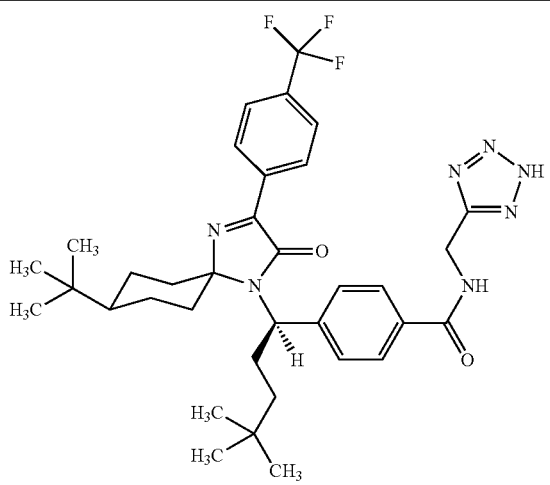 |
| 2.128 | 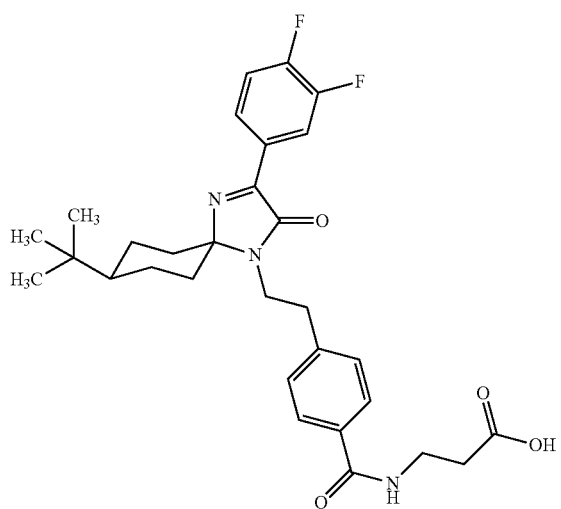 [SMILES: CC(C)(C)C1CCC2(CC1)N=C(c1ccc(F)c(F)c1)C(=O)N2CCc1ccc(C(=O)NCCC(=O)O)cc1] |
| 2.129 | 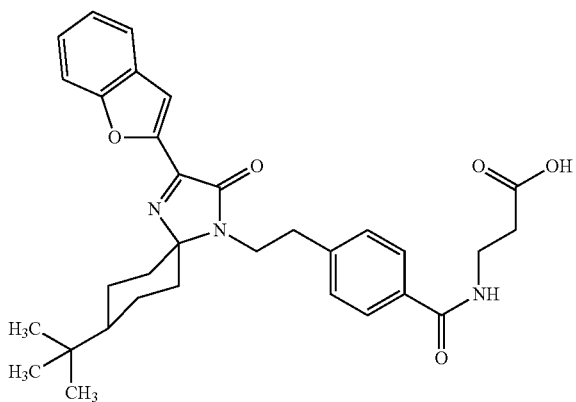 [SMILES: CC(C)(C)C1CCC2(CC1)N=C(c1cc3ccccc3o1)C(=O)N2CCc1ccc(C(=O)NCCC(=O)O)cc1] |

-continued
| Ex. | Structure |
|---|---|
| 2.130 | 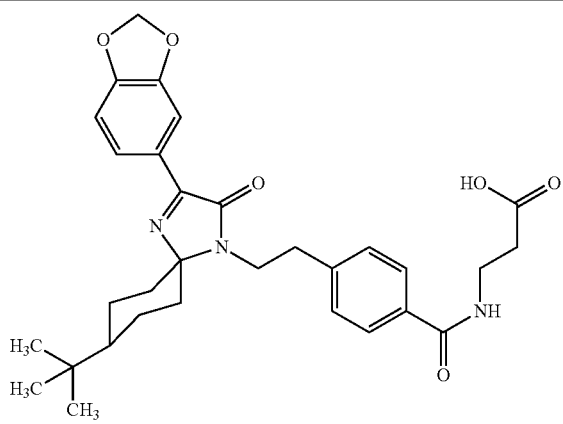 |
| 2.131 | 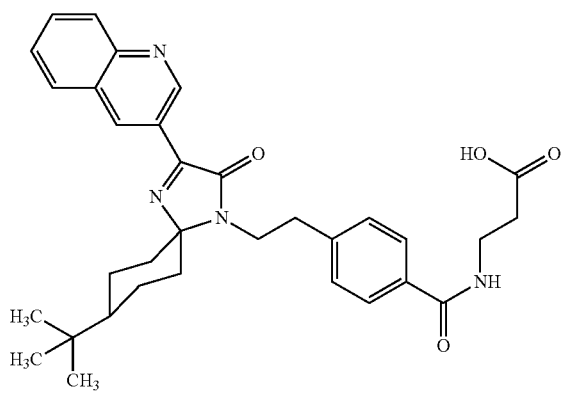 [SMILES: CC(C)(C)C1CCC2(CC1)N=C(c1cnc3ccccc3c1)C(=O)N2CCc1ccc(C(=O)NCCC(=O)O)cc1] |
| 2.134 | 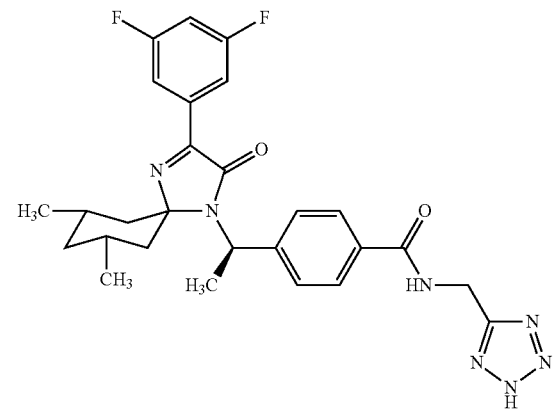 [SMILES: CC1CC(C)CC2(C1)N=C(c1cc(F)cc(F)c1)C(=O)N2[C@H](C)c1ccc(C(=O)NCc2nn[nH]n2)cc1] |
| 2.135 | 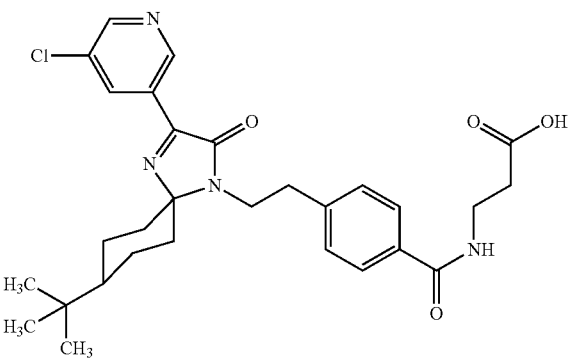 [SMILES: CC(C)(C)C1CCC2(CC1)N=C(c1cncc(Cl)c1)C(=O)N2CCc1ccc(C(=O)NCCC(=O)O)cc1] |

-continued
| Ex. | Structure |
|---|---|
| 2.136 | 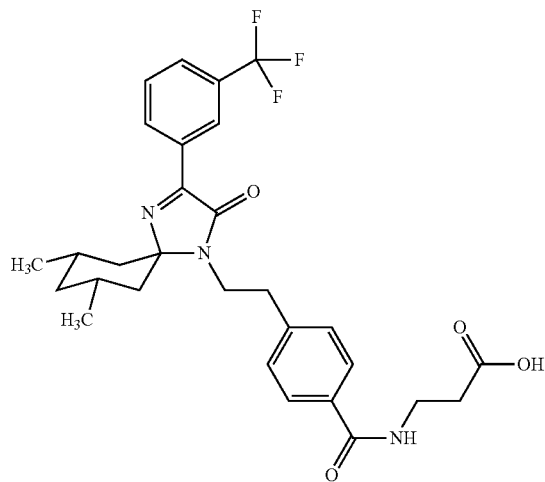 [SMILES: CC1CC(C)CC2(C1)N=C(c1cccc(C(F)(F)F)c1)C(=O)N2CCc1ccc(C(=O)NCCC(=O)O)cc1] |
| 2.137 | 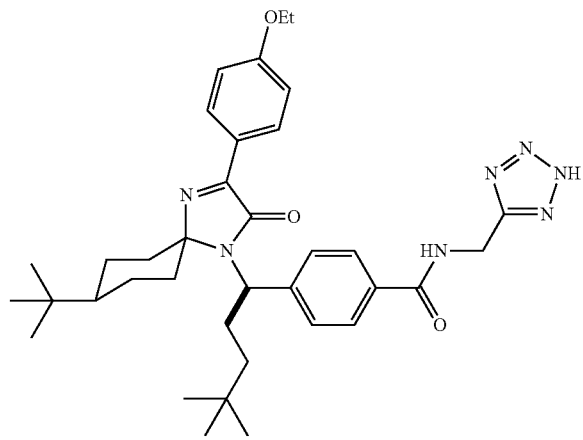 [SMILES: CCOc1ccc(C2=NC3(CCC(C(C)(C)C)CC3)N([C@H](CCC(C)(C)C)c3ccc(C(=O)NCc4nn[nH]n4)cc3)C2=O)cc1] |
| 3.1 | 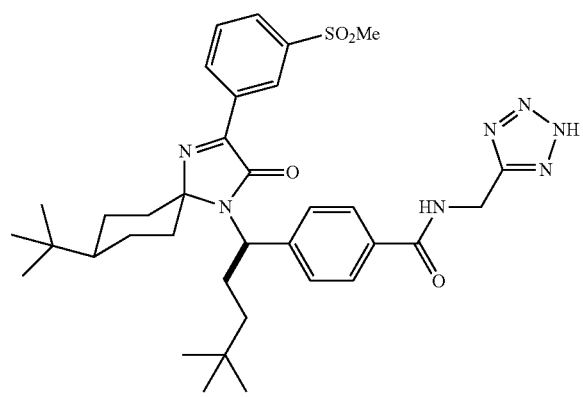 [SMILES: CC(C)(C)CC[C@H](c1ccc(C(=O)NCc2nn[nH]n2)cc1)N1C(=O)C(c2cccc(S(C)(=O)=O)c2)=NC12CCC(C(C)(C)C)CC2] |

| Ex. | Structure |
|---|---|
| 3.3 | 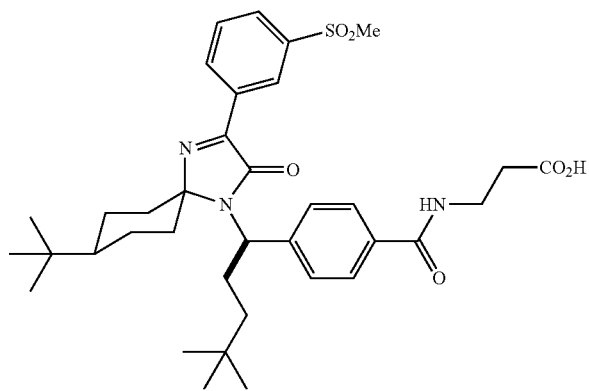 [SMILES: CC(C)(C)CC[C@H](c1ccc(C(=O)NCCC(=O)O)cc1)N1C(=O)C(c2cccc(S(C)(=O)=O)c2)=NC12CCC(C(C)(C)C)CC2] |
| 2.132 | 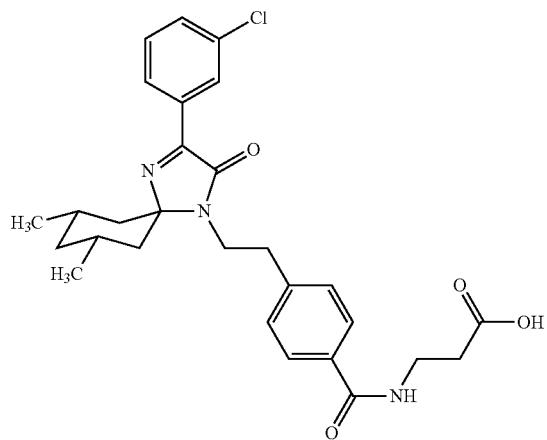 [SMILES: CC1CC(C)CC2(C1)N=C(c1cccc(Cl)c1)C(=O)N2CCc1ccc(C(=O)NCCC(=O)O)cc1] |
| 2.133 | 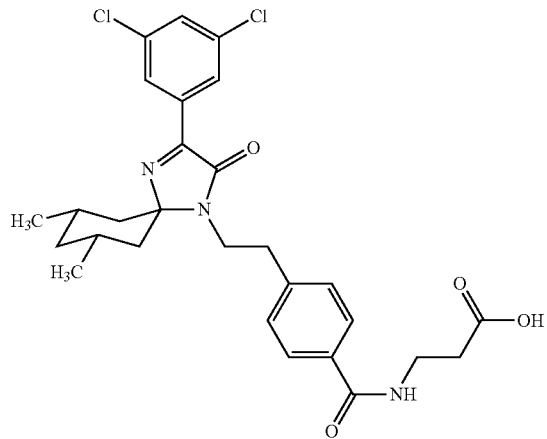 [SMILES: CC1CC(C)CC2(C1)N=C(c1cc(Cl)cc(Cl)c1)C(=O)N2CCc1ccc(C(=O)NCCC(=O)O)cc1] |

-continued
| Ex. | Structure |
|---|---|
| 4.1 | 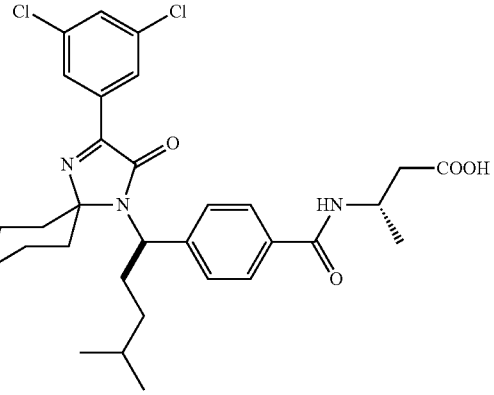 |
| 4.2 | 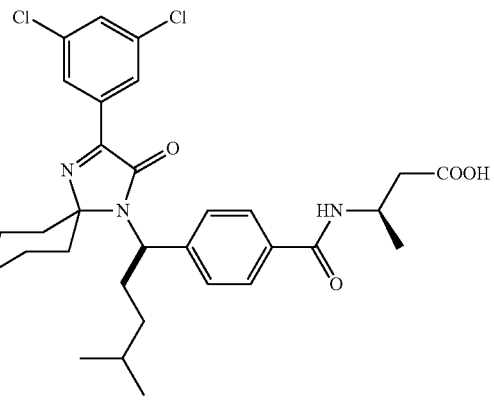 |
| 4.3 | 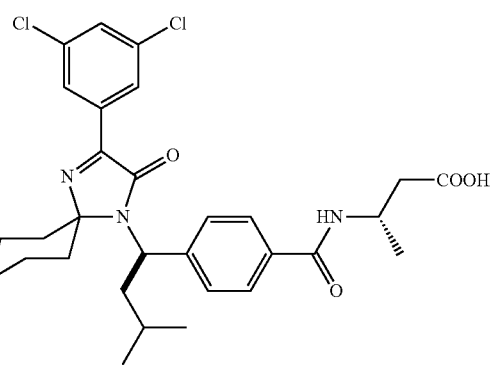 |
| 4.4 | 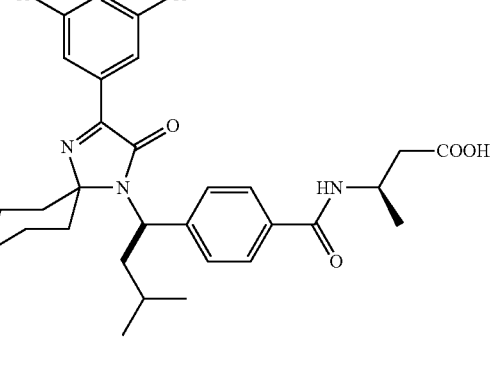 |

-continued
| Ex. | Structure |
|---|---|
| 4.11 | 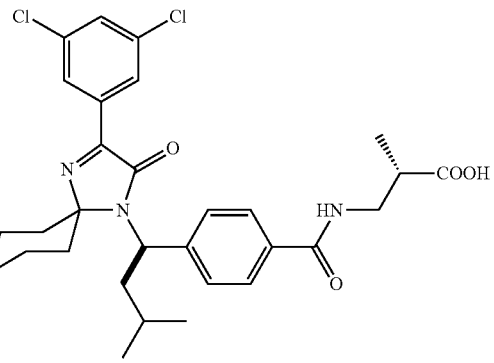 |
| 4.5 | 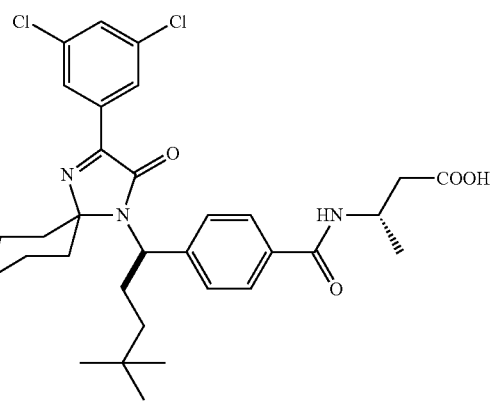 |
| 4.6 | 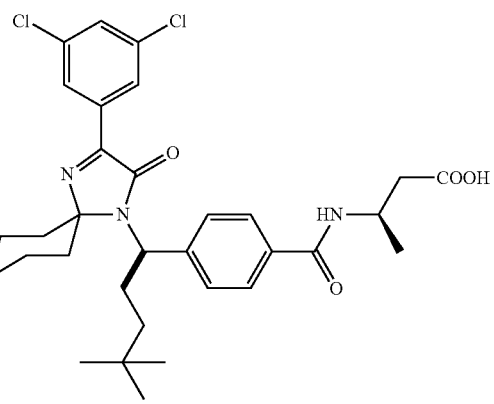 |
| 4.7 | 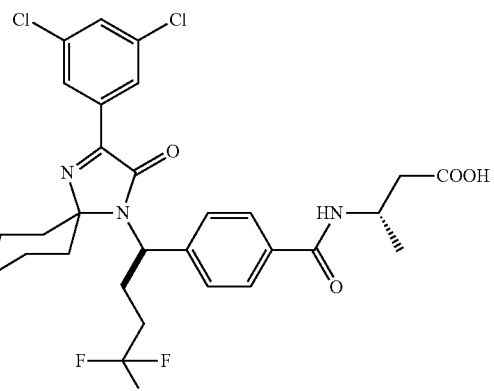 |

-continued

| Ex. | Structure |
|---|---|
| 4.8 | 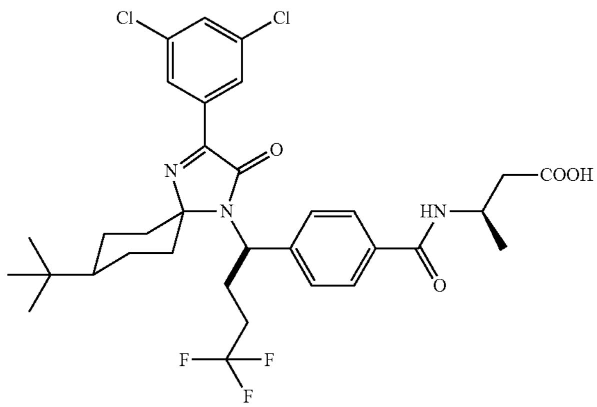 [SMILES: C[C@H](CC(=O)O)NC(=O)c1ccc([C@@H](CCC(F)(F)F)N2C(=O)C(c3cc(Cl)cc(Cl)c3)=NC23CCC(C(C)(C)C)CC3)cc1] |
| 4.9 | 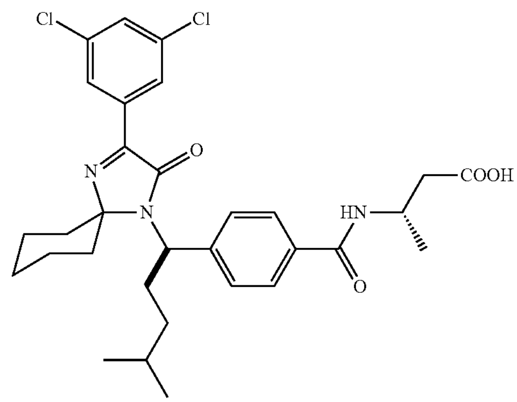 |
| 4.10 | 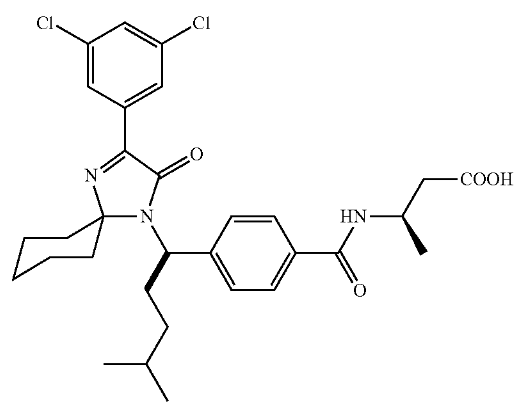 [SMILES: CC(C)CC[C@H](c1ccc(C(=O)N[C@H](C)CC(=O)O)cc1)N1C(=O)C(c2cc(Cl)cc(Cl)c2)=NC12CCCCC2] |
| 4.12 | 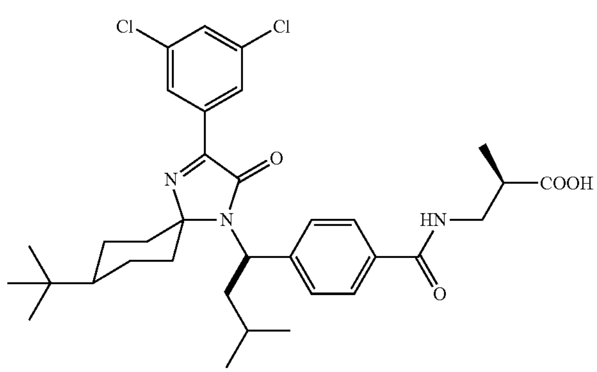 [SMILES: CC(C)C[C@H](c1ccc(C(=O)NC[C@@H](C)C(=O)O)cc1)N1C(=O)C(c2cc(Cl)cc(Cl)c2)=NC12CCC(C(C)(C)C)CC2] |

-continued
| Ex. | Structure |
|---|---|
| 1.1 | 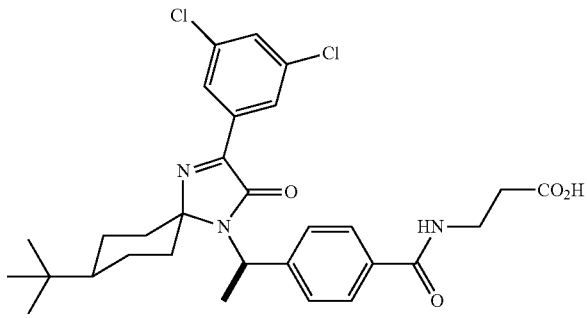 [SMILES: C[C@H](c1ccc(C(=O)NCCC(=O)O)cc1)N1C(=O)C(c2cc(Cl)cc(Cl)c2)=NC12CCC(C(C)(C)C)CC2] |
| 1.2 | 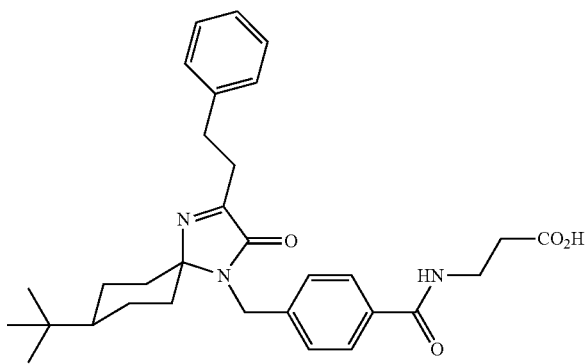 [SMILES: CC(C)(C)C1CCC2(CC1)N=C(CCc1ccccc1)C(=O)N2Cc1ccc(C(=O)NCCC(=O)O)cc1] |
| 1.3 | 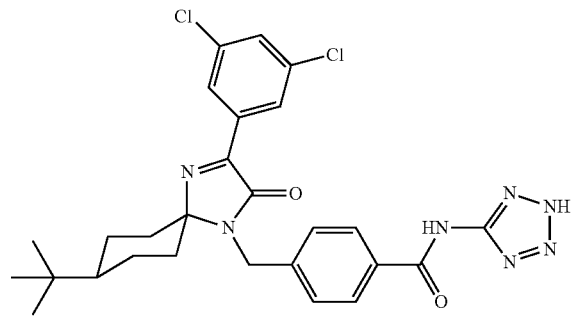 [SMILES: CC(C)(C)C1CCC2(CC1)N=C(c1cc(Cl)cc(Cl)c1)C(=O)N2Cc1ccc(C(=O)Nc2nn[nH]n2)cc1] |
| 1.4 | 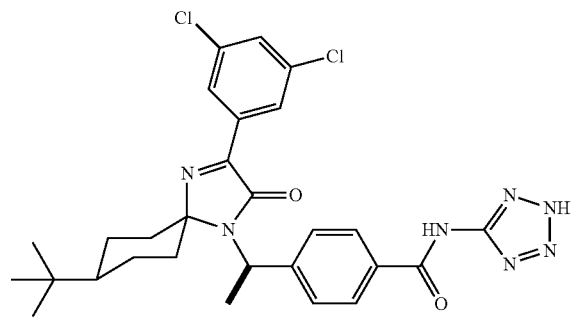 [SMILES: C[C@H](c1ccc(C(=O)Nc2nn[nH]n2)cc1)N1C(=O)C(c2cc(Cl)cc(Cl)c2)=NC12CCC(C(C)(C)C)CC2] |

-continued

| Ex. | Structure |
|---|---|
| 1.5 | 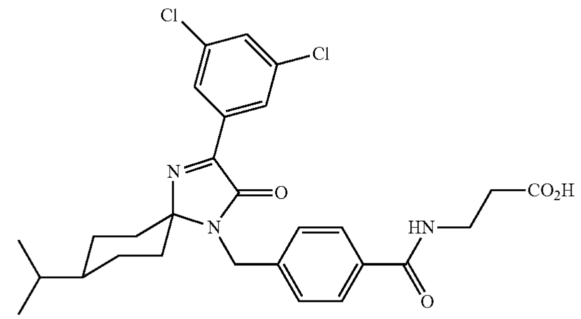 [SMILES: CC(C)C1CCC2(CC1)N=C(c1cc(Cl)cc(Cl)c1)C(=O)N2Cc1ccc(C(=O)NCCC(=O)O)cc1] |
| 1.6 | 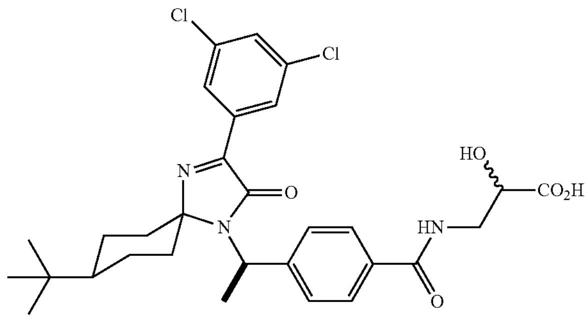 [SMILES: C[C@H](c1ccc(C(=O)NCC(O)C(=O)O)cc1)N1C(=O)C(c2cc(Cl)cc(Cl)c2)=NC12CCC(C(C)(C)C)CC2] |
| 1.7 | 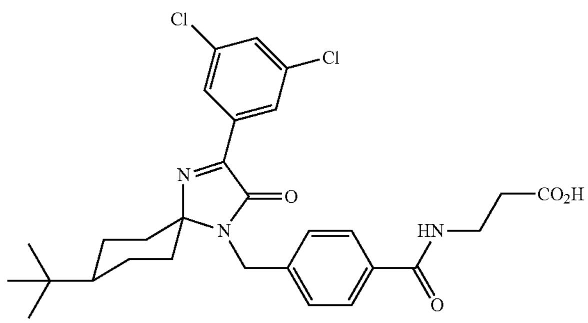 |
| 1.8 | 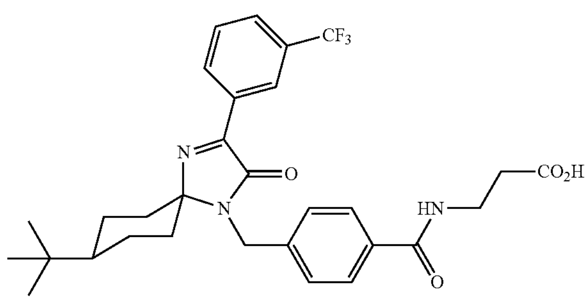 [SMILES: CC(C)(C)C1CCC2(CC1)N=C(c1cccc(C(F)(F)F)c1)C(=O)N2Cc1ccc(C(=O)NCCC(=O)O)cc1] |
| 1.9 | 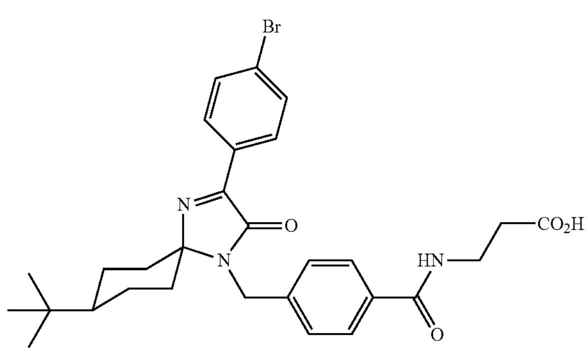 |

-continued
| Ex. | Structure |
|---|---|
| 1.10 | 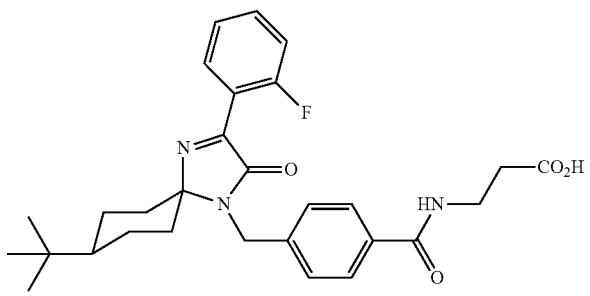 [SMILES: CC(C)(C)C1CCC2(CC1)N=C(c1ccccc1F)C(=O)N2Cc1ccc(C(=O)NCCC(=O)O)cc1] |
| 1.11 | 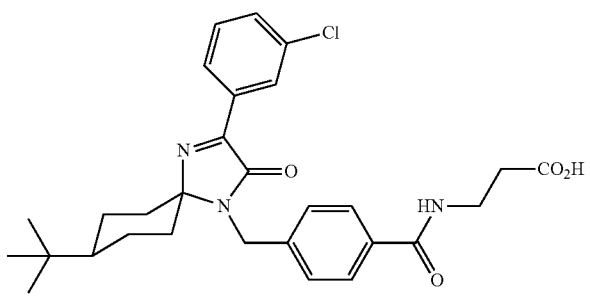 [SMILES: CC(C)(C)C1CCC2(CC1)N=C(c1cccc(Cl)c1)C(=O)N2Cc1ccc(C(=O)NCCC(=O)O)cc1] |
| 1.12 | 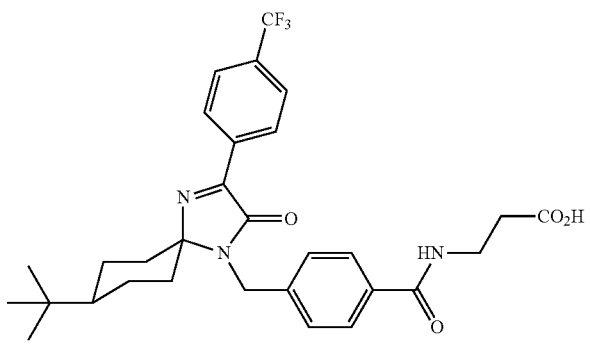 [SMILES: CC(C)(C)C1CCC2(CC1)N=C(c1ccc(C(F)(F)F)cc1)C(=O)N2Cc1ccc(C(=O)NCCC(=O)O)cc1] |
| 1.13 | 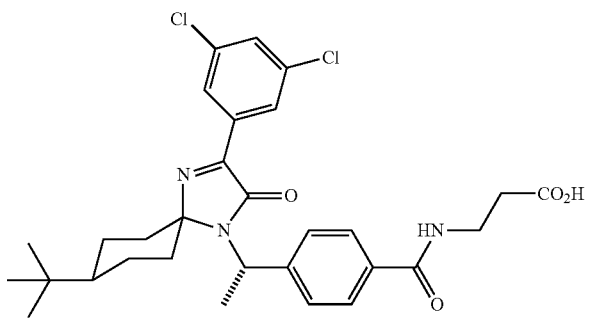 [SMILES: C[C@@H](c1ccc(C(=O)NCCC(=O)O)cc1)N1C(=O)C(c2cc(Cl)cc(Cl)c2)=NC12CCC(C(C)(C)C)CC2] |

| Ex. | Structure |
|---|---|
| 1.14 | 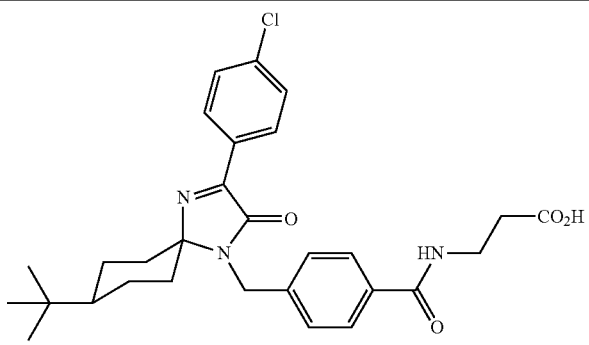 |
| 1.15 | 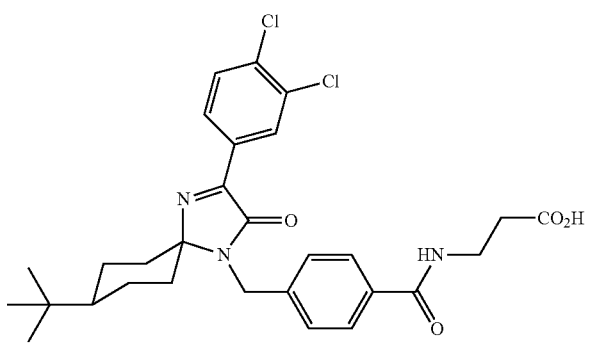 [SMILES: CC(C)(C)C1CCC2(CC1)N=C(c1ccc(Cl)c(Cl)c1)C(=O)N2Cc1ccc(C(=O)NCCC(=O)O)cc1] |
| 1.16 | 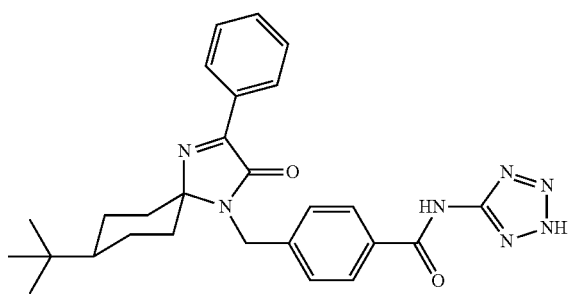 [SMILES: CC(C)(C)C1CCC2(CC1)N=C(c1ccccc1)C(=O)N2Cc1ccc(C(=O)Nc2nn[nH]n2)cc1] |
| 1.17 | 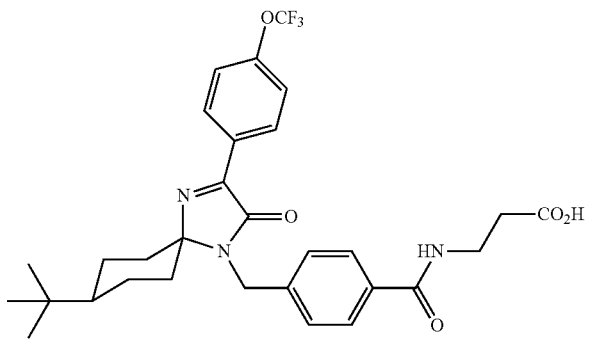 |

-continued
| Ex. | Structure |
|---|---|
| 1.18 | 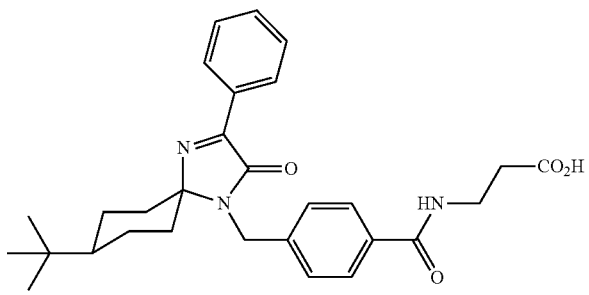 |
| 1.19 | 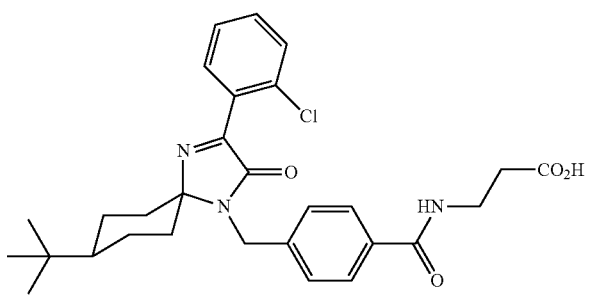 [SMILES: CC(C)(C)C1CCC2(CC1)N=C(c1ccccc1Cl)C(=O)N2Cc1ccc(C(=O)NCCC(=O)O)cc1] |
| 1.20 | 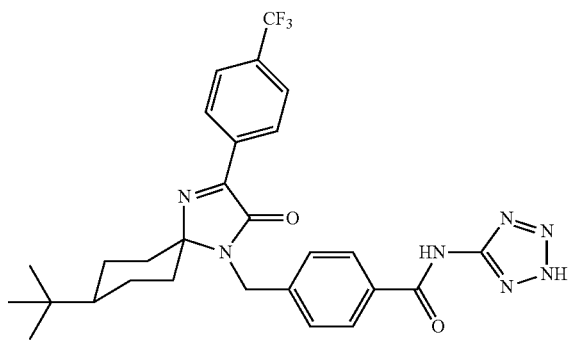 [SMILES: CC(C)(C)C1CCC2(CC1)N=C(c1ccc(C(F)(F)F)cc1)C(=O)N2Cc1ccc(C(=O)Nc2nn[nH]n2)cc1] |
| 1.21 | 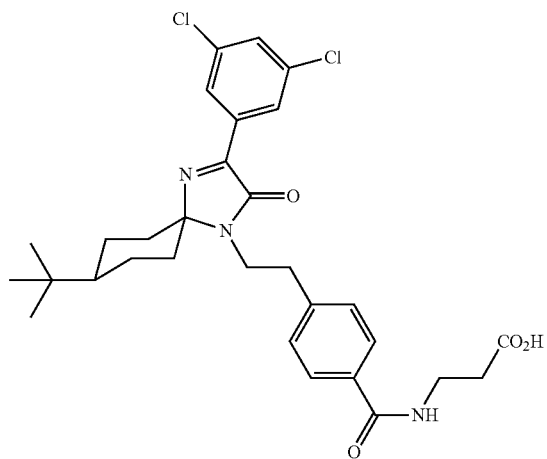 [SMILES: CC(C)(C)C1CCC2(CC1)N=C(c1cc(Cl)cc(Cl)c1)C(=O)N2CCc1ccc(C(=O)NCCC(=O)O)cc1] |

| Ex. | Structure |
|---|---|
| 1.22 | 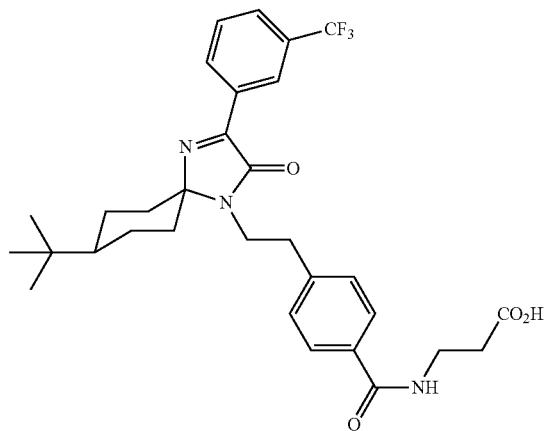 |
| 1.30 | 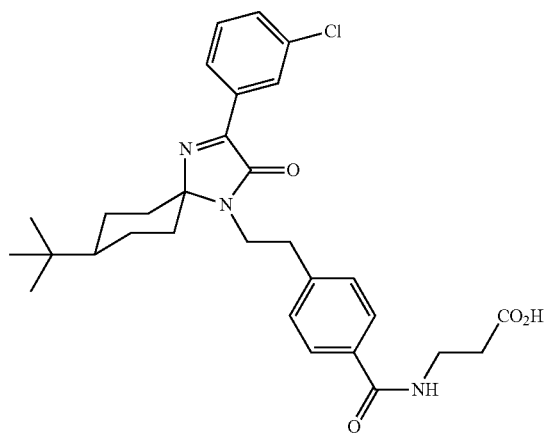 [SMILES: CC(C)(C)C1CCC2(CC1)N=C(c1cccc(Cl)c1)C(=O)N2CCc1ccc(C(=O)NCCC(=O)O)cc1] |
| 1.31 | 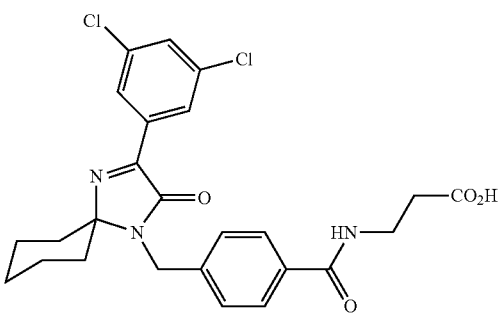 [SMILES: O=C(O)CCNC(=O)c1ccc(CN2C(=O)C(c3cc(Cl)cc(Cl)c3)=NC23CCCCC3)cc1] |

-continued
| Ex. | Structure |
|---|---|
| 1.32 | 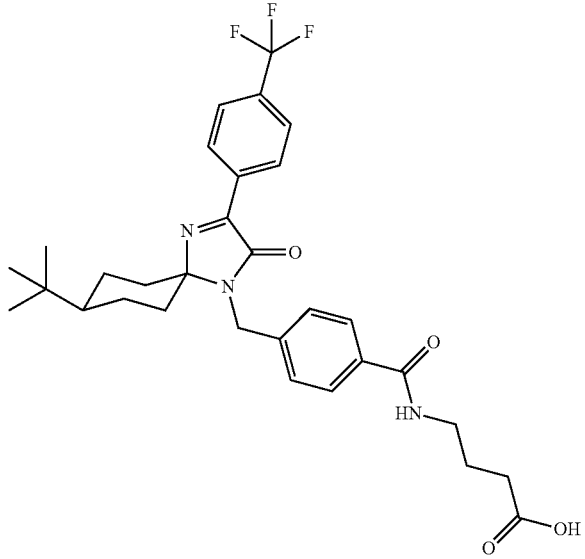 [SMILES: CC(C)(C)C1CCC2(CC1)N=C(c1ccc(C(F)(F)F)cc1)C(=O)N2Cc1ccc(C(=O)NCCCC(=O)O)cc1] |
| 1.33 | 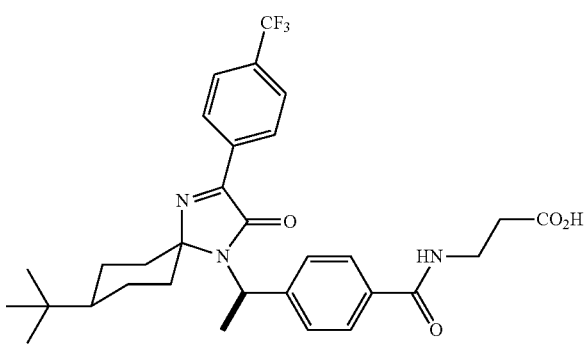 |
| 1.34 | 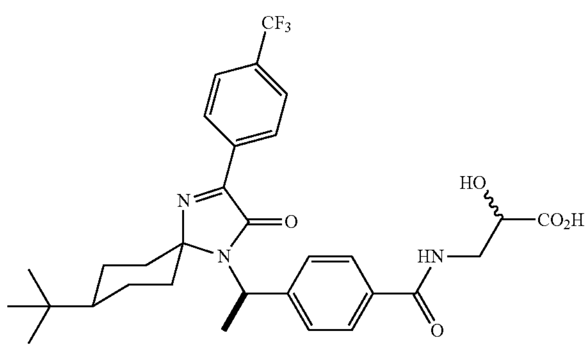 [SMILES: C[C@H](c1ccc(C(=O)NCC(O)C(=O)O)cc1)N1C(=O)C(c2ccc(F)cc2)=NC12CCC(C(C)(C)C)CC2] |
| 1.35 | 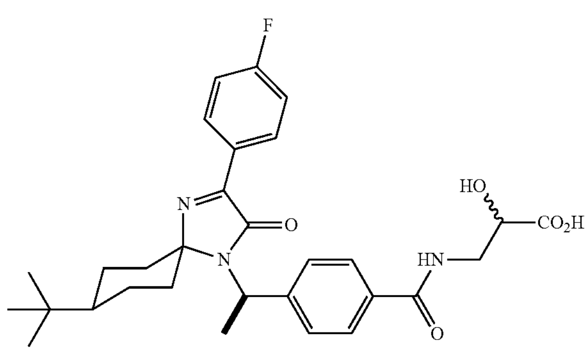 |

| Ex. | Structure |
|---|---|
| 1.23 | 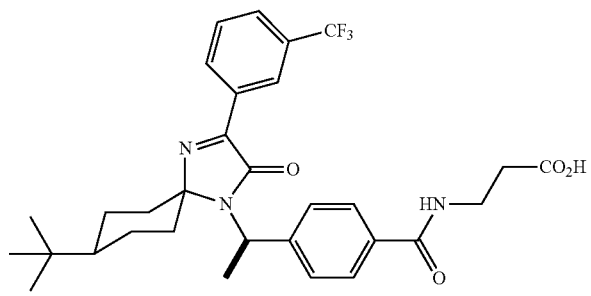 [SMILES: C[C@H](c1ccc(C(=O)NCCC(=O)O)cc1)N1C(=O)C(c2cccc(C(F)(F)F)c2)=NC12CCC(C(C)(C)C)CC2] |
| 1.24 | 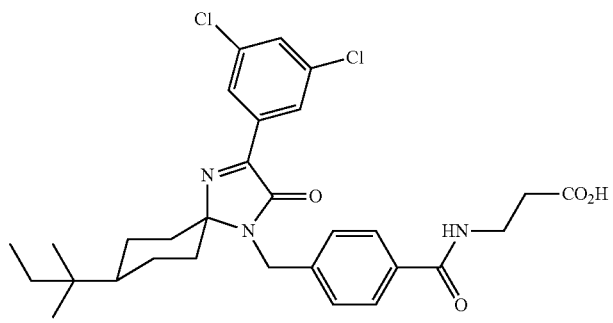 [SMILES: CCC(C)(C)C1CCC2(CC1)N=C(c1cc(Cl)cc(Cl)c1)C(=O)N2Cc1ccc(C(=O)NCCC(=O)O)cc1] |
| 1.25 | 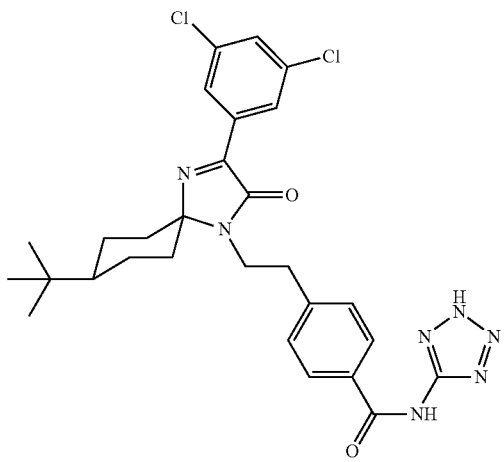 [SMILES: CC(C)(C)C1CCC2(CC1)N=C(c1cc(Cl)cc(Cl)c1)C(=O)N2CCc1ccc(C(=O)Nc2nn[nH]n2)cc1] |
| 1.26 | 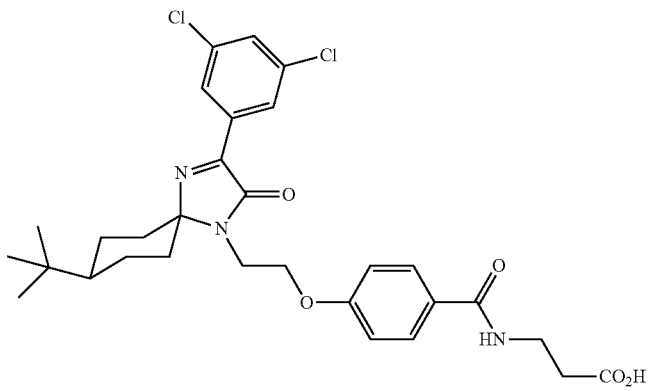 [SMILES: CC(C)(C)C1CCC2(CC1)N=C(c1cc(Cl)cc(Cl)c1)C(=O)N2CCOc1ccc(C(=O)NCCC(=O)O)cc1] |

| Ex. | Structure |
|---|---|
| 1.27 | 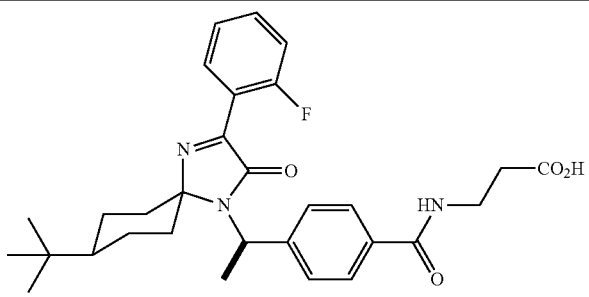 |
| 1.28 | 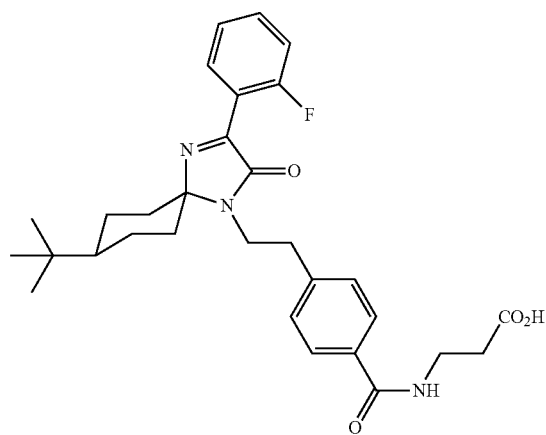 [SMILES: CC(C)(C)C1CCC2(CC1)N=C(c1ccccc1F)C(=O)N2CCc1ccc(C(=O)NCCC(=O)O)cc1] |
| 1.36 | 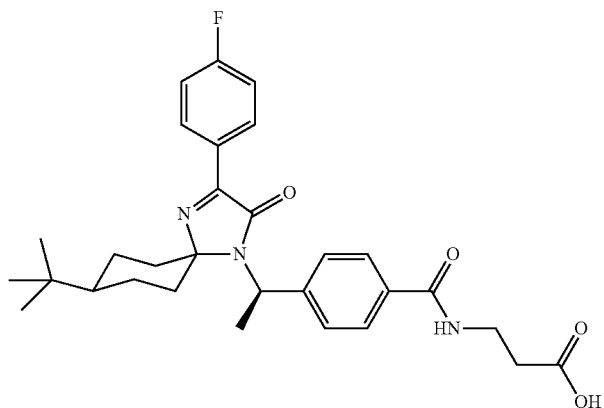 [SMILES: C[C@H](c1ccc(C(=O)NCCC(=O)O)cc1)N1C(=O)C(c2ccc(F)cc2)=NC12CCC(C(C)(C)C)CC2] |
| 1.37 | 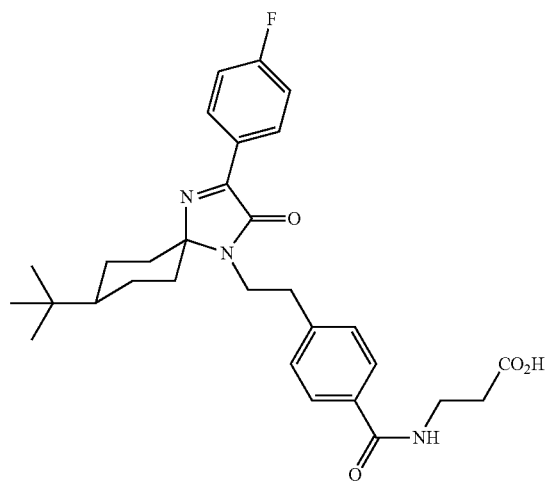 [SMILES: CC(C)(C)C1CCC2(CC1)N=C(c1ccc(F)cc1)C(=O)N2CCc1ccc(C(=O)NCCC(=O)O)cc1] |

-continued
| Ex. | Structure |
|---|---|
| 1.38 | 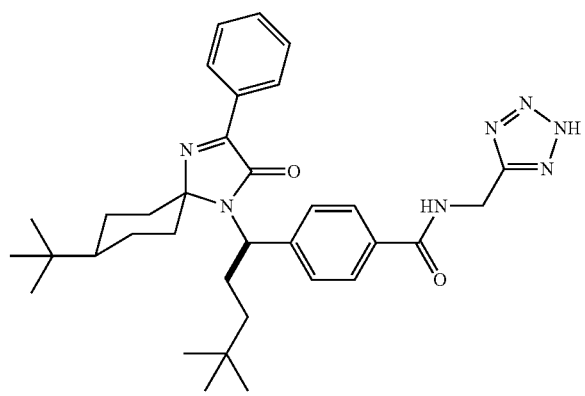 [SMILES: CC(C)(C)CC[C@H](c1ccc(C(=O)NCc2nn[nH]n2)cc1)N1C(=O)C(c2ccccc2)=NC12CCC(C(C)(C)C)CC2] |
| 1.39 | 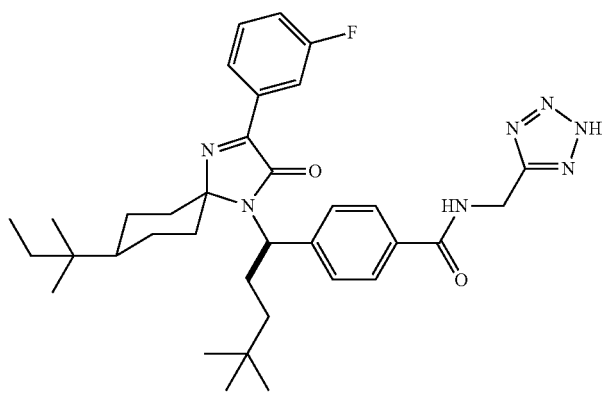 [SMILES: CCC(C)(C)C1CCC2(CC1)N=C(c1cccc(F)c1)C(=O)N2[C@H](CCC(C)(C)C)c1ccc(C(=O)NCc2nn[nH]n2)cc1] |
| 1.40 | 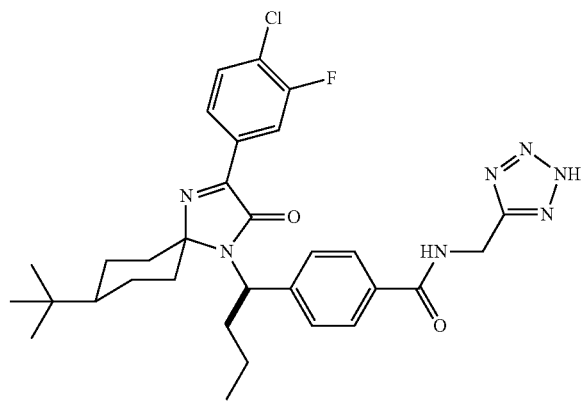 [SMILES: CCC[C@H](c1ccc(C(=O)NCc2nn[nH]n2)cc1)N1C(=O)C(c2ccc(Cl)c(F)c2)=NC12CCC(C(C)(C)C)CC2] |
| 1.41 | 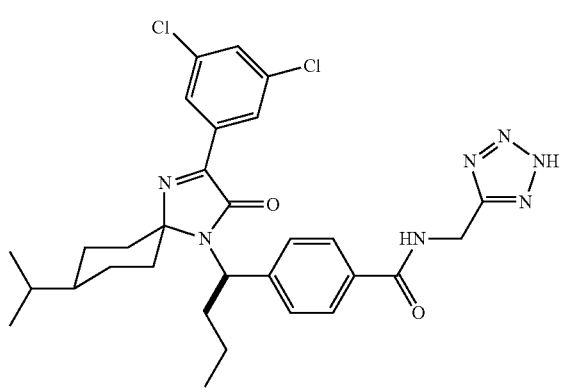 [SMILES: CCC[C@H](c1ccc(C(=O)NCc2nn[nH]n2)cc1)N1C(=O)C(c2cc(Cl)cc(Cl)c2)=NC12CCC(C(C)C)CC2] |

-continued
| Ex. | Structure |
|---|---|
| 1.29 | 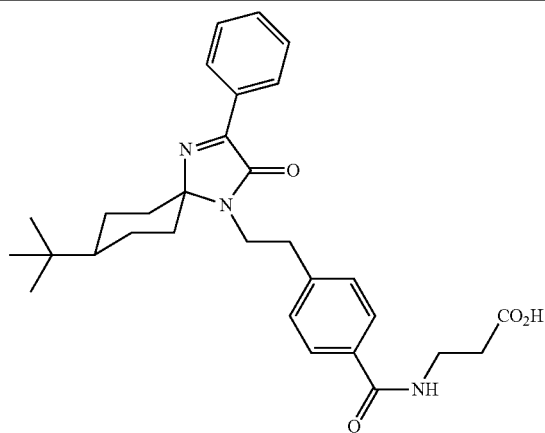 |
| 1.43 | 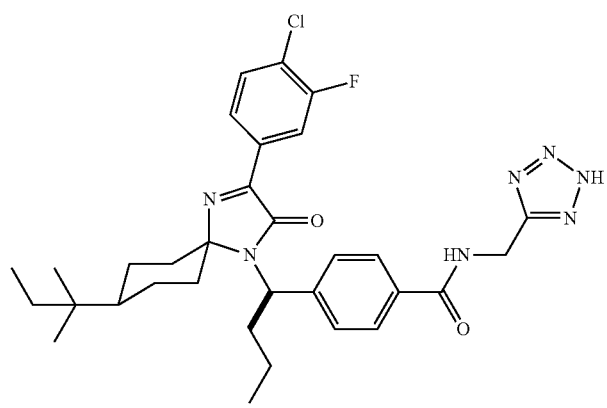 [SMILES: CCC[C@H](c1ccc(C(=O)NCc2nn[nH]n2)cc1)N1C(=O)C(c2ccc(Cl)c(F)c2)=NC12CCC(C(C)(C)CC)CC2] |
| 1.44 | 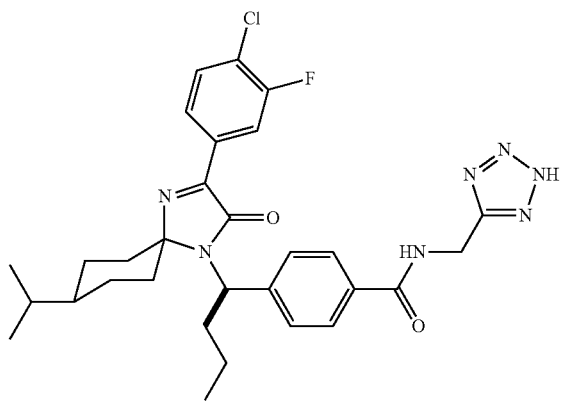 [SMILES: CCC[C@H](c1ccc(C(=O)NCc2nn[nH]n2)cc1)N1C(=O)C(c2ccc(Cl)c(F)c2)=NC12CCC(C(C)C)CC2] |

-continued
| Ex. | Structure |
|---|---|
| 1.45 | 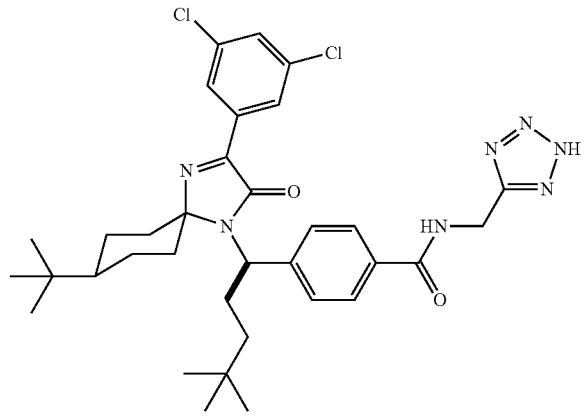 [SMILES: CC(C)(C)CC[C@H](c1ccc(C(=O)NCc2nn[nH]n2)cc1)N1C(=O)C(c2cc(Cl)cc(Cl)c2)=NC12CCC(C(C)(C)C)CC2] |
| 1.46 | 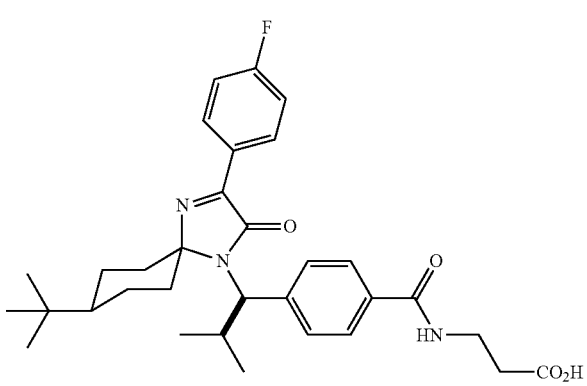 [SMILES: CC(C)[C@H](c1ccc(C(=O)NCCC(=O)O)cc1)N1C(=O)C(c2ccc(F)cc2)=NC12CCC(C(C)(C)C)CC2] |
| 1.47 | 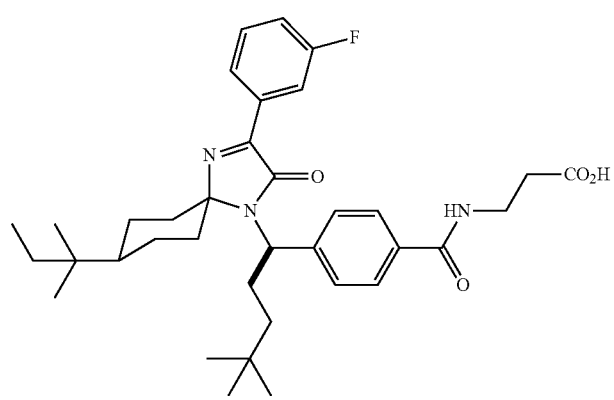 [SMILES: CCC(C)(C)C1CCC2(CC1)N=C(c1cccc(F)c1)C(=O)N2[C@H](CCC(C)(C)C)c1ccc(C(=O)NCCC(=O)O)cc1] |
| 1.48 | 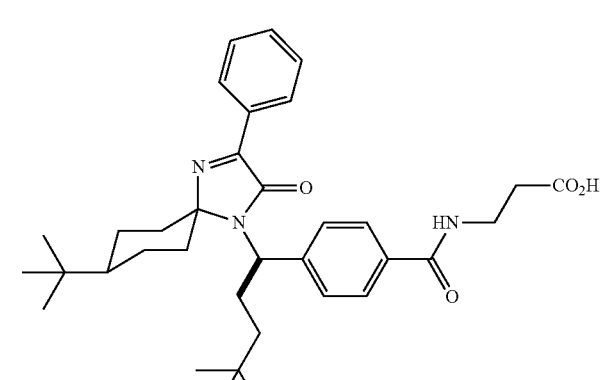 |

-continued
| Ex. | Structure |
|---|---|
| 1.42 | 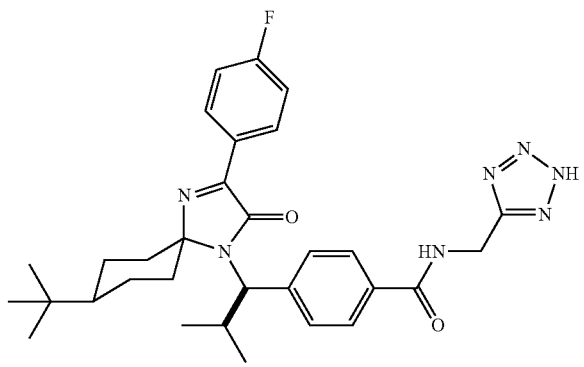 [SMILES: CC(C)[C@H](c1ccc(C(=O)NCc2nn[nH]n2)cc1)N1C(=O)C(c2ccc(F)cc2)=NC12CCC(C(C)(C)C)CC2] |
| 1.49 | 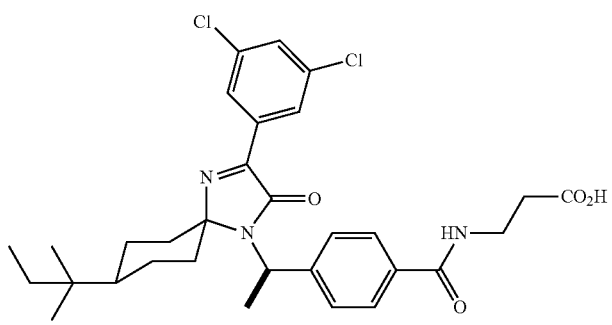 [SMILES: CCC(C)(C)C1CCC2(CC1)N=C(c1cc(Cl)cc(Cl)c1)C(=O)N2[C@H](C)c1ccc(C(=O)NCCC(=O)O)cc1] |
| 1.50 | 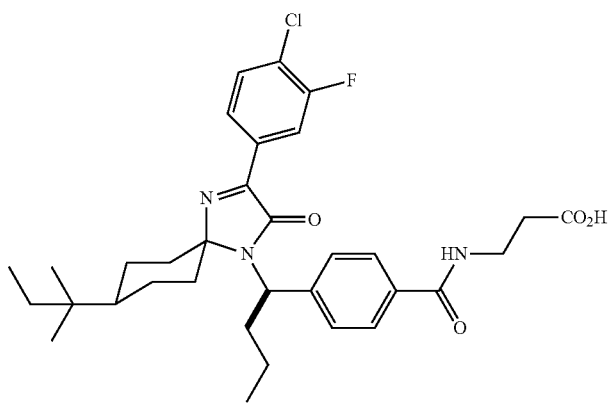 [SMILES: CCC[C@H](c1ccc(C(=O)NCCC(=O)O)cc1)N1C(=O)C(c2ccc(Cl)c(F)c2)=NC12CCC(C(C)(C)CC)CC2] |
| 1.60 | 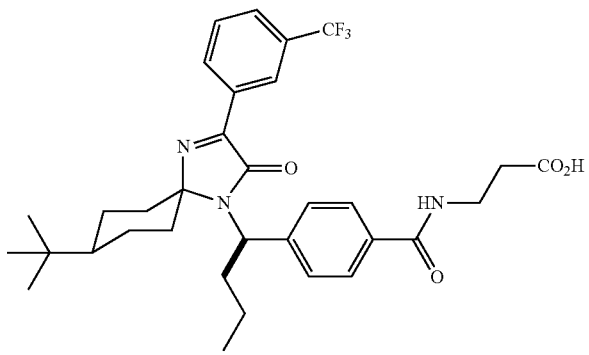 [SMILES: CCC[C@H](c1ccc(C(=O)NCCC(=O)O)cc1)N1C(=O)C(c2cccc(C(F)(F)F)c2)=NC12CCC(C(C)(C)C)CC2] |

-continued
| Ex. | Structure |
|---|---|
| 1.61 | 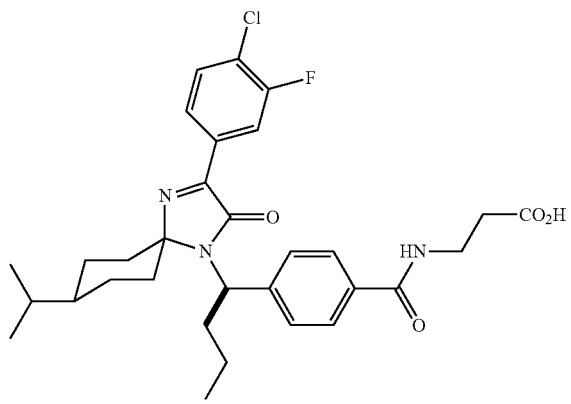 [SMILES: CCC[C@H](c1ccc(C(=O)NCCC(=O)O)cc1)N1C(=O)C(c2ccc(Cl)c(F)c2)=NC12CCC(C(C)C)CC2] |
| 1.62 | 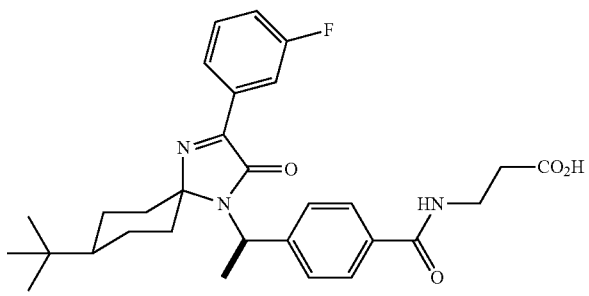 [SMILES: C[C@H](c1ccc(C(=O)NCCC(=O)O)cc1)N1C(=O)C(c2cccc(F)c2)=NC12CCC(C(C)(C)C)CC2] |
| 1.63 | 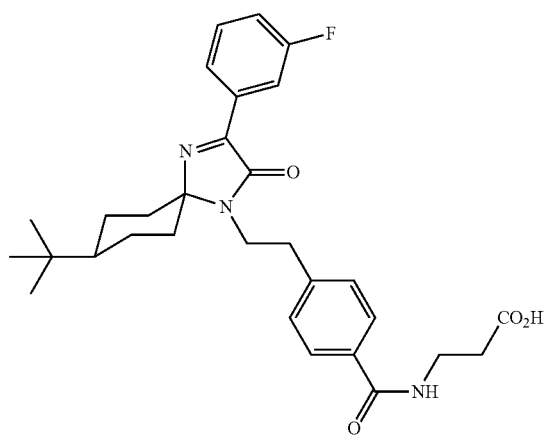 [SMILES: CC(C)(C)C1CCC2(CC1)N=C(c1cccc(F)c1)C(=O)N2CCc1ccc(C(=O)NCCC(=O)O)cc1] |
| 1.68 | 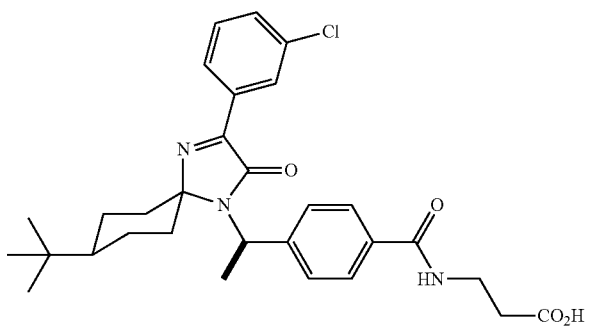 [SMILES: C[C@H](c1ccc(C(=O)NCCC(=O)O)cc1)N1C(=O)C(c2cccc(Cl)c2)=NC12CCC(C(C)(C)C)CC2] |

| Ex. | Structure |
|---|---|
| 1.69 | 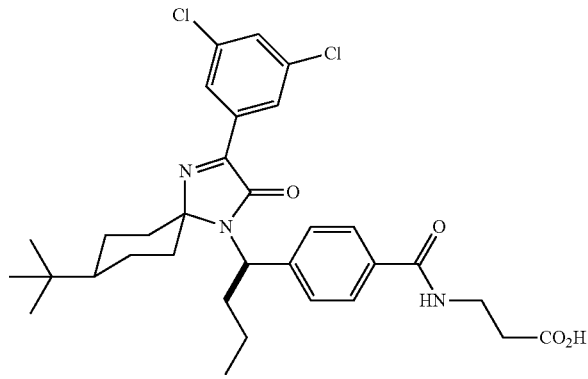 [SMILES: CCC[C@H](c1ccc(C(=O)NCCC(=O)O)cc1)N1C(=O)C(c2cc(Cl)cc(Cl)c2)=NC12CCC(C(C)(C)C)CC2] |
| 1.70 | 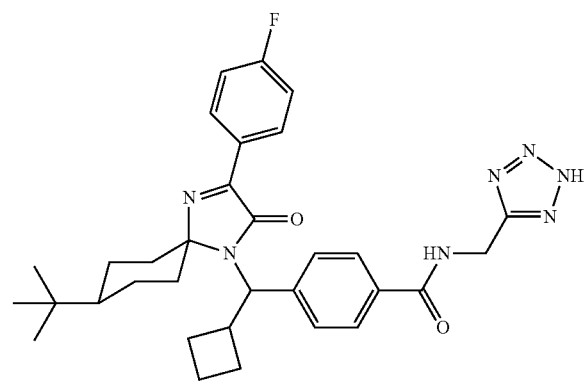 [SMILES: CC(C)(C)C1CCC2(CC1)N=C(c1ccc(F)cc1)C(=O)N2C(c1ccc(C(=O)NCc2nn[nH]n2)cc1)C1CCC1] |
| 1.71 | 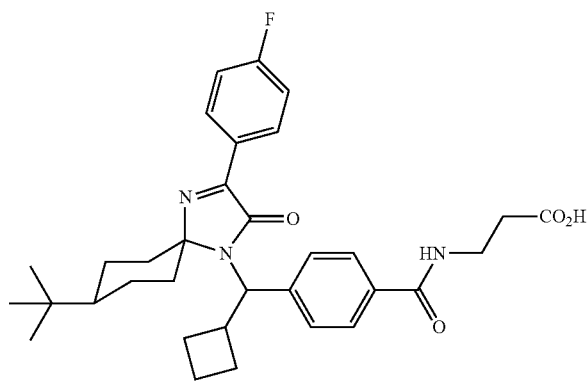 [SMILES: CC(C)(C)C1CCC2(CC1)N=C(c1ccc(F)cc1)C(=O)N2C(c1ccc(C(=O)NCCC(=O)O)cc1)C1CCC1] |
| 1.72 | 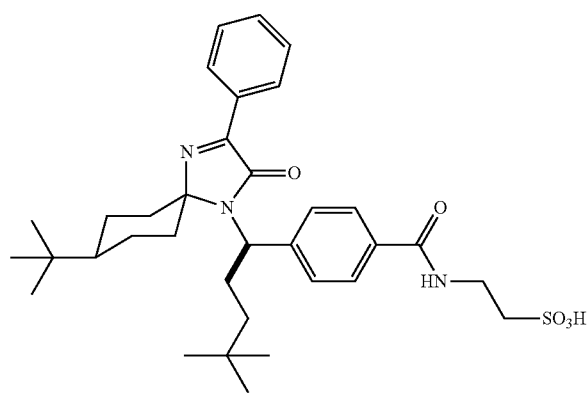 [SMILES: CC(C)(C)CC[C@H](c1ccc(C(=O)NCCS(=O)(=O)O)cc1)N1C(=O)C(c2ccccc2)=NC12CCC(C(C)(C)C)CC2] |

-continued
| Ex. | Structure |
|---|---|
| 1.73 | 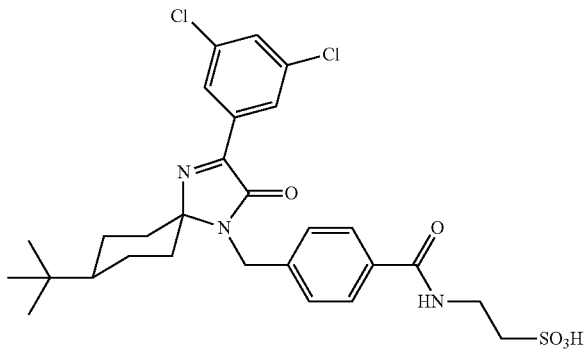 [SMILES: CC(C)(C)C1CCC2(CC1)N=C(c1cc(Cl)cc(Cl)c1)C(=O)N2Cc1ccc(C(=O)NCCS(=O)(=O)O)cc1] |
| 1.74 | 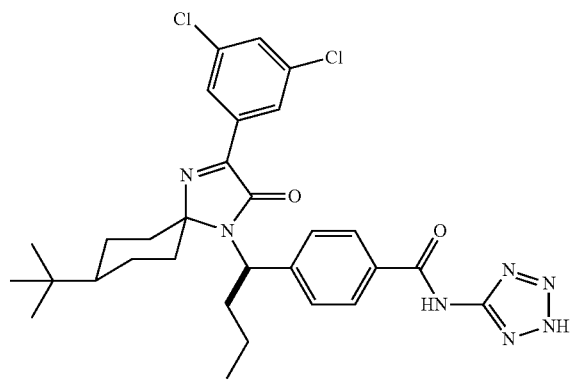 [SMILES: CCC[C@H](c1ccc(C(=O)Nc2nn[nH]n2)cc1)N1C(=O)C(c2cc(Cl)cc(Cl)c2)=NC12CCC(C(C)(C)C)CC2] |
| 1.64 | 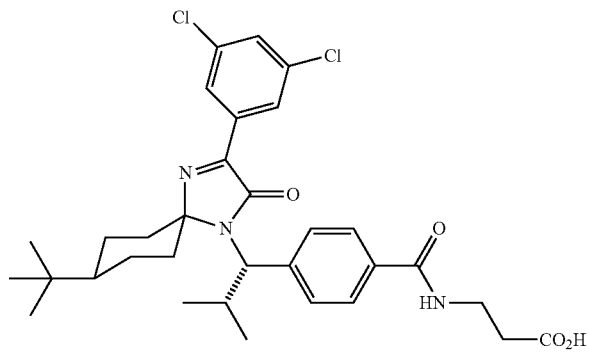 [SMILES: CC(C)[C@@H](c1ccc(C(=O)NCCC(=O)O)cc1)N1C(=O)C(c2cc(Cl)cc(Cl)c2)=NC12CCC(C(C)(C)C)CC2] |
| 1.65 | 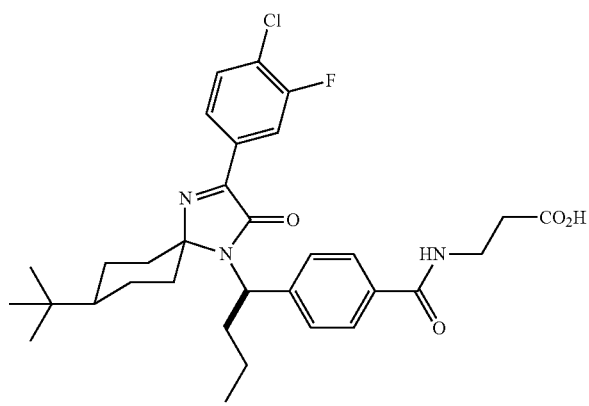 [SMILES: CCC[C@H](c1ccc(C(=O)NCCC(=O)O)cc1)N1C(=O)C(c2ccc(Cl)c(F)c2)=NC12CCC(C(C)(C)C)CC2] |

-continued
| Ex. | Structure |
|---|---|
| 1.66 | 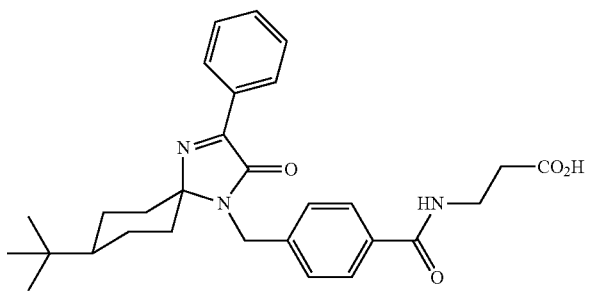 [SMILES: CC(C)(C)C1CCC2(CC1)N=C(c1ccccc1)C(=O)N2Cc1ccc(C(=O)NCCC(=O)O)cc1] |
| 1.67 | 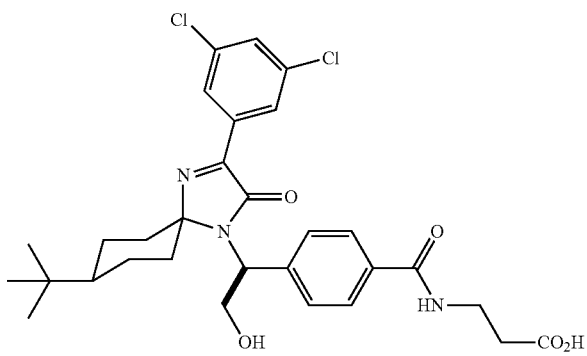 [SMILES: CC(C)(C)C1CCC2(CC1)N=C(c1cc(Cl)cc(Cl)c1)C(=O)N2[C@H](CO)c1ccc(C(=O)NCCC(=O)O)cc1] |
| 1.79 | 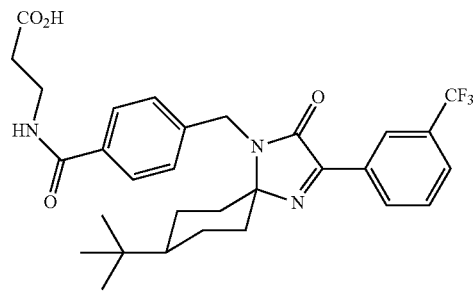 [SMILES: CC(C)(C)C1CCC2(CC1)N=C(c1cccc(C(F)(F)F)c1)C(=O)N2Cc1ccc(C(=O)NCCC(=O)O)cc1] |
| 1.80 | 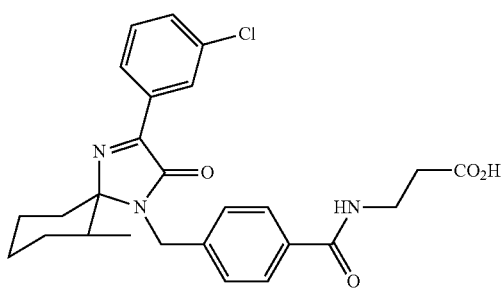 [SMILES: CC1CCCCC12N=C(c1cccc(Cl)c1)C(=O)N2Cc1ccc(C(=O)NCCC(=O)O)cc1] |

-continued
| Ex. | Structure |
|---|---|
| 1.81 | 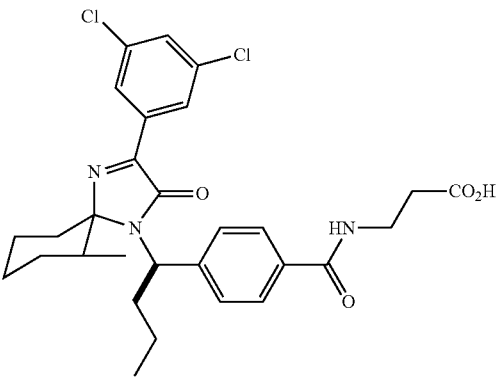 [SMILES: CCC[C@H](c1ccc(C(=O)NCCC(=O)O)cc1)N1C(=O)C(c2cc(Cl)cc(Cl)c2)=NC12CCCCC2C] |
| 1.75 | 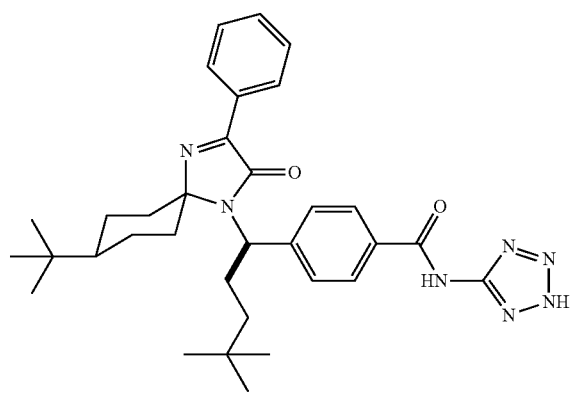 [SMILES: CC(C)(C)CC[C@H](c1ccc(C(=O)Nc2nn[nH]n2)cc1)N1C(=O)C(c2ccccc2)=NC12CCC(C(C)(C)C)CC2] |
| 1.76 | 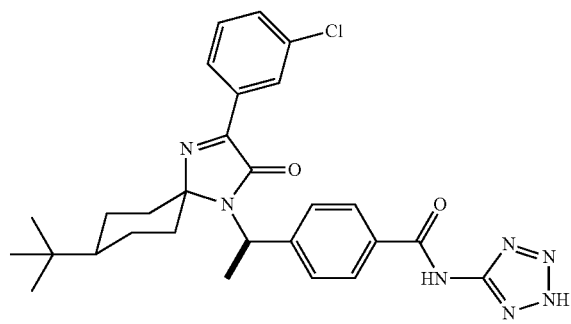 [SMILES: C[C@H](c1ccc(C(=O)Nc2nn[nH]n2)cc1)N1C(=O)C(c2cccc(Cl)c2)=NC12CCC(C(C)(C)C)CC2] |
| 1.77 | 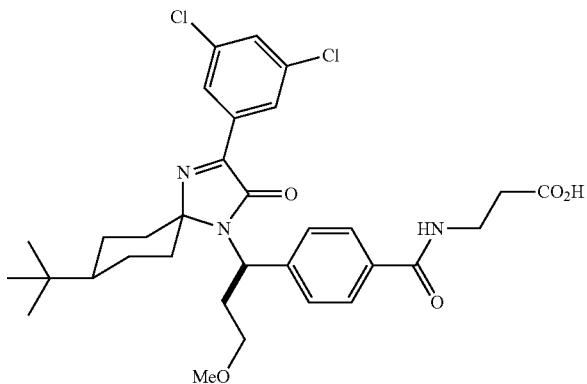 [SMILES: COCC[C@H](c1ccc(C(=O)NCCC(=O)O)cc1)N1C(=O)C(c2cc(Cl)cc(Cl)c2)=NC12CCC(C(C)(C)C)CC2] |

| Ex. | Structure |
|---|---|
| 1.78 | 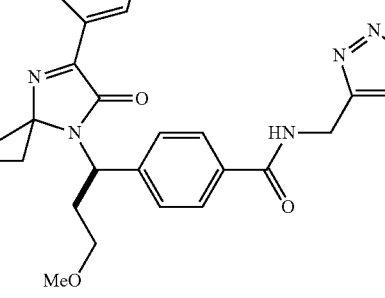 |
| 1.85 | 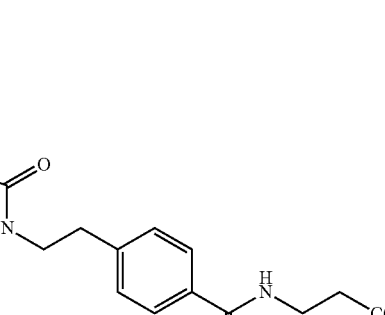 |
| 1.86 | 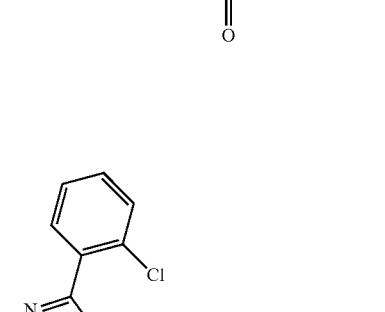 |
| 1.87 | 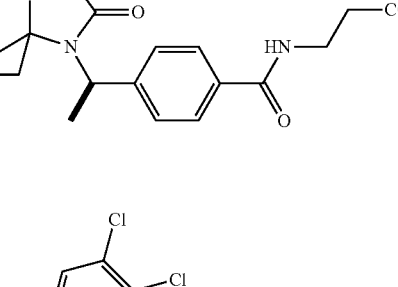 |

| Ex. | Structure |
|---|---|
| 1.82 | 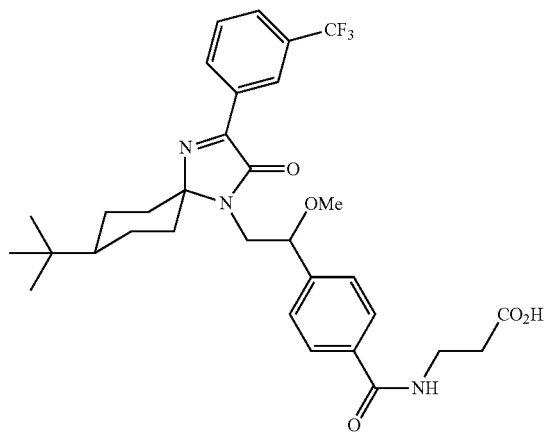 [SMILES: COC(CN1C(=O)C(c2cccc(C(F)(F)F)c2)=NC12CCC(C(C)(C)C)CC2)c1ccc(C(=O)NCCC(=O)O)cc1] |
| 1.83 | 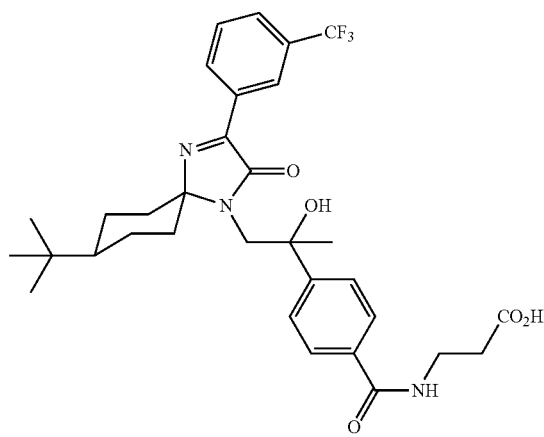 [SMILES: CC(O)(CN1C(=O)C(c2cccc(C(F)(F)F)c2)=NC12CCC(C(C)(C)C)CC2)c1ccc(C(=O)NCCC(=O)O)cc1] |
| 1.84 | 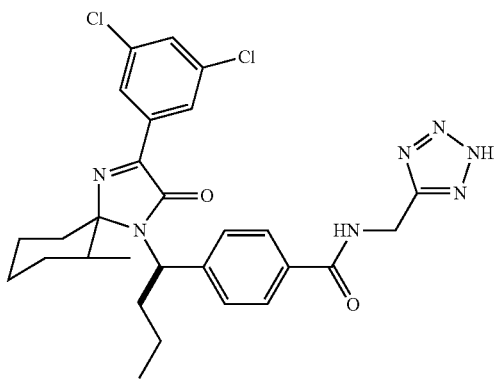 [SMILES: CCC[C@H](c1ccc(C(=O)NCc2nn[nH]n2)cc1)N1C(=O)C(c2cc(Cl)cc(Cl)c2)=NC12CCCCC2C] |

| Ex. | Structure |
|---|---|
| 1.92 | 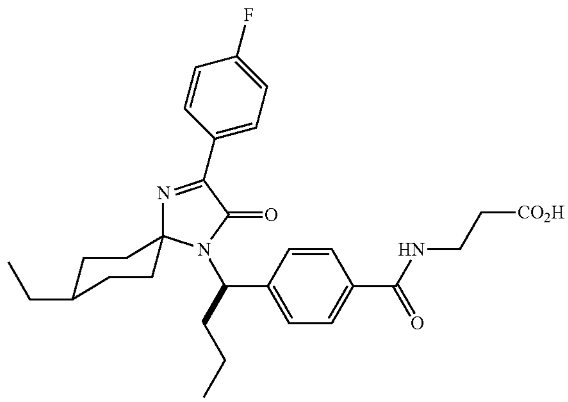 [SMILES: CCC[C@H](c1ccc(C(=O)NCCC(=O)O)cc1)N1C(=O)C(c2ccc(F)cc2)=NC12CCC(CC)CC2] |
| 1.93 | 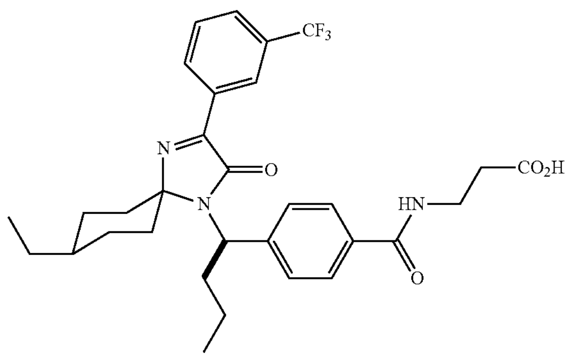 [SMILES: CCC[C@H](c1ccc(C(=O)NCCC(=O)O)cc1)N1C(=O)C(c2cccc(C(F)(F)F)c2)=NC12CCC(CC)CC2] |
| 1.94 | 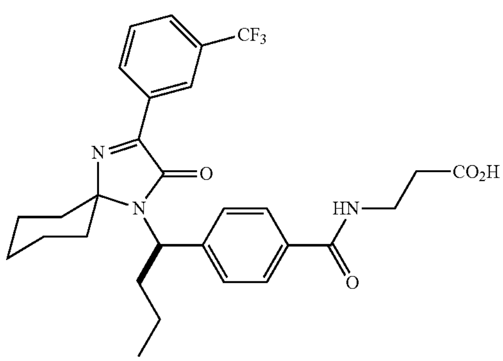 [SMILES: CCC[C@H](c1ccc(C(=O)NCCC(=O)O)cc1)N1C(=O)C(c2cccc(C(F)(F)F)c2)=NC12CCCCC2] |
| 1.95 | 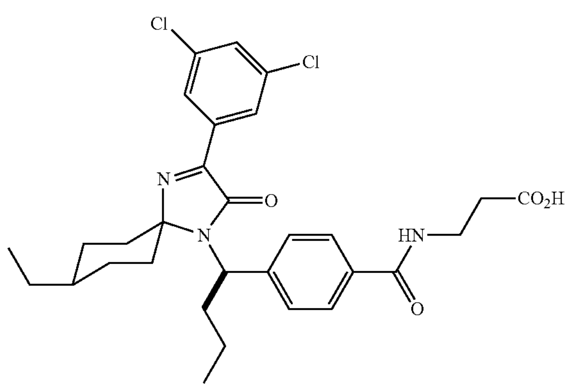 [SMILES: CCC[C@H](c1ccc(C(=O)NCCC(=O)O)cc1)N1C(=O)C(c2cc(Cl)cc(Cl)c2)=NC12CCC(CC)CC2] |

-continued
| Ex. | Structure |
|---|---|
| 1.88 | 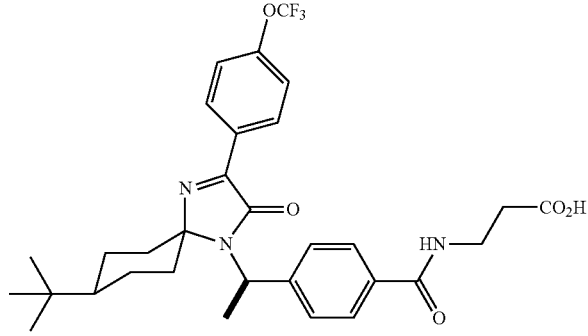 [SMILES: C[C@H](c1ccc(C(=O)NCCC(=O)O)cc1)N1C(=O)C(c2ccc(OC(F)(F)F)cc2)=NC12CCC(C(C)(C)C)CC2] |
| 1.89 | 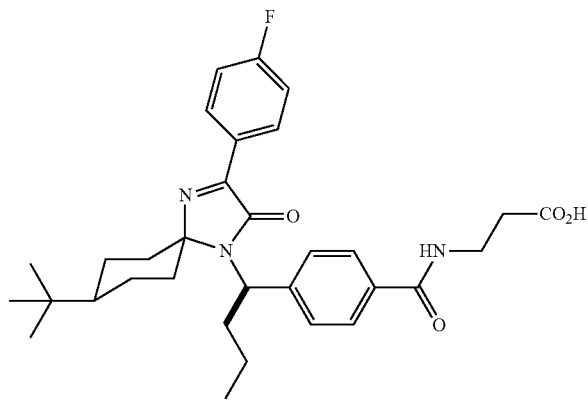 [SMILES: CCC[C@H](c1ccc(C(=O)NCCC(=O)O)cc1)N1C(=O)C(c2ccc(F)cc2)=NC12CCC(C(C)(C)C)CC2] |
| 1.90 | 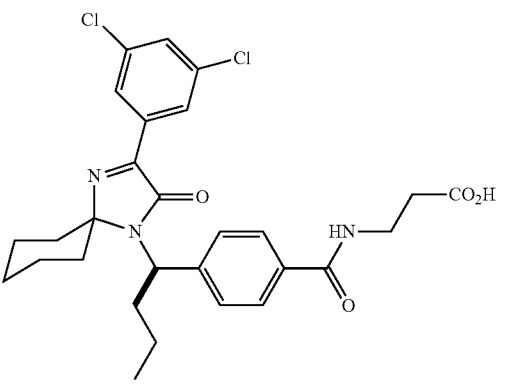 [SMILES: CCC[C@H](c1ccc(C(=O)NCCC(=O)O)cc1)N1C(=O)C(c2cc(Cl)cc(Cl)c2)=NC12CCCCC2] |
| 1.91 | 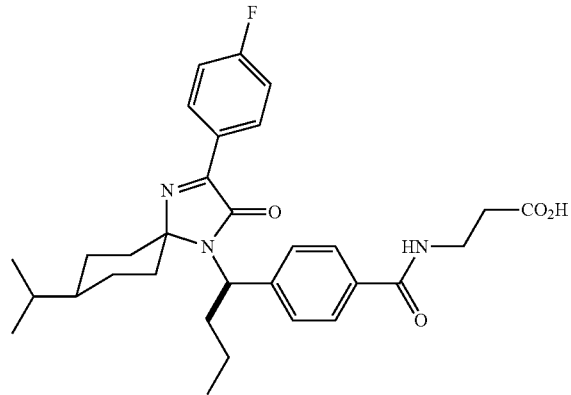 [SMILES: CCC[C@H](c1ccc(C(=O)NCCC(=O)O)cc1)N1C(=O)C(c2ccc(F)cc2)=NC12CCC(C(C)C)CC2] |

| Ex. | Structure |
|---|---|
| 1.98 | 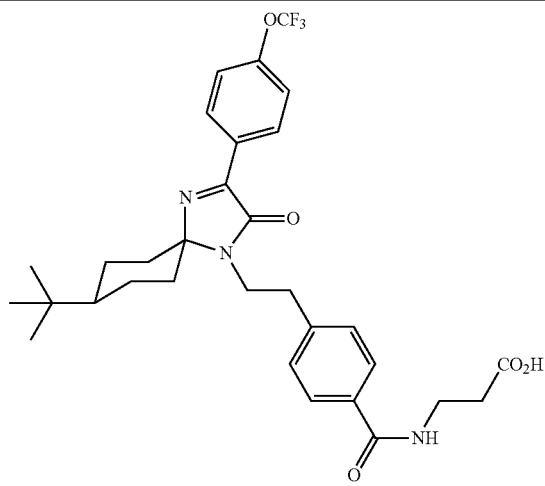 |
| 1.99 | 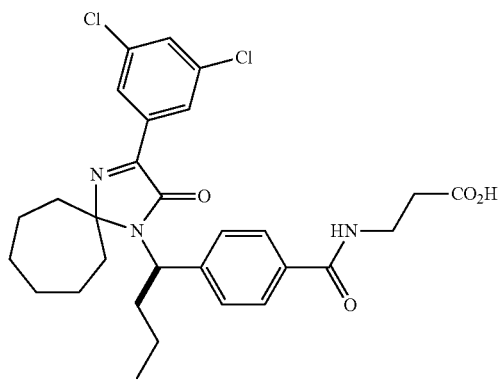 [SMILES: CCC[C@H](c1ccc(C(=O)NCCC(=O)O)cc1)N1C(=O)C(c2cc(Cl)cc(Cl)c2)=NC12CCCCCC2] |
| 1.96 | 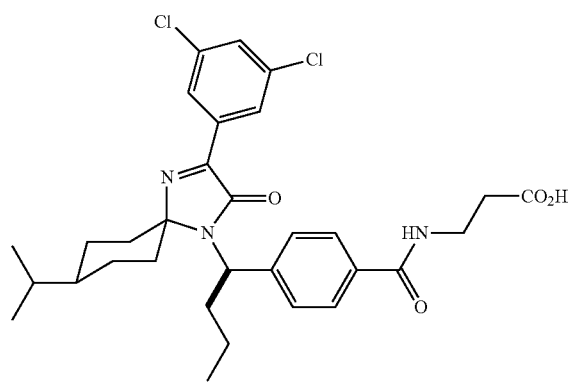 [SMILES: CCC[C@H](c1ccc(C(=O)NCCC(=O)O)cc1)N1C(=O)C(c2cc(Cl)cc(Cl)c2)=NC12CCC(C(C)C)CC2] |

-continued
| Ex. | Structure |
|---|---|
| 1.97 | 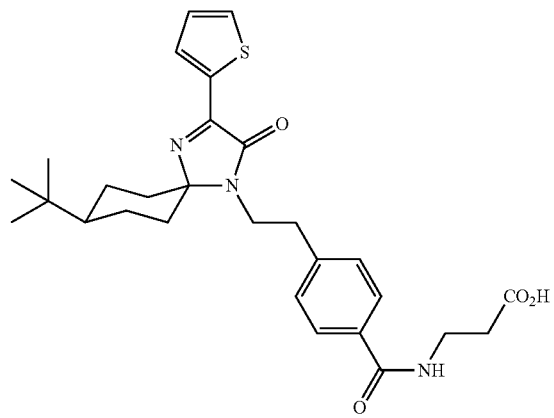 [SMILES: CC(C)(C)C1CCC2(CC1)N=C(c1cccs1)C(=O)N2CCc1ccc(C(=O)NCCC(=O)O)cc1] |
| 1.980 | 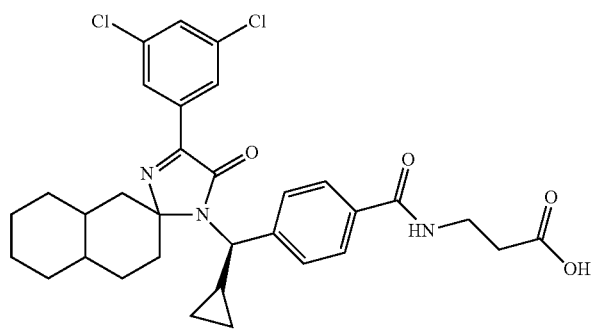
Mix of isomers |
| 1.104 | 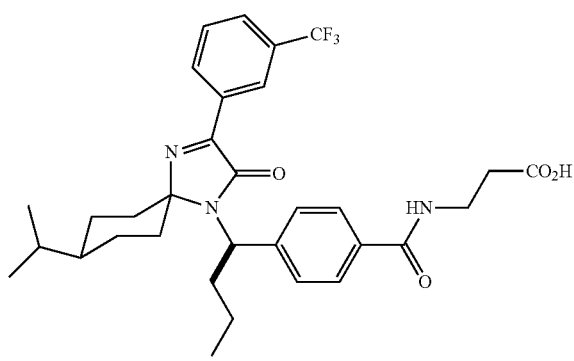 [SMILES: CCC[C@H](c1ccc(C(=O)NCCC(=O)O)cc1)N1C(=O)C(c2cccc(C(F)(F)F)c2)=NC12CCC(C(C)C)CC2] |
| 1.105 | 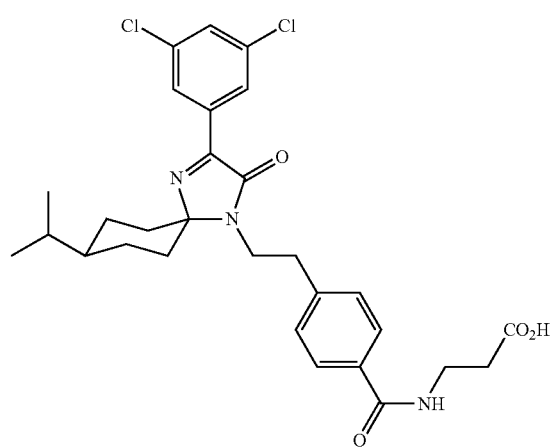 [SMILES: CC(C)C1CCC2(CC1)N=C(c1cc(Cl)cc(Cl)c1)C(=O)N2CCc1ccc(C(=O)NCCC(=O)O)cc1] |

| Ex. | Structure |
|---|---|
| 1.106 | 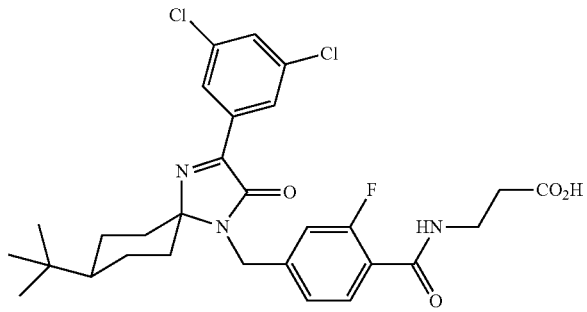 [SMILES: CC(C)(C)C1CCC2(CC1)N=C(c1cc(Cl)cc(Cl)c1)C(=O)N2Cc1ccc(C(=O)NCCC(=O)O)c(F)c1] |
| 1.100 | 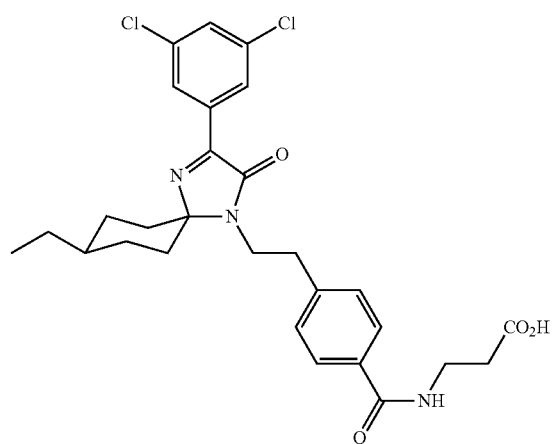 [SMILES: CCC1CCC2(CC1)N=C(c1cc(Cl)cc(Cl)c1)C(=O)N2CCc1ccc(C(=O)NCCC(=O)O)cc1] |
| 1.101 | 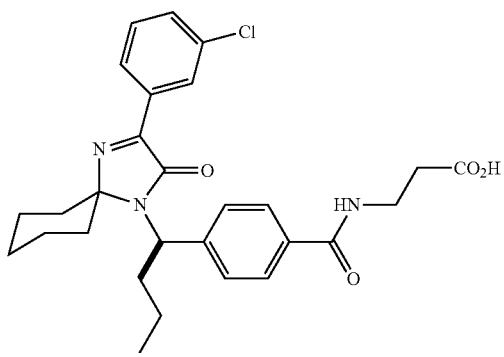 [SMILES: CCC[C@H](c1ccc(C(=O)NCCC(=O)O)cc1)N1C(=O)C(c2cccc(Cl)c2)=NC12CCCCC2] |
| 1.102 | 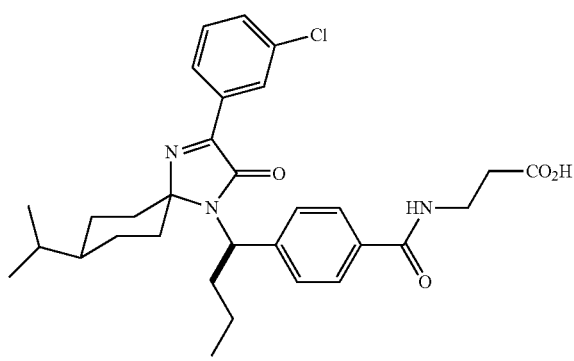 [SMILES: CCC[C@H](c1ccc(C(=O)NCCC(=O)O)cc1)N1C(=O)C(c2cccc(Cl)c2)=NC12CCC(C(C)C)CC2] |

-continued
| Ex. | Structure |
|---|---|
| 1.103 | 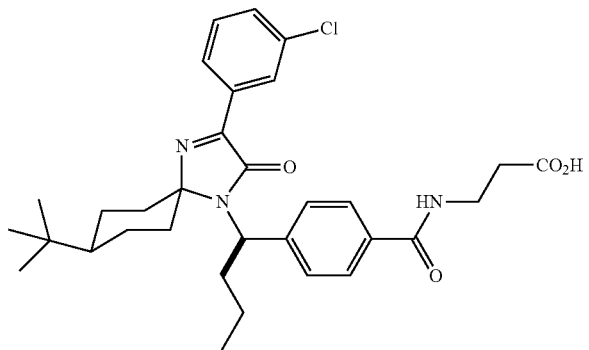 |
| 1.110 | 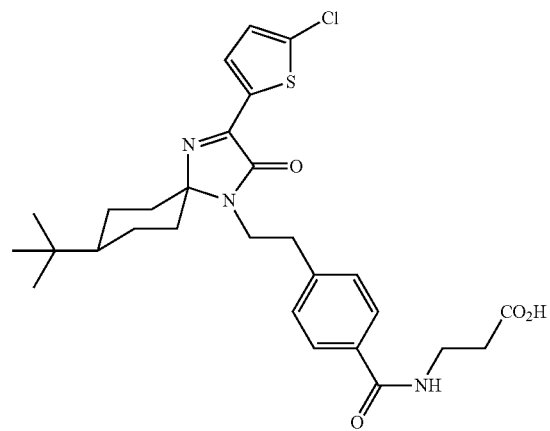 [SMILES: CC(C)(C)C1CCC2(CC1)N=C(c1ccc(Cl)s1)C(=O)N2CCc1ccc(C(=O)NCCC(=O)O)cc1] |
| 1.111 | 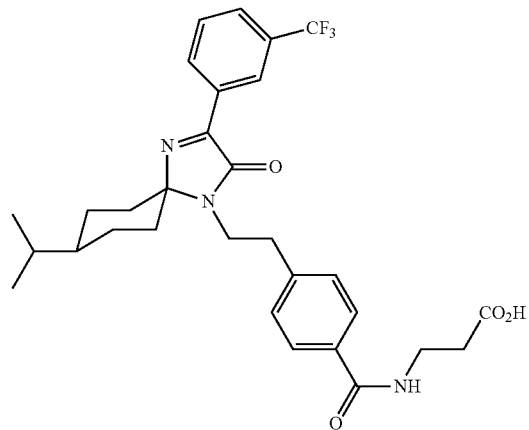 |
| 1.107 | 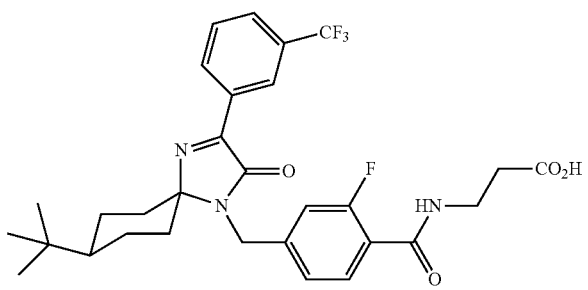 [SMILES: CC(C)(C)C1CCC2(CC1)N=C(c1cccc(C(F)(F)F)c1)C(=O)N2Cc1ccc(C(=O)NCCC(=O)O)c(F)c1] |

| Ex. | Structure |
|---|---|
| 1.108 | 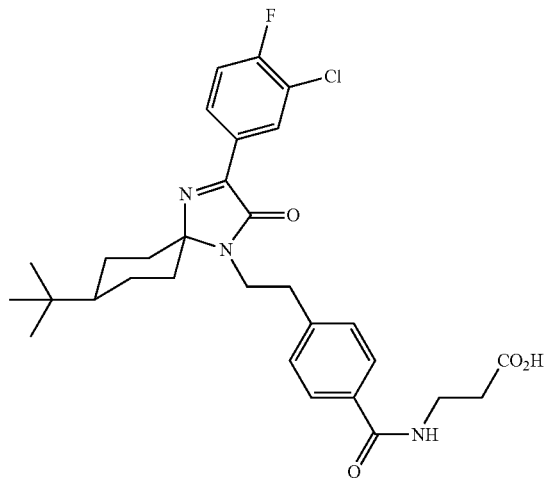 [SMILES: CC(C)(C)C1CCC2(CC1)N=C(c1ccc(F)c(Cl)c1)C(=O)N2CCc1ccc(C(=O)NCCC(=O)O)cc1] |
| 1.109 | 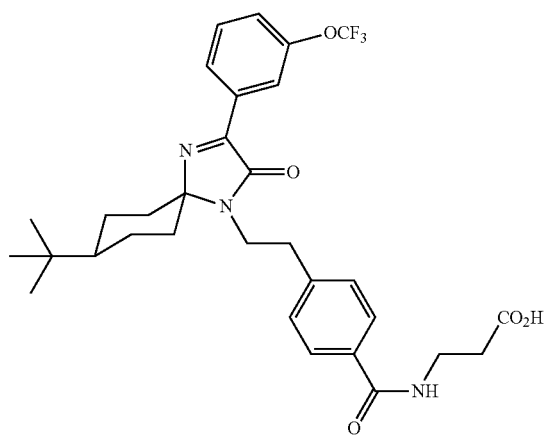 [SMILES: CC(C)(C)C1CCC2(CC1)N=C(c1cccc(OC(F)(F)F)c1)C(=O)N2CCc1ccc(C(=O)NCCC(=O)O)cc1] |
| 1.116 | 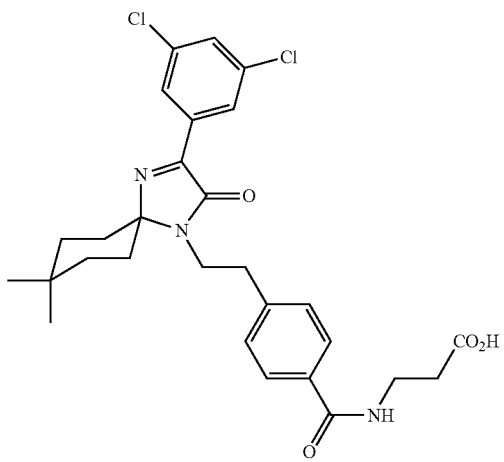 [SMILES: CC1(C)CCC2(CC1)N=C(c1cc(Cl)cc(Cl)c1)C(=O)N2CCc1ccc(C(=O)NCCC(=O)O)cc1] |

| Ex. | Structure |
|---|---|
| 1.117 | 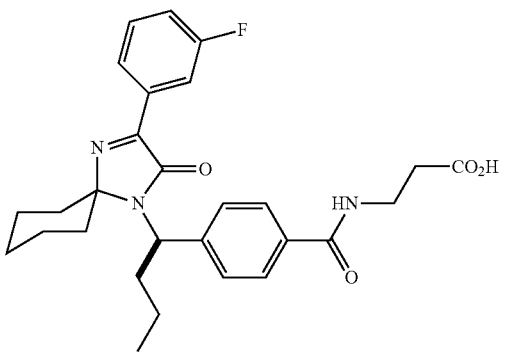 [SMILES: CCC[C@H](c1ccc(C(=O)NCCC(=O)O)cc1)N1C(=O)C(c2cccc(F)c2)=NC12CCCCC2] |
| 1.118 | 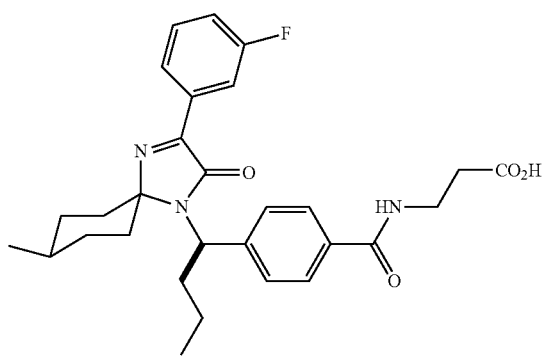 [SMILES: CCC[C@H](c1ccc(C(=O)NCCC(=O)O)cc1)N1C(=O)C(c2cccc(F)c2)=NC12CCC(C)CC2] |
| 1.112 | 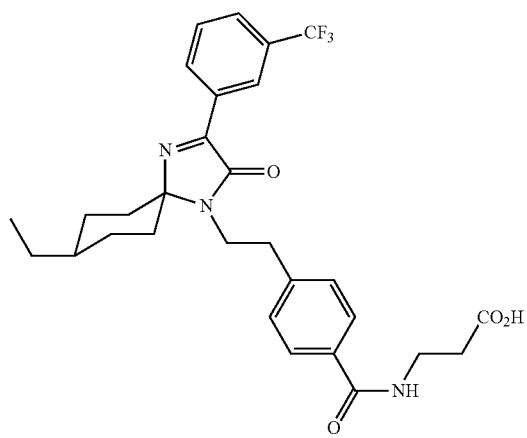 [SMILES: CCC1CCC2(CC1)N=C(c1cccc(C(F)(F)F)c1)C(=O)N2CCc1ccc(C(=O)NCCC(=O)O)cc1] |
| 1.113 | 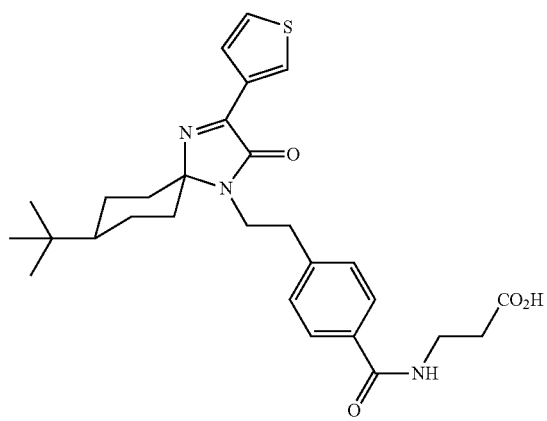 [SMILES: CC(C)(C)C1CCC2(CC1)N=C(c1ccsc1)C(=O)N2CCc1ccc(C(=O)NCCC(=O)O)cc1] |

-continued
| Ex. | Structure |
|---|---|
| 1.114 | 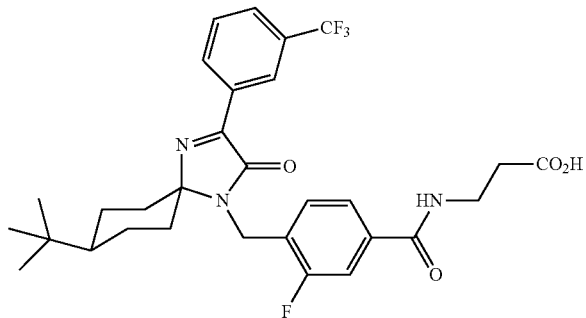 [SMILES: CC(C)(C)C1CCC2(CC1)N=C(c1cccc(C(F)(F)F)c1)C(=O)N2Cc1ccc(C(=O)NCCC(=O)O)cc1F] |
| 1.115 | 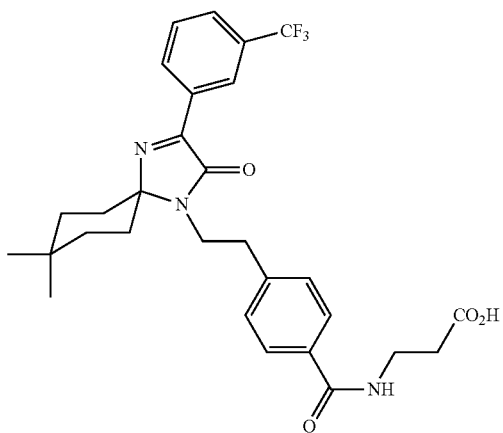 [SMILES: CC1(C)CCC2(CC1)N=C(c1cccc(C(F)(F)F)c1)C(=O)N2CCc1ccc(C(=O)NCCC(=O)O)cc1] |
| 1.122 | 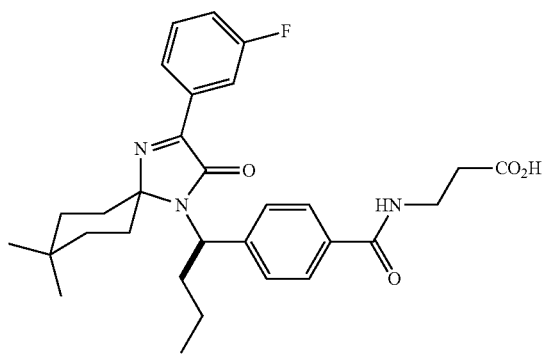 [SMILES: CCC[C@H](c1ccc(C(=O)NCCC(=O)O)cc1)N1C(=O)C(c2cccc(F)c2)=NC12CCC(C)(C)CC2] |
| 1.123 | 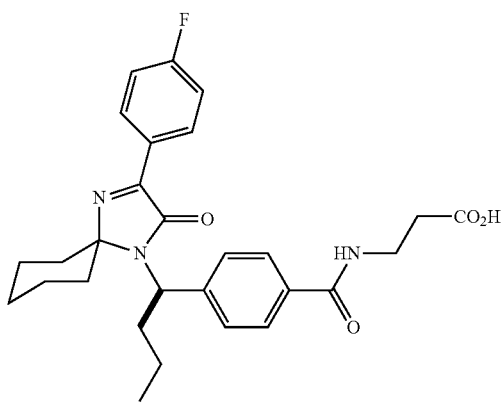 [SMILES: CCC[C@H](c1ccc(C(=O)NCCC(=O)O)cc1)N1C(=O)C(c2ccc(F)cc2)=NC12CCCCC2] |

-continued
| Ex. | Structure |
|---|---|
| 1.119 | 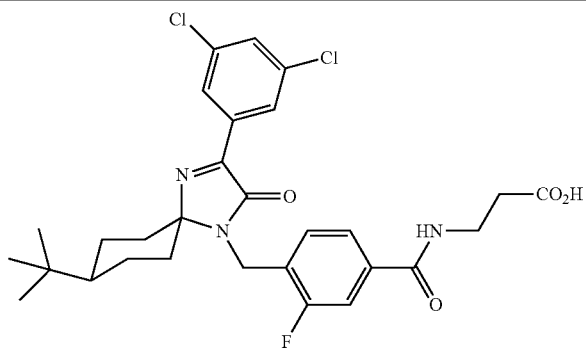 |
| 1.120 | 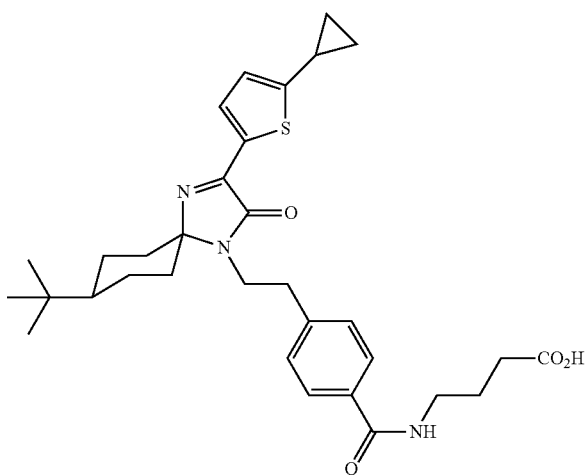 [SMILES: CC(C)(C)C1CCC2(CC1)N=C(c1ccc(C3CC3)s1)C(=O)N2CCc1ccc(C(=O)NCCCC(=O)O)cc1] |
| 1.121 | 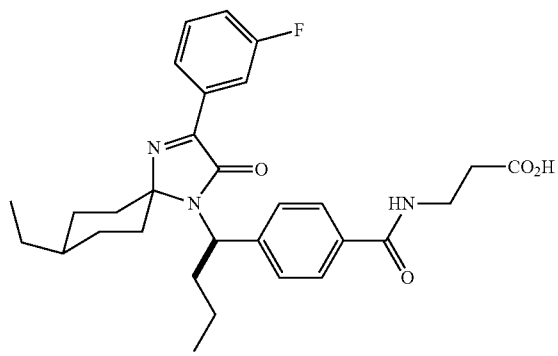 [SMILES: CCC[C@H](c1ccc(C(=O)NCCC(=O)O)cc1)N1C(=O)C(c2cccc(F)c2)=NC12CCC(CC)CC2] |
| 1.128 | 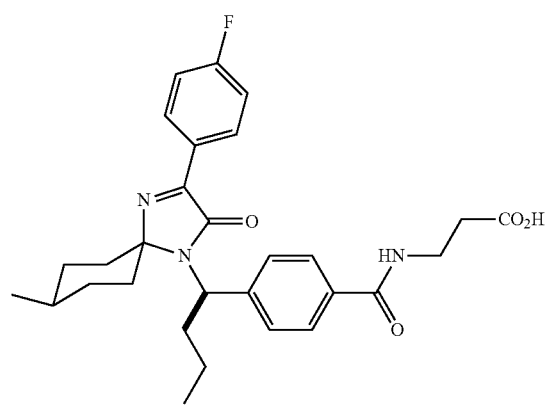 [SMILES: CCC[C@H](c1ccc(C(=O)NCCC(=O)O)cc1)N1C(=O)C(c2ccc(F)cc2)=NC12CCC(C)CC2] |

-continued
| Ex. | Structure |
|---|---|
| 1.129 | 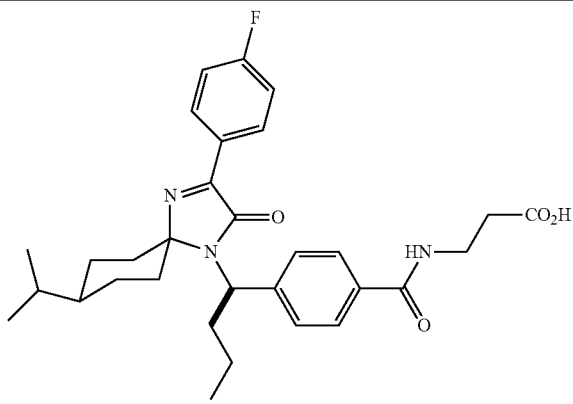 |
| 1.130 | 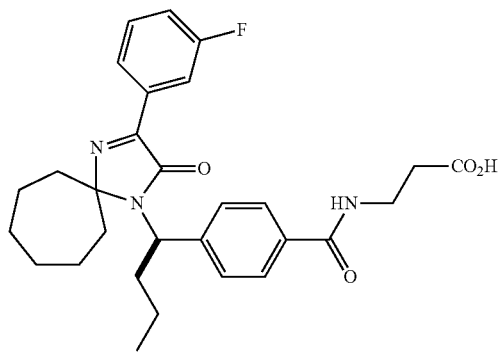 [SMILES: CCC[C@H](c1ccc(C(=O)NCCC(=O)O)cc1)N1C(=O)C(c2cccc(F)c2)=NC12CCCCCC2] |
| 1.124 | 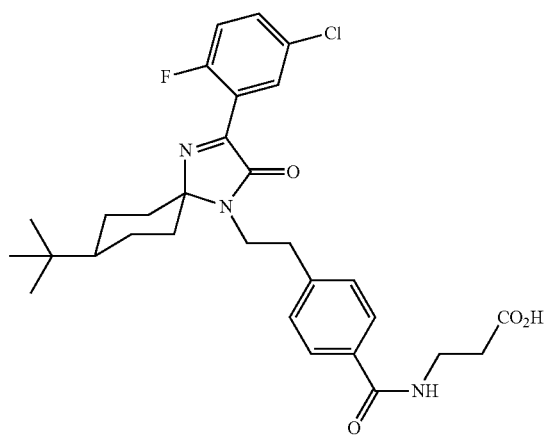 [SMILES: CC(C)(C)C1CCC2(CC1)N=C(c1cc(Cl)ccc1F)C(=O)N2CCc1ccc(C(=O)NCCC(=O)O)cc1] |
| 1.125 | 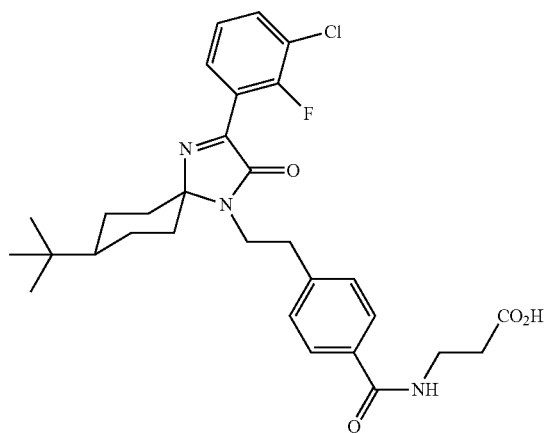 [SMILES: CC(C)(C)C1CCC2(CC1)N=C(c1cccc(Cl)c1F)C(=O)N2CCc1ccc(C(=O)NCCC(=O)O)cc1] |

| Ex. | Structure |
|---|---|
| 1.126 | 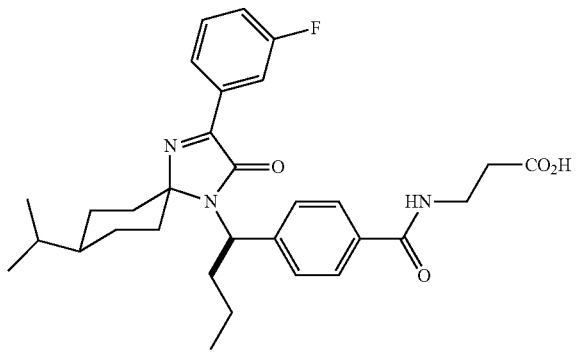 [SMILES: CCC[C@H](c1ccc(C(=O)NCCC(=O)O)cc1)N1C(=O)C(c2cccc(F)c2)=NC12CCC(C(C)C)CC2] |
| 1.127 | 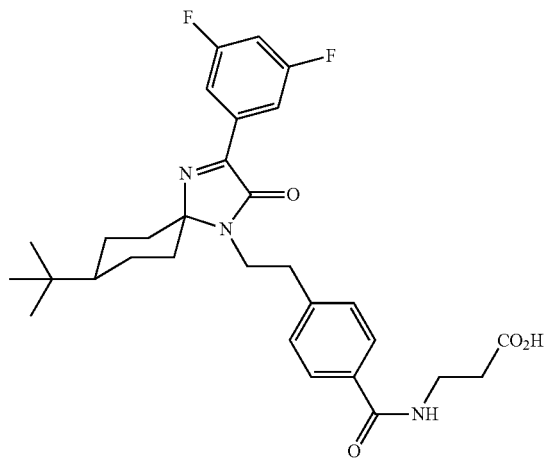 [SMILES: CC(C)(C)C1CCC2(CC1)N=C(c1cc(F)cc(F)c1)C(=O)N2CCc1ccc(C(=O)NCCC(=O)O)cc1] |
| 1.135 | 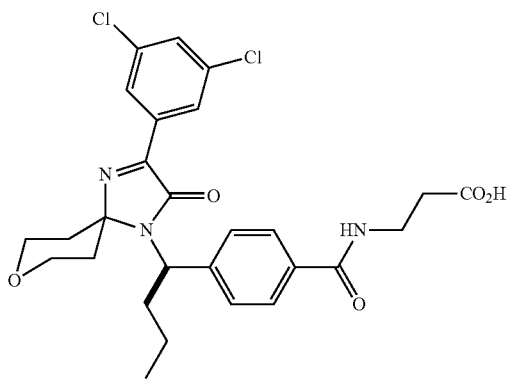 [SMILES: CCC[C@H](c1ccc(C(=O)NCCC(=O)O)cc1)N1C(=O)C(c2cc(Cl)cc(Cl)c2)=NC12CCOCC2] |
| 1.136 | 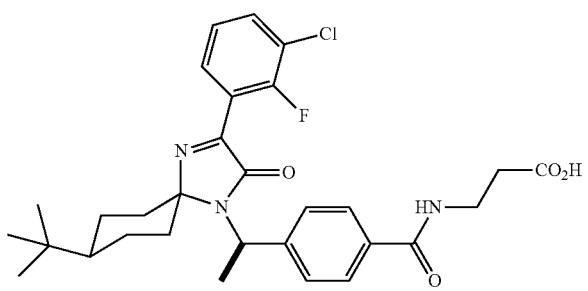 [SMILES: C[C@H](c1ccc(C(=O)NCCC(=O)O)cc1)N1C(=O)C(c2cccc(Cl)c2F)=NC12CCC(C(C)(C)C)CC2] |

| Ex. | Structure |
|---|---|
| 1.131 | 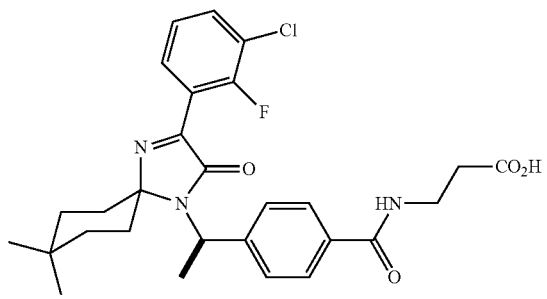 [SMILES: C[C@H](c1ccc(C(=O)NCCC(=O)O)cc1)N1C(=O)C(c2cccc(Cl)c2F)=NC12CCC(C)(C)CC2] |
| 1.132 | 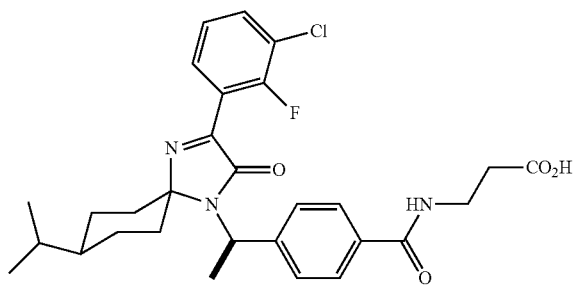 [SMILES: CC(C)C1CCC2(CC1)N=C(c1cccc(Cl)c1F)C(=O)N2[C@H](C)c1ccc(C(=O)NCCC(=O)O)cc1] |
| 1.133 | 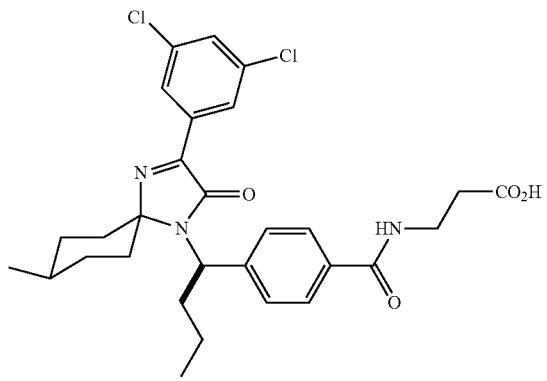 [SMILES: CCC[C@H](c1ccc(C(=O)NCCC(=O)O)cc1)N1C(=O)C(c2cc(Cl)cc(Cl)c2)=NC12CCC(C)CC2] |
| 1.134 | 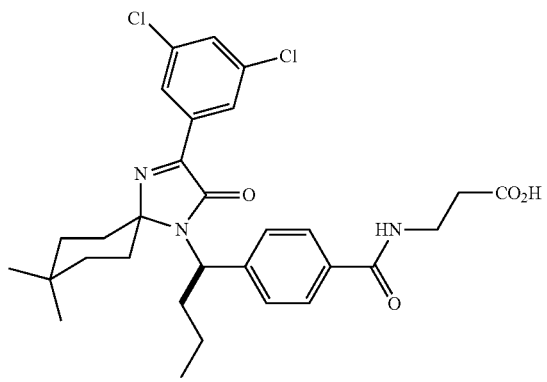 [SMILES: CCC[C@H](c1ccc(C(=O)NCCC(=O)O)cc1)N1C(=O)C(c2cc(Cl)cc(Cl)c2)=NC12CCC(C)(C)CC2] |

| Ex. | Structure |
|---|---|
| 1.142 | 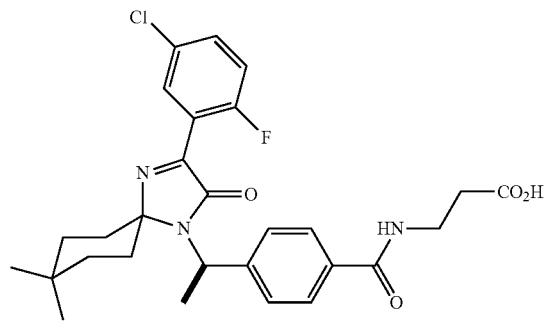 [SMILES: C[C@H](c1ccc(C(=O)NCCC(=O)O)cc1)N1C(=O)C(c2cc(Cl)ccc2F)=NC12CCC(C)(C)CC2] |
| 1.143 | 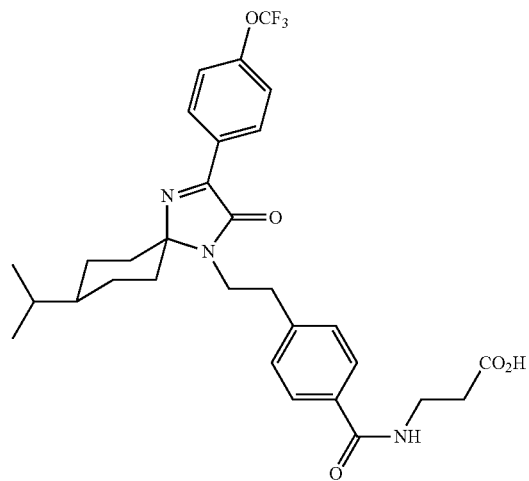 [SMILES: CC(C)C1CCC2(CC1)N=C(c1ccc(OC(F)(F)F)cc1)C(=O)N2CCc1ccc(C(=O)NCCC(=O)O)cc1] |
| 1.137 | 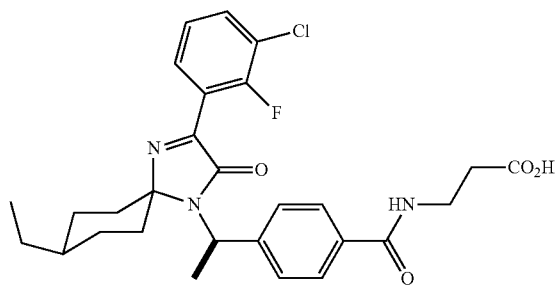 [SMILES: CCC1CCC2(CC1)N=C(c1cccc(Cl)c1F)C(=O)N2[C@H](C)c1ccc(C(=O)NCCC(=O)O)cc1] |
| 1.138 | 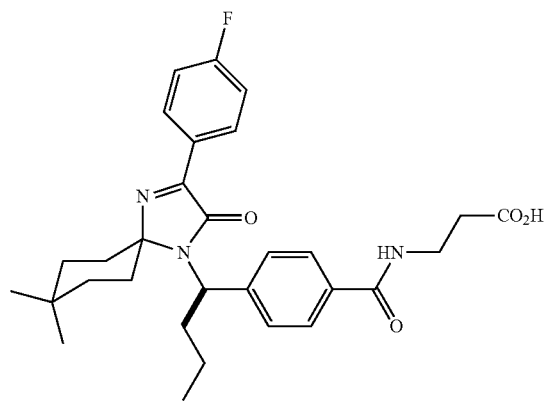 [SMILES: CCC[C@H](c1ccc(C(=O)NCCC(=O)O)cc1)N1C(=O)C(c2ccc(F)cc2)=NC12CCC(C)(C)CC2] |

| Ex. | Structure |
|---|---|
| 1.139 | 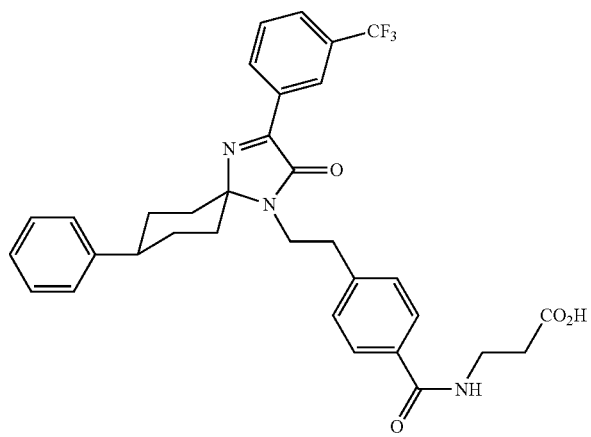 [SMILES: O=C(O)CCNC(=O)c1ccc(CCN2C(=O)C(c3cccc(C(F)(F)F)c3)=NC23CCC(c2ccccc2)CC3)cc1] |
| 1.140 | 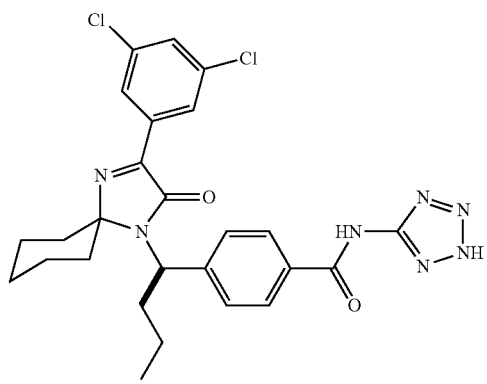 [SMILES: CCC[C@H](c1ccc(C(=O)Nc2nn[nH]n2)cc1)N1C(=O)C(c2cc(Cl)cc(Cl)c2)=NC12CCCCC2] |
| 1.141 | 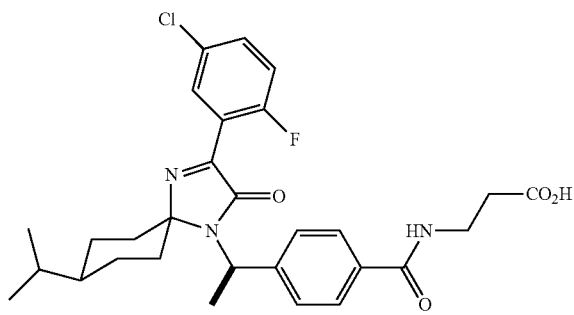 [SMILES: CC(C)C1CCC2(CC1)N=C(c1cc(Cl)ccc1F)C(=O)N2[C@H](C)c1ccc(C(=O)NCCC(=O)O)cc1] |
| 1.148 | 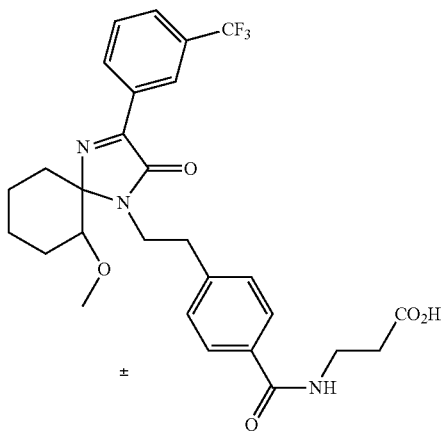 [SMILES: COC1CCCCC12N=C(c1cccc(C(F)(F)F)c1)C(=O)N2CCc1ccc(C(=O)NCCC(=O)O)cc1] |

-continued
| Ex. | Structure |
|---|---|
| 1.144 | 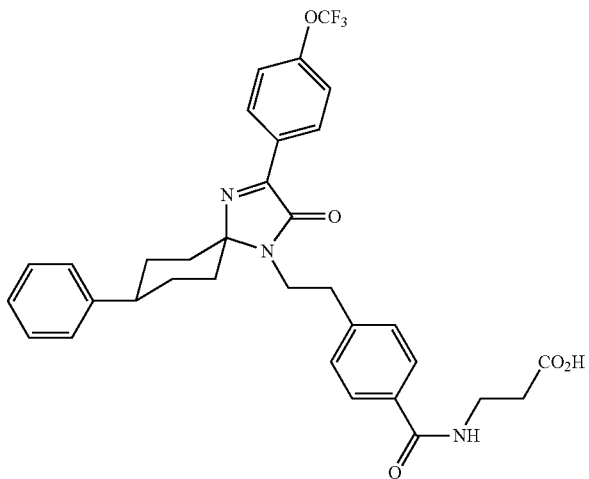 [SMILES: O=C(O)CCNC(=O)c1ccc(CCN2C(=O)C(c3ccc(OC(F)(F)F)cc3)=NC23CCC(c2ccccc2)CC3)cc1] |
| 1.145 | 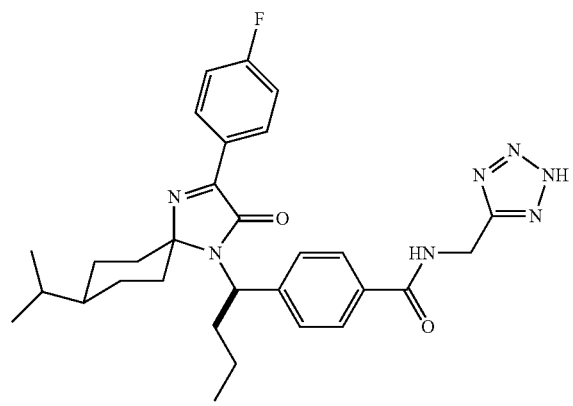 |
| 1.146 | 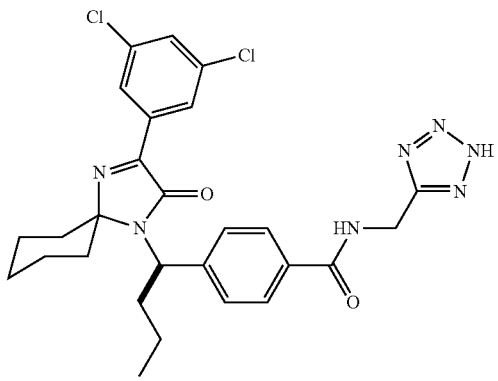 |

-continued
| Ex. | Structure |
|---|---|
| 1.147 | 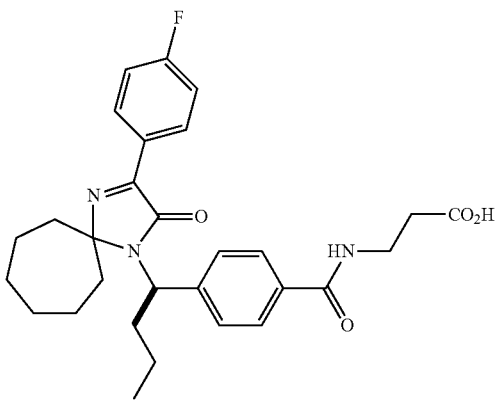 [SMILES: CCC[C@H](c1ccc(C(=O)NCCC(=O)O)cc1)N1C(=O)C(c2ccc(F)cc2)=NC12CCCCCC2] |
| 1.154 | 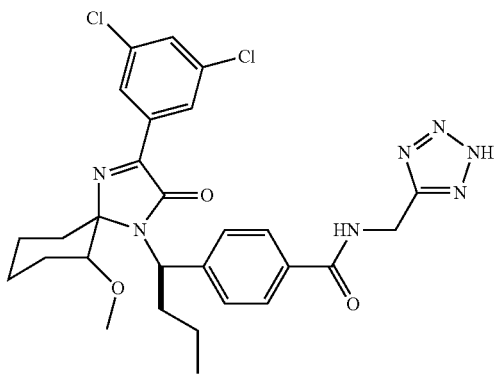 [SMILES: CCC[C@H](c1ccc(C(=O)NCc2nn[nH]n2)cc1)N1C(=O)C(c2cc(Cl)cc(Cl)c2)=NC12CCCCC2OC] |
| 1.155 | 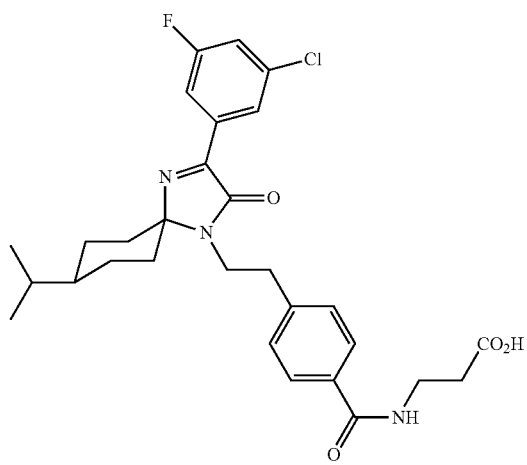 [SMILES: CC(C)C1CCC2(CC1)N=C(c1cc(F)cc(Cl)c1)C(=O)N2CCc1ccc(C(=O)NCCC(=O)O)cc1] |
| 1.149 | 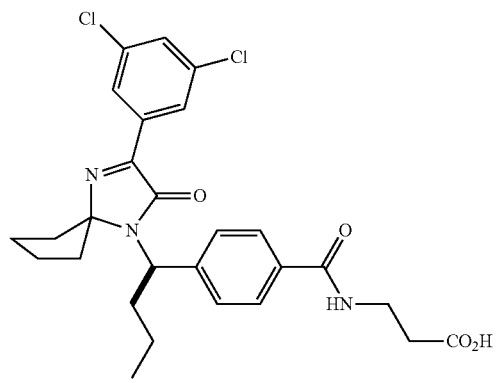 [SMILES: CCC[C@H](c1ccc(C(=O)NCCC(=O)O)cc1)N1C(=O)C(c2cc(Cl)cc(Cl)c2)=NC12CCCC2] |

-continued
| Ex. | Structure |
|---|---|
| 1.150 | 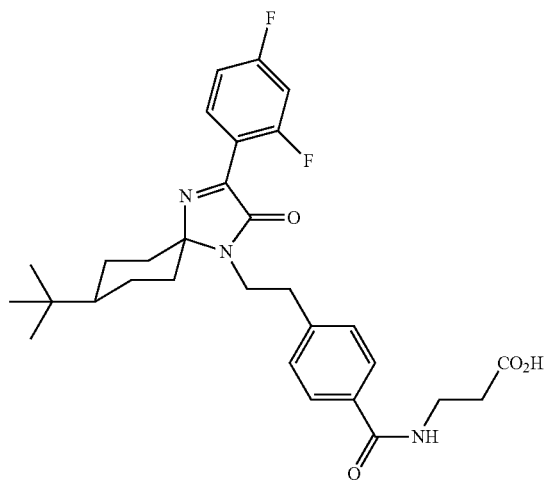 [SMILES: CC(C)(C)C1CCC2(CC1)N=C(c1ccc(F)cc1F)C(=O)N2CCc1ccc(C(=O)NCCC(=O)O)cc1] |
| 1.151 | 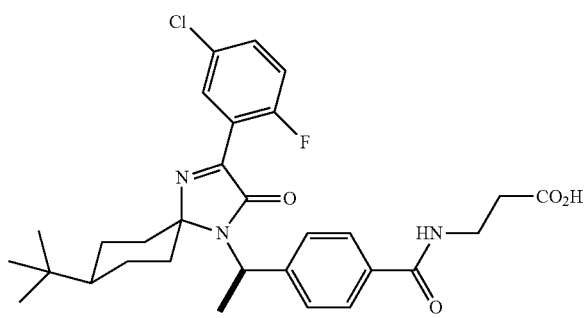 [SMILES: C[C@H](c1ccc(C(=O)NCCC(=O)O)cc1)N1C(=O)C(c2cc(Cl)ccc2F)=NC12CCC(C(C)(C)C)CC2] |
| 1.152 | 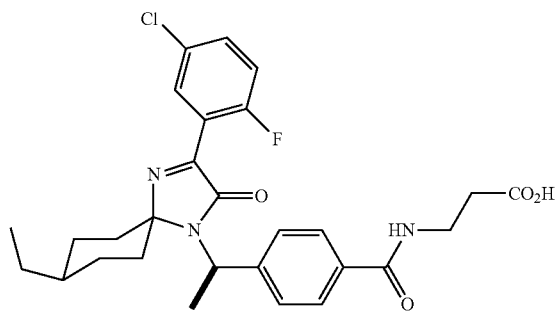 [SMILES: CCC1CCC2(CC1)N=C(c1cc(Cl)ccc1F)C(=O)N2[C@H](C)c1ccc(C(=O)NCCC(=O)O)cc1] |
| 1.153 | 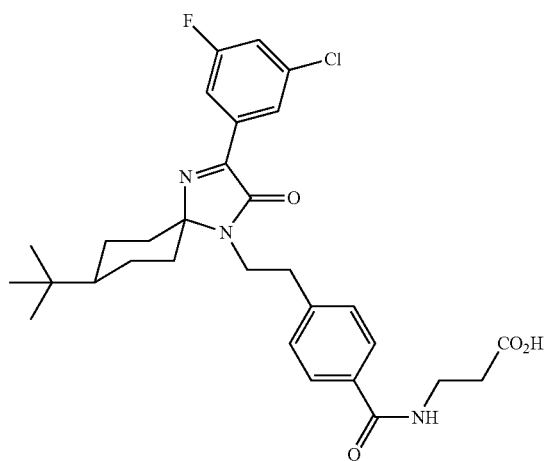 |

-continued
| Ex. | Structure |
|---|---|
| 1.160 | 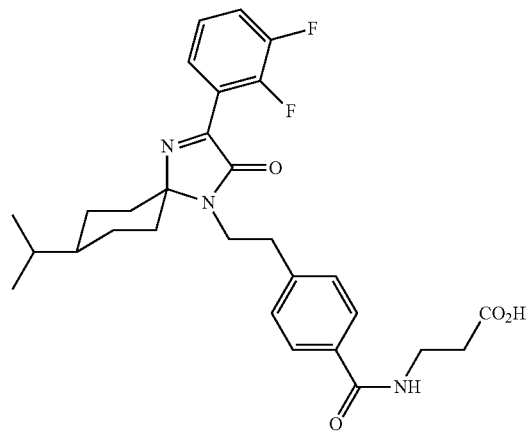 [SMILES: CC(C)C1CCC2(CC1)N=C(c1cccc(F)c1F)C(=O)N2CCc1ccc(C(=O)NCCC(=O)O)cc1] |
| 1.156 | 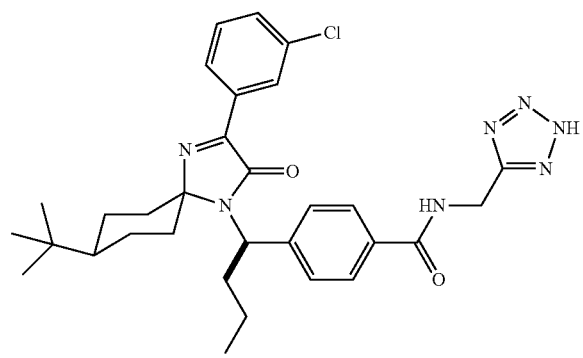 |
| 1.157 | 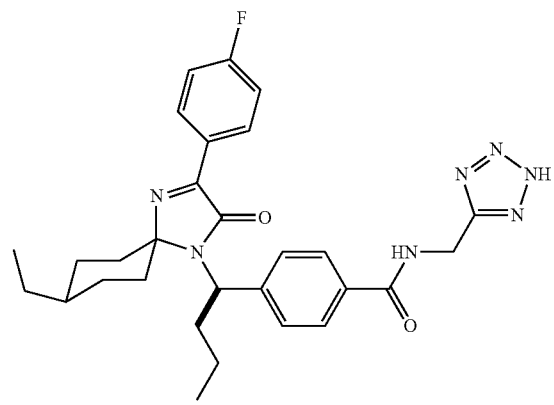 [SMILES: CCC[C@H](c1ccc(C(=O)NCc2nn[nH]n2)cc1)N1C(=O)C(c2ccc(F)cc2)=NC12CCC(CC)CC2] |

| Ex. | Structure |
|---|---|
| 1.158 | 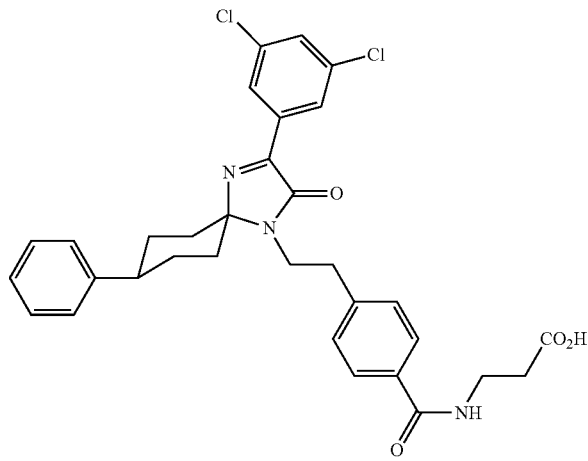 [SMILES: O=C(O)CCNC(=O)c1ccc(CCN2C(=O)C(c3cc(Cl)cc(Cl)c3)=NC23CCC(c2ccccc2)CC3)cc1] |
| 1.159 | 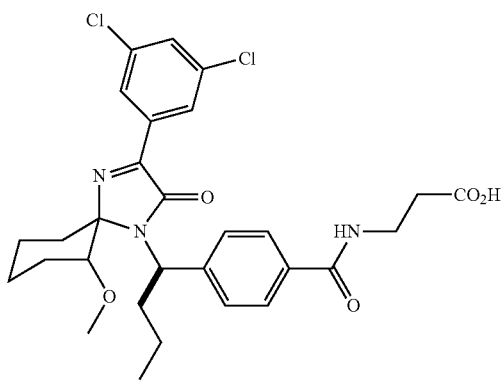 [SMILES: CCC[C@H](c1ccc(C(=O)NCCC(=O)O)cc1)N1C(=O)C(c2cc(Cl)cc(Cl)c2)=NC12CCCCC2OC] |
| 1.166 | 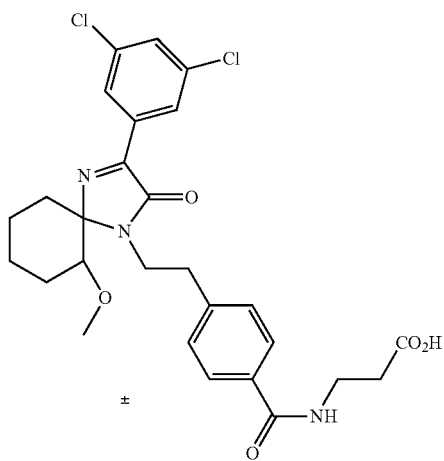 |

| Ex. | Structure |
|---|---|
| 1.167 | 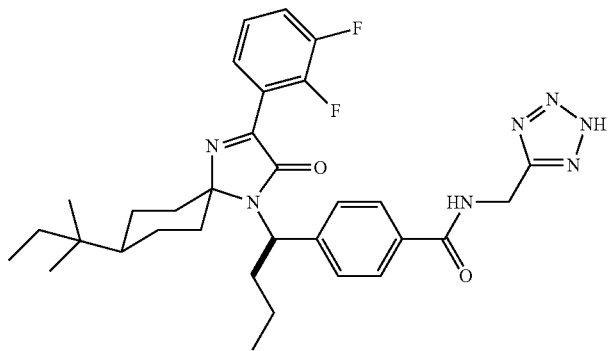 [SMILES: CCC[C@H](c1ccc(C(=O)NCc2nn[nH]n2)cc1)N1C(=O)C(c2cccc(F)c2F)=NC12CCC(C(C)(C)CC)CC2] |
| 1.161 | 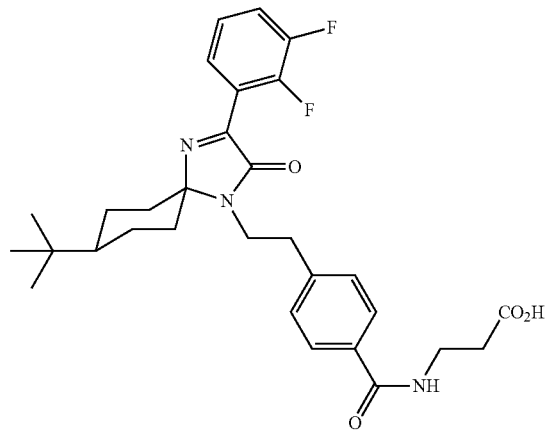 |
| 1.162 | 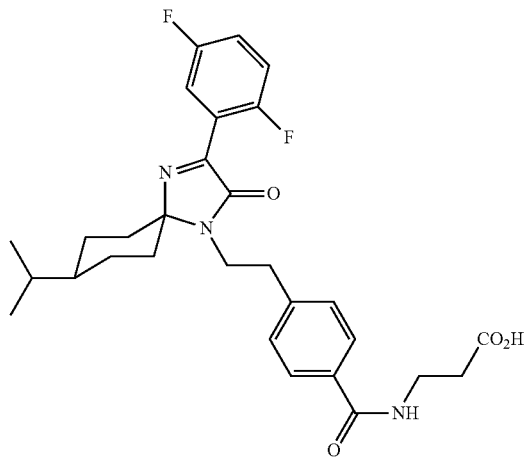 [SMILES: CC(C)C1CCC2(CC1)N=C(c1cc(F)ccc1F)C(=O)N2CCc1ccc(C(=O)NCCC(=O)O)cc1] |

-continued
| Ex. | Structure |
|---|---|
| 1.163 | 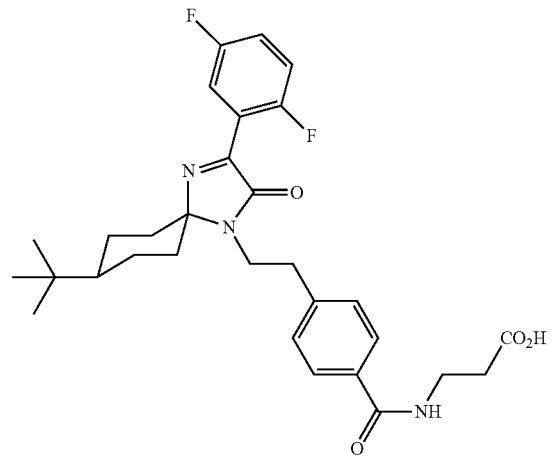 [SMILES: CC(C)(C)C1CCC2(CC1)N=C(c1cc(F)ccc1F)C(=O)N2CCc1ccc(C(=O)NCCC(=O)O)cc1] |
| 1.164 | 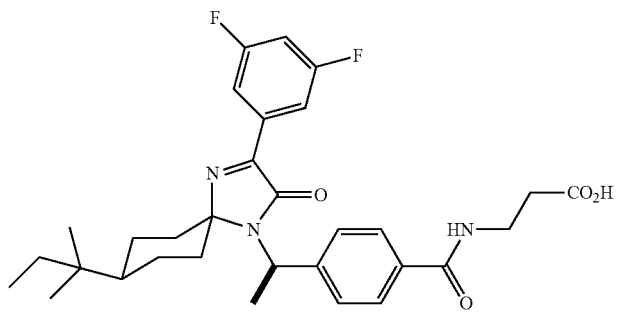 [SMILES: CCC(C)(C)C1CCC2(CC1)N=C(c1cc(F)cc(F)c1)C(=O)N2[C@H](C)c1ccc(C(=O)NCCC(=O)O)cc1] |
| 1.165 | 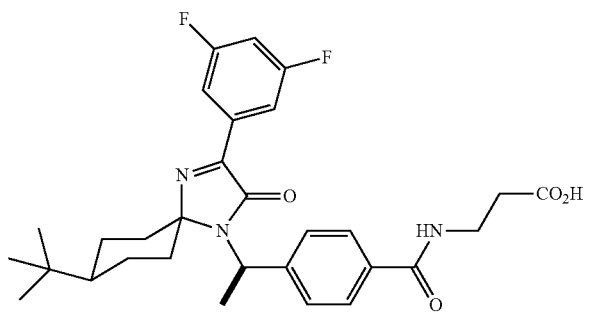 [SMILES: C[C@H](c1ccc(C(=O)NCCC(=O)O)cc1)N1C(=O)C(c2cc(F)cc(F)c2)=NC12CCC(C(C)(C)C)CC2] |
| 1.172 | 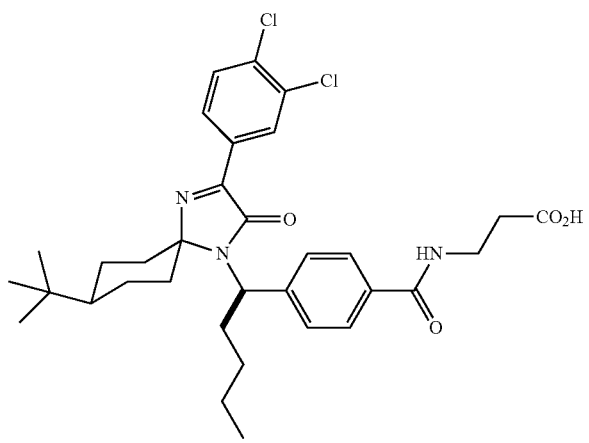 [SMILES: CCCC[C@H](c1ccc(C(=O)NCCC(=O)O)cc1)N1C(=O)C(c2ccc(Cl)c(Cl)c2)=NC12CCC(C(C)(C)C)CC2] |

| Ex. | Structure |
|---|---|
| 1.168 | 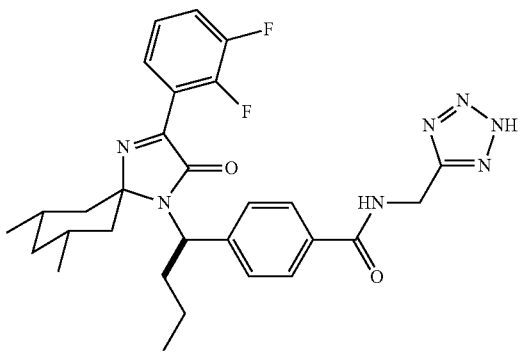 [SMILES: CCC[C@H](c1ccc(C(=O)NCc2nn[nH]n2)cc1)N1C(=O)C(c2cccc(F)c2F)=NC12CC(C)CC(C)C2] |
| 1.169 | 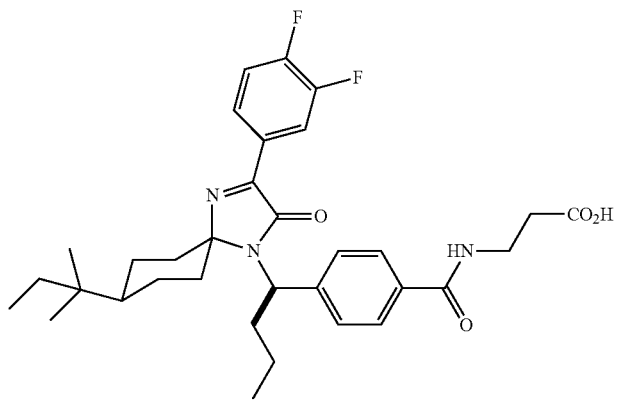 [SMILES: CCC[C@H](c1ccc(C(=O)NCCC(=O)O)cc1)N1C(=O)C(c2ccc(F)c(F)c2)=NC12CCC(C(C)(C)CC)CC2] |
| 1.170 | 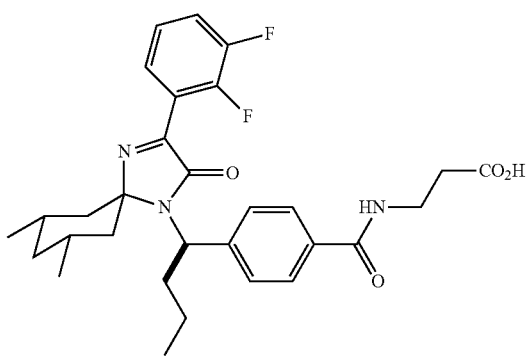 [SMILES: CCC[C@H](c1ccc(C(=O)NCCC(=O)O)cc1)N1C(=O)C(c2cccc(F)c2F)=NC12CC(C)CC(C)C2] |
| 1.171 | 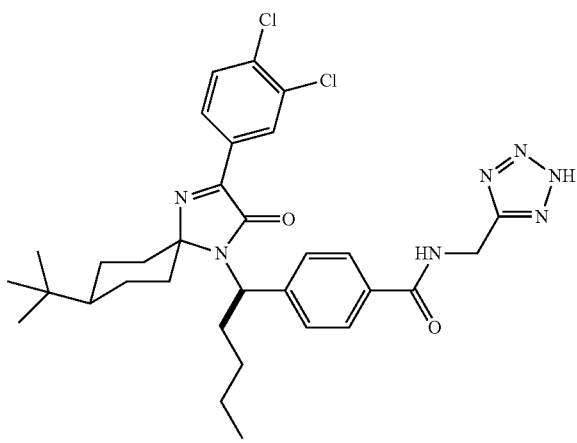 |

-continued
| Ex. | Structure |
|---|---|
| 1.178 | 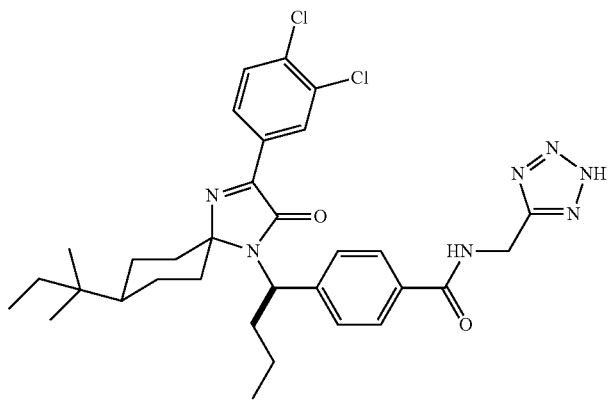 [SMILES: CCC[C@H](c1ccc(C(=O)NCc2nn[nH]n2)cc1)N1C(=O)C(c2ccc(Cl)c(Cl)c2)=NC12CCC(C(C)(C)CC)CC2] |
| 1.179 | 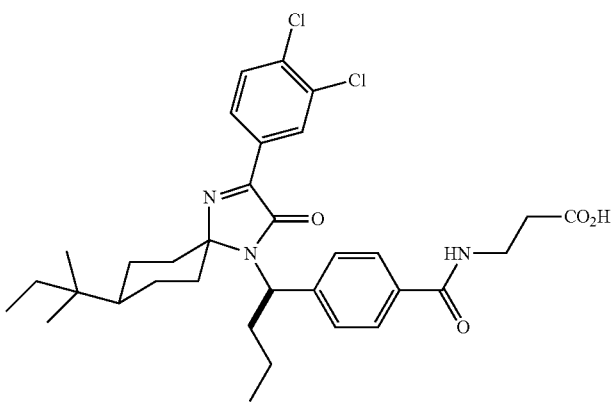 |
| 1.173 | 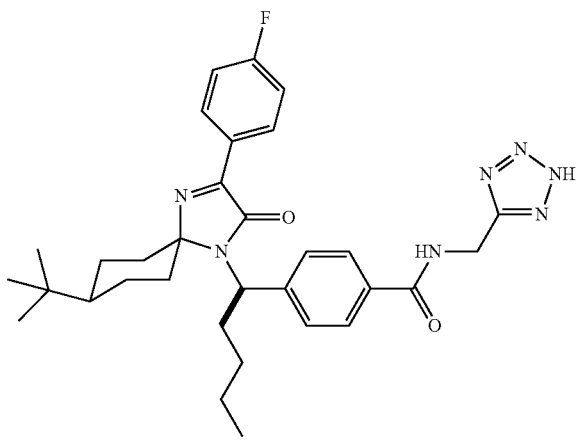 [SMILES: CCCC[C@H](c1ccc(C(=O)NCc2nn[nH]n2)cc1)N1C(=O)C(c2ccc(F)cc2)=NC12CCC(C(C)(C)C)CC2] |

| Ex. | Structure |
|---|---|
| 1.174 | 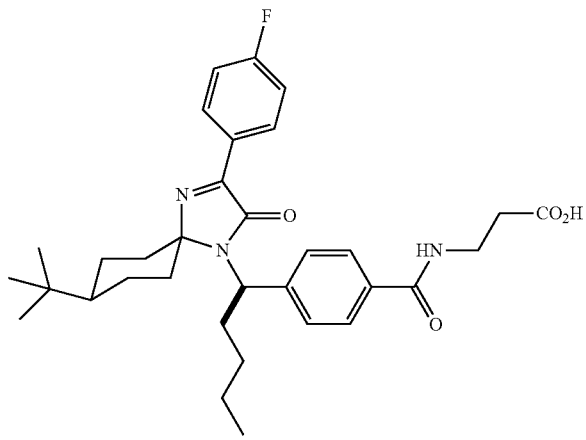 |
| 1.175 | 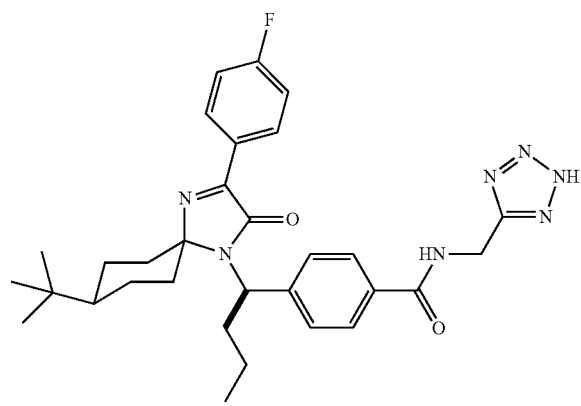 |
| 1.176 | 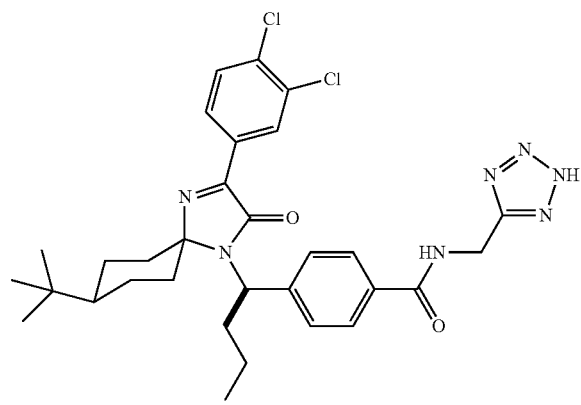 [SMILES: CCC[C@H](c1ccc(C(=O)NCc2nn[nH]n2)cc1)N1C(=O)C(c2ccc(Cl)c(Cl)c2)=NC12CCC(C(C)(C)C)CC2] |

-continued
| Ex. | Structure |
|---|---|
| 1.177 | 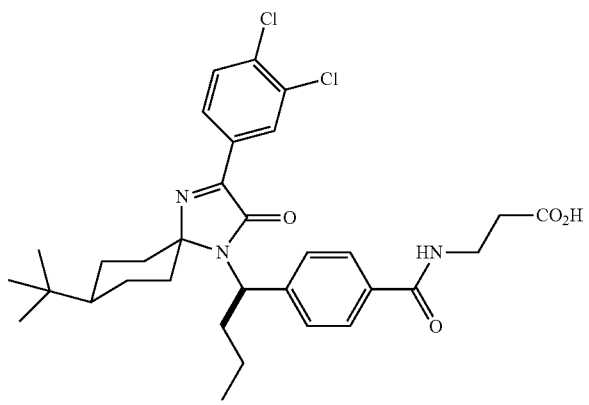 |
| 1.184 | 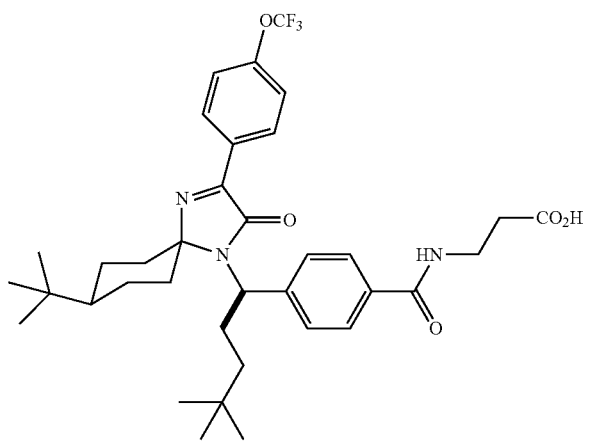 [SMILES: CC(C)(C)CC[C@H](c1ccc(C(=O)NCCC(=O)O)cc1)N1C(=O)C(c2ccc(OC(F)(F)F)cc2)=NC12CCC(C(C)(C)C)CC2] |
| 1.180 | 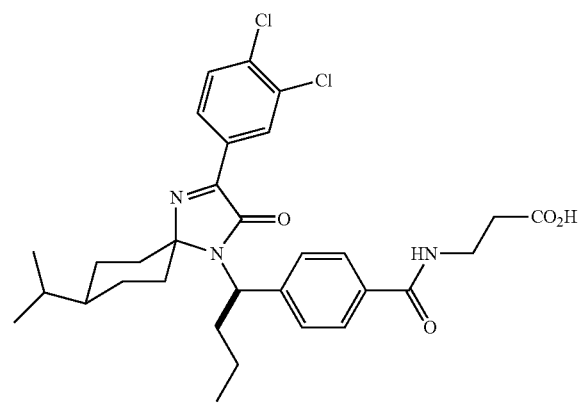 [SMILES: CCC[C@H](c1ccc(C(=O)NCCC(=O)O)cc1)N1C(=O)C(c2ccc(Cl)c(Cl)c2)=NC12CCC(C(C)C)CC2] |

-continued
| Ex. | Structure |
|---|---|
| 1.181 | 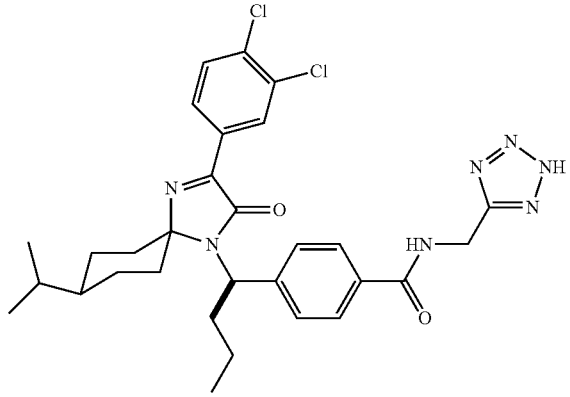 |
| 1.182 | 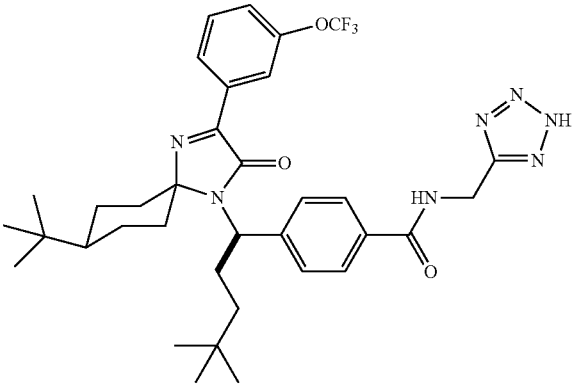 [SMILES: CC(C)(C)CC[C@H](c1ccc(C(=O)NCc2nn[nH]n2)cc1)N1C(=O)C(c2cccc(OC(F)(F)F)c2)=NC12CCC(C(C)(C)C)CC2] |
| 1.183 | 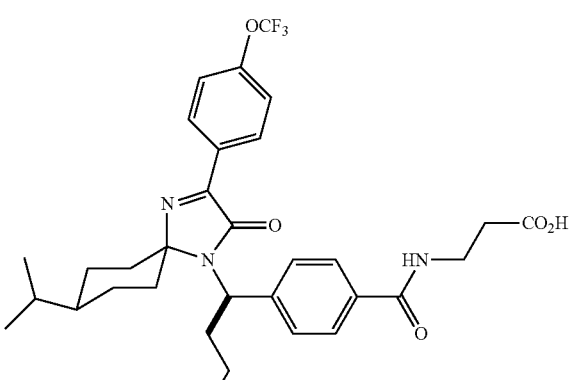 |
| 1.198 | 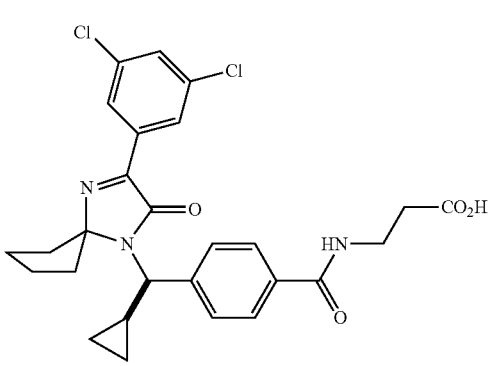 [SMILES: O=C(O)CCNC(=O)c1ccc([C@@H](C2CC2)N2C(=O)C(c3cc(Cl)cc(Cl)c3)=NC23CCCC3)cc1] |

-continued
| Ex. | Structure |
|---|---|
| 1.199 | 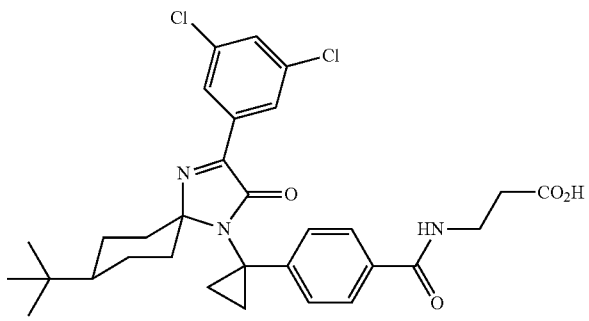 [SMILES: CC(C)(C)C1CCC2(CC1)N=C(c1cc(Cl)cc(Cl)c1)C(=O)N2C1(c2ccc(C(=O)NCCC(=O)O)cc2)CC1] |
| 1.185 | 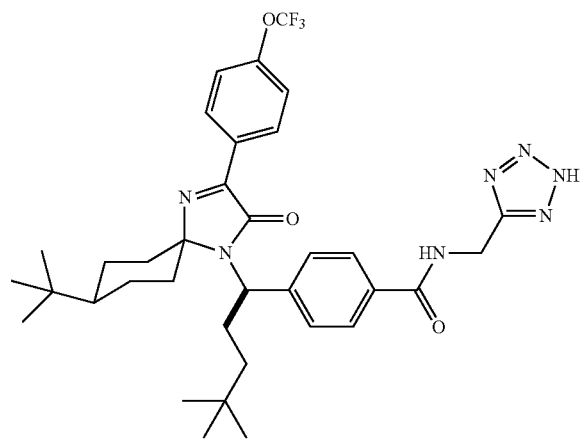 [SMILES: CC(C)(C)CC[C@H](c1ccc(C(=O)NCc2nn[nH]n2)cc1)N1C(=O)C(c2ccc(OC(F)(F)F)cc2)=NC12CCC(C(C)(C)C)CC2] |
| 1.186 | 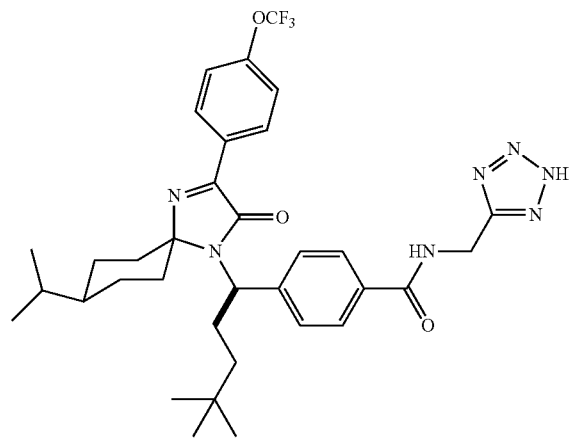 [SMILES: CC(C)C1CCC2(CC1)N=C(c1ccc(OC(F)(F)F)cc1)C(=O)N2[C@H](CCC(C)(C)C)c1ccc(C(=O)NCc2nn[nH]n2)cc1] |

-continued

| Ex. | Structure |
|---|---|
| 1.187 | 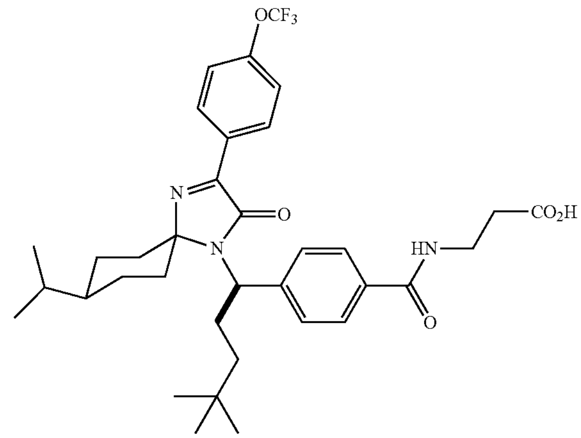 [SMILES: CC(C)C1CCC2(CC1)N=C(c1ccc(OC(F)(F)F)cc1)C(=O)N2[C@H](CCC(C)(C)C)c1ccc(C(=O)NCCC(=O)O)cc1] |
| 1.188 | 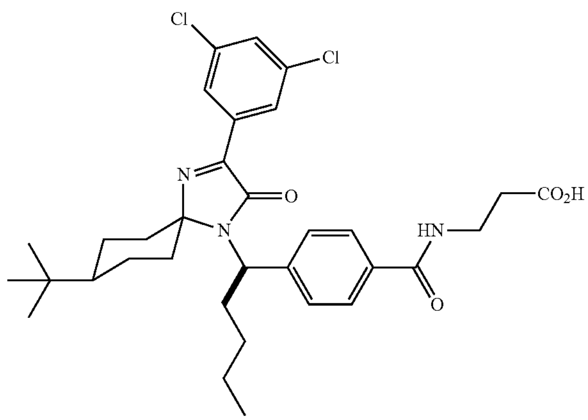 [SMILES: CCCC[C@H](c1ccc(C(=O)NCCC(=O)O)cc1)N1C(=O)C(c2cc(Cl)cc(Cl)c2)=NC12CCC(C(C)(C)C)CC2] |
| 1.189 | 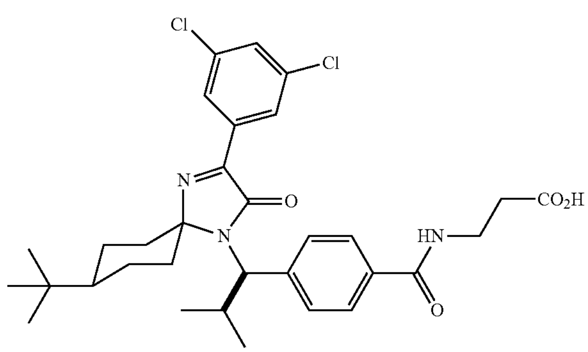 [SMILES: CC(C)[C@H](c1ccc(C(=O)NCCC(=O)O)cc1)N1C(=O)C(c2cc(Cl)cc(Cl)c2)=NC12CCC(C(C)(C)C)CC2] |
| 1.190 | 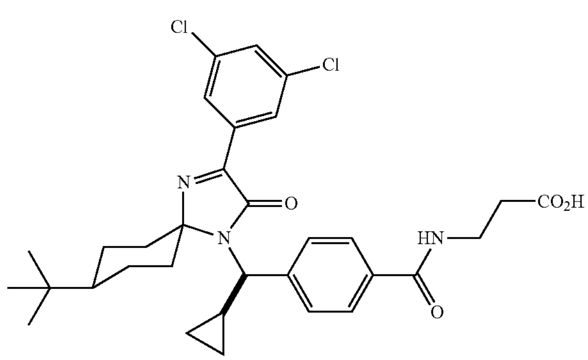 [SMILES: CC(C)(C)C1CCC2(CC1)N=C(c1cc(Cl)cc(Cl)c1)C(=O)N2[C@@H](c1ccc(C(=O)NCCC(=O)O)cc1)C1CC1] |

| Ex. | Structure |
|---|---|
| 1.191 | 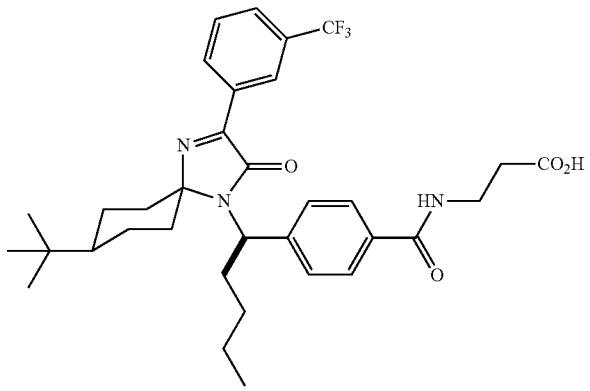 [SMILES: CCCC[C@H](c1ccc(C(=O)NCCC(=O)O)cc1)N1C(=O)C(c2cccc(C(F)(F)F)c2)=NC12CCC(C(C)(C)C)CC2] |
| 1.200 | 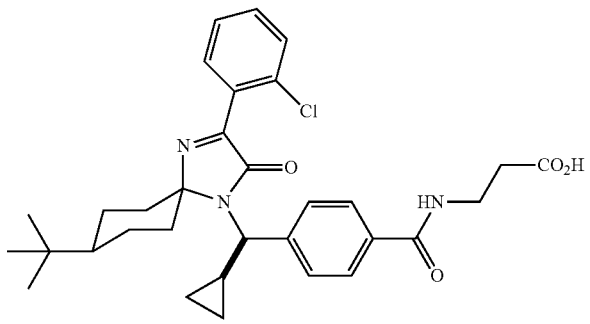 [SMILES: CC(C)(C)C1CCC2(CC1)N=C(c1ccccc1Cl)C(=O)N2[C@@H](c1ccc(C(=O)NCCC(=O)O)cc1)C1CC1] |
| 1.201 | 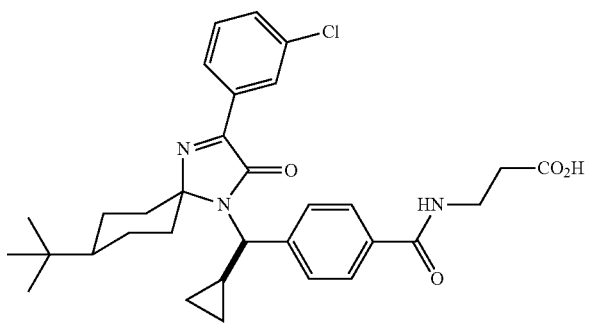 |
| 1.202 | 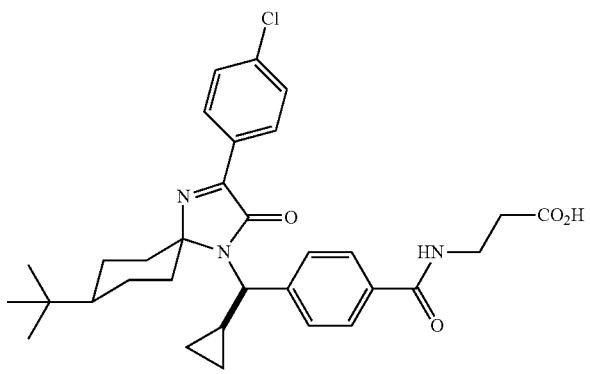 |

-continued
| Ex. | Structure |
|---|---|
| 1.203 | 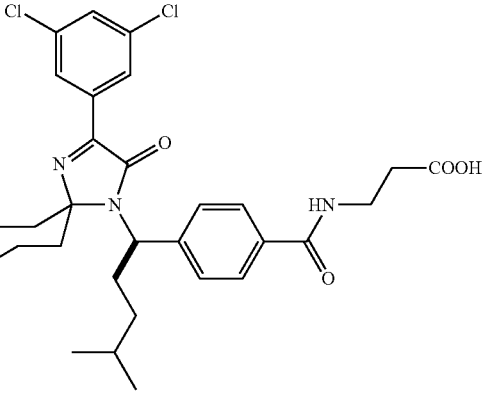 |
| 1.204 | 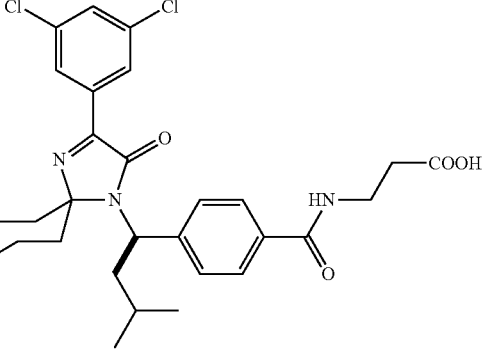 |
| 1.205 | 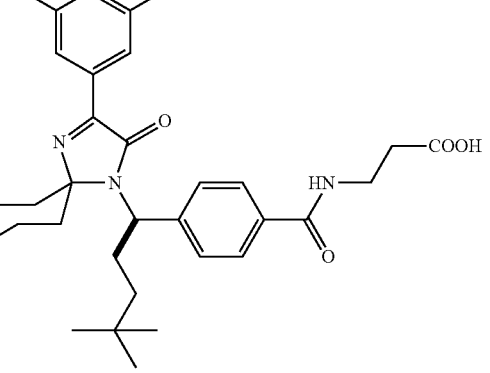 |
| 1.206 | 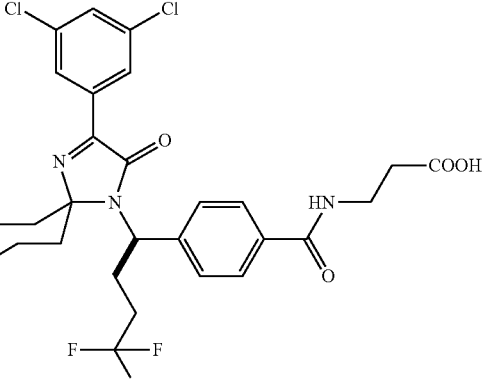 |

-continued
| Ex. | Structure |
|---|---|
| 1.192 | 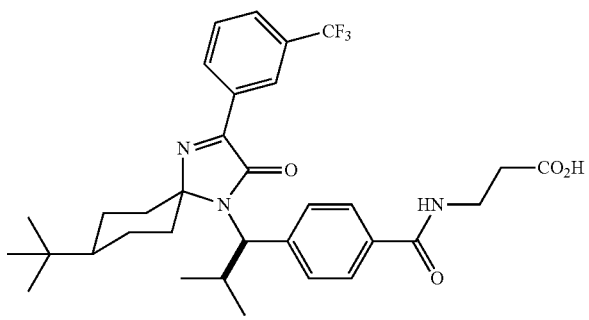 [SMILES: CC(C)[C@H](c1ccc(C(=O)NCCC(=O)O)cc1)N1C(=O)C(c2cccc(C(F)(F)F)c2)=NC12CCC(C(C)(C)C)CC2] |
| 1.193 | 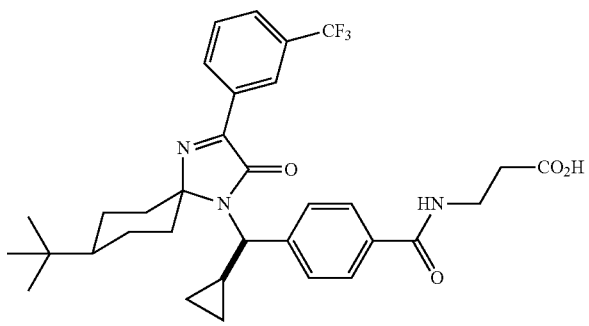 [SMILES: CC(C)(C)C1CCC2(CC1)N=C(c1cccc(C(F)(F)F)c1)C(=O)N2[C@@H](c1ccc(C(=O)NCCC(=O)O)cc1)C1CC1] |
| 1.194 | 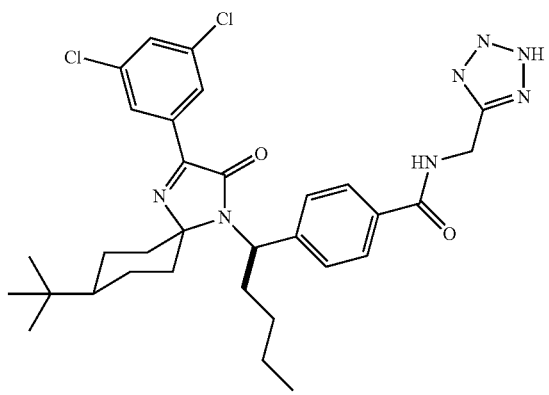 [SMILES: CCCC[C@H](c1ccc(C(=O)NCC2=NNNN2)cc1)N1C(=O)C(c2cc(Cl)cc(Cl)c2)=NC12CCC(C(C)(C)C)CC2] |
| 1.195 | 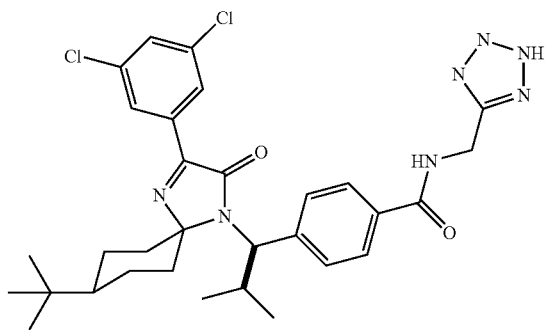 [SMILES: CC(C)[C@H](c1ccc(C(=O)NCC2=NNNN2)cc1)N1C(=O)C(c2cc(Cl)cc(Cl)c2)=NC12CCC(C(C)(C)C)CC2] |

-continued
| Ex. | Structure |
|---|---|
| 1.196 | 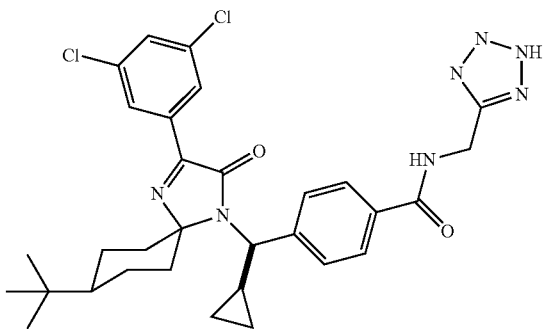 [SMILES: CC(C)(C)C1CCC2(CC1)N=C(c1cc(Cl)cc(Cl)c1)C(=O)N2[C@@H](c1ccc(C(=O)NCC2=NNNN2)cc1)C1CC1] |
| 1.197 | 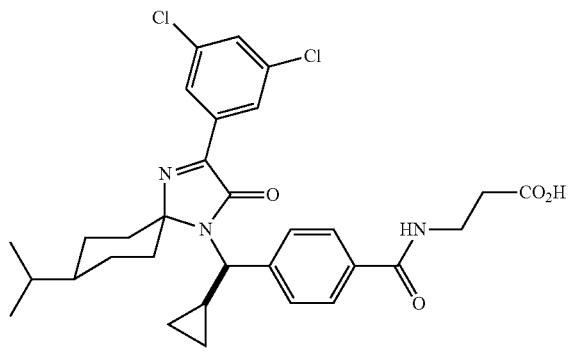 [SMILES: CC(C)C1CCC2(CC1)N=C(c1cc(Cl)cc(Cl)c1)C(=O)N2[C@@H](c1ccc(C(=O)NCCC(=O)O)cc1)C1CC1] |
| 1.213 | 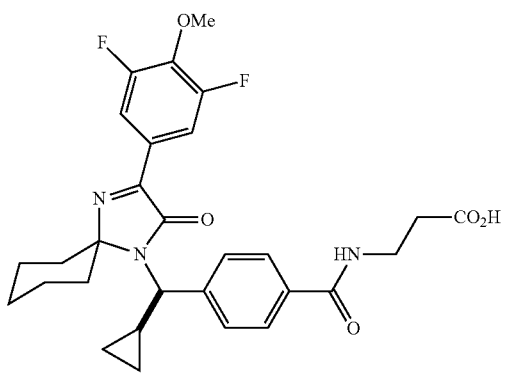 [SMILES: COc1c(F)cc(C2=NC3(CCCCC3)N([C@@H](c3ccc(C(=O)NCCC(=O)O)cc3)C3CC3)C2=O)cc1F] |
| 1.207 | 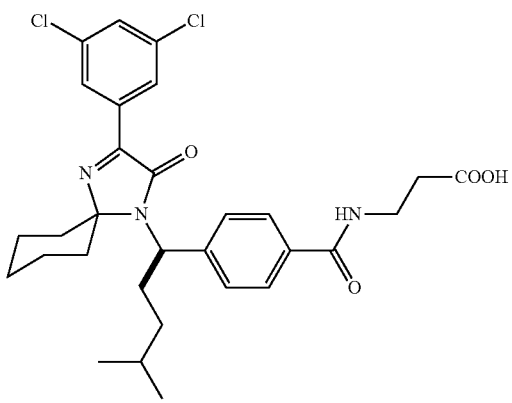 [SMILES: CC(C)CC[C@H](c1ccc(C(=O)NCCC(=O)O)cc1)N1C(=O)C(c2cc(Cl)cc(Cl)c2)=NC12CCCCC2] |

-continued
| Ex. | Structure |
|---|---|
| 1.208 | 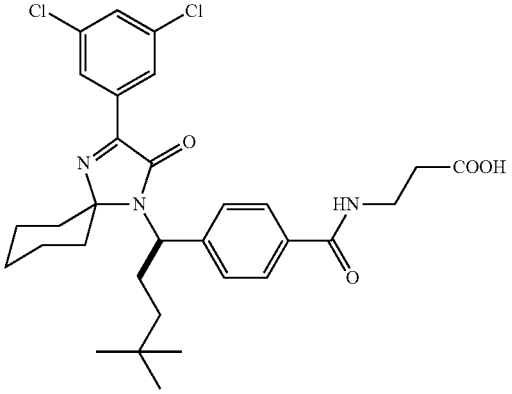 [SMILES: CC(C)(C)CC[C@H](c1ccc(C(=O)NCCC(=O)O)cc1)N1C(=O)C(c2cc(Cl)cc(Cl)c2)=NC12CCCCC2] |
| 1.209 | 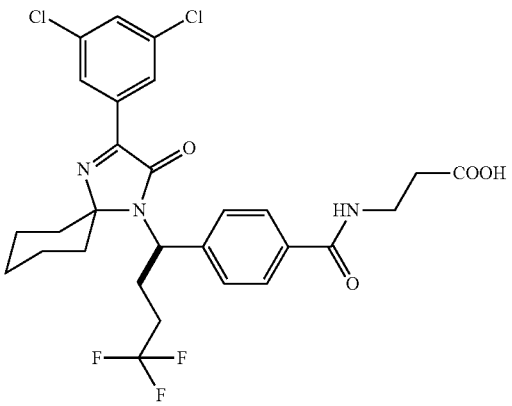 [SMILES: O=C(O)CCNC(=O)c1ccc([C@@H](CCC(F)(F)F)N2C(=O)C(c3cc(Cl)cc(Cl)c3)=NC23CCCCC3)cc1] |
| 1.210 | 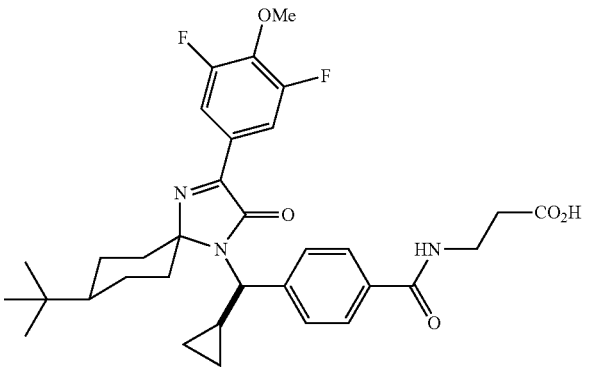 [SMILES: COc1c(F)cc(C2=NC3(CCC(C(C)(C)C)CC3)N([C@@H](c3ccc(C(=O)NCCC(=O)O)cc3)C3CC3)C2=O)cc1F] |
| 1.211 | 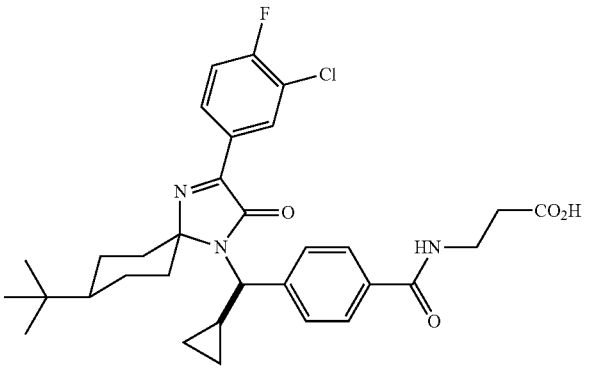 [SMILES: CC(C)(C)C1CCC2(CC1)N=C(c1ccc(F)c(Cl)c1)C(=O)N2[C@@H](c1ccc(C(=O)NCCC(=O)O)cc1)C1CC1] |

| Ex. | Structure |
|---|---|
| 1.212 | 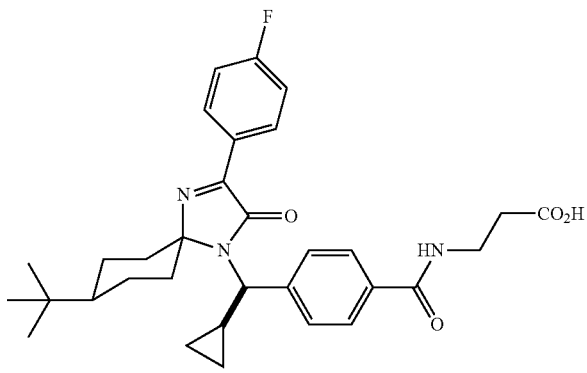 |
| 1.220 | 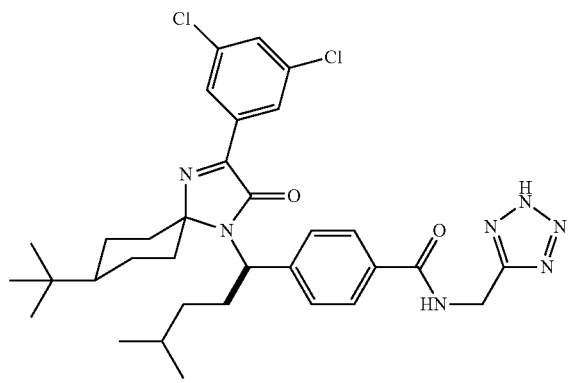 |
| 1.214 | 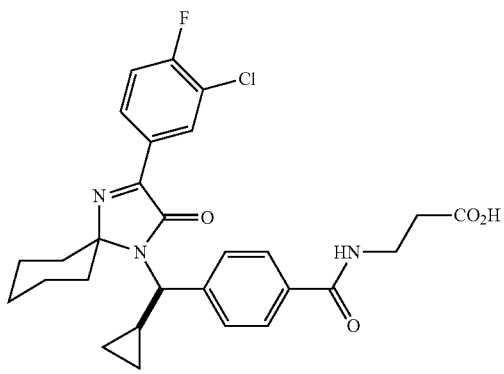 [SMILES: O=C(O)CCNC(=O)c1ccc([C@@H](C2CC2)N2C(=O)C(c3ccc(F)c(Cl)c3)=NC23CCCCC3)cc1] |
| 1.215 | 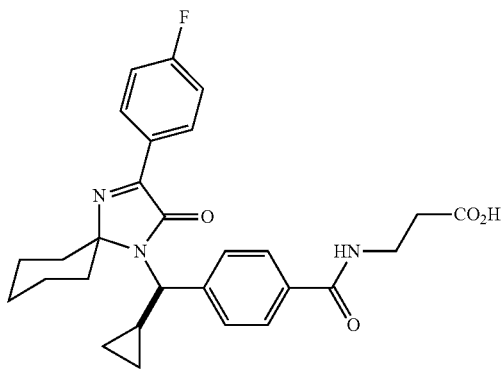 [SMILES: O=C(O)CCNC(=O)c1ccc([C@@H](C2CC2)N2C(=O)C(c3ccc(F)cc3)=NC23CCCCC3)cc1] |

| Ex. | Structure |
|---|---|
| 1.216 | 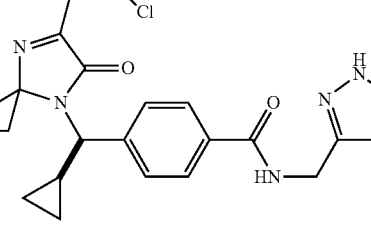 |
| 1.217 | 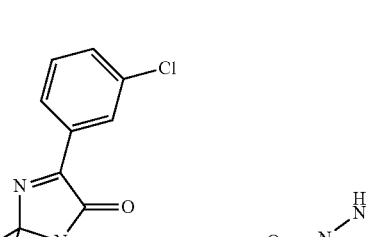 |
| 1.218 | 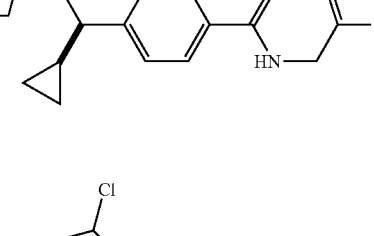 |
| 1.219 | 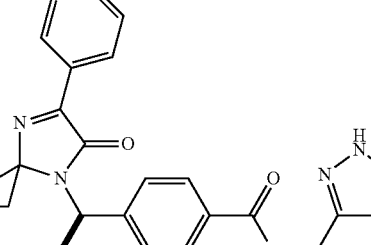 |

-continued
| Ex. | Structure |
|---|---|
| 1.227 | 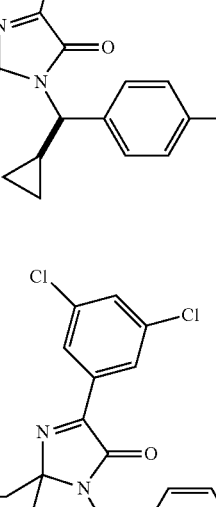 |
| 1.221 | 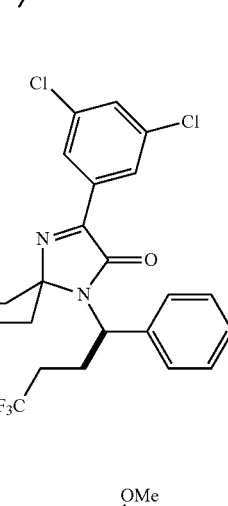 |
| 1.222 | 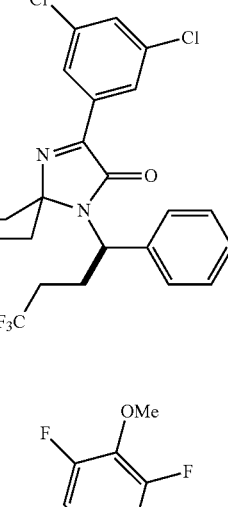 |
| 1.223 | 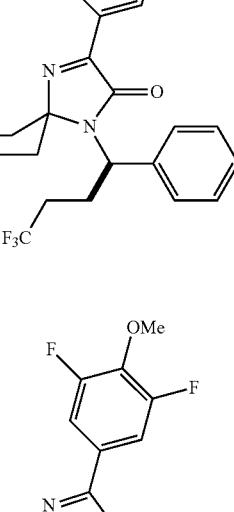 |

| Ex. | Structure |
|---|---|
| 1.224 | 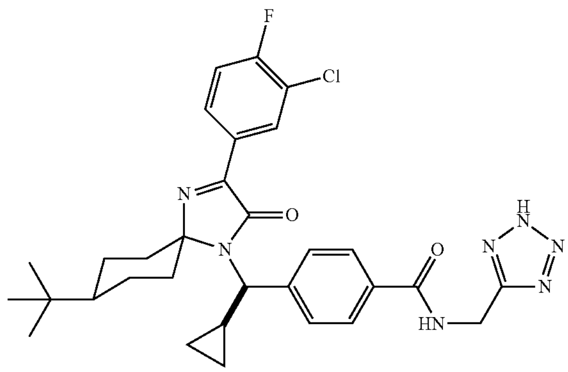 [SMILES: CC(C)(C)C1CCC2(CC1)N=C(c1ccc(F)c(Cl)c1)C(=O)N2[C@@H](c1ccc(C(=O)NCc2nn[nH]n2)cc1)C1CC1] |
| 1.225 | 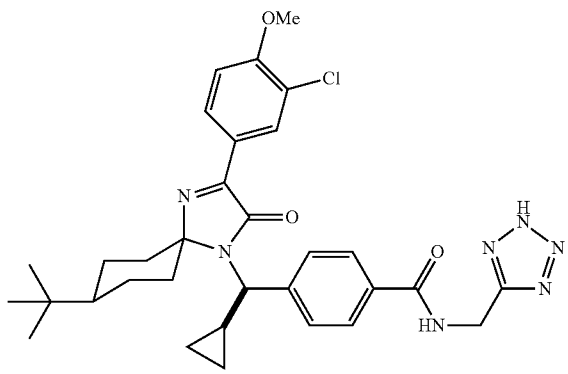 [SMILES: COc1ccc(C2=NC3(CCC(C(C)(C)C)CC3)N([C@@H](c3ccc(C(=O)NCc4nn[nH]n4)cc3)C3CC3)C2=O)cc1Cl] |
| 1.226 | 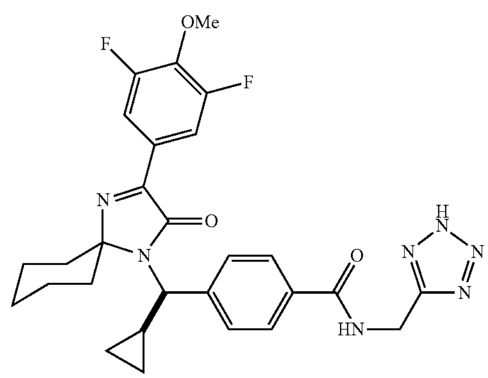 [SMILES: COc1c(F)cc(C2=NC3(CCCCC3)N([C@@H](c3ccc(C(=O)NCc4nn[nH]n4)cc3)C3CC3)C2=O)cc1F] |
| 1.234 | 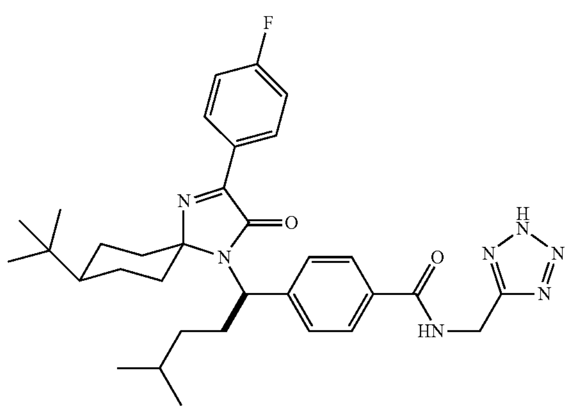 [SMILES: CC(C)CC[C@H](c1ccc(C(=O)NCc2nn[nH]n2)cc1)N1C(=O)C(c2ccc(F)cc2)=NC12CCC(C(C)(C)C)CC2] |

| Ex. | Structure |
|---|---|
| 1.228 | 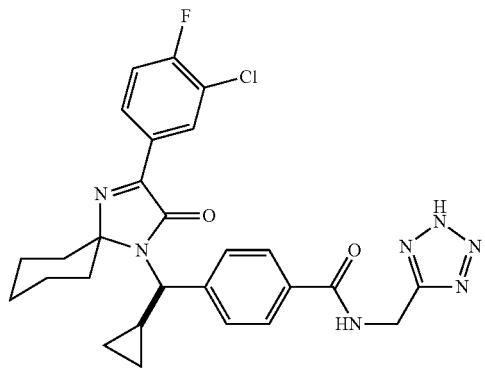 [SMILES: O=C(NCc1nn[nH]n1)c1ccc([C@@H](C2CC2)N2C(=O)C(c3ccc(F)c(Cl)c3)=NC23CCCCC3)cc1] |
| 1.229 | 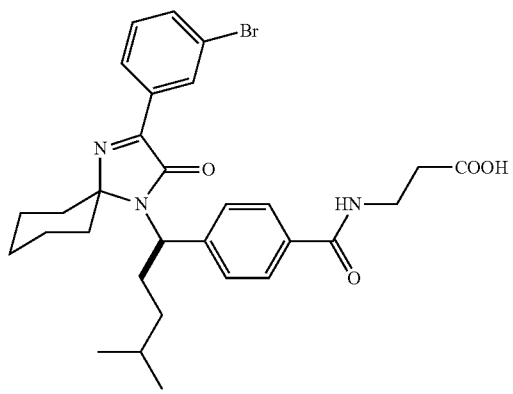 [SMILES: CC(C)CC[C@H](c1ccc(C(=O)NCCC(=O)O)cc1)N1C(=O)C(c2cccc(Br)c2)=NC12CCCCC2] |
| 1.230 | 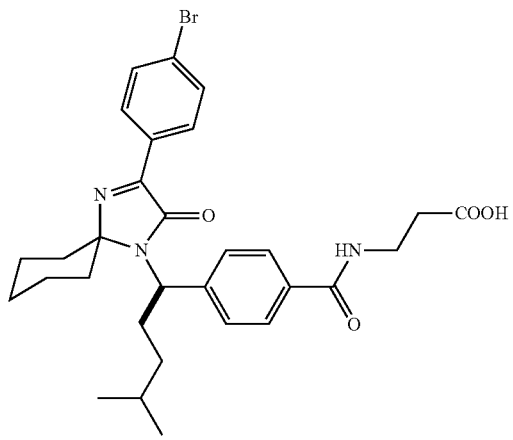 [SMILES: CC(C)CC[C@H](c1ccc(C(=O)NCCC(=O)O)cc1)N1C(=O)C(c2ccc(Br)cc2)=NC12CCCCC2] |
| 1.231 | 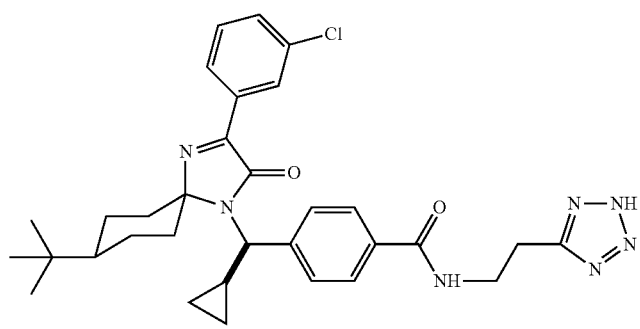 [SMILES: CC(C)(C)C1CCC2(CC1)N=C(c1cccc(Cl)c1)C(=O)N2[C@@H](c1ccc(C(=O)NCCc2nn[nH]n2)cc1)C1CC1] |

| Ex. | Structure |
|---|---|
| 1.232 | 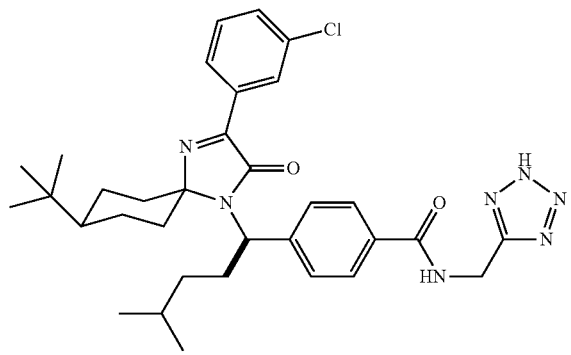 [SMILES: CC(C)CC[C@H](c1ccc(C(=O)NCc2nn[nH]n2)cc1)N1C(=O)C(c2cccc(Cl)c2)=NC12CCC(C(C)(C)C)CC2] |
| 1.233 | 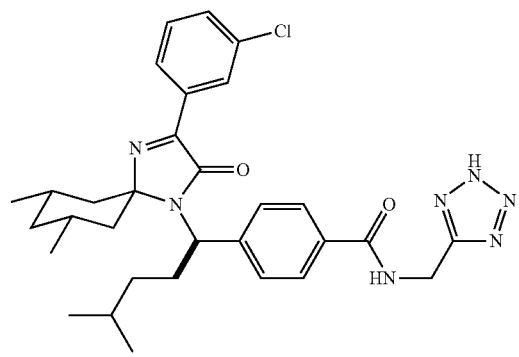 [SMILES: CC(C)CC[C@H](c1ccc(C(=O)NCc2nn[nH]n2)cc1)N1C(=O)C(c2cccc(Cl)c2)=NC12CC(C)CC(C)C2] |
| 1.241 | 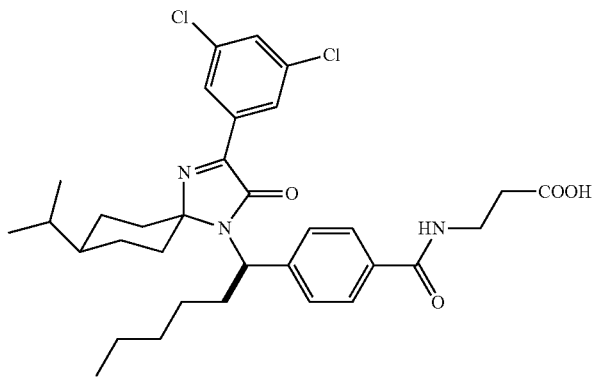 [SMILES: CCCCC[C@H](c1ccc(C(=O)NCCC(=O)O)cc1)N1C(=O)C(c2cc(Cl)cc(Cl)c2)=NC12CCC(C(C)C)CC2] |
| 1.235 | 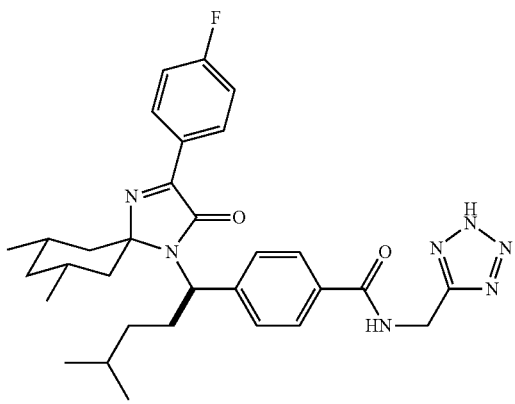 [SMILES: CC(C)CC[C@H](c1ccc(C(=O)NCc2nn[nH]n2)cc1)N1C(=O)C(c2ccc(F)cc2)=NC12CC(C)CC(C)C2] |

-continued

| Ex. | Structure |
|---|---|
| 1.236 | 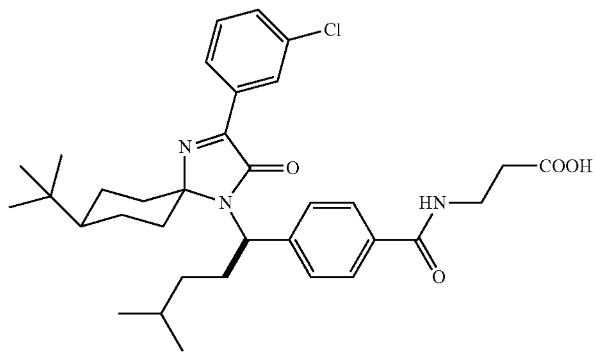 [SMILES: CC(C)CC[C@H](c1ccc(C(=O)NCCC(=O)O)cc1)N1C(=O)C(c2cccc(Cl)c2)=NC12CCC(C(C)(C)C)CC2] |
| 1.237 | 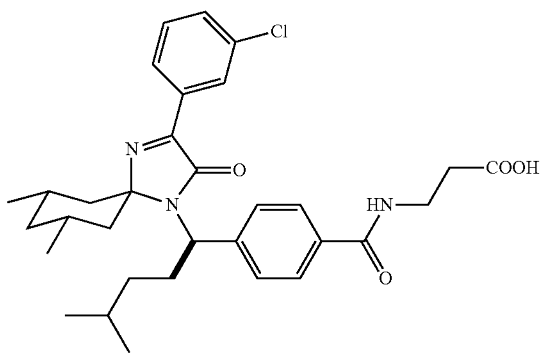 [SMILES: CC(C)CC[C@H](c1ccc(C(=O)NCCC(=O)O)cc1)N1C(=O)C(c2cccc(Cl)c2)=NC12CC(C)CC(C)C2] |
| 1.238 | 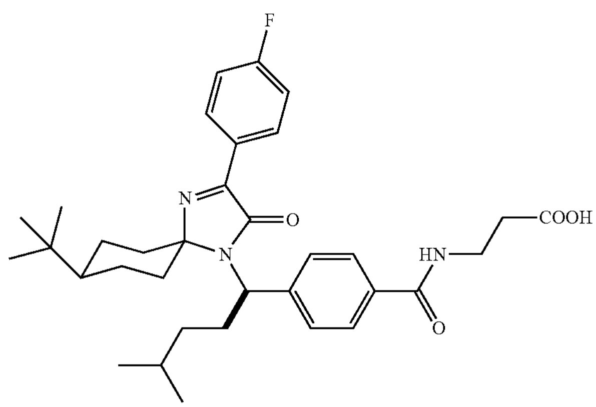 [SMILES: CC(C)CC[C@H](c1ccc(C(=O)NCCC(=O)O)cc1)N1C(=O)C(c2ccc(F)cc2)=NC12CCC(C(C)(C)C)CC2] |
| 1.239 | 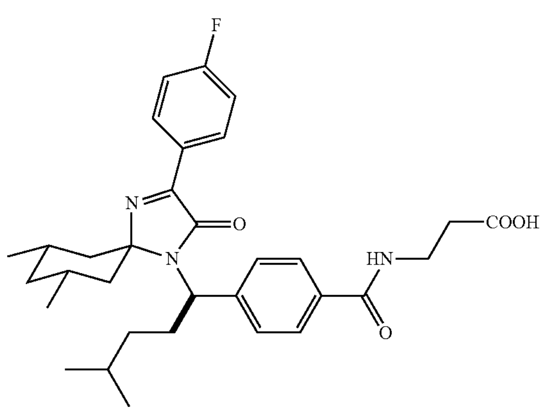 [SMILES: CC(C)CC[C@H](c1ccc(C(=O)NCCC(=O)O)cc1)N1C(=O)C(c2ccc(F)cc2)=NC12CC(C)CC(C)C2] |

-continued

| Ex. | Structure |
|---|---|
| 1.240 | 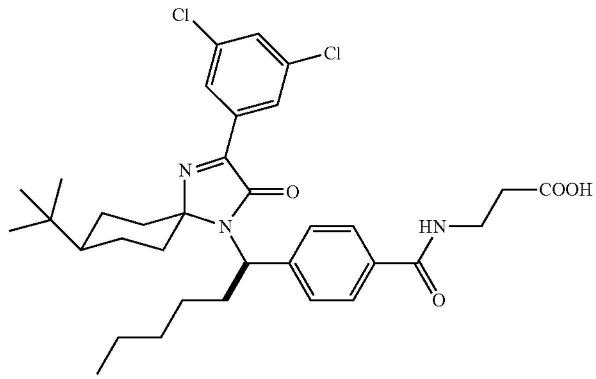 [SMILES: CCCCC[C@H](c1ccc(C(=O)NCCC(=O)O)cc1)N1C(=O)C(c2cc(Cl)cc(Cl)c2)=NC12CCC(C(C)(C)C)CC2] |
| 1.255 | 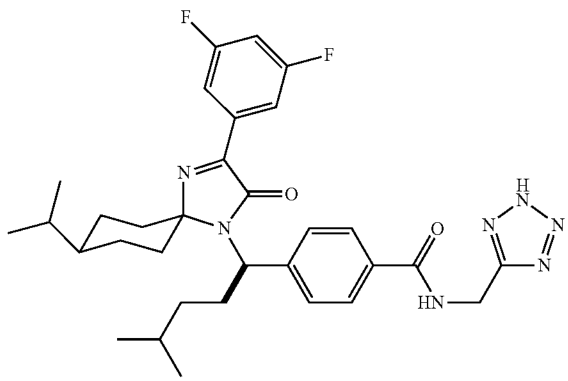 [SMILES: CC(C)CC[C@H](c1ccc(C(=O)NCc2nn[nH]n2)cc1)N1C(=O)C(c2cc(F)cc(F)c2)=NC12CCC(C(C)C)CC2] |
| 1.242 | 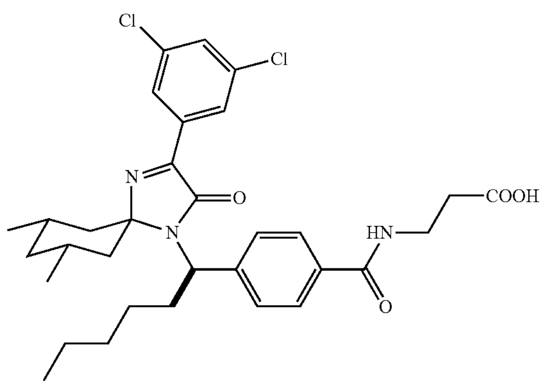 [SMILES: CCCCC[C@H](c1ccc(C(=O)NCCC(=O)O)cc1)N1C(=O)C(c2cc(Cl)cc(Cl)c2)=NC12CC(C)CC(C)C2] |
| 1.243 | 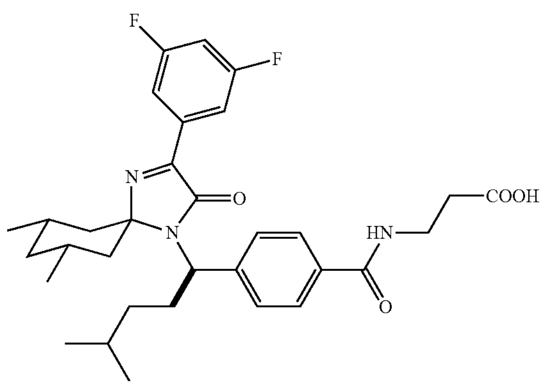 [SMILES: CC(C)CC[C@H](c1ccc(C(=O)NCCC(=O)O)cc1)N1C(=O)C(c2cc(F)cc(F)c2)=NC12CC(C)CC(C)C2] |

| Ex. | Structure |
|---|---|
| 1.244 | 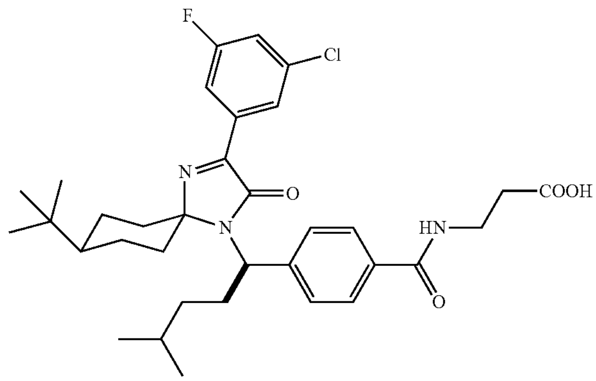 [SMILES: CC(C)CC[C@H](c1ccc(C(=O)NCCC(=O)O)cc1)N1C(=O)C(c2cc(F)cc(Cl)c2)=NC12CCC(C(C)(C)C)CC2] |
| 1.245 | 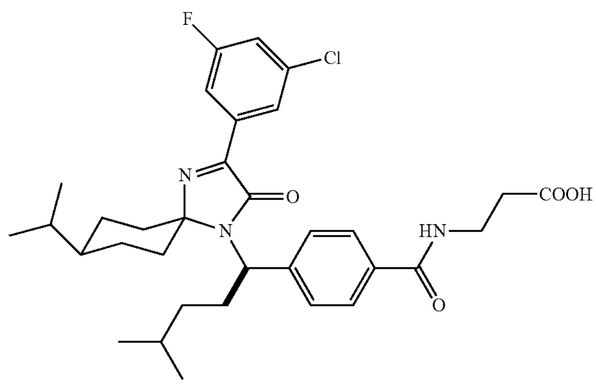 [SMILES: CC(C)CC[C@H](c1ccc(C(=O)NCCC(=O)O)cc1)N1C(=O)C(c2cc(F)cc(Cl)c2)=NC12CCC(C(C)C)CC2] |
| 1.246 | 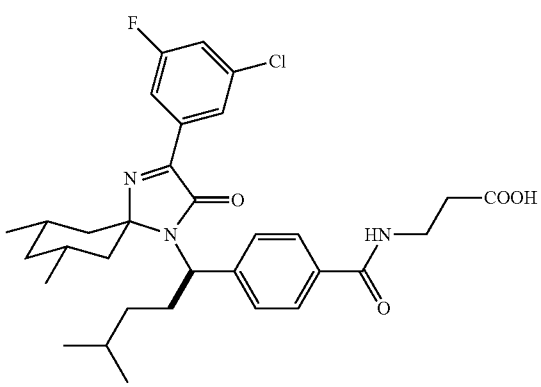 [SMILES: CC(C)CC[C@H](c1ccc(C(=O)NCCC(=O)O)cc1)N1C(=O)C(c2cc(F)cc(Cl)c2)=NC12CC(C)CC(C)C2] |
| 1.247 | 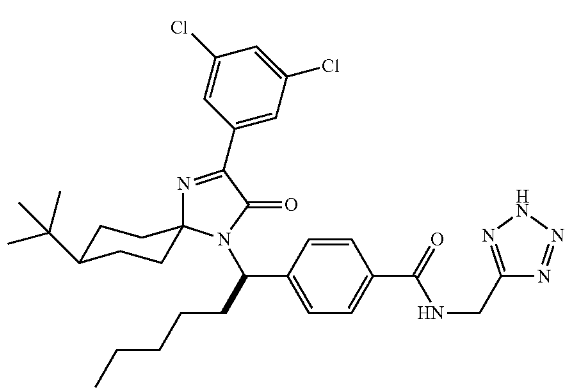 |

-continued
| Ex. | Structure |
|---|---|
| 1.248 | 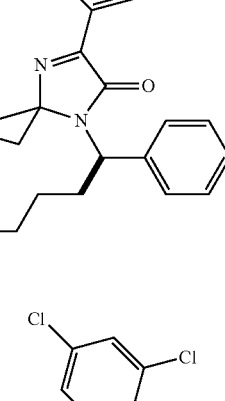 |
| 1.256 | 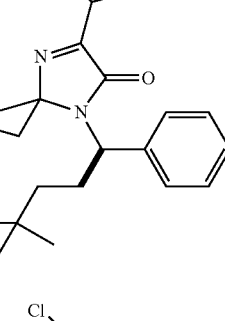 |
| 1.257 | 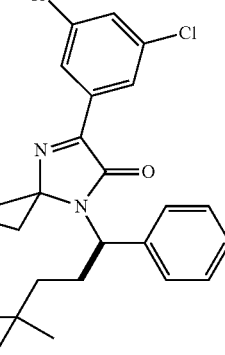 |
| 1.258 | 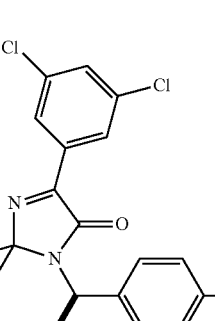 |

| Ex. | Structure |
|---|---|
| 1.259 | 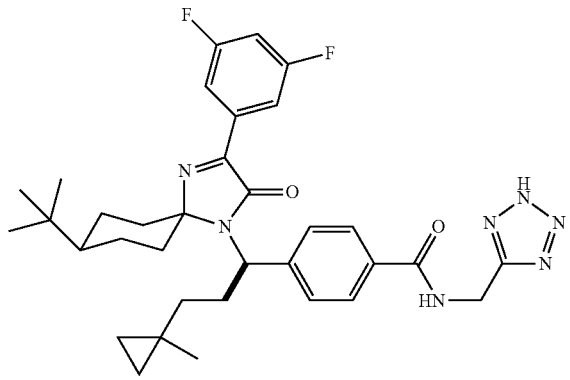 [SMILES: CC1(CC[C@H](c2ccc(C(=O)NCc3nn[nH]n3)cc2)N2C(=O)C(c3cc(F)cc(F)c3)=NC23CCC(C(C)(C)C)CC3)CC1] |
| 1.260 | 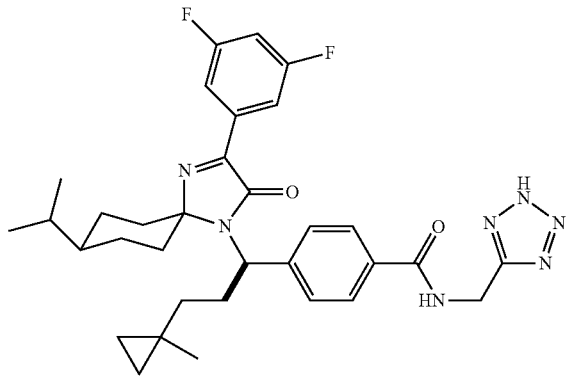 [SMILES: CC(C)C1CCC2(CC1)N=C(c1cc(F)cc(F)c1)C(=O)N2[C@H](CCC1(C)CC1)c1ccc(C(=O)NCc2nn[nH]n2)cc1] |
| 1.261 | 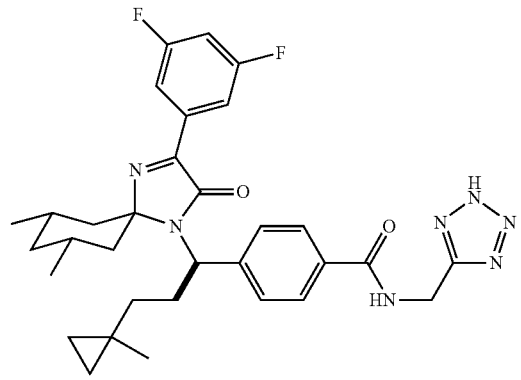 [SMILES: CC1CC(C)CC2(C1)N=C(c1cc(F)cc(F)c1)C(=O)N2[C@H](CCC1(C)CC1)c1ccc(C(=O)NCc2nn[nH]n2)cc1] |
| 1.262 | 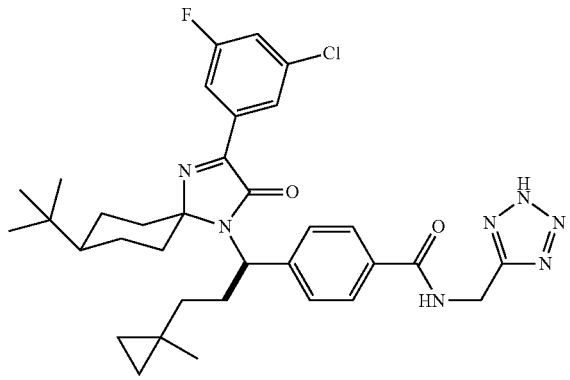 [SMILES: CC1(CC[C@H](c2ccc(C(=O)NCc3nn[nH]n3)cc2)N2C(=O)C(c3cc(F)cc(Cl)c3)=NC23CCC(C(C)(C)C)CC3)CC1] |

-continued

| Ex. | Structure |
|---|---|
| 1.249 | 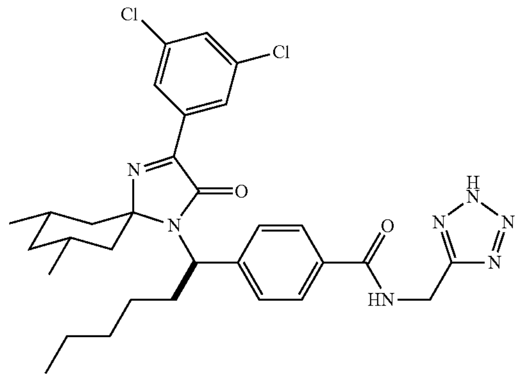 [SMILES: CCCCC[C@H](c1ccc(C(=O)NCc2nn[nH]n2)cc1)N1C(=O)C(c2cc(Cl)cc(Cl)c2)=NC12CC(C)CC(C)C2] |
| 1.250 | 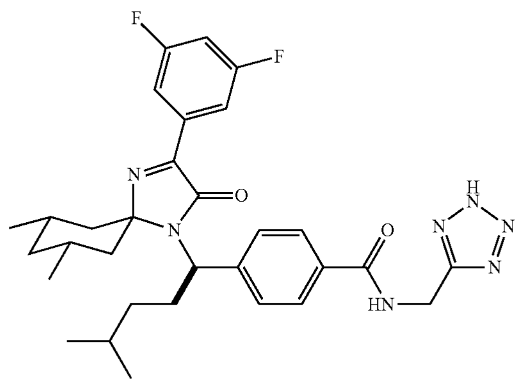 [SMILES: CC(C)CC[C@H](c1ccc(C(=O)NCc2nn[nH]n2)cc1)N1C(=O)C(c2cc(F)cc(F)c2)=NC12CC(C)CC(C)C2] |
| 1.251 | 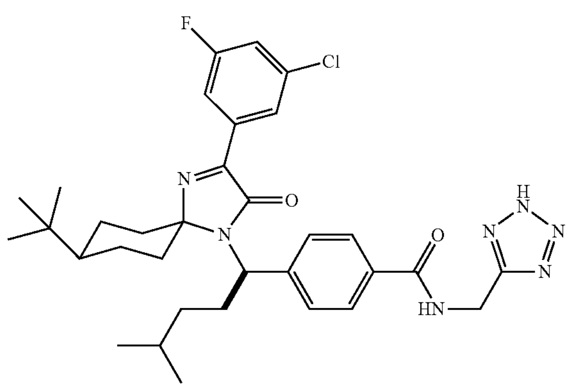 |
| 1.252 | 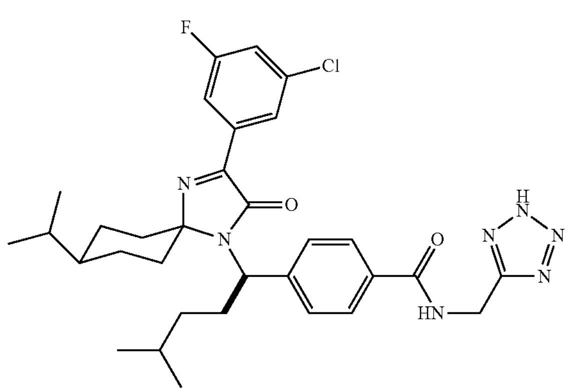 |

-continued

| Ex. | Structure |
|---|---|
| 1.253 | 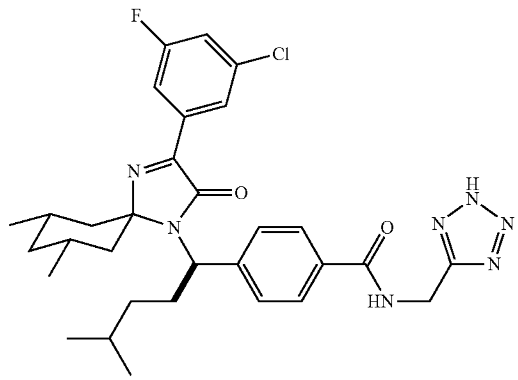 |
| 1.254 | 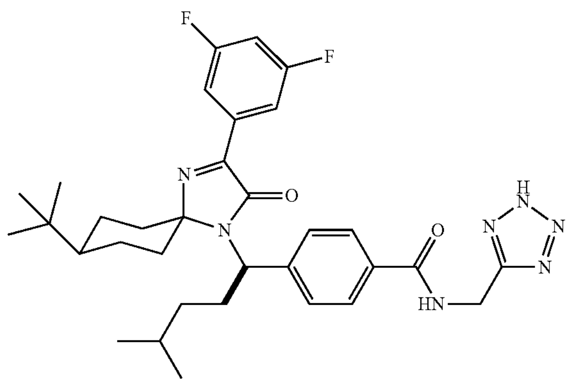 [SMILES: CC(C)CC[C@H](c1ccc(C(=O)NCc2nn[nH]n2)cc1)N1C(=O)C(c2cc(F)cc(Cl)c2)=NC12CCC(C(C)(C)C)CC2] |
| 1.269 | 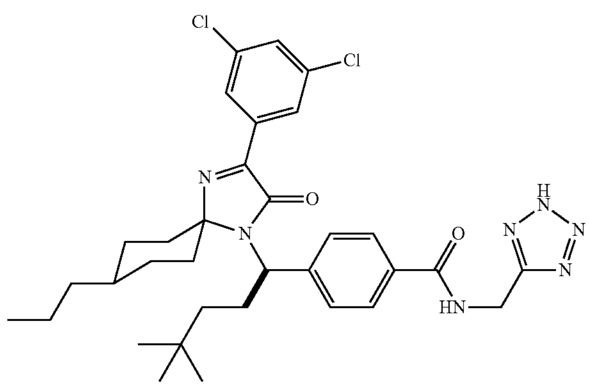 [SMILES: CCCC1CCC2(CC1)N=C(c1cc(Cl)cc(Cl)c1)C(=O)N2[C@H](CCC(C)(C)C)c1ccc(C(=O)NCc2nn[nH]n2)cc1] |
| 1.263 | 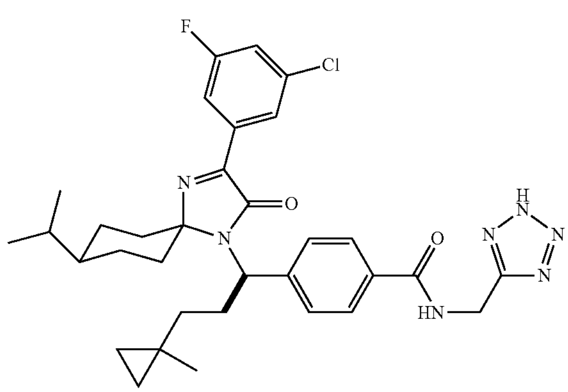 [SMILES: CC(C)C1CCC2(CC1)N=C(c1cc(F)cc(Cl)c1)C(=O)N2[C@H](CCC1(C)CC1)c1ccc(C(=O)NCc2nn[nH]n2)cc1] |

-continued
| Ex. | Structure |
|---|---|
| 1.264 | 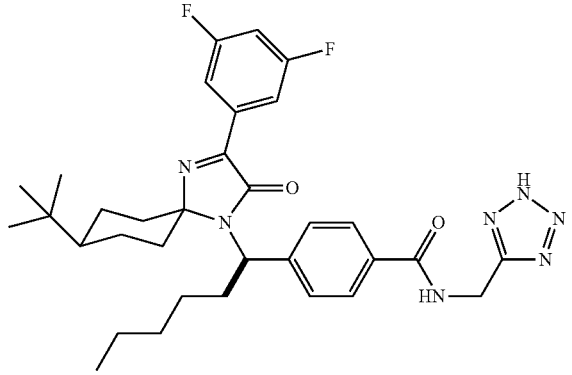 |
| 1.265 | 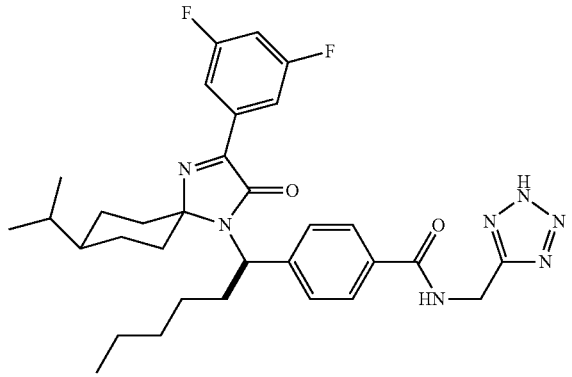 [SMILES: CCCCC[C@H](c1ccc(C(=O)NCc2nn[nH]n2)cc1)N1C(=O)C(c2cc(F)cc(F)c2)=NC12CCC(C(C)C)CC2] |
| 1.266 | 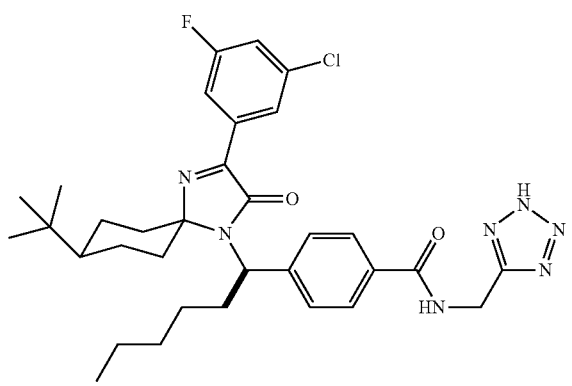 [SMILES: CCCCC[C@H](c1ccc(C(=O)NCc2nn[nH]n2)cc1)N1C(=O)C(c2cc(F)cc(Cl)c2)=NC12CCC(C(C)(C)C)CC2] |
| 1.267 | 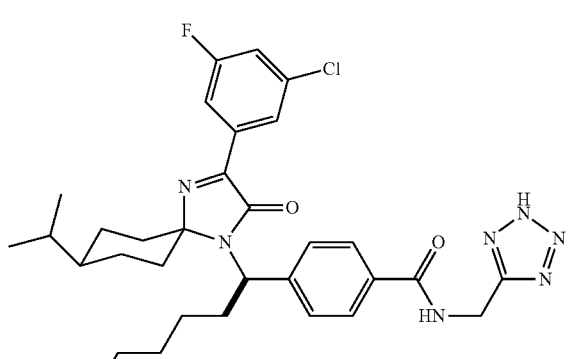 |

-continued
| Ex. | Structure |
|---|---|
| 1.268 | 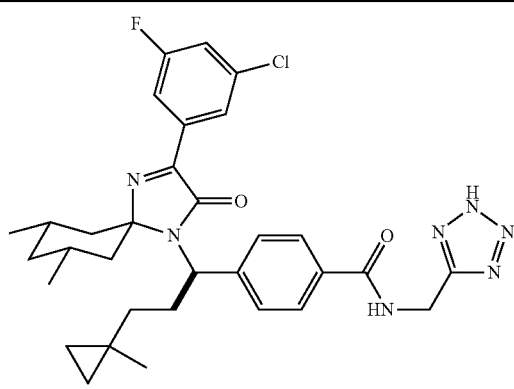 |
| 1.276 | 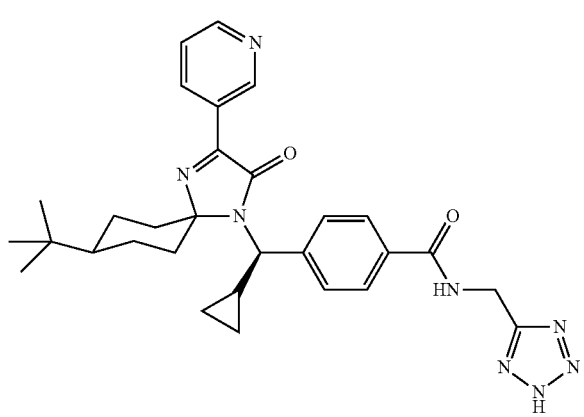 [SMILES: CC(C)(C)C1CCC2(CC1)N=C(c1cccnc1)C(=O)N2[C@@H](c1ccc(C(=O)NCc2nn[nH]n2)cc1)C1CC1] |
| 1.270 | 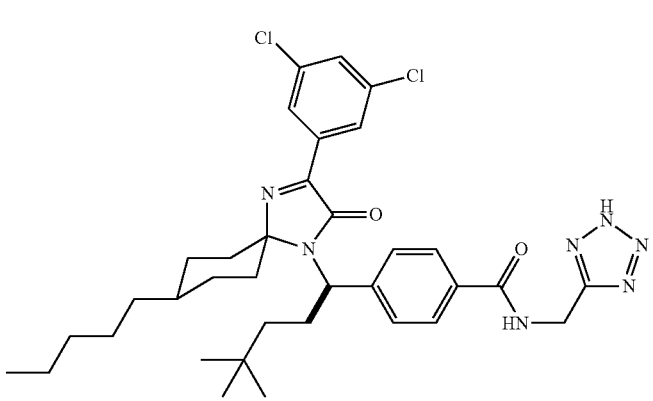 [SMILES: CCCCCC1CCC2(CC1)N=C(c1cc(Cl)cc(Cl)c1)C(=O)N2[C@H](CCC(C)(C)C)c1ccc(C(=O)NCc2nn[nH]n2)cc1] |
| 1.271 | 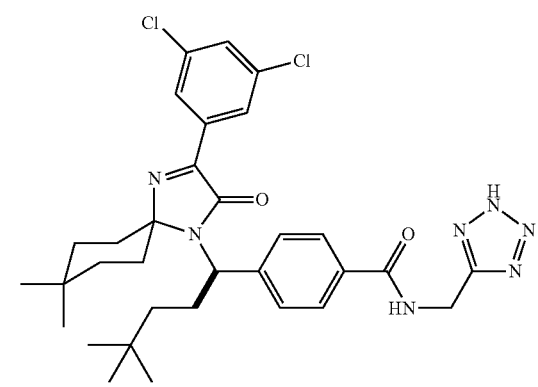 [SMILES: CC(C)(C)CC[C@H](c1ccc(C(=O)NCc2nn[nH]n2)cc1)N1C(=O)C(c2cc(Cl)cc(Cl)c2)=NC12CCC(C)(C)CC2] |

| Ex. | Structure |
|---|---|
| 1.272 | 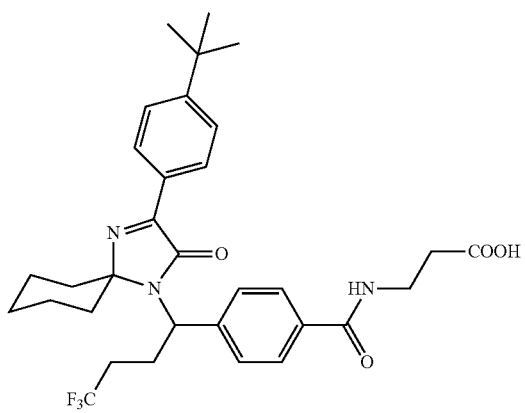 [SMILES: CC(C)(C)c1ccc(C2=NC3(CCCCC3)N(C(CCC(F)(F)F)c3ccc(C(=O)NCCC(=O)O)cc3)C2=O)cc1] |
| 1.273 | 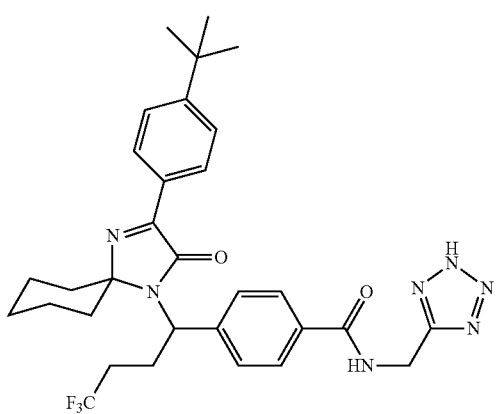 [SMILES: CC(C)(C)c1ccc(C2=NC3(CCCCC3)N(C(CCC(F)(F)F)c3ccc(C(=O)NCc4nn[nH]n4)cc3)C2=O)cc1] |
| 1.274 | 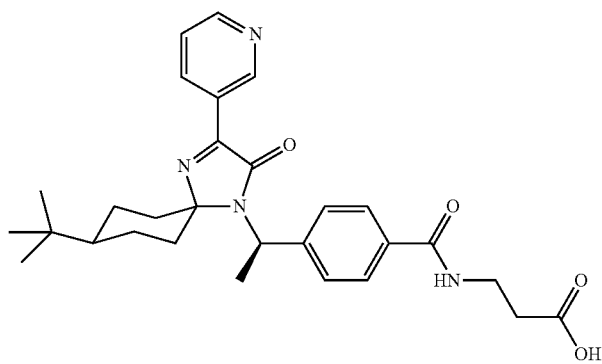 [SMILES: C[C@H](c1ccc(C(=O)NCCC(=O)O)cc1)N1C(=O)C(c2cccnc2)=NC12CCC(C(C)(C)C)CC2] |
| 1.275 | 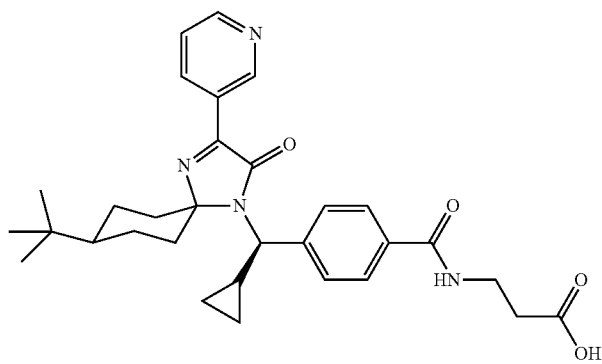 [SMILES: CC(C)(C)C1CCC2(CC1)N=C(c1cccnc1)C(=O)N2[C@@H](c1ccc(C(=O)NCCC(=O)O)cc1)C1CC1] |

-continued
| Ex. | Structure |
|---|---|
| 1.277 | 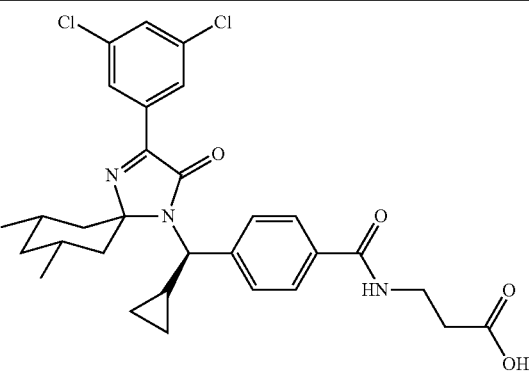 |
| 1.278 | 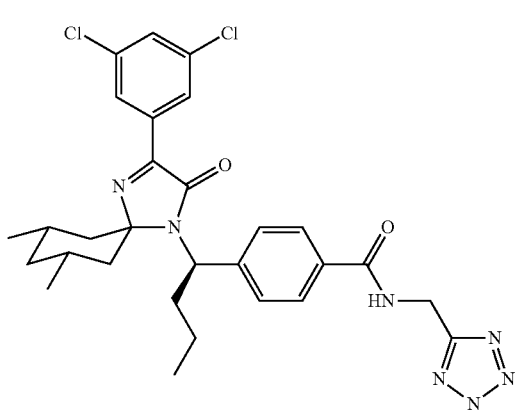 |
| 1.279 | 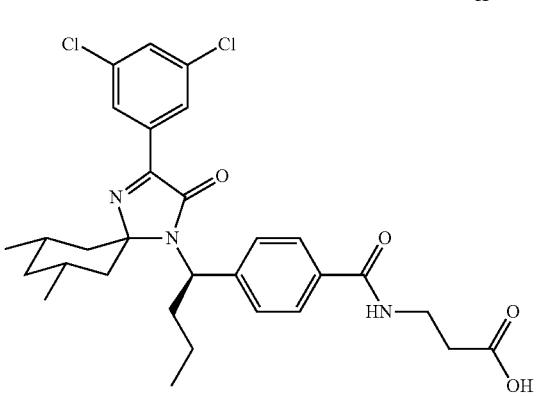 |
| 1.280 | 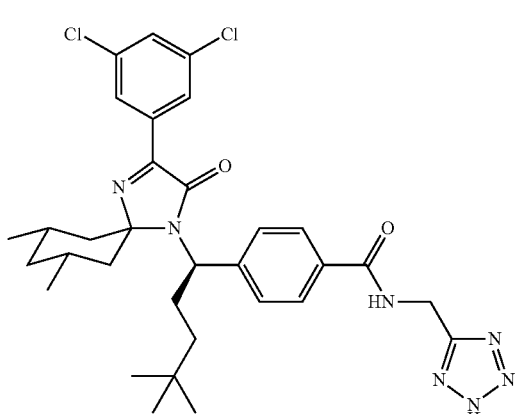 |

-continued
| Ex. | Structure |
|---|---|
| 1.281 | 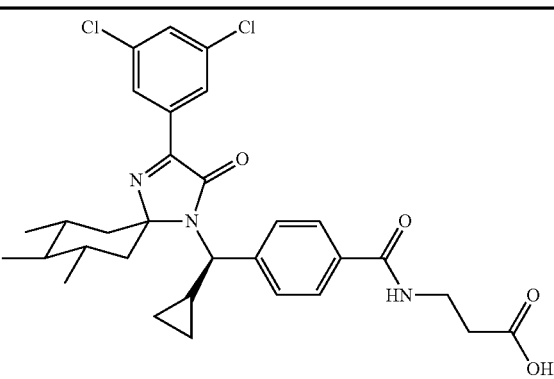 |
| 1.293 | 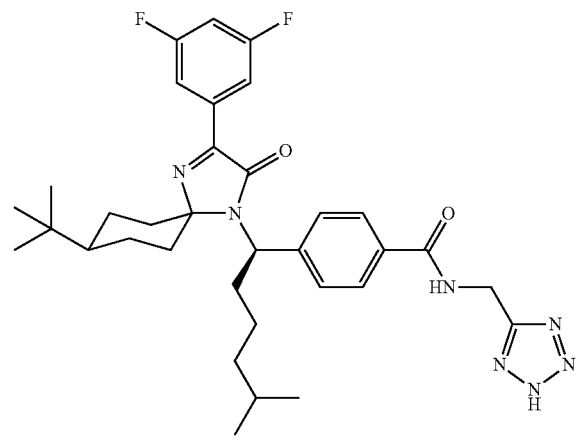 [SMILES: CC(C)CCC[C@H](c1ccc(C(=O)NCc2nn[nH]n2)cc1)N1C(=O)C(c2cc(F)cc(F)c2)=NC12CCC(C(C)(C)C)CC2] |
| 1.282 | 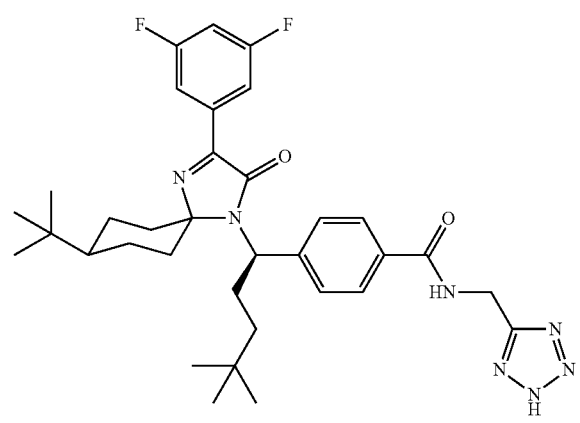 [SMILES: CC(C)(C)CC[C@H](c1ccc(C(=O)NCc2nn[nH]n2)cc1)N1C(=O)C(c2cc(F)cc(F)c2)=NC12CCC(C(C)(C)C)CC2] |
| 1.283 | 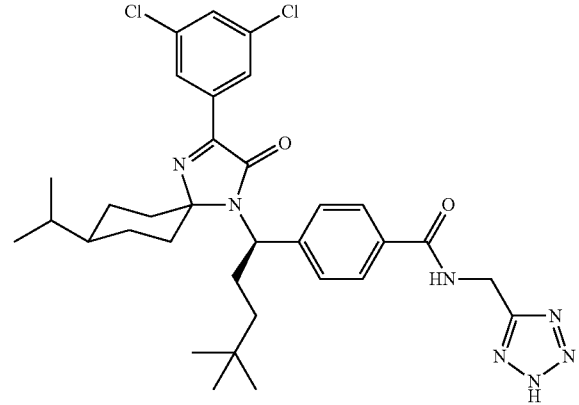 [SMILES: CC(C)C1CCC2(CC1)N=C(c1cc(Cl)cc(Cl)c1)C(=O)N2[C@H](CCC(C)(C)C)c1ccc(C(=O)NCc2nn[nH]n2)cc1] |

-continued
| Ex. | Structure |
|---|---|
| 1.284 | 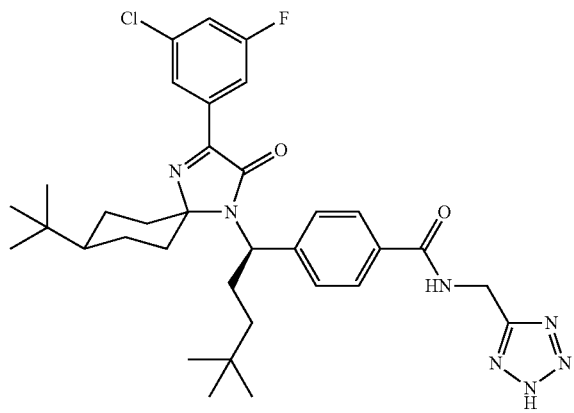 |
| 1.285 | 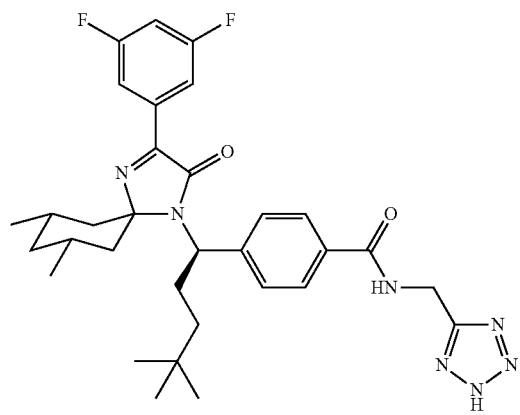 [SMILES: CC1CC(C)CC2(C1)N=C(c1cc(F)cc(Cl)c1)C(=O)N2[C@H](CCC(C)(C)C)c1ccc(C(=O)NCc2nn[nH]n2)cc1] |
| 1.286 | 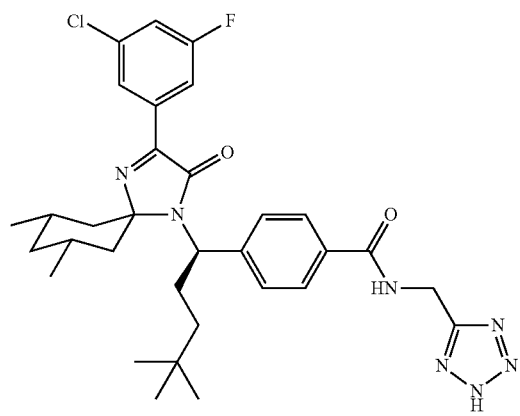 |

| Ex. | Structure |
|---|---|
| 1.290 | 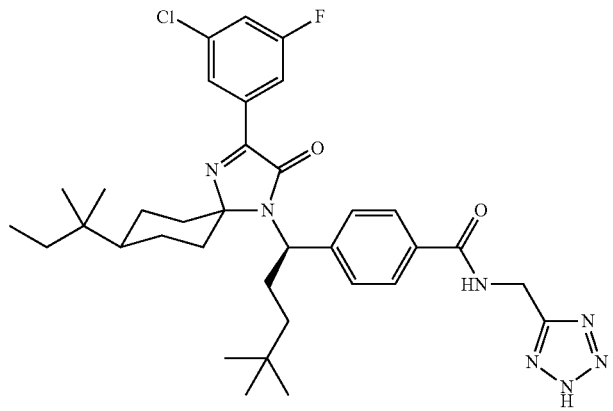 |
| 1.294 | 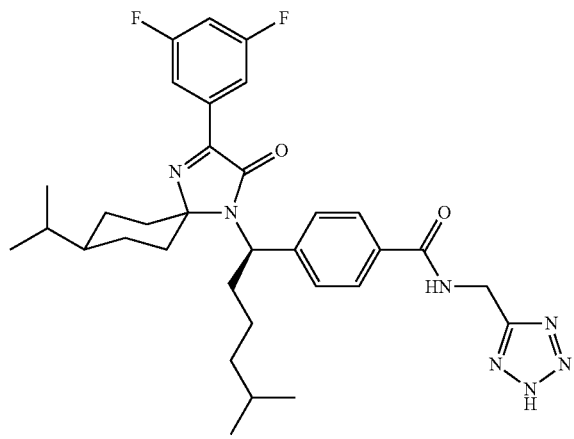 [SMILES: CC(C)CCC[C@H](c1ccc(C(=O)NCc2nn[nH]n2)cc1)N1C(=O)C(c2cc(F)cc(F)c2)=NC12CCC(C(C)C)CC2] |
| 1.295 | 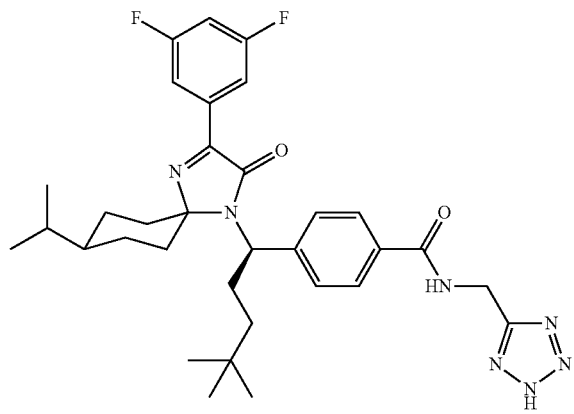 [SMILES: CC(C)C1CCC2(CC1)N=C(c1cc(F)cc(F)c1)C(=O)N2[C@H](CCC(C)(C)C)c1ccc(C(=O)NCc2nn[nH]n2)cc1] |

| Ex. | Structure |
|---|---|
| 1.287 | 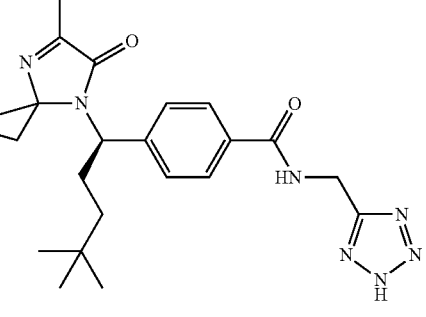 |
| 1.288 | 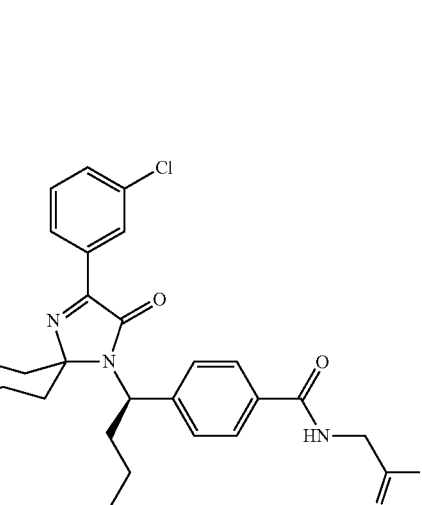 |
| 1.289 | 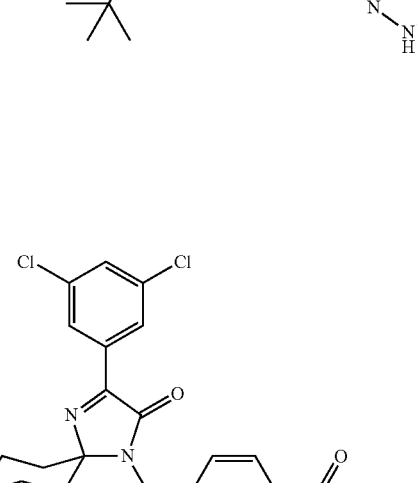 |

| Ex. | Structure |
|---|---|
| 1.296 | 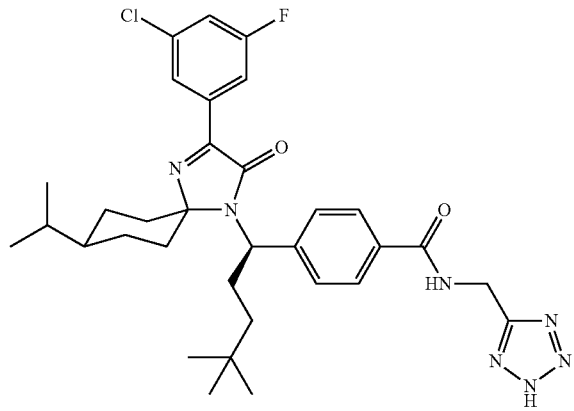 |
| 1.291 | 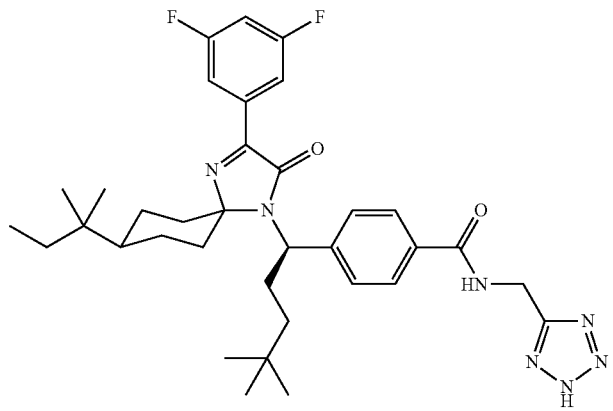 [SMILES: CCC(C)(C)C1CCC2(CC1)N=C(c1cc(Cl)cc(Cl)c1)C(=O)N2[C@H](CCC(C)(C)C)c1ccc(C(=O)NCc2nn[nH]n2)cc1] |
| 1.292 | 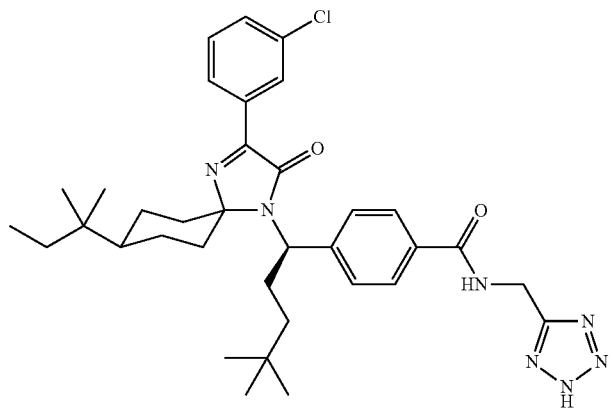 [SMILES: CCC(C)(C)C1CCC2(CC1)N=C(c1cccc(Cl)c1)C(=O)N2[C@H](CCC(C)(C)C)c1ccc(C(=O)NCc2nn[nH]n2)cc1] |

| Ex. | Structure |
|---|---|
| 1.299 | 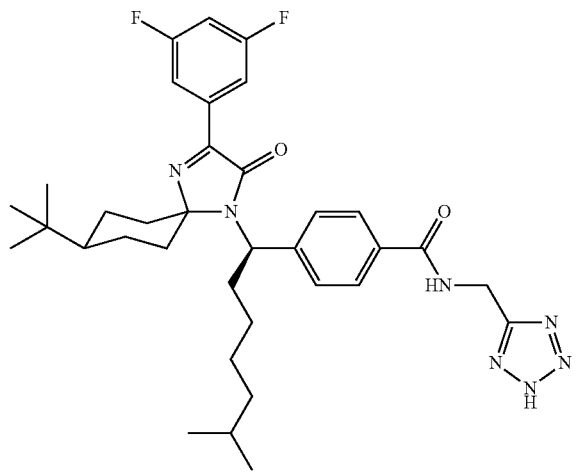 [SMILES: CC(C)CCCC[C@H](c1ccc(C(=O)NCc2nn[nH]n2)cc1)N1C(=O)C(c2cc(F)cc(F)c2)=NC12CCC(C(C)(C)C)CC2] |
| 1.300 | 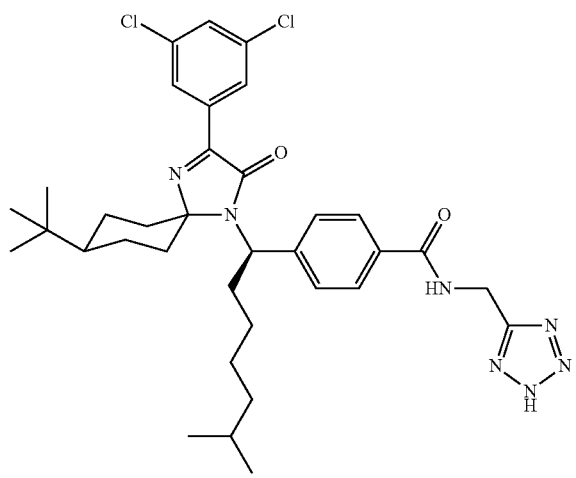 |
| 1.301 | 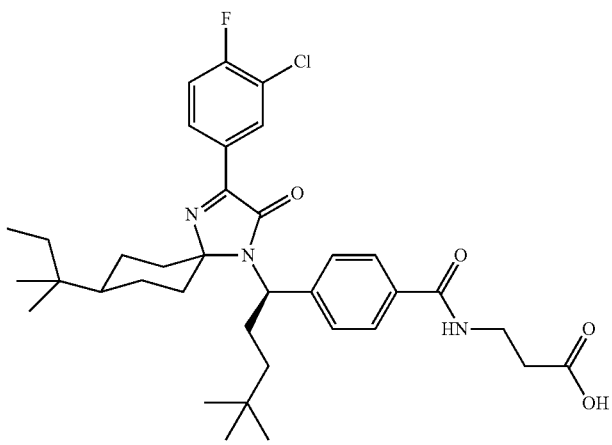 [SMILES: CCC(C)(C)C1CCC2(CC1)N=C(c1ccc(F)c(Cl)c1)C(=O)N2[C@H](CCC(C)(C)C)c1ccc(C(=O)NCCC(=O)O)cc1] |

| Ex. | Structure |
|---|---|
| 1.302 | 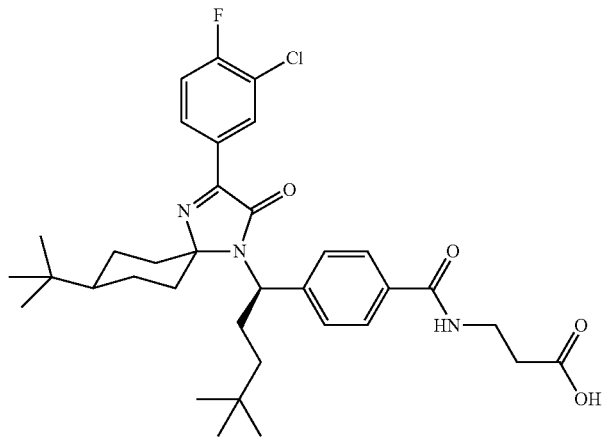 [SMILES: CC(C)(C)CC[C@H](c1ccc(C(=O)NCCC(=O)O)cc1)N1C(=O)C(c2ccc(F)c(Cl)c2)=NC12CCC(C(C)(C)C)CC2] |
| 1.297 | 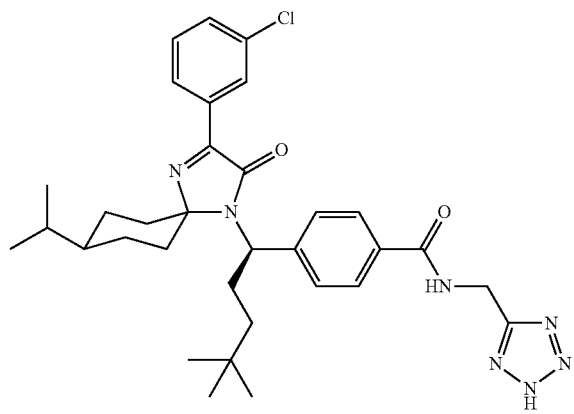 [SMILES: CC(C)C1CCC2(CC1)N=C(c1cccc(Cl)c1)C(=O)N2[C@H](CCC(C)(C)C)c1ccc(C(=O)NCc2nn[nH]n2)cc1] |
| 1.298 | 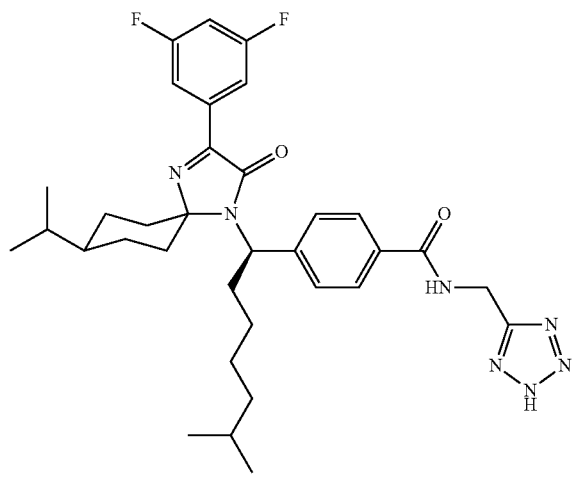 [SMILES: CC(C)CCCC[C@H](c1ccc(C(=O)NCc2nn[nH]n2)cc1)N1C(=O)C(c2cc(F)cc(F)c2)=NC12CCC(C(C)C)CC2] |

| Ex. | Structure |
|---|---|
| 1.310 | 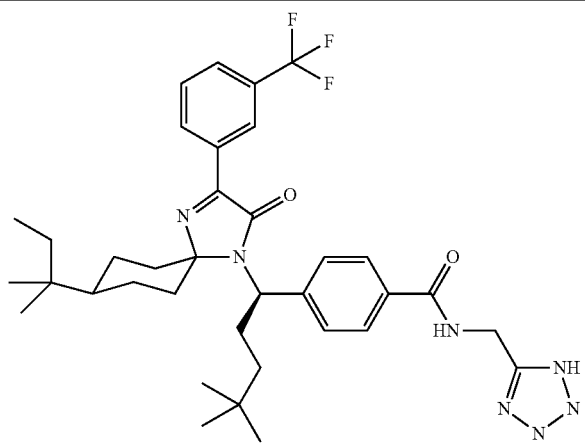 |
| 1.311 | 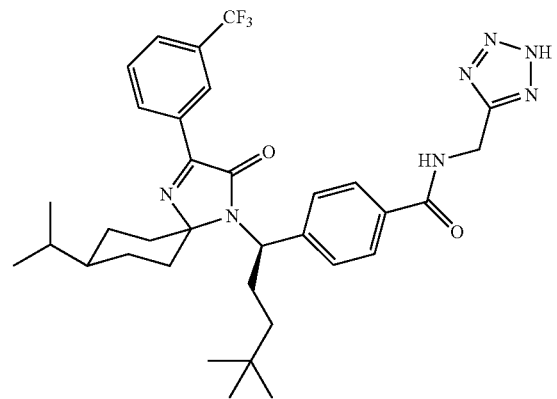 [SMILES: CC(C)C1CCC2(CC1)N=C(c1cccc(C(F)(F)F)c1)C(=O)N2[C@H](CCC(C)(C)C)c1ccc(C(=O)NCc2nn[nH]n2)cc1] |
| 1.312 | 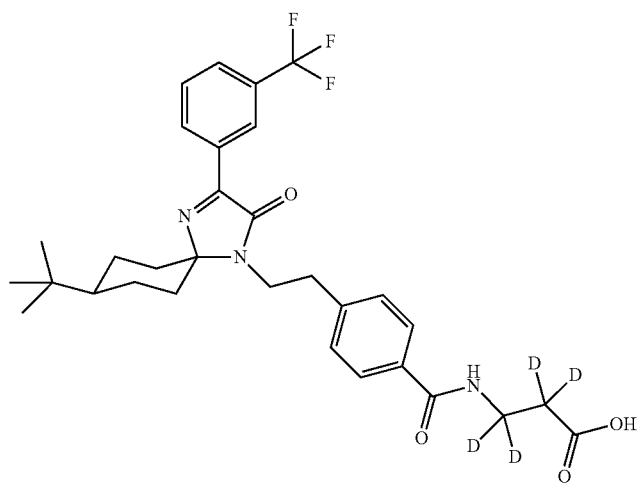 [SMILES: [2H]C([2H])(NC(=O)c1ccc(CCN2C(=O)C(c3cccc(C(F)(F)F)c3)=NC23CCC(C(C)(C)C)CC3)cc1)C([2H])([2H])C(=O)O] |
| 1.313 | 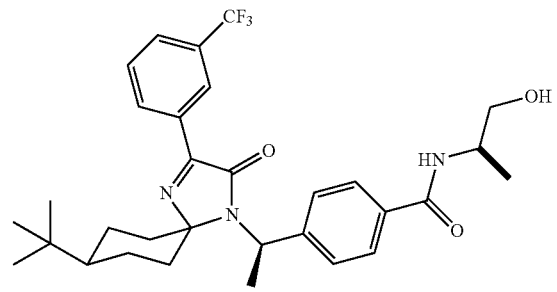 [SMILES: C[C@H](CO)NC(=O)c1ccc([C@@H](C)N2C(=O)C(c3cccc(C(F)(F)F)c3)=NC23CCC(C(C)(C)C)CC3)cc1] |

| Ex. | Structure |
|---|---|
| 1.303 | 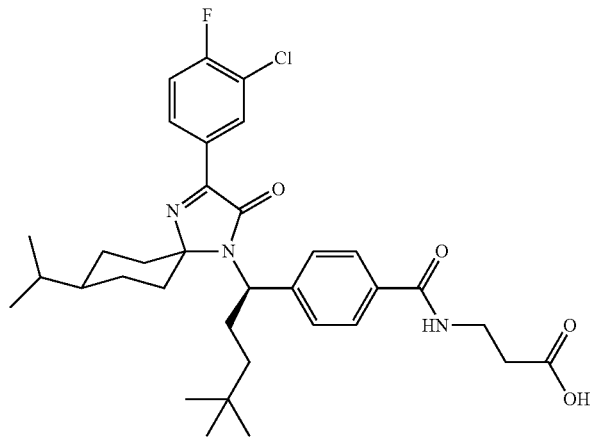 [SMILES: CC(C)C1CCC2(CC1)N=C(c1ccc(F)c(Cl)c1)C(=O)N2[C@H](CCC(C)(C)C)c1ccc(C(=O)NCCC(=O)O)cc1] |
| 1.304 | 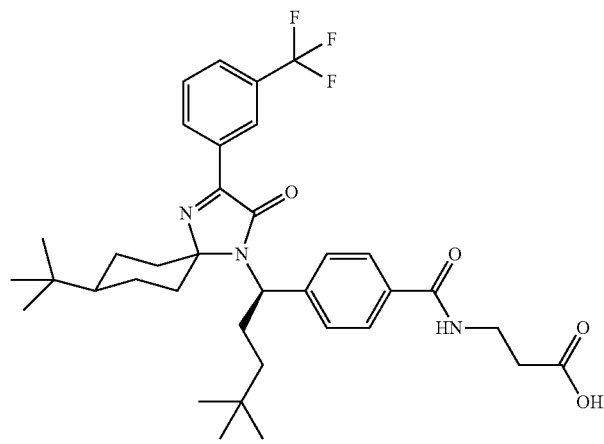 [SMILES: CC(C)(C)CC[C@H](c1ccc(C(=O)NCCC(=O)O)cc1)N1C(=O)C(c2cccc(C(F)(F)F)c2)=NC12CCC(C(C)(C)C)CC2] |
| 1.305 | 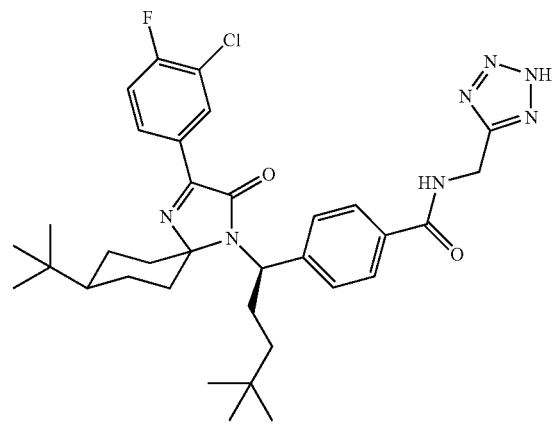 |

-continued
| Ex. | Structure |
|---|---|
| 1.306 | 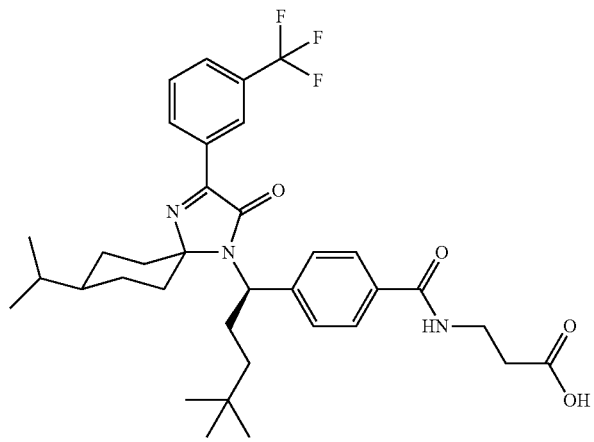 [SMILES: CC(C)C1CCC2(CC1)N=C(c1cccc(C(F)(F)F)c1)C(=O)N2[C@H](CCC(C)(C)C)c1ccc(C(=O)NCCC(=O)O)cc1] |
| 1.307 | 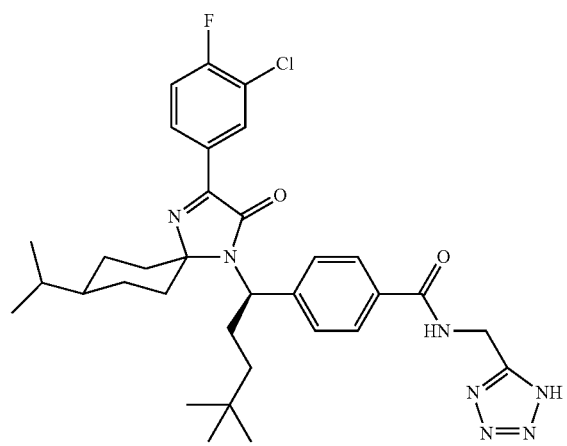 [SMILES: CC(C)C1CCC2(CC1)N=C(c1ccc(F)c(Cl)c1)C(=O)N2[C@H](CCC(C)(C)C)c1ccc(C(=O)NCc2nnn[nH]2)cc1] |
| 1.308 | 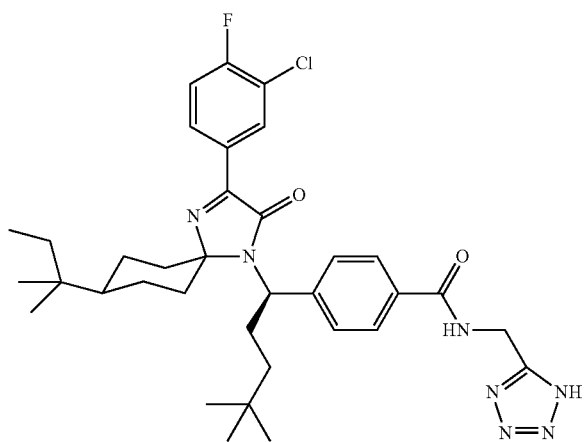 |

| Ex. | Structure |
|---|---|
| 1.314 | 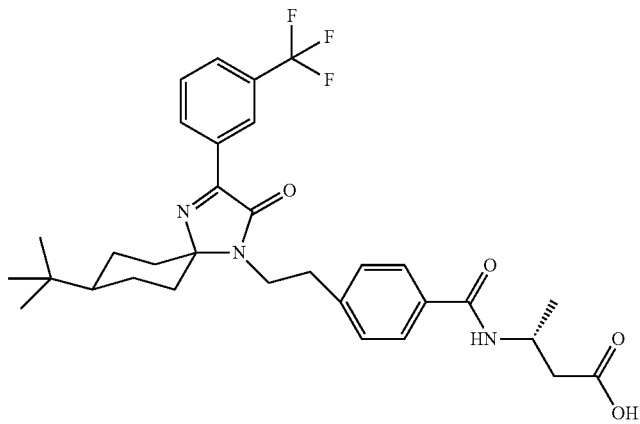 [SMILES: C[C@H](CC(=O)O)NC(=O)c1ccc(CCN2C(=O)C(c3cccc(C(F)(F)F)c3)=NC23CCC(C(C)(C)C)CC3)cc1] |
| 1.315 | 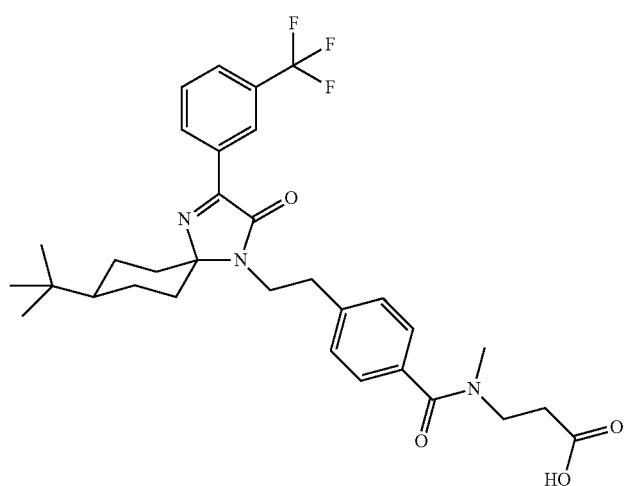 [SMILES: CN(CCC(=O)O)C(=O)c1ccc(CCN2C(=O)C(c3cccc(C(F)(F)F)c3)=NC23CCC(C(C)(C)C)CC3)cc1] |
| 1.316 | 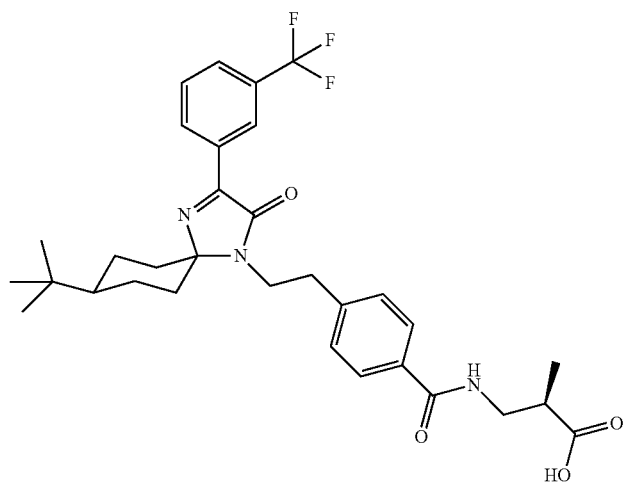 [SMILES: C[C@H](CNC(=O)c1ccc(CCN2C(=O)C(c3cccc(C(F)(F)F)c3)=NC23CCC(C(C)(C)C)CC3)cc1)C(=O)O] |

| Ex. | Structure |
|---|---|
| 1.317 | 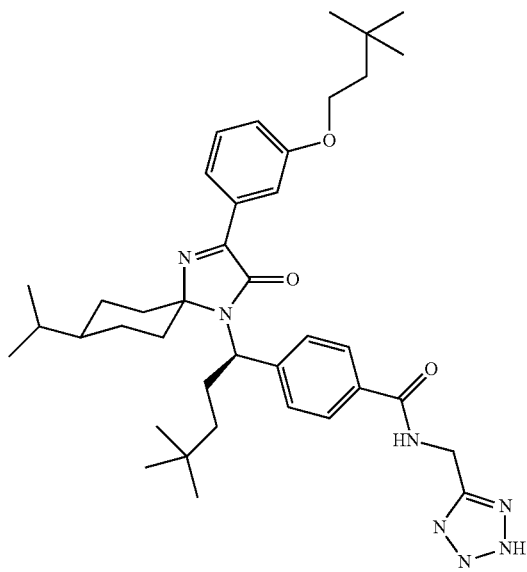 [SMILES: CC(C)C1CCC2(CC1)N=C(c1cccc(OCCC(C)(C)C)c1)C(=O)N2[C@H](CCC(C)(C)C)c1ccc(C(=O)NCC2=NNNN2)cc1] |
| 1.318 | 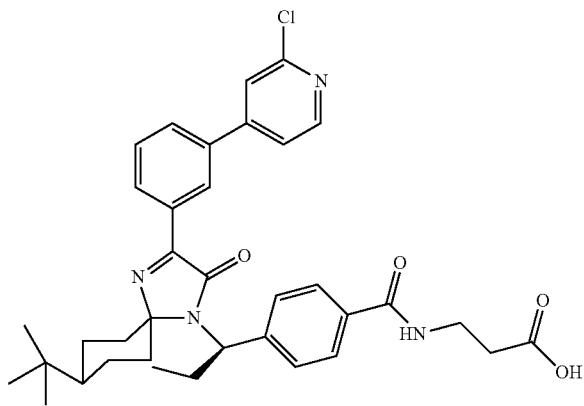 [SMILES: CC[C@H](c1ccc(C(=O)NCCC(=O)O)cc1)N1C(=O)C(c2cccc(-c3ccnc(Cl)c3)c2)=NC12CCC(C(C)(C)C)CC2] |
| 1.319 | 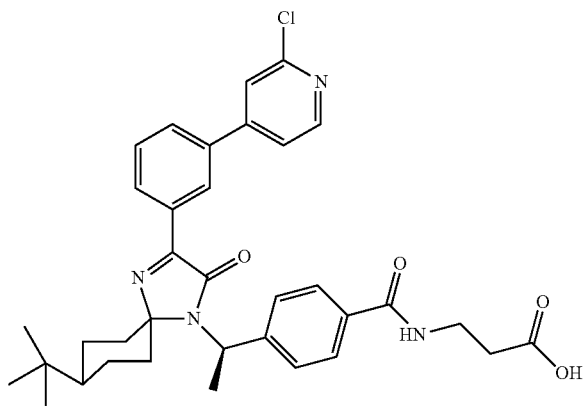 [SMILES: C[C@H](c1ccc(C(=O)NCCC(=O)O)cc1)N1C(=O)C(c2cccc(-c3ccnc(Cl)c3)c2)=NC12CCC(C(C)(C)C)CC2] |

-continued
| Ex. | Structure |
|---|---|
| 1.309 | 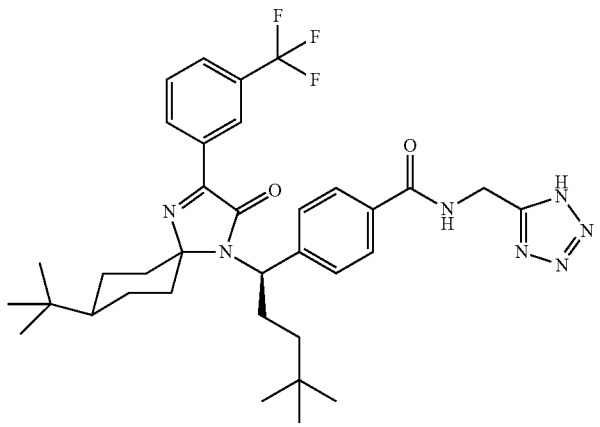 [SMILES: CC(C)(C)CC[C@H](c1ccc(C(=O)NCc2nnn[nH]2)cc1)N1C(=O)C(c2cccc(C(F)(F)F)c2)=NC12CCC(C(C)(C)C)CC2] |
| 1.321 | 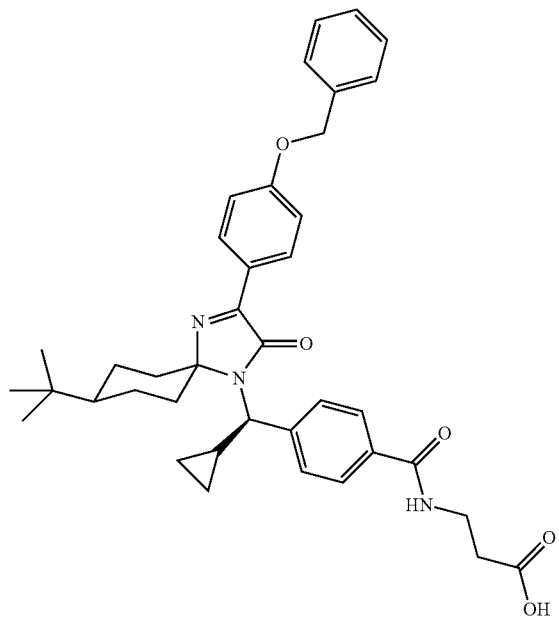 [SMILES: CC(C)(C)C1CCC2(CC1)N=C(c1ccc(OCc3ccccc3)cc1)C(=O)N2[C@@H](c1ccc(C(=O)NCCC(=O)O)cc1)C1CC1] |
| 1.322 | 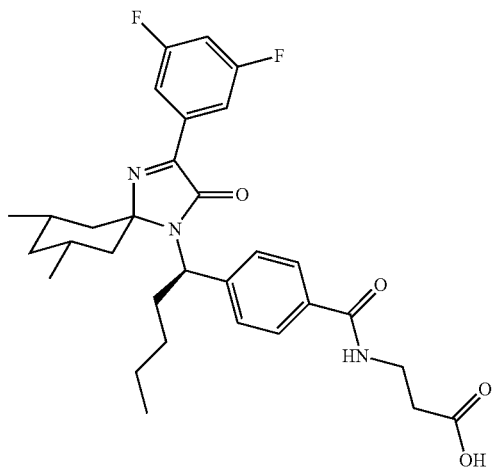 [SMILES: CCCC[C@H](c1ccc(C(=O)NCCC(=O)O)cc1)N1C(=O)C(c2cc(F)cc(F)c2)=NC12CC(C)CC(C)C2] |

| Ex. | Structure |
|---|---|
| 1.323 | 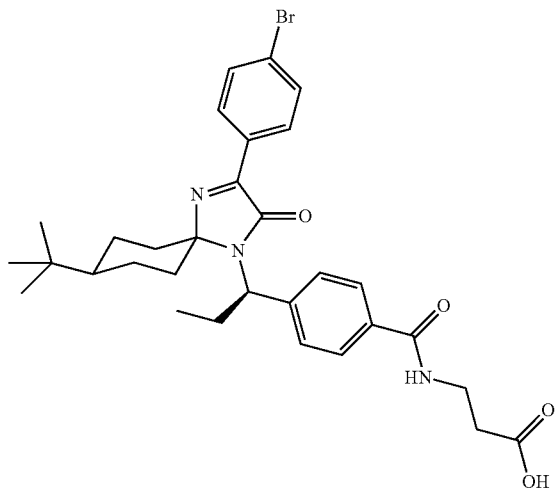 [SMILES: CC[C@H](c1ccc(C(=O)NCCC(=O)O)cc1)N1C(=O)C(c2ccc(Br)cc2)=NC12CCC(C(C)(C)C)CC2] |
| 1.324 | 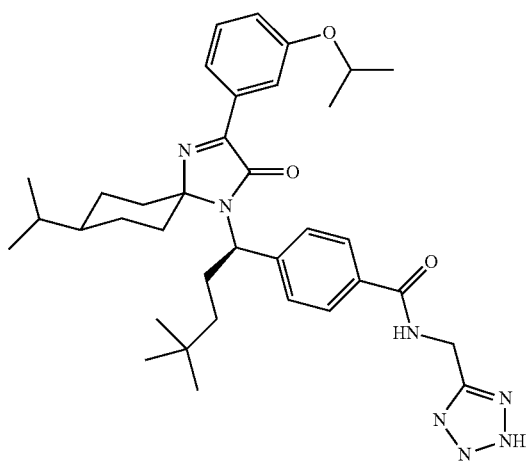 [SMILES: CC(C)Oc1cccc(C2=NC3(CCC(C(C)C)CC3)N([C@H](CCC(C)(C)C)c3ccc(C(=O)NCC4=NNNN4)cc3)C2=O)c1] |
| 1.320 | 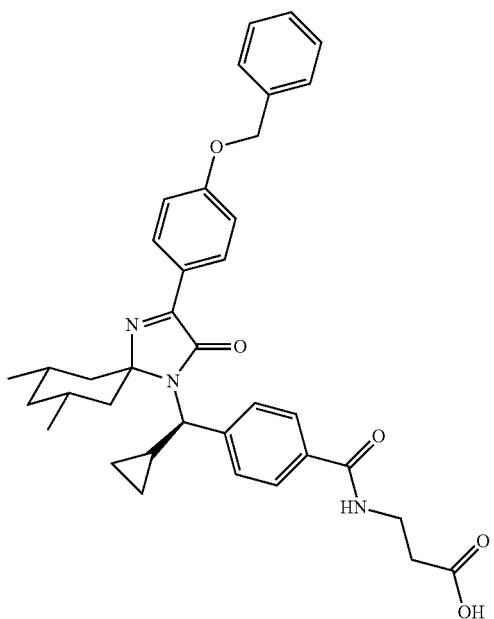 [SMILES: CC1CC(C)CC2(C1)N=C(c1ccc(OCc3ccccc3)cc1)C(=O)N2[C@@H](c1ccc(C(=O)NCCC(=O)O)cc1)C1CC1] |

| Ex. | Structure |
|---|---|
| 1.326 | 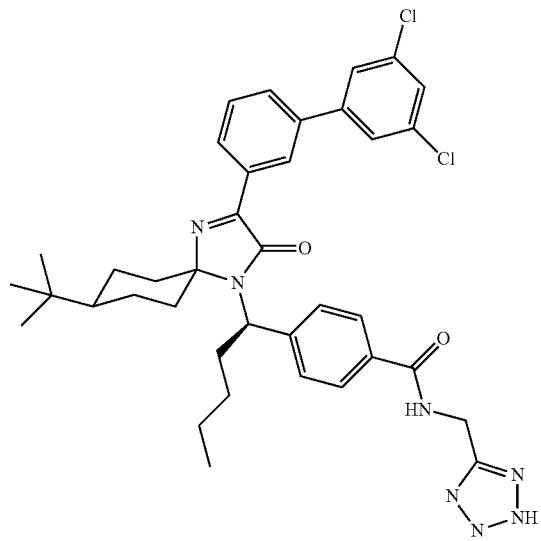 [SMILES: CCCC[C@H](c1ccc(C(=O)NCC2=NNNN2)cc1)N1C(=O)C(c2cccc(-c3cc(Cl)cc(Cl)c3)c2)=NC12CCC(C(C)(C)C)CC2] |
| 1.327 | 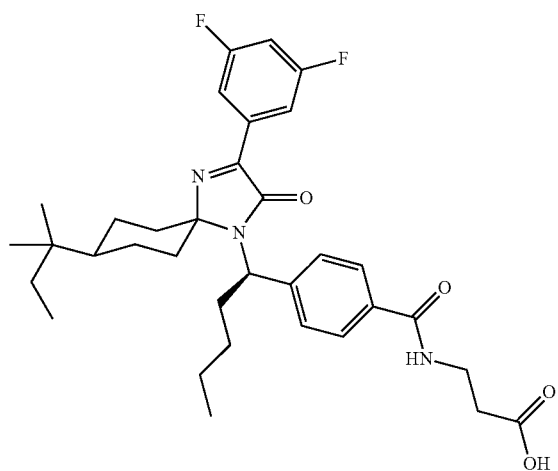 [SMILES: CCCC[C@H](c1ccc(C(=O)NCCC(=O)O)cc1)N1C(=O)C(c2cc(F)cc(F)c2)=NC12CCC(C(C)(C)CC)CC2] |
| 1.328 | 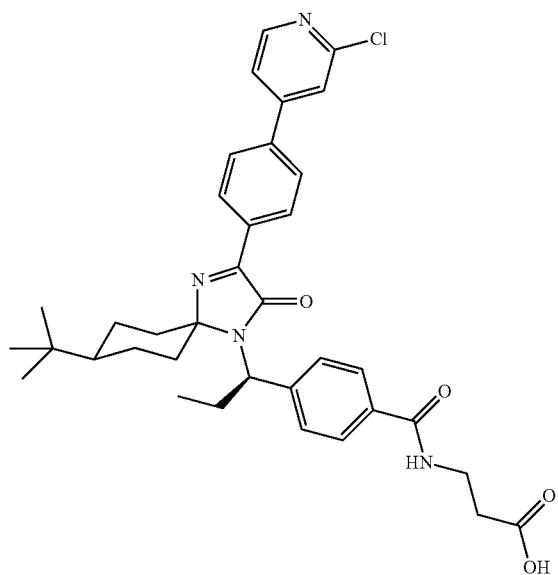 [SMILES: CC[C@H](c1ccc(C(=O)NCCC(=O)O)cc1)N1C(=O)C(c2ccc(-c3ccnc(Cl)c3)cc2)=NC12CCC(C(C)(C)C)CC2] |

| Ex. | Structure |
|---|---|
| 1.329 | 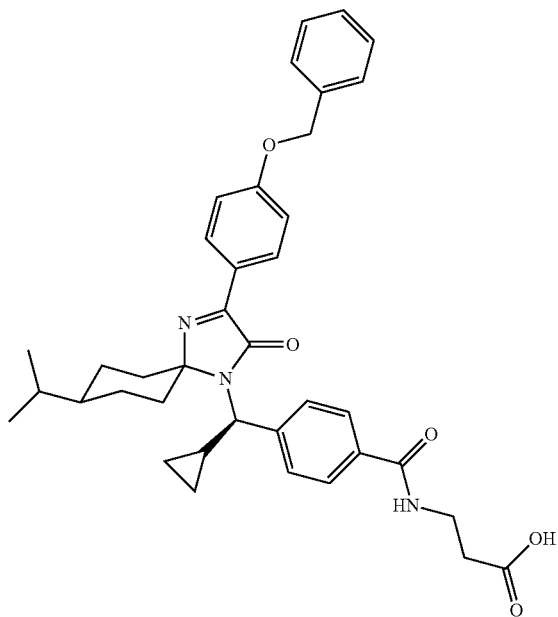 [SMILES: CC(C)C1CCC2(CC1)N=C(c1ccc(OCc3ccccc3)cc1)C(=O)N2[C@@H](c1ccc(C(=O)NCCC(=O)O)cc1)C1CC1] |
| 1.325 | 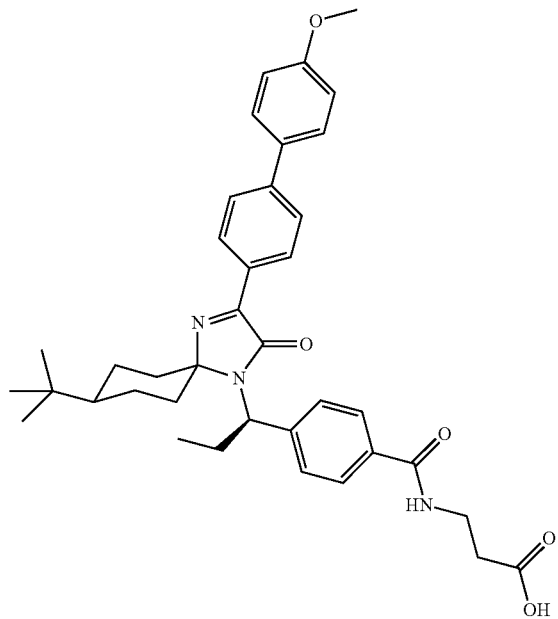 [SMILES: CC[C@H](c1ccc(C(=O)NCCC(=O)O)cc1)N1C(=O)C(c2ccc(-c3ccc(OC)cc3)cc2)=NC12CCC(C(C)(C)C)CC2] |

| Ex. | Structure |
|---|---|
| 1.331 | 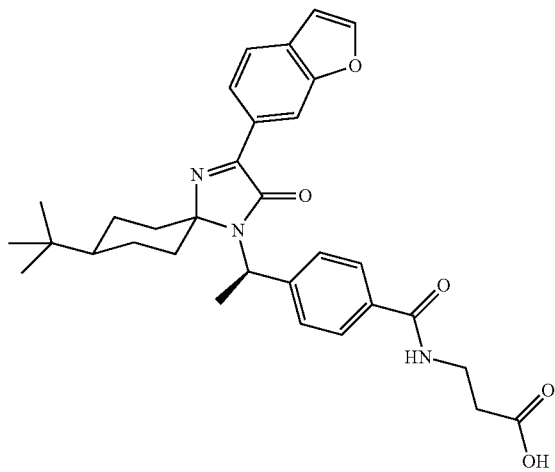 [SMILES: C[C@H](c1ccc(C(=O)NCCC(=O)O)cc1)N1C(=O)C(c2ccc3ccoc3c2)=NC12CCC(C(C)(C)C)CC2] |
| 1.332 | 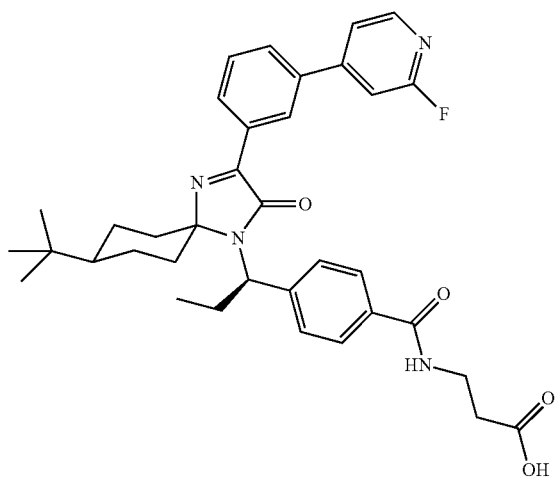 [SMILES: CC[C@H](c1ccc(C(=O)NCCC(=O)O)cc1)N1C(=O)C(c2cccc(-c3ccnc(F)c3)c2)=NC12CCC(C(C)(C)C)CC2] |
| 1.333 | 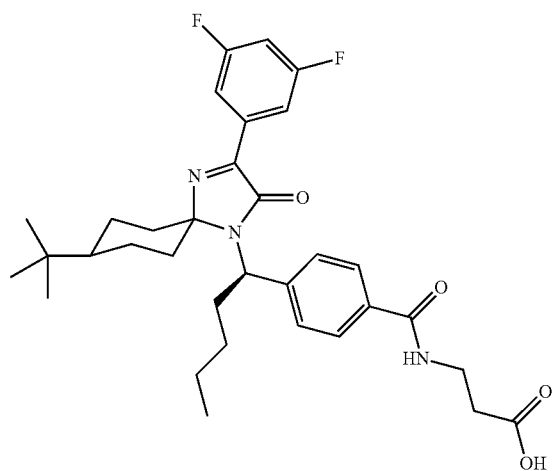 [SMILES: CCCC[C@H](c1ccc(C(=O)NCCC(=O)O)cc1)N1C(=O)C(c2cc(F)cc(F)c2)=NC12CCC(C(C)(C)C)CC2] |

-continued
| Ex. | Structure |
|---|---|
| 1.334 | 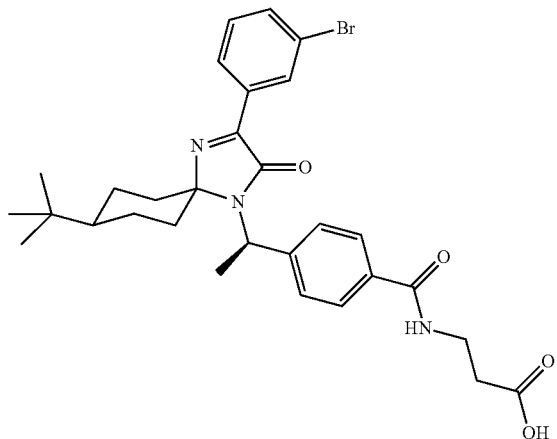 [SMILES: C[C@H](c1ccc(C(=O)NCCC(=O)O)cc1)N1C(=O)C(c2cccc(Br)c2)=NC12CCC(C(C)(C)C)CC2] |
| 1.330 | 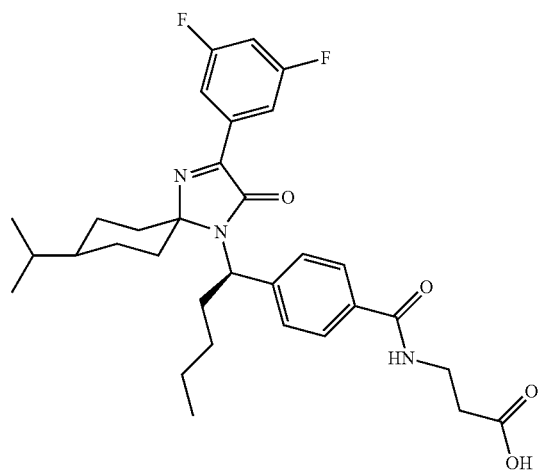 [SMILES: CCCC[C@H](c1ccc(C(=O)NCCC(=O)O)cc1)N1C(=O)C(c2cc(F)cc(F)c2)=NC12CCC(C(C)C)CC2] |
| 1.336 | 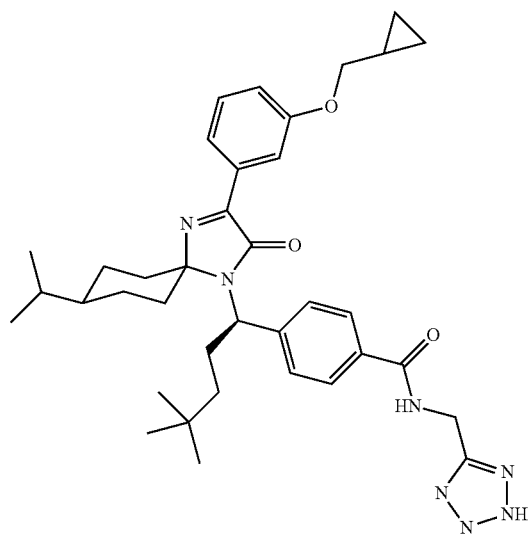 [SMILES: CC(C)C1CCC2(CC1)N=C(c1cccc(OCC3CC3)c1)C(=O)N2[C@H](CCC(C)(C)C)c1ccc(C(=O)NCC2=NNNN2)cc1] |

-continued
| Ex. | Structure |
|---|---|
| 1.337 | 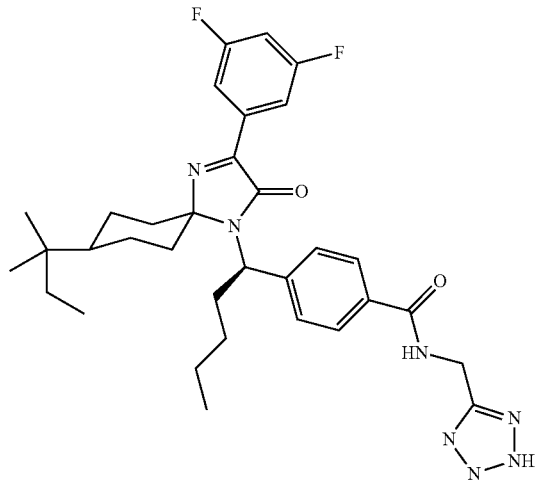 [SMILES: CCCC[C@H](c1ccc(C(=O)NCC2=NNNN2)cc1)N1C(=O)C(c2cc(F)cc(F)c2)=NC12CCC(C(C)(C)CC)CC2] |
| 1.338 | 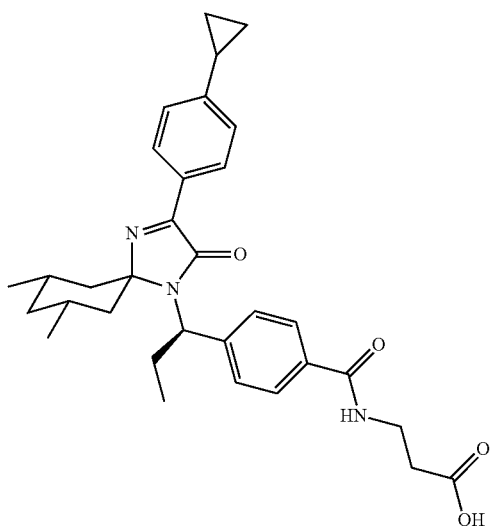 [SMILES: CC[C@H](c1ccc(C(=O)NCCC(=O)O)cc1)N1C(=O)C(c2ccc(C3CC3)cc2)=NC12CC(C)CC(C)C2] |
| 1.339 | 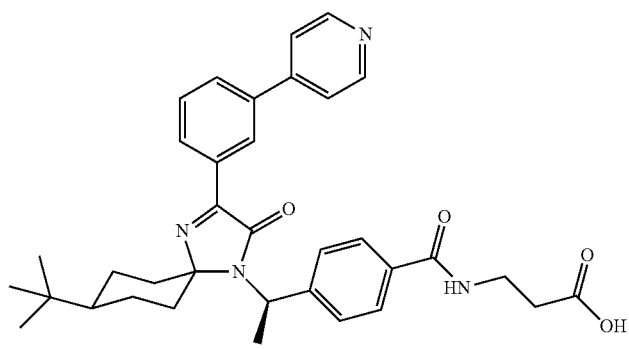 [SMILES: C[C@H](c1ccc(C(=O)NCCC(=O)O)cc1)N1C(=O)C(c2cccc(-c3ccncc3)c2)=NC12CCC(C(C)(C)C)CC2] |

| Ex. | Structure |
|---|---|
| 1.335 | 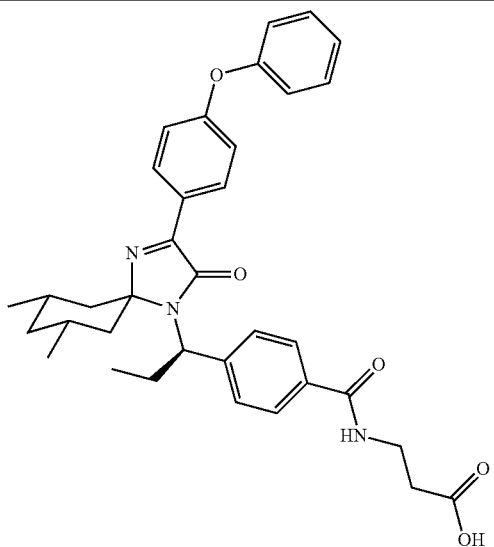 |
| 1.341 | 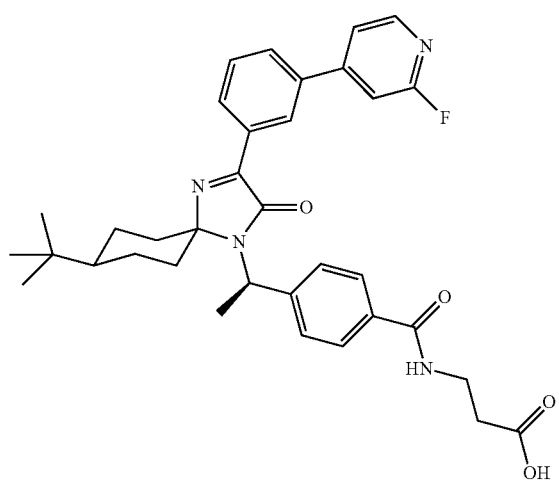 [SMILES: C[C@H](c1ccc(C(=O)NCCC(=O)O)cc1)N1C(=O)C(c2cccc(-c3ccnc(F)c3)c2)=NC12CCC(C(C)(C)C)CC2] |
| 1.342 | 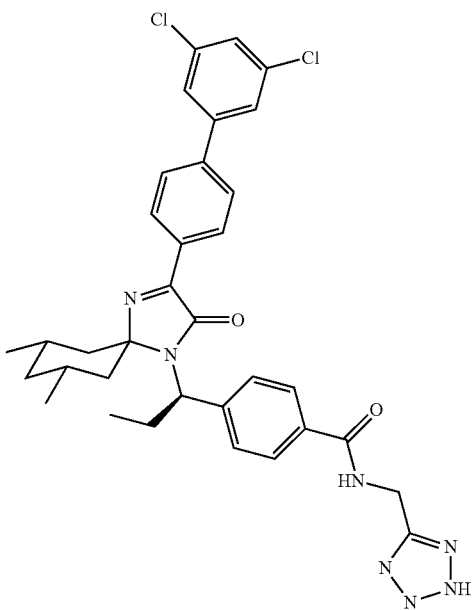 [SMILES: CC[C@H](c1ccc(C(=O)NCC2=NNNN2)cc1)N1C(=O)C(c2ccc(-c3cc(Cl)cc(Cl)c3)cc2)=NC12CC(C)CC(C)C2] |

| Ex. | Structure |
|---|---|
| 1.343 | 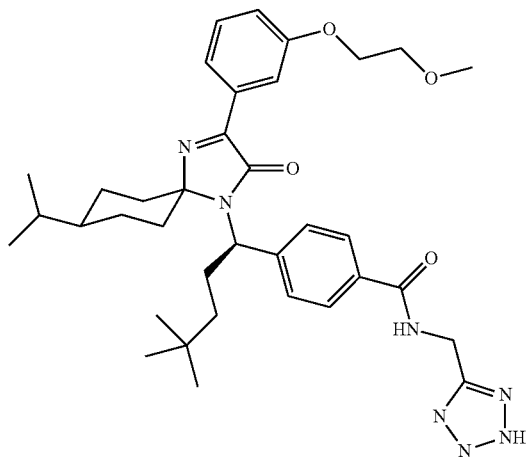 [SMILES: COCCOc1cccc(C2=NC3(CCC(C(C)C)CC3)N([C@H](CCC(C)(C)C)c3ccc(C(=O)NCC4=NNNN4)cc3)C2=O)c1] |
| 1.344 | 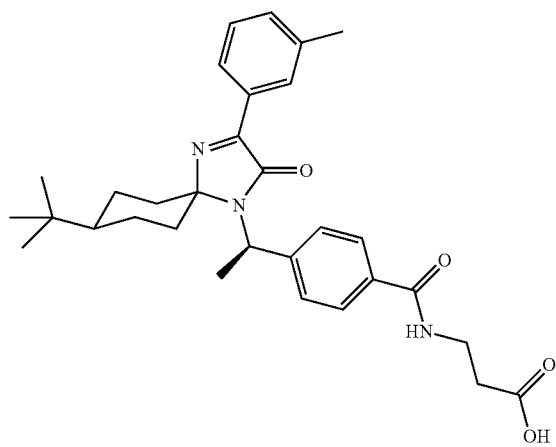 [SMILES: Cc1cccc(C2=NC3(CCC(C(C)(C)C)CC3)N([C@H](C)c3ccc(C(=O)NCCC(=O)O)cc3)C2=O)c1] |
| 1.340 | 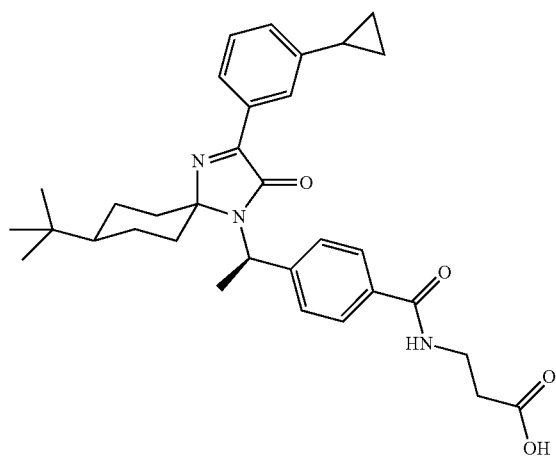 [SMILES: C[C@H](c1ccc(C(=O)NCCC(=O)O)cc1)N1C(=O)C(c2cccc(C3CC3)c2)=NC12CCC(C(C)(C)C)CC2] |

-continued

| Ex. | Structure |
|---|---|
| 1.347 | 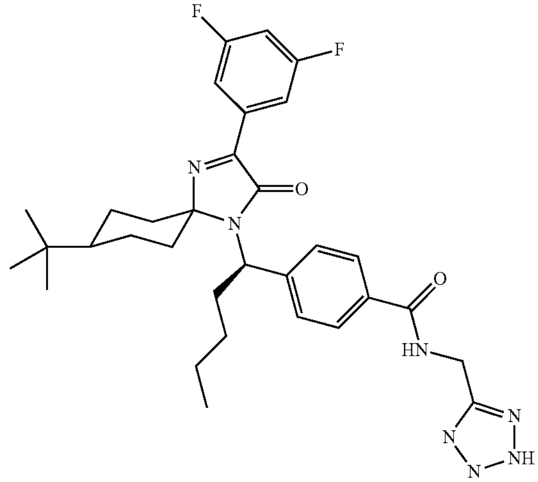 [SMILES: CCCC[C@H](c1ccc(C(=O)NCC2=NNNN2)cc1)N1C(=O)C(c2cc(F)cc(F)c2)=NC12CCC(C(C)(C)C)CC2] |
| 1.348 | 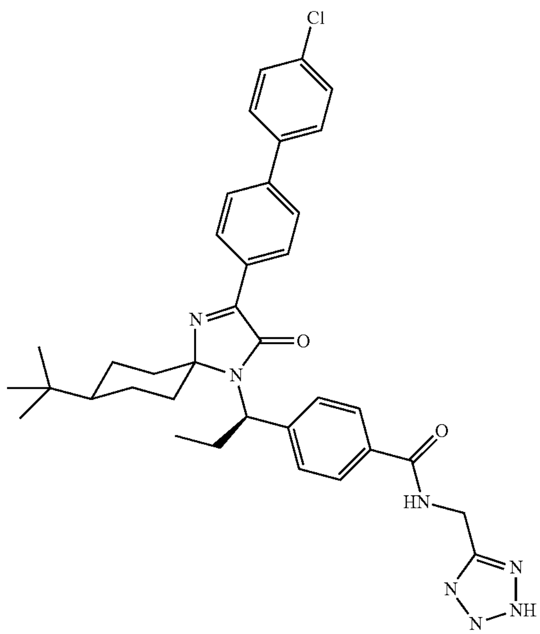 [SMILES: CC[C@H](c1ccc(C(=O)NCC2=NNNN2)cc1)N1C(=O)C(c2ccc(-c3ccc(Cl)cc3)cc2)=NC12CCC(C(C)(C)C)CC2] |
| 1.349 | 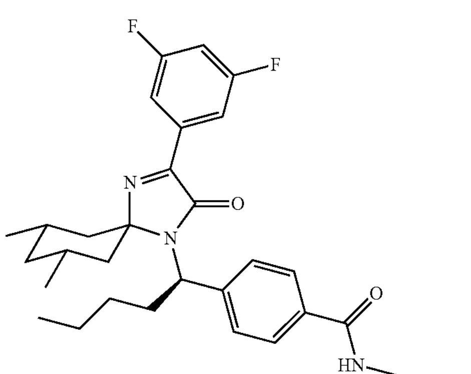 |

| Ex. | Structure |
|---|---|
| 1.350 | 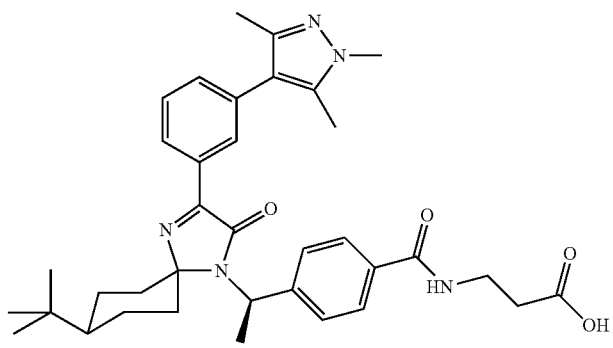 [SMILES: Cc1nn(C)c(C)c1-c1cccc(C2=NC3(CCC(C(C)(C)C)CC3)N([C@H](C)c3ccc(C(=O)NCCC(=O)O)cc3)C2=O)c1] |
| 1.345 | 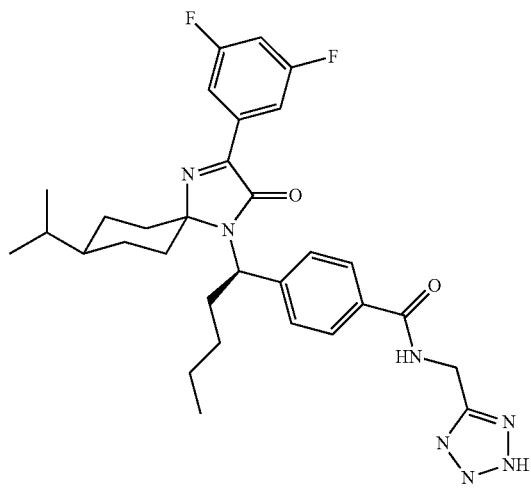 [SMILES: CCCC[C@H](c1ccc(C(=O)NCC2=NNNN2)cc1)N1C(=O)C(c2cc(F)cc(F)c2)=NC12CCC(C(C)C)CC2] |
| 1.346 | 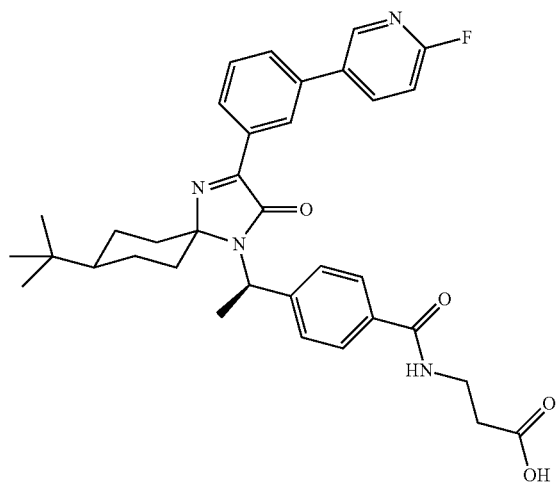 [SMILES: C[C@H](c1ccc(C(=O)NCCC(=O)O)cc1)N1C(=O)C(c2cccc(-c3ccc(F)nc3)c2)=NC12CCC(C(C)(C)C)CC2] |

| Ex. | Structure |
|---|---|
| 1.353 | 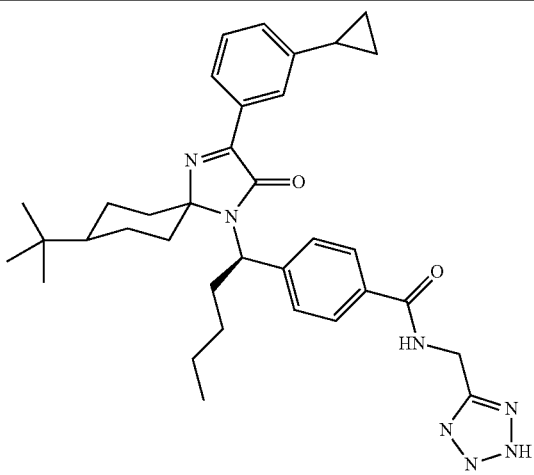 |
| 1.354 | 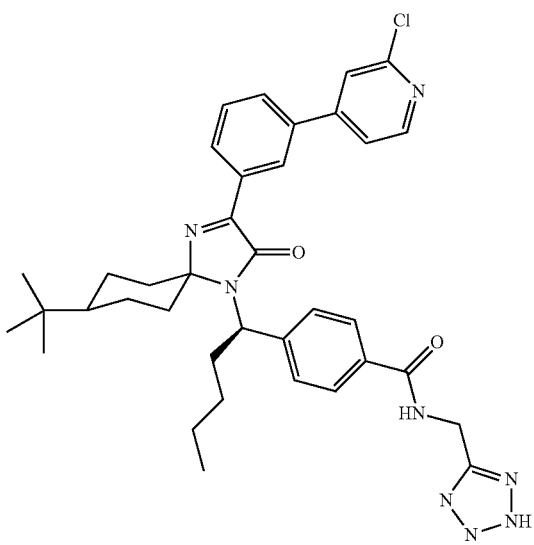 [SMILES: CCCC[C@H](c1ccc(C(=O)NCC2=NNNN2)cc1)N1C(=O)C(c2cccc(-c3ccnc(Cl)c3)c2)=NC12CCC(C(C)(C)C)CC2] |
| 1.351 | 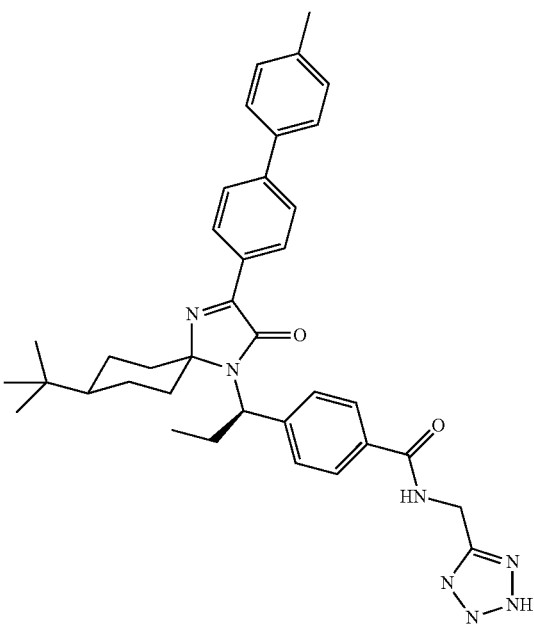 [SMILES: CC[C@H](c1ccc(C(=O)NCC2=NNNN2)cc1)N1C(=O)C(c2ccc(-c3ccc(C)cc3)cc2)=NC12CCC(C(C)(C)C)CC2] |

| Ex. | Structure |
|---|---|
| 1.352 | 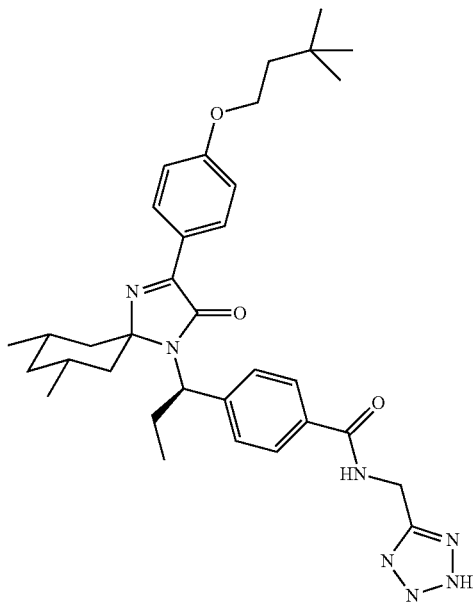 [SMILES: CC[C@H](c1ccc(C(=O)NCC2=NNNN2)cc1)N1C(=O)C(c2ccc(OCCC(C)(C)C)cc2)=NC12CC(C)CC(C)C2] |
| 1.358 | 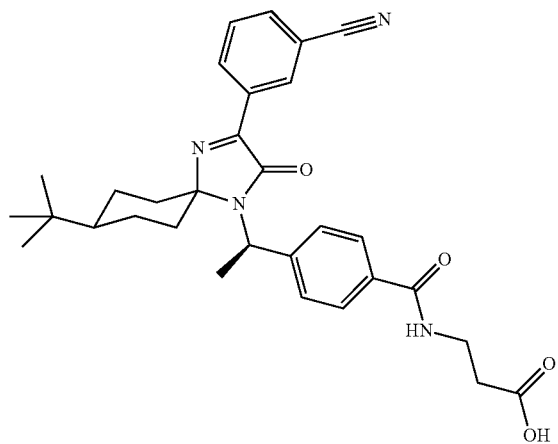 [SMILES: C[C@H](c1ccc(C(=O)NCCC(=O)O)cc1)N1C(=O)C(c2cccc(C#N)c2)=NC12CCC(C(C)(C)C)CC2] |

| Ex. | Structure |
|---|---|
| 1.359 | 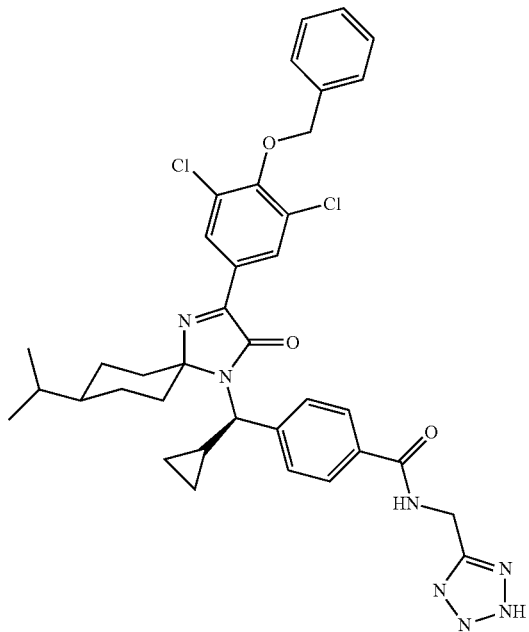 [SMILES: CC(C)C1CCC2(CC1)N=C(c1cc(Cl)c(OCc3ccccc3)c(Cl)c1)C(=O)N2[C@@H](c1ccc(C(=O)NCC2=NNNN2)cc1)C1CC1] |
| 1.355 | 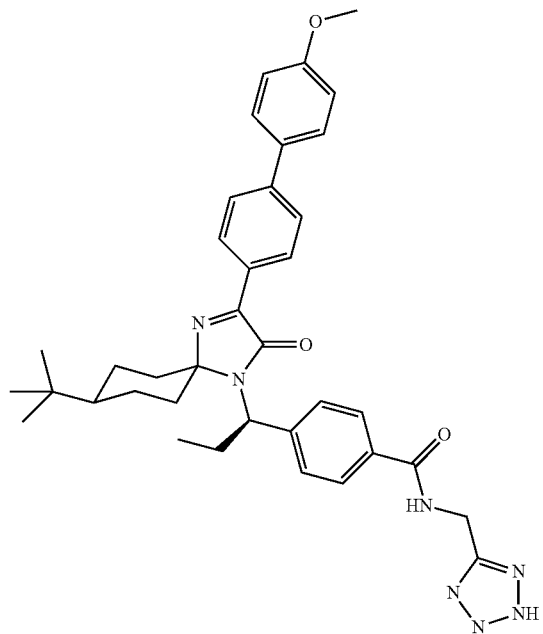 [SMILES: CC[C@H](c1ccc(C(=O)NCC2=NNNN2)cc1)N1C(=O)C(c2ccc(-c3ccc(OC)cc3)cc2)=NC12CCC(C(C)(C)C)CC2] |

| Ex. | Structure |
|---|---|
| 1.356 | 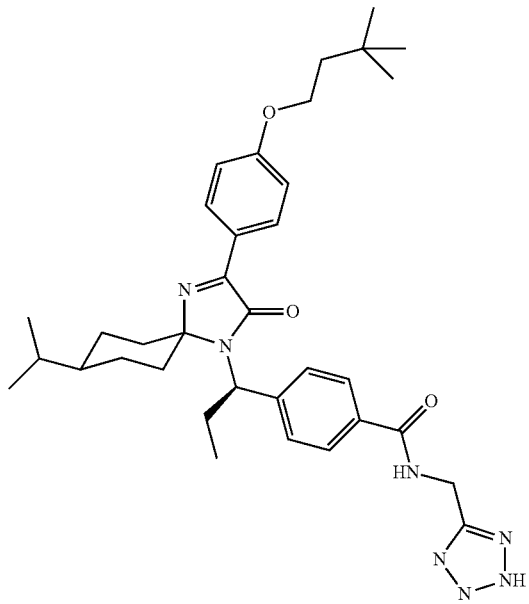 [SMILES: CC[C@H](c1ccc(C(=O)NCC2=NNNN2)cc1)N1C(=O)C(c2ccc(OCCC(C)(C)C)cc2)=NC12CCC(C(C)C)CC2] |
| 1.357 | 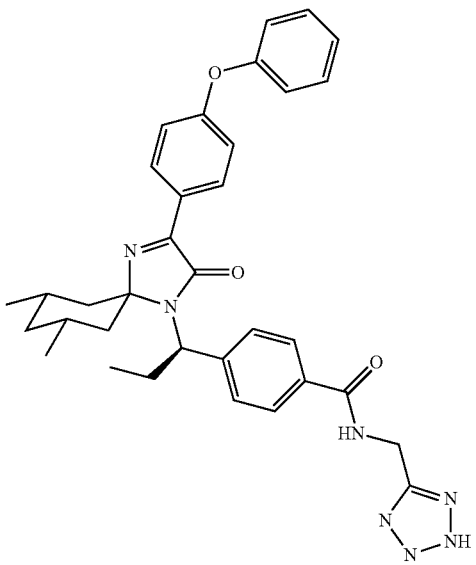 [SMILES: CC[C@H](c1ccc(C(=O)NCC2=NNNN2)cc1)N1C(=O)C(c2ccc(Oc3ccccc3)cc2)=NC12CC(C)CC(C)C2] |
| 1.369 | 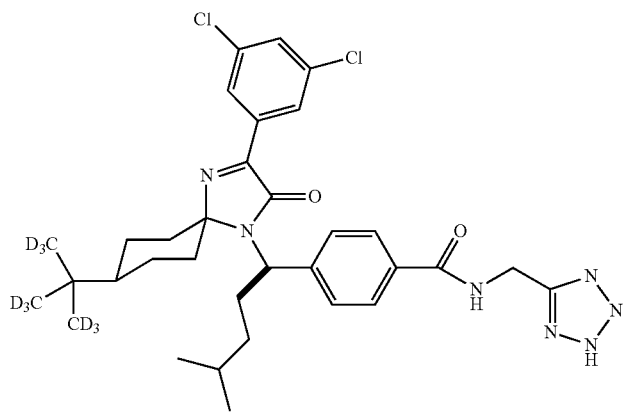 [SMILES: [2H]C([2H])([2H])C(C1CCC2(CC1)N=C(c1cc(Cl)cc(Cl)c1)C(=O)N2[C@H](CCC(C)C)c1ccc(C(=O)NCC2=NNNN2)cc1)(C([2H])([2H])[2H])C([2H])([2H])[2H]] |

| Ex. | Structure |
|---|---|
| 1.370 | 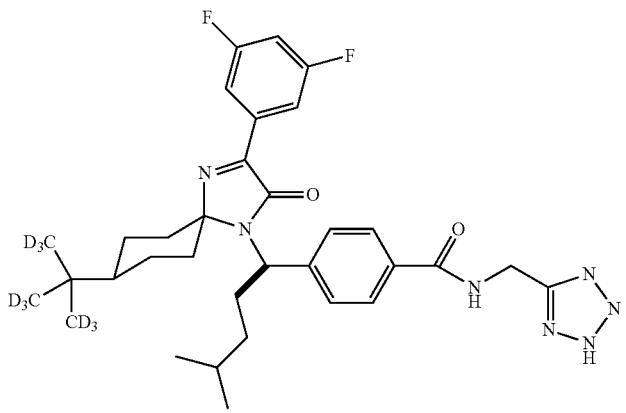 [SMILES: [2H]C([2H])([2H])C(C1CCC2(CC1)N=C(c1cc(F)cc(F)c1)C(=O)N2[C@H](CCC(C)C)c1ccc(C(=O)NCC2=NNNN2)cc1)(C([2H])([2H])[2H])C([2H])([2H])[2H]] |
| 1.360 | 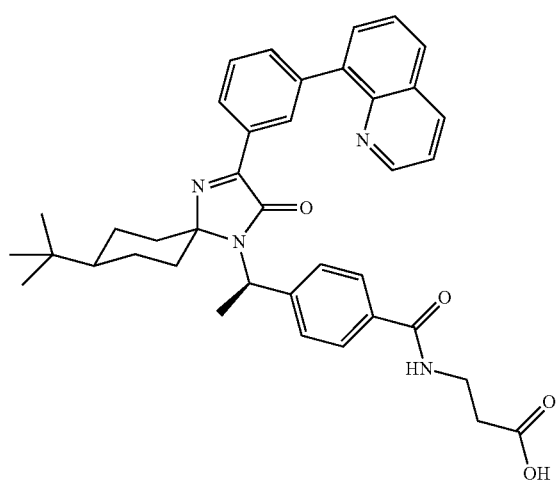 [SMILES: C[C@H](c1ccc(C(=O)NCCC(=O)O)cc1)N1C(=O)C(c2cccc(-c3cccc4cccnc34)c2)=NC12CCC(C(C)(C)C)CC2] |
| 1.361 | 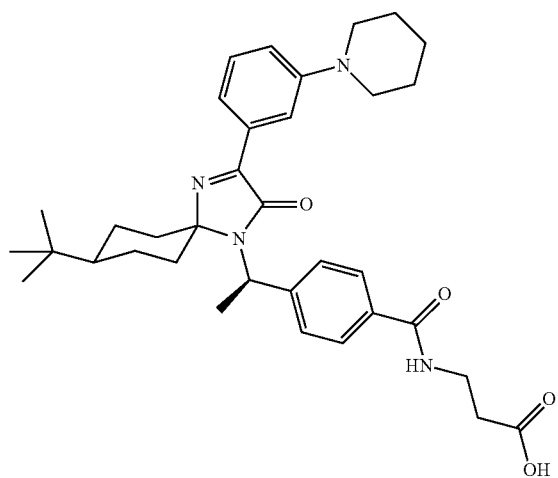 [SMILES: C[C@H](c1ccc(C(=O)NCCC(=O)O)cc1)N1C(=O)C(c2cccc(N3CCCCC3)c2)=NC12CCC(C(C)(C)C)CC2] |

| Ex. | Structure |
|---|---|
| 1.362 | 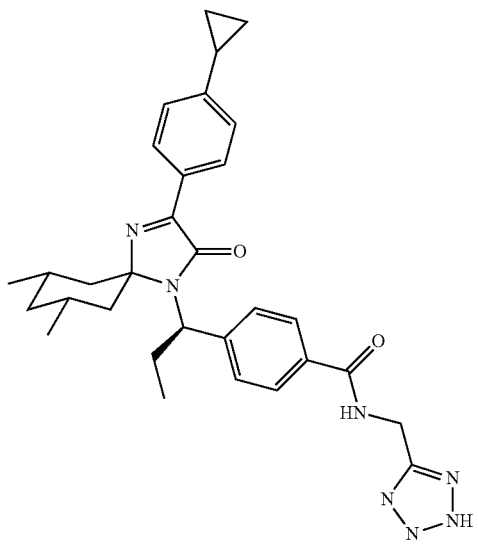 [SMILES: CC[C@H](c1ccc(C(=O)NCC2=NNNN2)cc1)N1C(=O)C(c2ccc(C3CC3)cc2)=NC12CC(C)CC(C)C2] |
| 1.363 | 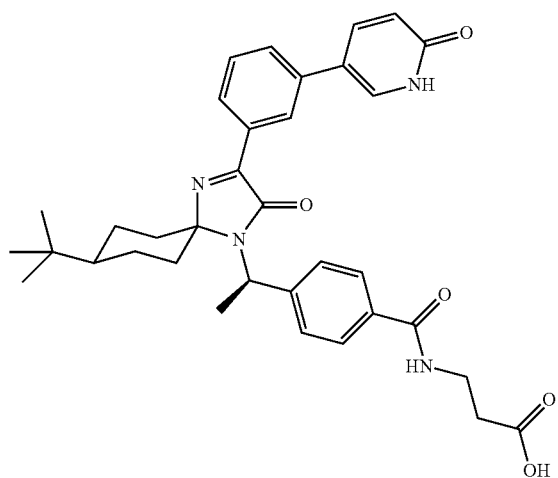 [SMILES: C[C@H](c1ccc(C(=O)NCCC(=O)O)cc1)N1C(=O)C(c2cccc(-c3ccc(=O)[nH]c3)c2)=NC12CCC(C(C)(C)C)CC2] |
| 1.364 | 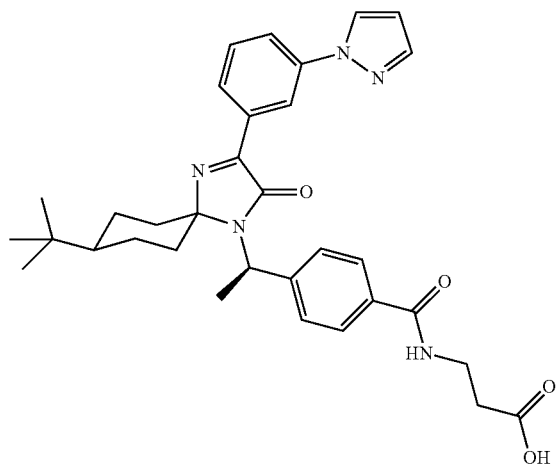 [SMILES: C[C@H](c1ccc(C(=O)NCCC(=O)O)cc1)N1C(=O)C(c2cccc(-n3cccn3)c2)=NC12CCC(C(C)(C)C)CC2] |

-continued

| Ex. | Structure |
|---|---|
| 1.371 | 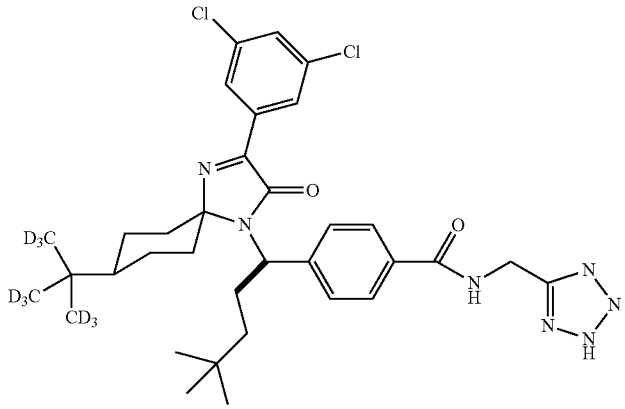 |
| 1.372 | 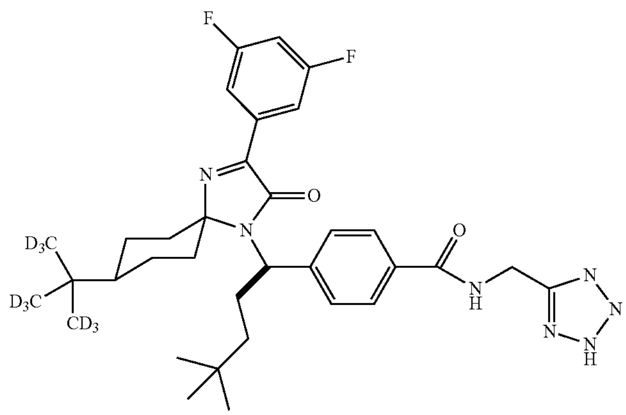 [SMILES: [2H]C([2H])([2H])C(C1CCC2(CC1)N=C(c1cc(F)cc(F)c1)C(=O)N2[C@H](CCC(C)(C)C)c1ccc(C(=O)NCC2=NNNN2)cc1)(C([2H])([2H])[2H])C([2H])([2H])[2H]] |
| 1.373 | 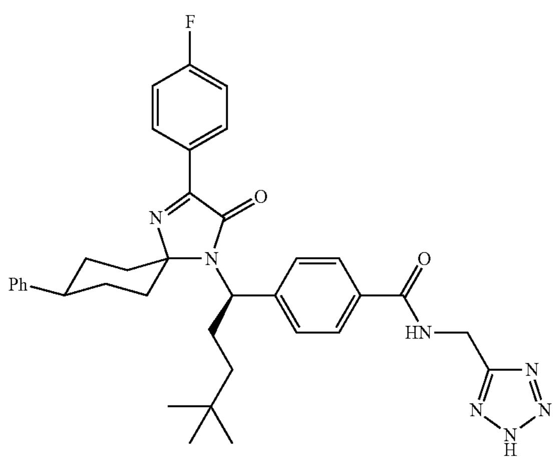 [SMILES: CC(C)(C)CC[C@H](c1ccc(C(=O)NCc2nn[nH]n2)cc1)N1C(=O)C(c2ccc(F)cc2)=NC12CCC(c1ccccc1)CC2] |
| 1.374 | 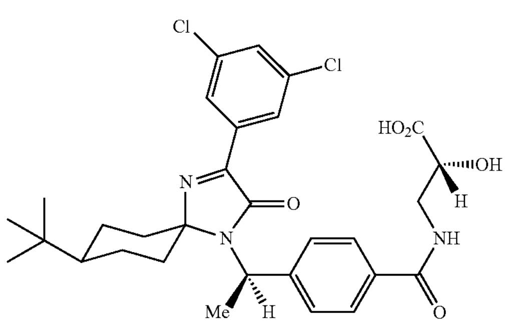 [SMILES: C[C@H](c1ccc(C(=O)NC[C@@H](O)C(=O)O)cc1)N1C(=O)C(c2cc(Cl)cc(Cl)c2)=NC12CCC(C(C)(C)C)CC2] |

| Ex. | Structure |
|---|---|
| 1.375 | 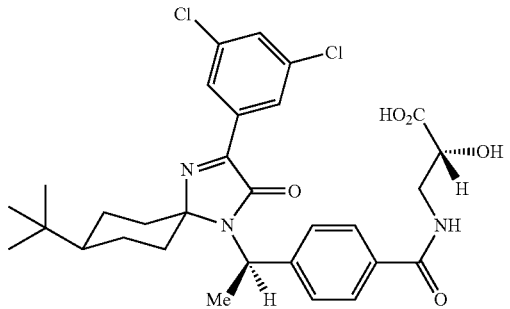 [SMILES: C[C@H](c1ccc(C(=O)NC[C@@H](O)C(=O)O)cc1)N1C(=O)C(c2cc(Cl)cc(Cl)c2)=NC12CCC(C(C)(C)C)CC2] |
| 1.365 | 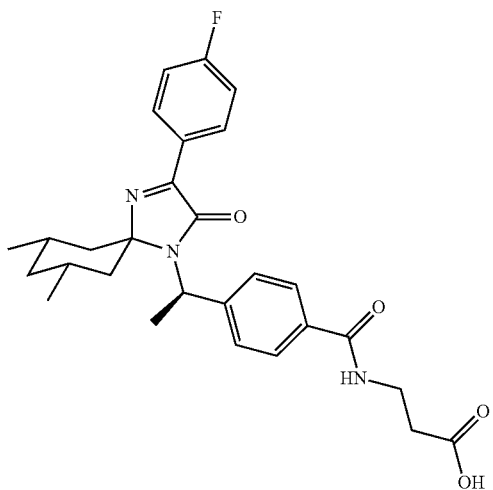 [SMILES: CC1CC(C)CC2(C1)N=C(c1ccc(F)cc1)C(=O)N2[C@H](C)c1ccc(C(=O)NCCC(=O)O)cc1] |
| 1.366 | 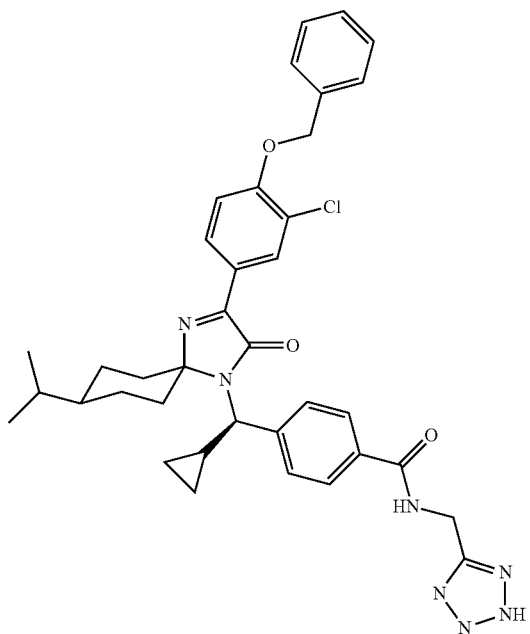 [SMILES: CC(C)C1CCC2(CC1)N=C(c1ccc(OCc3ccccc3)c(Cl)c1)C(=O)N2[C@@H](c1ccc(C(=O)NCC2=NNNN2)cc1)C1CC1] |

| Ex. | Structure |
|---|---|
| 1.367 | 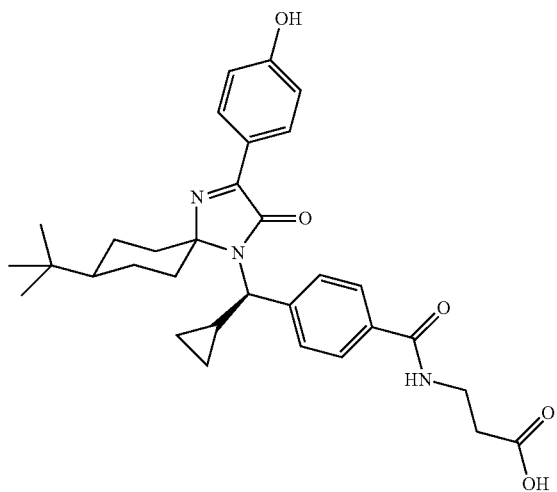 [SMILES: CC(C)(C)C1CCC2(CC1)N=C(c1ccc(O)cc1)C(=O)N2[C@@H](c1ccc(C(=O)NCCC(=O)O)cc1)C1CC1] |
| 1.368 | 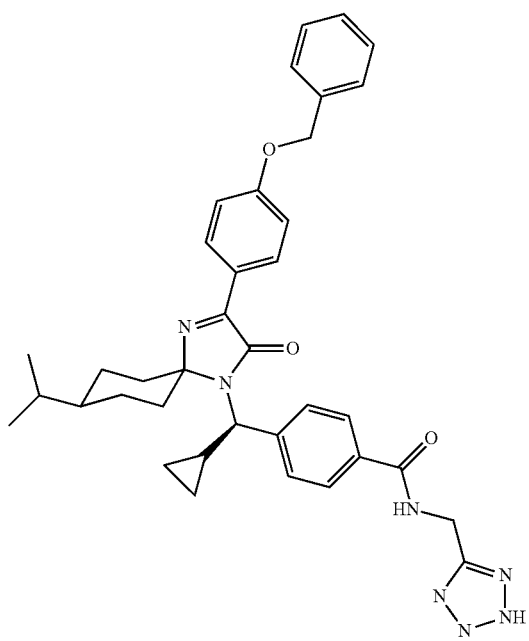 [SMILES: CC(C)C1CCC2(CC1)N=C(c1ccc(OCc3ccccc3)cc1)C(=O)N2[C@@H](c1ccc(C(=O)NCC2=NNNN2)cc1)C1CC1] |
| 1.500 | 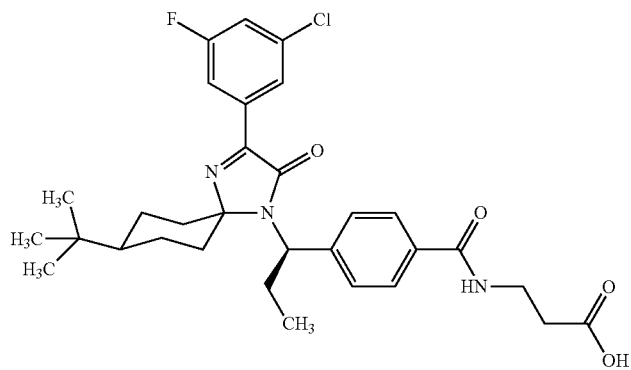 [SMILES: CC[C@H](c1ccc(C(=O)NCCC(=O)O)cc1)N1C(=O)C(c2cc(F)cc(Cl)c2)=NC12CCC(C(C)(C)C)CC2] |

| Ex. | Structure |
|---|---|
| 1.376 | 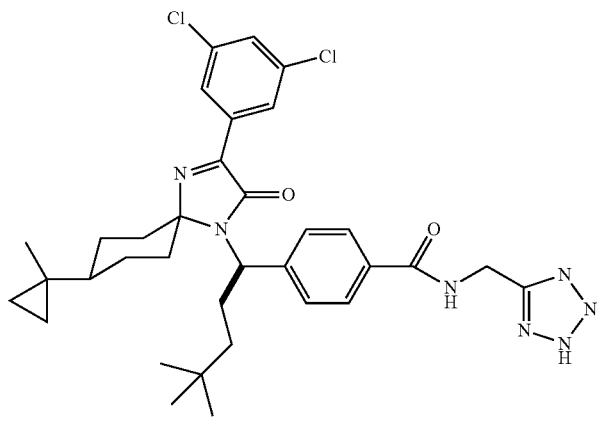 [SMILES: CC(C)(C)CC[C@H](c1ccc(C(=O)NCC2=NNNN2)cc1)N1C(=O)C(c2cc(Cl)cc(Cl)c2)=NC12CCC(C1(C)CC1)CC2] |
| 1.377 | 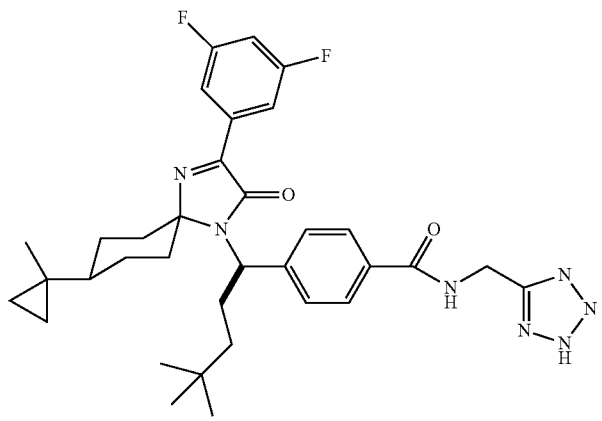 [SMILES: CC(C)(C)CC[C@H](c1ccc(C(=O)NCC2=NNNN2)cc1)N1C(=O)C(c2cc(F)cc(F)c2)=NC12CCC(C1(C)CC1)CC2] |
| 1.378 | 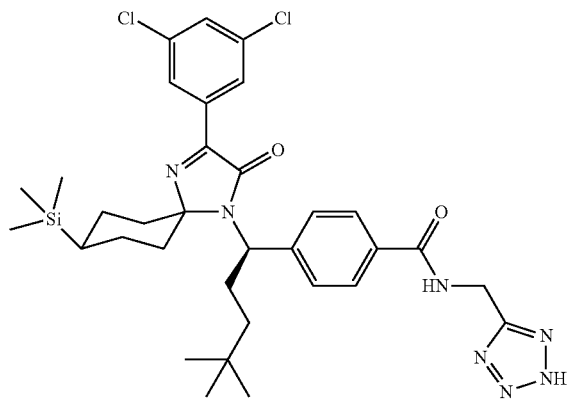 [SMILES: CC(C)(C)CC[C@H](c1ccc(C(=O)NCc2nn[nH]n2)cc1)N1C(=O)C(c2cc(Cl)cc(Cl)c2)=NC12CCC([Si](C)(C)C)CC2] |

| Ex. | Structure |
|---|---|
| 1.379 | 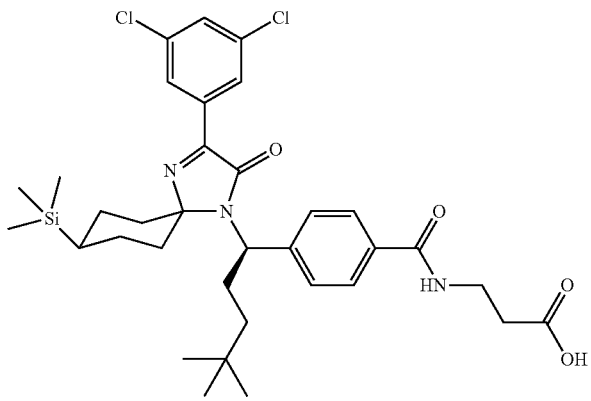 [SMILES: CC(C)(C)CC[C@H](c1ccc(C(=O)NCCC(=O)O)cc1)N1C(=O)C(c2cc(Cl)cc(Cl)c2)=NC12CCC([Si](C)(C)C)CC2] |
| 1.380 | 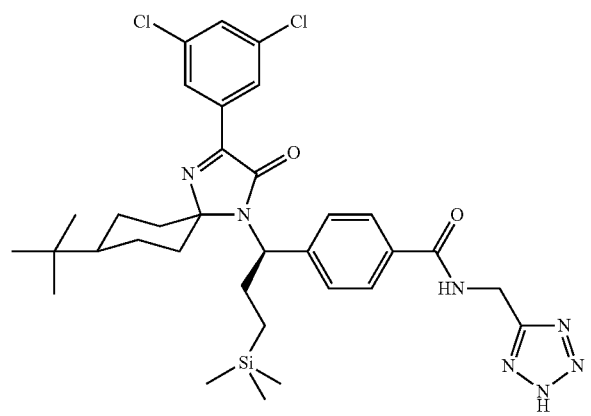 [SMILES: CC(C)(C)C1CCC2(CC1)N=C(c1cc(Cl)cc(Cl)c1)C(=O)N2[C@H](CC[Si](C)(C)C)c1ccc(C(=O)NCc2nn[nH]n2)cc1] |
| 1.506 | 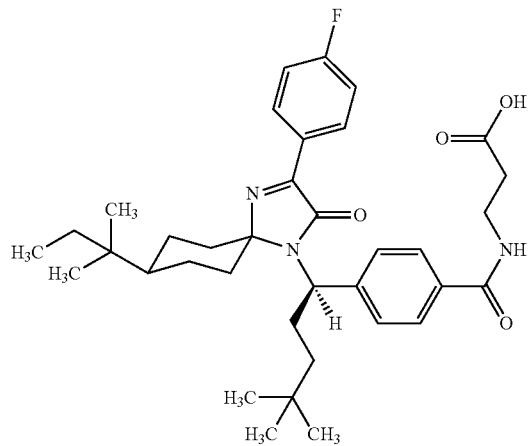 [SMILES: CCC(C)(C)C1CCC2(CC1)N=C(c1ccc(F)cc1)C(=O)N2[C@H](CCC(C)(C)C)c1ccc(C(=O)NCCC(=O)O)cc1] |

-continued
| Ex. | Structure |
|---|---|
| 1.507 | 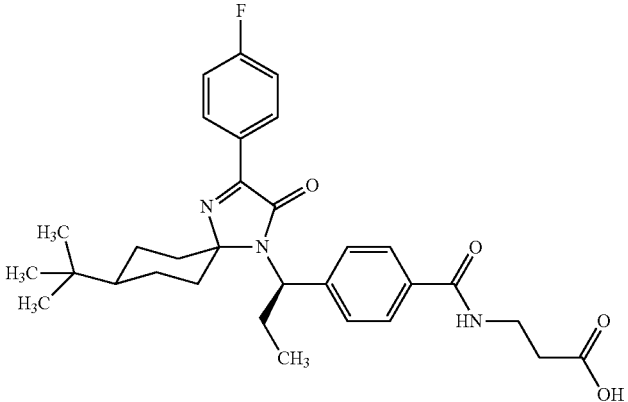 [SMILES: CC[C@H](c1ccc(C(=O)NCCC(=O)O)cc1)N1C(=O)C(c2ccc(F)cc2)=NC12CCC(C(C)(C)C)CC2] |
| 1.501 | 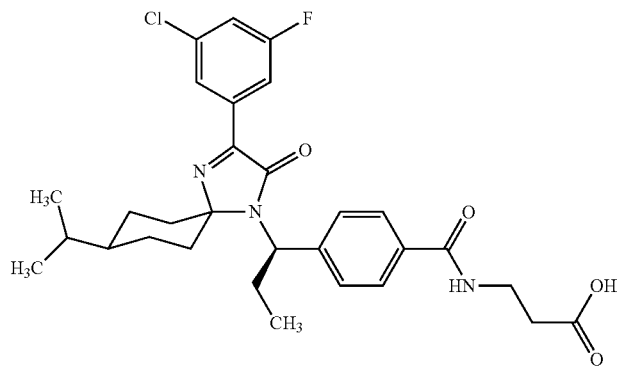 [SMILES: CC[C@H](c1ccc(C(=O)NCCC(=O)O)cc1)N1C(=O)C(c2cc(F)cc(Cl)c2)=NC12CCC(C(C)C)CC2] |
| 1.502 | 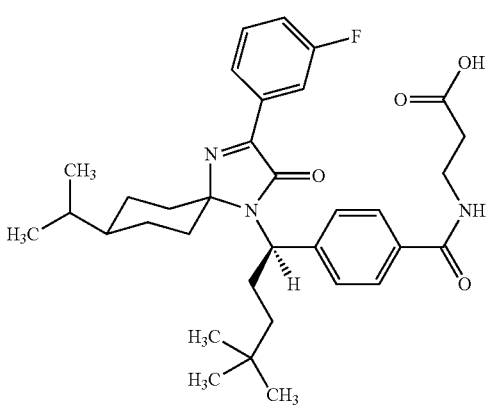 |
| 1.503 | 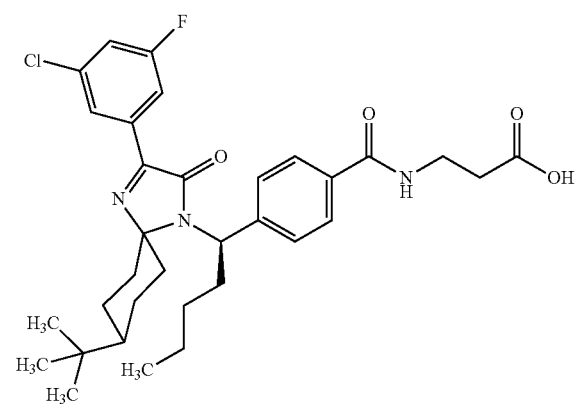 [SMILES: CCCC[C@H](c1ccc(C(=O)NCCC(=O)O)cc1)N1C(=O)C(c2cc(F)cc(Cl)c2)=NC12CCC(C(C)(C)C)CC2] |

| Ex. | Structure |
|---|---|
| 1.504 | 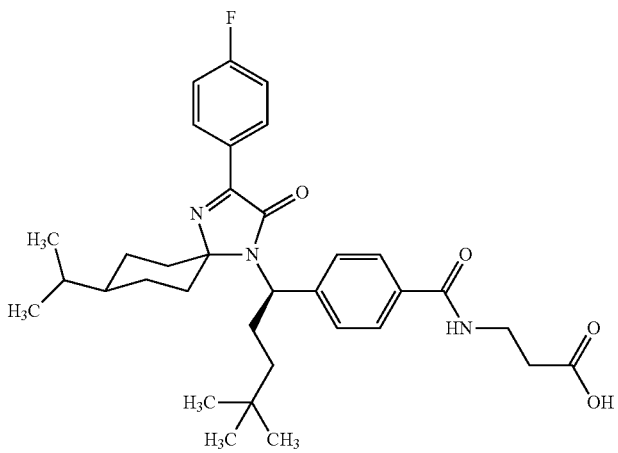 [SMILES: CC(C)C1CCC2(CC1)N=C(c1ccc(F)cc1)C(=O)N2[C@H](CCC(C)(C)C)c1ccc(C(=O)NCCC(=O)O)cc1] |
| 1.505 | 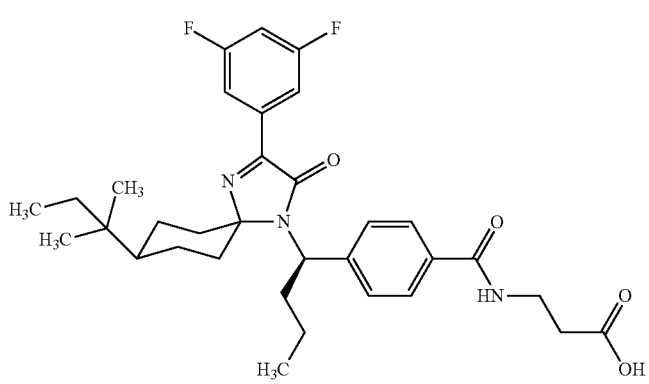 [SMILES: CCC[C@H](c1ccc(C(=O)NCCC(=O)O)cc1)N1C(=O)C(c2cc(F)cc(F)c2)=NC12CCC(C(C)(C)CC)CC2] |
| 1.512 | 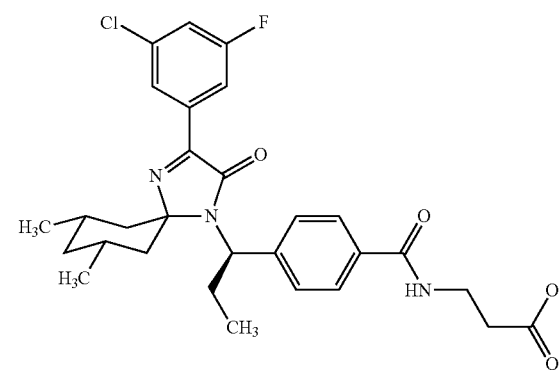 |
| 1.513 | 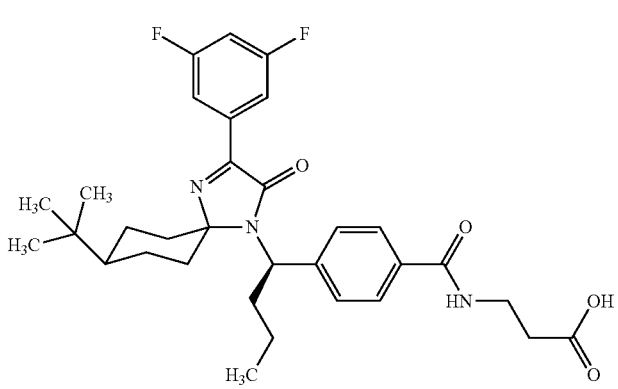 [SMILES: CCC[C@H](c1ccc(C(=O)NCCC(=O)O)cc1)N1C(=O)C(c2cc(F)cc(F)c2)=NC12CCC(C(C)(C)C)CC2] |

-continued
| Ex. | Structure |
|---|---|
| 1.508 | 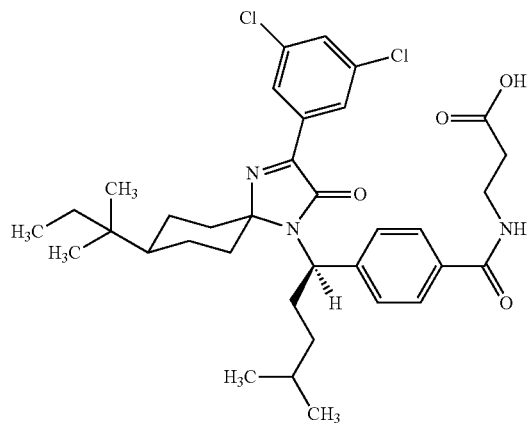 [SMILES: CCC(C)(C)C1CCC2(CC1)N=C(c1cc(Cl)cc(Cl)c1)C(=O)N2[C@H](CCC(C)C)c1ccc(C(=O)NCCC(=O)O)cc1] |
| 1.509 | 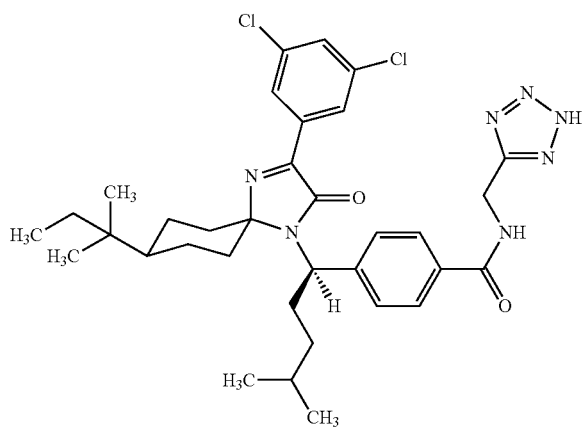 [SMILES: CCC(C)(C)C1CCC2(CC1)N=C(c1cc(Cl)cc(Cl)c1)C(=O)N2[C@H](CCC(C)C)c1ccc(C(=O)NCc2nn[nH]n2)cc1] |
| 1.510 | 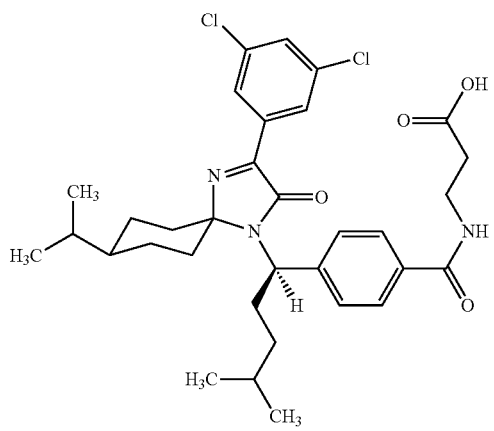 [SMILES: CC(C)CC[C@H](c1ccc(C(=O)NCCC(=O)O)cc1)N1C(=O)C(c2cc(Cl)cc(Cl)c2)=NC12CCC(C(C)C)CC2] |

-continued

| Ex. | Structure |
|---|---|
| 1.511 | 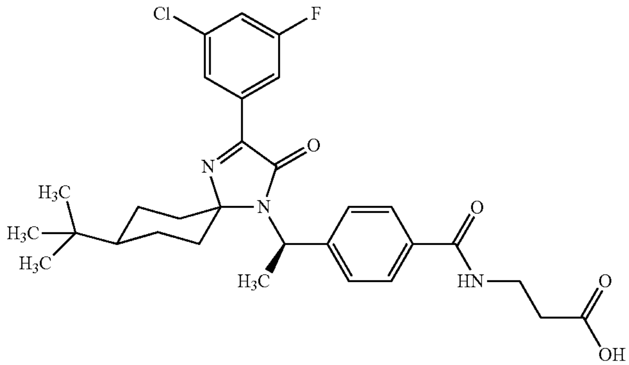 [SMILES: C[C@H](c1ccc(C(=O)NCCC(=O)O)cc1)N1C(=O)C(c2cc(F)cc(Cl)c2)=NC12CCC(C(C)(C)C)CC2] |
| 1.518 | 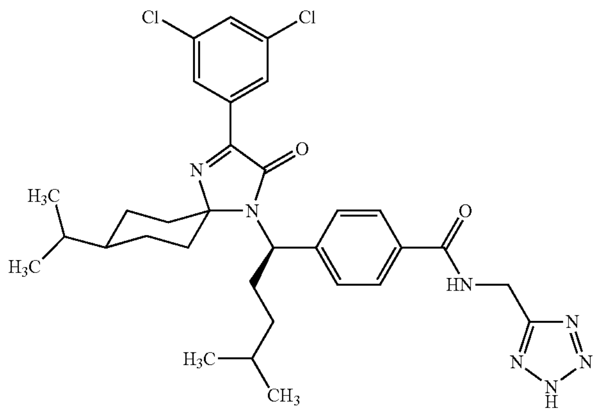 [SMILES: CC(C)CC[C@H](c1ccc(C(=O)NCc2nn[nH]n2)cc1)N1C(=O)C(c2cc(Cl)cc(Cl)c2)=NC12CCC(C(C)C)CC2] |
| 1.519 | 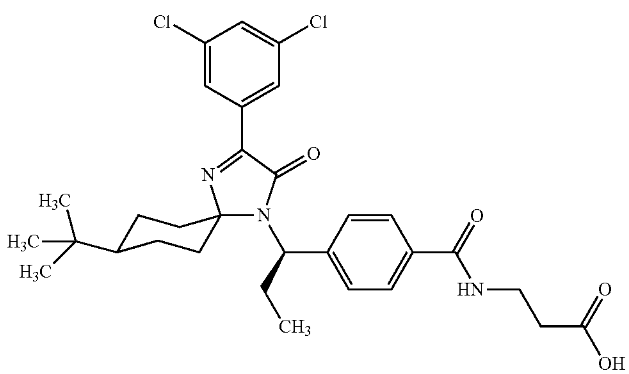 [SMILES: CC[C@H](c1ccc(C(=O)NCCC(=O)O)cc1)N1C(=O)C(c2cc(Cl)cc(Cl)c2)=NC12CCC(C(C)(C)C)CC2] |
| 1.520 | 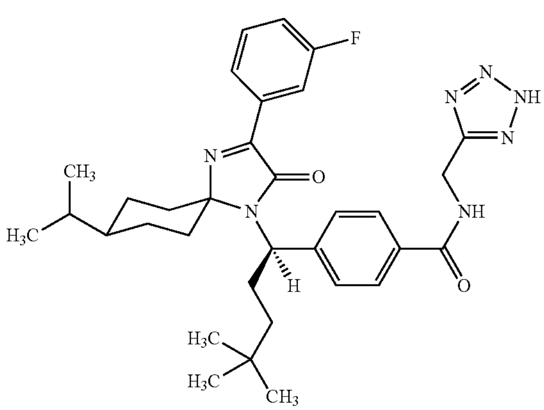 [SMILES: CC(C)C1CCC2(CC1)N=C(c1cccc(F)c1)C(=O)N2[C@H](CCC(C)(C)C)c1ccc(C(=O)NCc2nn[nH]n2)cc1] |

| Ex. | Structure |
|---|---|
| 1.514 | 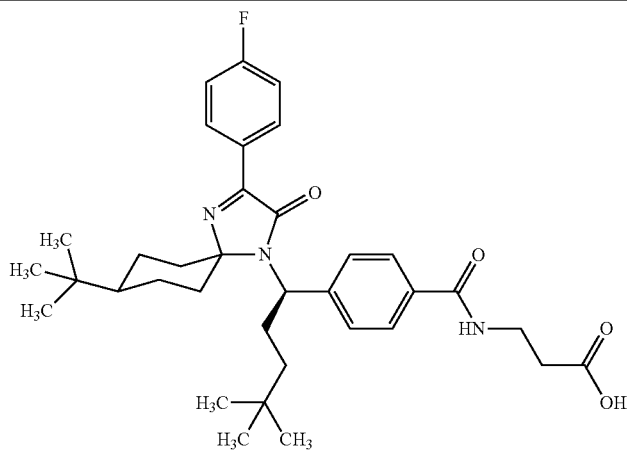 |
| 1.515 | 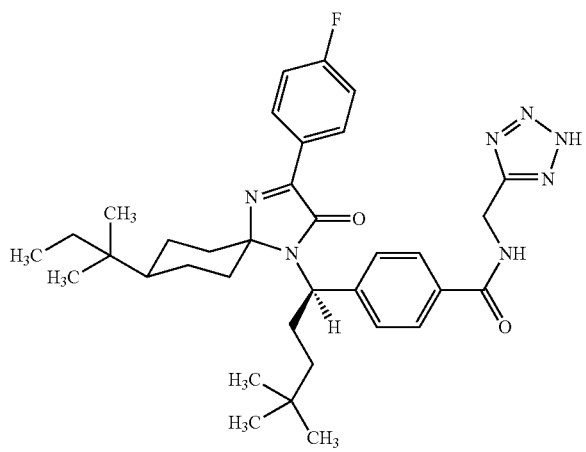 [SMILES: CCC(C)(C)C1CCC2(CC1)N=C(c1ccc(F)cc1)C(=O)N2[C@H](CCC(C)(C)C)c1ccc(C(=O)NCc2nn[nH]n2)cc1] |
| 1.516 | 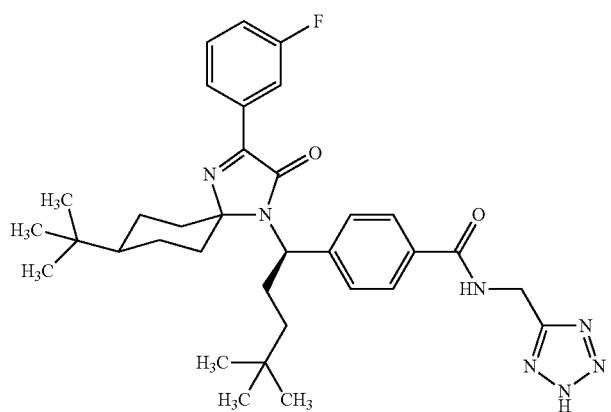 [SMILES: CC(C)(C)CC[C@H](c1ccc(C(=O)NCc2nn[nH]n2)cc1)N1C(=O)C(c2cccc(F)c2)=NC12CCC(C(C)(C)C)CC2] |

| Ex. | Structure |
|---|---|
| 1.517 | 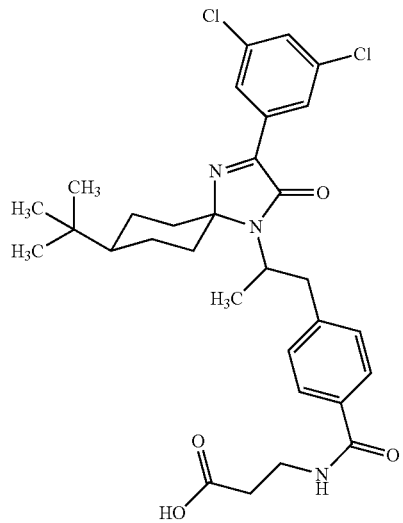 [SMILES: CC(Cc1ccc(C(=O)NCCC(=O)O)cc1)N1C(=O)C(c2cc(Cl)cc(Cl)c2)=NC12CCC(C(C)(C)C)CC2] |
| 1.524 | 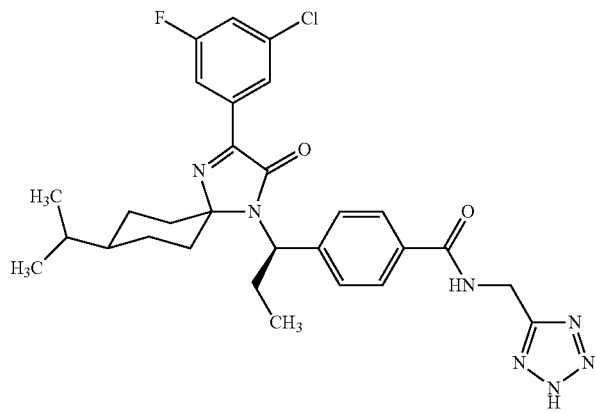 [SMILES: CC[C@H](c1ccc(C(=O)NCc2nn[nH]n2)cc1)N1C(=O)C(c2cc(F)cc(Cl)c2)=NC12CCC(C(C)C)CC2] |
| 1.525 | 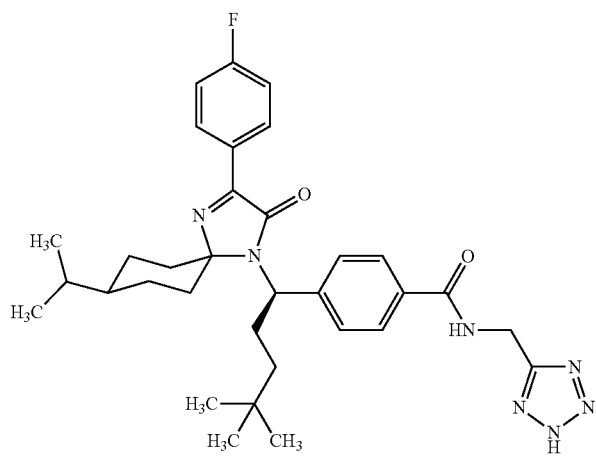 [SMILES: CC(C)C1CCC2(CC1)N=C(c1ccc(F)cc1)C(=O)N2[C@H](CCC(C)(C)C)c1ccc(C(=O)NCc2nn[nH]n2)cc1] |

-continued
| Ex. | Structure |
|---|---|
| 1.526 | 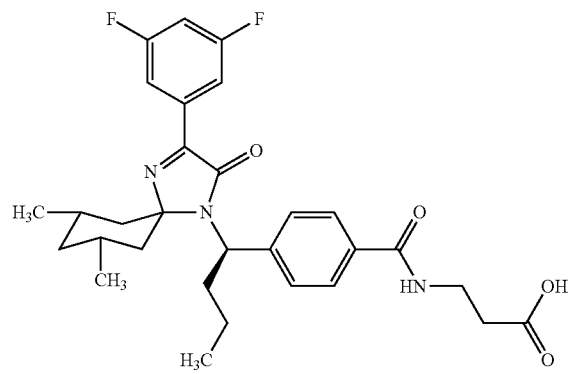 [SMILES: CCC[C@H](c1ccc(C(=O)NCCC(=O)O)cc1)N1C(=O)C(c2cc(F)cc(F)c2)=NC12CC(C)CC(C)C2] |
| 1.520 | 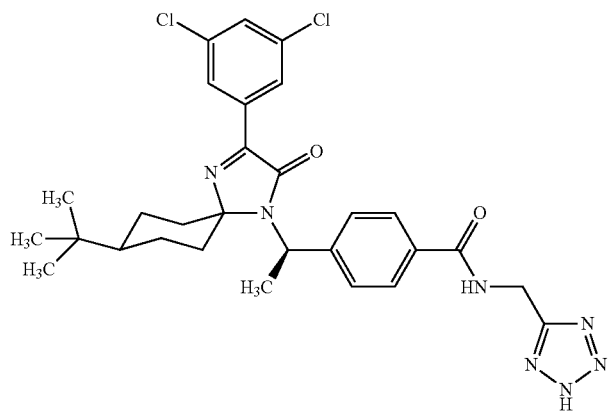 [SMILES: C[C@H](c1ccc(C(=O)NCc2nn[nH]n2)cc1)N1C(=O)C(c2cc(Cl)cc(Cl)c2)=NC12CCC(C(C)(C)C)CC2] |
| 1.521 | 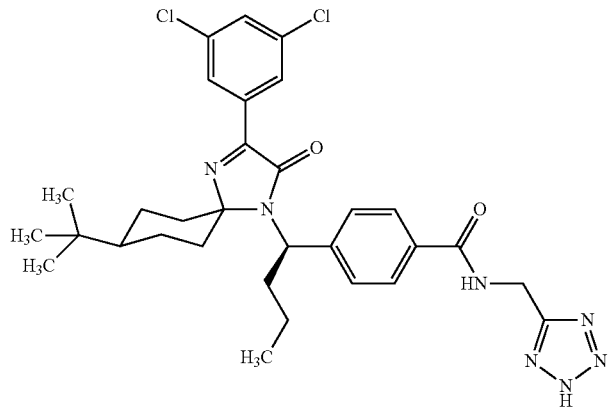 |

| Ex. | Structure |
|---|---|
| 1.522 | 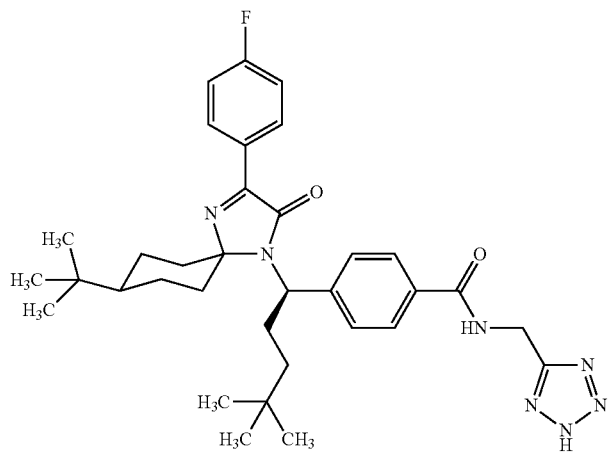 |
| 1.523 | 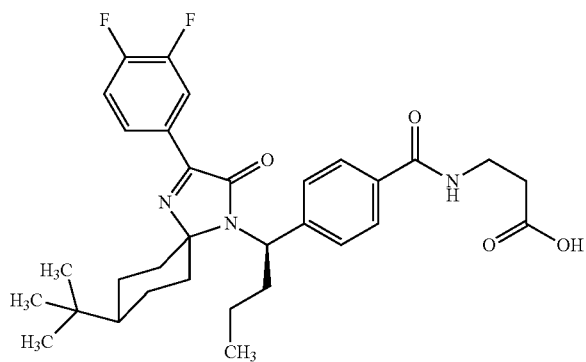 [SMILES: CCC[C@H](c1ccc(C(=O)NCCC(=O)O)cc1)N1C(=O)C(c2ccc(F)c(F)c2)=NC12CCC(C(C)(C)C)CC2] |
| 1.530 | 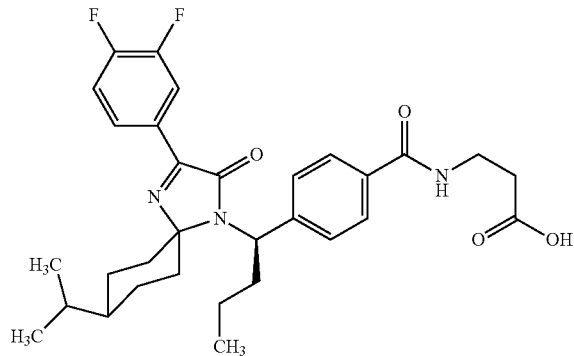 [SMILES: CCC[C@H](c1ccc(C(=O)NCCC(=O)O)cc1)N1C(=O)C(c2ccc(F)c(F)c2)=NC12CCC(C(C)C)CC2] |

| Ex. | Structure |
|---|---|
| 1.531 | 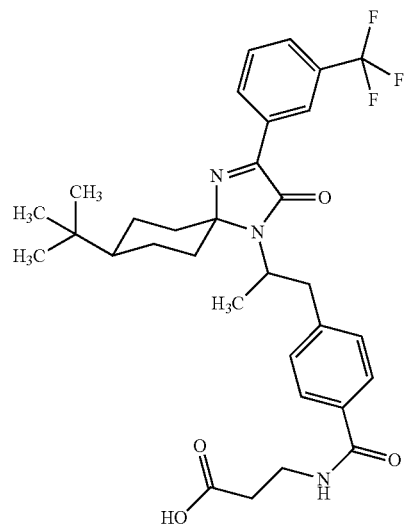 [SMILES: CC(Cc1ccc(C(=O)NCCC(=O)O)cc1)N1C(=O)C(c2cccc(C(F)(F)F)c2)=NC12CCC(C(C)(C)C)CC2] |
| 1.527 | 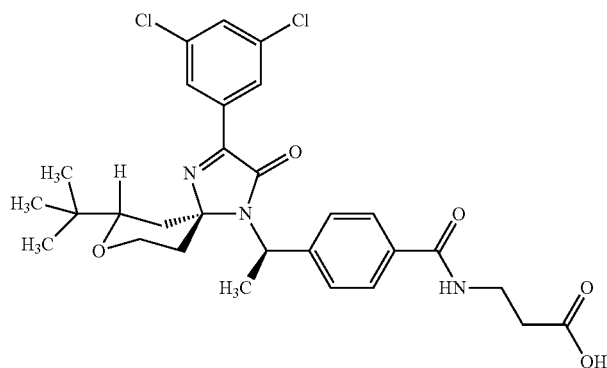 |
| 1.528 | 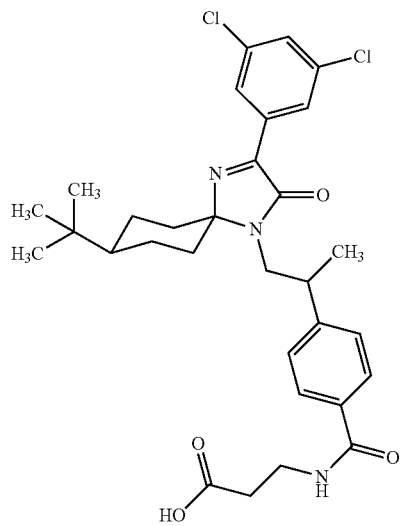 [SMILES: CC(CN1C(=O)C(c2cc(Cl)cc(Cl)c2)=NC12CCC(C(C)(C)C)CC2)c1ccc(C(=O)NCCC(=O)O)cc1] |

| Ex. | Structure |
|---|---|
| 1.529 | 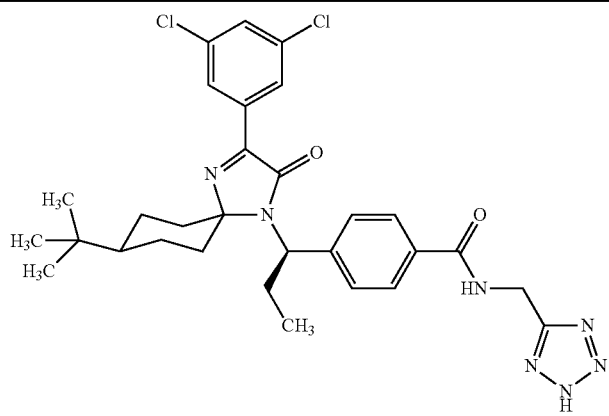 |
| 1.536 | 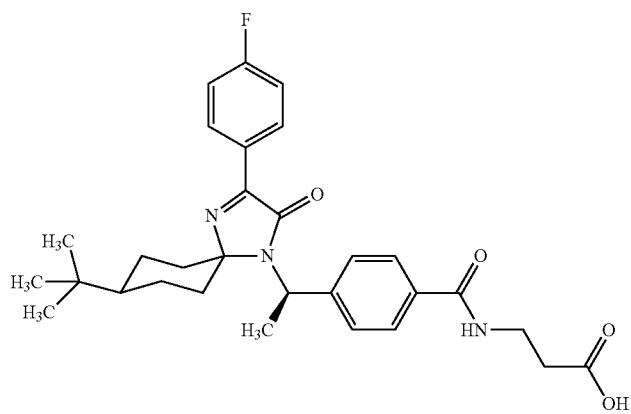 [SMILES: C[C@H](c1ccc(C(=O)NCCC(=O)O)cc1)N1C(=O)C(c2ccc(F)cc2)=NC12CCC(C(C)(C)C)CC2] |
| 1.537 | 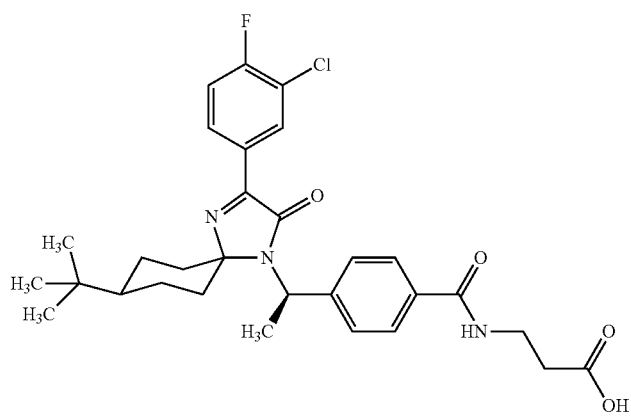 [SMILES: C[C@H](c1ccc(C(=O)NCCC(=O)O)cc1)N1C(=O)C(c2ccc(F)c(Cl)c2)=NC12CCC(C(C)(C)C)CC2] |

-continued
| Ex. | Structure |
|---|---|
| 1.538 | 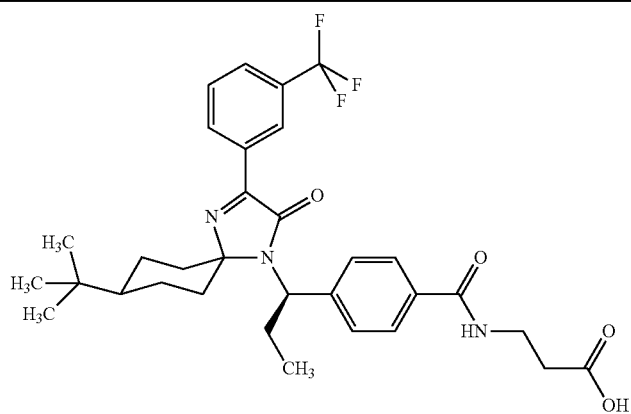 |
| 1.532 | 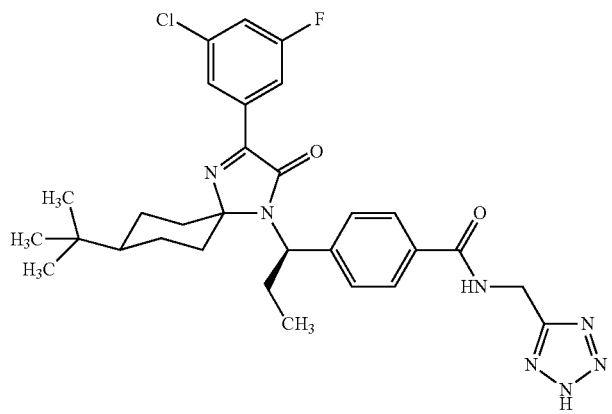 |
| 1.533 | 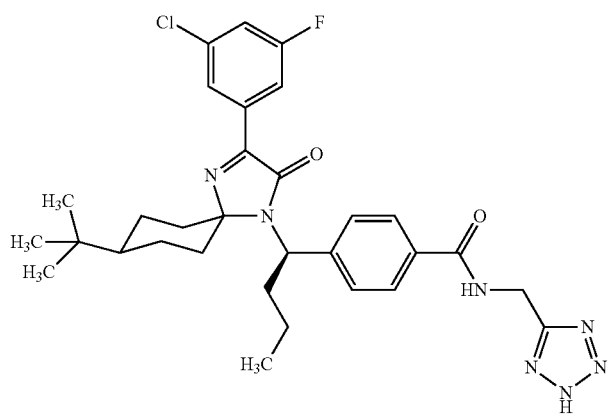 [SMILES: CCC[C@H](c1ccc(C(=O)NCc2nn[nH]n2)cc1)N1C(=O)C(c2cc(F)cc(Cl)c2)=NC12CCC(C(C)(C)C)CC2] |

| Ex. | Structure |
|---|---|
| 1.534 | 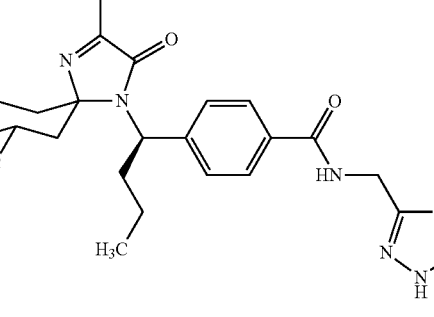 |
| 1.535 | 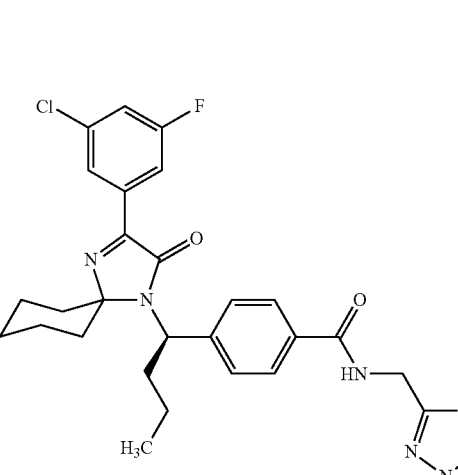 |
| 1.543 | 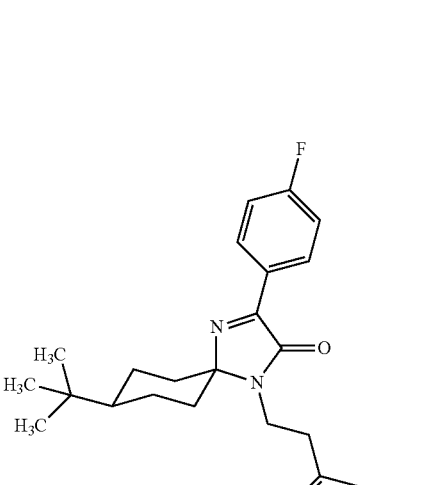 |

| Ex. | Structure |
|---|---|
| 1.544 | 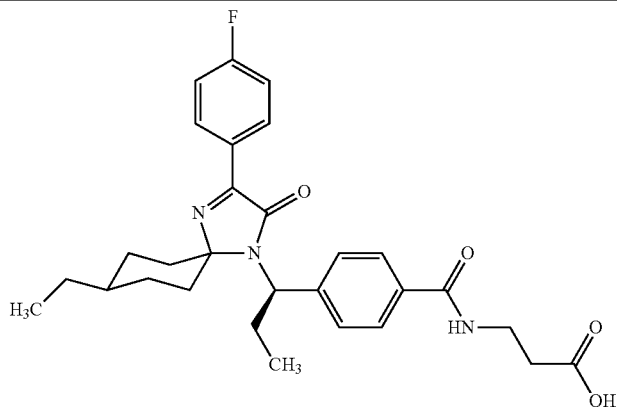 |
| 1.539 | 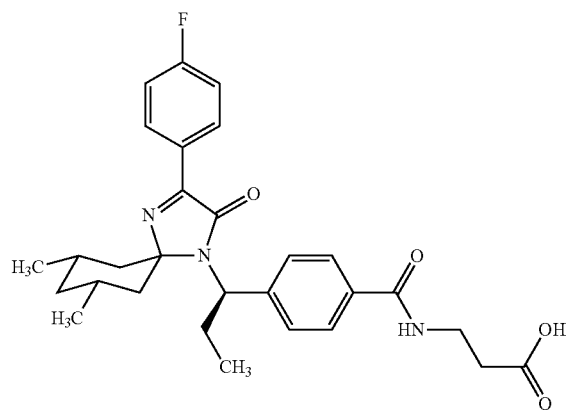 [SMILES: CC[C@H](c1ccc(C(=O)NCCC(=O)O)cc1)N1C(=O)C(c2ccc(F)cc2)=NC12CC(C)CC(C)C2] |
| 1.540 | 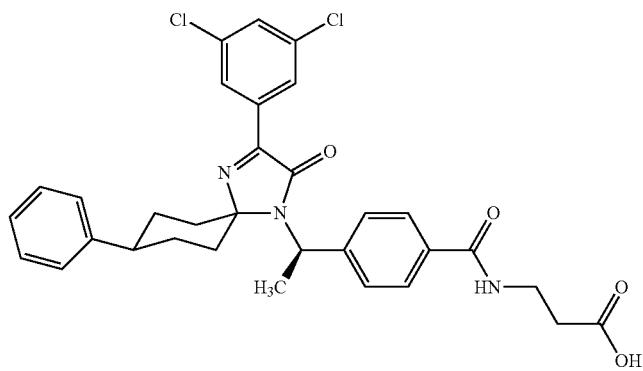 [SMILES: C[C@H](c1ccc(C(=O)NCCC(=O)O)cc1)N1C(=O)C(c2cc(Cl)cc(Cl)c2)=NC12CCC(c1ccccc1)CC2] |
| 1.541 | 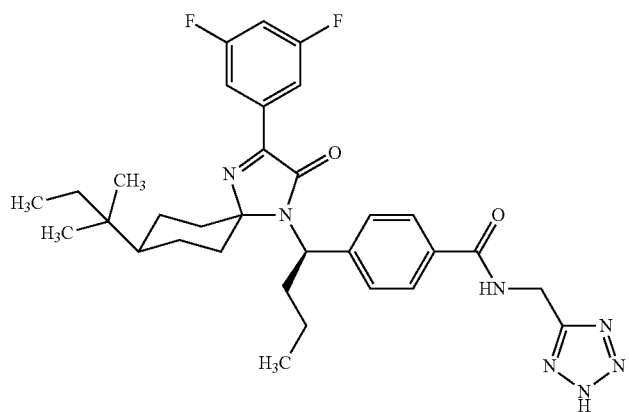 [SMILES: CCC[C@H](c1ccc(C(=O)NCc2nn[nH]n2)cc1)N1C(=O)C(c2cc(F)cc(F)c2)=NC12CCC(C(C)(C)CC)CC2] |

| Ex. | Structure |
|---|---|
| 1.542 | 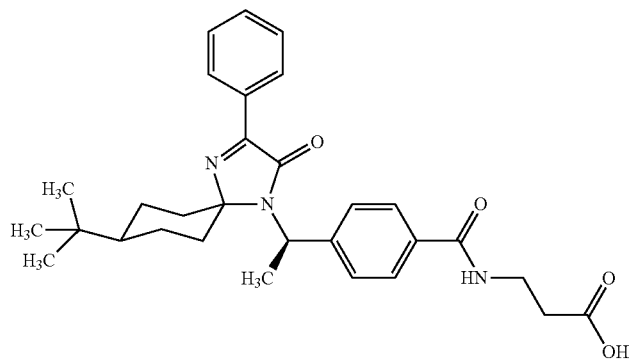 [SMILES: C[C@H](c1ccc(C(=O)NCCC(=O)O)cc1)N1C(=O)C(c2ccccc2)=NC12CCC(C(C)(C)C)CC2] |
| 1.549 | 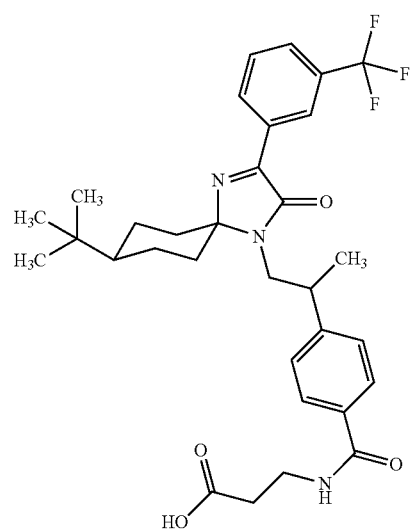 [SMILES: CC(CN1C(=O)C(c2cccc(C(F)(F)F)c2)=NC12CCC(C(C)(C)C)CC2)c1ccc(C(=O)NCCC(=O)O)cc1] |
| 1.550 | 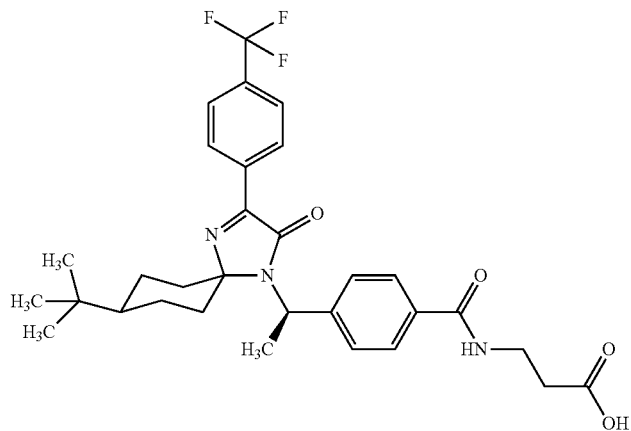 [SMILES: C[C@H](c1ccc(C(=O)NCCC(=O)O)cc1)N1C(=O)C(c2ccc(C(F)(F)F)cc2)=NC12CCC(C(C)(C)C)CC2] |

-continued
| Ex. | Structure |
|---|---|
| 1.545 | 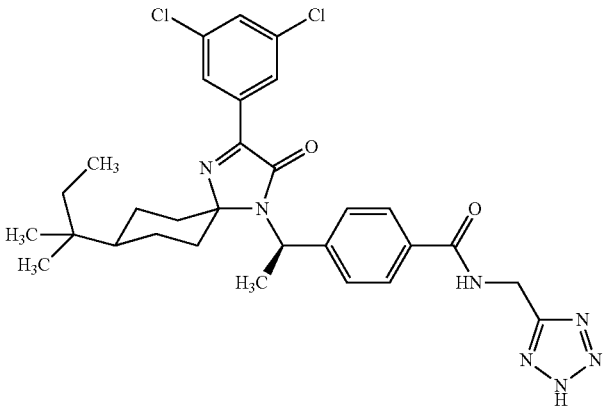 [SMILES: CCC(C)(C)C1CCC2(CC1)N=C(c1cc(Cl)cc(Cl)c1)C(=O)N2[C@H](C)c1ccc(C(=O)NCc2nn[nH]n2)cc1] |
| 1.546 | 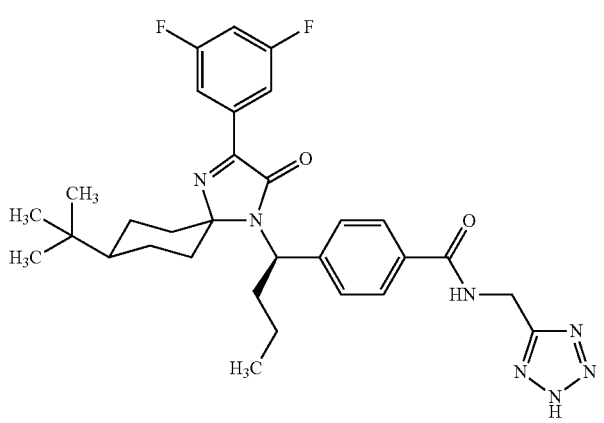 [SMILES: CCC[C@H](c1ccc(C(=O)NCc2nn[nH]n2)cc1)N1C(=O)C(c2cc(F)cc(F)c2)=NC12CCC(C(C)(C)C)CC2] |
| 1.547 | 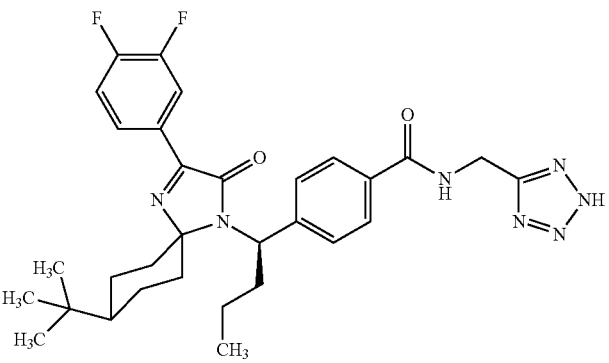 [SMILES: CCC[C@H](c1ccc(C(=O)NCc2nn[nH]n2)cc1)N1C(=O)C(c2ccc(F)c(F)c2)=NC12CCC(C(C)(C)C)CC2] |
| 1.548 | 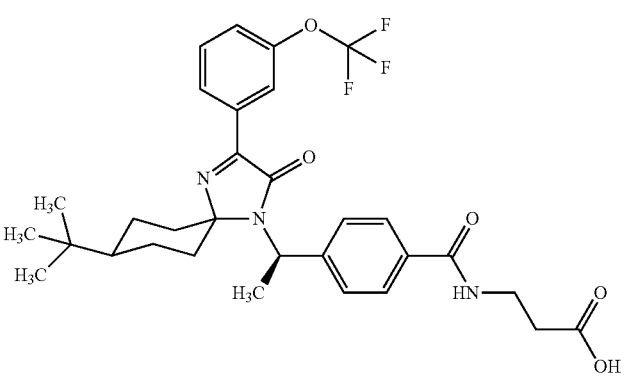 [SMILES: C[C@H](c1ccc(C(=O)NCCC(=O)O)cc1)N1C(=O)C(c2cccc(OC(F)(F)F)c2)=NC12CCC(C(C)(C)C)CC2] |

| Ex. | Structure |
|---|---|
| 1.555 | 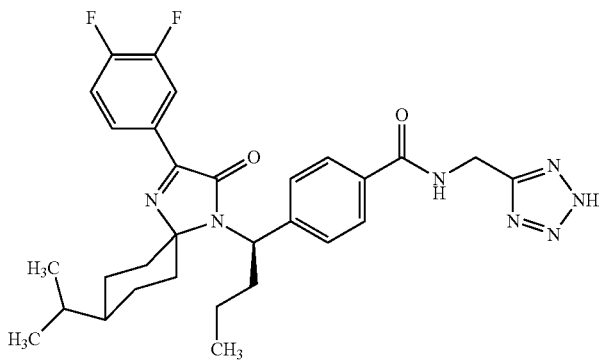 [SMILES: CCC[C@H](c1ccc(C(=O)NCc2nn[nH]n2)cc1)N1C(=O)C(c2ccc(F)c(F)c2)=NC12CCC(C(C)C)CC2] |
| 1.556 | 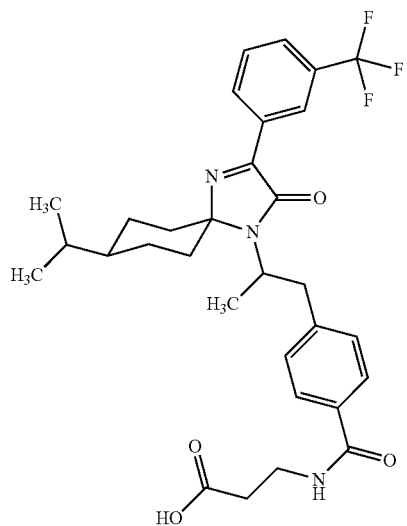 [SMILES: CC(C)C1CCC2(CC1)N=C(c1cccc(C(F)(F)F)c1)C(=O)N2C(C)Cc1ccc(C(=O)NCCC(=O)O)cc1] |
| 1.551 | 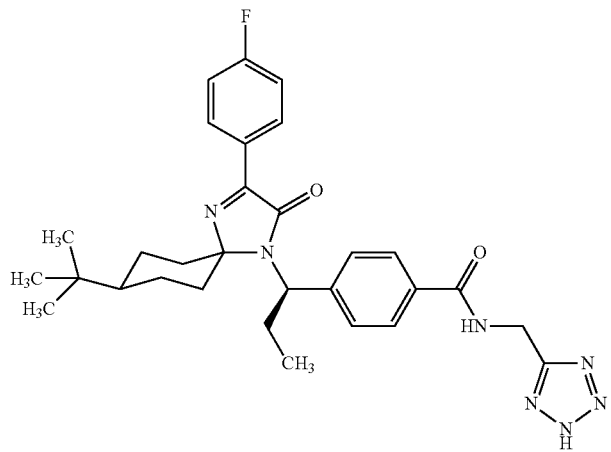 [SMILES: CC[C@H](c1ccc(C(=O)NCc2nn[nH]n2)cc1)N1C(=O)C(c2ccc(F)cc2)=NC12CCC(C(C)(C)C)CC2] |

-continued
| Ex. | Structure |
|---|---|
| 1.552 | 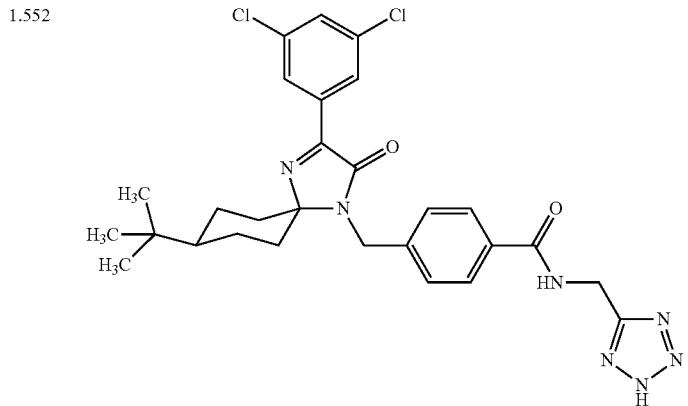 |
| 1.553 | 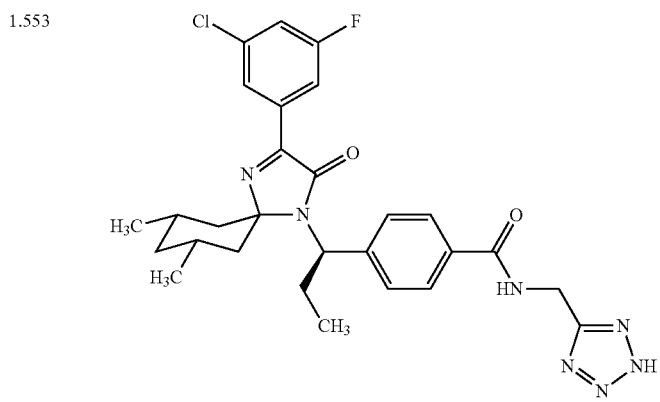 |
| 1.554 | 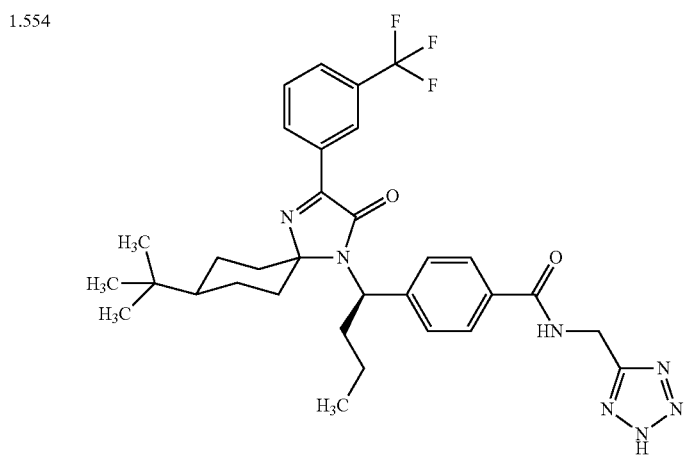 |

-continued
| Ex. | Structure |
|---|---|
| 1.561 | 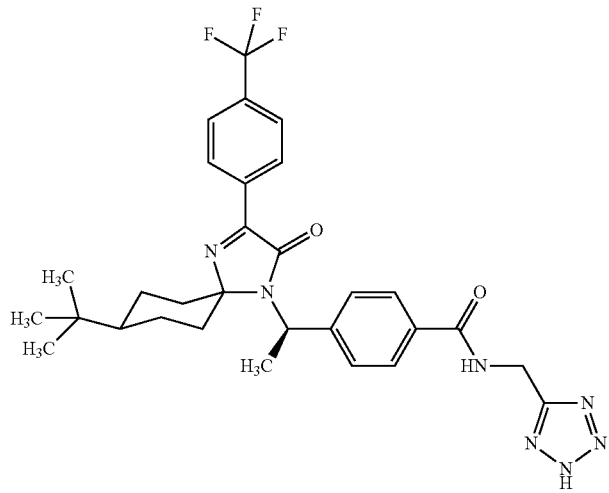 [SMILES: C[C@H](c1ccc(C(=O)NCc2nn[nH]n2)cc1)N1C(=O)C(c2ccc(C(F)(F)F)cc2)=NC12CCC(C(C)(C)C)CC2] |
| 1.562 | 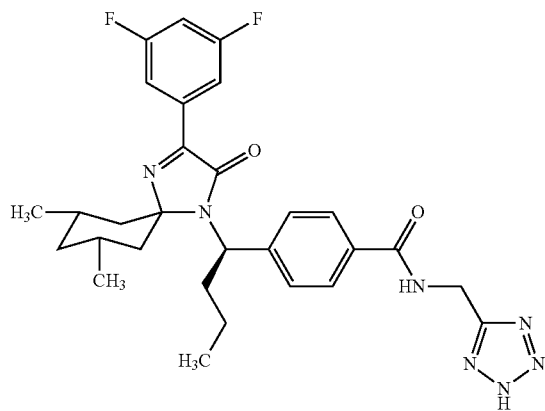 [SMILES: CCC[C@H](c1ccc(C(=O)NCc2nn[nH]n2)cc1)N1C(=O)C(c2cc(F)cc(F)c2)=NC12CC(C)CC(C)C2] |
| 1.557 | 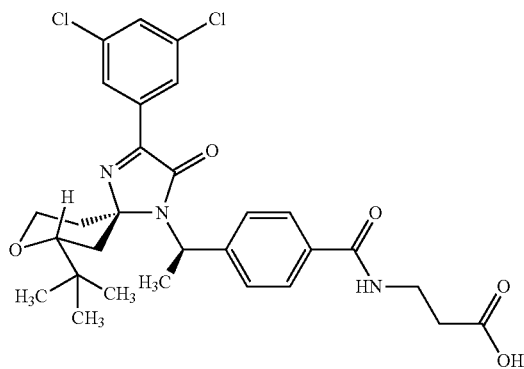 |

| Ex. | Structure |
|---|---|
| 1.558 | 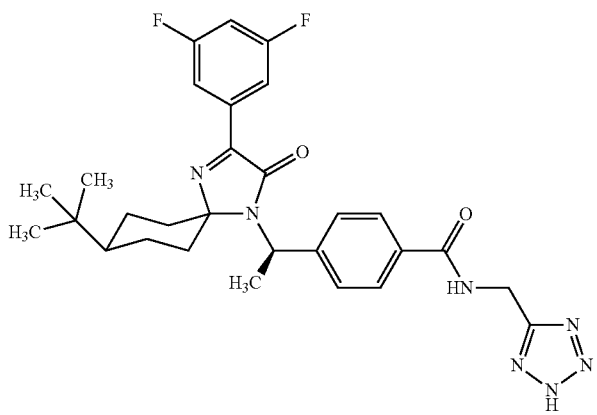 [SMILES: C[C@H](c1ccc(C(=O)NCc2nn[nH]n2)cc1)N1C(=O)C(c2cc(F)cc(F)c2)=NC12CCC(C(C)(C)C)CC2] |
| 1.559 | 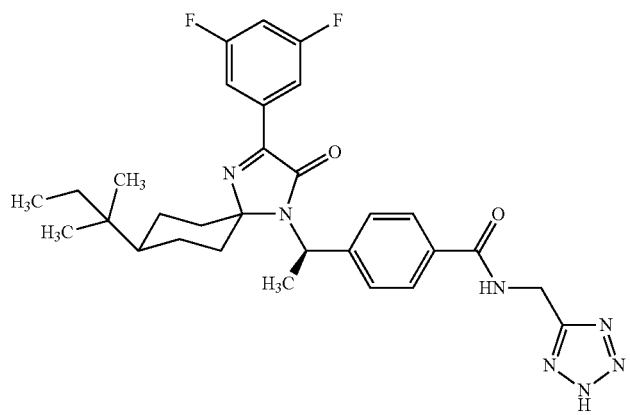 [SMILES: CCC(C)(C)C1CCC2(CC1)N=C(c1cc(F)cc(F)c1)C(=O)N2[C@H](C)c1ccc(C(=O)NCc2nn[nH]n2)cc1] |
| 1.560 | 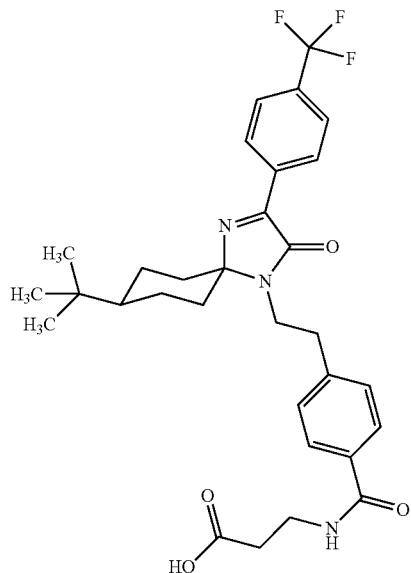 [SMILES: CC(C)(C)C1CCC2(CC1)N=C(c1ccc(C(F)(F)F)cc1)C(=O)N2CCc1ccc(C(=O)NCCC(=O)O)cc1] |

1423
-continued
| Ex. | Structure |
|---|---|
| 1.567 | 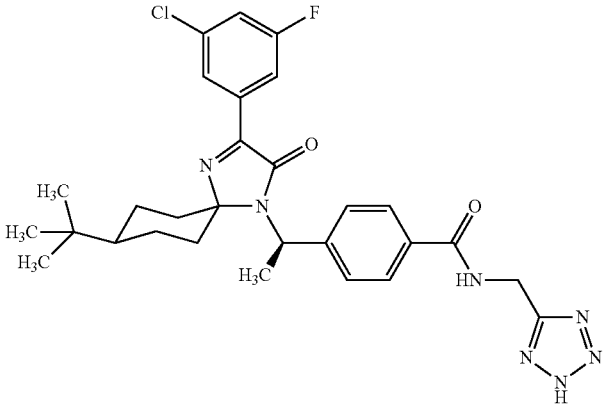 [SMILES: C[C@H](c1ccc(C(=O)NCc2nn[nH]n2)cc1)N1C(=O)C(c2cc(F)cc(Cl)c2)=NC12CCC(C(C)(C)C)CC2] |
| 1.568 | 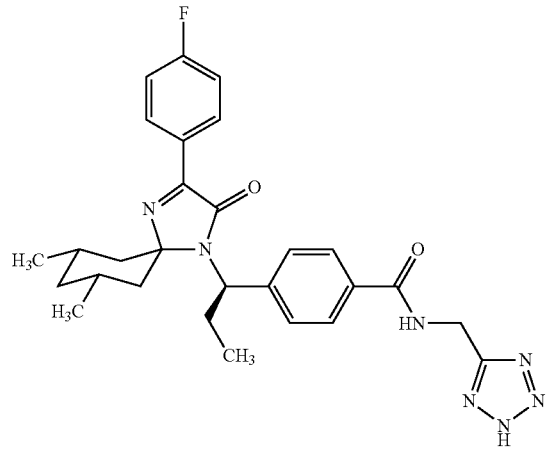 [SMILES: CC[C@H](c1ccc(C(=O)NCc2nn[nH]n2)cc1)N1C(=O)C(c2ccc(F)cc2)=NC12CC(C)CC(C)C2] |
| 1.563 | 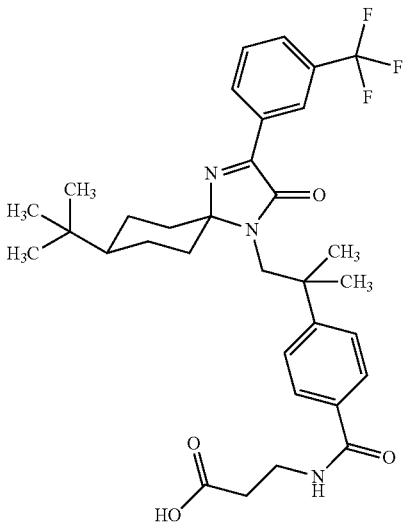 [SMILES: CC(C)(CN1C(=O)C(c2cccc(C(F)(F)F)c2)=NC12CCC(C(C)(C)C)CC2)c1ccc(C(=O)NCCC(=O)O)cc1] |
1424

| Ex. | Structure |
|---|---|
| 1.564 | 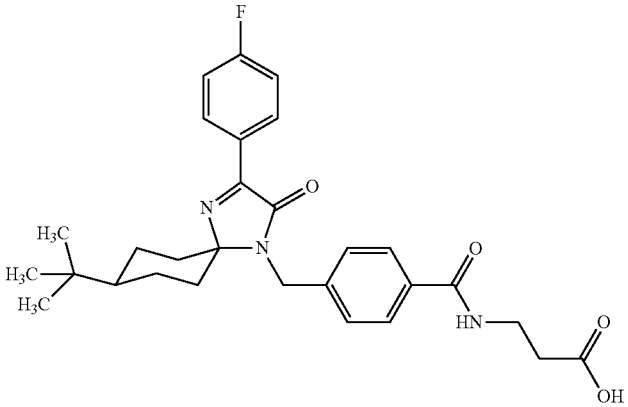 [SMILES: CC(C)(C)C1CCC2(CC1)N=C(c1ccc(F)cc1)C(=O)N2Cc1ccc(C(=O)NCCC(=O)O)cc1] |
| 1.565 | 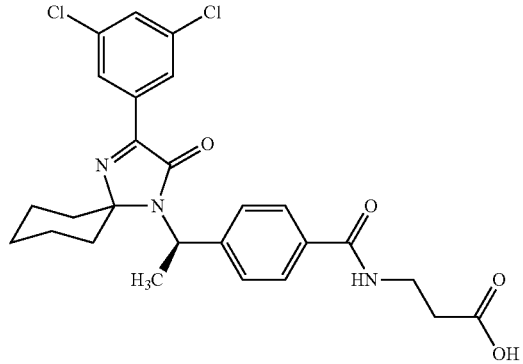 [SMILES: C[C@H](c1ccc(C(=O)NCCC(=O)O)cc1)N1C(=O)C(c2cc(Cl)cc(Cl)c2)=NC12CCCCC2] |
| 1.566 | 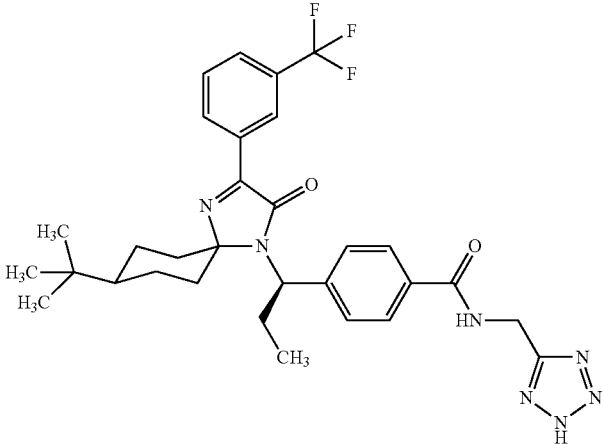 [SMILES: CC[C@H](c1ccc(C(=O)NCc2nn[nH]n2)cc1)N1C(=O)C(c2cccc(C(F)(F)F)c2)=NC12CCC(C(C)(C)C)CC2] |

| Ex. | Structure |
|---|---|
| 1.573 | 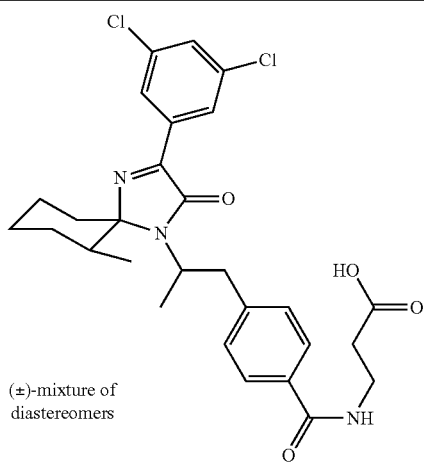<br>(±)-mixture of diastereomers |
| 1.574 | 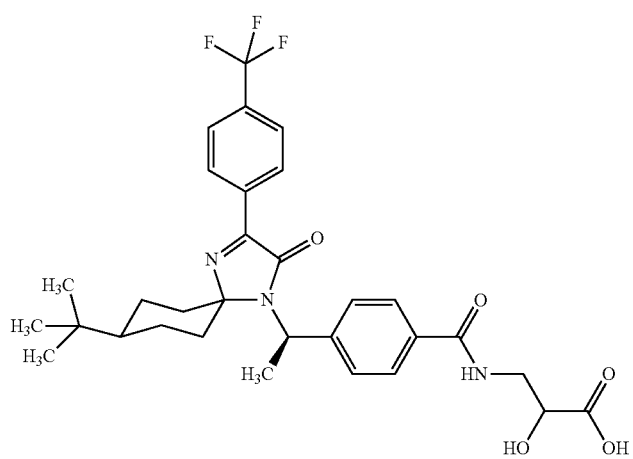 [SMILES: C[C@H](c1ccc(C(=O)NCC(O)C(=O)O)cc1)N1C(=O)C(c2ccc(C(F)(F)F)cc2)=NC12CCC(C(C)(C)C)CC2] |
| 1.569 | 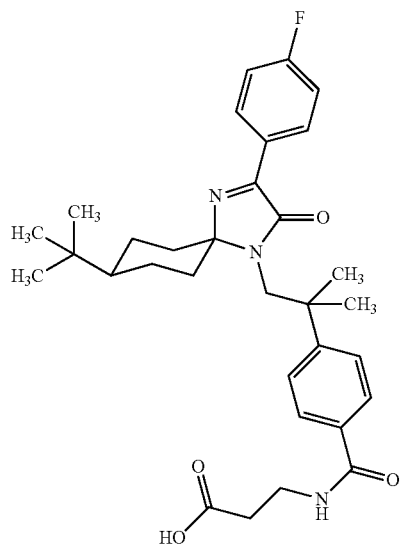 [SMILES: CC(C)(CN1C(=O)C(c2ccc(F)cc2)=NC12CCC(C(C)(C)C)CC2)c1ccc(C(=O)NCCC(=O)O)cc1] |

| Ex. | Structure |
|---|---|
| 1.570 | 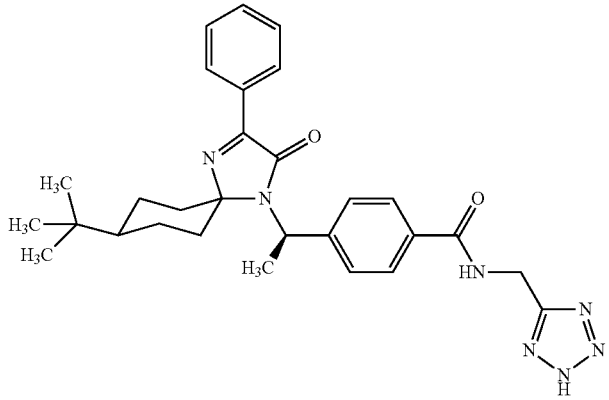 [SMILES: C[C@H](c1ccc(C(=O)NCc2nn[nH]n2)cc1)N1C(=O)C(c2ccccc2)=NC12CCC(C(C)(C)C)CC2] |
| 1.571 | 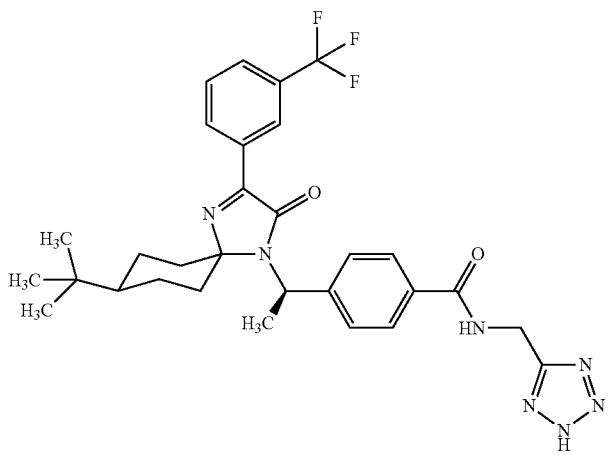 [SMILES: C[C@H](c1ccc(C(=O)NCc2nn[nH]n2)cc1)N1C(=O)C(c2cccc(C(F)(F)F)c2)=NC12CCC(C(C)(C)C)CC2] |
| 1.572 | 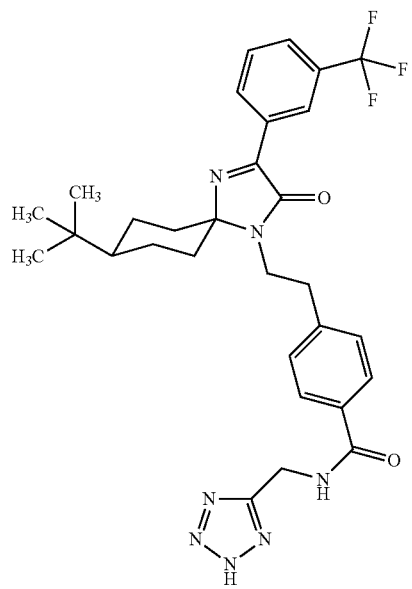 [SMILES: CC(C)(C)C1CCC2(CC1)N=C(c1cccc(C(F)(F)F)c1)C(=O)N2CCc1ccc(C(=O)NCc2nn[nH]n2)cc1] |

| Ex. | Structure |
|---|---|
| 1.903 | 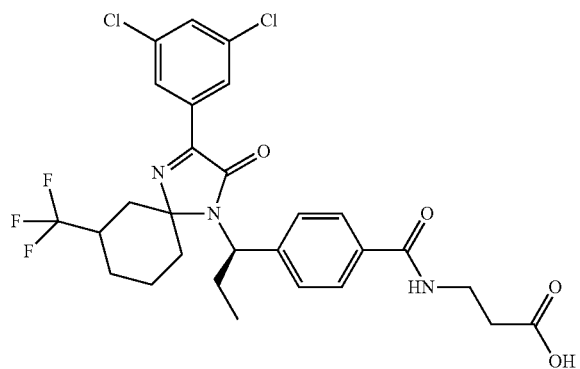 [SMILES: CC[C@H](c1ccc(C(=O)NCCC(=O)O)cc1)N1C(=O)C(c2cc(Cl)cc(Cl)c2)=NC12CCCC(C(F)(F)F)C2] |
| 1.904 | 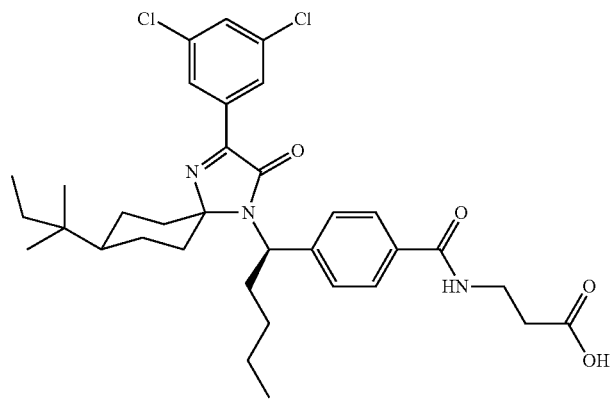 [SMILES: CCCC[C@H](c1ccc(C(=O)NCCC(=O)O)cc1)N1C(=O)C(c2cc(Cl)cc(Cl)c2)=NC12CCC(C(C)(C)CC)CC2] |
| 1.575 | 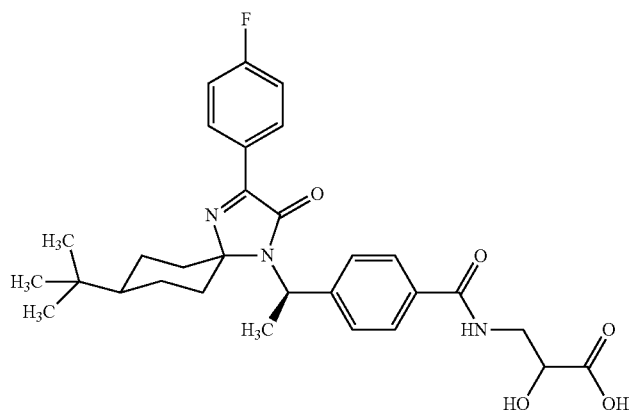 [SMILES: C[C@H](c1ccc(C(=O)NCC(O)C(=O)O)cc1)N1C(=O)C(c2ccc(F)cc2)=NC12CCC(C(C)(C)C)CC2] |
| 1.900 | 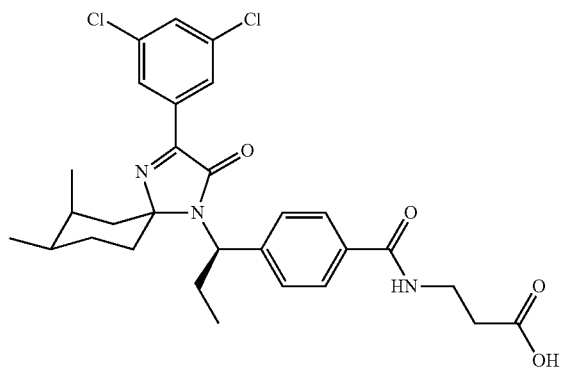 [SMILES: CC[C@H](c1ccc(C(=O)NCCC(=O)O)cc1)N1C(=O)C(c2cc(Cl)cc(Cl)c2)=NC12CCC(C)C(C)C2] |

-continued

| Ex. | Structure |
|---|---|
| 1.901 | 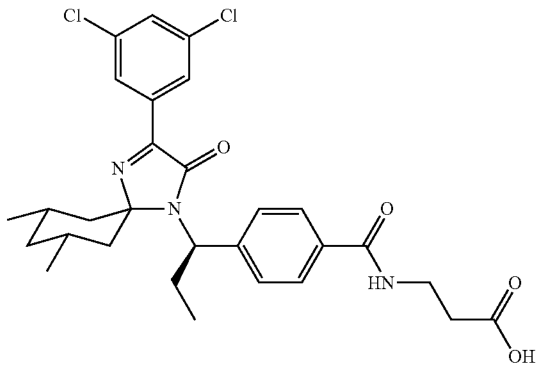 [SMILES: CC[C@H](c1ccc(C(=O)NCCC(=O)O)cc1)N1C(=O)C(c2cc(Cl)cc(Cl)c2)=NC12CC(C)CC(C)C2] |
| 1.902 | 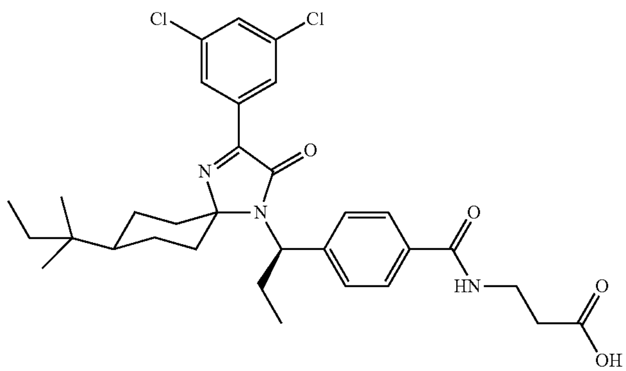 [SMILES: CC[C@H](c1ccc(C(=O)NCCC(=O)O)cc1)N1C(=O)C(c2cc(Cl)cc(Cl)c2)=NC12CCC(C(C)(C)CC)CC2] |
| 1.910 | 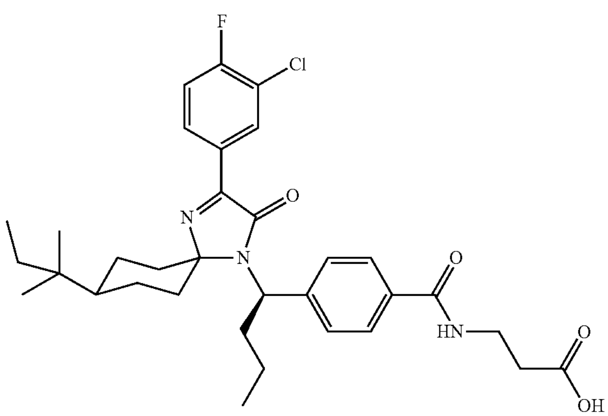 [SMILES: CCC[C@H](c1ccc(C(=O)NCCC(=O)O)cc1)N1C(=O)C(c2ccc(F)c(Cl)c2)=NC12CCC(C(C)(C)CC)CC2] |
| 1.911 | 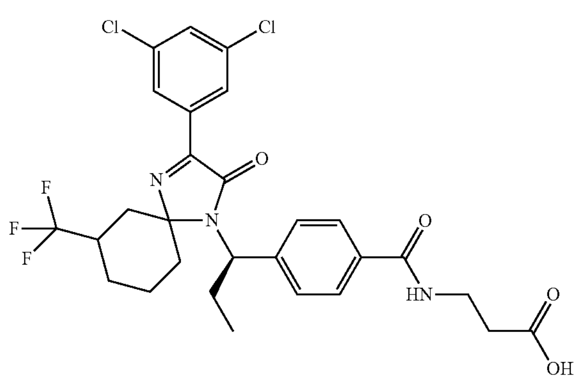 [SMILES: CC[C@H](c1ccc(C(=O)NCCC(=O)O)cc1)N1C(=O)C(c2cc(Cl)cc(Cl)c2)=NC12CCCC(C(F)(F)F)C2] |

| Ex. | Structure |
|---|---|
| 1.905 | 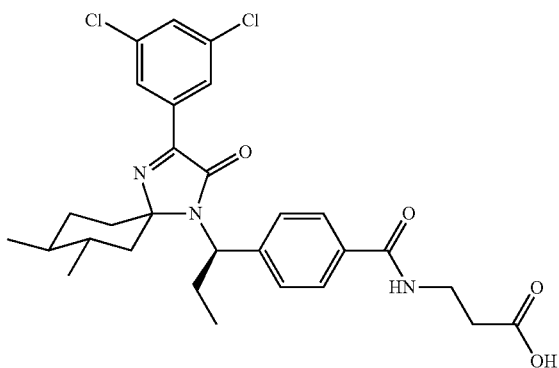 [SMILES: CC[C@H](c1ccc(C(=O)NCCC(=O)O)cc1)N1C(=O)C(c2cc(Cl)cc(Cl)c2)=NC12CCC(C)C(C)C2] |
| 1.906 | 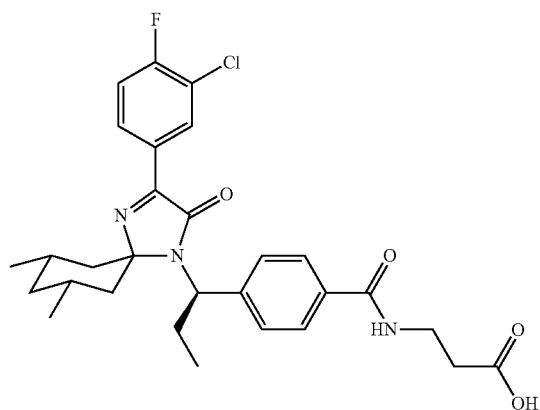 [SMILES: CC[C@H](c1ccc(C(=O)NCCC(=O)O)cc1)N1C(=O)C(c2ccc(F)c(Cl)c2)=NC12CC(C)CC(C)C2] |
| 1.907 | 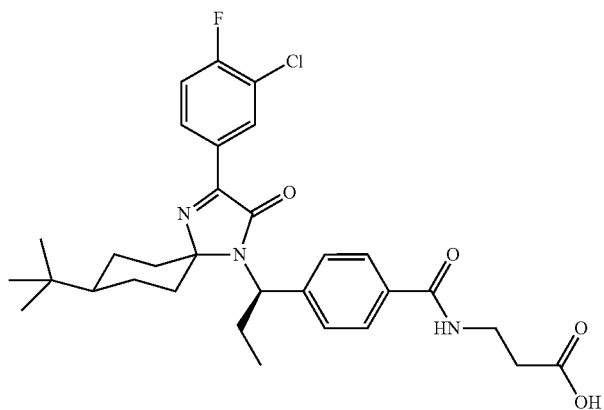 [SMILES: CC[C@H](c1ccc(C(=O)NCCC(=O)O)cc1)N1C(=O)C(c2ccc(F)c(Cl)c2)=NC12CCC(C(C)(C)C)CC2] |
| 1.908 | 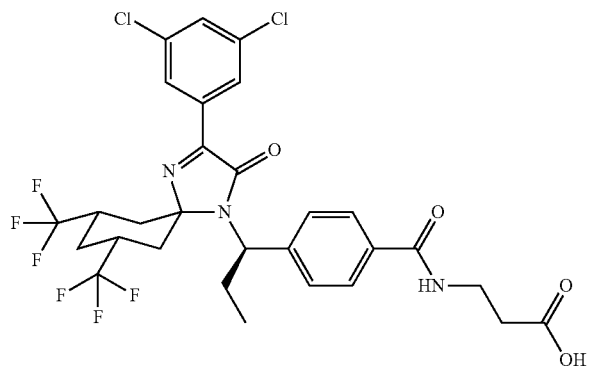 [SMILES: CC[C@H](c1ccc(C(=O)NCCC(=O)O)cc1)N1C(=O)C(c2cc(Cl)cc(Cl)c2)=NC12CC(C(F)(F)F)CC(C(F)(F)F)C2] |

| Ex. | Structure |
|---|---|
| 1.909 | 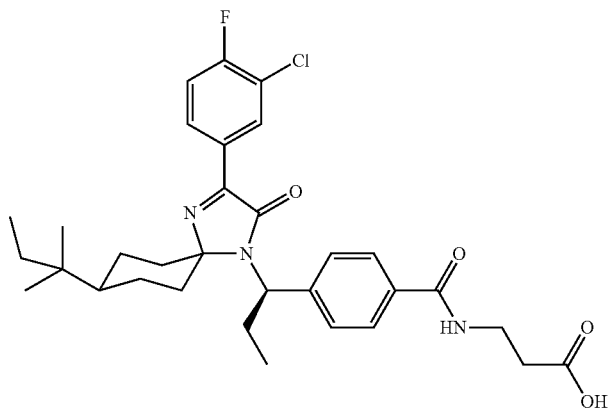 [SMILES: CC[C@H](c1ccc(C(=O)NCCC(=O)O)cc1)N1C(=O)C(c2ccc(F)c(Cl)c2)=NC12CCC(C(C)(C)CC)CC2] |
| 1.916 | 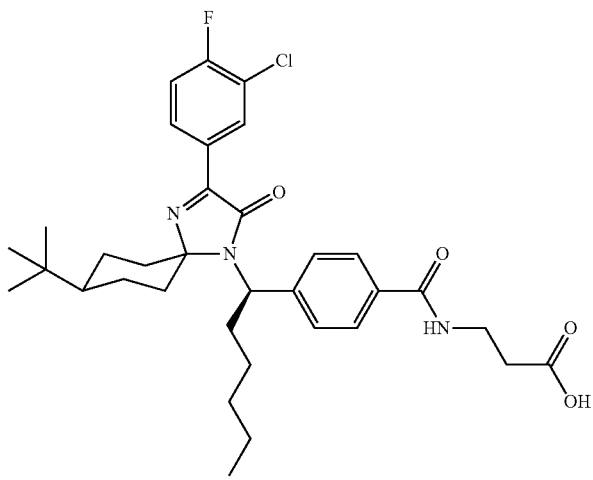 [SMILES: CCCCC[C@H](c1ccc(C(=O)NCCC(=O)O)cc1)N1C(=O)C(c2ccc(F)c(Cl)c2)=NC12CCC(C(C)(C)C)CC2] |
| 1.912 | 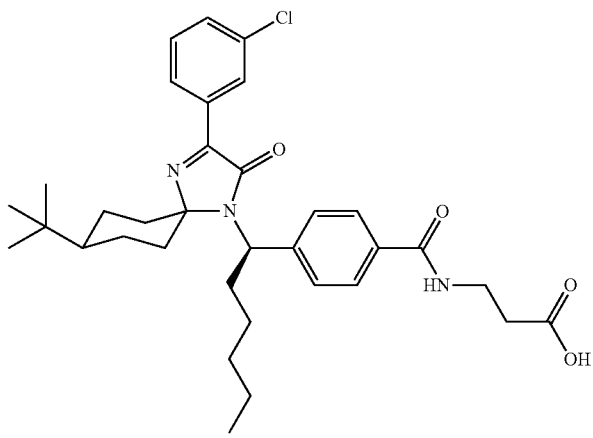 [SMILES: CCCCC[C@H](c1ccc(C(=O)NCCC(=O)O)cc1)N1C(=O)C(c2cccc(Cl)c2)=NC12CCC(C(C)(C)C)CC2] |

| Ex. | Structure |
|---|---|
| 1.913 | 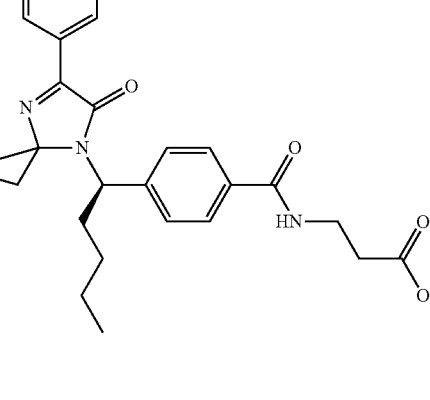 |
| 1.914 | 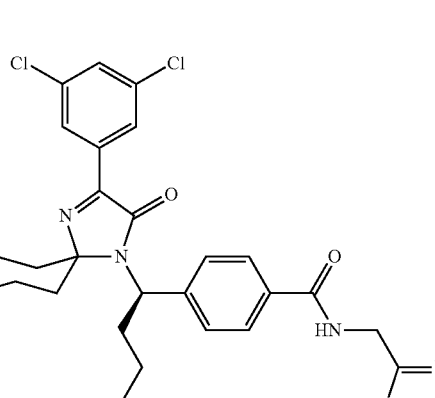 |
| 1.915 | 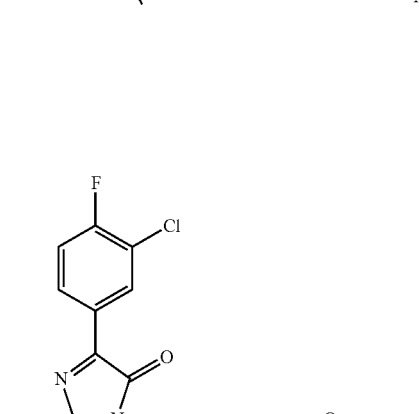 |

-continued
| Ex. | Structure |
|---|---|
| 1.922 | 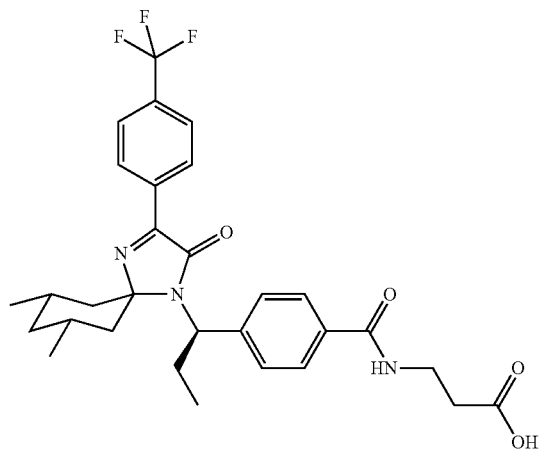 [SMILES: CC[C@H](c1ccc(C(=O)NCCC(=O)O)cc1)N1C(=O)C(c2ccc(C(F)(F)F)cc2)=NC12CC(C)CC(C)C2] |
| 1.923 | 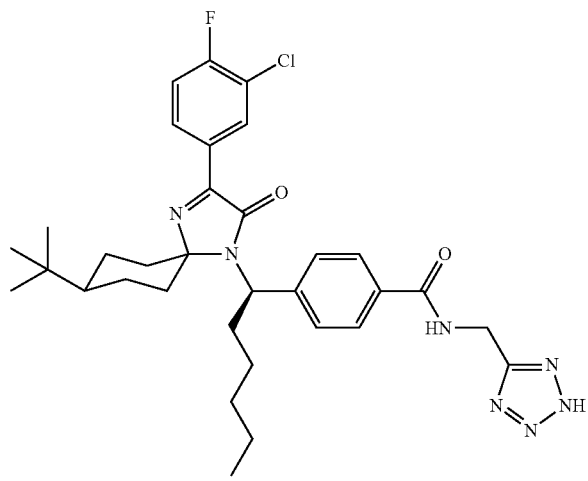 [SMILES: CCCCC[C@H](c1ccc(C(=O)NCc2nn[nH]n2)cc1)N1C(=O)C(c2ccc(F)c(Cl)c2)=NC12CCC(C(C)(C)C)CC2] |
| 1.917 | 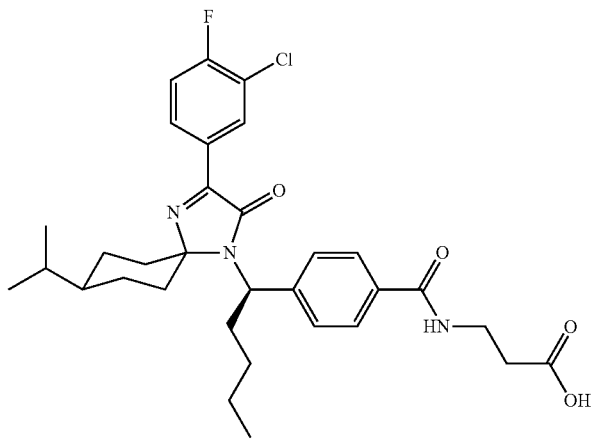 [SMILES: CCCC[C@H](c1ccc(C(=O)NCCC(=O)O)cc1)N1C(=O)C(c2ccc(F)c(Cl)c2)=NC12CCC(C(C)C)CC2] |

| Ex. | Structure |
|---|---|
| 1.918 | 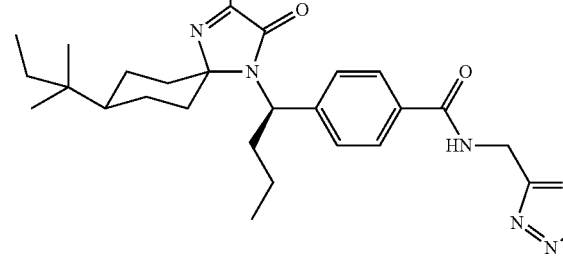 |
| 1.919 | 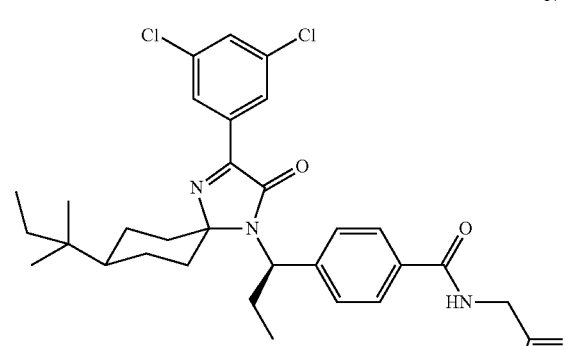 |
| 1.920 | 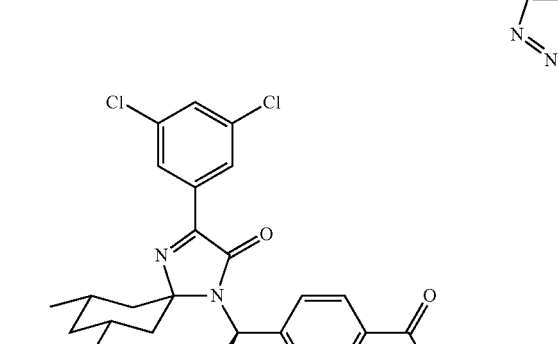 |
| 1.921 | 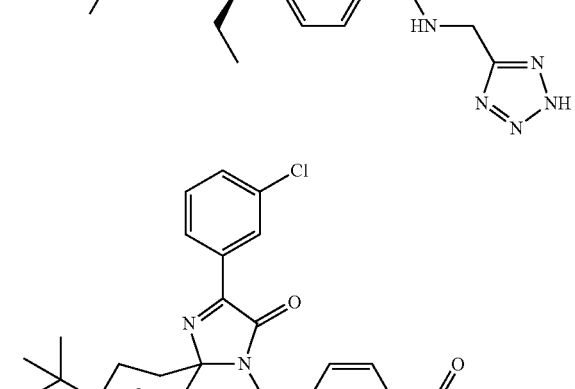 |

| Ex. | Structure |
|---|---|
| 1.928 | 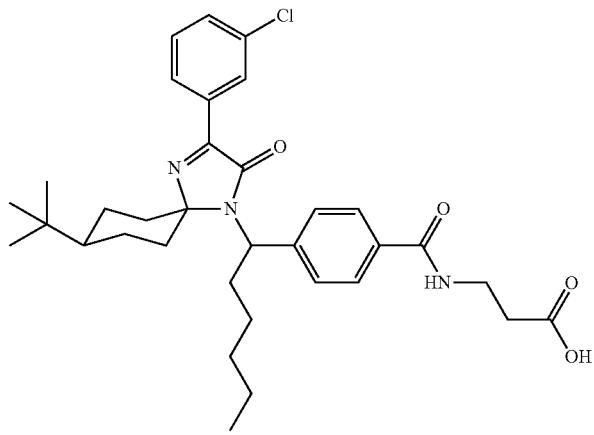 [SMILES: CCCCCC(c1ccc(C(=O)NCCC(=O)O)cc1)N1C(=O)C(c2cccc(Cl)c2)=NC12CCC(C(C)(C)C)CC2] |
| 1.924 | 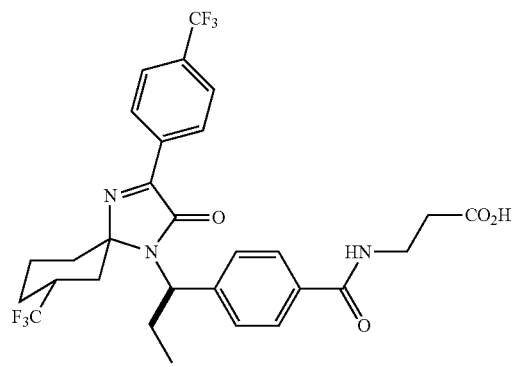
Isomer 2 |
| 1.925 | 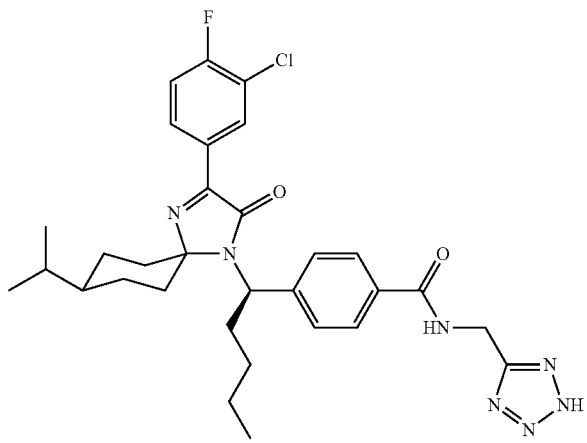 [SMILES: CCCC[C@H](c1ccc(C(=O)NCc2nn[nH]n2)cc1)N1C(=O)C(c2ccc(F)c(Cl)c2)=NC12CCC(C(C)C)CC2] |

| Ex. | Structure |
|---|---|
| 1.926 | 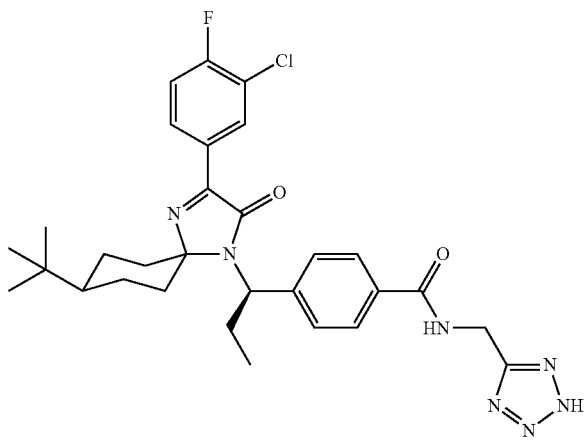 [SMILES: CC[C@H](c1ccc(C(=O)NCc2nn[nH]n2)cc1)N1C(=O)C(c2ccc(F)c(Cl)c2)=NC12CCC(C(C)(C)C)CC2] |
| 1.927 | 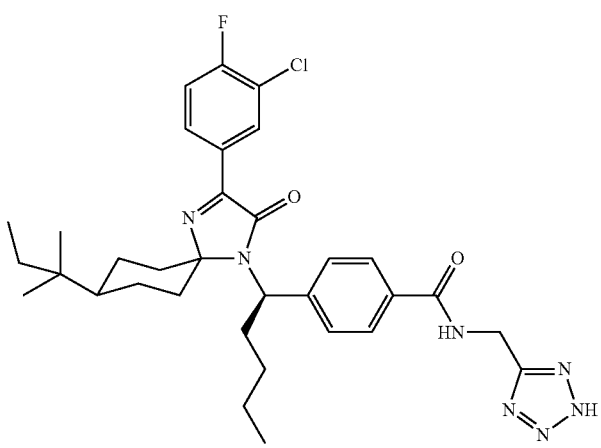 [SMILES: CCCC[C@H](c1ccc(C(=O)NCc2nn[nH]n2)cc1)N1C(=O)C(c2ccc(F)c(Cl)c2)=NC12CCC(C(C)(C)CC)CC2] |
| 1.934 | 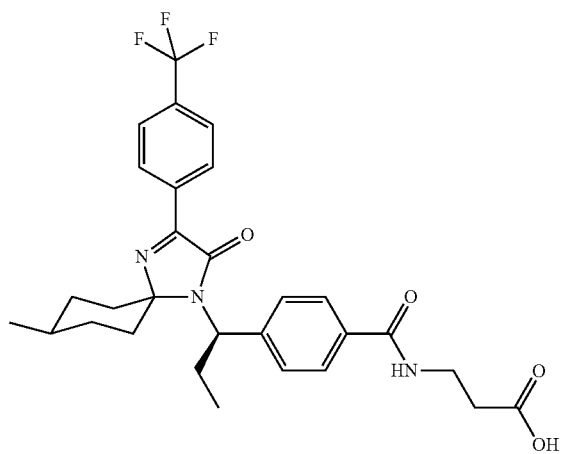 [SMILES: CC[C@H](c1ccc(C(=O)NCCC(=O)O)cc1)N1C(=O)C(c2ccc(C(F)(F)F)cc2)=NC12CCC(C)CC2] |

| Ex. | Structure |
|---|---|
| 1.935 | 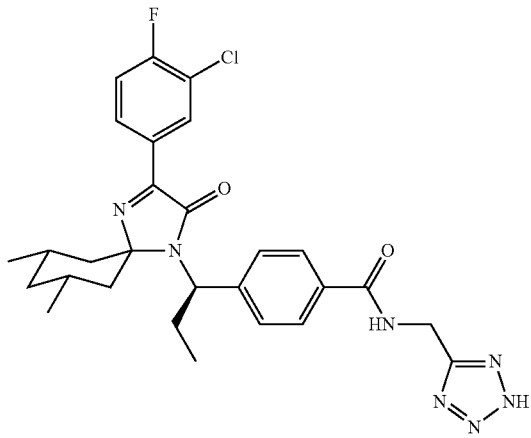 [SMILES: CC[C@H](c1ccc(C(=O)NCc2nn[nH]n2)cc1)N1C(=O)C(c2ccc(F)c(Cl)c2)=NC12CC(C)CC(C)C2] |
| 1.929 | 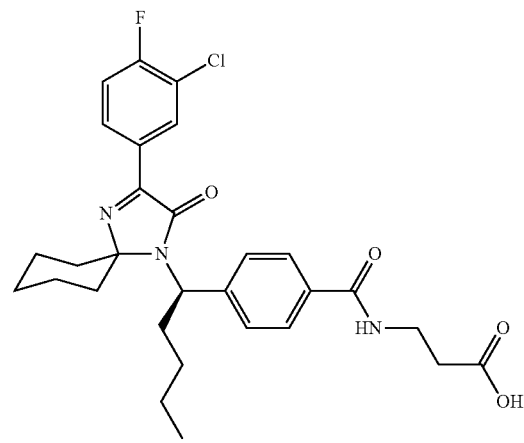 [SMILES: CCCC[C@H](c1ccc(C(=O)NCCC(=O)O)cc1)N1C(=O)C(c2ccc(F)c(Cl)c2)=NC12CCCCC2] |
| 1.930 | 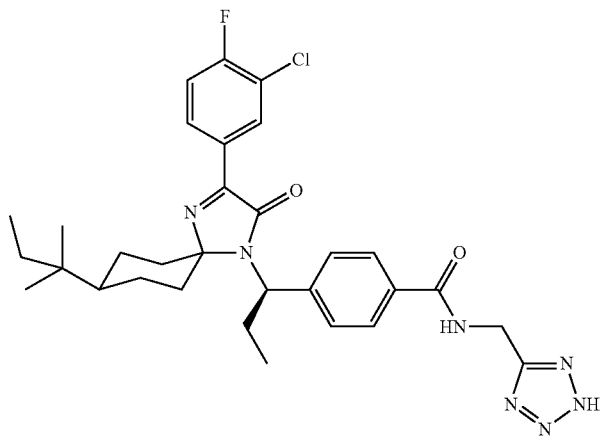 [SMILES: CC[C@H](c1ccc(C(=O)NCc2nn[nH]n2)cc1)N1C(=O)C(c2ccc(F)c(Cl)c2)=NC12CCC(C(C)(C)CC)CC2] |

| Ex. | Structure |
|---|---|
| 1.931 | 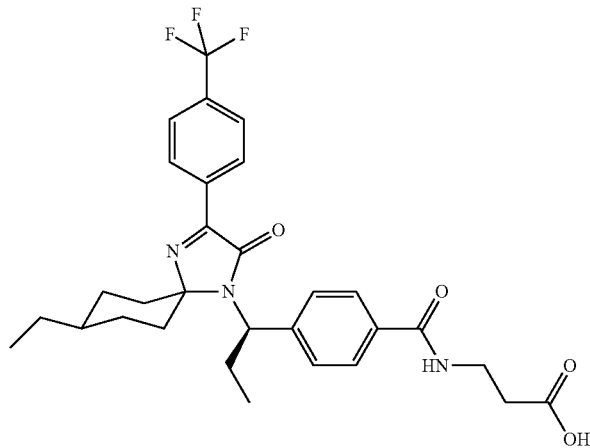 [SMILES: CCC1CCC2(CC1)N=C(c1ccc(C(F)(F)F)cc1)C(=O)N2[C@H](CC)c1ccc(C(=O)NCCC(=O)O)cc1] |
| 1.932 | 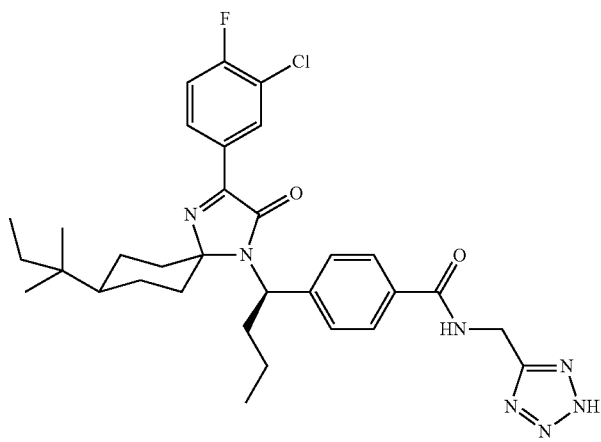 [SMILES: CCC[C@H](c1ccc(C(=O)NCc2nn[nH]n2)cc1)N1C(=O)C(c2ccc(F)c(Cl)c2)=NC12CCC(C(C)(C)CC)CC2] |
| 1.933 | 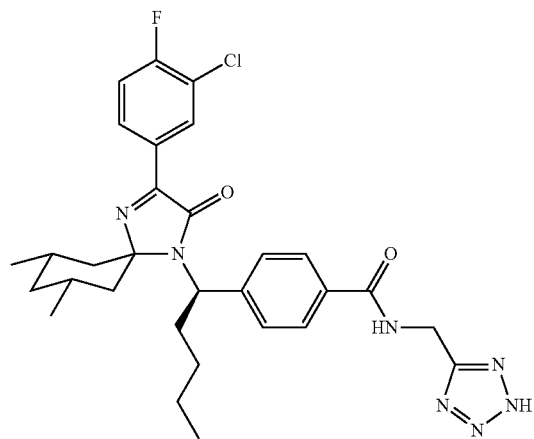 [SMILES: CCCC[C@H](c1ccc(C(=O)NCc2nn[nH]n2)cc1)N1C(=O)C(c2ccc(F)c(Cl)c2)=NC12CC(C)CC(C)C2] |

-continued
| Ex. | Structure |
|---|---|
| 1.940 | 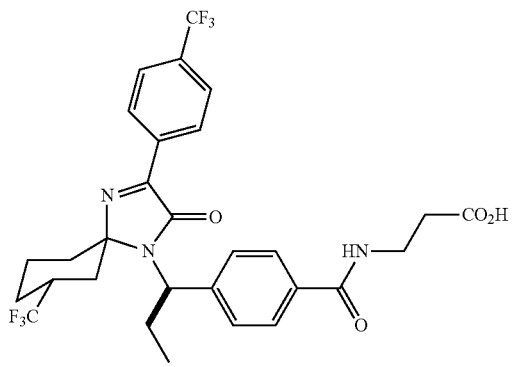<br>Isomer 1 |
| 1.936 | 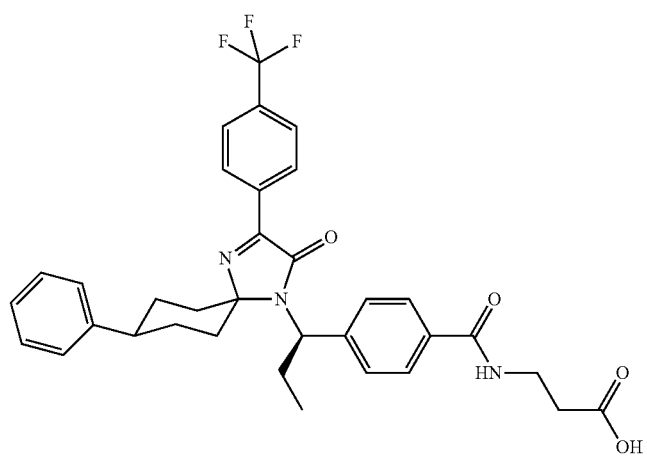 [SMILES: CC[C@H](c1ccc(C(=O)NCCC(=O)O)cc1)N1C(=O)C(c2ccc(C(F)(F)F)cc2)=NC12CCC(c1ccccc1)CC2] |
| 1.937 | 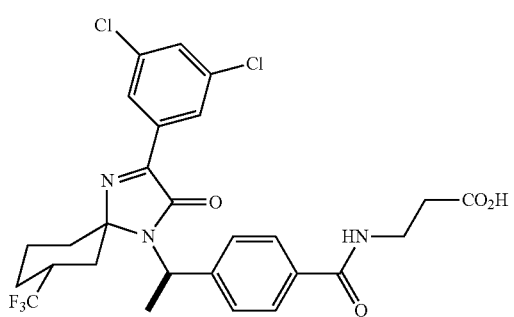<br>Isomer 2 |
| 1.938 | 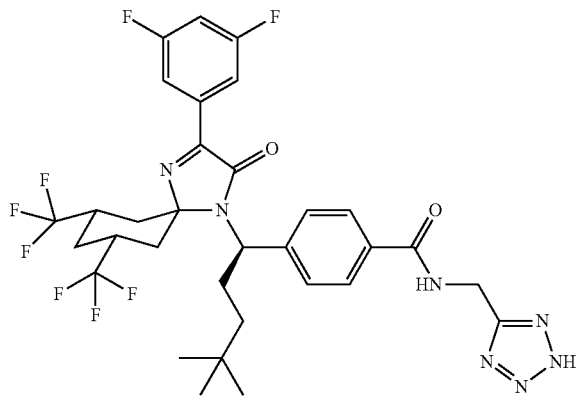 [SMILES: CC(C)(C)CC[C@H](c1ccc(C(=O)NCc2nn[nH]n2)cc1)N1C(=O)C(c2cc(F)cc(F)c2)=NC12CC(C(F)(F)F)CC(C(F)(F)F)C2] |

| Ex. | Structure |
|---|---|
| 1.939 | 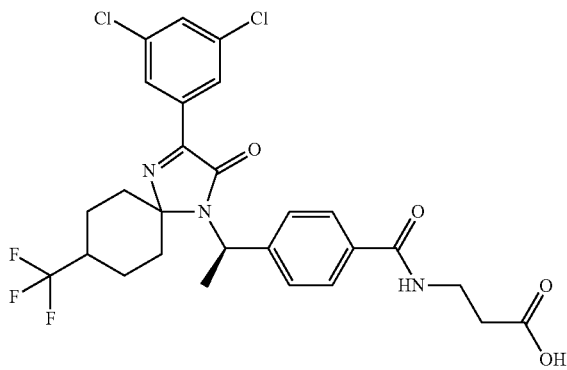<br>Isomer 2 |
| 1.946 | 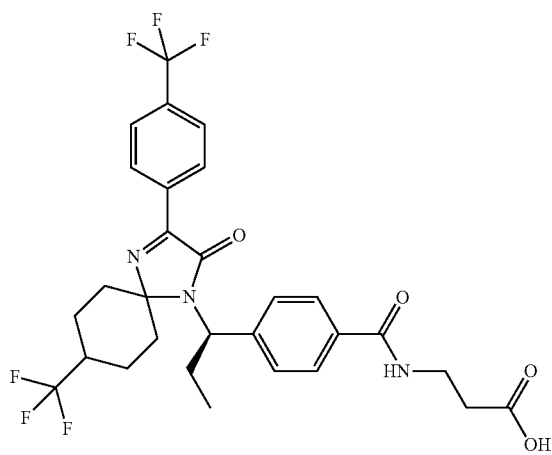<br>isomer 1 |
| 1.947 | 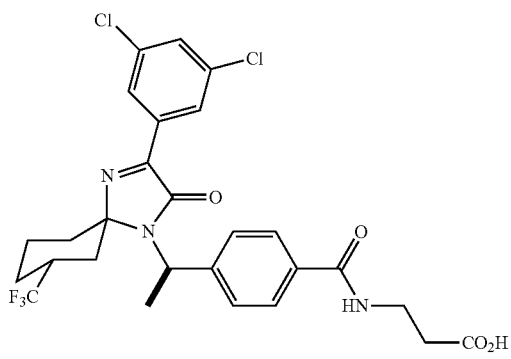<br>Isomer 1 |

-continued
| Ex. | Structure |
|---|---|
| 1.941 | 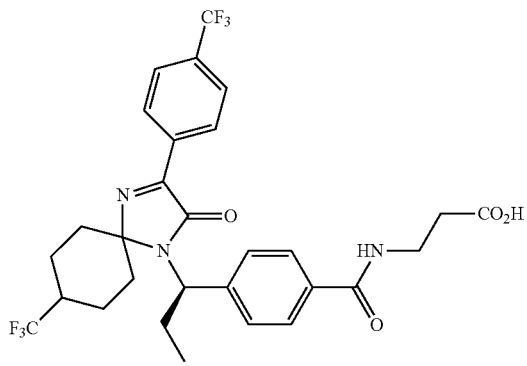<br>Isomer 2 |
| 1.942 | 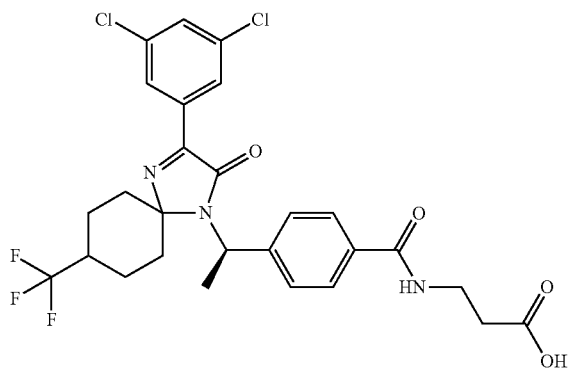<br>Isomer 1 |
| 1.943 | 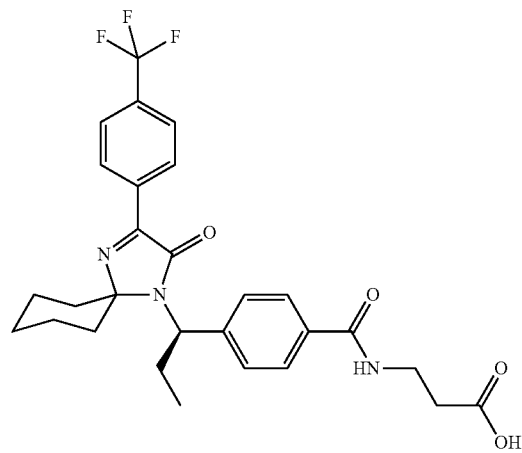 [SMILES: CC[C@H](c1ccc(C(=O)NCCC(=O)O)cc1)N1C(=O)C(c2ccc(C(F)(F)F)cc2)=NC12CCCCC2] |

| Ex. | Structure |
|---|---|
| 1,944 | 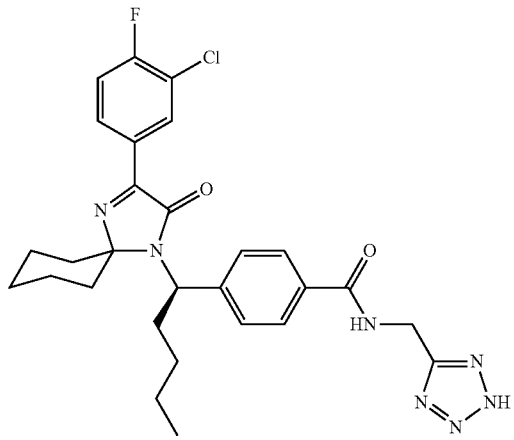 [SMILES: CCCC[C@H](c1ccc(C(=O)NCc2nn[nH]n2)cc1)N1C(=O)C(c2ccc(F)c(Cl)c2)=NC12CCCCC2] |
| 1,945 | 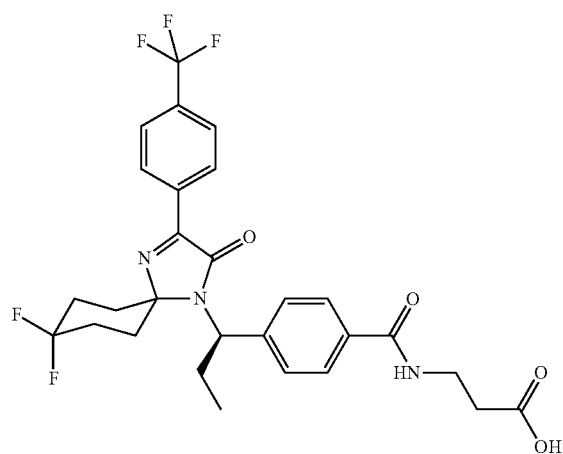 [SMILES: CC[C@H](c1ccc(C(=O)NCCC(=O)O)cc1)N1C(=O)C(c2ccc(C(F)(F)F)cc2)=NC12CCC(F)(F)CC2] |
| 1,952 | 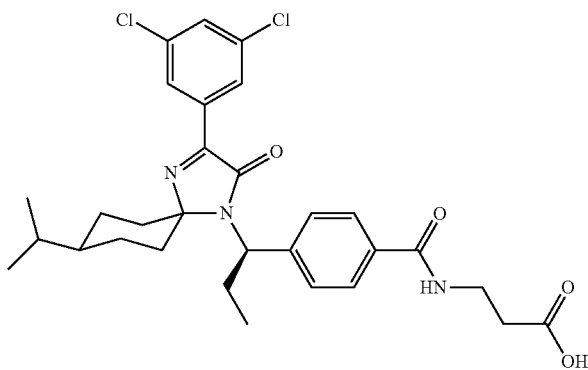 [SMILES: CC[C@H](c1ccc(C(=O)NCCC(=O)O)cc1)N1C(=O)C(c2cc(Cl)cc(Cl)c2)=NC12CCC(C(C)C)CC2] |

| Ex. | Structure |
|---|---|
| 1.948 | 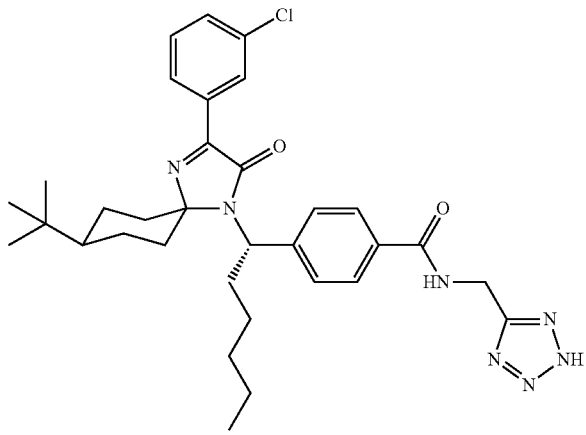 [SMILES: CCCCC[C@@H](c1ccc(C(=O)NCc2nn[nH]n2)cc1)N1C(=O)C(c2cccc(Cl)c2)=NC12CCC(C(C)(C)C)CC2] |
| 1.949 | 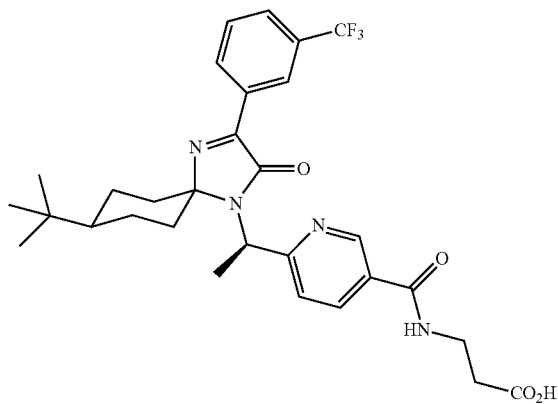 [SMILES: C[C@H](c1ccc(C(=O)NCCC(=O)O)cn1)N1C(=O)C(c2cccc(C(F)(F)F)c2)=NC12CCC(C(C)(C)C)CC2] |
| 1.950 | 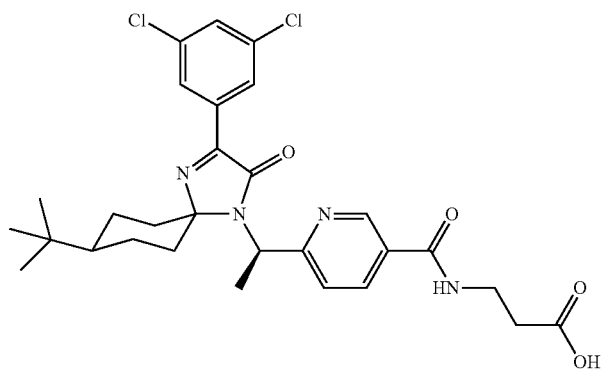 [SMILES: C[C@H](c1ccc(C(=O)NCCC(=O)O)cn1)N1C(=O)C(c2cc(Cl)cc(Cl)c2)=NC12CCC(C(C)(C)C)CC2] |

| Ex. | Structure |
|---|---|
| 1.959 | 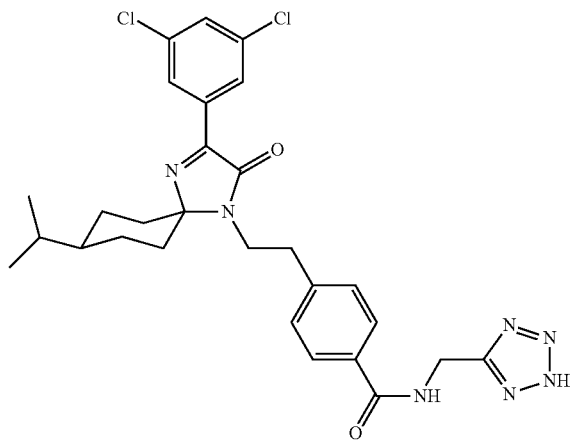 [SMILES: CC(C)C1CCC2(CC1)N=C(c1cc(Cl)cc(Cl)c1)C(=O)N2CCc1ccc(C(=O)NCc2nn[nH]n2)cc1] |
| 1.960 | 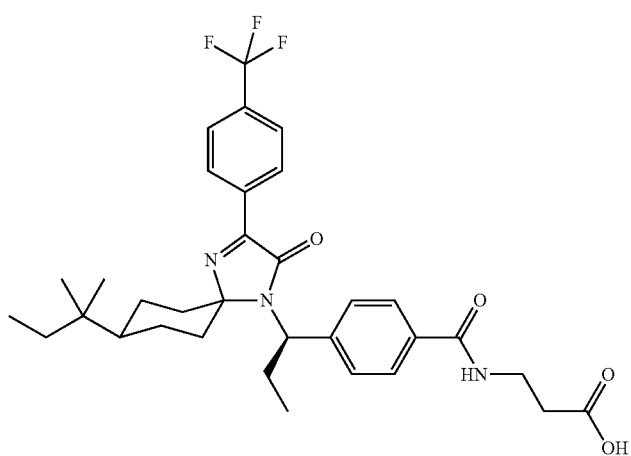 [SMILES: CC[C@H](c1ccc(C(=O)NCCC(=O)O)cc1)N1C(=O)C(c2ccc(C(F)(F)F)cc2)=NC12CCC(C(C)(C)CC)CC2] |
| 1.953 | 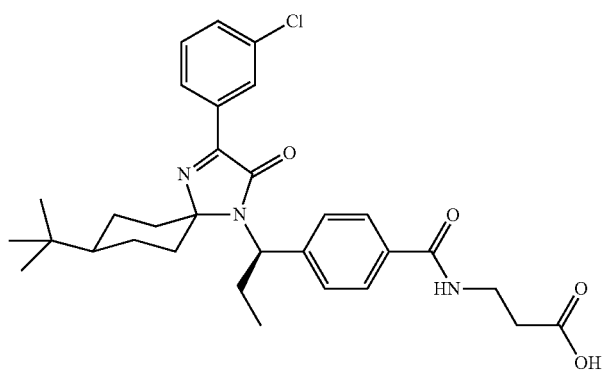 [SMILES: CC[C@H](c1ccc(C(=O)NCCC(=O)O)cc1)N1C(=O)C(c2cccc(Cl)c2)=NC12CCC(C(C)(C)C)CC2] |

-continued
| Ex. | Structure |
|---|---|
| 1.954 | 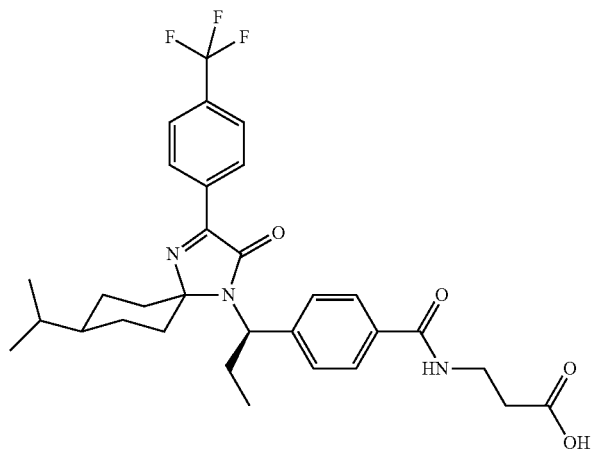 [SMILES: CC[C@H](c1ccc(C(=O)NCCC(=O)O)cc1)N1C(=O)C(c2ccc(C(F)(F)F)cc2)=NC12CCC(C(C)C)CC2] |
| 1.955 | 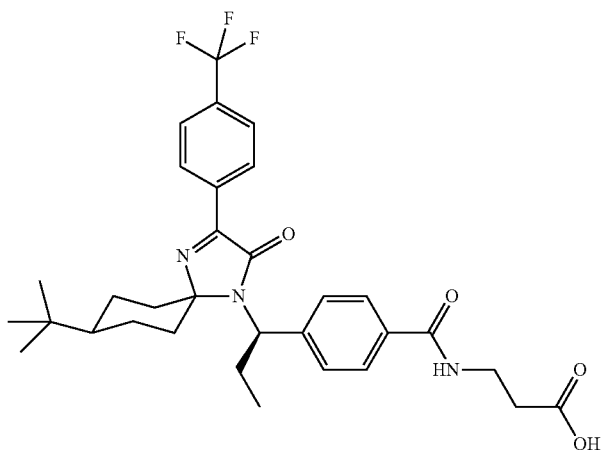 [SMILES: CC[C@H](c1ccc(C(=O)NCCC(=O)O)cc1)N1C(=O)C(c2ccc(C(F)(F)F)cc2)=NC12CCC(C(C)(C)C)CC2] |
| 1.956 | 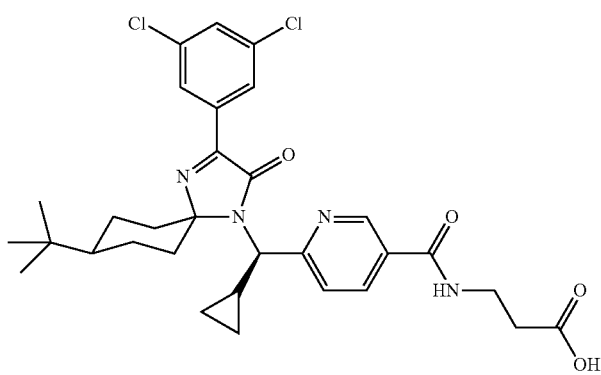 [SMILES: CC(C)(C)C1CCC2(CC1)N=C(c1cc(Cl)cc(Cl)c1)C(=O)N2[C@@H](c1ccc(C(=O)NCCC(=O)O)cn1)C1CC1] |

-continued
| Ex. | Structure |
|---|---|
| 1.957 | 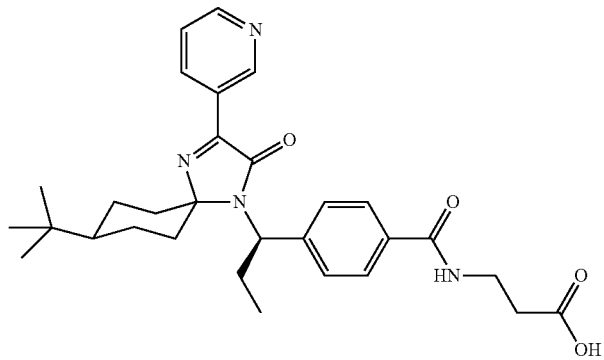 [SMILES: CC[C@H](c1ccc(C(=O)NCCC(=O)O)cc1)N1C(=O)C(c2cccnc2)=NC12CCC(C(C)(C)C)CC2] |
| 1.958 | 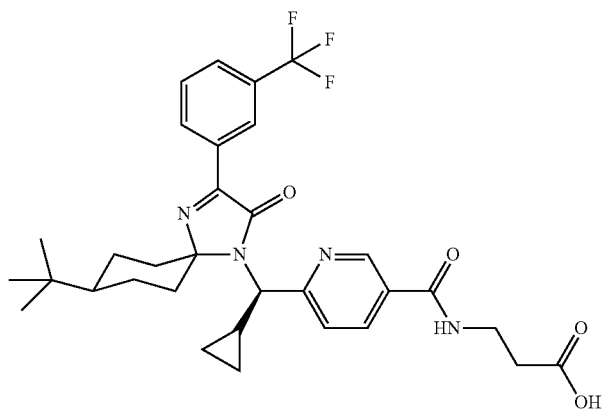 [SMILES: CC(C)(C)C1CCC2(CC1)N=C(c1cccc(C(F)(F)F)c1)C(=O)N2[C@@H](c1ccc(C(=O)NCCC(=O)O)cn1)C1CC1] |
| 1.966 | 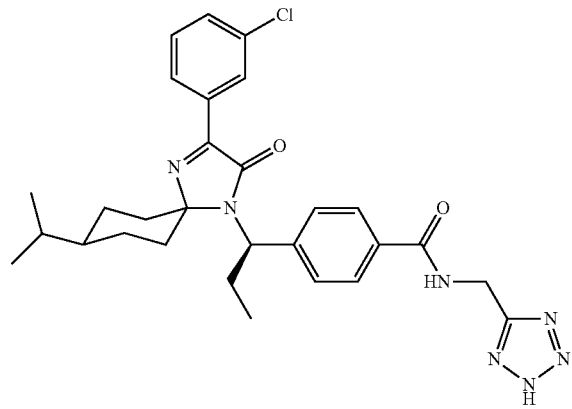 [SMILES: CC[C@H](c1ccc(C(=O)NCc2nn[nH]n2)cc1)N1C(=O)C(c2cccc(Cl)c2)=NC12CCC(C(C)C)CC2] |
| 1.961 | 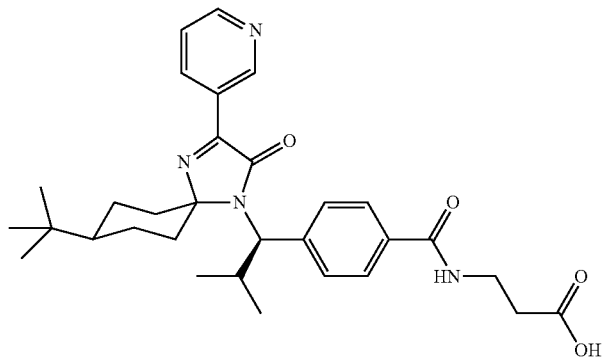 [SMILES: CC(C)[C@H](c1ccc(C(=O)NCCC(=O)O)cc1)N1C(=O)C(c2cccnc2)=NC12CCC(C(C)(C)C)CC2] |

| Ex. | Structure |
|---|---|
| 1.962 | 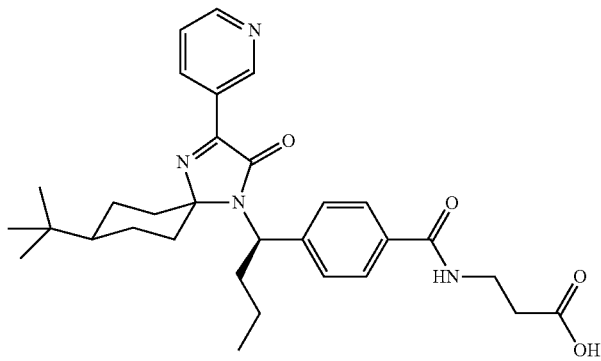 [SMILES: CCC[C@H](c1ccc(C(=O)NCCC(=O)O)cc1)N1C(=O)C(c2cccnc2)=NC12CCC(C(C)(C)C)CC2] |
| 1.963 | 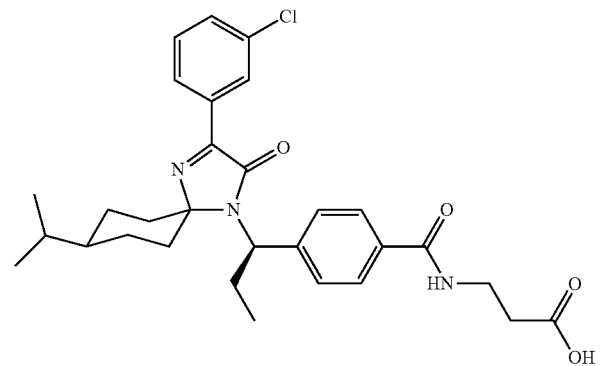 [SMILES: CC[C@H](c1ccc(C(=O)NCCC(=O)O)cc1)N1C(=O)C(c2cccc(Cl)c2)=NC12CCC(C(C)C)CC2] |
| 1.964 | 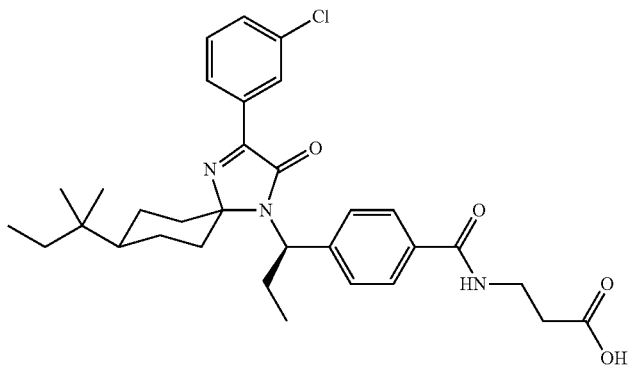 [SMILES: CC[C@H](c1ccc(C(=O)NCCC(=O)O)cc1)N1C(=O)C(c2cccc(Cl)c2)=NC12CCC(C(C)(C)CC)CC2] |
| 1.965 | 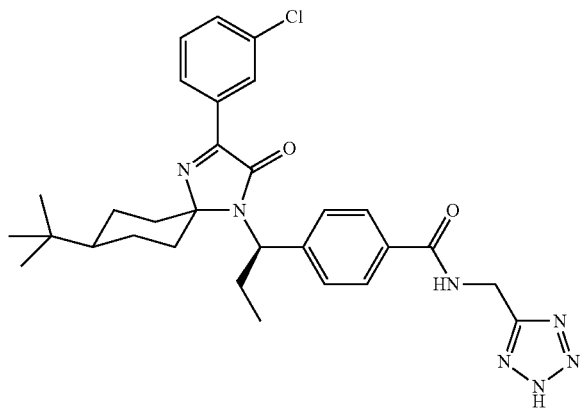 [SMILES: CC[C@H](c1ccc(C(=O)NCc2nn[nH]n2)cc1)N1C(=O)C(c2cccc(Cl)c2)=NC12CCC(C(C)(C)C)CC2] |

| Ex. | Structure |
|---|---|
| 1.978 | 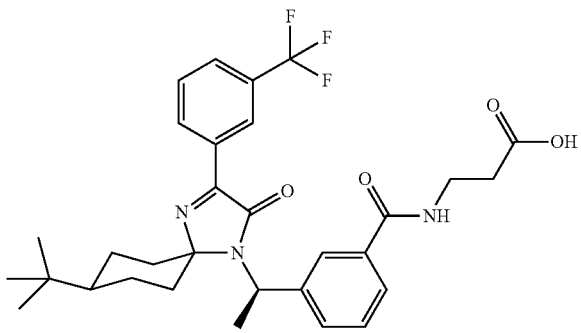 [SMILES: C[C@H](c1cccc(C(=O)NCCC(=O)O)c1)N1C(=O)C(c2cccc(C(F)(F)F)c2)=NC12CCC(C(C)(C)C)CC2] |
| 1.973 | 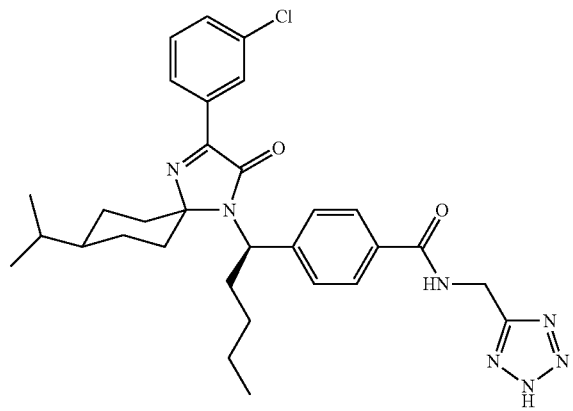 [SMILES: CCCC[C@H](c1ccc(C(=O)NCc2nn[nH]n2)cc1)N1C(=O)C(c2cccc(Cl)c2)=NC12CCC(C(C)C)CC2] |
| 1.967 | 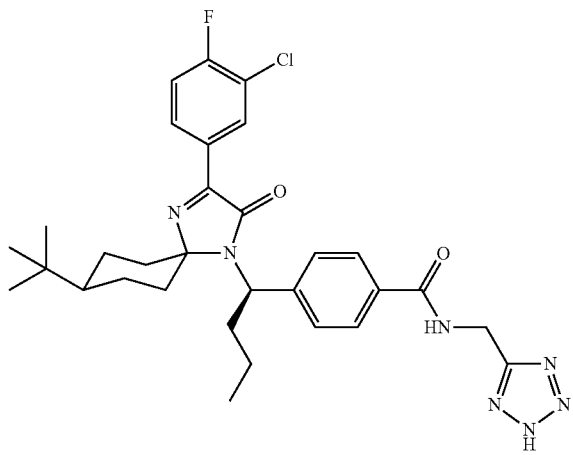 [SMILES: CCC[C@H](c1ccc(C(=O)NCc2nn[nH]n2)cc1)N1C(=O)C(c2ccc(F)c(Cl)c2)=NC12CCC(C(C)(C)C)CC2] |

| Ex. | Structure |
|---|---|
| 1.969 | 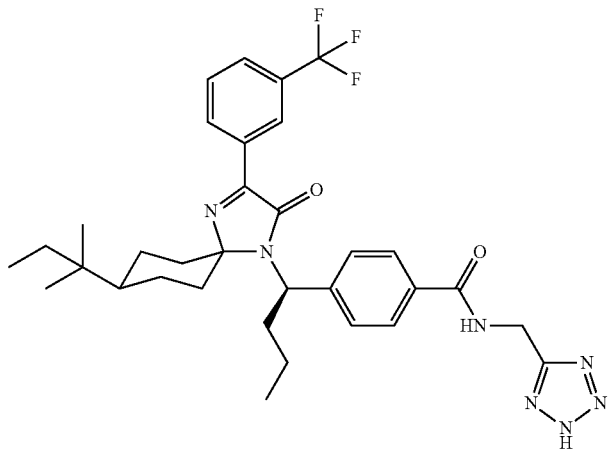 [SMILES: CCC[C@H](c1ccc(C(=O)NCc2nn[nH]n2)cc1)N1C(=O)C(c2cccc(C(F)(F)F)c2)=NC12CCC(C(C)(C)CC)CC2] |
| 1.970 | 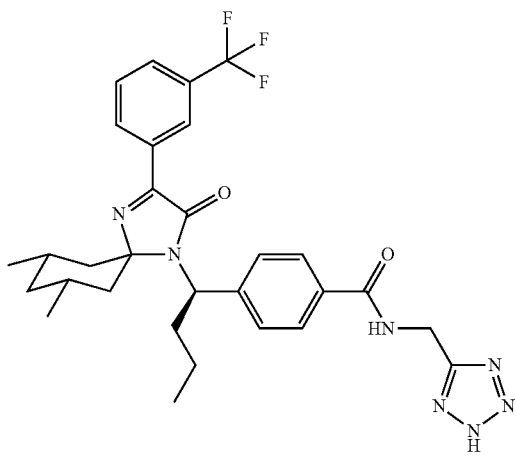 [SMILES: CCC[C@H](c1ccc(C(=O)NCc2nn[nH]n2)cc1)N1C(=O)C(c2cccc(C(F)(F)F)c2)=NC12CC(C)CC(C)C2] |
| 1.981 | 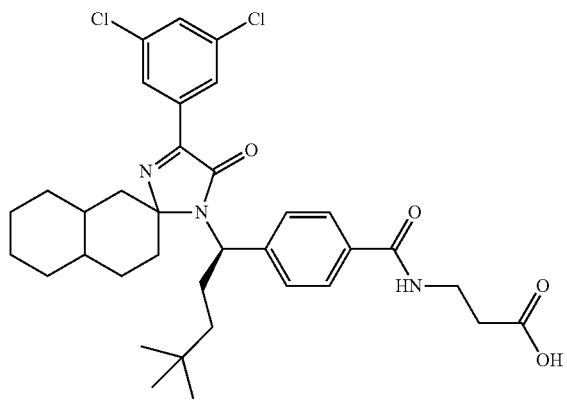  Mix of isomers |

-continued
| Ex. | Structure |
|---|---|
| 1.971 | 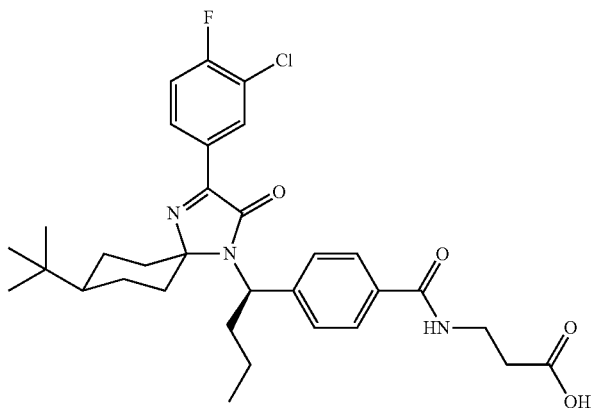 [SMILES: CCC[C@H](c1ccc(C(=O)NCCC(=O)O)cc1)N1C(=O)C(c2ccc(F)c(Cl)c2)=NC12CCC(C(C)(C)C)CC2] |
| 1.983 | 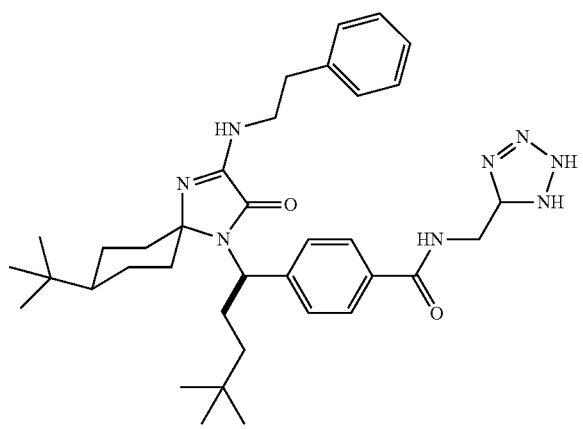 [SMILES: CC(C)(C)CC[C@H](c1ccc(C(=O)NCC2N=NNN2)cc1)N1C(=O)C(NCCc2ccccc2)=NC12CCC(C(C)(C)C)CC2] |
| 1.974 | 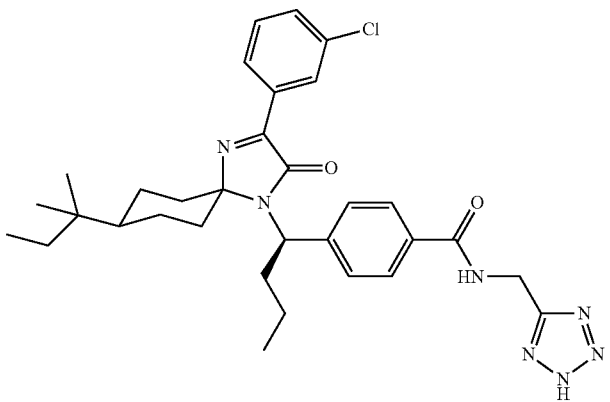 [SMILES: CCC[C@H](c1ccc(C(=O)NCc2nn[nH]n2)cc1)N1C(=O)C(c2cccc(Cl)c2)=NC12CCC(C(C)(C)CC)CC2] |

-continued
| Ex. | Structure |
|---|---|
| 1.975 | 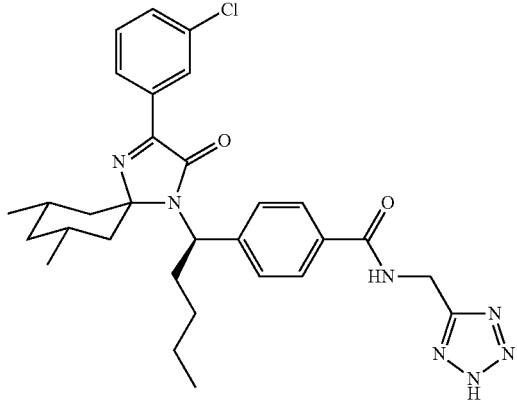 [SMILES: CCCC[C@H](c1ccc(C(=O)NCc2nn[nH]n2)cc1)N1C(=O)C(c2cccc(Cl)c2)=NC12CC(C)CC(C)C2] |
| 1.976 | 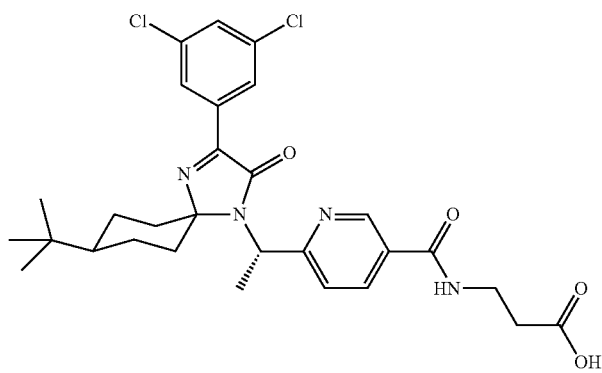 [SMILES: C[C@@H](c1ccc(C(=O)NCCC(=O)O)cn1)N1C(=O)C(c2cc(Cl)cc(Cl)c2)=NC12CCC(C(C)(C)C)CC2] |
| 1.982 | 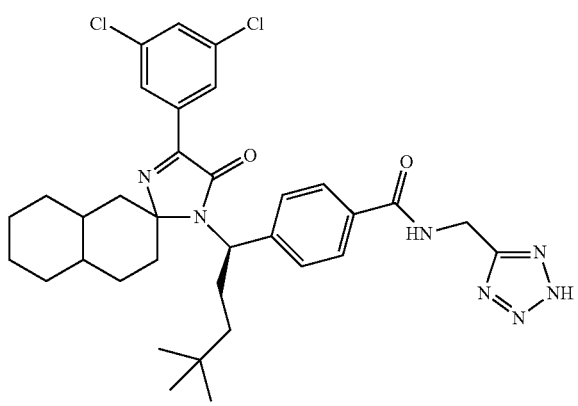<br>Mix of isomers |
| 1.977 | 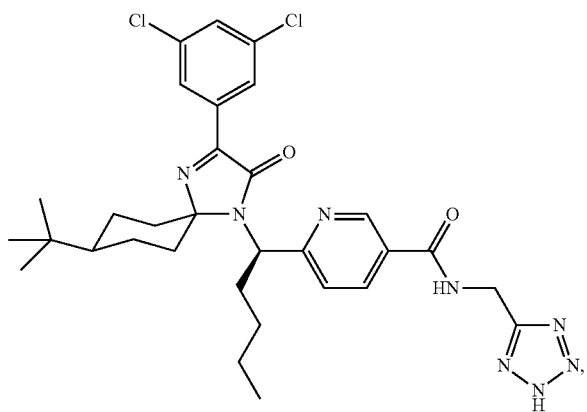 [SMILES: CCCC[C@H](c1ccc(C(=O)NCc2nn[nH]n2)cn1)N1C(=O)C(c2cc(Cl)cc(Cl)c2)=NC12CCC(C(C)(C)C)CC2] |

| Ex. | Structure |
|---|---|
| 1.984 | 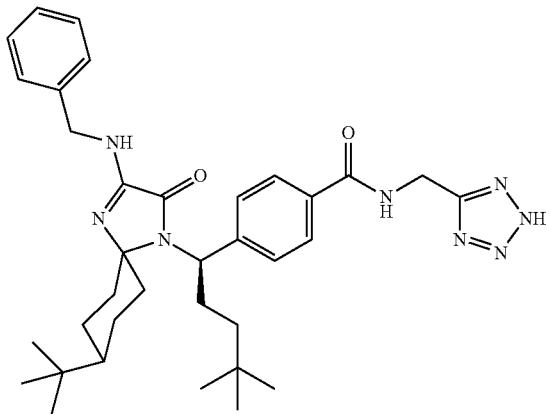 [SMILES: CC(C)(C)CC[C@H](c1ccc(C(=O)NCc2nn[nH]n2)cc1)N1C(=O)C(NCc2ccccc2)=NC12CCC(C(C)(C)C)CC2] |
| 1.985 | 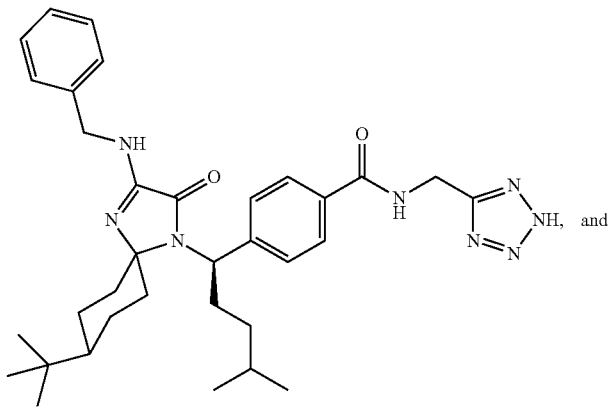 [SMILES: CC(C)CC[C@H](c1ccc(C(=O)NCc2nn[nH]n2)cc1)N1C(=O)C(NCc2ccccc2)=NC12CCC(C(C)(C)C)CC2 ; "and"] and |
| 1.972 | 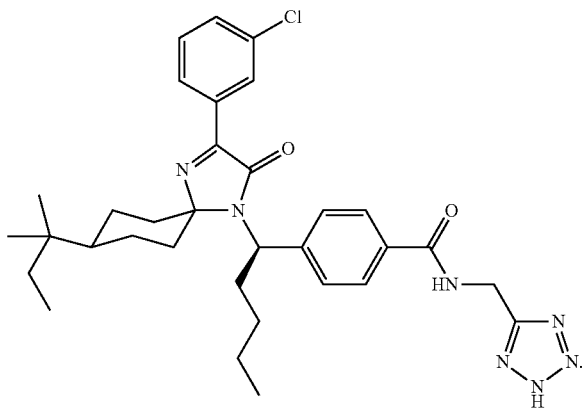 [SMILES: CCCC[C@H](c1ccc(C(=O)NCc2nn[nH]n2)cc1)N1C(=O)C(c2cccc(Cl)c2)=NC12CCC(C(C)(C)CC)CC2] |

14. A composition comprising a compound according to claim 1 and a pharmaceutically acceptable carrier.

15. A composition of claim 14, further comprising one or more antidiabetic agents other than a compound of claim 1.

16. A composition of claim 15, further comprising at least one pharmaceutically acceptable carrier.

17. A composition of claim 14, further comprising at least one additional therapeutic agent selected from the group consisting of: DPP-IV inhibitor, an insulin sensitizer, insulin, an insulin mimetic, an insulin secretagogue, a GLP-1 mimetic, a glucosidase inhibitor, an alpha glucosidase inhibitor, a glucagon receptor antagonist other than a compound of claim 1, glucophage, glucophage XR, an antihypertensive agent, a meglitinide, an alpha-glucosidase inhibitor, amlintide, pramlintide, exendin, a histamine $H_3$ receptor antagonist, dapagliflozin, sergliflozin, AVE2268 (Sanofi-Aventis) and T-1095 (Tanabe Seiyaku), a cholesterol lowering agent, a PACAP, a PACAP mimetic, a PACAP receptor 3 agonist, a PPAR delta agonist, an antiobesity agent, an ileal bile acid transporter inhibitor, an NSAID, and a CB1 receptor antagonist, and a CB1 receptor inverse agonist.

18. A compound of claim 1, or a pharmaceutically acceptable salt or tautomer of said compound, having the structure:

2.138

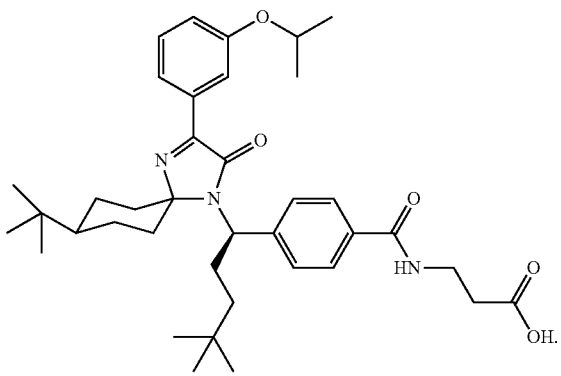

* * * * *